(12) United States Patent
Jakobovits et al.

(10) Patent No.: US 7,951,375 B2
(45) Date of Patent: May 31, 2011

(54) METHODS OF INDUCING AN IMMUNE RESPONSE

(75) Inventors: Aya Jakobovits, Beverly Hills, CA (US); Pia M. Challita-Eid, Encino, CA (US); Mary Faris, Los Angeles, CA (US); Wangmao Ge, Los Angeles, CA (US); Rene S. Hubert, Los Angeles, CA (US); Karen Jane Meyrick Morrison, Santa Monica, CA (US); Robert Kendall Morrison, Santa Monica, CA (US); Arthur B. Raitano, Los Angeles, CA (US); Daniel E. H. Afar, Fremont, CA (US)

(73) Assignee: Agensys, Inc., Santa Monica, CA (US)

( * ) Notice: Subject to any disclaimer, the term of this patent is extended or adjusted under 35 U.S.C. 154(b) by 268 days.

(21) Appl. No.: 11/156,231

(22) Filed: Jun. 17, 2005

(65) Prior Publication Data

US 2007/0041968 A1 Feb. 22, 2007

Related U.S. Application Data

(62) Division of application No. 10/121,024, filed on Apr. 10, 2002, now Pat. No. 7,736,654.

(60) Provisional application No. 60/286,630, filed on Apr. 25, 2001, provisional application No. 60/282,739, filed on Apr. 10, 2001, provisional application No. 60/283,112, filed on Apr. 10, 2001.

(51) Int. Cl.
*A61K 39/00* (2006.01)
(52) U.S. Cl. ...................... 424/184.1; 530/300
(58) Field of Classification Search ............... 424/184.1; 530/300
See application file for complete search history.

(56) References Cited

U.S. PATENT DOCUMENTS

| | | | |
|---|---|---|---|
| 6,150,090 A | 11/2000 | Baltimore | |
| 6,265,565 B1 | 7/2001 | Bandman et al. | |
| 6,410,516 B1 | 6/2002 | Baltimore et al. | |
| 6,414,220 B1 | 7/2002 | Vrontakis | |
| 6,500,938 B1 | 12/2002 | Au-Young et al. | |
| 6,518,411 B1 | 2/2003 | Murray et al. | |
| 6,639,063 B1 | 10/2003 | Edwards et al. | |
| 6,812,339 B1 | 11/2004 | Venter et al. | |
| 2001/0051335 A1 | 12/2001 | Lalgudi | |
| 2002/0022248 A1 | 2/2002 | Xu et al. | |
| 2002/0098543 A1 | 7/2002 | Bandman et al. | |
| 2002/0102543 A1 | 8/2002 | Friedrich et al. | |
| 2002/0103125 A1 | 8/2002 | Ashkenazi et al. | |
| 2002/0123463 A1 | 9/2002 | Ashkenazi et al. | |
| 2002/0127584 A1 | 9/2002 | Baker et al. | |
| 2002/0132252 A1 | 9/2002 | Ashkenazi et al. | |
| 2002/0137139 A1 | 9/2002 | Byatt et al. | |
| 2002/0142961 A1 | 10/2002 | Ashkenazi et al. | |
| 2002/0147140 A1 | 10/2002 | Rosen et al. | |
| 2002/0156263 A1 | 10/2002 | Chen | |
| 2002/0160384 A1 | 10/2002 | Ashkenazi et al. | |
| 2002/0169284 A1 | 11/2002 | Ashkenazi et al. | |
| 2002/0177164 A1 | 11/2002 | Ashkenazi et al. | |
| 2002/0192706 A1 | 12/2002 | Ashkenazi et al. | |
| 2002/0192763 A1 | 12/2002 | Xu et al. | |
| 2003/0003531 A1 | 1/2003 | Ashkenazi et al. | |
| 2003/0004102 A1 | 1/2003 | Ashkenazi et al. | |
| 2003/0004311 A1 | 1/2003 | Baker et al. | |
| 2003/0017542 A1 | 1/2003 | Baker et al. | |
| 2003/0017563 A1 | 1/2003 | Baker et al. | |
| 2003/0022298 A1 | 1/2003 | Baker et al. | |
| 2003/0027162 A1 | 2/2003 | Ashkenazi et al. | |
| 2003/0027163 A1 | 2/2003 | Ashkenazi et al. | |
| 2003/0027272 A1 | 2/2003 | Baker et al. | |
| 2003/0027280 A1 | 2/2003 | Baker et al. | |
| 2003/0027985 A1 | 2/2003 | Ashkenazi et al. | |
| 2003/0032023 A1 | 2/2003 | Ashkenazi et al. | |
| 2003/0032102 A1 | 2/2003 | Baker et al. | |
| 2003/0032104 A1 | 2/2003 | Baker et al. | |
| 2003/0032106 A1 | 2/2003 | Baker et al. | |
| 2003/0032110 A1 | 2/2003 | Baker et al. | |
| 2003/0032113 A1 | 2/2003 | Baker et al. | |
| 2003/0032155 A1 | 2/2003 | Baker et al. | |
| 2003/0036136 A1 | 2/2003 | Baker et al. | |
| 2003/0036137 A1 | 2/2003 | Baker et al. | |
| 2003/0036139 A1 | 2/2003 | Baker et al. | |
| 2003/0036143 A1 | 2/2003 | Baker et al. | |
| 2003/0036156 A1 | 2/2003 | Baker et al. | |
| 2003/0036157 A1 | 2/2003 | Baker et al. | |
| 2003/0036162 A1 | 2/2003 | Baker et al. | |
| 2003/0036180 A1 | 2/2003 | Baker et al. | |
| 2003/0105002 A1 | 6/2003 | Murray et al. | |
| 2004/0048253 A1 | 3/2004 | Panzer et al. | |

FOREIGN PATENT DOCUMENTS

CA 2255286 6/1999

(Continued)

OTHER PUBLICATIONS

White et al, 2001 (Ann Rev Med, 52: 125-145).*
Boon, 1992 (Adv Can Res, 58:177-210).*
Smith RT, 1994 (Clin Immunol, 41(4): 841-849).*
Bodey et al, 2000, Anticancer Res, 20: 2665-2676.*
Lee et al, 1999, J Immunol, 163: 6292-6300.*
Banki et al, 1994, JBC, 269 (4): 2847-5.*
Boller et al., J. Virol. (1997) 17:4581-4588.

(Continued)

*Primary Examiner* — Larry R. Helms
*Assistant Examiner* — Minh-Tam Davis
(74) *Attorney, Agent, or Firm* — Morrison & Foerster LLP

(57) ABSTRACT

Novel genes designated and set forth in FIG. 2 and their respective encoded proteins, and variants thereof, are described wherein a gene of the invention exhibits tissue specific expression in normal adult tissue, and is aberrantly expressed in the cancers such as those listed in Table I. Consequently, of gene products of a gene of FIG. 2 provide diagnostic, prognostic, prophylactic and/or therapeutic targets for cancer. A gene of FIG. 2 or fragment thereof, its encoded protein, or variants thereof, or a fragment thereof, can be used to elicit a humoral or cellular immune response; antibodies or T cells reactive with a gene product of FIG. 2 can be used in active or passive immunization.

5 Claims, 383 Drawing Sheets

FOREIGN PATENT DOCUMENTS

| | | |
|---|---|---|
| CA | 2401868 | 8/2001 |
| CN | 1352259 | 6/2002 |
| EP | 1 033 401 | 9/2000 |
| EP | 1 067 182 | 1/2001 |
| EP | 1 074 617 | 2/2001 |
| EP | 1 101 820 | 5/2001 |
| EP | 1 293 569 | 3/2003 |
| EP | 1 308 459 | 5/2003 |
| JP | 05-328975 | 12/1993 |
| JP | 07-145197 | 6/1995 |
| JP | 09-191883 | 7/1997 |
| JP | 11-332579 | 12/1999 |
| JP | 12-270871 | 10/2000 |
| WO | WO-89/07614 | 8/1989 |
| WO | WO-92/12997 | 8/1992 |
| WO | WO-92/15015 | 9/1992 |
| WO | WO-92/15681 | 9/1992 |
| WO | WO-93/16178 | 8/1993 |
| WO | WO-94/21783 | 9/1994 |
| WO | WO-95/14772 | 6/1995 |
| WO | WO-96/24379 | 8/1996 |
| WO | WO-97/39133 | 10/1997 |
| WO | WO-98/14568 | 4/1998 |
| WO | WO9814568 * | 4/1998 |
| WO | WO-98/21328 | 5/1998 |
| WO | WO-98/30585 | 7/1998 |
| WO | WO-98/32853 | 7/1998 |
| WO | WO-98/45435 | 10/1998 |
| WO | WO-98/46755 | 10/1998 |
| WO | WO-98/49299 | 11/1998 |
| WO | WO-99/03990 | 1/1999 |
| WO | WO-99/05272 | 2/1999 |
| WO | WO-99/06439 | 2/1999 |
| WO | WO-99/06548 | 2/1999 |
| WO | WO-99/06549 | 2/1999 |
| WO | WO-99/06550 | 2/1999 |
| WO | WO-99/06551 | 2/1999 |
| WO | WO-99/06552 | 2/1999 |
| WO | WO-99/06553 | 2/1999 |
| WO | WO-99/06554 | 2/1999 |
| WO | WO-99/18207 | 4/1999 |
| WO | WO-99/19469 | 4/1999 |
| WO | WO-99/22000 | 5/1999 |
| WO | WO-99/25825 | 5/1999 |
| WO | WO-99/31117 | 6/1999 |
| WO | WO-99/31236 | 6/1999 |
| WO | WO-99/33982 | 7/1999 |
| WO | WO-99/38972 | 8/1999 |
| WO | WO-99/40189 | 8/1999 |
| WO | WO-99/46281 | 9/1999 |
| WO | WO-99/48920 | 9/1999 |
| WO | WO-99/53051 | 10/1999 |
| WO | WO-99/58660 | 11/1999 |
| WO | WO-99/58675 | 11/1999 |
| WO | WO-99/63088 | 12/1999 |
| WO | WO-99/64576 | 12/1999 |
| WO | WO-00/04149 | 1/2000 |
| WO | WO-00/04153 | 1/2000 |
| WO | WO-00/06589 | 2/2000 |
| WO | WO-00/06714 | 2/2000 |
| WO | WO-00/09676 | 2/2000 |
| WO | WO-00/14251 | 3/2000 |
| WO | WO-00/18914 | 4/2000 |
| WO | WO-00/32221 | 6/2000 |
| WO | WO-00/34466 | 6/2000 |
| WO | WO-00/50629 | 8/2000 |
| WO | WO-00/52047 | 9/2000 |
| WO | WO-00/53756 | 9/2000 |
| WO | WO-00/53758 | 9/2000 |
| WO | WO-00/55173 | 9/2000 |
| WO | WO-00/55320 | 9/2000 |
| WO | WO-00/58473 | 10/2000 |
| WO | WO-00/61622 | 10/2000 |
| WO | WO-00/69900 | 11/2000 |
| WO | WO-00/70092 | 11/2000 |
| WO | WO-00/73454 | 12/2000 |
| WO | WO-00/73801 | 12/2000 |
| WO | WO-00/75279 | 12/2000 |
| WO | WO-00/75661 | 12/2000 |
| WO | WO-00/77024 | 12/2000 |
| WO | WO-01/00848 | 1/2001 |
| WO | WO-01/02568 | 1/2001 |
| WO | WO-01/09318 | 2/2001 |
| WO | WO-01/12660 | 2/2001 |
| WO | WO-01/22920 | 4/2001 |
| WO | WO-01/25272 | 4/2001 |
| WO | WO-01/30972 | 5/2001 |
| WO | WO-01/34802 | 5/2001 |
| WO | WO-01/40466 | 6/2001 |
| WO | WO-01/42467 | 6/2001 |
| WO | WO-01/42472 | 6/2001 |
| WO | WO-01/51628 | 7/2001 |
| WO | WO-01/51633 | 7/2001 |
| WO | WO-01/54477 | 8/2001 |
| WO | WO-01/55312 | 8/2001 |
| WO | WO-01/55314 | 8/2001 |
| WO | WO-01/55328 | 8/2001 |
| WO | WO-01/55367 | 8/2001 |
| WO | WO-01/57058 | 8/2001 |
| WO | WO-01/57182 | 8/2001 |
| WO | WO-01/57186 | 8/2001 |
| WO | WO-01/57188 | 8/2001 |
| WO | WO-01/57190 | 8/2001 |
| WO | WO-01/57272 | 8/2001 |
| WO | WO-01/57273 | 8/2001 |
| WO | WO-01/57274 | 8/2001 |
| WO | WO-01/57275 | 8/2001 |
| WO | WO-01/57276 | 8/2001 |
| WO | WO-01/57277 | 8/2001 |
| WO | WO-01/57278 | 8/2001 |
| WO | WO-01/59063 | 8/2001 |
| WO | WO-01/60860 | 8/2001 |
| WO | WO-01/60999 | 8/2001 |
| WO | WO-01/62785 | 8/2001 |
| WO | WO-01/62927 | 8/2001 |
| WO | WO-01/63293 | 8/2001 |
| WO | WO-01/66719 | 9/2001 |
| WO | WO-01/68848 | 9/2001 |
| WO | WO-01/70976 | 9/2001 |
| WO | WO-01/71042 | 9/2001 |
| WO | WO-01/72777 | 10/2001 |
| WO | WO-01/73032 | 10/2001 |
| WO | WO-01/75067 | 10/2001 |
| WO | WO-01/77137 | 10/2001 |
| WO | WO-01/77290 | 10/2001 |
| WO | WO-01/77291 | 10/2001 |
| WO | WO-01/85177 | 11/2001 |
| WO | WO-01/86003 | 11/2001 |
| WO | WO-01/87321 | 11/2001 |
| WO | WO-01/88188 | 11/2001 |
| WO | WO-01/92581 | 12/2001 |
| WO | WO-01/94629 | 12/2001 |
| WO | WO-01/96388 | 12/2001 |
| WO | WO-01/96390 | 12/2001 |
| WO | WO-02/00677 | 1/2002 |
| WO | WO-02/00927 | 1/2002 |
| WO | WO-02/08416 | 1/2002 |
| WO | WO-02/10449 | 2/2002 |
| WO | WO-02/12314 | 2/2002 |
| WO | WO-02/12328 | 2/2002 |
| WO | WO-02/12440 | 2/2002 |
| WO | WO-02/18424 | 3/2002 |
| WO | WO-02/18541 | 3/2002 |
| WO | WO-02/18632 | 3/2002 |
| WO | WO-02/24719 | 3/2002 |
| WO | WO-02/26936 | 4/2002 |
| WO | WO-02/28999 | 4/2002 |
| WO | WO-02/29086 | 4/2002 |
| WO | WO-02/29103 | 4/2002 |
| WO | WO-02/30268 | 4/2002 |
| WO | WO-02/31111 | 4/2002 |
| WO | WO-02/38759 | 5/2002 |
| WO | WO-02/41763 | 5/2002 |
| WO | WO-02/44331 | 6/2002 |
| WO | WO-02/46467 | 6/2002 |
| WO | WO-02/50301 | 6/2002 |
| WO | WO-02/052005 | 7/2002 |

| WO | WO-02/058534 | 8/2002 |
| WO | WO-02/059271 | 8/2002 |
| WO | WO-02/060317 | 8/2002 |
| WO | WO-02/064795 | 8/2002 |
| WO | WO-02/066064 | 8/2002 |
| WO | WO-02/069900 | 9/2002 |
| WO | WO-02/070539 | 9/2002 |
| WO | WO-02/077204 | 10/2002 |
| WO | WO-02/078516 | 10/2002 |
| WO | WO-02/079433 | 10/2002 |
| WO | WO-02/079449 | 10/2002 |
| WO | WO-02/083921 | 10/2002 |
| WO | WO-02/085298 | 10/2002 |
| WO | WO-02/090526 | 11/2002 |
| WO | WO-02/090992 | 11/2002 |
| WO | WO-02/095000 | 11/2002 |
| WO | WO-02/097031 | 12/2002 |
| WO | WO-02/097090 | 12/2002 |
| WO | WO-02/102982 | 12/2002 |
| WO | WO-03/012082 | 2/2003 |
| WO | WO-03/016549 | 2/2003 |
| WO | WO-03/022300 | 4/2003 |
| WO | WO-03/045989 | 6/2003 |

OTHER PUBLICATIONS

Danilczyk et al., Nature (2006) 444(7122):1088-1091.
Database EMBL, (2000) EBI accession No. EMBL:AW365784.
Database Geneseq, (1998) EBI accession No. GSN:AAV40540.
Database Geneseq, (2000) EBI accession No. GSP:AAB24430.
Database Geneseq, (2001) EBI accession No. GSN:AAH72870.
Database Geneseq, (2003) EBI accession No. GSP:ABB84525.
Database Geneseq, (2004) EBI accession No. GSP:ADK41492.
Partial European Search Report for EP 02747813.0, mailed Jul. 31, 2007, 13 pages.
Smogorzewska et al., Cell (2007) 129(2):289-301.
Zhang et al., The Journal of Biological Chemistry (2001) 276(20):17132-17139.
Office Action for Canadian Patent Application No. 2,443,123, mailed on Mar. 18, 2009, 4 pages.
Database EMBL, (2000) EBI Accession No. EMBL:BF674714.
Hubert et al., PNAS (1999) 96(25):14523-14528.
Nupponen et al., Amer. J. of Pathol. (1999) 154(6):1777-1783.
Porkka et al., J. of Pathol. (2001) 193(1):73-79.
Supplementary Partial European Search Report, Date Mailed on Apr. 18, 2007, for EP 02747813.0, 9 pages.
Alberts et al., Molecular Biology of the Cell, 3rd edition (1994) p. 465.
Boon, "Toward a genetic analysis of tumor rejection antigens," Adv. Can. Res. (1992) 58:177-210.
Bowie et al., "Deciphering the Message in Protein Sequences: Tolerance to Amino Acid Substitutions," Science (1990) 257:1306-1310.
Brennan et al., "Cytokine Production in Culture by Cells Isolated from the Synovial Membrane," Journal of Autoimmunity (1989) (2 suppl.):177-186.
Carrere et al., "Immunoreactive pancreatic Reg protein in sera from cystic fibrosis patients with and without pancreatic insufficiency," Gut (1999) 44:545-551.
Chaux et al., "Estimation of the frequencies of anti-mage-3 cytolytic t-lymphocyte precursors in blood from individuals without cancer," Int. J. Cancer (1998) 77:538-542.

Eriksson et al., "Insulin resistance in Type 2 (non-insulin-dependent) diabetic patients and their relatives is not associated with a defect in the expression of the insulin-responsive glucose transporter (GLUT-4) gene in human skeletal muscle," Diabetologia (1992) 35:143-147.
Ezzell, "Cancer "Vaccines": An Idea Whose Time Has Come?" J. NIH Res. (1995) 7:46-49.
Fu et al., Translational regulation of human p53 gene, EMBO Journal (1996) 15:4392-4401.
Greenbaum et al., "Comparing protein abundance and mRNA expression levels on a genomic scale," Genome Biology (2003) 4(9):117.1-117.8.
Greenspan et al., "Defining epitopes: It's not as easy as it seems," Nature Biotechnology (1999) 7:936-937.
Guo et al., "Induction Profile of Rat Organic Anion Transporting Polypeptide 2 (oatp2) by Prototypical Drug-Metabolizing Enzyme Inducers That Activate Gene Expression through Ligand-Activated Transcription Factor Pathways," Journal of Pharmacology and Experimental Therapeutics (2002) 300:206-212.
Gura, "Systems for Identifying New Drugs Are Often Faulty," Science (1997) 278:1041-1042.
Hell et al., "Hodgkin Cells Accumulate mRNA for *bcl-2*," Laboratory Investigation (1995) 73:492-496.
Herbert et al., The Dictionary of Immunology, Academic Press, 3rd edition, London (1985) pp. 58-59.
Holmes, "PSMA specific antibodies and their diagnostic and therapeutic use," Exp. Opin. Invest. Drugs (2001) 10(3):511-519.
Jang et al., "An examination of the effects of hypoxia, acidosis, and glucose starvation on the expression of metastasis-associated genes in murine tumor cells," Clinical and Experimental Metastasis (1997) 15:469-483.
Jansen et al., "Translational Control of Gene Expression," Pediatric Res. (1995) 37(6):681-686.
Kirkin et al., "Melanoma-associated antigens recognized by cytotoxic T lymphocytes," APMIS (1998) 106:665-679.
McClean and Hill, Evidence of Post-translational Regulation of P-Glycoprotein Associated with the Expression of a Distinctive Multiple Drug-resistant Phenotype in Chinese Hamster Ovary Cells, Eur. J. of Cancer (1993) 29A:2243-2248.
Powell et al., "Expression of cytochrome P4502E1 in human liver: assessment by mRNA, genotype and phenotype," Pharmacogenesis (1998) 8:411-421.
Roitt et al., Immunology 4th edition, Mosby, London (1993) pp. 7.7-7.8.
Shantz and Pegg, "Translational regulation of ornithine decarboxylase and other enzymes of the polyamine pathway," Int. J. of Biochem. and Cell Biol. (1999) 31:107-122.
Sherman et al., "Strategies for Tumor Elimination by Cytotoxic T Lymphocytes," Critical Reviews in Immunol. (1998) 18(1-2):47-54.
Smith, "Cancer and the Immune System," Clin. Immunol. (1994) 41(4):841-849.
Spitler, "Cancer Vaccines: The Interferon Analogy," Cancer Biotherapy (1995) 10:1-3.
Vallejo et al., "Evidence of tissue-specific, post-transcriptional regulation of NRF-2 expression," Biochimie (2000) 82:1129-1133.
Zimmer, "Examination of the Calcium-Modulated Protein S100α and Its Target Proteins in Adult and Developing Skeletal Muscle," Cell Motility and the Cytoskeleton (1991) 20:325-337.

* cited by examiner

Figure 1:

Figure 1A 74P3B3 SSH sequence of 217 nucleotides. (SEQ ID NO:1)

```
  1 GATCATCCGG AGTGGCCGCC TCCAATAAAG CAATGTAGCT TGGAGCCTTG GAGGTCTGAA
 61 TCTCAAATTT GCCCTGTTTC ACGAATGAAT GAATTGTGGC CTCAGGAACC ACGAGCGCAT
121 GGTGTAGCAC CAGTACAACA TAAGGCTGCA CTGCCATCTA ATGTTAATGA ATCGCCATTA
181 CAGTTTACTA TTCGGCAGGC TAGATTAGCC GGAGATC
```

Figure 1B 83P4B8 SSH sequence of 398 nucleotides. (SEQ ID NO:2)

```
  1 GATCAAGCAC CTGGTCCTGA AATCTTTGTA TTCTTGTTAC AGACAGAAGA AGAGCAATGC
 61 TGAAGGGACT TAAGTTATTA TTGGAATCTC CTTGCTGTCC TACCTTTAAG TGTTTCACGA
121 GTTCTCTGCC TAGTTCATAG TCCAATTTGA TGGCAAACAC AATGTGTAGA ATAATGGTGC
181 CTTCCACATG ACGAAGTTCA CCTGATGGCA CAGTGACAAC ATCCAATAGC TCGTCACCAC
241 TCTGTTCCTC ATTGNGCTGC TTATCTAGTG CACTGAAGAA GGCTATGATT CCTTNCAAAA
301 CACTCTTTNT GCTTCCTTGG AGGAGAGAAC CAGAAGCTGA TANACCAAAG GNGGTATTTC
361 TTGAAGATTC ATCTTGGAGA ACAAGCTCAA TGCTTTTT
```

Figure 1C 109P1D4 SSH sequence of 192 nucleotides. (SEQ ID NO:3)

```
  1 GATCCTGGTT GCAGCTGTTG CTGGCACCAT AACTGTCGTT GTAGTTATTT TCATCACTGC
 61 TGTAGTAAGA TGTCGCCAGG CACACACCTT AAGGCTGCTC AGAAAAACAT GCAGAATTCT
121 GAATGGGCTA CCCCAAACCC AGAAAACAGG CAGATGATAA AAAAAAAAAA AAAAAAAAAA
181 AAAAGCTTGA TC
```

Figure 1D 151P1C7A SSH sequence of 237 nucleotides. (SEQ ID NO:4)

```
  1 GATCTTGGAC CAGAAGTGTC TAGCACAACA CAATCCTGAG GCACAGTCTG ATGACCGGAG
 61 ACAAACAGAA CCTTCTTGTC CTTTGGTGTG ATACATTTTT GAAGACAAGG TGGTTCTTCT
121 GGAATACCCA TCCAAGGTGC TATGATCACG GGGCCCTTGT GGAATAAAGG CCGGTGGTTC
181 TCCTCATGCT TGTCCAGGCA GTTGGGATGC ACAGCATGGG CCATGTCTGC GCTGATC
```

Figure 1E 151P4E11 SSH sequence of 265 nucleotides. (SEQ ID NO:5)

```
  1 GATCTNCCCG CCGCAGCCTC CTCAGAAGAC ATCGAGCGGT CCTGAGAGCC TCCTGGGCAC
 61 GTTTGTCTGT GTGCTGTAAC CTGAAGTCAA ACCTTAAGAT AATGGATAAT CTTCGGCCAA
121 TTTATGCAGA GTCAGCCATT CCTGTTCTCT TTGCCTTGAT GTTGTGTTGT TATCATTNAA
181 GATNTTTTTT ATGGTAATTA TTTTGAGTGG CAAAATAAAG AATAGCANTT AAANAAAANA
241 NAAAAAAAAN ANAAANCGCT TGATC
```

Figure 1F 154P2A8 SSH sequence of 267 nucleotides. (SEQ ID NO:6)

```
  1 GATCCAGGCA ACATTACAC GCAGACAAGA AAAGTGTAAT TTCTTTGCAG TAATATAGGA
 61 TTTTTTGTGC AGATTCATCT AAAAGCCTGT CTAAGTGACT AAAAGTAAAA GGAATTCTGC
121 ACAAGTGATA TGGTAGAAAG CAGGTAAAAA ACACAGCCAC AACAACCCTG ATGCTCTGGT
181 TATGTTTTCG CTTTCGGCTT GACTGACTTA TGAATTGCCT GCTGGATTTG TGGATGTACC
241 TGGATATGGC TATGTAACAT CCCGATC
```

Figure 1G 156P1D4 SSH sequence of 212 nucleotides. (SEQ ID NO:7)

```
  1 GATCATATAT TTTGTTTCAC CATTCTTCTT TTGTAATAAA TTTTGAATGT GCTTGAAAGT
 61 GAAAAGCAAT CAATTATACC CACCAACACC ACTGAAATCA TAAGCTATTC ACGACTCAAA
121 ATATTCTAAA ATATTTTTCT GACAGTATAG TGTATAAATG TGGTCATGTG GTATTTGTAG
181 TTATTGATTT AAGCATTTTT AGAAATAAGA TC
```

Figure 1H 156P5C12 SSH sequence of 199 nucleotides. (SEQ ID NO:8)

```
  1 GATCTCTTTC TGTGTGTATT GGTCAGAATA GAATCCATTC AGCTGTAGCA GCAAGCAATC
 61 CCCAACCTTT CACTGCAATG ACCTTTCAAT GCAATAAAAG CTTATTGTCC ATTCAAAAAA
121 AAAAAAAAAA AAAAAAAAAA AAAAAAAAAA AAAAAAAAAA AAAAAAAAAA AAAAAAAAAA
181 AAAAAAAAAA GGNTTGATC
```

Figure 1I 159P2B5 SSH sequence of 110 nucleotides. (SEQ ID NO:9)

```
  1 GATCCTTGGC CCTCTAGGNA AGTANGTNAG NGCCCCAAGA CTGGANCTGG TCTCTTTCAA
 61 CGCCTTGGGA GACTGGGTGA AAGGCNAGCT TGNTTACGCT TAAAATGATC
```

Figure 1J 161P2B7A SSH sequence of 65 nucleotides. (SEQ ID NO:10)

```
  1 GATCAATTGA ATGAAAATAT CGTTTCAAAA AACAAAAAAA AAAAAAAAAA AAAAAAGGCT
 61 TGATC
```

Figure 1K 179P3G7 SSH sequence of 365 nucleotides. (SEQ ID NO:11)

```
  1 GATCTTAACT TTGCATGGAG AACAGAATGC TGTGTGTGAG TGCGTGGGTG AGTGAGGGTT
 61 TGACACACAC ACCAGCCACA CTCCCACCCC CATCTATGAG GGCACACACC ACACCCCACA
121 TCCCGGCACC CCATTTCTCA TGCTTTAAGT GGAAGCATCT TCGCAGCACG AACCACAGGT
181 CCCTTGGAAG GAGAGTCTGA GGTCTTTGCC TTTTTTGCAG TCGCATTGCA TTTATACTCA
241 GGGAGGAAAA AAAAATATAT CACCAGGCAC AAAGGGAGGA GGGGCGGGGA GAGGAAGGAG
301 CGGGAAGGGA GGAGGAGAGG CCGCGCTCTC AGGTGAAATT AAAATTGGAG GTCAGTTCCC
361 GGATC
```

Figure 1L 184P3C10B SSH sequence of 296 nucleotides. (SEQ ID NO:12)

```
  1 GATCATCAAG TTGTATAGCT GTATCATTGG CAACATGATT TCGCTGTTTC AGATAGAGAG
 61 CCTTGCCCGG GAGGCCTCCA CTGGAGTACT AAAAGACCTA ATGCATGGCC TCATCACCTT
121 AATGCTGGAT TCTCGGATTG AAGATCATTC CAGCCCCAGT GCTGTTCTCT GAATTCTTGG
181 GGAACACAGG GATGGGGGCT CCTAATGAGG ACCCCAGAAA CTCTGAGCTC TCACAACTTT
241 CAAAGGACAC TTGCCTCCCT CCTCTGCCCA CACCTCCACC ATTACAGCAT TTGATC
```

Figure 1M 184P3G10 SSH sequence of 406 nucleotides. (SEQ ID NO:13)

```
  1 GATCTCTGAA CTCCTGGGCT GAGGATGATT TGCTCCCTGC TGTAGAATCT GCCATTCCTT
 61 CCCTTAGCTG GTTCAGAAGG TCTCTGCTCT CACTGGGAGG CAAGTTACTC AGGAAGTATG
121 GAGGGGCCAA TTCCACCAGC ATCTGTGGTT GAATCTCAGA AACAATGGAA AGGCAGTTGT
181 CTTTGGATAT GGTGAAATTG TGGTAGAGCA CCCATGGTGG GGGTCTGGCA GGAGCTCTGC
241 GGCTTCGGTA GCAGCAGTAT GAGGAGAGCT GGGCCACATG CTTATGGGTT AGGAGAAGGT
301 AATTTCCAGT CCCGTCTGTG TCTCTGGCCA CCTTGAGAAA GTATCCTGAC ACCAGTGCTT
361 TCTGAAGGTC TCTGCGATTC TGCTCAGAGC CAAAGGCTGG TAGGGA
```

Figure 1N 185P2C9 SSH sequence of 163 nucleotides. (SEQ ID NO:14)

```
  1 GATCCTTATA TTATCCTACT TGGCTTGCAC GTCTTCGGGT GCATGTATAT ACCGCTACTG
 61 TGTCCTCGCC ATCACCTAAA TGTGACTCAG TCTGTTCCAC TGTAATATGT TGTGAATTTC
121 CTTGTACTGT ACTTTTATTG TTGGTCTTCT TGCATCGATG ATC
```

Figure 1(O) 185P3C2 SSH sequence of 287 nucleotides. (SEQ ID NO:15)

```
  1 GATCTGGGGA GCTCAGTGAA CCTCCTCACC CTCCTGCCAG TATGAAGTTG GGAAGCGCCT
 61 TCTCTGTCCC CCAGAACAGA ACAAACTCTT GTTCCCTGTG GTTGGGGAAA AGGTGTGGGG
121 GGCTTGGACC TAGGAAGAAG CTGAGCTGAA TTCCTCCAGG GCCCAGGTGA AACCCCCAGG
181 GGAGTTTCTG AGACTCTAGA CTTGCCATTT CTCCACTTTT CCTTCCCAAT GACTCCGGTG
241 AGCAGCTCAN AGTCTGGGCT AGGGCAACTG GTAGGACAGT GGGGATC
```

Figure 1P 186P1H9 SSH sequence of 210 nucleotides. (SEQ ID NO:16)

```
  1 GATCTCCGGT CCCTTCCCCC ATCATCCTTC CTTAGACTGA TGCTTTGACT GAATCATCAC
 61 TAGCTATGGC ATTAAAAGGC CTCTCTTCTC ATCTGGTGCC AAAGGTTCCG TTGCAGCTTT
121 TTACAACCAT CCGGTGTGGT TTGGAGGATT TGTTTTTTTT TTTCCCAACA NAAAGGAACA
181 GCCATTANAA GAAGGCTCCC ATTTTCTGAT
```

Figure 1Q 187P3F2 SSH sequence of 227 nucleotides. (SEQ ID NO:17)

```
  1 GATCTCGTTC ATACTGTGGT GGTGTTTCGT TTTTGTTTTT GTTTTTAAAG AAGGGTGAAG
 61 ATGCCTGACG CACGAAAACT GCACTCGTGA GGTTTTTCCA CCCTGAGATG ACCTACACGG
121 CAGCGGTGGA CAGCACCTGC CTCGTCTTCT CCTCTTTGAA AAAAAGAGAG AGAGAGAGTC
181 CCCTTTCCTT TCACTTTCTC CCTCCAAAAC AGCTGCCTAA AGAGATC
```

Figure 1R 192P2G7 SSH sequence of 381 nucleotides. (SEQ ID NO:18)

```
  1 GATCTTTCTA CCATTCGGGC GTGGCTCGCT CCTGATTCCC CTTGGAAATG AACTTTTATT
 61 TGGTTTACTG ACATTTATGT AGATTTCCAG TGAAAAGCTC TATAAAATAC AATAAATAAT
121 ACGGGGTTGA AAAGGCAGAC ATTCTAGTTG CATATATTAC AGGCTTTATC CTTACGGTCC
181 AGGCCATTGG AACTGCAATG TGGAGACTGT TTGTAATCAG ACATGGAAAG GCTGCACGTT
241 CTAAAGGCGA GACAGCTGCT TTCGGTTGGG AATCATCACA CTCCCTCCGC TCACGCCGCT
301 CTTCCCTTCC CCCGCTGTTT CACACGCTGC TTCCAGAGTT TGTCCAGCAA GGAATAAATG
361 AATGCATACA GGACTTTTGG C
```

Figure 2:

Figure 2A.1 The cDNA (SEQ ID NO:19) and amino acid sequence (SEQ ID NO:20) of 74P3B3 v.1A clone B. The start methionine is underlined. The open reading frame extends from nucleic acid 289-831 including the stop codon.

```
   1 ctccacgttgcgatggatccttggacccacttttgttaactcttaaactttgtgtctttg
  61 tctttatttcttttctcattccctcgtctccaccgggaaggggagagcctgcgggtggtg
 121 tatcaggcaggttcccctacatctttggcacccaacacggtctcctcgaacccaggtgaa
 181 gttacacctgagcgtggtcgttgtgaagaacggtctgtccaggaactcccgagaacgtgt
 1                                                     M  G  Q  S
 241 ggtcggccttgcggtaagcttgtgcactcggagcattccagggacaccATGGGACAATCC
 5  K  S  K  H  S  A  Y  L  H  F  I  K  L  L  L  K  R  A  G  I
 301 AAAAGTAAACATTCTGCATATTTACATTTTATTAAGCTCCTCTTAAAGAGGGCAGGAATT
 25 K  A  S  T  E  N  L  I  T  L  F  P  T  V  E  Q  Y  C  P  W
 361 AAGGCTAGCACAGAAAATTTGATTACTCTGTTTCCAACAGTAGAGCAATATTGTCCTTGG
 45 F  P  E  H  G  T  M  D  F  K  D  W  E  Q  V  G  I  A  L  K
 421 TTTCCTGAACATGGTACCATGGACTTCAAAGATTGGGAACAGGTGGGAATTGCCTTAAAA
 65 Q  V  C  K  E  G  K  F  I  P  L  T  A  W  S  N  W  A  I  V
 481 CAAGTTTGTAAGGAAGGAAAATTTATCCCCCTAACAGCCTGGTCAAACTGGGCTATAGTT
 85 K  A  A  S  E  P  F  Q  S  E  N  E  A  Y  P  P  A  E  R  I
 541 AAAGCAGCCTCGGAACCGTTTCAATCGGAAAATGAGGCTTATCCTCCAGCAGAAAGAATT
 105 S  A  E  E  G  G  D  A  A  E  G  G  E  D  S  E  E  D  F  E
 601 TCTGCAGAGGAAGGTGGTGATGCTGCTGAAGGAGGAGAGGATAGTGAAGAAGATTTTGAG
 125 E  N  T  D  K  P  G  D  E  L  I  S  F  E  E  H  V  G  P  S
 661 GAAAATACAGACAAACCTGGAGATGAGTTAATTTCTTTTGAGGAGCACGTGGGACCTTCA
 145 A  A  P  K  I  E  K  P  Y  M  P  R  C  L  K  Q  R  R  A  L
 721 GCTGCTCCTAAAATAGAGAAGCCATATATGCCAAGATGTTTAAAACAAAGAAGGGCCTTG
 165 R  S  S  R  L  L  I  G  I  I  I  R  S  G  R  L  Q  *
 781 AGGAGCAGTCGGCTCCTCATTGGGATCATCCGGAGTGGCCGCCTCCAATAAagcaatgta
 841 gcttggagccttggaggtctgaatctcaaatttgccctgtttcacgaatgaatgaattgt
 901 ggcctcaggaaccacaagcgcatggtgtagcaccagtacaacataaggctgcactgccat
 961 ctaatgttaatgaatcgccattacagtttattattcggcaggctagattagccggagatc
1021 ttgatgcctggcagtttgcagtagttttgcaaccccacgacagcaaggtggagcccatc
1081 aagcggtatgggaaccattttctttttaagctgctcaaagatcttaaagcagctgttggtc
1141 agtatggtcccaattcgcctttcatccgatcgctattgcaatctgtggctcagaataagc
1201 tattgactccgtgtgattgggagattttaacgaaagttacacttttcgcccctcccaatttc
1261 ttcagtttaagacttggtggaccgacgaggctcaaaatcaagatcgaaaaaaccgtgctg
1321 ctaatcctgctattgccattacatttgaacaacttctaggaataggggtcaatggggaa
1381 ctgtaaacaaccatcaggacttcgagatgatgccattgaacaaattcgcaattgctgttt
1441 gagggcatgggagaaaattcaggatctgggaactacttatcagtcttttaattctattag
1501 acaaggctcaaaggaaccatatcctgatttcattgctcgccttcaagacgcagcacagaa
1561 ggctctcactgatgaaagtgccaggaaggccgggtgcggtggctcatgcctgtaatccca
1621 gcactttgggaggccgaggtgggcggatcacctgaggtcgggagttggagaccagcctga
1681 ccaacatggagaaaccccgtctctactaaaaatataaaaattagccgggcgtgatggcac
1741 atgtctgtaatcccagctactcaggaggctgaggcaggagaattgcttgaacccaggagg
1801 cggaggttgcggtgagccgagatcacgccactgcactccagcctgggtaacaagagcgaa
1861 actccgcctcaaaaaaaaaaaaaaaaaaaaaaaaaaaaaaaaaaaaaa
```

Figure 2A.2. The cDNA (SEQ ID NO:21) and amino acid sequence (SEQ ID NO:22)
of 74P3B3 v.1B clone B. The start methionine is underlined. The open reading
frame extends from nucleic acid 756-1442 including the stop codon.

```
   1 ctccacgttgcgatggatccttggacccacttttgttaactcttaaactttgtgtctttg
  61 tctttatttcttttctcattccctcgtctccaccgggaaggggagagcctgcgggtggtg
 121 tatcaggcaggttcccctacatctttggcacccaacacggtctcctcgaacccaggtgaa
 181 gttacacctgagcgtggtcgttgtgaagaacggtctgtccaggaactcccgagaacgtgt
 241 ggtcggccttgcggtaagcttgtgcactcggagcattccagggacaccatgggacaatcc
 301 aaaagtaaacattctgcatatttacattttattaagctcctcttaaagagggcaggaatt
 361 aaggctagcacagaaaatttgattactctgtttccaacagtagagcaatattgtccttgg
 421 tttcctgaacatggtaccatggacttcaaagattgggaacaggtgggaattgccttaaaa
 481 caagtttgtaaggaaggaaaatttatcccctaacagcctggtcaaactgggctatagtt
 541 aaagcagcctcggaaccgtttcaatcggaaaatgaggcttatcctccagcagaaagaatt
 601 tctgcagaggaaggtggtgatgctgctgaaggaggagaggatagtgaagaagattttgag
 661 gaaaatacagacaaacctggagatgagttaatttcttttgaggagcacgtgggaccttca
   1                                            M  F  K  T  K  G  L  E
 721 gctgctcctaaaatagagaagccatatatgccaagATGTTTAAAACAAAGAAGGGCCTTG
  10  E  Q  S  A  P  H  W  D  H  P  E  W  P  P  P  I  K  Q  C  S
 781 AGGAGCAGTCGGCTCCTCATTGGGATCATCCGGAGTGGCCGCCTCCAATAAAGCAATGTA
  30  L  E  P  W  R  S  E  S  Q  I  C  P  V  S  R  M  N  E  L  W
 841 GCTTGGAGCCTTGGAGGTCTGAATCTCAAATTTGCCCTGTTTCACGAATGAATTGT
  50  P  Q  E  P  Q  A  H  G  V  A  P  V  Q  H  K  A  A  L  P  S
 901 GGCCTCAGGAACCACAAGCGCATGGTGTAGCACCAGTACAACATAAGGCTGCACTGCCAT
  70  N  V  N  E  S  P  L  Q  F  I  I  R  Q  A  R  L  A  G  D  L
 961 CTAATGTTAATGAATCGCCATTACAGTTTATTATTCGGCAGGCTAGATTAGCCGGAGATC
  90  D  A  W  Q  F  A  V  V  L  Q  P  P  R  Q  Q  G  G  A  H  Q
1021 TTGATGCCTGGCAGTTTGCAGTAGTTTTGCAACCCCCACGACAGCAAGGTGGAGCCCATC
 110  A  V  W  E  P  F  S  F  K  L  L  K  D  L  K  A  A  V  G  Q
1081 AAGCGGTATGGGAACCATTTTCTTTTAAGCTGCTCAAAGATCTTAAAGCAGCTGTTGGTC
 130  Y  G  P  N  S  P  F  I  R  S  L  L  Q  S  V  A  Q  N  K  L
1141 AGTATGGTCCCAATTCGCCTTTCATCCGATCGCTATTGCAATCTGTGGCTCAGAATAAGC
 150  L  T  P  C  D  W  E  I  L  T  K  V  T  L  S  P  S  Q  F  L
1201 TATTGACTCCGTGTGATTGGGAGATTTTAACGAAAGTTACACTTTCGCCCTCCCAATTTC
 170  Q  F  K  T  W  W  T  D  E  A  Q  N  Q  D  R  K  N  R  A  A
1261 TTCAGTTTAAGACTTGGTGGACCGACGAGGCTCAAAATCAAGATCGAAAAAACCGTGCTG
 190  N  P  A  I  A  I  T  F  E  Q  L  L  G  I  G  G  Q  W  G  T
1321 CTAATCCTGCTATTGCCATTACATTTGAACAACTTCTAGGAATAGGGGGTCAATGGGAA
 210  V  N  N  H  Q  D  F  E  M  M  P  L  N  K  F  A  I  A  V  *
1381 CTGTAAACAACCATCAGGACTTCGAGATGATGCCATTGAACAAATTCGCAATTGCTGTTT
1441 GAgggcatgggagaaaattcaggatctgggaactacttatcagtcttttaattctattag
1501 acaaggctcaaaggaaccatatcctgatttcattgctcgccttcaagacgcagcacagaa
1561 ggctctcactgatgaaagtgccaggaaggccgggtgcggtggctcatgcctgtaatccca
1621 gcactttgggaggccgaggtgggcggatcacctgaggtcgggagttggagaccagcctga
1681 ccaacatggagaaaccccgtctctactaaaaatataaaaattagccgggcgtgatggcac
1741 atgtctgtaatcccagctactcaggaggctgaggcaggagaattgcttgaacccaggagg
1801 cggaggttgcggtgagccgagatcacgccactgcactccagcctgggtaacaagagcgaa
1861 actccgcctcaaaaaaaaaaaaaaaaaaaaaaaaaaaaaaaa
```

Figure 2B  The cDNA (SEQ ID NO:23) and amino acid sequence (SEQ ID NO:24) of
83P4B8 clone 83P4B8.4AD.  The start methionine is underlined.  The open
reading frame extends from nucleic acid 25-4011 including the stop codon

```
  1                       M  D  Q  K  I  L  S  L  A  A  E  K
  1 cggagttctgtgatatgagcaacaATGGACCAGAAGATTTTATCTCTAGCAGCAGAAAAA
 13 T  A  D  K  L  Q  E  F  L  Q  T  L  R  E  G  D  L  T  N  L
 61 ACAGCAGACAAACTGCAAGAATTTCTTCAAACCCTGAGAGAAGGTGATTTGACTAATCTC
 33 L  Q  N  Q  A  V  K  G  K  V  A  G  A  L  L  R  A  I  F  K
121 CTTCAGAATCAAGCAGTGAAAGGAAAAGTTGCTGGAGCACTCCTGAGAGCCATCTTCAAA
 53 G  S  P  C  S  E  E  A  G  T  L  R  R  R  K  I  Y  T  C  C
181 GGTTCCCCCTGCTCTGAGGAAGCTGGAACACTTAGGAGACGTAAGATATACACTTGTTGT
 73 I  Q  L  V  E  S  G  D  L  Q  K  E  I  V  S  E  I  I  G  L
241 ATCCAGTTGGTGGAATCGGGGGATTTGCAGAAAGAAATAGTGTCTGAGATCATAGGATTA
 93 L  M  L  E  A  H  H  F  P  G  P  L  L  V  E  L  A  N  E  F
301 CTGATGCTGGAGGCTCACCATTTTCCAGGACCATTATTGGTTGAATTAGCCAATGAGTTT
113 I  S  A  V  R  E  G  S  L  V  N  G  K  S  L  E  L  L  P  I
361 ATTAGTGCTGTCAGAGAAGGCAGCCTAGTGAATGGAAAATCTTTGGAGTTACTACCTATC
133 I  L  T  A  L  A  T  K  K  E  N  L  A  Y  G  K  G  V  L  S
421 ATTCTCACTGCCCTGGCTACGAAAAAGGAAAATCTGGCTTATGGAAAAGGTGTACTGAGT
153 G  E  E  C  K  K  Q  L  I  N  T  L  C  S  G  R  W  D  Q  Q
481 GGGGAAGAATGTAAGAAACAGTTGATTAACACCCTGTGTTCTGGCAGGTGGGATCAGCAA
173 Y  V  I  Q  H  T  S  M  F  K  D  V  P  L  T  A  E  E  V  E
541 TATGTAATCCAACACACCTCCATGTTCAAGGATGTCCCTCTGACTGCAGAAGAGGTGGAA
193 F  V  V  E  K  A  L  S  M  F  S  K  M  N  L  Q  E  I  P  P
601 TTTGTGGTGGAAAAAGCATTGAGCATGTTCTCCAAGATGAATCTTCAAGAAATACCACCT
213 L  V  Y  Q  L  V  L  S  S  K  G  S  R  K  S  V  L  E  G
661 TTGGTCTATCAGCTTCTGGTTCTCTCCTCCAAGGGAAGCAGAAAGAGTGTTTTGAAGGA
233 I  I  A  F  F  S  A  L  D  K  Q  H  N  E  E  Q  S  G  D  E
721 ATCATAGCCTTCTTCAGTGCACTAGATAAGCAGCACAATGAGGAACAGAGTGGTGACGAG
253 L  L  D  V  V  T  V  P  S  G  E  L  R  H  V  E  G  T  I  I
781 CTATTGGATGTTGTCACTGTGCCATCAGGTGAACTTCGTCATGTGGAAGGCACCATTATT
273 L  H  I  V  F  A  I  K  L  D  Y  E  L  G  R  E  L  V  K  H
841 CTACACATTGTGTTTGCCATCAAATTGGACTATGAACTAGGCAGAGAACTCGTGAAACAC
293 L  K  V  G  Q  Q  G  D  S  N  N  N  L  S  P  F  S  I  A  L
901 TTAAAGGTAGGACAGCAAGGAGATTCCAATAATAACTTAAGTCCCTTCAGCATTGCTCTT
313 L  L  S  V  T  R  I  Q  R  F  Q  D  Q  V  L  D  L  L  K  T
961 CTTCTGTCTGTAACAAGAATACAAAGATTTCAGGACCAGGTGCTTGATCTTTTAAAGACT
333 S  V  V  K  S  F  K  D  L  Q  L  L  Q  G  S  K  F  L  Q  N
1021 TCGGTTGTAAAGAGCTTTAAGGATCTTCAACTCCTCCAAGGCTCAAAATTTCTTCAGAAT
353 L  V  P  H  R  S  Y  V  S  T  M  I  L  E  V  V  K  N  S  V
1081 CTAGTTCCTCATAGATCTTATGTTTCAACCATGATCTTGGAAGTAGTGAAGAATAGCGTT
373 H  S  W  D  H  V  T  Q  G  L  V  E  L  G  F  I  L  M  D  S
1141 CATAGCTGGGACCATGTTACTCAGGGCCTCGTAGAACTTGGTTTCATTTTGATGGATTCA
393 Y  G  P  K  K  V  L  D  G  K  T  I  E  T  S  P  S  L  S  R
1201 TATGGGCCAAAGAAGGTTCTTGATGGAAAAACTATTGAAACCAGCCCAAGTCTTTCTAGA
413 M  P  N  Q  H  A  C  K  L  G  A  N  I  L  L  E  T  F  K  I
1261 ATGCCAAACCAGCATGCATGTAAGCTCGGAGCTAATATCCTGTTGGAAACTTTTAAGATC
433 H  E  M  I  R  Q  E  I  L  E  Q  V  L  N  R  V  V  T  R  A
1321 CATGAGATGATCAGACAAGAAATTTTGGAGCAGGTCCTCAACAGGGTTGTTACCAGAGCA
453 S  S  P  I  S  H  F  L  D  L  L  S  N  I  V  M  Y  A  P  L
1381 TCTTCTCCCATCAGTCATTTCTTAGACCTGCTTTTCAAATATCGTCATGTATGCACCCTTA
473 V  L  Q  S  C  S  S  K  V  T  E  A  F  D  Y  L  S  F  L  P
1441 GTTCTTCAAAGTTGTTCTTCTAAAGTCACAGAAGCTTTTGACTATTTGTCCTTTCTGCCC
493 L  Q  T  V  Q  R  L  L  K  A  V  Q  P  L  L  K  V  S  M  S
1501 CTTCAGACTGTACAAAGGCTGCTTAAGGCAGTGCAGCCCCTTCTCAAAGTCAGCATGTCA
513 M  R  D  C  L  I  L  V  L  R  K  A  M  F  A  N  Q  L  D  A
1561 ATGAGAGACTGCTTGATACTTGTCCTTCGGAAAGCTATGTTTGCCAACCAGCTTGATGCC
533 R  K  S  A  V  A  G  F  L  L  L  K  N  F  K  V  L  G  S
1621 CGAAAATCTGCAGTTGCTGGGTTTTGCTGCTCCTGAAGAACTTTAAAGTTTTAGGCAGC
553 L  S  S  S  Q  C  S  Q  S  L  S  V  S  Q  V  H  V  D  V  H
1681 CTGTCATCCTCTCAGTGCAGTCAGTCTCTCAGTGTCAGTCAGGTTCATGTGGATGTTCAC
573 S  H  Y  N  S  V  A  N  E  T  F  C  L  E  I  M  D  S  L  R
1741 AGCCATTACAATTCTGTCGCCAATGAAACTTTTTGCCTTGAGATCATGGATAGTTTGAGG
593 R  C  L  S  Q  Q  A  D  V  R  L  M  L  Y  E  G  F  Y  D  V
1801 AGATGCTTAAGCCAGCAAGCTGATGTTCGACTCATGCTTTATGAGGGGTTTTATGATGTT
613 L  R  R  N  S  Q  L  A  N  S  V  M  Q  T  L  L  S  Q  L  K
1861 CTTCGAAGGAACTCTCAGCTGGCTAATTCAGTCATGCAAACTCTGCTCTCACAGTTAAAA
633 Q  F  Y  E  P  K  P  D  L  L  P  P  L  K  L  D  A  C  I  L
1921 CAGTTCTATGAGCCCAAAACCTGATCTGCTGCCTCCTCTGAAATTAGATGCTTGTATTCTG
653 T  Q  G  D  K  I  S  L  Q  E  P  L  D  Y  L  L  C  C  I  Q
1981 ACCCAAGGAGATAAGATCTCTCTACAAGAACCACTGGATTATCTGCTGTGTTGTATTCAG
673 H  C  L  A  W  Y  K  N  T  V  I  P  L  Q  Q  G  E  E  E  E
```

Figure 2B (continued)

```
2041 CATTGTTTGGCCTGGTATAAGAATACAGTCATACCCTTACAGCAGGGAGAGGAGGAAGAG
 693  E   E   E   A   F   Y   E   D   L   D   D   I   L   E   S   I   T   N   R
2101 GAGGAGGAAGAGGCATTCTACGAAGACCTAGATGATATATTGGAGTCCATTACTAATAGA
 713  M   I   K   S   E   L   E   D   F   E   L   D   K   S   A   D   F   S   Q   S
2161 ATGATTAAGAGTGAGCTGGAAGACTTTGAACTGGATAAATCAGCAGATTTTTCTCAGAGC
 733  T   S   I   G   I   K   N   N   I   S   A   F   L   V   M   G   V   C   E   V
2221 ACCAGTATTGGCATAAAAAATAATATCTCTGCTTTTCTTGTGATGGGAGTTTGTGAGGTT
 753  L   I   E   Y   N   F   S   I   S   S   F   S   K   N   R   F   E   D   I   L
2281 TTAATAGAATACAATTTCTCCATAAGTAGTTTCAGTAAGAATAGGTTTGAGGACATTCTG
 773  S   L   F   M   C   Y   K   K   L   S   D   I   L   N   E   K   A   G   K   A
2341 AGCTTATTTATGTGTTACAAAAAACTCTCTGACATTCTTAATGAAAAAGCGGGTAAAGCC
 793  K   T   K   M   A   N   K   T   S   D   S   L   L   S   M   K   F   V   S   S
2401 AAAACTAAAATGGCCAACAAGACAAGTGATAGTCTTTTGTCCATGAAATTTGTGTCCAGT
 813  L   L   T   A   L   F   R   D   S   I   Q   S   H   Q   E   S   L   S   V   L
2461 CTTCTCACTGCTCTTTTCAGGGATAGTATCCAAAGCCACCAAGAAAGCCTTTCTGTTCTC
 833  R   S   S   N   E   F   M   R   Y   A   V   N   V   A   L   Q   K   V   Q   Q
2521 AGGTCCAGCAATGAGTTTATGCGCTATGCAGTGAATGTAGCTCTGCAGAAAGTACAGCAG
 853  L   K   E   T   G   H   V   S   G   P   D   G   Q   N   P   E   K   I   F   Q
2581 CTAAAGGAAACAGGGCATGTGAGTGGCCCTGATGGCCAAAACCCAGAAAAGATCTTTCAG
 873  N   L   C   D   I   T   R   V   L   L   W   R   Y   T   S   I   P   T   S   V
2641 AACCTCTGTGACATAACTCGAGTCTTGCTATGGAGATACACTTCAATTCCTACTTCAGTG
 893  E   E   S   G   K   K   E   K   G   K   S   I   S   L   L   C   L   E   G   L
2701 GAAGAGTCGGGAAAGAAAGAGAAAGGAAAGAGCATCTCACTGCTGTGCTTGGAGGGTTTA
 913  Q   K   I   F   S   A   V   Q   Q   F   Y   Q   P   K   I   Q   Q   F   L   R
2761 CAGAAAATATTCAGTGCTGTGCAACAGTTCTATCAGCCCAAGATTCAGCAGTTTCTCAGA
 933  A   L   D   V   T   D   K   E   G   E   E   R   E   D   A   D   V   S   V   T
2821 GCTCTGGATGTCACAGATAAGGAAGGAGAAGAGAGAGAAGATGCAGATGTCAGTGTCACT
 953  Q   R   T   A   F   Q   I   R   Q   F   Q   R   S   L   L   N   L   L   S   S
2881 CAGAGAACAGCATTCCAGATCCGGCAATTTCAGAGGTCCTTGTTGAATTTACTTAGCAGT
 973  Q   E   E   D   F   N   S   K   E   A   L   L   L   V   T   V   L   T   S   L
2941 CAAGAGGAAGATTTTAATAGCAAAGAAGCCCTCCTGCTAGTCACGGTTCTTACCAGTTTG
 993  S   K   L   L   E   P   S   S   P   Q   F   V   Q   M   L   S   W   T   S   K
3001 TCCAAGTTACTGGAGCCCTCCTCTCCTCAGTTTGTGCAGATGTTATCCTGGACATCAAAG
1013  I   C   K   E   N   S   R   E   D   A   L   F   C   K   S   L   M   N   L   L
3061 ATTTGCAAGGAAAACAGCCGGGAGGATGCCTTGTTTTGCAAGAGCTTGATGAACTTGCTC
1033  F   S   L   H   V   S   Y   K   S   P   V   I   L   L   R   D   L   S   Q   D
3121 TTCAGCCTGCATGTTTCGTATAAGAGTCCTGTCATTCTGCTGCGTGACTTGTCCCAGGAT
1053  I   H   G   H   L   G   D   I   D   Q   D   V   E   V   E   K   T   N   H   F
3181 ATCCACGGGCATCTGGGAGATATAGACCAGGATGTAGAGGTGGAGAAAACAAACCACTTT
1073  A   I   V   N   L   R   T   A   A   P   T   V   C   L   L   V   L   S   Q   A
3241 GCAATAGTGAATTTGAGAACGGCTGCCCCCACTGTCTGTTTACTTGTTCTGAGTCAGGCC
1093  E   K   V   L   E   E   V   D   W   L   I   T   K   L   G   Q   V   S   Q
3301 GAGAAGGTTCTAGAAGAAGTGGACTGGCTAATCACCAAGCTTAAGGGACAAGTGAGCCAA
1113  E   T   L   S   E   E   A   S   S   Q   A   T   L   P   N   Q   P   V   E   K
3361 GAAACCTTATCAGAAGAGGCCTCTTCTCAGGCAACCCTACCAAATCAGCCTGTTGAGAAA
1133  A   I   I   M   Q   L   G   T   L   L   T   F   F   H   E   L   V   Q   T   A
3421 GCTATCATCATGCAACTGGGAACTCTGCTTACATTTTTCCACGAGCTGGTGCAGACAGCT
1153  L   P   S   G   S   C   V   D   T   L   L   K   D   L   C   K   M   Y   T   T
3481 CTGCCATCAGGCAGCTGTGTGGACACCTTGTTAAAGGACTTGTGCAAAATGTACACCACA
1173  L   T   A   L   V   R   Y   Y   L   Q   V   C   Q   S   S   G   G   I   P   K
3541 CTTACAGCCCTTGTCAGATATTATCTCCAGGTGTGTCAGAGCTCCGGAGGAATCCCAAAA
1193  N   M   E   K   L   V   K   L   S   G   S   H   L   T   P   L   C   Y   S   F
3601 AATATGGAAAAGCTGGTGAAGCTGTCTGGTTCTCATCTGACCCCCCTGTGTTATTCTTTC
1213  I   S   Y   V   Q   N   K   S   K   S   L   N   Y   T   G   E   K   E   K
3661 ATTTCTTACGTACAGAATAAGAGTAAGAGCCTGAACTATACGGGAGAGAAAAAGGAGAAA
1233  P   A   A   V   A   T   A   M   A   R   V   L   R   E   T   K   P   I   P   N
3721 CCTGCTGCCGTTGCCACAGCCATGGCCAGAGTTCTTCGGGAAACCAAGCCAATCCCTAAC
1253  L   I   F   A   I   E   Q   Y   E   K   F   L   I   H   L   S   K   K   S   K
3781 CTCATCTTTGCCATAGAACAGTATGAAAAATTTCTCATCCACCTTTCTAAGAAGTCCAAG
1273  V   N   L   M   Q   H   M   K   L   S   T   S   R   D   F   K   I   K   G   N
3841 GTGAACCTGATGCAGCACATGAAGCTCAGCACCTCACGAGACTTCAAGATCAAAGGAAAC
1293  I   L   D   M   V   L   R   E   D   G   E   D   E   N   E   E   G   T   A   S
3901 ATCCTAGACATGGTTCTTCGAGAGGATGGCGAAGATGAAAATGAAGAGGGCACTGCATCA
1313  E   H   G   G   Q   N   K   E   P   A   K   K   K   R   K   K   *
3961 GAGCATGGGGGACAGAACAAAGAACCAGCCAAGAAGAAAAGGAAAAAATAAatgaaatgc
4021 ctgagttaatgtg
```

Figure 2C The cDNA (SEQ ID NO:25) and amino acid sequence (SEQ ID NO:26) of
109P1D4 clone 109P1D4.9AD. The start methionine is underlined. The open
reading frame extends from nucleic acid 846-3911 including the stop codon

```
   1 ctggtggtccagtacctccaaagatatggaatacactcctgaaatatcctgaaaacttt
  61 tttttcagaatcctttaataagcagttatgtcaatctgaaagttgcttacttgtacttt
 121 atattaatagctattcttgtttttcttatccaaagaaaaatcctctaatccccttttcac
 181 atgatagttgttaccatgtttaggcattagtcacatcaaccctctcctctcccaaactt
 241 ctcttcttcaaatcaaactttattagtccctcctttataatgattccttgcctcgttta
 301 tccagatcaattttttttcactttgatgcccagagctgaagaaatggactactgtataaa
 361 ttattcattgccaagagaataattgcattttaaacccatattataacaaagaataatgat
 421 tatattttgtgatttgtaacaaatacccttatttttcccttaactattgaattaaatatt
 481 ttaattatttgtattctctttaactatcttggtatattaaagtattatctttttatatt
 541 tatcaatggtggacactttataggtactctgtgtcattttgatactgtaggtatctta
 601 tttcattatctttattcttaatgtacgaattcataatatttgattcagaacaaatttat
 661 cactaattaacagagtgtcaattatgctaacatctcatttactgatttaatttaaaaca
 721 gtttttgttaacatgcatgtttaggggttggcttcttaataatttcttcttcctcttctct
 781 ctctcctcttcttttggtcagtgttgtgcgggttaatacaacaaactgtaacaagtgtac
   1       M  D  L  L  S  G  T  Y  I  F  A  V  L  L  A  C  V  V  F
 841 ctggtATGGACTTGTTGTCCGGGACGTACATTTTCGCGGTCCTGCTAGCATGCGTGGTGT
  20 H  S  G  A  Q  E  K  N  Y  T  I  R  E  E  M  P  E  N  V  L
 901 TCCACTCTGGCGCCCAGGAGAAAAACTACACCATCCGAGAAGAAATGCCAGAAAACGTCC
  40 I  G  D  L  L  K  D  L  N  L  S  L  I  P  N  K  S  L  T  T
 961 TGATAGGCGACTTGTTGAAAGACCTTAACTTGTCGCTGATTCCAAACAAGTCCTTGACAA
  60 A  M  Q  F  K  L  V  Y  K  T  G  D  V  P  L  I  R  I  E  E
1021 CTGCTATGCAGTTCAAGCTAGTGTACAAGACCGGAGATGTGCCACTGATTCGAATTGAAG
  80 D  T  G  E  I  F  T  T  G  A  R  I  D  R  E  K  L  C  A  G
1081 AGGATACTGGTGAGATCTTCACTACTGGCGTCGCATTGATCGTGAGAAATTATGTGCTG
 100 I  P  R  D  E  H  C  F  Y  E  V  E  V  A  I  L  P  D  E  I
1141 GTATCCCAAGGGATGAGCATTGCTTTTATGAAGTGGAGGTTGCCATTTTGCCGGATGAAA
 120 F  R  L  V  K  I  R  F  L  I  E  D  I  N  D  N  A  P  L  F
1201 TATTTAGACTGGTTAAGATACGTTTTCTGATAGAAGATATAAATGATAATGCACCATTGT
 140 P  A  T  V  I  N  I  S  I  P  E  N  S  A  I  N  S  K  Y  T
1261 TCCCAGCAACAGTTATCAACATATCAATTCCAGAGAACTCGGCTATAAACTCTAAATATA
 160 L  P  A  A  V  D  P  D  V  G  I  N  G  V  Q  N  Y  E  L  I
1321 CTCTCCCAGCGGCTGTTGATCCTGACGTAGGAATAAACGGAGTTCAAAACTACGAACTAA
 180 K  S  Q  N  I  F  G  L  D  V  I  E  T  P  E  G  D  K  M  P
1381 TTAAGAGTCAAAACATTTTTGGCCTCGATGTCATTGAAACACCAGAAGGAGACAAGATGC
 200 Q  L  I  V  Q  K  E  L  D  R  E  E  K  D  T  Y  V  M  K  V
1441 CACAACTGATTGTTCAAAAGGAGTTAGATAGGGAAGAGAAGGATACCTACGTGATGAAAG
 220 K  V  E  D  G  G  F  P  Q  R  S  S  T  A  I  L  Q  V  S  V
1501 TAAAGGTTGAAGATGGTGGCTTTCCTCAAAGATCCAGTACTGCTATTTTGCAAGTGAGTG
 240 T  D  T  N  D  N  H  P  V  F  K  E  T  E  I  E  V  S  I  P
1561 TTACTGATACAAATGACAACCACCCAGTCTTTAAGGAGACAGAGATTGAAGTCAGTATAC
 260 E  N  A  P  V  G  T  S  V  T  Q  L  H  A  T  D  A  D  I  G
1621 CAGAAAATGCTCCTGTAGGCACTTCAGTGACACAGCTCCATGCCACAGATGCTGACATAG
 280 E  N  A  K  I  H  F  S  F  S  N  L  V  S  N  I  A  R  R  L
1681 GTGAAAATGCCAAGATCCACTTCTCTTTCAGCAATCTAGTCTCCAACATTGCCAGGAGAT
 300 F  H  L  N  A  T  T  G  L  I  T  I  K  E  P  L  D  R  E  E
1741 TATTTCACCTCAATGCCACCACTGGACTTATCACAATCAAAGAACCACTGGATAGGGAAG
 320 T  P  N  H  K  L  L  V  L  A  S  D  G  G  L  M  P  A  R  A
1801 AAACACCAAACCACAAGTTACTGGTTTTGGCAAGTGATGGTGGATTGATGCCAGCAAGAG
 340 M  V  L  V  N  V  T  D  V  N  D  N  V  P  S  I  D  I  R  Y
1861 CAATGGTGCTGGTAAATGTTACAGATGTCAATGATAATGTCCCATCCATTGACATAAGAT
 360 I  V  N  P  V  N  D  T  V  V  L  S  E  N  I  P  L  N  T  K
1921 ACATCGTCAATCCTGTCAATGACACAGTTGTTCTTTCAGAAAATATTCCACTCAACACCA
 380 I  A  L  I  T  V  T  D  K  D  A  D  H  N  G  R  V  T  C  F
1981 AAATTGCTCTCATAACTGTGACGGATAAGGATGCGGACCATAATGGCAGGGTGACATGCT
 400 T  D  H  E  I  P  F  R  L  R  P  V  F  S  N  Q  F  L  L  E
2041 TCACAGATCATGAAATCCCTTTCAGATTAAGGCCAGTATTCAGTAATCAGTTCCTCCTGG
 420 T  A  A  Y  L  D  Y  E  S  T  K  E  Y  A  I  K  L  L  A  A
2101 AGACTGCAGCATATCTTGACTATGAGTCCACAAAAGAATATGCCATTAAATTACTGGCTG
 440 D  A  G  K  P  P  L  N  Q  S  A  M  L  F  I  K  V  K  D  E
2161 CAGATGCTGGCAAACCTCCTTTGAATCAGTCAGCAATGCTCTTCATCAAAGTGAAAGATG
 460 N  D  N  A  P  V  F  T  Q  S  F  V  T  V  S  I  P  E  N  N
2221 AAAATGACAATGCTCCAGTTTTCACCCAGTCTTTCGTAACTGTTTCTATTCCTGAGAATA
 480 S  P  G  I  Q  L  T  K  V  S  A  M  D  A  D  S  G  P  N  A
2281 ACTCTCCTGGCATCCAGTTGACGAAAGTAAGTGCAATGGATGCAGACAGTGGGCCTAATG
 500 K  I  N  Y  L  L  G  P  D  A  P  P  E  F  S  L  D  C  R  T
2341 CTAAGATCAATTACCTGCTAGGCCCTGATGCTCCACCTGAATTCAGCCTGGATTGTCGTA
 520 G  M  L  T  V  V  K  K  L  D  R  E  K  E  D  K  Y  L  F  T
2401 CAGGCATGCTGACTGTAGTGAAGAAACTAGATAGAGAAAAAGAGGATAAATATTTATTCA
```

Figure 2C (continued)

```
540        I  L  A  K  D  N  G  V  P  P  L  T  S  N  V  T  V  F  V  S
2461  CAATTCTGGCAAAAGATAACGGGGTACCACCCTTAACCAGCAATGTCACAGTCTTTGTAA
560        I  I  D  Q  N  D  N  S  P  V  F  T  H  N  E  Y  N  F  Y  V
2521  GCATTATTGATCAGAATGACAATAGCCCAGTTTTCACTCACAATGAATACAACTTCTATG
580        P  E  N  L  P  R  H  G  T  V  G  L  I  T  V  T  D  P  D  Y
2581  TCCCAGAAAACCTTCCAAGGCATGGTACAGTAGGACTAATCACTGTAACTGATCCTGATT
600        G  D  N  S  A  V  T  L  S  I  L  D  E  N  D  D  F  T  I  D
2641  ATGGAGACAATTCTGCAGTTACGCTCTCCATTTTAGATGAGAATGATGACTTCACCATTG
620        S  Q  T  G  V  I  R  P  N  I  S  F  D  R  E  K  Q  E  S  Y
2701  ATTCACAAACTGGTGTCATCCGACCAAATATTTCATTTGATAGAGAAAAACAAGAATCTT
640        T  F  Y  V  K  A  E  D  G  G  R  V  S  R  S  S  S  A  K  V
2761  ACACTTTCTATGTAAAGGCTGAGGATGGTGGTAGAGTATCACGTTCTTCAAGTGCCAAAG
660        T  I  N  V  V  D  V  N  D  N  K  P  V  F  I  V  P  P  S  N
2821  TAACCATAAATGTGGTTGATGTCAATGACAACAAACCAGTTTTCATTGTCCCTCCTTCCA
680        C  S  Y  E  L  V  L  P  S  T  N  P  G  T  V  V  F  Q  V  I
2881  ACTGTTCTTATGAATTGGTTCTACCGTCCACTAATCCAGGCACAGTGGTCTTTCAGGTAA
700        A  V  D  N  D  T  G  M  N  A  E  V  C  Y  S  I  V  G  G  N
2941  TTGCTGTTGACAATGACACTGGCATGAATGCAGAGGTTTGTTACAGCATTGTAGGAGGAA
720        T  R  D  L  F  A  I  D  Q  E  T  G  N  I  T  L  M  E  K  C
3001  ACACAAGAGATCTGTTTGCAATCGACCAAGAAACAGGCAACATAACATTGATGGAGAAAT
740        D  V  T  D  L  G  L  H  R  V  L  V  K  A  N  D  L  G  Q  P
3061  GTGATGTTACAGACCTTGGTTTACACAGAGTGTTGGTCAAAGCTAATGACTTAGGACAGC
760        D  S  L  F  S  V  V  I  V  N  L  F  V  N  E  S  V  T  N  A
3121  CTGATTCTCTCTTCAGTGTTGTAATTGTCAATCTGTTCGTGAATGAGTCGGTGACCAATG
780        T  L  I  N  E  L  V  R  K  S  T  E  A  P  V  T  P  N  T  E
3181  CTACACTGATTAATGAACTGGTGCGCAAAAGCACTGAAGCACCAGTGACCCCAAATACTG
800        I  A  D  V  S  S  P  T  S  D  Y  V  K  I  L  V  A  A  V  A
3241  AGATAGCTGATGTATCCTCACCAACTAGTGACTATGTCAAGATCCTGGTTGCAGCTGTTG
820        G  T  I  T  V  V  V  I  F  I  T  A  V  V  R  C  R  Q  A
3301  CTGGCACCATAACTGTCGTTGTAGTTATTTTCATCACTGCTGTAGTAAGATGTCGCCAGG
840        P  H  L  K  A  A  Q  K  N  K  Q  N  S  E  W  A  T  P  N  P
3361  CACCACACCTTAAGGCTGCTCAGAAAAACAAGCAGAATTCTGAATGGGCTACCCCAAACC
860        E  N  R  Q  M  I  M  M  K  K  K  K  K  K  H  S  P  K
3421  CAGAAAACAGGCAGATGATAATGATGAAGAAAAAGAAAAAGAAGAAGAAGCATTCCCCTA
880        N  L  L  L  N  F  V  T  I  E  E  T  K  A  D  D  V  D  S  D
3481  AGAACTTGCTGCTTAATTTTGTCACTATTGAAGAAACTAAGGCAGATGATGTTGACAGTG
900        G  N  R  V  T  L  D  L  P  I  D  L  E  E  Q  T  M  G  K  Y
3541  ATGGAAACAGAGTCACACTAGACCTTCCTATTGATCTAGAAGAGCAAACAATGGGAAAGT
920        N  W  V  T  T  P  T  T  F  K  P  D  S  P  D  L  A  R  H  Y
3601  ACAATTGGGTAACTACACCTACTACTTTCAAGCCCGACAGCCCTGATTTGGCCCGACACT
940        K  S  A  S  P  Q  P  A  F  Q  I  Q  P  E  T  P  L  N  S  K
3661  ACAAATCTGCCTCTCCACAGCCTGCCTTCCAAATTCAGCCTGAAACTCCCCTGAATTCGA
960        H  H  I  I  Q  E  L  P  L  D  N  T  F  V  A  C  D  S  I  S
3721  AGCACCACATCATCCAAGAACTGCCTCTCGATAACACCTTTGTGGCCTGTGACTCTATCT
980        K  C  S  S  S  S  D  P  Y  S  V  S  D  C  G  Y  P  V  T
3781  CCAAGTGTTCCTCAAGCAGTTCAGATCCCTACAGCGTTTCTGACTGTGGCTATCCAGTGA
1000       T  F  E  V  P  V  S  V  H  T  R  P  V  G  I  Q  V  S  N  T
3841  CGACCTTCGAGGTACCTGTGTCCGTACACACCAGACCGGTAGGTATCCAAGTTTCTAACA
1020       T  F  *
3901  CAACTTTCTAActatttttttattattattttcagttgatgtagaactttacaaaatcta
3961  ttgacttcaaagagggatcaaaacaatcatattctacagatgtacccaatagatatatgg
4021  attcaattaagtttggtagaagatgagaacaaaataactactgatttaggaaaattggat
4081  gcagaataataattatagtaggggcaattttgtctgtagatggcagtatgacaattcttg
4141  ctagagaatatattgaaaaaaacttcaacacaaagggttgtagcactgtcctcagtacca
4201  ttgtgtgcatgaggatcagaatagtctgggctagatacatcacattaaagcttttcagaa
4261  tctgataaatagctctaaatactaatgatattgagaagcctagcttcacttgggaaaatc
4321  tgtggctgttcacagaaattcagcaccaagttattcccccatactctaccaggccttca
4381  ggtcctcataaagaaaagtgtcgttttcagattaggaactcaaaattattttggtgcatc
4441  aaatctacagtcacacaatataacaagaatgggattagaaaaatgaaagcctactcattc
4501  tcatctttaagccagagaatgaaatatatatgaggtctctggatagctatttaaatattt
4561  gcatatttatgcaaggtattttgagcccttcagaagacattct
```

Figure 2D The cDNA (SEQ ID NO:27) and amino acid sequence (SEQ ID NO:28) of
151P1C7A. The start methionine is underlined. The open reading frame extends
from nucleic acid 103-903 including the stop codon.

```
   1 ccacgcgtccgcggacgcgtgggcggcacggtttcgtggggacccaggcttgcaaagtga
   1                                                    M  M  A  L  G  A
  61 cggtcatttctctttctttctccctcttgagtccttctgagATGATGGCTCTGGGCGCA
   7 A  G  A  T  R  V  F  V  A  M  V  A  A  A  L  G  G  H  P  L
 121 GCGGGAGCTACCCGGGTCTTTGTCGCGATGGTAGCGGCGGCTCTCGGCGGCCACCCTCTG
  27 L  G  V  S  A  T  L  N  S  V  L  N  S  N  A  I  K  N  L  P
 181 CTGGGAGTGAGCGCCACCTTGAACTCGGTTCTCAATTCCAACGCTATCAAGAACCTGCCC
  47 P  P  L  G  G  A  A  G  H  P  G  S  A  V  S  A  A  P  G  I
 241 CCACCGCTGGGCGGCGCTGCGGGGCACCCAGGCTCTGCAGTCAGCGCCGCGCCGGGAATC
  67 L  Y  P  G  G  N  K  Y  Q  T  I  D  N  Y  Q  P  Y  P  C  A
 301 CTGTACCCGGGCGGGAATAAGTACCAGACCATTGACAACTACCAGCCGTACCCGTGCGCA
  87 E  D  E  E  C  G  T  D  E  Y  C  A  S  P  T  R  G  G  D  A
 361 GAGGACGAGGAGTGCGGCACTGATGAGTACTGCGCTAGTCCCACCCGCGGAGGGGACGCA
 107 G  V  Q  I  C  L  A  C  R  K  R  K  R  C  M  R  H  A  M
 421 GGCGTGCAAATCTGTCTCGCCTGCAGGAAGCGCCGAAAACGCTGCATGCGTCACGCTATG
 127 C  C  P  G  N  Y  C  K  N  G  I  C  V  S  S  D  Q  N  H  F
 481 TGCTGCCCCGGGAATTACTGCAAAAATGGAATATGTGTGTCTTCTGATCAAAATCATTTC
 147 R  G  E  I  E  E  T  I  T  E  S  F  G  N  D  H  S  T  L  D
 541 CGAGGAGAAATTGAGGAAACCATCACTGAAAGCTTTGGTAATGATCATAGCACCTTGGAT
 167 G  Y  S  R  R  T  T  L  S  S  K  M  Y  H  T  K  G  Q  E  G
 601 GGGTATTCCAGAAGAACCACCTTGTCTTCAAAAATGTATCACACCAAAGGACAAGAAGGT
 187 S  V  C  L  R  S  S  D  C  A  S  G  L  C  C  A  R  H  F  W
 661 TCTGTTTGTCTCCGGTCATCAGACTGTGCCTCAGGATTGTGTTGTGCTAGACACTTCTGG
 207 S  K  I  C  K  P  V  L  K  E  G  Q  V  C  T  K  H  R  R  K
 721 TCCAAGATCTGTAAACCTGTCCTGAAAGAAGGTCAAGTGTGTACCAAGCATAGGAGAAAA
 227 G  S  H  G  L  E  I  F  Q  R  C  Y  C  G  E  G  L  S  C  R
 781 GGCTCTCATGGACTAGAAATATTCCAGCGTTGTTACTGTGGAGAAGGTCTGTCTTGCCGG
 247 I  Q  K  D  H  H  Q  A  S  N  S  S  R  L  H  T  C  Q  R  H
 841 ATACAGAAAGATCACCATCAAGCCAGTAATTCTTCTAGGCTTCACACTTGTCAGAGACAC
 267 *
 901 TAAaccagctatccaaatgcagtgaactccttttatataatagatgctatgaaaacctttt
 961 tatgaccttcatcaactcaatcctaaggatatacaagttctgtggtttcagttaagcatt
1021 ccaataacaccttccaaaaacctggagtgtaagagctttgtttctttatggaactcccct
1081 gtgattgcagtaaattactgtattgtaaattctcagtgtggcacttacctgtaaatgcaa
1141 tgaaacttttaattattttctaaaggtgctgcactgcctattttcctcttgttatgta
1201 aattttgtacacattgattgttatcttgactgacaaatattctatattgaactgaagta
1261 aatcatttcagcttatagttcttaaaagcataacccttttaccccatttaattctagagtc
1321 tagaacgcaaggatctcttggaatgacaaatgataggtacctaaaatgtaacatgaaaat
1381 actagcttattttctgaaatgtactatcttaatgcttaaattatatttcccttaggctg
1441 tgatagttttgaaataaaatttaacatttaatatcatgaaatgttataagtagacataa
1501 aaaaaaaaaaaaaaaaaaaa
```

Figure 2E The cDNA (SEQ ID NO:29) and amino acid sequence (SEQ ID NO:30) of 151P4E11. The start methionine is underlined. The open reading frame extends from nucleic acid 3-374 including the stop codon.

```
  1     M   A   R   G   S   A   L   L   L   A   S   L   L   L   A   A   A   L   S   A
  1   agATGGCCCGAGGCAGCGCCCTCCTGCTCGCCTCCCTCCTCCTCGCCGCGGCCCTTTCTG
 21     S   A   G   L   W   S   P   A   K   E   K   R   G   W   T   L   N   S   A   G
 61   CCTCTGCGGGGCTCTGGTCGCCGGCCAAGGAAAAACGAGGCTGGACCCTGAACAGCGCGG
 41     Y   L   L   G   P   H   A   V   G   N   H   R   S   F   S   D   K   N   G   L
121   GCTACCTGCTGGGCCCACATGCCGTTGGCAACCACAGGTCATTCAGCGACAAGAATGGCC
 61     T   S   K   R   E   L   R   P   E   D   D   M   K   P   G   S   F   D   R   S
181   TCACCAGCAAGCGGGAGCTGCGGCCCGAAGATGACATGAAACCAGGAAGCTTTGACAGGT
 81     I   P   E   N   N   I   M   R   T   I   I   E   F   L   S   F   L   H   L   K
241   CCATACCTGAAAACAATATCATGCGCACAATCATTGAGTTTCTGTCTTTCTTGCATCTCA
101     E   A   G   A   L   D   R   L   L   D   L   P   A   A   A   S   S   E   D   I
301   AAGAGGCCGGTGCCCTCGACCGCCTCCTGGATCTCCCCGCCGCAGCCTCCTCAGAAGACA
121     E   R   S   *
361   TCGAGCGGTCCTGAgagcctcctgggcacgtttgtctgtgtgctgtaacctgaagtcaaa
421   ccttaagataatggataatcttcggccaatttatgcggagtcagccattcctgttctctt
481   tgccttgatgttgtgttgttatcatttaagattttttttttttggtaattattttgagtg
541   gcaaaataaagaatagcaatta
```

Figure 2F The cDNA (SEQ ID NO:31) and amino acid sequence (SEQ ID NO:32) of 154P2A8. The start methionine is underlined. The open reading frame extends from nucleic acid 250-1326 including the stop codon.

```
   1          ggcacgagggtttcgttttcatgctttaccagaaaatccacttccctgccgaccttagtt
  61          tcaaagcttattcttaattagagacaagaaacctgtttcaacttgaagacaccgtatgag
 121          gtgaatggacagccagccaccacaatgaaagaaatcaaaccaggaataacctatgctgaa
 181          cccacgcctcaatcgtccccaagtgtttcctgacacgcatctttgcttacagtgcatcac
   1                M  G  F  N  L  T  L  A  K  L  P  N  N  E  L  H  G
 241          aactgaagaATGGGGTTCAACTTGACGCTTGCAAAATTACCAAATAACGAGCTGCACGGC
  18   Q  E  S  H  N  S  G  N  R  S  D  G  P  G  K  N  T  T  L  H
 301          CAAGAGAGTCACAATTCAGGCAACAGGAGCGACGGGCCAGGAAAGAACACCACCCTTCAC
  38   N  E  F  D  T  I  V  L  P  V  L  Y  L  I  I  F  V  A  S  I
 361          AATGAATTTGACACAATTGTCTTGCCGGTGCTTTATCTCATTATATTTGTGGCAAGCATC
  58   L  L  N  G  L  A  V  W  I  F  F  H  I  R  N  K  T  S  F  I
 421          TTGCTGAATGGTTTAGCAGTGTGGATCTTCTTCCACATTAGGAATAAAACCAGCTTCATA
  78   F  Y  L  K  N  I  V  V  A  D  L  I  M  T  L  T  F  P  F  R
 481          TTCTATCTCAAAAACATAGTGGTTGCAGACCTCATAATGACGCTGACATTTCCATTTCGA
  98   I  V  H  D  A  G  F  G  P  W  Y  F  K  F  I  L  C  R  Y  T
 541          ATAGTCCATGATGCAGGATTTGGACCTTGGTACTTCAAGTTTATTCTCTGCAGATACACT
 118   S  V  L  F  Y  A  N  M  Y  T  S  I  V  F  L  G  L  I  S  I
 601          TCAGTTTTGTTTTATGCAAACATGTATACTTCCATCGTGTTCCTTGGGCTGATAAGCATT
 138   D  R  Y  L  K  V  V  K  P  F  G  D  S  R  M  Y  S  I  T  F
 661          GATCGCTATCTGAAGGTGGTCAAGCCATTTGGGGACTCTCGGATGTACAGCATAACCTTC
 158   T  K  V  L  S  V  C  V  W  V  I  M  A  V  L  S  L  P  N  I
 721          ACGAAGGTTTTATCTGTTTGTGTTTGGGTGATCATGGCTGTTTTGTCTTTGCCAAACATC
 178   I  L  T  N  G  Q  P  T  E  D  N  I  H  D  C  S  K  L  K  S
 781          ATCCTGACAAATGGTCAGCCAACAGAGGACAATATCCATGACTGCTCAAAACTTAAAAGT
 198   P  L  G  V  K  W  H  T  A  V  T  Y  V  N  S  C  L  F  V  A
 841          CCTTTGGGGGTCAAATGGCATACGGCAGTCACCTATGTGAACAGCTGCTTGTTTGTGGCC
 218   V  L  V  I  L  I  G  C  Y  I  A  I  S  R  Y  I  H  K  S  S
 901          GTGCTGGTGATTCTGATCGGATGTTACATAGCCATATCCAGGTACATCCACAAATCCAGC
 238   R  Q  F  I  S  Q  S  S  R  K  R  K  H  N  Q  S  I  R  V  V
 961          AGGCAATTCATAAGTCAGTCAAGCCGAAAGCGAAAACATAACCAGAGCATCAGGGTTGTT
 258   V  A  V  F  F  T  C  F  L  P  Y  H  L  C  R  I  P  F  T  F
1021          GTGGCTGTGTTTTTTACCTGCTTTCTACCATATCACTTGTGCAGAATTCCTTTTACTTTT
 278   S  H  L  D  R  L  L  D  E  S  A  Q  K  I  L  Y  Y  C  K  E
1081          AGTCACTTAGACAGGCTTTTAGATGAATCTGCACAAAAAATCCTATATTACTGCAAAGAA
 298   I  T  L  F  L  S  A  C  N  V  C  L  D  P  I  I  Y  F  F  M
1141          ATTACACTTTTCTTGTCTGCGTGTAATGTTTGCCTGGATCCAATAATTTACTTTTTCATG
 318   C  R  S  F  S  R  R  L  F  K  K  S  N  I  R  T  R  S  E  S
1201          TGTAGGTCATTTTCAAGAAGGCTGTTCAAAAAATCAAATATCAGAACCAGGAGTGAAAGC
 338   I  R  S  L  Q  S  V  R  R  S  E  V  R  I  Y  Y  D  Y  T  D
1261          ATCAGATCACTGCAAAGTGTGAGAAGATCGGAAGTTCGCATATATTATGATTACACTGAT
 358   V  *
1321          GTGTAGgcctttttattgtttgttggaatcgatatgtacaaagtgtaaataaatgtttctt
1381          ttcattatccttaaaaaaaaaa
```

Figure 2G The cDNA (SEQ ID NO:33) and amino acid sequence (SEQ ID NO:34) of 156P1D4. The start methionine is underlined. The open reading frame extends from nucleic acid 24-692 including the stop codon.

```
  1                         M   L   W   L   L   F   F   L   V   T   A   I   H
  1 cttgtgttttccaccctgaaagaATGTTGTGGCTGCTCTTTTTTCTGGTGACTGCCATTC
 14   A   E   L   C   Q   P   G   A   E   N   A   F   K   V   R   L   S   I   R   T
 61 ATGCTGAACTCTGTCAACCAGGTGCAGAAAATGCTTTTAAAGTGAGACTTAGTATCAGAA
 34   A   L   G   D   K   A   Y   A   W   D   T   N   E   E   Y   L   F   K   A   M
121 CAGCTCTGGGAGATAAAGCATATGCCTGGGATACCAATGAAGAATACCTCTTCAAAGCGA
 54   V   A   F   S   M   R   K   V   P   N   R   E   A   T   E   I   S   H   V   L
181 TGGTAGCTTTCTCCATGAGAAAAGTTCCCAACAGAGAAGCAACAGAAATTTCCCATGTCC
 74   L   C   N   V   T   Q   R   V   S   F   W   F   V   V   T   D   P   S   K   N
241 TACTTTGCAATGTAACCCAGAGGGTATCATTCTGGTTTGTGGTTACAGACCCTTCAAAAA
 94   H   T   L   P   A   V   E   V   Q   S   A   I   R   M   N   K   N   R   I   N
301 ATCACACCCTTCCTGCTGTTGAAGTGCAATCAGCCATAAGAATGAACAAGAACCGGATCA
114   N   A   F   L   N   D   Q   T   L   E   F   L   K   I   P   S   T   L   A
361 ACAATGCCTTCTTTCTAAATGACCAAACTCTGGAATTTTTAAAAATCCCTTCCACACTTG
134   P   P   M   D   P   S   V   P   I   W   I   I   I   F   G   V   I   F   C   I
421 CACCACCCATGGACCCATCTGTGCCCATCTGGATTATTATATTTGGTGTGATATTTTGCA
154   I   I   V   A   I   A   L   L   I   L   S   G   I   W   Q   R   R   R   K   N
481 TCATCATAGTTGCAATTGCACTACTGATTTTATCAGGGATCTGGCAACGTAGAAGAAAGA
174   K   E   P   S   E   V   D   D   A   E   D   K   C   E   N   M   I   T   I   E
541 ACAAAGAACCATCTGAAGTGGATGACGCTGAAGATAAGTGTGAAAACATGATCACAATTG
194   N   G   I   P   S   D   P   L   D   M   K   G   G   H   I   N   D   A   F   M
601 AAAATGGCATCCCCTCTGATCCCCTGGACATGAAGGGAGGGCATATTAATGATGCCTTCA
214   T   E   D   E   R   L   T   P   L   *
661 TGACAGAGGATGAGAGGCTCACCCCTCTCTGAagggctgttgttctgcttcctcaagaaa
721 ttaaacatttgtttctgtgtgactgctgagcatcctgaaataccaagagcagatcatata
781 ttttgtttcaccattcttcttttgtaataaattttgaatgtgcttgaaagtgaaaagcaa
841 tcaattatacccaccaacaccactgaaatcataagctattcacgactcaaaatattctaa
901 aatattttctgacagtatagtgtataaatgtggtcatgtggtatttgtagttattgatt
961 taagcatttttagaaataagatcaggcatatgtatatattttcacacttcaaagacctaa
1021 ggaaaaataaattttccagtggagaatacatataatatggtgtagaaatcattgaaaatg
1081 gatcctttttgacgatcacttatatcactctgtatatgactaagtaaacaaaagtgagaa
1141 gtaattattgtaaatggatggataaaaatggaattactcatatacagggtggaattttat
1201 cctgttatcacaccaacagttgattatatattttctgaatatcagcccctaataggacaa
1261 ttctatttgttgaccatttctacaatttgtaaaagtccaatctgtgctaacttaataaag
1321 taataatcatctcttttgattgtg
```

Figure 2H The cDNA (SEQ ID NO:35) and amino acid sequence (SEQ ID NO:36) of
156P5C12. The start methionine is underlined. The open reading frame extends
from nucleic acid 178-861 including the stop codon.

```
  1 ttcggcacgagcggcacgagaagccccagacggtatctccgagatgccagtgagcggctg
 61 agagctgaagccccctggacactcaaggctcttgtggtgacagtctgacgtaaaggcgtg
  1                                                            M
121 cagggaggcctagctctgtctcctggacttagagatttcagacacagaagtctgtccATG
  2 A  P  C  H  I  R  K  Y  Q  E  S  D  R  Q  W  V  V  G  L  L
181 GCTCCTTGTCACATCCGCAAATACCAGGAGAGCGACCGCCAGTGGGTTGTGGGCTTGCTC
 22 S  R  G  M  A  E  H  A  P  A  T  F  R  Q  L  L  K  L  P  R
241 TCCCGGGGGATGGCCGAGCATGCCCCAGCCACCTTCCGGCAATTGCTGAAGCTGCCTCGA
 42 T  L  I  L  L  G  G  P  L  A  L  L  V  S  G  S  W  L
301 ACCCTCATACTCTTACTTGGGGGGCCCCTCGCCCTACTCCTGGTCTCTGGATCCTGGCTT
 62 L  A  L  V  F  S  I  S  L  F  P  A  L  W  F  L  A  K  K  P
361 CTAGCCCTCGTGTTCAGCATCAGCCTCTTCCCTGCCCTGTGGTTCCTTGCCAAAAAACCC
 82 W  T  E  Y  V  D  M  T  L  C  T  D  M  S  D  I  T  K  S  Y
421 TGGACGGAGTATGTGGACATGACATTGTGCACAGACATGTCTGACATTACCAAATCCTAC
102 L  S  E  R  G  S  C  F  W  V  A  E  S  E  E  K  V  V  G  M
481 CTGAGTGAGCGTGGCTCCTGCTTCTGGGTGGCTGAGTCTGAAGAGAAGGTGGTGGGCATG
122 V  G  A  L  P  V  D  D  P  T  L  R  E  K  R  L  Q  L  F  H
541 GTAGGAGCTCTGCCTGTTGATGATCCCACCTTGAGGGAGAAGCGGTTGCAGCTGTTTCAT
142 L  S  V  D  S  E  H  R  R  Q  G  I  A  K  A  L  V  R  T  V
601 CTCTCTGTGGACAGTGAGCACCGTCGTCAGGGGATAGCAAAAGCCCTGGTCAGGACTGTC
162 L  Q  F  A  R  D  Q  G  Y  S  E  V  I  L  D  T  G  T  I  Q
661 CTCCAGTTTGCCCGGGACCAGGGCTACAGTGAAGTTATCCTGGACACCGGCACCATCCAG
182 L  S  A  M  A  L  Y  Q  S  M  G  F  K  K  T  G  Q  S  F  F
721 CTCTCTGCTATGGCCCTCTACCAGAGCATGGGCTTCAAGAAGACGGGCCAGTCCTTCTTC
202 C  V  W  A  R  L  V  A  L  H  T  V  H  F  I  Y  H  L  P  S
781 TGTGTGTGGGCCAGGCTAGTGGCTCTTCATACAGTTCATTTCATCTACCACCTCCCTTCT
222 S  K  V  G  S  L  *
841 TCTAAGGTAGGGAGTCTGTGAtctctttctgtgtgtattggtcagaatagaatccattca
901 gctgtagcagcaagcaatccccaacctttcactgcaatgacctttcaatgcaataaaagc
961 ttattgtccattcaaaaaaaaaaaaaaaaaaa
```

Figure 2I The cDNA (SEQ ID NO:37) and amino acid sequence (SEQ ID NO:38) of 159P2B5. The start methionine is underlined. The open reading frame extends from nucleic acid 1517-2191 including the stop codon.

```
   1 atcagtgggccagagctcgccgggtggccgcaagtacgccggcccagcccgcagcgcgcc
  61 cagccggaaggcggggaatccggctgacaccgcgccccgggttcccaggccacctcctct
 121 gttctgaggctgggctgggagaccgtggggcgtgaggagcgcatagaaccgtggtggag
 181 ggcgaggctgggccaccggctcttcaagctcggaatggaggggaagagcgcagagggct
 241 ggctgggaggaactcgggtgggcgtgaaggagacgagggcaagaaaagaaacttcccttc
 301 ttccaggagggtcttcgaaaccctctcccacagccctctcgtcattagcatggcaatg
 361 aggagtttctgtaattcgacttggaggggcggatgagccctggaaactcagagctcgccg
 421 gaaaaggccgggggcggccgggctcttcttccccaccttccctctcgtcgctctccgc
 481 cccttctctctttccccactcagttttgcaccgggagccctccgggatgcggagctactcga
 541 ccgccggatttttaggggtaggaggcggggagagagatgacgctggcggacgtggccag
 601 cgcggggccgggcggtgcgctgcaggccatctgccggcgccctgagacccaggagcctc
 661 cgcgctcccgcgtgggcctcacagggccggtccacagctccaacatagtagctgaactcc
 721 cttcgttgcgttcctcttttctggaggggaatgttagaagagagagagagcttcctttt
 781 ataaccttcctcattctgctgcacgtctagagtgggtgtgggggctggcaggtgggaggg
 841 gcggtggacaaatggctgatggtggacgcacttacccaacgacacctcctcccct
 901 ttccaactggctgtgtagttgcttatgagaaccttcaagtccttccctagagagacacat
 961 gcaaatctgagcctcatcccaggccaggggtcctgttcctcatcaccctacttccctgag
1021 gctgctgaggtcgttaaattgttgtttactattaggtttcacgtcaaccctgggcttgta
1081 gagagaaaaagccaaacggagaccaagaattgatgcagtcttgggtaggagaaatcgaga
1141 gcttgtccaggaagctttgctgtataaattataagcaatgctgtataaattttactccaa
1201 ccatgtgtacaatgttggaatcagatgaaatttatagtgaatgaatgtatgtgggttgg
1261 ggtttccactcctcttcagcctttcctccgttagaacaaggaagttttttttttttttca
1321 aggaaggtacatttcaaatatgttagtcacccttcagtcttctgtattctgttctccac
1381 gtaccgaagttccccccaaacctgtcctctcaagagaaaaaacccatgctgactctggact
1441 ccctcagtaacaatgaaacattctcccaaacatttcctttcagaatagtatttgtgact
   1                 M  V  K  R  E  H  G  Q  E  R  P  T  F  W  G
1501 ttgatccatcccaagcATGGTTAAGAGGGAGCACGGGCAGGAAAGGCCCACTTTCTGGGG
  16  W  A  A  T  P  A  P  V  S  A  P  G  N  P  P  T  G  E  G  E
1561 TTGGGCAGCCACCCCTGCCCCAGTTTCGGCTCCTGGGAATCCTCCGACTGGAGAAGGGGA
  36  R  Q  G  S  P  P  G  G  G  F  L  G  S  T  S  F  Q  R  R  G
1621 AAGGCAAGGCAGTCCTCCTGGAGGCGGCTTCCTTGGGAGCACCAGCTTCCAGCGGCGGGG
  56  E  K  E  L  L  W  E  R  G  Q  D  V  S  R  S  V  L  A  M  R
1681 AGAGAAGGAGCTCCTGTGGGAGAGGGGGCAGGATGTGAGTAGGTCGGTGCTGGCTATGCG
  76  A  I  L  P  P  S  L  S  K  S  V  H  F  P  P  L  P  H  S  C
1741 AGCAATCCTCCCTCCAAGCCTGAGCAAGTCGGTACATTTTCCCCGCTGCCTCATTCCTG
  96  T  L  V  A  L  L  S  L  G  L  Q  D  P  L  G  C  R  A  P  A
1801 TACCTTGGTTGCCCTCCTCAGCCTGGGTTTGCAGGACCCCCTCGGCTGCAGGGCGCCTGC
 116  T  K  P  T  P  A  G  A  T  L  S  A  S  S  L  P  R  P  C  S
1861 CACAAAGCCGACCCCGGCAGGAGCCACTCTCTCTGCTAGTTCGCTGCCTCGGCCCTGCTC
 136  P  S  A  S  L  L  L  S  W  P  L  F  W  G  I  L  G  G  V  F
1921 TCCCTCAGCCTCTCTTCTTCTCTCCTGGCCTCTTTTCTGGGGCATCCTGGGTGGAGTGTT
 156  F  L  G  S  R  A  C  T  R  T  Q  A  R  R  H  T  G  P  A  A
1981 TTTCTTGGGATCACGAGCTTGCACTCGCACACAGGCCCGCAGACACACAGGCCCGGCGGC
 176  A  L  R  L  L  F  P  A  P  R  R  P  G  A  R  S  R  A  G
2041 CGCCCTTCTCCGCTTACTGTTCCCGGCTCCCCGCAGGCCGGGTGCTCGCAGCCGGGCTGG
 196  Y  A  S  P  G  S  P  E  R  R  S  P  G  T  A  H  K  G  S  L
2101 CTATGCCTCGCCTGGCAGCCCAGAGCGCCGCTCCCCGGGAACAGCACACAAAGGCAGCCT
 216  P  W  P  L  A  L  R  L  L  *
2161 CCCCTGGCCTCTAGCCCTTAGGCTTCTGTAGctcagttctttcccacacccctccccca
2221 agaaattctgggggccgttccaccgagtaggagatccttggccctctaggcaagtaggtc
2281 agcgccccaagactggagctggtctctttcaacgccttgggagactgggtgaaaggcgag
2341 cttggttacgcttaaaatgatcgcctacaagcggttctcttggctcaaaacgcctcttc
2401 agggctcttatgctagaaaggaaaggaataaggaggagataaaatgacgccaggccctg
2461 aactgttcatggcatccgcggctcagccaagctgttgttttaaaagagcaataaaatga
2521 attatgact
```

Figure 2J The cDNA (SEQ ID NO:39) and amino acid sequence (SEQ ID NO:40) of 161P2B7A. The start methionine is underlined. The open reading frame extends from nucleic acid 198-770 including the stop codon.

```
   1 gccgcccaggattccacgaggggaaggattctctattcttttttgcgacaaatctggta
  61 acaggatttgctgtgctgttttcgtccgtgtgtgtgcgtgtgtgtgtgttcgtgtg
 121 gatgcacgtgtggccccgctggggtgcccctccagtgtccccggagctgaaagatcgca
   1                                        M  E  D  E  G  Q  T  K  I  K  Q  R  R  S  R
 181 aagaggatgcgaaagggATGGAGGACGAAGGCCAGACCAAAATCAAGCAGAGGCGAAGTC
  16  T  N  F  T  L  E  Q  L  N  E  L  R  L  F  D  E  T  H  Y
 241 GGACCAATTTCACCCTGGAACAACTCAATGAGCTGGAGAGGCTTTTTGACGAGACCCACT
  36  P  D  A  F  M  R  E  E  L  S  Q  R  L  G  L  S  E  A  R  V
```

Figure 2J (continued)

```
301 ATCCCGACGCCTTCATGCGAGAGGAACTGAGCCAGCGACTGGGCCTGTCGGAGGCCCGAG
 56   Q  V  W  F  Q  N  R  R  A  K  C  R  K  Q  E  N  Q  L  H  K
361 TGCAGGTTTGGTTTCAAAATCGAAGAGCTAAATGTAGAAAACAAGAAAATCAACTCCATA
 76   G  V  L  I  G  A  A  S  Q  F  E  A  C  R  V  A  P  Y  V  N
421 AAGGTGTTCTCATAGGGGCCGCCAGCCAGTTTGAAGCTTGTAGAGTCGCACCTTATGTCA
 96   V  G  A  L  R  M  P  F  Q  Q  V  Q  A  Q  L  Q  L  D  S  A
481 ACGTAGGTGCTTTAAGGATGCCATTTCAGCAGGTTCAGGCGCAGCTGCAGCTGGACAGCG
116   V  A  H  A  H  H  H  L  H  P  H  L  A  A  H  A  P  Y  M  M
541 CTGTGGCGCACGCGCACCACCACCTGCATCCGCACCTGGCCGCGCACGCGCCCTACATGA
136   F  P  A  P  P  F  G  L  P  L  A  T  L  A  A  D  S  A  S  A
601 TGTTCCCAGCACCGCCCTTCGGACTGCCGCTCGCCACGCTGGCCGCGGATTCGGCTTCCG
156   A  S  V  V  A  A  A  A  A  K  T  T  S  K  N  S  S  I  A
661 CCGCCTCGGTAGTGGCGGCCGCAGCAGCCGCCAAGACCACCAGCAAGAACTCCAGCATCG
176   D  L  R  L  K  A  K  K  H  A  A  A  L  G  L  *
721 CCGATCTCAGACTGAAAGCCAAAAAGCACGCCGCAGCCCTGGGTCTGTGAcgccaacgcc
781 agcaccaatgtcgcgcctgtcccgcggcactcagcctgcacgccctccgcgccccgctgc
841 ttctccgttacccctttgagacctcgggagccgccctcttcccgcctcactgaccatcc
901 ctcgtcccctatcgcatcttggactcggaaagccagactccacgcaggaccagggatctc
961 acgaggcacgcaggctccgtggctcctgcccgttttcctactcgagggcctagaattggg
1021 ttttgtaggagcgggtttgggggagtctggagagagactggacaggggagtgctggaacc
1081 gcggagtttggctcaccgcaaagctacaacgatggactcttgcatagaaaaaaaaatctt
1141 gttaacaatgaaaaaatgagcaaacaaaaaaatcgaaagacaaacgggagagaaaaagag
1201 gaaggaaacttattctctaactgctatttggcaggagctgaaattggagaaccaaggagc
1261 aaaaacaaattttaaaattaaagtattttatacatttaaaaatatggaaaaacaacccag
1321 acgattctcgagagactgggggggagttaccaacttaaatgtgtgtttttaaaaatgcgct
1381 aagaaggcaaagcagaaagaagaggtatacttatttaaaaaactaagatgaaaaaagtgc
1441 gcagctgggaagttcacaggttttgaaactgaccttttttctgcgaagttcacgttaatac
1501 gagaaatttgatgagagaggcggctcttttacgttgaatcagatgctttgagtttaaaac
1561 ccaccatgtatggaagagcaagaaaaggaaaatattaaaacgaggagagagaaaaataa
1621 tattaacacaaaaaaatgccacagacaatgatttctctgagaaattattatggcaaaact
1681 gtctggactgctgacagtaaattccggtttgcatgttacttgtattccattgatggtgtg
1741 tcttcctcccacccccttatctcccatgcactcactccattttcatcttcactatgaaaa
1801 acaataccaaaagtatctggaaattgatatatatatatccacatatatatatcatatatt
1861 tgccatatatatatatatatatatatatatatatatatatatatatatatatatatttgccc
1921 tgtctttgatcctggggaacaaaagaaaaaagtcagaaagggaaaaaaattacactcattg
1981 ccctaagaagacagaggtgggcagaatatgtggggaaaggaaaaagaaaacaagaccacc
2041 aaatgaaataatgaaggtacagcgcctcgctgtgccagacacagtaggcgctcaatcagt
2101 attagttcccaccattccccttttcttgtgttccttcttgttggttttcctgaagtcctat
2161 ttgaagacagtggtttatttcccccctctctatcccgtcaaattcaccttaaataacaccc
2221 agctagatacaggcactaggtttgtgtaagatatgttgatacacacgaacaaagtttatt
2281 ttgactataatgtgtggactgacttttcaacatttgcattttatctcacaaaggtgtatct
2341 attcaagtaacctttttttttttttgttttgtttctttttttgtttttttttttttcttttg
2401 gttgtttgtttcaattcatgtagctatttaaactgggataccttggactaagccagtctg
2461 tatcccaattcgctagcaagcctaagtttgtgggggttttgtttttgtttttgttttacct
2521 tctaatttacaagaaagaggaaaagctcttctaactgaactttggtatgcggttgagctt
2581 tgtaactatttgttctccatgaaaacaaaattatttatatttgacatatttttttctagt
2641 gtattaagttatttaaacaaaagatgttatctcatgacgtgttgtcagtacaaaatgtg
2701 tcgcctccaattctgttaaaccttttaaataagtgccaagttattaatt
```

Figure 2K The cDNA (SEQ ID NO:41) and amino acid sequence (SEQ ID NO:42) of 179P3G7. The start methionine is underlined. The open reading frame extends from nucleic acid 72-1100 including the stop codon.

```
  1 cggatggggaaaaaaaaagatgtcagctcctccgctgtagtattgctccttaaaaacccc
  1               M  T  C  P  R  N  V  T  P  N  S  Y  A  E  P  L  A
 61 tctctctgaaaATGACATGCCCTCGCAATGTAACTCCGAACTCGTACGCGGAGCCCTTGG
 18   A  P  G  G  E  R  Y  S  R  S  A  G  M  Y  M  Q  S  G  S
121 CTGCGCCCGGCGGAGGAGAGCGCTATAGCCGGAGCGCAGGCATGTATATGCAGTCTGGGA
 38   D  F  N  C  G  V  M  R  G  C  L  A  P  S  L  S  K  R  D
181 GTGACTTCAATTGCGGGGTGATGAGGGGCTGCGGGCTGCCCCCTCGCTCTCCAAGAGGG
 58   E  G  S  S  P  S  L  A  L  N  T  Y  P  S  Y  L  S  Q  L  D
241 ACGAGGGCAGCAGCCCCAGCCTCGCCCTCAACACCTATCCGTCCTACCTCTCGCAGCTGG
 78   S  W  G  D  P  K  A  A  Y  R  L  E  Q  P  V  G  R  P  L  S
301 ACTCCTGGGGCGACCCCAAAGCCGCCTATCGCCTGGAACAACCTGTTGGCAGGCCGCTGT
 98   S  C  S  Y  P  P  S  V  K  E  E  N  V  C  C  M  Y  S  A  E
361 CCTCCTGCTCCTACCCACCCTAGTGTCAAGGAGGAGAATGTCTGCTGCATGTACAGCGCAG
118   N  R  A  K  S  G  P  E  A  A  L  Y  S  H  P  L  P  E  S  C
421 AGAACCGGGCGAAAAGTGGCCCTGAGGCAGCTCTCTACTCCCACCCCTTGCCGGAGTCCT
138   L  G  E  H  E  V  P  V  P  S  Y  Y  R  A  S  P  S  Y  S  A
481 GCCTTGGGGAGCACGAGGTACCCGTCCCCAGCTACTACCGCGCCAGCCCGAGCTACTCCG
```

Figure 2K (continued)

```
158  L   D   K   T   P   H   C   S   G   A   N   D   F   E   A   P   F   E   Q   R
541 CGCTGGACAAGACGCCCCACTGTTCTGGGGCCAACGACTTCGAAGCCCCTTTCGAGCAGC
178  A   S   L   N   P   R   A   E   H   L   E   S   P   Q   L   G   G   K   V   S
601 GGGCCAGTCTCAACCCGCGCGCCGAACATCTGGAATCGCCTCAGCTGGGGGCAAAGTGA
198  F   P   E   T   P   K   S   D   S   Q   T   P   S   P   N   E   I   K   T   E
661 GTTTCCCTGAGACCCCCAAGTCCGACAGCCAGACCCCCAGCCCCAATGAAATCAAGACGG
218  Q   S   L   A   G   P   K   G   S   P   S   E   S   E   K   E   R   A   K   A
721 AGCAGAGCCTGGCGGGCCCTAAAGGGAGCCCCTCGGAGAGCGAAAAGGAGAGGGCCAAAG
238  A   D   S   S   P   D   T   S   D   N   E   A   K   E   E   I   K   A   E   N
781 CTGCCGACTCCAGCCCAGACACCTCGGATAACGAAGCGAAAGAGGAGATAAAGGCAGAAA
258  T   T   G   N   W   L   T   A   K   S   G   R   K   K   R   C   P   Y   T   K
841 ACACCACAGGAAATTGGCTGACTGCAAAGAGCGGAAGGAAGAAGAGGTGCCCCTATACTA
278  H   Q   T   L   E   L   E   K   E   F   L   F   N   M   Y   L   T   R   E   R
901 AACACCAGACGCTGGAATTGGAGAAAGAATTTCTGTTCAATATGTATTTGACGCGAGAGC
298  R   L   E   I   S   K   T   I   N   L   T   D   R   Q   V   K   I   W   F   Q
961 GCCGCCTGGAGATTAGCAAGACCATTAACCTTACAGACAGACAAGTCAAAATCTGGTTTC
318  N   R   R   M   K   L   K   K   M   N   R   E   N   R   I   R   E   L   T   S
1021 AAAATCGCAGAATGAAACTCAAGAAAATGAACCGAGAGAATCGGATCCGGGAACTGACCT
338  N   F   N   F   T   *
1081 CCAATTTTAATTTCACCTGAgagcgcggcctctcctcctcccttcccgctccttgctctc
1141 cccgccctcctcccttgtgcctggtgatatattttttttcctccctgagtataaatg
1201 caatgcgactgcaaaaaaggcaaagacctcagactctccttccaagggacctgtggttcg
1261 tgctgcgaagatgcttccacttaaagcatgagaaatggggtgccgggatgtgggtgtgg
1321 tgtgtgccctcatagatggggtgggagtgtggctggtgtgtgtcaaaccctcactca
1381 cccacgcactcacacacagcattctgttctccatgcaaagttaagatcgaatccatccgc
1441 ttgtaggggaaaaaaaggaaaaaaaattaaccagagagggtctgtaatctcgcagagcaca
1501 ggcagaatcgttccttccttgctgcatttcctccttagactaatagacgttttggaaagt
1561 tcggctagtgttcgtgtgtttgtcgtagcacccagagcctccaccaaaccctctccatgt
1621 ctttacctcccagtcgctctaagatctgcttgaagtctcgtatttgtactgctttctgct
1681 tttctcccaccccctcctagcaccccccacatcccccatctagtaacatctcagaaatttca
1741 tccagaggaacaaaaaaattaaaaatagaacataagcaaagcaaagacagaatgccccccc
1801 ccaaatattgtcctgtccctgtctgggagttgtgttatttaaagatattctgtatgttgt
1861 atcttttgcatgtagcttccttaatggagaaaaaaaaatcctaataaatttccagaatca
1921 taaaaaaaaaaaaaaaaaaaa
```

Figure 2L  The cDNA (SEQ ID NO:43) and amino acid sequence (SEQ ID NO:44) of 184P3C10B. The start methionine is underlined. The open reading frame extends from nucleic acid 118-1236 including the stop codon.

```
  1 actctttcttcggctcgcgagctgagaggagcaggtagaggggcagaggcgggactgtcg
  1                                                            M
 61 tctggggggagccgcccaggaggctcctcaggccgaccccagaccctggctggccaggATG
  2 K   Y   L   R   H   R   R   P   N   A   T   L   I   L   A   I   G   A   F   T
121 AAGTATCTCCGGCACCGGCGGCCCAATGCCACCCTCATTCTGGCCATCGGCGCTTTCACC
 22 L   L   L   F   S   L   L   V   S   P   P   T   C   K   V   Q   E   Q   P   P
181 CTCCTCCTCTTCAGTCTGCTAGTGTCACCACCCACCTGCAAGGTCCAGGAGCAGCCACCG
 42 A   I   P   E   A   L   A   W   P   T   P   P   T   R   P   A   P   A   P   C
241 GCGATCCCCGAGGCCCTGGCCTGGCCCACTCCACCCACCCGCCCAGCCCCGGCCCCGTGC
 62 H   A   N   T   S   M   V   T   H   P   D   F   A   T   Q   P   Q   H   V   Q
301 CATGCCAACACCTCTATGGTCACCCACCCGGACTTCGCCACGCAGCCGCAGCACGTTCAG
 82 N   F   L   L   Y   R   H   C   R   H   F   P   L   L   Q   D   V   P   P   S
361 AACTTCCTCCTGTACAGACACTGCCGCCACTTTCCCCTGCTGCAGGACGTGCCCCCCTCT
102 K   C   A   Q   P   V   F   L   L   L   V   I   K   S   S   P   S   N   Y   V
421 AAGTGCGCGCAGCCGGTCTTCCTGCTGCTGGTGATCAAGTCCTCCCCTAGCAACTATGTG
122 R   R   E   L   L   R   T   W   G   E   R   K   V   R   G   L   Q   L
481 CGCCGCGAGCTGCTGCGGCGCACGTGGGGCCGCGAGCGCAAGGTACGGGGTTTGCAGCTG
142 R   L   L   F   L   V   G   T   A   S   N   P   H   E   A   R   K   V   N   R
541 CGCCTCCTCTTCCTGGTGGGCACAGCCTCCAACCCGCACGAGGCCCGCAAGGTCAACCGG
162 L   L   E   L   E   A   Q   T   H   G   D   I   L   Q   W   D   F   H   D   S
601 CTGCTGGAGCTGGAGGCACAGACTCACGGAGACATCCTGCAGTGGGACTTCCACGACTCC
182 F   F   N   L   T   L   K   Q   V   L   F   L   Q   W   Q   E   T   R   C   A
661 TTCTTCAACCTCACGCTCAAGCAGGTCCTGTTCTTACAGTGGCAGGAGACAAGGTGCGCC
202 N   A   S   F   V   L   N   G   D   D   D   V   F   A   H   T   D   N   M   V
721 AACGCCAGCTTCGTGCTCAACGGGGATGATGACGTCTTTGCACACACAGACAACATGGTC
222 F   Y   L   Q   D   H   D   P   G   R   H   L   F   V   G   Q   L   I   Q   N
781 TTCTACCTGCAGGACCATGACCCTGGCCGCCACCTCTTCGTGGGGCAACTGATCCAAAAC
242 V   G   P   I   R   A   F   W   S   K   Y   Y   V   P   E   V   V   T   Q   N
841 GTGGGCCCCATCCGGGCTTTTTGGAGCAAGTACTATGTGCCAGAGGTGGTGACTCAGAAT
262 E   R   Y   P   P   Y   C   G   G   G   F   L   L   S   R   F   T   A   A
901 GAGCGGTACCCACCCTATTGTGGGGGTGGTGGCTTCTTGCTGTCCCGCTTCACGGCCGCT
```

Figure 2L (continued)

```
 282 A  L  R  R  A  A  H  V  L  D  I  F  P  I  D  D  V  F  L  G
 961 GCCCTGCGCCGTGCTGCCCATGTCTTGGACATCTTCCCCATTGATGATGTCTTCCTGGGT
 302 M  C  L  E  L  E  G  L  K  P  A  S  H  S  G  I  R  T  S  G
1021 ATGTGTCTGGAGCTTGAGGGACTGAAGCCTGCCTCCCACAGCGGCATCCGCACGTCTGGC
 322 V  R  A  P  S  Q  H  L  S  S  F  D  P  C  F  Y  R  D  L  L
1081 GTGCGGGCTCCATCGCAACACCTGTCCTCCTTTGACCCCTGCTTCTACCGAGACCTGCTG
 342 L  V  H  R  F  L  P  Y  E  M  L  L  M  W  D  A  L  N  Q  P
1141 CTGGTGCACCGCTTCCTACCTTATGAGATGCTGCTCATGTGGGATGCGCTGAACCAGCCC
 362 N  L  T  C  G  N  Q  T  Q  I  Y  *
1201 AACCTCACCTGCGGCAATCAGACACAGATCTACTGAgtcagcatcagggtccccagcctc
1261 tgggctcctgtttccataggaaggggcgacaccttcctcccaggaagctgagacctttgt
1321 ggtctgagcataagggagtgccagggaaggtttgaggtttgatgagtgaatattctggct
1381 ggcgaactcctacacatccttcaaaacccacctggtactgttccagcatcttccctggat
1441 ggctggaggaactccagaaaatatccatcttcttttttgtggctgctaatggcagaagtgc
1501 ctgtgctagagttccaactgtggatgcatccgtcccgtttgagtcaaagtcttacttccc
1561 tgctctcacctactcacagacgggatgctaagcagtgcacctgcagtggtttaatggcag
1621 ataagctccgtctgcagttccaggccagccagaaactcctgtgtccacatagagctgacg
1681 tgagaaatatctttcagcccaggagagggggtcctgatcttaaccctttcctgggtctc
1741 agacaactcagaaggttggggggataccagagaggtggtggaataggaccgcccctcct
1801 tacttgtgggatcaaatgctgtaatggtggaggtgtgggcagaggagggaggcaagtgtc
1861 ctttgaaagttgtgagagctcagagtttctggggtcctcattaggagcccccatccctgt
1921 gttccccaagaattcagagaacagcactggggctggaatgatctttaatgggcccaaggc
1981 caacaggcatatgcctcactactgcctggagaagggagagattcaggtcctccagcagcc
2041 tccctcacccagtatgttttacagattacgggggaccgggtgagccagtgaccccctgc
2101 agccccagcttcaggcctcagtgtctgccagtcaagcttcacaggcattgtgatgggc
2161 agccttggggaatataaaattttgtg
```

Figure 2M The cDNA (SEQ ID NO:45) and amino acid sequence (SEQ ID NO:46) of 184P3G10. The start methionine is underlined. The open reading frame extends from nucleic acid 14-2260 including the stop codon.

```
   1                   M  N  T  A  F  A  G  K  M  V  S  V  T  K  Y  D
   1 ctgatggcgatgaATGAACACTGCGTTTGCTGGGAAGATGGTGTCGGTCACCAAATATGA
  17 L  T  G  C  S  A  F  C  R  S  C  Q  R  A  T  M  T  S  Q  P
  61 CCTTACTGGCTGCTCTGCCTTCTGCAGGTCCTGCCAGAGAGCCACCATGACCTCTCAGCC
  37 L  R  L  A  E  E  Y  G  P  S  P  G  E  S  E  L  A  V  N  P
 121 TCTCAGGCTAGCAGAAGAGTATGGCCCAAGTCCTGGGGAGTCTGAACTGGCTGTGAACCC
  57 F  D  G  L  P  F  S  S  R  Y  Y  E  L  L  K  Q  R  Q  A  L
 181 CTTTGATGGGCTTCCCTTCTCTTCCCGCTACTATGAGCTGCTGAAGCAGCGCCAAGCCTT
  77 P  I  W  A  A  R  F  T  F  L  E  Q  L  E  S  N  P  T  G  V
 241 GCCCATCTGGGCTGCTCGCTTTACCTTCTTGGAGCAGTTGGAGAGTAACCCCACTGGAGT
  97 V  L  V  S  G  E  P  G  S  G  K  S  T  Q  I  P  Q  W  C  A
 301 GGTGCTGGTGTCTGGGGAGCCTGGTTCTGGCAAGAGCACCCAGATCCCTCAGTGGTGTGC
 117 E  F  A  L  A  R  G  F  Q  K  G  Q  V  T  V  T  Q  P  Y  P
 361 AGAGTTTGCGCTGGCCAGAGGGTTCCAGAAAGGACAGGTTACTGTTACTCAGCCCTACCC
 137 L  A  A  R  S  L  A  L  R  V  A  D  E  M  D  L  T  L  G  H
 421 TCTTGCAGCCCGGAGCCTGGCTCTGCGGGTTGCTGATGAGATGGACCTGACCCTGGGTCA
 157 E  V  G  Y  S  I  P  Q  E  D  C  T  G  P  N  T  L  L  R  F
 481 TGAGGTTGGATACAGCATCCCCCAGGAGGACTGCACGGGGCCCAACACCCTGCTCAGGTT
 177 C  W  D  R  L  L  L  Q  E  V  G  T  S  T  R  G  T  G  A  W  G
 541 CTGCTGGGACAGGCTGCTTCTGCAGGAGGTGGCCTCGACCCGAGGCACTGGAGCGCTGGGG
 197 V  L  V  L  D  E  A  Q  E  R  S  V  A  S  D  S  L  Q  G  L
 601 CGTGCTGGTACTAGATGAGGCTCAGGAGCGGTCGGTGGCATCAGATTCACTCCAGGGGCT
 217 L  Q  D  A  R  L  E  K  L  P  G  D  L  R  V  V  V  V  T  D
 661 ACTGCAAGATGCCAGGCTGGAAAAACTTCCGGGGGACCTCAGAGTGGTTGTGGTTACTGA
 237 P  A  L  E  P  K  L  R  A  F  W  G  N  P  P  I  V  H  I  P
 721 CCCAGCCCTTGAACCTAAGCTCCGAGCTTTCTGGGGCAATCCTCCTATTGTGCATATACC
 257 R  E  P  G  E  R  P  S  P  I  Y  W  D  T  I  P  P  D  R  V
 781 CAGAGAGCCTGGTGAGAGACCTTCCCCCATCTACTGGGACACCATCCCACCTGATCGGGT
 277 E  A  A  C  Q  A  V  L  E  L  C  R  K  E  L  P  G  D  V  L
 841 GGAAGCTGCCTGCCAAGCAGTGCTTGAATTGTGTCGGAAGGAGCTTCCAGGAGATGTGCT
 297 V  F  L  P  S  E  E  E  I  S  L  C  C  E  S  L  S  R  E  V
 901 AGTGTTCCTGCCCAGTGAGGAGGAAATTTCCCTGTGTGTGAATCCTTGTCCAGGGAGGT
 317 E  S  L  L  L  Q  G  L  P  P  R  V  L  P  L  H  P  D  C  G
 961 AGAGTCCTTGCTTCTCCAAGGGCTTCCACCACGAGTACTGCCCCTTCACCCAGACTGTGG
 337 R  A  V  Q  A  V  Y  E  D  M  D  A  R  K  V  V  V  T  H  W
1021 ACGAGCCGTTCAGGCTGTGTATGAGGACATGGATGCCCGAAAGGTTGTGGTCACTCACTG
 357 L  A  D  F  S  F  S  L  P  S  I  Q  H  V  I  D  S  G  L  E
1081 GCTGGCTGACTTCTCCTTCTCCCTCCCTTCCATCCAACATGTCATCGACTCAGGACTGGA
```

Figure 2M (continued)

```
     377  L  R  S  V  Y  N  P  R  I  R  A  E  F  Q  V  L  R  P  I  S
    1141 GCTCCGAAGTGTTTACAATCCTAGGATCCGAGCAGAATTCCAAGTGTTGAGGCCAATCAG
     397  K  C  Q  A  E  A  R  R  L  R  A  R  G  F  P  P  G  S  C  L
    1201 CAAGTGTCAGGCAGAGGCAAGACGATTGCGAGCAAGAGGGTTCCCACCAGGATCCTGCCT
     417  C  L  Y  P  K  S  F  L  E  L  E  A  P  P  L  P  Q  P  R  V
    1261 CTGCCTGTATCCTAAGTCCTTCTTAGAACTAGAAGCTCCACCATTGCCACAACCCAGGGT
     437  C  E  E  N  L  S  S  L  V  L  L  L  K  R  R  Q  I  A  E  P
    1321 GTGTGAGGAGAATCTGAGCTCCCTGGTGTTACTACTAAAAAGGAGACAGATTGCAGAGCC
     457  G  E  C  H  F  L  D  Q  P  A  P  E  A  L  M  Q  A  L  E  D
    1381 AGGGGAGTGTCACTTCCTGGACCAGCCTGCTCCAGAAGCACTGATGCAAGCCCTGGAAGA
     477  L  D  Y  L  A  A  L  D  D  D  G  D  L  S  D  L  G  V  I  L
    1441 TTTAGACTATCTGGCAGCCCTGGATGATGATGGGGACCTGTCAGATCTGGGTGTCATACT
     497  S  E  F  P  L  A  P  E  L  A  K  A  L  A  S  C  E  F  D
    1501 ATCAGAATTCCCTCTGGCCCCTGAGCTGGCCAAAGCCCTGCTGGCCTCATGCGAGTTTGA
     517  C  V  D  E  M  L  T  L  A  A  M  L  T  A  A  P  G  F  T  R
    1561 CTGTGTGGACGAGATGCTCACCCTGGCTGCCATGCTCACAGCTGCCCCTGGGTTTACCCG
     537  P  P  L  S  A  E  E  A  A  L  R  R  A  L  E  H  T  D  G  D
    1621 TCCTCCACTCAGTGCAGAAGAAGCTGCCCTGCGTCGGGCCCTGGAACACACGGATGGTGA
     557  H  S  S  L  I  Q  V  Y  E  A  F  I  Q  S  G  A  D  E  A  W
    1681 CCACAGTTCTCTGATCCAGGTGTATGAAGCCTTTATACAAAGTGGAGCAGATGAGGCTTG
     577  C  Q  A  R  G  L  N  W  A  A  L  C  Q  A  H  K  L  R  G  E
    1741 GTGCCAGGCTCGAGGTCTGAATTGGGCAGCATTGTGCCAAGCCCATAAACTTCGGGGAGA
     597  L  L  E  L  M  Q  R  I  E  L  P  L  S  L  P  A  F  G  S  E
    1801 ACTCCTAGAACTCATGCAACGAATTGAACTTCCCTTGTCCCTACCAGCCTTTGGCTCTGA
     617  Q  N  R  R  D  L  Q  K  A  L  V  S  G  Y  F  L  K  V  A  R
    1861 GCAGAATCGCAGAGACCTTCAGAAAGCACTGGTGTCAGGATACTTTCTCAAGGTGGCCAG
     637  D  T  D  G  T  G  N  Y  L  L  L  T  H  K  H  V  A  Q  L  S
    1921 AGACACAGACGGGACTGGAAATTACCTTCTCCTAACCCATAAGCATGTGGCCCAGCTCTC
     657  S  Y  C  C  Y  R  S  R  R  A  P  A  R  P  P  P  W  V  L  Y
    1981 CTCATACTGCTGCTACCGAAGCCGCAGAGCTCCTGCCAGACCCCCACCATGGGTGCTCTA
     677  H  N  F  T  I  S  K  D  N  C  L  S  I  V  S  E  I  Q  P  Q
    2041 CCACAATTTCACCATATCCAAAGACAACTGCCTTTCCATTGTTTCTGAGATTCAACCACA
     697  M  L  V  E  L  A  P  P  Y  F  L  S  N  L  P  P  S  E  S  R
    2101 GATGCTGGTGGAATTGGCCCCTCCATACTTCCTGAGTAACTTGCCTCCCAGTGAGAGCAG
     717  D  L  L  N  Q  L  R  E  G  M  A  D  S  T  A  G  S  K  S  S
    2161 AGACCTTCTGAACCAGCTAAGGGAAGGAATGGCAGATTCTACAGCAGGGAGCAAATCATC
     737  S  A  Q  E  F  R  D  P  C  V  L  Q  *
    2221 CTCAGCCCAGGAGTTCAGAGATCCCTGTGTCCTGCAGTGAcctgcctgcctatggaatgg
    2281 agctgggttcatctcatcacattagattatccctcagggtgacaccaaagcacccagaca
    2341 gatttagaagcccaaagtttagggtcaaatgtaaaccctggaacctgagtcccaagaaat
    2401 ggtagactgggaatggaaagaatgggtaaaccacagtctacatagggaaggactctttc
    2461 cttagccttctcttattgattggagagggactgacatgctcctcattctcttaactttgc
    2521 caaacccattcttgtactcccttgtgatctataaaagatttttctatgatgccaa
```

Figure 2N.1 The cDNA (SEQ ID NO:47) and amino acid sequence (SEQ ID NO:48) of 185P2C9 v.1. The start methionine is underlined. The open reading frame extends from nucleic acid 140-4063 including the stop codon.

```
       1 cacggggaagcaggcgggccccccagcacccgggaggccgagctgaagctgcggctaaa
      61 gctggtggaggaggaagccaacatcttgggccggaagatcgtggagctggaggtggagaa
       1                                        M  E  D  M  R  G  Q  Q  E  R  E  G  P  G
     121 ccgtggcctcaaggcagagATGGAGGACATGCGGGGCCAGCAGGAGCGGGAGGGCCCGGG
      15  R  D  H  A  P  S  I  P  T  S  P  F  G  D  S  L  E  S  S  T
     181 TCGGGACCACGCACCCAGCATTCCTACCTCACCCTTCGGTGACTCCCTGGAGTCCTCCAC
      35  E  L  R  R  H  L  Q  F  V  E  E  E  A  E  L  L  R  R  S  I
     241 TGAGCTCCGCCGCCACCTGCAGTTTGTAGAAGAGGAAGCGGAGTTGCTCCGGAGGTCCAT
      55  S  E  I  E  D  H  N  R  Q  L  T  L  S  K  F  K  F  E
     301 CTCCGAGATCGAAGACCACAACCGGCAACTGACCCACGAGCTCAGCAAGTTTAAGTTTGA
      75  P  P  R  E  P  G  W  L  G  E  G  A  S  P  G  A  G  G  G  A
     361 GCCTCCCCGGGAGCCGGGCTGGCTAGGAGAGGGTGCAAGTCCTGGTGCCGGGGGTGGGGC
      95  P  L  Q  E  E  L  K  S  A  R  L  Q  I  S  E  L  S  G  K  V
     421 CCCCCTGCAGGAGGAGCTGAAGTCAGCCAGGCTGCAGATCAGCGAGCTCAGCGGCAAGGT
     115  L  K  L  Q  H  E  N  H  A  L  L  S  N  I  Q  R  C  D  L  A
     481 GCTCAAACTGCAGCACGAGAACCACGCGCTGCTTCCAACATCCAGCGCTGCGACCTGGC
     135  A  H  L  G  L  R  A  P  S  P  R  D  S  D  A  E  S  D  A  G
     541 AGCCCACCTGGGGCTGCGTGCCCCCAGTCCCCGGGACAGCGATGCCGAGAGTGATGCGGG
     155  K  K  E  S  D  G  E  E  S  R  L  P  Q  P  K  R  E  G  P  V
     601 CAAGAAGGAGAGTGATGGGGAGGAGAGCCGCCTGCCCCAGCCCAAGCGGGAAGGGCCTGT
     175  G  G  E  S  D  S  E  E  M  F  E  K  T  S  G  F  G  S  G  K
     661 TGGCGGGGAGAGTGACTCGGAGGAAATGTTTGAGAAGACGTCGGGCTTCGGGAGCGGGAA
```

Figure 2N.1 (continued)

```
 195  P  S  E  A  S  E  P  C  P  T  E  L  L  K  A  R  E  D  S  E
 721 GCCATCGGAGGCCAGCGAGCCATGCCCCACGGAGCTCCTGAAGGCCCGGGAGGACTCTGA
 215  Y  L  V  T  L  K  H  E  A  Q  R  L  E  R  T  V  E  R  L  I
 781 GTACCTAGTGACCCTAAAACACGAGGCCCAGCGGCTAGAGCGGACGGTGGAGCGCCTCAT
 235  T  D  T  D  S  F  L  H  D  A  G  L  R  G  G  A  P  L  P  G
 841 CACGGACACCGACAGCTTCCTCCATGATGCGGGGCTGCGGGGTGGTGCGCCCTTACCGGG
 255  P  G  L  Q  G  E  E  E  Q  G  E  G  D  Q  Q  E  P  Q  L  L
 901 GCCTGGCCTCCAGGGCGAAGAGGAGCAGGGTGAGGGGGACCAGCAGGAGCCCCAGCTGCT
 275  G  T  I  N  A  K  M  K  A  F  K  K  E  L  Q  A  F  L  E  Q
 961 GGGGACCATCAACGCCAAGATGAAGGCTTTCAAGAAAGAGCTGCAGGCCTTCCTGGAGCA
 295  V  N  R  I  G  D  G  L  S  P  L  P  H  L  T  E  S  S  S  F
1021 GGTGAACCGCATTGGGGATGGCCTATCCCCCTTGCCCCACCTCACAGAGTCCTCTAGCTT
 315  L  S  T  V  T  S  V  S  R  D  S  P  I  G  N  L  G  K  E  L
1081 CCTCTCCACTGTGACTTCCGTGTCCCGGGACTCCCCCATCGGGAACCTGGGGAAGGAGCT
 335  G  P  D  L  Q  S  R  L  K  E  Q  L  E  W  Q  L  G  P  A  R
1141 GGGCCCAGACTTGCAGTCCAGACTGAAAGAGCAGCTGGAGTGGCAGCTCGGGCCGGCCCG
 355  G  D  E  R  E  S  L  R  L  R  A  A  R  E  L  H  R  R  A  D
1201 AGGGGACGAGCGGGAGAGCCTGCGCCTCCGAGCCGCGCGGGAGCTGCACCGCCGCGCAGA
 375  G  D  T  G  S  H  G  L  G  G  Q  T  C  F  S  L  E  M  E  E
1261 CGGGGACACCGGGAGCCACGGGCTGGGAGGCCAGACCTGCTTCAGCCTGGAGATGGAGGA
 395  E  H  L  Y  A  L  R  W  K  E  L  E  M  H  S  L  A  L  Q  N
1321 GGAGCACCTCTATGCCTTGAGGTGGAAAGAACTGGAAATGCACAGCCTGGCTTTGCAAAA
 415  T  L  H  E  R  T  W  S  D  E  K  N  L  M  Q  Q  E  L  R  S
1381 CACCCTCCATGAGCGAACCTGGAGTGATGAGAAGAATCTGATGCAGCAGGAGCTCCGGTC
 435  L  K  Q  N  I  F  L  F  Y  V  K  L  R  W  L  L  K  H  W  R
1441 CTTGAAGCAGAACATTTTCCTCTTCTACGTCAAACTCAGGTGGCTGCTGAAACACTGGCG
 455  Q  G  K  Q  M  E  E  E  G  E  E  F  T  E  G  E  H  P  E  T
1501 GCAAGGGAAGCAGATGGAGGAGGAAGGAGAGGAGTTCACTGAGGGTGAACATCCAGAGAC
 475  L  S  R  L  G  E  L  G  V  Q  G  G  H  Q  A  D  G  P  D  H
1561 CCTCTCCAGGCTCGGGGAGCTTGGAGTCCAGGGGGTCACCAGGCGGATGGCCCAGACCA
 495  D  S  D  R  G  C  G  F  P  V  G  E  H  S  P  H  S  R  V  Q
1621 CGACAGTGACCGAGGCTGTGGCTTTCCAGTGGGGGAGCACTCCCCACACTCCCGGGTGCA
 515  I  G  D  H  S  L  R  L  Q  T  A  D  R  G  Q  P  H  K  Q  V
1681 GATTGGAGATCACAGCTTGCGGCTGCAGACCGCGGACAGGGGACAGCCCCACAAACAGGT
 535  V  E  N  Q  Q  L  F  S  A  F  K  A  L  L  E  D  F  R  A  E
1741 GGTGGAAAACCAGCAGCTGTTCAGCGCCTTCAAGGCCTTGCTGGAGGACTTCCGTGCGGA
 555  L  R  E  D  E  R  A  R  L  R  L  Q  Q  Q  Y  A  S  D  K  A
1801 GCTGCGGGAGGATGAGCGTGCCCGACTACGGCTGCAGCAGCAATATGCCAGCGACAAGGC
 575  A  W  D  V  E  W  A  V  L  K  C  R  L  E  Q  L  E  E  K  T
1861 GGCCTGGGACGTGGAGTGGGCCGTGCTCAAGTGCCGTCTGGAACAGCTGGAAGAGAAGAC
 595  E  N  K  L  G  E  L  G  S  S  A  E  S  K  G  A  L  K  K  E
1921 TGAGAACAAGTTGGGAGAACTAGGCTCCTCCGCTGAGAGCAAGGGGGCCTTGAAGAAGGA
 615  R  E  V  H  Q  K  L  L  A  D  S  H  S  L  V  M  D  L  R  W
1981 GAGAGAGGTGCACCAGAAGCTCCTGGCAGACAGTCACAGCCTGGTCATGGACCTGCGCTG
 635  Q  I  H  H  S  E  K  N  W  N  R  E  K  V  E  L  L  D  R  L
2041 GCAGATCCATCACAGCGAGAAGAACTGGAACCGGGAGAAGGTGGAACTTCTCGACCGCCT
 655  D  R  D  R  Q  E  W  E  R  Q  K  K  E  F  L  W  R  I  E  Q
2101 GGACAGAGATCGGCAGGAGTGGGAGCGGCAGAAGGAATTCTTGTGGAGGATAGAGCA
 675  L  Q  K  E  N  S  P  R  R  G  G  S  F  L  C  D  Q  K  D  G
2161 GTTGCAGAAAGAGAACAGTCCCCGGAGAGGTGGCAGTTTCCTCTGTGATCAAAAAGACGG
 695  N  V  R  P  F  P  H  Q  G  S  L  R  M  P  R  P  V  A  M  W
2221 CAACGTTCGCCCCTTTCCCCACCAGGGAAGCCTCCGCATGCCCCGTCCAGTGGCCATGTG
 715  P  C  A  D  A  D  S  I  P  F  E  D  R  P  L  S  K  L  K  E
2281 GCCTTGTGCAGATGCTGACTCCATCCCGTTTGAAGACCGGCCGCTGTCCAAGCTGAAGGA
 735  S  D  R  C  S  A  S  E  N  L  Y  L  D  A  L  S  L  D  D  E
2341 GTCGGACAGGTGCTCGGCCAGTGAGAATCTCTACCTGGATGCCTTGTCCCTGGATGACGA
 755  P  E  E  P  P  A  H  R  P  E  R  E  F  R  N  R  L  P  E  E
2401 GCCAGAAGAGCCACCAGCCCACAGGCCCGAGAGGGAGTTCAGGAACCGCCTCCCTGAGGA
 775  E  E  N  H  K  G  N  L  Q  R  A  V  S  V  S  S  M  S  E  F
2461 AGAAGAAAATCACAAAGGAAATCTTCAAAGGGCGGTGTCCGTGTCCTCCATGTCAGAGTT
 795  Q  R  L  M  D  I  S  P  F  L  P  E  K  G  L  P  S  T  S  S
2521 CCAGCGTCTAATGGACATCTCCCCCTTCCTGCCTGAGAAGGGCCTGCCGTCCACCAGCAG
 815  K  E  D  V  T  P  P  L  S  P  D  D  L  K  Y  I  E  E  F  N
2581 CAAGGAGGATGTCACCCCACCCCTGTCTCCAGACGACCTCAAGTACATCGAGGAGTTCAA
 835  K  S  W  D  Y  T  P  N  R  G  H  N  G  G  G  P  D  L  W  A
2641 CAAGAGCTGGGACTACACACCCAACAGGGGCCACAATGGTGGGGGCCGGACCTTTGGGC
 855  D  R  T  E  V  G  R  A  G  H  E  D  S  T  E  P  F  P  D  S
2701 CGACAGGACCGAGGTGGGCGGGCAGGGCACGAGGACAGCACAGAGCCTTTCCCCGACTC
 875  S  W  Y  L  T  T  S  V  T  M  T  T  D  T  M  T  S  P  E  H
2761 CTCCTGGTACCTAACCACAAGTGTCACCATGACCACGGACACCATGACCAGCCCAGAGCA
 895  C  Q  K  Q  P  L  R  S  H  V  L  T  E  Q  S  G  L  R  V  L
```

Figure 2N.1 (continued)

```
2821 CTGCCAGAAGCAGCCACTGCGGAGCCACGTCCTCACCGAGCAGTCGGGGTTGCGCGTGTT
 915  H  S  P  P  A  V  R  R  V  D  S  I  T  A  A  G  G  E  G  P
2881 ACACAGCCCGCCTGCCGTGCGCAGGGTCGACAGCATCACGGCGGCAGGTGGTGAGGGTCC
 935  F  P  T  S  R  A  R  G  S  P  G  D  T  K  G  G  P  P  E  P
2941 CTTTCCCACAAGCAGAGCCAGAGGGAGCCCGGGAGACACCAAGGGGGGCCCTCCAGAACC
 955  M  L  S  R  W  P  C  T  S  P  R  H  S  R  D  Y  V  E  G  A
3001 CATGCTCAGCAGGTGGCCTTGCACCTCCCCCAGGCACTCCCGGGACTATGTGGAGGGGGC
 975  R  R  P  L  D  S  P  L  C  T  S  L  G  F  A  S  P  L  H  S
3061 ACGGCGCCCCCTTGATAGTCCCCTCTGTACCTCCCTGGGGTTTGCCTCCCCACTGCACAG
 995  L  E  M  S  K  N  L  S  D  D  M  K  E  V  A  P  S  V  R  N
3121 CCTGGAGATGTCCAAGAACTTGAGTGATGACATGAAGGAGGTGGCCTTCTCTGTCAGGAA
1015  A  I  C  S  G  P  G  E  L  Q  V  K  D  M  A  C  Q  T  N  G
3181 TGCCATCTGCTCCGGCCCTGGCGAGCTGCAAGTCAAGGACATGGCCTGCCAGACCAATGG
1035  S  R  T  M  G  T  Q  T  V  Q  T  I  S  V  G  L  Q  T  E  A
3241 GTCCCGGACGATGGGGACCCAGACTGTTCAGACCATCAGTGTGGGCTTGCAGACTGAAGC
1055  L  R  G  S  G  V  T  S  S  P  H  K  C  L  T  P  K  A  G  G
3301 CCTGCGTGGCAGCGGTGTCACCAGCAGCCCCCACAAGTGTCTCACTCCAAAGGCTGGGGG
1075  G  A  T  P  V  S  S  P  S  R  L  R  S  R  Q  V  A  P  A
3361 CGGTGCTACACCCGTGTCGTCTCCTTCCCGGAGCCTTAGGAGCAGACAGGTGGCCCCTGC
1095  I  E  K  V  Q  A  K  F  E  R  T  C  C  S  P  K  Y  G  S  P
3421 CATCGAGAAGGTGCAGGCCAAGTTTGAACGCACATGCTGCTCCCCCAAGTATGGTTCTCC
1115  K  L  Q  R  K  P  L  P  K  A  D  Q  P  N  N  R  T  S  P  G
3481 CAAGCTGCAGAGGAAGCCCCTCCCCAAAGCCGACCAGCCAAATAACAGGACGTCACCAGG
1135  M  A  Q  K  G  Y  S  E  S  A  W  A  R  S  T  T  T  R  E  S
3541 GATGGCCCAGAAAGGGTACAGTGAGTCAGCCTGGGCCCGCTCCACCACCACAAGGGAGAG
1155  P  V  H  T  T  I  N  D  G  L  S  S  L  F  N  I  I  D  H  S
3601 CCCCGTGCACACCACCATTAATGATGGCCTCTCCAGCCTCTTCAACATCATTGACCACAG
1175  P  V  V  Q  D  P  F  Q  K  G  L  R  A  G  S  R  S  R  S  A
3661 CCCCGTGGTGCAGGACCCCTTCCAGAAGGGGCTGCGGGCCGGCAGTCGGTCTCGCTCAGC
1195  E  P  R  P  E  L  G  P  G  Q  E  T  G  T  N  S  R  G  R  S
3721 AGAGCCCCGACCAGAGCTGGGCCCAGGCCAGGAAACAGGCACCAATTCCCGAGGAAGGTC
1215  P  S  P  I  G  V  G  S  E  M  C  R  E  E  G  G  E  G  T  P
3781 GCCTAGCCCCATTGGGGTGGGGTCAGAGATGTGCAGGGAGGAAGGGGGAGAGGGCACGCC
1235  V  K  Q  D  L  S  A  P  P  G  Y  T  L  T  E  N  V  A  R  I
3841 AGTGAAGCAGGACTTATCTGCTCCCCCTGGCTACACCCTCACTGAGAACGTGGCCCGGAT
1255  L  N  K  K  L  L  E  H  A  L  K  E  E  R  R  Q  A  A  H  G
3901 CCTCAACAAGAAGCTGCTGGAACATGCCTTAAAGGAGGAGGAGGAGGCAGGCTGCCCACGG
1275  P  P  G  L  H  S  D  S  H  S  L  G  D  T  A  E  P  G  P  M
3961 GCCCCCGGGTCTCCACAGTGACAGCCACTCGCTGGGGGACACAGCCGAGCCAGGGCCCAT
1295  E  N  Q  T  V  L  L  T  A  P  W  G  L  *
4021 GGAGAACCAAACTGTCTTGCTAACTGCCCCCTGGGGACTCTAGccctgcccgcctcacgc
4081 tgaactaccttgttctgcactagctccatccctagagccctgcttctccaggcccgagag
4141 accagcaaaccgtcgccctccgtccccgttgggccccacattcccccactgcctcacagcc
4201 tcagtcaccggagacccgacgtccttggaggagcatggtggcgaggagccgcccgagga
4261 gcagccacaccgagatgcaagcttgcatggattatcacagtataattcactgtaatttgc
4321 ataaccacaccatcaccatgaacaaaactctgcccaacaggagagatctagttttctcaa
4381 ggtcaaagaatgttttttaaaaacacaaagctgctgaatgttcaacctgtgaaactgaga
4441 tgtttctagaatgaaacagtaaatgtgcctgtaataacttaattttttttcatagctcaga
4501 aaactattttttgtctccatcttttttacacacagtatattaaacgaaaaggtaaataagg
4561 tataaatagatttaaaaaataaaagtttttaaaaaatgtacattttaagagattctgaaca
4621 ccctcgctgtcaataccctgactgcctctgttaaatttgcactgttacattttggttcagt
4681 ttatttccatgttgaattagagtggattaagttaattttattttgtcagtgttactgttt
4741 tttacgaatttttttaatgcttcagactgtctgattcagtgaacttttttgtagtgaaaaag
4801 ccatgaagccagtagacaagacagatattctgtatgctggaggggatacaggatgatttt
4861 gaaaaggtacaaagtcctcagtgggcttagaaaattcactgtatgatccttatattatcc
4921 tacttggcttgcacgtcttcgggtgcatgtatataccgctactgtgtcctcgccatcacc
4981 taaatgtgactcagtctgttccactgtaatatgttgtgaattccttgtactgtactttt
5041 attgttggtcttcttgcatcgatgatccaacagcaacaccattttttaaattattgtgaaa
5101 agattaactggcaatgtacagagtttactcaaagttttcttaagggaaaacactacaaaa
5161 agtcacaaggataccaaatggaaacacatgatgatgcctctgggtctgtatgagaccgtg
5221 atgaagtagaaataaagcccttctgagatggc
```

Figure 2N.2 The cDNA (SEQ ID NO:49) and amino acid sequence (SEQ ID NO:50) of 185P2C9 v.2 clone 1. The start methionine is underlined. The open reading frame extends from nucleic acid 140-3568 including the stop codon.

```
  1 cacgggggaagcaggcgggcccccagcacccgggaggccgagctgaagctgcggctaaa
 61 gctggtggaggaggaagccaacatcttgggccggaagatcgtggagctggaggtggagaa
  1                                 M  E  D  T  R  G  Q  Q  E  R  E  G  P  G
121 ccgtggcctcaaggcagagATGGAGGACACGCGGGGCCAGCAGGAGCGGGAGGGCCCGGG
```

Figure 2N.2 (continued)

```
 15         R  D  H  A  P  S  I  P  T  S  P  F  G  D  S  L  E  S  S  T
181 TCGGGACCACGCACCCAGCATTCCTACCTCACCCTTCGGTGACTCCCTGGAGTCCTCCAC
 35         E  L  R  R  H  L  Q  F  V  E  E  E  A  E  L  L  R  R  S  I
241 TGAGCTCCGCCGCCACCTGCAGTTTGTAGAAGAGGAAGCGGAGTTGCTCCGGAGGTCCAT
 55         S  E  I  E  D  H  N  R  Q  L  T  H  E  L  S  K  F  K  F  E
301 CTCCGAGATCGAAGACCACAACCGGCAACTGACCCACGAGCTCAGCAAGTTTAAGTTTGA
 75         P  P  R  E  P  G  W  L  G  E  G  A  S  P  G  A  G  G  G  A
361 GCCTCCCCGGGAGCCGGGCTGGCTAGGAGAGGGTGCAAGTCCTGGTGCCGGGGGTGGGGC
 95         P  L  Q  E  E  L  K  S  A  R  L  Q  I  S  E  L  S  G  K  V
421 CCCCCTGCAGGAGGAGCTGAAGTCAGCCAGGCTGCAGATCAGCGAGCTCAGCGGCAAGGT
115         L  K  L  Q  H  E  N  H  A  L  L  S  N  I  Q  R  C  D  L  A
481 GCTCAAACTGCAGCACGAGAACCACGCGCTGCTGTCCAACATCCAGCGCTGCGACCTGGC
135         A  H  L  G  L  R  A  P  S  P  R  D  S  D  A  E  S  D  A  G
541 AGCCCACCTGGGGCTGCGTGCCCCAGTCCCCGGGACAGCGATGCCGAGAGTGATGCGGG
155         K  K  E  S  D  G  E  E  S  R  L  P  Q  P  K  R  E  G  P  V
601 CAAGAAGGAGAGTGATGGGGAGGAGAGCCGCCTGCCCCAGCCCAAGCGGGAAGGGCCTGT
175         G  G  E  S  D  S  E  E  M  F  E  K  T  S  G  F  G  S  G  K
661 TGGCGGGGAGAGTGACTCGGAGGAGATGTTTGAGAAGACGTCGGGCTTCGGGAGCGGGAA
195         P  S  E  A  S  E  P  C  P  T  E  L  L  K  A  R  E  D  S  E
721 GCCATCGGAGGCCAGCGAGCCATGCCCCACGGAGCTCCTGAAGGCCCGGGAGGACTCTGA
215         Y  L  V  T  L  K  H  E  A  Q  R  L  E  R  T  V  E  R  L  I
781 GTACCTAGTGACCCTAAAACACGAGGCCCAGCGGCTAGAGCGGACGGTGGAGCGCCTCAT
235         T  D  T  D  S  F  L  H  D  G  A  P  L  P  G
841 CACGGACACCGACAGCTTCCTCCATGATGCGGGGCTGCGGGGTGGTGCGCCCTTACCGGG
255         P  G  L  Q  G  E  E  E  Q  G  E  G  D  Q  Q  E  P  Q  L  L
901 GCCTGGCCTCCAGGGCGAAGAGGAGCAGGGTGAGGGGGACCAGCAGGAGCCCCAGCTGCT
275         G  T  I  N  A  K  M  K  A  F  K  K  E  L  Q  A  F  L  Q  Q
961 GGGGACCATCAACGCCAAGATGAAGGCTTTCAAGAAAGAGCTGCAGGCCTTCCTGCAGCA
295         V  N  R  I  G  D  G  L  S  P  L  P  H  L  T  E  S  S  F
1021 GGTGAACCGCATTGGGGATGGCCTATCCCCCTTGCCCCACCTCACAGAGTCCTCTAGCTT
315         L  S  T  V  T  S  V  S  R  D  S  P  I  G  N  L  G  K  E  L
1081 CCTCTCCACTGTGACTTCCGTGTCCCGGGACTCCCCCATCGGGAACCTGGGGAAGGAGCT
335         G  P  D  L  Q  S  R  L  K  E  Q  L  E  W  Q  L  G  P  A  Q
1141 GGGCCCAGACTTGCAGTCCAGACTGAAAGAGCAGCTGGAGTGGCAGCTCGGGCCGGCCCA
355         G  D  E  R  E  S  L  R  L  R  A  A  R  E  L  H  R  R  A  D
1201 AGGGGACGAGCGGGAGAGCCTGCGCCTCCGAGCCGCGCGGGAGCTGCACCGCCGCGCAGA
375         G  D  T  G  S  H  G  L  G  G  Q  T  C  F  S  L  E  M  E  E
1261 CGGGGACACCGGGAGCCACGGGCTGGAGGCCAGACCTGCTTCAGCCTGGAGATGGAGGA
395         E  H  L  Y  A  L  R  W  K  E  L  E  M  H  S  L  A  L  Q  N
1321 GGAGCACCTCTATGCCTTGAGGTGGAAAGAACTGGAAATGCACAGCCTGGCTTTGCAAAA
415         T  L  H  E  R  T  W  S  D  E  K  N  L  M  Q  Q  E  L  R  S
1381 CACCCTCCATGAGCGAACCTGGAGTGATGAGAAGAATCTGATGCAGCAGGAGCTCCGGTC
435         L  K  Q  N  I  F  L  F  Y  V  K  L  R  W  L  L  K  H  W  R
1441 CTTGAAGCAGAACATTTTCCTCTTCTACGTCAAACTCAGGTGGCTGCTGAAACACTGGCG
455         Q  G  K  Q  M  E  E  G  E  E  F  T  E  G  E  H  P  E  T
1501 GCAAGGGAAGCAGATGGAGGAGGAAGGAGAGGAGTTCACTGAGGGTGAACATCCAGAGAC
475         L  S  R  L  G  E  L  G  V  Q  G  G  H  Q  A  D  G  P  D  H
1561 CCTCTCCAGGCTCGGGGAGCTTGGAGTCCAGGGGGGTCACCAGGCGGATGGCCCAGACCA
495         D  S  D  R  G  C  G  F  P  V  G  E  H  S  P  H  S  R  V  Q
1621 CGACAGTGACCGAGGCTGTGGCTTTCCAGTGGGGGAGCACTCCCCACACTCCCGGGTGCA
515         I  G  D  H  S  L  R  L  Q  T  A  D  R  G  Q  P  H  K  Q  V
1681 GATTGGAGATCACAGCTTGCGGCTGCAGACCGCGGACAGGGGACAGCCCCACAAACAGGT
535         V  E  N  Q  Q  L  F  S  A  F  K  A  L  L  E  D  F  R  A  E
1741 GGTGGAAAACCAGCAGCTGTTCAGCGCCTTCAAGGCCTTGCTGGAGGACTTCCGTGCGGA
555         L  R  E  D  E  R  A  R  L  R  L  Q  Q  Q  Y  A  S  D  K  A
1801 GCTGCGGGAGGATGAGCGTGCCCGACTACGGCTGCAGCAGCAATATGCCAGCGACAAGGC
575         A  W  D  V  E  W  A  V  L  K  C  R  L  E  Q  L  E  E  K  T
1861 GGCCTGGGACGTGGAGTGGGCCGTGCTCAAGTGCCGTCTGGAACAGCTGGAAGAGAAGAC
595         E  N  K  L  G  E  L  G  S  S  A  E  S  K  G  A  L  K  K  E
1921 TGAGAACAAGTTGGGAGAACTAGGCTCCTCCGCTGAGAGCAAGGGGCCTTGAAGAAGGA
615         R  E  V  H  Q  K  L  L  A  D  S  H  S  L  V  M  D  L  R  W
1981 GAGAGAGGTGCACCAGAAGCTCCTGGCAGACAGTCACAGCCTGGTCATGGACCTGCGCTG
635         Q  I  H  H  S  E  K  N  W  N  R  E  K  V  E  L  L  D  R  L
2041 GCAGATCCATCACAGCGAGAAGAACTGGAACCGGGAGAAGGTGGAACTTCTCGACCGCCT
655         D  R  D  R  Q  E  W  E  R  Q  K  K  E  F  L  W  R  I  E  Q
2101 GGACAGAGATCGCCAGGAGTGGGAGCGGCAGAAGAAGGAATTCTTGTGGAGGATAGAGCA
675         L  Q  K  E  N  S  P  R  R  G  G  S  F  L  C  D  Q  K  D  G
2161 GTTGCAGAAAGAGAACAGTCCCCGGAGAGGTGGCAGTTTCCTCTGTGATCAAAAAGACGG
695         N  V  R  P  F  P  H  Q  G  S  L  R  M  R  P  P  V  A  M  W
2221 CAACGTTCGCCCCTTTCCCCACCAGGGAAGCCTCCGCATGCCCCGTCCAGTGGCCATGTG
715         P  C  A  D  A  D  S  I  P  F  E  D  R  P  L  S  K  L  K  E
```

Figure 2N.2 (continued)

```
2281 GCCTTGTGCAGATGCTGACTCCATCCCGTTTGAAGACCGGCCGCTGTCCAAGCTGAAGGA
 735  S  D  R  C  S  A  S  E  N  L  Y  L  D  A  L  S  L  D  D  E
2341 GTCGGACAGGTGCTCGGCCAGTGAGAATCTCTACCTGGATGCCTTGTCCCTGGATGACGA
 755  P  E  E  P  P  A  H  R  P  E  R  E  F  R  N  R  L  P  E  E
2401 GCCAGAAGAGCCACCAGCCCACAGGCCCGAGAGGGAGTTCAGGAACCGCCTCCCTGAGGA
 775  E  E  N  H  K  G  N  L  Q  R  A  V  S  V  S  S  M  S  E  F
2461 AGAAGAAAATCACAAAGGAAATCTTCAAAGGGCGGTGTCCGTGTCCTCCATGTCTGAGTT
 795  Q  R  L  M  D  I  S  P  F  L  P  E  K  G  L  P  S  T  S  S
2521 CCAGCGTCTAATGGACATCTCCCCCTTCCTGCCTGAGAAGGGCCTGCCGTCCACCAGCAG
 815  K  E  D  V  T  P  P  L  S  P  D  D  L  K  Y  I  E  E  F  N
2581 CAAGGAGGATGTCACCCCACCCCTGTCTCCAGACGACCTCAAGTACATCGAGGAGTTCAA
 835  K  S  W  D  Y  T  P  N  R  G  H  N  G  G  G  P  D  L  W  A
2641 CAAGAGCTGGGACTACACACCCAACAGGGGCCACAATGGTGGGGGCCGGACCTTTGGGC
 855  D  R  T  E  V  G  R  A  G  H  E  D  S  T  E  P  F  P  D  S
2701 CGACAGGACCGAGGTGGGGCGGGCAGGGCACGAGGACAGCACAGAGCCTTTCCCCGACTC
 875  S  W  Y  L  T  T  S  V  T  M  T  T  D  T  M  T  S  P  E  H
2761 CTCCTGGTACCTAACCACAAGTGTCACCATGACCACGGACACCATGACCAGCCCAGAGCA
 895  C  Q  K  Q  P  L  R  S  H  V  L  T  E  Q  S  G  L  R  V  L
2821 CTGCCAGAAGCAGCCACTGCGGAGCCACGTCCTCACCGAGCAGTCGGGGTTGCGCGTGTT
 915  H  S  P  P  A  V  R  R  V  D  S  I  T  A  A  G  G  E  G  P
2881 ACACAGCCCGCCTGCCGTGCGCAGGGTCGACAGCATCACGGCGGCAGGTGGTGAGGGTCC
 935  F  P  T  S  R  A  R  G  S  P  G  D  T  K  G  G  P  E  P
2941 CTTTCCCACAAGCAGAGCCAGAGGGAGCCCGGGAGACACCAAGGGGGCCCTCCAGAACC
 955  M  L  S  R  W  P  C  T  S  P  R  H  S  R  D  Y  V  E  G  A
3001 CATGCTCAGCAGGTGGCCTTGCACCTCCCCCAGGCACTCCCGGGACTATGTGGAGGGGGC
 975  R  R  P  L  D  S  P  L  C  T  S  L  G  F  A  S  P  L  H  S
3061 ACGGCGCCCCCTTGATAGTCCCCTCTGTACCTCCCTGGGGTTTGCCTCCCCACTGCACAG
 995  L  E  M  S  K  N  L  S  D  D  M  K  E  V  A  F  S  V  R  N
3121 CCTGGAGATGTCCAAGAACTTGAGTGATGACATGAAGGAGGTGGCCTTCTCTGTCAGGAA
1015  A  I  C  S  G  P  G  E  L  Q  V  K  D  M  A  C  Q  T  N  G
3181 TGCCATCTGCTCCGGCCCTGGCGAGCTGCAAGTCAAGGACATGGCCTGCCAGACCAATGG
1035  S  R  T  M  G  T  Q  T  V  Q  T  I  S  V  G  L  Q  T  E  A
3241 GTCCCGGACGATGGGGACCCAGACTGTTCAGACCATCAGTGTGGGCTTGCAGACTGAAGC
1055  L  R  G  S  G  V  T  S  S  P  H  K  C  L  T  P  K  A  G  G
3301 CCTGCGTGGCAGCGGTGTCACCAGCAGCCCCCACAAGTGTCTCACTCCAAAGGCTGGGGG
1075  G  A  T  P  V  S  S  P  S  R  S  L  R  S  R  Q  V  A  P  A
3361 CGGTGCTACACCCGTGTCGTCTCCTTCCCGGAGCCTTAGGAGCAGACAGGTGGCCCCTGC
1095  I  E  K  V  Q  A  K  F  E  R  T  C  C  S  P  K  Y  G  S  P
3421 CATCGAGAAGGTGCAGGCCAAGTTTGAACGCACATGCTGCTCCCCCAAGTATGGTTCTCC
1115  K  L  Q  R  K  P  L  P  K  A  D  Q  P  N  N  R  P  G  N  R
3481 CAAGCTGCAGAGGAAGCCCCTCCCCAAAGCCGACCAGCCAAATAACAGGCCAGGAAACAG
1135  H  Q  F  P  R  K  V  A  *
3541 GCACCAATTCCCGAGGAAGGTCGCCTAGcccattggggtgggtcagagatgtgcaggg
3601 aggaaggggagagggcacgccagtgaagcaggacttatctgctcccctggctacaccc
3661 tcactgagaacgtggcccggatcctcaacaagaagctgctggaacatgccttaaaggagg
3721 agaggaggcaggctgcccacgggcccccgggtctccacagtgacagccactcgctgggg
3781 acacagccgagccagggcccatggaggaactaccttgttctgcactagctcc
```

Figure 2N.3 The cDNA (SEQ ID NO:51) and amino acid sequence (SEQ ID NO:52) of 185P2C9 v.3 clone 2. The start methionine is underlined. The open reading frame extends from nucleic acid 140-4078 including the stop codon.

```
   1 cacggggaagcaggcgggccccccagcacccgggaggccgagctgaagctgcggctaaa
  61 gctggtggaggaggaagccaacatcttgggccggaagatcgtggagctggaggtggagaa
   1                    M  E  D  T  R  G  Q  Q  E  R  E  G  P  G
 121 ccgtggcctcaaggcagagATGGAGGACACGCGGGGCCAGCAGGAGCGGGAGGGCCCGGG
  15  R  D  H  A  P  S  I  P  T  S  P  F  G  D  S  L  E  S  S  T
 181 TCGGGACCACGCACCCAGCATTCCTACCTCACCCTTCGGTGACTCCCTGGAGTCCTCCAC
  35  E  L  R  R  H  L  Q  F  V  E  E  E  A  E  L  L  R  R  S  I
 241 TGAGCTCCGCCGCCACCTGCAGTTTGTAGAAGAGGAAGCGGAGTTGCTCCGGAGGTCCAT
  55  S  E  I  E  D  H  N  R  Q  L  T  H  E  L  S  K  F  K  F  E
 301 CTCCGAGATCGAAGACCACAACCGGCAACTGACCCACGAGCTCAGCAAGTTTAAGTTTGA
  75  P  P  R  E  P  G  W  L  G  E  G  A  S  P  G  A  G  G  G  A
 361 GCCTCCCCGGGAGCCGGGCTGGCTAGGAGAGGGTGCAAGTCCTGGTGCCGGGGGTGGGGC
  95  P  L  Q  E  E  L  K  S  A  R  L  Q  I  S  E  L  S  G  K  V
 421 CCCCCTGCAGGAGGAGCTGAAGTCAGCCAGGCTGCAGATCAGCGAGCTCAGCGGCAAGGT
 115  L  K  L  Q  H  E  N  H  A  L  L  S  N  I  Q  R  C  D  L  A
 481 GCTCAAACTGCAGCACGAGAACCACGCGCTGCTGTCCAACATCCAGCGCTGCGACCTGGC
 135  A  H  L  G  L  R  A  P  S  P  R  D  S  D  A  E  S  D  A  G
 541 AGCCCACCTGGGGCTGCGTGCCCCCAGTCCCCGGGACAGCGATGCCGAGAGTGATGCGGG
```

Figure 2N.3 (continued)

```
155  K  K  E  S  D  G  E  E  S  R  L  P  Q  P  K  W  E  G  P  V
601 CAAGAAGGAGAGTGATGGGGAGGAGAGCCGCCTGCCCCAGCCCAAGTGGGAAGGGCCTGT
175  G  G  E  S  D  S  E  E  M  F  E  K  T  S  G  F  G  S  G  K
661 TGGCGGGGAGAGTGACTCGGAGGAGATGTTTGAGAAGACGTCGGGCTTCGGGAGCGGGAA
195  P  S  E  A  S  E  P  C  P  T  E  L  L  K  A  R  E  D  S  E
721 GCCATCGGAGGCCAGCGAGCCATGCCCCACGGAGCTCCTGAAGGCCCGGGAGGACTCTGA
215  Y  L  V  T  L  K  H  E  A  Q  R  L  E  R  T  V  E  R  L  I
781 GTACCTAGTGACCCTAAAACACGAGGCCCAGCGGCTAGAGCGGACGGTGGAGCGCCTCAT
235  T  D  T  D  S  F  L  H  D  A  G  L  R  G  G  A  P  L  P  G
841 CACGGACACCGACAGCTTCCTCCATGATGCGGGGCTGCGGGGTGGTGCGCCCTTACCGGG
255  P  G  L  Q  G  E  E  E  Q  G  E  G  D  Q  Q  E  P  Q  L  L
901 GCCTGGCCTCCAGGGCGAAGAGGAGCAGGGTGAGGGGGACCAGCAGGAGCCCCAGCTGCT
275  G  T  I  N  A  K  M  K  A  F  K  K  E  L  Q  A  F  L  E  Q
961 GGGGACCATCAACGCCAAGATGAAGGCTTTCAAGAAAGAGCTGCAGGCCTTCCTGGAGCA
295  V  N  R  I  G  D  G  L  S  P  L  P  H  L  T  E  S  S  S  F
1021 GGTGAACCGCATTGGGGATGGCCTATCCCCCTTGCCCCACCTCACAGAGTCCTCTAGCTT
315  L  S  T  V  T  S  V  S  R  D  S  P  I  G  N  L  G  K  E  L
1081 CCTCTCCACTGTGACTTCCGTGTCCCGGGACTCCCCCATCGGGAACCTGGGGAAGGAGCT
335  G  P  D  L  Q  S  R  L  K  E  Q  L  E  W  Q  L  G  P  A  R
1141 GGGCCCAGACTTGCAGTCCAGACTGAAAGAGCAGCTGGAGTGGCAGCTCGGGCCGGCCCG
355  G  D  E  R  E  S  L  R  L  A  A  R  E  L  H  R  R  A  D
1201 AGGGGACGAGCGGGAGAGCCTGCGCCTCCGAGCCGCGCGGGAGCTGCACCGCCGCGCAGA
375  G  D  T  G  S  H  G  L  G  G  Q  T  C  F  S  L  E  M  E  E
1261 CGGGGACACCGGGAGCCACGGGCTGGGAGGCCAGACCTGCTTCAGCCTGGAGATGGAGGA
395  E  H  L  Y  A  L  R  W  K  E  L  E  M  H  S  L  A  L  Q  N
1321 GGAGCACCTCTATGCCTTGAGGTGGAAAGAACTGGAAATGCACAGCCTGGCTTTGCAAAA
415  T  L  H  E  R  T  W  S  D  E  K  N  L  M  Q  Q  E  L  R  S
1381 CACCCTCCATGAGCGAACCTGGAGTGATGAGAAGAATCTGATGCAGCAGGAGCTCCGGTC
435  L  K  Q  N  I  F  L  F  Y  V  K  L  R  W  L  L  K  H  W  R
1441 CTTGAAGCAGAACATTTTCCTCTTCTACGTCAAACTCAGGTGCTGCTGAAACACTGGCG
455  Q  G  K  Q  M  E  E  E  G  E  E  F  T  E  G  E  H  P  E  T
1501 GCAAGGGAAGCAGATGGAGGAGGAAGGAGAGGAGTTCACTGAGGGTGAACATCCAGAGAC
475  L  S  R  L  G  E  L  G  V  Q  G  G  H  Q  A  D  G  P  D  H
1561 CCTCTCCAGGCTCGGGGAGCTTGGAGTCCAGGGGGGTCACCAGGCGGATGGCCCAGACCA
495  D  S  D  R  G  C  G  F  P  V  G  E  H  S  P  H  S  R  V  Q
1621 CGACAGTGACCGAGGCTGTGTGGCTTTCCAGTGGGGGAGCACTCCCCACACTCCCGGGTGCA
515  I  G  D  H  S  L  R  L  Q  T  A  D  R  G  Q  P  H  K  Q  V
1681 GATTGGAGATCACAGCTTGCGGCTGCAGACCGCGGACAGGGGACAGCCCCACAAACAGGT
535  V  E  N  Q  Q  L  F  S  A  F  K  A  L  L  E  D  F  R  A  E
1741 GGTGGAAAACCAGCAGCTGTTCAGCGCCTTCAAGGCCTTGCTGGAGGACTTCCGTGCGGA
555  L  R  E  D  E  R  A  R  L  R  L  Q  Q  Q  Y  A  S  D  K  A
1801 GCTGCGGGAGGATGAGCGTGCCCGACTACGGCTGCAGCAATATGCCAGCGACAAGGC
575  A  W  D  V  E  W  A  V  L  K  C  R  L  E  Q  N  C  C  G  Y
1861 GGCCTGGGACGTGGAGTGGGCCGTGCTCAAGTGCCGTCTGGAACAGAATTGTTGTGGATA
595  P  R  I  N  I  E  E  E  T  L  G  F  T  R  L  P  A  G  S  T
1921 TCCCAGAATTAACATTGAGGAGGAGACTTTAGGCTTCACCAGGCTGCCAGCTGGGTCCAC
615  V  K  T  L  K  S  L  G  L  Q  R  L  E  L  E  E  K  T  E  N
1981 GGTAAAAACGTTGAAGAGCCTTGGGTTGCAGAGATTGGAGCTGGAAGAGAAGACTGAGAA
635  K  L  G  E  L  G  S  S  A  E  S  K  G  A  L  K  K  E  R  E
2041 CAAGTTGGGAGAACTAGGCTCCTCCGCTGAGAGCAAGGGGGCCTTGAAGAAGGAGAGAGA
655  V  H  Q  K  L  L  A  D  S  H  S  L  V  M  D  L  R  W  Q  I
2101 GGTGCACCAGAAGCTCCTGGCAGACAGTCACAGCCTGGTCATGGACCTGCGCTGGCAGAT
675  H  H  S  E  K  N  W  N  R  E  K  V  E  L  L  D  R  L  D  R
2161 CCATCACAGCGAGAAGAACTGGAACCGGGAGAAGGTGGAACTTCTCGACCGCCTGGACAG
695  D  R  Q  E  W  E  R  Q  K  E  F  L  W  R  I  E  Q  G
2221 AGATCGGCAGGAGTGGGAGCGGCAGAAGAAGGAATTCTTGTGGAGGATAGAGCAGGGAAG
715  L  R  M  P  R  P  V  A  M  W  P  C  A  D  A  D  S  I  P  F
2281 CCTCCGCATGCCCCGTCCAGTGGCCATGTGGCCTTGTGCAGATGCTGACTCCATCCCGTT
735  E  D  R  P  L  S  K  L  K  E  S  D  R  C  S  A  S  E  N  L
2341 TGAAGACCGGCCGCTGTCCAAGCTGAAGGAGTCGGACAGGTGCTCGGCCAGTGAGAATCT
755  Y  L  D  A  L  S  L  D  D  E  P  E  E  P  P  A  H  R  P  E
2401 CTACCTGGATGCCTTGTCCCTGGATGACGAGCCAGAAGAGCCACCAGCCCACAGGCCCGA
775  R  E  F  R  N  R  L  P  E  E  E  E  N  H  K  G  N  L  Q  R
2461 GAGGGAGTTCAGGAACCGCCTCCCTGAGGAAGAAGAAAATCACAAAGGAAATCTTCAAAG
795  A  V  S  V  S  S  M  S  E  F  Q  R  L  M  D  I  S  P  F  L
2521 GGCGGTGTCCGTGTCCTCCATGTCTGAGTTCCAGCGTCTAATGGACATCTCCCCCTTCCT
815  P  E  K  G  L  P  S  T  S  S  K  E  D  V  T  P  P  L  S  P
2581 GCCTGAGAAGGGCCTGCCGTCCACCAGCAGCAAGGAGGATGTCACCCCACCCCTGTCTCC
835  D  D  L  K  Y  I  E  E  F  N  K  S  W  D  Y  T  P  N  R  G
2641 AGACGACCTCAAGTACATCGAGGAGTTCAACAAGAGCTGGGACTACACACCCAACAGGGG
855  H  N  G  G  P  D  L  W  A  D  R  T  E  V  G  R  A  G  H
```

Figure 2N.3 (continued)

```
2701 CCACAATGGTGGGGGGCCGGACCTTTGGGCCGACAGGACCGAGGTGGGGCGGGCAGGGCA
 875   E  D  S  T  E  P  F  P  D  S  S  W  Y  L  T  T  S  V  T  M
2761 CGAGGACAGCACAGAGCCTTTCCCCGACTCCTCCTGGTACCTAACCACAAGTGTCACCAT
 895   T  T  D  T  M  T  S  P  E  H  C  Q  K  Q  P  L  R  S  H  V
2821 GACCACGGACACCATGACCAGCCCAGAGCACTGCCAGAAGCAGCCACTGCGGAGCCACGT
 915   L  T  E  Q  S  G  L  R  V  L  H  S  P  P  A  V  R  R  V  D
2881 CCTCACCGAGCAGTCGGGGTTGCGCGTGTTACACAGCCCGCCTGCCGTGCGCAGGGTCGA
 935   S  I  T  A  A  G  G  E  G  P  F  P  T  S  R  A  R  G  S  P
2941 CAGCATCACGGCGGCAGGTGGTGAGGGTCCCTTTCCCACAAGCAGAGCCAGAGGGAGCCC
 955   G  D  T  K  G  G  P  P  E  P  M  L  S  R  W  P  C  T  S  P
3001 GGGAGACACCAAGGGGGGCCCTCCAGAACCCATGCTCAGCAGGTGGCCTTGCACCTCCCC
 975   R  H  S  R  D  Y  V  E  G  A  R  R  P  L  D  S  P  L  C  T
3061 CAGGCACTCCCGGGACTATGTGGAGGGGGCACGGCGCCCCCTTGATAGTCCCCTCTGTAC
 995   S  L  G  F  A  S  P  L  H  S  L  E  M  S  K  N  L  S  D  D
3121 CTCCCTGGGGTTTGCCTCCCCACTGCACAGCCTGGAGATGTCCAAGAACTTGAGTGATGA
1015   M  K  E  V  A  F  S  V  R  N  A  I  C  S  G  P  G  E  L  Q
3181 CATGAAGGAGGTGGCCTTCTCTGTCAGGAATGCCATCTGCTCCGGCCCTGGCGAGCTGCA
1035   V  K  D  M  A  C  Q  T  N  G  S  R  T  M  G  T  Q  T  V  Q
3241 AGTCAAGGACATGGCCTGCCAGACCAATGGGTCCCGGACGATGGGGACCCAGACTGTTCA
1055   T  I  S  V  G  L  Q  T  E  A  L  R  G  S  G  V  T  S  S  P
3301 GACCATCAGTGTGGGCTTGCAGACTGAAGCCCTGCGTGGCAGCGGTGTCACCAGCAGCCC
1075   H  K  C  L  T  P  K  A  G  G  A  T  P  V  S  S  P  S  R
3361 CCACAAGTGTCTCACTCCAAAGGCTGGGGGCGGTGCTACACCCGTGTCGTCTCCTTCCCG
1095   S  L  R  S  R  Q  V  A  P  A  I  E  K  V  Q  A  K  F  E  R
3421 GAGCCTTAGGAGCAGACAGGTGGCCCCTGCCATCGAGAAGGTGCAGGCCAAGTTTGAACG
1115   T  C  C  S  P  K  Y  G  S  P  K  L  Q  R  K  P  L  P  K  A
3481 CACATGCTGCTCCCCCAAGTATGGTTCTCCCAAGCTGCAGAGGAAGCCCCTCCCCAAAGC
1135   D  Q  P  N  N  R  T  S  P  G  M  A  Q  K  G  Y  S  E  S  A
3541 CGACCAGCCAAATAACAGGACGTCACCAGGGATGGCCCAGAAAGGGTACAGTGAGTCAGC
1155   W  A  R  S  T  T  T  R  E  S  P  V  H  T  T  I  N  D  G  L
3601 CTGGGCCCGCTCCACCACCACAAGGGAGAGCCCCGTGCACACCACCATTAATGATGGCCT
1175   S  S  L  F  N  I  I  D  H  S  P  V  V  Q  D  P  F  Q  K  G
3661 CTCCAGCCTCTTCAACATCATTGACCACAGCCCCGTGGTGCAGGACCCCTTCCAGAAGGG
1195   L  R  A  G  S  R  S  R  S  A  E  P  R  P  E  L  G  P  G  Q
3721 GCTGCGGGCCGGCAGTCGGTCTCGCTCAGCAGAGCCCCGACCAGAGCTGGGCCCAGGCCA
1215   E  T  G  T  N  S  R  G  R  S  P  I  G  V  G  S  E  M
3781 GGAAACAGGCACCAATTCCCGAGGAAGGTCGCCTAGCCCCATTGGGGTGGGGTCAGAGAT
1235   C  R  E  E  G  G  E  G  T  P  V  K  Q  D  L  S  A  P  P  G
3841 GTGCAGGGAGGAAGGGGGAGAGGGCACGCCAGTGAAGCAGGACTTATCTGCTCCCCCTGG
1255   Y  T  L  T  E  N  V  A  R  I  L  N  K  K  L  L  E  H  A  L
3901 CTACACCCTCACTGAGAACGTGGCCCGGATCCTCAACAAGAAGCTGCTGGAACATGCCTT
1275   K  E  E  R  R  Q  A  A  H  G  P  P  G  L  H  S  D  S  H  S
3961 AAAGGAGGAGAGGAGGCAGGCTGCCCACGGGCCCCGGGTCTCCACAGTGACAGCCACTC
1295   L  G  D  T  A  E  P  G  P  M  E  E  L  P  C  S  A  L  A
4021 GCTGGGGGACACAGCCGAGCCAGGGCCCATGGAGGAACTACCTTGTTCTGCACTAGCTCC
```

Figure 2O The cDNA (SEQ ID NO:53) and amino acid sequence (SEQ ID NO:54) of 185P3C2. The open reading frame extends from nucleic acid 3-1658 including the stop codon.

```
   1   N  C  L  L  R  P  K  N  K  S  V  R  W  G  P  G  A  G  A  A
   1 acAACTGTCTGCTGCGCCCGAAAAACAAGTCGGTGCGCTGGGGACCCGGGGCCGGGGCCG
  21   L  L  R  P  S  P  A  A  L  G  A  G  S  R  A  C  S  V  P  P
  61 CCTTACTCCGGCCTAGCCCCGCGGCCCTCGGTGCGGGCTCCAGGGCATGCTCGGTACCCC
  41   A  A  P  A  Q  T  P  R  P  Q  V  S  A  P  A  W  G  P  G  R
 121 CCGCGGCTCCAGCCCAGACGCCCCGGCCTCAGGTCTCGGCCCCGCTTGGGCCCCGGCC
  61   A  A  R  G  S  G  R  M  E  R  R  M  K  A  G  Y  L  D  Q  Q
 181 GTGCGGCGCGAGGGAGCGGCCGGATGGAGCGGAGGATGAAAGCCGGATACTTGGACCAGC
  81   V  P  Y  T  F  S  S  K  S  P  G  N  G  S  L  R  E  A  L  I
 241 AAGTGCCCTACACCTTCAGCAGCAAATCGCCCGGAAATGGGAGCTTGCGCGAAGCGCTGA
 101   G  P  L  G  K  L  M  D  P  G  S  L  P  P  L  P  D  S  E  D  L
 301 TCGGCCCGCTGGGGAAGCTCATGGACCCGGGCTCCCTGCCGCCCCTCGACTCTGAAGATC
 121   F  Q  D  L  S  H  F  Q  E  T  W  L  A  E  A  Q  V  P  D  S
 361 TCTTCCAGGATCTAAGTCACTTCCAGGAGACGTGGCTCGCTGAAGCTCAGGTACCAGACA
 141   D  E  Q  F  V  P  D  F  H  S  E  N  L  A  F  H  S  P  T  T
 421 GTGATGAGCAGTTTGTTCCTGATTTCCATTCAGAAAACCTAGCTTTCCACAGCCCCACCA
 161   R  I  K  K  E  P  Q  S  P  R  T  D  P  A  L  S  C  S  R  K
 481 CCAGGATCAAGAAGGAGCCCCAGAGTCCCCGCACAGACCCGGCCCTGTCCTGCAGCAGGA
 181   P  P  L  P  Y  H  H  G  E  Q  C  L  Y  S  S  A  Y  D  P  P
 541 AGCCGCCACTCCCCTACCACCATGGCGAGCAGTGCCTTTACTCCAGTGCCTATGACCCCC
```

Figure 20 (continued)

```
    201  R  Q  I  A  I  K  S  P  A  P  G  A  L  G  Q  S  P  L  Q  P
    601 CCAGACAAATCGCCATCAAGTCCCCTGCCCCTGGTGCCCTTGGACAGTCGCCCCTACAGC
    221  F  P  R  A  E  Q  R  N  F  L  R  S  S  G  T  S  Q  P  H  P
    661 CCTTTCCCCGGGCAGAGCAACGGAATTTCCTGAGATCCTCTGGCACCTCCCAGCCCCACC
    241  G  H  G  Y  L  G  E  H  S  S  V  F  Q  Q  P  L  D  I  C  H
    721 CTGGCCATGGGTACCTCGGGGAACATAGCTCCGTCTTCCAGCAGCCCCTGGACATTTGCC
    261  S  F  T  S  Q  G  G  G  R  E  P  L  P  A  P  Y  Q  H  Q  L
    781 ACTCCTTCACATCTCAGGGAGGGGGCCGGGAACCCCTCCCAGCCCCCTACCAACACCAGC
    281  S  E  P  C  P  P  Y  P  Q  Q  S  F  K  Q  E  Y  H  D  P  L
    841 TGTCGGAGCCCTGCCCACCCTATCCCCAGCAGAGCTTTAAGCAAGAATACCATGATCCCC
    301  Y  E  Q  A  G  Q  P  A  V  D  Q  G  G  V  N  G  H  R  Y  P
    901 TGTATGAACAGGCGGGCCAGCCAGCCGTGGACCAGGGTGGGGTCAATGGGCACAGGTACC
    321  G  A  G  V  V  I  K  Q  E  Q  T  D  F  A  Y  D  S  D  V  T
    961 CAGGGGCGGGGGTGGTGATCAAACAGGAACAGACGGACTTCGCCTACGACTCAGATGTCA
    341  G  C  A  S  M  Y  L  H  T  E  G  F  S  G  P  S  P  G  D  G
   1021 CCGGGTGCGCATCAATGTACCTCCACACAGAGGGCTTCTCTGGGCCCTCTCCAGGTGACG
    361  A  M  G  Y  G  Y  E  K  P  L  R  P  F  P  D  D  V  C  V  V
   1081 GGGCCATGGGCTATGGCTATGAGAAACCTCTGCGACCATTCCCAGATGATGTCTGCGTTG
    381  P  E  K  F  E  G  D  I  K  Q  E  G  V  G  A  F  R  E  G  P
   1141 TCCCTGAGAAATTTGAAGGAGACATCAAGCAGGAAGGGGTCGGTGCATTTCGAGAGGGGC
    401  P  Y  Q  R  R  G  A  L  Q  L  W  Q  F  L  V  A  L  L  D  D
   1201 CGCCCTACCAGCGCCGGGGTGCCCTGCAGCTGTGGCAATTTCTGGTGGCCTTGCTGGATG
    421  P  T  N  A  H  F  I  A  W  T  G  R  G  M  E  F  K  L  I  E
   1261 ACCCAACAAATGCCCATTTCATTGCCTGGACGGGCCGGGGAATGGAGTTCAAGCTCATTG
    441  P  E  E  V  A  R  L  W  G  I  Q  K  N  R  P  A  M  N  Y  D
   1321 AGCCTGAGGAGGTCGCCAGGCTCTGGGGCATCCAGAAGAACCGGCCAGCCATGAATTACG
    461  K  L  S  R  S  L  R  Y  Y  Y  E  K  G  I  M  Q  K  V  A  G
   1381 ACAAGCTGAGCCGCTCGCTCCGATACTATTATGAGAAAGGCATCATGCAGAAGGTGGCTG
    481  E  R  Y  V  Y  K  F  V  C  E  P  E  A  L  F  S  L  A  F  P
   1441 GTGAGCGTTACGTGTACAAGTTTGTGTGTGAGCCCGAGGCCCTCTTCTCTTTGGCCTTCC
    501  D  N  Q  R  P  A  L  K  A  E  F  D  R  P  V  S  E  E  D  T
   1501 CGGACAATCAGCGTCCAGCTCTCAAGGCTGAGTTTGACCGGCCTGTCAGTGAGGAGGACA
    521  V  P  L  S  H  L  D  E  S  P  A  Y  L  P  E  L  A  G  P  A
   1561 CAGTCCCTTTGTCCCACTTGGATGAGAGCCCCGCCTACCTCCCAGAGCTGGCTGGCCCCG
    541  Q  P  F  G  P  K  G  G  Y  S  Y  *
   1621 CCCAGCCATTTGGCCCCAAGGGTGGCTACTCTTACTAGccccccagcggctgttccccctg
   1681 ccgcaggtgggtgctgccctgtgtacatataaatgaatctggtgttggggaaaccttcat
   1741 ctgaaacccacagatgtctctggggcagatccccactgtcctaccagttgccctagccca
   1801 gactctgagctgctcaccggagtcattgggaaggaaaagtggagaaatggcaagtctaga
   1861 gtctcagaaactcccctgggggtttcacctgggcctggaggaattcagctcagcttctt
   1921 cctaggtccaagcccccacaccttttcccaaccacagagaacaagagtttgttctgtt
   1981 ctgggggacagagaaggcgcttcccaacttcatactggcaggagggtgaggaggttcact
   2041 gagctccccagatctcccactgcggggagacagaagcctggactctgccccacgctgtgg
   2101 ccctggagggtcccggtttgtcagttcttggtgctctgtgttcccagaggcaggcggagg
   2161 ttgaagaaaggaacctgggatgaggggtgctgggtataagcagagagggatgggttcctg
   2221 ctccaagggaccctttgcctttcttctgccctttcctaggcccaggcctgggtttgtact
   2281 tccacctccaccacatctgccagaccttaataaaggcccccacttctcccatt
```

Figure 2P  The cDNA (SEQ ID NO:55) and amino acid sequence (SEQ ID NO:56) of 186P1H9. The start methionine is underlined. The open reading frame extends from nucleic acid 170-1462 including the stop codon.

```
      1 gagcagcgcggtgggtgcggctgtgagacggcaggagacttctgccccgcggtgcacgcg
     61 accctcgagacgacagcgcggctactgccagcagcgaaggcgcctcccgcggagcgcccc
      1                                                       M  L  A  L
    121 gacggcgcccgctcgcccatgccgagctgagcgcggcagcggcggcgggATGCTGGCGCT
      5  L  A  A  S  V  A  L  A  V  A  A  G  A  Q  D  S  P  A  P  G
    181 GCTGGCCGCCAGCGTGGCGCTCGCCGTGGCCGCTGGGGCCCAGGACAGCCCGGCGCCCGG
     25  S  R  F  V  C  T  A  L  P  P  P  E  A  V  H  A  G  C  P  L  P
    241 TAGCCGCTTCGTGTGCACGGCACTGCCCCCAGAGGCGGTGCACGCCGGCTGCCCGCTGCC
     45  A  M  P  M  Q  G  G  A  Q  S  P  E  E  E  L  R  A  A  V  L
    301 CGCGATGCCCATGCAGGGCGGCGCGCAGAGTCCCGAGGAGGAGCTGAGGGCCGCGGTGCT
     65  Q  L  R  E  T  V  V  Q  Q  K  E  T  L  A  S  A  R  A  I  R
    361 GCAGCTGCGCGAGACCGTCGTGCAGCAGAAGGAGACGCTGGCCAGCGCGAGGGCCATCCG
     85  E  L  T  G  K  L  A  R  C  E  G  L  A  G  G  K  A  R  G  A
    421 CGAGCTCACGGGCAAGCTAGCGCGCTGCGAGGGGCTGGCGGGCGGCAAGGCGCGCGGCGC
    105  G  A  T  G  K  D  T  M  G  D  L  P  R  D  P  G  H  V  V  E
    481 GGGGGCCACGGGCAAGGACACTATGGGCGACCTGCCGCGGGACCCCGGCCACGTCGTGGA
    125  Q  L  S  R  S  L  Q  T  L  K  D  R  L  E  S  L  E  H  Q  L
    541 GCAGCTCAGCCGCTCGCTGCAGACCCTCAAGGACCGCCTGGAGAGCCTCGAGCACCAGCT
    145  R  A  N  V  S  N  A  G  L  P  G  D  F  R  E  V  L  Q  Q  R
```

Figure 2P (continued)

```
 601 CAGAGCAAACGTGTCCAATGCTGGGCTGCCCGGCGACTTCCGCGAGGTGCTCCAGCAGCG
 165  L  G  E  L  E  R  Q  L  L  R  K  V  A  E  L  E  D  E  K  S
 661 GCTGGGGGAGCTGGAGAGGCAGCTTCTGCGCAAGGTGGCAGAGCTGGAGGACGAGAAGTC
 185  L  L  H  N  E  T  S  A  H  R  Q  K  T  E  S  T  L  N  A  L
 721 CCTGCTGCACAATGAGACCTCGGCTCACCGGCAGAAGACCGAGAGCACCCTGAACGCGCT
 205  L  Q  R  V  T  E  L  E  R  G  N  S  A  F  K  S  P  D  A  F
 781 GCTGCAGAGGGTCACCGAGCTGGAGCGAGGCAATAGCGCCTTTAAGTCACCAGATGCGTT
 225  K  V  S  L  P  L  R  T  N  Y  L  Y  G  K  I  K  K  T  L  P
 841 CAAGGTGTCCCTCCCACTCCGCACAAACTACCTATACGGCAAGATCAAGAAGACGCTGCC
 245  E  L  Y  A  F  T  I  C  L  W  L  R  S  S  A  S  P  G  I  G
 901 TGAGCTGTACGCCTTCACCATCTGCCTGTGGCTGCGGTCCAGCGCCTCACCAGGCATTGG
 265  T  P  F  S  Y  A  V  P  G  Q  A  N  E  I  L  L  I  E  W  G
 961 CACCCCCTTCTCCTATGCGGTGCCAGGGCAGGCCAACGAGATCTTGCTGATCGAGTGGGG
 285  N  N  P  I  E  L  L  I  N  D  K  V  A  Q  L  P  L  F  V  S
1021 CAACAACCCCATCGAGCTGCTCATCAACGACAAGGTTGCGCAGCTGCCCCTGTTTGTCAG
 305  D  G  K  W  H  H  I  C  V  T  W  T  T  R  D  G  M  W  E  A
1081 TGACGGCAAGTGGCACCACATCTGTGTCACCTGGACGACACGGGATGGCATGTGGGAGGC
 325  F  Q  D  G  E  K  L  A  P  W  H  P  I  K
1141 ATTCCAGGACGGAGAGAAGCTGGGCACTGGGGAGAACCTGGCCCCCTGGCACCCCATCAA
 345  P  G  G  V  L  I  L  G  Q  E  Q  D  T  V  G  G  R  F  D  A
1201 GCCCGGGGGCGTGCTGATCCTTGGACAAGAGCAGGACACCGTGGGGGGTAGGTTTGATGC
 365  T  Q  A  F  V  G  E  L  S  Q  F  N  I  W  D  R  V  L  R  A
1261 CACTCAGGCATTTGTCGGGGAGCTCAGCCAGTTCAACATATGGGACCGCGTCCTTCGCGC
 385  Q  E  I  V  N  I  A  N  C  G  N  I  I  P  W
1321 ACAAGAAATTGTCAACATCGCCAACTGCTCCACAAACATGCCGGGCAACATCATCCCGTG
 405  V  D  N  N  V  D  V  F  G  G  A  S  K  W  P  V  E  T  C  E
1381 GGTGGACAATAACGTCGATGTGTTCGGAGGGGCCTCCAAGTGGCCCGTGGAGACGTGTGA
 425  E  A  L  L  D  L  *
1441 GGAGGCTCTCCTTGACTTGTAGccgccttctcctctgtccaggaggccgggatcaggctg
1501 ttgccatggaagttcagggccatagactgccccacttaaactcttgtcagtctgggctca
1561 gggttcccagagctcattcccaggaatctctaagaccagggctggggcagtgtctgtca
1621 ctggcttgtttgttccctaccaatattctgttgctgtttgaagtagtgccagggtcccct
1681 gggaagatgcccccaagacacctgccccaagtgggtggatatctgccttcctgctgcaag
1741 tggaggcaggtccagcagcccctcttcagagccctgtaaatgctatcgcagcctgagtc
1801 ctgccgccttccagttccttggtgtcccgtgcacccttctgtctgtcccctttcatgct
1861 gtgcagccgtcccgctggagtggccatgtcccttgtgcattgagtgcatcccgctggtg
1921 actaagctcgcagcaagcgctacccccgatctgcaaagggcctctcccctttgtgttcta
1981 tacattgtgaatcttcccgtctgaagaacgcccagcctgcccagacaaagccccgccttc
2041 cccaaagcagaggggctgtctgtgtctccagaaaggggacatcggggggggagggggggct
2101 cagaaaggagaagggctgtgatctccggtcccttcccccatcatccttccttagactgat
2161 gctttgactgaatcatcactagctatggcattaaaaggcctctcttctcatctggtgcca
2221 aaggttccgttgcagcttttttacaaccatccggtgtggtttggaggatttgttttttttt
2281 tttcccaacagaaaagaacagccattagaagaaggctcccattttctgatgttccgcccc
2341 actgtgaagagtgtgctcgttttaaattcatgttgattcttgtaagcactggactgtctt
2401 catcaagtatttcccctacagaactcctcaagaaaaacagagatcatttggctagagatt
2461 gtctgagtgactccaagctactcactgtattggacgggagtagtaatttatttaaagat
2521 aaagtgactaagtggggaaatttataaagctaaatattatatatttttattttcatacat
2581 gtttgaagtgcaaatctgtggatattccatttgtaggaccaagtcgacatgcccatcctg
2641 acattgtatgctacgagaactcttctgatgatggaatttcgattaaagtgcactgaaaga
2701 tg
```

Figure 2Q The cDNA (SEQ ID NO:57) and amino acid sequence (SEQ ID NO:58) of 187P3F2. The start methionine is underlined. The open reading frame extends from nucleic acid 60-1562 including the stop codon.

```
   1                                                              M
   1 ctgctgctgcggcggcggcggtggtggcggcggtggggtggcgggagcggagcggcA
   2     A  T  A  A  S  N  P  Y  L  P  G  N  S  L  L  A  A  G  S  I
  61 TGGCCACGGCGGCTTCTAACCCCTACCTGCCGGGGAACAGCCTGCTCGCGGCCGGCTCTA
  22  V  H  S  D  A  A  G  A  G  G  G  G  G  G  G  S  G  G
 121 TTGTGCACTCGGACGCGGCGGGGGCTGGCGGCGGCGGGGGTGGCGGCGGCGGCAGCGGCG
  42  G  G  A  G  G  G  G  G  M  Q  P  G  S  A  A  V  T  S  G
 181 GGGGCGGCGCAGGGGGCGGGGGCGGCGGCATGCAGCCGGGCAGCGCCGCCGTGACCTCGG
  62  A  Y  R  G  D  P  S  S  V  K  M  V  Q  S  D  F  M  Q  G  A
 241 GCGCCTACCGGGGGGACCCGTCCTCTGTCAAGATGGTCCAGAGCGACTTCATGCAGGGGG
  82  M  A  A  S  N  G  G  H  M  L  S  H  A  H  Q  W  V  T  A  L
 301 CCATGGCCGCCAGCAACGGCGGCCATATGCTGAGCCACGCGCACCAGTGGGTCACAGCCC
 102  P  H  A  A  A  A  A  A  A  A  A  A  A  V  E  A  S  S  P
 361 TGCCCCACGCCGCCGCCGCCGCCGCCGCTGCCGCCGCCGCCGTGGAGGCGAGCTCGC
 122  W  S  G  S  A  V  G  M  A  G  S  P  Q  Q  P  P  Q  P  P  P
 421 CGTGGTCGGGCAGCGCCGTGGGCATGGCTGGCAGCCCCCAGCAGCCACCGCAGCCGCCGC
```

Figure 2Q (continued)

```
142        P  P  P  Q  G  P  D  V  K  G  G  A  G  R  D  D  L  H  A  G
481  CGCCACCGCCGCAGGGCCCCGACGTGAAGGGCGGCGCCGGGCGCGACGACCTGCACGCGG
162        T  A  L  H  H  R  G  P  P  H  L  G  P  P  P  P  P  P  H  Q
541  GCACAGCGCTGCACCACCGCGGGCCCGCACCTCGGACCCCCGCCGCCGCCCCCACACC
182        G  H  P  G  G  W  G  A  A  A  A  A  A  A  A  A  A  A
601  AGGGCCACCCTGGGGGCTGGGGGGCGGCCGCCGCTGCCGCAGCCGCAGCCGCCGCCGCCG
202        A  A  A  H  L  P  S  M  A  G  G  Q  Q  P  P  P  Q  S  L  L
661  CCGCCGCCGCGCACCTCCCGTCCATGGCCGGGGGCCAGCAGCCGCCGCCGCAGAGTCTGC
222        Y  S  Q  P  G  G  F  T  V  N  G  M  L  S  A  P  P  G  P  G
721  TCTACTCGCAGCCCGGAGGCTTCACGGTGAACGGCATGCTGAGCGCGCCACCGGGGCCCG
242        G  G  G  G  A  G  G  G  A  Q  S  L  V  H  P  G  L  V  R
781  GCGGCGGCGGCGGCGGCGCGGGCGGTGGAGCCCAGAGCTTGGTGCACCCGGGGCTGGTGC
262        G  D  T  P  E  L  A  E  H  H  H  H  H  H  H  A  H  P  H
841  GCGGGGACACGCCAGAGCTGGCCGAGCACCACCACCACCACCACCACCACGCGCATCCTC
282        P  P  H  P  H  H  A  Q  G  P  P  H  G  G  G  G  G  A
901  ACCCGCCGCACCCGCACCACGCGCAGGGACCCCCGCACCACGGCGGCGGCGGCGGCGGCG
302        G  P  G  L  N  S  H  D  P  H  S  D  E  D  T  P  T  S  D  D
961  CGGGGCCTGGACTCAACAGCCACGACCCGCACTCGGACGAGGACACGCCGACGTCGGACG
322        L  E  Q  F  A  K  Q  F  K  Q  R  R  I  K  L  G  F  T  Q  A
1021 ACCTGGAGCAGTTCGCCAAGCAGTTCAAGCAGCGGCGCATCAAGCTGGGCTTCACGCAGG
342        D  V  G  L  A  L  G  T  L  Y  G  N  V  F  S  Q  T  T  I  C
1081 CCGACGTGGGGTTGGCGCTGGGCACACTCTACGGCAACGTGTTCTCGCAGACCACCATCT
362        R  F  E  A  L  Q  L  S  F  K  N  M  C  K  L  K  P  L  L  N
1141 GCCGCTTCGAGGCCCTGCAGCTGAGCTTCAAGAACATGTGCAAGCTCAAGCCGCTGCTGA
382        K  W  L  E  E  A  D  S  S  T  G  S  P  T  S  I  D  K  I  A
1201 ACAAGTGGCTGGAGGAGGCGGACTCAAGCACCGGCAGCCCCACAAGCATCGACAAGATCG
402        A  Q  G  R  K  R  K  K  R  T  S  I  E  V  S  V  K  G  A  L
1261 CGGCGCAGGGTCGCAAGCGCAAGAAGCGGACCTCTATCGAGGTGAGCGTCAAGGGCGCGC
422        E  S  H  F  L  K  C  P  K  P  S  A  Q  E  I  T  N  L  A  D
1321 TGGAGAGCCACTTCCTCAAGTGCCCCAAGCCCTCCGCGCAGGAGATCACCAACCTGGCCG
442        S  L  Q  L  E  K  E  V  V  R  V  W  F  C  N  R  R  Q  K  E
1381 ACAGCCTGCAGCTCGAGAAGGAGGTGGTGCGGGTCTGGTTCTGCAATCGGCGCCAAAAGG
462        K  R  M  T  P  P  G  I  Q  Q  Q  T  P  D  D  V  Y  S  Q  V
1441 AGAAGCGCATGACGCCGCCCGGGATCCAACAGCAGACGCCCGACGACGTCTACTCGCAGG
482        G  T  V  S  A  D  T  P  P  P  H  H  G  L  Q  T  S  V  Q  *
1501 TGGGCACCGTGAGCGCCGACACGCCGCCGCCTCACCACGGGCTGCAGACGAGCGTTCAGT
1561 GAagccagggcgcagagcgaagagtgccgccgccgccgccgcctccgcagccgccgtcag
1621 caccgccgccgccctgccgccgccgccgccgccgccgccgctgccgccgccgcgc
```

Figure 2R The cDNA (SEQ ID NO:59) and amino acid sequence (SEQ ID NO:60) of 192P2G7. The start methionine is underlined. The open reading frame extends from nucleic acid 84-938 including the stop codon.

```
  1  ccacgcgtccggcgcgggcgcgggcgcgggcgcgtgcgggctgcgagccgggaggcggcg
  1                              M  A  E  S  E  A  E  T  P  S  T  P  G
 61  gcggcgacggcgacggcggcggcATGGCGGAGAGCGAGGCCGAGACCCCCAGCACCCCGG
 14    E  F  E  S  K  Y  F  E  F  H  G  V  R  L  P  P  F  C  R  G
121  GGGAGTTCGAGAGCAAGTACTTCGAGTTCCATGGCGTGCGGCTGCCGCCCTTCTGCCGCG
 34    K  M  E  E  I  A  N  F  P  V  R  P  S  D  V  W  I  V  T  Y
181  GGAAGATGGAGGAGATCGCCAACTTCCCGGTGCGGCCCAGCGACGTGTGGATCGTCACCT
 54    P  K  S  G  T  S  L  L  Q  E  V  V  Y  L  V  S  Q  G  A  D
241  ACCCCAAGTCCGGCACCAGCTTGCTGCAGGAGGTGGTCTACTTGGTGAGCCAGGGCGCTG
 74    P  D  E  I  G  L  M  N  I  D  E  Q  L  P  V  L  E  Y  P  Q
301  ACCCCGATGAGATCGGCTTGATGAACATCGACGAGCAGCTCCCGGTCCTGGAGTACCCAC
 94    P  G  L  D  I  I  K  E  L  T  S  P  R  L  I  K  S  H  L  P
361  AGCCGGGCCTGGACATCATCAAGGAACTGACCTCTCCCCGCCTCATCAAGAGCCACCTGC
114    Y  R  F  L  P  S  D  L  H  N  G  D  S  K  V  I  Y  M  A  R
421  CCTACCGCTTTCTGCCCTCTGACCTCCACAATGGAGACTCCAAGGTCATCTATATGGCTC
134    N  P  K  D  L  V  V  S  Y  Y  Q  F  H  R  S  L  R  T  M  S
481  GCAACCCCAAGGATCTGGTGGTGTCTTATTATCAGTTCCACCGCTCTCTGCGGACCATGA
154    Y  R  G  T  F  Q  E  F  C  R  R  F  M  N  D  K  L  G  Y  G
541  GCTACCGAGGCACCTTTCAAGAATTCTGCCGGAGGTTTATGAATGATAAGCTGGGCTACG
174    S  W  F  E  H  V  Q  E  F  W  E  H  R  M  D  S  N  V  L  F
601  GCTCCTGGTTTGAGCACGTGCAGGAGTTCTGGGAGCACCGCATGGACTCGAACGTGCTTT
194    L  K  Y  E  D  M  H  R  D  L  V  T  M  V  E  Q  L  A  R  F
661  TTCTCAAGTATGAAGACATGCATCGGGACCTGGTGACGATGGTGGAGCAGCTGGCCAGAT
214    L  G  V  S  C  D  K  A  Q  L  E  A  L  T  E  H  C  H  Q  L
721  TCCTGGGGGTGTCCTGTGACAAGGCCCAGCTGGAAGCCCTGACGGAGCACTGCCACCAGC
234    V  D  Q  C  C  N  A  E  A  L  P  V  G  R  G  R  V  G  L  W
781  TGGTGGACCAGTGCTGCAACGCTGAGGCCCTGCCCGTGGGCCGGGGAAGAGTTGGGCTGT
254    K  D  I  F  T  V  S  M  N  E  K  F  D  L  V  Y  K  Q  K  M
```

Figure 2R (continued)

```
 841 GGAAGGACATCTTCACCGTCTCCATGAATGAGAAGTTTGACTTGGTGTATAAACAGAAGA
 274  G  K  C  D  L  T  F  D  F  Y  L  *
 901 TGGGAAAGTGTGACCTCACGTTTGACTTTTATTTATAAtaacagaaacaacaacctgcat
 961 gctcacaatacccagacagtctactagccaaaagtcctgtatgcattcatttattccttg
1021 ctggacaaactctggaagcagcgtgtgaaacagcggggaagggaagagcggcgtgagcg
1081 gagggagtgtgatgattcccaaccgaaagcagctgtctcgcctttagaacgtgcagcctc
1141 tccatgtctgattacaaacagtctccacattgcagttccaatggcctggaccgtaaggat
1201 aaagcctgtaatatatgcaactagaatgtctgccttttcaacccgtattatttattgta
1261 ttttatagagcttttcactggaaatctacataaatgtcagtaaaccaaataaaagttcat
1321 ttccaaggggaatcaggagcgagccacacccgaatggtagaaagatctcagggttaactc
1381 tttattttgtagttttattatctaaggcacagccattctgttctcacttggttctgaga
1441 tagtggtgagaacagaggatgagttgggtctgttgggggaatctggacacttgtttatt
1501 ctgacggagttcacttcttcagaaccttcctgaaatgagcagaaattgttcactaggtct
1561 tcagaatggacgtccttctgccagagacttccagcgggcggctccaaaggcccaatgcag
1621 aggagcccgcggagcatgtgctgagggaagtctgcctggtgaggctggcaggtgggagtc
1681 taatgcagtcaggagcatttgcatgcagtgggtggagagtcggccaccaaaggaccgagt
1741 tgcgctcggaatttgagctgaattccacagccttactttgtttcctgaagtgatagccta
1801 ctaatgctggcaagcagatgcttaatagtaaatttctaaaatcccgggtctttatcatt
1861 cagtttgttctgtgcacctgaggcgctcagccgtgggaggaccattttgcgagtgtagcc
1921 ctgtttcactcggatcaggttggcacggccgcctgcgtgtctgtccacctcatccctccg
1981 tgtatctgagggagtaaaggtgaggtcttattgcttcactgcctaatttctcacccac
2041 attcgctgaagcgatggagagtcgggggccagtagccagccaacccgtggggaccgggg
2101 ttgtctgtcatttatgtggctggaaagcacccaaagtggtggtcaggagggtcgctgctg
2161 tggaagggtctccgttcttggtgctgtatttgaaacgggtgtagagagaagcttgtgtt
2221 tttgtttgtaatggggagaagcgtggccaggcagtggcacgtggcatcgcatggtgggct
2281 cggcagcaccttgcctgtgtttctgtgagggaggctgctttctgtgaaatttctttatat
2341 ttttctatttttagtactgtatggatgttactgagcactacacatgatccttctgtgctt
2401 gcttgcatctttaataaagacatgttcccggcaaaaaaaaaaaaaaaaaaaaaaaaaaaa
2461 aaaaaaaaaaaaaaaaaaaaaaaaaaaaaaaaaa
```

Figure 3:

Figure 3A.1  74P3B3 v.1A amino acid sequence (SEQ ID NO:61) of 180 amino acids.

```
  1 MGQSKSKHSA YLHFIKLLLK RAGIKASTEN LITLFPTVEQ YCPWFPEHGT MDFKDWEQVG
 61 IALKQVCKEG KFIPLTAWSN WAIVKAASEP FQSENEAYPP AERISAEEGG DAAEGGEDSE
121 EDFEENTDKP GDELISFEEH VGPSAAPKIE KPYMPRCLKQ RRALRSSRLL IGIIRSGRLQ
```

Figure 3A.2  74P3B3 v.1B amino acid sequence (SEQ ID NO: 62) of 228 amino acids.

```
  1 MFKTKKGLEE QSAPHWDHPE WPPPIKQCSL EPWRSESQIC PVSRMNELWP QEPQAHGVAP
 61 VQHKAALPSN VNESPLQFII RQARLAGDLD AWQFAVVLQP PRQQGGAHQA VWEPFSFKLL
121 KDLKAAVGQY GPNSPFIRSL LQSVAQNKLL TPCDWEILTK VTLSPSQFLQ FKTWWTDEAQ
181 NQDRKNRAAN PAIAITFEQL LGIGGQWGTV NNHQDFEMMP LNKFAIAV
```

Figure 3B  83P4B8 amino acid sequence (SEQ ID NO:63) of 1328 amino acids.

```
   1 MDQKILSLAA EKTADKLQEF LQTLREGDLT NLLQNQAVKG KVAGALLRAI FKGSPCSEEA
  61 GTLRRRKIYT CCIQLVESGD LQKEIVSEII GLLMLEAHHF PGPLLVELAN EFISAVREGS
 121 LVNGKSLELL PIILTALATK KENLAYGKGV LSGEECKKQL INTLCSGRWD QQYVIQHTSM
 181 FKDVPLTAEE VEFVVEKALS MFSKMNLQEI PPLVYQLLVL SSKGSRKSVL EGIIAFFSAL
 241 DKQHNEEQSG DELLDVVTVP SGELRHVEGT IILHIVFAIK LDYELGRELV KHLKVGQQGD
 301 SNNNLSPFSI ALLLSVTRIQ RFQDQVLDLL KTSVVKSFKD LQLLQGSKFL QNLVPHRSYV
 361 STMILEVVKN SVHSWDHVTQ GLVELGFILM DSYGPKKVLD GKTIETSPSL SRMPNQHACK
 421 LGANILLETF KIHEMIRQEI LEQVLNRVVT RASSPISHFL DLLSNIVMYA PLVLQSCSSK
 481 VTEAFDYLSF LPLQTVQRLL KAVQPLLKVS MSMRDCLILV LRKAMFANQL DARKSAVAGF
 541 LLLLKNFKVL GSLSSSQCSQ SLSVSQVHVD VHSHYNSVAN ETFCLEIMDS LRRCLSQQAD
 601 VRLMLYEGFY DVLRRNSQLA NSVMQTLLSQ LKQFYEPKPD LLPPLKLDAC ILTQGDKISL
 661 QEPLDYLLCC IQHCLAWYKN TVIPLQQGEE EEEEEEAFYE DLDDILESIT NRMIKSELED
 721 FELDKSADFS QSTSIGIKNN ISAFLVMGVC EVLIEYNFSI SSFSKNRFED ILSLFMCYKK
 781 LSDILNEKAG KAKTKMANKT SDSLLSMKFV SSLLTALFRD SIQSHQESLS VLRSSNEFMR
 841 YAVNVALQKV QQLKETGHVS GPDGQNPEKI FQNLCDITRV LLWRYTSIPT SVEESGKKEK
 901 GKSISLLCLE GLQKIFSAVQ QFYQPKIQQF LRALDVTDKE GEEREDADVS VTQRTAFQIR
 961 QFQRSLLNLL SSQEEDFNSK EALLLVTVLT SLSKLLEPSS PQFVQMLSWT SKICKENSRE
1021 DALFCKSLMN LLFSLHVSYK SPVILLRDLS QDIHGHLGDI DQDVEVEKTN HFAIVNLRTA
1081 APTVCLLVLS QAEKVLEEVD WLITKLKGQV SQETLSEEAS SQATLPNQPV EKAIIMQLGT
1141 LLTFFHELVQ TALPSGSCVD TLLKDLCKMY TTLTALVRYY LQVCQSSGGI PKNMEKLVKL
1201 SGSHLTPLCY SFISYVQNKS KSLNYTGEKK EKPAAVATAM ARVLRETKPI PNLIFAIEQY
1261 EKFLIHLSKK SKVNLMQHMK LSTSRDFKIK GNILDMVLRE DGEDENEEGT ASEHGGQNKE
1321 PAKKKRKK
```

Figure 3C  109P1D4 amino acid sequence (SEQ ID NO:64) of 1021 amino acids.

```
   1 MDLLSGTYIF AVLLACVVFH SGAQEKNYTI REEMPENVLI GDLLKDLNLS LIPNKSLTTA
  61 MQFKLVYKTG DVPLIRIEED TGEIFTTGAR IDREKLCAGI PRDEHCFYEV EVAILPDEIF
 121 RLVKIRFLIE DINDNAPLFP ATVINISIPE NSAINSKYTL PAAVDPDVGI NGVQNYELIK
 181 SQNIFGLDVI ETPEGDKMPQ LIVQKELDRE EKDTYVMKVK VEDGGFPQRS STAILQVSVT
 241 DTNDNHPVFK ETEIEVSIPE NAPVGTSVTQ LHATDADIGE NAKIHFSFSN LVSNIARRLF
 301 HLNATTGLIT IKEPLDREET PNHKLLVLAS DGGLMPARAM VLVNVTDVND NVPSIDIRYI
 361 VNPVNDTVVL SENIPLNTKI ALITVTDKDA DHNGRVTCFT DHEIPFRLRP VFSNQFLLET
 421 AAYLDYESTK EYAIKLLAAD AGKPPLNQSA MLFIKVKDEN DNAPVFTQSF VTVSIPENNS
 481 PGIQLTKVSA MDADSGPNAK INYLLGPDAP PEFSLDCRTG MLTVVKKLDR EKEDKYLFTI
 541 LAKDNGVPPL TSNVTVFVSI IDQNDNSPVF THNEYNFYVP ENLPRHGTVG LITVTDPDYG
 601 DNSAVTLSIL DENDDFTIDS QTGVIRPNIS FDREKQESYT FYVKAEDGGR VSRSSSAKVT
 661 INVVDVNDNK PVFIVPPSNC SYELVLPSTN PGTVVFQVIA VDNDTGMNAE VCYSIVGGNT
 721 RDLFAIDQET GNITLMEKCD VTDLGLHRVL VKANDLGQPD SLFSVVIVNL FVNESVTNAT
 781 LINELVRKST EAPVTPNTEI ADVSSPTSDY VKILVAAVAG TITVVVVIFI TAVVRCRQAP
 841 HLKAAQKNKQ NSEWATPNPE NRQMIMMKKK KKKKKHSPKN LLLNFVTIEE TKADDVDSDG
 901 NRVTLDLPID LEEQTMGKYN WVTTPTTFKP DSPDLARHYK SASPQPAFQI QPETPLNSKH
 961 HIIQELPLDN TFVACDSISK CSSSSSDPYS VSDCGYPVTT FEVPVSVHTR PVGIQVSNTT
1021 F
```

Figure 3D   151P1C7A amino acid sequence (SEQ ID NO:65) of 266 amino acids.

```
  1 MMALGAAGAT RVFVAMVAAA LGGHPLLGVS ATLNSVLNSN AIKNLPPPLG GAAGHPGSAV
 61 SAAPGILYPG GNKYQTIDNY QPYPCAEDEE CGTDEYCASP TRGGDAGVQI CLACRKRRKR
121 CMRHAMCCPG NYCKNGICVS SDQNHFRGEI EETITESFGN DHSTLDGYSR RTTLSSKMYH
181 TKGQEGSVCL RSSDCASGLC CARHFWSKIC KPVLKEGQVC TKHRRKGSHG LEIFQRCYCG
241 EGLSCRIQKD HHQASNSSRL HTCQRH
```

Figure 3E   151P4E11 amino acid sequence (SEQ ID NO:66) of 123 amino acids.

```
  1 MARGSALLLA SLLLAAALSA SAGLWSPAKE KRGWTLNSAG YLLGPHAVGN HRSFSDKNGL
 61 TSKRELRPED DMKPGSFDRS IPENNIMRTI IEFLSFLHLK EAGALDRLLD LPAAASSEDI
121 ERS
```

Figure 3F   154P2A8 amino acid sequence (SEQ ID NO:67) of 358 amino acids.

```
  1 MGFNLTLAKL PNNELHGQES HNSGNRSDGP GKNTTLHNEF DTIVLPVLYL IIFVASILLN
 61 GLAVWIFFHI RNKTSFIFYL KNIVVADLIM TLTFPFRIVH DAGFGPWYFK FILCRYTSVL
121 FYANMYTSIV FLGLISIDRY LKVVKPFGDS RMYSITFTKV LSVCVWVIMA VLSLPNIILT
181 NGQPTEDNIH DCSKLKSPLG VKWHTAVTYV NSCLFVAVLV ILIGCYIAIS RYIHKSSRQF
241 ISQSSRKRKH NQSIRVVVAV FFTCFLPYHL CRIPFTFSHL DRLLDESAQK ILYYCKEITL
301 FLSACNVCLD PIIYFFMCRS FSRRLFKKSN IRTRSESIRS LQSVRRSEVR IYYDYTDV
```

Figure 3G   156P1D4 amino acid sequence (SEQ ID NO:68) of 222 amino acids.

```
  1 MLWLLFFLVT AIHAELCQPG AENAFKVRLS IRTALGDKAY AWDTNEEYLF KAMVAFSMRK
 61 VPNREATEIS HVLLCNVTQR VSFWFVVTDP SKNHTLPAVE VQSAIRMNKN RINNAFFLND
121 QTLEFLKIPS TLAPPMDPSV PIWIIIFGVI FCIIIVAIAL LILSGIWQRR RKNKEPSEVD
181 DAEDKCENMI TIENGIPSDP LDMKGGHIND AFMTEDERLT PL
```

Figure 3H   156P5C12 amino acid sequence (SEQ ID NO:69) of 227 amino acids.

```
  1 MAPCHIRKYQ ESDRQWVVGL LSRGMAEHAP ATFRQLLKLP RTLILLLGGP LALLLVSGSW
 61 LLALVFSISL FPALWFLAKK PWTEYVDMTL CTDMSDITKS YLSERGSCFW VAESEEKVVG
121 MVGALPVDDP TLREKRLQLF HLSVDSEHRR QGIAKALVRT VLQFARDQGY SEVILDTGTI
181 QLSAMALYQS MGFKKTGQSF FCVWARLVAL HTVHFIYHLP SSKVGSL
```

Figure 3I   159P2B5 amino acid sequence (SEQ ID NO:70) of 224 amino acids.

```
  1 MVKREHGQER PTFWGWAATP APVSAPGNPP TGEGERQGSP PGGGFLGSTS FQRRGEKELL
 61 WERGQDVSRS VLAMRAILPP SLSKSVHFPP LPHSCTLVAL LSLGLQDPLG CRAPATKPTP
121 AGATLSASSL PRPCSPSASL LLSWPLFWGI LGGVFFLGSR ACTRTQARRH TGPAAALLRL
181 LFPAPRRPGA RSRAGYASPG SPERRSPGTA HKGSLPWPLA LRLL
```

Figure 3J   161P2B7A amino acid sequence (SEQ ID NO:71) of 190 amino acids.

```
  1 MEDEGQTKIK QRRSRTNFTL EQLNELERLF DETHYPDAFM REELSQRLGL SEARVQVWFQ
 61 NRRAKCRKQE NQLHKGVLIG AASQFEACRV APYVNVGALR MPFQQVQAQL QLDSAVAHAH
121 HHLHPHLAAH APYMMFPAPP FGLPLATLAA DSASAASVVA AAAAAKTTSK NSSIADLRLK
181 AKKHAAALGL
```

Figure 3K   179P3G7 amino acid sequence (SEQ ID NO:72) of 342 amino acids.

```
  1 MTCPRNVTPN SYAEPLAAPG GGERYSRSAG MYMQSGSDFN CGVMRGCGLA PSLSKRDEGS
 61 SPSLALNTYP SYLSQLDSWG DPKAAYRLEQ PVGRPLSSCS YPPSVKEENV CCMYSAENRA
121 KSGPEAALYS HPLPESCLGE HEVPVPSYYR ASPSYSALDK TPHCSGANDF EAPFEQRASL
181 NPRAEHLESP QLGGKVSFPE TPKSDSQTPS PNEIKTEQSL AGPKGSPSES EKERAKAADS
241 SPDTSDNEAK EEIKAENTTG NWLTAKSGRK KRCPYTKHQT LELEKEFLFN MYLTRERRLE
301 ISKTINLTDR QVKIWFQNRR MKLKKMNREN RIRELTSNFN FT
```

Figure 3L  184P3C10B amino acid sequence (SEQ ID NO:73) of 372 amino acids.

```
  1 MKYLRHRRPN ATLILAIGAF TLLLFSLLVS PPTCKVQEQP PAIPEALAWP TPPTRPAPAP
 61 CHANTSMVTH PDFATQPQHV QNFLLYRHCR HFPLLQDVPP SKCAQPVFLL LVIKSSPSNY
121 VRRELLRRTW GRERKVRGLQ LRLLFLVGTA SNPHEARKVN RLLELEAQTH GDILQWDFHD
181 SFFNLTLKQV LFLQWQETRC ANASFVLNGD DDVFAHTDNM VFYLQDHDPG RHLFVGQLIQ
241 NVGPIRAFWS KYYVPEVVTQ NERYPPYCGG GGFLLSRFTA AALRRAAHVL DIFPIDDVFL
301 GMCLELEGLK PASHSGIRTS GVRAPSQHLS SFDPCFYRDL LLVHRFLPYE MLLMWDALNQ
361 PNLTCGNQTQ IY
```

Figure 3M  184P3G10 amino acid sequence (SEQ ID NO:74) of 748 amino acids.

```
  1 MNTAFAGKMV SVTKYDLTGC SAFCRSCQRA TMTSQPLRLA EEYGPSPGES ELAVNPFDGL
 61 PFSSRYYELL KQRQALPIWA ARFTFLEQLE SNPTGVVLVS GEPGSGKSTQ IPQWCAEFAL
121 ARGFQKGQVT VTQPYPLAAR SLALRVADEM DLTLGHEVGY SIPQEDCTGP NTLLRFCWDR
181 LLLQEVASTR GTGAWGVLVL DEAQERSVAS DSLQGLLQDA RLEKLPGDLR VVVVTDPALE
241 PKLRAFWGNP PIVHIPREPG ERPSIYWDT IPPDRVEAAC QAVLELCRKE LPGDVLVFLP
301 SEEEISLCCE SLSREVESLL LQGLPPRVLP LHPDCGRAVQ AVYEDMDARK VVVTHWLADF
361 SFSLPSIQHV IDSGLELRSV YNPRIRAEFQ VLRPISKCQA EARRLRARGF PPGSCLCLYP
421 KSFLELEAPP LPQPRVCEEN LSSLVLLLKR RQIAEPGECH FLDQPAPEAL MQALEDLDYL
481 AALDDDGDLS DLGVILSEFP LAPELAKALL ASCEFDCVDE MLTLAAMLTA APGFTRPPLS
541 AEEAALRRAL EHTDGDHSSL IQVYEAFIQS GADEAWCQAR GLNWAALCQA HKLRGELLEL
601 MQRIELPLSL PAFGSEQNRR DLQKALVSGY FLKVARDTDG TGNYLLLTHK HVAQLSSYCC
661 YRSRRAPARP PPWVLYHNFT ISKDNCLSIV SEIQPQMLVE LAPPYFLSNL PPSESRDLLN
721 QLREGMADST AGSKSSSAQE FRDPCVLQ
```

Figure 3N.1  185P2C9 v.1 amino acid sequence (SEQ ID NO:75) of 1307 amino acids.

```
   1 MEDMRGQQER EGPGRDHAPS IPTSPFGDSL ESSTELRRHL QFVEEEAELL RRSISEIEDH
  61 NRQLTHELSK FKFEPPREPG WLGEGASPGA GGGAPLQEEL KSARLQISEL SGKVLKLQHE
 121 NHALLSNIQR CDLAAHLGLR APSPRDSDAE SDAGKKESDG EESRLPQPKR EGPVGGESDS
 181 EEMFEKTSGF GSGKPSEASE PCPTELLKAR EDSEYLVTLK HEAQRLERTV ERLITDTDSF
 241 LHDAGLRGGA PLPGPGLQGE EEQGEGDQQE PQLLGTINAK MKAFKKELQA FLEQVNRIGD
 301 GLSPLPHLTE SSSFLSTVTS VSRDSPIGNL GKELGPDLQS RLKEQLEWQL GPARGDERES
 361 LRLRAARELH RRADGDTGSH GLGGQTCFSL EMEEEHLYAL RWKELEMHSL ALQNTLHERT
 421 WSDEKNLMQQ ELRSLKQNIF LFYVKLRWLL KHWRQGKQME EEGEEFTEGE HPETLSRLGE
 481 LGVQGGHQAD GPDHDSDRGC GFPVGEHSPH SRVQIGDHSL RLQTADRGQP HKQVVENQQL
 541 FSAFKALLED FRAELREDER ARLRLQQQYA SDKAAWDVEW AVLKCRLEQL EEKTENKLGE
 601 LGSSAESKGA LKKEREVHQK LLADSHSLVM DLRWQIHHSE KNWNREKVEL LDRLDRDRQE
 661 WERQKKEFLW RIEQLQKENS PRRGGSFLCD QKDGNVRPFP HQGSLRMPRP VAMWPCADAD
 721 SIPFEDRPLS KLKESDRCSA SENLYLDALS LDDEPEEPPA HRPEREFRNR LPEEEENHKG
 781 NLQRAVSVSS MSEFQRLMDI SPFLPEKGLP STSSKEDVTP PLSPDDLKYI EEFNKSWDYT
 841 PNRGHNGGGP DLWADRTEVG RAGHEDSTEP FPDSSWYLTT SVTMTTDTMT SPEHCQKQPL
 901 RSHVLTEQSG LRVLHSPPAV RRVDSITAAG GEGPFPTSRA RGSPGDTKGG PPEPMLSRWP
 961 CTSPRHSRDY VEGARRPLDS PLCTSLGFAS PLHSLEMSKN LSDDMKEVAF SVRNAICSGP
1021 GELQVKDMAC QTNGSRTMGT QTVQTISVGL QTEALRGSGV TSSPHKCLTP KAGGGATPVS
1081 SPSRSLRSRQ VAPAIEKVQA KFERTCCSPK YGSPKLQRKP LPKADQPNNR TSPGMAQKGY
1141 SESAWARSTT TRESPVHTTI NDGLSSLFNI IDHSPVVQDP FQKGLRAGSR SRSAEPRPEL
1201 GPGQETGTNS RGRSPSPIGV GSEMCREEGG EGTPVKQDLS APPGYTLTEN VARILNKKLL
1261 EHALKEERRQ AAHGPPGLHS DSHSLGDTAE PGPMENQTVL LTAPWGL
```

Figure 3N.2  185P2C9 v.2 clone 1 amino acid sequence (SEQ ID NO:76) of 1142 amino acids.

```
   1 MEDTRGQQER EGPGRDHAPS IPTSPFGDSL ESSTELRRHL QFVEEEAELL RRSISEIEDH
  61 NRQLTHELSK FKFEPPREPG WLGEGASPGA GGGAPLQEEL KSARLQISEL SGKVLKLQHE
 121 NHALLSNIQR CDLAAHLGLR APSPRDSDAE SDAGKKESDG EESRLPQPKR EGPVGGESDS
 181 EEMFEKTSGF GSGKPSEASE PCPTELLKAR EDSEYLVTLK HEAQRLERTV ERLITDTDSF
 241 LHDAGLRGGA PLPGPGLQGE EEQGEGDQQE PQLLGTINAK MKAFKKELQA FLQQVNRIGD
 301 GLSPLPHLTE SSSFLSTVTS VSRDSPIGNL GKELGPDLQS RLKEQLEWQL GPAQGDERES
 361 LRLRAARELH RRADGDTGSH GLGGQTCFSL EMEEEHLYAL RWKELEMHSL ALQNTLHERT
 421 WSDEKNLMQQ ELRSLKQNIF LFYVKLRWLL KHWRQGKQME EEGEEFTEGE HPETLSRLGE
 481 LGVQGGHQAD GPDHDSDRGC GFPVGEHSPH SRVQIGDHSL RLQTADRGQP HKQVVENQQL
 541 FSAFKALLED FRAELREDER ARLRLQQQYA SDKAAWDVEW AVLKCRLEQL EEKTENKLGE
 601 LGSSAESKGA LKKEREVHQK LLADSHSLVM DLRWQIHHSE KNWNREKVEL LDRLDRDRQE
 661 WERQKKEFLW RIEQLQKENS PRRGGSFLCD QKDGNVRPFP HQGSLRMPRP VAMWPCADAD
 721 SIPFEDRPLS KLKESDRCSA SENLYLDALS LDDEPEEPPA HRPEREFRNR LPEEEENHKG
 781 NLQRAVSVSS MSEFQRLMDI SPFLPEKGLP STSSKEDVTP PLSPDDLKYI EEFNKSWDYT
 841 PNRGHNGGGP DLWADRTEVG RAGHEDSTEP FPDSSWYLTT SVTMTTDTMT SPEHCQKQPL
 901 RSHVLTEQSG LRVLHSPPAV RRVDSITAAG GEGPFPTSRA RGSPGDTKGG PPEPMLSRWP
 961 CTSPRHSRDY VEGARRPLDS PLCTSLGFAS PLHSLEMSKN LSDDMKEVAF SVRNAICSGP
1021 GELQVKDMAC QTNGSRTMGT QTVQTISVGL QTEALRGSGV TSSPHKCLTP KAGGGATPVS
1081 SPSRSLRSRQ VAPAIEKVQA KFERTCCSPK YGSPKLQRKP LPKADQPNNR PGNRHQFPRK
1141 VA
```

Figure 3N.3  185P2C9 v.3 clone 2 amino acid sequence ((SEQ ID NO:77) of 1313 amino acids.

```
   1 MEDTRGQQER EGPGRDHAPS IPTSPFGDSL ESSTELRRHL QFVEEEAELL RRSISEIEDH
  61 NRQLTHELSK FKFEPPREPG WLGEGASPGA GGGAPLQEEL KSARLQISEL SGKVLKLQHE
 121 NHALLSNIQR CDLAAHLGLR APSPRDSDAE SDAGKKESDG EESRLPQPKW EGPVGGESDS
 181 EEMFEKTSGF GSGKPSEASE PCPTELLKAR EDSEYLVTLK HEAQRLERTV ERLITDTDSF
 241 LHDAGLRGGA PLPGPGLQGE EEQGEGDQQE PQLLGTINAK MKAFKKELQA FLEQVNRIGD
 301 GLSPLPHLTE SSSFLSTVTS VSRDSPIGNL GKELGPDLQS RLKEQLEWQL GPARGDERES
 361 LRLRAARELH RRADGDTGSH GLGGQTCFSL EMEEEHLYAL RWKELEMHSL ALQNTLHERT
 421 WSDEKNLMQQ ELRSLKQNIF LFYVKLRWLL KHWRQGKQME EEGEEFTEGE HPETLSRLGE
 481 LGVQGGHQAD GPDHDSDRGC GFPVGEHSPH SRVQIGDHSL RLQTADRGQP HKQVVENQQL
 541 FSAFKALLED FRAELREDER ARLRLQQQYA SDKAAWDVEW AVLKCRLEQN CCGYPRINIE
 601 EETLGFTRLP AGSTVKTLKS LGLQRLELEE KTENKLGELG SSAESKGALK KEREVHQKLL
 661 ADSHSLVMDL RWQIHHSEKN WNREKVELLD RLDRDRQEWE RQKKEFLWRI EQGSLRMPRP
 721 VAMWPCADAD SIPFEDRPLS KLKESDRCSA SENLYLDALS LDDEPEEPPA HRPEREFRNR
 781 LPEEEENHKG NLQRAVSVSS MSEFQRLMDI SPFLPEKGLP STSSKEDVTP PLSPDDLKYI
 841 EEFNKSWDYT PNRGHNGGGP DLWADRTEVG RAGHEDSTEP FPDSSWYLTT SVTMTTDTMT
 901 SPEHCQKQPL RSHVLTEQSG LRVLHSPPAV RRVDSITAAG GEGPFPTSRA RGSPGDTKGG
 961 PPEPMLSRWP CTSPRHSRDY VEGARRPLDS PLCTSLGFAS PLHSLEMSKN LSDDMKEVAF
1021 SVRNAICSGP GELQVKDMAC QTNGSRTMGT QTVQTISVGL QTEALRGSGV TSSPHKCLTP
1081 KAGGGATPVS SPSRSLRSRQ VAPAIEKVQA KFERTCCSPK YGSPKLQRKP LPKADQPNNR
1141 TSPGMAQKGY SESAWARSTT TRESPVHTTI NDGLSSLFNI IDHSPVVQDP FQKGLRAGSR
1201 SRSAEPRPEL GPGQETGTNS RGRSPSPIGV GSEMCREEGG EGTPVKQDLS APPGYTLTEN
1261 VARILNKKLL EHALKEERRQ AAHGPPGLHS DSHSLGDTAE PGPMEELPCS ALA
```

Figure 3(O)  185P3C2 amino acid sequence (SEQ ID NO:78) of 551 amino acids.

```
   1 NCLLRPKNKS VRWGPGAGAA LLRPSPAALG AGSRACSVPP AAPAQTPRPQ VSAPAWGPGR
  61 AARGSGRMER RMKAGYLDQQ VPYTFSSKSP GNGSLREALI GPLGKLMDPG SLPPLDSEDL
 121 FQDLSHFQET WLAEAQVPDS DEQFVPDFHS ENLAFHSPTT RIKKEPQSPR TDPALSCSRK
 181 PPLPYHHGEQ CLYSSAYDPP RQIAIKSPAP GALGQSPLQP FPRAEQRNFL RSSGTSQPHP
 241 GHGYLGEHSS VFQQPLDICH SFTSQGGGRE PLPAPYQHQL SEPCPPYPQQ SFKQEYHDPL
 301 YEQAGQPAVD QGGVNGHRYP GAGVVIKQEQ TDFAYDSDVT GCASMYLHTE GFSGPSPGDG
 361 AMGYGYEKPL RPFPDDVCVV PEKFEGDIKQ EGVGAFREGP PYQRRGALQL WQFLVALLDD
 421 PTNAHFIAWT GRGMEFKLIE PEEVARLWGI QKNRPAMNYD KLSRSLRYYY EKGIMQKVAG
 481 ERYVYKFVCE PEALFSLAFP DNQRPALKAE FDRPVSEEDT VPLSHLDESP AYLPELAGPA
 541 QPFGPKGGYS Y
```

Figure 3P  186P1H9 amino acid sequence (SEQ ID NO:79) of 430 amino acids.

```
  1 MLALLAASVA LAVAAGAQDS PAPGSRFVCT ALPPEAVHAG CPLPAMPMQG GAQSPEEELR
 61 AAVLQLRETV VQQKETLASA RAIRELTGKL ARCEGLAGGK ARGAGATGKD TMGDLPRDPG
121 HVVEQLSRSL QTLKDRLESL EHQLRANVSN AGLPGDFREV LQQRLGELER QLLRKVAELE
181 DEKSLLHNET SAHRQKTEST LNALLQRVTE LERGNSAFKS PDAFKVSLPL RTNYLYGKIK
241 KTLPELYAFT ICLWLRSSAS PGIGTPFSYA VPGQANEILL IEWGNNPIEL LINDKVAQLP
301 LFVSDGKWHH ICVTWTTRDG MWEAFQDGEK LGTGENLAPW HPIKPGGVLI LGQEQDTVGG
361 RFDATQAFVG ELSQFNIWDR VLRAQEIVNI ANCSTNMPGN IIPWVDNNVD VFGGASKWPV
421 ETCEEALLDL
```

Figure 3Q  187P3F2 amino acid sequence (SEQ ID NO:80) of 500 amino acids.

```
  1 MATAASNPYL PGNSLLAAGS IVHSDAAGAG GGGGGGGGSG GGGAGGGGGG MQPGSAAVTS
 61 GAYRGDPSSV KMVQSDFMQG AMAASNGGHM LSHAHQWVTA LPHAAAAAAA AAAAAVEASS
121 PWSGSAVGMA GSPQQPPQPP PPPPQGPDVK GGAGRDDLHA GTALHHRGPP HLGPPPPPPH
181 QGHPGGWGAA AAAAAAAAA AAAAHLPSMA GGQQPPPQSL LYSQPGGFTV NGMLSAPPGP
241 GGGGGGAGGG AQSLVHPGLV RGDTPELAEH HHHHHHHAHP HPPHPHHAQG PPHHGGGGGG
301 AGPGLNSHDP HSDEDTPTSD DLEQFAKQFK QRRIKLGFTQ ADVGLALGTL YGNVFSQTTI
361 CRFEALQLSF KNMCKLKPLL NKWLEEADSS TGSPTSIDKI AAQGRKRKKR TSIEVSVKGA
421 LESHFLKCPK PSAQEITNLA DSLQLEKEVV RVWFCNRRQK EKRMTPPGIQ QQTPDDVYSQ
481 VGTVSADTPP PHHGLQTSVQ
```

Figure 3R  192P2G7 amino acid sequence (SEQ ID NO:81) of 284 amino acids.

```
  1 MAESEAETPS TPGEFESKYF EFHGVRLPPF CRGKMEEIAN FPVRPSDVWI VTYPKSGTSL
 61 LQEVVYLVSQ GADPDEIGLM NIDEQLPVLE YPQPGLDIIK ELTSPRLIKS HLPYRFLPSD
121 LHNGDSKVIY MARNPKDLVV SYYQFHRSLR TMSYRGTFQE FCRRFMNDKL GYGSWFEHVQ
181 EFWEHRMDSN VLFLKYEDMH RDLVTMVEQL ARFLGVSCDK AQLEALTEHC HQLVDQCCNA
241 EALPVGRGRV GLWKDIFTVS MNEKFDLVYK QKMGKCDLTF DFYL
```

Figure 4:

74P3B3 (SEQ ID NO 82) Alignment with Gag-Pro-Pol-Env protein (SEQ ID NO 83).

Score = 149 bits (375), Expect = 3e-35
Identities = 92/219 (42%), Positives = 121/219 (55%), Gaps = 21/219 (9%)

```
Query:    5 KKGLEEQSAPHWDHPEWPPIKQCSLEPWRSESQ------ICPVSRMNELWPQEPQAHGVA  59
            K+ E ++ P  +   WPP  Q   ESQ           +PQ P
Sbjct:  197 KQVKENKTQPPVAYQYWPPAELQYRPPP---ESQYGYPGMPAPQGRAPYPQPPTR----  249

Query:   60 PVQHKAALPSNVNESPLQFIIRQARLAGDLDAWQFAVVLQPPRQQGAH------QAVW  112
            P +    S L II ++R  GD +AWQF + L+P     GA        +A +
Sbjct:  250 --RLNPTAPPSRQGSELHEIIDKSRKEGDTEAWQFPITLEPMPGEGAQEGEPPTVEARY  307

Query:  113 EPFSFKLLKDLKAAVGQYGPNSPFIRSLLQSVAQNKLLTPCDWEILTKVTLSPSQFLQFK  172
            + FS K+LKD+K V QYGPNSP++R+LL S+A    L P DWEIL K +LSPSQFLQFK
Sbjct:  308 KSFSIKMLKDMKEGVKQYGPNSPYMRTLLDSIAYGHRLIPYDWEILAKSSLSPSQFLQFK  367

Query:  173 TWWTDEAQNQDRKNRAANPAIATTFEQLLGIGGQWGTVN  211
            TWW D  Q Q R+NRAANP + I   +QLLGIG  W T++
Sbjct:  368 TWWIDGVQEQVRRNRAANPPVNIDADQILLGIGQNWSTIS  406
```

83P4B8 (SEQ ID NO 84) Alignment with KIAA1794 protein (SEQ ID NO 85).

Score = 1416 bits (3665), Expect = 0.0
Identities = 793/796 (99%), Positives = 796/796 (99%)

```
Query:  547 ANQLDARKSAVAGFLLLLKNFKVLGSLSSSQCSQSLSVSQVHVDHSHYNSVANETFCLE  606
            A+QLDARKSAVAGFLLLLKNFKVLGSLSSSQCSQSLSVSQVHVDHSHYNSVANETFCLE
Sbjct:    1 ASQLDARKSAVAGFLLLLKNFKVLGSLSSSQCSQSLSVSQVHVDHSHYNSVANETFCLE   60

Query:  607 IMDSLRRCLSQQADVRLMLYEGFYDVLRRNSQLANSVMQTLLSQLKQFYEPKPDLLPPLK  666
            IMDSLRRCLSQQADVRLMLYEGFYDVLRRNSQLANSVMQTLLSQLKQFYEPKPDLLPPLK
Sbjct:   61 IMDSLRRCLSQQADVRLMLYEGFYDVLRRNSQLANSVMQTLLSQLKQFYEPKPDLLPPLK  120

Query:  667 LDACILTQGDKISLQEPLDYLLCCIQHCLAWYKNTVIPLQQGEEEEEEAFYEDLDDIL  726
            L+ACILTQGDKISLQEPLDYLLCCIQHCLAWYKNTVIPLQQGEEEEEEAFYEDLDDIL
Sbjct:  121 LEACILTQGDKISLQEPLDYLLCCIQHCLAWYKNTVIPLQQGEEEEEEAFYEDLDDIL  180

Query:  727 ESITNRMIKSELEDFELDKSADFSQSTSIGIKNNISAFLVMGVCEVLIEYNFSISSFSKN  786
            ESITNRMIKSELEDFELDKSADFSQSTSIGIKNNISAFLVMGVCEVLIEYNFSISSFSKN
Sbjct:  181 ESITNRMIKSELEDFELDKSADFSQSTSIGIKNNISAFLVMGVCEVLIEYNFSISSFSKN  240

Query:  787 RFEDIISLFMCYKKLSDILNEKAGKAKTKMANKTSDSLLSMKFVSSLLTALFRDSIQSHQ  846
            RFEDIISLFMCYKKLSDILNEKAGKAKTKMANKTSDSLLSMKFVSSLLTALFRDSIQSHQ
Sbjct:  241 RFEDIISLFMCYKKLSDILNEKAGKAKTKMANKTSDSLLSMKFVSSLLTALFRDSIQSHQ  300
```

Figure 4 (continued)

```
Query:  847  ESLSVLRSSNEFMRYAVNVALQKVQQLKETGHVSGPDGQNPEKIFQNLCDITRVLLWRYT  906
             ESLSVLRSSNEFMRYAVNVALQKVQQLKETGHVSGPDGQNPEKIFQNLCD+TRVLLWRYT
Sbjct:  301  ESLSVLRSSNEFMRYAVNVALQKVQQLKETGHVSGPDGQNPEKIFQNLCDLTRVLLWRYT  360

Query:  907  SIPTSVEESGKKEKGKSISLLCLEGLQKIFSAVQQFYQPKIQQFLRALDVTDKEGEERED  966
             SIPTSVEESGKKEKGKSISLLCLEGLQKIFSAVQQFYQPKIQQFLRALDVTDKEGEERED
Sbjct:  361  SIPTSVEESGKKEKGKSISLLCLEGLQKIFSAVQQFYQPKIQQFLRALDVTDKEGEERED  420

Query:  967  ADVSVTQRTAFQIRQFQRSLLNLLSSQEEDFNSKEALLLVTVLTSLSKLLEPSSPQFVQM  1026
             ADVSVTQRTAFQIRQFQRSLLNLLSSQEEDFNSKEALLLVTVLTSLSKLLEPSSPQFVQM
Sbjct:  421  ADVSVTQRTAFQIRQFQRSLLNLLSSQEEDFNSKEALLLVTVLTSLSKLLEPSSPQFVQM  480

Query:  1027 LSWTSKICKENSREDALFCKSLMNLLFSLHVSYKSPVILLRDLSQDIHGHLGDIDQDVEV  1086
             LSWTSKICKENSREDALFCKSLMNLLFSLHVSYKSPVILLRDLSQDIHGHLGDIDQDVEV
Sbjct:  481  LSWTSKICKENSREDALFCKSLMNLLFSLHVSYKSPVILLRDLSQDIHGHLGDIDQDVEV  540

Query:  1087 EKTNHFAIVNLRTAAPTVCLLVLSQAEKVLEEVDWLITKLKGQVSQETLSEEASSQATLP  1146
             EKTNHFAIVNLRTAAPTVCLLVLSQAEKVLEEVDWLITKLKGQVSQETLSEEASSQATLP
Sbjct:  541  EKTNHFAIVNLRTAAPTVCLLVLSQAEKVLEEVDWLITKLKGQVSQETLSEEASSQATLP  600

Query:  1147 NQPVEKAIIMQLGTLLITFFHELVQTALPSGSCVDTLLKDLCKMYTTLTALVRYYLQVCQS  1206
             NQPVEKAIIMQLGTLLITFFHELVQTALPSGSCVDTLLKDLCKMYTTLTALVRYYLQVCQS
Sbjct:  601  NQPVEKAIIMQLGTLLITFFHELVQTALPSGSCVDTLLKDLCKMYTTLTALVRYYLQVCQS  660

Query:  1207 SGGIPKNMEKLVKLSGSHLTPLCYSFISYVQNKSKSLNYTGEKKEKPAAVATAMARVLRE  1266
             SGGIPKNMEKLVKLSGSHLTPLCYSFISYVQNKSKSLNYTGEKKEKPAAVATAMARVLRE
Sbjct:  661  SGGIPKNMEKLVKLSGSHLTPLCYSFISYVQNKSKSLNYTGEKKEKPAAVATAMARVLRE  720

Query:  1267 TKPIPNLIFAIEQYEKFLIHLSKKSKVNLMQHMKLSTSRDFKIKGNILDMVLREDGEDEN  1326
             TKPIPNLIFAIEQYEKFLIHLSKKSKVNLMQHMKLSTSRDFKIKGNILDMVLREDGEDEN
Sbjct:  721  TKPIPNLIFAIEQYEKFLIHLSKKSKVNLMQHMKLSTSRDFKIKGNILDMVLREDGEDEN  780

Query:  1327 EEGTASEHGGQNKEPA  1342
             EEGTASEHGGQNKEPA
Sbjct:  781  EEGTASEHGGQNKEPA  796
```

109P1D4 (SEQ ID NO 86) Alignment with protocadherin 11 (SEQ ID NO 87).
Score = 1896 bits (4912), Expect = 0.0
Identities = 1010/1011 (99%), Positives = 1010/1011 (99%)

```
Query:  1  MDLLSGTYIFAVLLACVVFHSGAQEKNYTIREEMPENVLIGDLLKDLNLSLIPNKSLTTA  60
           MDLLSGTYIFAVLLACVVFHSGAQEKNYTIREEMPENVLIGDLLKDLNLSLIPNKSLTTA
Sbjct:  1  MDLLSGTYIFAVLLACVVFHSGAQEKNYTIREEMPENVLIGDLLKDLNLSLIPNKSLTTA  60
```

Figure 4 (continued)

```
Query:  61  MQFKLVYKTGDVPLIRIEEDTGEIFTTGARIDREKLCAGIPRDEHCFYEVEVAILPDEIF  120
Sbjct:  61  MQFKLVYKTGDVPLIRIEEDTGEIFTTGARIDREKLCAGIPRDEHCFYEVEVAILPDEIF  120

Query: 121  RLVKIRFLIEDINDNAPLFPATVINISIPENSAINSKYTLPAAVDPDVGINGVQNYELIK  180
Sbjct: 121  RLVKIRFLIEDINDNAPLFPATVINISIPENSAINSKYTLPAAVDPDVGINGVQNYELIK  180

Query: 181  SQNIFGLDVIETPEGDKMPQLIVQKELDREEKDTYVMKVKVEDGGFPQRSSTAILQVSVT  240
Sbjct: 181  SQNIFGLDVIETPEGDKMPQLIVQKELDREEKDTYVMKVKVEDGGFPQRSSTAILQVSVT  240

Query: 241  DTNDNHPVFKETEIEVSIPENAPVGTSVTQLHATDADIGENAKIHFSFSNLVSNIARRLF  300
Sbjct: 241  DTNDNHPVFKETEIEVSIPENAPVGTSVTQLHATDADIGENAKIHFSFSNLVSNIARRLF  300

Query: 301  HLNATTGLITIKEPLDREETPNHKLLVLASDGGLMPARAMVLVNVTDVNDNVPSIDIRYI  360
Sbjct: 301  HLNATTGLITIKEPLDREETPNHKLLVLASDGGLMPARAMVLVNVTDVNDNVPSIDIRYI  360

Query: 361  VNPVNDTVVLSENIPLNTKIALITVTDKDADHNGRVTCFTDHEIPFRLRPVFSNQFLLET  420
Sbjct: 361  VNPVNDTVVLSENIPLNTKIALITVTDKDADHNGRVTCFTDHEIPFRLRPVFSNQFLLET  420

Query: 421  AAYLDYESTKEYAIKLLAADAGKPPLNQSAMLFIKVKDENDNAPVFTQSFVTVSIPENNS  480
Sbjct: 421  AAYLDYESTKEYAIKLLAADAGKPPLNQSAMLFIKVKDENDNAPVFTQSFVTVSIPENNS  480

Query: 481  PGIQLTKVSAMDADSGPNAKINYLLGPDAPPEFSLDCRTGMLTVVKKLDREKEDKYLFTI  540
Sbjct: 481  PGIQLTKVSAMDADSGPNAKINYLLGPDAPPEFSLDCRTGMLTVVKKLDREKEDKYLFTI  540

Query: 541  LAKDNGVPPLTSNVTVFVSIIDQNDNSPVFTHNEYNFYVPENLPRHGTVGLITVTDPDYG  600
Sbjct: 541  LAKDNGVPPLTSNVTVFVSIIDQNDNSPVFTHNEYNFYVPENLPRHGTVGLITVTDPDYG  600

Query: 601  DNSAVTLSILDENDDFTIDSQTGVIRPNISFDREKQESYTFYVKAEDGGRVSRSSSAKVT  660
Sbjct: 601  DNSAVTLSILDENDDFTIDSQTGVIRPNISFDREKQESYTFYVKAEDGGRVSRSSSAKVT  660

Query: 661  INVVDVNDNKPVFIVPSNCSYELVLPSTNPGTVVFQVIAVDNDTGMNAEVCYSIVGGNT  720
Sbjct: 661  INVVDVNDNKPVFIVPSNCSYELVLPSTNPGTVVFQVIAVDNDTGMNAEV YSIVGGNT  720

Query: 721  RDLFAIDQETGNITLMEKCDVTDLGLHRVLVKANDLGQPDSLFSVVIVNLFVNESVTNAT  780
```

Figure 4 (continued)

```
Sbjct: 721  RDLFAIDQETGNITLMEKCDVTDLGLHRVLVKANDLGQPDSLFSVIVNLFVNESVTNAT 780

Query: 781  LINELVRKSTEAPVTPNTEIADVSSPTSDYVKILVAAVAGTITVVVIFITAVVRCRQAP 840
            LINELVRKSTEAPVTPNTEIADVSSPTSDYVKILVAAVAGTITVVVIFITAVVRCRQAP
Sbjct: 781  LINELVRKSTEAPVTPNTEIADVSSPTSDYVKILVAAVAGTITVVVIFITAVVRCRQAP 840

Query: 841  HLKAAQKNKQNSEWATPNPENRQMIMMKKKKKKKKHSPKNLLLNFVTIEETKADDVDSDG 900
            HLKAAQKNKQNSEWATPNPENRQMIMMKKKKKKKKHSPKNLLLNFVTIEETKADDVDSDG
Sbjct: 841  HLKAAQKNKQNSEWATPNPENRQMIMMKKKKKKKKHSPKNLLLNFVTIEETKADDVDSDG 900

Query: 901  NRVTLDLPIDLEEQTMGKYNWVTTPTTFKPDSPDLARHYKSASPQPAFQIQPETPLNSKH 960
            NRVTLDLPIDLEEQTMGKYNWVTTPTTFKPDSPDLARHYKSASPQPAFQIQPETPLNSKH
Sbjct: 901  NRVTLDLPIDLEEQTMGKYNWVTTPTTFKPDSPDLARHYKSASPQPAFQIQPETPLNSKH 960

Query: 961  HIIQELPLDNTFVACDSISKCSSSSSDPYSVSDCGYPVTTFEVPVSVHTRP 1011
            HIIQELPLDNTFVACDSISKCSSSSSDPYSVSDCGYPVTTFEVPVSVHTRP
Sbjct: 961  HIIQELPLDNTFVACDSISKCSSSSSDPYSVSDCGYPVTTFEVPVSVHTRP 1011
```

154P2A8 (SEQ ID NO 88) Alignment with orphan G protein-coupled receptor 87 (SEQ ID NO 89).

Score = 526 bits (1356), Expect = e-149
Identities = 288/288 (100%), Positives = 288/288 (100%)

```
Query:   1  RNKTSFIFYLKNIVVADLIMTLTFPFRIVHDAGFGPWYFKFILCRYTSVLFYANMYTSIV  60
            RNKTSFIFYLKNIVVADLIMTLTFPFRIVHDAGFGPWYFKFILCRYTSVLFYANMYTSIV
Sbjct:  71  RNKTSFIFYLKNIVVADLIMTLTFPFRIVHDAGFGPWYFKFILCRYTSVLFYANMYTSIV 130

Query:  61  FLGLISIDRYLKVVKPFGDSRMYSITFFTKVLSVCVWVIMAVLSLPNIILTNGQPTEDNIH 120
            FLGLISIDRYLKVVKPFGDSRMYSITFFTKVLSVCVWVIMAVLSLPNIILTNGQPTEDNIH
Sbjct: 131  FLGLISIDRYLKVVKPFGDSRMYSITFFTKVLSVCVWVIMAVLSLPNIILTNGQPTEDNIH 190

Query: 121  DCSKLKSPLGVKWHTAVTVYNSCLFVAVLVILIGCYIAISRYIHKSSRQFISQSSRKRKH 180
            DCSKLKSPLGVKWHTAVTVYNSCLFVAVLVILIGCYIAISRYIHKSSRQFISQSSRKRKH
Sbjct: 191  DCSKLKSPLGVKWHTAVTVYNSCLFVAVLVILIGCYIAISRYIHKSSRQFISQSSRKRKH 250

Query: 181  NQSIRVVVAVFFTCFLPYHLCRIPFTFSHLDRLLDESAQKILYYCKEITLFLSACNVCLD 240
            NQSIRVVVAVFFTCFLPYHLCRIPFTFSHLDRLLDESAQKILYYCKEITLFLSACNVCLD
Sbjct: 251  NQSIRVVVAVFFTCFLPYHLCRIPFTFSHLDRLLDESAQKILYYCKEITLFLSACNVCLD 310

Query: 241  PIIYFFMCRSFSRRLFKKSNIRTRSESIRSLQSVRRSEVRIYYDYTDV 288
            PIIYFFMCRSFSRRLFKKSNIRTRSESIRSLQSVRRSEVRIYYDYTDV
Sbjct: 311  PIIYFFMCRSFSRRLFKKSNIRTRSESIRSLQSVRRSEVRIYYDYTDV 358
```

Figure 4 (continued)

156P1D4 (SEQ ID NO 90) Alignment with kidney-specific membrane protein NX-17 (SEQ ID NO 91).
Score = 424 bits (1089), Expect = e-118
Identities = 222/222 (100%), Positives = 222/222 (100%)

```
Query:   1  MLWLLFFLVTAIHAELCQPGAENAFKVRLSIRTALGDKAYAWDTNEEYLFKAMVAFSMRK   60
            MLWLLFFLVTAIHAELCQPGAENAFKVRLSIRTALGDKAYAWDTNEEYLFKAMVAFSMRK
Sbjct:   1  MLWLLFFLVTAIHAELCQPGAENAFKVRLSIRTALGDKAYAWDTNEEYLFKAMVAFSMRK   60

Query:  61  VPNREATEISHVLLCNVTQRVSFWFVVTDPSKNHTLPAVEVQSAIRMNKNRINNAFFLND  120
            VPNREATEISHVLLCNVTQRVSFWFVVTDPSKNHTLPAVEVQSAIRMNKNRINNAFFLND
Sbjct:  61  VPNREATEISHVLLCNVTQRVSFWFVVTDPSKNHTLPAVEVQSAIRMNKNRINNAFFLND  120

Query: 121  QTLEFLKIPSTLAPPMDPSVPIWIIIFGVIFCIIIVAIALLILSGIWQRRRKNKEPSEVD  180
            QTLEFLKIPSTLAPPMDPSVPIWIIIFGVIFCIIIVAIALLILSGIWQRRRKNKEPSEVD
Sbjct: 121  QTLEFLKIPSTLAPPMDPSVPIWIIIFGVIFCIIIVAIALLILSGIWQRRRKNKEPSEVD  180

Query: 181  DAEDKCENMITIENGIPSDPLDMKGGHINDAFMTEDERLTPL  222
            DAEDKCENMITIENGIPSDPLDMKGGHINDAFMTEDERLTPL
Sbjct: 181  DAEDKCENMITIENGIPSDPLDMKGGHINDAFMTEDERLTPL  222
```

156P5C12 (SEQ ID NO 92) Alignment with N-ACETYLTRANSFERASE CML1 (SEQ ID NO 93).
Score = 416 bits (1070), Expect = e-116
Identities = 227/227 (100%), Positives = 227/227 (100%)

```
Query:   1  MAPCHIRKYQESDRQWVGLLSRGMAEHAPATFRQLLKLPRTLILLLGGPLALLIVSGSW    60
            MAPCHIRKYQESDRQWVGLLSRGMAEHAPATFRQLLKLPRTLILLLGGPLALLIVSGSW
Sbjct:   1  MAPCHIRKYQESDRQWVGLLSRGMAEHAPATFRQLLKLPRTLILLLGGPLALLIVSGSW    60

Query:  61  LLALVFSISLFPALWFLAKKPWTEYDMTLCTDMSDITKSYLSERGSCFWVAESEEKVVG  120
            LLALVFSISLFPALWFLAKKPWTEYDMTLCTDMSDITKSYLSERGSCFWVAESEEKVVG
Sbjct:  61  LLALVFSISLFPALWFLAKKPWTEYDMTLCTDMSDITKSYLSERGSCFWVAESEEKVVG  120

Query: 121  MVGALPVDDPTLREKRLQLFHLSVDSEHRRQGIAKALVRTVLQFARDQGYSEVILDTGTI  180
            MVGALPVDDPTLREKRLQLFHLSVDSEHRRQGIAKALVRTVLQFARDQGYSEVILDTGTI
Sbjct: 121  MVGALPVDDPTLREKRLQLFHLSVDSEHRRQGIAKALVRTVLQFARDQGYSEVILDTGTI  180

Query: 181  QLSAMALYQSMGFKKTGQSFFCVWARLVALHTVHFIYHLPSSKVGSL  227
            QLSAMALYQSMGFKKTGQSFFCVWARLVALHTVHFIYHLPSSKVGSL
Sbjct: 181  QLSAMALYQSMGFKKTGQSFFCVWARLVALHTVHFIYHLPSSKVGSL  227
```

161P2B7a (SEQ ID NO 94) Alignment with OG-12b homeodomain protein (SEQ ID NO 95).
Score = 283 bits (723), Expect = 9e-76
Identities = 190/190 (100%), Positives = 190/190 (100%)

Figure 4 (continued)

```
Query:   1  MEDEGQTKIKQRRSRTNFTLEQLNELERLFDETHYPDAFMREELSQRLGLSEARVQVWFQ   60
Sbjct:   9  MEDEGQTKIKQRRSRTNFTLEQLNELERLFDETHYPDAFMREELSQRLGLSEARVQVWFQ   68

Query:  61  NRRAKCRKQENQLHKGVLIGAASQFEACRVAPYVNVGALRMPFQQVQAQLQLDSAVAHAH  120
Sbjct:  69  NRRAKCRKQENQLHKGVLIGAASQFEACRVAPYVNVGALRMPFQQVQAQLQLDSAVAHAH  128

Query: 121  HHLHPHLAAHAPYMMFPAPPFGLPLATLAADSASAASVAAAAAAKTTSKNSSIADLRLK   180
Sbjct: 129  HHLHPHLAAHAPYMMFPAPPFGLPLATLAADSASAASVAAAAAAKTTSKNSSIADLRLK   188

Query: 181  AKKHAAALGL                                                    190
Sbjct: 189  AKKHAAALGL                                                    198

179P3G7- (SEQ ID NO 96) Alignment with homeo box C10 (SEQ ID NO 97).
Score =  619 bits (1595), Expect = e-176
Identities = 342/342 (100%), Positives = 342/342 (100%)

Query:   1  MTCPRNVTPNSYAEPLAAPGGGERYSRSAGMYMQSGSDFNCGVMRGCGLAPSLSKRDEGS   60
Sbjct:   1  MTCPRNVTPNSYAEPLAAPGGGERYSRSAGMYMQSGSDFNCGVMRGCGLAPSLSKRDEGS   60

Query:  61  SPSLALNTYPSYLSQLDSWGDPKAAYRLEQPVGRPLSSCSYPPSVKEENVCCMYSAENRA  120
Sbjct:  61  SPSLALNTYPSYLSQLDSWGDPKAAYRLEQPVGRPLSSCSYPPSVKEENVCCMYSAENRA  120

Query: 121  KSGPEAALYSHPLPESCLGEHEVPVPSYYRASPSYSALDKTPHCSGANDFEAPFEQRASL  180
Sbjct: 121  KSGPEAALYSHPLPESCLGEHEVPVPSYYRASPSYSALDKTPHCSGANDFEAPFEQRASL  180

Query: 181  NPRAEHLESPQLGGKVSFPETPKSDSQTPSPNEIKTEQSLAGPKGSPSESEKERAKAADS  240
Sbjct: 181  NPRAEHLESPQLGGKVSFPETPKSDSQTPSPNEIKTEQSLAGPKGSPSESEKERAKAADS  240

Query: 241  SPDTSDNEAKEEIKAENTTGNWLTAKSGRKKRCPYTKHQTLELEKEFLFNMYLTRERRLE  300
Sbjct: 241  SPDTSDNEAKEEIKAENTTGNWLTAKSGRKKRCPYTKHQTLELEKEFLFNMYLTRERRLE  300

Query: 301  ISKTINLTDRQVKIWFQNRRMKLKKMNRENRIRELTSNFNFT                   342
Sbjct: 301  ISKTINLTDRQVKIWFQNRRMKLKKMNRENRIRELTSNFNFT                   342
```

Figure 4 (continued)

184P3C10B (SEQ ID NO 98) Alignment with type II membrane protein (SEQ ID NO 99).

Score = 720 bits (1859), Expect = 0.0
Identities = 372/372 (100%), Positives = 372/372 (100%)

```
Query:   1   MKYLRHRRPNATLLIAIGAFTLLLFSLLVSPPTCKVQEQPPAIPEALAWPTPTRPAPAP    60
             MKYLRHRRPNATLLIAIGAFTLLLFSLLVSPPTCKVQEQPPAIPEALAWPTPTRPAPAP
Sbjct:   1   MKYLRHRRPNATLLIAIGAFTLLLFSLLVSPPTCKVQEQPPAIPEALAWPTPTRPAPAP    60

Query:  61   CHANTSMVTHPDFATQPQHVQNFLLYRHCRHFPLLQDVPPSKCCAQPVFLLLVIKSSPSNY   120
             CHANTSMVTHPDFATQPQHVQNFLLYRHCRHFPLLQDVPPSKCCAQPVFLLLVIKSSPSNY
Sbjct:  61   CHANTSMVTHPDFATQPQHVQNFLLYRHCRHFPLLQDVPPSKCCAQPVFLLLVIKSSPSNY   120

Query: 121   VRRELLRRTWGRERKVRGLQLRLLFLVGTASNPHEARKVNRLLELEAQTHGDILQWDFHD   180
             VRRELLRRTWGRERKVRGLQLRLLFLVGTASNPHEARKVNRLLELEAQTHGDILQWDFHD
Sbjct: 121   VRRELLRRTWGRERKVRGLQLRLLFLVGTASNPHEARKVNRLLELEAQTHGDILQWDFHD   180

Query: 181   SFFNLTLKQVLFLQWQETRCANASFVLNGDDDVFAHTDNMVFYLQDHDPGRHLFVGQLIQ   240
             SFFNLTLKQVLFLQWQETRCANASFVLNGDDDVFAHTDNMVFYLQDHDPGRHLFVGQLIQ
Sbjct: 181   SFFNLTLKQVLFLQWQETRCANASFVLNGDDDVFAHTDNMVFYLQDHDPGRHLFVGQLIQ   240

Query: 241   NVGPIRAFWSKYYVPEVVTQNERYPPYCGGGGFLLSRFTAAALRRAAHVLDIFPIDDVFL   300
             NVGPIRAFWSKYYVPEVVTQNERYPPYCGGGGFLLSRFTAAALRRAAHVLDIFPIDDVFL
Sbjct: 241   NVGPIRAFWSKYYVPEVVTQNERYPPYCGGGGFLLSRFTAAALRRAAHVLDIFPIDDVFL   300

Query: 301   GMCLELEGLKPASHSGIRTSGVRAPSQHLSSFDPCFYRDLLLVHRFLPYEMLLMWDALNQ   360
             GMCLELEGLKPASHSGIRTSGVRAPSQHLSSFDPCFYRDLLLVHRFLPYEMLLMWDALNQ
Sbjct: 301   GMCLELEGLKPASHSGIRTSGVRAPSQHLSSFDPCFYRDLLLVHRFLPYEMLLMWDALNQ   360

Query: 361   PNLTCGNQTQIY   372
             PNLTCGNQTQIY
Sbjct: 361   PNLTCGNQTQIY   372
```

185P3C2 (SEQ ID NO 100) Alignment with E1A ENHANCER BINDING FACTOR (SEQ ID NO 101).

```
Query:   1   NCLLRPKNKSVRWGPGAGAALLRPSPAALGAGSRACSVPPAAPAQTPRPQVSAPAWGPGR    60
             NCLLRPKNKSVRWGPGAGAALLRPSPAALGAGSRACSVPPAAPAQTPRPQVSAPAWGPGR
Sbjct:   1   NCLLRPKNKSVRWGPGAGAALLRPSPAALGAGSRACSVPPAAPAQTPRPQVSAPAWGPGR    60

Query:  61   AARGSGRMERRMKAGYLDQQVPYTFSSKSPGNGSLREALIGPLGKLMDPGSLPPLDSEDL   120
             AARGSGRMERRMKAGYLDQQVPYTFSSKSPGNGSLREALIGPLGKLMDPGSLPPLDSEDL
Sbjct:  61   AARGSGRMERRMKAGYLDQQVPYTFSSKSPGNGSLREALIGPLGKLMDPGSLPPLDSEDL   120

Query: 121   FQDLSHFQETWLAEAQVPDSDEQFVPDFHSENLAFHSPTTRIKKEPQSPRTDPALSCSRK   180
             FQDLSHFQETWLAEAQVPDSDEQFVPDFHSENLAFHSPTTRIKKEPQSPRTDPALSCSRK
```

Figure 4 (continued)

```
Sbjct:  121  FQDLSHFQETWLAEAQVPDSDEQFVPDFHSENLAFHSPTTRIKKEPQSPRTDPALSCSRK  180

Query:  181  PPLPYHHGEQCLYSSAYDPPRQIAIKSPAPGALGQSPLQPFPRAEQRNFLRSSGTSQPHP  240
             PPLPYHHGEQCLYSSAYDPPRQIAIKSPAPGALGQSPLQPFPRAEQRNFLRSSGTSQPHP
Sbjct:  181  PPLPYHHGEQCLYSSAYDPPRQIAIKSPAPGALGQSPLQPFPRAEQRNFLRSSGTSQPHP  240

Query:  241  GHGYLGEHSSVFQQPLDICHSFTSQGGGREPLPAPYQHQLSEPCPPYPQQSFKQEYHDPL  300
             GHGYLGEHSSVFQQPLDICHSFTSQGGGREPLPAPYQHQLSEPCPPYPQQSFKQEYHDPL
Sbjct:  241  GHGYLGEHSSVFQQPLDICHSFTSQGGGREPLPAPYQHQLSEPCPPYPQQSFKQEYHDPL  300

Query:  301  YEQAGQPAVDQGGVNGHRYPGAGVVIKQEQTDFAYDSDVTGCASMYLHTEGFSGPSPGDG  360
             YEQAGQPAVDQGGVNGHRYPGAGVVIKQEQTDFAYDSDVTGCASMYLHTEGFSGPSPGDG
Sbjct:  301  YEQAGQPAVDQGGVNGHRYPGAGVVIKQEQTDFAYDSDVTGCASMYLHTEGFSGPSPGDG  360

Query:  361  AMGYGYEKPLRPFPDDVCVVPEKFEGDIKQEGVGAFREGPPYQRRGALQLWQFLVALLDD  420
             AMGYGYEKPLRPFPDDVCVVPEKFEGDIKQEGVGAFREGPPYQRRGALQLWQFLVALLDD
Sbjct:  361  AMGYGYEKPLRPFPDDVCVVPEKFEGDIKQEGVGAFREGPPYQRRGALQLWQFLVALLDD  420

Query:  421  PTNAHFIAWTGRGMEFKLIEPEEVARLWGIQKNRPAMNYDKLSRSLRYYYEKGIMQKVAG  480
             PTNAHFIAWTGRGMEFKLIEPEEVARLWGIQKNRPAMNYDKLSRSLRYYYEKGIMQKVAG
Sbjct:  421  PTNAHFIAWTGRGMEFKLIEPEEVARLWGIQKNRPAMNYDKLSRSLRYYYEKGIMQKVAG  480

Query:  481  ERYVYKFVCEPEALFSLAFPDNQRPALKAEFDRPVSEEDTVPLSHLDESPAYLPELAGPA  540
             ERYVYKFVCEPEALFSLAFPDNQRPALKAEFDRPVSEEDTVPLSHLDESPAYLPELAGPA
Sbjct:  481  ERYVYKFVCEPEALFSLAFPDNQRPALKAEFDRPVSEEDTVPLSHLDESPAYLPELAGPA  540

Query:  541  QPFGPKGGYSY  551
             QPFGPKGGYSY
Sbjct:  541  QPFGPKGGYSY  551
```

186P1H9-PENTRAXIN II (SEQ ID NO 102).
gi|9931976|gb|AAA68980.2| neuronal pentraxin II [Homo sapiens], 430 amino acids, 2F6 checksum.
MLALLAASVALAVAAGAQDSPAPGSRFVCTALPPEAVHAGCPLPAMPMQG
GAQSPEELRAAVLQLRETVVQQKETLASARAIRELTGKLARCEGLAGGK
ARGAGATGKDTMGDLPRDPGHVVEQLSRSLQTLKDRLESLEHQLRANVSN
AGLPGDFREVLQQRLGELERQLLRKVAELEDEKSLLHNETSAHRQKTEST
LNALLQRVTELERGNSAFKSPDAFKVSLPLRTNYLYGKIKKTLPELYAFT
ICLWLRSSASPGIGTPFSYAVPGQANEILLIEWGNNPIELLINDKVAQLP
LFVSDGKWHHICVTWTTRDGMWEAFQDGEKLGTGENLAPWHPIKPGGVLI
LGQEQDTVGGRFDATQAFVGELSQFNIWDRVLRAQEIVNIANCSTNMPGN
IIPWDNNVDVFGGASKWPVETCEEALLDL

Figure 4 (continued)

192P2G7 (SEQ ID NO 103) Alignment with sulfotransferase-related protein (SEQ ID NO 104).
Score = 591 bits (1524), Expect = e-168
Identities = 284/284 (100%), Positives = 284/284 (100%)

```
Query:   1   MAESEAETPSTPGEFESKYFEFHGVRLPPFCRGKMEEIANFPVRPSDVWIVTYPKSGTSL      60
             MAESEAETPSTPGEFESKYFEFHGVRLPPFCRGKMEEIANFPVRPSDVWIVTYPKSGTSL
Sbjct:   1   MAESEAETPSTPGEFESKYFEFHGVRLPPFCRGKMEEIANFPVRPSDVWIVTYPKSGTSL      60

Query:  61   LQEVVYLVSQGADPDEIGLMNIDEQLPVLEYPQPGLDIIKELTSPRLIKSHLPYRFLPSD     120
             LQEVVYLVSQGADPDEIGLMNIDEQLPVLEYPQPGLDIIKELTSPRLIKSHLPYRFLPSD
Sbjct:  61   LQEVVYLVSQGADPDEIGLMNIDEQLPVLEYPQPGLDIIKELTSPRLIKSHLPYRFLPSD     120

Query: 121   LHNGDSKVIYMARNPKDLVVSYYQFHRSLRTMSYRGTFQEFCRRFMNDKLGYGSWFEHVQ     180
             LHNGDSKVIYMARNPKDLVVSYYQFHRSLRTMSYRGTFQEFCRRFMNDKLGYGSWFEHVQ
Sbjct: 121   LHNGDSKVIYMARNPKDLVVSYYQFHRSLRTMSYRGTFQEFCRRFMNDKLGYGSWFEHVQ     180

Query: 181   EFWEHRMDSNVLFLKYEDMHRDLVTMVEQLARFLGVSCDKAQLEALTEHCHQLVDQCCNA     240
             EFWEHRMDSNVLFLKYEDMHRDLVTMVEQLARFLGVSCDKAQLEALTEHCHQLVDQCCNA
Sbjct: 181   EFWEHRMDSNVLFLKYEDMHRDLVTMVEQLARFLGVSCDKAQLEALTEHCHQLVDQCCNA     240

Query: 241   EALPVGRGRVGLWKDIFTVSMNEKFDLVYKQKMGKCDLTFDFYL     284
             EALPVGRGRVGLWKDIFTVSMNEKFDLVYKQKMGKCDLTFDFYL
Sbjct: 241   EALPVGRGRVGLWKDIFTVSMNEKFDLVYKQKMGKCDLTFDFYL     284
```

187P3F2 (SEQ ID NO 105) Alignment with POU domain, class 3, transcription factor 3 (SEQ ID NO 106).
Score = 616 bits (1589), Expect = e-175
Identities = 499/500 (99%), Positives = 499/500 (99%)

```
Query:   1   MATAASNPYLPGNSLLAAGSIVHSDAAGSIVHSDAAGAGGGGGGGGGGGGGAGGGGMQPGSAAVTS      60
             MATAASNPYLPGNSLLAAGSIVHSDAAGAGGGGGGGGG  GGGAGGGGGGMQPGSAAVTS
Sbjct:   1   MATAASNPYLPGNSLLAAGSIVHSDAAGAGGGGGGGGGGGGGAGGGGGGMQPGSAAVTS      60

Query:  61   GAYRGDPSSVKMVQSDFMQGAMAASNGGHMLSHAHQWVTALPHAAAAAAAAAAVEASS     120
             GAYRGDPSSVKMVQSDFMQGAMAASNGGHMLSHAHQWVTALPHAAAAAAAAAAVEASS
Sbjct:  61   GAYRGDPSSVKMVQSDFMQGAMAASNGGHMLSHAHQWVTALPHAAAAAAAAAAAVEASS     120

Query: 121   PWSGSAVGMAGSPQQPQQPPQQPPPPPQGPDVKGGAGRDDLHAGTALHHRGPPHLGPPPPPH     180
             PWSGSAVGMAGSPQQPQQPPQQPPPPPQGPDVKGGAGRDDLHAGTALHHRGPPHLGPPPPPH
Sbjct: 121   PWSGSAVGMAGSPQQPQQPPQQPPPPPQGPDVKGGAGRDDLHAGTALHHRGPPHLGPPPPPH     180

Query: 181   QGHPGGWGAAAAAAAAAAAAAAAAAHLPSMAGGQQPPPQSLLYSQPGGFTVNGMLSAPPGP     240
             QGHPGGWGAAAAAAAAAAAAAAAAAHLPSMAGGQQPPPQSLLYSQPGGFTVNGMLSAPPGP
Sbjct: 181   QGHPGGWGAAAAAAAAAAAAAAAAAHLPSMAGGQQPPPQSLLYSQPGGFTVNGMLSAPPGP     240
```

Figure 4 (continued)

```
Query: 241 GGGGGGAGGAQSLVHPGLVRGDTPELAEHHHHHHHHAHPHPPHPHHAQGPPHHGGGGGG 300
Sbjct: 241 GGGGGGAGGAQSLVHPGLVRGDTPELAEHHHHHHHHAHPHPPHPHHAQGPPHHGGGGGG 300

Query: 301 AGPGLNSHDPHSDEDTPTSDDLEQFAKQFKQRRIKLGFTQADVGLALGTLYGNVFSQTTI 360
Sbjct: 301 AGPGLNSHDPHSDEDTPTSDDLEQFAKQFKQRRIKLGFTQADVGLALGTLYGNVFSQTTI 360

Query: 361 CRFEALQLSFKNMCKLKPLLNKWLEEADSSTGSPTSIDKIAAQGRKRKKRTSIEVSVKGA 420
Sbjct: 361 CRFEALQLSFKNMCKLKPLLNKWLEEADSSTGSPTSIDKIAAQGRKRKKRTSIEVSVKGA 420

Query: 421 LESHFLKCPKPSAQEITNLADSLQLEKEVRVWFCNRRQKEKRMTPPGIQQQTPDDVYSQ 480
Sbjct: 421 LESHFLKCPKPSAQEITNLADSLQLEKEVRVWFCNRRQKEKRMTPPGIQQQTPDDVYSQ 480

Query: 481 VGTVSADTPPPHHGLQTSVQ 500
Sbjct: 481 VGTVSADTPPPHHGLQTSVQ 500

185P2C9 v.1 (SEQ ID NO 107) Alignment with KIAA0802 protein (SEQ ID NO 108).
Score = 2335 bits (6052), Expect = 0.0
Identities = 1307/1307 (100%), Positives = 1307/1307 (100%)

Query: 1   MEDMRGGQQEREGPGRDHAPSIPTSPFGDSLESSTELRRHLQFVEEEAELLRRSISEIEDH 60
Sbjct: 1   MEDMRGGQQEREGPGRDHAPSIPTSPFGDSLESSTELRRHLQFVEEEAELLRRSISEIEDH 60

Query: 61  NRQLTHELSKFKFEPPREPGWLGEGASPGAGGGAPLQEELKSARLQISELSGKVLKLQHE 120
Sbjct: 61  NRQLTHELSKFKFEPPREPGWLGEGASPGAGGGAPLQEELKSARLQISELSGKVLKLQHE 120

Query: 121 NHALLSNIQRCDLAAHLGLRAPSPRDSDAESDAGKKESDGEESRLPQPKREGPVGGESDS 180
Sbjct: 121 NHALLSNIQRCDLAAHLGLRAPSPRDSDAESDAGKKESDGEESRLPQPKREGPVGGESDS 180

Query: 181 EEMFEKTSGFGSGKPSEASEPCPTELLKAREDSEYLVTLKHEAQRLERTVERLITDTDSF 240
Sbjct: 181 EEMFEKTSGFGSGKPSEASEPCPTELLKAREDSEYLVTLKHEAQRLERTVERLITDTDSF 240

Query: 241 LHDAGLRGGAPLPGPGLQGEEEQGEGDQQEPQLLGTINAKMKAFKKELQAFLEQVNRIGD 300
Sbjct: 241 LHDAGLRGGAPLPGPGLQGEEEQGEGDQQEPQLLGTINAKMKAFKKELQAFLEQVNRIGD 300

Query: 301 GLSPLPHLTESSSFLSTVTVSRDSPIGNLGKELGPDLQSRLKEQLEWQLGPARGDERES 360
```

Figure 4 (continued)

```
Sbjct: 301  GLSPLPHLTESSSFLSTVTSVSRDSPIGNLGKELGPDLQSRLKEQLEWQLGPARGDERES  360

Query: 361  LRLRAARELHRRADGDTGSHGLGGQTCFSLEMEEEHLYALRWKELEMHSLALQNTLHERI  420
Sbjct: 361  LRLRAARELHRRADGDTGSHGLGGQTCFSLEMEEEHLYALRWKELEMHSLALQNTLHERI  420

Query: 421  WSDEKNLMQQELRSLKQNIFLFYVKLRWLLKHWRQGKQMEEEGEEFTEGEHPETLSRLGE  480
Sbjct: 421  WSDEKNLMQQELRSLKQNIFLFYVKLRWLLKHWRQGKQMEEEGEEFTEGEHPETLSRLGE  480

Query: 481  LGVQGGHQADGPDHDSDRGCGFPVGEHSPHSRVQIGDHSLRLQTADRGQPHKQVVENQQL  540
Sbjct: 481  LGVQGGHQADGPDHDSDRGCGFPVGEHSPHSRVQIGDHSLRLQTADRGQPHKQVVENQQL  540

Query: 541  FSAFKALLEDFRAELREDERARLRLQQQYASDKAAWDVEWAVLKCRLEQLEEKTENKLGE  600
Sbjct: 541  FSAFKALLEDFRAELREDERARLRLQQQYASDKAAWDVEWAVLKCRLEQLEEKTENKLGE  600

Query: 601  LGSSAESKGALKKEREVHQKLLADSHSLVMDLRWQIHHSEKNWNREKVELLDRLDRDRQE  660
Sbjct: 601  LGSSAESKGALKKEREVHQKLLADSHSLVMDLRWQIHHSEKNWNREKVELLDRLDRDRQE  660

Query: 661  WERQKKEFLWRIEQLQKENSPRRGGSFLCDQKDGNVRPFPHQGSLRMPRPVAMWPCADAD  720
Sbjct: 661  WERQKKEFLWRIEQLQKENSPRRGGSFLCDQKDGNVRPFPHQGSLRMPRPVAMWPCADAD  720

Query: 721  SIPFEDRPLSKLKESDRCSASENLYLDALSLDDEPEEPPAHRPEREFRNRLPEEEENHKG  780
Sbjct: 721  SIPFEDRPLSKLKESDRCSASENLYLDALSLDDEPEEPPAHRPEREFRNRLPEEEENHKG  780

Query: 781  NLQRAVSVSSMSEFQRLMDISPFLPEKGLPSTSSKEDVTPPLSPDDLKYIEEFNKSWDYT  840
Sbjct: 781  NLQRAVSVSSMSEFQRLMDISPFLPEKGLPSTSSKEDVTPPLSPDDLKYIEEFNKSWDYT  840

Query: 841  PNRGHNGGGPDLWADRTEVGRAGHEDSTEPFPDSSWYLTTSVTMTTDTMTSPEHCQKQPL  900
Sbjct: 841  PNRGHNGGGPDLWADRTEVGRAGHEDSTEPFPDSSWYLTTSVTMTTDTMTSPEHCQKQPL  900

Query: 901  RSHVLTEQSGLRVLHSPPAVRRVDSITAAGGEGPFPTSRARGSPGDTKGGPPEPMLSRWP  960
Sbjct: 901  RSHVLTEQSGLRVLHSPPAVRRVDSITAAGGEGPFPTSRARGSPGDTKGGPPEPMLSRWP  960

Query: 961  CTSPRHSRDYVEGARRPLDSPLCTSLGFASPLHSLEMSKNLSDDMKEVAFSVRNAICSGP  1020
```

Figure 4 (continued)

```
Sbjct:  961 CTSPRHSRDYVEGARRPLDSPLICTSLGFASPLHSLEMSKNLSDDMKEVAFSVRNAICSGP 1020

Query: 1021 GELQVKDMACQTNGSRTMGTQTVQTISVGLQTEALRGSGVTSSPHKCLTPKAGGGATPVS 1080
Sbjct: 1021 GELQVKDMACQTNGSRTMGTQTVQTISVGLQTEALRGSGVTSSPHKCLTPKAGGGATPVS 1080

Query: 1081 SPSRSLRSRQVAPAIEKVQAKFERTCCSPKYGSPKLQRKPLPKADQPNNRTSPGMAQKGY 1140
Sbjct: 1081 SPSRSLRSRQVAPAIEKVQAKFERTCCSPKYGSPKLQRKPLPKADQPNNRTSPGMAQKGY 1140

Query: 1141 SESAWARSTTTRESPVHTTINDGLSSLFNIIDHSPVVQDPFQKGLRAGSRSRSAEPRPEL 1200
Sbjct: 1141 SESAWARSTTTRESPVHTTINDGLSSLFNIIDHSPVVQDPFQKGLRAGSRSRSAEPRPEL 1200

Query: 1201 GPGQETGTNSRGRSPSPIGVGSEMCREEGGEGTPVKQDLSAPPGYTLTENVARILNKKLL 1260
Sbjct: 1201 GPGQETGTNSRGRSPSPIGVGSEMCREEGGEGTPVKQDLSAPPGYTLTENVARILNKKLL 1260

Query: 1261 EHALKEERRQAAHGPPGLHSDSHSLGDTAEPGPMENQTVLLTAPWGL 1307
Sbjct: 1261 EHALKEERRQAAHGPPGLHSDSHSLGDTAEPGPMENQTVLLTAPWGL 1307

185P2C9 v.2 (SEQ ID NO 109) Alignment with human KIAA0802 protein (SEQ ID NO 110).

Score = 1999 bits (5180), Expect = 0.0
 Identities = 1128/1130 (99%), Positives = 1130/1130 (99%)

Query:   1 MEDTRGQQEREGPGRDHAPSIPTSPFGDSLESSTELRRHLQFVEEEAELLRRSISEIEDH 60
Sbjct:  47 MEDTRGQQEREGPGRDHAPSIPTSPFGDSLESSTELRRHLQFVEEEAELLRRSISEIEDH 106

Query:  61 NRQLTHELSKFKFEPPREPGWLGEGASPGAGGGAPLQEELKSARLQISELSGKVLKLQHE 120
Sbjct: 107 NRQLTHELSKFKFEPPREPGWLGEGASPGAGGGAPLQEELKSARLQISELSGKVLKLQHE 166

Query: 121 NHALLSNIQRCDLAAHLGLRAPSPRDSDAESDAGKKESDGEESRLPQPKREGPVGGESDS 180
Sbjct: 167 NHALLSNIQRCDLAAHLGLRAPSPRDSDAESDAGKKESDGEESRLPQPKREGPVGGESDS 226

Query: 181 EEMFEKTSGFGSGKPSEASEPCPTELLKAREDSEYLVTLKHEAQRLERTVERLITDTDSF 240
Sbjct: 227 EEMFEKTSGFGSGKPSEASEPCPTELLKAREDSEYLVTLKHEAQRLERTVERLITDTDSF 286

Query: 241 LHDAGLRGGAPLPGPGLQEEEQEGEGDQQEPQLLGTINAKMKAFKKELQAFLQQVNRIGD 300
```

Figure 4 (continued)

```
Sbjct:  287  LHDAGLRGGAPLPGPGLQGEEEQEGEGDQQEPQLLGTINAKMKAFKKELQAFL+QVNRIGD  346

Query:  301  GLSPLPHLTESSSFLSTVTSVSRDSPIGNLGKELGPDLQSRLKEQLEWQLGPAQGDERES  360
Sbjct:  347  GLSPLPHLTESSSFLSTVTSVSRDSPIGNLGKELGPDLQSRLKEQLEWQLGPA+GDERES  406

Query:  361  LRLRAARELHRRADGDTGSHGLGGQTCFSLEMEEEHLYALRWKELEMHSLALQNTLHERT  420
Sbjct:  407  LRLRAARELHRRADGDTGSHGLGGQTCFSLEMEEEHLYALRWKELEMHSLALQNTLHERT  466

Query:  421  WSDEKNLMQQELRSLKQNIFLFYVKLRWLLKHWRQGKQMEEEGEEFTEGEHPETLSRLGE  480
Sbjct:  467  WSDEKNLMQQELRSLKQNIFLFYVKLRWLLKHWRQGKQMEEEGEEFTEGEHPETLSRLGE  526

Query:  481  LGVQGGHQADGPDHDSDRGCGFPVGEHSPHSRVQIGDHSLRLQTADRGQPHKQVVENQQL  540
Sbjct:  527  LGVQGGHQADGPDHDSDRGCGFPVGEHSPHSRVQIGDHSLRLQTADRGQPHKQVVENQQL  586

Query:  541  FSAFKALLEDFRAELREDERARLRLQQQYASDKAAWDVEWAVLKCRLEQLEEKTENKLGE  600
Sbjct:  587  FSAFKALLEDFRAELREDERARLRLQQQYASDKAAWDVEWAVLKCRLEQLEEKTENKLGE  646

Query:  601  LGSSAESKGALKKEREVHQKLLADSHSLVMDLRWQIHHSEKNWNREKVELLDRLDRDRQE  660
Sbjct:  647  LGSSAESKGALKKEREVHQKLLADSHSLVMDLRWQIHHSEKNWNREKVELLDRLDRDRQE  706

Query:  661  WERQKKEFLWRIEQLQKENSPRRGGSFLCDQKDGNVRPFPHQGSLRMPRPVAMWPCADAD  720
Sbjct:  707  WERQKKEFLWRIEQLQKENSPRRGGSFLCDQKDGNVRPFPHQGSLRMPRPVAMWPCADAD  766

Query:  721  SIPFEDRPLSKLKESDRCSASENLYLDALSLDDEPEEPPAHRPEREFRNRLPEEEENHKG  780
Sbjct:  767  SIPFEDRPLSKLKESDRCSASENLYLDALSLDDEPEEPPAHRPEREFRNRLPEEEENHKG  826

Query:  781  NLQRAVSVSSMSEFQRLMDISPFLPEKGLPSTSSKEDVTPPLSPDDLKYIEEFNKSWDYT  840
Sbjct:  827  NLQRAVSVSSMSEFQRLMDISPFLPEKGLPSTSSKEDVTPPLSPDDLKYIEEFNKSWDYT  886

Query:  841  PNRGHNGGGPDLWADRTEVGRAGHEDSTEPFPDSSWYLTTSVTMTTDTMTSPEHCQKQPL  900
Sbjct:  887  PNRGHNGGGPDLWADRTEVGRAGHEDSTEPFPDSSWYLTTSVTMTTDTMTSPEHCQKQPL  946

Query:  901  RSHVLTEQSGLRVLHSPPAVRRVDSITAAGGEGPFPTSRARGSPGDTKGGPPEPMLSRWP  960
```

Figure 4 (continued)

```
Sbjct:  947  RSHVLTEQSGLRVLHSPPAVRRVDSITAAGGEGPFPTSRARGSPGDTKGGPPEPMLSRWP  1006
Query:  961  CTSPRHSRDYVEGARRPLDSPLCTSLGFASPLHSLEMSKNLSDDMKEVAFSVRNAICSGP  1020
             CTSPRHSRDYVEGARRPLDSPLCTSLGFASPLHSLEMSKNLSDDMKEVAFSVRNAICSGP
Sbjct: 1007  CTSPRHSRDYVEGARRPLDSPLCTSLGFASPLHSLEMSKNLSDDMKEVAFSVRNAICSGP  1066
Query: 1021  GELQVKDMACQTNGSRTMGTQTVQTISVGLQTEALRGSGVTSSPHKCLTPKAGGATPVS  1080
             GELQVKDMACQTNGSRTMGTQTVQTISVGLQTEALRGSGVTSSPHKCLTPKAGGATPVS
Sbjct: 1067  GELQVKDMACQTNGSRTMGTQTVQTISVGLQTEALRGSGVTSSPHKCLTPKAGGATPVS  1126
Query: 1081  SPSRSLRSRQVAPAIEKVQAKFERTCCSPKYGSPKLQRKPLPKADQPNNR  1130
             SPSRSLRSRQVAPAIEKVQAKFERTCCSPKYGSPKLQRKPLPKADQPNNR
Sbjct: 1127  SPSRSLRSRQVAPAIEKVQAKFERTCCSPKYGSPKLQRKPLPKADQPNNR  1176
```

185P2C9 v.3 (same gene as above)

159P2B5 (SEQ ID NO 111) Alignment with hypothetical protein XP_040796 (SEQ ID NO 112).
Score = 348 bits (893), Expect = 2e-95
Identities = 224/224 (100%), Positives = 224/224 (100%)

```
Query:   1  MVKREHGQERPTFWGWAATPAPVSAPGNPPTGEGERQGSPPGGGFLGSTSFQRRGEKELL   60
            MVKREHGQERPTFWGWAATPAPVSAPGNPPTGEGERQGSPPGGGFLGSTSFQRRGEKELL
Sbjct:   1  MVKREHGQERPTFWGWAATPAPVSAPGNPPTGEGERQGSPPGGGFLGSTSFQRRGEKELL   60

Query:  61  WERGQDVSRSVLAMRAILPPSLSKSVHFPPLPHSCTLVALLSLGLQDPLGCRAPATKPTP  120
            WERGQDVSRSVLAMRAILPPSLSKSVHFPPLPHSCTLVALLSLGLQDPLGCRAPATKPTP
Sbjct:  61  WERGQDVSRSVLAMRAILPPSLSKSVHFPPLPHSCTLVALLSLGLQDPLGCRAPATKPTP  120

Query: 121  AGATLSASSLPRPCSPSASLLLSWPLFWGILGGVFFLGSRACTRTQARRHTGPAAALLRL  180
            AGATLSASSLPRPCSPSASLLLSWPLFWGILGGVFFLGSRACTRTQARRHTGPAAALLRL
Sbjct: 121  AGATLSASSLPRPCSPSASLLLSWPLFWGILGGVFFLGSRACTRTQARRHTGPAAALLRL  180

Query: 181  LFPAPRRPGARSRAGYASPGSPERRSPGTAHKGSLPWPLALRLL  224
            LFPAPRRPGARSRAGYASPGSPERRSPGTAHKGSLPWPLALRLL
Sbjct: 181  LFPAPRRPGARSRAGYASPGSPERRSPGTAHKGSLPWPLALRLL  224
```

184P3G10 (SEQ ID NO 113) Alignment with human hypothetical protein XP_092661 (SEQ ID NO 114).
Score = 1318 bits (3410), Expect = 0.0
Identities = 700/717 (97%), Positives = 701/717 (97%), Gaps = 16/717 (2%)

Figure 4 (continued)

```
Query:  32  MTSQPLRLAEEYGPSPGESELAVNPFDGLPFSSRYYELLKQRQALPIWAARFTFLEQLES    91
Sbjct:   1  MTSQPLRLAEEYGPSPGESELAVNPFDGLPFSSRYYELLKQRQALPIWAARFTFLEQLES    60

Query:  92  NPTGVVLVSGEPGSGKSTQIPQWCAEFALARGFQKGQVTVTQPYPLAARSLALRVADEMD   151
Sbjct:  61  NPTGVVLVSGEPGSGKSTQIPQWCAEFALARGFQKGQVTVTQPYPLAARSLALRVADEMD   120

Query: 152  LTLGHEVGYSIPQEDCTGPNTLLRFCWDRLLLQEVASTRGTGAWGVLVLDEAQERSVASD   211
Sbjct: 121  LTLGHEVGYSIPQEDCTGPNTLLRFCWDRLLLQEVASTRGTGAWGVLVLDEAQERSVASD   180

Query: 212  SLQGLLQDARLEKLPGDLRVVVTDPALEPKLRAFWGNPPIVHIPREPGERPSPIYWDTI   271
Sbjct: 181  SLQGLLQDARLEKLPGDLRVVVTDPALEPKLRAFWGNPPIVHIPREPGERPSPIYWDTI   240

Query: 272  PPDRVEAACQAVLELCRKELPGDVIVFLPSEEEISLCCESLSREVESLLLQGLPPRVLPL   331
Sbjct: 241  PPDRVEAACQAVLELCRKELPGDVIVFLPSEEEISLCCESLSREVESLLLQGLPPRVLPL   300

Query: 332  HPDCGRAVQAVYEDMDARKVVTHWLADFSFSLPSIQHVIDSGLELRSVYNPRIRAEFQV   391
Sbjct: 301  HPDCGRAVQAVYEDMDARKVVTHWLADFSFSLPSIQHVIDSGLELRSVYNPRIRAEFQV   360

Query: 392  LRPISKCQAEARRLRARGFPPGSCLCLYPKSFLELEAPPLPQPRVCEENLSSIVLLLKRR   451
Sbjct: 361  LRPISKCQAEARRLRARGFPPGSCLCLYPKSFLELEAPPLPQPRVCEENLSSIVLLLKRR   420

Query: 452  QIAEPGECHFLDQPAPEALMQALEDIDYLAALDDDGDLSDLGVILSEFPLAPELAKALLA   511
Sbjct: 421  QIAEPGECHFLDQPAPEALMQALEDIDYLAALDDDGDLSDLGVILSEFPLAPELAKALLA   480

Query: 512  SCEFDCVDEMLTLAAMLTAAPGFTRPPLSAEEAALRRALEHTDGDHSSLIQVYEAFIQSG   571
Sbjct: 481  SCEFDCVDEMLTLAAMLTAAPGFTRPPLSAEEAALRRALEHTDGDHSSLIQVYEAFIQSG   540

Query: 572  ADEAWCQARGLNWAALCQAHKLRGELLELMQRIELPLSLPAFGSEQNRRDLQKALVSGYF   631
Sbjct: 541  ADEAWCQARGLNWAALCQAHKLRGELLELMQRIELPLSLPAFGSEQNRRDLQKALVSGYF   600

Query: 632  LKVARDTDGTGNYLLLTHKHVAQLSSYCCYRSRRAPARPPPWVLYHNFTISKDNCLSIVS   691
Sbjct: 601  LKVARDTDGTGNYLLLTHKHVAQLSSYCCYRSRRAPARPPPWVLYHNFTISKDNCLSIVS   660

Query: 692  EIQPQMLVELAPPYFLSNLPPSESRDLLNQLREGMADSTAGSKSSSAQEFRDPCVLQ    748
```

Figure 4 (continued)

```
          EIQPQ+        ESRDLINQLREGMADSTAGSKSSSAQEFRDPCVLQ
Sbjct: 661 EIQPQI--------ESRDLINQLREGMADSTAGSKSSSAQEFRDPCVLQ 701
```

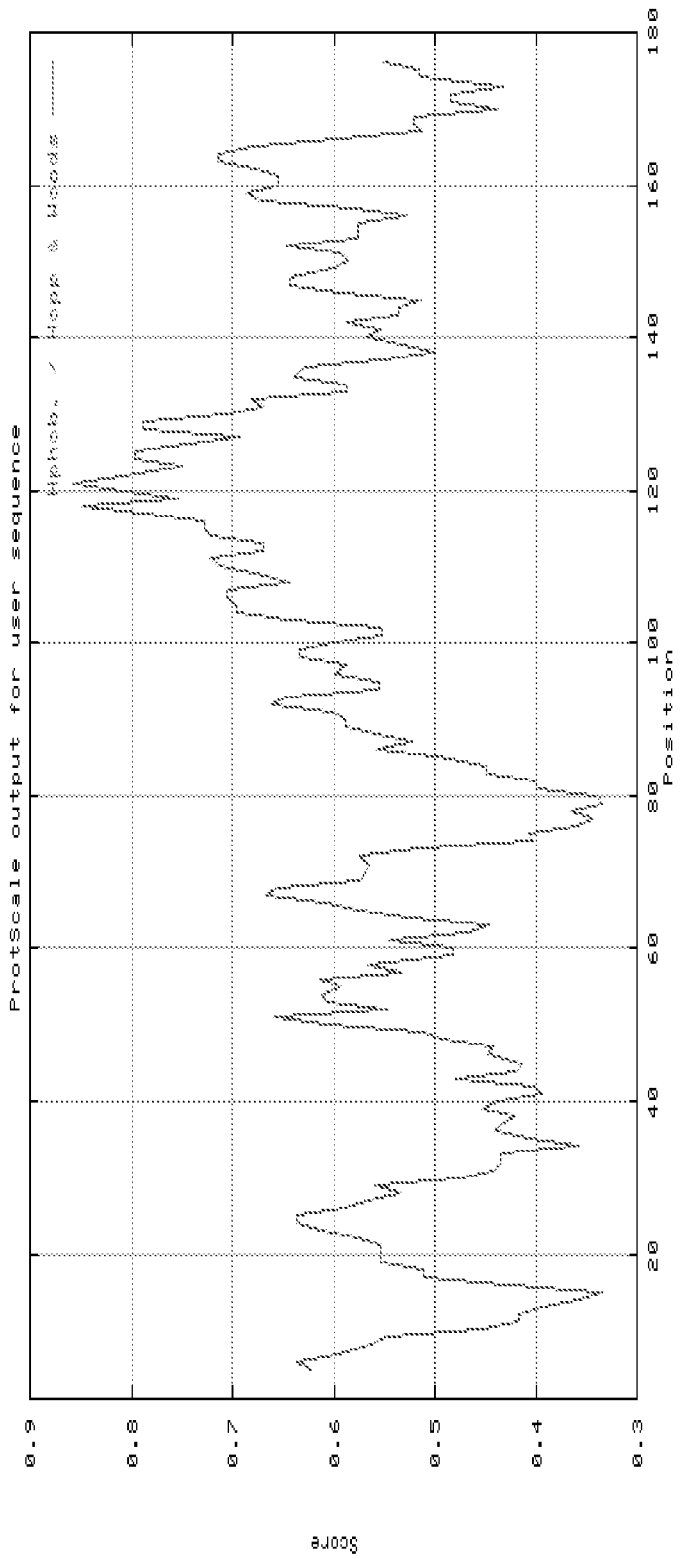
Figure 5A: 74P3B3 variant 1a Hydrophilicity profile
(Hopp T.P., Woods K.R., 1981. Proc. Natl. Acad. Sci. U.S.A. 78:3824-3828)

74P3B3 variant 1b Hydrophilicity profile
(Hopp T.P., Woods K.R., 1981. Proc. Natl. Acad. Sci. U.S.A. 78:3824-3828)

83P4B8 Hydrophilicity profile
(Hopp T.P., Woods K.R., 1981. Proc. Natl. Acad. Sci. U.S.A. 78:3824-3828)

109P1D4 Hydrophilicity profile
(Hopp T.P., Woods K.R., 1981. Proc. Natl. Acad. Sci. U.S.A. 78:3824-3828)

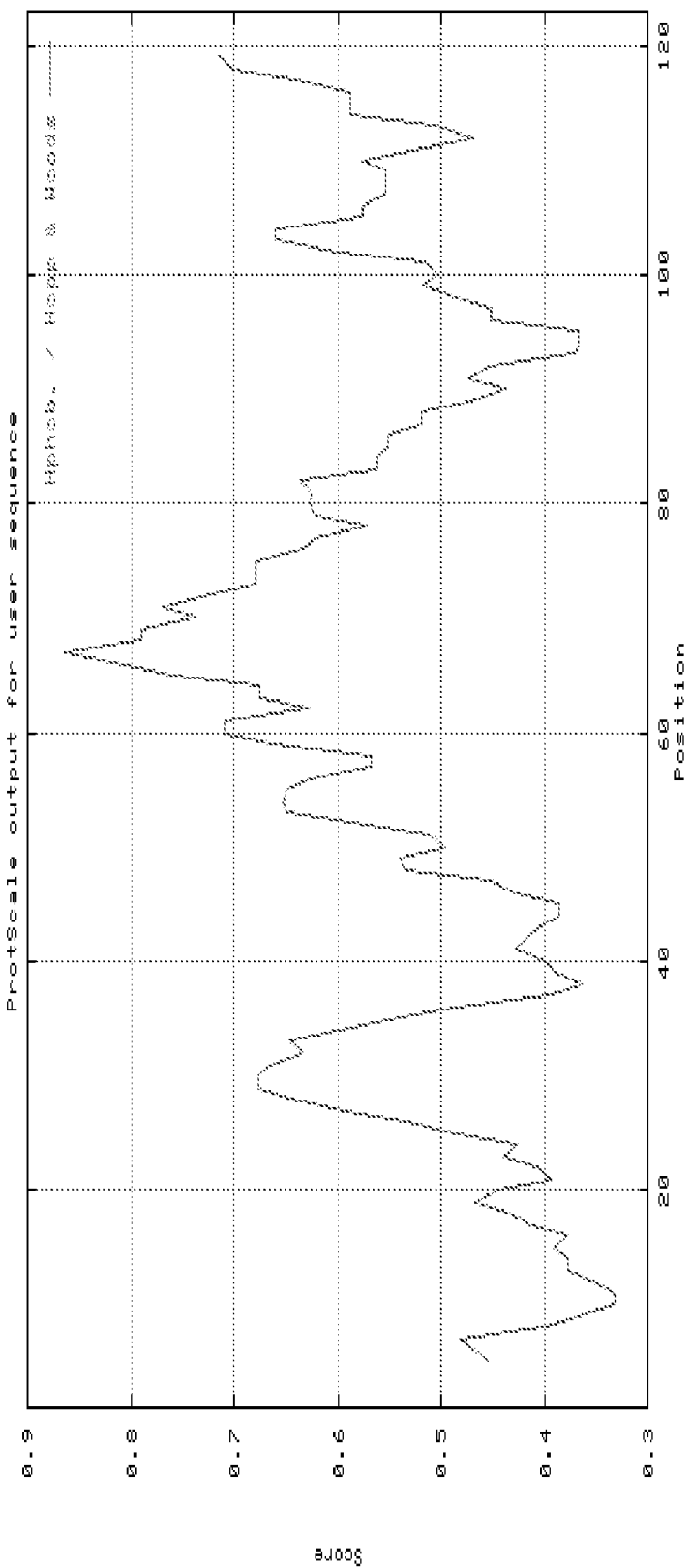
Figure 5E: 151P4E11 Hydrophilicity profile
(Hopp T.P., Woods K.R., 1981. Proc. Natl. Acad. Sci. U.S.A. 78:3824-3828)

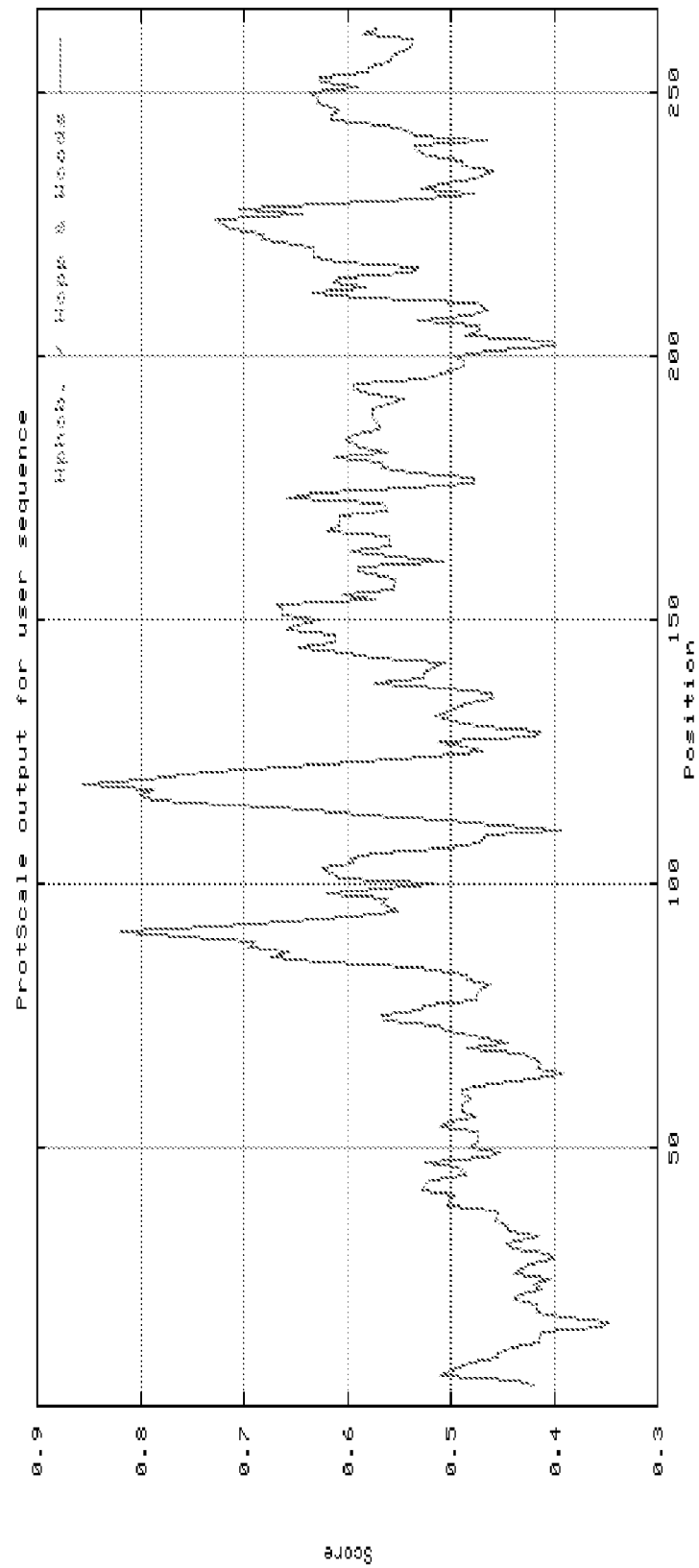
Figure 5F: 151P1C7a Hydrophilicity profile
(Hopp T.P., Woods K.R., 1981. Proc. Natl. Acad. Sci. U.S.A. 78:3824-3828)

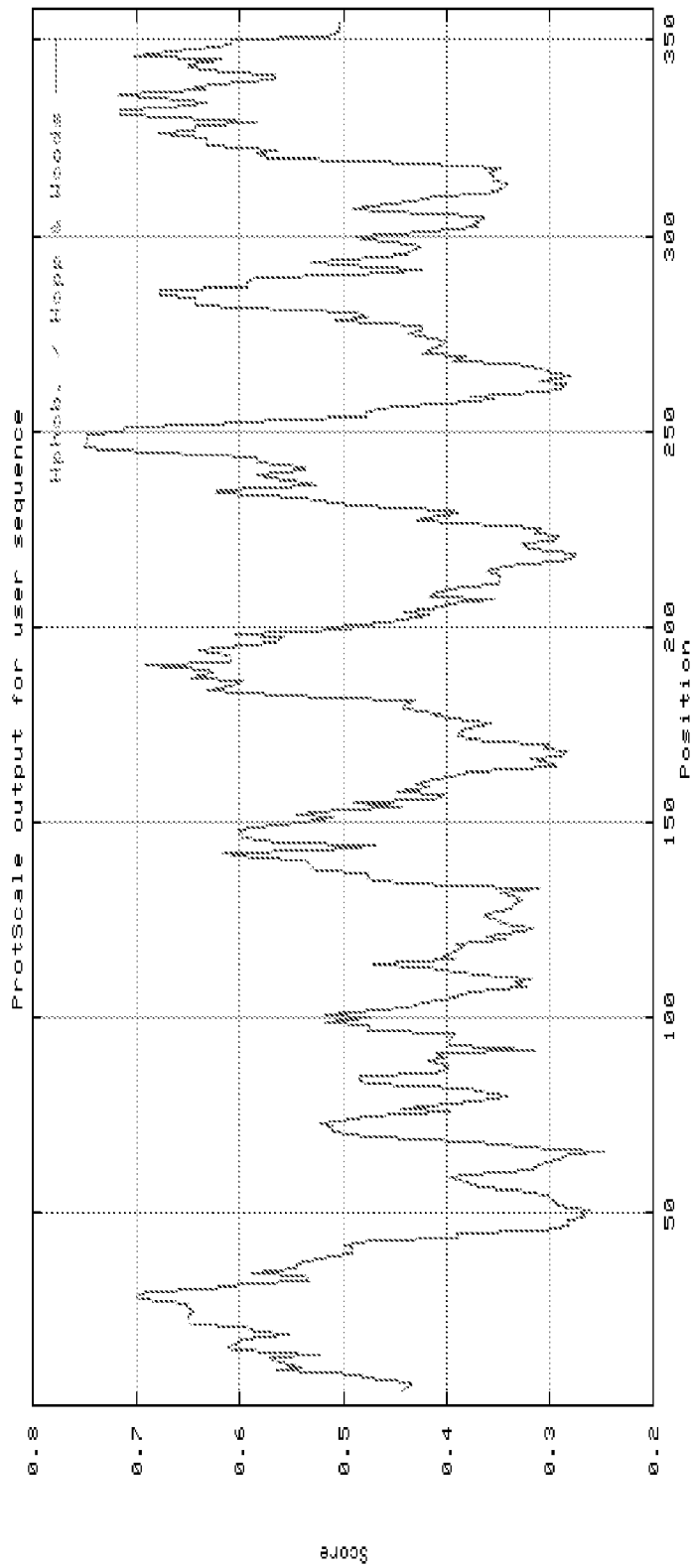
Figure 5G: 154P2A8 Hydrophilicity profile
(Hopp T.P., Woods K.R., 1981. Proc. Natl. Acad. Sci. U.S.A. 78:3824-3828)

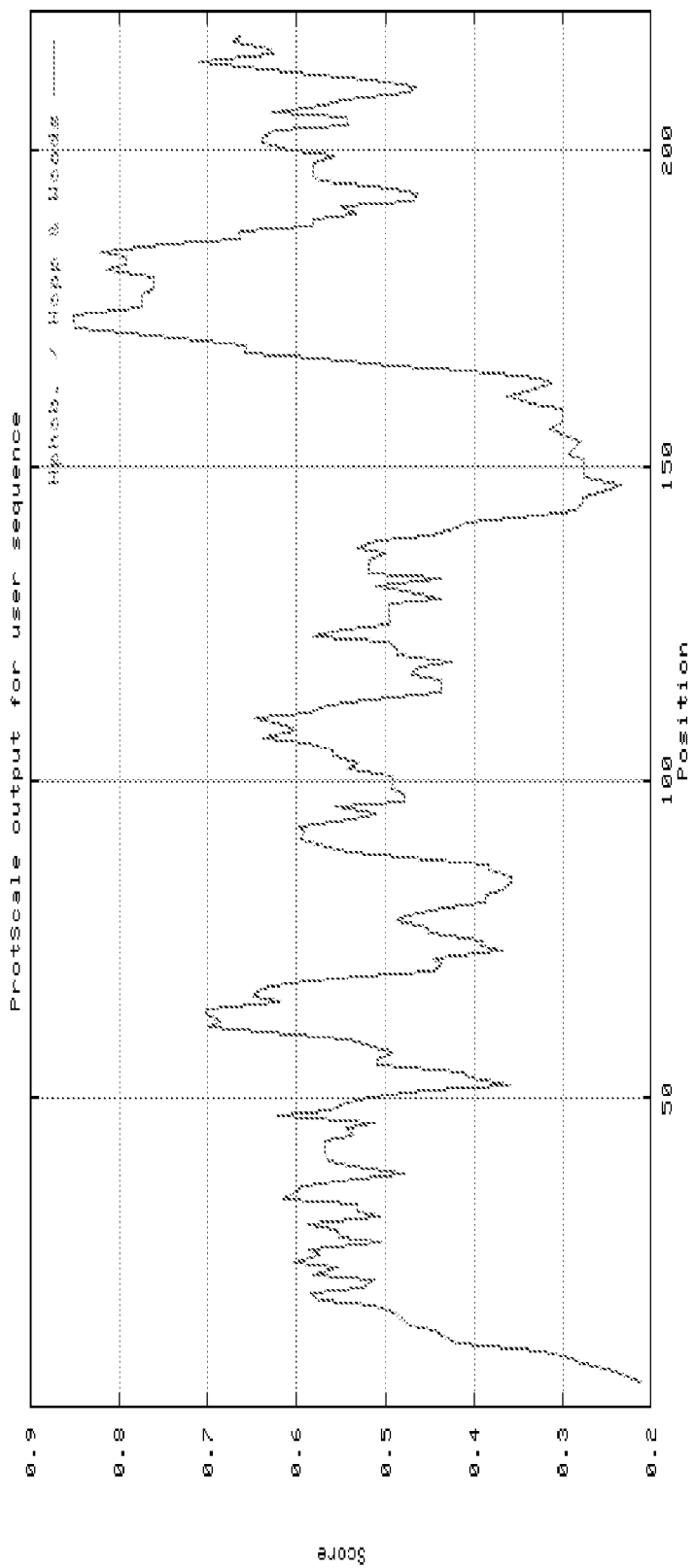
Figure 5H: 156P1D4 Hydrophilicity profile
(Hopp T.P., Woods K.R., 1981. Proc. Natl. Acad. Sci. U.S.A. 78:3824-3828)

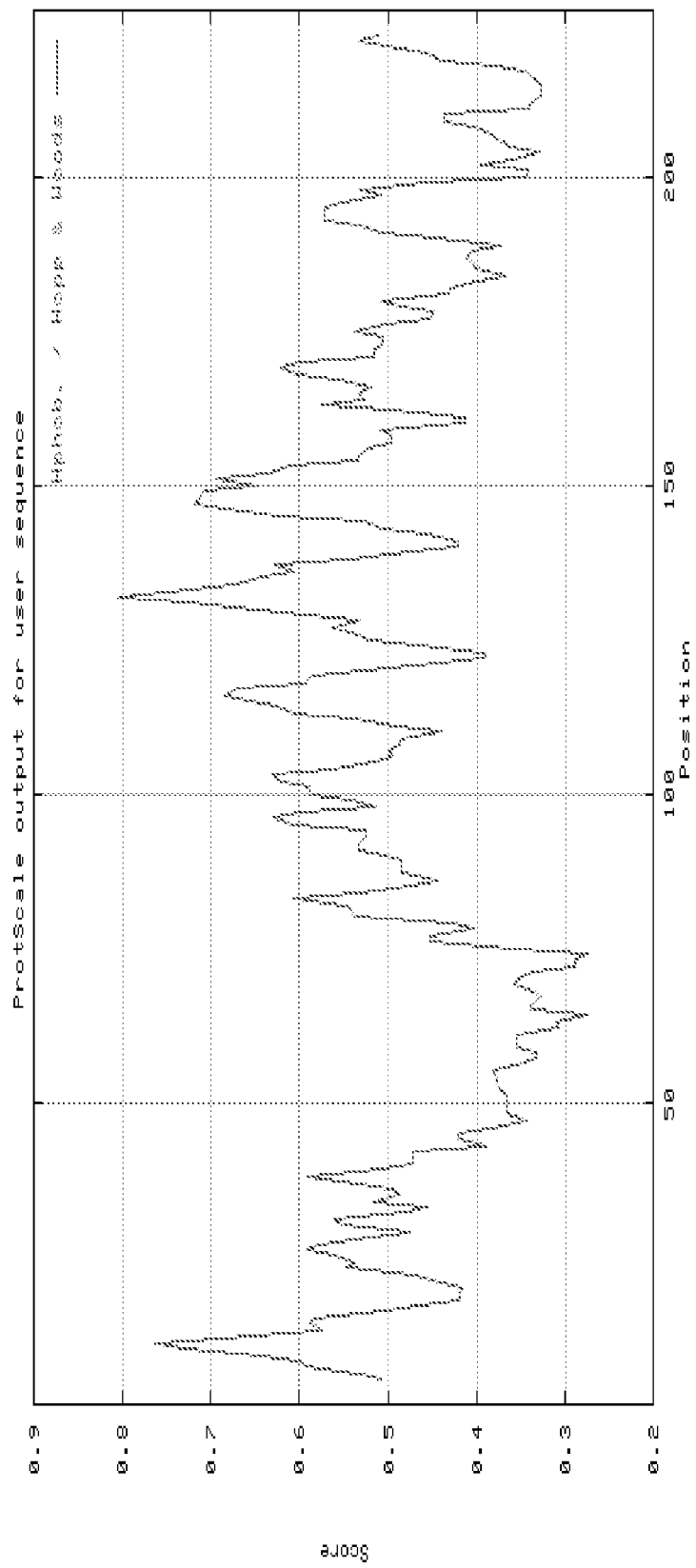
Figure 5I: 156P5C12 Hydrophilicity profile
(Hopp T.P., Woods K.R., 1981. Proc. Natl. Acad. Sci. U.S.A. 78:3824-3828)

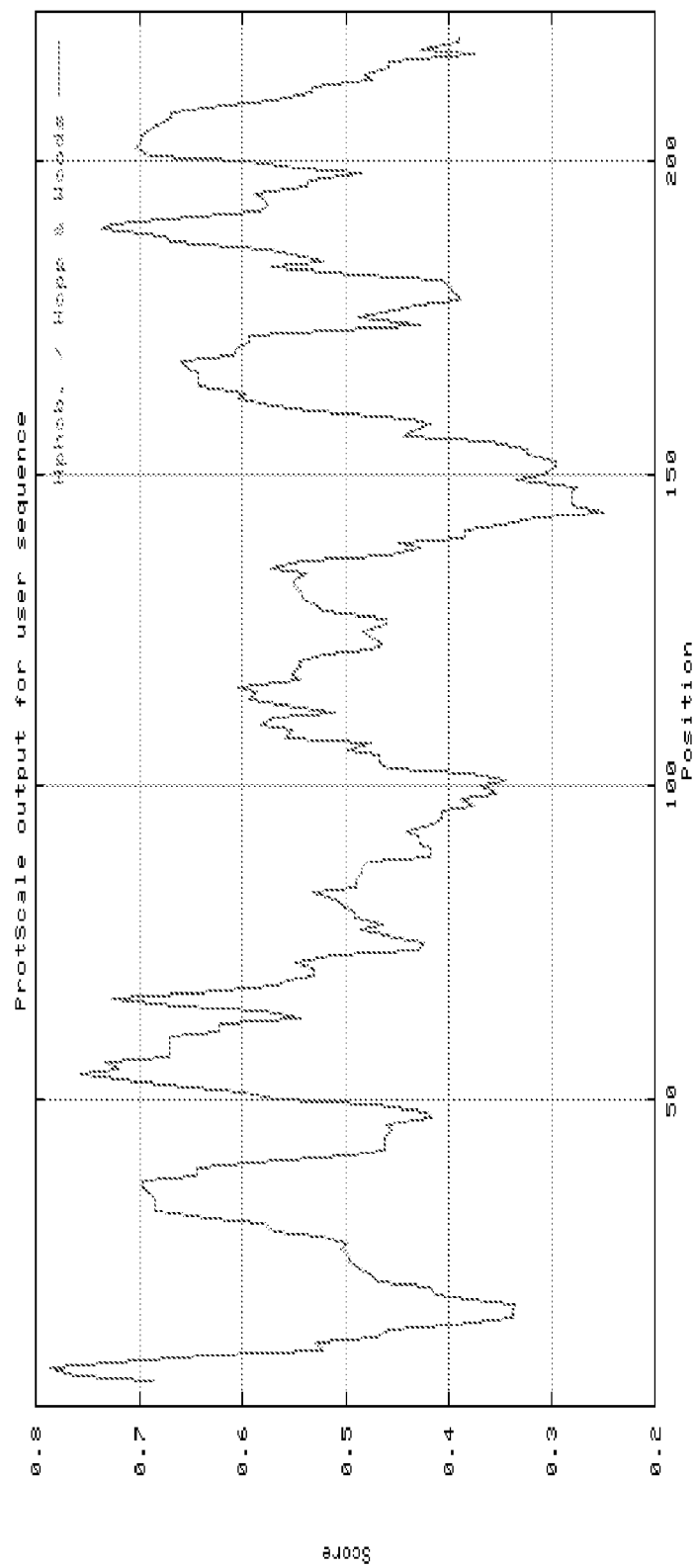
Figure 5J: 159P2B5 Hydrophilicity profile
(Hopp T.P., Woods K.R., 1981. Proc. Natl. Acad. Sci. U.S.A. 78:3824-3828)

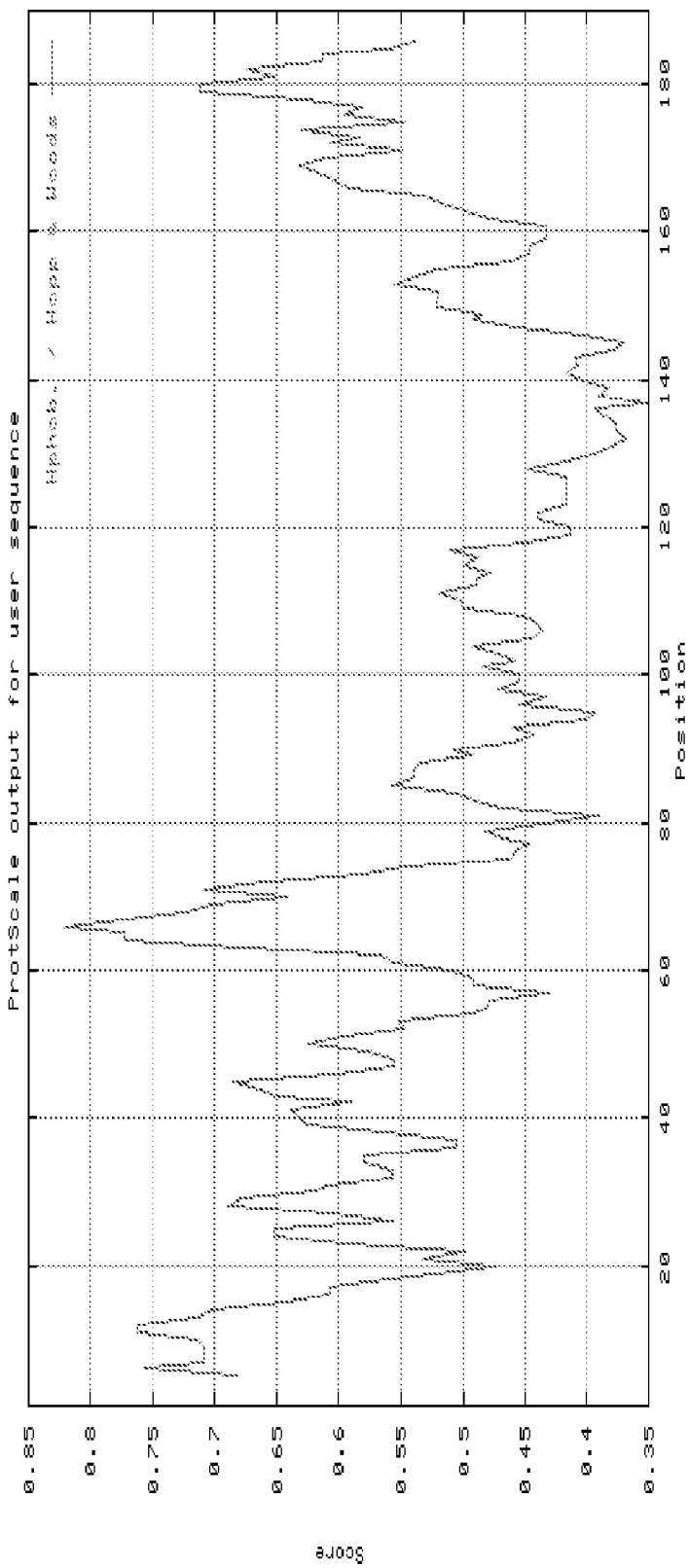
Figure 5K: 161P2B7a Hydrophilicity profile
(Hopp T.P., Woods K.R., 1981. Proc. Natl. Acad. Sci. U.S.A. 78:3824-3828)

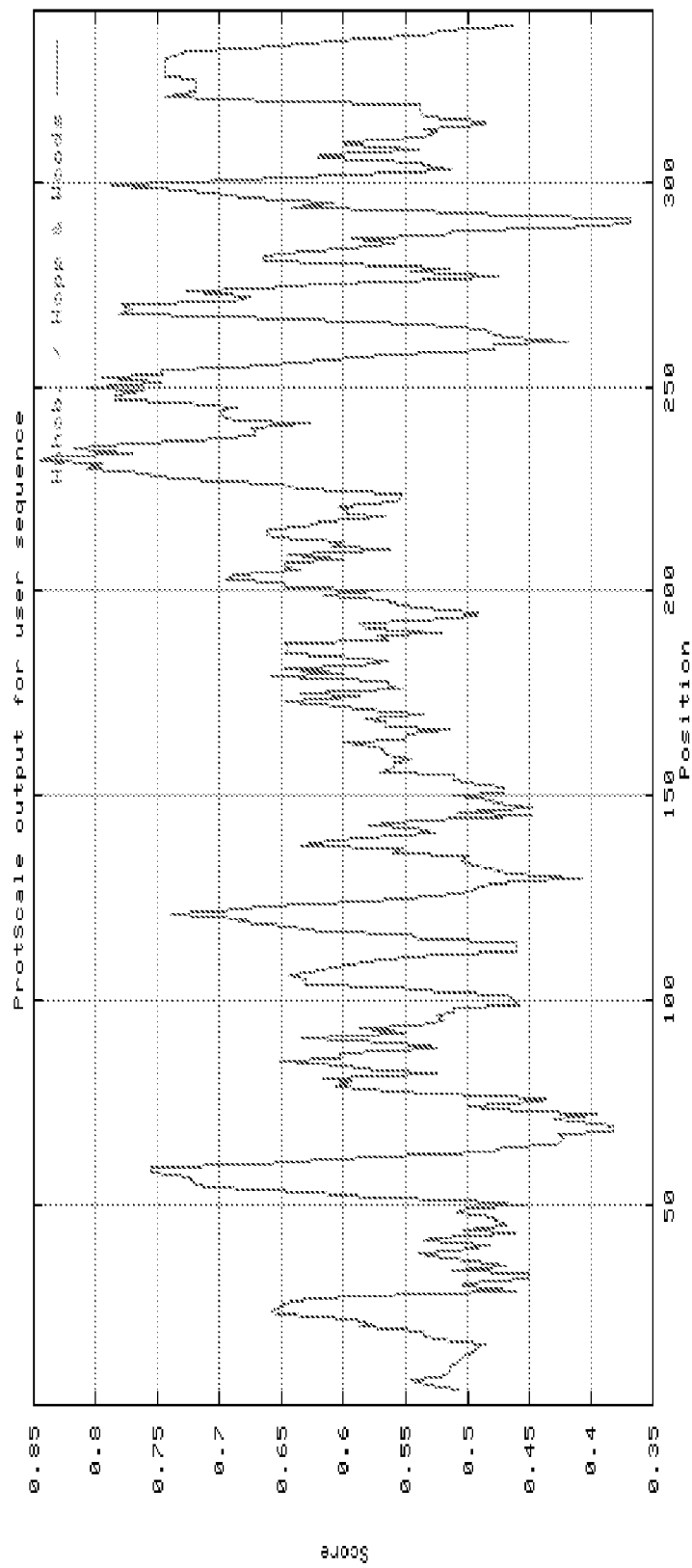
Figure 5L: 179P3G7 Hydrophilicity profile
(Hopp T.P., Woods K.R., 1981. Proc. Natl. Acad. Sci. U.S.A. 78:3824-3828)

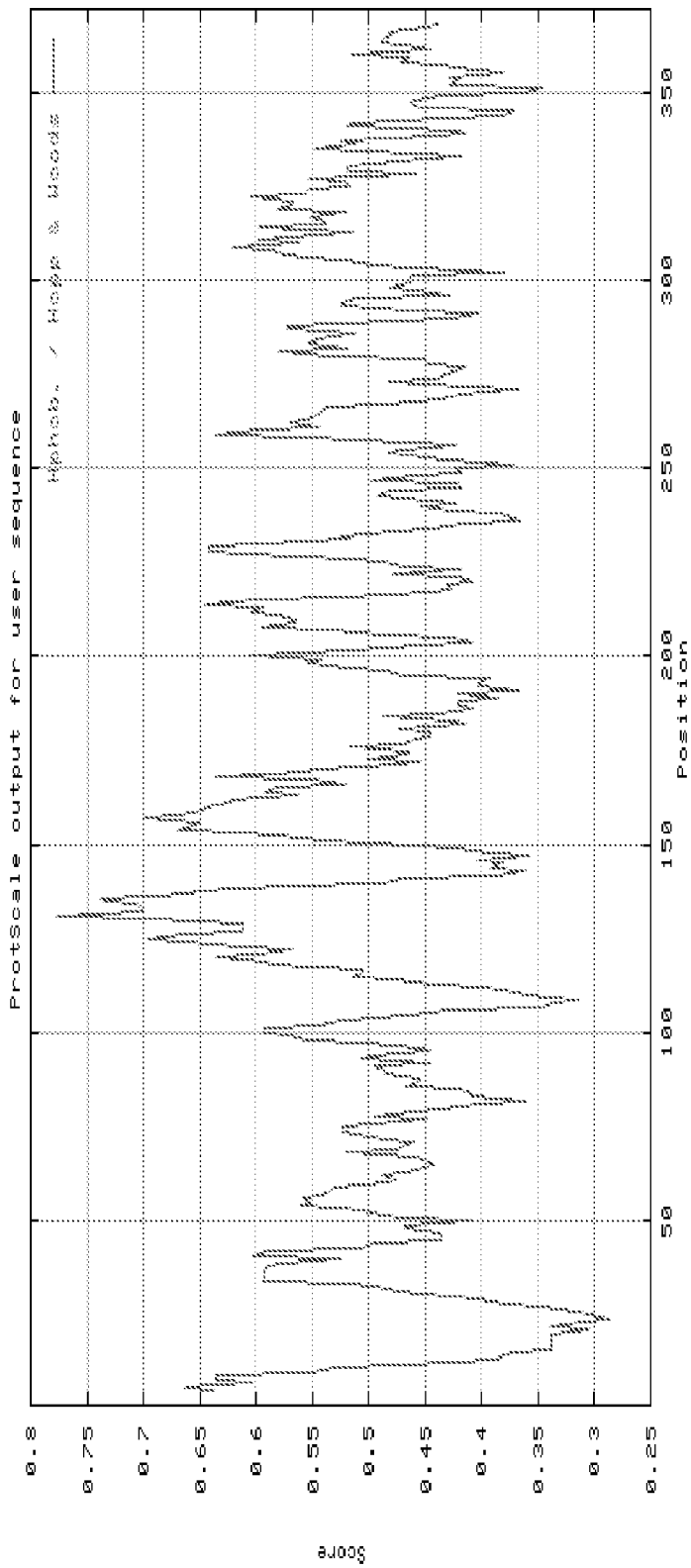
Figure 5M: 184P3C10b Hydrophilicity profile
(Hopp T.P., Woods K.R., 1981. Proc. Natl. Acad. Sci. U.S.A. 78:3824-3828)

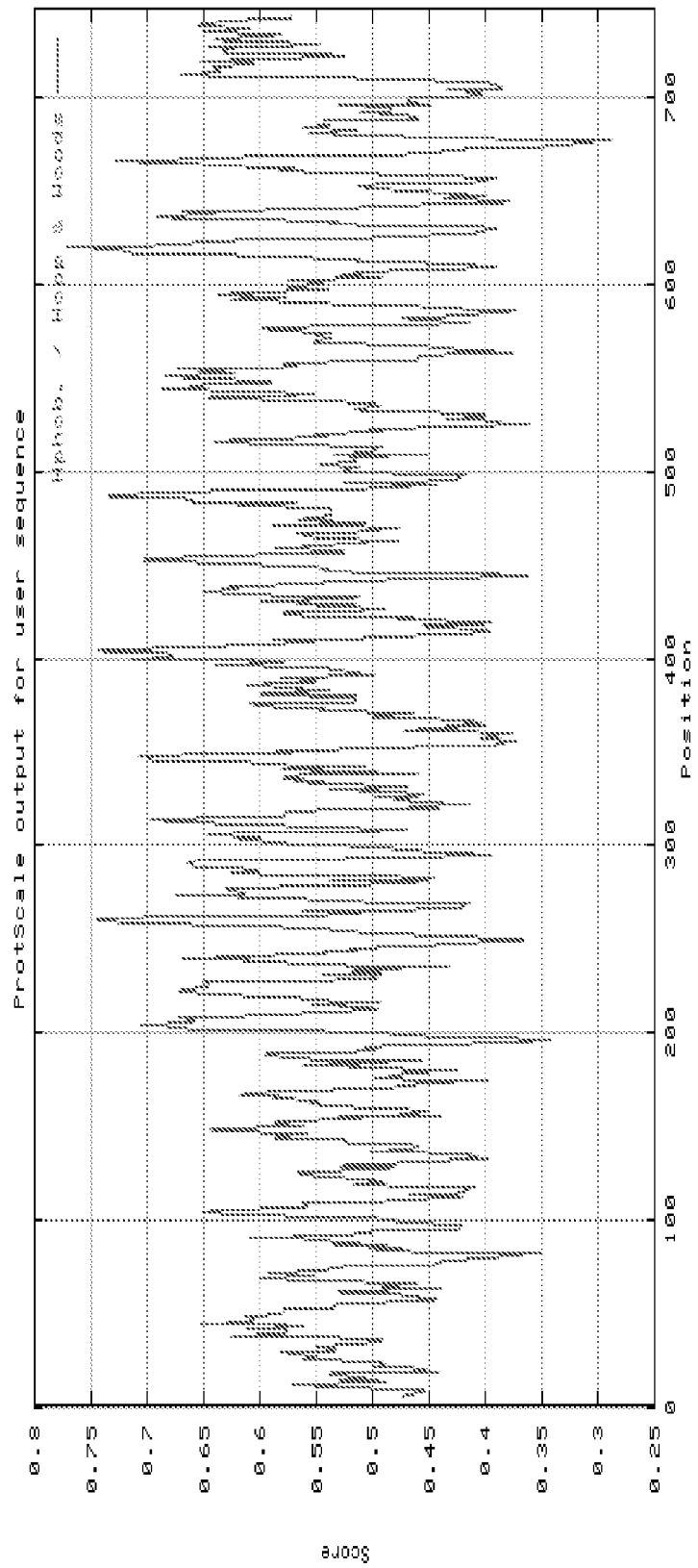
Figure 5N: 184P3G10 Hydrophilicity profile
(Hopp T.P., Woods K.R., 1981. Proc. Natl. Acad. Sci. U.S.A. 78:3824-3828)

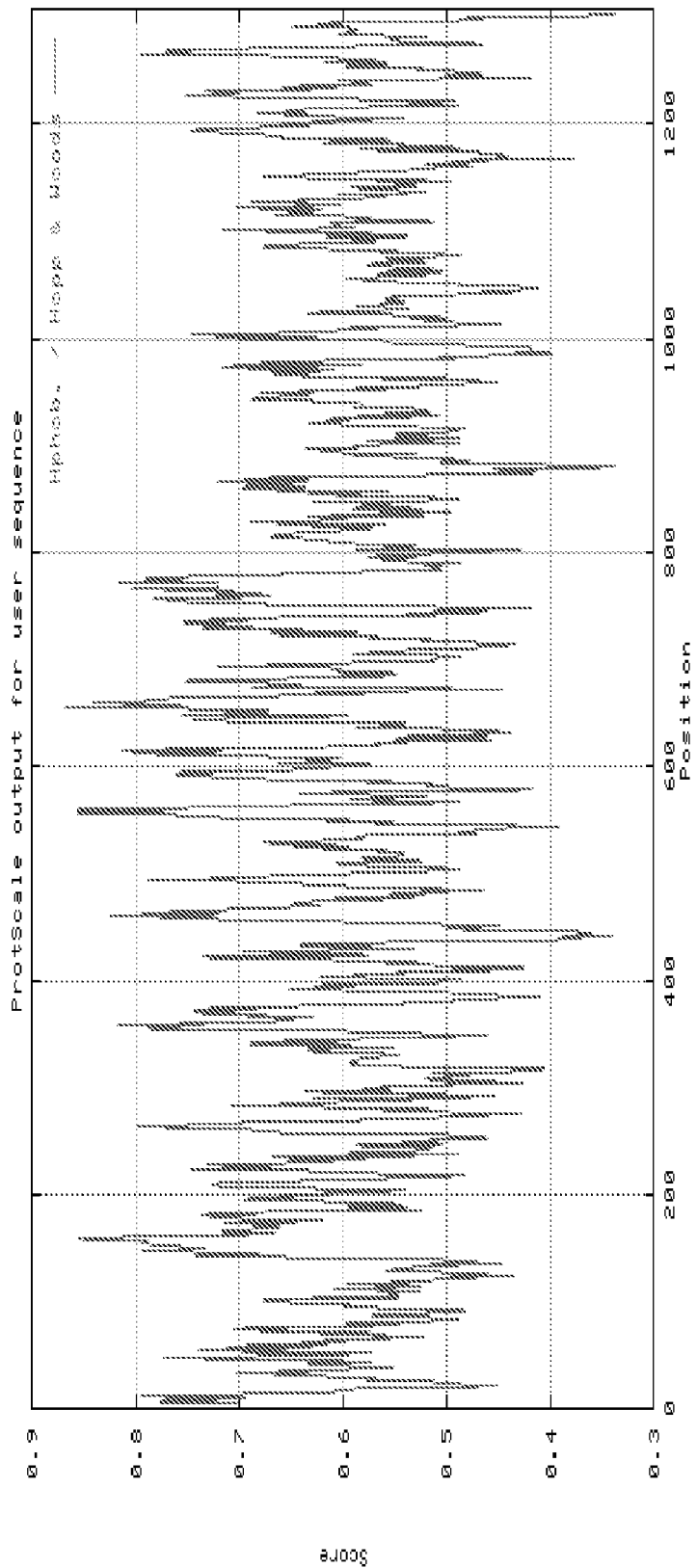
Figure 5O: 185P2C9 variant 1 Hydrophilicity profile
(Hopp T.P., Woods K.R., 1981. Proc. Natl. Acad. Sci. U.S.A. 78:3824-3828)

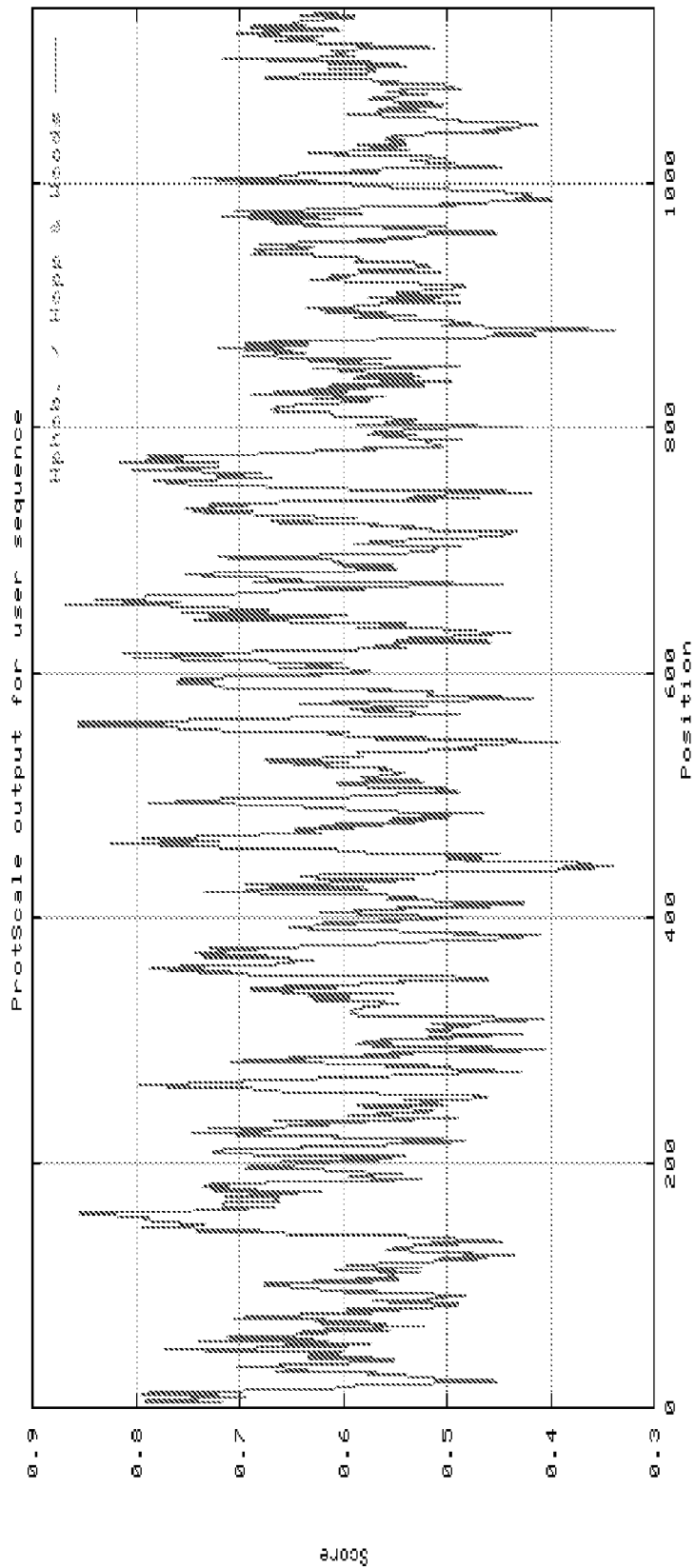
Figure 5P: 185P2C9 variant 2 Hydrophilicity profile
(Hopp T.P., Woods K.R., 1981. Proc. Natl. Acad. Sci. U.S.A. 78:3824-3828)

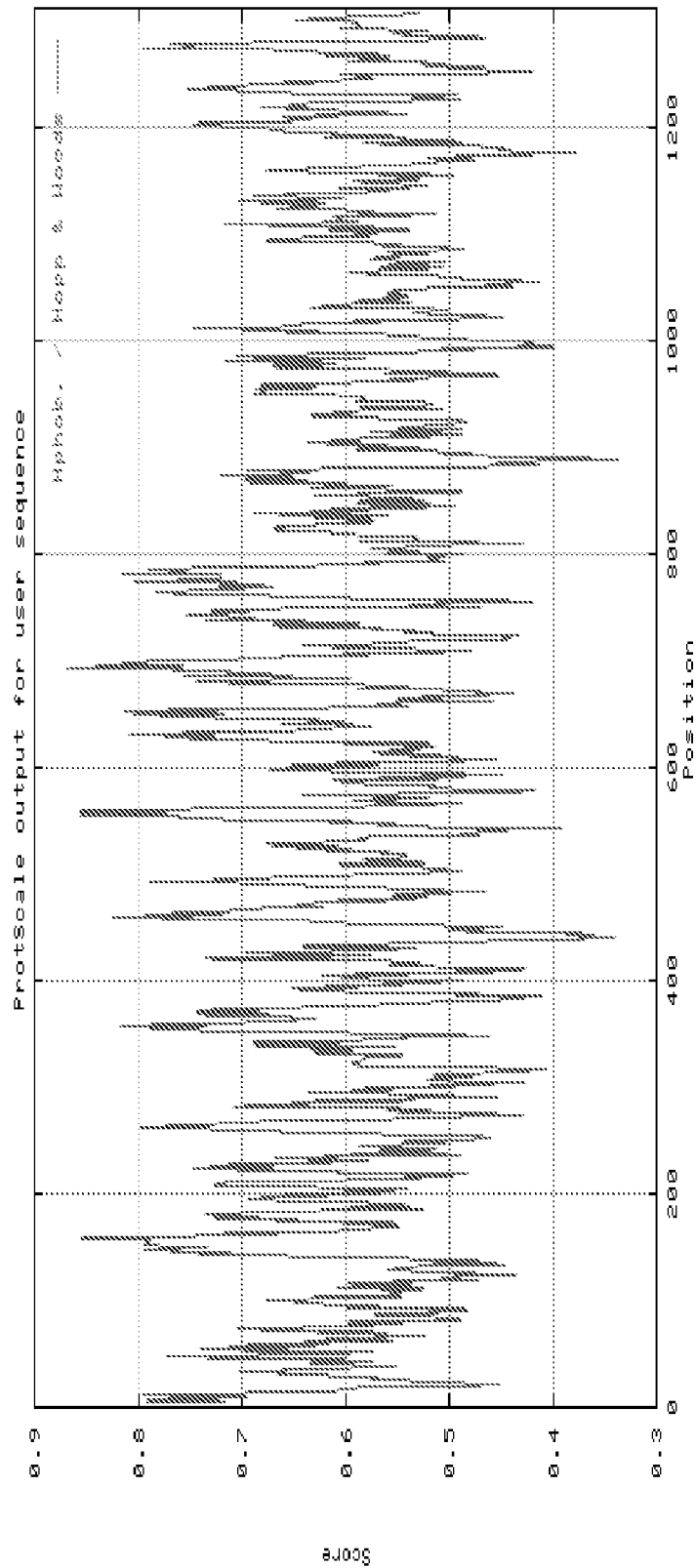
Figure 5Q: 185P2C9 variant 3 Hydrophilicity profile
(Hopp T.P., Woods K.R., 1981. Proc. Natl. Acad. Sci. U.S.A. 78:3824-3828)

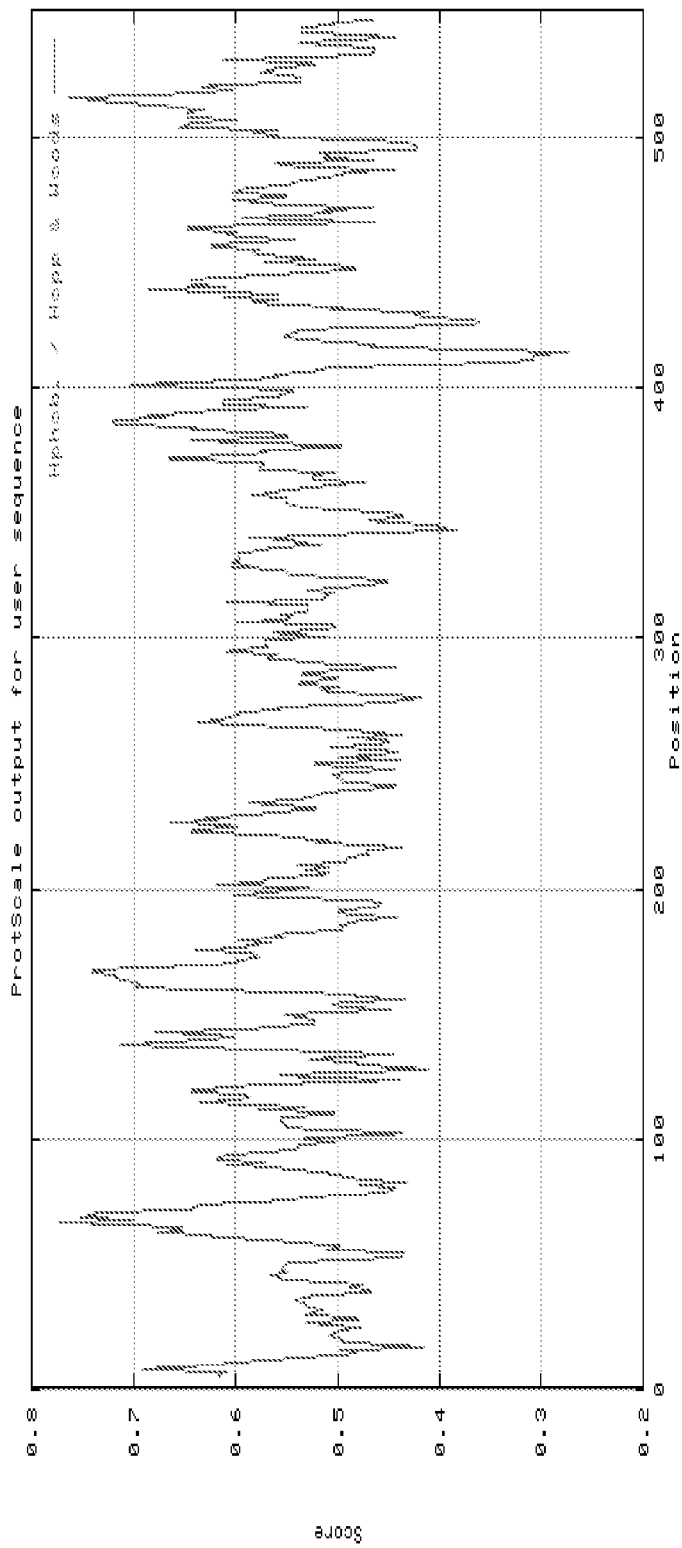
Figure 5R: 185P3C2 Hydrophilicity profile
(Hopp T.P., Woods K.R., 1981. Proc. Natl. Acad. Sci. U.S.A. 78:3824-3828)

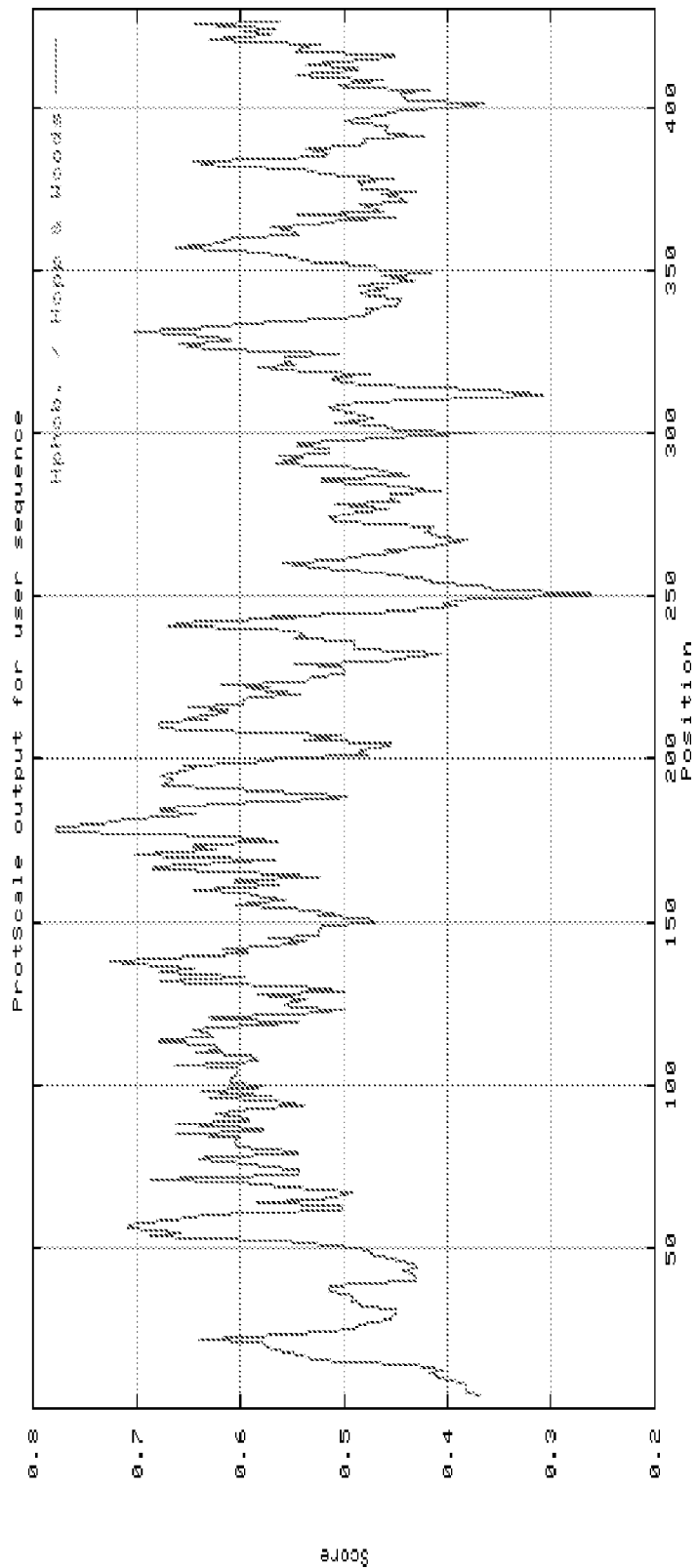
Figure 5S: 186P1H9 Hydrophilicity profile
(Hopp T.P., Woods K.R., 1981. Proc. Natl. Acad. Sci. U.S.A. 78:3824-3828)

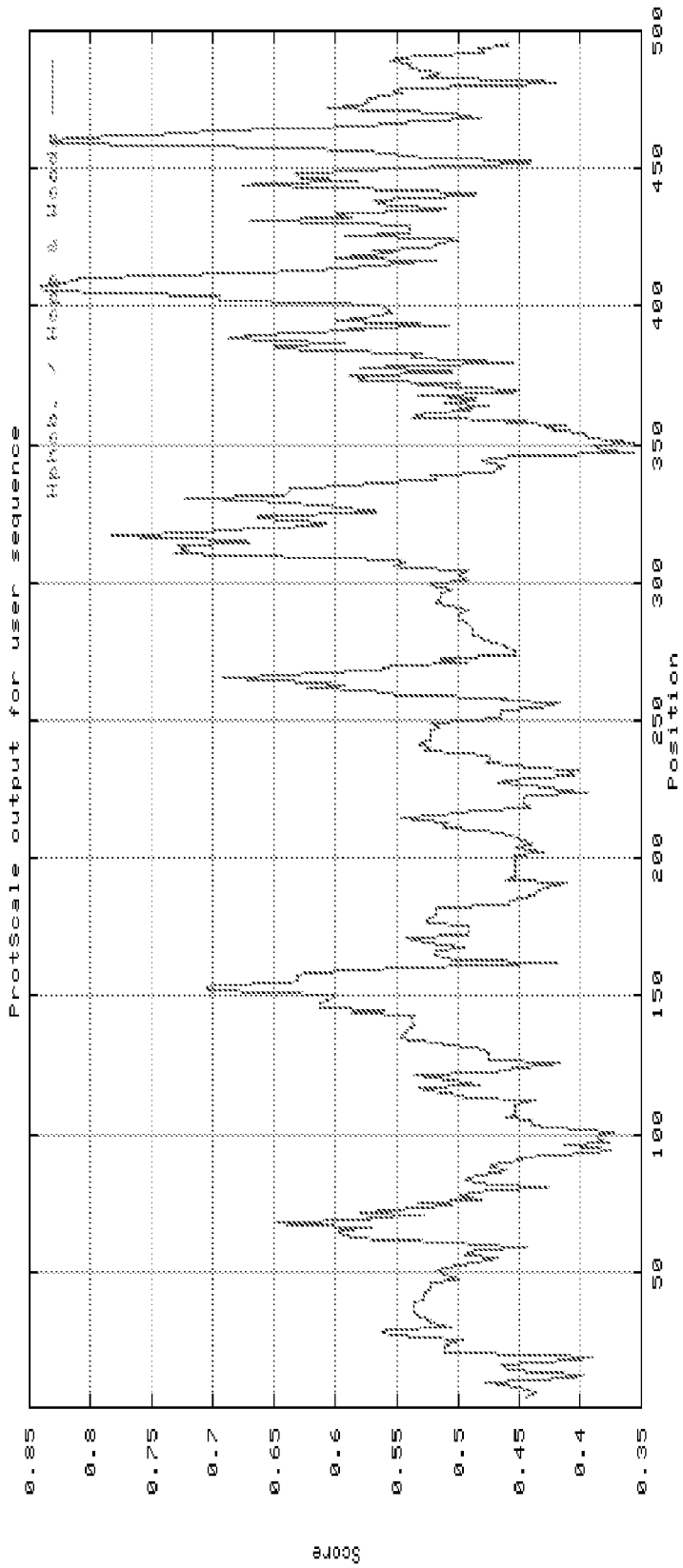
Figure 5T: 187P3F2 Hydrophilicity profile
(Hopp T.P., Woods K.R., 1981. Proc. Natl. Acad. Sci. U.S.A. 78:3824-3828)

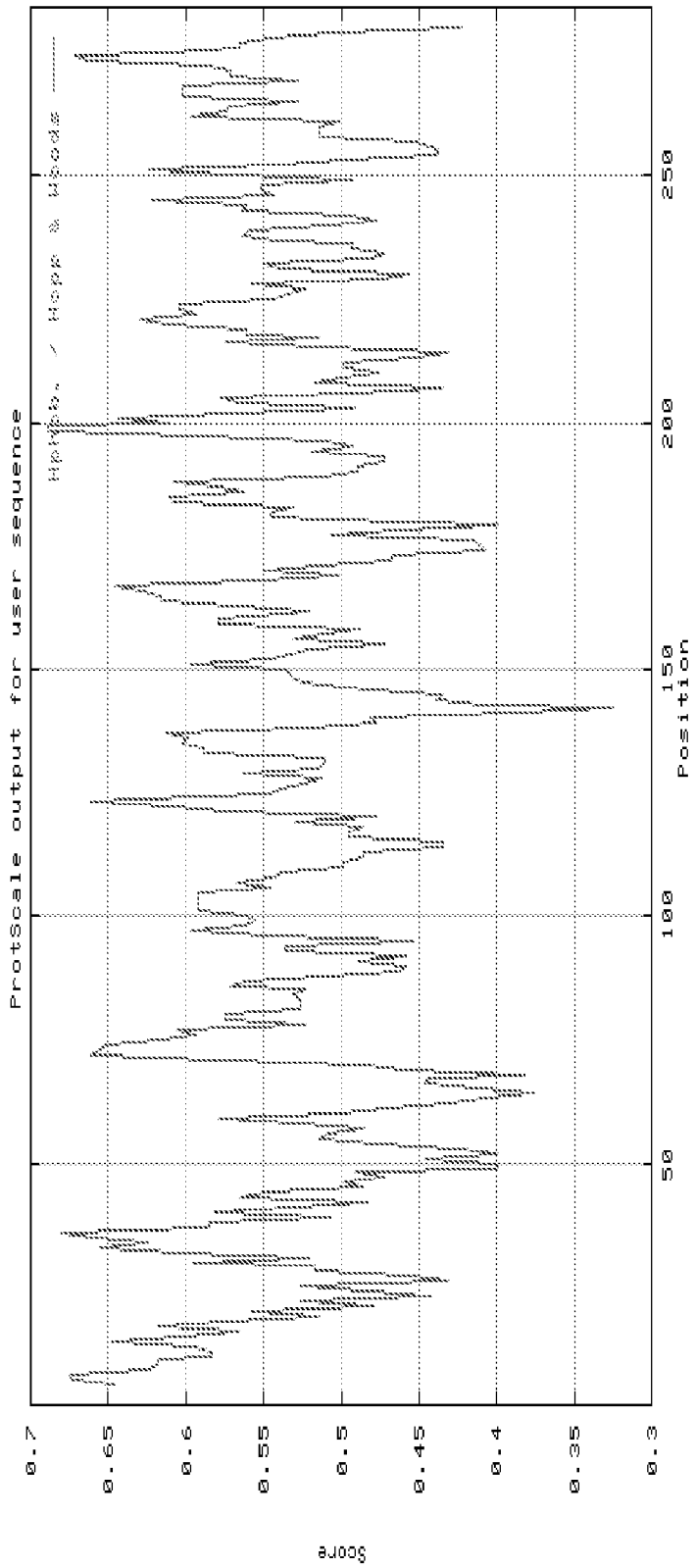
Figure 5U: 192P2G7 Hydrophilicity profile
(Hopp T.P., Woods K.R., 1981. Proc. Natl. Acad. Sci. U.S.A. 78:3824-3828)

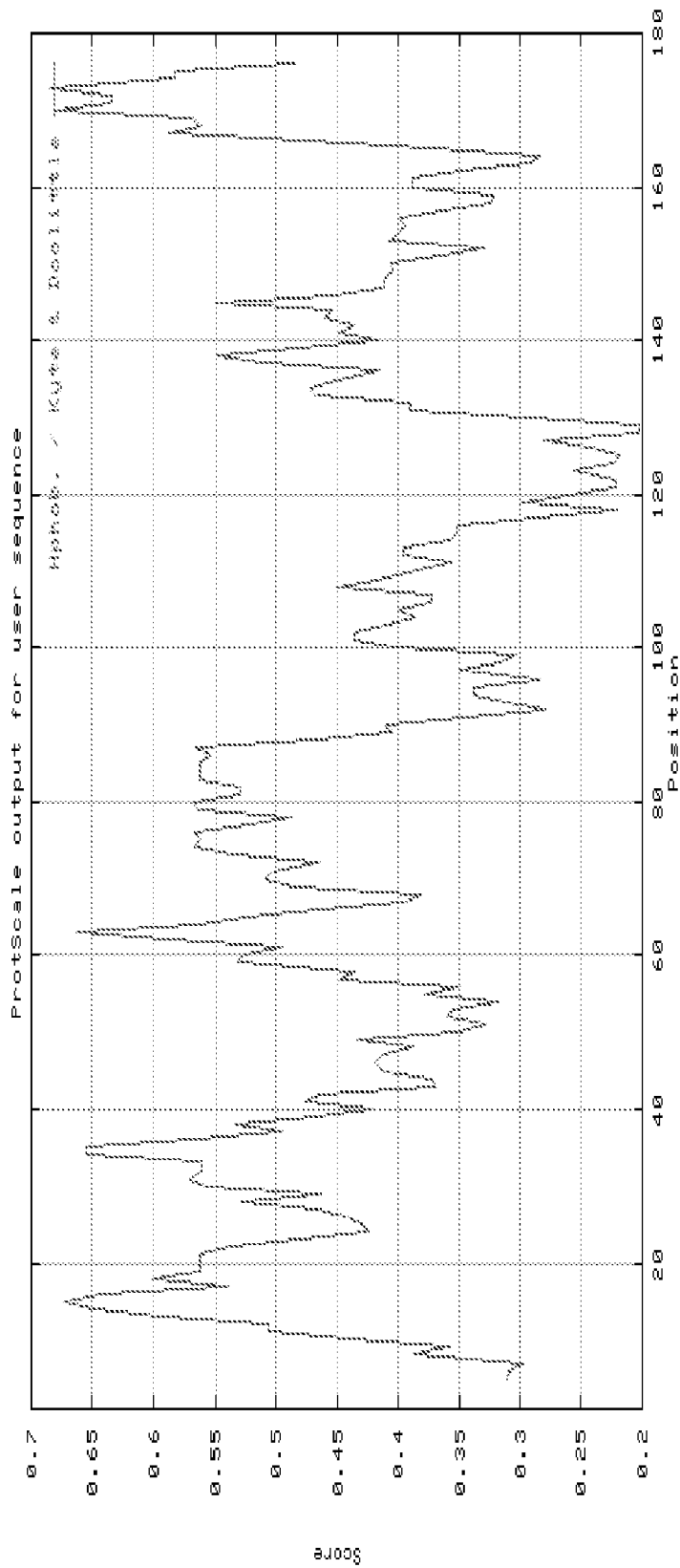
Figure 6A: 74P3B3 variant 1a Hydropathicity Profile
(Kyte J., Doolittle R.F., 1982. J. Mol. Biol. 157:105-132)

74P3B3 variant 1b Hydropathicity Profile
(Kyte J., Doolittle R.F., 1982. J. Mol. Biol. 157:105-132)

83P4B8 Hydropathicity Profile
(Kyte J., Doolittle R.F., 1982. J. Mol. Biol. 157:105-132)

109P1D4 Hydropathicity Profile
(Kyte J., Doolittle R.F., 1982. J. Mol. Biol. 157:105-132)

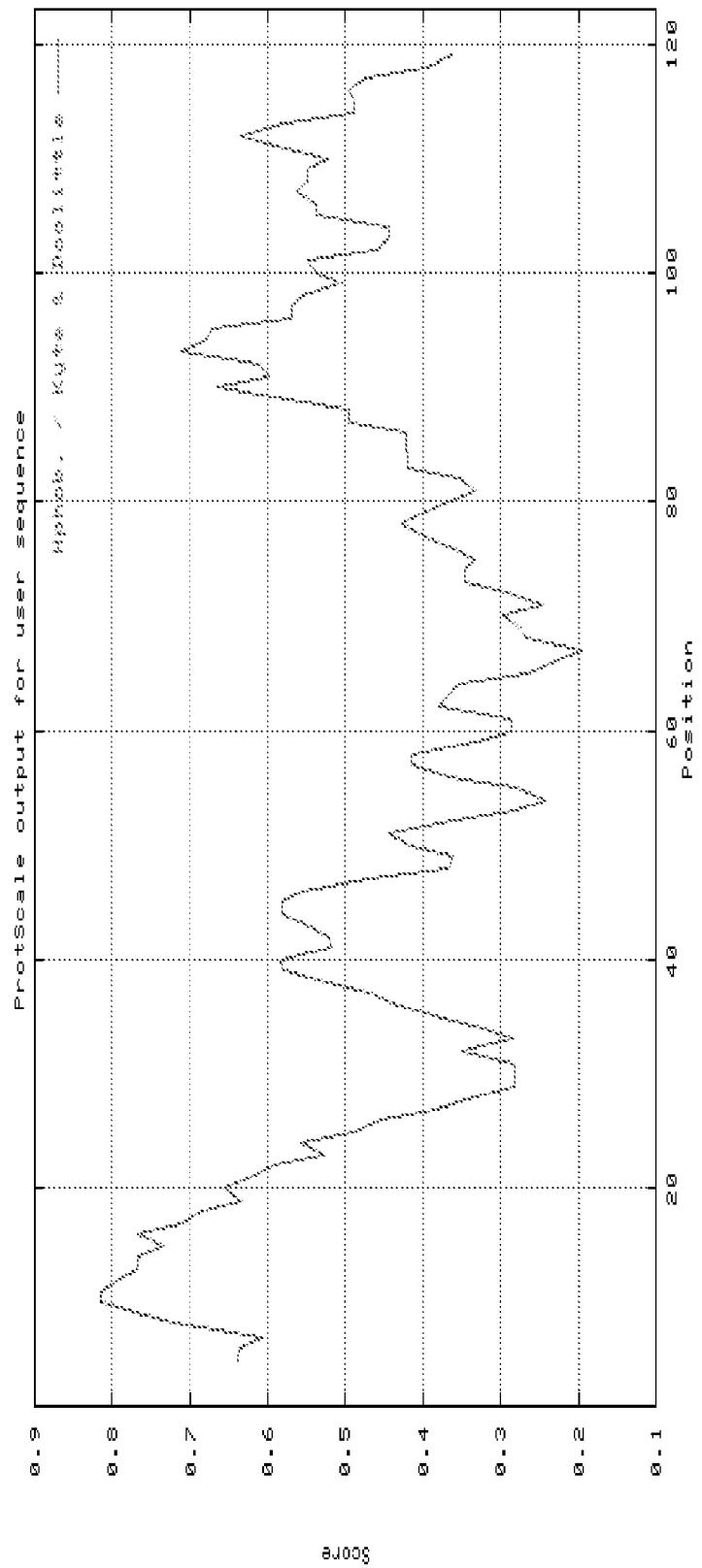
Figure 6E: 151P4E11 Hydropathicity Profile
(Kyte J., Doolittle R.F., 1982. J. Mol. Biol. 157:105-132)

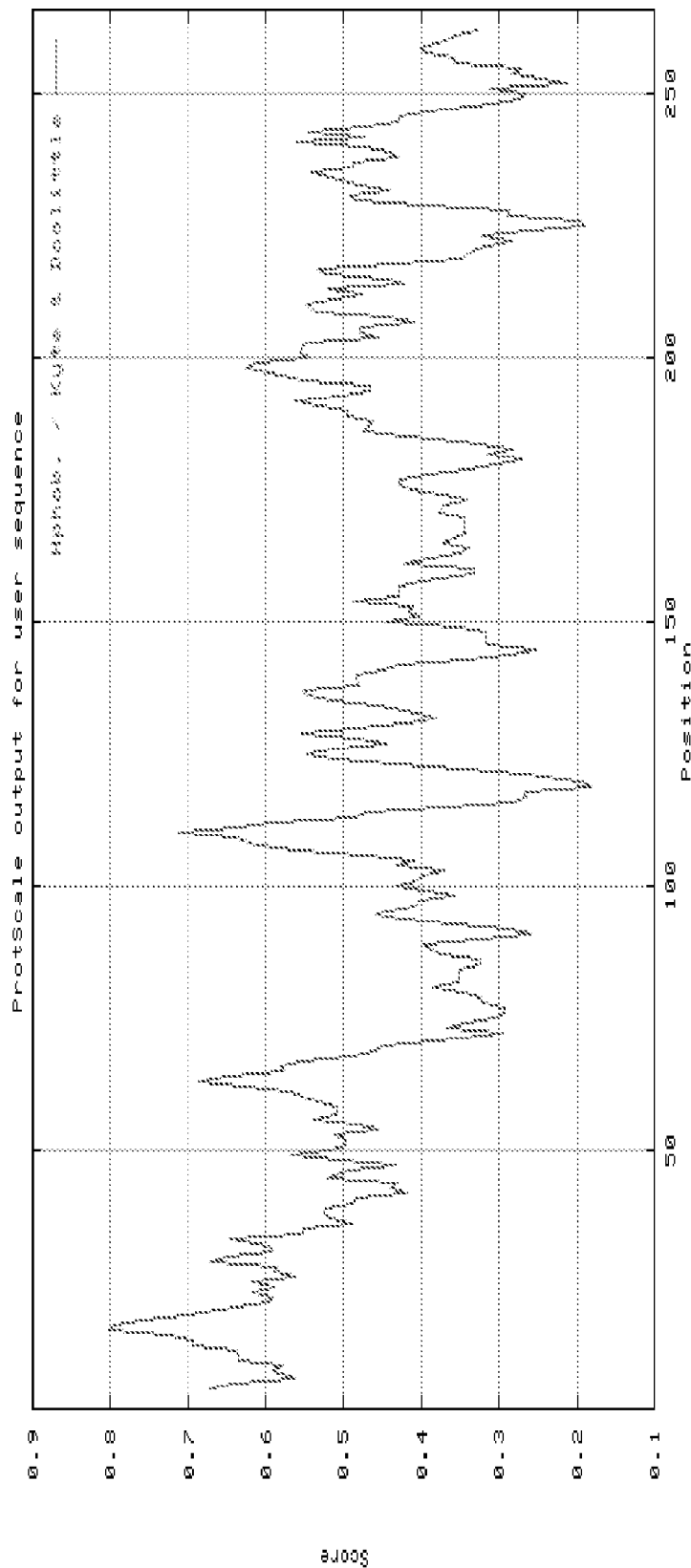
Figure 6F: 151P1C7a Hydropathicity Profile
(Kyte J., Doolittle R.F., 1982. J. Mol. Biol. 157:105-132)

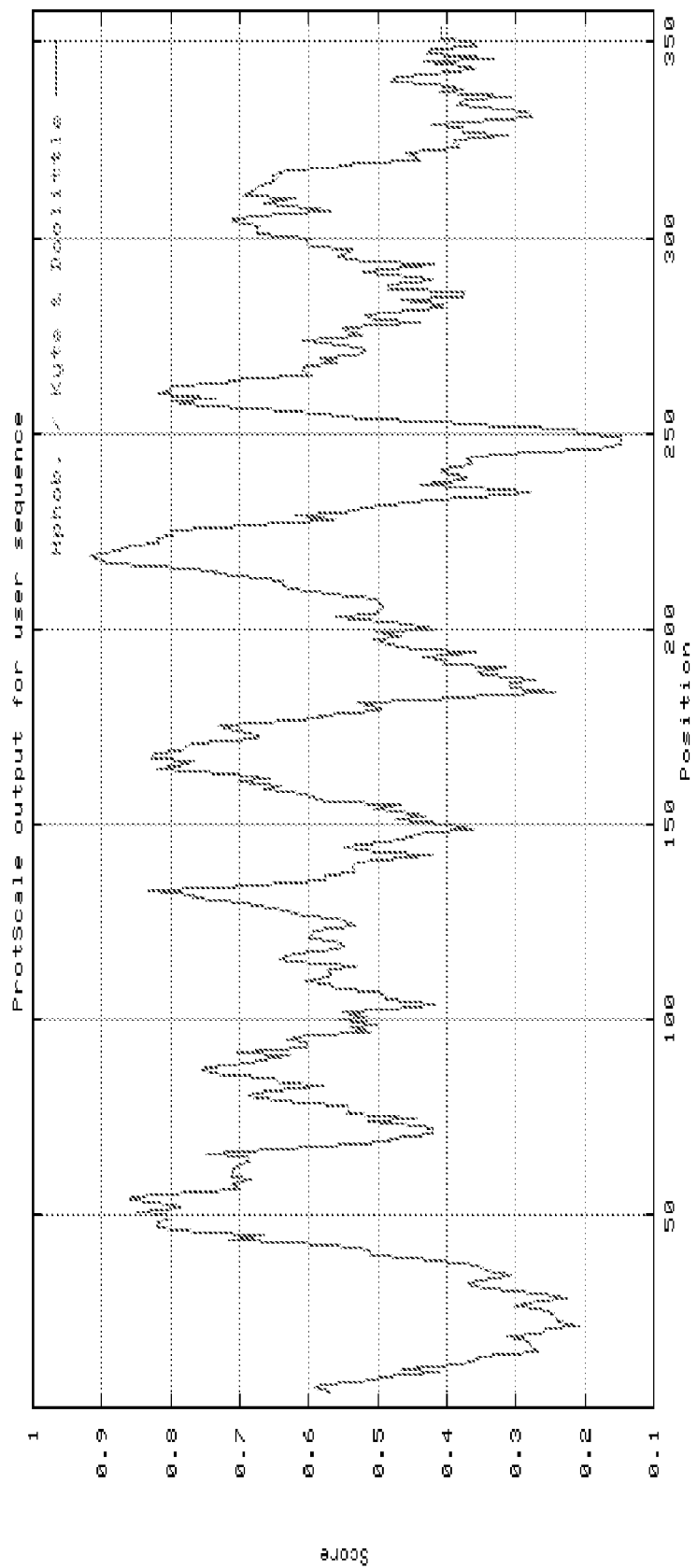
Figure 6G: 154P2A8 Hydropathicity Profile
(Kyte J., Doolittle R.F., 1982. J. Mol. Biol. 157:105-132)

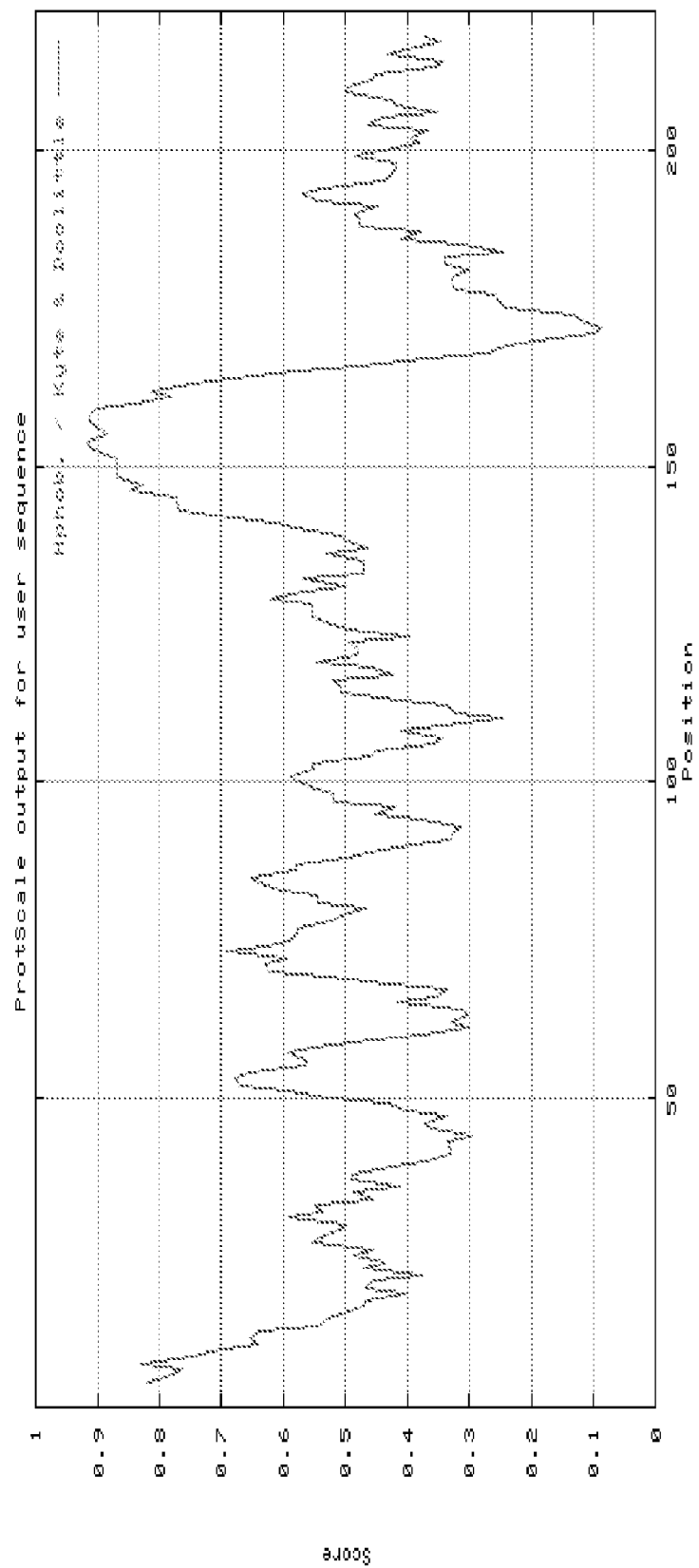
Figure 6H: 156P1D4 Hydropathicity Profile
(Kyte J., Doolittle R.F., 1982. J. Mol. Biol. 157:105-132)

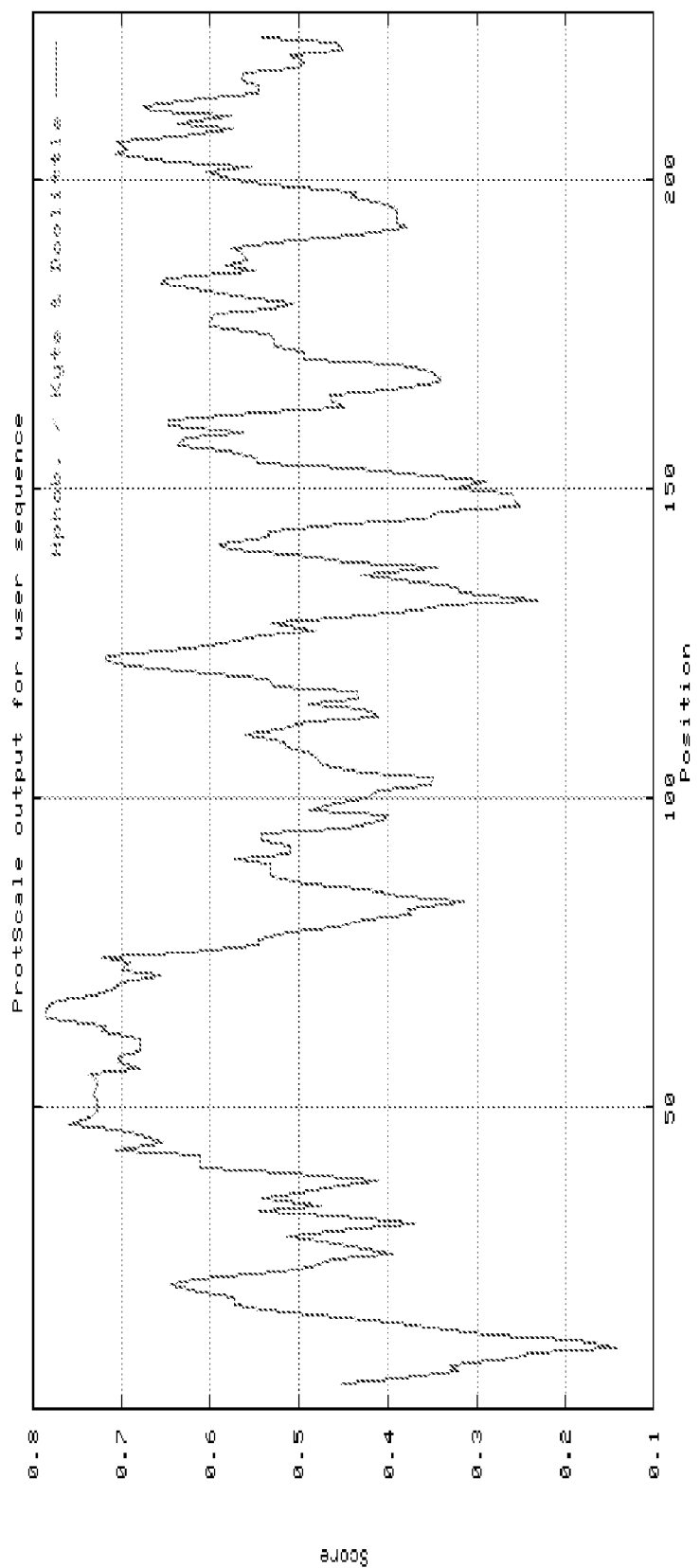
Figure 6I: 156P5C12 Hydropathicity Profile
(Kyte J., Doolittle R.F., 1982. J. Mol. Biol. 157:105-132)

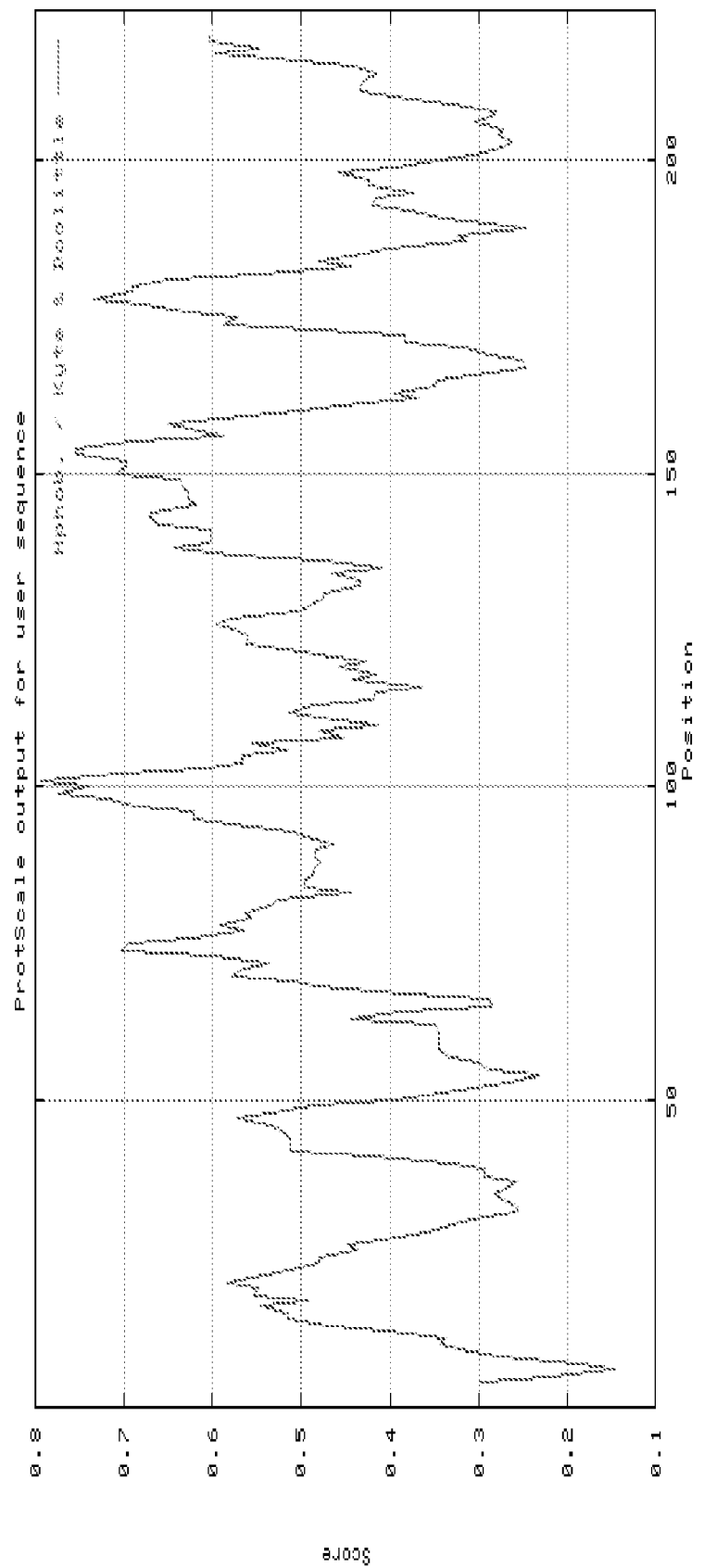
Figure 6J: 159P2B5 Hydropathicity Profile
(Kyte J., Doolittle R.F., 1982. J. Mol. Biol. 157:105-132)

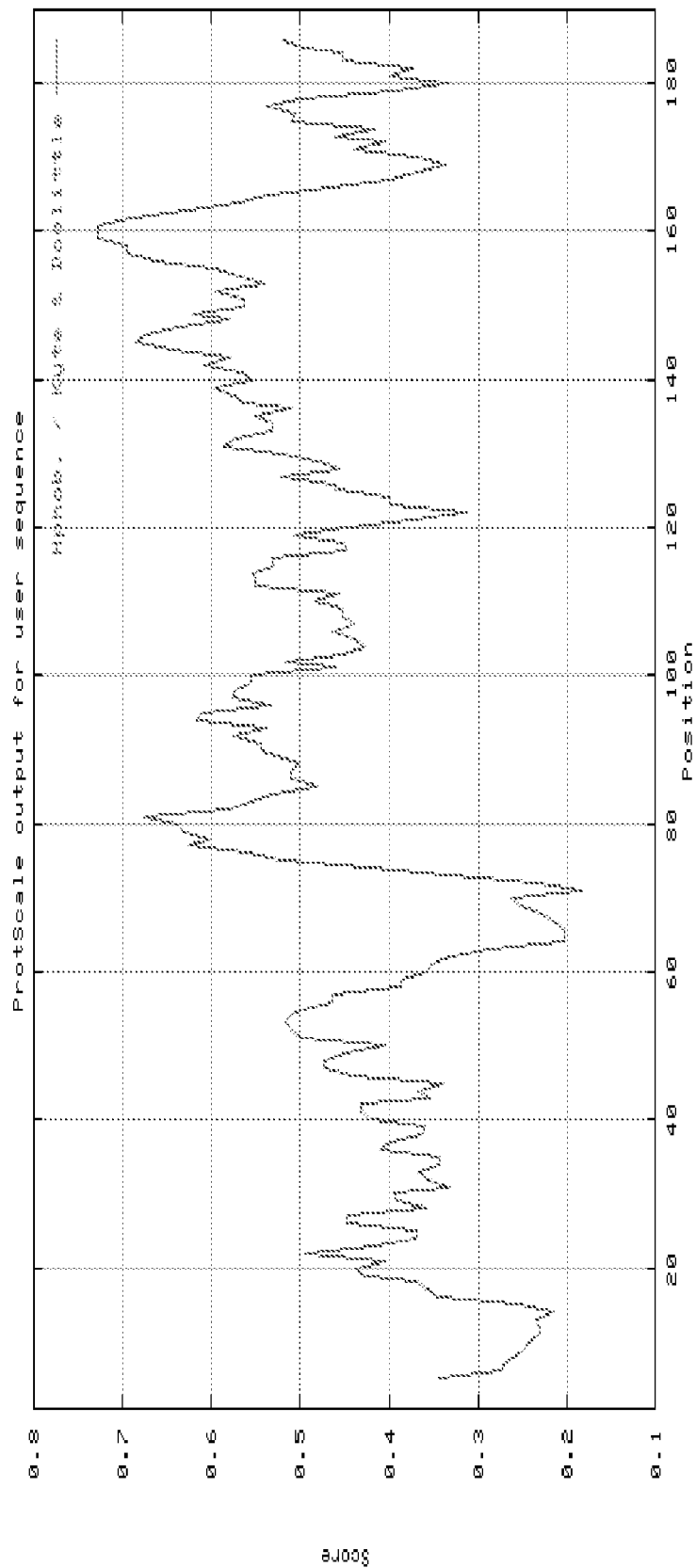
Figure 6K: 161P2B7a Hydropathicity Profile
(Kyte J., Doolittle R.F., 1982. J. Mol. Biol. 157:105-132)

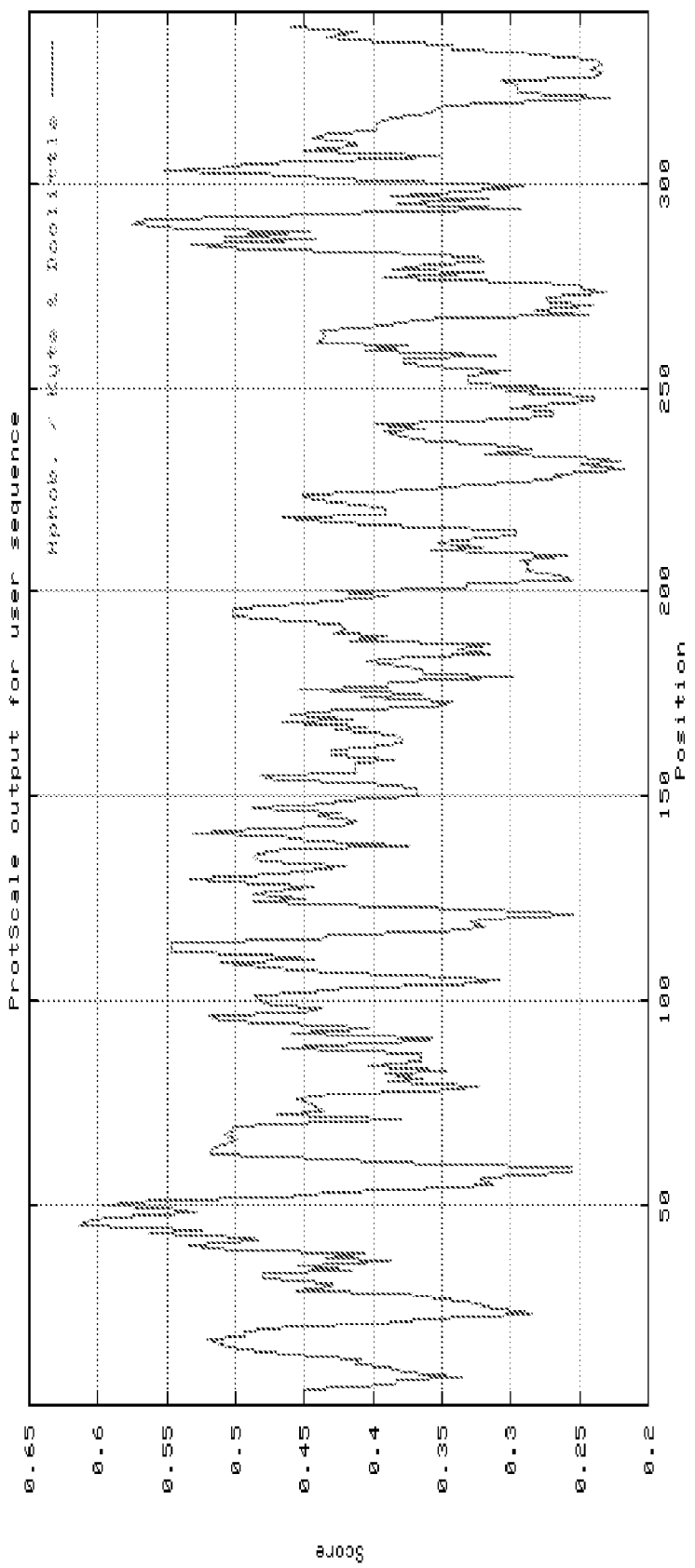
Figure 6L: 179P3G7 Hydropathicity Profile
(Kyte J., Doolittle R.F., 1982. J. Mol. Biol. 157:105-132)

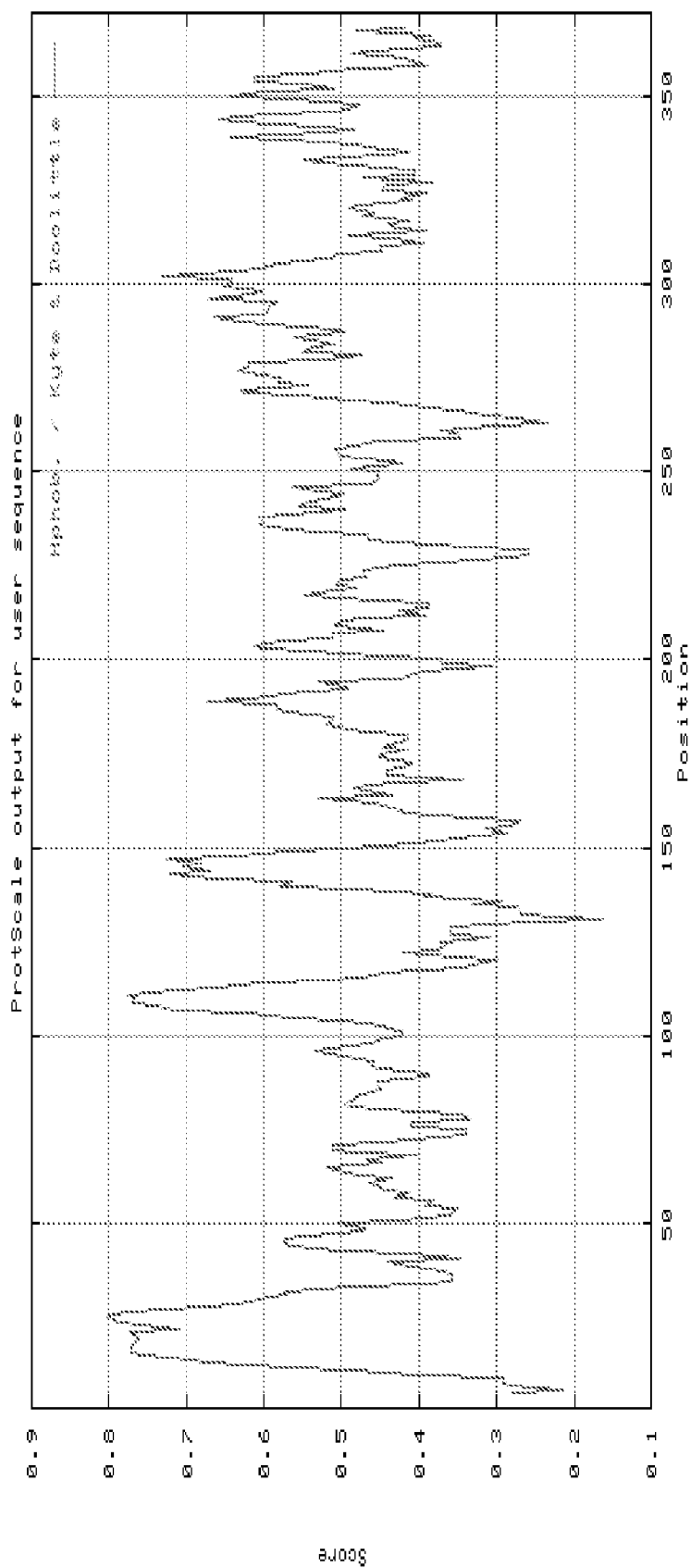
Figure 6M: 184P3C10b Hydropathicity Profile
(Kyte J., Doolittle R.F., 1982. J. Mol. Biol. 157:105-132)

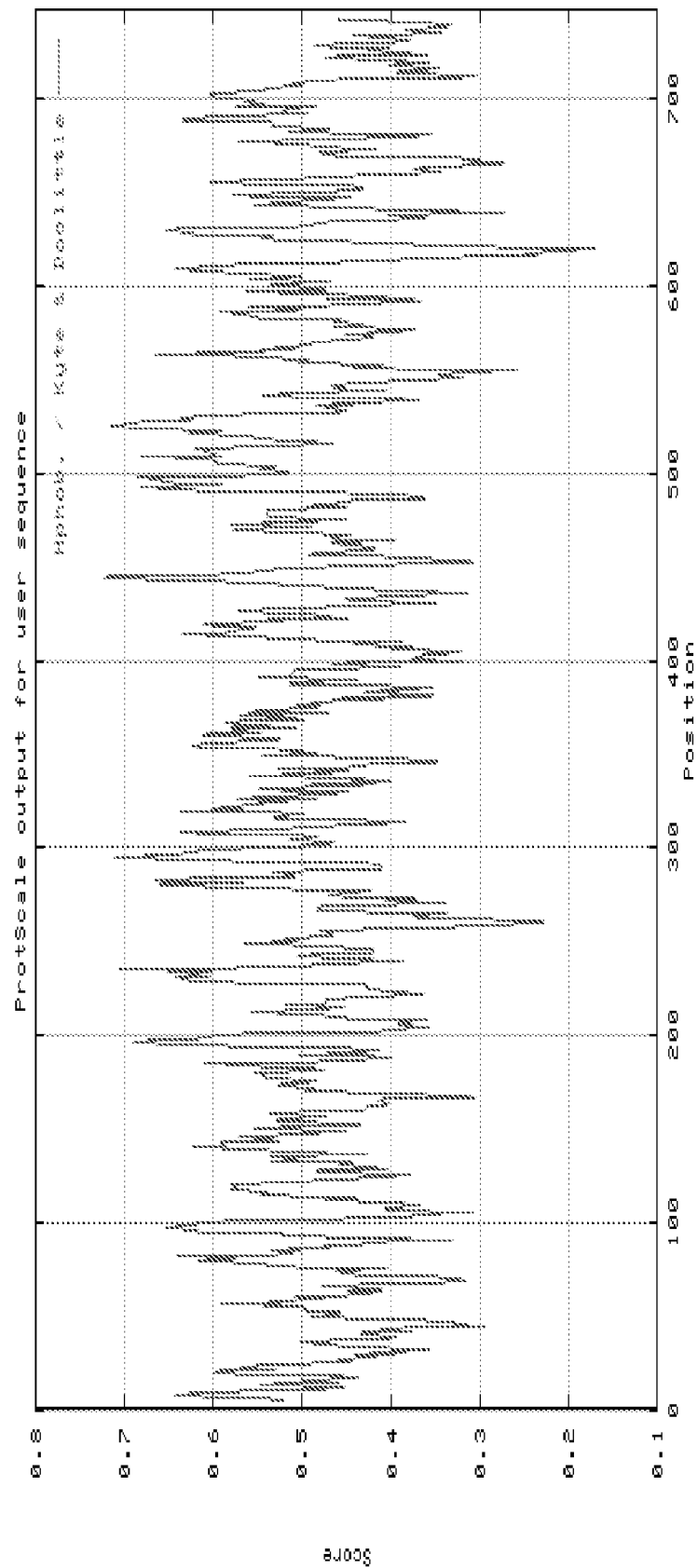
Figure 6N: 184P3G10 Hydropathicity Profile
(Kyte J., Doolittle R.F., 1982. J. Mol. Biol. 157:105-132)

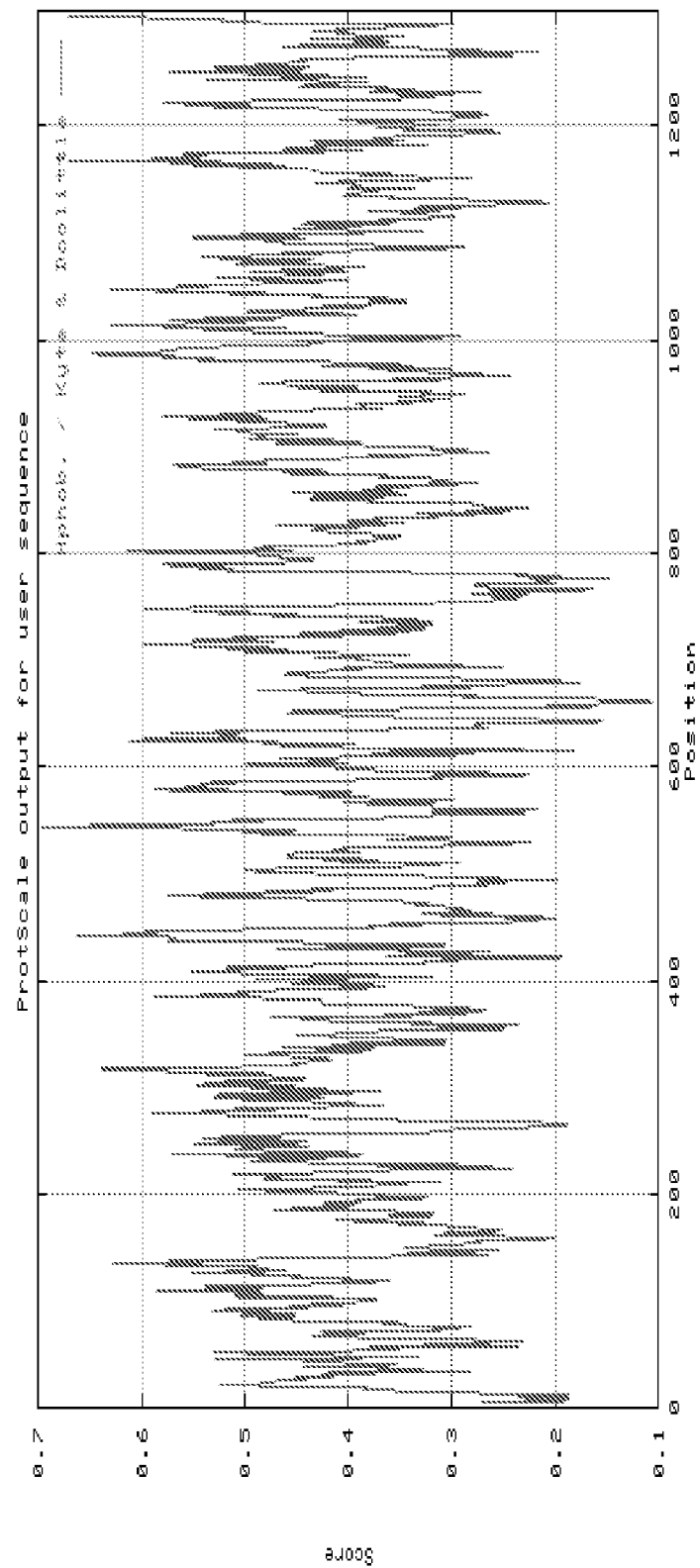
Figure 60: 185P2C9 variant 1 Hydropathicity Profile
(Kyte J., Doolittle R.F., 1982. J. Mol. Biol. 157:105-132)

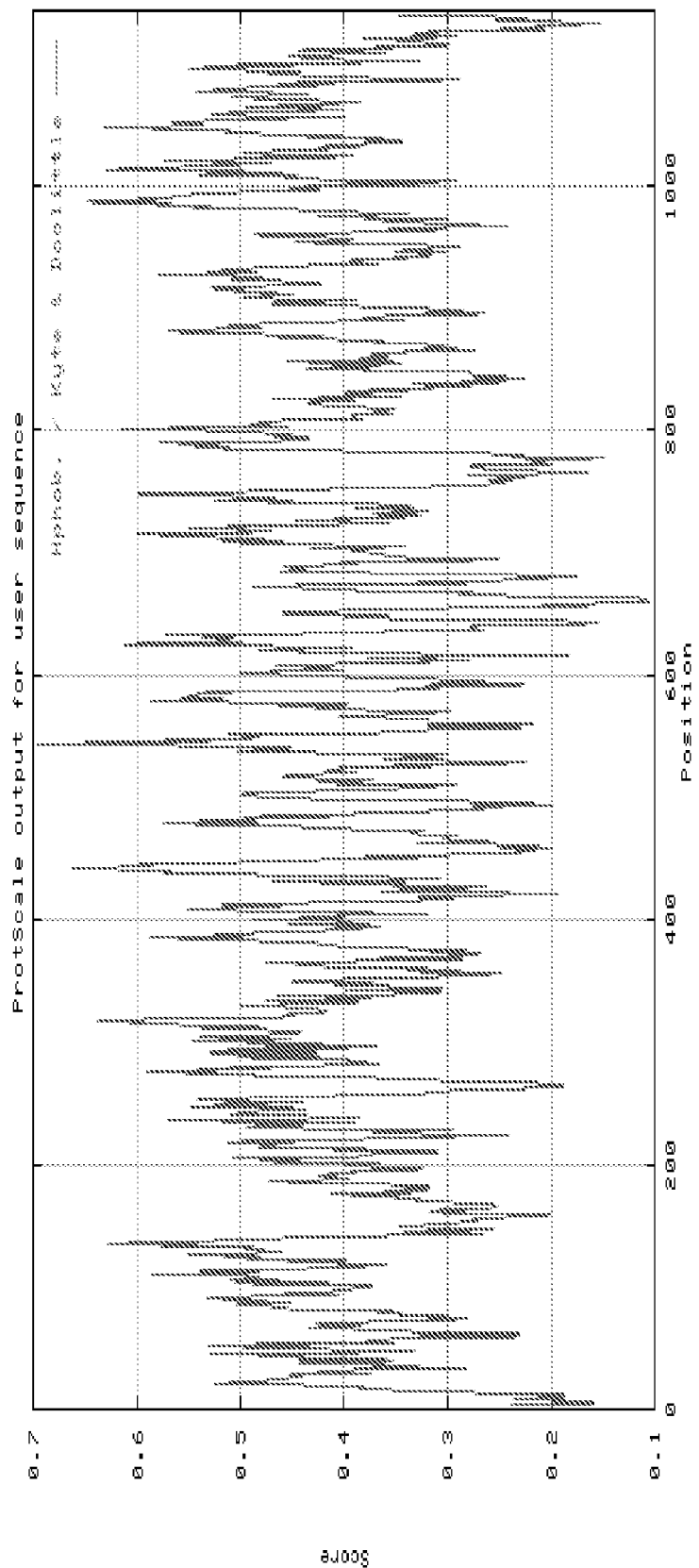
Figure 6P: 185P2C9 variant 2 Hydropathicity Profile
(Kyte J., Doolittle R.F., 1982. J. Mol. Biol. 157:105-132)

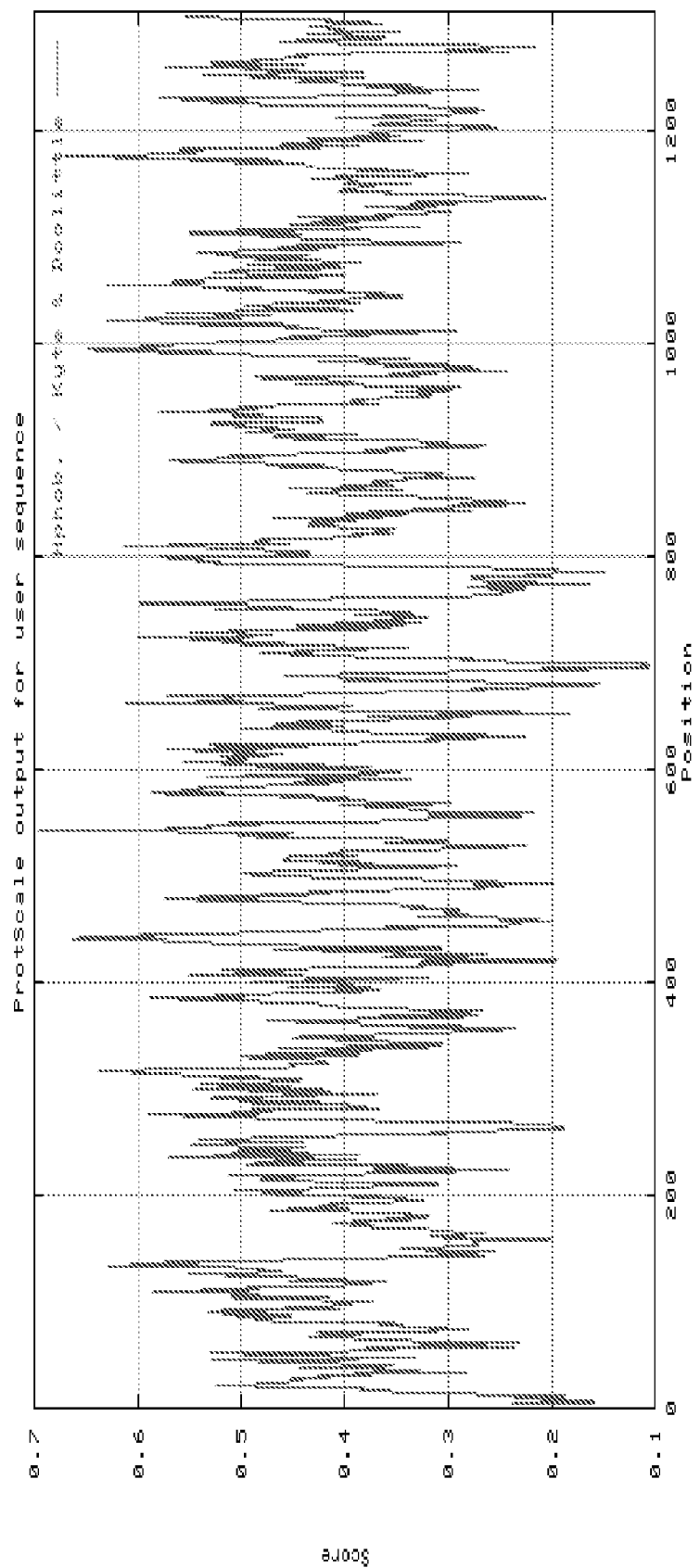
Figure 6Q: 185P2C9 variant 3 Hydropathicity Profile
(Kyte J., Doolittle R.F., 1982. J. Mol. Biol. 157:105-132)

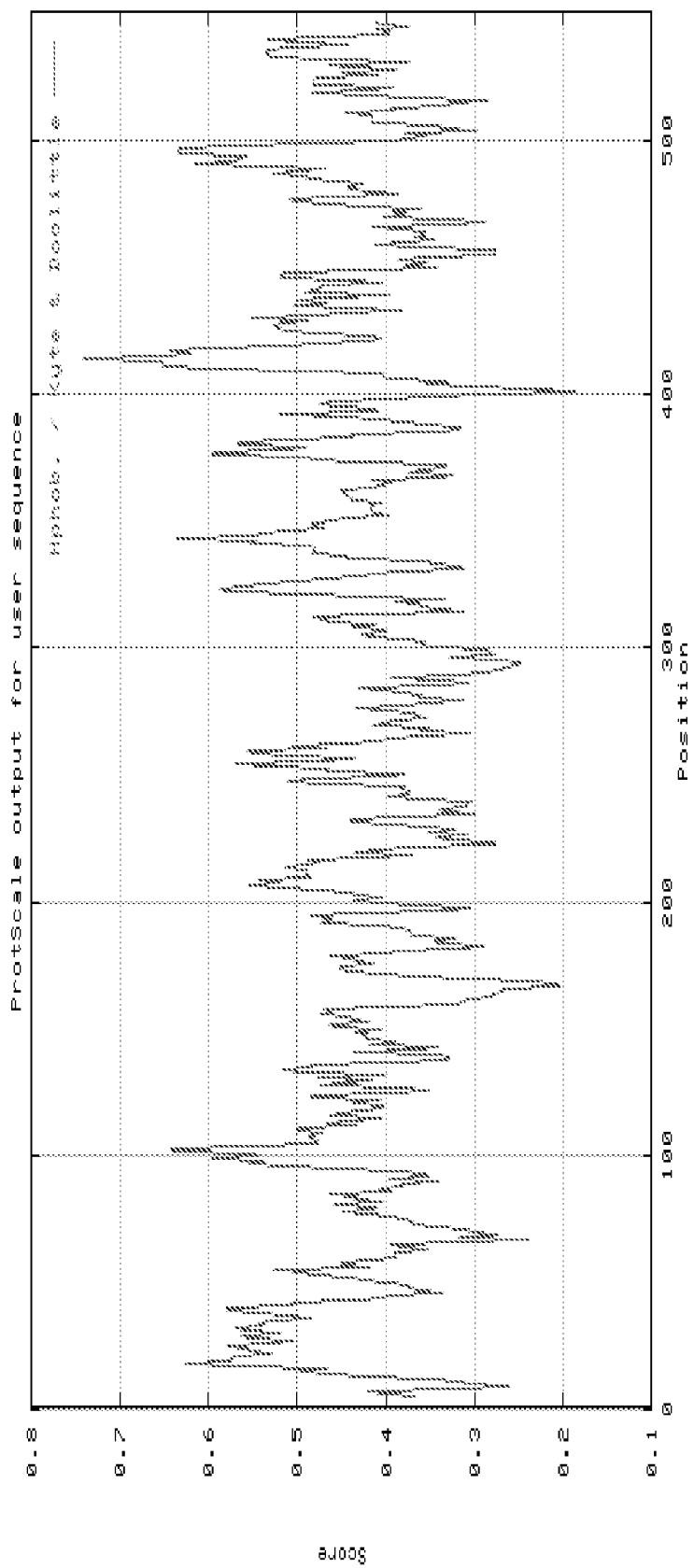
Figure 6R: 185P3C2 Hydropathicity Profile
(Kyte J., Doolittle R.F., 1982. J. Mol. Biol. 157:105-132)

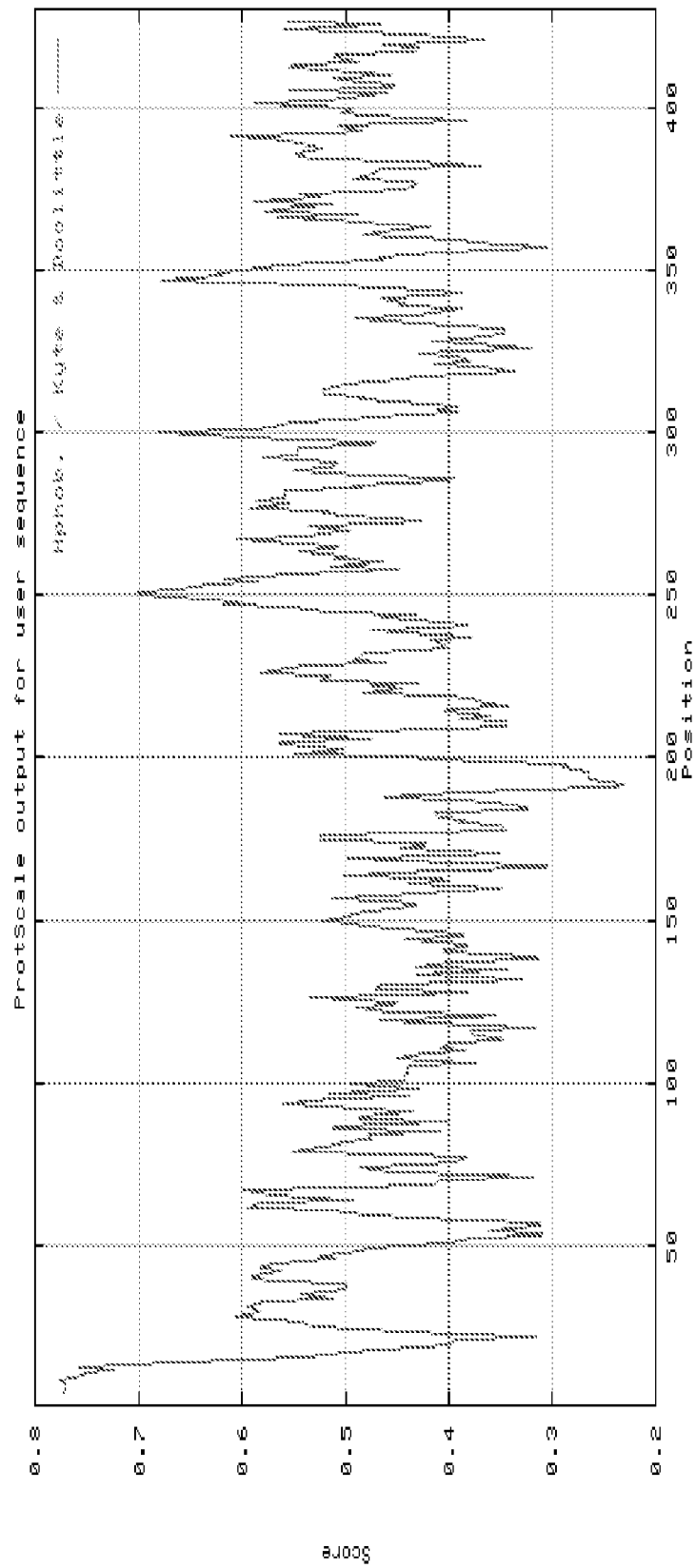
Figure 6S: 186P1H9 Hydropathicity Profile
(Kyte J., Doolittle R.F., 1982. J. Mol. Biol. 157:105-132)

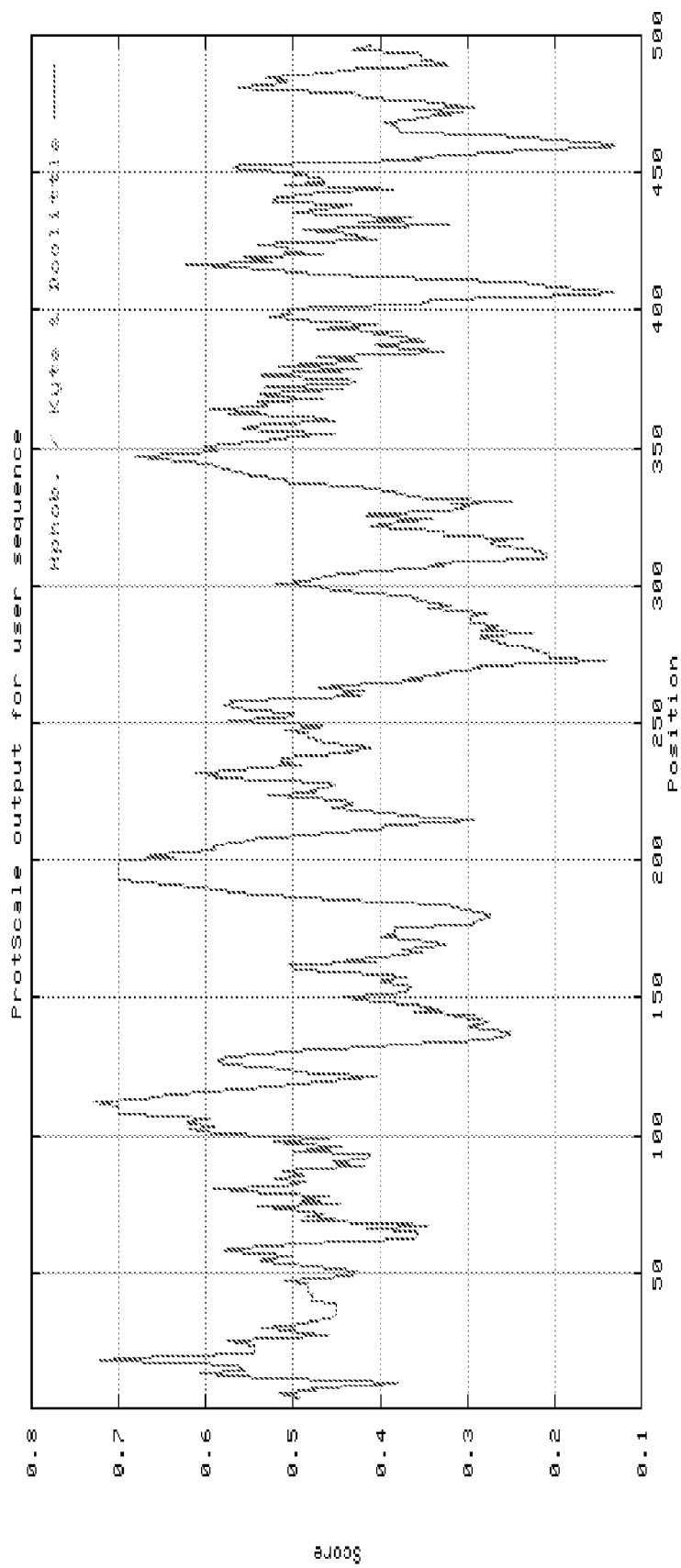
Figure 6T: 187P3F2 Hydropathicity Profile
(Kyte J., Doolittle R.F., 1982. J. Mol. Biol. 157:105-132)

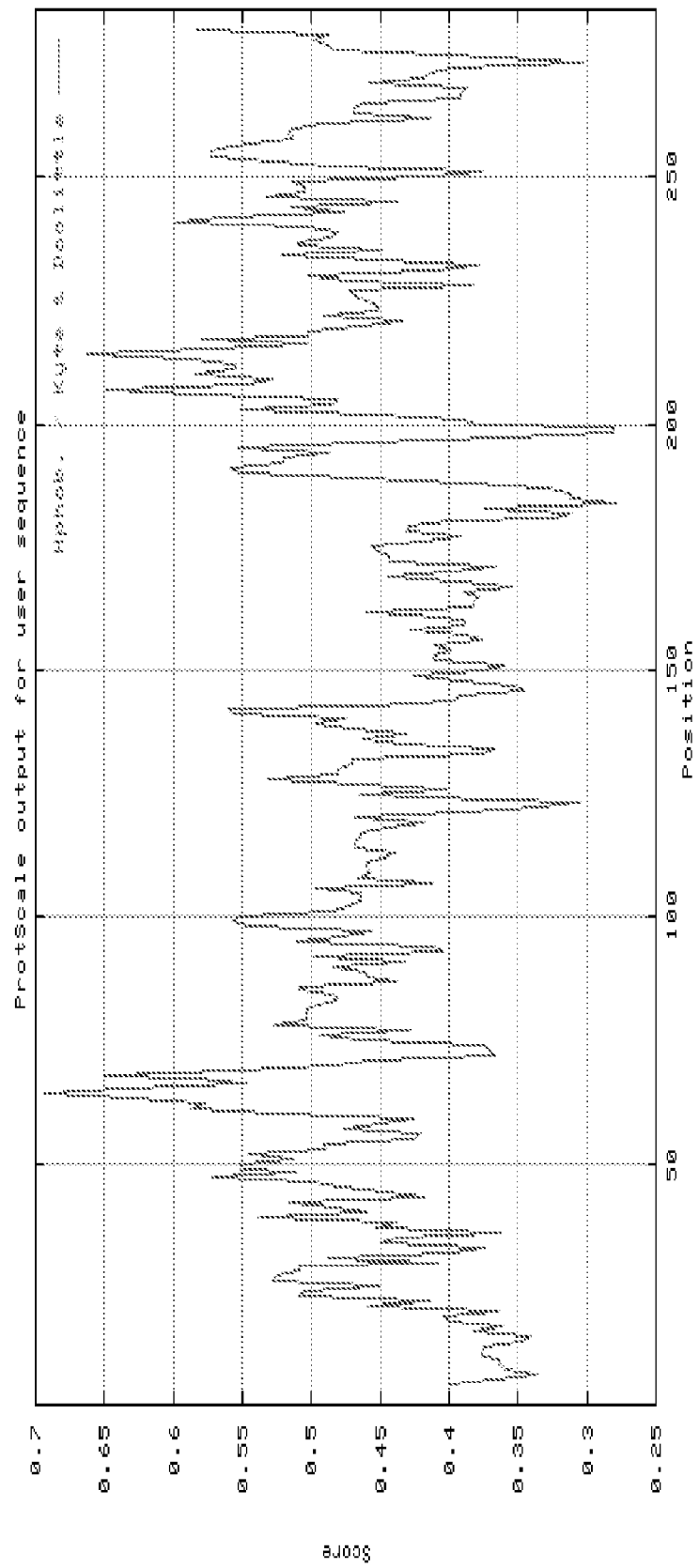
Figure 6U: 192P2G7 Hydropathicity Profile
(Kyte J., Doolittle R.F., 1982. J. Mol. Biol. 157:105-132)

74P3B3 variant 1a % Accessible Residues Profile
(Janin J., 1979. Nature 277:491-492)

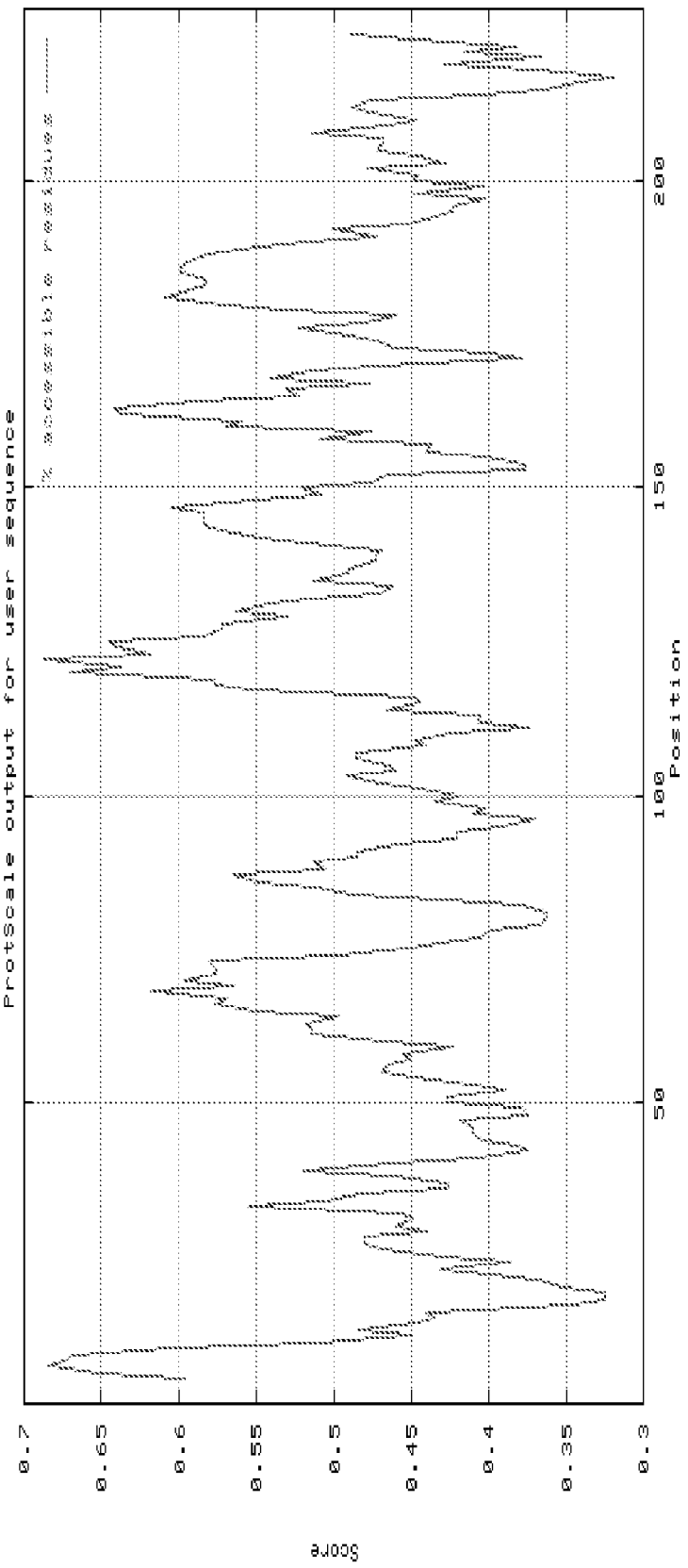

83P4B8 % Accessible Residues Profile
(Janin J., 1979. Nature 277:491-492)

109P1D4 % Accessible Residues Profile
(Janin J., 1979. Nature 277:491-492)

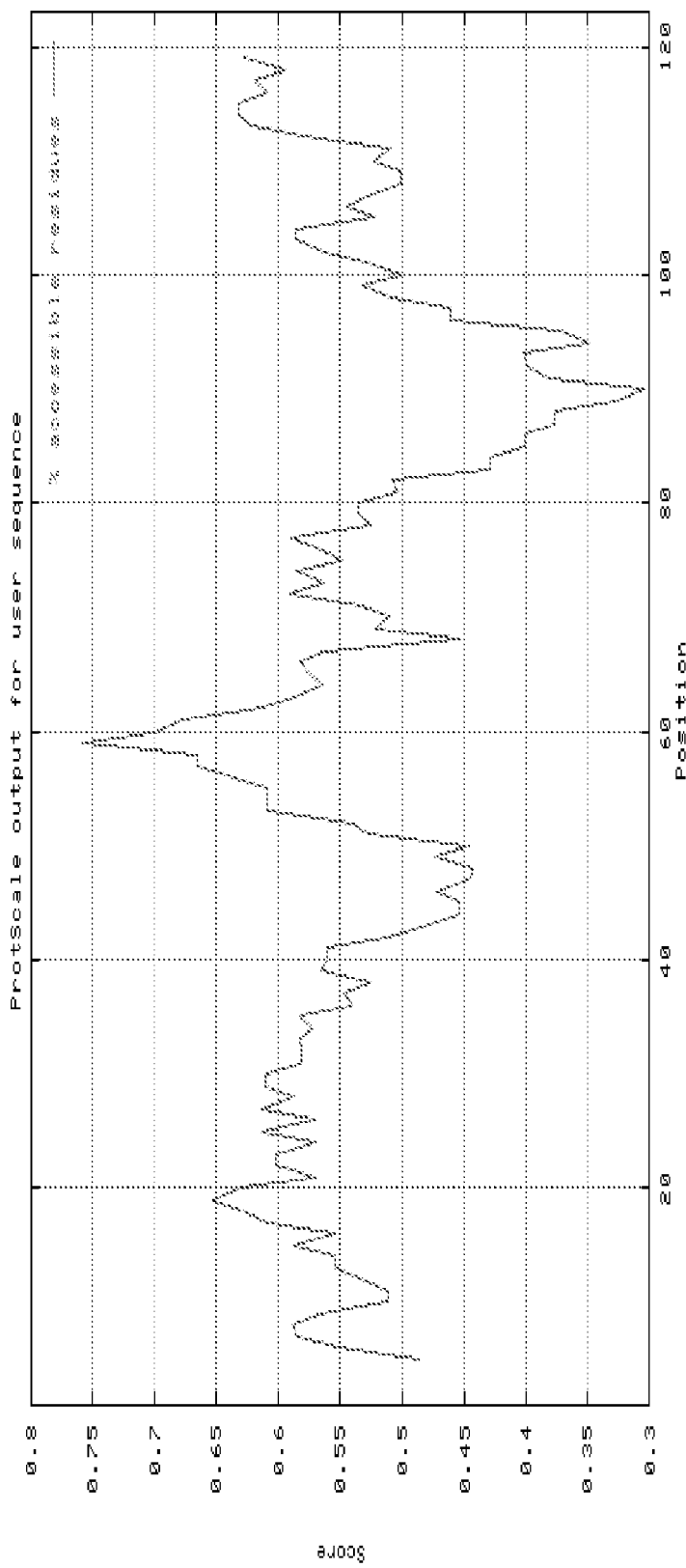
Figure 7E: 151P4E11 % Accessible Residues Profile
(Janin J., 1979. Nature 277:491-492)

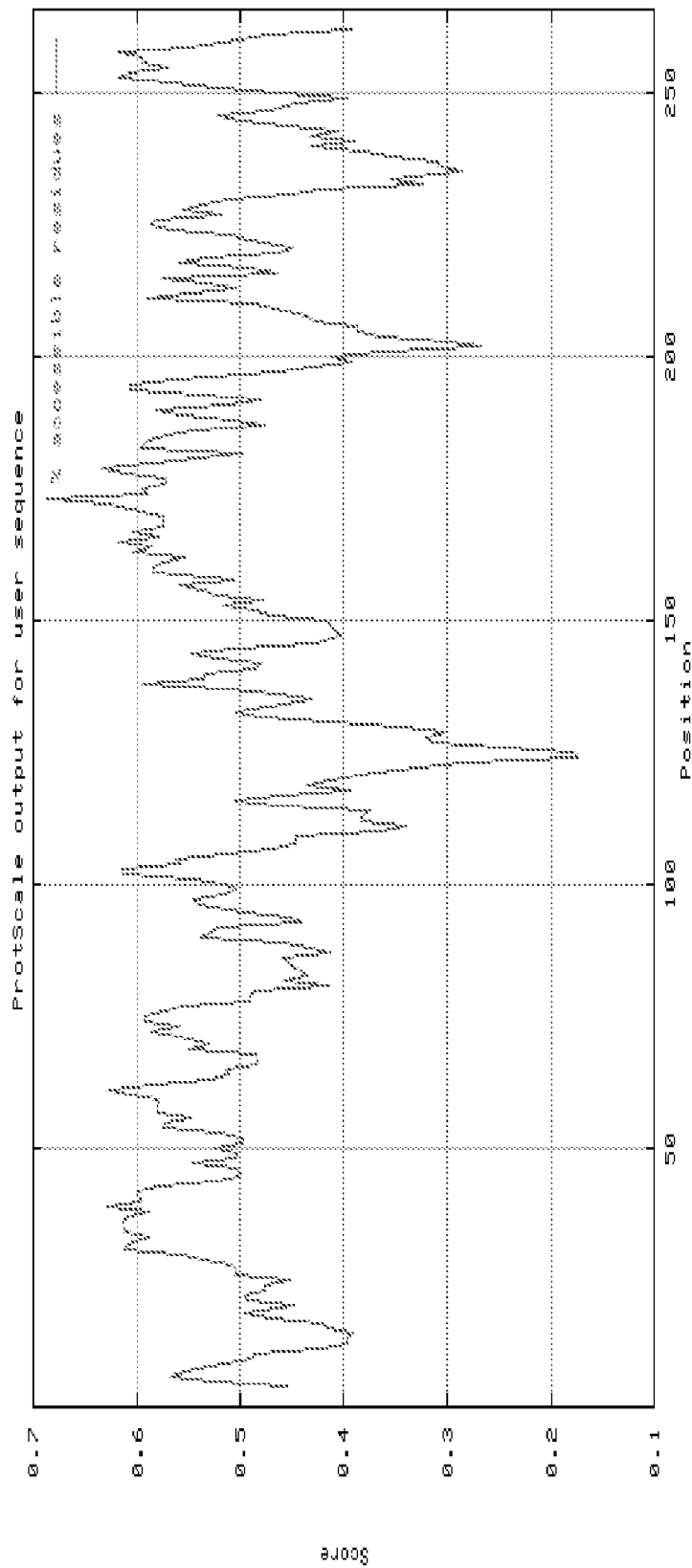
Figure 7F: 151P1C7a % Accessible Residues Profile
(Janin J., 1979. Nature 277:491-492)

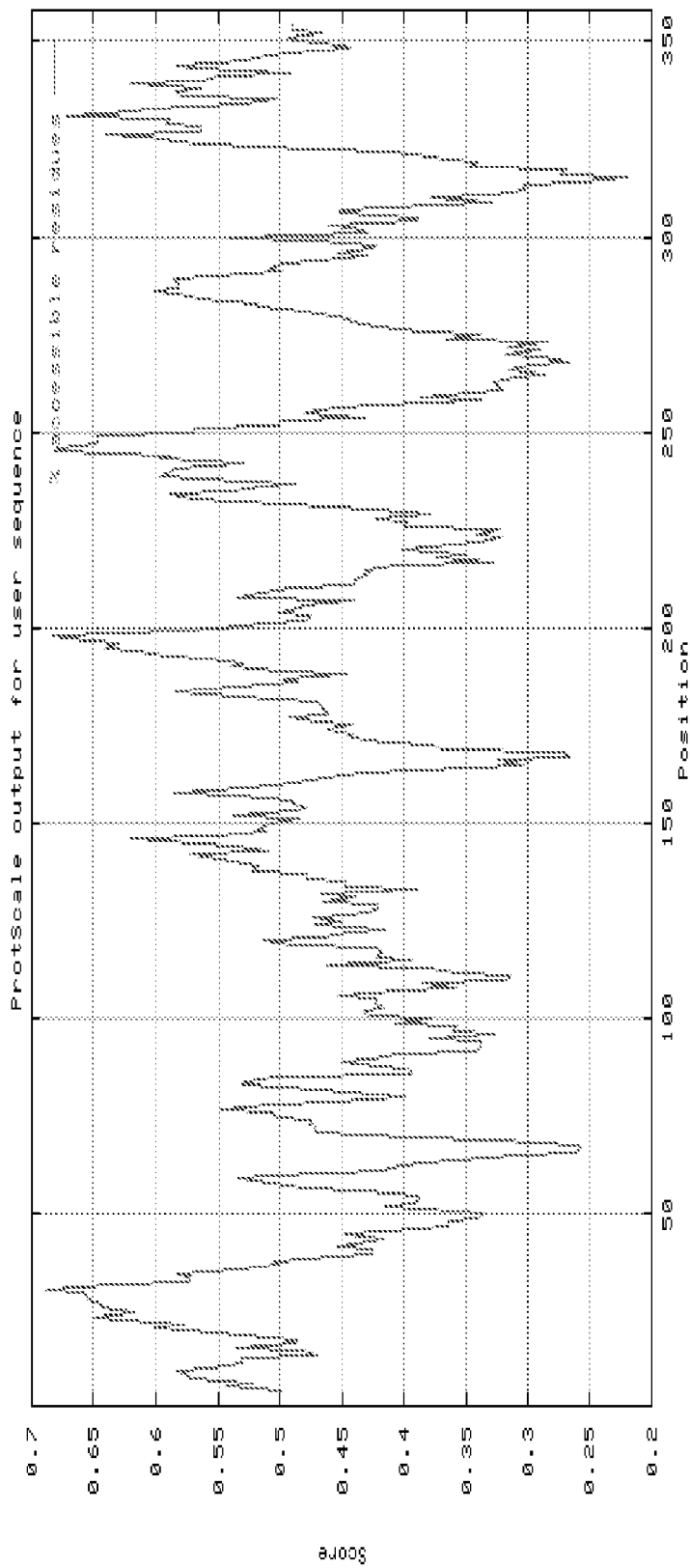
Figure 7G: 154P2A8 % Accessible Residues Profile
(Janin J., 1979. Nature 277:491-492)

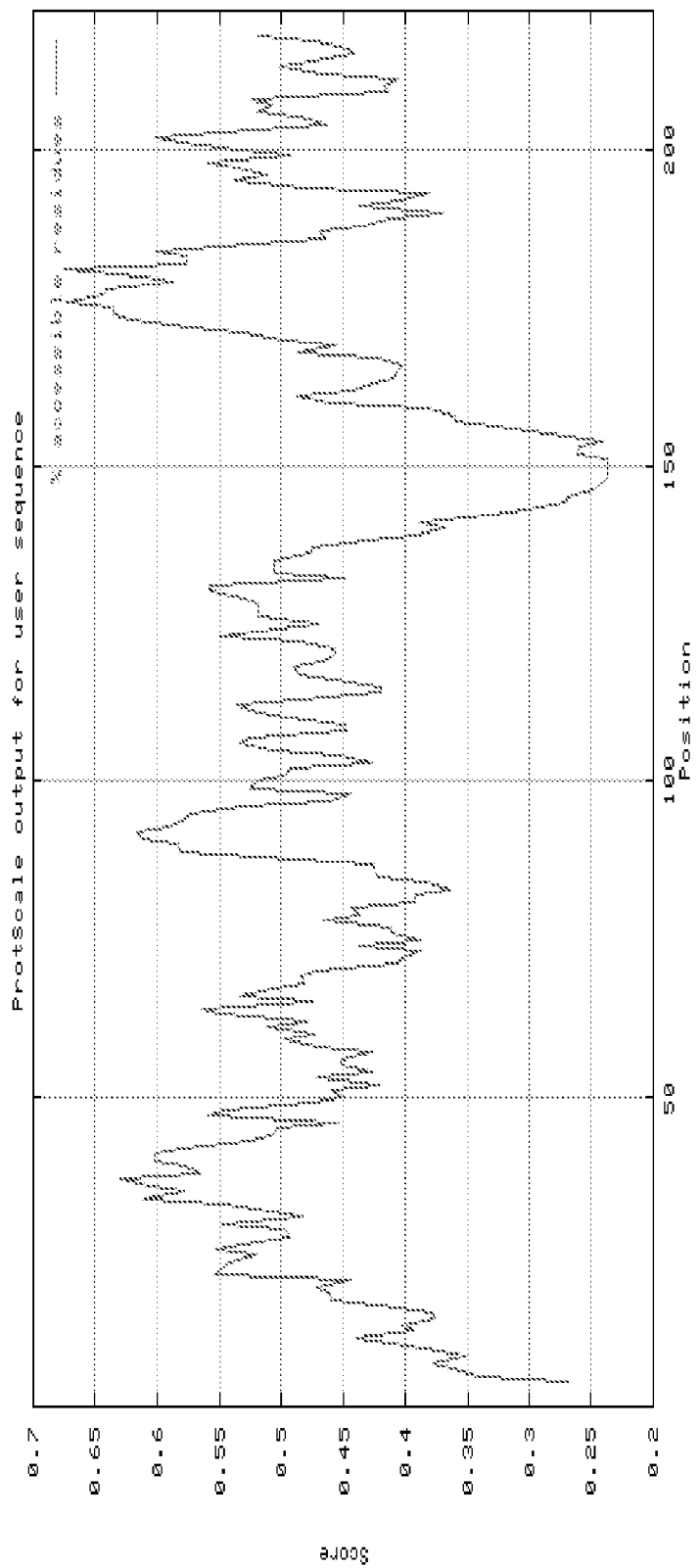
Figure 7H: 156P1D4 % Accessible Residues Profile
(Janin J., 1979. Nature 277:491-492)

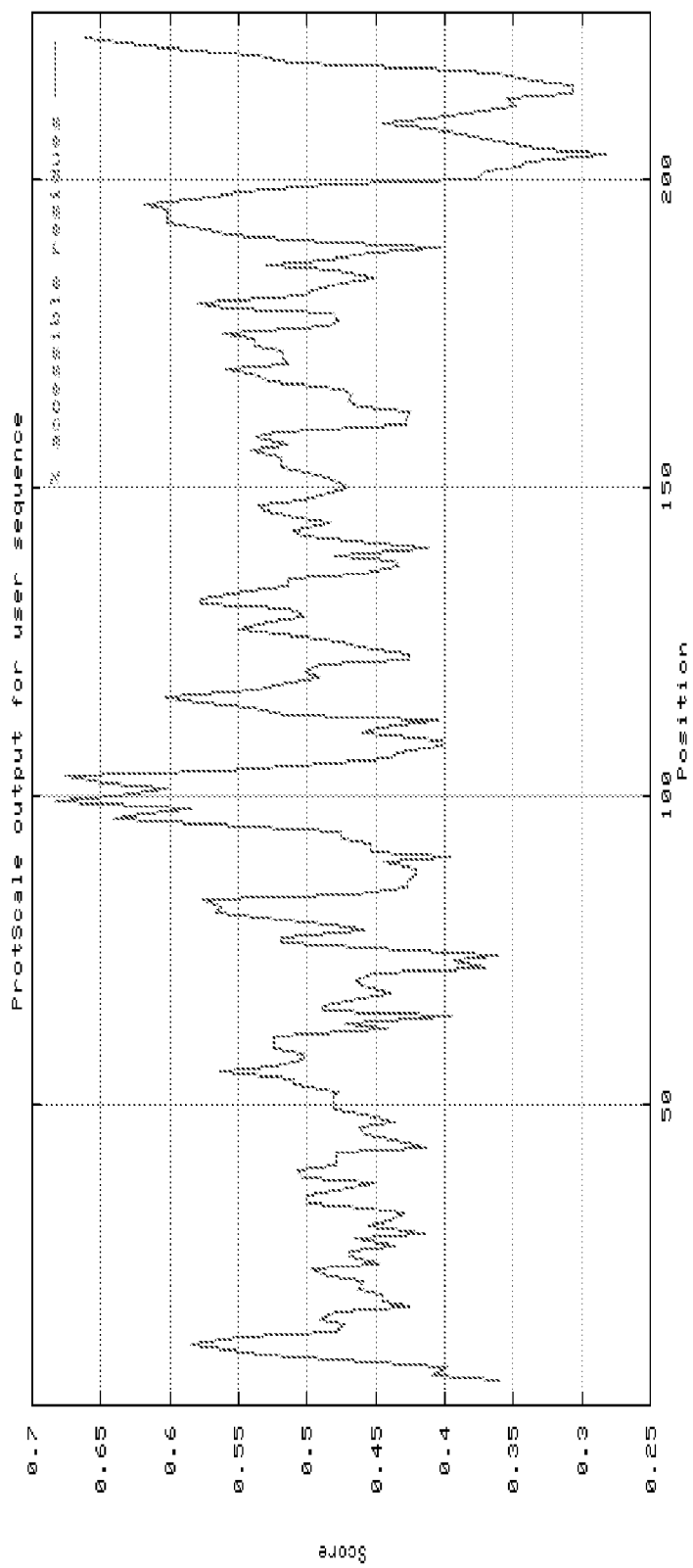
Figure 7l: 156P5C12 % Accessible Residues Profile
(Janin J., 1979. Nature 277:491-492)

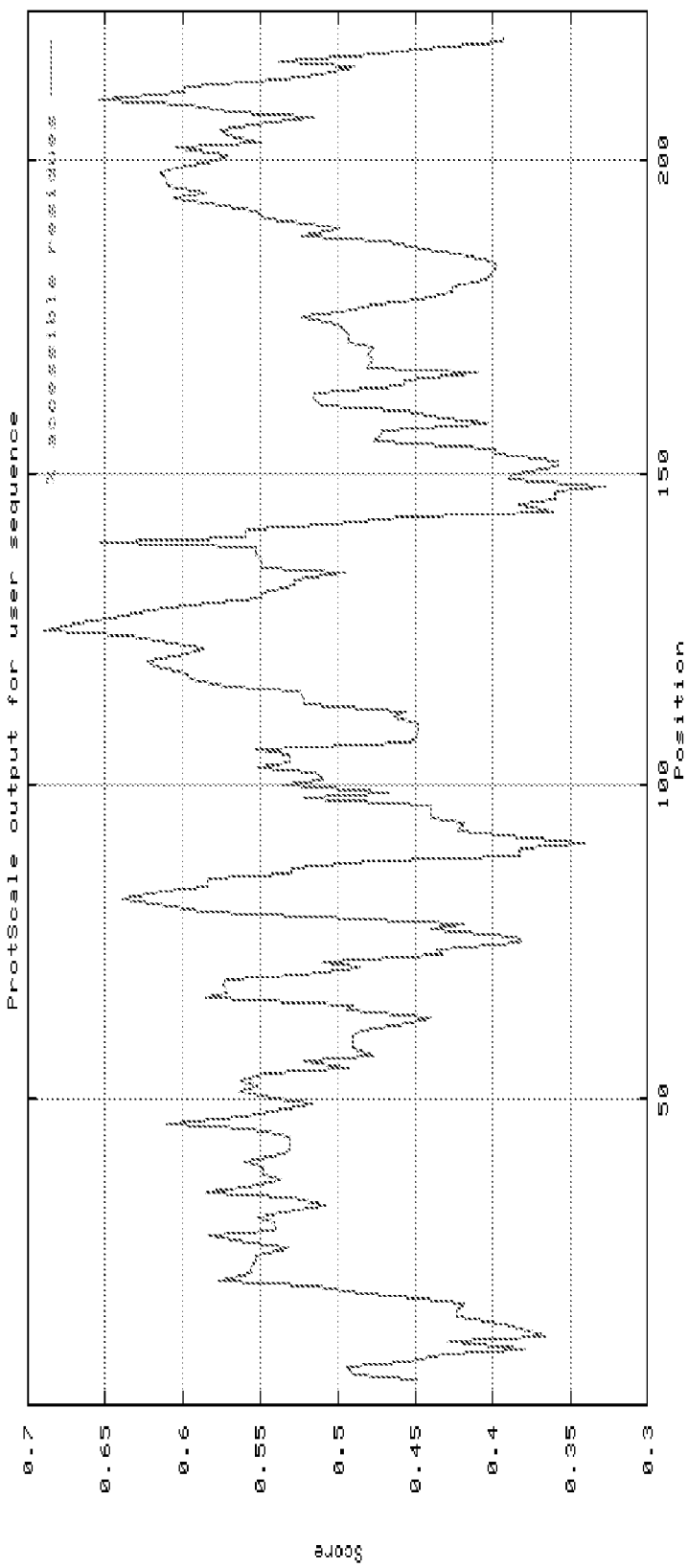
Figure 7J: 159P2B5 % Accessible Residues Profile
(Janin J., 1979. Nature 277:491-492)

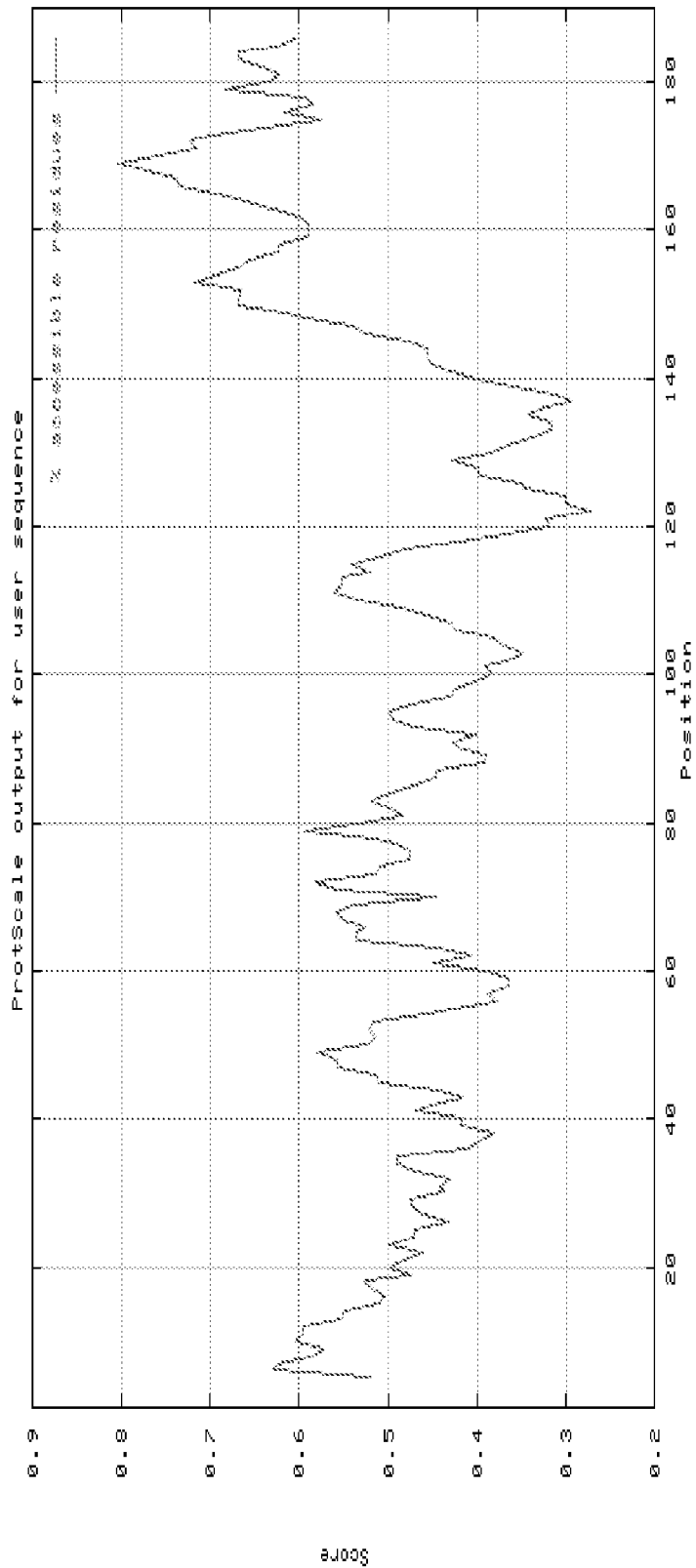
Figure 7K: 161P2B7a % Accessible Residues Profile
(Janin J., 1979. Nature 277:491-492)

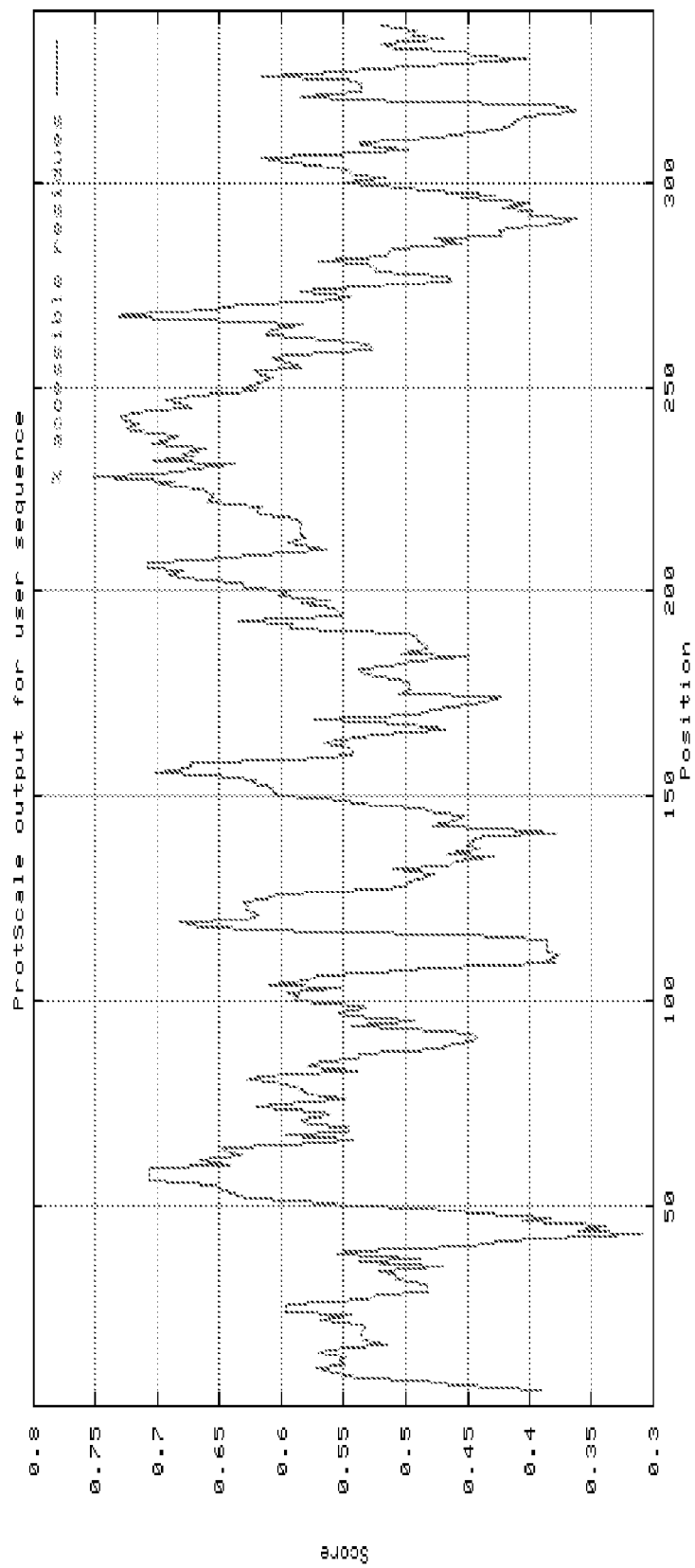
Figure 7L: 179P3G7 % Accessible Residues Profile
(Janin J., 1979. Nature 277:491-492)

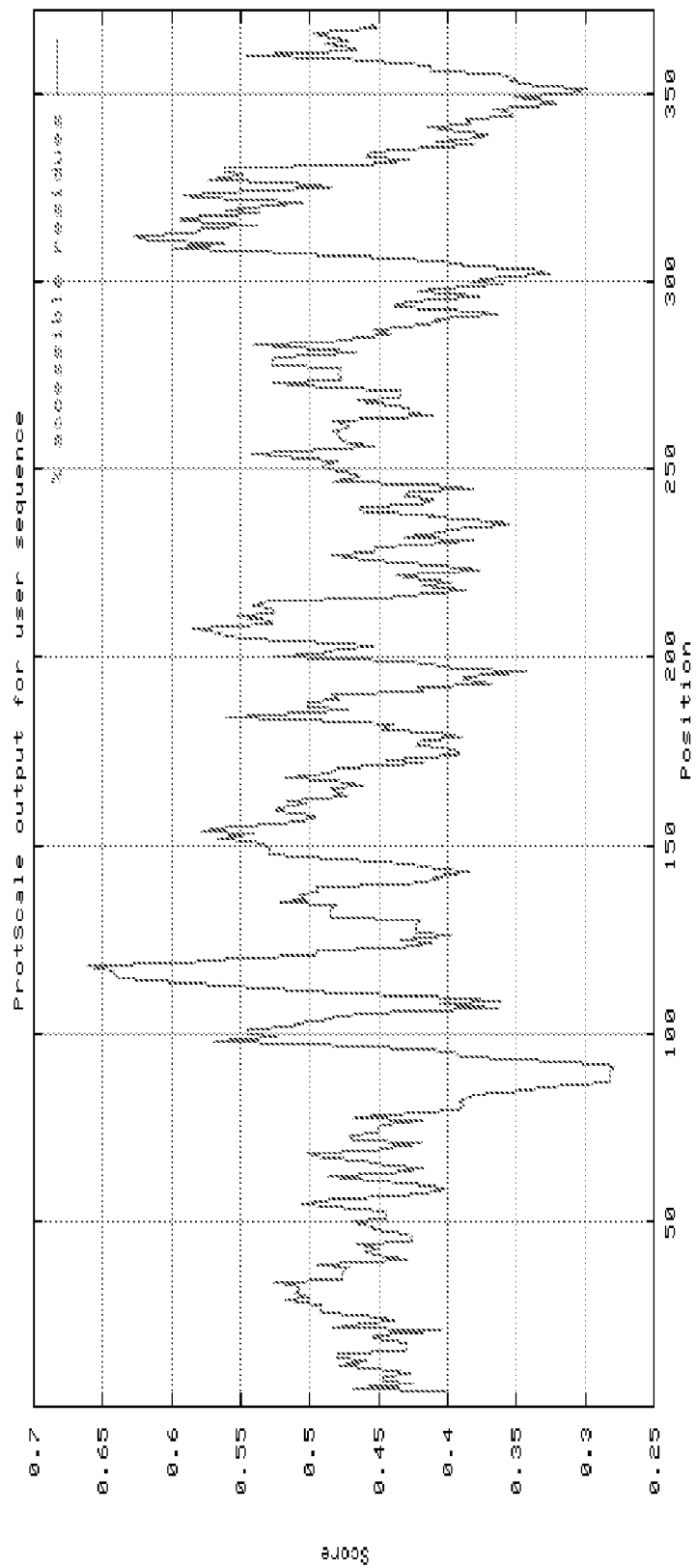
Figure 7M: 184P3C10b % Accessible Residues Profile
(Janin J., 1979. Nature 277:491-492)

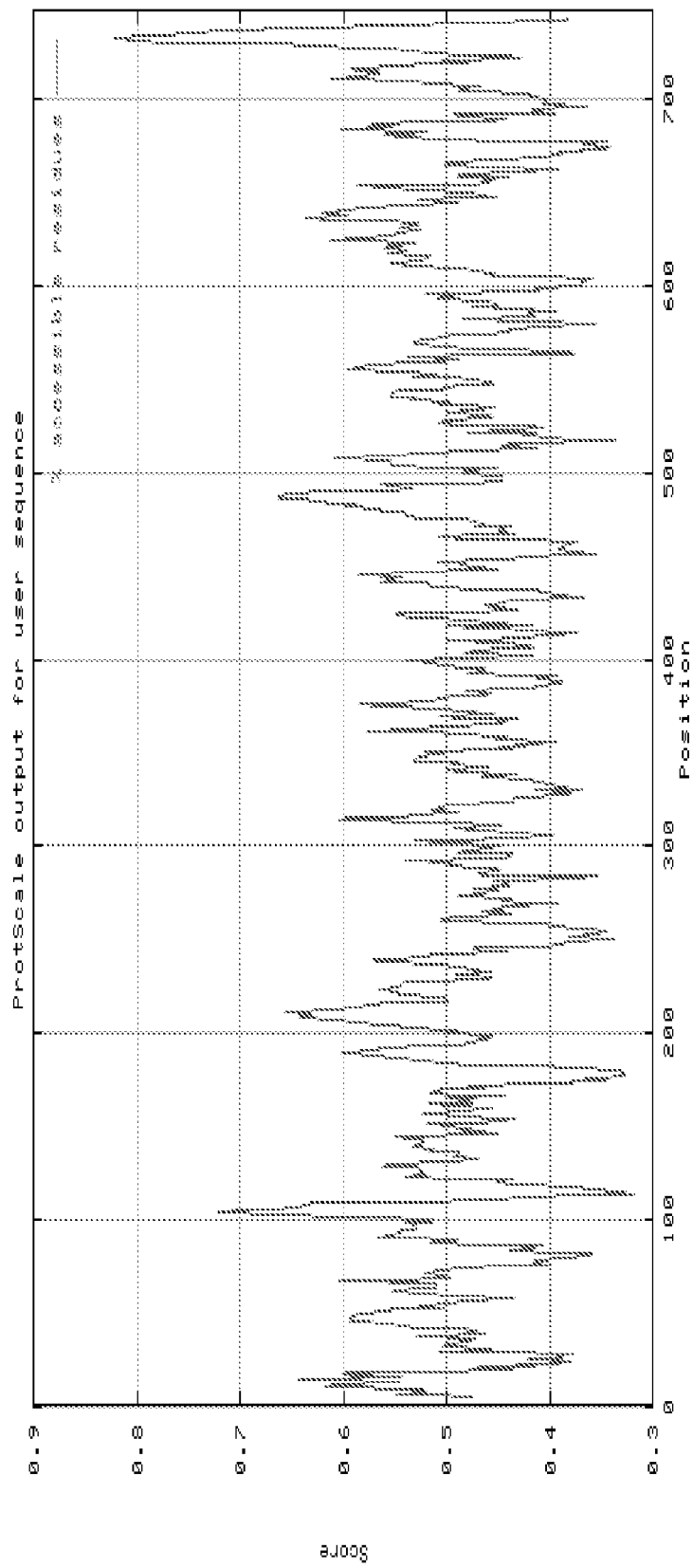
Figure 7N: 184P3G10 % Accessible Residues Profile
(Janin J., 1979. Nature 277:491-492)

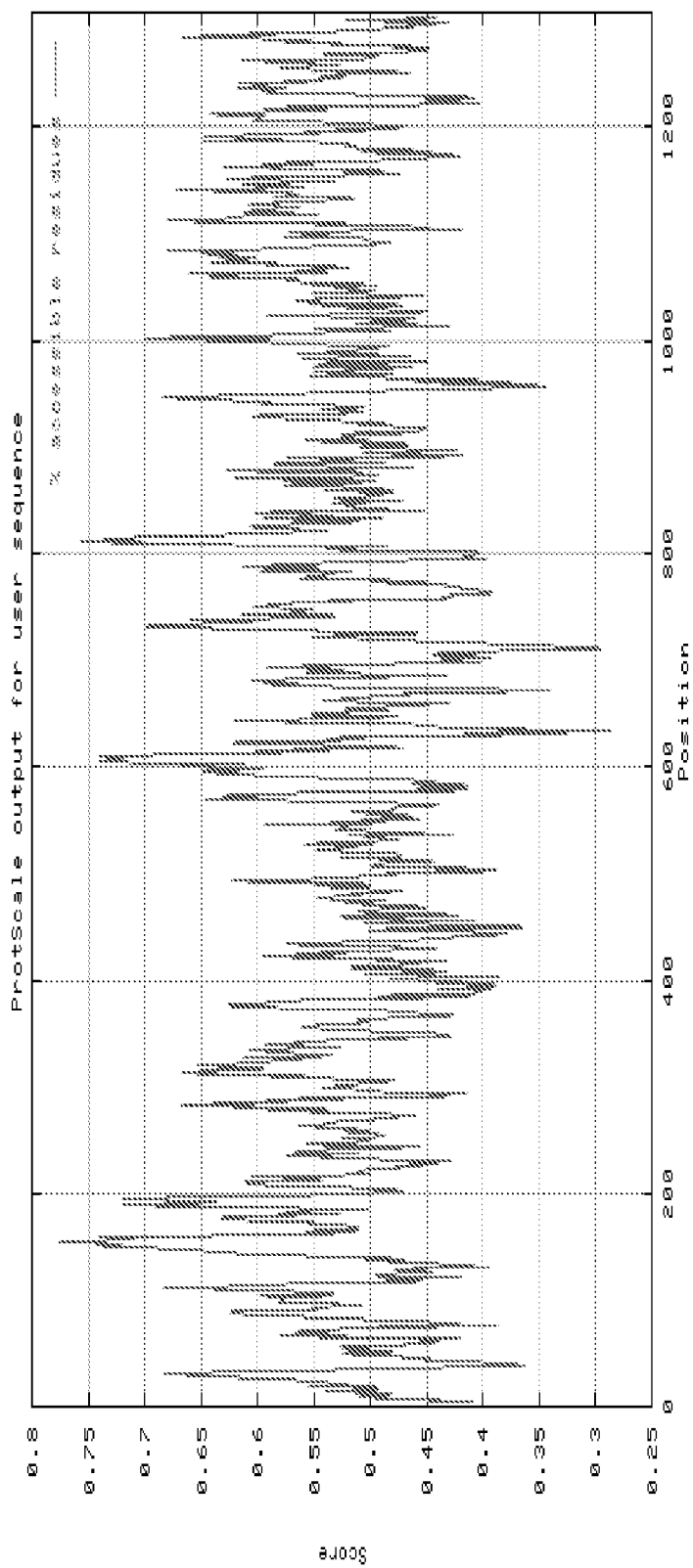

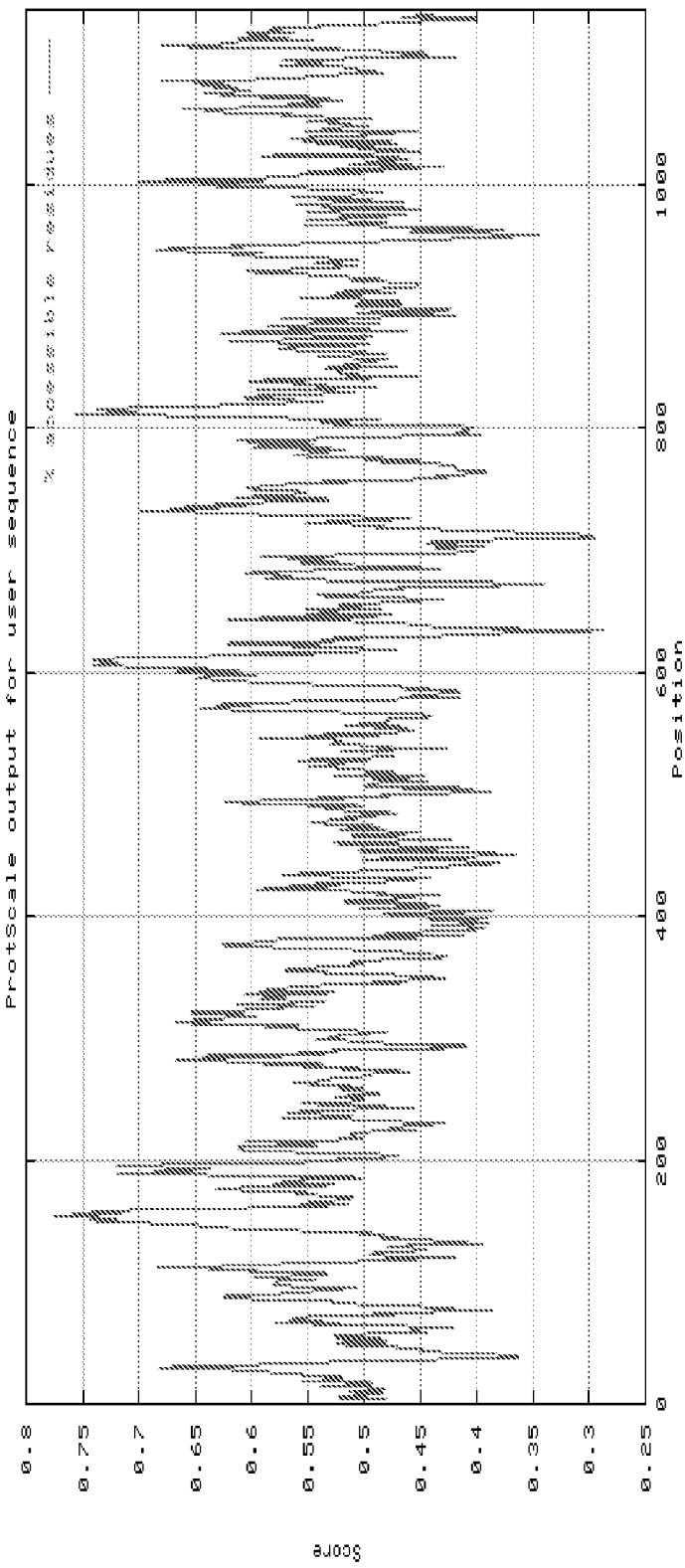
Figure 7P: 185P2C9 variant 2 % Accessible Residues Profile
(Janin J., 1979. Nature 277:491-492)

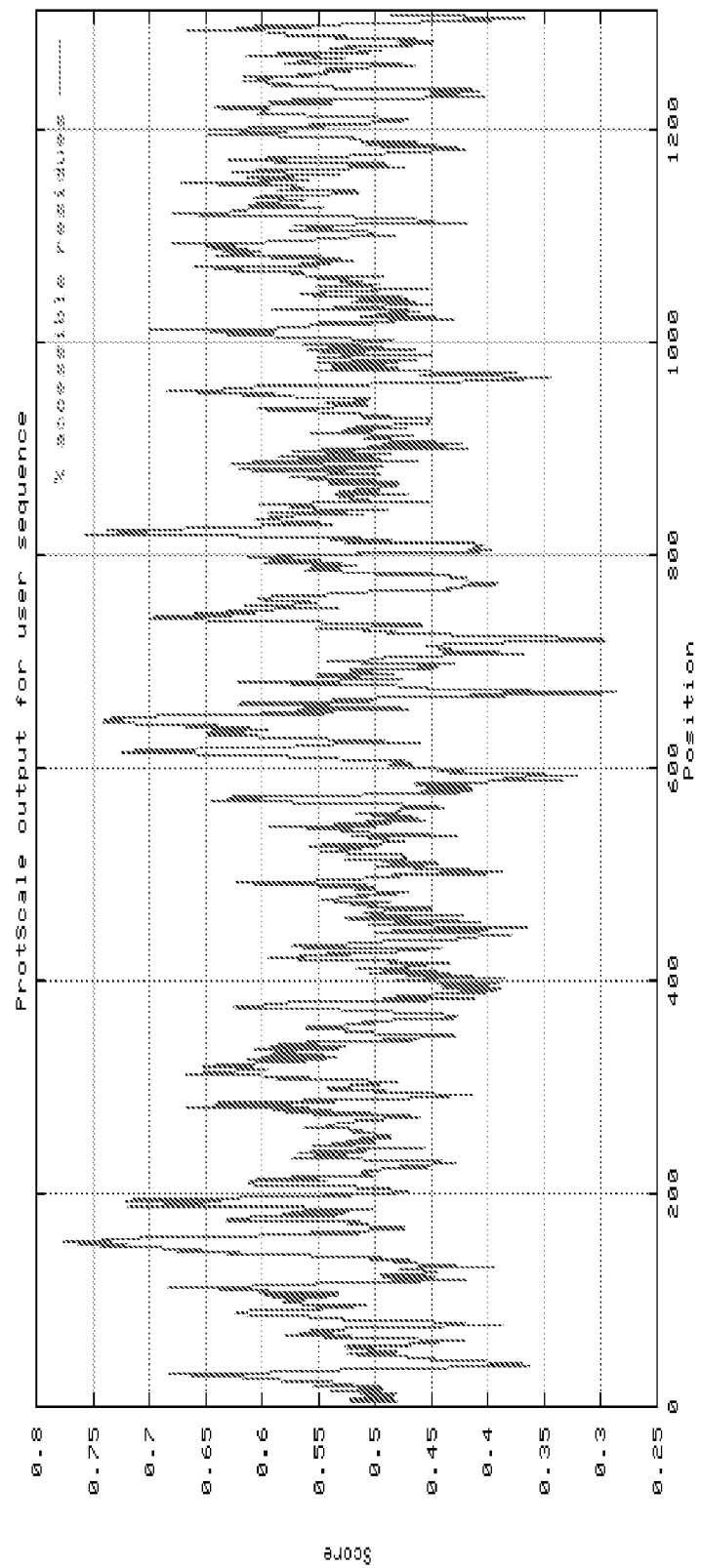
Figure 7Q: 185P2C9 variant 3 % Accessible Residues Profile
(Janin J., 1979. Nature 277:491-492)

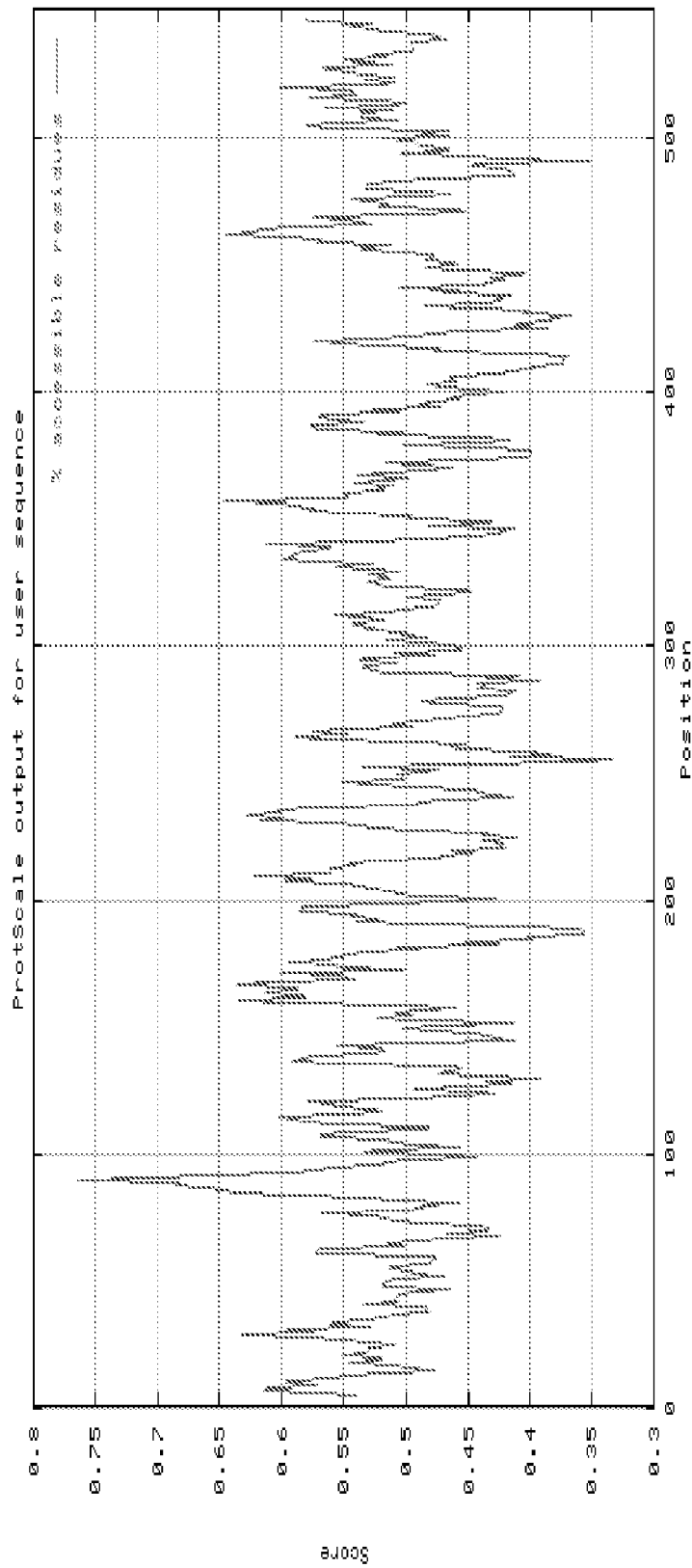
Figure 7R: 185P3C2 % Accessible Residues Profile
(Janin J., 1979. Nature 277:491-492)

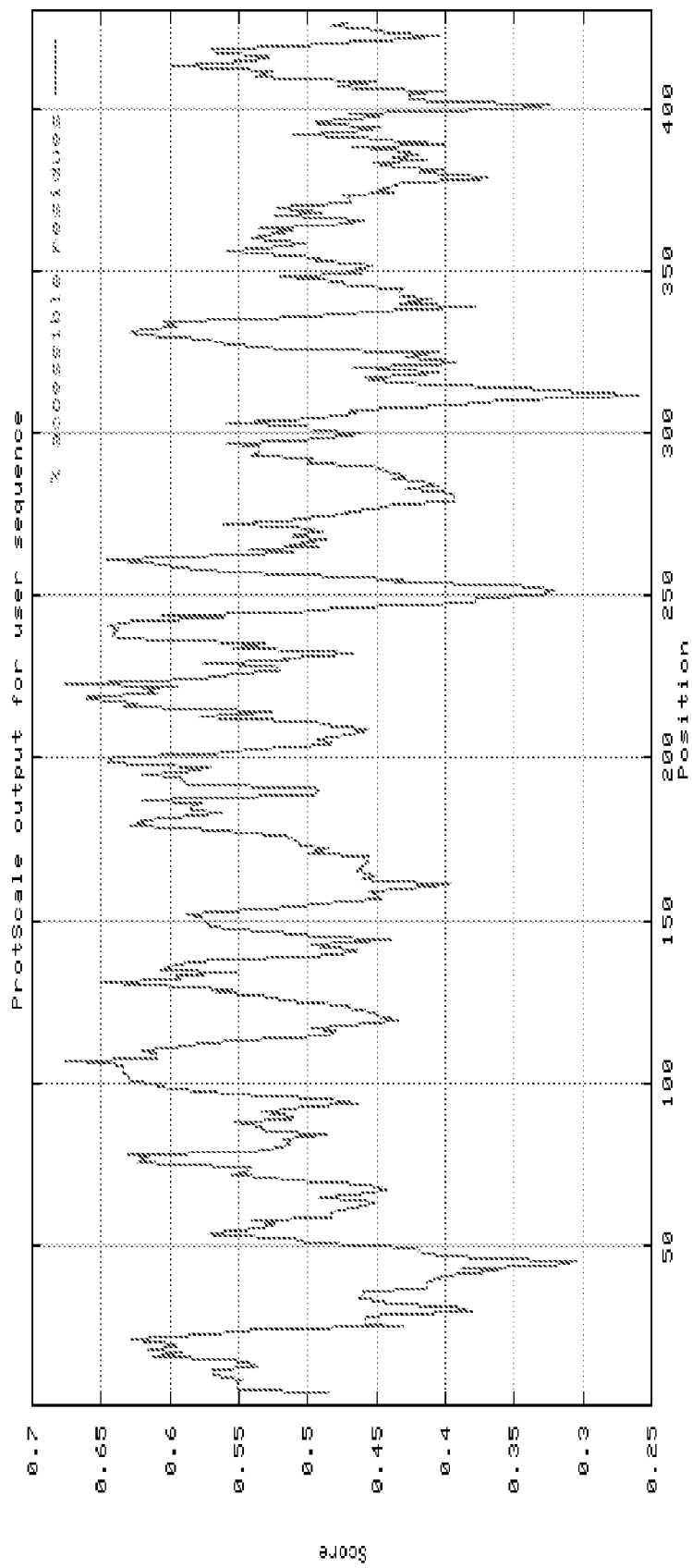
Figure 7S: 186P1H9 % Accessible Residues Profile
(Janin J., 1979. Nature 277:491-492)

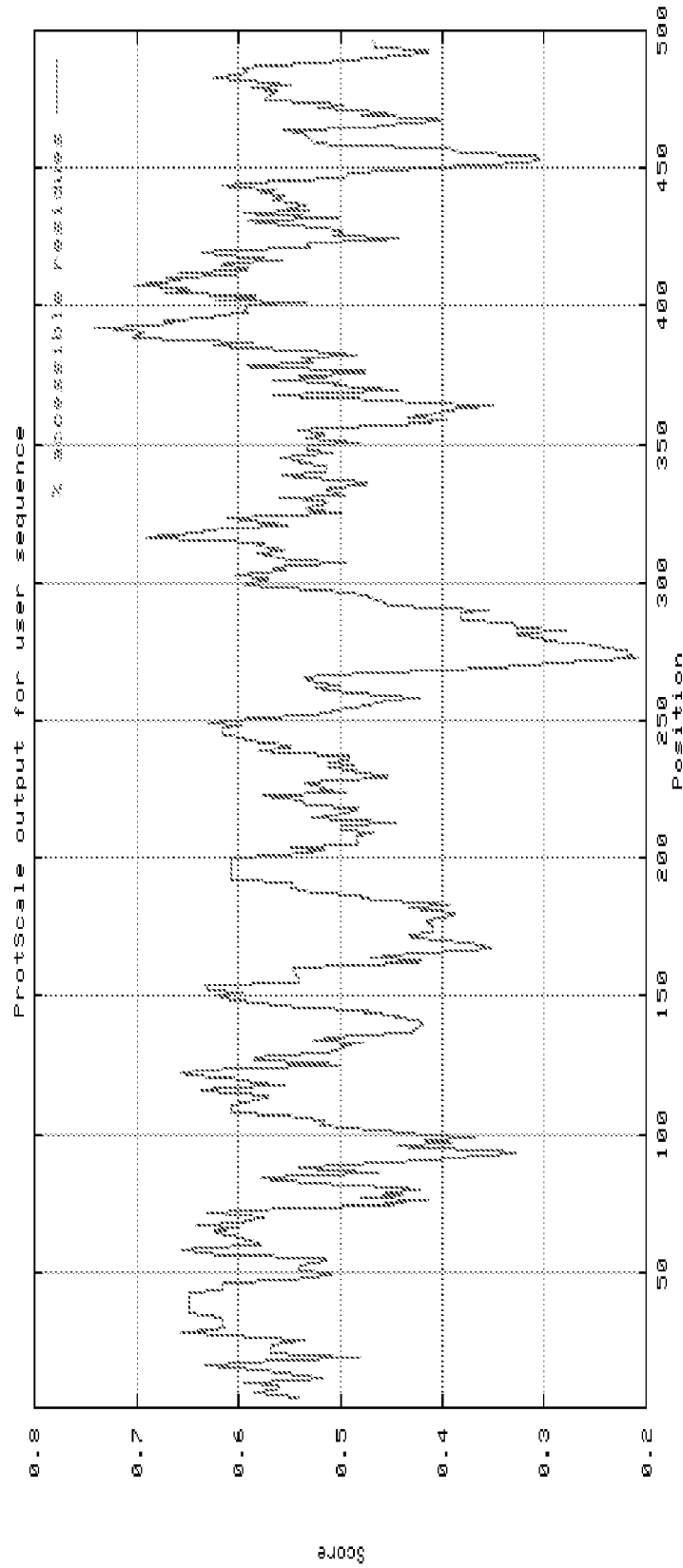
Figure 7T: 187P3F2 % Accessible Residues Profile
(Janin J., 1979. Nature 277:491-492)

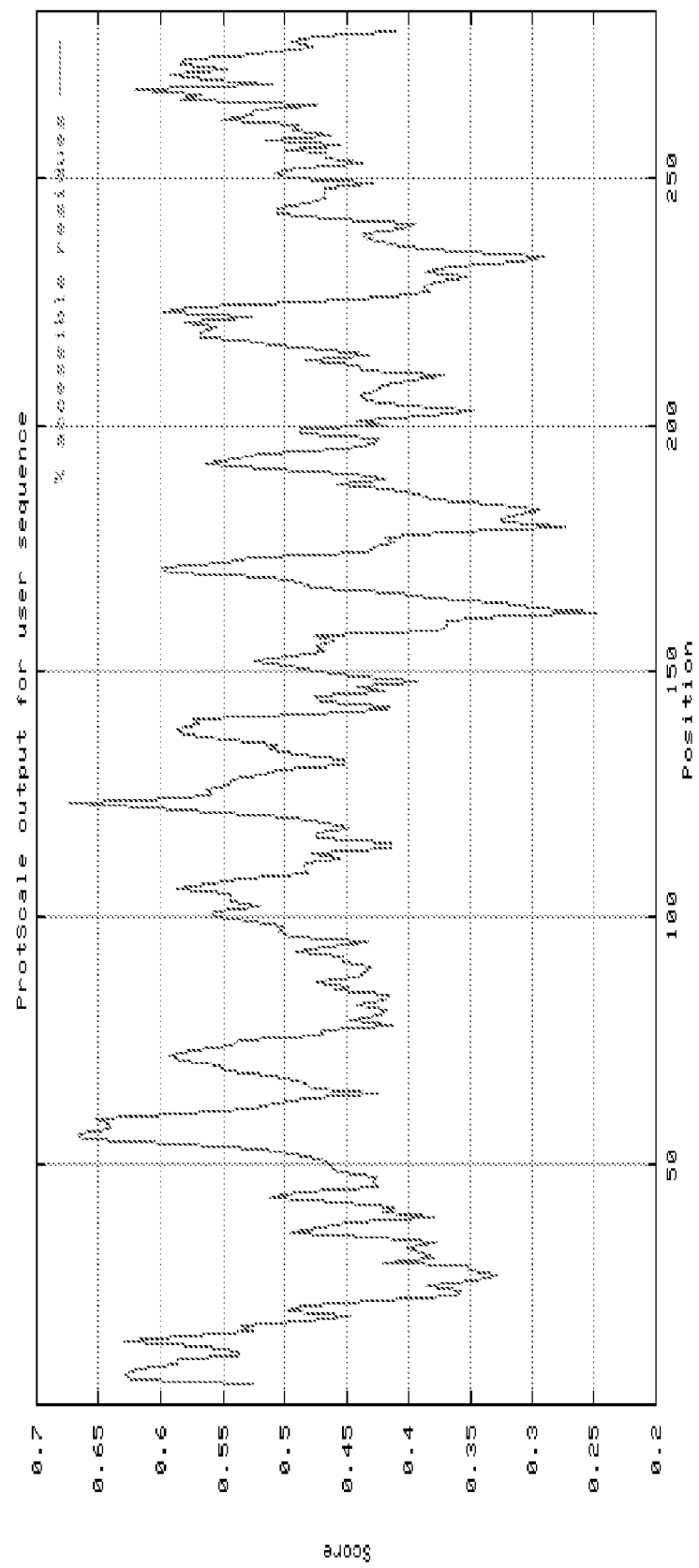
Figure 7U: 192P2G7 % Accessible Residues Profile
(Janin J., 1979. Nature 277:491-492)

74P3B3 variant 1a Average Flexibility Profile
(Bhaskaran R., Ponnuswamy P.K., 1988.
Int. J. Pept. Protein Res. 32:242-255)

74P3B3 variant 1b Average Flexibility Profile
(Bhaskaran R., Ponnuswamy P.K., 1988.
Int. J. Pept. Protein Res. 32:242-255)

83P4B8 Average Flexibility Profile
(Bhaskaran R., Ponnuswamy P.K., 1988.
Int. J. Pept. Protein Res. 32:242-255)

109P1D4 Average Flexibility Profile
(Bhaskaran R., Ponnuswamy P.K., 1988.
Int. J. Pept. Protein Res. 32:242-255)

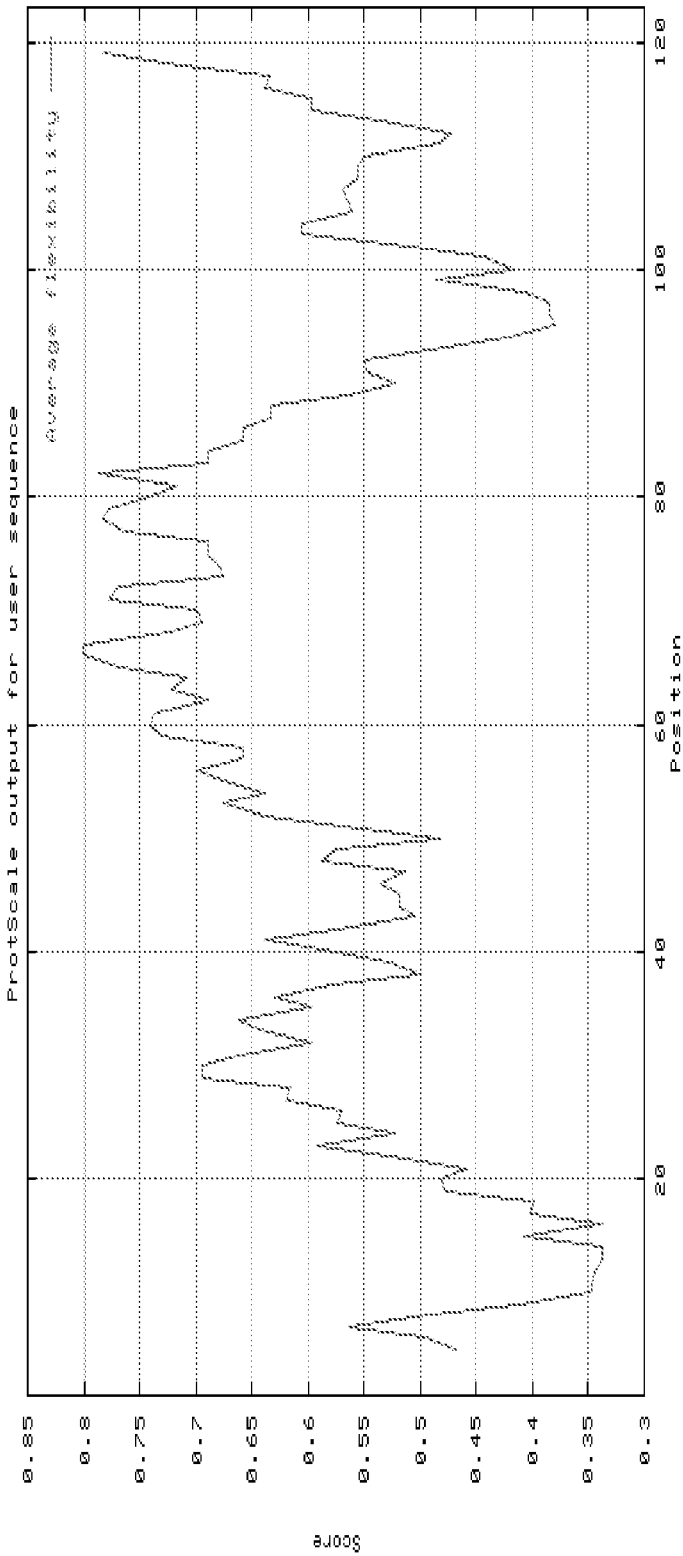
Figure 8E: 151P4E11 Average Flexibility Profile
(Bhaskaran R., Ponnuswamy P.K., 1988.
Int. J. Pept. Protein Res. 32:242-255)

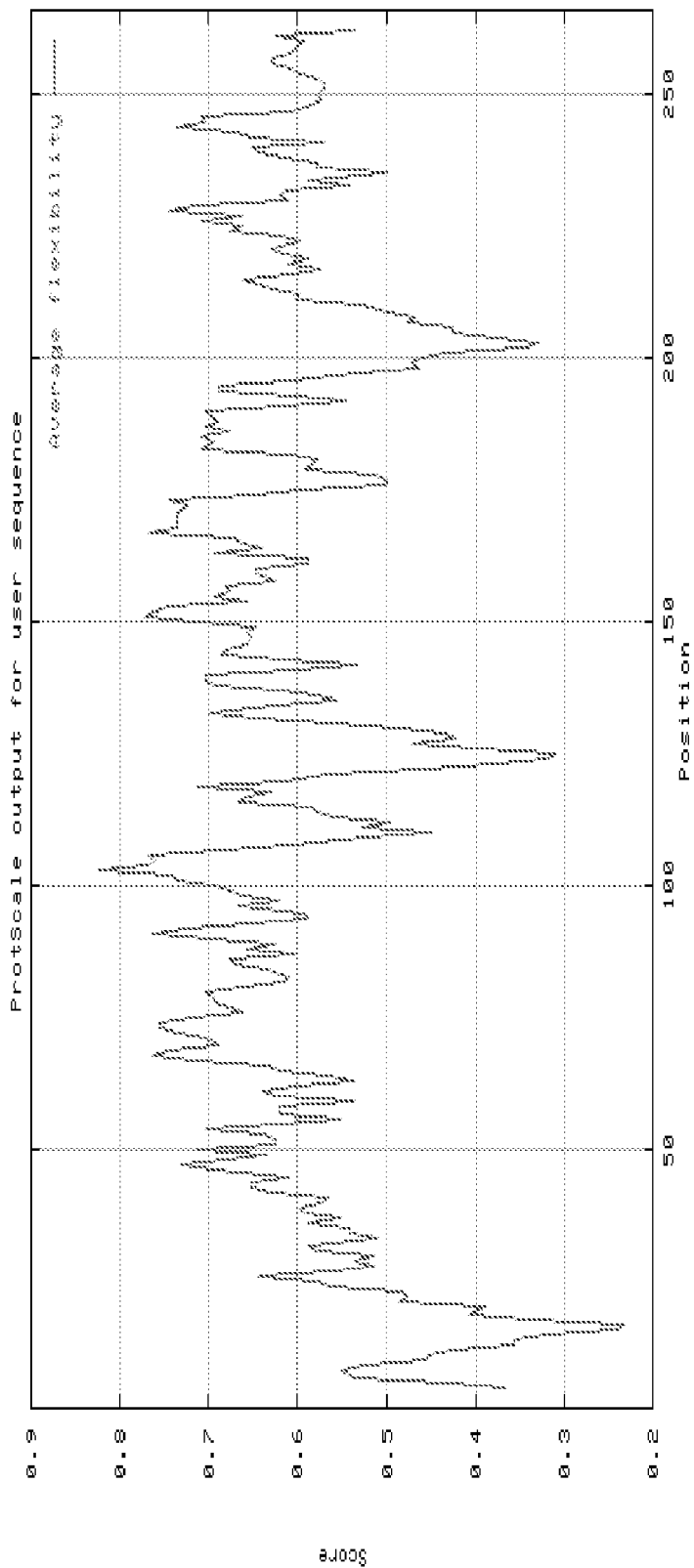
Figure 8F: 151P1C7a Average Flexibility Profile
(Bhaskaran R., Ponnuswamy P.K., 1988.
Int. J. Pept. Protein Res. 32:242-255)

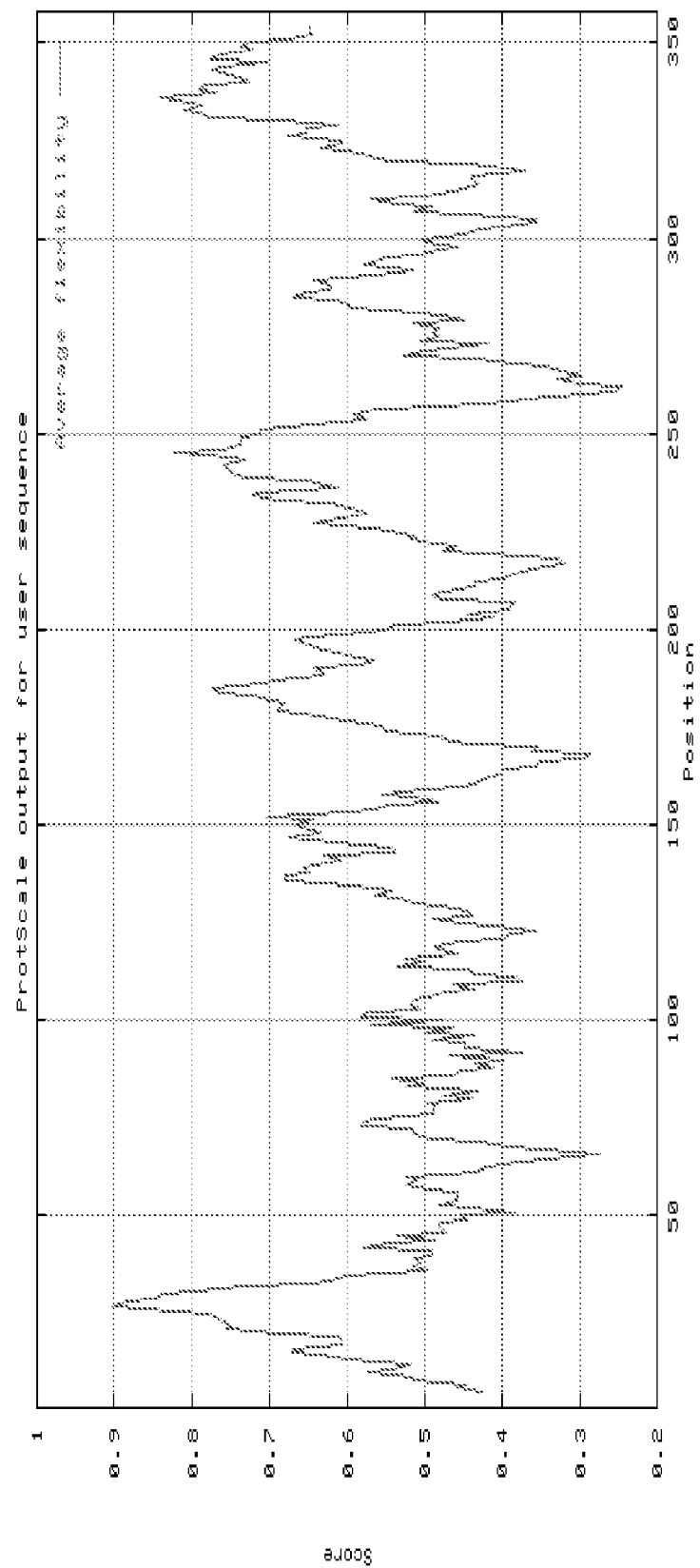
Figure 8G: 154P2A8 Average Flexibility Profile
(Bhaskaran R., Ponnuswamy P.K., 1988.
Int. J. Pept. Protein Res. 32:242-255)

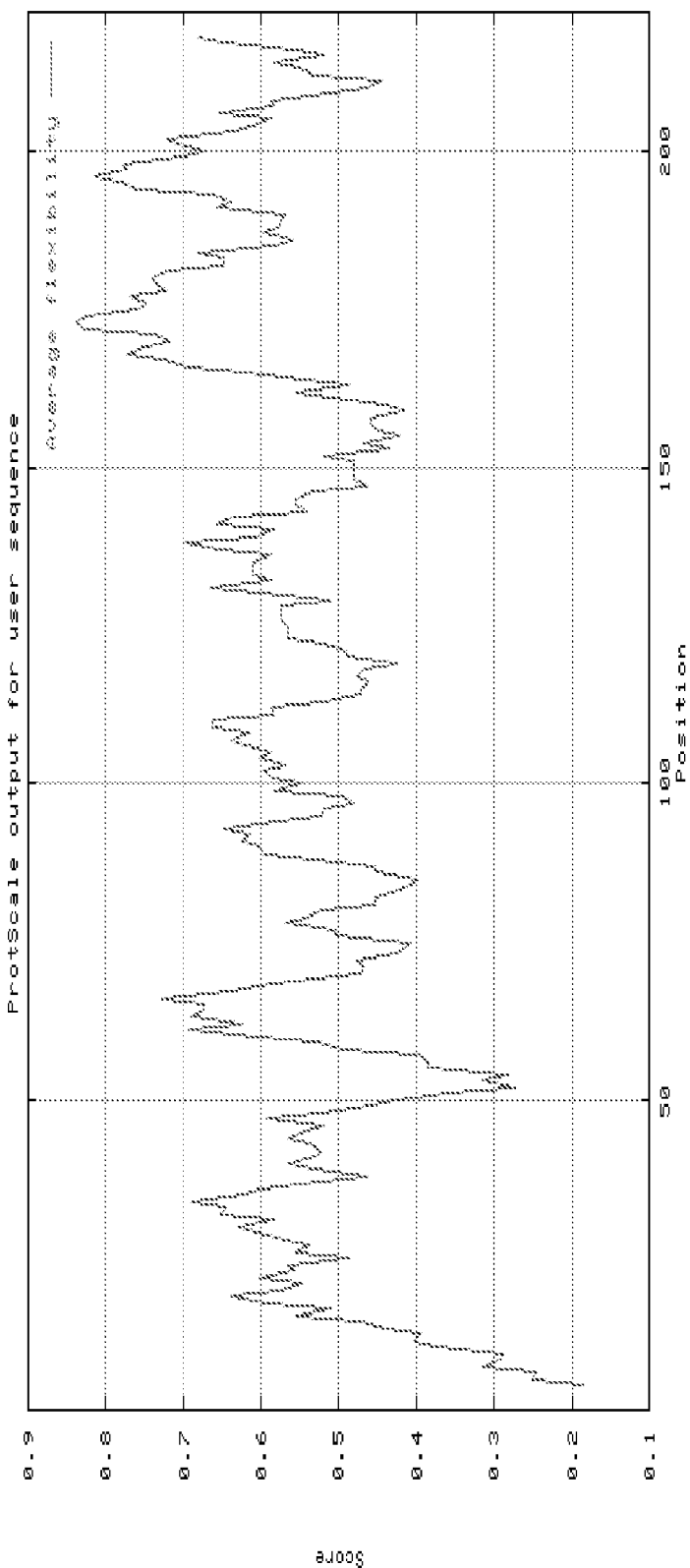
Figure 8H: 156P1D4 Average Flexibility Profile
(Bhaskaran R., Ponnuswamy P.K., 1988.
Int. J. Pept. Protein Res. 32:242-255)

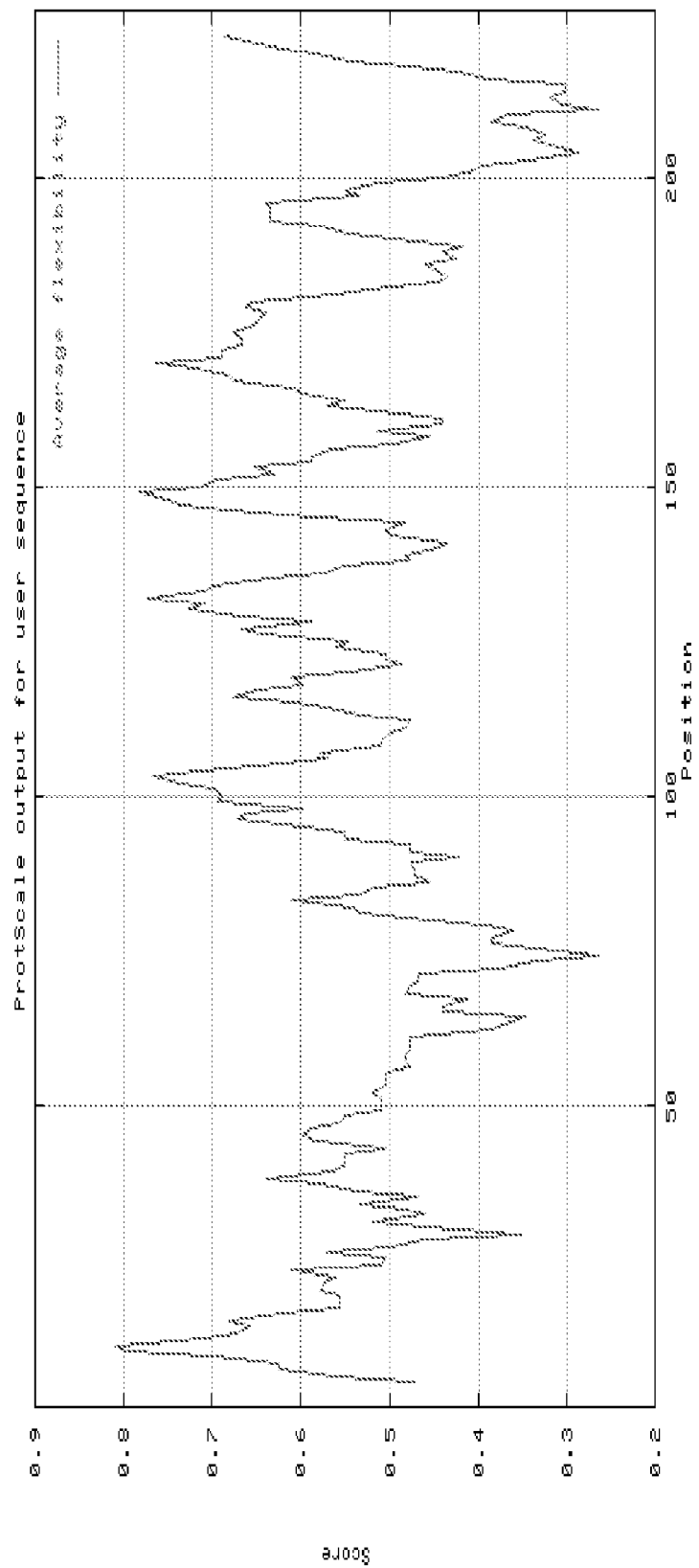
Figure 8I: 156P5C12 Average Flexibility Profile
(Bhaskaran R., Ponnuswamy P.K., 1988. Int. J. Pept. Protein Res. 32:242-255)

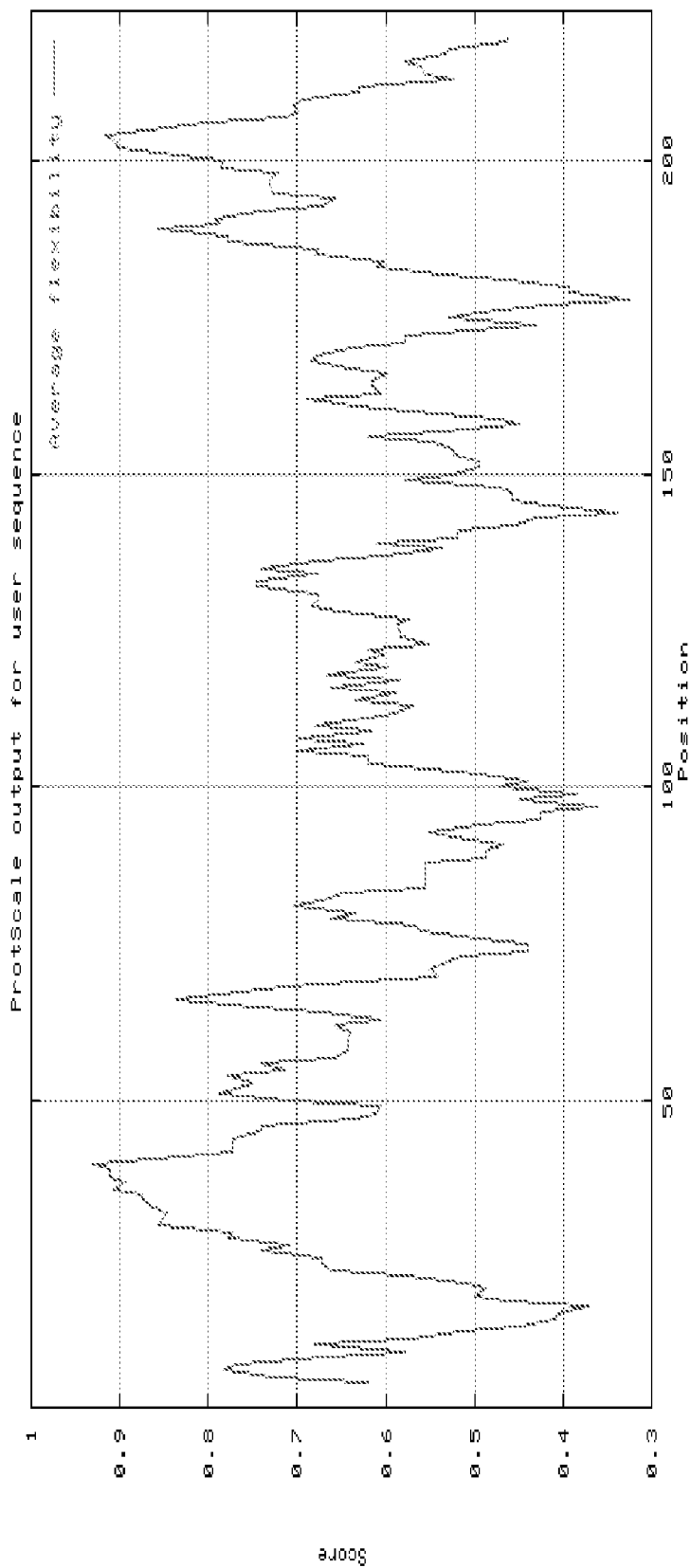
Figure 8J: 159P2B5 Average Flexibility Profile
(Bhaskaran R., Ponnuswamy P.K., 1988.
Int. J. Pept. Protein Res. 32:242-255)

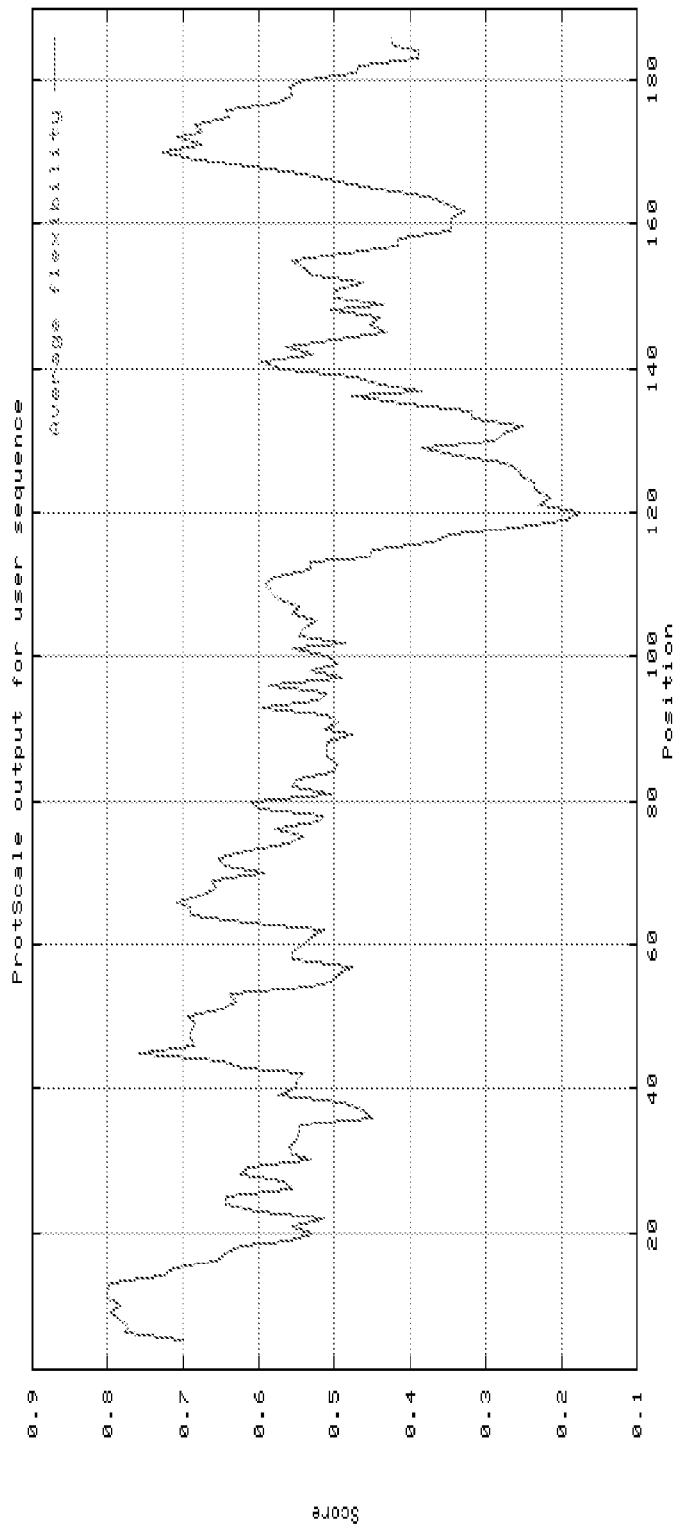
Figure 8K: 161P2B7a Average Flexibility Profile
(Bhaskaran R., Ponnuswamy P.K., 1988.
Int. J. Pept. Protein Res. 32:242-255)

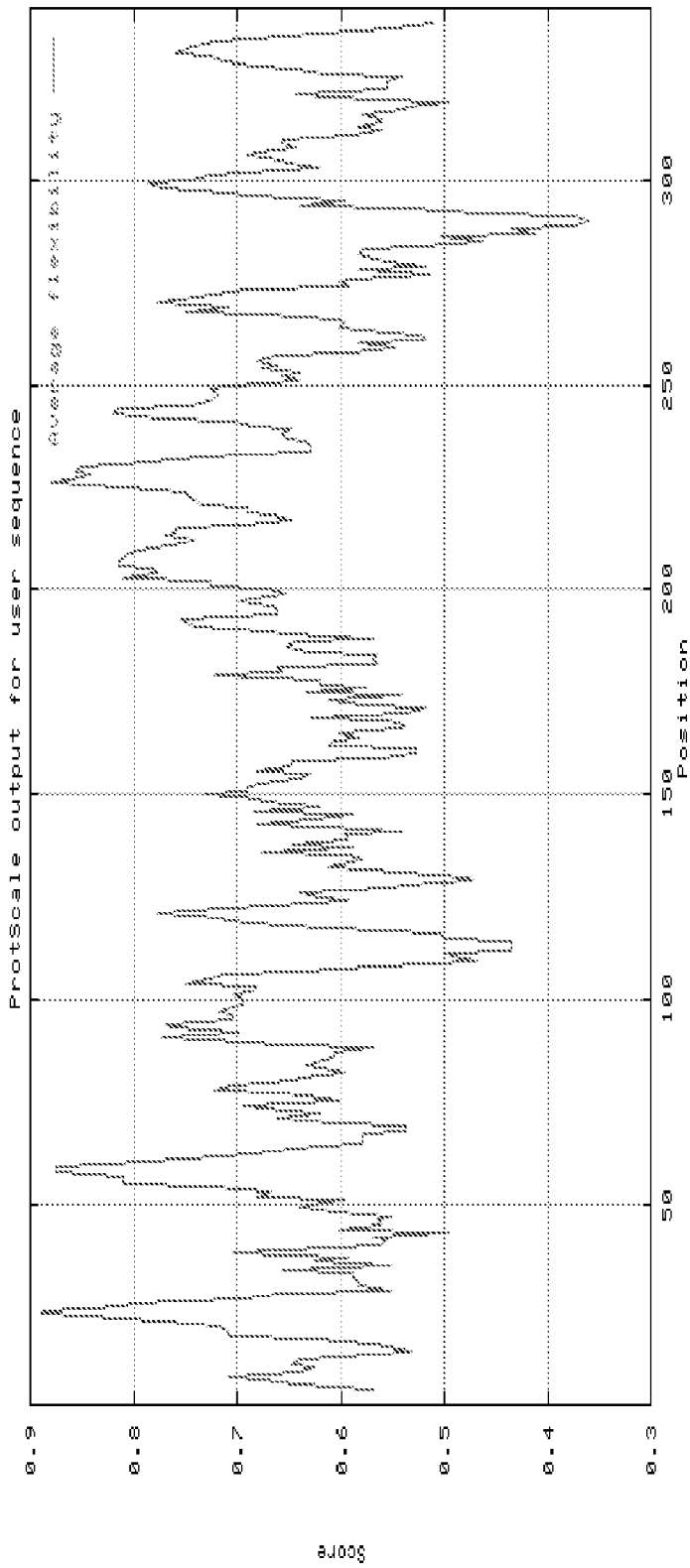
Figure 8L: 179P3G7 Average Flexibility Profile
(Bhaskaran R., Ponnuswamy P.K., 1988.
Int. J. Pept. Protein Res. 32:242-255)

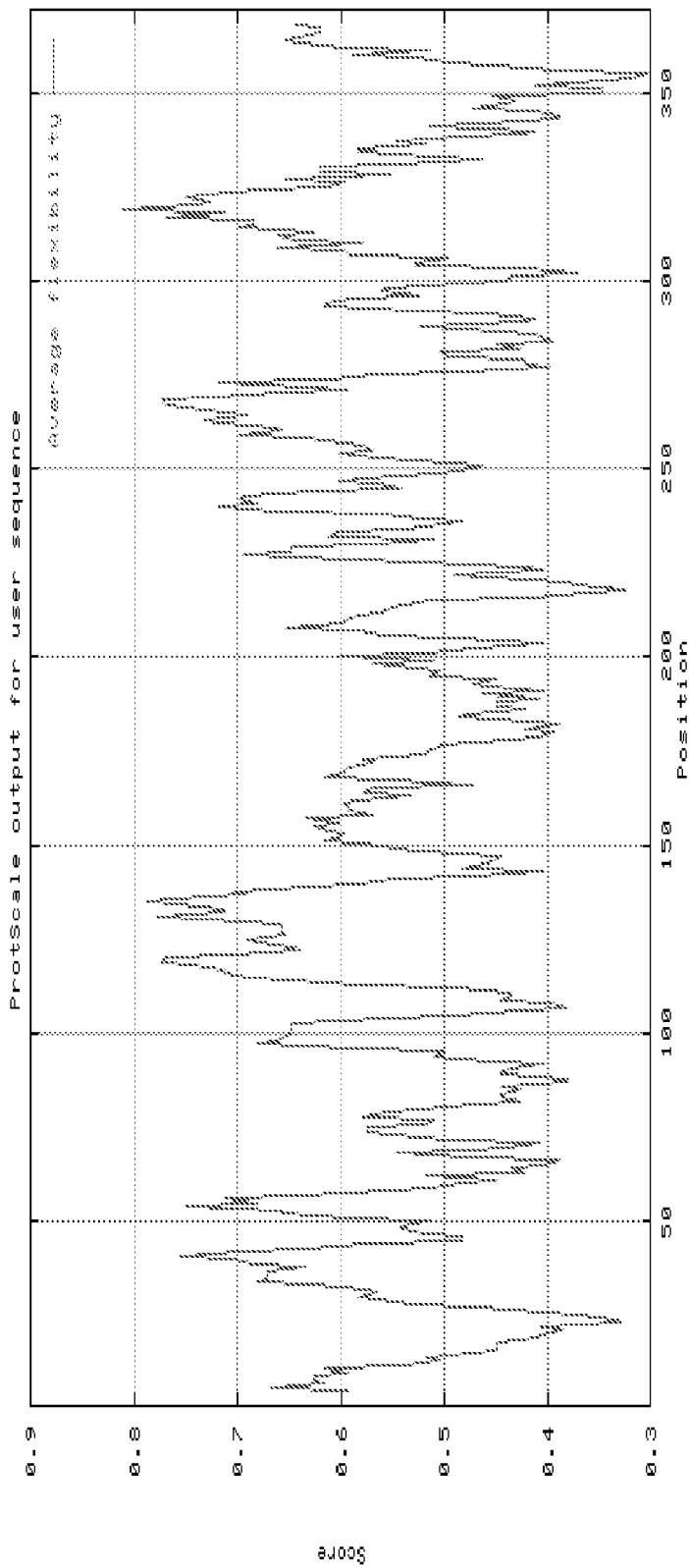
Figure 8M: 184P3C10b Average Flexibility Profile
(Bhaskaran R., Ponnuswamy P.K., 1988.
Int. J. Pept. Protein Res. 32:242-255)

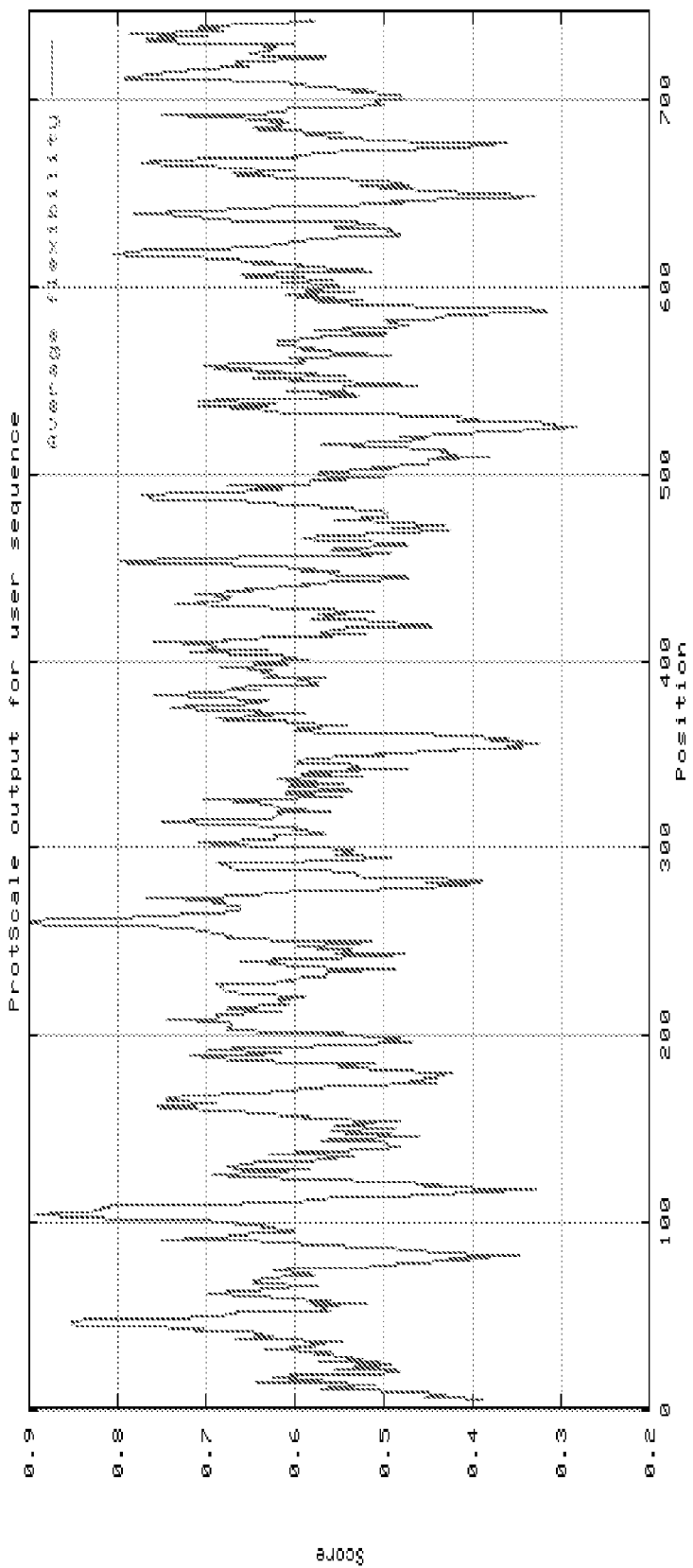
Figure 8N: 184P3G10 Average Flexibility Profile
(Bhaskaran R., Ponnuswamy P.K., 1988.
Int. J. Pept. Protein Res. 32:242-255)

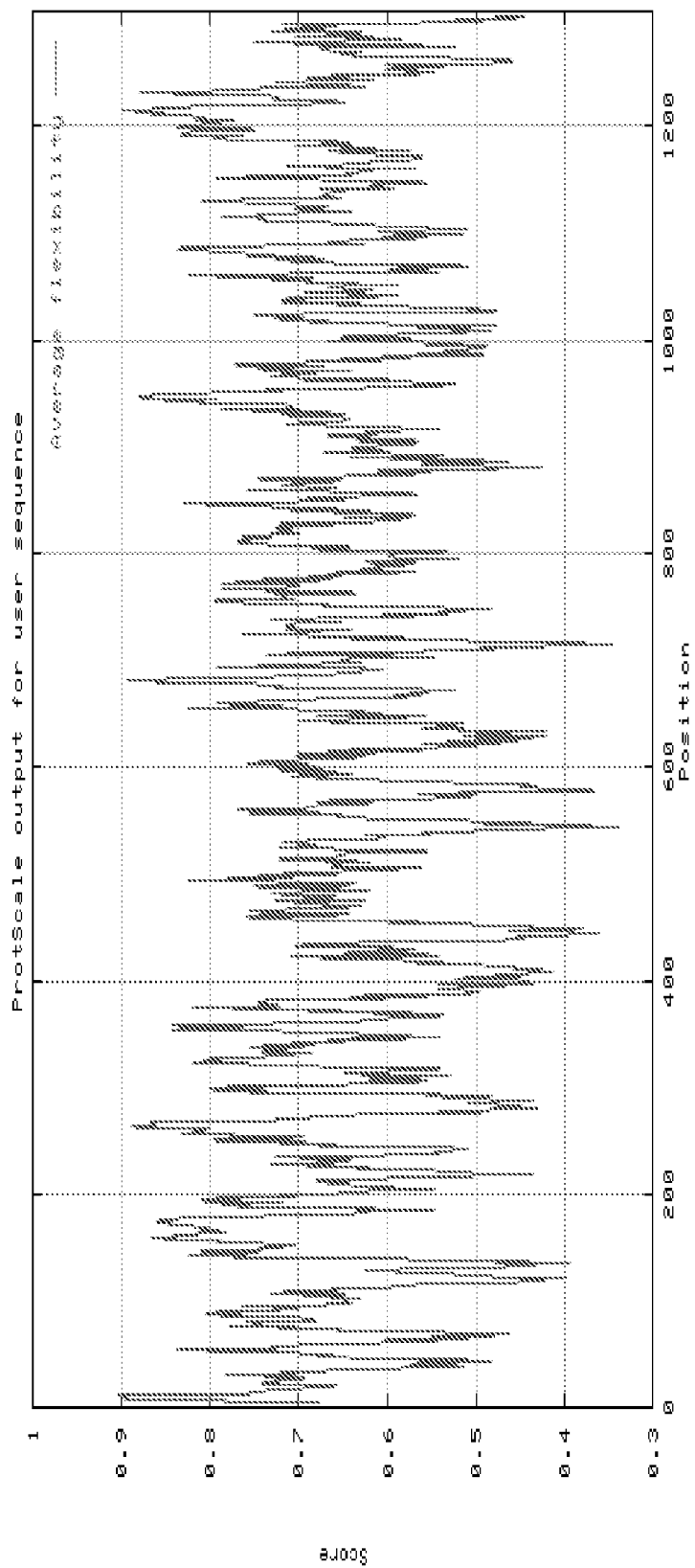
Figure 8O: 185P2C9 variant 1 Average Flexibility Profile
(Bhaskaran R., Ponnuswamy P.K., 1988.
Int. J. Pept. Protein Res. 32:242-255)

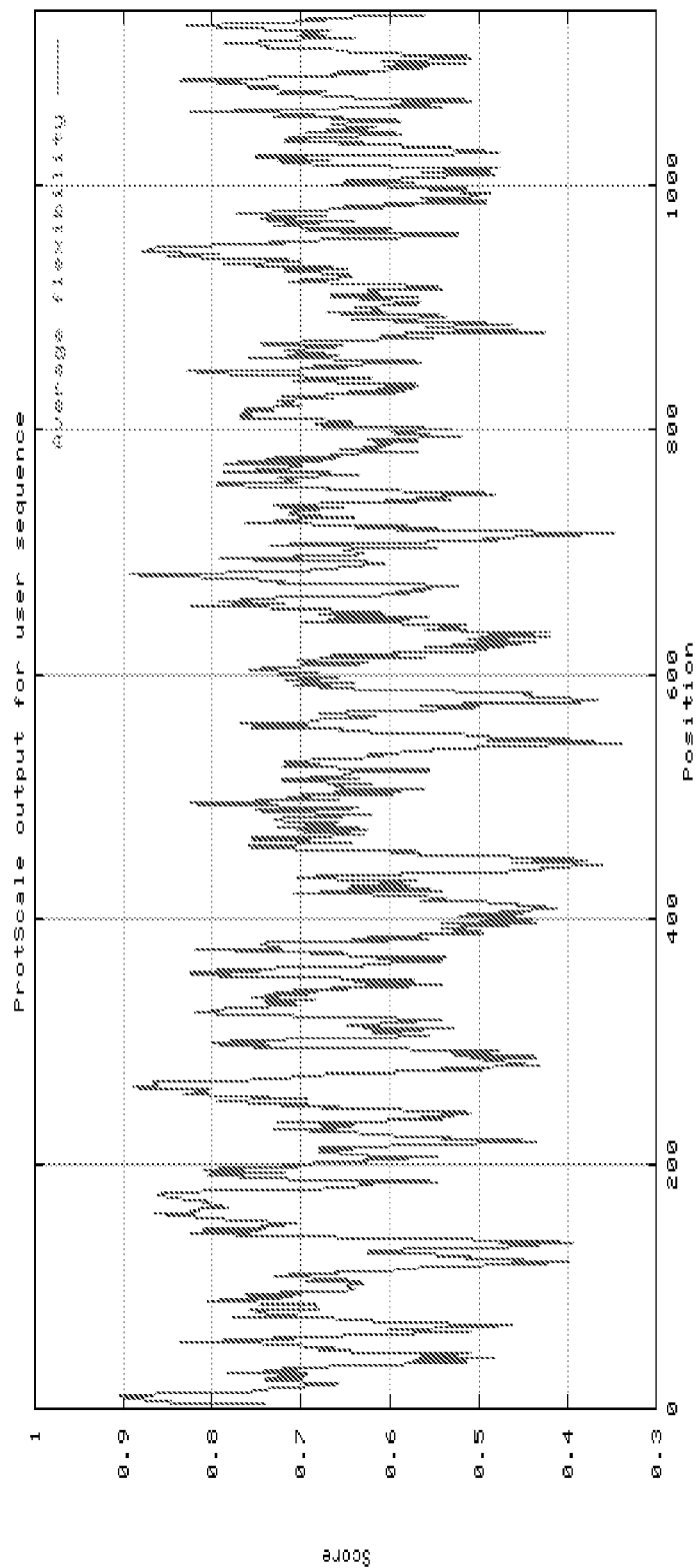

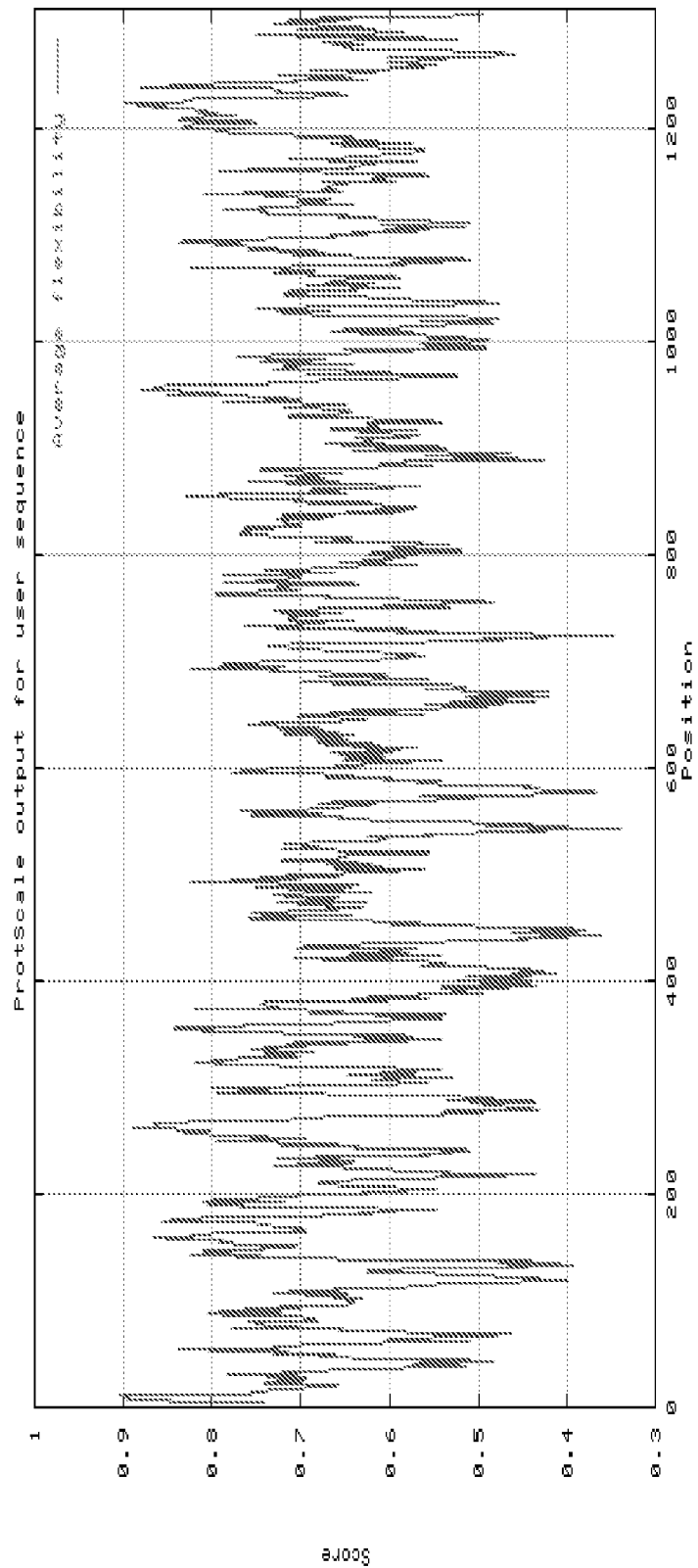
Figure 8Q: 185P2C9 variant 3 Average Flexibility Profile
(Bhaskaran R., Ponnuswamy P.K., 1988.
Int. J. Pept. Protein Res. 32:242-255)

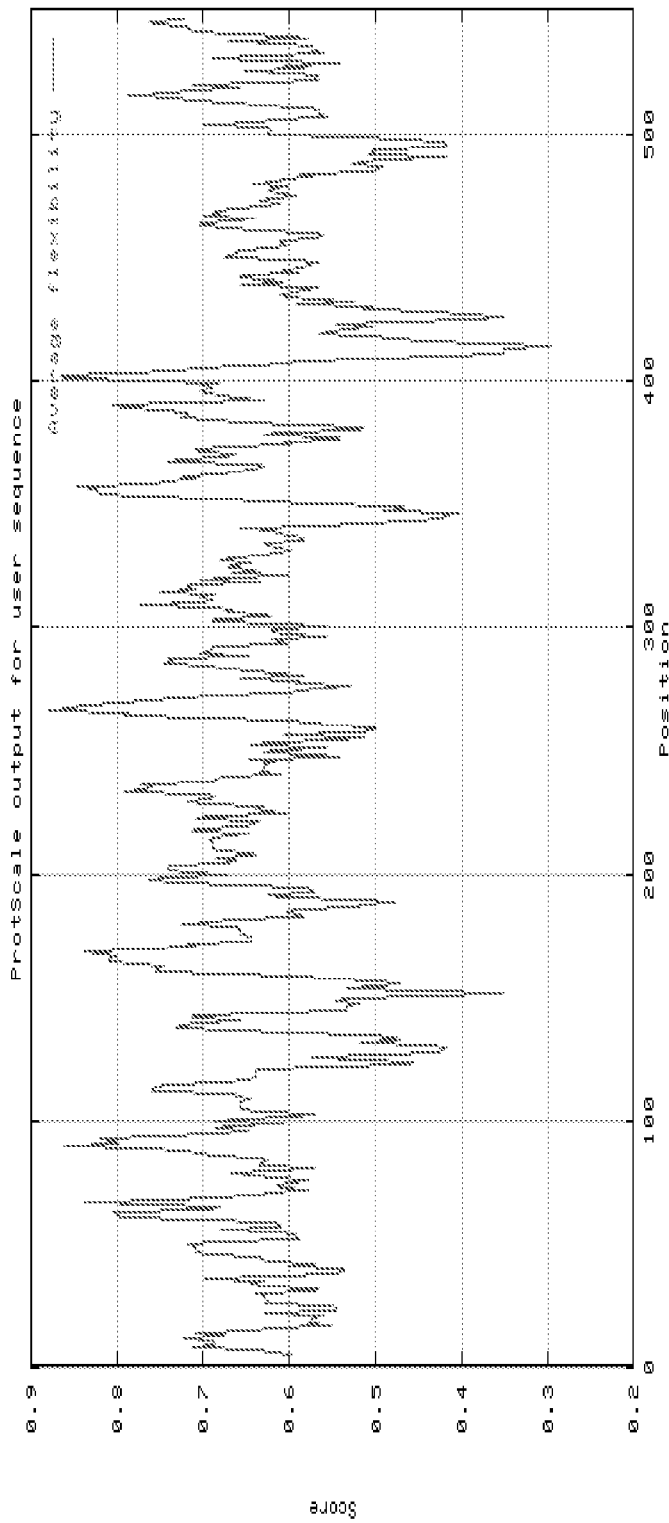
Figure 8R: 185P3C2 Average Flexibility Profile
(Bhaskaran R., Ponnuswamy P.K., 1988.
Int. J. Pept. Protein Res. 32:242-255)

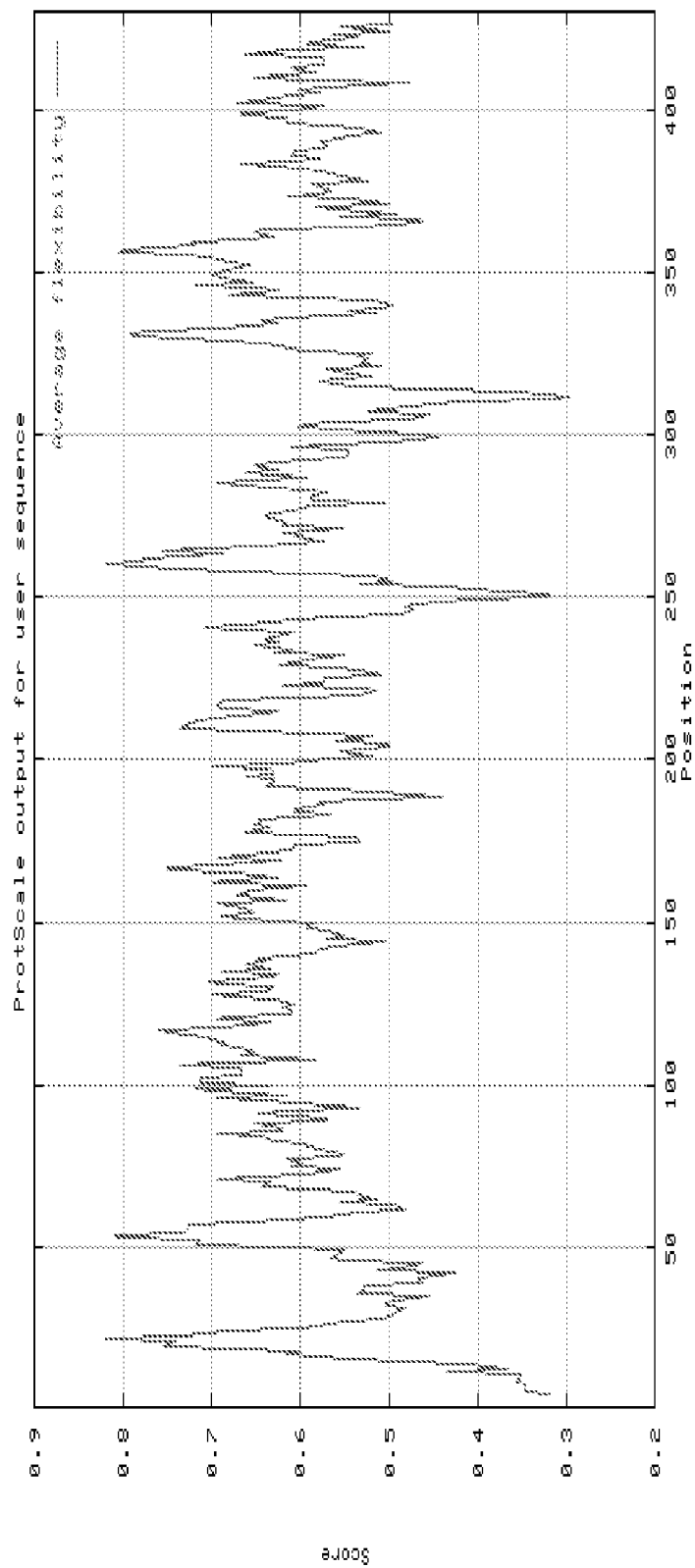
Figure 8S: 186P1H9 Average Flexibility Profile
(Bhaskaran R., Ponnuswamy P.K., 1988.
Int. J. Pept. Protein Res. 32:242-255)

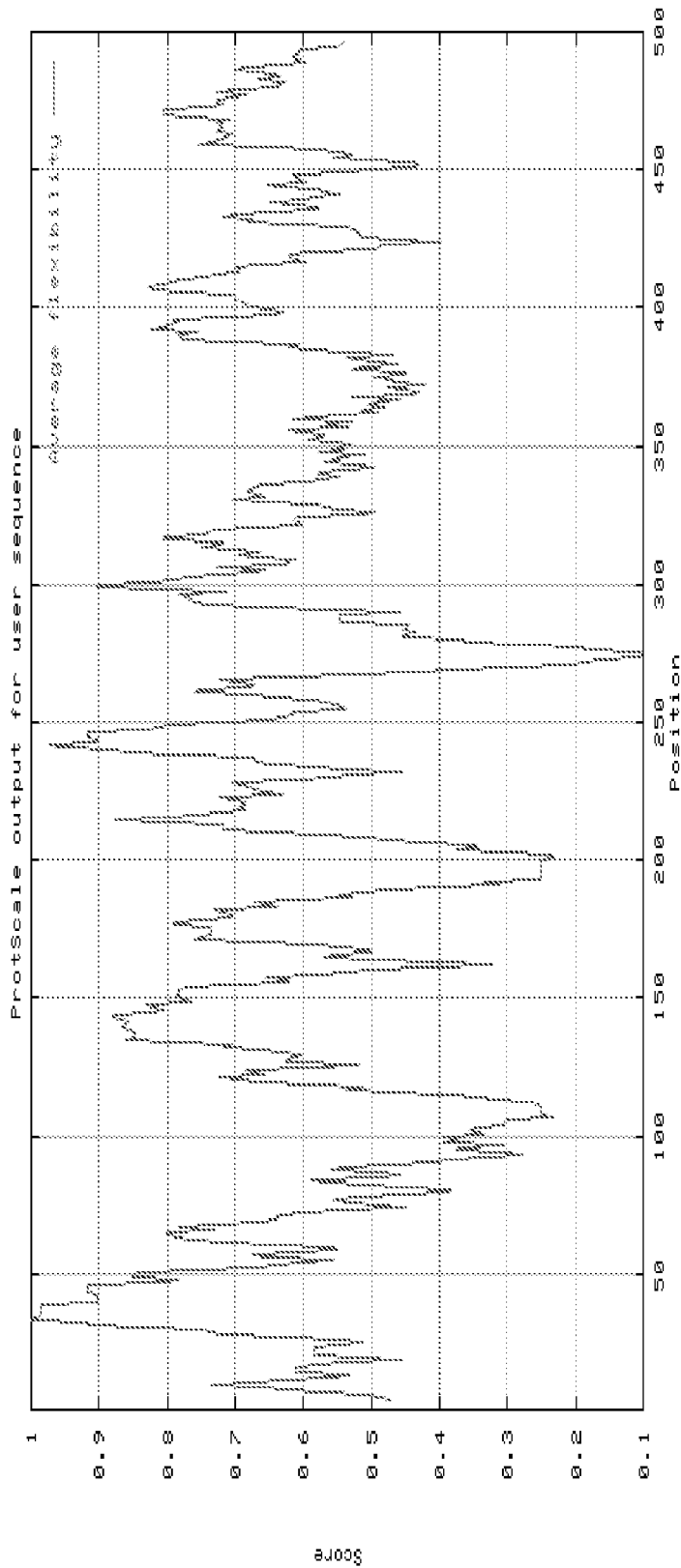
Figure 8T: 187P3F2 Average Flexibility Profile
(Bhaskaran R., Ponnuswamy P.K., 1988.
Int. J. Pept. Protein Res. 32:242-255)

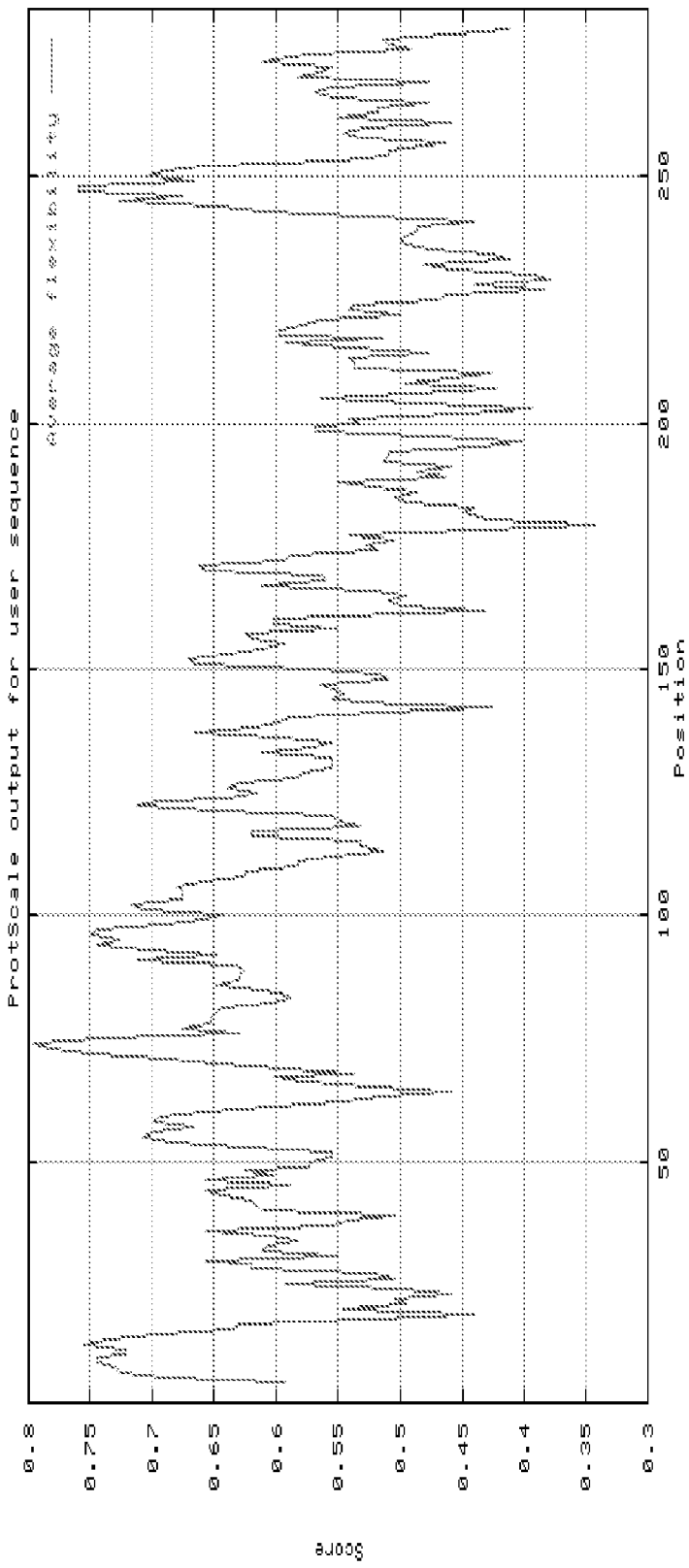
Figure 8U: 192P2G7 Average Flexibility Profile
(Bhaskaran R., Ponnuswamy P.K., 1988.
Int. J. Pept. Protein Res. 32:242-255)

74P3B3 variant 1a Beta-turn Profile
(Deleage, G., Roux B. 1987. Protein Engineering 1:289-294)

74P3B3 variant 1b Beta-turn Profile
(Deleage, G., Roux B. 1987. Protein Engineering 1:289-294)

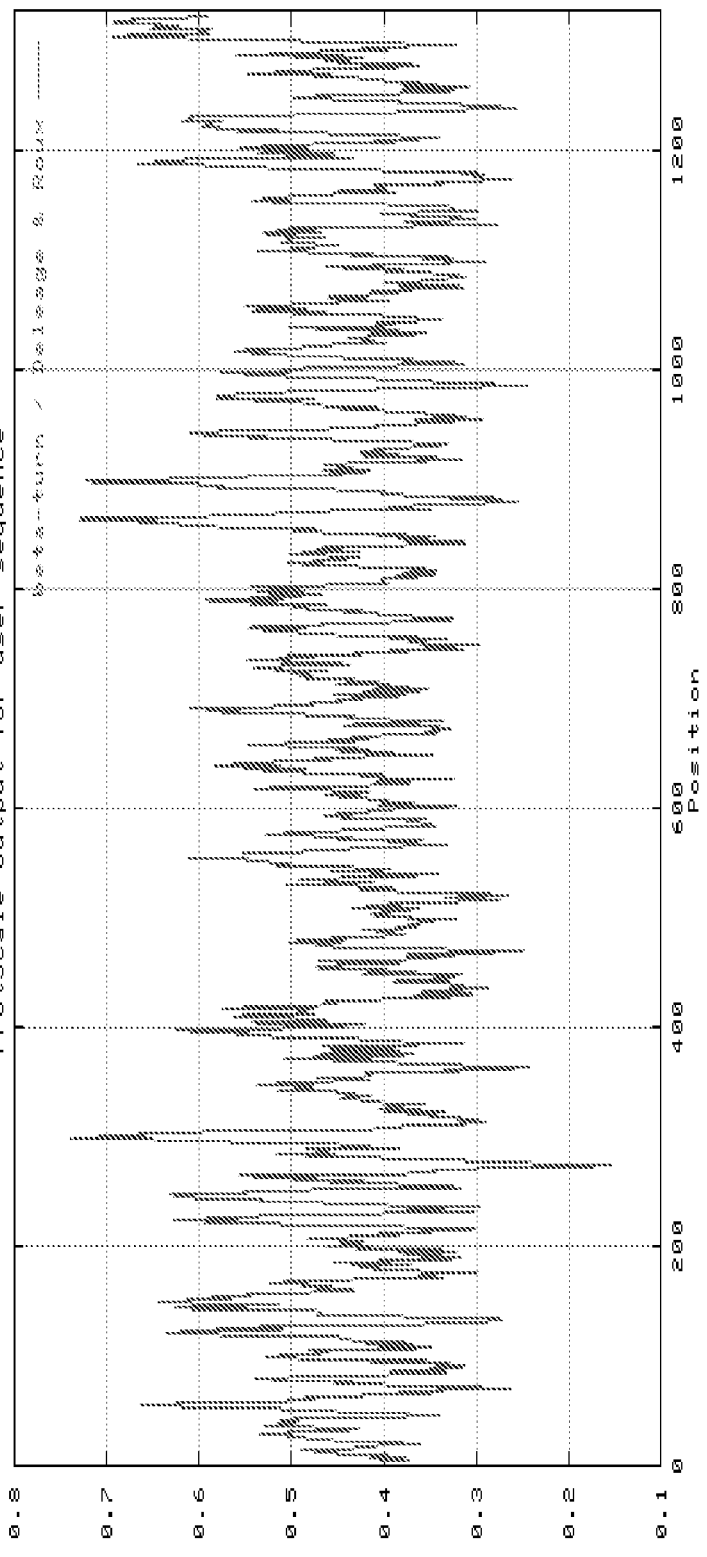

109P1D4 Beta-turn Profile
(Deleage, G., Roux B. 1987. Protein Engineering 1:289-294)

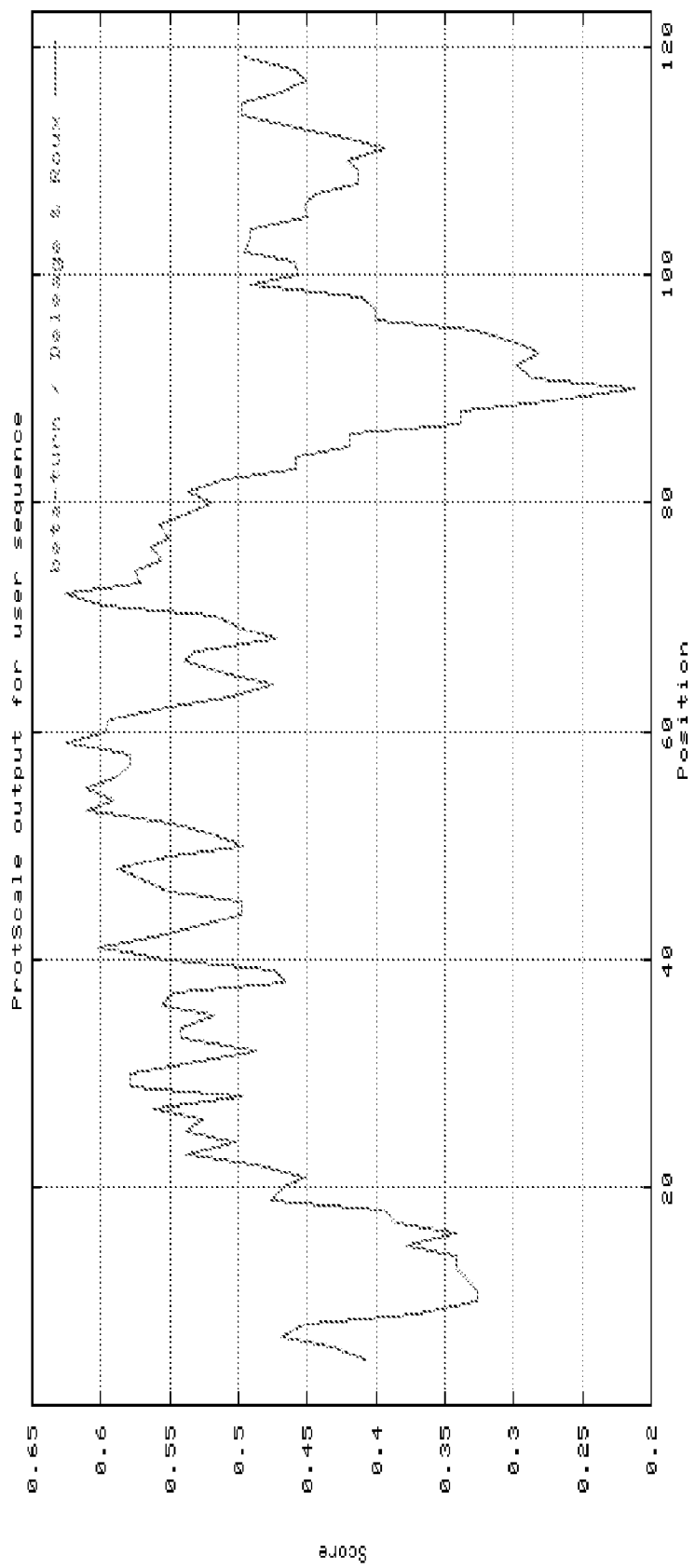
Figure 9E: 151P4E11 Beta-turn Profile
(Deleage, G., Roux B. 1987. Protein Engineering 1:289-294)

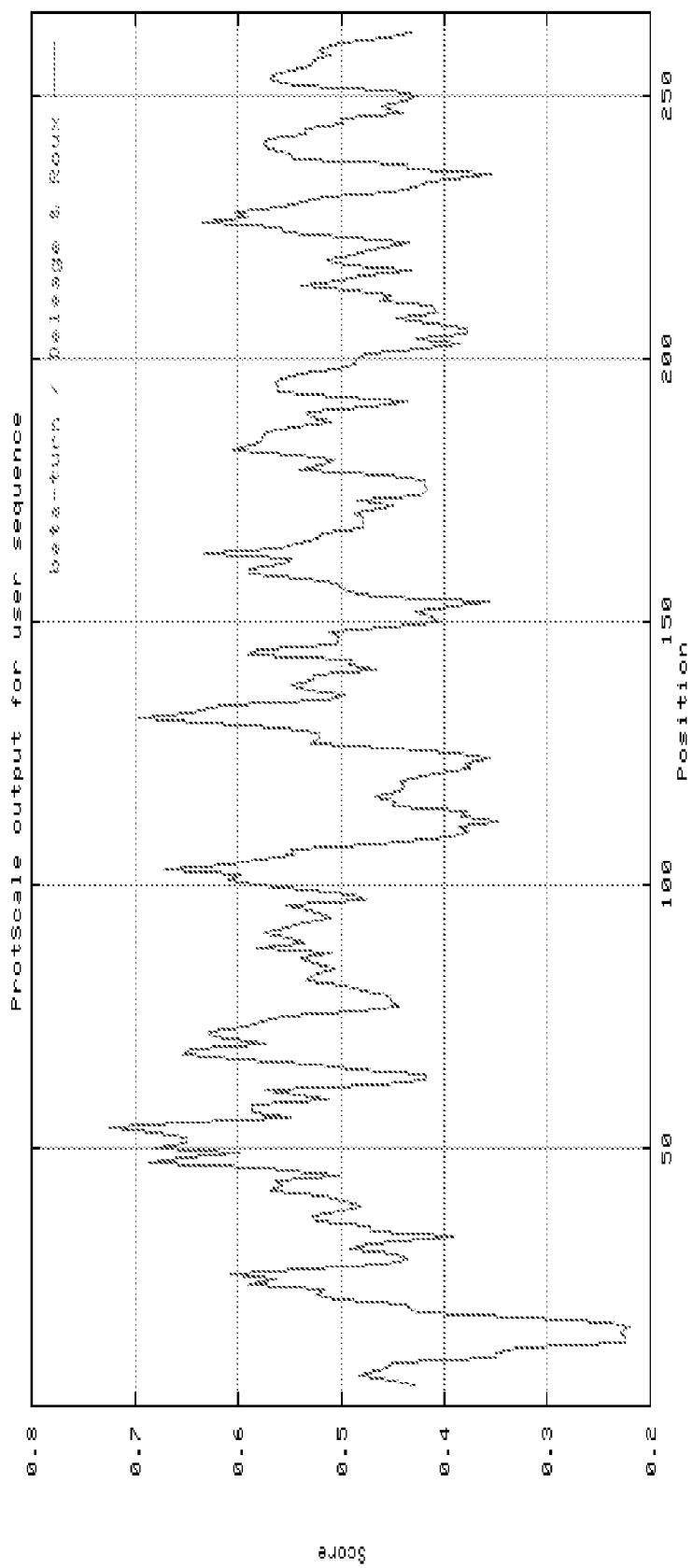
Figure 9F: 151P1C7a Beta-turn Profile
(Deleage, G., Roux B. 1987. Protein Engineering 1:289-294)

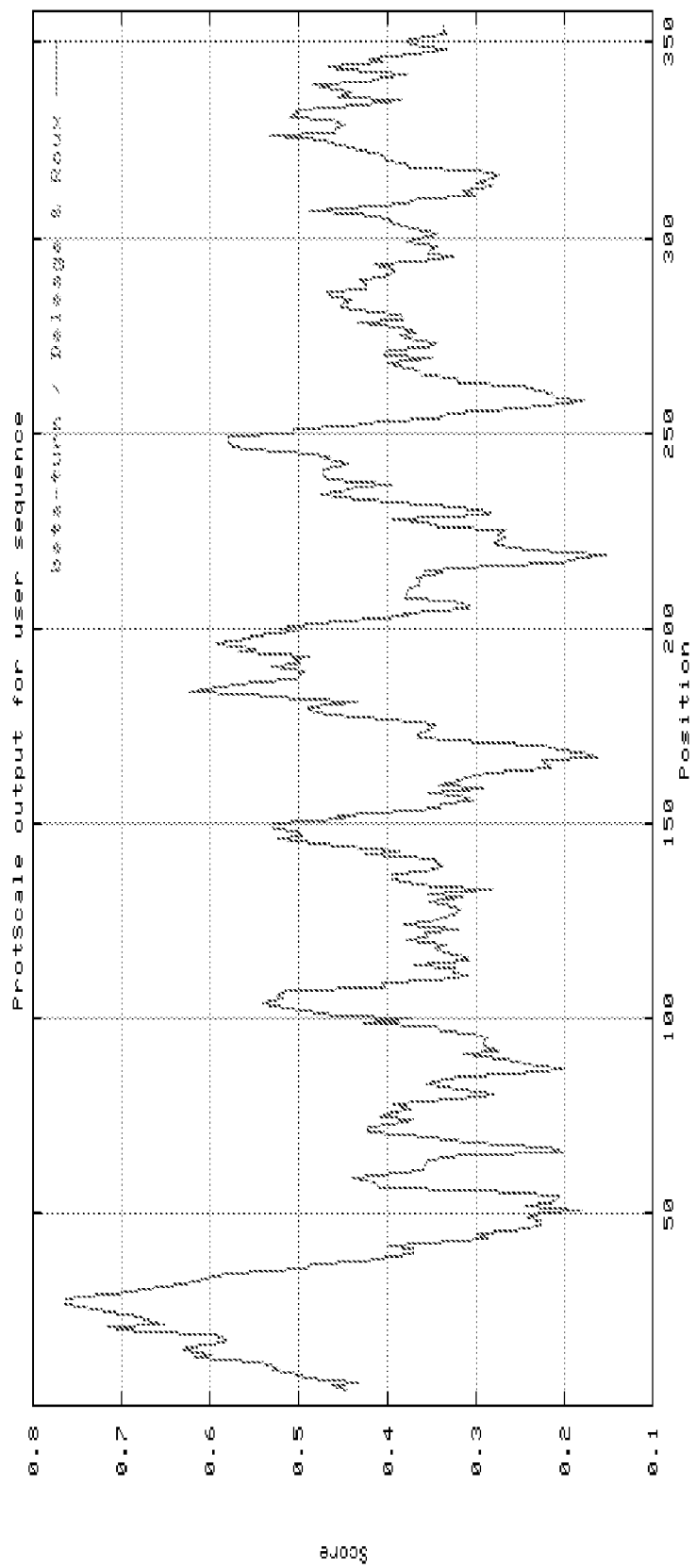
Figure 9G: 154P2A8 Beta-turn Profile
(Deleage, G., Roux B. 1987. Protein Engineering 1:289-294)

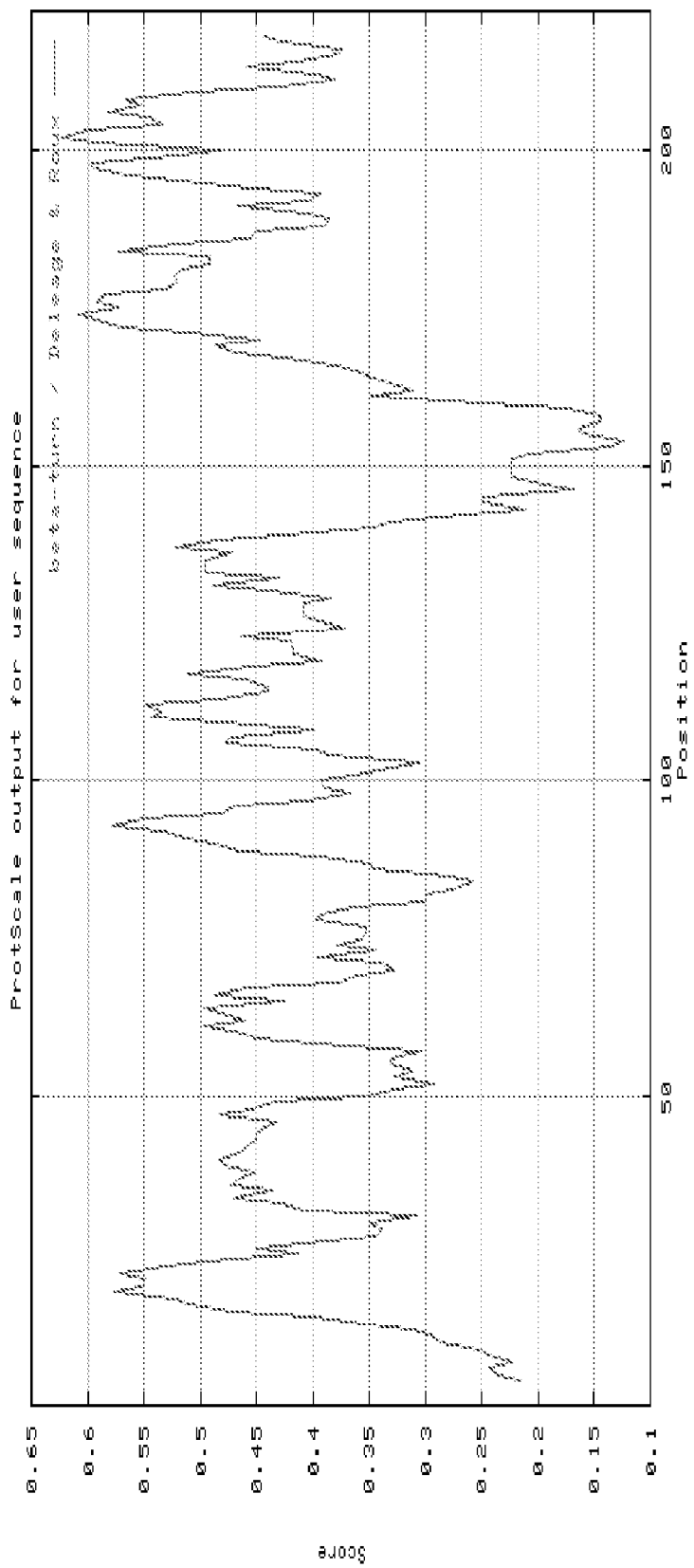
Figure 9H: 156P1D4 Beta-turn Profile
(Deleage, G., Roux B. 1987. Protein Engineering 1:289-294)

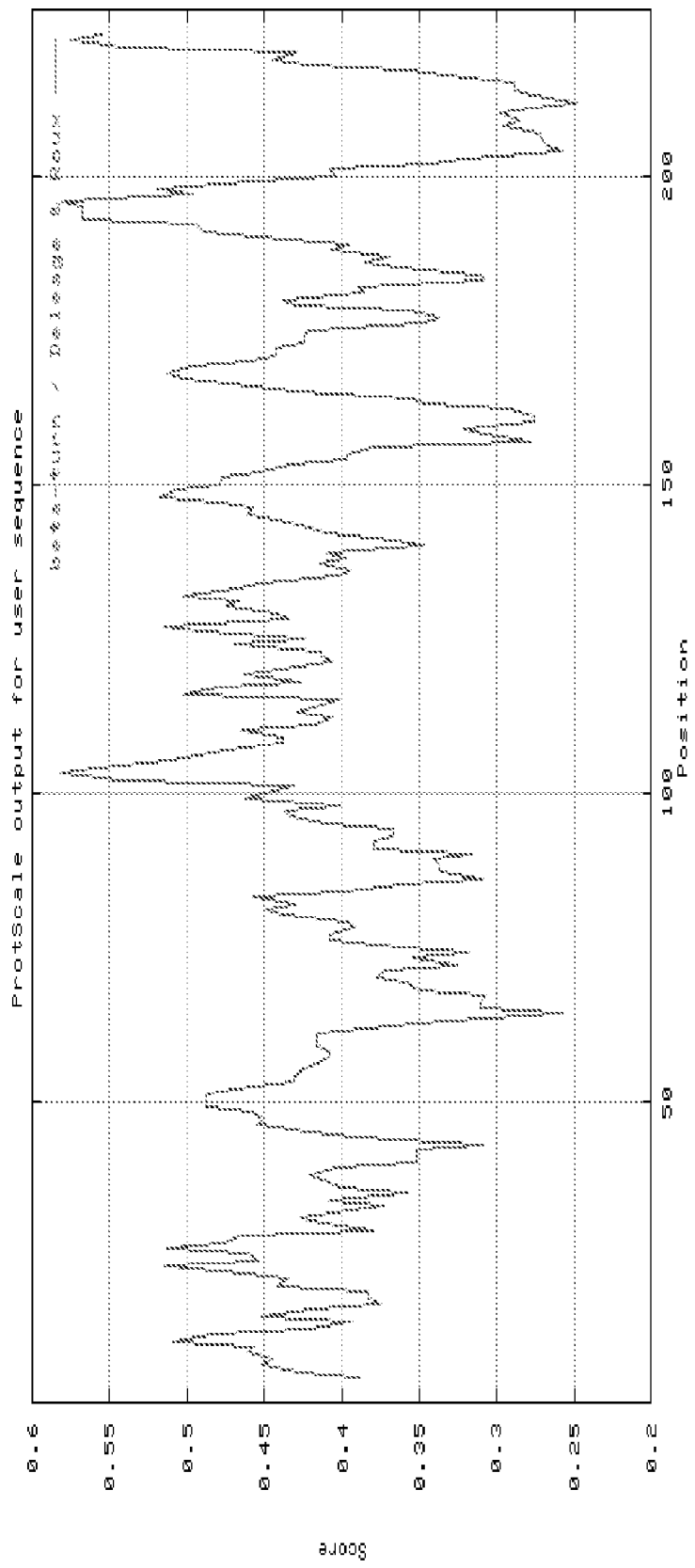
Figure 9l: 156P5C12 Beta-turn Profile
(Deleage, G., Roux B. 1987. Protein Engineering 1:289-294)

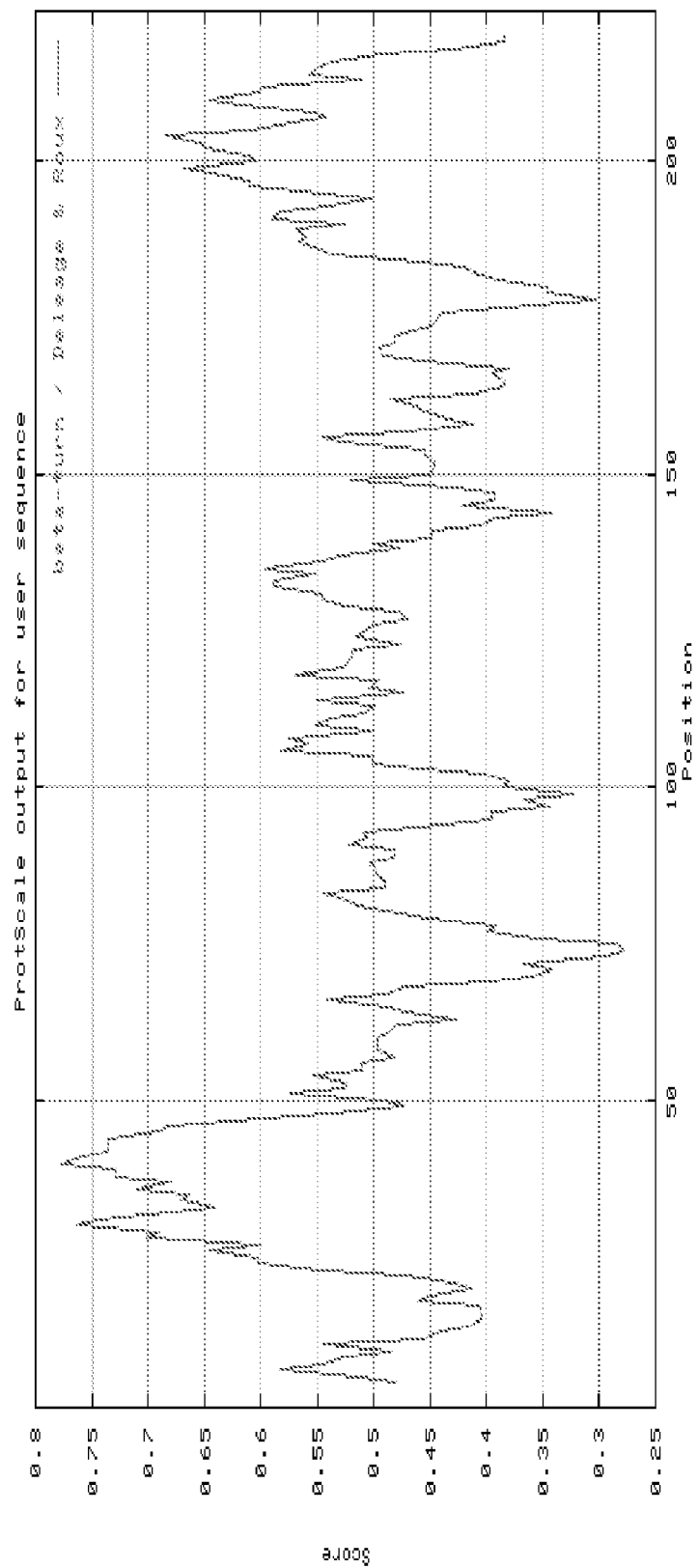
Figure 9J: 159P2B5 Beta-turn Profile
(Deleage, G., Roux B. 1987. Protein Engineering 1:289-294)

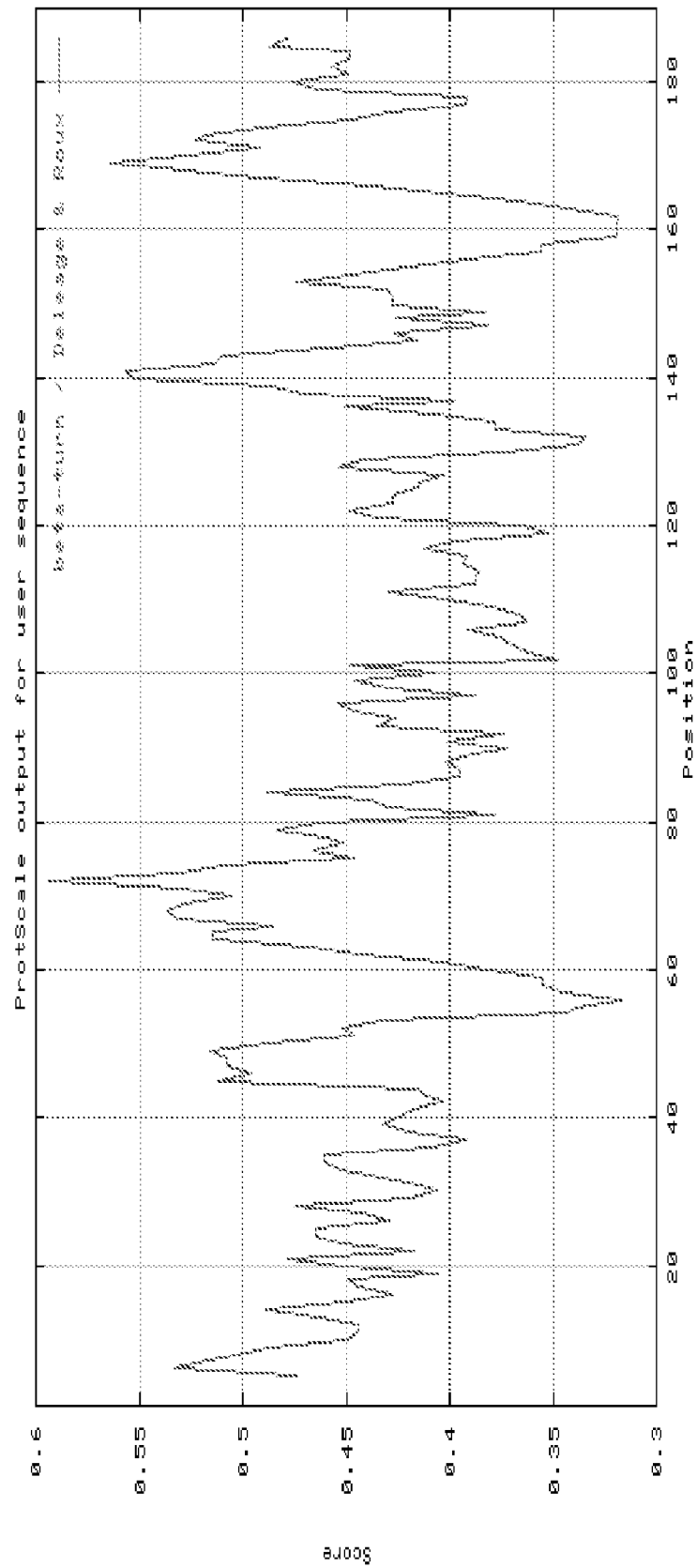
Figure 9K: 161P2B7a Beta-turn Profile
(Deleage, G., Roux B. 1987. Protein Engineering 1:289-294)

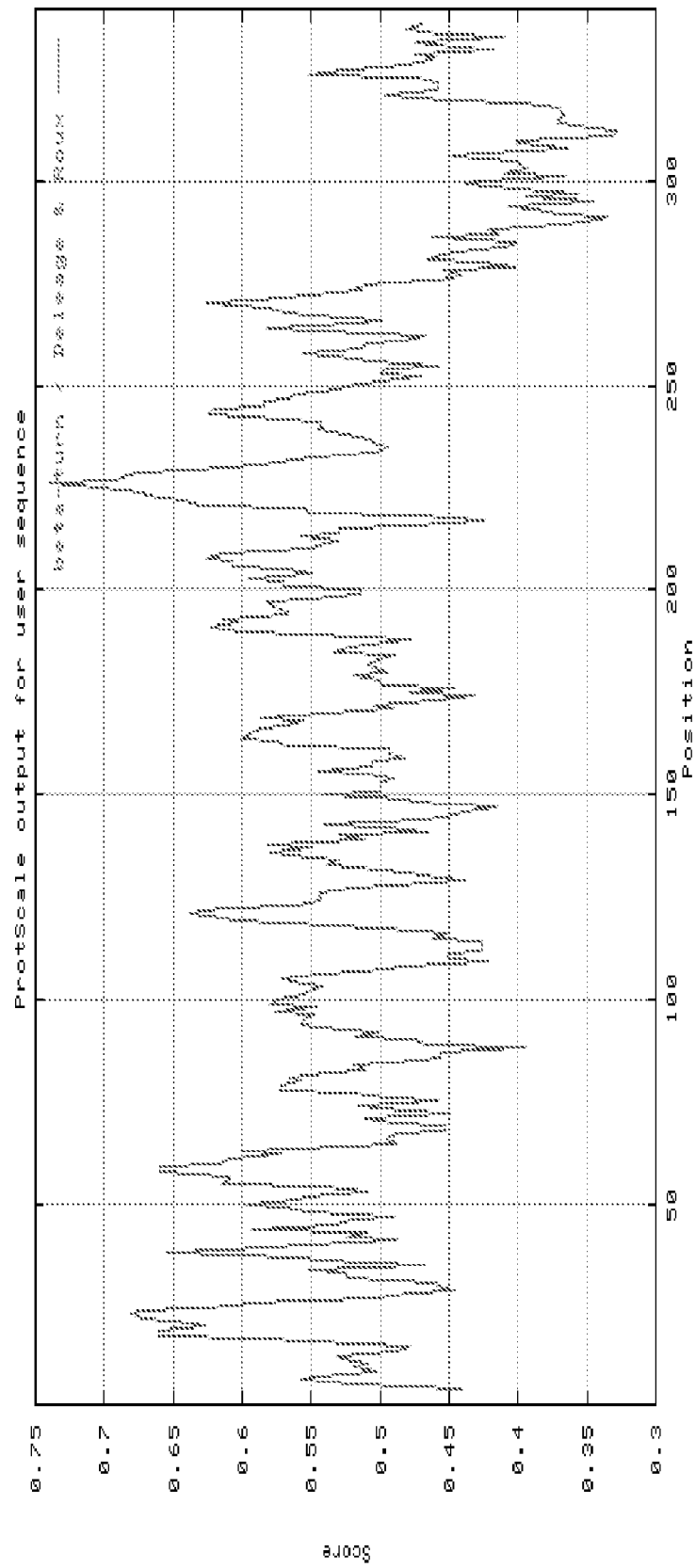
Figure 9L: 179P3G7 Beta-turn Profile
(Deleage, G., Roux B. 1987. Protein Engineering 1:289-294)

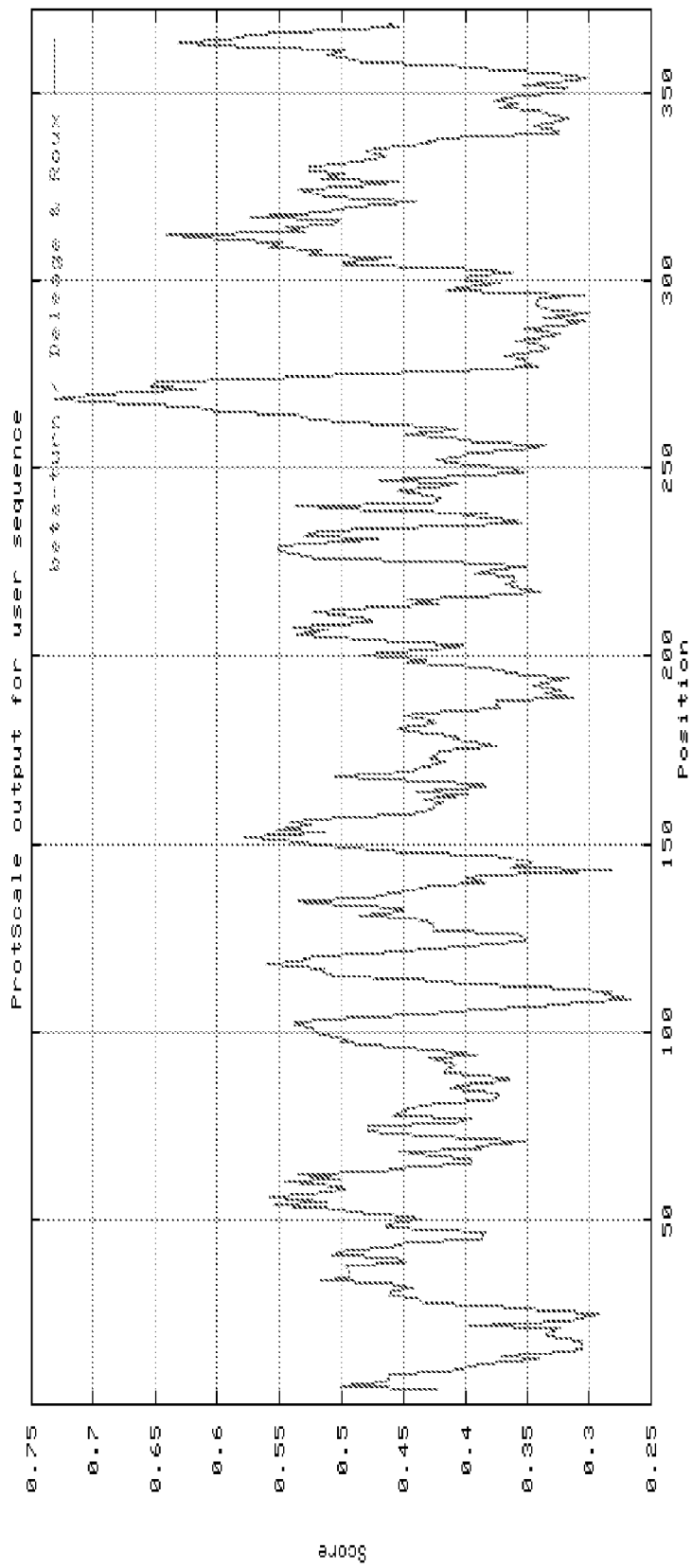
Figure 9M: 184P3C10b Beta-turn Profile
(Deleage, G., Roux B. 1987. Protein Engineering 1:289-294)

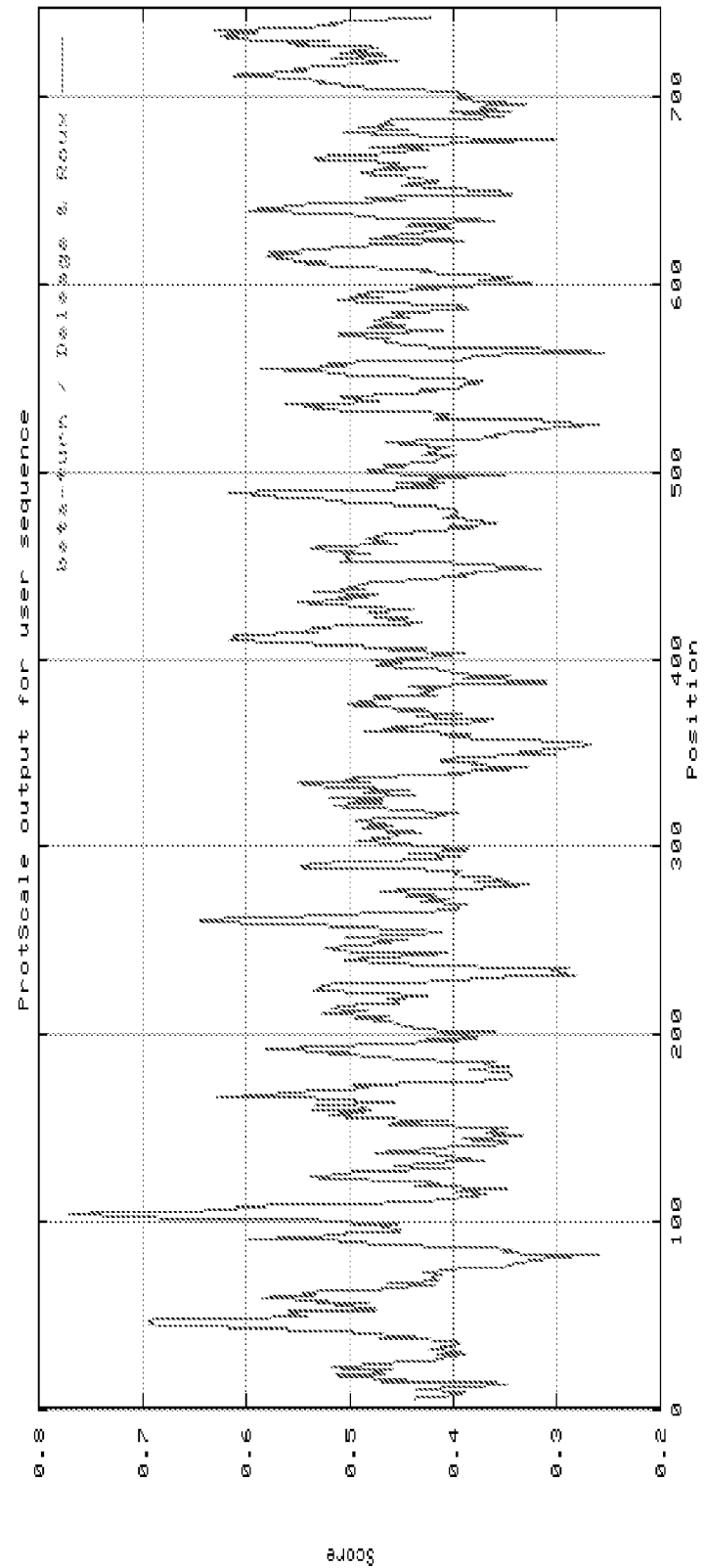
Figure 9N: 184P3G10 Beta-turn Profile
(Deleage, G., Roux B. 1987. Protein Engineering 1:289-294)

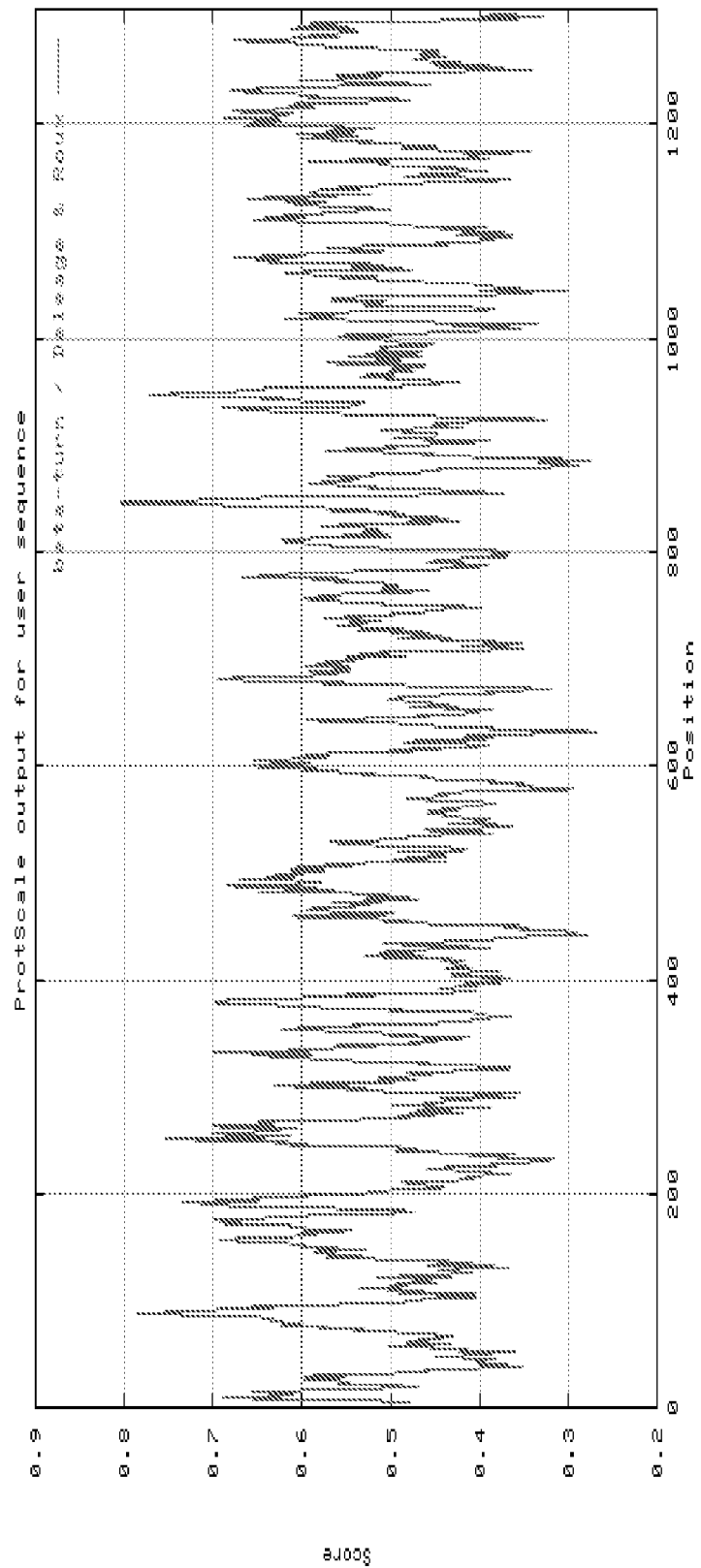
Figure 9O: 185P2C9 variant 1 Beta-turn Profile
(Deleage, G., Roux B. 1987. Protein Engineering 1:289-294)

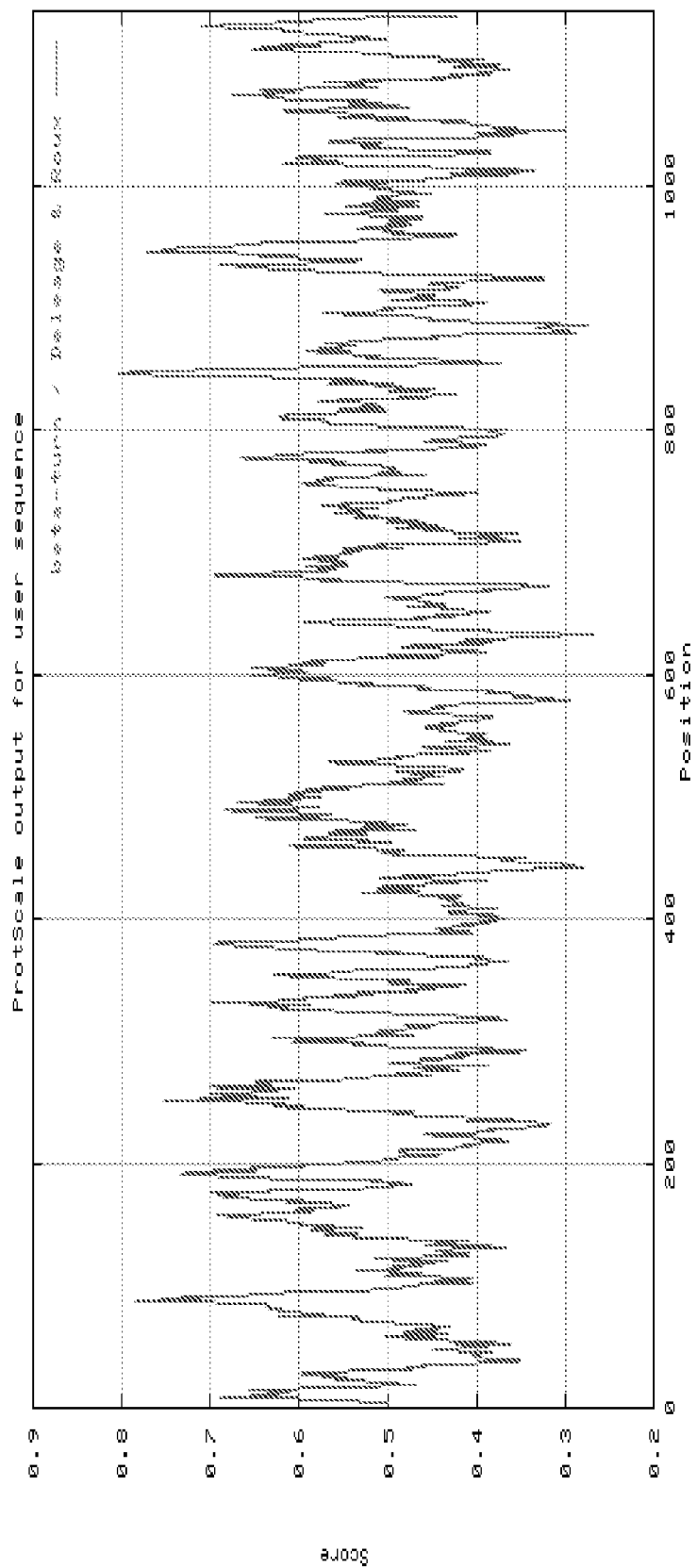
Figure 9P: 185P2C9 variant 2 Beta-turn Profile
(Deleage, G., Roux B. 1987. Protein Engineering 1:289-294)

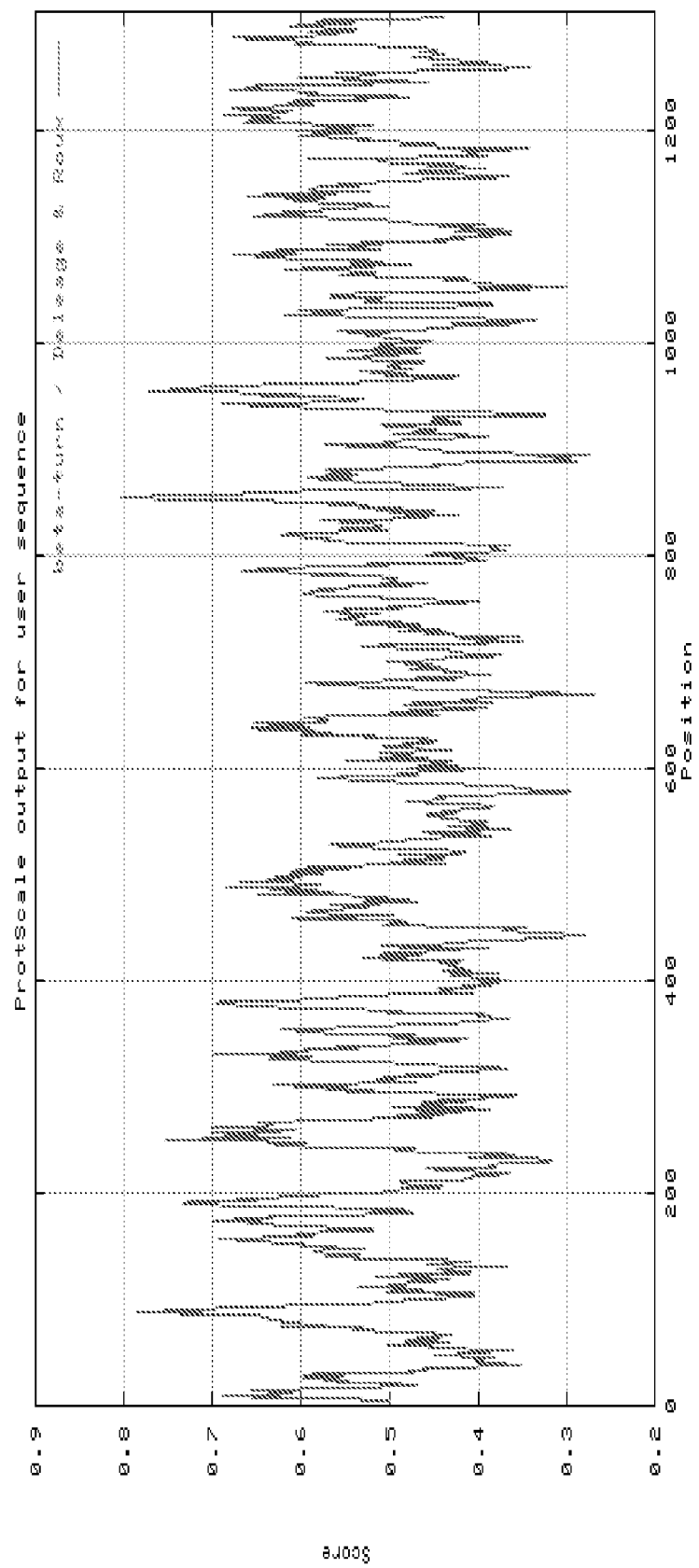
Figure 9Q: 185P2C9 variant 3 Beta-turn Profile
(Deleage, G., Roux B. 1987. Protein Engineering 1:289-294)

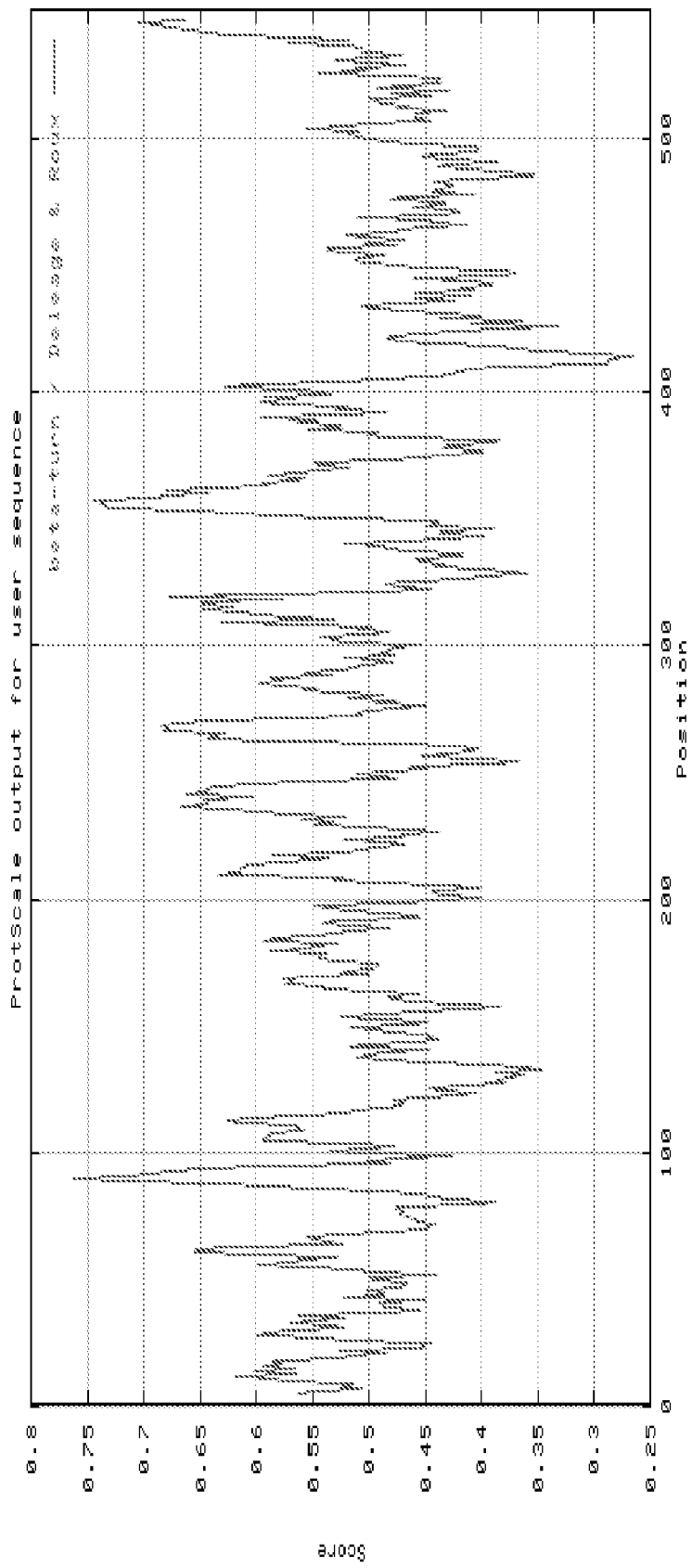
Figure 9R: 185P3C2 Beta-turn Profile
(Deleage, G., Roux B. 1987. Protein Engineering 1:289-294)

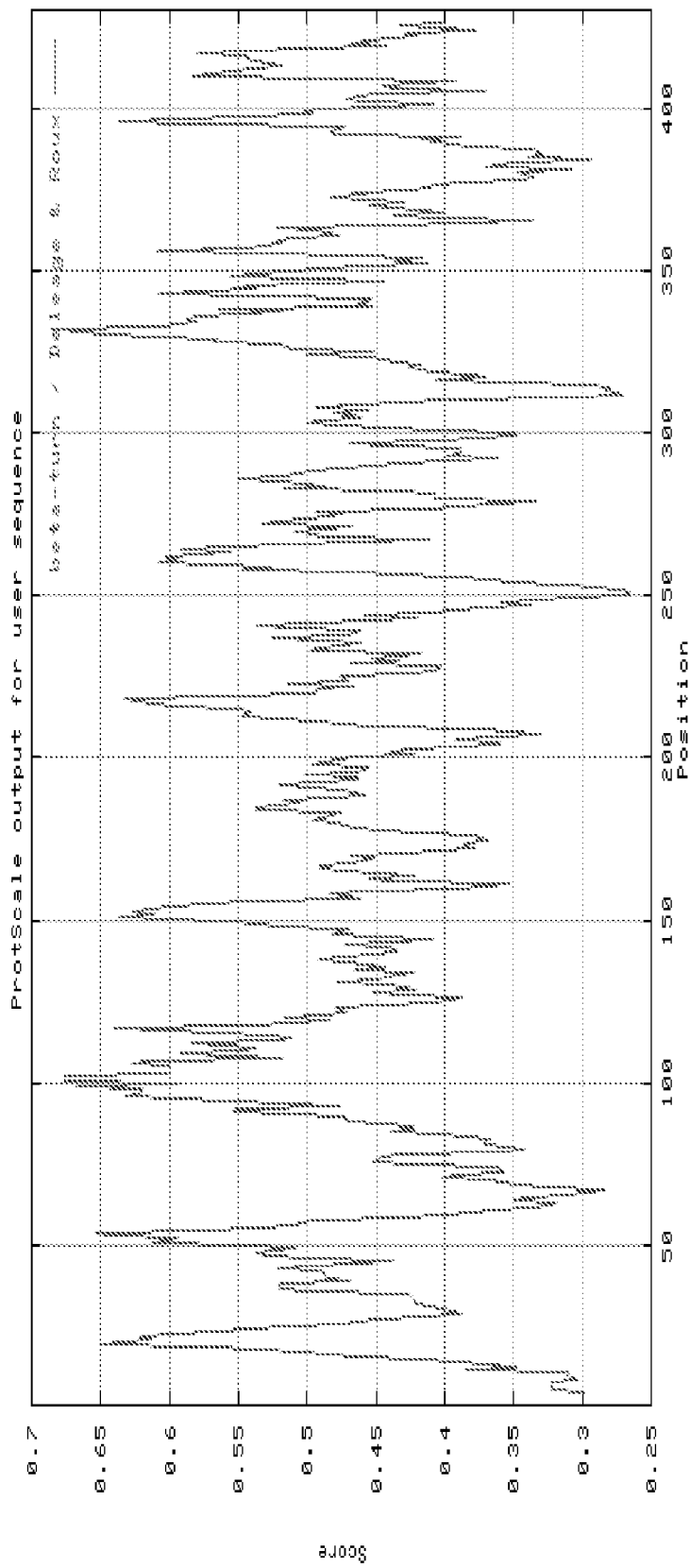
Figure 9S: 186P1H9 Beta-turn Profile
(Deleage, G., Roux B. 1987. Protein Engineering 1:289-294)

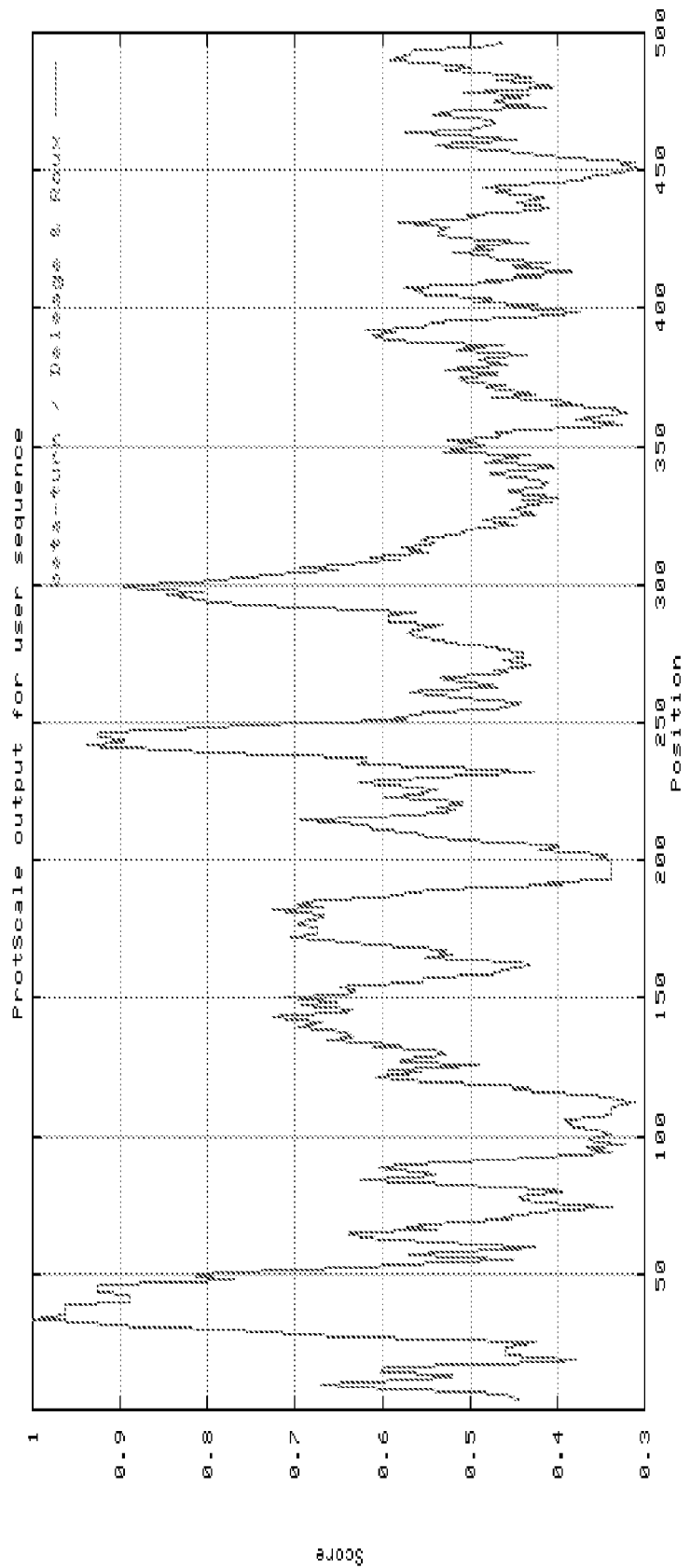
Figure 9T: 187P3F2 Beta-turn Profile
(Deleage, G., Roux B. 1987. Protein Engineering 1:289-294)

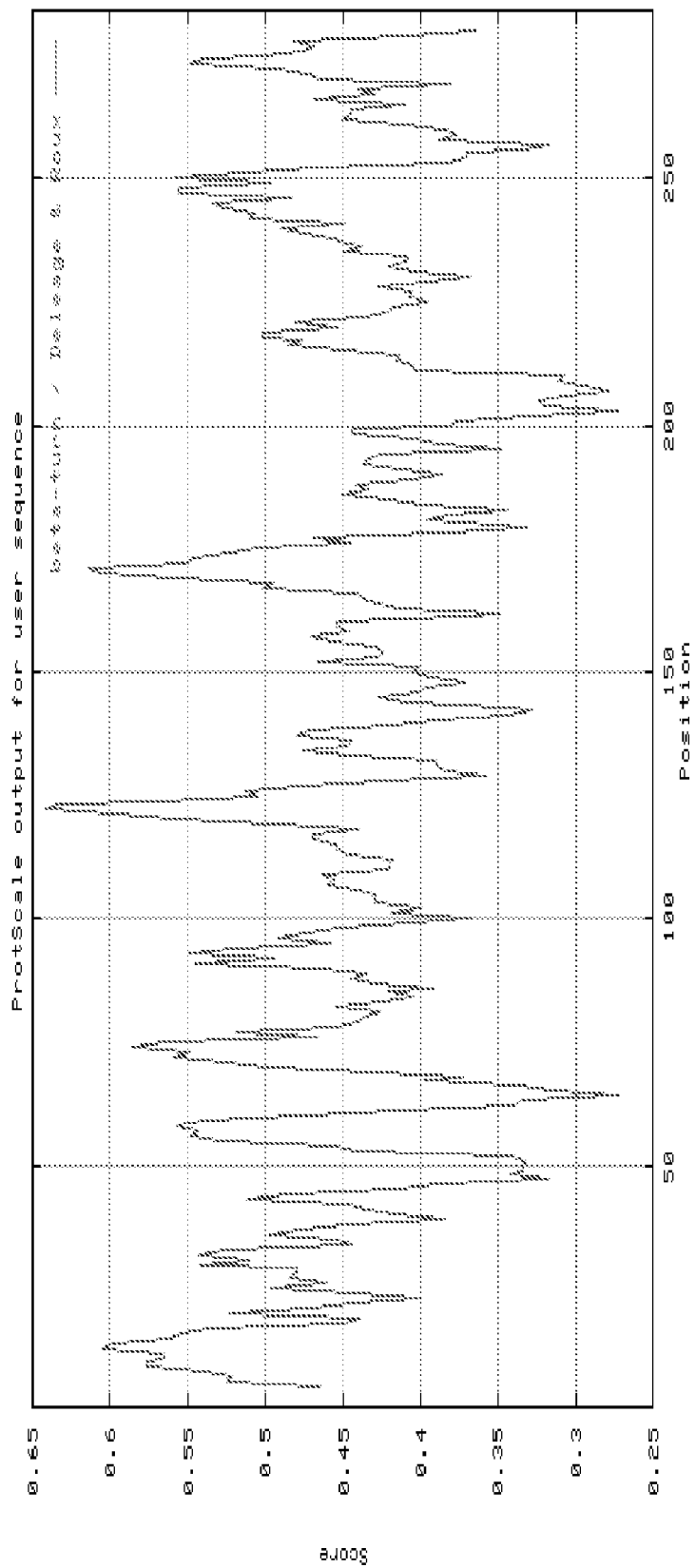
Figure 9U: 192P2G7 Beta-turn Profile
(Deleage, G., Roux B. 1987. Protein Engineering 1:289-294)

Figure 10A: Secondary structure of 74P3B3 variant 1

```
         10         20         30         40         50         60         70
          |          |          |          |          |          |          |
MGQSKSKHSAYLHFIKLLLKRAGIKASTENLITLFPTVEQYCPWFPEHGTMDFKDWEQVGIALKQVCKEG
cccccchhhhhhhhhhhcccccchhhheeecccccccccccccccchhhhhhhhhhhcc KFIPLTAWSNWAIVKAASEPFQSENEAYPPAERISAEEGGDAAEGGEDSEEDFEENTDKPGDELISFEEH
cceeeeecchehhhhhcccccccccccccchccccccccccccccchcccceeeeecc VGPSAAPKIEKPYMPRCLKQRRALRSSRLLIGIIRSGRLQ
cccccccccchhcchhhhhhhhcheeheeeccccccc Alpha helix       (h):   31.67%
Extended strand   (e):   11.67%
Random coil       (c):   56.67%
```

Figure 10B: Secondary structure of 74P3B3 variant 2

```
        10          20          30          40          50          60          70
         |           |           |           |           |           |           |
MFKTKKGLEEQSAPHWDHPEWPPPIKQCSLEPWRSESQICPVSRMNELWPQEPQAHGVAPVQHKAALPSN
ccccccccccccccccccccccccccccccccccccccccccccccccccccccccccccccccccccc
VNESPLQFIIRQARLAGDLDAWQFAVVLQPPRQQGGAHQAVWEPFSFKLLKDLKAAVGQYGPNSPFIRSL
cchhhhhhhhhhccccheeeeeccccccccccccchhhhhchhhhhhhhccccccchhhhhhhhhhhhhhh
LQSVAQNKLLTPCDWEILTKVTLSPSQFLQFKTWWTDEAQNQDRKNRAANPAIAITFEQLLGIGGQWGTV
hhhhhhhccccccceeeeeecccccccccceeeeehhccccccchhccccchhehhhhhccccccc
NNHQDFEMMPLNKFAIAV
cccccchhchcheeecc Alpha helix       (h):    29.82%
Extended strand   (e):     9.65%
Random coil       (c):    60.53%
```

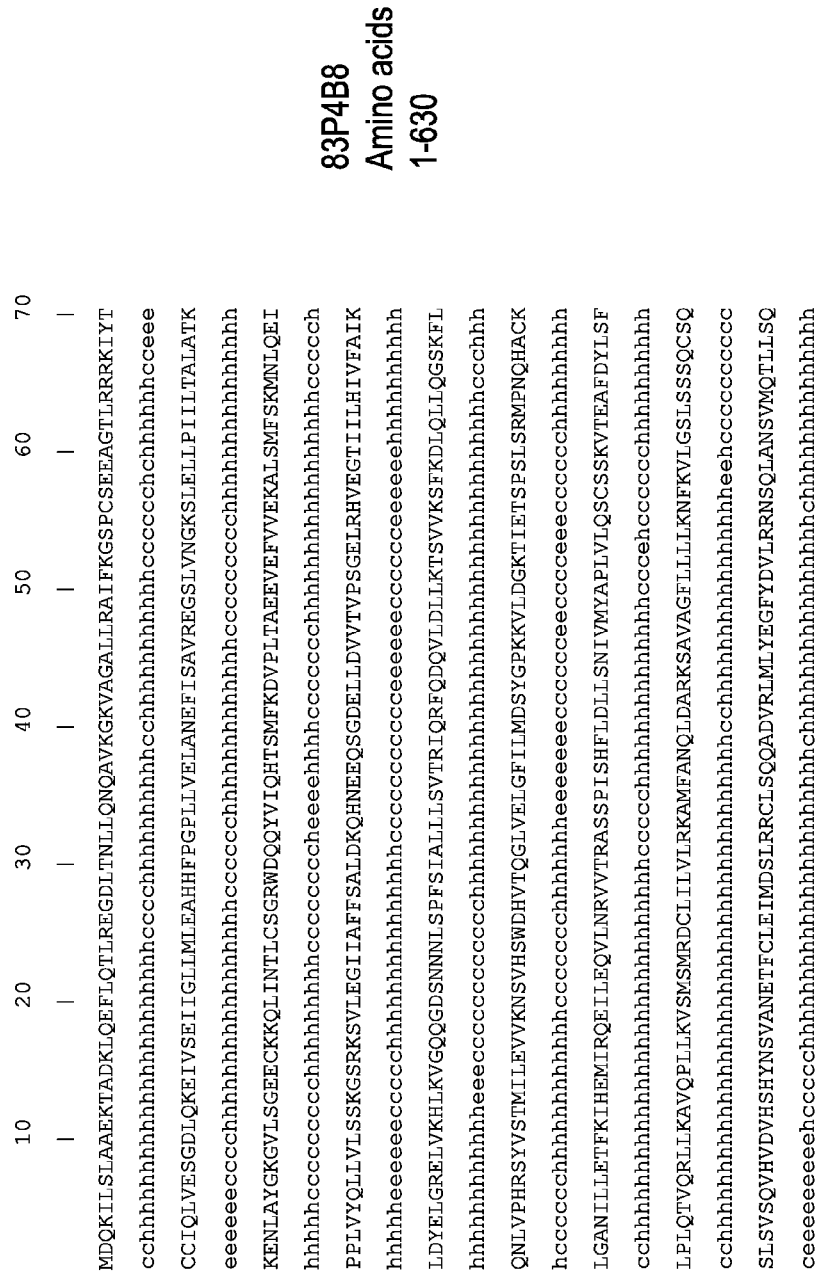
Figure 10C: Secondary structure of 83P4B8

Figure 10D: Secondary structure of 83P4B8

83P4B8
Amino acids
631-1328

```
         640         650         660         670         680         690         700
          |           |           |           |           |           |           |
LKQFYEPKPDLLPPLKLDACILTQGDKISLQEPLDYLLCCIQHCLAWYKNTVIPLQQGEEEEEEAAFYE
hhhhhccccccccccccceeeecccccchhhhhhhhhhhhhcccceeccccccchhhhhhhhh
DLDDILESITNRMIKSELEDFELDKSADFSQSTSIGIKNNISAFLVMGVCEVLIEYNFSISSFSKNRFED
hhhhhhhhhhhhhhhhhhhhccccccccccceehhhhhhhhhhhhheeeceeecccchhhhh
ILSLFMCYKKLSDILNEKAGKAKTKMANKTSDSLLSMKFVSSLLTALFRDSIQSHQESLSVLRSSNEFMR
hhhhhhhhhhhhhhhhccccccccccccchhhhhhhhhhhhhhhhhhhchehecchhhhh
YAVNVALQKVQQLKETGHVSGPDGQNPEKIFQNLCDITRVLLWRYTSIPTSVEESGKKEKGKSISLLCLE
hhhhhhhhhhhhhhhccccccccccchhhhhhhhhheeeeccccccccccceeeeeehh
GLQKIFSAVQQFYQPKIQQFLRALDVTDKEGEEREDADVSVTQRTAFQIRQFQRSLLNLLSSQEEDFNSK
hhhhhhhhhhhhhhhhhhhhhcccccccchhhhhhhhhhhhhhhhhccccccch
EALLLVTVLTSLSKLLEPSSPQFVQMLSWTSKICKENSREDALFCKSIMNLLFSLHVSYKSPVILLRDLS
hhhhhhhhhhhhhhhhhcccccchehhhhcccccccchhhhhhhhhhhecccceeeehhc
QDIHGHLGDIDQDVEVEKTNHFAIVNLRTAAPTVCLLVLSQAEKVLEEVDWLITKLKGQVSQETLSEEAS
hhhcccccccceehhccceeeeecccccccchhhhhhhhhhhhcccccchcchhccc
SQATLPNQPVEKAIIMQLGTLLTFFHELVQTALPSGSCVDTLLKDLCKMYTTLTALVRYYLQVCQSSGGI
ccccccccccchhhhhhhhhhhhhhhhcccccchhhhhhhhhhhhhhhhhecccccc
PKNMEKIVKLSGSHLTPLCYSFISYVQNKSKSLNYTGEKKEKPAAVATAMARVLRETKPIPNLIFAIEQY
hhhhhhhhhhccccccchheehhccccccccccccchhhhhhhhhhccchhheehhhh
EKFLIHLSKKSKVNLMQHMKLSTSRDFKIKGNILDMVLREDGEDENEEGTASEHGGQNKEPAKKKRKK
hhhhheeccccchhhhhhhccccccceeeccccccccccccccccchhhhccc
```

Figure 10E: Secondary structure of 109P1D4

109P1D4
Amino acids
1-490

```
         10        20        30        40        50        60        70
         |         |         |         |         |         |         |
MDLLSGTYIFAVLLACVVFHSGAQEKNYTIREEMPENVLIGDLLKDLNLSLIPNKSLTTAMQFKLVYKTG
cchhhhhhhhhhheeccccccccccccceeeeccccccchehhhhhhhhccccccccchhhhheeeehccc
DVPLIRIEEDTGEIFTTGARIDREKLCAGIPRDEHCFYEVEVAILPDEIFRLVKIRFLIEDINDNAPLFP
cceeeeecccccccccccccceeeccccchhhhhccccccccccceeeeeehchhhhhheeeehhhcccccccccc
ATVINISIPENSAINSKYTLPAAVDPDVGINGVQNYELIKSQNIFGLDVIETPEGDKMPQLIVQKELDRE
ceeeeeecccccccccccccccccccccccccchheeeeeeecccccccccccccceeehhhhchc
EKDTYMKVKVEDGGFPQRSSTAILQVSVTDTNDNHPVFKETEIEVSIPENAPVGTSVTQLHATDADIGE
ccceeeeeeccccccccccccccccceeeeeeeeeeccccceeeeeeeeccccccceeeeecccccccc
NAKIHFSFSNLVSNIARRLFHLNATTGLITIKEPLDREETPNHKLLVLASDGGLMPARAMVLVNVTDVND
cceeeeehhhhhhhhhhhhhhheccccceeeeeecccccccccccccceeeeeeeccccceeeeeeccccc
NVPSIDIRYIVNPVNDTVVLSENIPLNTKTALITVTDKDADHNGRVTCFTDHEIPFRLRPVFSNQFTLET
ccccceeeeecccccccceeeeeeeccccccccccccccceeeeeeeeccccccccccccchccchhhhh
AAYLDYESTKEYAIKLLAADAGKPPLNQSAMLFIKVKDENDNAPVFTQSFVTVSIPFNNSPGIQLTKVSA
hhhccccchhhhhhhhhhccccccchhheeeeeeccccccccccceeeeeeeeeeeeecccccceeeeee
```

Alpha helix       (h):  16.75%
Extended strand   (e):  29.48%
Random coil       (c):  53.77%

Figure 10F: Secondary structure of 109P1D4

109P1D4
Amino acids
491-1021

```
          500        510        520        530        540        550        560
           |          |          |          |          |          |          |
MDADSGPNAKINYLLGPDAPPEFSLDCRTGMLTVVKKLDREKEDKYLFTILAKDNGVPPLTSNVTVFVSI
cccccccccceeeeeeccccccccccccccccccccceehehccccccccceeeeccccccccccceeeeeee
IDQNDNSPVFTHNEYNFYVPENLPRHGTVGLITVTDPDYGDNSAVTLSILDENDDFTIDSQTGVIRPNIS
eccccccccceeeeecccccccccccccccccceeeeeeecccccccccccccccceeeeccccccccccc
FDREKQESYTFYVKAEDGGRVSRSSSAKVTINVVDVNDNKPVFIVPPSNCSYELVLPSTNPGTVVFQVIA
ccccccceeeeeccccccccccccccceeeeeeeccccccccccccccccccceeeeeeccccceeeeeee
VDNDTGMNAEVCYSIVGNTRDLFAIDQETGNITLMEKCDVTDLGLHRVLVKANDLGQPDSLFSVVIVNL
eccccccceeeeeeeeccchheeeeecccccccceeeeeeccccccccccchhehecccccchhhhhhhhh
FVNESVTNATLINELVRKSTEAPVTPNTEIADVSSPTSDYVKILVAAVAGTITVVVVIFITAVVRCRQAP
ehcccccchhhhhcccccccccccccccccchhhhhhhhhhcccceeeeeeehhhhhhchcc
HLKAAQKNKQNSEWATPNPENRQMIMKKKKKHSPKNLLLNFVTIEETKADDVDSDGNRVTLDLPID
cchhhhccccccccccchhhhhhhhhhhhccccccceeeeeeeeecccccccccccccccccccc
LEEQTMGKYNMVTTPTTFKPDSPDLARHYKSASPQPAFQIQPETPINSKHHIIQELPLDNTFVACDSISK
cchccccccccccccccccccccccccchhcccccccccccccccceeeecccccccceeeccccc
CSSSSSDPYSVSDCGYPVTTFEVPVSVHTRPVGIQVSNTTF
cccccccccccccccccccceeeeeeecccceeeeccccc
```

Figure 10G: Secondary structure of 151P4E11

```
         10        20        30        40        50        60        70
          |         |         |         |         |         |         |
MARGSALLLASLLLAAALSASAGLWSPAKEKRGWTLNSAGYLLGPHAVGNHRSFSDKNGLTSKRELRPED
ccchhhhhhhhhhhhhhhhhhhhhhhcccccccccceecccccccccccccccccccccccccccccc
DMKPGSFDRSIPENNIMRTIIEFLSFLHLKEAGALDRLLDLPAAASSEDIERS
cccccccccccchhhhhhhhhhhhhhhhhhhhhccccccccchchccc Alpha helix       (h):   39.02%
Extended strand   (e):    1.63%
Random coil       (c):   59.35%
```

Figure 10H: Secondary structure of 151P1C7a

```
        10         20         30         40         50         60         70
         |          |          |          |          |          |          |
MMALGAAGATRVFVAMVAAALGGHPLLGVSATLNSVLNSNAIKNLPPPLGGAAGHPGSAVSAAPGILYPG
ceeecccchhhhhhhhhhhccccceeeeechhhhccchhhccccccchhccccccccccccccccccc
GNKYQTIDNYQPYPCAEDEECGTDEYCASPTRGGDAGVQICLACRKRKRKRCMRHAMCCPGNYCKNGICVS
cccceeccccccccccccccccccccccccccccchhhehhhhhhhhhhhhhhcccccccccceeee
SDQNHFRGEIEETITESFGNDHSTLDGYSRRTTLSSKMYHTKGQEGSVCLRSSDCASGLCCARHFWSKIC
ccccccccceheeehccccccccccccccccccceeeeccccccceeeccccccchhhhhhhhhhh
KPVLKEGQVCTKHRRKGSHGLEIFQRCYCGEGLSCRIQKDHHQASNSSRLHTCQRH
ccccccccceeccccccccccccccchhhhhccccccccceeecccccccccccccc Alpha helix       (h):  22.56%
Extended strand   (e):  13.91%
Random coil       (c):  63.53%
```

Figure 10I: Secondary structure of 154P2A8

```
         10        20        30        40        50        60        70
         |         |         |         |         |         |         |
MGFNLTLAKLPNNELHGQESHNSGNRSDGPGKNTTLHNEFDTIVLPVLYLIIFVASILLNGLAVWIFFHI
cccceehecccccccccccccccccccccccccchhhhhhhhhhhhhhhhhhhhhhhhhhhhhhehee
RNKTSFIFYLKNIVVADLIMTLTFPFRIVHDAGFGPWYFKFILCRYTSVLFYANMYTSIVFLGLISIDRY
ccchhhhhhhhhhhhhhhhhhhhccceeecccccccchhhhhhhhhhhhhhhhhhhhhhhhhhhhchh
LKVVKPFGDSRMYSITFTKVLSVCVWVIMAVLSLPNIILTNGQPTEDNIHDCSKLKSPLGVKWHTAVTYV
heeeecccccceeehhhhhhhhhhhccceeecccccccccccccccccccccccccceeeeeeeeec
NSCLFVAVLVILIGCYIAISRYIHKSSRQFISQSSRKRKHNQSIRVVVAVFFTCFLPYHLCRIPFTFSHL
hhhhhhhhhhhhhhhhhhhhhhccchheeccccccccceeeeehhhhhccchhccccccchhh
DRLLDESAQKILYYCKEITLFLSACNVCLDPIIYFFMCRSFSRRLFKKSNIRTRSESIRSLQSVRRSEVR
hhhhhhhhhhhhhhhhhhhhhhhcccchhehhhhhccccccchhhhhhhccceee
IYYDYTDV
eeeeccccc Alpha helix       (h):  53.35%
Extended strand   (e):  13.69%
Random coil       (c):  32.96%
```

Figure 10J: Secondary structure of 156P1D4

```
         10         20         30         40         50         60         70
         |          |          |          |          |          |          |
MLWLLFFLVTAIHAELCQPGAENAFKVRLSIRTALGDKAYAWDTNEEYLFKAMVAFSMRKVPNREATEIS
ceeeeehhhhhhhhcccchhhhheeeehhhccccceeccchhhhhhhhhhhhhhhccchhhhh
HVLLCNVTQRVSFWFVVTDPSKNHTLPAVEVQSAIRMNKNRINNAFFLNDQTLEFLKIPSTLAPPMDPSV
hhhhccccceeeeeecccccchhhhhhhhhccccheeeccccchehhecccccccc
PIWIIFGVIFCIIIVAIALLILSGIWQRRRKNKEPSEVDDAEDKCENMITIENGIPSDPLDMKGGHIND
chhehhhhhhhhhhhhhhhhhccccccccchhhcccccccccccccccccch
AFMTEDERLTPL
heeccccccccc Alpha helix      (h):  43.69%
Extended strand  (e):  13.96%
Random coil      (c):  42.34%
```

Figure 10K: Secondary of 156P5C12

```
         10        20        30        40        50        60        70
          |         |         |         |         |         |         |
MAPCHIRKYQESDRQWVVGLLSRGMAEHAPATFRQLLKLPRTLILLLGGPLALLLVSGSWLLALVFSISL
ccccccccccccchhhhhhcchhhhhhhhhhhcchhhhcccchheecccchhhhhchhhhhhhhhhhh
FPALWFLAKKPWTEYVDMTLCTDMSDITKSYLSERGSCFWVAESEEKVVGMVGALPVDDDPTLREKRLQLF
hhhhhhhccccheeeeeecccheeeeeeccccceeeeeecccceeeeeeeecccccccchhhhhhee
HLSVDSEHRRQGIAKALVRTVLQFARDQGYSEVILDTGTIQLSAMALYQSMGFKKTGQSFFCVWARLVAL
eeccccchhhhhhhhhhhhhhhhccccceeeeecccceehhhhhhccccccchhhhhhhhhhhhhhh
HTVHFIYHLPSSKVGSL
ceeeeeeccccccccc Alpha helix        (h) :   49.78%
Extended strand    (e) :   16.30%
Random coil        (c) :   33.92%
```

Figure 10L: Secondary structure of 159P2B5

```
         10        20        30        40        50        60        70
          |         |         |         |         |         |         |
MVKREHGQERPTFWGWAATPAPVSAPGNPPTGEGERQGSPPGGGFLGSTSFQRRGEKELLWERGQDVSRS
ccccccccccccceeecccccccccccccccccccccccccccccchhhcchhhhhcchhhhcchhhhh VLAMRAILPPSLSKSVHFPPLPHSCTLVALLSLGLQDPLGCRAPATKPTPAGATLSASSLPRPCSPSASL
hhhhhhhccccccccccccccccccchhhhhhcccccccccccccccccccccccccccccccccchhh LLSWPLFWGILGGVFFLGSRACTRTQARRHTGPAAALLRLLFPAPRRPGARSRAGYASPGSPERRSPGTA
hechchhhhcccceeecccccccchhhhhccchhhhhcccccccccccccccccccccccccccccccc HKGSLPWPLALRLL
cccccccchhhhcc Alpha helix       (h):   25.00%
Extended strand   (e):    3.57%
Random coil       (c):   71.43%
```

Figure 10M: Secondary structure of 161P2B7a

```
         10        20        30        40        50        60        70
         |         |         |         |         |         |         |
MEDEGQTKIKQRRSRTNFTLEQLNELERLFDETHYPDAFMREELSQRLGLSEARVQVWFQNRRAKCRKQE
cchhhhhhhhccccccchhhhhhhhhhhhhhhhccccchhhhhhhhhhccccchhhhhhhhchhhhhhhh
NQLHKGVLIGAASQFEACRVAPYVNVGALRMPFQQVQAQLQLDSAVAHAHHHLHPHLAAHAPYMMFPAPP
hcccceeeecchhhhhhccccccccchhhhccchhhcccchhhhhhhhhhcccccccccccccccccccc
FGLPLATLAADSASAASVVAAAAAKTTSKNSSIADLRLKAKKHAAALGL
cccchhhccchhhhhhhhhcccccccchhhhhhhhhhhhhhhccc Alpha helix      (h):    59.47%
Extended strand  (e):     2.11%
Random coil      (c):    38.42%
```

Figure 10N: Secondary structure of 179P3G7

```
         10         20         30         40         50         60         70
          |          |          |          |          |          |          |
MEDEGQTKIKQRRSRTNFTLEQLNELERLFDETHYPDAFMREELSQRLGLSEARVQVWFQNRRAKCRKQE
cchhhhhhhhccccccccchhhhhhhhhhhcccccchhhhhhhhhccccchhhhhhhhhchhhhhhhh
NQLHKGVLIGAASQFEACRVAPYVNVGALRMPFQQVQAQLQLDSAVAHAHHHLHPHLAAHAPYMMFPAPP
hccceeeecchhhhhhhcccccccchhhhhhhhcccchhhhhhhhhhhhhcccccccccccccccccc
FGLPLATLAADSASAASVVAAAAAKTTSKNSSIADLRLKAKKHAAALGL
ccchhhccccchhhhhhcccccccchhhhhhhhhhhhhhhccc Alpha helix     (h) : 59.47%
Extended strand (e) :  2.11%
Random coil     (c) : 38.42%
```

Figure 100: Secondary structure of 184P3C10b

```
         10        20        30        40        50        60        70
          |         |         |         |         |         |         |
MKYLRHRRPNATLIAIGAFTLLIFSLIVSPPTCKVQEQPPAIPEALAWPTPPTRPAPAPCHANTSMVTH
cccccccccchhhhhhhhhhhhhhhhhhhhhcccccccccccccccccccccccccccccccccccc
PDFATQPQHVQNFLLYRHCRHFPLLQDVPPSKCAQPVFLLLVIKSSPSNYVRRELLRRTWGRERKVRGLQ
ccccchhhhhhhhhhhhhhhccccccccccccccccheeeeeecccchhhhhcccchhhhhhhhe
LRLLFLVGTASNPHEARKVNRLLELEAQTHGDILQWDFHDSFFNLTLKQVLFLQWQETRCANASFVLNGD
eeeeeecccccccchhhhhhhhhhhhcccceeechhhhhhhhhhhhhhcccceeeeccc
DDVFAHTDNMVFYLQDHDPGRHLFVGQLIQNVGPIRAFWSKYYVPEVVTQNERYPPYCGGGFLLSRFTA
cceeecccceeeehhhhcccccehhcccccccehhcccccccccccchhhhhhh
AALRRAAHVLDIFPIDDVFLGMCLELEGLKPASHSGIRTSGVRAPSQHLSSFDPCFYRDLLLVHRFLPYE
hhhhhhhhccccccchhhhheeeccccccccccccccccchhhhhhhhhhhcchh
MLLMWDALNQPNLTCGNQTQIY
hhhhhhhhcccccccccccccc Alpha helix      (h):  38.17%
Extended strand  (e):  11.83%
Random coil      (c):  50.00%
```

Figure 10P: Secondary structure of 184P3G10

```
         10        20        30        40        50        60        70
         |         |         |         |         |         |         |
MNTAFAGKMVSVTKYDLTGCSAFCRSCQRATMTSQPLRLAEEYGPSPGESELAVNPFDGLPFSSRYYELL
ccccccccceeeeecccccccccccccccchhhhhhhhhhcccccccccccccccccccchhhhhh
KQRQALPIWAARFTFLEQLESNPTGVVLVSGEPGSGKSTQIPQWCAEFALARGFQKGQVTVTQPYPLAAR
hhhcccchhhhhhhhhhccccceeeeeecccccccccchhhhhhhhhhhccccceeeccccchhhh
SLALRVADEMDLTLGHEVGYSIPQEDCTGPNTLLRFCWDRLLLQEVASTRGTGAWGVLVLDEAQERSVAS
hhhhhhhhhhheccccccccccccccccchhhhhhhhhhhhhhhhcccccceeeeeeccccccccch
DSLQGLLQDARLEKLPGDLRVVVTDPALEPKLRAFWGNPPIVHIPREPGERPSPIYWDTIPPDRVEAAC
hhhhhhhhhhhhhccccceeeeeecccccccccccccccccccccccccccccccchhhhh
QAVLELCRKELPGDVLVFLPSEEEISLCCESLSREVESLLLQGLPPRVLPLHPDCGRAVQAVYEDMDARK
hhhhhhhhhhcccceeeeccccccceeehhhhhhhhhhhhhhhcccccccccchhhhhhhhcccce
VVVTHWLADFSFSLPSIQHVIDSGLELRSVYNPRIRAEFQVLRPISKCQAEARRLRARGFPPGSCLCLYP
eeeeeeecccccccccchhheccceecccccccceehhhhhccccchhhhhhhhccccccceeecc
KSFLELEAPPLPQPRVCEENLSSIVLLLKRRQIAEPGECHFLDQPAPEALMQALEDLDYLAALDDDGDLS
cceeeccccccccccccccchhhhhhhhhhhhcccccccchhhhhhhhhhhhhhhhcccccccc
DLGVILSEFPLAPELAKALLASCEFDCVDEMLTLAAMLTAAPGFTRPPLSAEEAALRALEHTDGDHSSL
cceeeccccchhhhhhhhhhhhhhhcccchhhhhhhhhhhhhhhccccccccchhhhhhhcccccchh
IQVYEAFIQSGADEAWCQARGLNWAALCQAHKLRGELLELMQRIELPLSLPAFGSEQNRDLQKALVSGY
hhhhhccchhhhhhhhhhccchhhhhhhhcccchhhhhhhhhhhhhhhhhhhhhhhcccchhhhhhhhccc
FLKVARDTDGTGNYLLLTHKHVAQLSSYCCYRSRRAPARPPWVLYHNFTISKDNCLSIVSEIQPQMLVE
eeeeccccccchehhhhhhhhhhccceeeeccccccccccccccceeeeeeeccccccceehccccheeh
LAPPYFLSNLPPSESRDLLNQLREGMADSTAGSKSSSAQEFRDPCVLQ
ccccccccccccccchhhhhhhhhhcccccccccccccchhccccccc
```

Alpha helix   (h): 41.71%
Extended strand (e): 11.76%
Random coil   (c): 46.52%

Figure 10Q: Secondary structure of 185P2C9 variant 1

185P2C9 variant 1
Amino acids
1-630

```
         10        20        30        40        50        60        70
          |         |         |         |         |         |         |
MEDMRGQQEREGPGRDHAPSIPTSPFGDSLESSTELRRHLQFVEEEAELLRRSISEIEDHNRQLTHELSK
cccccccccccccccccccccccccccccchhhhhhhhhhhhhhhhhhhhhhhhhhhhhhhhhhhhhh
FKFEPPREPGWLGEGASPGAGGAPLQEELKSARLQISELSGKVLKLQHENHALLSNIQRCDLAAHLGLR
ecccccccccccccccccccchhhhhhhhhchhhhhhhhchhhhhhhchhhhhhhhhhhhhhhhcccc
APSPRDSDAESDAGKKESDGEESRLPQPKREGPVGGESDSEEMFEKTSGFGSGKPSEASEPCPTELLKAR
ccccccccccccccccccccccccccccccccccccchhhhhccccccccccccccccccchhhhccc
EDSEYLVTLKHEAQRLERTVERLITDTDSFLHDAGLRGGAPLPGPGLQGEEEQEGEGDQQEPQLLGTINAK
ccchhhhhhhhhhhhhhhhhhhhhccchehccccccccccccccccccccccccccccchhhhhhhhh
MKAFKKELQAFLEQVNRIGDGLSPLPHLITESSSFLSTVTSVSRDSPIGNLGKELIGPDLQSRLKEQLEWQL
hhhhhhhhhhhhhhhhhhhhcccccccccccccccccceeeccccccccccccchhhhhhhhhhhhhc
GPARGDERESLRLRAARELHRRADGDTGSHGLGGQTCFSLEMEEEHLYALRWKELEMHSLALQNTLHERT
ccccchhhhhhhhhhhhhhhccccccccccccccceeeechhhhhhhhhhhhhhhhhhhhhhhcchcc
WSDEKNLMQQELRSLKQNIFLFYVKLRWLLKHWRQGKQMEEGEEFTEGEHPETLSRIGELGVQGGHQAD
cchhhhhhhhhhhhhhhhhhhhhhhhhccccccccccccccccccccchhhhhhccceecccccccc
GPDHDSDRGCGFPVGEHSPHSRVQIGDHSLRLQTADRGQPHKQVVENQQLFSAFKALLEDFRAELREDER
ccccccccccccccccccccccccceeeeccccccccccccchhhhhhhhhhhhhhhhhhhhhhhhh
ARLRLQQQYASDKAAWDVEWAVLKCRLEQLEEKTENKLGEIGSSAESKGALKKEREVHQKLLADSHSLVM
hhhhhhhhhhccccchhhhhhhhhhhhhhhhcccccccchhhhhcccchhhhhhhhhhhhhchhhhh Alpha helix     (Hh) :   472 is  36.11%
Extended strand (Ee) :    75 is   5.74%
Random coil     (Cc) :   760 is  58.15%
```

Figure 10R: Secondary structure of 185P2C9 variant 1

185P2C9 variant 1
Amino acids
631-1307

```
        640       650       660       670       680       690       700
         |         |         |         |         |         |         |
DLRWQIHHSEKNWNREKVELLDRLDRDRQEWERQKKEFLWRIEQLQKENSPRRGGSFLCDQKDGNVRPFP
hhhheccccccchhhhhhhhhhhhhhhhhhhhhhhhhhhhhhhhhhhhhhccccccccccceecccccccccc
HQGSLRMPRPVAMWPCADADSIPFEDRPLSKLKESDRCSASENLYLDALSLDDEPEEPPAHRPEREFRNR
ccccccccccccccccccccccccccccccccheeeehecccccccccccccccchhhhcc
LPEEEENHKGNLQRAVSVSSMSEFQRLMDISPFLPEKGLPSTSSKEDVTPPLSPDDLKYIEEFNKSWDYT
ccchhhhhcccceeeeecchhhhhhhhccccccccccccccccccchhhhhhcccccccc
PNRGHNGGGPDLWADRTEVGRAGHEDSTEPFPDSSWYLTTSVTMTTDTMTSPEHCQKQPLRSHVLTEQSG
cccccccccccccccccccccceeeeeeeeeecccccccccccccccccccceeeeecccc
LRVLHSPPAVRRVDSITAAGGEGEPFPTSRARGSPGDTKGGPPEPMLSRWPCTSPRHSRDYVEGARRPLDS
eeeecccccccceeecccccccccccccccccchhhhhhhhhhhhcccccccccccccccchhcchccccccc
PLCTSLGFASPLHSLEMSKNLSDDMKEVAFSVRNAICSGPGELQVKDMACQTNGSRTMGTQTVQTISVGL
cccccccccccccccccccccchhhhhhhhhhhhhhhhcccccccccccccccceeeeeeecc
QTEALRGSGVTSSPHKCLITPKAGGATPVSSPSRSLRSRQVAPAIEKVQAKFERTCCSPKYGSPKLQRKP
chhhccccccccccccccccccccccccchhhhhhhhhhhhccccccccccccccccccc
LPKADQPNNRTSPGMAQKGYSESAWARSTTRESPVHTTINDGLSSLFNIIDHSPVVQDPFQKGLRAGSR
cccccccccccccccccccheccccccccccccccccccchhhhhhccccccc
SRSAEPRPELGPGQETGTNSRGRSPSPSPIGVGSEMCREEGEGGTPVKQDLSAPPGYTLTENVARILNKKLL
ccccccccccccccccccccccccccccccccccccccccccccccchhhhhhhhhhhh
EHALKEERRQAAHGPPGLHSDSHSLGDTAEPGMENQTVLLTAPWGL
hhhhhhhhhhhccccccccccccccccccccceeeeeecccccc
```

Figure 10S: Secondary structure of 185P2C9 variant 2

185P2C9 variant 2
Amino acids
1-630

```
         10        20        30        40        50        60        70
          |         |         |         |         |         |         |
MEDTRGQQEREGPGRDHAPSIPTSPFGDSLESSTELRRHLQFVEEEAELLRRSISEIEDHNRQLTHELSK
cccccccccccccccccccccccccccccccchhhhhhhhhhhhhhhhhhhhhhhhhhhhhhhhhhhh
FKFEPPREPGWLGEGASPGAGGGAPLQEELKSARLQISELSGKVLKLQHENHALLSNIQRCDLAAHLGLR
eccccccccccccccccccccccccccccccccchhhhhhhhhhcchhhhhhhhhhhhhhhhhhcccc
APSPRDSDAESDAGKKESDGEESRLPQPKREGPVGGESDSEEMFEKTSGFGSGKPSEASEPCPTELLKAR
cccccccccccccccccccccccccccccccccccccccccchhhhhhcccccccccccchhhccc
EDSEYLVTLKHEAQRLERTVERLITDTDSFLHDAGLRGGAPLPGPGLQGEEEQGEGDQQEPQLLGTINAK
ccchhhhhhhhhhhhhcccchehccccccccccccccccccccccccccccccccchhhhhhhhh
MKAFKKELQAFLQQVNRIGDGLSLPLPHLTESSSFLSTVTSVSRDSPIGNLGKELGPDLQSRLKEQLEWQL
hhhhhhhhhhhhhhhhcccccccccccccccceeeeccccccccccccccccccchhhhhhhhhhhc
GPAQGDERESLRLRAARELHRRADGDTGSHGLGGQTCFSLEMEEEHLYALRWKELEMHSLALQNTLHERT
ccccchhhhhhhhhhhhhhhhhccccccccccceeeehhhhhhhhhhhhhhhhhhhhhhhhccchcc
WSDEKNLMQQELRSLKQNIFLFYVKLRWLLKHWRQGKQMEEEGEFTEGEHPETLSRLGELGVQGHQAD
cchhhhhhhhhhhhhhhhhhhhhhhhhhhhccccccccchhhhcccccccccccceecccccccc
GPDHDSDRGCGFPVGEHSPHSRVQIGDHSLRLIQTADRGQPHKQVVENQQLFSAFKALLEDFRAELREDER
cccccccccccccccccccccccceeeccccccccccccchhhhhhhhhhhhhhhhhhhhhhhhh
ARLRLQQQYASDKAAWDVEWAVLKCRLEQLEEKTENKLGELGSSAESKGALKKEREVHQKLLADSHSLVM
hhhhhhhhccccccchhhhhhhhhhhhhhhhhhcccccccchhccchhhhhhhhhhhhhhhchhhhh Alpha helix      (h): 37.57%
Extended strand  (e):  5.87%
Random coil      (c): 56.57%
```

Figure 10T: Secondary structure of 185P2C9 variant 2

185P2C9 variant 2
Amino acids 631-1142

```
         640        650        660        670        680        690        700
          |          |          |          |          |          |          |
DLRWQIHHSEKNWNREKVELLDRLDRDRQEWERQKKEFLWRIEQLQKENSPRRGGSFLCDQKDGNVRPFP
hhhhheccccchhhhhhhhchcccchhhhhhhhhhhhhhhhhhhhhcccccccceecccccccccccc HQGSLRMPRPVAMWPCADADSIPFEDRPLSKLKESDRCSASENLYLDALSLDDEPEEPPAHRPEREFRNR
ccccccccccccccccccccccccccchcccccccccccccheeeeheccccccccccccchhhhhcc LPEEEENHKGNLQRAVSVSSMSEFQRLMDISPFLPEKGLPSTSSKEDVTPPLSPDDLKYIEEFNKSWDYT
ccchhhhcccceeeecchhhhhhhhcccccccccccccccccccccccccccccccchhhhhccccccc PNRGHNGGGPDLWADRTEVGRAGHEDSTEPFPDSSWYLTTSVTMTTDTMTSPEHCQKQPLRSHVLTEQSG
ccccccccccccccccccccccccccccccccccccccceeeeeeecccccccccccccceeeeeccc LRVLHSPPAVRRVDSITAAGGEGPFPTSRARGSPGDTKGGPPEPMLSRWPCTSPRHSRDYVEGARRPLDS
eeeecccccceecccccceeecccccccccccccccccccccccccccccccccchhhcchccccccc PLCTSLGFASPLHSLEMSKNLSDDMKEVAFSVRNAICSGPGELQVKDMACQTNGSRTMGTQTVQTISVGL
ccccccccccccccccccccccccccchhhhhhhhcccccccccccchhhhhhhccccccccceeeeeecc QTEALRGSGVTSSPHKCLTPKAGGGATPVSSPSRSLRSRQVAPAIEKVQAKFERTCCSPKYGSPKLQRKP
chhhcccccccccccccccccccccccccccccccccccccccccchhhhhhhhhhhhcccccccccccc LPKADQPNNRPGNRHQFPRKVA
cccccccccccccccccccccc
```

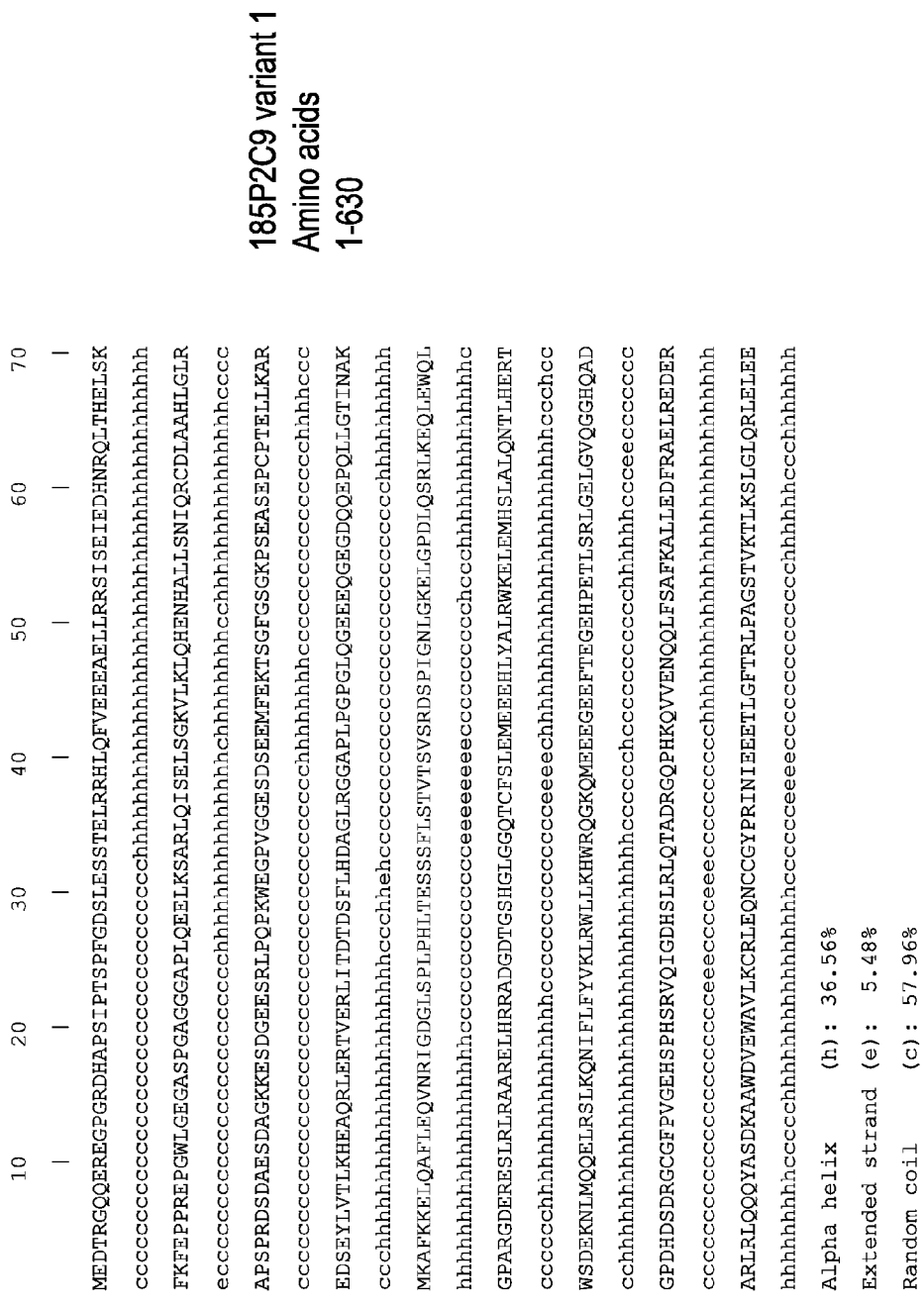
Figure 10U: Secondary structure of 185P2C9 variant 1
185P2C9 variant 1
Amino acids
1-630

Figure 10V: Secondary structure of 185P2C9 variant 1

185P2C9 variant 1
Amino acids
631-1313

```
       640        650        660        670        680        690        700
         |          |          |          |          |          |          |
KTENKLGELGSSAESKGALKKEREVHQKLLADSHSLVMDLRWQIHHSEKNWNREKVELLDRLDRDRQEWE
hhhhhhhccccchhhhhhhhhhhhhhhhhhhhhhhhhhheccccchhhhhhhhhhhhhhhhhhcccchhhh
RQKKEFLWRIEQGSLRMPRPVAMWPCADADSIPFEDRPLSKLKESDRCSASENLYLDALSLDDEPEPPA
hhhhhhhhhhcccccccccccccccccccccccccccchheeeeheccccccccc
HRPEREFRNRLPEEEENHKGNLQRAVSVSSMSEFQRLMDISPFLPEKGLPSTSSKEDVTPPLSPDDLKYI
ccchhhhhccccchhhhhcccccceeeecchhhhhhhccccccccccccccccccccccccccccchhh
EEFNKSWDYTPNRGHNGGGPDLWADRTEVGRAGHEDSTEPFPDSSWYLTTSVTMTTDTMTSPEHCQKQPL
hhhccccccccccccccccccccccccccccccccccceeeeeeeeeccccccccccccccccccc
RSHVLTEQSGLRVLHSPPAVRRVDSITAAGGEGPFPTSRARGSPGDTKGGPPEPMLSRWPCTSPRHSRDY
ceeeeeecceeeecccccccccccccccccccccccccccccccccccccccccccccccccccccch
VEGARRPLDSPLCTSLGFASPLHSLEMSKNLSDDMKEVAFSVRNAICSGPGELQVKDMACQTNGSRTMGT
hhcchccccccccccccccccchhhhhhhhhccccchhhhhhhhccccccccccc
QTVQTISVGLQTEALRGSGVTSSPHKCLTPKAGGGATPVSSPSRSLRSRQVAPAIEKVQAKFERTCCSPK
ceeeeeeecchhhccccccccccccccccccccccccchhhhhhhhhhccccccc
YGSPKLQRKPLPKADQPNNRTSPGMAQKGYSESAWARSTTTRESPVHTTINDGLSSLFNIIDHSPVVQDP
cccccccccccccccccccccccccccccchecccccccccccchhhhhhhehheccccchhh
FQKGLRAGSRSRSAEPRPELGPGQETGTNSRGRSPSPIGVGSEMCREEGGEGTPVKQDLSAPPGYTLTEN
hhhccccccccccccccccccccccccccccccccccccccccccccccccccccccchhhh
VARILNKKLLEHALKEERRQAAHGPPGLHSDSHSLGDTAEPGPMEELPCSALA
hhhhhhhhhhhhhhhccccccccccccccccccccccccccccc
```

Figure 10W: Secondary structure of 185P3C2

```
         10        20        30        40        50        60        70
          |         |         |         |         |         |         |
NCLLRPKNKSVRWGPGAGAALLRPSPAALGAGSRACSVPPAAPAQTPRPQVSAPAWGPGRAARGSGRMER
cccccccccccccccccccccchhccccccccccccccccccccccccccccccccccccccchhhhh
RMKAGYLDQQVPYTFSSKSPGNGSLREALIGPLGKLMDPGSLPPLDSEDLFQDLSHFQETWLAEAQVPDS
hhhccccccccceeecccccccccccccchhhhhcccccccccccccccchhhhhhhhhhhcccccc
DEQFVPDFHSENLAFHSPTTRIKKEPQSPRTDPALSCSRKPPLPYHHGEQCLYSSAYDPPRQIAIKSPAP
ccccccccccccccccccccccccccccccccccccccccccccccccccccccccccceeecccc
GALGQSPLQPFPRAEQRNFLRSSGTSQPHPGHGYLGEHSSVFQQPLDICHSFTSQGGGREPLPAPYQHQL
cccccccchhhhhhhhhhccccccccccccccccccchhhhhcccceeecccccccccccccccccc
SEPCPPYPQQSFKQEYHDPLIYEQAGQPAVDQGGVNGHRYPGAGVVIKQEQTDFAYDSDVTGCASMYLHTE
ccccccccccccchhccccccccccccccccccccccccccccceeeeccccceeccccccceeeeecc
GFSGPSPGDGAMGYGYEKPLRPFPDDVCVVPEKFEGDIKQEGVGAFREGPPYQRRGALQLWQFIVALLDD
ccccccccccccccccccccccccccccccccccccccccchhchhhhhhhhhhhhhhhhhhhhhcc
PTNAHFIAWTGRGMEFKLIEPEEVARLWGIQKNRPAMNYDKLSRSLRYYYEKGIMQKVAGERYVYKFVCE
cccceeeeecccccccceehcchhhhhhhhhhhcccccccchhhhhhhhhhhhhhhhcccceeeeeeec
PEALFSLAFPDNQRPALKAEFDRPVSEEDTVPLSHLDESPAYLPELAGPAQPFGPKGGYSY
ccheeeeccccchhcccchhhhcccccccccccccccccccccccccccccccccccccc Alpha helix      (h):   19.42%
Extended strand  (e):    8.53%
Random coil      (c):   72.05%
```

Figure 10X: Secondary structure of 186P1H9

```
          10         20         30         40         50         60         70
           |          |          |          |          |          |          |
MLALLAASVALAVAAGAQDSPAPGSRFVCTALPPEAVHAGCPLPAMPMQGGAQSPEEELRAAVLQLRETV
chhhhhhhhhhhhhhhcccccccccceeecccccccccccccccccccccccchhhhhhhhhhhhhhhh
VQQKETLASARAIRELTGKLARCEGLAGGKARGAGATGKDTMGDLPRDPGHVVEQLSRSLQTLKDRLESL
hhhhhhhhhhhhhhhhhhhhhhcccccccccccccccccccccccchhhhhhhhhhhhhhhhhhhhh
EHQLRANVSNAGLPGDFREVLQQRLGELERQLLRKVAELEDEKSLLHNETSAHRQKTESTLNALLQRVTE
hhhhhcccccccccccchhhhhhhhhhhhhhhhhhhhhhhhhheccccccccchhhhhhhhhhhhhh
LERGNSAFKSPDAFKVSLPLRTNYLYGKIKKTLPELYAFTICLWLRSSASPGIGTPFSYAVPGQANEILL
hhcccccccccccceeecccccccccchhhhchhhhhheeeeecccccccccccccccccccceeee
IEWGNNPIELLINDKVAQLPLFVSDGKWHHICVTWTTRDGMWEAFQDGEKLGTGENLAPWHPIKPGGVLI
eeccccchhehhhhhhcceeeeeeeeecccchhhhhhcccccccchhhccccccccccccccceee
LGQEQDTVGGRFDATQAFVGELSQFNIWDRVLRAQEIVNIANCSTNMPGNIIPWVDNNVDVFGGASKWPV
eeccccccccccchhhhcchchhhhhhhhhhhhhhhhhchccccceeecccccccccccccccccc
ETCEEALLDL
chhhhhhcc Alpha helix       (h):    43.95%
Extended strand   (e):     9.30%
Random coil       (c):    46.74%
```

Figure 10Y: Secondary structure of 187P3F2

```
         10        20        30        40        50        60        70
         |         |         |         |         |         |         |
MATAASNPYLPGNSLLAAGSIVHSDAAGAGGGGGSGGGAGGGGGMQPGSAAVTSGAYRGDPSSV
ccccccccccccccccccheeccheeccccccccccccccccccccccccceeecccccccccc
KMVQSDFMQGAMAASNGGHMLSHAHQWVTALPHAAAAAAAAAAAAVFASSPWSGSAVGMAGSPQQPPQPP
eeehhhhhhhhhhccccchhhhhhhhhhchhhhhhhhhhhhhhhccccccccecccccccccccccc
PPPPQGPDVKGGAGRDDLHAGTALHHRGPPHLGPPPPPHQGHPGGWGAAAAAAAAAAAAHLPSMA
cccccccccccccccccccccccccccccccccccccccccccccchhhhhhhhhhhhhhcccc
GGQQPPPQSLLYSQPGGFTVNGMLSAPPGPGGGGGGAGGAQSLVHPGLVRGDTPELAEHHHHHHHAHP
cccccccccccccccceeccccccccccccccccccccccceecccccccccchhhcccccccccc
HPPHPHHAQGPPHHGGGGGAGPGLNSHDPHSDEDTPTSDDLEQFKQRRIKLGFTQADVGLALGTL
ccccccccccccccccccccccccccccccccccccccchhhhhhhhhhhccchhhhhehhhhh
YGNVFSQTTICRFEALQLSFKNMCKLKPLLNKWLEEADSSTGSPTSIDKIAAQGRKRKKRTSIEVSVKGA
cccccccchhhhhhhhhhhhhhhhhhhchhhhhhhhhhhcccccccccchhhhhhhhccchccccceeeeecccc
LESHFLKCPKPSAQEITNLADSLQLEKEVVRVWFCNRRQKEKRMTPPGIQQQTPDDVYSQVGTVSADTPP
hhhhccccccccchhhhhhhhhhhhhhhhhhhhcccchhccccccccccccccceeeecccccccc
PHHGLQTSVQ
cccccccccc Alpha helix      (h):  30.80%
Extended strand  (e):   5.80%
Random coil      (c):  63.40%
```

Figure 10Z: Secondary structure of 192P2G7

```
         10        20        30        40        50        60        70
          |         |         |         |         |         |         |
MAESEAETPSTPGEFESKYFEFHGVRLPPFCRGKMEEIANFPVRPSDVWIVTYPKSGTSLLQEVVYLVSQ
ccccccccccccccccceeeecccccccccchhhhcccccccccceeeecccccchhhhhhhheec
GADPDEIGLMNIDEQLPVLEYPQPGLDIIKELTSPRLIKSHLPYRFLPSDLHNGDSKVIYMARNPKDLVV
cccccceeeeccccccccccccccccchhhhhcccceeeccccccccccccceeeeeeccccheee
SYYQFHRSLRTMSYRGTFQEFCRRFMNDKLGYGSWFEHVQEFWEHRMDSNVLFLKYEDMHRDLVTMVEQL
eeeehhhhhchccccccchhhhhhhhhhhcccccceeeehhhhhhhhcccccceeeehhhhhhhhhhh
ARFLGVSCDKAQLEALTEHCHQLVDQCCNAEALPVGRGRVGLWKDIFTVSMNEKFDLVYKQKMGKCDLTF
hhhhccccchhhhhhhhhhhhhccccccccccccccccceehhhhhehechhhhhhhhhccccceee
DFYL
eecc Alpha helix      (h):  36.27%
Extended strand  (e):  16.20%
Random coil      (c):  47.54%
```

Figure 11:

Figure 11b   Nucleotide sequences of transcript variants of 83P4B8 (SEQ ID NO:115).
>83P4B8 v.2

```
cggagttctg tgatatgagc aacaatggac cagaagattt tatctctagc agcagaaaaa     60
acagcagaca aactgcaaga atttcttcaa acctgagag aagtgattt gactaatctc    120
cttcagaatc aagcagtgaa aggaaaagtt gctggagcac tcctgagagc catcttcaaa    180
ggttcccct gctctgagga agctggaaca cttaggaaga gtaagatata cacttgttgt    240
atccagttgg tggaatcgg ggatttgcag aagaaatag tgtctgagat cacaggatta    300
ctgatgctgg aggctcacca ttttccagga ccattattgg ttgaattagc caatgagttt    360
attagtgctg tcagagaagg cagcctagtg aatgaaaaat ctttggagtt actacctatc    420
atctcactg ccctggctac gaaaaggaa aatctggctt atgaaaaagg tgggatcagc    480
aatatgtaat ccaacacacc tccatgttca aggatgtccc tctgactgca gaagaggtgg    540
aatttgtgt ggaaaaagca ttgagcatgt tctccaagat gaatcttcaa gaaataccac    600
cttttgtcta tcagttctg gttctctcct ccaaggaag cagaaagagt gttttggaag    660
gaatcatagc cttcttcagt gcactagata agcagcacaa tgaggaacag agtggtgacg    720
agctattga tgttgtcact gtgccatcag gtgaacttcg tcatgtggaa ggcaccatta    780
ttctacacat tgtgtttgcc atcaaattgg actatgaact agcagagaa ctcgtgaaac    840
acttaaaggt aggacagcaa ggagattcca ataataactt aagtcccttc agcattgctc    900
ttctctgtc tgtaacaaga atacaaagat ttcaggacca ggtgcttgat cttttaaaga    960
cttcggttgt aaagagcttt aaggatctc aactcctcca aggctcaaaa tttcttcaga   1020
atctagttcc tcatagatct tatgtttcaa coatgatctt ggaagtagtg aagaatagcg   1080
ttcatagctg ggaccatgtt actcaggcc tcgtagaact tggtttcatt ttgatggatt   1140
catatggcc aagaaggtt cttgatgaa aaactattga aaccagccca agtctttcta   1200
gaatgccaaa ccagcatgca tgtaagctg agcaggtcct ctgttgaa actttaaga   1260
tccatgagat gatcagacaa gaaattttgg agcaggtcct caacaggttt gttaccagag   1320
catcttctcc catcagtcat ttcttagacc tgcttcaaa tatcgtcatg tatgcaccct   1380
tagttcttca aagttgttct tctaagtca cagaagcttt tgactattg tccttctgc   1440
ccctcagac tgtacaaagg ctgcttaagg cagtgcagcc cctctcaaa gtcagcatgt   1500
caatgagaga ctgcttgata cttgtcctc ggaaagctat gtttgccaac cagcttgatg   1560
cccgaaaatc tgcagttgct ggttttttgc tgtcctgaa gaacttaaa gttttaggca   1620
gctgtcatc ctctcagtgc agtcagtctc tcagtgtcag tcaggttcat gtggatgttc   1680
acagccatta caattctgtc gccaatgaaa cttttgcct tgaatcatg gataatgagt   1740
ggagatgctt aagccagcaa gctgatgttc gactctgct ttatgagggg ttttatgatg   1800
ttcttcgaag gaactctcag ctgcctaatt cagtcatgca aactctgctc tcacagttaa   1860
aacagttcta tgagccaaaa cctgatctgc tgcctcctct gaaattagat gcttgtattc   1920
tgacccaagg agataagatc tctctacaag aaccactgga ttatctgctg tgttgtattc   1980
agcattgttt ggcctggtat aagaatacag tcataccctt aatgtgatat attggagtcc   2040
aggaggagga agaggcattc tacgaagacc tagactttg aactgataa atcagcagat   2100
gaatgattaa gagtgagctg gaagacttg aactgataa atcagcagat ttttctcaga   2160
gcaccagtat tggcataaaa aataatatct ctgcttttct tgtgatggga gtttgtgagg   2220
```

Figure 11b (continued)

```
tttaataga atacaattte tccataagta gtttcagtaa gaataggttt gaggacatte    2280
tgagcttatt tatgtgttac aaaaaactct ctgacattct taatgaaaaa gcgggtaaag    2340
ccaaaactaa aatgccaac aagacaagtg atagtctttt gtccatgaaa tttgtgtcca    2400
gtcttctcac tgctctttc agggatagta tccaaagcca ccaagaaagc ctttctgttc    2460
tcagtccag caatgagttt atgcgctatg cagtgaatgt cagtggcca aaagtacagc    2520
agctaaagga aacagggcat gtgagtggcc ctgatggcca aaaccagaa aagatctttc    2580
agaacctctg tgacataact cgagtctgc tatggagata cacttcaatt cctacttcag    2640
tggaagagtc gggaaagaaa gagaaaggaa agagcatctc cagattcag ttggagggtt    2700
tacagaaat attcagtgct gtgcacagt tctatcagcc caagattcag cagttctca    2760
gagctctgga tgtcacagat aaggaggag agatgcagat cttgttgaat gtcagtgtca    2820
ctcagagaac agcattccag atccggcaat ttcagaggtc ctgttgaat cttaccagtt    2880
gtcaagagga agattttaat agcaaagaag ccctcctgct agtcacgtt cttaccagtt    2940
tgtccaagtt actggagccc tcctctcctc agttgtgca gatgttatc tggacatcaa    3000
agatttgcaa ggaaaacagc cggaggatg cctgtttttg caagagcttg atgaacttgc    3060
tcttcagcct gcatgtttcg tataagagtc ctgtcattct gctgcgtgac ttgtcccagg    3120
atatccacgg gcatctggga gatatagaco aggatgtaga ggtggaaaa acaaaccact    3180
ttgcaatagt gaatttgaga acggctgccc ccactgtctg tttacttgtt ctgagtcagg    3240
ccgagaaggt tctagagaa gtgcagtgaa gcttaaggga taatcaacag gcttaaggga    3300
aagaaacctt atcagaagag gcctcttcte aggcaaccct accaatcag ctgttgaga    3360
aagctatcat catgcaactg ggaactctgc ttacattttt ccacgagctg gtgcagacag    3420
ctctgccatc agcagctgca gtggacacct tgttaaagga cttgtgcaaa atgtacacca    3480
cacttagagc ccttgtcaga tattatctcc agtgtgtca gagctcgga gaccccctg    3540
aaaatatga aaagtgtg aagctgtctg gctcatct gacccccctg tgttattctt    3600
tcatttctta cgtacagaat aagagtaaga gcctgaacta tacgggagag aaaaaggaga    3660
aacctgctgc cgttgcaca gccatggcca gagttcttcg ggaaacaaag ccaatcccta    3720
acctcatctt tgccataga cagtatgaaa aatttctcat ccacctttct aagaagtcca    3780
agtgaacat gatgcaacag atgaagctca cgacctcacg agacttcaag atcaaaggaa    3840
acatcctaga catgttctt cgagaggatg gcgaagatga aaatgaagag ggcactgcat    3900
cagagcatgg gggacagaac aaagaaccag ccaagaagaa aaggaaaaaa taaatgaaat    3960
gcctgagtta atgtg                                                    3975
```

>83P4B8 v.3 (SEQ ID NO:116).

```
cggagttctg tgatatgagc aacaatggac cagaagagttt tatcctctagc agcagaaaaa    60
acagcagaca aactgcaaga atttcttcaa accctgagag aagttgattt gactaatctc     120
cttcagaatc aagcagtgaa aggaaaagtt gctggagcac tcctgagagc catcctcaaa     180
ggttcccct gctctgagga agctgaaca cttaggagac gtaagatata cacttgttgt      240
atccagttgg tggaatcggg ggatttgcag aaagaaatag tgtctgagat cataggatta     300
ctgatgctgg aggctcacca tttccagga ccattattgg ttgaattagc caatgagttt     360
```

Figure 11b (continued)

```
attagtgctg tcagagaagg cagcctagtg aatgaaaat ctttggagtt actacctatc 420
attctcactg ccctggctac gaaaaaggaa aatctggctt atgaaaagg tgtactgagt 480
gggaagaat gtaagaaaca gttgattaac accctgtgtt ctggcagtg ggatcagcaa 540
tatgtaatcc aacacacctc catgttcaag gatgtccctc tgactgcaga agaggtggaa 600
tttgtggtgg aaaaagcatt gagcatgttc tccaagatga atcttcaaga aataccacct 660
ttggtctatc agcttctggt tctctcctcc aagggaagca cagcacaatg gaaagtgt tttggaagga 720
atcatagcct tcttcagtgc actagataag cagcacaatg agaacagag tggtgacgag 780
ctattggatg ttgtcactgt gccatcagt gaacttgtc atgtgaagg caccattatt 840
ctacacattg tgtttgccat caaattggac tatgaactag gcagagact cgtgaaacac 900
ttaaagtag gacagcaagg agattccaat aataacttaa gtcccttcag cattgctctt 960
ctctgtctg taacaagaat acaaagattt caggacaagg tgctgatct tttaaagact 1020
tcggttgtaa agagctttaa ggatcttcaa ctctccaag gctcaaaatt tcttcagaat 1080
ctagttcctc atagatctta tgtttcaacc atgatcttgg aagtagtgaa gaatagcgtt 1140
catagctggg accagttac tcagggcctc gtagaacttg gtttcattt gatggattca 1200
tatgggccaa agaaggttct tgatgaaaa actattgaaa ccagccaag tctttctaga 1260
atgccaaacc agcatgcatg taagctcgga gctaatatcc tgttgaaaac ttttaagatc 1320
catgagatga tcagacaaga aatttggag caggtcctca acaggttgt taccagagca 1380
tctctccca tcagtcattt cttagacctg ctttcaaata tcgtcatgta tgcaccctta 1440
gttcttcaaa gttgttcttc taaagtcaca gaagcttttg actattgtc ctttctgccc 1500
cttcagactg tacaaggct gcttaaggca gtgcagcccc ttcaagt cagcatgtca 1560
atgagagact gcttgatact tgtccttcgg aaagctatgt ttgccaacca gcttgatgcc 1620
cgaaaatctg cagtgctgg gttttttgctg tccctgaaga acttaaagt tttagggcagc 1680
ctgtcatcct ctcagtgcag tcagtctctc agtgtcagtc aggttcatgt ggatgttcac 1740
agccattaca attctgtcgc caatgaaact tttgccttg agatcatgaa tagtttgagg 1800
agatgcttaa gccagcaagc tgatgttcga ctcatgcttt atgaggggtt ttatgatgtt 1860
cttcgaagga actctcagct ggctaattca gtcatgcaaa ctctgtctc acagttaaaa 1920
cagttctatg agccaaaacc tgatctgctg cctcctctga aattagatgc ttgtattctg 1980
acccaaggag ataagatctc tctacaagaa ccactggatt atctgctgtg ttgtattcag 2040
cattgtttgg cctgtataa gaatacagtc atacccttac agcaggaga ggaggaagag 2100
gaggaggaag aggcattca ggatgtccat tgagtccat tactaataga 2160
atgattaaga gtgagctgga agacttgaa ctgataaat cagcagatt tctcagagc 2220
accagtattg gcataaaaaa taatatctct gctttttctg tgatgggagt ttgtgaggtt 2280
ttaatagaat acaattctc cataagtagt ttcagtaaga ataggtttga ggacattctg 2340
agcttattta tgttacaa aaaactctct gacattctta atgaaaaagc gggtaaagcc 2400
aaaactaaaa tggccaacaa gacaagtgat agtcttttgt ccatgaaatt tgtgtccagt 2460
cttctcactg ctcttttcag gtccagcaat gtccagcaat agtttatgc gctatgcagt gaatgtagct 2520
ctcagaaag tacagcagct aaaggaaaca cggcatgtga gtggcctga tggccaaaac 2580
ccagaaaga tctttcagaa cctctgtgac ataactcgag tcttgctatg gagatacact 2640
tcaattccta cttcagtgga agagtcggga aggaaagaga aggaaagaga catctcactg 2700
```

Figure 11b (continued)

```
ctgtgcttgg agggtttaca gaaaatattc agtgctgtgc aacagttcta tcagcccaag 2760
attcagcagt ttctcagagc tctgatgtc acagataagg aaggagaaga gagaagagat 2820
gcagatgtca gtgtcactca gagaacagca ttccagatcc gccaatttca gagtccttg 2880
ttgaatttac ttagcagtca agaggaagat tttaatagca aagaagccct cctgctagtc 2940
acggttctta ccagtttgtc caagttactg gagccctcct ctccagtt tgtgcagatg 3000
ttatcctgga catcaaagat ttgcaaggaa aacagccggg agatgcctt gtttgcaag 3060
agcttgatga acttgctctt cagcctgcat gtttcgtata agagtcctgt cattctgctg 3120
cgtgacttgt ccaggatat ccagggcat ctggagata tagaccagga tgtagaggtg 3180
gagaaaacaa accactttgc aatagtgaat ttgagaacgg ctgccccac tgtctgttta 3240
cttgttctga gtcaggccga gaagttctca gaagaagtgg actgctaat caccaagctt 3300
aaggacaaag tgagccaaga aacttatca gaactggaa ctctcaggc aacctacca 3360
aatcactg ttgagaagc tatcatcatg caactggtgg ctctgcttac attttccac 3420
gagctgtgc agacagctct gccatcagc agctgtgtgg acacctgtt aaaggacttg 3480
tgcaaaatgt acaccacact tacagccctt gtcagatatt atctccagt gtgtcagagc 3540
tccggagaa tcccaaaa tatgaaaag ctggtgaagc tgtctggttc tcatctgacc 3600
cccctgtgtt attctttcat ttcttacgta cagaataaga gtaagagcct gaactatacg 3660
ggagagaaaa aggagaaacc tgctgccgtt gccacagcca tgaaaaatt tctcatccac 3720
accaagcaa tccctaacct catctttgcc ataagaacagt agctcagcac ctcacgacac 3780
ctttctaaga agtccaggt gaacctgatg cagcacatg gttcttcgag aggatggcga agatgaaat 3840
ttcaagatca aaggaaacat cctagacatg gttcttcgag aggatggcga agatgaaaat 3900
gaagagggca ctgcatcaga gcatggggga cagaacaaag aaccagccaa gagaaaagg 3960
aaaaaataaa tgaaatgcct gagttaatgt g                                3991

>83P4B8 v.4 (SEQ ID NO:117).
cggagttctg tgatatgagc aacaatggac cagaagattt tatctctagc agcagaaaa   60
acagcagaca aactgcaaga atttcttcaa accctgagag aagtgatt gactaatctc  120
cttcagaatc aagcagtgaa aggaaagtt gctggagcac tcctgagagc catcttcaaa  180
ggttccccct gctctgagga agtggaaca cttaggagac gtaagatata cacttgttgt  240
atccagttgg tggaatcggg ggattgcag aagaaatag tgtctgagat cataggatta  300
ctgatgctgg aggctcacca tttccagga ccattattgg ttgaattagc caatgagttt  360
attagtgctg tcagagaagg cagcctagtg aaaaaggaa aatctggctt atggaaaagg  420
attctcactg cctggctac gttgattaac acctgtgtt ctggcaggtg ggatcagcaa  480
gggaagaaat gtaagaaaca cacacctc catgtccaag gatgtccctc tgactgcaga gaggtggaa  540
tatgtaatcc aaaaagcatt catgtccaag gatcatcaag atcttcaaga aataccacct  600
tttgtgtgg aaaaagcatt ctgtctgtc aaggaagca gcacacaatg tttggaagga  660
ttgtctatc agcttctgc tctctcctcc aagataaag cagcacaatg aggaacagag tggtgacgag  720
atcatagcct tcttcagtgc actagataag cagcacaatg aggaacagag tggtgacgag  780
ctattggatg ttgtcactgt gcatcaggt gaacttcgtc atgtggaagg caccattatt  840
```

Figure 11b (continued)

```
ctacacattg tgtttgccat caaattggac tatgaactag gcagagaact cgtgaaacac   900
ttaaagtag gacagcaagg agattccaat aataacttaa gtcccttcag cattgctctt   960
cttctgtctg taacaagaat acaaagattt caggaccagg tgcttgatct tttaaagact  1020
tcggttgtaa agagctttaa ggatcttcaa ctcctccaag gctcaaaatt tcttcagaat  1080
ctagttcctc atagatctta tgtttcaacc atgatcttgg aagtagtgaa gaatagcgtt  1140
catagctggg accatgttac tcaggcctc gtagaacttg gtttcattt gatggattca   1200
tatggcaa agaaggttct tgatgaaaa actattgaaa ccagcccaag tcttctcaga   1260
atgccaaacc agcatgcatg taagctcgga gctaatatcc tgttgaaac ttttaagatc   1320
catgagatga tcagacaaga aattggaag caggtcctca acagggttgt taccagagca   1380
tcttctccca tcagtcattt cttagacctg cttcaaata tcgtcatgta tgcaccctta   1440
gttcttcaaa gtgttcttc taaagtcaca gaagcttttg actattgtc ctttctgccc   1500
cttcagactg tacaaggct gcttaaggca gtgcagcccc ttctcaaagt cagcatgtca   1560
atgagagact gcttgatact tgtccttcgg aagctatgt ttgccaacca gctgatgcc   1620
cgaaaatctg cagttgctgg gtttttgctg ctcctgaaga actttaaagt tttaggcagc   1680
ctgtcatcct ctcagtgcag tcagtctctc agtgtcagtc agttcatgt ggatgttcac   1740
agccattaca atctgtcgc caatgaaact tttgccttg agatcatgga tagttgagg   1800
agatgcttaa gccagcaagc tgatgttcga ctcatgcttt ctcatgcttt atgaggggtt ttatgatgtt   1860
cttcgaagga actctcagct ggctaattca gtcatgcaaa ctctgctctc acagttaaaa   1920
cagttctatg agccaaacc tgatctgctg cctcctctga aattagatgc ttgtattctg   1980
acccaaggag ataagatctc tctacaagaa ccactgatt atctgctgtg ttgtattcag   2040
cattgtttgg cctggtataa gaatcagtc ataccttac agcagggaga ggaggaagag   2100
gaggagaag aggcattcta cgaagaccta gatgatatat tggagtccat tactaataga   2160
atgattaaga gtgagctgga agactttgaa ctggataat cagcagattt ttctcagagc   2220
accagtattg gcataaaaaa taatactct gcttttcttg tgatggggt ttgtgaggtt   2280
ttaatagaat acaattctc cataagtagt ttcagtaaga ataggtttga ggacattctg   2340
agcttattta tgtgttacaa aaaactctct gacattctta atgaaaaagc gggtaaagcc   2400
aaaactaaaa tggccaacaa gacaagtgat agtctttttgt ccatgaaatt tgtgtccagt   2460
cttctcactg ctcttttcag agtcttgcta tggagataca cttcaattcc tacttcagtg   2520
gaagagtcgg gaaagaaaga gaaggaaag agcatctcac tgctgtgctt ggagggttta   2580
cagaaaatat tcagtgctgt gcaacagttc tatcagccca agattcagca gttctcaga   2640
gctctgatg tcacagataa ggaaggagaa gagagagaag atgcagatgt cagtgtcact   2700
cagaacag cattccagat ccggcaattc cagcaaatct cagaggtcct tgttgaattt acttagcagt   2760
caagagaag atttaatag caaagaagcc ctcctgctag tcacggttct taccagtttg   2820
tccaagttac tggagccctc ctctcctcag tttgtgcaga tgttatcctg gacatcaaag   2880
atttgcaagg aaaacagccg ggggatgcc ttgttttgca agagcttgat gaacttgctc   2940
ttcagcctgc atgttcgta taagtcct gtcattctgc tgcgtgactt gtcccaggat   3000
atccacgggc atctgggaga tatagaccag gatgtagagg tggagaaaac aaaccactt   3060
gcaatagtga atttgagaac ggctgcccc actgtctgtt tacttgttct gagtcaggcc   3120
gagaaggttc tagaagaagt ggactggcta atccaccaag ttaaggggaca agtgagccaa   3180
```

Figure 11b (continued)

```
gaaacccttat cagaagaggc ctcttctcag gcaaccctac caaatcagcc tgttgagaaa    3240
gctatcatca tgcaactggg aactctgctt acatttttcc acgagctggt gcagacagct    3300
ctgccatcag gcagctgtgt ggacaccttg ttaaaggact tgtgcaaaat gtaccacaca    3360
ctacagccc ttgtcagata ttatctccag gtgtgtcaga gctccggagg aatcccaaaa    3420
aatatgaaa agctggtgaa gctgtctgt tctcatctga tgtctgagat tgattctttc    3480
atttcttacg tacgaataa gagtaagagc ctgaactata cggagagaa aaaggagaaa    3540
cctgctccg ttgccacaga catgccacaga gttcttcggg aaaccagcaa aatccctaac    3600
ctcatctttg ccatagaaca gtatgaaaaa tttctcatcc actttctaa gaagtccaag    3660
gtgaacctga tgcagcacat gaagcttcgc acctcacgag acttcacgat caaaggaaac    3720
atcctagaca tggttcttcg agaggattgg gaagatgaaa atgaagaggg cactgcatca    3780
gagcatgggg gacagaacaa agaaccagcc aagaagaaaa aagaagaaata gaaaaaata    3840
ctgagttaat gtg                                                        3853

>83P4B8 v.5 (SEQ ID NO:118).
cggagttctg tgatatgagc aacaatggac cagaagatttt tatctctagc agcagaaaaa      60
acagcagaca aactgcaaga atttcttcaa acctgagag aagtgatttt gactaatctc     120
cttcagaatc aagcagtgaa aggaaaagtt gctggagcac tcctgagagc catcttcaaa     180
ggttccccct gctctgagga agctggaaca cttaggagac gtaagatata cacttgttgt     240
atccagttgg tggaatcggg ggattgcag aaagaaatag tgtctgagat caggagatta     300
ctgtgctgg aggctcacca tttccagga ccattattgg ttgaattagc caatgagttt     360
attagtgctg tcagagaagg cagcctgagt aatgaaaat ctttggagtt actacctatc     420
attctcactg ccctgctac gttgattaac acctgtgtt ctgcaggtg tgtactgagt     480
ggggaagaat gtaagaaaca aacacaccctc catgttcaag gatgcccctc tgactcaga ggagtgcaa     540
tatgtaatcc aacacaccctc catgttcaag gatgcccctc tgactcaga aataccacct     600
tttgtgtgg aaaaagcatt gagcagttc tccaagatga atcttcaaga aataccacct     660
ttgtctatc agcttctgt tctctcctcc aagggaagca gcacacatg aaaagagtgt tttggaagga     720
atcatagcct tcttcagtgc actagataag gccatcagtg gaacttgtc atgtggaagg tggtgacgag     780
ctattggatg ttgtcactgt tgtgccat caaattggac tatgaactag gcagagaact cgtgaaacac     840
ctacacattg tgtttgccat caaattggac tatgaactag gcagagaact cgtgaaacac     900
ttaaggtag gacagcaagg agattccaat aataacttaa gtccccttcag cattgctctt     960
cttctgtctg taacaagaat acaaagattt caggaccagg tgcttgatct tttaaagact    1020
tcggttgtaa agagcttaa ggatcttcaa ctcctccaag gctcaaaatt tcttcagaat    1080
ctagttcctc atagatctta tgtttcaacc atgatcttgg aagtagtgaa gaatagcgtt    1140
catagctggg accatgttac tcagggcctc gtagaacttg gtttcatttt gatgattca    1200
tatggccaa agaaggttct tgatgaaaa actattgaaa ccagcccaag gtttctctaga    1260
atgccaaacc agcatgcatg taagctcgga gctaatatcc tgttggaaac ttttaagatc    1320
catgagatga tcagacaaga aattttggag caggtcctca acaggggttgt taccagagca    1380
ctgtctccca tcagtcatt cttagacctg tcgtcaaata tcgtcatgta tgcaccctta    1440
```

Figure 11b (continued)

```
gttcttcaaa gttgttcttc taaagtcaca gaagcttttg actatttgtc ctttctgccc 1500
cttcagactg tacaaaggct gcttaaggca gtgcagcccc ttctcaaagt cagcatgtca 1560
atgagagact gcttgatact tgtccttcgg aaagctatgt ttgccaacca gcttgatgcc 1620
cgaaaatctg cagttgctgg gtttttgctg ctcctgaaga actttaaagt tttaggcagc 1680
ctgtcatcct ctcagtgcag tcagtctctc agtgtcagtc agttcatgt ggatgttcac 1740
agccattaca atctctgcgc caatgaaact tttgcctg agatcatgaa tagttgagg 1800
agatgcttaa gccagcaagc tgatgttcga ctcatgcttt atgaggggtt ttatgatgtt 1860
cttcgaagga actctcagct ggctaattca gtcatgcaaa ctctgctctc acagttaaaa 1920
cagttctatg agccaaaacc tgatctgctg cctccctga aattagatgc ttgtattctg 1980
acccaaggag ataagatctc tctacaagaa ccactggatt atctgctgtg ttgtattcag 2040
cattgtttgg cctggtataa gaatacagtc ataccctac agcagggaga ggaggaagag 2100
gaggaggaag aggcattcta cgaagaccta gatgatatat tggagtccat tactaataga 2160
atgattaaga gtgagctgga agactttgaa ctgataaat cagcagattt ttctcagagc 2220
accagtattg gcataaaaaa taatatctct gcttttcttg tgatgggagt ttgtgaggtt 2280
ttaatagaat acaattctc cataagtagt ttcagtaaga ataggtttga ggacattctg 2340
agcttattta tgtgttacaa aaaactctct gacattctta atgaaaaagc gggtaaagcc 2400
aaaactaaaa tggccaacaa gacaagtgat agtcttttgt ccatgaaatt tgtgtccagt 2460
cttctcactg ctcttttcag ggatagtatc caaagccacc aagaaagcct ttctgttctc 2520
agtccagca atgagtttat gcgctatgca gtgaatgtag ctctgcagaa agtacagcag 2580
ctaaagaaag caggcatgt gagtgcct gatgccaaa acccagaaa gatctttcag 2640
aacctctgtg acataactcg agtcttgcta tggagataca cttcaattcc tacttcagtg 2700
gaagagtcgg gaaagaaaga gaaagaaag agcatctcac tgctgtgctt ggaggttta 2760
cagaaaatat tcagtgctgt gcaacagttc tatcagccca agattcagca gtttctcaga 2820
gctctggatg tcacagataa ggaaggagaa gagagagaag atgcagatgt cagtgtcact 2880
cagagaacag cattccagat ccggcaattt cagaggtcct tgttgaattt acttagcagt 2940
caagaggaag attttaatag caaagaagcc ctcctgctag tcacgttct taccagtttg 3000
tccaagttac tggagccctc ctctcctcag tttgtgcaga tgttatcctg gacatcaaag 3060
atttgcaagg aaaacagccg ggaggatgcc ttgttttgca agagcttgat gaacttgctc 3120
ttcagcctgc atgtttcgta taagagtcct gtcattctgc tgcgtgactt gtcccaggat 3180
atccacgggc atctggagaa tataaccag gatgtagagg tgagaaaac aaccactttt 3240
gcaatagtga atttgagaac ggctgccccc actgtctgtt tactgttct gagtcaggcc 3300
gagaaggttc tagaagaagt ggactggcta atcaccaagc ttaagggaca agtgagccaa 3360
gaaacctttat cagtatctcc agtgtgtca gagctccgga ggaatcccaa aaaatatgga 3420
aaagctggtg aagctgctg gttctcatct gaccccctg tgttattctt tcatttctta 3480
cgtacagaat aagagtaaga gcctgaacta tacgggagaa aaaaggaga aacctgctgc 3540
cgttgccaca gccatggcca gagttcttcg ggaaaccaag ccaatcccta acctcatctt 3600
tgccatagaa cagtatgaaa aatttctcat ccacctttct aagaagtcca aggtgaacct 3660
gatgcagcac atgaagctca gcacctcacg agacttcaag atcaaaggaa acatcctaga 3720
catggttctt cgagaggatg gcgaagatga aaatgaagag ggcactgcat cagagcatgg 3780
```

Figure 11b (continued)

```
gggacagaac aaagaaccag ccaagaagaa aaggaaaaaa taaatgaaat gctgagtta   3840
atgtg                                                               3845
```

>83P4B8 v.6 (SEQ ID NO:119).

```
cggagttctg tgatatgagc aacaatgac  cagagatttt tatctctagc agcagaaaaa     60
acagcagaca aactgcaaga atttcttcaa accctgagag aagtgatttt gactaatctc    120
cttcagaatc aagcagtgaa aggaaaagtt gctggagcac tcctgagagc catcttcaaa    180
ggttcccct  gctctgagga agctgaaca  cttaggagac gtaagatata cacttgttgt    240
atccagttgg tggaatcggg gatttgcag  aaagaaatag tgtctgagat cataggatta    300
ctgatgctgg aggctcacca tttccagga  ccattattgg ttgaattagc caatgagttt    360
attagtgctg tcagagaagg cagcctagtg gaaaaggaa  ctttggagtt actacctatc    420
attctcactg ccctggctac gaaaaggaa  aatctggctt atgaaaagg  tgtactgagt    480
ggggaagaat gtaagaaaca gttgattaac accctgtgtt ctggcaggtg ggatcagcaa    540
tatgtaatcc aacacacctc catgttcaag gatgtccctc tgactgcaga agaggtggaa    600
tttgtggtgg aaaaagcatt gagcatgttc tccaagatga atcttcaaga aataccacct    660
ttgtctatc  agcttctgt  tctctcctcc aaggaagca  gaaagagtgt tttggaagga    720
atcatagcct tcttcagtgc actagataag ggacacagag aggtgacgag tggtgacgag    780
ctattgatg  ttgtcactgt gccatcagtc gaacttgtc  atgtgaagg  caccattatt    840
ctacacattg tgtttgccat caaattgcat tatgaactag gcagagaact cgtgaaacac    900
ttaaaggtag gacagcaagg agattccaat aataacttaa gtcccttcag cattgctctt    960
cttctgtctg taacaagaat acaaagattt caggaccagg tgcttgatct tttaaagact   1020
tcggttgtaa agagctttaa ggatcttcaa ctcctccaag gctcaaaatt tcttcagaat   1080
ctagttcctc atagatctta tgtttcaacc atgatcttgg aagtagtgaa aatagcgtt    1140
catagctggg accatgttac tcagggcctc gtagaacttg gttcatttt  gatggattca   1200
tatggccaa  agaaggttct tgatgaaga  actattgaaa ccagcccaag tctttctaga   1260
atgccaaacc agcatgcatg taagctcgga gctaatatcc tgttgaaac  ttttaagatc   1320
catgagatga tcagaacaga aatttggag  caggtcctca acagggttgt taccagagca   1380
tcttctccca tcagtcattt cttagacctg cttcaaata  tcgtcatgta tgcacccta    1440
gttcttcaaa gttgttcttc taaagtcaca gaagcttttg gtgcagccc  tctattgtc   1500
cttcagactg tacaaaggct gcttaaggca gtgcagccc  ttctcaaagt cagcatgtca   1560
atgagagact gcttgatact tgtccttcgg aaagctatgt ttgccaacca gcttagcagc   1620
cgaaatctg  cagttgctgg gtttttgctg ctcctgaaga acttaagt   tttaggcagc   1680
ctgtcatcct ctcagtgcag tcagtctctc agtgtcagtc aggttcatgt ggatgttcac   1740
agccattaca attctgtcgc caatgaaact tttgccttg  agatcatgaa tagtttgagg   1800
agatgcttaa gccagcaagc tgatgttcga ctcatgcttt atgaggggtt ttatgatgtt   1860
cttcgaagga actctcagct ggctaattca gtcatgcaaa ctctgctctc acagttaaaa   1920
cagttctatg agccaaaacc tgatctgctg cctcctctga aattagatgc ttgtattctg   1980
acccaaggag ataagatctc tctacaagaa ccactggatt atctgctgtg ttgtattcag   2040
```

Figure 11b (continued)

```
cattgtttgg cctggtataa gaatacagtc ataccctcac agcagggaga ggaggaagag     2100
gaggaggaag aggcattcta cgaagaccta gatgatatat tggagtccat tactaataga     2160
atgattaaga gtgagctgga agactttgaa ctggataaat cagcagattt ttctcagagc     2220
accagtattg gcataaaaaa taatatctct gctttcttg tgatgggagt ttgtgaggtt      2280
ttaatagaat acaattctc cataagtagt ttcagtaaga ataggttga ggacattctg      2340
agcttattta tgtgttacaa aaaactctct gacattctta atgaaaaagc gggtaaagcc     2400
aaaactaaaa tggccaacaa gacaagtgat agtcttttgt ccatgaaatt tgtgtccagt     2460
ctctcactg ctcttttcag agtcttgcta tggagataca cttcaattcc tacttcagtg     2520
gaagagtcgg gaaagaaaga agcatctcac tgctgtgctt ggagggttta                2580
cagaaaatat tcagtgctgt gcaacagttc tatcagccca agattcagca gtttctcaga     2640
gctctggatg tcacagataa ggaaggagaa gagagaaag atgcagatgt cagtgtcact      2700
cagagaacag cattccagat ccggcaattt cagaggtcct tgttgaattt acttagcagt     2760
caagaggaag atttaatag ctctcctcag ctcctgctag tcacggttct tacagttg       2820
tccagttac tggagccctc ctctcctcag tttgtgcaga tgttatcctg gacatcaaag     2880
atttgcaagg aaaacagccg ggaggatgcc ttgttttgca agagcttgat gaacttgctc     2940
ttcagcctgc atgtttcgta taagagtcct gtcattctgc tgcgtgactt gtccaggat     3000
atccacgggc atctggagaa tatagaccag gatgtagagg actgtctgtt tacttgttct    3060
gcaatagtga atttgagaac ggctgcccc ggactggcta atcaccaagc ttaagggaca     3120
gagaaggttc tagaagaagt ggactctcc agtgtgtca gagctccgga ggaatcccaa      3180
gaaaccttat cagtatctcc agtgtgtca gttctcatct gacccccctg tgttattctt    3240
aaagctggtg aagctgtctg gtctcatct gcctgaacta tacgggagag aaaaaggaga    3300
cgtacagaat aagagtaaga gccatggcca gagttcttcg ggaaaccaag ccaatccta    3360
cgttgccaca gccatggcca gagttcttcg ggaaaccaag ccaatccta acctcatctt    3420
tgccatagaa cagtatgaaa aatttctcat ccaacttct aagaagtcca agtgaacct    3480
gatgcagcac atgaagctca gcacctcacg agacttcaag atcaaaggaa acatcctaga   3540
catggttctt cgagaggatg gcgaagatga aatgaagag ggcactgcat cagagcatgg   3600
gggacagaac aaagaaccag ccaagaagaa aaggaaaaaa taaatgaaat gcctgagtta   3660
atgtg                                                                 3665
```

Figure 12b Protein sequences of transcript variants of 83P4B8
>83P4B8 v.2 (SEQ ID NO:120).

```
MFKDVPLTAE EVEFVVEKAL SMFSKMNLQE IPPLVYQLLV LSSKGSRKSV LEGIIAFFSA       60
LDKQHNEEQS GDELLDVVTV PSGELRHVEG TIILHIVFAI KLDYELGREL VKHLKVGQQG      120
DSNNNLSPFS IALLLSVTRI QRFQDQVLDL LKTSVVKSFK DLQLLQGSKF LQNLVPHRSY      180
VSTMILEVVK NSVHSWDHVT QGLIVELGFIL MDSYGPKKVL DGKTIETSPS LSRMPNQHAC      240
KLGANILLET FKIHEMIRQE ILEQVLNRVV TRASSPISHF LDLLSNIVMY APLVLQSCSS      300
KVTEAFDYLS FLPLQTVQRL LKAVQPLLKV SMSMRDCLIL VLRKAMFANQ LDARKSAVAG      360
FLLLKNFKV  LGSLSSSQCS QSLSVSQVHV DVHSHYNSVA NETFCLEIMD SLRRCLSQQA      420
DVRLMLYEGF YDVLRRNSQL ANSVMQTLLS QIKQFYEPKP DLIPPLKLDA CILTQGDKIS      480
LQEPLDYLLC CIQHCLAWYK NTVIPLQQGE EEEEEEAFY  EDLDDILESI TNRMIKSELE      540
DFELDKSADF SQSTSIGIKN NISAFLVMGV CEVLIEYNFS ISSFSKNRFE DILSLFMCYK      600
KLSDILNEKA GKAKTKMANK TSDSLLSMKF VSSLLTALFR DSIQSHQESL SVLRSSNEFM      660
RYAVNVALQK VQQLKETGHV SGPDGQNPEK IFQNLCDITR VLLWRYTSIP TSVEESGKKE      720
KGKSISLLCL EGLQKIFSAV QQFYQPKIQQ FLRALDVTDK EGEEREDADV SVTQRTAFQI      780
RQFQRSLINL LSSQEEDFNS KEALLLVTVL TSLSKLLEPS SPQFVQMLSW TSKICKENSR      840
EDALFCKSLM NLLFSLHVSY KSPVILLRDL SQDIHGHLGD IDQDVEVEKT NHFAIVNLRT      900
AAPTVCLIVL SQAEKVLEEV DWLITKLKGQ VSQETLSEEA SSQATLPNQP VEKAIIMQLG      960
TLLTFFHELV QTALPSGSCV DTLLKDLCKM YTTLTALVRY YLQVCQSSGG IPKNMEKLVK     1020
LSGSHLTPLC YSFTSYVQNK SKSLNYTGEK KEKPAAVATA MARVLRETKP IPNLIFAIEQ     1080
YEKFLIHLSK KSKVNLMQHM KLSTSRDFKI KGNILDMVLR EDGEDENEEG TASEHGGQNK     1140
EPAKKKRKK                                                              1149
```

>83P4B8 v.3 (SEQ ID NO:121).

```
MDQKILSLAA EKTADKLQEF LQTLREGDLT NLLQNQAVKG KVAGALLRAI FKGSPCSEEA       60
GTLRRRKIYT CCIQLVESGD LQKEIVSEII GLLMLEAHHF PGPLLVELAN EFISAVREGS      120
IVNGKSLELL PIILTALATK KENLAYGKGV LSGEECKKQL INTLCSGRWD QQYVIQHTSM      180
FKDVPLTAEE VEFVVEKALS MFSKMNLQEI PPLVYQLLVL SSKGSRKSVL EGIIAFFSAL      240
DKQHNEEQSG DELLDVVTVP SGELRHVEGT IILHIVFAIK LDYELGRELV KHLKVGQQGD      300
SNNNLSPFSI ALLLSVTRIQ RFQDQVLDLL KTSVVKSFKD LQLLQGSKFL QNLVPHRSYV      360
STMILEVVKN SVHSWDHVTQ GLIVELGFIL MDSYGPKKVL DGKTIETSPSL SRMPNQHACK     420
LGANILLETF KIHEMIRQEI LEQVLNRVVT RASSPISHFL DLLSNIVMYA PLVLQSCSSK      480
VTEAFDYLSF LPLQTVQRLL KAVQPLLKVS MSMRDCLILV LRKAMFANQL DARKSAVAGF      540
LLLLKNFKVL GSLSSSQCSQ SLSVSQVHVD VHSHYNSVAN ETFCLEIMDS LRRCLSQQAD      600
VRLMLYEGFY DVLRRNSQLA NSVMQTLLSQ LKQFYEPKPD LLPPLKLDAC ILTQGDKISL      660
QEPLDYLLCC IQHCLAWYKN TVIPLQQGEE EEEEEAFYE  DLDDILESIT NRMIKSELED      720
FELDKSADFS QSTSIGIKNN ISAFLVMGVC EVLIEYNFSI SSFSKNRFED ILSLFMCYKK      780
LSDILNEKAG KAKTKMANKT SDSLLSMKFV SSLLTALFRS NEFMRYAVN VALQKVQQIK      840
ETGHVSGPDG QNPEKIFQNL CDITRVLLWR YTSIPTSVEE SGKKEKGKSI SLLCLEGLQK      900
```

Figure 12b (continued)

```
IFSAVQQFYQ PKIQQFLRAL DVTDKEGEER EDADVSVTQR TAFQIRQFQR SLLNLLSSQE    960
EDFNSKEALL LVTVLTSLSK LLEPSSPQFV QMLSWTSKIC KENSREDALF CKSLMNLLFS   1020
LHVSYKSPVI LLRDLSQDIH GHLGDIDQDV EVEKTNHFAI VNLRTAAPTV CLLVLSQAEK   1080
VLEEVDWLIT KLKGQVSQET LSEEASSQAT LPNQPVEKAI IMQLGTLLTF FHELVQTALP   1140
SGSCVDTLLK DLCKMYTTLT ALVRYYLQVC QSSGGIPKNM EKLVKLSGSH LTPLCYSFIS   1200
YVQNKSKSLN YTGEKKEKPA AVATAMARVL RETKGPIPNLI FAIEQYEKFL IHLSKKSKVN   1260
LMQHMKLSTS RDFKIKGNIL DMVLREDGED ENEEGTASEH GGQNKEPAKK KRKK         1314

>83P4B8 v.4 (SEQ ID NO:122).
MDQKILSLAA EKTADKIQEF LQTLREGDLT NLLQNQAVKG KVAGALLRAI FKGSPCSEEA     60
GTLRRRKIYT CCIQLVESGD LQKEIVSEII GLLMLEAHHF PGPLLVELAN EFISAVREGS    120
LVNGKSLELL PIILTALATK KENLAYGKGV LSGEECKKQL INTLCSGRWD QQYVIQHTSM    180
FKDVPLTAEE VEFVVEKALS MFSKMNLQEI PPLVYQLLVL SSKGSRKSVL EGIIAFFSAL    240
DKQHNEEQSG DELLDVVTVP SGELRHVEGT IILHIVFAIK LDYELGREIV KHLKVGQQGD    300
SNNNLSPFSI ALLLSVTRIQ RFQDQVLDLL KTSVVKSFKD LQLLQGSKFL QNLVPHRSYV    360
STMILEVVKN SVHSWDHVTQ GLVELGFILM DSYGPKKVLD GKTIETSPSL SRMPNQHACK    420
LGANILLETF KTHEMIRQEI LEQVLNRVVT RASSPISHFL DLLSNIVMYA PIVLQSCSSK    480
VTEAFDYLSF LPLQTVQRLL KAVQPLLKVS MSMRDCLILV LRKAMFANQL DARKSAVAGF    540
LLLLKNFKVL GSLSSSQCSQ SLSVSQVHVD VHSHYNSVAN ETFCLEIMDS LRRCLSQQAD    600
VRIMLYEGFY DVLRRNSQLA NSVMQTLLSQ LKQFYEPKPD LLPPLKLDAC ILTQGDKISL    660
QEPLDYLLCC IQHCLAWYKN TVIPLQQGEE EEEEEEAFYE DLDDILESIT NRMIKSLED    720
FELDKSADFS QSTSIGIKNN ISAFLVMGVC EVLIEYNFSI SSFSKNRFED ILSLFMCYKK    780
LSDIINEKAG KAKTKMANKT SDSLLSMKFV SSLLTALFRV LLWRYTSIPT SVEESGKKEK    840
GKSISLLCLE GLQKIFSAVQ QFYQPKIQQF LRALDVTDKE GEEREDADVS VTQRTAFQIR    900
QFQRSLINLL SSQEEDFNSK EALLLVTVLT SLSKLLEPSS PQFVQMLSWT SKICKENSRE    960
DALFCKSLMN LLFSLHVSYK SPVILLRDLS QDIHGHLGDI DQDVEVEKTN HFAIVNLRTA   1020
APTVCLLVLS QAEKVLEEVD WLITKLKGQV SQETLSEEAS SQATLPNQPV EKAIIMQLGT   1080
LLTFFHEIVQ TALPSGSCVD TLLKDLCKMY TTLTALVRYY LQVCQSSGGI PKNMEKLVKL   1140
SGSHLTPLCY SFISYVQNKS KSLNYTGEKK EKPAAVATAM ARVLRETKPI PNLIFAIEQY   1200
EKFLIHLSKK SKVNLMQHMK LSTSRDFKIK GNILDMVLRE DGEDENEEGT ASEHGGQNKE   1260
PAKKKRKK                                                            1268

>83P4B8 v.5 (SEQ ID NO:123).
MDQKILSLAA EKTADKIQEF LQTLREGDLT NLLQNQAVKG KVAGALLRAI FKGSPCSEEA     60
GTLRRRKIYT CCIQLVESGD LQKEIVSEII GLLMLEAHHF PGPLLVELAN EFISAVREGS    120
LVNGKSLELL PIILTALATK KENLAYGKGV LSGEECKKQL INTLCSGRWD QQYVIQHTSM    180
FKDVPLTAEE VEFVVEKALS MFSKMNLQEI PPLVYQLLVL SSKGSRKSVL EGIIAFFSAL    240
```

Figure 12b (continued)

```
DKQHNEEQSG DELLDVVTVP SGELRHVEGT IILHIVFAIK LDYELGRELV KHLKVGQQGD    300
SNNNLSPFSI ALLLSVTRIQ RFQDQVLDLL KTSVVKSFKD LQLLQGSKFL QNLVPHRSYV    360
STMILEVVKN SVHSWDHVTQ GLVELGFILM DSYGPKKVLD GKTIETSPSL SRMPNQHACK    420
LGANILLETF KIHEMIRQEI LEQVLNRVVI RASSPISHFL DLLSNIVMYA PLVLQSCSSK    480
VTEAFDYLSF LPLQTVQRLL KAVQPLLKVS MSMRDCLIIV LRKAMFANQL DARKSAVAGF    540
LLLLKNFKVL GSLSSSQCSQ SLSVSQVHVD VHSHYNSVAN ETFCLEIMDS LRRCLSQQAD    600
VRIMLYEGFY DVLRRNSQLA NSVMQTLLSQ LKQFYEPKPD LLPPLKLDAC ILTQGDKISL    660
QEPLDYILLCC IQHCLAWYKN TVIPLQQGEE EEEEEAFYE DLDDILESIT NRMIKSELED    720
FELDKSADFS QSTSIGIKNN ISAFLVMGVC EVLIEYNFSI SSFSKNRFED ILSLFMCYKK    780
LSDILNEKAG KAKTKMANKT SDSLLSMKFV SSLLTALFRD SIQSHQESLS VLRSSNEFMR    840
YAVNVALQKV QQLKETGHVS GPDGQNPEKI FQNLCDITRV LLWRYTSIPT SVEESGKKEK    900
GKSISLLCLE GLQKIFSAVQ QFYQPKIQQF LRALDVTDKE GEEREDADVS VTQRTAFQIR    960
QFQRSLLNLL SSQEEDFNSK EALLLVTVLI SLSKLLEPSS PQFVQMLSWT SKICKENSRE   1020
DALFCKSLMN LLFSLHVSYK SPVILLRDLS QDIHGHLGDI DQDVEVEKTN HFAIVNLRTA   1080
APTVCLLVLS QAEKVLEEVD WLITKLKGQV SQETLSVSPG VSELRRNPKK YGKAGEAVWF   1140
SSDPPVLFFH FLRTE                                                   1155

>83P4B8 v.6 (SEQ ID NO:124).
MDQKILSLAA EKTADKLQEF LQTLREGDLT NLLQNQAVKG KVAGALLRAI FKGSPCSEEA    60
GTLRRRKIYT CCIQLVESGD LQKEIVSEII GLLMLEAHHF PGPLIVELAN EFISAVREGS   120
IVNGKSLELL PILLTALATK KENLAYGKGV LSGEECKKQL INTLCSGRWD QQYVIQHTSM   180
FKDVPLTAEE VEFVVEKALS MFSKMNLQEI PPLVYQLIVL SSKGSRKSVL EGIIAFFSAL   240
DKQHNEEQSG DELLDVVTVP SGELRHVEGT IILHIVFAIK LDYELGRELV KHLKVGQQGD   300
SNNNLSPFSI ALLLSVTRIQ RFQDQVLDLL KTSVVKSFKD LQLLQGSKFL QNLVPHRSYV   360
STMILEVVKN SVHSWDHVTQ GLVELGFILM DSYGPKKVLD GKTIETSPSL SRMPNQHACK   420
LGANILLETF KIHEMIRQEI LEQVLNRVVI RASSPISHFL DLLSNIVMYA PLVLQSCSSK   480
VTEAFDYLSF LPLQTVQRLL KAVQPLLKVS MSMRDCLIIV LRKAMFANQL DARKSAVAGF   540
LLLLKNFKVL GSLSSSQCSQ SLSVSQVHVD VHSHYNSVAN ETFCLEIMDS LRRCLSQQAD   600
VRIMLYEGFY DVLRRNSQLA NSVMQTLLSQ LKQFYEPKPD LLPPLKLDAC ILTQGDKISL   660
QEPLDYILLCC IQHCLAWYKN TVIPLQQGEE EEEEEAFYE DLDDILESIT NRMIKSELED   720
FELDKSADFS QSTSIGIKNN ISAFLVMGVC EVLIEYNFSI SSFSKNRFED ILSLFMCYKK   780
LSDILNEKAG KAKTKMANKT SDSLLSMKFV SSLLTALFRV LLWRYTSIPT SVEESGKKEK   840
GKSISLLCLE GLQKIFSAVQ QFYQPKIQQF LRALDVTDKE GEEREDADVS VTQRTAFQIR   900
QFQRSLLNLL SSQEEDFNSK EALLLVTVLI SLSKLLEPSS PQFVQMLSWT SKICKENSRE   960
DALFCKSLMN LLFSLHVSYK SPVILLRDLS QDIHGHLGDI DQDVEVEKTN HFAIVNLRTA  1020
APTVCLLVLS QAEKVLEEVD WLITKLKGQV SQETLSVSPG VSELRRNPKK YGKAGEAVWF  1080
SSDPPVLFFH FLRTE                                                  1095
```

Figure 13b Alignment of nucleotide sequences of 83P4B8 transcript variants
(SEQ ID NOs:23, 115, 116, 117, 118, 119).

```
83P4B8v.3        CGGAGTTCTGTGATATGAGCAACAATGACCAGAAGATTTATCTCTAGCAGCAGAAAAA   60
83P4B8v.4        CGGAGTTCTGTGATATGAGCAACAATGACCAGAAGATTTATCTCTAGCAGCAGAAAAA   60
83P4B8v.2        CGGAGTTCTGTGATATGAGCAACAATGACCAGAAGATTTATCTCTAGCAGCAGAAAAA   60
83P4B8v.1        CGGAGTTCTGTGATATGAGCAACAATGACCAGAAGATTTATCTCTAGCAGCAGAAAAA   60
83P4B8v.5        CGGAGTTCTGTGATATGAGCAACAATGACCAGAAGATTTATCTCTAGCAGCAGAAAAA   60
83P4B8v.6        CGGAGTTCTGTGATATGAGCAACAATGACCAGAAGATTTATCTCTAGCAGCAGAAAAA   60
                 ************************************************************

83P4B8v.3        ACAGCAGACAAACTGCAAGAATTCTTCAAACCCTGAGAGAAGGTGATTTGACTAATCTC  120
83P4B8v.4        ACAGCAGACAAACTGCAAGAATTCTTCAAACCCTGAGAGAAGGTGATTTGACTAATCTC  120
83P4B8v.2        ACAGCAGACAAACTGCAAGAATTCTTCAAACCCTGAGAGAAGGTGATTTGACTAATCTC  120
83P4B8v.1        ACAGCAGACAAACTGCAAGAATTCTTCAAACCCTGAGAGAAGGTGATTTGACTAATCTC  120
83P4B8v.5        ACAGCAGACAAACTGCAAGAATTCTTCAAACCCTGAGAGAAGGTGATTTGACTAATCTC  120
83P4B8v.6        ACAGCAGACAAACTGCAAGAATTCTTCAAACCCTGAGAGAAGGTGATTTGACTAATCTC  120
                 ************************************************************

83P4B8v.3        CTTCAGAATCAAGCAGTCAGCAGTCAGCAGAAAAGTTGCTGGAGCACTCCTGAGAGCCATCTTCAAA  180
83P4B8v.4        CTTCAGAATCAAGCAGTCAGCAGTCAGCAGAAAAGTTGCTGGAGCACTCCTGAGAGCCATCTTCAAA  180
83P4B8v.2        CTTCAGAATCAAGCAGTCAGCAGTCAGCAGAAAAGTTGCTGGAGCACTCCTGAGAGCCATCTTCAAA  180
83P4B8v.1        CTTCAGAATCAAGCAGTCAGCAGTCAGCAGAAAAGTTGCTGGAGCACTCCTGAGAGCCATCTTCAAA  180
83P4B8v.5        CTTCAGAATCAAGCAGTCAGCAGTCAGCAGAAAAGTTGCTGGAGCACTCCTGAGAGCCATCTTCAAA  180
83P4B8v.6        CTTCAGAATCAAGCAGTCAGCAGTCAGCAGAAAAGTTGCTGGAGCACTCCTGAGAGCCATCTTCAAA  180
                 ************************************************************

83P4B8v.3        GGTTCCCCCTGCTCTGAGGAAGCTGGAACACTTAGGAGACGTAAGATATACACTTGTTGT  240
83P4B8v.4        GGTTCCCCCTGCTCTGAGGAAGCTGGAACACTTAGGAGACGTAAGATATACACTTGTTGT  240
83P4B8v.2        GGTTCCCCCTGCTCTGAGGAAGCTGGAACACTTAGGAGACGTAAGATATACACTTGTTGT  240
83P4B8v.1        GGTTCCCCCTGCTCTGAGGAAGCTGGAACACTTAGGAGACGTAAGATATACACTTGTTGT  240
83P4B8v.5        GGTTCCCCCTGCTCTGAGGAAGCTGGAACACTTAGGAGACGTAAGATATACACTTGTTGT  240
83P4B8v.6        GGTTCCCCCTGCTCTGAGGAAGCTGGAACACTTAGGAGACGTAAGATATACACTTGTTGT  240
                 ************************************************************

83P4B8v.3        ATCCAGTTGGTGAATCGGGGGATTTGCAGAAAGAAATAGTGTCTGAGATCATAGGATTA  300
83P4B8v.4        ATCCAGTTGGTGAATCGGGGGATTTGCAGAAAGAAATAGTGTCTGAGATCATAGGATTA  300
83P4B8v.2        ATCCAGTTGGTGAATCGGGGGATTTGCAGAAAGAAATAGTGTCTGAGATCATAGGATTA  300
83P4B8v.1        ATCCAGTTGGTGAATCGGGGGATTTGCAGAAAGAAATAGTGTCTGAGATCATAGGATTA  300
83P4B8v.5        ATCCAGTTGGTGAATCGGGGGATTTGCAGAAAGAAATAGTGTCTGAGATCATAGGATTA  300
```

Figure 13b (continued)

```
83P4B8v.6   ATCCAGTTGGTGGAATCGGGGGATTTGCAGAAAGAAATAGTGTCTGAGATCATAGGATTA   300
            ************************************************************

83P4B8v.3   CTGATGCTGGAGGCTCACCATTTCCAGGACCATTATTGGTTGAATTAGCCAATGAGTTT   360
83P4B8v.4   CTGATGCTGGAGGCTCACCATTTCCAGGACCATTATTGGTTGAATTAGCCAATGAGTTT   360
83P4B8v.2   CTGATGCTGGAGGCTCACCATTTCCAGGACCATTATTGGTTGAATTAGCCAATGAGTTT   360
83P4B8v.1   CTGATGCTGGAGGCTCACCATTTCCAGGACCATTATTGGTTGAATTAGCCAATGAGTTT   360
83P4B8v.5   CTGATGCTGGAGGCTCACCATTTCCAGGACCATTATTGGTTGAATTAGCCAATGAGTTT   360
83P4B8v.6   CTGATGCTGGAGGCTCACCATTTCCAGGACCATTATTGGTTGAATTAGCCAATGAGTTT   360
            ***********************************************************

83P4B8v.3   ATTAGTGCTGTCAGAGAAGGCAGCCTAGTGAATGGAAAATCTTTGGAGTTACTACCTATC   420
83P4B8v.4   ATTAGTGCTGTCAGAGAAGGCAGCCTAGTGAATGGAAAATCTTTGGAGTTACTACCTATC   420
83P4B8v.2   ATTAGTGCTGTCAGAGAAGGCAGCCTAGTGAATGGAAAATCTTTGGAGTTACTACCTATC   420
83P4B8v.1   ATTAGTGCTGTCAGAGAAGGCAGCCTAGTGAATGGAAAATCTTTGGAGTTACTACCTATC   420
83P4B8v.5   ATTAGTGCTGTCAGAGAAGGCAGCCTAGTGAATGGAAAATCTTTGGAGTTACTACCTATC   420
83P4B8v.6   ATTAGTGCTGTCAGAGAAGGCAGCCTAGTGAATGGAAAATCTTTGGAGTTACTACCTATC   420
            ************************************************************

83P4B8v.3   ATTCTCACTGCCCTGCCTACGAAAAGGAAAATCTGGCTTATGGAAAAGGTGTACTGAGT   480
83P4B8v.4   ATTCTCACTGCCCTGCCTACGAAAAGGAAAATCTGGCTTATGGAAAAGGTGTACTGAGT   480
83P4B8v.2   ATTCTCACTGCCCTGCCTACGAAAAGGAAAATCTGGCTTATGGAAAAGGTG-------   472
83P4B8v.1   ATTCTCACTGCCCTGCCTACGAAAAGGAAAATCTGGCTTATGGAAAAGGTGTACTGAGT   480
83P4B8v.5   ATTCTCACTGCCCTGCCTACGAAAAGGAAAATCTGGCTTATGGAAAAGGTGTACTGAGT   480
83P4B8v.6   ATTCTCACTGCCCTGCCTACGAAAAGGAAAATCTGGCTTATGGAAAAGGTGTACTGAGT   480
            **************************************************

83P4B8v.3   GGGGAAGAATGTAAGAAAACAGTTGATTAACACCCTGTGTTCTGGCAGGTGGATCAGCAA   540
83P4B8v.4   GGGGAAGAATGTAAGAAAACAGTTGATTAACACCCTGTGTTCTGGCAGGTGGATCAGCAA   540
83P4B8v.2   ----------------------------------------GGATCAGCAA   482
83P4B8v.1   GGGGAAGAATGTAAGAAAACAGTTGATTAACACCCTGTGTTCTGGCAGGTGGATCAGCAA   540
83P4B8v.5   GGGGAAGAATGTAAGAAAACAGTTGATTAACACCCTGTGTTCTGGCAGGTGGATCAGCAA   540
83P4B8v.6   GGGGAAGAATGTAAGAAAACAGTTGATTAACACCCTGTGTTCTGGCAGGTGGATCAGCAA   540
                                                    **********

83P4B8v.3   TATGTAATCCAACACACCTCCATGTTCAAGGATGTCCCTCGACTGCAGAAGAGGTGGAA   600
83P4B8v.4   TATGTAATCCAACACACCTCCATGTTCAAGGATGTCCCTCGACTGCAGAAGAGGTGGAA   600
83P4B8v.2   TATGTAATCCAACACACCTCCATGTTCAAGGATGTCCCTCGACTGCAGAAGAGGTGGAA   542
83P4B8v.1   TATGTAATCCAACACACCTCCATGTTCAAGGATGTCCCTCGACTGCAGAAGAGGTGGAA   600
            ***********
```

Figure 13b (continued)

```
83P4B8v.5    TATGTAATCCAACACACCTCCATGTTCAAGGATGTCCCTCTGACTGCAGAAGAGTGGAA  600
83P4B8v.6    TATGTAATCCAACACACCTCCATGTTCAAGGATGTCCCTCTGACTGCAGAAGAGTGGAA  600
             ************************************************************

83P4B8v.3    TTTGTGGTGGAAAAAGCATTGAGCATGTTCTCCAAGATGAATCTTCAAGAAATACCACCT  660
83P4B8v.4    TTTGTGGTGGAAAAAGCATTGAGCATGTTCTCCAAGATGAATCTTCAAGAAATACCACCT  660
83P4B8v.2    TTTGTGGTGGAAAAAGCATTGAGCATGTTCTCCAAGATGAATCTTCAAGAAATACCACCT  602
83P4B8v.1    TTTGTGGTGGAAAAAGCATTGAGCATGTTCTCCAAGATGAATCTTCAAGAAATACCACCT  660
83P4B8v.5    TTTGTGGTGGAAAAAGCATTGAGCATGTTCTCCAAGATGAATCTTCAAGAAATACCACCT  660
83P4B8v.6    TTTGTGGTGGAAAAAGCATTGAGCATGTTCTCCAAGATGAATCTTCAAGAAATACCACCT  660
             ************************************************************

83P4B8v.3    TTGGTCTATCAGCTTCTGGTTCTCTGGTTCTCTTCTCTCCTCCAAGGAAGCAGAAAGAGTGTTTTGGAAGGA  720
83P4B8v.4    TTGGTCTATCAGCTTCTGGTTCTCTGGTTCTCTTCTCTCCTCCAAGGAAGCAGAAAGAGTGTTTTGGAAGGA  720
83P4B8v.2    TTGGTCTATCAGCTTCTGGTTCTCTGGTTCTCTTCTCTCCTCCAAGGAAGCAGAAAGAGTGTTTTGGAAGGA  662
83P4B8v.1    TTGGTCTATCAGCTTCTGGTTCTCTGGTTCTCTTCTCTCCTCCAAGGAAGCAGAAAGAGTGTTTTGGAAGGA  720
83P4B8v.5    TTGGTCTATCAGCTTCTGGTTCTCTGGTTCTCTTCTCTCCTCCAAGGAAGCAGAAAGAGTGTTTTGGAAGGA  720
83P4B8v.6    TTGGTCTATCAGCTTCTGGTTCTCTGGTTCTCTTCTCTCCTCCAAGGAAGCAGAAAGAGTGTTTTGGAAGGA  720
             ************************************************************

83P4B8v.3    ATCATAGCCTTCTTCAGTGCACTAGATAAGCACAGCAGCACAATGAGGAACAGAGTGGTGACGAG  780
83P4B8v.4    ATCATAGCCTTCTTCAGTGCACTAGATAAGCACAGCAGCACAATGAGGAACAGAGTGGTGACGAG  780
83P4B8v.2    ATCATAGCCTTCTTCAGTGCACTAGATAAGCACAGCAGCACAATGAGGAACAGAGTGGTGACGAG  722
83P4B8v.1    ATCATAGCCTTCTTCAGTGCACTAGATAAGCACAGCAGCACAATGAGGAACAGAGTGGTGACGAG  780
83P4B8v.5    ATCATAGCCTTCTTCAGTGCACTAGATAAGCACAGCAGCACAATGAGGAACAGAGTGGTGACGAG  780
83P4B8v.6    ATCATAGCCTTCTTCAGTGCACTAGATAAGCACAGCAGCACAATGAGGAACAGAGTGGTGACGAG  780
             ************************************************************

83P4B8v.3    CTATTGGATGTTGTCACTGTGCCATCAGGTGAACTTCGTCATGTGGAAGGCACCATTATT  840
83P4B8v.4    CTATTGGATGTTGTCACTGTGCCATCAGGTGAACTTCGTCATGTGGAAGGCACCATTATT  840
83P4B8v.2    CTATTGGATGTTGTCACTGTGCCATCAGGTGAACTTCGTCATGTGGAAGGCACCATTATT  782
83P4B8v.1    CTATTGGATGTTGTCACTGTGCCATCAGGTGAACTTCGTCATGTGGAAGGCACCATTATT  840
83P4B8v.5    CTATTGGATGTTGTCACTGTGCCATCAGGTGAACTTCGTCATGTGGAAGGCACCATTATT  840
83P4B8v.6    CTATTGGATGTTGTCACTGTGCCATCAGGTGAACTTCGTCATGTGGAAGGCACCATTATT  840
             ************************************************************

83P4B8v.3    CTACACATTGTGTTGCCATCAAATTGGACTATGAACTAGGCAGAGAACTCGTGAAACAC  900
83P4B8v.4    CTACACATTGTGTTGCCATCAAATTGGACTATGAACTAGGCAGAGAACTCGTGAAACAC  900
83P4B8v.2    CTACACATTGTGTTGCCATCAAATTGGACTATGAACTAGGCAGAGAACTCGTGAAACAC  842
```

Figure 13b (continued)

```
83P4B8v.1    CTACACATTGTGTTTGCCATCAAATTGGACTATGAACTAGGCAGAGAACTCGTGAAACAC  900
83P4B8v.5    CTACACATTGTGTTTGCCATCAAATTGGACTATGAACTAGGCAGAGAACTCGTGAAACAC  900
83P4B8v.6    CTACACATTGTGTTTGCCATCAAATTGGACTATGAACTAGGCAGAGAACTCGTGAAACAC  900
             ************************************************************

83P4B8v.3    TTAAAGGTAGGACAGCAGCAAGGAGATTCCAATAATAACTTAAGTCCCTTCAGCATTGCTCTT  960
83P4B8v.4    TTAAAGGTAGGACAGCAGCAAGGAGATTCCAATAATAACTTAAGTCCCTTCAGCATTGCTCTT  960
83P4B8v.2    TTAAAGGTAGGACAGCAGCAAGGAGATTCCAATAATAACTTAAGTCCCTTCAGCATTGCTCTT  902
83P4B8v.1    TTAAAGGTAGGACAGCAGCAAGGAGATTCCAATAATAACTTAAGTCCCTTCAGCATTGCTCTT  960
83P4B8v.5    TTAAAGGTAGGACAGCAGCAAGGAGATTCCAATAATAACTTAAGTCCCTTCAGCATTGCTCTT  960
83P4B8v.6    TTAAAGGTAGGACAGCAGCAAGGAGATTCCAATAATAACTTAAGTCCCTTCAGCATTGCTCTT  960
             ************************************************************

83P4B8v.3    CTTCTGTCTGTAACAAGAATACAAAGATTTCAGGACCAGGTGCTTGATCTTTTAAAGACT  1020
83P4B8v.4    CTTCTGTCTGTAACAAGAATACAAAGATTTCAGGACCAGGTGCTTGATCTTTTAAAGACT  1020
83P4B8v.2    CTTCTGTCTGTAACAAGAATACAAAGATTTCAGGACCAGGTGCTTGATCTTTTAAAGACT   962
83P4B8v.1    CTTCTGTCTGTAACAAGAATACAAAGATTTCAGGACCAGGTGCTTGATCTTTTAAAGACT  1020
83P4B8v.5    CTTCTGTCTGTAACAAGAATACAAAGATTTCAGGACCAGGTGCTTGATCTTTTAAAGACT  1020
83P4B8v.6    CTTCTGTCTGTAACAAGAATACAAAGATTTCAGGACCAGGTGCTTGATCTTTTAAAGACT  1020
             ************************************************************

83P4B8v.3    TCGGTTGTAAAGAGCTTTAAGGATCTTCAACTCCTCCAAGGCTCAAAATTTCTTCAGAAT  1080
83P4B8v.4    TCGGTTGTAAAGAGCTTTAAGGATCTTCAACTCCTCCAAGGCTCAAAATTTCTTCAGAAT  1080
83P4B8v.2    TCGGTTGTAAAGAGCTTTAAGGATCTTCAACTCCTCCAAGGCTCAAAATTTCTTCAGAAT  1022
83P4B8v.1    TCGGTTGTAAAGAGCTTTAAGGATCTTCAACTCCTCCAAGGCTCAAAATTTCTTCAGAAT  1080
83P4B8v.5    TCGGTTGTAAAGAGCTTTAAGGATCTTCAACTCCTCCAAGGCTCAAAATTTCTTCAGAAT  1080
83P4B8v.6    TCGGTTGTAAAGAGCTTTAAGGATCTTCAACTCCTCCAAGGCTCAAAATTTCTTCAGAAT  1080
             ************************************************************

83P4B8v.3    CTAGTTCCTCATAGATCTTATGTTTCAACCATGATCTTGGAAGTAGTAGTGAAGAATAGCGTT  1140
83P4B8v.4    CTAGTTCCTCATAGATCTTATGTTTCAACCATGATCTTGGAAGTAGTAGTGAAGAATAGCGTT  1140
83P4B8v.2    CTAGTTCCTCATAGATCTTATGTTTCAACCATGATCTTGGAAGTAGTAGTGAAGAATAGCGTT  1082
83P4B8v.1    CTAGTTCCTCATAGATCTTATGTTTCAACCATGATCTTGGAAGTAGTAGTGAAGAATAGCGTT  1140
83P4B8v.5    CTAGTTCCTCATAGATCTTATGTTTCAACCATGATCTTGGAAGTAGTAGTGAAGAATAGCGTT  1140
83P4B8v.6    CTAGTTCCTCATAGATCTTATGTTTCAACCATGATCTTGGAAGTAGTAGTGAAGAATAGCGTT  1140
             ************************************************************

83P4B8v.3    CATAGCTGGGACCATGTTACTCAGGGCCTCGTAGAACTTGGTTTCATTTTGATGGATTCA  1200
83P4B8v.4    CATAGCTGGGACCATGTTACTCAGGGCCTCGTAGAACTTGGTTTCATTTTGATGGATTCA  1200
```

Figure 13b (continued)

```
83P4B8v.2    CATAGCTGGACCATGTTACTCAGGGCCTCGTAGAACTTGGTTCATTTTGATGGATTCA   1142
83P4B8v.1    CATAGCTGGACCATGTTACTCAGGGCCTCGTAGAACTTGGTTCATTTTGATGGATTCA   1200
83P4B8v.5    CATAGCTGGACCATGTTACTCAGGGCCTCGTAGAACTTGGTTCATTTTGATGGATTCA   1200
83P4B8v.6    CATAGCTGGACCATGTTACTCAGGGCCTCGTAGAACTTGGTTCATTTTGATGGATTCA   1200
             **********************************************************

83P4B8v.3    TATGGGCCAAAGAAGAAGGTTCTTGATGAAAAAACTATTGAAACCAGCCCAAGTCTTTCTAGA   1260
83P4B8v.4    TATGGGCCAAAGAAGAAGGTTCTTGATGAAAAAACTATTGAAACCAGCCCAAGTCTTTCTAGA   1260
83P4B8v.2    TATGGGCCAAAGAAGAAGGTTCTTGATGAAAAAACTATTGAAACCAGCCCAAGTCTTTCTAGA   1202
83P4B8v.1    TATGGGCCAAAGAAGAAGGTTCTTGATGAAAAAACTATTGAAACCAGCCCAAGTCTTTCTAGA   1260
83P4B8v.5    TATGGGCCAAAGAAGAAGGTTCTTGATGAAAAAACTATTGAAACCAGCCCAAGTCTTTCTAGA   1260
83P4B8v.6    TATGGGCCAAAGAAGAAGGTTCTTGATGAAAAAACTATTGAAACCAGCCCAAGTCTTTCTAGA   1260
             ************************************************************

83P4B8v.3    ATGCCAAACCAGCCATGCATGTAAGCTCGGAGCTAATATCCTGTTGGAAACTTTTAAGATC   1320
83P4B8v.4    ATGCCAAACCAGCCATGCATGTAAGCTCGGAGCTAATATCCTGTTGGAAACTTTTAAGATC   1320
83P4B8v.2    ATGCCAAACCAGCCATGCATGTAAGCTCGGAGCTAATATCCTGTTGGAAACTTTTAAGATC   1262
83P4B8v.1    ATGCCAAACCAGCCATGCATGTAAGCTCGGAGCTAATATCCTGTTGGAAACTTTTAAGATC   1320
83P4B8v.5    ATGCCAAACCAGCCATGCATGTAAGCTCGGAGCTAATATCCTGTTGGAAACTTTTAAGATC   1320
83P4B8v.6    ATGCCAAACCAGCCATGCATGTAAGCTCGGAGCTAATATCCTGTTGGAAACTTTTAAGATC   1320
             ************************************************************

83P4B8v.3    CATGAGATGATCAGACAAGAAGAAATTTTGGAGCAGGTTCCTCAACAGGGTTGTTGTTACCAGAGCA   1380
83P4B8v.4    CATGAGATGATCAGACAAGAAGAAATTTTGGAGCAGGTTCCTCAACAGGGTTGTTGTTACCAGAGCA   1380
83P4B8v.2    CATGAGATGATCAGACAAGAAGAAATTTTGGAGCAGGTTCCTCAACAGGGTTGTTGTTACCAGAGCA   1322
83P4B8v.1    CATGAGATGATCAGACAAGAAGAAATTTTGGAGCAGGTTCCTCAACAGGGTTGTTGTTACCAGAGCA   1380
83P4B8v.5    CATGAGATGATCAGACAAGAAGAAATTTTGGAGCAGGTTCCTCAACAGGGTTGTTGTTACCAGACCA   1380
83P4B8v.6    CATGAGATGATCAGACAAGAAGAAATTTTGGAGCAGGTTCCTCAACAGGGTTGTTGTTACCAGACCA   1380
             ****************************************************************

83P4B8v.3    TCTTCTCCCATCAGTCATTTCTTAGACCTGCTTTCAAATATCGTCATGTATGCACCCTTA   1440
83P4B8v.4    TCTTCTCCCATCAGTCATTTCTTAGACCTGCTTTCAAATATCGTCATGTATGCACCCTTA   1440
83P4B8v.2    TCTTCTCCCATCAGTCATTTCTTAGACCTGCTTTCAAATATCGTCATGTATGCACCCTTA   1382
83P4B8v.1    TCTTCTCCCATCAGTCATTTCTTAGACCTGCTTTCAAATATCGTCATGTATGCACCCTTA   1440
83P4B8v.5    TCTTCTCCCATCAGTCATTTCTTAGACCTGCTTTCAAATATCGTCATGTATGCACCCTTA   1440
83P4B8v.6    TCTTCTCCCATCAGTCATTTCTTAGACCTGCTTTCAAATATCGTCATGTATGCACCCTTA   1440
             ************************************************************

83P4B8v.3    GTTCTTCAAAGTTGTTCTTCTAAAGTCACAGAAGCTTTTGACTATTTGTCCTTTCTGCCC   1500
```

Figure 13b (continued)

```
83P4B8v.4   GTTCTTCAAAGTTGTTCTTCTAAAGTCACAGAAGCTTTGACTATTGTCCTTTCTGCCC  1500
83P4B8v.2   GTTCTTCAAAGTTGTTCTTCTAAAGTCACAGAAGCTTTGACTATTGTCCTTTCTGCCC  1442
83P4B8v.1   GTTCTTCAAAGTTGTTCTTCTAAAGTCACAGAAGCTTTGACTATTGTCCTTTCTGCCC  1500
83P4B8v.5   GTTCTTCAAAGTTGTTCTTCTAAAGTCACAGAAGCTTTGACTATTGTCCTTTCTGCCC  1500
83P4B8v.6   GTTCTTCAAAGTTGTTCTTCTAAAGTCACAGAAGCTTTGACTATTGTCCTTTCTGCCC  1500
            **********************************************************

83P4B8v.3   CTTCAGACTGTACAAAGGCTGCTTAAGGCAGTGCAGCCCCTTCTCAAAGTCAGCATGTCA  1560
83P4B8v.4   CTTCAGACTGTACAAAGGCTGCTTAAGGCAGTGCAGCCCCTTCTCAAAGTCAGCATGTCA  1560
83P4B8v.2   CTTCAGACTGTACAAAGGCTGCTTAAGGCAGTGCAGCCCCTTCTCAAAGTCAGCATGTCA  1502
83P4B8v.1   CTTCAGACTGTACAAAGGCTGCTTAAGGCAGTGCAGCCCCTTCTCAAAGTCAGCATGTCA  1560
83P4B8v.5   CTTCAGACTGTACAAAGGCTGCTTAAGGCAGTGCAGCCCCTTCTCAAAGTCAGCATGTCA  1560
83P4B8v.6   CTTCAGACTGTACAAAGGCTGCTTAAGGCAGTGCAGCCCCTTCTCAAAGTCAGCATGTCA  1560
            ************************************************************

83P4B8v.3   ATGAGAGACTGCTTGATACTTGTCCTTCGGAAAGCTATGTTTGCCAACCAGCTTGATGCC  1620
83P4B8v.4   ATGAGAGACTGCTTGATACTTGTCCTTCGGAAAGCTATGTTTGCCAACCAGCTTGATGCC  1620
83P4B8v.2   ATGAGAGACTGCTTGATACTTGTCCTTCGGAAAGCTATGTTTGCCAACCAGCTTGATGCC  1562
83P4B8v.1   ATGAGAGACTGCTTGATACTTGTCCTTCGGAAAGCTATGTTTGCCAACCAGCTTGATGCC  1620
83P4B8v.5   ATGAGAGACTGCTTGATACTTGTCCTTCGGAAAGCTATGTTTGCCAACCAGCTTGATGCC  1620
83P4B8v.6   ATGAGAGACTGCTTGATACTTGTCCTTCGGAAAGCTATGTTTGCCAACCAGCTTGATGCC  1620
            ************************************************************

83P4B8v.3   CGAAAATCTGCAGTTGCTGGGTTTTGCTGCTCCTGAAGAACTTTAAAGTTTTAGGCAGC  1680
83P4B8v.4   CGAAAATCTGCAGTTGCTGGGTTTTGCTGCTCCTGAAGAACTTTAAAGTTTTAGGCAGC  1680
83P4B8v.2   CGAAAATCTGCAGTTGCTGGGTTTTGCTGCTCCTGAAGAACTTTAAAGTTTTAGGCAGC  1622
83P4B8v.1   CGAAAATCTGCAGTTGCTGGGTTTTGCTGCTCCTGAAGAACTTTAAAGTTTTAGGCAGC  1680
83P4B8v.5   CGAAAATCTGCAGTTGCTGGGTTTTGCTGCTCCTGAAGAACTTTAAAGTTTTAGGCAGC  1680
83P4B8v.6   CGAAAATCTGCAGTTGCTGGGTTTTGCTGCTCCTGAAGAACTTTAAAGTTTTAGGCAGC  1680
            ***********************************************************

83P4B8v.3   CTGTCATCCTCCTCAGTGCAGTCAGTCTCCAGTGTCAGTCAGTTCATGTGGATGTTCAC  1740
83P4B8v.4   CTGTCATCCTCCTCAGTGCAGTCAGTCTCCAGTGTCAGTCAGTTCATGTGGATGTTCAC  1740
83P4B8v.2   CTGTCATCCTCCTCAGTGCAGTCAGTCTCCAGTGTCAGTCAGTTCATGTGGATGTTCAC  1682
83P4B8v.1   CTGTCATCCTCCTCAGTGCAGTCAGTCTCCAGTGTCAGTCAGTTCATGTGGATGTTCAC  1740
83P4B8v.5   CTGTCATCCTCCTCAGTGCAGTCAGTCTCCAGTGTCAGTCAGTTCATGTGGATGTTCAC  1740
83P4B8v.6   CTGTCATCCTCCTCAGTGCAGTCAGTCTCCAGTGTCAGTCAGTTCATGTGGATGTTCAC  1740
            ***********************************************************
```

Figure 13b (continued)

```
83P4B8v.3    AGCCATTACAATTCTGTCGCCAATGAAACTTTTGCCTTGAGATCATGGATAGTTTGAGG 1800
83P4B8v.4    AGCCATTACAATTCTGTCGCCAATGAAACTTTTGCCTTGAGATCATGGATAGTTTGAGG 1800
83P4B8v.2    AGCCATTACAATTCTGTCGCCAATGAAACTTTTGCCTTGAGATCATGGATAGTTTGAGG 1742
83P4B8v.1    AGCCATTACAATTCTGTCGCCAATGAAACTTTTGCCTTGAGATCATGGATAGTTTGAGG 1800
83P4B8v.5    AGCCATTACAATTCTGTCGCCAATGAAACTTTTGCCTTGAGATCATGGATAGTTTGAGG 1800
83P4B8v.6    AGCCATTACAATTCTGTCGCCAATGAAACTTTTGCCTTGAGATCATGGATAGTTTGAGG 1800
             ***********************************************************

83P4B8v.3    AGATGCTTAAGCCAGCAAGCTGATGTTCGACTCATGCTTTATGAGGGGTTTTATGATGTT 1860
83P4B8v.4    AGATGCTTAAGCCAGCAAGCTGATGTTCGACTCATGCTTTATGAGGGGTTTTATGATGTT 1860
83P4B8v.2    AGATGCTTAAGCCAGCAAGCTGATGTTCGACTCATGCTTTATGAGGGGTTTTATGATGTT 1802
83P4B8v.1    AGATGCTTAAGCCAGCAAGCTGATGTTCGACTCATGCTTTATGAGGGGTTTTATGATGTT 1860
83P4B8v.5    AGATGCTTAAGCCAGCAAGCTGATGTTCGACTCATGCTTTATGAGGGGTTTTATGATGTT 1860
83P4B8v.6    AGATGCTTAAGCCAGCAAGCTGATGTTCGACTCATGCTTTATGAGGGGTTTTATGATGTT 1860
             ***********************************************************

83P4B8v.3    CTTCGAAGGAACTCTCAGCTGCTAATTCAGTCATGCAAACTCTGCTCTCACAGTTAAAA 1920
83P4B8v.4    CTTCGAAGGAACTCTCAGCTGCTAATTCAGTCATGCAAACTCTGCTCTCACAGTTAAAA 1920
83P4B8v.2    CTTCGAAGGAACTCTCAGCTGCTAATTCAGTCATGCAAACTCTGCTCTCACAGTTAAAA 1862
83P4B8v.1    CTTCGAAGGAACTCTCAGCTGCTAATTCAGTCATGCAAACTCTGCTCTCACAGTTAAAA 1920
83P4B8v.5    CTTCGAAGGAACTCTCAGCTGCTAATTCAGTCATGCAAACTCTGCTCTCACAGTTAAAA 1920
83P4B8v.6    CTTCGAAGGAACTCTCAGCTGCTAATTCAGTCATGCAAACTCTGCTCTCACAGTTAAAA 1920
             ***********************************************************

83P4B8v.3    CAGTTCTATGAGCCAAAACCTGATCTGCCTCCTCTGAAATTAGATGCTTGTATTCTG 1980
83P4B8v.4    CAGTTCTATGAGCCAAAACCTGATCTGCCTCCTCTGAAATTAGATGCTTGTATTCTG 1980
83P4B8v.2    CAGTTCTATGAGCCAAAACCTGATCTGCCTCCTCTGAAATTAGATGCTTGTATTCTG 1922
83P4B8v.1    CAGTTCTATGAGCCAAAACCTGATCTGCCTCCTCTGAAATTAGATGCTTGTATTCTG 1980
83P4B8v.5    CAGTTCTATGAGCCAAAACCTGATCTGCCTCCTCTGAAATTAGATGCTTGTATTCTG 1980
83P4B8v.6    CAGTTCTATGAGCCAAAACCTGATCTGCCTCCTCTGAAATTAGATGCTTGTATTCTG 1980
             ********************************************************

83P4B8v.3    ACCCAAGGAGATAAGATCTCTCTACAAGAACCACTGATTATCTGCTGTGTTGTTATTCAG 2040
83P4B8v.4    ACCCAAGGAGATAAGATCTCTCTACAAGAACCACTGATTATCTGCTGTGTTGTTATTCAG 2040
83P4B8v.2    ACCCAAGGAGATAAGATCTCTCTACAAGAACCACTGATTATCTGCTGTGTTGTTATTCAG 1982
83P4B8v.1    ACCCAAGGAGATAAGATCTCTCTACAAGAACCACTGATTATCTGCTGTGTTGTTATTCAG 2040
83P4B8v.5    ACCCAAGGAGATAAGATCTCTCTACAAGAACCACTGATTATCTGCTGTGTTGTTATTCAG 2040
83P4B8v.6    ACCCAAGGAGATAAGATCTCTCTACAAGAACCACTGATTATCTGCTGTGTTGTTATTCAG 2040
             ************************************************************
```

Figure 13b (continued)

```
83P4B8v.3    CATTGTTTGGCCTGGTATAAGAATACAGTCATACCCTTACAGCAGGGAGAGGAGGAAGAG  2100
83P4B8v.4    CATTGTTTGGCCTGGTATAAGAATACAGTCATACCCTTACAGCAGGGAGAGGAGGAAGAG  2100
83P4B8v.2    CATTGTTTGGCCTGGTATAAGAATACAGTCATACCCTTACAGCAGGGAGAGGAGGAAGAG  2042
83P4B8v.1    CATTGTTTGGCCTGGTATAAGAATACAGTCATACCCTTACAGCAGGGAGAGGAGGAAGAG  2100
83P4B8v.5    CATTGTTTGGCCTGGTATAAGAATACAGTCATACCCTTACAGCAGGGAGAGGAGGAAGAG  2100
83P4B8v.6    CATTGTTTGGCCTGGTATAAGAATACAGTCATACCCTTACAGCAGGGAGAGGAGGAAGAG  2100
             ************************************************************

83P4B8v.3    GAGGAGGAAGAGAGCATTCTACGAAGACCTAGATGATATATATTGGAGTCCATTACTAATAGA  2160
83P4B8v.4    GAGGAGGAAGAGAGCATTCTACGAAGACCTAGATGATATATATTGGAGTCCATTACTAATAGA  2160
83P4B8v.2    GAGGAGGAAGAGAGCATTCTACGAAGACCTAGATGATATATTGGAGTCCATTACTAATAGA  2102
83P4B8v.1    GAGGAGGAAGAGAGCATTCTACGAAGACCTAGATGATATATTGGAGTCCATTACTAATAGA  2160
83P4B8v.5    GACGAGGAAGACGCATTCTACGAAGACCTAGATGATATATTGCAGTCCATTACTAATAGA  2160
83P4B8v.6    GAGGAGGAAGAGAGCATTCTACGAAGACCTAGATGATATATTGGAGTCCATTACTAATAGA  2160
             ************************************************************

83P4B8v.3    ATGATTAAGAGTGAGCTGGAAGACTTTGAACTGGATAAATCAGCAGATTTTTCTCAGAGC  2220
83P4B8v.4    ATGATTAAGAGTGAGCTGGAAGACTTTGAACTGGATAAATCAGCAGATTTTTCTCAGAGC  2220
83P4B8v.2    ATGATTAAGAGTGAGCTGGAAGACTTTGAACTGGATAAATCAGCAGATTTTTCTCAGAGC  2162
83P4B8v.1    ATGATTAAGAGTGAGCTGGAAGACTTTGAACTGGATAAATCAGCAGATTTTTCTCAGAGC  2220
83P4B8v.5    ATGATTAAGAGTGAGCTGGAAGACTTTGAACTGGATAAATCAGCAGATTTTTCTCAGAGC  2220
83P4B8v.6    ATGATTAAGAGTGAGCTGGAAGACTTTGAACTGGATAAATCAGCAGATTTTTCTCAGAGC  2220
             ************************************************************

83P4B8v.3    ACCAGTATTGGCATAAAAATAATAATATCTCTGCTTTTCTTGTGATGGGAGTTTGTGAGGTT  2280
83P4B8v.4    ACCAGTATTGGCATAAAAATAATAATATCTCTGCTTTTCTTGTGATGGGAGTTTGTGAGGTT  2280
83P4B8v.2    ACCAGTATTGGCATAAAAATAATAATATCTCTGCTTTTCTTGTGATGGGAGTTTGTGAGGTT  2222
83P4B8v.1    ACCAGTATTGGCATAAAAATAATAATATCTCTGCTTTTCTTGTGATGGGAGTTTGTGAGGTT  2280
83P4B8v.5    ACCAGTATTGGCATAAAAATAATAATATCTCTGCTTTTCTTGTGATGGGAGTTTGTGAGGTT  2280
83P4B8v.6    ACCAGTATTGGCATAAAAATAATAATATCTCTGCTTTTCTTGTGATGGGAGTTTGTGAGGTT  2280
             ************************************************************

83P4B8v.3    TTAATAGAATACAATTTCTCCATAAGTAGTTTCAGTAAGAATAGGTTTGAGGACATTCTG  2340
83P4B8v.4    TTAATAGAATACAATTTCTCCATAAGTAGTTTCAGTAAGAATAGGTTTGAGGACATTCTG  2340
83P4B8v.2    TTAATAGAATACAATTTCTCCATAAGTAGTTTCAGTAAGAATAGGTTTGAGGACATTCTG  2282
83P4B8v.1    TTAATAGAATACAATTTCTCCATAAGTAGTTTCAGTAAGAATAGGTTTGAGGACATTCTG  2340
83P4B8v.5    TTAATAGAATACAATTTCTCCATAAGTAGTTTCAGTAAGAATAGGTTTGAGGACATTCTG  2340
83P4B8v.6    TTAATAGAATACAATTTCTCCATAAGTAGTTTCAGTAAGAATAGGTTTGAGGACATTCTG  2340
             ************************************************************
```

Figure 13b (continued)

```
83P4B8v.3  AGCTTATTTATGTGTTACAAAAAAACTCTCTGACATTCTTAATGAAAAAGCGGGTAAAGCC 2400
83P4B8v.4  AGCTTATTTATGTGTTACAAAAAAACTCTCTGACATTCTTAATGAAAAAGCGGGTAAAGCC 2400
83P4B8v.2  AGCTTATTTATGTGTTACAAAAAAACTCTCTGACATTCTTAATGAAAAAGCGGGTAAAGCC 2342
83P4B8v.1  AGCTTATTTATGTGTTACAAAAAAACTCTCTGACATTCTTAATGAAAAAGCGGGTAAAGCC 2400
83P4B8v.5  AGCTTATTTATGTGTTACAAAAAAACTCTCTGACATTCTTAATGAAAAAGCGGGTAAAGCC 2400
83P4B8v.6  AGCTTATTTATGTGTTACAAAAAAACTCTCTGACATTCTTAATGAAAAAGCGGGTAAAGCC 2400
           ************************************************************

83P4B8v.3  AAAACTAAAATGGCCAACAAGACAAGTGATAGTCTTTGTCCATGAAATTTGTGTCCAGT 2460
83P4B8v.4  AAAACTAAAATGGCCAACAAGACAAGTGATAGTCTTTTGTCCATGAAATTGTGTCCAGT 2460
83P4B8v.2  AAAACTAAAATGGCCAACAAGACAAGTGATAGTCTTTTGTCCATGAAATTTGTGTCCAGT 2402
83P4B8v.1  AAAACTAAAATGGCCAACAAGACAAGTGATAGTCTTTTGTCCATGAAATTTGTGTCCAGT 2460
83P4B8v.5  AAAACTAAAATGGCCAACAAGACAAGTGATAGTCTTTTGTCCATGAAATTTGTGTCCAGT 2460
83P4B8v.6  AAAACTAAAATGGCCAACAAGACAAGTGATAGTCTTTTGTCCATGAAATTTGTGTCCAGT 2460
           ************************************************************

83P4B8v.3  CTTCTCACTGCTCTCTTTTCAGG------------------------------------ 2481
83P4B8v.4  CTTCTCACTGCTCTCTTTTCAG-------------------------------------- 2480
83P4B8v.2  CTTCTCACTGCTCTCTTTTCAGGGATAGTAGTATCCAAAGCCACCAAGAAAGCCTTTCTGTTCTC 2462
83P4B8v.1  CTTCTCACTGCTCTCTTTTCAGGGATAGTAGTATCCAAAGCCACCAAGAAAGCCTTTCTGTTCTC 2520
83P4B8v.5  CTTCTCACTGCTCTCTTTTCAGGGATAGTAGTATCCAAAGCCACCAAGAAAGCCTTTCTGTTCTC 2520
83P4B8v.6  CTTCTCACTGCTCTTTTCAG---------------------------------------- 2480
           **********************

83P4B8v.3  ---TCCAGCAATGAGTTTATGCGCTATGCAGTGAATGTAGCTCTGCAGAAAGTACAGCAG 2538
83P4B8v.4  ------------------------------------------------------------
83P4B8v.2  AGGTCCAGCAATGAGTTTATGCGCTATGCAGTGAATGTAGCTCTGCAGAAAGTACAGCAG 2522
83P4B8v.1  AGGTCCAGCAATGAGTTTATGCGCTATGCAGTGAATGTAGCTCTGCAGAAAGTACAGCAG 2580
83P4B8v.5  AGGTCCAGCAATGAGTTTATGCGCTATGCAGTGAATGTAGCTCTGCAGAAAGTACAGCAG 2580
83P4B8v.6  ------------------------------------------------------------

83P4B8v.3  CTAAAGGAAACAGGGCATGTGAGTGGCCCTGATGGCCAAAACCCAGAAAAGATCTTTCAG 2598
83P4B8v.4  ------------------------------------------------------------
83P4B8v.2  CTAAAGGAAACAGGGCATGTGAGTGGCCCTGATGGCCAAAACCCAGAAAAGATCTTTCAG 2582
83P4B8v.1  CTAAAGGAAACAGGGCATGTGAGTGGCCCTGATGGCCAAAACCCAGAAAAGATCTTTCAG 2640
83P4B8v.5  CTAAAGGAAACAGGGCATGTGAGTGGCCCTGATGGCCAAAACCCAGAAAAGATCTTTCAG 2640
83P4B8v.6  ------------------------------------------------------------
```

Figure 13b (continued)

```
83P4B8v.3    AACCCTCTGTGACATAACTCGAGTCTTGCTATGGAGATACACTTCAATTCCTACTTCAGTG  2658
83P4B8v.4    ------------------AGTCTTGCTATGGAGATACACTTCAATTCCTACTTCAGTG    2520
83P4B8v.2    AACCCTCTGTGACATAACTCGAGTCTTGCTATGGAGATACACTTCAATTCCTACTTCAGTG  2642
83P4B8v.1    AACCCTCTGTGACATAACTCGAGTCTTGCTATGGAGATACACTTCAATTCCTACTTCAGTG  2700
83P4B8v.5    AACCCTCTGTGACATAACTCGAGTCTTGCTATGGAGATACACTTCAATTCCTACTTCAGTG  2700
83P4B8v.6    ------------------AGTCTTGCTATGGAGATACACTTCAATTCCTACTTCAGTG    2520
                               ******************************************

83P4B8v.3    GAAGAGTCGGGAAAGAGAAAGAGAAAGAGAGCATCTCACTGCTGTGCTTGGAGGGTTTA    2718
83P4B8v.4    GAAGAGTCGGGAAAGAGAAAGAGAAAGAGAGCATCTCACTGCTGTGCTTGGAGGGTTTA    2580
83P4B8v.2    GAAGAGTCGGGAAAGAGAAAGAGAAAGAGAGCATCTCACTGCTGTGCTTGGAGGGTTTA    2702
83P4B8v.1    GAAGAGTCGGGAAAGAGAAAGAGAAAGAGAGCATCTCACTGCTGTGCTTGGAGGGTTTA    2760
83P4B8v.5    GAAGAGTCGGGAAAGAGAAAGAGAAAGAGAGCATCTCACTGCTGTGCTTGGAGGGTTTA    2760
83P4B8v.6    GAAGAGTCGGGAAAGAGAAAGAGAAAGAGAGCATCTCACTGCTGTGCTTGGAGGGTTTA    2580
             ************************************************************

83P4B8v.3    CAGAAAATATTCAGTGCTGTGCAACAGTTCTATCAGCCCAAGATTCAGCAGTTTCTCAGA   2778
83P4B8v.4    CAGAAAATATTCAGTGCTGTGCAACAGTTCTATCAGCCCAAGATTCAGCAGTTTCTCAGA   2640
83P4B8v.2    CAGAAAATATTCAGTGCTGTGCAACAGTTCTATCAGCCCAAGATTCAGCAGTTTCTCAGA   2762
83P4B8v.1    CAGAAAATATTCAGTGCTGTGCAACAGTTCTATCAGCCCAAGATTCAGCAGTTTCTCAGA   2820
83P4B8v.5    CAGAAAATATTCAGTGCTGTGCAACAGTTCTATCAGCCCAAGATTCAGCAGTTTCTCAGA   2820
83P4B8v.6    CAGAAAATATTCAGTGCTGTGCAACAGTTCTATCAGCCCAAGATTCAGCAGTTTCTCAGA   2640
             ************************************************************

83P4B8v.3    GCTCTGGATGTCACAGATAAGGAAGGAGAGAGAGAAGATGCAGATGTCAGTGTCACT      2838
83P4B8v.4    GCTCTGGATGTCACAGATAAGGAAGGAGAGAGAGAAGATGCAGATGTCAGTGTCACT      2700
83P4B8v.2    GCTCTGGATGTCACAGATAAGGAAGGAGAGAGAGAAGATGCAGATGTCAGTGTCACT      2822
83P4B8v.1    GCTCTGGATGTCACAGATAAGGAAGGAGAGAGAGAAGATGCAGATGTCAGTGTCACT      2880
83P4B8v.5    GCTCTGGATGTCACAGATAAGGAAGGAGAGAGAGAAGATGCAGATGTCAGTGTCACT      2880
83P4B8v.6    GCTCTGGATGTCACAGATAAGGAAGGAGAGAGAGAAGATGCAGATGTCAGTGTCACT      2700
             ************************************************************

83P4B8v.3    CAGAGAACAGCATTCCAGATCCGGCAATTCAGAGGTCCTTGTTGAATTACTTAGCAGT     2898
83P4B8v.4    CAGAGAACAGCATTCCAGATCCGGCAATTCAGAGGTCCTTGTTGAATTACTTAGCAGT     2760
83P4B8v.2    CAGAGAACAGCATTCCAGATCCGGCAATTCAGAGGTCCTTGTTGAATTACTTAGCAGT     2882
83P4B8v.1    CAGAGAACAGCATTCCAGATCCGGCAATTCAGAGGTCCTTGTTGAATTACTTAGCAGT     2940
83P4B8v.5    CAGAGAACAGCATTCCAGATCCGGCAATTCAGAGGTCCTTGTTGAATTACTTAGCAGT     2940
83P4B8v.6    CAGAGAACAGCATTCCAGATCCGGCAATTCAGAGGTCCTTGTTGAATTACTTAGCAGT     2760
             ************************************************************
```

Figure 13b (continued)

```
83P4B8v.3    CAAGAGGAAGATTTTAATAGCAAAGAAGCCCTCCTGCTAGTCACGGTTCTTACCAGTTTG 2958
83P4B8v.4    CAAGAGGAAGATTTTAATAGCAAAGAAGCCCTCCTGCTAGTCACGGTTCTTACCAGTTTG 2820
83P4B8v.2    CAAGAGGAAGATTTTAATAGCAAAGAAGCCCTCCTGCTAGTCACGGTTCTTACCAGTTTG 2942
83P4B8v.1    CAAGAGGAAGATTTTAATAGCAAAGAAGCCCTCCTGCTAGTCACGGTTCTTACCAGTTTG 3000
83P4B8v.5    CAAGAGGAAGATTTTAATAGCAAAGAAGCCCTCCTGCTAGTCACGGTTCTTACCAGTTTG 3000
83P4B8v.6    CAAGAGGAAGATTTTAATAGCAAAGAAGCCCTCCTGCTAGTCACGGTTCTTACCAGTTTG 2820
             ************************************************************

83P4B8v.3    TCCAAGTTACTGGAGCCCTCCTCCTCCTCCTCAGTTTGTGCAGATGTTATCCTGGACATCAAAG 3018
83P4B8v.4    TCCAAGTTACTGGAGCCCTCCTCCTCCTCCTCAGTTTGTGCAGATGTTATCCTGGACATCAAAG 2880
83P4B8v.2    TCCAAGTTACTGGAGCCCTCCTCCTCCTCCTCAGTTTGTGCAGATGTTATCCTGGACATCAAAG 3002
83P4B8v.1    TCCAAGTTACTGGAGCCCTCCTCCTCCTCCTCAGTTTGTGCAGATGTTATCCTGGACATCAAAG 3060
83P4B8v.5    TCCAAGTTACTGGAGCCCTCCTCCTCCTCCTCAGTTTGTGCAGATGTTATCCTGGACATCAAAG 3060
83P4B8v.6    TCCAAGTTACTGGAGCCCTCCTCCTCCTCCTCAGTTTGTGCAGATGTTATCCTGGACATCAAAG 2880
             ************************************************************

83P4B8v.3    ATTTGCAAGGAAAACAGCCGGAGGATGCCTTGTTGTTTGCAAGAGCTTGATGAACTTGCTC 3078
83P4B8v.4    ATTTGCAAGGAAAACAGCCGGAGGATGCCTTGTTGTTTGCAAGAGCTTGATGAACTTGCTC 2940
83P4B8v.2    ATTTGCAAGGAAAACAGCCGGAGGATGCCTTGTTGTTTGCAAGAGCTTGATGAACTTGCTC 3062
83P4B8v.1    ATTTGCAAGGAAAACAGCCGGAGGATGCCTTGTTGTTTGCAAGAGCTTGATGAACTTGCTC 3120
83P4B8v.5    ATTTGCAAGGAAAACAGCCGGAGGATGCCTTGTTGTTTGCAAGAGCTTGATGAACTTGCTC 3120
83P4B8v.6    ATTTGCAAGGAAAACAGCCGGAGGATGCCTTGTTGTTTGCAAGAGCTTGATGAACTTGCTC 2940
             ************************************************************

83P4B8v.3    TTCAGCCTGCATGTTTCGTATAAGAGTCCTGTCATTCTGCGCTGCCGTGACTTGTCCCAGGAT 3138
83P4B8v.4    TTCAGCCTGCATGTTTCGTATAAGAGTCCTGTCATTCTGCGCTGCCGTGACTTGTCCCAGGAT 3000
83P4B8v.2    TTCAGCCTGCATGTTTCGTATAAGAGTCCTGTCATTCTGCGCTGCCGTGACTTGTCCCAGGAT 3122
83P4B8v.1    TTCAGCCTGCATGTTTCGTATAAGAGTCCTGTCATTCTGCGCTGCCGTGACTTGTCCCAGGAT 3180
83P4B8v.5    TTCAGCCTGCATGTTTCGTATAAGAGTCCTGTCATTCTGCGCTGCCGTGACTTGTCCCAGGAT 3180
83P4B8v.6    TTCAGCCTGCATGTTTCGTATAAGAGTCCTGTCATTCTGCGCTGCCGTGACTTGTCCCAGGAT 3000
             ************************************************************

83P4B8v.3    ATCCACGGGCATCTGGGAGATATAGACCAGGATGTAGAGGTGGAGAAAACAAACCACTTT 3198
83P4B8v.4    ATCCACGGGCATCTGGGAGATATAGACCAGGATGTAGAGGTGGAGAAAACAAACCACTTT 3060
83P4B8v.2    ATCCACGGGCATCTGGGAGATATAGACCAGGATGTAGAGGTGGAGAAAACAAACCACTTT 3182
83P4B8v.1    ATCCACGGGCATCTGGGAGATATAGACCAGGATGTAGAGGTGGAGAAAACAAACCACTTT 3240
83P4B8v.5    ATCCACGGGCATCTGGGAGATATAGACCAGGATGTAGAGGTGGAGAAAACAAACCACTTT 3240
83P4B8v.6    ATCCACGGGCATCTGGGAGATATAGACCAGGATGTAGAGGTGGAGAAAACAAACCACTTT 3060
             ************************************************************
```

Figure 13b (continued)

```
83P4B8v.3    GCAATAGTGAATTTGAGAACGGCTGCCCCCACTGTCTGTTTACTTGTTCTGAGTCAGGCC  3258
83P4B8v.4    GCAATAGTGAATTTGAGAACGGCTGCCCCCACTGTCTGTCTGTTCTGAGTCAGCC      3120
83P4B8v.2    GCAATAGTGAATTTGAGAACGGCTGCCCCCACTGTCGCCCCACTGTCTGTTCTGAGTCAGGCC  3242
83P4B8v.1    GCAATAGTGAATTTGAGAACGGCTGCCCCCACTGTCGCCCCACTGTCTGTTCTGAGTCAGGCC  3300
83P4B8v.5    GCAATAGTGAATTTGAGAACGGCTGCCCCCACTGTCGCCCCACTGTCTGTTCTGAGTCAGGCC  3300
83P4B8v.6    GCAATAGTGAATTTGAGAACGGCTGCCCCCACTGTCGCCCCACTGTCTGTTCTGAGTCAGCC   3120
             ******************************************

83P4B8v.3    GAGAAGGTTCTAGAAGAAGTGGACTGGCTAATCACCAAGCTTAAGGGACAAGTGAGCCAA  3318
83P4B8v.4    GAGAAGGTTCTAGAAGAAGTGGACTGGCTAATCACCAAGCTTAAGGACAAGTGAGCCAA   3180
83P4B8v.2    GAGAAGGTTCTAGAAGAAGTGGACTGGCTAATCACCAAGCTTAAGGACAAGTGAGCCAA   3302
83P4B8v.1    GAGAAGGTTCTAGAAGAAGTGGACTGGCTAATCACCAAGCTTAAGGGACAAGTGAGCCAA  3360
83P4B8v.5    GAGAAGGTTCTAGAAGAAGTGGACTGGCTAATCACCAAGCTTAAGGGACAAGTGAGCCAA  3360
83P4B8v.6    GAGAAGGTTCTAGAAGAAGTGGACTGGCTAATCACCAAGCTTAAGGGACAAGTGAGCCAA  3180
             ******************************************

83P4B8v.3    GAAACCTTATCAGAAGAGAGGCCTCTTCTCAGGCAACCCTACCAAATCAGCCTGTTGAGAAA  3378
83P4B8v.4    GAAACCTTATCAGAAGAAGAGGCCTCTTCTCAGGCAACCCTACCAAATCAGCCTGTTGAGAAA 3240
83P4B8v.2    GAAACCTTATCAGAAGAAGAGGCCTCTTCTCAGGCAACCCTACCAAATCAGCCTGTTGAGAAA 3362
83P4B8v.1    GAAACCTTATCAGAAGAAGAGGCCTCTTCTCAGGCAACCCTACCAAATCAGCCTGTTGAGAAA 3420
83P4B8v.5    GAAACCTTATCAG-----------------------------------------------   3373
83P4B8v.6    GAAACCTTATCAG-----------------------------------------------   3193
             *************

83P4B8v.3    GCTATCATCATGCAACTGGGAACTCTGCTTACATTTTTCCACGAGCTGGTGCAGACAGCT  3438
83P4B8v.4    GCTATCATCATGCAACTGGGAACTCTGCTTACATTTTTCCACGAGCTGGTGCAGACAGCT  3300
83P4B8v.2    GCTATCATCATGCAACTGGGAACTCTGCTTACATTTTTCCACGAGCTGGTGCAGACAGCT  3422
83P4B8v.1    GCTATCATCATGCAACTGGGAACTCTGCTTACATTTTTCCACGAGCTGGTGCAGACAGCT  3480
83P4B8v.5    ------------------------------------------------------------
83P4B8v.6    ------------------------------------------------------------

83P4B8v.3    CTGCCATCAGGCAGCTGTGTGGACACCTTGTTAAAGGACTTGTGCAAAATGTACACCACA  3498
83P4B8v.4    CTGCCATCAGGCAGCTGTGTGGACACCTTGTTAAAGGACTTGTGCAAAATGTACACCACA  3360
83P4B8v.2    CTGCCATCAGGCAGCTGTGTGGACACCTTGTTAAAGGACTTGTGCAAAATGTACACCACA  3482
83P4B8v.1    CTGCCATCAGGCAGCTGTGTGGACACCTTGTTAAAGGACTTGTGCAAAATGTACACCACA  3540
83P4B8v.5    ------------------------------------------------------------
83P4B8v.6    ------------------------------------------------------------
```

Figure 13b (continued)

```
83P4B8v.3  CTTACAGCCCTTGTCAGATATTATCTCCAGTGTGTCAGAGCTCCGAGGAATCCCAAAA  3558
83P4B8v.4  CTTACAGCCCTTGTCAGATATTATCTCCAGTGTGTCAGAGCTCCGAGGAATCCCAAAA  3420
83P4B8v.2  CTTACAGCCCTTGTCAGATATTATCTCCAGTGTGTCAGAGCTCCGAGGAATCCCAAAA  3542
83P4B8v.1  CTTACAGCCCTTGTCAGATATTATCTCCAGTGTGTCAGAGCTCCGAGGAATCCCAAAA  3600
83P4B8v.5  ------------TATCTCCAGTGTGTCAGAGCTCCGAGGAATCCCAAAA  3412
83P4B8v.6  ------------TATCTCCAGTGTGTCAGAGCTCCGAGGAATCCCAAAA  3232
                       ******************************************

83P4B8v.3  AATATGGAAAAGCTGGTGAAGCTGTCTGGTTCTCATCTGACCCCCCTGTGTTATTCTTTC  3618
83P4B8v.4  AATATGGAAAAGCTGGTGAAGCTGTCTGGTTCTCATCTGACCCCCCTGTGTTATTCTTTC  3480
83P4B8v.2  AATATGGAAAAGCTGGTGAAGCTGTCTGGTTCTCATCTGACCCCCCTGTGTTATTCTTTC  3602
83P4B8v.1  AATATGGAAAAGCTGGTGAAGCTGTCTGGTTCTCATCTGACCCCCCTGTGTTATTCTTTC  3660
83P4B8v.5  AATATGGAAAAGCTGGTGAAGCTGTCTGGTTCTCATCTGACCCCCCTGTGTTATTCTTTC  3472
83P4B8v.6  AATATGGAAAAGCTGGTGAAGCTGTCTGGTTCTCATCTGACCCCCCTGTGTTATTCTTTC  3292
           ************************************************************

83P4B8v.3  ATTTCTTACGTACAGAATAAGAGTAAGAGCCTGAACTATACGGGAGAGAAAAAGGAGAAA  3678
83P4B8v.4  ATTTCTTACGTACAGAATAAGAGTAAGAGCCTGAACTATACGGGAGAGAAAAAGGAGAAA  3540
83P4B8v.2  ATTTCTTACGTACAGAATAAGAGTAAGAGCCTGAACTATACGGGAGAGAAAAAGGAGAAA  3662
83P4B8v.1  ATTTCTTACGTACAGAATAAGAGTAAGAGCCTGAACTATACGGGAGAGAAAAAGGAGAAA  3720
83P4B8v.5  ATTTCTTACGTACAGAATAAGAGTAAGAGCCTGAACTATACGGGAGAGAAAAAGGAGAAA  3532
83P4B8v.6  ATTTCTTACGTACAGAATAAGAGTAAGAGCCTGAACTATACGGGAGAGAAAAAGGAGAAA  3352
           ************************************************************

83P4B8v.3  CCTGCTGCCGTTGCCACAGCCATGGCCAGAGTTCTTCGGGAAACCAAGCCAATCCCTAAC  3738
83P4B8v.4  CCTGCTGCCGTTGCCACAGCCATGGCCAGAGTTCTTCGGGAAACCAAGCCAATCCCTAAC  3600
83P4B8v.2  CCTGCTGCCGTTGCCACAGCCATGGCCAGAGTTCTTCGGGAAACCAAGCCAATCCCTAAC  3722
83P4B8v.1  CCTGCTGCCGTTGCCACAGCCATGGCCAGAGTTCTTCGGGAAACCAAGCCAATCCCTAAC  3780
83P4B8v.5  CCTGCTGCCGTTGCCACAGCCATGGCCAGAGTTCTTCGGGAAACCAAGCCAATCCCTAAC  3592
83P4B8v.6  CCTGCTGCCGTTGCCACAGCCATGGCCAGAGTTCTTCGGGAAACCAAGCCAATCCCTAAC  3412
           ************************************************************

83P4B8v.3  CTCATCTTTGCCATAGAACAGTATGAAAAATTTCTCATCCACCTTTCTAAGAAGTCCAAG  3798
83P4B8v.4  CTCATCTTTGCCATAGAACAGTATGAAAAATTTCTCATCCACCTTTCTAAGAAGTCCAAG  3660
83P4B8v.2  CTCATCTTTGCCATAGAACAGTATGAAAAATTTCTCATCCACCTTTCTAAGAAGTCCAAG  3782
83P4B8v.1  CTCATCTTTGCCATAGAACAGTATGAAAAATTTCTCATCCACCTTTCTAAGAAGTCCAAG  3840
83P4B8v.5  CTCATCTTTGCCATAGAACAGTATGAAAAATTTCTCATCCACCTTTCTAAGAAGTCCAAG  3652
83P4B8v.6  CTCATCTTTGCCATAGAACAGTATGAAAAATTTCTCATCCACCTTTCTAAGAAGTCCAAG  3472
           ************************************************************
```

Figure 13b (continued)

```
83P4B8v.3    GTGAACCTGATGCAGCACACATGAAGCTCAGCACCTCACGAGACTTCAAGATCAAAGGAAAC  3858
83P4B8v.4    GTGAACCTGATGCAGCACACATGAAGCTCAGCACCTCACGAGACTTCAAGATCAAAGGAAAC  3720
83P4B8v.2    GTGAACCTGATGCAGCACACATGAAGCTCAGCACCTCACGAGACTTCAAGATCAAAGGAAAC  3842
83P4B8v.1    GTGAACCTGATGCAGCACACATGAAGCTCAGCACCTCACGAGACTTCAAGATCAAAGGAAAC  3900
83P4B8v.5    GTGAACCTGATGCAGCACACATGAAGCTCAGCACCTCACGAGACTTCAAGATCAAAGGAAAC  3712
83P4B8v.6    GTGAACCTGATGCAGCACACATGAAGCTCAGCACCTCACGAGACTTCAAGATCAAAGGAAAC  3532
             ************************************************************

83P4B8v.3    ATCCTAGACATGGTTCTTCGAGAGGATGGCGAAGATGAAAATGAAGAGGGCACTGCATCA   3918
83P4B8v.4    ATCCTAGACATGGTTCTTCGAGAGGATGGCGAAGATGAAAATGAAGAGGGCACTGCATCA   3780
83P4B8v.2    ATCCTAGACATGGTTCTTCGAGAGGATGGCGAAGATGAAAATGAAGAGGGCACTGCATCA   3902
83P4B8v.1    ATCCTAGACATGGTTCTTCGAGAGGATGGCGAAGATGAAAATGAAGAGGGCACTGCATCA   3960
83P4B8v.5    ATCCTAGACATGGTTCTTCGAGAGGATGGCGAAGATGAAAATGAAGAGGGCACTGCATCA   3772
83P4B8v.6    ATCCTAGACATGGTTCTTCGAGAGGATGGCGAAGATGAAAATGAAGAGGGCACTGCATCA   3592
             ************************************************************

83P4B8v.3    GAGCATGGGGGACAGAACAAAGAACCAGCCCAAGAAGAAGGAAAAATAAATGAAATGC    3978
83P4B8v.4    GAGCATGGGGGACAGAACAAAGAACCAGCCCAAGAAGAAGGAAAAATAAATGAAATGC    3840
83P4B8v.2    GAGCATGGGGGACAGAACAAAGAACCAGCCCAAGAAGAAGGAAAAATAAATGAAATGC    3962
83P4B8v.1    GAGCATGGGGGACAGAACAAAGAACCAGCCCAAGAAGAAGGAAAAATAAATGAAATGC    4020
83P4B8v.5    GAGCATGGGGGACAGAACAAAGAACCAGCCCAAGAAGAAGGAAAAATAAATGAAATGC    3832
83P4B8v.6    GAGCATGGGGGACAGAACAAAGAACCAGCCCAAGAAGAAGGAAAAATAAATGAAATGC    3652
             ************************************************************

83P4B8v.3    CTGAGTTAATGTG  3991
83P4B8v.4    CTGAGTTAATGTG  3853
83P4B8v.2    CTGAGTTAATGTG  3975
83P4B8v.1    CTGAGTTAATGTG  4033
83P4B8v.5    CTGAGTTAATGTG  3845
83P4B8v.6    CTGAGTTAATGTG  3665
             *************
```

Figure 14b Alignment of protein sequences of 83P4B8 transcript variants
(SEQ ID NOs: 24, 120, 121, 122, 123, 124).

```
83P4B8v.1    MDQKILSLAAEKTADKLQEFLQTLREGDLTNLLQNQAVKGKVAGALLRAIFKGSPCSEEA    60
83P4B8v.2    ------------------------------------------------------------
83P4B8v.3    MDQKILSLAAEKTADKLQEFLQTLREGDLTNLLQNQAVKGKVAGALLRAIFKGSPCSEEA    60
83P4B8v.4    MDQKILSLAAEKTADKLQEFLQTLREGDLTNLLQNQAVKGKVAGALLRAIFKGSPCSEEA    60
83P4B8v.5    MDQKILSLAAEKTADKLQEFLQTLREGDLTNLLQNQAVKGKVAGALLRAIFKGSPCSEEA    60
83P4B8v.6    MDQKILSLAAEKTADKLQEFLQTLREGDLTNLLQNQAVKGKVAGALLRAIFKGSPCSEEA    60

83P4B8v.1    GTLRRRKIYTCCIQLVESGDLQKEIVSEIIGLLMLEAHHFPGPLLVELANEFISAVREGS   120
83P4B8v.2    ------------------------------------------------------------
83P4B8v.3    GTLRRRKIYTCCIQLVESGDLQKEIVSEIIGLLMLEAHHFPGPLLVELANEFISAVREGS   120
83P4B8v.4    GTLRRRKIYTCCIQLVESGDLQKEIVSEIIGLLMLEAHHFPGPLLVELANEFISAVREGS   120
83P4B8v.5    GTLRRRKIYTCCIQLVESGDLQKEIVSEIIGLLMLEAHHFPGPLLVELANEFISAVREGS   120
83P4B8v.6    GTLRRRKIYTCCIQLVESGDLQKEIVSEIIGLLMLEAHHFPGPLLVELANEFISAVREGS   120

83P4B8v.1    LVNGKSLELLPIIILTALALATKKENLAYGKGVLSGEECKKQLINTLCSGRWDQQYVIQHTSM   180
83P4B8v.2    -----------------------------------------------------------M     1
83P4B8v.3    LVNGKSLELLPIIILTALALATKKENLAYGKGVLSGEECKKQLINTLCSGRWDQQYVIQHTSM   180
83P4B8v.4    LVNGKSLELLPIIILTALALATKKENLAYGKGVLSGEECKKQLINTLCSGRWDQQYVIQHTSM   180
83P4B8v.5    LVNGKSLELLPIIILTALALATKKENLAYGKGVLSGEECKKQLINTLCSGRWDQQYVIQHTSM   180
83P4B8v.6    LVNGKSLELLPIIILTALALATKKENLAYGKGVLSGEECKKQLINTLCSGRWDQQYVIQHTSM   180
                                                                        *

83P4B8v.1    FKDVPLTAEEVEFVVEKALSMFSKMNLQEIPPLVYQLLVLSSKGSRKSVLEGIIAFFSAL   240
83P4B8v.2    FKDVPLTAEEVEFVVEKALSMFSKMNLQEIPPLVYQLLVLSSKGSRKSVLEGIIAFFSAL    61
83P4B8v.3    FKDVPLTAEEVEFVVEKALSMFSKMNLQEIPPLVYQLLVLSSKGSRKSVLEGIIAFFSAL   240
83P4B8v.4    FKDVPLTAEEVEFVVEKALSMFSKMNLQEIPPLVYQLLVLSSKGSRKSVLEGIIAFFSAL   240
83P4B8v.5    FKDVPLTAEEVEFVVEKALSMFSKMNLQEIPPLVYQLLVLSSKGSRKSVLEGIIAFFSAL   240
83P4B8v.6    FKDVPLTAEEVEFVVEKALSMFSKMNLQEIPPLVYQLLVLSSKGSRKSVLEGIIAFFSAL   240
             ************************************************************

83P4B8v.1    DKQHNEEQSGDELLDVVTVPSGELRHVEGTIILHIVFAIKLDYELGRELVKHLKVGQQGD   300
83P4B8v.2    DKQHNEEQSGDELLDVVTVPSGELRHVEGTIILHIVFAIKLDYELGRELVKHLKVGQQGD   121
83P4B8v.3    DKQHNEEQSGDELLDVVTVPSGELRHVEGTIILHIVFAIKLDYELGRELVKHLKVGQQGD   300
83P4B8v.4    DKQHNEEQSGDELLDVVTVPSGELRHVEGTIILHIVFAIKLDYELGRELVKHLKVGQQGD   300
83P4B8v.5    DKQHNEEQSGDELLDVVTVPSGELRHVEGTIILHIVFAIKLDYELGRELVKHLKVGQQGD   300
```

Figure 14b (continued)

```
83P4B8v.6_  DKQHNEEQSGDELLDVTVPSGELRHVEGTIILHTVFAIKLDYELGRELVKHLKVGQQGD 300
            *********************************************************

83P4B8v.1_  SNNNLSPFSIALLLSVTRIQRFQDQVLDLLKTSVVKSFKDLQLLQGSKFLQNLVPHRSYV 360
83P4B8v.2_  SNNNLSPFSIALLLSVTRIQRFQDQVLDLLKTSVVKSFKDLQLLQGSKFLQNLVPHRSYV 181
83P4B8v.3_  SNNNLSPFSIALLLSVTRIQRFQDQVLDLLKTSVVKSFKDLQLLQGSKFLQNLVPHRSYV 360
83P4B8v.4_  SNNNLSPFSIALLLSVTRIQRFQDQVLDLLKTSVVKSFKDLQLLQGSKFLQNLVPHRSYV 360
83P4B8v.5_  SNNNLSPFSIALLLSVTRIQRFQDQVLDLLKTSVVKSFKDLQLLQGSKFLQNLVPHRSYV 360
83P4B8v.6_  SNNNLSPFSIALLLSVTRIQRFQDQVLDLLKTSVVKSFKDLQLLQGSKFLQNLVPHRSYV 360
            *********************************************************

83P4B8v.1_  STMLEVVKNSVHSWDHVTQGLVELGFILMDSYGPKKVLDGKTIETSPSLSRMPNQHACK 420
83P4B8v.2_  STMLEVVKNSVHSWDHVTQGLVELGFILMDSYGPKKVLDGKTIETSPSLSRMPNQHACK 241
83P4B8v.3_  STMLEVVKNSVHSWDHVTQGLVELGFILMDSYGPKKVLDGKTIETSPSLSRMPNQHACK 420
83P4B8v.4_  STMLEVVKNSVHSWDHVTQGLVELGFILMDSYGPKKVLDGKTIETSPSLSRMPNQHACK 420
83P4B8v.5_  STMLEVVKNSVHSWDHVTQGLVELGFILMDSYGPKKVLDGKTIETSPSLSRMPNQHACK 420
83P4B8v.6_  STMLEVVKNSVHSWDHVTQGLVELGFILMDSYGPKKVLDGKTIETSPSLSRMPNQHACK 420
            *********************************************************

83P4B8v.1_  LGANILLETFKIHEMIRQEILEQVLNRVVTRASSPISHFLDLLSNIVMYAPLVLQSCSSK 480
83P4B8v.2_  LGANILLETFKIHEMIRQEILEQVLNRVVTRASSPISHFLDLLSNIVMYAPLVLQSCSSK 301
83P4B8v.3_  LGANILLETFKIHEMIRQEILEQVLNRVVTRASSPISHFLDLLSNIVMYAPLVLQSCSSK 480
83P4B8v.4_  LGANILLETFKIHEMIRQEILEQVLNRVVTRASSPISHFLDLLSNIVMYAPLVLQSCSSK 480
83P4B8v.5_  LGANILLETFKIHEMIRQEILEQVLNRVVTRASSPISHFLDLLSNIVMYAPLVLQSCSSK 480
83P4B8v.6_  LGANILLETFKIHEMIRQEILEQVLNRVVTRASSPISHFLDLLSNIVMYAPLVLQSCSSK 480
            *********************************************************

83P4B8v.1_  VTEAFDYLSFLPLQTVQRLLKAVQPLLKVSMSMRDCLIIVLRKAMFANQLDARKSAVAGF 540
83P4B8v.2_  VTEAFDYLSFLPLQTVQRLLKAVQPLLKVSMSMRDCLIIVLRKAMFANQLDARKSAVAGF 361
83P4B8v.3_  VTEAFDYLSFLPLQTVQRLLKAVQPLLKVSMSMRDCLIIVLRKAMFANQLDARKSAVAGF 540
83P4B8v.4_  VTEAFDYLSFLPLQTVQRLLKAVQPLLKVSMSMRDCLIIVLRKAMFANQLDARKSAVAGF 540
83P4B8v.5_  VTEAFDYLSFLPLQTVQRLLKAVQPLLKVSMSMRDCLIIVLRKAMFANQLDARKSAVAGF 540
83P4B8v.6_  VTEAFDYLSFLPLQTVQRLLKAVQPLLKVSMSMRDCLIIVLRKAMFANQLDARKSAVAGF 540
            *********************************************************

83P4B8v.1_  LLLKNFKVLGSLSSSQCSQSLSVSQVHVDSHYNSVANETFCLEIMDSLRRCLSQQAD 600
83P4B8v.2_  LLLKNFKVLGSLSSSQCSQSLSVSQVHVDSHYNSVANETFCLEIMDSLRRCLSQQAD 421
83P4B8v.3_  LLLKNFKVLGSLSSSQCSQSLSVSQVHVDSHYNSVANETFCLEIMDSLRRCLSQQAD 600
83P4B8v.4_  LLLKNFKVLGSLSSSQCSQSLSVSQVHVDSHYNSVANETFCLEIMDSLRRCLSQQAD 600
```

Figure 14b (continued)

```
83P4B8v.5  LLLLKNFKVIGSLSSSQCSQSLSVSQVHVDVHSHYNSVANETFCLEIMDSLRRCLSQQAD 600
83P4B8v.6  LLLLKNFKVIGSLSSSQCSQSLSVSQVHVDVHSHYNSVANETFCLEIMDSLRRCLSQQAD 600
           ************************************************************

83P4B8v.1  VRLMLYEGFYDVLRRNSQLANSVMQTLLSQLKQFYEPKPDLLPPLKLDACIITQGDKISL 660
83P4B8v.2  VRLMLYEGFYDVLRRNSQLANSVMQTLLSQLKQFYEPKPDLLPPLKLDACIITQGDKISL 481
83P4B8v.3  VRLMLYEGFYDVLRRNSQLANSVMQTLLSQLKQFYEPKPDLLPPLKLDACIITQGDKISL 660
83P4B8v.4  VRLMLYEGFYDVLRRNSQLANSVMQTLLSQLKQFYEPKPDLLPPLKLDACIITQGDKISL 660
83P4B8v.5  VRLMLYEGFYDVLRRNSQLANSVMQTLLSQLKQFYEPKPDLLPPLKLDACIITQGDKISL 660
83P4B8v.6  VRLMLYEGFYDVLRRNSQLANSVMQTLLSQLKQFYEPKPDLLPPLKLDACIITQGDKISL 660
           ************************************************************

83P4B8v.1  QEPLDYLLCCIQHCLAWYKNTVIPLQQGEEEEEEAFYEDLDDILESITNRMIKSELED 720
83P4B8v.2  QEPLDYLLCCIQHCLAWYKNTVIPLQQGEEEEEEAFYEDLDDILESITNRMIKSELED 541
83P4B8v.3  QEPLDYLLCCIQHCLAWYKNTVIPLQQGEEEEEEAFYEDLDDILESITNRMIKSELED 720
83P4B8v.4  QEPLDYLLCCIQHCLAWYKNTVIPLQQGEEEEEEAFYEDLDDILESITNRMIKSELED 720
83P4B8v.5  QEPLDYLLCCIQHCLAWYKNTVIPLQQGEEEEEEAFYEDLDDILESITNRMIKSELED 720
83P4B8v.6  QEPLDYLLCCIQHCLAWYKNTVIPLQQGEEEEEEAFYEDLDDILESITNRMIKSELED 720
           ***********************************************************

83P4B8v.1  FELDKSADFSQSTSIGIKNNISAFLVMGVCEVLIEYNFSISSFSKNRFEDIISLFMCYKK 780
83P4B8v.2  FELDKSADFSQSTSIGIKNNISAFLVMGVCEVLIEYNFSISSFSKNRFEDIISLFMCYKK 601
83P4B8v.3  FELDKSADFSQSTSIGIKNNISAFLVMGVCEVLIEYNFSISSFSKNRFEDIISLFMCYKK 780
83P4B8v.4  FELDKSADFSQSTSIGIKNNISAFLVMGVCEVLIEYNFSISSFSKNRFEDIISLFMCYKK 780
83P4B8v.5  FELDKSADFSQSTSIGIKNNISAFLVMGVCEVLIEYNFSISSFSKNRFEDIISLFMCYKK 780
83P4B8v.6  FELDKSADFSQSTSIGIKNNISAFLVMGVCEVLIEYNFSISSFSKNRFEDIISLFMCYKK 780
           ************************************************************

83P4B8v.1  LSDIINEKAGKAKTKMANKTSDSLLSMKFVSSLLTALFRDSIQHQESLSVLRSSNEFMR 840
83P4B8v.2  LSDIINEKAGKAKTKMANKTSDSLLSMKFVSSLLTALFRDSIQHQESLSVLRSSNEFMR 661
83P4B8v.3  LSDIINEKAGKAKTKMANKTSDSLLSMKFVSSLLTALFR---------SSNEFMR 826
83P4B8v.4  LSDIINEKAGKAKTKMANKTSDSLLSMKFVSSLLTALFR--------------- 819
83P4B8v.5  LSDIINEKAGKAKTKMANKTSDSLLSMKFVSSLLTALFRDSIQHQESLSVLRSSNEFMR 840
83P4B8v.6  LSDIINEKAGKAKTKMANKTSDSLLSMKFVSSLLTALFR--------------- 819
           ***************************************               *

83P4B8v.1  YAVNVALQKVQQLKETGHVSGPDGQNPEKIFQNLCDITRVLLWRYTSIPTSVEESGKKEK 900
83P4B8v.2  YAVNVALQKVQQLKETGHVSGPDGQNPEKIFQNLCDITRVLLWRYTSIPTSVEESGKKEK 721
83P4B8v.3  YAVNVALQKVQQLKETGHVSGPDGQNPEKIFQNLCDITRVLLWRYTSIPTSVEESGKKEK 886
```

Figure 14b (continued)

```
83P4B8v.4    ------------------------------------------------VLLWRYTSIPTSVEESGKKEK  840
83P4B8v.5    YAVNVALQKVQQLKETGHVSGPDGQNPEKIFQNLCDITRVLLWRYTSIPTSVEESGKKEK  900
83P4B8v.6    ------------------------------------------------VLLWRYTSIPTSVEESGKKEK  840
                                                             ************

83P4B8v.1    GKSISLLCLEGLQKIFSAVQQFYQPKIQQFLRALDVTDKEGEEREDADVSVTQRTAFQIR  960
83P4B8v.2    GKSISLLCLEGLQKIFSAVQQFYQPKIQQFLRALDVTDKEGEEREDADVSVTQRTAFQIR  781
83P4B8v.3    GKSISLLCLEGLQKIFSAVQQFYQPKIQQFLRALDVTDKEGEEREDADVSVTQRTAFQIR  946
83P4B8v.4    GKSISLLCLEGLQKIFSAVQQFYQPKIQQFLRALDVTDKEGEEREDADVSVTQRTAFQIR  900
83P4B8v.5    GKSISLLCLEGLQKIFSAVQQFYQPKIQQFLRALDVTDKEGEEREDADVSVTQRTAFQIR  960
83P4B8v.6    GKSISLLCLEGLQKIFSAVQQFYQPKIQQFLRALDVTDKEGEEREDADVSVTQRTAFQIR  900
             ************************************************************

83P4B8v.1    QFQRSLLNLLSSQEEDFNSKEALLLVTLTSLSKLLEPSSPQFVQMLSWTSKICKENSRE  1020
83P4B8v.2    QFQRSLLNLLSSQEEDFNSKEALLLVTLTSLSKLLEPSSPQFVQMLSWTSKICKENSRE   841
83P4B8v.3    QFQRSLLNLLSSQEEDFNSKEALLLVTLTSLSKLLEPSSPQFVQMLSWTSKICKENSRE  1006
83P4B8v.4    QFQRSLLNLLSSQEEDFNSKEALLLVTLTSLSKLLEPSSPQFVQMLSWTSKICKENSRE   960
83P4B8v.5    QFQRSLLNLLSSQEEDFNSKEALLLVTLTSLSKLLEPSSPQFVQMLSWTSKICKENSRE  1020
83P4B8v.6    QFQRSLLNLLSSQEEDFNSKEALLLVTLTSLSKLLEPSSPQFVQMLSWTSKICKENSRE   960
             ***********************************************************

83P4B8v.1    DALFCKSLMNLLFSLHVSYKSPVILLRDLSQDIHGHLGDIDQDVEVEKTNHFAIVNLRTA  1080
83P4B8v.2    DALFCKSLMNLLFSLHVSYKSPVILLRDLSQDIHGHLGDIDQDVEVEKTNHFAIVNLRTA   901
83P4B8v.3    DALFCKSLMNLLFSLHVSYKSPVILLRDLSQDIHGHLGDIDQDVEVEKTNHFAIVNLRTA  1066
83P4B8v.4    DALFCKSLMNLLFSLHVSYKSPVILLRDLSQDIHGHLGDIDQDVEVEKTNHFAIVNLRTA  1020
83P4B8v.5    DALFCKSLMNLLFSLHVSYKSPVILLRDLSQDIHGHLGDIDQDVEVEKTNHFAIVNLRTA  1080
83P4B8v.6    DALFCKSLMNLLFSLHVSYKSPVILLRDLSQDIHGHLGDIDQDVEVEKTNHFAIVNLRTA  1020
             ************************************************************

83P4B8v.1    APTVCLLVLSQAEKVLEEVDWLITKLKGQVSQETLSEEASSQATLPNQPVEKAIIMQLGT  1140
83P4B8v.2    APTVCLLVLSQAEKVLEEVDWLITKLKGQVSQETLSEEASSQATLPNQPVEKAIIMQLGT   961
83P4B8v.3    APTVCLLVLSQAEKVLEEVDWLITKLKGQVSQETLSEEASSQATLPNQPVEKAIIMQLGT  1126
83P4B8v.4    APTVCLLVLSQAEKVLEEVDWLITKLKGQVSQETLSEEASSQATLPNQPVEKAIIMQLGT  1080
83P4B8v.5    APTVCLLVLSQAEKVLEEVDWLITKLKGQVSQETLSVSPG-------------------  1120
83P4B8v.6    APTVCLLVLSQAEKVLEEVDWLITKLKGQVSQETLSVSPG-------------------  1060
             ************************************

83P4B8v.1    LLTFFHELVQTALPSGSCVDTLLKDLCKMYTTLTALVRYYLQVCQSSGGIPKNMEKLVKL  1200
83P4B8v.2    LLTFFHELVQTALPSGSCVDTLLKDLCKMYTTLTALVRYYLQVCQSSGGIPKNMEKLVKL  1021
```

Figure 14b (continued)

```
83P4B8v.3   LLTFFHELVQTALPSGSCVDTLLKDLCKMYTTLTALVRYYLQVCQSSGGIPKNMEKLVKL 1186
83P4B8v.4   LLTFFHELVQTALPSGSCVDTLLKDLCKMYTTLTALVRYYLQVCQSSGGIPKNMEKLVKL 1140
83P4B8v.5   ------------------------------------------------------------
83P4B8v.6   ------------------------------------------------------------

83P4B8v.1   SGSHLTPLCYSFISYVQNKSKSLNYTGEKKEKPAAVATAMARVLRETKPIPNLIFAIEQY 1260
83P4B8v.2   SGSHLTPLCYSFISYVQNKSKSLNYTGEKKEKPAAVATAMARVLRETKPIPNLIFAIEQY 1081
83P4B8v.3   SGSHLTPLCYSFISYVQNKSKSLNYTGEKKEKPAAVATAMARVLRETKPIPNLIFAIEQY 1246
83P4B8v.4   SGSHLTPLCYSFISYVQNKSKSLNYTGEKKEKPAAVATAMARVLRETKPIPNLIFAIEQY 1200
83P4B8v.5   ---------------------VSELRRNPKKYGKAGEAVWFSSDP-PVLFFHFLRT 1154
83P4B8v.6   ---------------------VSELRRNPKKYGKAGEAVWFSSDP-PVLFFHFLRT 1094
                                 .. *  ..:.*   .::.*  * *:* * :  :

83P4B8v.1   EKFLIHLSKKKSKVNLMQHMKLSTSRDFKIKGNILDMVLREDGEDENEEGTASEHGGQNKE 1320
83P4B8v.2   EKFLIHLSKKKSKVNLMQHMKLSTSRDFKIKGNILDMVLREDGEDENEEGTASEHGGQNKE 1141
83P4B8v.3   EKFLIHLSKKKSKVNLMQHMKLSTSRDFKIKGNILDMVLREDGEDENEEGTASEHGGQNKE 1306
83P4B8v.4   EKFLIHLSKKKSKVNLMQHMKLSTSRDFKIKGNILDMVLREDGEDENEEGTASEHGGQNKE 1260
83P4B8v.5   E----------------------------------------------------------- 1155
83P4B8v.6   E----------------------------------------------------------- 1095
             *

83P4B8v.1   PAKKKRKK 1328
83P4B8v.2   PAKKKRKK 1149
83P4B8v.3   PAKKKRKK 1314
83P4B8v.4   PAKKKRKK 1268
83P4B8v.5   --------
83P4B8v.6   --------
```

Figure 11c  Nucleotide sequences of transcript variants of 109P1D4
>109P1D4 v.2 (SEQ ID NO:125).

```
cccctttctc ccctcggtt  aagtccctcc ccctcgccat tcaaagggc  tggctcggca      60
ctggctcctt gcagtcggcg aactgtcggg gcggaggag  ccgtgagcag tagctgcact     120
cagctgcccg ccgcgcaaag aggaaggcaa gccaaacaga gtgccagag  tggcagtgcc     180
agcggcgaca caggcagcac aggcagcccg ggctgcctga atagcctcag aaacaacctc     240
agcgactccg gctgctctgc ggactgcgag ctgtggcgt  agaccccgct acagcagtcg     300
agcctccgt  ggagcgggcg gaagccttt  ttctcccttt cgttacctc  ttcattctac     360
cagtctccgt ggagcgggcg gaagccttt  ttctcccttt cgttacctc  ttcattctac     360
tctaaaggca tcgttattag gaaaatcctg ttgcgaataa gaaggattcc acagatcaca     420
taccggagag gttttgcctc agctgctctc aactttgtaa tcttgtgaag aagctgacaa     480
gcttggctga ttgcagagca ctatgaggac tgaacgacag tgggttttaa ttcagatatt     540
tcaagtgttg tgcggttaa  tacaacaaac tgtaacaagt gtacctggta tggacttgtt     600
gtccgggacg tacattttcg cggtcctgct agcatgcgtg gtgttccact ctggcgccca     660
ggagaaaaac tacaccatcc gagaagaaat gccagaaaac gtcctgatag gcgacttgtt     720
gaaagacctt aacttgtcgc tgattccaaa caagtccttg acaactgcta tgcagttcaa     780
gctagtgtac agaccggaca atgtgccact gattcgaatt gaagaggata ctggtgagat     840
cttcactact ggcgctcgca ttgatctgtg gaaattatgt gctgtatcc  caaggatga     900
gcattgcttt tatgaagtgg aggttgccat tttgccggat gaatattta  gactggttaa     960
gatacgtttt ctgatagaag atataaatga taatgcacca ttgttcccag caacagttat    1020
caacatatca attccagaga actcggctat aaactctaaa tatactctcc cagcggctgt    1080
tgatcctgac gtaggaataa acggagttca aaactacgaa ctaattaaga gtcaaaacat    1140
tttggcctc  gatgtcattg aaacaccaga aggagacaag atgccacaag tgattgttca    1200
aaaggagtta gataggaag  agaaggatac ctacgtgatg aaagtaaagg ttgaagatgg    1260
tggctttcct caaagatcca gtactgctat tttgcaagtg agtgttactg atacaaatga    1320
caaccaccca gtcttaagg  agacagagat tgaagtcagt tgaagtgaaa atgctcctgt    1380
aggcacttca gtgacacagc tccatgccac agatgctgac ataggtgaaa atgccaagat    1440
ccacttctct ttcacaaatc tagtctccaa cattgccagg agattatttc acctcaatgc    1500
caccactgaa cttatcacaa tcaaagaaac actgaggaaa agagaaaacc caaaccacaa    1560
gttactggtt ttggcaagtg atggtggatt gatgccagca agaccaatgg tgctggtaaa    1620
tgttacagat gtcaatgata gtgtccatc  cattgacata agatacatcg tcaatcctgt    1680
caatgacaca gttgttcttt cagaaaatat tccactcaac accaaaattg ctctccataac   1740
tgtgacggat aaggatgcgg accataatgg caggtgaca  tgcttcacag atcatgaaat    1800
cccttttcaga ttaaggccag tattcagtaa tcagttcctc ctggagactg cagcatatct    1860
tgactatgag tccacaaaag aatatgccat tgctcttcat caaagtgaaa gctgcagatg    1920
tcctttgaat cagtcagcaa tgctcttcg  tattcctgag ataactctc  acaatgctcc    1980
agtttcacc  cagtctttcg taactgtttc tattcctag  cagtgggcct aatgctaaga    2040
gttgacgaaa gtaagtgcaa tggatgcaa  cagtgcaga  cctgattgt  cgtacaggca    2100
gctaggccct gatgctccac ctgaattcag ctgaattcag aatgctaaga tgctgactgt    2160
agtgaagaaa ctagatagag aaaaagagga taaatattta ttcacaattc tggcaaaaga    2220
```

Figure 11c (continued)

```
taacggggta ccacccttaa ccagcaatgt cacagtcttt gtaagcatta ttgatcagaa 2280
tgacaatagc ccagttttca ctcacaatga atacaacttc tatgtcccag aaaaccttcc 2340
aaggcatgtt acagtaggac taatcactgt aactgatcct gattatgag acaattctgc 2400
agttacgctc tccattttag atgagaatga tgacttcacc attgattcac aaactgg tgt 2460
catccgacca aatatttcat ttgatagaga aaaacaagaa tcttacactt tctatgtaaa 2520
ggctgaggat ggtggtagag tatcacgttc ttcaagtgcc aagtaacca taaatggt 2580
tgatgtcaat gacaacaaac cagtttcat tgtccctcct tccaactgtt cttatgaatt 2640
ggttctaccg tccactaatc caggcacagt ggtctttcag gtaattgctg ttgacaatga 2700
cactggcatg aatgcagagg ttcgttacag cattgtagga ggaaacacaa gagatctgtt 2760
tgcaatcgac caagaaacag gcaacataac attgatggag aaatgtgatg ttacagacct 2820
tggtttacac agagtgttgg tcaaagctaa tgacttagga cagcctgatt ctctcttcag 2880
tgttgtaatt gtcaatctgt tcgtgaatga gtcggtgacc aatgctacac tgattaatga 2940
actggtgcgc aaaagcactg aagcaccagt gacccaaat actgagatag ctgatgtatc 3000
ctcaccaact agtgactatg tcaagatcct ggttgcagct gttgctggca ccataactgt 3060
cgttgtagtt atttcatca ctgctgtagt aagatgtcgc caggcaccac accttaaggc 3120
tgctcagaaa acaagcaga attctgaatg ggctacccca aaccagaaa acaggcagat 3180
gataatgatg aagaaaaaga aaagaaagaa gaagcattcc cctaagaact tgctgcttaa 3240
ttttgtcact attgaagaaa ctaagcagga tagtgttgac agtgatgaa acagagtcaa 3300
actagaccttt cctattgatc tagaagagca aacaatggga aagtaacatt gggtaactac 3360
acctactact ttcaagcccg acagccctga tttggcccga cactacaaat ctgcctctcc 3420
acagcctgcc ttccaaattc agcctgaaac tccccctgaat tcgaagcacc acatcatcca 3480
agaactgcct ctcgataaca cctttgtggc cctgactct atctccaagt gttcctcaag 3540
cagttcagat ccctacagcg tttctgactg tggctatcca gtgacgacct tcgaggtacc 3600
tgtgtccgta cacaccagac cgactgattc caggacatca actattgaaa tctgcagtga 3660
gataacctt tctaggaaca acaaaattcc attcccttc caaaaattt caatgattgt 3720
gatttcaaa ttaggctaag atcattaatt ttgtaatcta gatttcccat tataaagca 3780
agcaaaatc atcttaaaaa tgatgtccta gtgaaccttg tgctttcttt agctgtaatc 3840
tggcaatgga aatttaaaat ttatggaaga gacagtgcag cacaataaca gagtactctc 3900
atgctgtttc tctgtttgct ctgaatcaac agccatgatg taatataagg ctgtcttggt 3960
gtatacactt atggttaata tatcagtcat gaaacatgca attacttgcc ctgtctgatt 4020
gttgaataat taaaacatta tctccaggag tttgaagtg agctgaacta gccaaactac 4080
tctctgtcag gtatccaggg caagagacat ttttaagacc ccaaaaacaa aaaaaacaaa 4140
accaaaacac tctgtttcag tgttttgaaa atattcacta acatatatt gctgagaaaa 4200
tcattttat tacccaccac tctgcttaaa agttgagtgg gcgggcgcg gtgctcacg 4260
cctgtaatcc cagcactttg ggaggccgag gcgggtgat cacgaggtca ggagattgag 4320
accatcctgg ctaacacggt gaaacccat ctccactaaa aatacaaaaa attagcctgg 4380
cgtggtggcg ggcgcctgta gtcccagcta ctcgggaggc tgaggcagga gatagcgtg 4440
aacccgggag gcggaggttg cagtgagccg agatggcgcc actgcactcc agcctgggtg 4500
acagagcaag actctgtctc aaaaagaaaa aaatgttcaa tgatagaaaa taattact 4560
```

Figure 11c (continued)

```
aggtttttat gttgattgta ctcatgctgt tccactcctt ttaattatta aaaagttatt    4620
tttgctggg tgtgtggct cacacctgta atcccagcac tttgggaggc cgaggtggt      4680
ggatcacctg aggtcaggag ttcaagacca gtctgccaa cat                       4723

>109P1D4 v.3  (SEQ ID NO:126)
ctggtggtcc agtacctcca aagatatgga atacactcct gaaatatcct gaaaacttt      60
tttttcaga atcctttaat aagcagttat gtcaatctga aagttgtta cttgtacttt     120
atattaatag ctattctgt tttcttatc caagaaaaa tcctctaatc ccctttcac       180
atgatagttg ttaccatgtt taggcattag tcacatcaac ccctctcctc tccaaacct    240
ctcttcttca aatcaaactt tattagtccc tccttataa tgattccttg cctcgtttta    300
tccagatcaa tttttttca ctttgatgcc cagagctgaa gaaatgact actgtataaa     360
ttattcattg ccaagagaat aattgcattt taaacccata ttataacaaa gaataatgat    420
tatattttgt gattgtaac aaatacccct tattctcct taactattga attaaaatatt    480
ttaattattt gtattctctt taactatctt ggtatattaa agtattatct tttatatatt    540
tatcaatggt ggacacttt atagtactc tgtgtcattt ttgatactgt aggtatctta    600
tttcatttat ctttattctt aatgtacgaa ttcataatat ttgattcaga acaaatttat    660
cactaattaa cagagtgtca attatgctaa catctccattt actgattttta attaaaaca    720
gttttttgtta acatgcatgt ttaggttgg cttcttaata attctctctt cctctctct    780
ctctctcttt ctttggtca gtgttgtgcg ggttaataca acaaactgta acaagtgtac    840
ctgtatgga ctgttgtcc gggacgtaca tttcgcggt cctgtagca tgcgtgtgt       900
tccactctgg cgcccaggag aaaaactaca ccatccgaga agaaatgcca gaaaacgtcc    960
tgataggcga ctgtgttgaaa gaccttaact tgtcgctgat tccaaacaag tccttgacaa   1020
ctgtcaatga gttcaagcta gtgtacaaga ccggagatgt gccactgatt cgaattgaag   1080
aggatactgg tgagatcttc actactgggg ctcgcattga tcgtgagaaa ttatgtgctg   1140
gtatcccaag ggatgagcat tgcttttatg aagtggaggt tgccatttg ccggatgaaa   1200
tatttagact gttaagata cgttttctga tagaagatat aatgataat gcaccattgt    1260
tccagcaac agttatcaac atatcaattc cagagaactc ggctataaac tctaaatata   1320
ctctcccagc ggctgttgat cctgacgtag gaataaacgg agttcaaaac tacgaactaa   1380
ttaagagtca aacatttttt ggcctcgatg tcattgaaac accagaagga gacaagtgc    1440
cacaactgat tgttcaaag gagttagata gggaagaga ggataacctac gtgatgaaag   1500
taaggttga agatgcgcat tttcctcaga gatccagtac tgctatttg caagtgagtg    1560
ttactgatac aaatgacaac caccagtct cacttcagtga agagattgaa gtcagtatac   1620
cagaaaatgc tcctgtaggc actcagtga cacagctcca tgccacagat gctgacatag   1680
gtgaaaatgc caagatccac actgccacc acttctttca gcaatctagt ctccaacatt   1740
tatttcacct caatgccacc actgactta tcaatcaa agaaccactg gataggaag       1800
aacaccaaga ccacaagtta ctggttttgg caagtgatgg ccagcagag ccaatagat    1860
caatgtgct ggtaaatgtt acagatgtca atgataatgt cccatccatt gacataagat   1920
acactgtcaa tcctgtcaat gacacagttg ttcctttcaga aatatttcca ctcaacacca   1980
```

Figure 11c (continued)

```
aaattgctct cataactgtg acggataagg atgccgacca taatgcgcagg gtgacatgct    2040
tcacagatca tgaaatccct ttcagattaa ggccagtatt cagtaatcag ttcctcctgg    2100
agactgcagc atatcttgac tatgagtcca caaagaata tgccattaaa ttactgcctg    2160
cagatgctgg caaacctcct ttgaatcagt cagcaatgct cttcatcaaa gtgaaagatg    2220
aaaatgacaa tgctccagtt ttcaccagt cttcgtaac tgtttctatt cctgagaata    2280
actcctctgg catccagttg acgaaagtaa gtgcaatgga tgcagacagt gggcctaatg    2340
ctaagatcaa ttacctgcta ggccctgatg ctccacctga attcagcctg gattgtcgta    2400
caggcatgct gactgtagtg aagaaactag atagagaaaa agaggataaa tatttattca    2460
caattctggc aaaagataac gggtaccac cctaaccag caatgtcaca gtcttgtaa     2520
gcattattga tcagaatgac aatagcccag tttcactca caatgatgac aacttctatg    2580
tccagagaca ccttccaagg catgtccagt taggactaat cactgtaact gatcctgatt    2640
atggagacaa ttctgcagtt acgctctcca tttagatga gaatgatgac ttcaccattg    2700
attcacaaac tggtgtcatc cgaccaaata tttcattga tagagaaaaa caagaatctt    2760
acactttcta tgtaaaggct gaggatggtg gtagagtatc acgttcttca agtgccaaag    2820
taaccataaa tgtggttgat gtcaatgaca acaaaccagt tttcattgtc cctccttcca    2880
actgttctta tgaattggtt ctaccgtcca ctaatccagg cagaggttcg cacagtggtc tttcagtaa   2940
ttgctgttga caatgacact tctgtttgca ggcatgaatg cagaggttcg ttacagcatt gtaggagaa   3000
acacaagaga tctgtttgca atcgaccaag aaacagcca cataacattg atgagaaat    3060
gtgatgttac agaccttgt ttacacagag tgttgtcaa agctaatgac ttaggacagc    3120
ctgattctct cttcagtgtt gtaattgtca atcgttcgt gaatgagtcg gtgaccaatg    3180
ctacactgat taatgaactg gtgcgcaaaa gcactgaagc accagtgacc ccaaatactg    3240
agatagctga tgtatcctca ccaactagtg actatgtcaa gatcctggtt gcagctgttg    3300
ctggcaccat aactgtcgtt gtagttattt tcatcactgc tgtagtaaga tgtcgccagg    3360
caccacacct taagctgct cagaaaaaca agcagaattc tgaatgggct accccaaacc    3420
cagaaaacag gcagatgata atgatgaaga aaaagaaaaa gaagaagaag cattcccccta   3480
agaacttgct gcttaatttt gtcactattg aagaaacaca ggcagatgat gttgacagtg    3540
atgaaacag agtcacacta gaccttccta ttgatctaga agagcaaaca atggaaagt    3600
acaattgggt aactacacct actacttca agcccgacag cctgatttg gccgacact    3660
acaaatctgc ctctccacag ctgcctctg aaattcagcc tgaaactccc ctgaattga    3720
agcaccacat catccaagaa ctgcctctg ataacacctt tgtggcctgt gactctatct    3780
ccaagtgttc ctcaagcagt tcagatccct acagcgtttc tgactgtggc tatccagtga    3840
cgaccttcga ggtacctgtg tccgtacaca ccagaccgcc aatgaaggag gttgtgcgat    3900
cttgcacccc catgaaagag tctacaacta tgatctg gattcatccc caaccacagc       3960
ggaaatctga aggaaagtg gcaggaagt cccagcggcg tgtcacattt cacctgccag    4020
aaggctctca ggaaagcagc agtgatggtg gactgggaga catgatgca ggcagcctta    4080
ccagcacatc tcatggcctg ccccttggct atcctcagga ggagtacttt gatcgtgcta    4140
caccagcaa tcgcactgaa gggatggca atcctcgatcc accactgttc aaccactgta    4200
gactaaagaa agctgcagaa ataactgttc aaccactgtt gaagaggcc tctgacaact    4260
gcactcaaga atgtctcatc tatgccatt ctgatgccg ctggatgccg gcatctctgg    4320
```

Figure 11c (continued)

```
atcattccag ctcttcgcaa gcacaggcct ctgctctatg ccacagccca ccactgtcac 4380
aggcctctac tcagcaccaa agcccacgag tgacacagac cattgctctc tgccacagcc 4440
ctccagtgac acagaccatc gcattgtgcc acagccacc  accgatacag gtgtctgctc 4500
tccaccacag tcctcctcta gtgcaggcta ctgcacttca ccacagccca ccatcagcac 4560
aggcctcagc cctctgctac agccctcctt tagcacaggc tgctgcaatc agccacagct 4620
ctcctctgcc acaggttatt gccctccatc gtagtcaggc ccaatcatca gtcagtttgc 4680
agcaaggttg ggtgcaaggt gctgatggc  tatgctctgt tgatcaggga gtgcaaggta 4740
gtgcaacatc tcagttttac accatgtctg aaagacttca tcccagtgat gattcaatta 4800
aagtcattcc tttgacaacc ttcactccac gccaacaggc cagaccgtcc agaggtgatt 4860
ccccattat  ggaagaacat cccttgtaaa gctaaaatag ttacttcaaa ttttcagaaa 4920
agatgtatat agtcaaaatt taagatacaa ttccaatgag tattctgatt atcagatttg 4980
taaataacta tgtaaataga acagatacc  agaataaatc tacagctaga ccctagtca  5040
atagttaacc aaaaaattgc aatttgttta attcagaatg tgtatttaaa aagaaaaagga 5100
atttaacaat ttgcatcccc ttgtacagta aggcttatca tgacagagcg cactatttct 5160
gatgtacagt atttttgtt  gtttttatca tcatgtgcaa tattactgat ttgtttccat  5220
gctgattgtg tgaaccagt  atgtagcaaa tggaaagcct agaaatatct tattttctaa  5280
gtttacctt  agttaccta  aactttgtt  cagataacgt taaaagtat  acgtactcta  5340
gccttttttt gggctttctt tttgatttt  gtttgttgtt ttcagttttt ttgttgttgt  5400
tagtgagtct cccttcaaaa tacgcagtag gtagtgtaaa tactgcttgt ttgtgtctct  5460
ctgctgtcat gttttctacc ttattccaat actatattgt tgataaaatt tgtatataca  5520
ttttcaataa agaatatgta taaactgtac agatctagat ctacaaccta tttctctact  5580
ctttagtaga gttcgagaca cagaagtgca ataactgccc taattaagca actatttgtt  5640
aaaaagggc  tcttttact  ttaatagttt agtgtaaagt acatcagaaa taaagctgta  5700
tctgccattt taagcctgta gtccattatt actgggtct  ttacttctgg gaattgtat   5760
gtaacagcct agaaattaa  aaggaggtgg atgcatccaa agcacgagtc acttaaaata  5820
tcgacggtaa actactattt tgtagagaaa ctcaggaaga tttaaatgtt gatttgacag  5880
ccaataggc  tgttaccaaa gggtgttcag taaaaataac aaatacatgt aactgtagat  5940
aaaccatat  actaaatcta taagactaag ggattttgt  tattctagct caacttactg  6000
aagaaaacca ctaataacaa caagaatatc aggaaggaac ttttcaagaa atgtaattat  6060
aatctacat  caaacagaat tttaaggaaa aatgcagagg gagaataaag gcacatgact  6120
gcttctgca  gtcaacaata ttcttctaag acaccaata  aacaaaaacc atcaaaatct  6180
catatatgaa ataaatata  ttcttctaag caaagaaaca gtactattca tagaaaacat  6240
tagttttctt ctgttgtctg ttatttcctt cttgtatcct cttaactgcc cattatcttg  6300
tatgtgcaca tttataaat  gtacagaaac atcaccaact taattttctt ccatagcaaa  6360
actgagaaaa taccttgttt cagtataaca ctaaaccaag agacaattga tgtttaatgg  6420
gggcggttgg ggtggggggg ggagtcaata tctcctattg attaacttag acatagattt  6480
tgtaatgtat aacttgatat ttaatttatg attaaactgt gtgtaaattt tgtaacataa  6540
actgtggtaa ttgcataatt tcattggtga ggatttccac tgaatattga gaaagttct   6600
tttcatgtgc ccagcaggtt aagtagcgtt ttcagaatat acattattcc catccattgt  6660
```

Figure 11c (continued)

```
aagttcctt aagtcatatt tgactggcg tgcagaataa cttcttaact tttaactatc    6720
agagtttgat taataaaatt aattaatgtt ttttctcctt cgtgttgtta atgttccaag  6780
ggattggag catactggtt ttccagtgc atgtgaatcc cgaaggactg atgatatttg    6840
aatgtttatt aattattat catacaaatg tgttgatatt gtggctattg ttgatgttga   6900
aaatttaaa cttgggaag attaagaaaa gaaccaatag tgacaaaaat cagtgcttcc    6960
agtagattt agaacattct ttgcctcaaa aaacctgcaa agatgatgtg agattttttc   7020
ttgtgttta attattttca cattttctct ctgcaaaact ttagttttct gatgatctac   7080
acacacacac acacacacac gtgcacacac acacacattt aaatgatata aaaagaagag  7140
gttgaaagat tattaaataa cttatcaggc atccaatgg ttactatcta tgttagtgaa   7200
aatcaaatag gactcaaagt tggatatttg ggatttttct tctgacagta taattattg   7260
agttactagg gaggttctta aatcctcata tctggaaact tgtgacgttt tgacaccttt  7320
cctatagatg atataggaat gaaccaatac gctttatta ccctttctaa ctctgatttt   7380
ataatcagac ttagattgtg tttagaatat taaatgactg gcacccctct tcttggtttt  7440
taccagagag gctttgaatg gaagcaggct gagagtagcc aaagaggcaa gggtattag   7500
cccagttatt ctcccctatg cctccctct ctttctaagc gtccactagg tctggcctttg  7560
gaaacctgtt acttctaggg cttcagatct gatgatatct ttttcatcac attacaagtt  7620
atttctctga ctgaatagac agtggtatag gttgacacag cacacaagtg gctattgtga  7680
tgtatgatgt atgtagtcct acaactgcaa aacgtcttac tgaaccaaca atcaaaaaat  7740
ggttctgttt taaaaaggat tttgtttgat ttgaaattaa aacttcaagc tgaatgactt  7800
atatgagaat aatacgttca atcaaagtag ttattctatt ttgtgtccat attccattag  7860
atgtgatta ttaatttct agctatggta ttactatatc acacttgtga gtatgtattc    7920
aaatactaag tatcttatat gctacgtgca tacacattct ttcttaaac ttcttacctgtg 7980
tttaactaa tattgtgtca gtgtattaaa aattagcttt tacatatgat atctacaatg   8040
taataaattt agagagtaat tttgtgtatt cttattact taacattta ctttaatta     8100
tgtaaatttg gttagaaaat aataataaat ggttagtgct attgtgtaat ggtagcagtt  8160
acaaagagcc tctgccttcc caaactaata tttatcacac atggtcatta aatgggaaaa  8220
aaatagacta aacaaatcac aaattgttca gttcttaaaa tgtaattatg tcacacacac  8280
aaaaaatcct tttcaatcct gagaaaatta aaggcttttt actcacatgg ctattccaac  8340
attagttttt ttgtttgtt tcttttcat ggtattactg aaggtgtta tactcctaa      8400
tacacattta tgaaatcta cttgtttagg cttttattta tactcttctg attttatttt   8460
tttattataa ttattattc ttattatgac cattagaaac tttttgaaa ccaaatttat    8520
agttagttta ggtaaacttt ttattatgac cattagaaac tattttgaat gcttccaact  8580
ggctcaattg gccgggaaaa catggagca agagaagctg aaatatattt ctgcaagaac   8640
cttctatat tatgtgccaa ttaccacacc agatcaattt tatgcagagg ccttaaaata   8700
ttctttcaca gtagctttct tacactaacc gtcatgtgct tttagtaaat atgattttta  8760
aagcagttc aagttgacaa cagcagaaac agtaacaaaa aaatctgctc agaaaaatgt   8820
atgtgcacaa ataaaaaaaa ttaatgcaa ttgtttagtg attgtaagtg atacttttta   8880
aagagtaaac tgtgtgaaat ttatactatc cctgcttaaa atattaagat ttttatgaaa  8940
tatgtattta tgtttgtatt gtgggaagat tcctcctctg tgatatcata cagcatctga  9000
```

Figure 11c (continued)

```
aagtgaacag tatcccaaag cagttccaac catgctttgg aagtaagaag gttgactatt    9060
gtatggccaa ggatggcagt atgtaatcca gaagcaaact tgtattaatt gttctatttc    9120
aggttctgta ttgcatgttt tcttattaat atatattaat aaaagttatg agaaataaaa    9180
aaaaaaaaaa aaaaaa                                                    9196
```

>109P1D4 v.4  (SEQ ID NO:127)

```
ctggtggtcc agtacctcca aagatatgga atacactcct gaaatatcct gaaaactttt      60
ttttttcaga atcctttaat aagcagttat gtcaatctga aagttgctta cttgtacttt     120
atattaatag ctattcctgt ttttcttatc caaagaaaaa tcctctaatc cccttttcac     180
atgatagttg ttaccatgtt taggcattag tcacatcaac ccctctcctc tcccaaactt     240
ctcttcttca aatcaaactt tattagtccc tcctttataa tgattccttg cctcgtttta     300
tccagatcaa tttttttca ctttgatgcc cagactgaa gaaatggact actgtataaa      360
ttattcattg ccaagagaat aattgcattt taaaccata ttataacaaa gaataatgat     420
tatattttgt gattgtaac aaatacccct tattttccct taactattga attaaatatt     480
ttaattattt gtattctctt taactatctt ggtatattaa agtattatct tttatatatt     540
tatcaatggt ggacactttt ataggtactc tgtgtcattt ttgatactgt aggtatctta     600
tttcatttat ctttattctt aatgtacgaa ttcataatat ttgattcaga acaaatttat     660
cactaattaa cagagtgtca attatgctaa catctcattt actgatttta atttaaaaca     720
gtttttgtta acatgcatgt ttaggggttgg gtgttgtgcg cttcttaata acaaactgta     780
ctctctcctt ctttggtca gtgttgtgcc ggtaataca acaaactgta acaagtgtac        840
ctggtatgga cttgttgtcc gggacgtaca ttttcgccgt cctgctagca tgcgtggtgt     900
tccactctgg cgcccaggag aaaaactaca ccatccgaga agaaatgcca gaaaacgtcc     960
tgataggcga cttgttgaaa gaccttaact tgtcgctgat tccaaacaag tccttgacaa    1020
ctgctatgca gttcaagcta gtgtacaaga ccggagatgt gccactgatt cgaattgaag    1080
aggatactgg tgagatcttc actactggcg ctcgcattga tcgtgagaaa ttatgtgctg    1140
gtatcccaag ggatgagcat tgcttttatg aagtggaggt tgccattttg ccggatgaaa    1200
tattagact ggttaagata cgttttctga tagaagatat aaatgataat gcaccattgt     1260
tcccagcaac agttatcaac atatcaattc cagagaactc ggctataaac tctaaatata    1320
ctctcccagc ggctgttgat cctgacgtga gaatcaaaacgg agttcaaaac tacgaactaa  1380
ttaagagtca aaacattttt ggcctcgatg tcattgaaac accagaagga gacaagatgc    1440
cacaactgat tgttcaaaag gagttagata gggaagagaa ggataccac gtgatgaaag     1500
taaaggttga agatggtggc tttcctcaaa gatccagtac tgctattttg caagtgagtg    1560
ttactgatac aaatgacaac caccagtct ttaaggagac cacagctcca agagattgaa    1620
cagaaaatgc tcctgtaggc acttcagtga cacagctcca tgccacagat gctgacatag   1680
gtgaaaatgc caagatccac ttctctttca gcaatctagt ctccaacatt gccaggagat   1740
tatttcacct caatgccacc actgacctta tcacaatcaa agaaccactg gataggaag    1800
aaacaccaaa ccacaagtta ctggttttgg caagtgatgg tggattgatg ccagcaagag   1860
caatggtgct ggtaaatgtt acagatgtca atgataatgt cccatccatt gacataagat   1920
```

Figure 11c (continued)

```
acatcgtcaa tcctgtcaat gacacagttg ttctttcaga aaatattcca ctcaacacca 1980
aaattgctct cataactgtg acggataagg atgcgacca taatgcagg gtgacatgct 2040
tcacagatca tgaaatccct ttcagattaa ggcagtatt cagtaatcag ttcctcctgg 2100
agactgcagc atatcttgac tatgagtcca caaagaata tgccattaaa ttactgctg 2160
cagatgctgg caaacctcct ttgaatcagt cagcaatgct cttcatcaaa gtgaaagatg 2220
aaaatgacaa tgctccagtt ttcaccagt ctttcgtaac tgtttctatt cctgagaata 2280
actctcctgg catccagttg acgaagtaa gtgcaatgga tgcagacagt gggcctaatg 2340
ctaagatcaa ttacctgcta ggccctgatg ctccacctga attcagcctg gattgtcgta 2400
caggcatgct gactgtagtg aagaaactag agagagaaaa agaggataaa tatttattca 2460
caattctggc aaaagataac gggtaccaac cttaaccag caatgtcaca gtcttttgtaa 2520
gcattattga tcagaatgac aatgcccag tttcactca caatgaatac aacttctatg 2580
tcccagaaaa ccttccaagg catgtacag taggactaat cactgtaact gatcctgatt 2640
atggagacaa ttctgcagtt acgctctcca tttagatga gaatgatgac ttcaccattg 2700
attcacaaac tggtgtcatc cgaccaaata tttcattga tagagaaaaa caagaatctt 2760
acactttcta tgtaaaggct gaggatggtg gtagtatc acgttcttca agtgccaaag 2820
taaccataaa tgtggttgat gtcaatgaca acaaccagt tttcattgtc cctccttcca 2880
actgttctta tgaattgtt ctaccgtcca ctaatccagg cacagtggtc tttcaggtaa 2940
ttgctgttga caatgacact ggcatgaatg cagaggttcg ttacagcatt gtaggaggaa 3000
acacaagaga tctgtttgca atcgaccaag aaacaggcaa cataacattg atggagaaat 3060
gtgatgttac agacctggt ttacacagag tgttggtcaa agctaatgac ttaggacagc 3120
ctgattctct cttcagtgtt gtaattgtca atcgttcgt gaatgagtcg gtgaccaatg 3180
ctcactgat taatgaactg gtgcgcaaaa gcactgaagc accagtgacc ccaaatactg 3240
agatagctga tgtatcctca ccaactagtg actatgtcaa gatcctgttt gcagctgttg 3300
ctgcaccat aactgtcgtt gtagttattt tcatcaactg tgtagtaaga tgtcgccagg 3360
caccacacct taaggctgct cagaaaaaca agcagaattc agcagaaaaa tgaatggct accccaaacc 3420
cagaaaacag gcagatgata atgatgaaga aaaagaaaaa gaagaagaag cattcccta 3480
agaacttgct gcttaatttt gtcactattg aagaaactaa ggcagatgat gttgacagtg 3540
atggaaacag agtcacacta gaccttccta ttgatctaga agagcaaaca atgggaaagt 3600
acaattgggt aactacacct actactttca agcccgacag ccctgatttg gcccgacact 3660
acaaatctgc ctctccacag cctgccttcc aaattagcc tgaaactccc ctgaattcga 3720
agcaccacat catccaagaa ctgcctctcg ataacacctt tgtgcctgt gactctatct 3780
ccaagtgttc ctcaagcagt tcagatccct acagcgtttc acagccgcc tatccagtga 3840
cgaccttcga ggtacctgtg tccgtacaca ccgagatctg aatgaaggag gttgtgcgat 3900
cttgcaccc catgaaagag tgtcacattt cacctgccag aaggtctca gattcatccc caaccacagt 3960
ccagcgggcg ccatgatgca caccgcctta cagcagccta ccacaccatc tcatgcctg ccccttgct 4020
gactggagga ggagtacttt gatcgtgcta ggcagccttg catgcactga tcgcactgaa gggatgcca 4080
atcctccagg gaatctact ttcataccctg gactaaagaa agctgcagaa ataactgttc 4140
actccgatcc tgaatctact ttcataccctg gactaaagaa agctgcagaa ataactgttc 4200
aaccaactgt ggaagaggcc tctgacaact gcactcaaga atgtctcatc tatgccatt 4260
```

Figure 11c (continued)

```
ctgatgcctg ctgatgccg gcatctctgg atcattccag ctcttgcaa gcacaggcct    4320
ctgctctatg ccacgccca ccactgtcac aggcctctac tcagcaccac agcccaggag    4380
tgacacagac cattgctctc tgccacagcc ctccagtgac acagaccatc gcattgtgcc    4440
acagcccacc accgatacag gtgtctgctc tccaccacag tctcctctca gtgcaggcta    4500
ctgcacttca ccacagccca ccatcagcac aggcctcagc cctctgctac agccctcctt    4560
tagcacaggc tgctgcaatc agccacagct ctcctctgcc acaggttatt gccctccatc    4620
gtagtcaggc ccaatcatca gtcagtttgc agcaagttg ggtgcaaggt gctgatgggc    4680
tatgtctgt tgatcaggga gtgcaaggta gtgcaacatc tcagttttac accatgtctg    4740
aaagacttca tcccagtgat gattcaatta aagtcattcc tttgacaacc ttcactccac    4800
gccaacaggc cagaccgtcc agaggtgatt cccattat ggaagaacat cccttgtaaa    4860
gctaaaatag ttacttcaaa tttcagaaa agatgtatat agtcaaaatt taagatacaa    4920
ttccaatgag tattctgatt atcagatttg taaataacta tgtaaataga acagataacc    4980
agaataaatc tacagctaga cccttagtca ataagttaacc aaaaaattgc aatttgttta    5040
attcagaatg tgtatttaaa aagaaaagga atttaacaat ttgcatcccc ttgtacagta    5100
aggcttatca tgcagagcg cactattctt gatgtacagt attttttgtt gttttttatca    5160
tcatgtgcaa tattactgat ttgtttccat gctgattgtg tggaaccagt atgtagcaaa    5220
tggaaagcct agaaatatct tatttctaa gtttaccttt agtttaccta aacttttgtt    5280
cagataacgt taaaggtat acgtactcta gccttttttt gggcttttct tttgatttt    5340
gttttgttgtt ttcagttttt ttgttgttgt tagtgagtct cccttcaaaa tacgcagtag    5400
gtagtgtaaa tactgcttgt ttgtgtctct ctgctgtcat gtttctacc ttattccaat    5460
actatattgt tgataaaatt tgtatataca tttccaataa agaatatgta taaactgtac    5520
agatctagat ctacaaccta tttctctact ctttagtaga gttcgagaca cagaagtgca    5580
ataactgccc taattaagca actatttgtt aaaaagggcc tcttttact ttaatagttt    5640
agtgtaaagt acatcagaaa taaagctgta tctgccattt taagcctgta gtccattatt    5700
acttgggtct ttacttctgg gaatttgtat gtaacagcct agaaaattaa aaggaggtgg    5760
atgcatccaa agcacgagtc acttaaaata tcgacggtaa acttcctgtt tgtagagaaa    5820
ctcaggaaga tttaaatgtt gatttgacag ctcaatagc tgttcactga gggtgttcag    5880
taaaaataac aaatacatgt aactgtagat aaaaccatat actaaatcta taagactaag    5940
ggatttttgt tattctagct caacttactg aagaaaacca ctaataacaa caagaatatc    6000
aggaaggaac ttttcaagaa atgtaattat aaatctacat caaacagaat tttaaggaaa    6060
aatgcagagg gagaaataag gcacatgact gcttccttgca gtcaacaaga aataccaata    6120
acacacacag aacaaaaaacc atcaaaatct catatatgaa ataaaatata ttcttctaag    6180
caagaaaca gtactattca tagaaaacat tagttttctt ctgttgtctg ttatttcctt    6240
ccttgtatcct cttaactggc cattatcttg tatgtgcaca tttttataaat gtacagaaac    6300
atcaccaact taattttctt ccatagcaca actgagaaaa tacctttgtt cagtataaca    6360
ctaaccaag agacaattga tgtttaatgg gggcggttgg ggtgggggg ggagtcaata    6420
tctcctattg attaacttag acatagattt tgtaatgtat aacttgatat ttaattttatg    6480
attaaactgt gtgtaaattt tgtaacata actgtggtaa ttgcataatt tcattggtga    6540
ggattccac tgaattga gaaagttct tttcatgtgc ccagcaggtt ccagcaggtt aagtagcgtt    6600
```

Figure 11c (continued)

```
ttcagaatat acattattcc catccattgt aaagttcctt aagtcatatt tgactgggcg        6660
tgcagaataa cttcttaact tttaactatc agagtttgat taataaaatt aattaatgtt        6720
tttctcctt cgtgttgtta atgttccaag ggattggag catactgtt ttccaggtgc           6780
atgtgaatcc cgaaggactg atgatattg aatgttatt aaattattat catacaaatg          6840
tgttgatatt gtggctattg ttgatgttga aaattttaaa cttggggaag attaagaaaa        6900
gaaccaatag tgacaaaaat cagtgcttcc agtagatttt agaacattct ttgcctcaaa        6960
aaacctgcaa agatgatgtg agatttttc ttgtgttta attattttca catttctct           7020
ctgcaaaact ttagtttct gatgatctac acacacacac acacacacac gtgcacacac         7080
acacaattt aaatgatata aaagaagag gttgaagat tattaaataa ctatcaggc            7140
atctcaatgg ttactatcta tgttagtgaa aatcaaatag gactcaaagt tgatatttg         7200
ggattttct tctgacagta taattattg agttactagg gaggttctta aatcctcata         7260
tctggaaact tgtgacgttt tgacacctt cctatagatg atataggaat gaaccaatac         7320
gcttttatta cccttttctaa ctctgatttt ataatcagac ttagattgtg tttagaatat       7380
taaatgactg ggcaccctct tcttggtttt taccagagag gctttgaatg gaagcaggct        7440
gagagtagcc aaagaggcaa gggtattag cccagttatt ctcccctatg ccttccttct        7500
ctttctaagc gtccactagg tctgccctg gaaacctgtt acttctaggg cttcagatct         7560
gatgatatct tttcatcac attacaagtt attcctga ctgaatagac agtggtatag           7620
gttgacacag cacacaagtg gctattgta tgtatgatgt atgtagtcct acaactgcaa         7680
aacgtcttac tgaaccaaca atcaaaaaat ggttcctgt taaaaggat tttgtttgat          7740
ttgaaattaa aacttcaagc tgaatgactt atatgagaat aatacgttca atcaaagtag        7800
ttattctatt tttgtgtccat attccattag attgtgatta ttaattttct agctatggta      7860
ttactaatc acacttgtga gtatgtattc aatactaag tatcttatat gctacgtgca         7920
tacaaatctt tttctttaaac tttcctgtg ttttaactaa tattgtgtca gtgtattaaa      7980
aattagcttt tacatattta atctacaatg taataaattt agagagtaat tttgtgtatt      8040
cttattact taacatttta ctttttaatta tgtaaattg gttagaaaat aataataaat         8100
ggttagtgct atttgtaat ggtagcagtt acaaagagcc tctgccttcc caaactaata        8160
tttatcacac atggtcatta aatgggaaaa aaatagacta aacaaatcac aaattgttca        8220
gttcttaaaa tgtaattatg tcacacacac aaaaaatcct ttcaatcct gagaaaaatta       8280
aaggcgtttt actcacatgg ctatttcaac attagttttt tttgtttgtt tctttttcat       8340
ggtattactg aagtgtgta tactcctaa tacacattta tgaaaatcta cttgtttagg        8400
cttttattta tactcttctg atttatattt tttattataa ttattattc ttatcttct        8460
tctttatat tttttggaaa ccaatttat agttagttta gtaaactttt ttattatgac         8520
cattagaaac tatttgaat gcttccaact ggctccaattg gccgggaaaa catgggagca        8580
agagaagctg aaatatattt ctgcaagaac cttctatat tatgtgcaa ttaccacacc          8640
agatcaattt tatgcagagg ccttaaaata ttctttcaca gtagctttct tacactaacc       8700
gtcatgtgct tttagtaaat atgatttta aaagcagttc aagttgacaa cagcagaaac        8760
agtaacaaaa aaatctgctc agaaaatgt atgtgcaaa ataaaaaaa ttaatgcaa           8820
ttgtttagtg attgtaagtg atacttttta aagagtaaaa tgtgtgaaaat ttatactatc      8880
cctgcttaaa atattaagat ttttatgaaa tatgtattta tgtttgtatt gtgggaagat       8940
```

Figure 11c (continued)

```
tcctcctctg tgatatcata cagcatctga aagtgaacag tatccaaaag cagttccaac    9000
catgctttgg aagtaagaag gttgactatt gtatgccaaa ggatgccagt atgtaatcca    9060
gaagcaaact tgtattaatt gttctatttc aggttctgta ttgcatgttt tcttattaat    9120
atatattaat aaaagttatg agaaataaaa aaaaaaaaaa aaaaa                    9166
```

>109P1D4 v.5 (SEQ ID No 128).

```
atggactgt  tgtccggac  gtacattttc gcggtcctgc tagcatgcgt ggtgttccac      60
tctgcgccc  aggagaaaaa ctacaccatc cgagaagaaa tgccagaaaa cgtcctgata     120
ggcgacttgt tgaaagacct taacttgtcg ctgattccaa acaagtcctt gacaactgct     180
atgcagttca agctagtgta caagaccgga gatgtgccac tgattgaat  tgaagaggat     240
actggtgaga tcttcactac tggcgctcgc attgatcgtg agaaattatg tgctggtatc     300
ccaagggatg agcattgctt ttatgaagtg gaggttgcca tttgccgga  tgaaatattt     360
agactggtta agatacgttt tctgatagaa gatataaatg ataatgcacc attgttccca     420
gcaacagtta tcaacatatc aattccagag aactcggcta taaactctaa atatactctc     480
ccagcggctg ttgatcctga cgtaggcata acggagttc  aaaactacga actaattaag     540
agtcaaaaca tttttggcct cgatgtcatt gaaacaccag aaggagacaa gatgccacaa     600
ctgattgttc aaaaggagtt agataggga  gagaaggata cctacgtgat gaaagtaaag     660
gttgaagatg gtggctttcc tcaaagatcc agtactgcta tttgcaagt  tagtgttact     720
gatccaaatg ccaaccaccc agtctttaag agcccagaga tgaagtcag  tataccagaa     780
aatgctcctg taggcacttc agtgacacag ctccatgcca cagtgctga  cataggtgaa     840
aatgccaaga tccacttctc tttcagcaat ctagtctcca acattgccag agattattt      900
cacctcaatg ccaccactgg acttatcaca atcaaagaac cactgagata  ggaagaaaca     960
ccaaacacca agttactggt tttgcaagt  gatggtgat  tgatgccagc aagagcaatg    1020
gtgctgtaa  atgttacaga tgtcaatgat aatgtcccat ccattgacat aagatacatc    1080
gtcaatcctg tcaatgacac agttgttctt tcagaaaata ttccactcaa caccaaaatt    1140
gctctcataa ctgtgacgga taagggatcg gaccataatg gcagggtgac atgcttcaca    1200
gatcatgaaa tcccttcag  attaaggcca gtattcagta atcagttcct cctggagact    1260
gcagcatatc ttgactatga gtccacaaaa gaatatgcca ttaaattact ggctgcagat    1320
gctgcaaac  ctccttgaa  tcagtcagca atgctcttca caaagtgaa  agatgaaaat    1380
gacaatgctc cagtttcac  ccagtctttc gtaactgttt ctattcctga gaataactct    1440
cctggcatcc agttgacgaa agtaagtgca atggatgcag acagtgggcc taatgctaag    1500
atcaattacc tgctaggccc tgatgctcca cctgaattca gcctggattg tcgtacaggc    1560
atgctgactg tagtgaagaa actagataga gaaaaagagg ataaatattt attcacaatt    1620
ctggcaaaag ataacgggt  accaccctta accagcaatg tcacagtctt tgtaagcatt    1680
attgatcaga atgacaatag cccagttttc actacaactt aatacaactt ctatgtccca    1740
gaaaacttc  caaggcatgg tagactatga ctaatcactg taactcactg taacttatga    1800
gacaattctg cagttacgct ctccattta  gatgagaatg atgacttcac cattgattca    1860
caaactggtg tcatccgacc aaatatttca tttgataga  tttgatagag aaaaacaaga    atcttacact    1920
```

Figure 11c (continued)

```
ttctatgtaa aggctgagga tggtggtaga gtatcacgtt cttcaagtgc caaagtaacc    1980
ataaatgtgg ttgatgtcaa tgacaacaaa ccagtttca ttgtccctcc ttccaactgt    2040
tcttatgaat tggttctacc gtccactaat ccaggcacag tgtcttca gtaattgct     2100
gttgacaatg acactggcat gaatgcagag gttcgttaca gcattgtagg aggaaacaca   2160
agagatctgt ttgcaatcga ccaagaaaca ggcaacataa cattgatgga gaaatgtgat   2220
gttacagacc ttgtttaca cagagtgttg gtcaaagcta atgacttagg acagcctgat   2280
tctctcttca gtgttgtaat tgtcaatctg ttcgtgaatg agtcggtgac caatgctaca   2340
ctgattaatg aactggtgcg caaaagcact gaagcaccag tgacccaaa tactgagata   2400
gctgatgtat cctcaccaac tagtgactat gtcaagatcc tggttgcagc tgttgctgc   2460
accataactg tcgttgtagt tatttcatc actgctgtag gggctaccc ccaggcacca   2520
caccttaagg ctgctcagaa aacaagcag aattctgaat gggctaccc aaaccagaa    2580
aacaggcaga tgataatgat gaagaaaaag aaaaagaaga agaagcattc cctaagaac   2640
ttgctgctta attttgtcac cactagacct tattgaagaa actaaggcag atgatgttga cagtgatgga   2700
aacagagtca cacctactac tcctattgat ctagaagagc ctagacagcc atttgcccg acactacaaa   2760
tgggtaacta cacctgcctg cttccaaatt cagcctgaaa ctcccctgaa ttcgaagcac   2820
tctgcctctc cacacactgc tctcgataac accttgtgg cctgtgactc tatctccaag   2880
cacatcatcc aagaactgcc tccctacagc gtttctgact gtggctatcc agtgacgacc   2940
tgttcctcaa gcagttcaga tccctacagc cgtccccagc gcgtgtcac atttcacctg   3000
ttcgaggtac ctgtgtccgt acacaccaga cagcagtgat ggtggactgg gagaccatga tgcaggcagc   3060
ccagaaggct ctcaggaaag cagcagtgat cctgcccctt ggctatcctc aggagagta cttttgatcgt   3120
cttaccagca catctcatgg gcaatcgcac tgaagggat gggaactccg atcctgaatc tactttcata   3240
gctacaccca gcacacccca agaaactgc agaaataact gttcaaccaa ctgtggaaga ggcctctgac   3300
cctggactaa agaagcactc aagaatgtct catctatggc cattctgatg cctgctggat gccggcatct   3360
aactgcactc ccagctcttc gcaagcacag gcctctgctc tatgccacag cccaccactg   3420
ctggatcatt ctactcagca ccacagccca cgagtgacac agaccattgc tctctgccac   3480
tcacaggcct ctactcagca ccacagccca cgagtgacac agaccattgc acaggtgtct   3540
agccctccag tgacacagac catcgcattg tgccacagcc caccaccag cccaccatca   3600
gctctccacc acagtcctcc tctagtgcag gctactgcac ttcaccacag aatcagccac   3660
gcacaggcct cagccgtctc ctacagccct cctttagcac catcgtagtc aggctgctgc atcagtcagt   3720
agctctcctc tgccacaggt tattgccctc tattgctgat gggctatgct ctgttgatca gggagtgcaa   3780
ttgcagcaag gttgggtgca catctcagtt ttacaccatg tctgaaagac ttcatcccag tgatgattca   3840
gtagtgcaa catctcagtt ttacaccatg tctgaaagac ttcatcccag tgatgattca   3840
attaaagtca ttcctttgac aaccttcact ccacgccaac gtccagaggt   3900
gattcccca ttatgaaga acatccctta taaagctaaa atagttactt caaattttca   3960
gaaagatgt atatagtcaa aatttaagat acaattccaa tgagtattct gattatcaga   4020
tttgtaaata actatgtaaa tagaaacaga taccagaata a                       4061
```

Figure 11c (continued)

>109P1D4 v.6 (SEQ ID NO 129).

```
gccagtcggc gaactgtctg ggcgggagga gccgtgagca gtagctgcac tcagctgccc    60
gcgcggcaaa gaggaaggca agccaaacag agtgcgcaga gtggcagtgc cagcggcgac   120
acaggcagca caggcagccc gggctgcctg aatagcctca gaaacaacct cagcgactcc   180
ggctgctctg cggactgcga gctgtggcgg tagagcccgc tacagcagtc gcagtctccg   240
tggagcgggc ggaagccttt tttctccctt tcgtttacct cttcattcta ctctaaaggc   300
atcgttatta gagggtgctt aaaaagtaca gatcaactgg atggatgaat ggatggaaga   360
ggatgaata tcttaacaaa acacattttc cttaagtaaa ttcatgcata ctccaaataa   420
aatacagaat gtgaagtatc tctgaactgt gctgttgaat atggtagcta ctagctacat   480
gaaaatcctg ttgtgaataa gaaggattcc acagatcaca taccagagcg gttttgcctc   540
agctgctctc aactttgtaa tctttgtgaag aagctgacaa gcttgcctga ttgcagtgca   600
ctatgaggac tgaatgacag tgggttttaa ttcagatatt tcaagtgttg tgcgggttaa   660
tacaacaaac tgtcacaagt gtttgttgtc cgggacgtac attttcgcgg tcctgctagt   720
atgcgtggtg ttccactctg gcgcccagga gaaaaactac accatccgag aagaaattcc   780
agaaaacgtc ctgataggca actgttgaca agaccttaac agtgtacaag ttgtcgctga   840
gtccttgaca actactatgc agttcaagct cactaccggc gctcgcattg atcgtgagaa   900
tcgaattgaa gaggatactg gtgagatctt ccagatcgtg atcgcgattg ttgccattt    960
attatgtgct gtatcccaa ggatgagca ttgcttttat gaagtggagg ttgccatttt   1020
gccgatgaa atatttagac tggttaagat acgttttctg atagaagata taaatgataa   1080
gccaccattg ttccagcaa cagttatcaa catatcaatt ccagagaact cggctataaa   1140
ctctaaatat actctcccag cggctgttga tcctgacgta ggcataaacg gagttcaaaa   1200
ctaccaacta attaagagtc aaaacatttt tggcctcgat gtcattgaaa caccagaagg   1260
agacaagatg ccacaactga ttgttcaaaa ggagttagat agggaagaga aggataccta   1320
tgtgatgaaa gtaaaggttg aagatggtgg ctttcctcaa agatccagta ctgctatttt   1380
gcaagtaagt gttactgata caaatgacaa ccaccagtc tttaaggaga cagagattga   1440
agtcagtata cacatcgtca atcctgtcaa tgacacagtt gttctttcag catgcggacc ataatgcag   1500
tgctgacata gtgaaaatg ccaagatcca tttcagatta gatgcgacc agccagtat tcagtaatca   1560
tgccaggaga ttatttcacc tcaatgccac cactgactt ctatgagtcc acaaagaat atgccattaa   1620
ggataggaa gaaacaccaa accacaagtt actggttttg ctatgagtcc tcagcaatgc tcttcatcaa   1680
gccagcaaga gcaatggtgc tggtaaatgt tacagatgtc aatgataatg gcaagtgatg gtggattgat   1740
tgacataaga tacatcgtca atcctgtcaa tgacacagtt gttctttcag tccatccat aaatattcc   1800
actcaacacc aaaattgctc tcataactgt gacggataag gatgcggacc ataatgcag  1860
ggtgacatgc ttcacagatc atgaaattcc tttcagatta agccagtat  tcagtaatca   1920
gttcctcctg gagaatgcag catatcttga ctatgagtcc acaaagaat atgccattaa   1980
attactggct gcagatgctg gcaaacctcc tttgaatcag tcagcaatgc tcttcatcaa   2040
agtgaaagat gaaaatgaca atgctccagt tttcacccag tctttcgtaa ctgtttctat   2100
tcctgagaat aactctcctg gcatccagtt gatgaaagta agtgcaacgg atgcagacag   2160
tgggcctaat gctgagatca attacctgct aggcccctgat gctccacctg aattcagcct   2220
ggatcgtcgt acaggcatgc tgactgtagt gaagaaacta gatagagaaa aagaggataa   2280
```

Figure 11c (continued)

```
atattattc acaattctgg caaaagtaa tgggtacca cccttaacca gcaatgtcac 2340
agtctttgta agcattattg atcagaatga caatagccca gttttcactc acaatgaata 2400
caaattctat gtcccagaaa accttccaag gcatggtaca gtaggactaa tcactgtaac 2460
tgatcctgat tatggagaca attctgcagt tacgctctcc atttagatg agaatgatga 2520
cttcaccatt gattcacaaa ctgtgtcat ccgaccaaat atttcatttg atagagaaaa 2580
acaagaatct tacactttct atgtaaagc tgaggatggt ggtagagtat cacgttcttc 2640
aagtgccaaa gtaaccataa atgtggttga tgtcaatgac aacaaaccag ttttcattgt 2700
ccctccttac aactattctt atgaattggt tctaccgtcc actaatccag gcacagtggt 2760
ctttcaggta attgctgttg acaatgacac tggcatgaat gcagaggttc gttacagcat 2820
tgtaggagga aacacaagag atctgtttgc aatcgaccaa gaaacaggca acataacatt 2880
gatggagaaa tgtgatgtta cagacctgg tttacacaga gtgttggtca aagctaatga 2940
cttaggacag cctgattctc tcttcagtgt tgtaattgtc aatctgttcg tgaatgagtc 3000
agtgaccaat gctacactga ttaatgaact gtgtgcgaaa agcattgaag caccagtgac 3060
cccaaatact gagatagctg atgtatcctc accaactagt gactatgtca agatcctggt 3120
tgcagctgtt gctgcacca taactgtcgt tgtagttatt ttcatcactg ctgtagtaag 3180
atgtcgccag gcaccacacc ttaaggctgc tcagaaaaac atgcagaatt ctgaatgggc 3240
tacccaaaac ccagaaaaca gcgagatgat aatgatgaag aaaaagaaaa agaagaaaga 3300
gcattcccct aagaacctgc tgcttaattt tgtcactatt gaagaaacta aggcagatga 3360
tgttgacagt gatgaaaca gagtcacact agaccttcct attgatctag aagagcaaac 3420
aatggaaag tacaattggg taactacacc tactacttc aagcctgaca gccctgattt 3480
ggcccgacac tacaaatctg cctctccaca gctgcctc caaattcagc ctgaaactcc 3540
cctgaatttg aagcaccaca tcatccaaga actgcctctc actgccctc gataacacct ttgtgcctg 3600
tgactctatc tccaagtgtt cctcaagcag tgtacctgt ttcagatccc tacagcgttt ctgactgtgg 3660
ctatccagtg acaaccttcg agtacctgt gtccgtacac accagaccga ctgattccag 3720
gacatgaact attgaaatct gcagtgagat gtaacttct aggaacaaca aaattccatt 3780
cccttccaa aaaattcaa tggattgtga tttcaagcag aggctaagat cattccatt atgtcctagt 3840
gtaatctaga tttcccatta taaaagcag ctgtaatctg gcaatgaaa tttaaaattt atggaagaga 3900
gaacctgtg ctttctttag ctgtaatctg gcaatgaaa tttaaaattt atggaagaga 3960
cagtgcagca caataacaga gtactctcat gctgttctct tgtttgctct gaatcaacag 4020
ccatgatgta atataaggct gtcttgtgt atacacttat ggttaatata tcagtcatga 4080
aacatgcaat tacttgccct gtctgattgt tgaataatta aacattatc ttccaggagt 4140
ttgaagtga gctgaactag ccaaactact ctctgaaagg tatccagggc aagagacatt 4200
tttaagaccc caaacaaaca aaaaacaaaa ccaaactact ctgttcagt gttttgaaaa 4260
tattcactaa cataatattg ctgagaaaat cattttttatt acccaccact ctgcttaaaa 4320
gttgagtggg ccgggcgcgg tggctcacgc ctgtaatccc agcactttgg gaggccgagg 4380
cgggtggatc acgaggtcag gagattgaga catcctggc taacacggtg aaaccccatc 4440
tccactaaaa atacaaaaa ttagcctggc gtggtggcgg gcgcctgtag tcccagctac 4500
tcgggaggct gaggcaggag aatagcgtga acccgggagg cggagcttgc agtgagccga 4560
gatgcgcca ctctgcactc cagcctggt gacagacaa gacagagaca gactctgtct caaaagaaa 4620
```

Figure 11c (continued)

```
aaaatgttca atgatagaaa ataattttac taggtttta tgttgattgt actcatggtg    4680
ttccactcct tttaattatt aaaagttat tttggggtg ggtgtggtgg ctcacaccgt    4740
aatcccagca ctttggagg ccgaggtggg tggatcacct gaggtcagga gttcaagacc   4800
agtntggcca acatgccga acccgtttt aaaaaaaaaa aaaaaaaaaa aaaagaaaaa    4860
```

>109P1D4 v.7 (SEQ ID NO:130).

```
ggtggtccag tacctccaaa gatatggaat acactcctga aatatcctga aaccttttt     60
ttttcagaat cctttaataa gcagttatgt caatctgaaa gttgcttact tgtactttat   120
attaatagct attcttgttt ttcttatcca aagaaaaatc ctctaatccc cttttcacat   180
gatagttgtt accatgttta ggcgttagtc acatcaaccc ctttataatg attccttgcc  240
cttcttcaaa tcaaacttta ttagtccctc ctttataatg gagctgaaga aatggactat  300
cagatcaatt ttttttcact ttgatgccca ttgcattta aaccatgtt ataacaaaga   360
attcattgcc aagagaataa ttgcatttta atacccttta tttcccta actattgaat   420
tatttgtga tttgtaacca atacctttta actatcttgg tatattaaag tattatcttt   480
aattatttgt attctcttta acactttat agtactcctg tgtcatttt gatactgtag   540
tcaatggtgg acactttat ttattcttaa tgtacgaatt cataatattt gattcagaac  600
tcattatct ttattcttaa gagtgtcaat tatgctaaca tctcattac tgattaat    660
ctaattaaca gagtgtcaat atgcatgttt aggttgcca tcttaataat ttcttcttcc  720
tttttgttaa catgcatgttt tttggtcagt gttgtgcggg ttaatcaac aaacgtcac  780
ctctctctct tttggtcagt gtacatttc gcggtcctgc tagtatgcgt ggtgttccac  840
tgtccgggac gtacatttc gcggtcctgc tagtatgcgt ggtgttccac tctggcgcc  900
aggagaaaaa ctacaccatc cgagaagaaa ttccagaaaa cgtcctgata ggcaacttgt 960
tgaaagacct taactgtcg ctgattccaa acaagtcctt gacaactact atgcagttca 1020
agctagtgta caagaccgga gatgtgccac tgattcgaat tgaagaggat actggtgaga 1080
tcttcactac cggcgctgc attgatcgtg agaaattatg tgctggtatc ccaagggatg 1140
agcattgctt ttatgaagtg gaggttgcca tttgccgga tgaaatattt agactggtta 1200
agatacgttt tctgatagaa gatataaatg ataatgcacc attgttccca gcaacagtta 1260
tcaacatatc aattccagag aactcggcta taaactctaa atatactctc ccagcggctg 1320
ttgatcctga cgtaggcata acggagttc aaaactacga actaattaag agtcaaaaca 1380
tttttggcct cgatgtcatt gaaacaccag aaggagacaa gatgccacaa ctgattgttc 1440
aaaggagtt agataggga gagaaggata cctatgtgat gaagtaaag gttgaagatg 1500
gtggctttcc tcaaagatcc agtactgcta ttttgcaagt aagtgttact gatacaaatg 1560
acaaccaccc agtcttaag gagacagaga ttgaagtcag tataccagaa aatgctcctg 1620
taggcacttc agtgacacag ctccatgcca cagatgctga cataggtgaa catgccaaga 1680
tccactctc tttcagcaat acattgccag agattattt cacctcaatg 1740
ccaccactgg acttatccca atcaaagaac cactgaatag ggaagaaaca ccaaacaaca 1800
agttactggt tttggcaagt gatgtggat tgatgccagc aagagcaatg gtgctgtaa  1860
atgttacaga tgtcaatgat aatgtcccat ccattgacat aagatacatc gtcaatcctg 1920
```

Figure 11c (continued)

```
tcaatgacac agttgttctt tcagaaaata ttccactcaa caccaaaatt gctctcataa       1980
ctgtgacgga taaggatgcg gaccataatg gcaggtgac atgcttcaca gatcatgaaa        2040
ttcctttcag attaaggcca gtattcagta atcagttcct cctggagaat gcagcatatc      2100
ttgactatga gtccacaaaa gaatatgcca ttaaattact ggctgcagat gctgcaaac       2160
ctcctttgaa tcagtcagca atgctcttca tcaaagtgaa aatgaaaat gacaatgctc       2220
cagttttcac ccagtctttc gtaactgttt ctattcctga gaataactct cctggcatcc      2280
agttgatgaa agtaagtgca acggatgcag acagtgggcc taatgctgag atcaattacc      2340
tgctaggccc tgatgctcca cctgaattca gctctgatcg tcgtacaggc atgctgactg      2400
tagtgaagaa actagataga gaaaagagg ataaatatttt attcacaatt ctggcaaaag      2460
ataatgggt accacccta accagcaatg tcacagtctt tgtaagcatt attgatcaga        2520
atgacaatag cccagttttc actcacactg aatacaaatt ctatgtccca gaaaaccttc      2580
caaggcatgg tacagtagga ctaatcactg atgacttcac taactgatcc tgattatgga      2640
cagttacgct ctccatttta gatgagaatg atgacttcac cattgattca caaactggtg      2700
tcatccgacc aaatatttca tttgatagag aaaacaaga atcttacact ttctatgtaa       2760
aggctgagga tggtggtaga gtatcacgtt cttcaagtgc caaagtaacc ataaatgtgg      2820
ttgatgtcaa tgacaacaaa ccagtttca ttgtccctcc ttacaactat tcttatgaat       2880
tggttctacc gtccactaat ccaggcacag tggtcttca gtaattgct gttgacaatg        2940
acactgcat gaatgcagag gttcgttaca gcattgtagg aggaaacaca agagatctgt      3000
ttgcaatcga ccaagaaaca ggcaacataa catgatgaa gaaatgtgat gttacagacc      3060
ttgtttaca cagagtgttg gtcaaagcta atgactaggg acagcctgat tctctcttca      3120
gtgttgtaat tgtcaatctg ttcgtgaatg agtcagtgac caatgctaca ctgattaatg     3180
aactggtgcg caaaagcatt gaagcaccag tgaccccaaa tactgagata gctgatgtat      3240
cctcaccaac tagtgactat gtcaagatcc tggttgcagc tgttgctggc accataactg      3300
tcgttgtagt tatttcatc actgctgtag taagatgtcg ccaggcacca caccttaagg      3360
ctgctcagaa aaacatgcag aattctgaat gggctacccc agaagcattc aacaggcaga      3420
tgataatgat gaagaaaag aaaaagagaa agaagcattc cctaagaac ctgctgctta       3480
atgttgtcac tattgaagaa actaaggcag atgattgga cagtgatgga aacagagtca      3540
cactagacct tcctattgat ctagaagagc aacaatggg aagtacaat tgggtaacta       3600
cacctactac tttcaagcct gacagccctg atttggcccg acactacaaa tctgcctctc      3660
cacagcctgc cttccaaatt cagccaaatt cctgtgactc tttgaagcac cacatcatcc      3720
aagaactgcc tctcgataac acctttgtgg cctgtgactc tatctccaat tgttcctcaa      3780
gcagttcgt tcctcacagc gtttctgact gtgctatcc agtgacaacc ttcgaggtac       3840
ctgtccgt acaccacaga ccgactgatt ccaggacatg aactattgaa atctgcagtg      3900
agatgtaact ttctaggaac aacaaattc cattcccctt ccaaaaaatt tcaatgattg      3960
tgatttcaaa attaggctaa gatcattaat ttttgtaatct agatttccca ttataaaagc    4020
aagcaaaat catcttaaaa atgatgtcct agtgaacctt gtgctttctt tagctgtaat      4080
ctggcaatgg aaatttaaaa tttatggaag agacagtgca gcgcaataac agagtactct     4140
catgctgttt ctctgttttgc tctgaatcaa cagccatgat gtaatataag gctgtcttgg    4200
tgtatacact tatggttaat                                                  4220
```

Figure 11c (continued)

>109P1D4 v.8 (SEQ ID NO:131).

```
gtggtccag tacctccaaa gatatggaat acactcctga aatatcctga aacctttttt        60
ttttcagaat cctttaataa gcagttatgt caatctgaaa gttgcttact tgtactttat      120
attaatagct attccttgttt ttcttatcca aagaaaaatc ctctaatccc ctttcacat      180
gatagttgtt accatgtttta gcgttagtc acatcaaccc ctctcctctc ccaaacttct     240
cttcttcaaa tcaaactttta ttagtccctc ctttataatg attccttgcc tccttttatc    300
cagatcaatt ttttttcact ttgatgccca gagctgaaga aatgactat tgtataaatt      360
attcattgcc aagagaataa ttgcatttta aaccatgtt ataacaaaga ataatgatta     420
tattttgtga tttgtaacaa atacccttta ttttcccta actattgaat taaatatttt     480
aattatttgt attctcttta actatcttgg tatattaaag tattatcttt tatatattta    540
tcaatggtgg acacttttat aggtactctg tgtcatttt gatactgtag gtatcttatt    600
tcatttatct ttattcttaa tgtacgaatt cataatattt gattcagaac agatttatca   660
ctaattaaca gagtgtcaat tatgctaaca tctcatttac tgatttttaat ttaaaacagt 720
ttttgttaac atgcatgttt agggtttggct tcttaataat ttcttcttcc tcttctctct  780
ctcctcttct tttggtcagt gttgtgcggg ttaatacaac aaactgtcac aagtgtttgt   840
tgtccgggac gtacatttc gcggtcctgc tagtatgcgt gtgttccac tctgcgccc      900
aggagaaaaaa ctacaccatc cgagaagaaa ttccagaaaa cgtcctgata ggcaacttgt  960
tgaaagacct taacttgtcg ctgattccaa acaagtcctt gacaactact atgcagttca 1020
agctagtgta caagaccgga gatgtgccac tgattcgaat tgaagaggat actgtgaga 1080
tcttcactac cggcgctcgc attgatcgtg agaaattatg tgctggtatc ccaagggatg 1140
agcattgctt ttatgaagtg gaggttgcca tttgccgga aaactgtcac agactggtta 1200
agatacgttt tctgatagaa gatataaatg ataactctaa taaactctaa ataatctctc 1260
tcaacatatc aattccagag aacggagttc aaaactacga aggagacaa gatgccacaa 1320
ttgatcctga cgtaggcata aacggagtte caaaactacga agtgttact agatgccaca 1380
tttttggcct cgatgtcatt gaaacaccag agaaggata cctatgtgat gaaagtaaag 1440
aaaggagttt agataggaa gagaaggata cctatgtgat gaaagtaaag gttgaagatg 1500
gtgcttttcc tcaaagatcc agtactgcta tttttgcaagt aagtgttact gatacaaatg 1560
acaaccaccc agtcttaag gagacagaga ttgaagtcga tataccagaa aatgctcctg 1620
taggcacttc agtgacacag ctccatgcca cagatgctga caggtgaa aatgccaaga 1680
tccacttctc tttcagcaat ctagtctcca acattgccag gagattatttt cacctcaatg 1740
ccaactacta acttatcaca atcaaagaac cactggatag ggaagaaaca ccaaaccaca 1800
agtactggt tttgcaagt gatgttgat tgatgccagc aagatcaatg gtgctggtaa 1860
atgttacaga tgtcaatgat aatgttccca ccattgccag aagatacatc gtcaatcctg 1920
tcaatgacac agttgttctt tcagaaaata ttccactcaa caccaaaatt gctctcataa 1980
ctgtgacgga taagatgcg gaccataatg gcaggtgac atgcttcaca gatcatgaaa 2040
ttcctttcag attaaggcca gtattcagta atcagttcct cctgagaat gcagcatatc 2100
ttgactatga gtccacaaaa gaatatgcca ttaaattact ggctgcagat gctgcaaac 2160
ctcctttgaa tcagtcagca atgctcttca tcaaagtgaa agatgaaaat gacaatgctc 2220
cagtttccac ccagtctttc gtaactgttt ctattcctga gaataactct cctggcatcc 2280
```

Figure 11c (continued)

```
agttgatgaa agtaagtgca acggatgcag acagtgggcc taatgctgag atcaattacc   2340
tgctcaggcc tgatgctcca cctgaattca gcctggatcg tcgtacaggc atgctgactg   2400
tagtgaagaa actagataga gaaaaagagg ataaatatttt attcacaatt ctggcaaaag   2460
atatgggggt accaccctta accagccatg tcacagtctt tgtaagcatt attgatcaga   2520
atgacaatag cccagttttc actcacactg aatacaaatt ctatgtccca gaaaaccttc   2580
caaggcatgg tacagtagga ctaatcactg taactgatcc tgattatgga gacaattctg   2640
cagtacgct ctccattta gatgagaatg atgacttcac cattgattca caaactggtg   2700
tcatccgacc aaatatttca tttgatagag aaaaacaaga atcttacact ttctatgtaa   2760
aggctgagga tgtggtaga gtatcacgtt cttcaagtgc caaagtaacc ataaatgtgg   2820
ttgatgtcaa tgacaacaaa ccagttttca ttgtccctcc ttacaactat tcttatgaat   2880
tgttctacc gtccactaat ccaggcacag tgttcttcta ggtaattgct gttgacaatg   2940
acactggcat gaatgcagag gttcgttaca gcattgtagg aggaaacaca agagatctgt   3000
ttgcaatcga ccaagaaaca ggcaacataa cattgatgga gaaatgtgat gttacagacc   3060
ttgtttaca cagagtgttg gtcaaagcta atgacttagg acagcctgat tctctcttca   3120
gtgttgtaat tgtcaatctg ttcgtgaatg agtcagtgac caatgctaca gctgattaatg   3180
aactgtgcg caaaagcatt gaagcaccag tgacccccaa tactgagata gctgatgtat   3240
cctccaccac tagtgactat gtcaagatcc tgttgcagc tgttgctgcc accataactg   3300
tcgttgtagt tattttcatc actgctgtag taagatgtcg ccaggcacca caccttaagg   3360
ctgctcagaa aaacatgcag aattctgaat gggctacccc aaacccagaa aacaggcaga   3420
tgataatgat gaagaaaaag aaaaagaaga agaagcattc ccctaagaac ctgctgctta   3480
atgttgtcac tattgaagaa actaagccag atgatgttga cagtgatgga aacagagtca   3540
cactgacct tcctattgat ctagaagagc aaacaatggg aaagtacaat ggtaacta   3600
cacctactac tttcaagcct gacagccctg atttggcccg acactacaaa tctgcctctc   3660
cacagcctgc cttccaaatt cagcctgaaa ctcccctgaa tttgaagcac cacatcatcc   3720
aagaactgcc tctcgataaac accttttgtg cctgtgactc tatctccaat tgttcctcaa   3780
gcagttcaga tcccacagc gttttctgact gtggctatcc agtgacaacc ttcgaggtac   3840
ctgtgcccgt acacacagc ccgtccaagc ggcgtgtcac atttcaacctg ccagaaggct   3900
ctcaggaaag cagcagtgat ggtgactgg gagaccatga tgcaggcagc cttaccagca   3960
catcccatgg cctgccccttt ggctatcctc aggaggagta ctttgatcgt gctacacca   4020
gcaatcgcac tgaaggggat ggcaacttccg atcctgaatc tactttcata cctgactaa   4080
agaaagaaat aactgttcaa ccaactgtgg aagaggcctc tgacaactgc actcaagat   4140
gtctcatcta tggccattct gatgcctgct ggatgccggc atctctgat cattccagct   4200
cttacaagc acaggcctct gctctatgcc acgcccacc actgtcacag gcctctactc   4260
agcaccacag cccaaccagtg acacagacca ttgttctctg ccacagccct ccagtgacac   4320
agaccatcgc attgtgccac agcccaccac cgataacggt gtctgctctc caccacagtc   4380
ctcctctagt gcaggtact gcacttcacc acagccaccc atcaggcacag ccctcagccc   4440
tctgctacac cctcccttta gcacaggctg gtcaggcctc ctgcaatcag ccacacctct cctctgccac   4500
aggttattgc cctccatcgt agtcaggccc aatcatcagt cagtttgcag caagttggg   4560
tgcaaggtgc taatggacta tgctctgttg tgtctctgttg atcagggagt gcaaggtagt gcaacatctc   4620
```

Figure 11c (continued)

```
agttttacac catgtctgaa agacttcatc ccagtgatga ttcaattaaa gtcattcctt  4680
tgacaacctt cgctccacgc caacaggcca gaccgtccag aggtgattcc cccattatgg  4740
aaacacatcc cttgtaaagc taaaatagtt acttcaaatt ttcagaaaag atgtatatag  4800
tcaaaattta agatacaatt ccaatgagta ttctgattat cagattgta aataactatg  4860
taaatagaaa cagataccag aataaatcta cagctagacc cttagtcaat agttaaccaa  4920
aaaattgcaa ttgtttaat tcagaatgtg tatttaaaaa gaaaaggaat ttaacaattt  4980
gcatcccctt gtacagtaag gcttatcatg acagagcgta ctattctga tgtacagtat  5040
ttttgttgt ttttatcatc atgtgcaata ttactgattt gtttccatgc tgattgtgtg  5100
gaaccagtat gtagcaaatg gaaagcctag aaatatctta ttttctaagt ttacctttag  5160
tttacctaaa cttttgttca gataatgtta aaagtatac gtactctagc cttttttggg  5220
gcttctttt tgattttgt ttgtggtttt cagtttttt gttgttgtta gtgagtctcc  5280
cttcaaaata cacagtaggt agtgtaaata ctgcttgttt gtgtctctct gctgtcatgt  5340
tttctacctt attccaatac tatattgttg ataaaattg tatatacatt ttcaataaag  5400
aatatgtata aactgtacag atctagatct acaacctatt tctctactct ttagtagagt  5460
tcgagacaca gaagtgcaat aactgccta attaagcaac tatttgttaa aaagggcccc  5520
tttttactt aatagtttag tgtaaagtac actctggga aacgtatc tgacatttta  5580
agcctgtagt ccattattac ttgggtcttt actctggga attgtatgt acagcctag  5640
aaaattaaaa ggaggtgat gcatccaaag cacgagtcac ttaaaatatc gacggtaaac  5700
tactattttg tagagaaact caggaagatt taaatgttga tttgacagct caataggctg  5760
ttaccaaagg gtgttcagta aaaataacaa atacatgtaa ctgtagataa aaccacatac  5820
taaatctata agactaaggg attttgtta ttctagctca acttactgaa gaaacact  5880
aataacaaca agaatatcag gaaggaactt ttcaagaaat gtaattataa atctacatca  5940
aacagaattt taaggaaaaa tgcagaggga gaaataaggc acatgactgc ttcttgcagt  6000
caagaagaaa taccaataac acacacagaa caaaaaccat caaatctca tatatgaaat  6060
aaatatatt cttctaagca aagaaacagt actattcata gaaaacatta gttttctcct  6120
gttgtctgtt atttccttct tttatcctct taactgccca ttatcttgta tgtgcacatt  6180
ttataatgt acagaaacat caccaacttg attttcttcc atagcaaaac tgaaaaata  6240
ccttgtttca gtataacact aaaccaagag acaattgatg tttaatgggg gcggttgggg  6300
ttgggggga gtcaatatct cctattgatt aacttagaca tagatttgt aatgtataac  6360
ttgatatta atttatgatt aaactgtaat tttgtaacat aactgtggt aattgcataa  6420
tttcattggt gaggatttcc tttgaatatt gagaaagttt cttttcatgt gcccagcagg  6480
ttaagtagcg ttttcagaat atacatatt cccattcat gtaagttcc ttaagtcata  6540
tttgactggg cgtgcagaat aacttcttaa ctattaacta tcaagtttg attaataaaa  6600
ttaattaatt tttttctcc ttcgtgttgt taatgtttca agggatttgg agcatactgg  6660
ttttccaggt gcatgtgaat cccgaaggac tgatgatatt tgaatgttta ttaaattatt  6720
atcacacaaa tgtgttgata ttgtggctat tgttgatgtt gaaattgta aacttggga  6780
agattaagaa aagaaccaat agtgacaaaa atcagtgctt ccagtagatt ttagaacatt  6840
ctttgcctca aaaacctgc aaagatgatg tgagattttt tcttgtgttt taattattt  6900
cacatttct ctctgcaaac ctttagtttt ctgatgatct acacacacac atacacacac  6960
```

Figure 11c (continued)

```
acacacacac agtgcacac acacacattt aaaggatata aaagaagag gttgaaagat 7020
tattaaataa cttatcaggc atctcaatgg ttactatcta tgttagtgaa aatcaaatag 7080
gactcaaagt tggatatttg ggattttctt tctgacagta taatttattg agttactagg 7140
gaggtcctta aatcctcata tctggaaact tgtgaagttt tgacaccttt cctatagata 7200
taggaatgaa ccaatacgct tttattaccc tttctaactc tgattttata atcagactta 7260
gattgtgttt agaatattaa atgactgggc accctcttct tggttttac cagagaggct 7320
ttgaatggaa gcaggctgag agtagccaaa gaggcaaggg gtattagccc agttattctc 7380
cgctatgcct tctcttccta agcgtccact agtctggcc ttggaaatct gttacttcta 7440
cgcttcaga tctgatgata tctttttcat cacattacaa gttattctt tgactgaata 7500
gacagtggta taggttgaca tactgaagca gtgctattg tgatgtatga tgtgtagt 7560
cccacaactg caaaacgtct tactgaagca acaatcgaaa aatggttctg ttttaaaaag 7620
gatttgttt gatttgaaat taaaacttca aactgaatga cttatatgag aataatatgt 7680
tcaatcaaag tagttattct attttgtgtc catattccat tagattgtga ttattaattt 7740
tctagctatg gtattactat atcacacttg tgagtatgta ttcaaatact aagtatctta 7800
tatgctacgt gcatacacat tcttttctta aacttacct gtgtttaac taatattgtg 7860
tcagtgtatt aaaaattagc tttacatat gatatctaca atgtaataaa tttagagagt 7920
aattttgtgt attcttattt acttaacatt ttactttaa ttatgtaaat ttggttagaa 7980
aataataata aatggttagt gctattgtgt aatgtagca gttacaaaga gcctctgcct 8040
tcccaaacta atatttatca cacatggtca ttaaatggga aaaaaataga ctaacaaat 8100
cacaaattgt tcagttctta aaatgtaatt atgtcacaca atgatatttt cacaaaaaaa tccttttcaa 8160
tcctgagaaa attaaaggtg tttactcac atgaagttg tgtatactcc caacattagt tttttttgtt 8220
tgttcttttt tcatggtatt actgaaggtg tttatactct tctgatttat atttttatt tttatgaaaa 8280
tctacttgtt tagactttta ttttttgaaa ccaaatttat agttagttta ataattatta 8340
tttcttatct tctttttat tttttgaat gtttccaact gctcaattg ggtaaacttt 8400
ttattatgac cattagaaac tatttttgaat gtttccaact ggctcaattg gctgggaaaa 8460
catgggaaca agagaagctg aaatatatt ctgcaagaac cttctatat tatgtgccaa 8520
ttaccaaccc agatcaattt tatgcagagg ccttaaaata ttcttcaca gtagctttct 8580
tacactaacc gtcatgtgct tttagtaaat atgattttta aaagcagttc aagttgacaa 8640
cagcagaaac agtaacaaaa aaatctgctc agaaaaatgt atgtgcacaa ataaaaaaaa 8700
ttaatggcaa ttgtttagtg actgtaagtg atactttta aagagtaaac tgtgtgaaat 8760
ttatactatc cctgcttaaa atattaagat ttttatgaaa tatgtattta tgtttgtatt 8820
gtgggaagat tcctcctctg tgatatcata cagcatctga aagtgaacag tatcccaaag 8880
cagttccaag catgctttgg aagtaagaag gttgactatt gtatgccaa ggatggcagt 8940
atgtaatcca gaagcaaact tgtattaatt gttctatttc aggttct 8987
```

Figure 12c  Protein sequences of transcript variants of 109P1D4
>109P1D4 v.2 (SEQ ID NO:132).

```
MDLLSGTYIF AVLLACVVFH SGAQEKNYTI REEMPENVLI GDLLKDLNLS LIPNKSLTTA     60
MQFKLVYKTG DVPLIRIEED TGEIFTTGAR IDREKLCAGI PRDEHCFYEV EVAILPDEIF    120
RLVKIRFLIE DINDNAPLFP ATVINISIPE NSAINSKYTL PAAVDPDVGI NGVQNYELIK    180
SQNIFGLDVI ETPEGDKMPQ LIVQKELDRE EKDTYVMKVK VEDGGFPQRS STAILQVSVT    240
DTNDNHPVFK ETEIEVSIPE NAPVGTSVTQ LHATDADIGE NAKIHFSFSN LVSNIARRLF    300
HLNATTGLIT IKEPLDREET PNHKLLVLAS DGGLMPARAM VLVNVTDVND NVPSIDIRYI    360
VNPVNDTVVL SENIPLNTKI ALITVTDKDA DHNGRVTCFT DHEIPFRLRP VFSNQFLLET    420
AAYLDYESTK EYAIKLLAAD AGKPPLNQSA MLFIKVKDEN DNAPVFTQSF VTVSIPENNS    480
PGIQLTKVSA MDADSGPNAK INYLLGPDAP PEFSLDCRTG MLTVVKKLDR EKEDKYLFTI    540
LAKDNGVPPL TSNVTVFVSI IDQNDNSPVF THNEYNFYVP ENLPRHGTVG LITVTDPDYG    600
DNSAVTLSIL DENDDFTIDS QTGVIRPNIS FDREKQESYT FYVKAEDGGR VSRSSSAKVT    660
INVVDVNDNK PVFIVPPSNC SYELVLPSTN PGTVVFQVIA VDNDTGMNAE VRYSIVGGNT    720
RDLFAIDQET GNITLMEKCD VTDLGLHRVL VKANDLGQPD SLFSVVIVNL FVNESVTNAT    780
LINELVRKST EAPVTPNTEI ADVSSPTSDY VKILVAAVAG TITVVVVIFI TAVVRCRQAP    840
HLKAAQKNKQ NSEWATPNPE NRQMIMMKKK KKKKKHSPKN LLLNFVTIEE TKADDVDSDG    900
NRVTLDLPID LEEQTMGKYN WVTTPTTFKP DSPDLARHYK SASPQPAFQI QPETPLNSKH    960
HIIQELPLDN TFVACDSISK CSSSSSDPYS VSDCGYPVTT FEVPVSVHTR PTDSRTSTIE   1020
ICSEI                                                              1025
```

>109P1D4 v.3 (SEQ ID NO:133).

```
MDLLSGTYIF AVLLACVVFH SGAQEKNYTI REEMPENVLI GDLLKDLNLS LIPNKSLTTA     60
MQFKLVYKTG DVPLIRIEED TGEIFTTGAR IDREKLCAGI PRDEHCFYEV EVAILPDEIF    120
RLVKIRFLIE DINDNAPLFP ATVINISIPE NSAINSKYTL PAAVDPDVGI NGVQNYELIK    180
SQNIFGLDVI ETPEGDKMPQ LIVQKELDRE EKDTYVMKVK VEDGGFPQRS STAILQVSVT    240
DTNDNHPVFK ETEIEVSIPE NAPVGTSVTQ LHATDADIGE NAKIHFSFSN LVSNIARRLF    300
HLNATTGLIT IKEPLDREET PNHKLLVLAS DGGLMPARAM VLVNVTDVND NVPSIDIRYI    360
VNPVNDTVVL SENIPLNTKI ALITVTDKDA DHNGRVTCFT DHEIPFRLRP VFSNQFLLET    420
AAYLDYESTK EYAIKLLAAD AGKPPLNQSA MLFIKVKDEN DNAPVFTQSF VTVSIPENNS    480
PGIQLTKVSA MDADSGPNAK INYLLGPDAP PEFSLDCRTG MLTVVKKLDR EKEDKYLFTI    540
LAKDNGVPPL TSNVTVFVSI IDQNDNSPVF THNEYNFYVP ENLPRHGTVG LITVTDPDYG    600
DNSAVTLSIL DENDDFTIDS QTGVIRPNIS FDREKQESYT FYVKAEDGGR VSRSSSAKVT    660
INVVDVNDNK PVFIVPPSNC SYELVLPSTN PGTVVFQVIA VDNDTGMNAE VRYSIVGGNT    720
RDLFAIDQET GNITLMEKCD VTDLGLHRVL VKANDLGQPD SLFSVVIVNL FVNESVTNAT    780
LINELVRKST EAPVTPNTEI ADVSSPTSDY VKILVAAVAG TITVVVVIFI TAVVRCRQAP    840
HLKAAQKNKQ NSEWATPNPE NRQMIMMKKK KKKKKHSPKN LLLNFVTIEE TKADDVDSDG    900
NRVTLDLPID LEEQTMGKYN WVTTPTTFKP DSPDLARHYK SASPQPAFQI QPETPLNSKH    960
HIIQELPLDN TFVACDSISK CSSSSSDPYS VSDCGYPVTT FEVPVSVHTR PMKEVVRSC   1020
```

Figure 12c (continued)

```
TPMKESTTME IWIHPQPQRK SEGKVAGKSQ RRVTFHLPEG SQESSSDGGL GDHDAGSLTS    1080
TSHGLPLGYP QEEYFDRATP SNRTEGDGNS DPESTFIPGL KKAAEITVQP TVEEASDNCT    1140
QECLIYGHSD ACWMPASLDH SSSSQAQASA LCHSPPLSQA STQHHSPRVT QTIALCHSPP    1200
VTQTIALCHS PPPIQVSALH HSPPLVQATA LHHSPPSAQA SALCYSPPLA QAAAISHSSP    1260
LPQVIALHRS QAQSSVSLQQ GWVQGADGLC SVDQGVQGSA TSQFYTMSER LHPSDDSIKV    1320
IPLTFTFTPRQ QARPSRGDSP IMEEHPL                                      1347
```

>109P1D4 v.4 (SEQ ID NO:134).

```
MDLLSGTYIF AVLLACVVFH SGAQEKNYTI REEMPENVLI GDLLKDLNLS LIPNKSLTTA      60
MQFKLVYKTG DVPLIRIEED TGEIFTTGAR IDREKLCAGI PRDEHCFYEV EVAILPDEIF     120
RLVKIRFLIE DINDNAPLFP ATVINISIPE NSAINSKYTL PAAVDPDVGI NGVQNYELIK     180
SQNIFGLDVI ETPEGDKMPQ LIVQKELDRE EKDTYVMKVK VEDGGFPQRS STAILQVSVT     240
DTNDNHPVFK ETEIEVSIPE NAPVGTSVTQ LHATDADIGE NAKIHFSFSN LVSNIARRLF     300
HLNATTGLIT IKEPLDREET PNHKLLVLAS DGGLMPARAM VLVNVTDVND NVPSIDIRYI     360
VNPVNDTVVL SENIPINTKI ALITVTDKDA DHNGRVTCFT DHEIPFRLRP VFSNQFLLET     420
AAYLDYESTK EYAIKLLAAD AGKPPLNQSA MLFIKVKDEN DNAPVTQSF VTVSIPENNS      480
PGIQLTKVSA MDADSGPNAK INYLLGPDAP PEFSLDCRTG MLTVVKKLDR EKEDKYLFTI     540
LAKDNGVPPL TSNVTVFVSI IDQNDNSPVF THNEYNFYVP ENLPRHGTVG LITVTDPDYG     600
DNSAVTLSIL DENDDFTIDS QTGVIRPNIS FDREKQESYT FYKAEDGGR VSRSSSAKVT     660
INVVDVNDNK PVFVPPSNC SYELVLPSTN PGTVVFQVIA VDNDTGMNAE VRYSIVGGNT     720
RDLFAIDQET GNITILMEKCD VTDLGLHRVL VKANDLGQPD SLFSVVIVNL FVNESVTNAT    780
LINELVRKST EAPVTPNTEI ADVSSPTSDY VKILVAAVAG TITVVVIFI TAVRCRQAP      840
HLKAAQKNKQ NSEWATPNPE NRQMIMMKKK KKKKKHSPKN LLLNFVTIEE TKADDVDSDG    900
NRVTLDLPID LEEQIMGKYN WTTPTTFKP DSPDLARHYK SASPQPAFQI QPETPLNSKH     960
HIQELPLDN TFVACDSISK CSSSSDPYS VSDCGYPVTT FEVPVSVHTR PPMKEVVRSC     1020
TPMKESTTME IWIHPQPSQ RRVTFHLPEG SQESSSDGGL GDHDAGSLTS TSHGLPLGYP     1080
QEEYFDRATP SNRTEGDGNS DPESTFIPGL KKAAEITVQP TVEEASDNCT QECLIYGHSD    1140
ACWMPASLDH SSSSQAQASA LCHSPPLSQA STQHHSPRVT QTIALCHSPP VTQTIALCHS    1200
PPPIQVSALH HSPPLVQATA LHHSPPSAQA SALCYSPPLA QAAAISHSSP LPQVIALHRS    1260
QAQSSVSLQQ GWVQGADGLC SVDQGVQGSA TSQFYTMSER LHPSDDSIKV IPLTFTFTPRQ   1320
QARPSRGDSP IMEEHPL                                                   1337
```

>109P1D4 v.5 (SEQ ID NO:135).

```
MDLLSGTYIF AVLLACVVFH SGAQEKNYTI REEMPENVLI GDLLKDLNLS LIPNKSLTTA      60
MQFKLVYKTG DVPLIRIEED TGEIFTTGAR IDREKLCAGI PRDEHCFYEV EVAILPDEIF     120
RLVKIRFLIE DINDNAPLFP ATVINISIPE NSAINSKYTL PAAVDPDVGI NGVQNYELIK     180
SQNIFGLDVI ETPEGDKMPQ LIVQKELDRE EKDTYVMKVK VEDGGFPQRS STAILQVSVT     240
```

Figure 12c (continued)

```
DPNANHPVFK EPEIEVSIPE NAPVGTSVTQ LHATDADIGE NAKIHFSFSN LVSNIARRLF    300
HLNATTGLIT IKEPLDREET PNHKLIVLAS DGGLMPARAM VLVNVTDVND NVPSIDIRYI    360
VNPVNDTVVL SENIPLNTKI ALITVTDKDA DHNGRVTCFT DHEIPFRLRP VFSNQFLLET    420
AAYLDYESTK EYAIKLLAAD AGKPPLNQSA MLFIKVKDEN DNAPVFTQSF VTVSIPENNS    480
PGIQLTKVSA MDADSGPNAK INYLLGPDAP PEFSLDCRTG MLTVVKKLDR EKEDKYLFTI    540
LAKDNGVPPL TSNVTVFVSI IDQNDNSPVF THNEYNFYVP ENLPRHGTVG LITVTDPDYG    600
DNSAVTLSIL DENDDFTIDS QTGVIRPNIS FDREKQESYT FYVKAEDGGR VSRSSSAKVT    660
INVVDVNDNK PVFIVPPSNC SYELVLPSTN PGTVVFQVIA VDNDTGMNAE VRYSIVGGNT    720
RDLFAIDQET GNITLMEKCD VTDLGLHRVL VKANDLGQPD SLFSVVIVNL FVNESVTNAT    780
LINELVRKST EAPVTPNTEI ADVSSPTSDY VKILVAAVAG TITVVVIFI TAVVRCRQAP     840
HLKAAQKNKQ NSEWATPNPE NRQMIMMKKK KKKKKHSPKN LLLNFVTIEE TKADDVDSDG    900
NRVTLDLPID LEEQTMGKYN WVTTPTTFKP DSPDLARHYK SASPQPAFQI QPETPLNSKH    960
HIIQELPLDN TFVACDSISK CSSSSSDPYS VSDCGYPVTT FEVPVSVHTR PSQRRVTFHL   1020
PEGSQESSSD GGLGDHDAGS LTSTSHGLPL GYPQEEYFDR ATPSNRTEGD GNSDPESTFI   1080
PGLKKAAEIT VQPTVEEASD NCTQECLLYG HSDACWMPAS LDHSSSSQAQ ASALCHSPPL   1140
SQASTQHHSP RVTQTIALCH SPVTQTIAL HRSAQSSVS LQQGWVQGAD ATALHHSPPS    1200
AQASALCYSP PLAQAAAISH SSPLPQVIAL HRSAQSSVS LQQGWVQGAD GLCSVDQGVQ    1260
GSATSQFYTM SERLHPSDDS IKVIPLTTFT PRQQARPSRG DSPIMEEHPL              1310

>109P1D4 v.6 (SEQ ID NO:136).
MTVGFNSDIS SVVRVNTTNC HKCLLSGTYI FAVLLVCVVF HSGAQEKNYT IREEIPENVL     60
IGNLIKDLNL SLIPNKSLTT TMQFKLVYKT GDVPLIRIEE DTGEIFTTGA RIDREKLCAG    120
IPRDEHCFYE VEVAILPDEI FRLVKIRFLI EDINDNAPLF PATVINISIP ENSAINSKYT    180
LPAAVDPDVG INGVQNYELI KSQNIFGLDV IETPEGDKMP QLIVQKELDR EEKDTYVMKV    240
KVEDGGFPQR SSTAILQVSV TDTNDNHPVF KETEIEVSIP ENAPVGTSVT QLHATDADIG    300
ENAKIHFSFS NLVSNIARRL FHLNATTGLI TIKEPLDREE TPNHKLIVLA SDGGLMPARA    360
MVLVNVTDVN DNVPSIDIRY IVNPVNDTVV LSENIPLNTK IALITVTDKD ADHNGRVTCF    420
TDHEIPFRLR PVFSNQFLLE NAAYLDYEST KEYAIKLLAA DAGKPPLNQS AMLFIKVKDE    480
NDNAPVFTQS FVTVSIPENN SPGIQLMKVS ATDADSGPNA EINYLLGPDA PPEFSLDRRI    540
GMLTVVKKLD REKEDKYLFT ILAKDNGVPP LTSNVTVFVS IIDQNDNSPV FTHNEYKFYV    600
PENLPRHGTV GLITVTDPDY GDNSAVTLSI LDENDDFTID SQTGVIRPNI SFDREKQESY    660
TFYVKAEDGG RVSRSSSAKV TINVVDVNDN KPVFIVPPYN YSYELVLPST NPGTVVFQVI    720
AVDNDTGMNA EVRYSIVGGN TRDLFAIDQE TGNITLMEKC DVTDLGLHRV LVKANDLGQP    780
DSLFSVVIVN LFVNESVTNA TLINELVRKS IEAPVTPNTE IADVSSPTSD YVKILVAAVA    840
GTITVVVIF ITAVVRCRQA PHLKAAQKNM QNSEWATPNP ENRQMIMMKK KKKKKHSPK     900
NLLLNFVTIE ETKADDVDSD GNRVTLDLPI DLEEQTMGKY NWTTPTTFK PDSPDLARHY    960
KSASPQPAFQ IQPETPLNLK HHIIQELPLD NTFVACDSIS KCSSSSSDPY SVSDCGYPVT   1020
TFEVPVSVHT RPTDSRT                                                  1037
```

Figure 12c (continued)

>109P1D4 v.7 (SEQ ID NO:137)

```
MFRVGFLIIS SSSSLSPLLL VSVVRVNTTN CHKCLLSGTY IFAVLLVCVV FHSGAQEKNY          60
TIREEIPENV LIGNLLKDLN LSLIPNKSLT TTMQFKLVYK TGDVPLIRIE EDTGEIFTTG         120
ARIDREKLCA GIPRDEHCFY EVEVAILPDE IFRLVKIRFL IEDINDNAPL FPATVINISI         180
PENSAINSKY TLPAAVDPDV GINGVQNYEL IKSQNIFGLD VIETPEGDKM PQLIVQKELD         240
REEKDTYVMK VKVEDGGFPQ RSSTAILQVS VTDTNDNHPV FKETEIEVSI PENAPVGTSV         300
TQLHATDADI GENAKIHFSF SNLVSNIARR LFHLNATTGL ITIKEPLDRE ETPNHKLLVL         360
ASDGGLMPAR AMVLVNVTDV NDNVPSIDIR YIVNPVNDTV VLSENIPLNT KIALITVTDK         420
DADHNGRVTC FTDHEIPFRL RPVFSNQFLL ENAAYLDYES TKFYAIKLLA ADAGKPPLNQ         480
SAMLFIKVKD ENDNAPVFTQ SFVTVSIPEN NSPGIQLMKV SATDADSGPN AEINYLLGPD         540
APPEFSLDRR TGMLTVVKKL DREKEDKYLF TILAKDNGVP PLTSNVTVFV SIIDQNDNSP         600
VFTHNEYKFY VPENLPRHGT VGLITVTDPD YGDNSAVTLS ILDENDDFTI DSQTGVIRPN         660
ISFDREKQES YTFYKAEDG GRVSRSSSAK VTINVDVND NKPVFIVPPY NYSYELVLPS           720
TNPGTVFQV  IAVDNDTGMN AEVRYSIVGG NTRDLFAIDQ ETGNITLMEK CDVTDLGLHR         780
VLVKANDLGQ PDSLFSVVIV NLFVNESVTN ATLINELVRK SIEAPVTPNT EIADVSSPTS         840
DYVKILVAAV AGTITVVVVI FITAVVRCRQ APHLKAAQKN MQNSEWATPN PENRQMIMMK         900
KKKKKKKHSP KNLLLNVVTI EETKADDVDS DGNRVTLDLP IDLEEQTMGK YNWVTTPTTF         960
KPDSPDLARH YKSASPQPAF QIQPETPLNL KHHIIQELPL DNTFVACDSI SNCSSSSSDP        1020
YSVSDCGYPV TTFEVPVSVH TRPTDSRT                                          1048
```

>109P1D4 v.8 (SEQ ID NO:138).

```
MFRVGFLIIS SSSSLSPLLL VSVVRVNTTN CHKCLLSGTY IFAVLLVCVV FHSGAQEKNY          60
TIREEIPENV LIGNLLKDLN LSLIPNKSLT TTMQFKLVYK TGDVPLIRIE EDTGEIFTTG         120
ARIDREKLCA GIPRDEHCFY EVEVAILPDE IFRLVKIRFL IEDINDNAPL FPATVINISI         180
PENSAINSKY TLPAAVDPDV GINGVQNYEL IKSQNIFGLD VIETPEGDKM PQLIVQKELD         240
REEKDTYVMK VKVEDGGFPQ RSSTAILQVS VTDTNDNHPV FKETEIEVSI PENAPVGTSV         300
TQLHATDADI GENAKIHFSF SNLVSNIARR LFHLNATTGL ITIKEPLDRE ETPNHKLLVL         360
ASDGGLMPAR AMVLVNVTDV NDNVPSIDIR YIVNPVNDTV VLSENIPLNT KIALITVTDK         420
DADHNGRVTC FTDHEIPFRL RPVFSNQFLL ENAAYLDYES TKFYAIKLLA ADAGKPPLNQ         480
SAMLFIKVKD ENDNAPVFTQ SFVTVSIPEN NSPGIQLMKV SATDADSGPN AEINYLLGPD         540
APPEFSLDRR TGMLTVVKKL DREKEDKYLF TILAKDNGVP PLTSNVTVFV SIIDQNDNSP         600
VFTHNEYKFY VPENLPRHGT VGLITVTDPD YGDNSAVTLS VTINVDVND  NKPVFIVPPY         660
ISFDREKQES YTFYVKAEDG GRVSRSIVGG AEVRYSIVGG NTRDLFAIDQ ETGNITLMEK         720
TNPGTVFQV  IAVDNDTGMN AEVRYSIVGG NTRDLFAIDQ ETGNITLMEK CDVTDLGLHR         780
VLVKANDLGQ PDSLFSVVIV NLFVNESVTN ATLINELVRK SIEAPVTPNT EIADVSSPTS         840
DYVKILVAAV AGTITVVVVI FITAVVRCRQ APHLKAAQKN MQNSEWATPN PENRQMIMMK         900
KKKKKKKHSP KNLLLNVVTI EETKADDVDS DGNRVTLDLP IDLEEQTMGK YNWVTTPTTF         960
KPDSPDLARH YKSASPQPAF QIQPETPLNL KHHIIQELPL DNTFVACDSI SNCSSSSSDP        1020
```

Figure 12c (continued)

```
YSVSDCGYPV TTFEVPVSVH TRPSQRRVTF HLPEGSQESS SDGGLGDHDA GSLTSTSHGL     1080
PLGYPQEEYF DRATPSNRTE GDGNSDPEST FIPGLKKEIT VQPTVEEASD NCTQECLIYG     1140
HSDACWMPAS LDHSSSSQAQ ASALCHSPPL SQASTQHHSP PVTQTIVLCH SPPVTQTIAL     1200
CHSPPPIQVS ALHHSPPLVQ GTALHHSPPS AQASALCYSP PLAQAAAISH SSSLPQVIAL     1260
HRSQAQSSVS LQQGWVQGAN GLCSVDQGVQ GSATSQFYTM SERLHPSDDS IKVIPLTTFA     1320
PRQQARPSRG DSPIMETHPL                                                1340
```

Figure 13c Alignment of nucleotide sequences of 109P1D4 transcript variants (data not shown)

Figure 14c Alignment of protein sequences of 109P1D4 transcript variants
(SEQ ID NOS:26, 132, 133, 134, 135, 136, 137, 138).

```
109P1D4v.1  ----------------------------------MDLLSGTYIFAVLLACVVFHSGAQEKNY   28
109P1D4v.2  ----------------------------------MDLLSGTYIFAVLLACVVFHSGAQEKNY   28
109P1D4v.3  ----------------------------------MDLLSGTYIFAVLLACVVFHSGAQEKNY   28
109P1D4v.4  ----------------------------------MDLLSGTYIFAVLLACVVFHSGAQEKNY   28
109P1D4v.5  ----------------------------------MDLLSGTYIFAVLLACVVFHSGAQEKNY   28
109P1D4v.6  ---------------SVVRVNTTNCHKCLLSGTYIFAVLLVCVVFHSGAQEKNY            49
109P1D4v.7  MFRVGFLIISSSSSLSPLLLVSVVRVNTTNCHKCLLSGTYIFAVLLVCVVFHSGAQEKNY      60
109P1D4v.8  MFRVGFLIISSSSSLSPLLLVSVVRVNTTNCHKCLLSGTYIFAVLLVCVVFHSGAQEKNY      60
                                              ****************.************

109P1D4v.1  TIREEMPENVLIGDLLKDINLSLIPNKSLTTAMQFKLVYKTGDVPLIRIEEDTGEIFTTG   88
109P1D4v.2  TIREEMPENVLIGDLLKDINLSLIPNKSLTTAMQFKLVYKTGDVPLIRIEEDTGEIFTTG   88
109P1D4v.3  TIREEMPENVLIGDLLKDINLSLIPNKSLTTAMQFKLVYKTGDVPLIRIEEDTGEIFTTG   88
109P1D4v.4  TIREEMPENVLIGDLLKDINLSLIPNKSLTTAMQFKLVYKTGDVPLIRIEEDTGEIFTTG   88
109P1D4v.5  TIREEMPENVLIGDLLKDINLSLIPNKSLTTAMQFKLVYKTGDVPLIRIEEDTGEIFTTG   88
109P1D4v.6  TIREEMPENVLIGNLLKDINLSLIPNKSLTTTMQFKLVYKTGDVPLIRIEEDTGEIFTTG  109
109P1D4v.7  TIREEIPENVLIGNLLKDINLSLIPNKSLTTTMQFKLVYKTGDVPLIRIEEDTGEIFTTG  120
109P1D4v.8  TIREEIPENVLIGNLLKDINLSLIPNKSLTTTMQFKLVYKTGDVPLIRIEEDTGEIFTTG  120
            *****:*******:***********:*************************

109P1D4v.1  ARIDREKLCAGIPRDEHCFYEVEVAILPDEIFRLVKIRFLIEDINDNAPLFPATVINISI  148
109P1D4v.2  ARIDREKLCAGIPRDEHCFYEVEVAILPDEIFRLVKIRFLIEDINDNAPLFPATVINISI  148
109P1D4v.3  ARIDREKLCAGIPRDEHCFYEVEVAILPDEIFRLVKIRFLIEDINDNAPLFPATVINISI  148
```

Figure 14c (continued)

```
109P1D4v.4    ARIDREKLCAGIPRDEHCFYEVEVAILPDEIFRLVKIRFLIEDINDNAPLFPATVINISI    148
109P1D4v.5    ARIDREKLCAGIPRDEHCFYEVEVAILPDEIFRLVKIRFLIEDINDNAPLFPATVINISI    148
109P1D4v.6    ARIDREKLCAGIPRDEHCFYEVEVAILPDEIFRLVKIRFLIEDINDNAPLFPATVINISI    169
109P1D4v.7    ARIDREKLCAGIPRDEHCFYEVEVAILPDEIFRLVKIRFLIEDINDNAPLFPATVINISI    180
109P1D4v.8    ARIDREKLCAGIPRDEHCFYEVEVAILPDEIFRLVKIRFLIEDINDNAPLFPATVINISI    180
              ************************************************************

109P1D4v.1    PENSAINSKYTLPAAVDPDVGINGVQNYELIKSQNIFGLDVIETPEGDKMPQLIVQKELD    208
109P1D4v.2    PENSAINSKYTLPAAVDPDVGINGVQNYELIKSQNIFGLDVIETPEGDKMPQLIVQKELD    208
109P1D4v.3    PENSAINSKYTLPAAVDPDVGINGVQNYELIKSQNIFGLDVIETPEGDKMPQLIVQKELD    208
109P1D4v.4    PENSAINSKYTLPAAVDPDVGINGVQNYELIKSQNIFGLDVIETPEGDKMPQLIVQKELD    208
109P1D4v.5    PENSAINSKYTLPAAVDPDVGINGVQNYELIKSQNIFGLDVIETPEGDKMPQLIVQKELD    208
109P1D4v.6    PENSAINSKYTLPAAVDPDVGINGVQNYELIKSQNIFGLDVIETPEGDKMPQLIVQKELD    229
109P1D4v.7    PENSAINSKYTLPAAVDPDVGINGVQNYELIKSQNIFGLDVIETPEGDKMPQLIVQKELD    240
109P1D4v.8    PENSAINSKYTLPAAVDPDVGINGVQNYELIKSQNIFGLDVIETPEGDKMPQLIVQKELD    240
              ************************************************************

109P1D4v.1    REEKDTYVMKVKVEDGGFPQRSSTAILQVSVTDTNDNHPVFKETEIEVSIPENAPVGTSV    268
109P1D4v.2    REEKDTYVMKVKVEDGGFPQRSSTAILQVSVTDTNDNHPVFKETEIEVSIPENAPVGTSV    268
109P1D4v.3    REEKDTYVMKVKVEDGGFPQRSSTAILQVSVTDTNDNHPVFKETEIEVSIPENAPVGTSV    268
109P1D4v.4    REEKDTYVMKVKVEDGGFPQRSSTAILQVSVTDTNDNHPVFKETEIEVSIPENAPVGTSV    268
109P1D4v.5    REEKDTYVMKVKVEDGGFPQRSSTAILQVSVTDPNANHPVFKEPEIEVSIPENAPVGTSV    268
109P1D4v.6    REEKDTYVMKVKVEDGGFPQRSSTAILQVSVTDTNDNHPVFKETEIEVSIPENAPVGTSV    289
109P1D4v.7    REEKDTYVMKVKVEDGGFPQRSSTAILQVSVTDTNDNHPVFKETEIEVSIPENAPVGTSV    300
109P1D4v.8    REEKDTYVMKVKVEDGGFPQRSSTAILQVSVTDTNDNHPVFKETEIEVSIPENAPVGTSV    300
              *********************************.* ***********************

109P1D4v.1    TQLHATDADIGENAKIHFSFSNLVSNIARRLFHLNATTGLITIKEPLDREETPNHKLLVL    328
109P1D4v.2    TQLHATDADIGENAKIHFSFSNLVSNIARRLFHLNATTGLITIKEPLDREETPNHKLLVL    328
109P1D4v.3    TQLHATDADIGENAKIHFSFSNLVSNIARRLFHLNATTGLITIKEPLDREETPNHKLLVL    328
109P1D4v.4    TQLHATDADIGENAKIHFSFSNLVSNIARRLFHLNATTGLITIKEPLDREETPNHKLLVL    328
109P1D4v.5    TQLHATDADIGENAKIHFSFSNLVSNIARRLFHLNATTGLITIKEPLDREETPNHKLLVL    328
109P1D4v.6    TQLHATDADIGENAKIHFSFSNLVSNIARRLFHLNATTGLITIKEPLDREETPNHKLLVL    349
109P1D4v.7    TQLHATDADIGENAKIHFSFSNLVSNIARRLFHLNATTGLITIKEPLDREETPNHKLLVL    360
109P1D4v.8    TQLHATDADIGENAKIHFSFSNLVSNIARRLFHLNATTGLITIKEPLDREETPNHKLLVL    360
              ************************************************************

109P1D4v.1    ASDGGLMPARAMVLVNVTDVNDNVPSIDIRYIVNPVNDTVVLSENIPLNTKIALITVTDK    388
109P1D4v.2    ASDGGLMPARAMVLVNVTDVNDNVPSIDIRYIVNPVNDTVVLSENIPLNTKIALITVTDK    388
```

Figure 14c (continued)

```
109P1D4v.3    ASDGGLMPARAMVLVNVTDVNDNVPSIDIRYIVNPVNDTVVLSENIPLNTKIALITVTDK 388
109P1D4v.4    ASDGGLMPARAMVLVNVTDVNDNVPSIDIRYIVNPVNDTVVLSENIPLNTKIALITVTDK 388
109P1D4v.5    ASDGGLMPARAMVLVNVTDVNDNVPSIDIRYIVNPVNDTVVLSENIPLNTKIALITVTDK 388
109P1D4v.6    ASDGGLMPARAMVLVNVTDVNDNVPSIDIRYIVNPVNDTVVLSENIPLNTKIALITVTDK 409
109P1D4v.7    ASDGGLMPARAMVLVNVTDVNDNVPSIDIRYIVNPVNDTVVLSENIPLNTKIALITVTDK 420
109P1D4v.8    ASDGGLMPARAMVLVNVTDVNDNVPSIDIRYIVNPVNDTVVLSENIPLNTKIALITVTDK 420
              ************************************************************

109P1D4v.1    DADHNGRVTCFTDHEIPFRLRPVFSNQFLLETAAYLDYESTKEYAIKLLAADAGKPPLNQ 448
109P1D4v.2    DADHNGRVTCFTDHEIPFRLRPVFSNQFLLETAAYLDYESTKEYAIKLLAADAGKPPLNQ 448
109P1D4v.3    DADHNGRVTCFTDHEIPFRLRPVFSNQFLLETAAYLDYESTKEYAIKLLAADAGKPPLNQ 448
109P1D4v.4    DADHNGRVTCFTDHEIPFRLRPVFSNQFLLETAAYLDYESTKEYAIKLLAADAGKPPLNQ 448
109P1D4v.5    DADHNGRVTCFTDHEIPFRLRPVFSNQFLLETAAYLDYESTKEYAIKLLAADAGKPPLNQ 448
109P1D4v.6    DADHNGRVTCFTDHEIPFRLRPVFSNQFLLENAAYLDYESTKEYAIKLLAADAGKPPLNQ 469
109P1D4v.7    DADHNGRVTCFTDHEIPFRLRPVFSNQFLLENAAYLDYESTKEYAIKLLAADAGKPPLNQ 480
109P1D4v.8    DADHNGRVTCFTDHEIPFRLRPVFSNQFLLENAAYLDYESTKEYAIKLLAADAGKPPLNQ 480
              *****************************.*****************************

109P1D4v.1    SAMLFIKVKDENDNAPVFTQSFVTVSIPENNSPGIQLTKVSAMDADSGPNAKINYLLGPD 508
109P1D4v.2    SAMLFIKVKDENDNAPVFTQSFVTVSIPENNSPGIQLTKVSAMDADSGPNAKINYLLGPD 508
109P1D4v.3    SAMLFIKVKDENDNAPVFTQSFVTVSIPENNSPGIQLTKVSAMDADSGPNAKINYLLGPD 508
109P1D4v.4    SAMLFIKVKDENDNAPVFTQSFVTVSIPENNSPGIQLTKVSAMDADSGPNAKINYLLGPD 508
109P1D4v.5    SAMLFIKVKDENDNAPVFTQSFVTVSIPENNSPGIQLTKVSAMDADSGPNAKINYLLGPD 508
109P1D4v.6    SAMLFIKVKDENDNAPVFTQSFVTVSIPENNSPGIQLMKVSATDADSGPNAEINYLLGPD 529
109P1D4v.7    SAMLFIKVKDENDNAPVFTQSFVTVSIPENNSPGIQLMKVSATDADSGPNAEINYLLGPD 540
109P1D4v.8    SAMLFIKVKDENDNAPVFTQSFVTVSIPENNSPGIQLMKVSATDADSGPNAEINYLLGPD 540
              *************************************:*****.***************

109P1D4v.1    APPEFSLDCRTGMLTVVKKLDREKEDKYLFTILAKDNGVPPLTSNVTVFVSIIDQNDNSP 568
109P1D4v.2    APPEFSLDCRTGMLTVVKKLDREKEDKYLFTILAKDNGVPPLTSNVTVFVSIIDQNDNSP 568
109P1D4v.3    APPEFSLDCRTGMLTVVKKLDREKEDKYLFTILAKDNGVPPLTSNVTVFVSIIDQNDNSP 568
109P1D4v.4    APPEFSLDCRTGMLTVVKKLDREKEDKYLFTILAKDNGVPPLTSNVTVFVSIIDQNDNSP 568
109P1D4v.5    APPEFSLDCRTGMLTVVKKLDREKEDKYLFTILAKDNGVPPLTSNVTVFVSIIDQNDNSP 568
109P1D4v.6    APPEFSLDRRTGMLTVVKKLDREKEDKYLFTILAKDNGVPPLTSNVTVFVSIIDQNDNSP 589
109P1D4v.7    APPEFSLDRRTGMLTVVKKLDREKEDKYLFTILAKDNGVPPLTSNVTVFVSIIDQNDNSP 600
109P1D4v.8    APPEFSLDRRTGMLTVVKKLDREKEDKYLFTILAKDNGVPPLTSNVTVFVSIIDQNDNSP 600
              ********  **************************************************

109P1D4v.1    VFTHNEYNFYVPENLPRHGTVGLIITVDPPDYGDNSAVTLSILDENDDFTIDSQTGVIRPN 628
```

Figure 14c (continued)

```
109P1D4v.2    VFTHNEYNFYVPENLPRHGTVGLITVTDPDYGDNSAVTLSILDENDDFTIDSQTGVIRPN    628
109P1D4v.3    VFTHNEYNFYVPENLPRHGTVGLITVTDPDYGDNSAVTLSILDENDDFTIDSQTGVIRPN    628
109P1D4v.4    VFTHNEYNFYVPENLPRHGTVGLITVTDPDYGDNSAVTLSILDENDDFTIDSQTGVIRPN    628
109P1D4v.5    VFTHNEYNFYVPENLPRHGTVGLITVTDPDYGDNSAVTLSILDENDDFTIDSQTGVIRPN    628
109P1D4v.6    VFTHNEYKFYVPENLPRHGTVGLITVTDPDYGDNSAVTLSILDENDDFTIDSQTGVIRPN    649
109P1D4v.7    VFTHNEYKFYVPENLPRHGTVGLITVTDPDYGDNSAVTLSILDENDDFTIDSQTGVIRPN    660
109P1D4v.8    VFTHNEYKFYVPENLPRHGTVGLITVTDPDYGDNSAVTLSILDENDDFTIDSQTGVIRPN    660
              *******:.***************************************************

109P1D4v.1    ISFDREKQESYTFYVKAEDGGRVSRSSSAKVTINVVDVNDNKPVFIVPPSNCSYELVLPS    688
109P1D4v.2    ISFDREKQESYTFYVKAEDGGRVSRSSSAKVTINVVDVNDNKPVFIVPPSNCSYELVLPS    688
109P1D4v.3    ISFDREKQESYTFYVKAEDGGRVSRSSSAKVTINVVDVNDNKPVFIVPPSNCSYELVLPS    688
109P1D4v.4    ISFDREKQESYTFYVKAEDGGRVSRSSSAKVTINVVDVNDNKPVFIVPPSNCSYELVLPS    688
109P1D4v.5    ISFDREKQESYTFYVKAEDGGRVSRSSSAKVTINVVDVNDNKPVFIVPPYNYSYELVLPS    688
109P1D4v.6    ISFDREKQESYTFYVKAEDGGRVSRSSSAKVTINVVDVNDNKPVFIVPPYNYSYELVLPS    709
109P1D4v.7    ISFDREKQESYTFY-KAEDGGRVSRSSSAKVTINVVDVNDNKPVFIVPPYNYSYELVLPS    719
109P1D4v.8    ISFDREKQESYTFYVKAEDGGRVSRSSSAKVTINVVDVNDNKPVFIVPPYNYSYELVLPS    720
              **************  ******************************* * **********

109P1D4v.1    TNPGTVVFQVIAVDNDTGMNAEVCYSIVGGNTRDLFAIDQETGNITLMEKCDVTDLGLHR    748
109P1D4v.2    TNPGTVVFQVIAVDNDTGMNAEVRYSIVGGNTRDLFAIDQETGNITLMEKCDVTDLGLHR    748
109P1D4v.3    TNPGTVVFQVIAVDNDTGMNAEVRYSIVGGNTRDLFAIDQETGNITLMEKCDVTDLGLHR    748
109P1D4v.4    TNPGTVVFQVIAVDNDTGMNAEVRYSIVGGNTRDLFAIDQETGNITLMEKCDVTDLGLHR    748
109P1D4v.5    TNPGTVVFQVIAVDNDTGMNAEVRYSIVGGNTRDLFAIDQETGNITLMEKCDVTDLGLHR    748
109P1D4v.6    TNPGTVVFQVIAVDNDTGMNAEVRYSIVGGNTRDLFAIDQETGNITLMEKCDVTDLGLHR    769
109P1D4v.7    TNPGTVVFQVIAVDNDTGMNAEVRYSIVGGNTRDLFAIDQETGNITLMEKCDVTDLGLHR    779
109P1D4v.8    TNPGTVVFQVIAVDNDTGMNAEVRYSIVGGNTRDLFAIDQETGNITLMEKCDVTDLGLHR    780
              ********************** *************************************

109P1D4v.1    VLVKANDLGQPDSLFSVVIVNLFVNESVTNATLINELVRKSTEAPVTPNTEIADVSSPTS    808
109P1D4v.2    VLVKANDLGQPDSLFSVVIVNLFVNESVTNATLINELVRKSTEAPVTPNTEIADVSSPTS    808
109P1D4v.3    VLVKANDLGQPDSLFSVVIVNLFVNESVTNATLINELVRKSTEAPVTPNTEIADVSSPTS    808
109P1D4v.4    VLVKANDLGQPDSLFSVVIVNLFVNESVTNATLINELVRKSTEAPVTPNTEIADVSSPTS    808
109P1D4v.5    VLVKANDLGQPDSLFSVVIVNLFVNESVTNATLINELVRKSTEAPVTPNTEIADVSSPTS    808
109P1D4v.6    VLVKANDLGQPDSLFSVVIVNLFVNESVTNATLINELVRKSIEAPVTPNTEIADVSSPTS    829
109P1D4v.7    VLVKANDLGQPDSLFSVVIVNLFVNESVTNATLINELVRKSIEAPVTPNTEIADVSSPTS    839
109P1D4v.8    VLVKANDLGQPDSLFSVVIVNLFVNESVTNATLINELVRKSIEAPVTPNTEIADVSSPTS    840
              ***************************************** ******************
```

Figure 14c (continued)

```
109P1D4v.1    DYVKILVAAVAGTITTVVVIFITAVVRCRQAPHLKAAQKNKQNSEWATPNPENRQMIMMK  868
109P1D4v.2    DYVKILVAAVAGTITTVVVIFITAVVRCRQAPHLKAAQKNKQNSEWATPNPENRQMIMMK  868
109P1D4v.3    DYVKILVAAVAGTITTVVVIFITAVVRCRQAPHLKAAQKNKQNSEWATPNPENRQMIMMK  868
109P1D4v.4    DYVKILVAAVAGTITTVVVIFITAVVRCRQAPHLKAAQKNKQNSEWATPNPENRQMIMMK  868
109P1D4v.5    DYVKILVAAVAGTITTVVVIFITAVVRCRQAPHLKAAQKNKQNSEWATPNPENRQMIMMK  868
109P1D4v.6    DYVKILVAAVAGTITTVVVIFITAVVRCRQAPHLKAAQKNKQNSEWATPNPENRQMIMMK  868
109P1D4v.7    DYVKILVAAVAGTITTVVVIFITAVVRCRQAPHLKAAQKNMQNSEWATPNPENRQMIMMK  889
109P1D4v.8    DYVKILVAAVAGTITTVVVIFITAVVRCRQAPHLKAAQKNMQNSEWATPNPENRQMIMMK  899
              DYVKILVAAVAGTITTVVVIFITAVVRCRQAPHLKAAQKNMQNSEWATPNPENRQMIMMK  900
              ************************************************ ***********

109P1D4v.1    KKKKKKKHSPKNLLLNFVTIEETKADDVDSDGNRVTLDLPIDLEEQTMGKYNWVTTPTTF  928
109P1D4v.2    KKKKKKKHSPKNLLLNFVTIEETKADDVDSDGNRVTLDLPIDLEEQTMGKYNWVTTPTTF  928
109P1D4v.3    KKKKKKKHSPKNLLLNFVTIEETKADDVDSDGNRVTLDLPIDLEEQTMGKYNWVTTPTTF  928
109P1D4v.4    KKKKKKKHSPKNLLLNFVTIEETKADDVDSDGNRVTLDLPIDLEEQTMGKYNWVTTPTTF  928
109P1D4v.5    KKKKKKKHSPKNLLLNFVTIEETKADDVDSDGNRVTLDLPIDLEEQTMGKYNWVTTPTTF  928
109P1D4v.6    KKKKKKKHSPKNLLLNFVTIEETKADDVDSDGNRVTLDLPIDLEEQTMGKYNWVTTPTTF  928
109P1D4v.7    KKKKKKKHSPKNLLLNFVTIEETKADDVDSDGNRVTLDLPIDLEEQTMGKYNWVTTPTTF  949
109P1D4v.8    KKKKKKKHSPKNLLLNVVTIEETKADDVDSDGNRVTLDLPIDLEEQTMGKYNWVTTPTTF  959
              KKKKKKKHSPKNLLLNVVTIEETKADDVDSDGNRVTLDLPIDLEEQTMGKYNWVTTPTTF  960
              ****************.*******************************************

109P1D4v.1    KPDSPDLARHYKSASPQPAFQIQPETPLNSKHHIIQELPLDNTFVACDSISKCSSSSSDP  988
109P1D4v.2    KPDSPDLARHYKSASPQPAFQIQPETPLNSKHHIIQELPLDNTFVACDSISKCSSSSSDP  988
109P1D4v.3    KPDSPDLARHYKSASPQPAFQIQPETPLNSKHHIIQELPLDNTFVACDSISKCSSSSSDP  988
109P1D4v.4    KPDSPDLARHYKSASPQPAFQIQPETPLNSKHHIIQELPLDNTFVACDSISKCSSSSSDP  988
109P1D4v.5    KPDSPDLARHYKSASPQPAFQIQPETPLNSKHHIIQELPLDNTFVACDSISKCSSSSSDP  988
109P1D4v.6    KPDSPDLARHYKSASPQPAFQIQPETPLNLKHHIIQELPLDNTFVACDSISKCSSSSSDP  1009
109P1D4v.7    KPDSPDLARHYKSASPQPAFQIQPETPLNLKHHIIQELPLDNTFVACDSISNCSSSSSDP  1019
109P1D4v.8    KPDSPDLARHYKSASPQPAFQIQPETPLNLKHHIIQELPLDNTFVACDSISNCSSSSSDP  1020
              ***************************** *****************.*;**********

109P1D4v.1    YSVSDCGYPVTFEVPVSVHTRP--------------------------------------  1011
109P1D4v.2    YSVSDCGYPVTFEVPVSVHTRP--------------------------------------  1011
109P1D4v.3    YSVSDCGYPVTFEVPVSVHTRPPMKEVVRSCTPMKESTTMEIWIHPQPQRKSEGKVAGK   1048
109P1D4v.4    YSVSDCGYPVTFEVPVSVHTRPPMKEVVRSCTPMKESTTMEIWIHPQPQ------------  1038
109P1D4v.5    YSVSDCGYPVTFEVPVSVHTRP--------------------------------------  1011
109P1D4v.6    YSVSDCGYPVTFEVPVSVHTRP--------------------------------------  1032
109P1D4v.7    YSVSDCGYPVTFEVPVSVHTRP--------------------------------------  1042
109P1D4v.8    YSVSDCGYPVTFEVPVSVHTRP--------------------------------------  1043
              **********************
```

Figure 14c (continued)

```
109P1D4v.1  ----------------VGIQVSN-----------------------------------  1018
109P1D4v.2  ----------------TDSRTST-----------------------------------  1018
109P1D4v.3  SQRRVTFHLPEGSQESSSDGGLGDHDAGSLTSTSHGLPLGYPQEEYFDRATPSNRTEGDG  1108
109P1D4v.4  SQRRVTFHLPEGSQESSSDGGLGDHDAGSLTSTSHGLPLGYPQEEYFDRATPSNRTEGDG  1098
109P1D4v.5  SQRRVTFHLPEGSQESSSDGGLGDHDAGSLTSTSHGLPLGYPQEEYFDRATPSNRTEGDG  1071
109P1D4v.6  ----------------TDSRT-------------------------------------  1037
109P1D4v.7  ----------------TDSRT-------------------------------------  1047
109P1D4v.8  ----------SQRRVTFHLPEGSQESSSDGGLGDHDAGSLTSTSHGLPLGYPQEEYFDRA  1093

109P1D4v.1  ----TTF-----------------------------------------------------  1021
109P1D4v.2  ----IEICSEI-------------------------------------------------  1025
109P1D4v.3  NSDPESTFIPGLKKAAEITVQPTVEEASDNCTQECLIYGHSDACWMPASLDHSSSSQAQA  1168
109P1D4v.4  NSDPESTFIPGLKKAAEITVQPTVEEASDNCTQECLIYGHSDACWMPASLDHSSSSQAQA  1158
109P1D4v.5  NSDPESTFIPGLKKAAEITVQPTVEEASDNCTQECLIYGHSDACWMPASLDHSSSSQAQA  1131
109P1D4v.6  ------------------------------------------------------------
109P1D4v.7  ------------------------------------------------------------
109P1D4v.8  TPSNRTEGDGNSDPESTFIPGLKKEITVQPTVEEASDNCTQECLIYGHSDACWMPASLDH  1153

109P1D4v.1  ------------------------------------------------------------
109P1D4v.2  ------------------------------------------------------------
109P1D4v.3  SALCHSPPLSQASTQHHSPRVTQTIALCHSPPVTQTIALCHSPPPIQVSALHHSPPLVQA  1228
109P1D4v.4  SALCHSPPLSQASTQHHSPRVTQTIALCHSPPVTQTIALCHSPPPIQVSALHHSPPLVQA  1218
109P1D4v.5  SALCHSPPLSQASTQHHSPRVTQTIALCHSPPVTQTIALCHSPPPIQVSALHHSPPLVQA  1191
109P1D4v.6  ------------------------------------------------------------
109P1D4v.7  ------------------------------------------------------------
109P1D4v.8  SSSSQAQASALCHSPPLSQASTQHHSPPVTQTIVLCHSPPVTQTIALCHSPPPIQVSALH  1213

109P1D4v.1  ------------------------------------------------------------
109P1D4v.2  ------------------------------------------------------------
109P1D4v.3  TALHHSPPSAQASALCYSPPLAQAAAISHSSSPLPQVIALHRSQAQSSVSLQQGWVQGADG  1288
109P1D4v.4  TALHHSPPSAQASALCYSPPLAQAAAISHSSSPLPQVIALHRSQAQSSVSLQQGWVQGADG  1278
109P1D4v.5  TALHHSPPSAQASALCYSPPLAQAAAISHSSSPLPQVIALHRSQAQSSVSLQQGWVQGADG  1251
109P1D4v.6  ------------------------------------------------------------
109P1D4v.7  ------------------------------------------------------------
109P1D4v.8  HSPPLVQGTALHHSPPSAQASALCYSPPLAQAAAISHSSSLPQVIALHRSQAQSSVSLQQ  1273
```

Figure 14c (continued)

```
109P1D4v.1  ------------------------------------------------------------  1347
109P1D4v.2  ------------------------------------------------------------  1337
109P1D4v.3  LCSVDQGVQGSATSQFYTMSERLHPSDDSIKVIPLTTFTPRQQARPSRGDSPIMEEHPL-  1347
109P1D4v.4  LCSVDQGVQGSATSQFYTMSERLHPSDDSIKVIPLTTFTPRQQARPSRGDSPIMEEHPL-  1337
109P1D4v.5  LCSVDQGVQGSATSQFYTMSERLHPSDDSIKVIPLTTFTPRQQARPSRGDSPIMEEHPL-  1310
109P1D4v.6  ------------------------------------------------------------
109P1D4v.7  ------------------------------------------------------------
109P1D4v.8  GWVQGANGLCSVDQGVQGSATSQFYTMSERLHPSDDSIKVIPLTTFAPRQQARPSRGDSP  1333

109P1D4v.1  ----------
109P1D4v.2  ----------
109P1D4v.3  ----------
109P1D4v.4  ----------
109P1D4v.5  ----------
109P1D4v.6  ----------
109P1D4v.7  ----------
109P1D4v.8  IMETHPL    1340
```

Figure 11e Nucleotide sequences of transcript variants of 151P4E11
>151P4E11 v.2 (SEQ ID NO:139).

```
gaaggtcttg gaaaaggcgg tgttcattag aaatctcaaa accgagtcac caagttccct    60
ctgttggagc ccagtggagc ctctgggaga aaagctgggg tgactttcc tacaaggggc    120
agaggactc tgctagattt ttgttttca tttgtttta attttgtaac atggaaactc     180
tttccttagg ataccagc tctcattact cagctaggaa ttatacctct ttaaagcctg    240
aatttaaaag tctgacagtt ttaaatgctt actaactgtg ggagttaaat cattacgaag    300
tgaggaatac agagtgttgt ccctgattct ggtttaatc tggtttaagaat ctttacagag    360
gacgaccaca cgccgcttcc tgtagcatgt gtcgtggttg taattctctc atgtgcatat    420
taagaagttg ctgtcagat gtggctcctc cctttgcaga ggccggtgcc ctcgaccgcc    480
tcctgatct cccgccgca gctccctgaa agacatcga gcggtcctga gagcctcctg    540
ggcatgtttg tctgtgtgct gtaaccctga gtcaaacctt aagataatgg ataatcttcg    600
gccaatttat gcagagtcag ccattcctgt tctctttgcc ttgatgttgt gttgttatca    660
tttaagattt tttttttg gtaattattt tgagtggcaa aataaagaat agcaattact    720
tg                                                                 722
```

Figure 12e Protein sequences of transcript variants of 151P4E11
>151P4E11 v.2 (SEQ ID NO:140).
MCRGCNSLMC ILRSCCSDVA LPFAEAGALD RLLDLPAAAS SEDIERS        47

Figure 13e Alignment of nucleotide sequences of 151P4E11 transcript variants
(SEQ ID NOS:29, 139)

```
151P4E11v.1   ------------------------------------------------------------
151P4E11v.2   GAAGGTCTTGGAAAAGGCGGTGTTCATTAGAAATCTCAAAACCGAGTCACCAAGTTCCCT   60

151P4E11v.1   ------------------------------------------------------------
151P4E11v.2   CTGTTGGAGAGCCCAGTGAGCCTCTGGGAGAAAAGCTGGGGTGACTTTTCCTACAAGGGGC  120

151P4E11v.1   AGATGGCCCGAGGCAGCGCCCTCCTGCTCCTCGCCCTCC---TCCTCGCCGCGGCCCTTT   57
151P4E11v.2   AGAGGGACTCTGCTAGATTTTGTTTTTCATTTGTTTTTAATTTTGTAACATGGAAACTC  180
              ***  **          *   * **  ** *   *    *  **  *   *    * *

151P4E11v.1   CTGCCTCTGCGGG-----GCTCTGGTCGCCGCCAAGGAA--AAACGAGGCTGGACCCTG  110
151P4E11v.2   TTTCCTTAGGATATACCAGTCTGACAGTTTTAAATGCTTACAGCTAGGAATTATACCTCTTTAAAGCTG  240
              * ***  *         ****       *       *    *  * *  ** ****

151P4E11v.1   AACAGGCCGGGCTACCTGCT-----GGGCCCACATGCCGTTGGCAACCACCAGTCATTCAG  166
151P4E11v.2   AATTTAAAAGTCTGACAGTTTTAAATGCTTACTACTGTGGGAGTTAAATCATTACGAAG  300
              **  *       *  *         *  * *   *  *     **      *    **

151P4E11v.1   CGACAAGAATGG--CCTCACCAGCAAGCGGGAGCTGCGGCCG-AAGA----TGACATGA  219
151P4E11v.2   TGAGGAATACAGAGTGTGTCCCTGATTCTGGGTTTAATCTGTAAGAATCTTTACAGAG  360
              **  *    *    ** ***      *     *    *   * * **** * ***

151P4E11v.1   AAC------CAGGAAGCTT-----TGACAGGT-CCATACCTGAAAACAATATCATGCGACA  269
151P4E11v.2   GACGACCACACGCCGCCTTCCTGTAGCATGTCGTCGTTGTAATTC-TCTCATGTGCATA  419
              **        **   *  ****       *   ** **    *  **   * ***  *

151P4E11v.1   ATCATTGAGTTTCTGTCTT-------TCTTGCATCTCAAAGAGGAGGCCGGTGCCCTCGACCG  322
151P4E11v.2   -TTAAGAAGTTGCTGCTCAGATGTGGCTCTTCCCTTTGCAGAGGCCGGCCCTCGACCG  478
              * *  *****        *       *  *                    *************

151P4E11v.1   CCTCCTGGATCTCCCCGCCGCAGCCTCCTCAGAAGACATCGAGCGGTCCTGAGAGCCTCC  382
151P4E11v.2   CCTCCTGGATCTCCCCGCCGCAGCCTCCTCAGAAGACATCGAGCGGTCCTGAGAGCCTCC  538
              ************************************************************
```

Figure 13e (continued)

```
151P4E11v.1    TGGGCACGTTTGTCTGTGTGCTGTAACCTGAAGTCAAACCTTAAGATAATGGATAATCTT 442
151P4E11v.2    TGGGCATGTTTGTCTGTGTGCTGTAACCTGAAGTCAAACCTTAAGATAATGGATAATCTT 598
               ****** ***************************************************

151P4E11v.1    CGGCCAATTTATGCGGAGTCAGCCATTCCTGTTCTCTTTGCCTTGATGTTGTGTGTTAT 502
151P4E11v.2    CGGCCAATTTATGCAGAGTCAGCCATTCCTGTTCTCTTTGCCTTGATGTTGTGTGTTAT 658
               ************** *********************************************

151P4E11v.1    CATTTAAGATTTTTTTTTTGGTAATTATTTGAGTGGCAAAATAAAGAATAGCAATTA 562
151P4E11v.2    CATTTAAGATTTTTTTTTTTTGGTAATTATTTGAGTGGCAAAATAAAGAATAGCAATTA 718
               ****************    ****************************************

151P4E11v.1    ----
151P4E11v.2    CTTG 722
```

Figure 14e Alignment of protein sequences of 151P4E11 transcript variants (SEQ ID NO:30, 140).

```
151P4E11v.1    MARGSALLLASLLLAAALSASAGLWSPAKEKRGWTLNSAGYLLGPHAVGNHRSFSDKNGL 60
151P4E11v.2    MCRG-------------------------------------------CNSLMCIL--------RSCCS---- 17
               * **                                            **   *   **  ..

151P4E11v.1    TSKRELRPEDDMKPGSFDRSIPENNIMRTIIEFLSFLHKEAGALDRLLDLPAAASSEDI 120
151P4E11v.2    -----------------DVALP--------------FAEAGALDRLLDLPAAASSEDI 44
                                 * ::*              : *********************

151P4E11v.1    ERS 123
151P4E11v.2    ERS 47
               ***
```

Figure 11j Nucleotide sequences of transcript variants of 161P2B7A
>161P2B7A v.2 (SEQ ID NO:141)

```
gccgcccagg attccacgag ggggaaggat tctctattct ttttgcgac aaatctggta    60
acaggatttg ctgtgctgtt ttcgtccgtg ttgtcgtgtg tgtgtcgtgtg tgttcgtgtg   120
gatgcacgtg tggcccgct gggtgcccc ctccagtgtc ccggagctg aaagatcgca       180
aagaggatgc gaaagggatg gaggacgaag gccagaccaa aatcaagcag aggcgaagtc    240
```

Figure 11j (continued)

```
ggaccaattt caccctggaa caactcaatg agctggagag gctttttgac gagaccact    300
atccgacgc cttcatgcga gaggaactga gccagcgact gggcctgtcg gaggccgag    360
tgcaggtttg gtttcaaaat cgaagagcta aatgtagaaa acaagaaaat caactccata  420
aagtgttct catagggcc gccagccagt ttgaagcttg tagagtcgca ccttatgtca    480
acgtagtgc tttaaggatg ccattcagc agttcaggc gcagctgcag ctggacagcg    540
ctgtgcgca cgcgcaccac cacctgcatc cgcacctggc cgcacgcg ccctacatga    600
tgttcccagc accgcccttc ggactgccgc tcgccacgct ggccggat tcggcttccg    660
ccgctcggt agtggcggcc gcacgagccg ccaagaccac cagcaaggac tccagcatcg  720
ccgatctcag actgaaagcc aaaaagcacg ccgcagccct gggtctgtga cgccaacgcc  780
agcaccaatg tcgcgcctgt ccccggcac tcagcctgca ccccctccgc cgccatcgc    840
ttctccgtta cccctttgg acctcggaga ccggccctc tcccgcctca ctgaccatcc    900
ctcgtcccct atcgcatctt ggactcggaa agccagactc cacgcaggac cagggatctc  960
acgaggcacg caggctccgt ggctcctgcc cgtttccta ctcgagggcc tagaattggg   1020
tttgtagga gcgggtttgg ggggtctgg agagactg gacaggtag tgctgaacc       1080
gcggagttg gctcaccgca aagctacaac gatggactct tgcatagaaa aaaaaaatct   1140
tgttaacat gaaaaatga gcaaacaaaa aaatcgaaag acaaacggga gagaaaaaga   1200
ggaaggcaac ttattctta actgtatttt gcagaagct gaaattggag aaccaaggag   1260
caaaaacaaa tttttaaatt aagtatttt atacatttaa aatatatgaa aacaaccca   1320
gacgattctc gagagactgg ggggagttac caacttaaat gtgtgtttta aaaatgcgc   1380
taagaaggca aagcagaaag aagagagag gtttgaaac cttattttaaa aactaagat   1440
gaaaaagtg 1440
cgcaggtggg aagttcacag gcggcctcc ttttacgttg ctgcgaagtt cacgttaata  1500
cgagaaattt gatgagagag gcggcctcc ttttacgttg aatcagatgc tttgagttta  1560
aacccaccat gtatgcaaga gcaagaaaag agaaaatatt aaaacgagga gagaaaaa   1620
taatgcaaa actgtctga ctgtgacag taaattccgg tttgcatga aaaaaaaa      1680
aaaaaaaa aaaaaa                                                   1696
```

>161P2B7A v.3 (SEQ ID NO:142).

```
gagcgccggg ctgacgtgcg gcggcgatgg aagaacttac ggcgttcgtc tccaagtctt   60
ttgaccagaa agtgaaggag aagaaggagg cgatcacgta cgggagagtg ctggagagcg  120
ggccgctgcg cgggccaag gagccgaccg gctgcaccga gcggcggcgg gcggcgaccg ca 180
gcagcccggc agtccgggcg gccggggcgg gaggcggga aggaggcgga gcggcgcgcg  240
gaggaggcgg aggaggcgga atgggcgcg ggagctgga aggaggcgg ggaggcgct    300
ctcccgtccg ggagctggac gtgcccg gagtgcgaaa cggagagaaa ggcagcccgc    360
ggctgacgga gtgtccccg gagctgaaag atcgcaaaga cgatgcgaaa gggatggagg   420
acgaaggcca gaccaaaatc agcagaggc gaagtcggac caattcacc ctggaacaac    480
tcaatgagct ggagagctt tttgacgaga cccactatcc cgagtcgag gttttgttt caaatcgaa 540
aactgagcca gcgactggcc gtgcgagg ctgtcgagag ccgagtgca caaatcgaa    600
gagctaaatg tagaaaacaa gaaaatcaac tccataaagg tccataaagg tgttctcata ggggccgcca  660
gccagtttga gcttgtaga gtcgcacctt atgtcaacgt aggtgcttta aggatgccat  720
```

Figure 11j (continued)

```
ttcagcagga tagtcattgc aacgtgacgc ccttgccctt tcaggttcag gcgcagctgc    780
agctgacag  cgctgtggcg cacgcgcacc accacctgca tccgcacctg gccgcgcacg    840
cgccctacat gatgttccca gcaccgccct tcggactgcc gctcgccacg ctggccgcgg    900
attcggcttc cgccgcctcg gtagtggcgg ccgcagcagc cgccaagacc accagcaagg    960
actccagcat cgccgatctc agactgaaag ccaaaaagca cccgcagcc  ctggtctgt    1020
gacgccaacg ccagccaccaa tgtcgcgcct gtcccgcggc actcagcctg cacgccctcc    1080
gcgccccgct gcttctccgt tacccctttg agacctcggg agccggccct cttcccgcct    1140
cactgaccat ccctcgtccc ctatcgcatc ttggactcgg aaagccagac tccacgcagg    1200
accaggatc  tcacgaggca cgcaggctcc gtggctcctg cccgttttcc tactcgaggg    1260
cctagaattg ggttttgtag gagcgggttt ggggagtct  ggagagagac tggacaggt    1320
agtgctggaa ccgcggagtt tggctcaccg caaagctaca acgatgact  cttgcataga    1380
aaaaaaaaat cttgttaaca atgaaaaaat gagcaaacaa aaaaatcgaa agacaaacgg    1440
gagagaaaaa gaggaaggca acttattct  taactgctat ttggcagaag ctgaaattgg    1500
agaaccaagg agcaaaaaca aatttaaaa  ttaaagtatt ttatacattt aaaaatatgg    1560
aaaacaaacc cagaacgattc tcgagagact gggggagtt  accaacttaa atgtgtgttt    1620
taaaaaatgc gctaagaagg caaagcagaa agaagaggta tacttattta aaaaactaag    1680
atgaaaaaag tgcgcaggtg ggaagttcac aggttttgaa actgacctt  ttctgcgaag    1740
ttcacgttaa tacgagaaat ttgatgagag agcgggcct  cctttttacgt tgaatcagat    1800
gctttgagtt taaaaccacc atgtatggaa gagcaagaaa gagagaaata ttaaaacgag    1860
gagagaaaaa aataatgcca aaactgtctg gactgctgac agtaaattcc ggttttgcatg    1920
gaaaaaaaaaa aaaaaaaaaa aaaaaaaa                                      1948
```

Figure 12j Protein sequences of transcript variants of 161P2B7A

>161P2B7A v.2 (SEQ ID NO:143).

```
MEDEGQTKIK QRRSRTNFTL EQLNELERLF DETHYPDAFM REELSQRLGL SEARVQWWFQ     60
NRRAKCRKQE NQLHKGVLIG AASQFEACRV APYVNVGALR MPFQQVQAQL QLDSAVAHAH    120
HHLHPHLAAH APYMMFPAPP FGLPLATLAA DSASAASVVA AAAAAKTTSK DSSIADLRLK    180
AKKHAAALGL                                                          190
```

>161P2B7A v.3 (SEQ ID NO:144).

```
MEELTAFVSK SFDQKVKEKK EAITYREVLE SGPLRGAKEP TGCTEAGRDD RSSPAVRAAG     60
GGGGGGGGG  GGGGGGGVGG GGAGGAGGG  RSPVRELDMG AAERSREPGS PRLTEVSPEL    120
KDRKDDAKGM EDEGQTKIKQ RRSRTNFTLE QLNELERLFD ETHYPDAFMR EELSQRLGLS    180
EARVQWFQN  RRAKCRKQEN QLHKGVLIGA ASQFEACRVA PYVNVGALRM PFQQDSHCNV    240
TPLPFVQAQ  LQLDSAVAHA HHHLHPHLAA HAPYMMFPAP PFGLPLATLA ADSASAASVV    300
AAAAAKTTS  KDSSIADLRL KAKKHAAALG L                                   331
```

Figure 13j Alignment of nucleotide sequences of 161P2B7A transcript variants
(SEQ ID NOS:39, 141, 142).

```
161P2B7Av.1   ------------------------------------------------------------
161P2B7Av.2   ------------------------------------------------------------
161P2B7Av.3   GAGCGCCGGCTGACGTGCGCGCGGCGATGCGAAGAACTTACGCGCCGTTCGTCTCCAAGTCTT   60

161P2B7Av.1   ------------------------------------------------------------
161P2B7Av.2   ------------------------------------------------------------
161P2B7Av.3   TTGACCAGAAAGTGAAGGAGAAGAAGGAGGCGATCACGTACCGGAGGTGCTGGAGAGCG    120

161P2B7Av.1   ------------------------------------------------------------
161P2B7Av.2   ------------------------------------------------------------
161P2B7Av.3   GGCCCGCTGCGCGGGGCCAAGGAGCCGACCGGCTGCACCGAGGCCGGCCGCGACGACCGCA    180

161P2B7Av.1   ------------------------------GCCGCCCAGGATTCCACGAGG            21
161P2B7Av.2   ------------------------------GCCGCCCAGGATTCCACGAGG            21
161P2B7Av.3   GCAGCCCGGCAGTCCGGCGGCCGCGGGCGGCGGCGGAGGCCGAGGCCGGGCG           240
                                            *  ***  *  ** *   *

161P2B7Av.1   GGGAAGGATTCTCTATTCTTTTTTGCGACAAATCTGGTAACAGGATTTGCTGTGCTGTTT    81
161P2B7Av.2   GGGAAGGATTCTCTATTCTTTTTTGCGACAAATCTGGTAACAGGATTTGCTGTGCTGTTT    81
161P2B7Av.3   GAGGAGGCCGAGGAGGTGTAGGAGGAGGTGGAGCAGGCGG-AGGAGCTGGAGGAGGGCGC   299
              * * ***                              ****  **      *   *

161P2B7Av.1   TCGTCCGTGTGTGTGTGCGTGTGTGCGTGTGTGTGTGTGTTCGTGTGTTGAATGCACGTGTGGCCCCGCTG   141
161P2B7Av.2   TCGTCCGTGTGTGTGTGCGTGTGTGCGTGTGTGTGTGTGTTCGTGTGTTGAATGCACGTGTGGCCCCGCTG   141
161P2B7Av.3   TCTCCCGTTCCGGGAGC-TGGACATGGGCGCCGCCGAGAGAA----GCAGGGAGCCCGGCAG         355
              ** *****  *        *   **   *   **  *  *       *  **** **  **

161P2B7Av.1   --GGGTGCCCCCTCCAGTGTCCCCGGAGCTGAAAGATCGCAAAGAGGATGCGAAAGGGAT    199
161P2B7Av.2   --GGGTGCCCCCTCCAGTGTCCCCGGAGCTGAAAGATCGCAAAGAGGATGCGAAAGGGAT    199
161P2B7Av.3   CCCGGCGCTGACGGAGGTGTCCCCGGAGCTGAAAGATCGCAAAGATGCGAAAGGGAT    415
                 **        *   * **************************    ************

161P2B7Av.1   GGAGGACGAAGGCCAGACCAAAATCAAGCAGAGGCGAAGTCGGACCAATTTCACCCTGGA    259
161P2B7Av.2   GGAGGACGAAGGCCAGACCAAAATCAAGCAGAGGCGAAGTCGGACCAATTTCACCCTGGA    259
161P2B7Av.3   GGAGGACGAAGGCCAGACCAAAATCAAGCAGAGGCGAAGTCGGACCAATTTCACCCTGGA    475
              ************************************************************
```

Figure 13j (continued)

```
161P2B7Av.1    ACAACTCAATGAGCTGGAGAGGCTTTTTGACGAGACCCACTATCCCGACGCCTTCATGCG  319
161P2B7Av.2    ACAACTCAATGAGCTGGAGAGGCTTTTTGACGAGACCCACTATCCCGACGCCTTCATGCG  319
161P2B7Av.3    ACAACTCAATGAGCTGGAGAGGCTTTTTGACGAGACCCACTATCCCGACGCCTTCATGCG  535
               ************************************************************

161P2B7Av.1    AGAGGAACTGAGCCAGCCAGCGACTGGGCCTGTCGGAGGCCCGAGTGCAGGTTTGGTTTCAAAA  379
161P2B7Av.2    AGAGGAACTGAGCCAGCCAGCGACTGGGCCTGTCGGAGGCCCGAGTGCAGGTTTGGTTTCAAAA  379
161P2B7Av.3    AGAGGAACTGAGCCAGCCAGCGACTGGGCCTGTCGGAGGCCCGAGTGCAGGTTTGGTTTCAAAA  595
               ************************************************************

161P2B7Av.1    TCGAAGAGAGCTAAATGTAGAAAACAAGAAAAATCAACTCCATAAAGGTGTTCTCATAGGGGC  439
161P2B7Av.2    TCGAAGAGAGCTAAATGTAGAAAACAAGAAAAATCAACTCCATAAAGGTGTTCTCATAGGGGC  439
161P2B7Av.3    TCGAAGAGAGCTAAATGTAGAAAACAAGAAAAATCAACTCCATAAAGGTGTTCTCATAGGGGC  655
               ************************************************************

161P2B7Av.1    CGCCAGCCAGTTTGAAGCTTGTAGAGTCGCACCTTATGTCAACGTAGTAGTGCTTTAAGGAT  499
161P2B7Av.2    CGCCAGCCAGTTTGAAGCTTGTAGAGTCGCACCTTATGTCAACGTAGTAGTGCTTTAAGGAT  499
161P2B7Av.3    CGCCAGCCAGTTTGAAGCTTGTAGAGTCGCACCTTATGTCAACGTAGTAGTGCTTTAAGGAT  715
               ************************************************************

161P2B7Av.1    GCCATTTCAGCAGG---------------------------------TTCAGGCGCA  523
161P2B7Av.2    GCCATTTCAGCAGG---------------------------------TTCAGGCGCA  523
161P2B7Av.3    GCCATTTCAGCAGGATAGTCATTGCAACGTGACGCCTTGCCCTTTCAGGTTCAGGCGCA  775
               **************                                 **********

161P2B7Av.1    GCTGCAGCTGGACAGCGCTGTGGCGCACCGCGCACCACCTGCATCCGCACCTGGCCGC  583
161P2B7Av.2    GCTGCAGCTGGACAGCGCTGTGGCGCACCGCGCACCACCTGCATCCGCACCTGGCCGC  583
161P2B7Av.3    GCTGCAGCTGGACAGCGCTGTGGCGCACCGCGCACCACCTGCATCCGCACCTGGCCGC  835
               ************************************************************

161P2B7Av.1    GCACGCGCCCTACAATGATGTTCCCAGCACCGCCCTTCGGACTGCCGCTCGCCACGCTGGC  643
161P2B7Av.2    GCACGCGCCCTACAATGATGTTCCCAGCACCGCCCTTCGGACTGCCGCTCGCCACGCTGGC  643
161P2B7Av.3    GCACGCGCCCTACAATGATGTTCCCAGCACCGCCCTTCGGACTGCCGCTCGCCACGCTGGC  895
               ************************************************************

161P2B7Av.1    CGCGGATTCGGCTTCCGCCGCCTTCCGCCTCGGTAGTGGCGGCCCAGCAGCCGCCAAGACCACCAG  703
161P2B7Av.2    CGCGGATTCGGCTTCCGCCGCCTTCCGCCTCGGTAGTGGCGGCCCAGCAGCCGCCAAGACCACCAG  703
161P2B7Av.3    CGCGGATTCGGCTTCCGCCGCCTTCCGCCTCGGTAGTGGCGGCCCAGCAGCCGCCAAGACCACCAG  955
               ************************************************************
```

Figure 13j (continued)

```
161P2B7Av.1      CAAGAACTCCAGCATCGCCGATCTCAGACTGAAAGCCAAAAAGCACGCCGCAGCCCTGGG    763
161P2B7Av.2      CAAGGACTCCAGCATCGCCGATCTCAGACTGAAAGCCAAAAAGCACGCCGCAGCCCTGGG    763
161P2B7Av.3      CAAGGACTCCAGCATCGCCGATCTCAGACTGAAAAGCCAAAAAGCACGCCGCAGCCCTGGG   1015
                 ****  ******************************************************

161P2B7Av.1      TCTGTGACGCCAACGCCAGCACCAATGTCGCGCCTGTCCCGCGCACTCAGCCTGCACGC    823
161P2B7Av.2      TCTGTGACGCCAACGCCAGCACCAATGTCGCGCCTGTCCCGCGCACTCAGCCTGCACGC    823
161P2B7Av.3      TCTGTGACGCCAACGCCAGCACCAATGTCGCGCCTGTCCCGCGCACTCAGCCTGCACGC   1075
                 ************************************************************

161P2B7Av.1      CCTCCGCGCCCCCGCTGCTTCTCCGTTACCCCTTTGAGACCTCGGGAGCCGGCCCTCTTCC    883
161P2B7Av.2      CCTCCGCGCCCCCGCTGCTTCTCCGTTACCCCTTTGAGACCTCGGGAGCCGGCCCTCTTCC    883
161P2B7Av.3      CCTCCGCGCCCCCGCTGCTTCTCCGTTACCCCTTTGAGACCTCGGGAGCCGGCCCTCTTCC   1135
                 ************************************************************

161P2B7Av.1      CGCCTCACTGACCATCCCTCGTCCGCCTATCGGACTCTTGGACTCGGAAAGCCAGACTCCAC    943
161P2B7Av.2      CGCCTCACTGACCATCCCTCGTCCGCCTATCGGACTCTTGGACTCGGAAAGCCAGACTCCAC    943
161P2B7Av.3      CGCCTCACTGACCATCCCTCGTCCGCCTATCGGACTCTTGGACTCGGAAAGCCAGACTCCAC   1195
                 ************************************************************

161P2B7Av.1      GCAGGACCAGGATCTCACGAGGCACGCAGGCTCCGTGGCTCCTGCCCGTTTTCCTACTC   1003
161P2B7Av.2      GCAGGACCAGGATCTCACGAGGCACGCAGGCTCCGTGGCTCCTGCCCGTTTTCCTACTC   1003
161P2B7Av.3      GCAGGACCAGGATCTCACGAGGCACGCAGGCTCCGTGGCTCCTGCCCGTTTTCCTACTC   1255
                 ************************************************************

161P2B7Av.1      GAGGGCCTAGAATTGGGTTTTGTAGGAGCGGGTTTGGGGAGTCTGGAGAGAGACTGGAC   1063
161P2B7Av.2      GAGGGCCTAGAATTGGGTTTTGTAGGAGCGGGTTTGGGGAGTCTGGAGAGAGACTGGAC   1063
161P2B7Av.3      GAGGGCCTAGAATTGGGTTTTGTAGGAGCGGGTTTGGGGAGTCTGGAGAGAGACTGGAC   1315
                 ************************************************************

161P2B7Av.1      AGGGGAGTGCTGGAACCGCGGAGTTTGGCTCACCGCAAAGCTACAACGATGGACTCTTGC   1123
161P2B7Av.2      AGGGTAGTGCTGGAACCGCGGAGTTTGGCTCACCGCAAAGCTACAACGATGGACTCTTGC   1123
161P2B7Av.3      AGGGTAGTGCTGGAACCGCGGAGTTTGGCTCACCGCAAAGCTACAACGATGGACTCTTGC   1375
                 ****  ******************************************************

161P2B7Av.1      ATAGAAAAAAAA-TCTTGTTAACAATGAAAAAATGAGCAAACAAAAAAATCGAAAGACA   1182
161P2B7Av.2      ATAGAAAAAAAAATCTTGTTAACAATGAAAAAATGAGCAAACAAAAAAATCGAAAGACA   1183
161P2B7Av.3      ATAGAAAAAAAAATCTTGTTAACAATGAAAAAATGAGCAAACAAAAAAATCGAAAGACA   1435
                 ************ ***********************************************
```

Figure 13j (continued)

```
161P2B7Av.1    AACGGGAGAGAAAAAGAGGAAGGAAGGAAACTTATTTCTTAACTGCTATTTGGCAGAAGCTGAA    1242
161P2B7Av.2    AACGGGAGAGAAAAAGAGGAAGGAAGGAAGGCAACTTATTTCTTAACTGCTATTTGGCAGAAGCTGAA  1243
161P2B7Av.3    AACGGGAGAGAAAAAGAGGAAGGAAGGCAACTTATTTCTTAACTGCTATTTGGCAGAAGCTGAA    1495
               ************************        ********************************

161P2B7Av.1    ATTGGAGAACCAAGGAGCAAAAACAAATTTAAAATTAAAGTATTTTATACATTTAAAAA        1302
161P2B7Av.2    ATTGGAGAACCAAGGAGCAAAAACAAATTTAAAATTAAAGTATTTTATACATTTAAAAA        1303
161P2B7Av.3    ATTGGAGAACCAAGGAGCAAAAACAAATTTAAAATTAAAGTATTTTATACATTTAAAAA        1555
               **********************************************************

161P2B7Av.1    TATGGAAAAACAACCCAGACGATTCTCGAGAGACTGGGGGAGTTACCAACTTAAATGTG        1362
161P2B7Av.2    TATGGAAAAACAACCCAGACGATTCTCGAGAGACTGGGGGAGTTACCAACTTAAATGTG        1363
161P2B7Av.3    TATGGAAAAACAACCCAGACGATTCTCGAGAGACTGGGGGAGTTACCAACTTAAATGTG        1615
               ***********************************************************

161P2B7Av.1    TGTTTTAAAAATGCGCTAAGAGGCAAAGCAGAAGAAGAGGTATACTTATTTAAAAAA         1422
161P2B7Av.2    TGTTTTAAAAATGCGCTAAGAGGCAAAGCAGAAGAAGAGGTATACTTATTTAAAAAA         1423
161P2B7Av.3    TGTTTTAAAAATGCGCTAAGAGGCAAAGCAGAAGAAGAGGTATACTTATTTAAAAAA         1675
               *********************************************************

161P2B7Av.1    CTAAGATGAAAAAGTCGCAGCTGCGCAGGTCACAGGTTTTGAAACTGACCTTTTCTG         1482
161P2B7Av.2    CTAAGATGAAAAAGTCGCAGCTGCGCAGGTCACAGGTTTTGAAACTGACCTTTTCTG         1483
161P2B7Av.3    CTAAGATGAAAAAGTCGCAGCTGCGCAGGTCACAGGTTTTGAAACTGACCTTTTCTG         1735
               *********************************************************

161P2B7Av.1    CGAAGTTCACGTTAATACGAGAAATTTGATGAGAGAGGCGG---CTCTTTTACGTTGAAT      1539
161P2B7Av.2    CGAAGTTCACGTTAATACGAGAAATTTGATGAGAGAGGCCCTCCTTTTACGTTGAAT         1543
161P2B7Av.3    CGAAGTTCACGTTAATACGAGAAATTTGATGAGAGAGGCCGCCTCCTTTTACGTTGAAT      1795
               ***************************************        **************

161P2B7Av.1    CAGATGCTTTGAGTTTAAAACCCACCATGTATGCAAGAGCAAGAAAAACAGAAAATATTAA    1599
161P2B7Av.2    CAGATGCTTTGAGTTTAAA-CCCACCATGTATGCAAGAGCAAGAAGAGAAAATATTAA       1602
161P2B7Av.3    CAGATGCTTTGAGTTTAAA-CCCACCATGTATGCAAGAGCAAGAAGAGAAAATATTAA       1854
               *******************  *************************  *** *********

161P2B7Av.1    AACGAGGAGAGAGAAAAATAATTAACACAAAAAATGCCACAGACAATGATTCTCTG         1659
161P2B7Av.2    AACGAGGAGAGAGAAAAATAATTAATGCAAAACTGTCTGG-ACTGCTGACAGTAAATTCC---  1658
161P2B7Av.3    AACGAGGAGAGAGAAAAATAATTAATGCAAAACTGTCTGG-ACTGCTGACAGTAAATTCC---  1910
               *********************  *  *  ****      *  ****  *  ***
```

Figure 13j (continued)

```
161P2B7Av.1  AGAAATTATTATGGCAAAACTGTCTGGACTGCTGACAGTAAATTCCGGTTTGCATGTTAC 1719
161P2B7Av.2  ---GGTTTGCATGGAAAAAAAAAAAAAAAAAAAAAAAAAA-------------------- 1696
161P2B7Av.3  ---GGTTTGCATGGAAAAAAAAAAAAAAAAAAAAAAAA---------------------- 1948
                ** ****  ****           *                 * * **

161P2B7Av.1  TTGTATTCCATTGATGGTGTGTCTTCCTCCCACCCCCTTATCTCCCATGCACTCACTCCA 1779
161P2B7Av.2  ------------------------------------------------------------
161P2B7Av.3  ------------------------------------------------------------

161P2B7Av.1  TTTTCATCTTCACTATGAAAAACAATACCAAAAGTATCTGGAAATTGATATATATATATC 1839
161P2B7Av.2  ------------------------------------------------------------
161P2B7Av.3  ------------------------------------------------------------

161P2B7Av.1  CACATATATATATCATATATATTGCCATATATATATATATATATATATATATATATATA 1899
161P2B7Av.2  ------------------------------------------------------------
161P2B7Av.3  ------------------------------------------------------------

161P2B7Av.1  TATATATATATATATATTTGCCCTGTCTTTGATCCTGGGGAACAAAAGAAAAAAGTCAGAAA 1959
161P2B7Av.2  ------------------------------------------------------------
161P2B7Av.3  ------------------------------------------------------------

161P2B7Av.1  GGGAAAAAAATTACACTCATTGCCCTAAGAAGACAGAGGTGGGCAGAATATGTGGGAAAG 2019
161P2B7Av.2  ------------------------------------------------------------
161P2B7Av.3  ------------------------------------------------------------

161P2B7Av.1  GAAAAAGAAAAACAAGACCACCAAATGAAATAATGAAGGTACAGCGCCTCGCTGTGCCAGA 2079
161P2B7Av.2  ------------------------------------------------------------
161P2B7Av.3  ------------------------------------------------------------

161P2B7Av.1  CACAGTAGGCGCTCAATCAGTATTAGTTCCCACCATTCCCCTTTTCTTGTGTTCCTTCTT 2139
161P2B7Av.2  ------------------------------------------------------------
161P2B7Av.3  ------------------------------------------------------------
```

Figure 13j (continued)

```
161P2B7Av.1    GTTGGTTTCCTGAAGTCCTATTTGAAGACAGTGGTTTATTTCCCCCTCTCTATCCCGTCA 2199
161P2B7Av.2    ------------------------------------------------------------
161P2B7Av.3    ------------------------------------------------------------

161P2B7Av.1    AATTCACCTTAAATAACACCCAGCTAGATACAGGCACTAGGTTTGTGTAAGATATGTTGA 2259
161P2B7Av.2    ------------------------------------------------------------
161P2B7Av.3    ------------------------------------------------------------

161P2B7Av.1    TACACACGAACAAAGTTTATTTGACTATAATGTGTGGACTGACTTTCAACATTTGCATT 2319
161P2B7Av.2    ------------------------------------------------------------
161P2B7Av.3    ------------------------------------------------------------

161P2B7Av.1    TTATCTCACAAAGGTGTATCTATTCAAGTAACCTTTTTTTTTTGTTGTTGTTGTTCTTT 2379
161P2B7Av.2    ------------------------------------------------------------
161P2B7Av.3    ------------------------------------------------------------

161P2B7Av.1    TTTGTTTTTTTTTTCTTTTTGGTTGTTGTTTCAATTCATGTAGCTATTTAAACTGGGAT 2439
161P2B7Av.2    ------------------------------------------------------------
161P2B7Av.3    ------------------------------------------------------------

161P2B7Av.1    ACCTTGGACTAAGCCAGTCTGTATCCCAATTCGCTAGCAAGCCTAAGTTTGTGGGGTTTT 2499
161P2B7Av.2    ------------------------------------------------------------
161P2B7Av.3    ------------------------------------------------------------

161P2B7Av.1    GTTTTTGTTTTTGTTTTACCTTCTAATTTACAAGAAAGAGGAAAAGCTCTTCTAACTGAA 2559
161P2B7Av.2    ------------------------------------------------------------
161P2B7Av.3    ------------------------------------------------------------

161P2B7Av.1    CTTTGGTATGCGGTTGAGCTTTGTAACTATTGTTCTCCATGAAAACAAAATTATTTATA 2619
161P2B7Av.2    ------------------------------------------------------------
161P2B7Av.3    ------------------------------------------------------------
```

Figure 13j (continued)

```
161P2B7Av.1    TTGACATATTTTTTCTAGTGTATTAAGTTATTTAAACAAAAGATGTTATCTCATGAC  2679
161P2B7Av.2    ----------------------------------------------------------
161P2B7Av.3    ----------------------------------------------------------

161P2B7Av.1    GTGTTGTCAGTACAAAATGTGTCGCCTCCAATTCTGTTAAACCTTTTAAATAAGTGCCAA  2739
161P2B7Av.2    ------------------------------------------------------------
161P2B7Av.3    ------------------------------------------------------------

161P2B7Av.1    GTTATTAATT  2749
161P2B7Av.2    ----------
161P2B7Av.3    ----------
```

Figure 14j Alignment of protein sequences of 161P2B7A transcript variants
(SEQ ID NOS: 40, 143, 144).

```
161P2B7Av.1    ------------------------------------------------------------
161P2B7Av.2    ------------------------------------------------------------
161P2B7Av.3    MEELTAFVSKSFDQKVKEKKEAITYREVLESGPLRGAKEPTGCTEAGRDDRSSPAVRAAG   60

161P2B7Av.1    ------------------------------------------------------------
161P2B7Av.2    ------------------------------------------------------------
161P2B7Av.3    GGGGGGGGGGGGGGGVGGGAGGGAGGGRSPVRELDMGAAERSREPGSPRLTEVSPEL    120

161P2B7Av.1    -------MEDEGQTKIKQRRSRTNFTLEQLNELERLFDETHYPDAFMREELSQRLGLS    51
161P2B7Av.2    -------MEDEGQTKIKQRRSRTNFTLEQLNELERLFDETHYPDAFMREELSQRLGLS    51
161P2B7Av.3    KDRKDDAKGMEDEGQTKIKQRRSRTNFTLEQLNELERLFDETHYPDAFMREELSQRLGLS  180
                      *********************************************

161P2B7Av.1    EARVQVWFQNRRAKCRKQENQLHKGVLIGAASQFEACRVAPYVNVGALRMPFQQ-------   105
161P2B7Av.2    EARVQVWFQNRRAKCRKQENQLHKGVLIGAASQFEACRVAPYVNVGALRMPFQQ-------   105
161P2B7Av.3    EARVQVWFQNRRAKCRKQENQLHKGVLIGAASQFEACRVAPYVNVGALRMPFQQDSHCNV   240
               ******************************************************

161P2B7Av.1    -------VQAQLQLDSAVAHAHHHLHPHLAAHAPYMMFPAPPFGLPLATLAADSASAASVV   159
```

Figure 14j (continued)

```
161P2B7Av.2    ------VQAQLQLDSAVAHAHHHLHPHLAAHAPYMFPAPPFGLPLATLAADSASAASVV 159
161P2B7Av.3    TPLPFQVQAQLQLDSAVAHAHHHLHPHLAAHAPYMFPAPPFGLPLATLAADSASAASVV 300
                     ************************************************

161P2B7Av.1    AAAAAKTTSKNSSIADLRLKAKKHAAALGL 190
161P2B7Av.2    AAAAAKTTSKDSSIADLRLKAKKHAAALGL 190
161P2B7Av.3    AAAAAKTTSKDSSIADLRLKAKKHAAALGL 331
               **********:******************
```

Figure 11k Nucleotide sequences of transcript variants of 179P3G7

>179P3G7 v.2 (SEQ ID NO:145).

```
cggatgggga aaaaaaaaga tgtcagctcc tccgctgtag tattgctcct taaaaacccc      60
tctctctgaa aatgacatgc cctcgcaatg ctcgtacgcg gagcccttgg               120
ctgcgcccgg cggaggagag cgctatagcc ggagcgcagg catgtatatg cagtctggga    180
gtgacttcaa ttgcggggtg atgaggggct gcgggctcgc ccctcgctc tccaagaggg     240
acgagggcag cagcccagc ctcgcctca acacctatcc gtcctacctc tcgcagctgg      300
actcctgggg cgacccaaa gccgctatc gctgaaca acctgttggc agccgctgt         360
cctcctgctc ctaccacct agtgtcaagg agagaatgt ctgctgcatg tacagcgcag      420
agaaccggc gaaaagtgc cctgaggcag ctctctactc ccaccccttg ccggactcct      480
gccttggga gcacgaggta ccgtccca gctactaccg cgccagcccg agctactccg       540
cgctggacaa gacgcccac tgttctgggg ccaacgactt cgaagccctt ttcgagcagc    600
gggccagtct caaccccgc gccgaacatc tggaatcgcc tcagctgggg ggcaaagtga    660
gtttccctga gacccccaag tccgacagcc agacccccag cccaatgaa atcaagacgg    720
agcagagcct ggcgggccct aaagggaccct cctcggagag cgaaaaggag aggccaaag   780
ctgccgactc cagccagac acctcggata acgaagcgaa agtaaggcc gcctgggccg     840
cgggcgccac tgggacgttc cggcacttgg tcttcgcggc cgggagggg ggcaggggag    900
agggtttgggc ccaggagcc ccagaccatt tcggaatgc gacctggct ttcgactagc     960
gtccgctgag ctccaggctg gtggcgcgtc acttagctgg ggaagaggag ataaggcag   1020
aaaacaccac aggaaattgg ctgactgcaa agagcggaag gaagaaagg tgccctata    1080
ctaaacaccc gacgctgaa ttggagaaag aattctgtt caatatgtat ttgacgcag    1140
agccgccct ggagattgaa aagaccatta acttacaga cagacaagtc aaaatctggt    1200
ttcaaaatcg cagaatgaaa ctcaagaaaa tgaaccgaga gaatcgatc cgggactga   1260
cctccaattt taattttcacc tgaggcgcg gctctctccc ctccttgct gctccttgct   1320
ctccccgccc ctcctccctt tgtgctggt gatatattt tttttcctcc ctgagtataa    1380
atgcaatgcg actgcaaaaa agcaaagac ctcagactct ccttccaagg gacctgtggt   1440
tcgtgctgcg aagatgcttc cacttaaagc atgagaaatg gggtgccggg atgtgggtg   1500
tggtgtgtgc cctcatagat gggggtggga gtgtggctgg tgtgtgtc aaaccctcac    1560
tcacccacgc actcacaca agcattctgt tctccatgca agttaagat cgaatccatc    1620
```

Figure 11k (continued)

```
cgcttgtagg ggaaaaaaag gaaaaaaatt aaccagagag ggtctgtaat ctcgcagagc    1680
acaggcagaa tcgttccttc cttgctgcat ttcctcctta gactaataga cgttttggaa    1740
agttcggcta gtgttcgtgt gtttgtcgta gcacccagag cctccaccaa accctctcca    1800
tgtctttacc tccagtcgc tctaagatct gcttgaagtc tgtatttgt actgctttct    1860
gcttttctcc caccccctcct agcaccccca catccccat ctagtaacat ctcagaaatt    1920
tcatccagag gaacaaaaaa attaaaaata gaacatagca aagcaaagac agaatgcccc    1980
ccccaaata ttgtcctgtc cctgtctggg agttgtgtta tttaaagata ttctgtatgt    2040
tgtatctttt gcatgtagct tccttaatgg agaaaaaaaa atcctaataa atttccagaa    2100
tca                                                                  2103
```

Figure 12k Protein sequences of transcript variants of 179P3G7

>179P3G7 v.2 (SEQ ID NO 146)
```
MTCPRNVTPN SYAEPLAAPG GGERYSRSAG MYMQSGSDFN CGVMRGCGLA PSLSKRDEGS     60
SPSLALNTYP SYLSQLDSWG DPKAAYRLEQ PVGRPLSSCS YPPSVKEENV CCMYSAENRA   120
KSGPEAALYS HPLPESCLGE HEVPVPSYYR ASPSYSALDK TPHCSGANDF EAPFEQRASL   180
NPRAEHLESP QLGGKVSFPE TPKSDSQTPS PNEIKTEQSL AGPKGSPSES EKERAKAADS   240
SPDTSDNEAK GKAAWAAGAT GTFRHLVFAA CEGGRGEGWA QEAPDHFGNA TLAFD        295
```

Figure 13k Alignment of nucleotide sequences of 179P3G7 transcript variants (SEQ ID NOS 41, 145).

```
179P3G7v.1    CGGATGGGGAAAAAAAAAAAAGATGTCAGCTCCTCCGCTGTAGTATTGCTCCTTAAAAACCCC    60
179P3G7v.2    CGGATGGGGAAAAAAAAAAAAGATGTCAGCTCCTCCGCTGTAGTATTGCTCCTTAAAAACCCC    60
              ****************************************************************

179P3G7v.1    TCTCTCTGAAAATGACATGCCCTCGCAATGTAACTCCGAACTCGTACGCGGAGCCCTTGG   120
179P3G7v.2    TCTCTCTGAAAATGACATGCCCTCGCAATGTAACTCCGAACTCGTACGCGGAGCCCTTGG   120
              ************************************************************

179P3G7v.1    CTGCGCCCGGCGGAGGAGAGAGCGCTATAGCCGGAGCCGCAGGCATGTATATGCAGTCTGGGA   180
179P3G7v.2    CTGCGCCCGGCGGAGGAGAGAGCGCTATAGCCGGAGCCGCAGGCATGTATATGCAGTCTGGGA   180
              ****************************************************************

179P3G7v.1    GTGACTTCAATTGCGGGGTGATGAGGGGCTGCGGGGCTGCGCTCTCCAAGAGGG   240
179P3G7v.2    GTGACTTCAATTGCGGGGTGATGAGGGGCTGCGGGGCTGCGCTCTCCAAGAGGG   240
              *************************************************************

179P3G7v.1    ACGAGGGCAGCAGCCCAGCCTCGCCCTCAACACCTATCCGTCCTACCTCTCGCAGCTGG    300
```

Figure 13k (continued)

```
179P3G7v.2    ACGAGGGCAGCAGCCCAGCCTCGCCCCTCAACACCTATCGTCGTCCTACCTCTCCGCAGCTGG    300
              ****************************************************************

179P3G7v.1    ACTCCTGGGGCGACCCCCAAAGCCGCTATCGCCTGGAACAACCTGTTGGCAGGCCGCTGT    360
179P3G7v.2    ACTCCTGGGGCGACCCCCAAAGCCGCTATCGCCTGGAACAACCTGTTGGCAGGCCGCTGT    360
              ****************************************************************

179P3G7v.1    CCTCCTGCTCCTACCCACCTAGTGTCAAGGAGGAGAATGTCTGCTGCATGTACAGCGCAG    420
179P3G7v.2    CCTCCTGCTCCTACCCACCTAGTGTCAAGGAGGAGAATGTCTGCTGCATGTACAGCGCAG    420
              ****************************************************************

179P3G7v.1    AGAACCGGGCGAAAAGTGGCCCTGAGGCAGCTCTCTACTCCCACCCCTTGCCGGAGTCCT    480
179P3G7v.2    AGAACCGGGCGAAAAGTGGCCCTGAGGCAGCTCTCTACTCCCACCCCTTGCCGGAGTCCT    480
              ****************************************************************

179P3G7v.1    GCCTTGGGGAGCACGAGGTACCCGTCCCCAGCTACTACCGCGCCAGCCCGAGCTACTCCG    540
179P3G7v.2    GCCTTGGGGAGCACGAGGTACCCGTCCCCAGCTACTACCGCGCCAGCCCGAGCTACTCCG    540
              ****************************************************************

179P3G7v.1    CGCTGACAAGACGCCCCACTGTTCTGGGGCCAACATCTGAAGCCCCTTTCGAGCAGC    600
179P3G7v.2    CGCTGACAAGACGCCCCACTGTTCTGGGGCCAACATCTGAAGCCCCTTTCGAGCAGC    600
              ****************************************************************

179P3G7v.1    GGGCCAGTCTCAACCGCGCGCGCCGAACATCTGGAATCGCCTCAGCTGGGGGCAAAGTGA    660
179P3G7v.2    GGGCCAGTCTCAACCGCGCGCGCCGAACATCTGGAATCGCCTCAGCTGGGGGCAAAGTGA    660
              ****************************************************************

179P3G7v.1    GTTTCCCTGAGACCCCCAAGTCCGACAGCCAGACCCCCAATGAAATCAAGACGG    720
179P3G7v.2    GTTTCCCTGAGACCCCCAAGTCCGACAGCCAGACCCCCAATGAAATCAAGACGG    720
              ****************************************************************

179P3G7v.1    AGCAGAGCCTGGCGGGCCCTAAAGGAGCCCTCGGAGAGCGAAAAGGAGAGGGCCAAAG    780
179P3G7v.2    AGCAGAGCCTGGCGGGCCCTAAAGGAGCCCTCGGAGAGCGAAAAGGAGAGGGCCAAAG    780
              ****************************************************************

179P3G7v.1    CTGCCGACTCCAGCCCAGACACCTCGGATAACGAAGCGAAAG------------         822
179P3G7v.2    CTGCCGACTCCAGCCCAGACACCTCGGATAACGAAGCGAAAGGTAAGGCCGCTGGGCCG    840
              ******************************************
```

Figure 13k (continued)

```
179P3G7v.1  ------------------------------------------------------------
179P3G7v.2  CGGGCGCCACTGGACGTTCCGGCACTTGGTCTTCGCGGCCGCGGGAGGGGGCAGGGGAG   900

179P3G7v.1  ------------------------------------------------------------
179P3G7v.2  AGGGTTGGGCCCCAGGAGGCCCCAGACCATTTCGGGAATGCGACCCTGGCTTTCGACTAGC   960

179P3G7v.1  ---------------------AGGAGATAAAGGCAG                          837
179P3G7v.2  GTCCGCTGAGCTCCAGGCTGTGGCGCTGTCACTTAGCTGGGAAGAGGAGATAAAGGCAG  1020
                                 ***************

179P3G7v.1  AAAACACCACAGGAAATTGGCTGACTGCAAAGAGCGGAAGAAGAAGAGTCGCCCCTATA   897
179P3G7v.2  AAAACACCACAGGAAATTGGCTGACTGCAAAGAGCGGAAGAAGAAGAGTGCCCCTATA  1080
            ************************************************ *********

179P3G7v.1  CTAAACACCAGACGCTGGAATTGGAGAAAAGAATTTCTGTTCAATATGTATTTGACGCGAG   957
179P3G7v.2  CTAAACACCAGACGCTGGAATTGGAGAAAAGAATTTCTGTTCAATATGTATTTGACGCGAG  1140
            ************************************************************

179P3G7v.1  AGCGCGCTGGAGATTAGCAAGACCATTAACCTTACAGACAGACAAGTCAAAATCTGGT  1017
179P3G7v.2  AGCGCGCTGGAGATTAGCAAGACCATTAACCTTACAGACAGACAAGTCAAAATCTGGT  1200
            *********************************************************

179P3G7v.1  TTCAAAAATCGCAGAATGAAACTCAAGAAAAATGAACCGAGAGAATCGGATCCGGGAACTGA  1077
179P3G7v.2  TTCAAAAATCGCAGAATGAAACTCAAGAAAAATGAACCGAGAGAATCGGATCCGGGAACTGA  1260
            *************************************************************

179P3G7v.1  CCTCCAATTTTAATTTCACCTGAGAGCGCGGCGCGCCTCTCCTCCCTTCCCGCTCCTTGCT  1137
179P3G7v.2  CCTCCAATTTTAATTTCACCTGAGAGCGCGGCGCGCCTCTCCTCCCTTCCCGCTCCTTGCT  1320
            ************************************************************

179P3G7v.1  CTCCCCGCCCCTCCTCCTCCCTTTGTGCCTGGTGATATATATTTTTTCCTCCCCTGAGTATAA  1197
179P3G7v.2  CTCCCCGCCCCTCCTCCTCCCTTTGTGCCTGGTGATATATATTTTTTCCTCCCCTGAGTATAA  1380
            ****************************************************************

179P3G7v.1  ATGCAATGCGACTGCAAAAAGGCAAAGACCTCAGACTCTCCTTCCAAGGACCTGTGGT  1257
179P3G7v.2  ATGCAATGCGACTGCAAAAAGGCAAAGACCTCAGACTCTCCTTCCAAGGACCTGTGGT  1440
            *********************************************************
```

Figure 13k (continued)

```
179P3G7v.1    TCGTGCTGCGAAGATGCTTCCACTTAAAGCATGAGAAATGGGGTGCCGGATGTGGGGTG   1317
179P3G7v.2    TCGTGCTGCGAAGATGCTTCCACTTAAAGCATGAGAAATGGGGTGCCGGATGTGGGGTG   1500
              ************************************************************

179P3G7v.1    TGGTGTGTGCCCTCATAGATGGGGTGGGAGTGTGGCTGGTGTGTGTCAAACCCTCAC     1377
179P3G7v.2    TGGTGTGTGCCCTCATAGATGGGGTGGGAGTGTGGCTGGTGTGTGTCAAACCCTCAC     1560
              ************************************************************

179P3G7v.1    TCACCCACGCACTCACACACAGCATTCTGTTCTCCATGCAAAGTTAAGATCGAATCCATC  1437
179P3G7v.2    TCACCCACGCACTCACACACAGCATTCTGTTCTCCATGCAAAGTTAAGATCGAATCCATC  1620
              ************************************************************

179P3G7v.1    CGCTTGTAGGGGAAAAAAAGGAAAAAAAATTAACCAGAGAGAGGGTCTGTAATCTCGCAGAGC  1497
179P3G7v.2    CGCTTGTAGGGGAAAAAAAGGAAAAAAAATTAACCAGAGAGAGGGTCTGTAATCTCGCAGAGC  1680
              ************************************************************

179P3G7v.1    ACAGGCAGAATCGTTCCTTCCTTCCTTGCTCGCATTTCCTCCTTAGACTAATAGACGTTTTGGAA  1557
179P3G7v.2    ACAGGCAGAATCGTTCCTTCCTTCCTTGCTCGCATTTCCTCCTTAGACTAATAGACGTTTTGGAA  1740
              ************************************************************

179P3G7v.1    AGTTCGGCTAGTGTTCGTGTGTTCGTGTGTTCGTAGCACCCAGAGCCTCCACCAAACCCTCTCCA  1617
179P3G7v.2    AGTTCGGCTAGTGTTCGTGTGTTCGTGTGTTCGTAGCACCCAGAGCCTCCACCAAACCCTCTCCA  1800
              ************************************************************

179P3G7v.1    TGTCTTTTACCTCCCAGTCGCTCGCTCTAAGATCTGCTTGAAGTCTCGTATTTGTACTGCTTTCT  1677
179P3G7v.2    TGTCTTTTACCTCCCAGTCGCTCGCTCTAAGATCTGCTTGAAGTCTCGTATTTGTACTGCTTTCT  1860
              ************************************************************

179P3G7v.1    GCTTTTCTCCCACCCCTCCTAGCACCCCACATCCCCCATCTAGTAACATCTCAGAAATT  1737
179P3G7v.2    GCTTTTCTCCCACCCCTCCTAGCACCCCACATCCCCCATCTAGTAACATCTCAGAAATT  1920
              ************************************************************

179P3G7v.1    TCATCCAGAGGAACAAAAAATTAAAAATAGAACATAGCAAAGCAAAGACAGAATGCCCC  1797
179P3G7v.2    TCATCCAGAGGAACAAAAAATTAAAAATAGAACATAGCAAAGCAAAGACAGAATGCCCC  1980
              ************************************************************

179P3G7v.1    CCCCCAAATATTGTCCCTGTCCCTGTCGGGAGTGTGTTATTTAAAGATATTCTGTATGT  1857
179P3G7v.2    CCCCCAAATATTGTCCCTGTCCCTGTCGGGAGTGTGTTATTTAAAGATATTCTGTATGT  2040
              ************************************************************
```

Figure 13k (continued)

```
179P3G7v.1    TGTATCTTTTGCATGTAGCTTCCTTAATGGAGAAAAAAAATCCTAATAAATTTCCAGAA 1917
179P3G7v.2    TGTATCTTTTGCATGTAGCTTCCTTAATGGAGAAAAAAAAATCCTAATAAATTTCCAGAA 2100
              ************************************************************

179P3G7v.1    TCATAAAAAAAAAAAAAAAAAAAA 1941
179P3G7v.2    TCA---------------------  2103
              ***
```

Figure 14k Alignment of protein sequences of 179P3G7 transcript variants (SEQ ID NOS:42, 146).

```
179P3G7v.1    MTCPRNVTPNSYAEPLAAPGGGERYSRSAGMYMQSGSDFNCGVMRGCGLAPSLSKRDEGS  60
179P3G7v.2    MTCPRNVTPNSYAEPLAAPGGGERYSRSAGMYMQSGSDFNCGVMRGCGLAPSLSKRDEGS  60
              ************************************************************

179P3G7v.1    SPSLAINTYPSYLSQLDSWGDPKAAYRLEQPVGRPLSSCSYPPSVKEENVCCMYSAENRA 120
179P3G7v.2    SPSLAINTYPSYLSQLDSWGDPKAAYRLEQPVGRPLSSCSYPPSVKEENVCCMYSAENRA 120
              ************************************************************

179P3G7v.1    KSGPEAAALYSHPLPESCLGEHEVPSYYRASPSYSALDKTPHCSGANDFEAPFEQRASL 180
179P3G7v.2    KSGPEAAALYSHPLPESCLGEHEVPSYYRASPSYSALDKTPHCSGANDFEAPFEQRASL 180
              ************************************************************

179P3G7v.1    NPRAEHLESPQLGGKVSFPETPKSDSQTPSPNEIKTEQSLAGPKGSPSESEKERAKAADS 240
179P3G7v.2    NPRAEHLESPQLGGKVSFPETPKSDSQTPSPNEIKTEQSLAGPKGSPSESEKERAKAADS 240
              ************************************************************

179P3G7v.1    SPDTSDNEAKEEIKAENTTGNWLTAKSGRKKRCPYTKHQTLELEKEFLFNMYLTRERRLE 300
179P3G7v.2    SPDTSDNEAKG-------KAAWAAGATG--------------TFRHLVFAAGE---- 272
              ***********         *  ::  :*                  *  . .:: :    *

179P3G7v.1    ISKTINLTDRQVKIWFQNRRMKLKKMNRENRIRELTSNFNFT 342
179P3G7v.2    ------GGRGEGWAQ-------EAPDHFGNATLAFD--     295
                     .  :: * *         :    * :::  :*   *:
```

Figure 11m  Nucleotide sequences of transcript variants of 184P3G10
>184P3G10 v.2 (SEQ ID NO:147).

```
gactacgtgg gtctggagct gactgccgtc ctgacacgtc ctagagctgc aagcaggtcc    60
tgccagagag ccaccatgac ctctcagcct ctcaggctag cagaagagta tggcccaagt   120
cctgggagt  ctgaactggc tgtgaacccc tttgatggc  ttcccttctc ttcccgctac   180
tatgagctgc tgaagcagcg ccaagccttg cccatctgg  ctgctcgctt tacttcttg   240
gagcagttgg agagtaaccc cactgagtg  gtgctggtgt ctggggagcc tggttctggc   300
aagagcaccc agatccctca gtggtgtgca gagtttgcgc tggcagagg  gttccagaaa   360
ggacaggtta ctgttactca gccctaccct cttgcagccc ggagcctggc tctgcgggtt   420
gctgatgaga tggacctgac cctggttcat gaggttgat  acagcatccc ccaggaggac   480
tgcacgggc  ccaacaccct gtcaggttc  tgctggaca  ggctgcttct gcaggagttg   540
gcctcgaccc gaggcactgg agcctgggc  gtgctgtac  ccaggctgga tcaggagcgg   600
tcggtggcat cagattcact ccagggcta  ctgcaagatg ccaggctgga aaaacttccg   660
ggggacctca gagtgttgt  ggttactgac aacctaagct cgagctttc                720
tgggcaatc  ctccattgt  gcatataccc agagagcctg gtgagacc  gcttgaattg    780
tactgggaca ccatcccacc tgatccggtg gaagctgcct gccaagcagt gctgaaattg    840
tgtcgaagg  agcttccagg agatgtgcta gtgttcctgc ccagtgagga ggaaattcc    900
ctgtgctgtg aatccttgtc cagggaggta gagtcctgc  ttctccaagg gcttccacca    960
cgagtactgc ccctcaccc  agactgtgga cgagccgttc aggctgtgta tgaggacatg   1020
gatgcccgaa agttgtggt  cactcactgg ctgctgact  tctccttctc cctccttcc   1080
atccaacatg tcatcgactc aggactgag  ctccgaagtg tttacaatcc taggatccga   1140
gcagaattcc aagtgttgag gccaatcagc aagtgtcagg cagaggcaag acgattgcga   1200
gcaagagggt tcccaccagg atcctgcctc tgcctgtatc ctaagtcctt cttagaacta   1260
gaagctccac cattgcaaca accagggtg  tgtgagaga  atctgagctc cctggtgtta   1320
ctactaaaaa ggagacagat tgcagagcca gggagtgtc  acttcctgga ccagcctgct   1380
ccagaagcac tgatgcaagc cctgaagca  ttagactatc tgcagccct  ggatgatgat   1440
gggaacctgt cagatgctgg tgtcatacta tcagaattcc ctctgagccc cctgctgcc   1500
aaagccctgc tgcccatg   cgagtttgac tgtgtgacg  agatgctcac cctgcctgcc   1560
atgctcacag ctgcccctgg gtttaccgt  cctccactca gtgcagaaga agctgccctg   1620
cgtcgggcc  tggaacacac ggatggtgac cacagttctc tgatccaggt gtatgaagcc   1680
tttatacaaa gtgagcaga  tgaggcttgg tgccagctc  gaggtctgaa ttgggcagca   1740
ttgtgccaag cccataaact tcgggagaa  ctcctagaac tcatgcaacg aattgaactt   1800
cccttgtccc taccagcctt tggctctgag cagaatgca  cagaacccttca gaaagcactg   1860
gtgtcaggat acttttctcaa ggtgccagga gatggccaga gacacagacg ggactggaaa ttacctctc   1920
ctaaccata  agcatggcc  ccagctctcc tcatactgct gctaccgaag cgcagagct   1980
cctgccacac cccaccatg  gtgctctac  cacaatttca ccatatccaa agacaactgc   2040
ctttccattg tttcgagat  tcaaccacag atgctgttgg aattgcccc  tccatacttc   2100
ctgagtaact tgccctccag tgcaggagga gacctctga  accagcttga ggaaggaatg   2160
gcagattcta cagcagggag cgcctgcct  caaatcatcc tcagcccagg agttcagaga   2220
ctgcagtgac ctgcctgcct atggaatgga gctggttca  tctcatcaca ttagattatc   2280
cctcagggtg acaccaaagc acccagacag atttagaagc ccaaagttta gggtcaaatg   2340
```

Figure 11m (continued)

```
taaaccctgg aacctgagtc ccaagaaatg gtagactggg aatgaaaaga atgggtaaa      2400
ccacagtcta cataggaaag gactcttcc ttagccttct cttattgatt ggagagggac      2460
tgacatgctc ctcattctct taactttgcc aaaccattc ttgtactccc ttgtgatcta      2520
taaaagattt ttctatgatg ccaa                                             2544

>184P3G10 v.3 (SEQ ID NO:148).
ctgatggcga tgaatgaaca ctgcgtttgc tggaagatg gtgtcggtca ccaaatatga        60
ccttactggc tgctctgcct tctgcaggtc ctgccagaga gccaccatga cctctcagcc      120
tctcaggcta gcagaagagt atggcccaag tcctggggag tctgaactgg ctgtgaaccc      180
ctttgatggg cttccctttct cttcccgcta ctatgagctg ctgaagcagc gccaagcctt    240
gccatctgg gctgctcgct ttaccttctt ggagcagttg gagagtaacc ccactggagt       300
ggtgctggtg tctgggagc ctggttctgg caagagcacc cagatccctc agtggtgtgc       360
agagttgcg ctggccagag gttccagaa aggacaggtt actgttactc agccctaccc         420
tcttgcagcc cggagcctgg ctctgcgggt tgctgatgag atggacctga cctgggtca       480
tgaggttgga tacagcatcc cccaggagga ctgcacgggg ccaacaccc cggagcactg       540
ctgctgggac agctgcttc tgcaggagt ggcctcgacc gtcggtggca tcagattcac gagcctgggg  600
cgtgctgta ctagatgagg ctcaggagc caggagagcc gtcggtggca tcagattcac tccagggct  660
actgcaagat gccaggctgg aaaaacttcc gggggacctc agagtggttg tggttactga       720
cccagccctt gaacctaagc tccgagcttt ctgggcaat cctcctattg tgcatatacc       780
cagagagcct ggtgagagac cttccccat ctactggac accatcccac ctgatcggt         840
ggaagctgcc tgccaagcag tgcttgaatt gtgtcggaag gagcttcag gagatgtgct       900
agtgttcctg cccagtgagg agtaaaaa acaaaacaaa acaaaaaaa cagcctgcaa          960
aatgagcctg caaaaggagg aaattccct gtgctgtga tccttgtcca gggagtaga        1020
gtccttgctt ctccaaggc ttccaccacg agtactgccc cttcaccag actgtggacg       1080
agccgttcag gctgtgtatg aggacatgga tgcccgaaag gttgtggtca ctcactgct     1140
ggctgacttc tccttctccc tccccttcat ccaacatgtc atcgactcag gactggagct    1200
ccgaagtgtt tacaatccta ggatccgagc agaattccaa gtgttgaggc caatcagcaa    1260
gtgtcaggca gaggcaagac gattgcgagc aagagggttc ccaccaggat cctgcctctg    1320
cctgtatcct aagtcctttct tagaactaga agctccacca ttgccacaac ccagggtgtg    1380
tgaggagaat ctgagctccc tgttgttact actaaaaagg agacagattg cagagccagg     1440
ggagtgtcac ttcctgacc agctgctcc agaagcactg atgcaagccc tggaagattt      1500
agactatctg gcagccctg atgatgatgg agctgcaa agcctgtgtg gatctggtg tcatactatc  1560
agaattccct ctgccctg agctgccaa agccctgctg gcctcatgcg agtttgactg        1620
tgtggacgag atgctcaccc tgctgccat gctcacagct gccctgggt ttaccgtcc       1680
tccactcagt gcagaagaag atccaggtgt gcagaagaag atccaggtgt cgggcctgcg tcggcctgcg gaacacacgg atggtgacca  1740
cagttcctg atccaggtgt ggtctgaatt gggcagcatt tatacaaagt ggagcagatg aggcttggtg   1800
caggctcga ggtctgaatt gggcagcatt tgtccaagcc cataaacttc ggggagaact        1860
cctagaactc atgcaacgaa ttgaacttcc cttgtcccta ccagcctttg gctctgagca        1920
gaatcgcaga gaccttcaga aagcactggt gtcaggatac ttcttcaagg tggccagaga        1980
```

Figure 11m (continued)

```
cacagacggg actgaaatt acctttctcct aacccataag catgtggccc agctctcctc 2040
atactgctgc taccgaagcc gcagagctcc tgccagaccc ccaccatggg tgtcttacca 2100
caatttcacc atatccaaag acaactgcct ttccattgtt tctgagattc aaccacagat 2160
gctggtggaa ttgccccctc catacttcct gagtaacttg cctcccagtg agagcagaga 2220
ccttctgaac cagctaaggg aaggaatggc agattctaca gcagggagca aatcatcctc 2280
agcccaggag ttcagtaaggg cctgtgtcct gcagtgacct gcctgcctat ggaatggagc 2340
tgggttcatc tcatcacatt agattatccc tcaggtgac accaaagcac ccagacagat 2400
ttagaagccc aaagttaagg gtcaaatgta aaccctgaa cctgagtccc aagaatggt 2460
agactgggaa tggaaagaat gggtaaaacc acagtctaca tagggaagga ctcttcctt 2520
agccttctct tattgattgg agagggactg acatgctcct cattctctta actttgccaa 2580
acccattctt gtactccctt gtgatctata aaagattttt ctatgatgcc aa 2632
```

>184P3G10 v.4 (SEQ ID NO:149).

```
ctgatggcga tgaatgaaca ctgcgtttgc tgggaagatg gtgtcggtca ccaaatatga   60
ccttactggc tgctctgcct tctgcaggtc ctgccagaga gccaccatga cctctcagcc  120
tctcaggcta gcagaagagt atggcccaag tcctggggag tctgaactgg ctgtgaaccc  180
cttttgatgg cttcccgtct cttacttctt ctatgagctg ctgaagcagc gccaagcctt  240
gccatctgg gctgctcgct ttaccttctt ggagcagcac cagatcccta cactgagtgagt  300
ggtgctggtg tctgggagc ctggttctgg caagagcacc cagatcccctc agtggtgtgc  360
agagtttgcg ctggccagag ggttccagaa aggacaggtt actgttactc agcoctaccc  420
tcttgcagcc cggagcctgg ctctgcgggt tgctgatgag atggacctga cctggtca    480
tgaggttgga tacagcatcc cccaggagga ctgcacgggg cccaacaccc tgctcaggtt  540
ctgctgggac aggctgcttc tgcaggaggt tcaggagag gcctcgacc cgaggcactg gagcctgggg  600
cgtgctggta ctagatgagg ctcaggagcg gtcggtgca tcagattcac tcaggggct   660
actgcaagat gccaggctgg aaaaacttcc ggggacctc agagtggttg tggttactga  720
cccagccctt gaacctaagc tccgagcttt ctgggcaat cctcctattg tgcatataacc 780
cagagagcct ggtgagagac cttccccccat ctactgggac accatcccac ctgatcgggt 840
ggaagctgcc tgccaagcag tgcttgaatt gtgtcggaag gagcttccag gagatgtgct   900
agtgttcctg cccagtgagg aggaaatttc cctgtctgt gaatccttgt ccaggaggt   960
agagtcctg cttctccaag ggcttccacc acgagtactg ccccttcacc cagactgtgg  1020
acgagccgtt caggctgtgt atgaggacat ggatgcccga aaggttgtgg tcactcactg  1080
gctggctgac ttctccttct ccctcccttc catccaacat gtcatcgact caggactgga  1140
gctccgaagt gtgagtgaga gagagagata gcggtggggt agtaaagaca gaatgcccc  1200
actctgatct gtcttggcct tgttgggg acgggcaaca ggtttacaat cctaggatcc  1260
gagcagaatt ccaagtgttg aggccaatca gcaagtgtca gcagaggca agacgattgc  1320
gagcagagg gttcccacca ggatcctgcc tctgcctgta tcctaagtcc ttcttagaac  1380
tagaagctcc accattgcca caacccaggg tgtgtgagga gaatctgagc tccctgtgt   1440
tactactaaa aaggagacag attgcagagc caggggagtg tcacttcctg gaccagcctg  1500
```

Figure 11m (continued)

```
ctccagaagc actgatgcaa gccctgaag atttagacta tctgcagcc ctggatgatg 1560
atggggacct gtcagatctg ggtgtcatac tatcagaatt ccctctggcc cctgagctgg 1620
ccaaagccct gctgcctca tgcgagtttg actgtgtgga cgatgtctc accctggctg 1680
ccatgctcac agctgcccct ggttacccc gtcctccact cagtgcagaa acctgtgccc 1740
tgcgtcgggc cctggaacac acggatggtg accacagttc tctgatccag gtgtatgaag 1800
ccttatatca aagtgagca gatgaggctt ggtgccaggc tcgagttcag aattggcag 1860
cattgtgcca agcccataaa cttcggggag aactcctaga actcatgcaa cgaattgaac 1920
ttcccttgtc cctaccagcc tttggctctg agcagaaatcg cagagaccctt cagaaagcac 1980
tggtgtcagg atactttctc aagtggcca gagacacaga cgggactgga aattaccttc 2040
tcctaaccca taagcatgtg gcccagctct cctcatactg ctgctaccga agccgcagag 2100
ctcctgccag accccacca tggtgtctct accacaattt caccatatcc aaagacaact 2160
gcctttccat tgtttctgag attcaaccac agatgctgt ggaattggcc cctccatact 2220
tcctgagtaa cttgcctccc agtgagagca gagaccttct cctcagccca gaaccagcta 2280
tggcagattc tacagcaggg agcaaatcat cctcagccca ggagttcaga gatccctgtg 2340
tcctgcagtg acctgcctgc ctatggaatg gagctgggtt catctcatca cattagatta 2400
tccctcaggg tgacaccaaa gcaccagac agatttagaa gccaaagtt tagggtcaaa 2460
tgtaaaccct ggaacctgag tcccaagaaa cttgtagactg tggtagactg gaatgggta 2520
aaccaagtc tacataggga aggacttctt cttagcctt ctctattga ttggagagg 2580
actgacatgc tcctcattct cttaacttg ccaaaccat tcttgtactc ccttgtatc 2640
tataaaagat ttttctatga tgccaa                                   2666
```

>184P3G10 v.5 (SEQ ID NO:150).

```
ctgatggcga tgaatgaaca ctgcgttgc tgggaagatg gtgtcggtca ccaaatatga   60
ccttactggc tgctctgcct tctgcagtc ctgcagaga gccaccatga cctctcagcc  120
tctcaggcta gcagaagagt atggcccaag tcctccgcta tctgagctg tctgaactgg ctgtgaaccc  180
ctttgatggg cttcccttct cttccctct ttaccttctt gagcagttg ctgaagcagc gccaagcctt  240
gccatctgg gctgctcgct gctgggag ctggttctgg caagcacc cagatccctc agtggtgtgc  300
ggtgctggtg tctgggag ctggccagag gttccagaa aggacaggtt actgttactc agcctaccc  420
agagtttgcg ctgccagag ctctgcggt tctgatgag atgacctga cctggtca  480
tcttgcagcc cggcagctg tccagcatcc ccaggagga ctgcaggg cccaacacc tgctcagtt  540
tgaggttgga tacagcatcc ccaggagga ctgcaggg cccaacacc tgctcagtt  540
ctgctgggca agctgcttc tgcaggagt ggcctggca gtcggtggca gcagcactg gagccgtggg  600
cgtgctggta ctagatgagg ctcaggagcg aaaaacttcc gtcggtggca tcagattcac tcaggggct  660
actgcaagat gccagctga aaaaacttcc tccgagcttt ggggaccct agagtgttg tgttactga  720
cccagagcct gaacctaagc tccgagcttt ctcccccat ctggggcaat cctcctattg tgcatatacc  780
cagagagcct gtgagagac cttccccat ctactggaag gagcttccag ctgatcggt  840
ggaagctgcc tgccaagcag tgcttgaatt gtgtcggaag gagcttccag gagatgtgct  900
agtgttcctg cccagtgagg aggaaatttc cctgctgt gaatccttgt ccaggaggt  960
agagtcctg cttctccaag ggcttccacc acgagtactg cccttcacc cagactgtgg  1020
```

Figure 11m (continued)

```
acgagccgtt caggctgtgt atgaggacat ggatgcccga aggttgtgg tcactcactg   1080
gctggctgac ttctccttct ccctccctt catccaacat gtcatgact caggactgga   1140
gctccgaagt gtttacaatc ctaggatccg agcagaattc caagtgttga ggccaatcag   1200
caagtgtcag gcagaggcaa gacgattgcg agcaagaggg ttccaccag tggtcttctt   1260
tcccagtgtc ttttcccctc aggatcctgc ctctgcctgt atcctaagtc cttcttagaa   1320
ctagaagctc accattgcc acaacccagg gtgtgtgagg agaatcgag ctccctggtg   1380
ttactactaa aaaggagaca gattgcagca ccagggagt gtcacttcct ggaccagcct   1440
gctccagaag cactgatgca agccctgaa gattagact atctgcagc cctgatgat    1500
gatgggacc tgtcagatct gggtgtcata ctatcagaat tccctctgc cctgagctg   1560
gccaaagccc tgctggcctc atgcgagttt gactgtgtg acgagatgct caccctggct   1620
gccatgctca cagctgcccc tgggtttacc cgtcctccac tcagtgcaga agaagtgcc   1680
ctgcgtcggg cctgaaaca cacggatggt gaccacagtt ctctgatcca gtgtatgaa   1740
gcctttatac aaagtggagc agatggagct tgggccagg gaactcctag aactcatgca acgaattgaa   1800
gcattgtgcc aagccataa acttcgggga cttggctct gcagagaatc gcagagacct tcagaaagca   1860
cttcccttgt cctaccagc caaggtggcc agagacacag acggactgg aaattacctt   1920
ctggtgtcag gatactttct aaggcatgt ggcccagctc tcctcatact gctgctaccg aagccgaga   2040
ctctaaccc ataagcatgt ggcccagctc tcctcatact gctgctaccg aagccgaga   2040
gctcctgcca gaccccacc atggtgctc taccacatt tcaccatatc caagacaac   2100
tgcctttcca ttgtttctga gattcaacca cagatgctgg tgaattggc ccctccatac   2160
ttcctgagta acttgcctcc cagtgagagc agagaccttc tgaaccagct aaggaagga   2220
atgcagatt ctacagcagg gacctgcctg cctatgaat ggagttcag agatcccctgt   2280
gtcctgcagt gacctgcctg gtgacaccaa agcaccagaa cagatttaga agcccaaagt ttaggtcaa   2400
atgtaaaccc tggaacctga gtcccaagaa atgtagact gggaatgaa agaatgggt   2460
aaaccacagt ctacataggg aaggactctt tccttagcct tctcttattg attggagagg   2520
gactgacatg ctcctcattc tcttaacttt gccaaaccca ttcttgtact cccttgtgat   2580
ctataaaaga tttttctatg atgccaa                                      2607
```

Figure 12m Protein sequences of transcript variants of 184P3G10

>184P3G10 v.2 (SEQ ID NO:151).

```
MTSQPLRLAE EYGPSPGESE LAVNPFDGLP FSSRYYELLK QRQALPIWAA RFTFLEQLES    60
NPTGVLVSG EPGSGKSTQI PQWCAEFALA RGFQKGQVTV TQPYPLAARS LALRVADEMD   120
LTLGHEVGYS IPQEDCTGPN TLLRFCWDRL LLQEVASTRG TGAWGVLVLD EAQERSVASD   180
SLQGLLQDAR LEKLPGDLRV VVTDPALEP KLRAFWGNPP IVHIPREPGE RPSPIYWDTI   240
PPDRVEAACQ AVLELCRKEL PGDVLVFLPS EEEISLCCES LSREVESLLL QGLPPRVLPL   300
HPDCGRAVQA VYEDMDARKV VVTHWLADFS FSLPSIQHVI DSGLELRSVY NPRIRAFFQV   360
LRPISKCQAE ARRLRARGFP PGSCLCLYPK SFLELEAPPL PQPRVCEENL SSLVLLLKRR   420
QIAEPGECHF LDQPAPEALM QALEDLDYLA ALDDDGDLSD LGVILSEFPL APELAKALLA   480
```

Figure 12m (continued)

```
SCEFDCVDEM LTLAAMLTAA PGFTRPPLSA EEAALRRALE HTDGDHSSLI QVYEAFIQSG    540
ADEAWCQARG LNWAALCQAH KLRGELLELM QRIELPLSLP AFGSEQNRRD LQKALVSGYF    600
LKVARDTDGT GNYLLLTHKH VAQLSSYCCY RSRRAPARPP PWVLYHNFTI SKDNCLSIVS    660
EIQPQMIVEL APPYFLSNLP PSESRDLLNQ LREGMADSTA GSKSSSAQEF RDPCVLQ       717

>184P3G10 v.3 (SEQ ID NO:152).
MNTAFAGKMV SVTKYDLTGC SAFCRSCQRA TMTSQPLRLA EEYGPSPGES ELAVNPFDGL     60
PFSSRYYELL KQRQALPIWA ARFTFLEQLE SNPTGVVLVS GEPGSGKSTQ IPQWCAEFAL    120
ARGFQKGQVT VTQPYPLAAR SLALRVADEM DLTIGHEVGY SIPQEDCTGP NTLLRFCWDR    180
LLLQEVASTR GTGAWGVLVL DEAQERSVAS DSLQGLLQDA RLEKLPGDLR VVVVTDPALE    240
PKLRAFWGNP PIVHIPREPG ERPSPITWDT IPPDRVEAAC QAVLELCRKE LPGDVLVFLP    300
SEEVKKQNKT KKTACKMSLQ KEEISLCCES LSREVESLLL QGLPPRVLPL HPDCGRAVQA    360
VYEDMDARKV VVTHWLADFS FSLPSIQHVI DSGLELRSVY NPRIRAEFQV LRPISKCQAE    420
ARRLRARGFP PGSCLCLYPK SFLELEAPPL PQPRVCEENL SSLVLLLKRR QIAEPGECHF    480
LDQPAPEALM QALEDLDYLA ALDDDGDLSD LGVILSEFPL APELAKALLA SCEFDCVDEM    540
LTLAAMLTAA PGFTRPPLSA EEAALRRALE HTDGDHSSLI QVYEAFIQSG ADEAWCQARG    600
LNWAALCQAH KLRGELLELM QRIELPLSLP AFGSEQNRRD LQKALVSGYF LKVARDTDGT    660
GNYLLLTHKH VAQLSSYCCY RSRRAPARPP PWVLYHNFTI SKDNCLSIVS EIQPQMIVEL    720
APPYFLSNLP PSESRDLLNQ LREGMADSTA GSKSSSAQEF RDPCVLQ                  767

>184P3G10 v.4A (SEQ ID NO:153).
MNTAFAGKMV SVTKYDLTGC SAFCRSCQRA TMTSQPLRLA EEYGPSPGES ELAVNPFDGL     60
PFSSRYYELL KQRQALPIWA ARFTFLEQLE SNPTGVVLVS GEPGSGKSTQ IPQWCAEFAL    120
ARGFQKGQVT VTQPYPLAAR SLALRVADEM DLTIGHEVGY SIPQEDCTGP NTLLRFCWDR    180
LLLQEVASTR GTGAWGVLVL DEAQERSVAS DSLQGLLQDA RLEKLPGDLR VVVVTDPALE    240
PKLRAFWGNP PIVHIPREPG ERPSPITWDT IPPDRVEAAC QAVLELCRKE LPGDVLVFLP    300
SEEEISLCCE SLSREVESLL LQGLPPRVLP LHPDCGRAVQ AVYEDMDARK VVVTHWLADF    360
SFSLPSIQHV IDSGLELRSV SERER                                         385

>184P3G10 v.4B (SEQ ID NO:154).
MAHSDLSWPW LGDGQQVYNP RIRAEFQVLR PISKCQAEAR RLRARGFPPG SCLCLYPKSF     60
LELEAPPLPQ PRVCEENLSS LVLLLKRRQI AEPGECHFLD QPAPEALMQA LEDLDYLAAL    120
DDDGDLSDLG VILSEFPLAP ELAKALLASC EFDCVDEMLT LAAMLTAAPG FTRPPLSAEE    180
AALRRALEHT DGDHSSLIQV YEAFIQSGAD EAWCQARGLN WAALCQAHKL RGELLELMQR    240
IELPLSLPAF GSEQNRRDLQ KALVSGYFLK VARDTDGTGN YLLLTHKHVA QLSSYCCYRS    300
RRAPARPPPW VLYHNFTISK DNCLSIVSEI QPQMIVELAP PYFLSNLPPS ESRDLLNQLR    360
EGMADSTAGS KSSSAQEFRD PCVLQ                                         385
```

Figure 12m (continued)

>184P3G10 v.5A (SEQ ID NO:155).
MNTAFAGKMV SVTKYDLTGC SAFCRSCQRA TMTSQPLRLA EEYGPSPGES ELAVNPFDGL    60
PFSSRYYELL KQRQALPIWA ARFTTLEQLE SNPTGVVLVS GEPGSGKSTQ IPQWCAEFAL   120
ARGFQKGQVT VTQPYPLAAR SLALRVADEM DLTLGHEVGY SIPQEDCTGP NTLLRFCWDR   180
LLLQEVASTR GTGAWGVLVL DEAQERSVAS DSLQGLIQDA RLEKLPGDLR VVVTDPALE    240
PKLRAFWGNP PIVHIPREPG ERPSPIYWDT IPPDRVEAAC QAVLELCRKE LPGDVLVFLP   300
SEEEISLCCE SLSREVESLL LQGLPPRVLP LHPDCGRAVQ AVYEDMDARK VVVTHWLADF   360
SFSLPSIQHV IDSGLELRSV YNPRIRAEFQ VLRPISKCQA EARRLRARGF PPVVFFPRSF   420
SPQDPASACI LSPS                                                    434

>184P3G10 v.5B (SEQ ID NO:156).
MQALEDLDYL AALDDDGDLS DLGVILSEFP LAPELAKALL ASCEFDCVDE MLTLAAMLTA    60
APGFTRPPLS AEEAALRRAL EHTDGDHSSL IQVYEAFIQS GADEAWCQAR GLNWAALCQA   120
HKLRGELLEL MQRIELPLSL PAFGSEQNRR DLQKALVSGY FLKVARDTDG TGNYLLLTHK   180
HVAQLSSYCC YRSRRAPARP PPWVLYHNFT ISKDNCLSIV SEIQPQMLVE LAPPYFLSNL   240
PPSESRDLLN QLREGMADST AGSKSSSAQE FRDPCVLQ                          278

Figure 13m  Alignment of nucleotide sequences of 184P3G10 transcript variants
(SEQ ID NOS:45, 147, 148, 149, 150)

```
184P3G10v.1  CTGATGGCGATGAATGAACACTGCCGTTTCTCTGGAAGATGGTCGGTCACCAAATATGA   60
184P3G10v.2  ----------------------GACTACGTGGGTCTGGAGCTGACTGCCGT---CCTGACACGT   39
184P3G10v.3  CTGATGGCGATGAATGAATGAACACTGCCGTTTGCTCTGGAAGATGGTCGGTCACCAAATATGA   60
184P3G10v.4  CTGATGGCGATGAATGAATGAACACTGCCGTTTGCTCTGGAAGATGGTCGGTCACCAAATATGA   60
184P3G10v.5  CTGATGGCGATGAATGAATGAACACTGCCGTTTGCTCTGGAAGATGGTCGGTCACCAAATATGA   60
                                   ***   ***  *    **  ** ** **  *

184P3G10v.1  CCTTACTGGCTGCTCTGCCTTCTGCCAGGTCCTGCCAGAGAGCCACCATGACCTCTCAGCC   120
184P3G10v.2  CCTAG--AGCTGCAA------GCAGGTCCTGCCAGAGAGCCACCATGACCTCTCAGCC    89
184P3G10v.3  CCTTACTGGCTGCTCTGCCTTCTGCCAGGTCCTGCCAGAGAGCCACCATGACCTCTCAGCC   120
184P3G10v.4  CCTTACTGGCTGCTCTGCCTTCTGCCAGGTCCTGCCAGAGAGCCACCATGACCTCTCAGCC   120
184P3G10v.5  CCTTACTGGCTGCTCTGCCTTCTGCCAGGTCCTGCCAGAGAGCCACCATGACCTCTCAGCC   120
             ***         *****                ******* ******************

184P3G10v.1  TCTCAGGCTAGCAGAAGAGAGTATGGCCCAAGTCCTGGGAGTTCTGAACTGGCTGTGAACCC   180
184P3G10v.2  TCTCAGGCTAGCAGAAGAGAGTATGGCCCAAGTCCTGGGAGTTCTGAACTGGCTGTGAACCC   149
184P3G10v.3  TCTCAGGCTAGCAGAAGAGAGTATGGCCCAAGTCCTGGGAGTTCTGAACTGGCTGTGAACCC   180
184P3G10v.4  TCTCAGGCTAGCAGAAGAGAGTATGGCCCAAGTCCTGGGAGTTCTGAACTGGCTGTGAACCC   180
184P3G10v.5  TCTCAGGCTAGCAGAAGAGAGTATGGCCCAAGTCCTGGGAGTTCTGAACTGGCTGTGAACCC   180
```

Figure 13m (continued)

```
                 ************************************************************
184P3G10v.1      CTTTGATGGGCTTCCCTTCTCTTCCCGCTACTATGAGCTGCTGAAGCAGCGCCAAGCCTT   240
184P3G10v.2      CTTTGATGGGCTTCCCTTCTCTTCCCGCTACTATGAGCTGCTGAAGCAGCGCCAAGCCTT   209
184P3G10v.3      CTTTGATGGGCTTCCCTTCTCTTCCCGCTACTATGAGCTGCTGAAGCAGCGCCAAGCCTT   240
184P3G10v.4      CTTTGATGGGCTTCCCTTCTCTTCCCGCTACTATGAGCTGCTGAAGCAGCGCCAAGCCTT   240
184P3G10v.5      CTTTGATGGGCTTCCCTTCTCTTCCCGCTACTATGAGCTGCTGAAGCAGCGCCAAGCCTT   240
                 ************************************************************

184P3G10v.1      GCCCATCTGGGCTGCTCGCTTTACCTTCTTGGAGCAGTTGGAGAGTAACCCCACTGGAGT   300
184P3G10v.2      GCCCATCTGGGCTGCTCGCTTTACCTTCTTGGAGCAGTTGGAGAGTAACCCCACTGGAGT   269
184P3G10v.3      GCCCATCTGGGCTGCTCGCTTTACCTTCTTGGAGCAGTTGGAGAGTAACCCCACTGGAGT   300
184P3G10v.4      GCCCATCTGGGCTGCTCGCTTTACCTTCTTGGAGCAGTTGGAGAGTAACCCCACTGGAGT   300
184P3G10v.5      GCCCATCTGGGCTGCTCGCTTTACCTTCTTGGAGCAGTTGGAGAGTAACCCCACTGGAGT   300
                 ************************************************************

184P3G10v.1      GGTGCTGGTGTCTGGGAGCCTGGTTCTGCAAGACCACCCAGATCCCTCAGTGGTGTGC   360
184P3G10v.2      GGTGCTGGTGTCTGGGAGCCTGGTTCTGCAAGACCACCCAGATCCCTCAGTGGTGTGC   329
184P3G10v.3      GGTGCTGGTGTCTGGGAGCCTGGTTCTGCAAGACCACCCAGATCCCTCAGTGGTGTGC   360
184P3G10v.4      GGTGCTGGTGTCTGGGAGCCTGGTTCTGCAAGACCACCCAGATCCCTCAGTGGTGTGC   360
184P3G10v.5      GGTGCTGGTGTCTGGGAGCCTGGTTCTGCAAGACCACCCAGATCCCTCAGTGGTGTGC   360
                 ************************************************************

184P3G10v.1      AGAGTTTGCGCTGGCCAGAGGGTTCCAGAAAGGACAGGTTACTGTTACTCAGCCCTACCC   420
184P3G10v.2      AGAGTTTGCGCTGGCCAGAGGGTTCCAGAAAGGACAGGTTACTGTTACTCAGCCCTACCC   389
184P3G10v.3      AGAGTTTGCGCTGGCCAGAGGGTTCCAGAAAGGACAGGTTACTGTTACTCAGCCCTACCC   420
184P3G10v.4      AGAGTTTGCGCTGGCCAGAGGGTTCCAGAAAGGACAGGTTACTGTTACTCAGCCCTACCC   420
184P3G10v.5      AGAGTTTGCGCTGGCCAGAGGGTTCCAGAAAGGACAGGTTACTGTTACTCAGCCCTACCC   420
                 ************************************************************

184P3G10v.1      TCTTGCAGCCCGGAGCCCGGAGCCTGGCTCTGCGGGTTGCTGATGAGATGGACCCTGGGTCA   480
184P3G10v.2      TCTTGCAGCCCGGAGCCCGGAGCCTGGCTCTGCGGGTTGCTGATGAGATGGACCCTGGGTCA   449
184P3G10v.3      TCTTGCAGCCCGGAGCCCGGAGCCTGGCTCTGCGGGTTGCTGATGAGATGGACCCTGGGTCA   480
184P3G10v.4      TCTTGCAGCCCGGAGCCCGGAGCCTGGCTCTGCGGGTTGCTGATGAGATGGACCCTGGGTCA   480
184P3G10v.5      TCTTGCAGCCCGGAGCCCGGAGCCTGGCTCTGCGGGTTGCTGATGAGATGGACCCTGGGTCA   480
                 ************************************************************

184P3G10v.1      TGAGGTTGGATACAGCATCCCCAGGAGGACTGCACGGGCCCAACACCCTGCTCTCAGTT   540
184P3G10v.2      TGAGGTTGGATACAGCATCCCCCAGGAGGACTGCACGGGCCCAACACCCTGCTCTCAGTT   509
                 ************************************************************
```

Figure 13m (continued)

```
184P3G10v.3    TGAGGTTGGATACAGCCATCCCCCAGGAGGACTGCACGGGGCCCAACACCCTGCTCAGGTT   540
184P3G10v.4    TGAGGTTGGATACAGCCATCCCCCAGGAGGACTGCACGGGGCCCAACACCCTGCTCAGGTT   540
184P3G10v.5    TGAGGTTGGATACAGCCATCCCCCAGGAGGACTGCACGGGGCCCAACACCCTGCTCAGGTT   540
               ************************************************************

184P3G10v.1    CTGCTGGGACAGGCTGCTTCTGCAGGAGGTGGCCTCGACCCGAGGCACTGGAGCCTGGGG   600
184P3G10v.2    CTGCTGGGACAGGCTGCTTCTGCAGGAGGTGGCCTCGACCCGAGGCACTGGAGCCTGGGG   569
184P3G10v.3    CTGCTGGGACAGGCTGCTTCTGCAGGAGGTGGCCTCGACCCGAGGCACTGGAGCCTGGGG   600
184P3G10v.4    CTGCTGGGACAGGCTGCTTCTGCAGGAGGTGGCCTCGACCCGAGGCACTGGAGCCTGGGG   600
184P3G10v.5    CTGCTGGGACAGGCTGCTTCTGCAGGAGGTGGCCTCGACCCGAGGCACTGGAGCCTGGGG   600
               ************************************************************

184P3G10v.1    CGTGCTGGTACTAGATGAGGCTCAGGAGCCGGTCGGTGGCATCAGATTCACTCCAGGGGCT   660
184P3G10v.2    CGTGCTGGTACTAGATGAGGCTCAGGAGCCGGTCGGTGGCATCAGATTCACTCCAGGGGCT   629
184P3G10v.3    CGTGCTGGTACTAGATGAGGCTCAGGAGCCGGTCGGTGGCATCAGATTCACTCCAGGGGCT   660
184P3G10v.4    CGTGCTGGTACTAGATGAGGCTCAGGAGCCGGTCGGTGGCATCAGATTCACTCCAGGGGCT   660
184P3G10v.5    CGTGCTGGTACTAGATGAGGCTCAGGAGCCGGTCGGTGGCATCAGATTCACTCCAGGGGCT   660
               ************************************************************

184P3G10v.1    ACTGCAAGATGCCAGGCTGGAAAAACTTCCGGGGAGACCTCAGAGTGGTTGTGGTTACTGA   720
184P3G10v.2    ACTGCAAGATGCCAGGCTGGAAAAACTTCCGGGGAGACCTCAGAGTGGTTGTGGTTACTGA   689
184P3G10v.3    ACTGCAAGATGCCAGGCTGGAAAAACTTCCGGGGAGACCTCAGAGTGGTTGTGGTTACTGA   720
184P3G10v.4    ACTGCAAGATGCCAGGCTGGAAAAACTTCCGGGGAGACCTCAGAGTGGTTGTGGTTACTGA   720
184P3G10v.5    ACTGCAAGATGCCAGGCTGGAAAAACTTCCGGGGAGACCTCAGAGTGGTTGTGGTTACTGA   720
               ************************************************************

184P3G10v.1    CCCAGCCCTTGAACCTAAGCTCCGAGCTTTCTGGGGCAATCCTCCTATTGTGCATATACC   780
184P3G10v.2    CCCAGCCCTTGAACCTAAGCTCCGAGCTTTCTGGGGCAATCCTCCTATTGTGCATATACC   749
184P3G10v.3    CCCAGCCCTTGAACCTAAGCTCCGAGCTTTCTGGGGCAATCCTCCTATTGTGCATATACC   780
184P3G10v.4    CCCAGCCCTTGAACCTAAGCTCCGAGCTTTCTGGGGCAATCCTCCTATTGTGCATATACC   780
184P3G10v.5    CCCAGCCCTTGAACCTAAGCTCCGAGCTTTCTGGGGCAATCCTCCTATTGTGCATATACC   780
               ************************************************************

184P3G10v.1    CAGAGAGCCTGGTGAGAGACCTTCCCCCATCTACTGGACACCATCCCACCTGATCGGGT   840
184P3G10v.2    CAGAGAGCCTGGTGAGAGACCTTCCCCCATCTACTGGACACCATCCCACCTGATCGGGT   809
184P3G10v.3    CAGAGAGCCTGGTGAGAGACCTTCCCCCATCTACTGGACACCATCCCACCTGATCGGGT   840
184P3G10v.4    CAGAGAGCCTGGTGAGAGACCTTCCCCCATCTACTGGACACCATCCCACCTGATCGGGT   840
184P3G10v.5    CAGAGAGCCTGGTGAGAGACCTTCCCCCATCTACTGGACACCATCCCACCTGATCGGGT   840
               ************************************************************
```

Figure 13m (continued)

```
184P3G10v.1    GGAAGCTGCCTGCCAAGCAGTGCTTGAATTGTGTCGGAAGGAGCTTCCAGGAGATGTGCT    900
184P3G10v.2    GGAAGCTGCCTGCCAAGCAGTGCTTGAATTGTGTCGGAAGGAGCTTCCAGGAGATGTGCT    869
184P3G10v.3    GGAAGCTGCCTGCCAAGCAGTGCTTGAATTGTGTCGGAAGGAGCTTCCAGGAGATGTGCT    900
184P3G10v.4    GGAAGCTGCCTGCCAAGCAGTGCTTGAATTGTGTCGGAAGGAGCTTCCAGGAGATGTGCT    900
184P3G10v.5    GGAAGCTGCCTGCCAAGCAGTGCTTGAATTGTGTCGGAAGGAGCTTCCAGGAGATGTGCT    900
               ************************************************************

184P3G10v.1    AGTGTTCCTGCCCAGTGAGGAGG-------------------------------------    923
184P3G10v.2    AGTGTTCCTGCCCAGTGAGGAGG-------------------------------------    892
184P3G10v.3    AGTGTTCCTGCCCAGTGAGGAGGTAAAAAAACAAAACAAAAAAAAACAGCCTGCAA       960
184P3G10v.4    AGTGTTCCTGCCCAGTGAGGAGG-------------------------------------    923
184P3G10v.5    AGTGTTCCTGCCCAGTGAGGAGG-------------------------------------    923
               ***********************

184P3G10v.1    ------------AAATTTCCCTGTGCTGTGAATCCTTGTCCAGGGAGGTAGA           963
184P3G10v.2    ------------AAATTTCCCTGTGCTGTGAATCCTTGTCCAGGGAGGTAGA           932
184P3G10v.3    AATGAGCCTGCAAAAGGAGAAATTTCCCTGTGCTGTGAATCCTTGTCCAGGGAGGTAGA    1020
184P3G10v.4    ------------AAATTTCCCTGTGCTGTGAATCCTTGTCCAGGGAGGTAGA           963
184P3G10v.5    ------------AAATTTCCCTGTGCTGTGAATCCTTGTCCAGGGAGGTAGA           963
                           *****************************************

184P3G10v.1    GTCCTTGCTTCTCCAAGGGCTTCCACCACGAGTACTGCCCCTTCACCCAGACTGTGGACG    1023
184P3G10v.2    GTCCTTGCTTCTCCAAGGGCTTCCACCACGAGTACTGCCCCTTCACCCAGACTGTGGACG     992
184P3G10v.3    GTCCTTGCTTCTCCAAGGGCTTCCACCACGAGTACTGCCCCTTCACCCAGACTGTGGACG    1080
184P3G10v.4    GTCCTTGCTTCTCCAAGGGCTTCCACCACGAGTACTGCCCCTTCACCCAGACTGTGGACG    1023
184P3G10v.5    GTCCTTGCTTCTCCAAGGGCTTCCACCACGAGTACTGCCCCTTCACCCAGACTGTGGACG    1023
               ************************************************************

184P3G10v.1    AGCCGTTCAGGCTGTGTATGAGGAGGACATGGATGCCCGAAAGGTTGTGGTCACTCACTGGCT    1083
184P3G10v.2    AGCCGTTCAGGCTGTGTATGAGGAGGACATGGATGCCCGAAAGGTTGTGGTCACTCACTGGCT    1052
184P3G10v.3    AGCCGTTCAGGCTGTGTATGAGGAGGACATGGATGCCCGAAAGGTTGTGGTCACTCACTGGCT    1140
184P3G10v.4    AGCCGTTCAGGCTGTGTATGAGGAGGACATGGATGCCCGAAAGGTTGTGGTCACTCACTGGCT    1083
184P3G10v.5    AGCCGTTCAGGCTGTGTATGAGGAGGACATGGATGCCCGAAAGGTTGTGGTCACTCACTGGCT    1083
               ************************************************************

184P3G10v.1    GGCTGACTTCTCCTTCTCCTCCCCTCCCCCTTCCATCCAACATGTCATCGACTCAGGACTGGAGCT    1143
184P3G10v.2    GGCTGACTTCTCCTTCTCCTCCCCTCCCCCTTCCATCCAACATGTCATCGACTCAGGACTGGAGCT    1112
184P3G10v.3    GGCTGACTTCTCCTTCTCCTCCCCTCCCCCTTCCATCCAACATGTCATCGACTCAGGACTGGAGCT    1200
184P3G10v.4    GGCTGACTTCTCCTTCTCCTCCCCTCCCCCTTCCATCCAACATGTCATCGACTCAGGACTGGAGCT    1143
               ************************************************************
```

Figure 13m (continued)

```
184P3G10v.5   GGCTGACTTCTCCTTCTCCCTCCCTTCCATCCAACATGTCATCGACTCAGGACTGGAGCT 1143
              ************************************************************

184P3G10v.1   CCGAAGTGT--------------------------------------------------- 1152
184P3G10v.2   CCGAAGTGT--------------------------------------------------- 1121
184P3G10v.3   CCGAAGTGT--------------------------------------------------- 1209
184P3G10v.4   CCGAAGTGTGAGTGAGAGAGAGAGAGATAGCGGTGGGGTAGTAAAGACAGAAATGGCCCACT 1203
184P3G10v.5   CCGAAGTGT--------------------------------------------------- 1152
              *********

184P3G10v.1   ------------------------------------------TTACAATCCTAGGATCCGAG 1172
184P3G10v.2   ------------------------------------------TTACAATCCTAGGATCCGAG 1141
184P3G10v.3   ------------------------------------------TTACAATCCTAGGATCCGAG 1229
184P3G10v.4   CTGATCTGTCTTGGCCTTGGTTGGGGACGGGCAACAGGTTTACAATCCTAGGATCCGAG 1263
184P3G10v.5   ------------------------------------------TTACAATCCTAGGATCCGAG 1172
                                                         *******************

184P3G10v.1   CAGAATTCCAAGTGTTGAGGCCAATCAGCCAATCAGCAAGTGTCAGGCAGAGGCAAGACGATTGCGAG 1232
184P3G10v.2   CAGAATTCCAAGTGTTGAGGCCAATCAGCCAATCAGCAAGTGTCAGGCAGAGACAAGACGATTGCGAG 1201
184P3G10v.3   CAGAATTCCAAGTGTTGAGGCCAATCAGCCAATCAGCAAGTGTCAGGCAGACGCAAGACGATTGCGAG 1289
184P3G10v.4   CAGAATTCCAAGTGTTGAGGCCAATCAGCCAATCAGCAAGTGTCAGGCAGAGGCAAGACGATTGCGAG 1323
184P3G10v.5   CAGAATTCCAAGTGTTGAGGCCAATCAGCCAATCAGCAAGTGTCAGGCAGAGGCAAGACGATTGCGAG 1232
              ****************************************************************

184P3G10v.1   CAAGAGGGTTCCCACCAG----------------------GATCCTGCCT 1260
184P3G10v.2   CAAGAGGGTTCCCACCAG----------------------GATCCTGCCT 1229
184P3G10v.3   CAAGAGGGTTCCCACCAG----------------------GATCCTGCCT 1317
184P3G10v.4   CAAGAGGGTTCCCACCAG----------------------GATCCTGCCT 1351
184P3G10v.5   CAAGAGGGTTCCCACCAGTGGTCTTCTTTTTCCCCTCAGGATCCTGCCT 1292
              ******************                      **********

184P3G10v.1   CTGCCTGTATCCTAAGTCCTTCTTAGAACTAGAAGCTCCACCATTGCCACAACCAGGGT 1320
184P3G10v.2   CTGCCTGTATCCTAAGTCCTTCTTAGAACTAGAAGCTCCACCATTGCCACAACCAGGGT 1289
184P3G10v.3   CTGCCTGTATCCTAAGTCCTTCTTAGAACTAGAAGCTCCACCATTGCCACAACCAGGGT 1377
184P3G10v.4   CTGCCTGTATCCTAAGTCCTTCTTAGAACTAGAAGCTCCACCATTGCCACAACCAGGGT 1411
184P3G10v.5   CTGCCTGTATCCTAAGTCCTTCTTAGAACTAGAAGCTCCACCATTGCCACAACCAGGGT 1352
              **********************************************************

184P3G10v.1   GTGTGAGGAGAATCTGAGCTCCCTGGTGTTACTACTAAAAGGAGACAGATTGCAGAGCC 1380
```

Figure 13m (continued)

```
184P3G10v.2   GTGTGAGGAGAATCTGAGCTCCCTGGTGTTACTACTAAAAAGGAGACAGATTGCAGAGCC  1349
184P3G10v.3   GTGTGAGGAGAATCTGAGCTCCCTGGTGTTACTACTAAAAAGGAGACAGATTGCAGAGCC  1437
184P3G10v.4   GTGTGAGGAGAATCTGAGCTCCCTGGTGTTACTACTAAAAAGGAGACAGATTGCAGAGCC  1471
184P3G10v.5   GTGTGAGGAGAATCTGAGCTCCCTGGTGTTACTACTAAAAAGGAGACAGATTGCAGAGCC  1412
              ********************************************************

184P3G10v.1   AGGGGAGTGTCACTTCCTGGACCAGCCTGCTCCAGAAGCACTGATGCAAGCCCTGGAAGA  1440
184P3G10v.2   AGGGGAGTGTCACTTCCTGGACCAGCCTGCTCCAGAAGCACTGATGCAAGCCCTGGAAGA  1409
184P3G10v.3   AGGGGAGTGTCACTTCCTGGACCAGCCTGCTCCAGAAGCACTGATGCAAGCCCTGGAAGA  1497
184P3G10v.4   AGGGGAGTGTCACTTCCTGGACCAGCCTGCTCCAGAAGCACTGATGCAAGCCCTGGAAGA  1531
184P3G10v.5   AGGGGAGTGTCACTTCCTGGACCAGCCTGCTCCAGAAGCACTGATGCAAGCCCTGGAAGA  1472
              ********************************************************

184P3G10v.1   TTTAGACTATCTGGCAGCCCTGGATGATGATGATGGGACCCTGTCAGATCTGGGTGTCATACT  1500
184P3G10v.2   TTTAGACTATCTGGCAGCCCTGGATGATGATGATGGGACCCTGTCAGATCTGGGTGTCATACT  1469
184P3G10v.3   TTTAGACTATCTGGCAGCCCTGGATGATGATGATGGGACCCTGTCAGATCTGGGTGTCATACT  1557
184P3G10v.4   TTTAGACTATCTGGCAGCCCTGGATGATGATGATGGGACCCTGTCAGATCTGGGTGTCATACT  1591
184P3G10v.5   TTTAGACTATCTGGCAGCCCTGGATGATGATGATGGGACCCTGTCAGATCTGGGTGTCATACT  1532
              ********************************************************

184P3G10v.1   ATCAGAATTCCCTCTGGCCTCTGAGCTGGCAGCTGGCCAAAGCCCTGCTGGCCTCATGCGAGTTTGA  1560
184P3G10v.2   ATCAGAATTCCCTCTGGCCTCTGAGCTGGCAGCTGGCCAAAGCCCTGCTGGCCTCATGCGAGTTTGA  1529
184P3G10v.3   ATCAGAATTCCCTCTGGCCTCTGAGCTGGCAGCTGGCCAAAGCCCTGCTGGCCTCATGCGAGTTTGA  1617
184P3G10v.4   ATCAGAATTCCCTCTGGCCTCTGAGCTGGCAGCTGGCCAAAGCCCTGCTGGCCTCATGCGAGTTTGA  1651
184P3G10v.5   ATCAGAATTCCCTCTGGCCTCTGAGCTGGCAGCTGGCCAAAGCCCTGCTGGCCTCATGCGAGTTTGA  1592
              ********************************************************

184P3G10v.1   CTGTGTGGACGAGAGATGCTCACCCTGGCCATGCTGCCATGCTGCCATGCTCACAGCTCACACCCTGGGTTTACCCG  1620
184P3G10v.2   CTGTGTGGACGAGAGATGCTCACCCTGGCCATGCTGCCATGCTGCCATGCTCACAGCTCACACCCTGGGTTTACCCG  1589
184P3G10v.3   CTGTGTGGACGAGAGATGCTCACCCTGGCCATGCTGCCATGCTGCCATGCTCACAGCTCACACCCTGGGTTTACCCG  1677
184P3G10v.4   CTGTGTGGACGAGAGATGCTCACCCTGGCCATGCTGCCATGCTGCCATGCTCACAGCTCACACCCTGGGTTTACCCG  1711
184P3G10v.5   CTGTGTGGACGAGAGATGCTCACCCTGGCCATGCTGCCATGCTGCCATGCTCACAGCTCACACCCTGGGTTTACCCG  1652
              ********************************************************

184P3G10v.1   TCCTTCCACTCAGTGCAGAAGAAGCTGCCCTGCCGTCGGGCCCTGAACACACGGATGGTGA  1680
184P3G10v.2   TCCTTCCACTCAGTGCAGAAGAAGCTGCCCTGCCGTCGGGCCCTGAACACACGGATGGTGA  1649
184P3G10v.3   TCCTTCCACTCAGTGCAGAAGAAGCTGCCCTGCCGTCGGGCCCTGAACACACGGATGGTGA  1737
184P3G10v.4   TCCTTCCACTCAGTGCAGAAGAAGCTGCCCTGCCGTCGGGCCCTGAACACACGGATGGTGA  1771
184P3G10v.5   TCCTTCCACTCAGTGCAGAAGAAGCTGCCCTGCCGTCGGGCCCTGAACACACGGATGGTGA  1712
              ********************************************************
```

Figure 13m (continued)

```
                   ****************************************************************
184P3G10v.1        CCACAGTTCTCTGATCCAGTGTATGAAGCCTTTATACAAAGTGGAGCAGATGAGGCTTG   1740
184P3G10v.2        CCACAGTTCTCTGATCCAGTGTATGAAGCCTTTATACAAAGTGGAGCAGATGAGGCTTG   1709
184P3G10v.3        CCACAGTTCTCTGATCCAGTGTATGAAGCCTTTATACAAAGTGGAGCAGATGAGGCTTG   1797
184P3G10v.4        CCACAGTTCTCTGATCCAGTGTATGAAGCCTTTATACAAAGTGGAGCAGATGAGGCTTG   1831
184P3G10v.5        CCACAGTTCTCTGATCCAGTGTATGAAGCCTTTATACAAAGTGGAGCAGATGAGGCTTG   1772
                   ****************************************************************

184P3G10v.1        GTGCCAGGCTCGAGGTCTGAATTGGGCAGCATTGTGCCAAGCCCATAAAACTTCGGGGAGA   1800
184P3G10v.2        GTGCCAGGCTCGAGGTCTGAATTGGGCAGCATTGTGCCAAGCCCATAAAACTTCGGGGAGA   1769
184P3G10v.3        GTGCCAGGCTCGAGGTCTGAATTGGGCAGCATTGTGCCAAGCCCATAAAACTTCGGGGAGA   1857
184P3G10v.4        GTGCCAGGCTCGAGGTCTGAATTGGGCAGCATTGTGCCAAGCCCATAAAACTTCGGGGAGA   1891
184P3G10v.5        GTGCCAGGCTCGAGGTCTGAATTGGGCAGCATTGTGCCAAGCCCATAAAACTTCGGGGAGA   1832
                   ****************************************************************

184P3G10v.1        ACTCCTAGAACTCATGCAACGAATTGAACTTCCCTTGTCCCTACCAGCCTTTGGCTCTGA   1860
184P3G10v.2        ACTCCTAGAACTCATGCAACGAATTGAACTTCCCTTGTCCCTACCAGCCTTTGGCTCTGA   1829
184P3G10v.3        ACTCCTAGAACTCATGCAACGAATTGAACTTCCCTTGTCCCTACCAGCCTTTGGCTCTGA   1917
184P3G10v.4        ACTCCTAGAACTCATGCAACGAATTGAACTTCCCTTGTCCCTACCAGCCTTTGGCTCTGA   1951
184P3G10v.5        ACTCCTAGAACTCATGCAACGAATTGAACTTCCCTTGTCCCTACCAGCCTTTGGCTCTGA   1892
                   ****************************************************************

184P3G10v.1        GCAGAATCGCAGAGACCTTCAGAAAGCACTGGTGTCAGGATACTTTCTCAAGGTGGCCAG   1920
184P3G10v.2        GCAGAATCGCAGAGACCTTCAGAAAGCACTGGTGTCAGGATACTTTCTCAAGGTGGCCAG   1889
184P3G10v.3        GCAGAATCGCAGAGACCTTCAGAAAGCACTGGTGTCAGGATACTTTCTCAAGGTGGCCAG   1977
184P3G10v.4        GCAGAATCGCAGAGACCTTCAGAAAGCACTGGTGTCAGGATACTTTCTCAAGGTGGCCAG   2011
184P3G10v.5        GCAGAATCGCAGAGACCTTCAGAAAGCACTGGTGTCAGGATACTTTCTCAAGGTGGCCAG   1952
                   ****************************************************************

184P3G10v.1        AGACACAGACGGACTGGAAATTACCTTCTCCTAACCCATAAGCATGTGGCCCAGCTCTC   1980
184P3G10v.2        AGACACAGACGGACTGGAAATTACCTTCTCCTAACCCATAAGCATGTGGCCCAGCTCTC   1949
184P3G10v.3        AGACACAGACGGACTGGAAATTACCTTCTCCTAACCCATAAGCATGTGGCCCAGCTCTC   2037
184P3G10v.4        AGACACAGACGGACTGGAAATTACCTTCTCCTAACCCATAAGCATGTGGCCCAGCTCTC   2071
184P3G10v.5        AGACACAGACGGACTGGAAATTACCTTCTCCTAACCCATAAGCATGTGGCCCAGCTCTC   2012
                   ****************************************************************

184P3G10v.1        CTCATACTGCTGCTACCGAAGCCGCAGAGCTCCTGCCAGACCCCACCATGGTGGTGCTCTA   2040
184P3G10v.2        CTCATACTGCTGCTACCGAAGCCGCAGAGCTCCTGCCAGACCCCACCATGGTGGTGCTCTA   2009
```

Figure 13m (continued)

```
184P3G10v.3   CTCATACTGCTGCTACCGAAGCCGCAGAGCTCCTGCCAGACCCCACCATGGGTGCTCTA 2097
184P3G10v.4   CTCATACTGCTGCTACCGAAGCCGCAGAGCTCCTGCCAGACCCCACCATGGGTGCTCTA 2131
184P3G10v.5   CTCATACTGCTGCTACCGAAGCCGCAGAGCTCCTGCCAGACCCCACCATGGGTGCTCTA 2072
              ********************************************************

184P3G10v.1   CCACAATTTCACCATATCCAAAGACAACTGCCTTTCCATTGTTTCTGAGATTCAACCACA 2100
184P3G10v.2   CCACAATTTCACCATATCCAAAGACAACTGCCTTTCCATTGTTTCTGAGATTCAACCACA 2069
184P3G10v.3   CCACAATTTCACCATATCCAAAGACAACTGCCTTTCCATTGTTTCTGAGATTCAACCACA 2157
184P3G10v.4   CCACAATTTCACCATATCCAAAGACAACTGCCTTTCCATTGTTTCTGAGATTCAACCACA 2191
184P3G10v.5   CCACAATTTCACCATATCCAAAGACAACTGCCTTTCCATTGTTTCTGAGATTCAACCACA 2132
              ************************************************************

184P3G10v.1   GATGCTGGTGGAATTGGCCCCTCCATACTTCCTGAGTAACTTGCCTCCCAGTGAGAGCAG 2160
184P3G10v.2   GATGCTGGTGGAATTGGCCCCTCCATACTTCCTGAGTAACTTGCCTCCCAGTGAGAGCAG 2129
184P3G10v.3   GATGCTGGTGGAATTGGCCCCTCCATACTTCCTGAGTAACTTGCCTCCCAGTGAGAGCAG 2217
184P3G10v.4   GATGCTGGTGGAATTGGCCCCTCCATACTTCCTGAGTAACTTGCCTCCCAGTGAGAGCAG 2251
184P3G10v.5   GATGCTGGTGGAATTGGCCCCTCCATACTTCCTGAGTAACTTGCCTCCCAGTGAGAGCAG 2192
              ************************************************************

184P3G10v.1   AGACCTTCTGAACCAGCTAAGGGAAGGAATGGCAGATTCTACACAGCAGGGAGCAAATCATC 2220
184P3G10v.2   AGACCTTCTGAACCAGCTAAGGGAAGGAATGGCAGATTCTACACAGCAGGGAGCAAATCATC 2189
184P3G10v.3   AGACCTTCTGAACCAGCTAAGGGAAGGAATGGCAGATTCTACACAGCAGGGAGCAAATCATC 2277
184P3G10v.4   AGACCTTCTGAACCAGCTAAGGGAAGGAATGGCAGATTCTACACAGCAGGGAGCAAATCATC 2311
184P3G10v.5   AGACCTTCTGAACCAGCTAAGGGAAGGAATGGCAGATTCTACACAGCAGGGAGCAAATCATC 2252
              ************************************************************

184P3G10v.1   CTCAGCCCAGGAGTTCAGAGATCCCTGTCCTGTCCTGTCCTGTCCTGCCAGTGACCTGCCTATGGAATGG 2280
184P3G10v.2   CTCAGCCCAGGAGTTCAGAGATCCCTGTCCTGTCCTGTCCTGTCCTGCCAGTGACCTGCCTATGGAATGG 2249
184P3G10v.3   CTCAGCCCAGGAGTTCAGAGATCCCTGTCCTGTCCTGTCCTGTCCTGCCAGTGACCTGCCTATGGAATGG 2337
184P3G10v.4   CTCAGCCCAGGAGTTCAGAGATCCCTGTCCTGTCCTGTCCTGTCCTGCCAGTGACCTGCCTATGGAATGG 2371
184P3G10v.5   CTCAGCCCAGGAGTTCAGAGATCCCTGTCCTGTCCTGTCCTGTCCTGCCAGTGACCTGCCTATGGAATGG 2312
              ************************************************************

184P3G10v.1   AGCTGGGTTCATCTCATCACATTAGATTATCCCTCAGGGTGACACCAAAGCACCCAGACA 2340
184P3G10v.2   AGCTGGGTTCATCTCATCACATTAGATTATCCCTCAGGGTGACACCAAAGCACCCAGACA 2309
184P3G10v.3   AGCTGGGTTCATCTCATCACATTAGATTATCCCTCAGGGTGACACCAAAGCACCCAGACA 2397
184P3G10v.4   AGCTGGGTTCATCTCATCACATTAGATTATCCCTCAGGGTGACACCAAAGCACCCAGACA 2431
184P3G10v.5   AGCTGGGTTCATCTCATCACATTAGATTATCCCTCAGGGTGACACCAAAGCACCCAGACA 2372
              ************************************************************
```

Figure 13m (continued)

```
184P3G10v.1    GATTTAGAAGCCCAAAGTTTAGGGTCAAATGTAAACCCTGAGTCCCAAGAAAT 2400
184P3G10v.2    GATTTAGAAGCCCAAAGTTTAGGGTCAAATGTAAACCCTGAGTCCCAAGAAAT 2369
184P3G10v.3    GATTTAGAAGCCCAAAGTTTAGGGTCAAATGTAAACCCTGAGTCCCAAGAAAT 2457
184P3G10v.4    GATTTAGAAGCCCAAAGTTTAGGGTCAAATGTAAACCCTGAGTCCCAAGAAAT 2491
184P3G10v.5    GATTTAGAAGCCCAAAGTTTAGGGTCAAATGTAAACCCTGAGTCCCAAGAAAT 2432
               *****************************************************

184P3G10v.1    GGTAGACTGGGAATGGAAAGAATGGGTAAACCACAGTCTACATAGGAAGGACTCTTTC 2460
184P3G10v.2    GGTAGACTGGGAATGGAAAGAATGGGTAAACCACAGTCTACATAGGAAGGACTCTTTC 2429
184P3G10v.3    GGTAGACTGGGAATGGAAAGAATGGGTAAACCACAGTCTACATAGGAAGGACTCTTTC 2517
184P3G10v.4    GGTAGACTGGGAATGGAAAGAATGGGTAAACCACAGTCTACATAGGAAGGACTCTTTC 2551
184P3G10v.5    GGTAGACTGGGAATGGAAAGAATGGGTAAACCACAGTCTACATAGGAAGGACTCTTTC 2492
               *********************************************************

184P3G10v.1    CTTAGCCTTCTCTTATTGATTGGAGAGGGACTGACATGCTCCTCATTCTCTCTTAACTTTGC 2520
184P3G10v.2    CTTAGCCTTCTCTTATTGATTGGAGAGGGACTGACATGCTCCTCATTCTCTCTTAACTTTGC 2489
184P3G10v.3    CTTAGCCTTCTCTTATTGATTGGAGAGGGACTGACATGCTCCTCATTCTCTCTTAACTTTGC 2577
184P3G10v.4    CTTAGCCTTCTCTTATTGATTGGAGAGGGACTGACATGCTCCTCATTCTCTCTTAACTTTGC 2611
184P3G10v.5    CTTAGCCTTCTCTTATTGATTGGAGAGGGACTGACATGCTCCTCATTCTCTCTTAACTTTGC 2552
               ************************************************************

184P3G10v.1    CAAACCCATTCTTGTACTCCCTTGTGATCTATAAAAGATTTTCTATGATGATGCCAA 2575
184P3G10v.2    CAAACCCATTCTTGTACTCCCTTGTGATCTATAAAAGATTTTCTATGATGATGCCAA 2544
184P3G10v.3    CAAACCCATTCTTGTACTCCCTTGTGATCTATAAAAGATTTTCTATGATGATGCCAA 2632
184P3G10v.4    CAAACCCATTCTTGTACTCCCTTGTGATCTATAAAAGATTTTCTATGATGATGCCAA 2666
184P3G10v.5    CAAACCCATTCTTGTACTCCCTTGTGATCTATAAAAGATTTTCTATGATGATGCCAA 2607
               *********************************************************
```

Figure 14m Alignment of protein sequences of 184P3G10 transcript variants
(SEQ ID NOS 46, 151, 152, 153, 154, 155, 156).

```
184P3G10v.1     -----MNTAFAGKMVSVTKYDLTGCSAFCRSCQRATMTSQPLR------------ 38
184P3G10v.2     ---------------------------------------MTSQPLR--------  7
184P3G10v.3     -----MNTAFAGKMVSVTKYDLTGCSAFCRSCQRATMTSQPLR------------ 38
184P3G10v.4A    -----MNTAFAGKMVSVTKYDLTGCSAFCRSCQRATMTSQPLR------------ 38
184P3G10v.4B    MAHSDLSWPWLGDGQQVYNPRIRAEFQVLRPISKCQAEARRLRARGFPPGSCLCLYPKSF 60
184P3G10v.5A    -----MNTAFAGKMVSVTKYDLTGCSAFCRSCQRATMTSQPLR------------ 38
184P3G10v.5B    ------------------------------------------------------
                                                   ***********
```

Figure 14m (continued)

```
184P3G10v.1    LAEEYGPSPGESELAVNPFDGLPFSSRYYELLKQRQALPIWAARFTFLEQLESNPTGVVL  98
184P3G10v.2    LAEEYGPSPGESELAVNPFDGLPFSSRYYELLKQRQALPIWAARFTFLEQLESNPTGVVL  67
184P3G10v.3    LAEEYGPSPGESELAVNPFDGLPFSSRYYELLKQRQALPIWAARFTFLEQLESNPTGVVL  98
184P3G10v.4A   LELEAPPLPQPRVCEENLSSLVLLLKRRQIAEPGECHFLDQPAPEALMQALEDIDYLAAL 120
184P3G10v.4B   LAEEYGPSPGESELAVNPFDGLPFSSRYYELLKQRQALPIWAARFTFLEQLESNPTGVVL  98
184P3G10v.5A   ------------------------------------------------MQALEDIDYLAAL  13
184P3G10v.5B
                                                                :: ** . ..*

184P3G10v.1    VSGEPGSGKSTQIPQWCAEFALARGFQKGQVTVTQPYPLAARSLALRVADEMDLTLGHEV 158
184P3G10v.2    VSGEPGSGKSTQIPQWCAEFALARGFQKGQVTVTQPYPLAARSLALRVADEMDLTLGHEV 127
184P3G10v.3    VSGEPGSGKSTQIPQWCAEFALARGFQKGQVTVTQPYPLAARSLALRVADEMDLTLGHEV 158
184P3G10v.4A   VSGEPGSGKSTQIPQWCAEFALARGFQKGQVTVTQPYPLAARSLALRVADEMDLTLGHEV 158
184P3G10v.4B   DDDGDLSDLGVILSEFPLAPELAKALLASCEFDCVDEMLTLAAMLTAAPGFTRPPLSAEE 180
184P3G10v.5A   VSGEPGSGKSTQIPQWCAEFALARGFQKGQVTVTQPYPLAARSLALRVADEMDLTLGHEV 158
184P3G10v.5B   DDDGDLSDLGVILSEFPLAPELAKALLASCEFDCVDEMLTLAAMLTAAPGFTRPPLSAEE  73
                 * . ..:::            . ** ::   ...     . .*.  . .*

184P3G10v.1    GYSIPQEDCTGPNTLLRFCWDRLLLQEVASTRGTGAWGVLVLDEAQERSVASDSLQGLLQ 218
184P3G10v.2    GYSIPQEDCTGPNTLLRFCWDRLLLQEVASTRGTGAWGVLVLDEAQERSVASDSLQGLLQ 187
184P3G10v.3    GYSIPQEDCTGPNTLLRFCWDRLLLQEVASTRGTGAWGVLVLDEAQERSVASDSLQGLLQ 218
184P3G10v.4A   GYSIPQEDCTGPNTLLRFCWDRLLLQEVASTRGTGAWGVLVLDEAQERSVASDSLQGLLQ 218
184P3G10v.4B   AALRRALEHTDGHSSLIQVYEAFIQSGADEAWCQARGLNWAALCQAHKLRGELLELMQR  240
184P3G10v.5A   GYSIPQEDCTGPNTLLRFCWDRLLLQEVASTRGTGAWGVLVLDEAQERSVASDSLQGLLQ 218
184P3G10v.5B   AALRRALEHTDGHSSLIQVYEAFIQSGADEAWCQARGLNWAALCQAHKLRGELLELMQR  133
                     *.:  ..  ::    :   ::::*. *     .:    * :::::*  *  .  :

184P3G10v.1    DARLEKLPGDLRVVVVTDPALEPKLRAFWGNPPIVHIPREPGERPSPIYWDTIPPDRVEA 278
184P3G10v.2    DARLEKLPGDLRVVVVTDPALEPKLRAFWGNPPIVHIPREPGERPSPIYWDTIPPDRVEA 247
184P3G10v.3    DARLEKLPGDLRVVVVTDPALEPKLRAFWGNPPIVHIPREPGERPSPIYWDTIPPDRVEA 278
184P3G10v.4A   DARLEKLPGDLRVVVVTDPALEPKLRAFWGNPPIVHIPREPGERPSPIYWDTIPPDRVEA 278
184P3G10v.4B   IELPLSLP-----AFGSEQNRRDIQKALVSGYFLKVARDTDGTGNYLLLTHKHVAQLSS  294
184P3G10v.5A   DARLEKLPGDLRVVVVTDPALEPKLRAFWGNPPIVHIPREPGERPSPIYWDTIPPDRVEA 278
184P3G10v.5B   IELPLSLP-----AFGSEQNRRDIQKALVSGYFLKVARDTDGTGNYLLLTHKHVAQLSS  187
                 * *         .      *:         *.*   ::::*  .

184P3G10v.1    ACQAVLELCRKELPGDVLVFLPSE-----------------EEISLCCESLSREVESL 319
184P3G10v.2    ACQAVLELCRKELPGDVLVFLPSE-----------------EEISLCCESLSREVESL 288
184P3G10v.3    ACQAVLELCRKELPGDVLVFLPSEEVKKQNKTKKTACKMSLQKEEISLCCESLSREVESL 338
```

Figure 14m (continued)

```
184P3G10v.4A    ACQAVLELCRKELPGDVLVFLPSE------------------------EEISLCCESLSREVESL  319
184P3G10v.4B    YCCYRSRRAPARPPPWVLYHNFTI------------------------SKDNCLSIVSEIQPQML  335
184P3G10v.5A    ACQAVLELCRKELPGDVLVFLPSE------------------------EEISLCCESLSREVESL  319
184P3G10v.5B    YCCYRSRRAPARPPPWVLYHNFTI------------------------SKDNCLSIVSEIQPQML  228
                  *       .  . *        **    :                  .  :    .:      *

184P3G10v.1     LLQGLPPRVLPLHPDCGRAVQAVYEDMDARKVVTHWLADFSFSLPSIQHVIDSGLELRS        379
184P3G10v.2     LLQGLPPRVLPLHPDCGRAVQAVYEDMDARKVVTHWLADFSFSLPSIQHVIDSGLELRS        348
184P3G10v.3     LLQGLPPRVLPLHPDCGRAVQAVYEDMDARKVVTHWLADFSFSLPSIQHVIDSGLELRS        398
184P3G10v.4A    LLQGLPPRVLPLHPDCGRAVQAVYEDMDARKVVTHWLADFSFSLPSIQHVIDSGLELRS        379
184P3G10v.4B    VELAPPYFLSNLPPSESRDLLNQLREGMADSTAGSKSSSAQEFRDPCVLQ---------        385
184P3G10v.5A    LLQGLPPRVLPLHPDCGRAVQAVYEDMDARKVVTHWLADFSFSLPSIQHVIDSGLELRS        379
184P3G10v.5B    VELAPPYFLSNLPPSESRDLLNQLREGMADSTAGSKSSSAQEFRDPCVLQ---------        278
                  .:    * *. .  *       :: ::  . *  ::   *  .         .

184P3G10v.1     VYNPRIRAEFQVLRPISKCQAEAARRLRARGFPPGSCLCLYPKSFLELEAPPLPQPRVCEE      439
184P3G10v.2     VYNPRIRAEFQVLRPISKCQAEAARRLRARGFPPGSCLCLYPKSFLELEAPPLPQPRVCEE      408
184P3G10v.3     VYNPRIRAEFQVLRPISKCQAEAARRLRARGFPPGSCLCLYPKSFLELEAPPLPQPRVCEE      458
184P3G10v.4A    VSERER------------------------------------------------------      385
184P3G10v.4B    ------------------------------------------------------------        
184P3G10v.5A    VYNPRIRAEFQVLRPISKCQAEAARRLRARGFPPVVEFPRSFSPQDPASACILSPS----      434
184P3G10v.5B    ------------------------------------------------------------

184P3G10v.1     NLSSLVLLLKRRQIAEPGECHFLDQPAPEALMQALEDLDYLAALDDDGDLSDLGVILSEF      499
184P3G10v.2     NLSSLVLLLKRRQIAEPGECHFLDQPAPEALMQALEDLDYLAALDDDGDLSDLGVILSEF      468
184P3G10v.3     NLSSLVLLLKRRQIAEPGECHFLDQPAPEALMQALEDLDYLAALDDDGDLSDLGVILSEF      518
184P3G10v.4A    ------------------------------------------------------------        
184P3G10v.4B    ------------------------------------------------------------        
184P3G10v.5A    ------------------------------------------------------------        
184P3G10v.5B    ------------------------------------------------------------

184P3G10v.1     PLAPELAKALLASCEFDCVDEMLTLAAMLTAAPGFTRPPLSAEEAALRRALEHTDGDHSS      559
184P3G10v.2     PLAPELAKALLASCEFDCVDEMLTLAAMLTAAPGFTRPPLSAEEAALRRALEHTDGDHSS      528
184P3G10v.3     PLAPELAKALLASCEFDCVDEMLTLAAMLTAAPGFTRPPLSAEEAALRRALEHTDGDHSS      578
184P3G10v.4A    ------------------------------------------------------------        
184P3G10v.4B    ------------------------------------------------------------        
184P3G10v.5A    ------------------------------------------------------------
```

184P3G10v.1    LIQVYEAFIQSGADEAWCQARGLNWAALCQAHKLRGELLELMQRIELPLSLPAFGSEQNR 619
184P3G10v.2    LIQVYEAFIQSGADEAWCQARGLNWAALCQAHKLRGELLELMQRIELPLSLPAFGSEQNR 588
184P3G10v.3    LIQVYEAFIQSGADEAWCQARGLNWAALCQAHKLRGELLELMQRIELPLSLPAFGSEQNR 638
184P3G10v.4A   ------------------------------------------------------------
184P3G10v.4B   ------------------------------------------------------------
184P3G10v.5A   ------------------------------------------------------------
184P3G10v.5B   ------------------------------------------------------------

184P3G10v.1    RDLQKALVSGYFLKVARDTDGTGNYLLLITHKHVAQLSSYCCYRSRRAPARPPPWVLYHNF 679
184P3G10v.2    RDLQKALVSGYFLKVARDTDGTGNYLLLITHKHVAQLSSYCCYRSRRAPARPPPWVLYHNF 648
184P3G10v.3    RDLQKALVSGYFLKVARDTDGTGNYLLLITHKHVAQLSSYCCYRSRRAPARPPPWVLYHNF 698
184P3G10v.4A   ------------------------------------------------------------
184P3G10v.4B   ------------------------------------------------------------
184P3G10v.5A   ------------------------------------------------------------
184P3G10v.5B   ------------------------------------------------------------

184P3G10v.1    TISKDNCLSIVSEIQPQMLVELAPPYFLSNLPPSESRDLLNQLREGMADSTAGSKSSSAQ 739
184P3G10v.2    TISKDNCLSIVSEIQPQMLVELAPPYFLSNLPPSESRDLLNQLREGMADSTAGSKSSSAQ 708
184P3G10v.3    TISKDNCLSIVSEIQPQMLVELAPPYFLSNLPPSESRDLLNQLREGMADSTAGSKSSSAQ 758
184P3G10v.4A   ------------------------------------------------------------
184P3G10v.4B   ------------------------------------------------------------
184P3G10v.5A   ------------------------------------------------------------
184P3G10v.5B   ------------------------------------------------------------

184P3G10v.1    EFRDPCVLQ 748
184P3G10v.2    EFRDPCVLQ 717
184P3G10v.3    EFRDPCVLQ 767
184P3G10v.4A   ---------
184P3G10v.4B   ---------
184P3G10v.5A   ---------
184P3G10v.5B   ---------
```

Figure 11n Nucleotide sequences of transcript variants of 185P2C9
>185P2C9 v.2 (SEQ ID NO:157).

```
cacggggaa gcaggcgggc ccccagcac cgggaggcc gagctgaagc tgcggctaaa    60
gctggtggag gaggaagcca acatcttggg ccgaaagatc gtggagctgg aggtggagaa   120
ccgtggcctc aagcagaga tggaggacac gcggggccag caggagcggg agggcccggg   180
tcgggaccac gcaccccagca ttcctacctc acccttcggt gactccctgg agtcctccac   240
tgagctccgc cgccacctgc agtttgtaga agaggaagcg gagttgctcc ggaggtccat   300
ctccgagatc gaagaccaca accggcaact gacccacgag ctcagcaagt ttaagtttga   360
gcctccccgg gagccgggct ggctaggaga gggtgcaagt cctggtgccg ggggtggggc   420
cccctgcag gaggagctga agtcagccag gctgcagatc agcgagctca gcgcaaggt   480
gctcaaactg cagcacgaga accagcgct cctgtccaac atccagcgct gcgacctggc   540
agccacctg gggctgcgtg ccccagtcc ccggacagc gatgccgaga gtgatgcggg   600
caagaagag agtgatgggg aggaagccg cctgcccag ccaagcggg aaggcctgt   660
tgcgggag agtgactcgg aggagatgtt tgaagaagcg tcggcttcg ggagcgggaa   720
gccatccgag gccagcgagc catgccccac ggagctcctg aaggcccggg aggactctga   780
gtactagtg acctaaaac acgaggccca gcggctagag gcgacgtgg acgcctcat   840
cacggacacc gacagcttcc tccatgatgc gggctgcgg gtggtgcgc ccttaccggg   900
gcctgcctc cagggcgaag aggagcaggg tgaggggac cagcaggcg cccagctgct   960
gggaccatc aacgccaaga tgaaggcttt caagaaagag ctgcaggcct tcctctagctt  1020
ggtgaaccgc attgggatg gcctatcccc cttgcccac ctcacagagt cctctagctt  1080
cctctccact gtgacttccg tgtccccgga ctcccccatc gggaacctgg ggaaggagct  1140
gggccagac ttgcagtcca gactgaaaga gcagctggag tggcagctcg ggccggccca  1200
agggacgag cgggagagcc tgcgcctccg agccgcgcgg gagctgcacc gccgcgcaga  1260
cgggacacc gggagccacg ggctggagg ccagacctgc ttcagcctgg agatggagga  1320
ggagcacctc tatgccttga ggtgaaaga actgaaatg cacagcctgg ctttgcaaaa  1380
caccctccat gagcgaacct tcttctacgt ggagtgatga caaactcagg atgcagcagg  1440
cttgaagcag aacattttcc tctctacgt aggaaggaga ggagttcact gagggtgaac  1500
gcaagggaag cagatggagg aggaaggaga ttggagtcca ggggggtcac caggcggatg  1560
cctctccagg ctcgggggagc ttgagtcca gctttccagt gggggagcac tccccacact  1620
cgacagtgac cgaggctgtg gctctgcagac ggctgcagag ggcgacagg gagacgcccc  1680
gattggagat cacagcttgc ggctgcagac tcagcgcctt caaggcctg ctggaggact  1740
ggtggaaaac cagcagctgt tcagcagcgtg cccgactacg gctgcagcag caatatgcca  1800
gctgcgggag gatgagcgtg gtggagtggg ccgtgctcaa gtgccgtctg gaacagctgg  1860
ggcctgggac gtggagtggg ttggagaaac taggctccct cgctgagagc aagggggcct  1920
tgagaacaag ttggagaaac caccagaagc tcctgcaga cagtcacagc ctggtcatgg  1980
gagagaggtg caccagaagc cacagcgaga agaactggaa ccggagagaa gtggaacttc  2040
gcagatccat cacagcgaga agaactggca cccggagaag gaagaaggaa ttcttgtgga  2100
gacagagat cggcaggagt ggggagcggca ccccgagagg tggcagtttc ctctgtgatc  2160
gttgcagaaa gagaacagtc cccggagagt gaagaaggaa tgcagttttc aaaaagacgg  2220
caacgttcgc cccttccccc accagggaag cctccgcatg ccccgtccag tggccatgtg  2280
```

Figure 11n (continued)

```
gccttgtgca gatgctgact ccatcccgtt tgaagaccgg ccgctgtcca agctgaagga 2340
gtcggacagg tgctcggcca gtgagaatct ctacctggat gccttgtccc tgatgacga 2400
gccagaagag ccaccagccc acaggcccga gagggagttc aggaaccgcc tccctgagga 2460
agagaaaat cacaaaggaa atcttcaaag gcgtgtcc gtgtcctcca tgtctgagtt 2520
ccagcgtcta atggacatct cccctcct gctgagaag gcctgcgt ccaccagcag 2580
caaggaggat gtcaccccac ccctgtctcc agacgacctc agtacatcg aggagttcaa 2640
caagagctgg gactacacac ccaacagggg ccaaatggt ggggggccgg acctttggc 2700
cgacaggacc gaggtggggc gggcagggca cgaggacagc acagagcctt tccccgactc 2760
ctcctggtac ctaaccacaa gtgtcaccat gaccacggac accatgacca gcccagagca 2820
ctgccagaag cagccactgc ggagccactgt ctcaccgag cagtcgggt tgcgcgtgtt 2880
acacagcccg cctgccgtgc gcagggtcga cagcatcacg gcggcaggtg gtgagggtcc 2940
cttcccaca agcagagcca gaggagccc gggagacacc aaggggggcc ctccagaacc 3000
catgctcagc agtggccttt gcaactcccc caggcactcc cggactatg tgagggggc 3060
acggcgcccc cttgatagtc ccctctgtac ctccctgggg tttgcctccc cactgcacag 3120
cctgagatg tccaagaact tgagtgatga catgaaggag gtgccttct ctgtcaggaa 3180
tgccatctgc tccggccctg gcgagctgca agtcaagagc accaagtgt atggcctgc agaccaatgg 3240
gtcccggacc atgggaccc agactgttca gaccatcagt gaccatccaa gtggctggc agactgaagc 3300
cctgcgtggc agcggtgtca ccagcagccc ccacaagtgt ctcacttcaa aggctggggg 3360
cggtgctaca cccgtgtcgt ctccttcccg gagccttagg agcagacagg tggccctgc 3420
catcgagaag gtgcaggcca agtttgaacg cacatgctgc tcccccaagt atggttctcc 3480
caagctgcag aggaagcccc tcccaaagc cgaccagcca ccattggggt aataacaggc caggaaacag 3540
gcaccaattc ccgaggaagg tcgcctagcc ccagtgaagc aggacttatc tgctccccct gctacaccc 3600
aggaagggg agaggcacg ccagtgaagc aggacttatc aggacttatc tgctccccct gctacaccc 3660
tcactgagaa cgtggcccgg atcctcaaca agaagctgct gaacatgcc ttaaagagg 3720
agaggaggca ggctgcccac gggcccccgg gtctccacag tgacagccac tcgctggggg 3780
acacagccga gccaggcccc atgaggaaac taccttgttc tgcactagct ccatccctag 3840
agcctgctt ctccaggccc gagagaccag caaacgtcg ccctccgtcc cgttggcccc 3900
cacattcccc cactgcctca cagcctcagt caccggaga ccgacgtcc ttggaggagc 3960
atgtggcga ggagccgccc gaggagcagc cacacaggag tgcaagcttg catgattat 4020
cacagtataa ttcactgaaa ttgcataac cacaccatca ccatgaacaa aactctgccc 4080
caccaggagag atctagtttt ctcaaggtca aagaatgttt tttaaaaaca caaagctgct 4140
gaatgttcaa cctgtgaaac tgagatgttt ctagaatgaa acagtaaatg tgcctgtaat 4200
aacttaattt tttcatagc tcagaaaact attttgtct catctttttt tacacacagt 4260
atattaaacg aaaaggtaaa taaggtataa atagatttaa aaaataaaag ttttaaaaaa 4320
tgtacatttt aagagattct gaacaccctc gctgtcaata cctgactgcc tctgttaat 4380
ttgcatttt acatttttgt tcagtttatt tccatgttga attagagtgg attaagttaa 4440
tttattttg tcactgttac tgttttttac gaattttttta atgcttcaga ctgtctgatt 4500
cagtgaactt tttgtagtga aaaagccatg aagccagtag acaagacaga tattctgtat 4560
gctggagggg atacaggatg atttgaaaa ggtacaaagt cctcagtggt cttagaaaat 4620
```

Figure 11n (continued)

```
tcactgtatg atccttatat tatcctactt ggcttgcacg tcttcgggtg catgtatata     4680
ccgctactgt gtcctgcgca tcacctaaat gtgactcagt ctgttccact gtaatatgtt    4740
gtgatttcc ttgtactgta cttttattgt tgtccttctt gcatcgatga tccaacagca    4800
acaccatttt taaattattg tgaaaagatt aactggcaat gtacagagtt tactcaaagt    4860
tttcttaagg gaaaacacta caaaaagtca caaggatacc aaatgaaaac acatgatgat    4920
gcctctgggt ctgtatgaga ccgtgatgaa gtagaaataa agcccttctg agatggc      4977
```

>185P2C9 v.3 (SEQ ID NO:158).

```
cacggggaa gcaggcgggc ccccagcac ccggggaggcc gagctgaagc tgcggctaaa      60
gctggtggag gaggaagcca acatcttggg ccggaagatc gtggagctgg aggtggagaa   120
ccgtggcctc aaggcagaga tggaggacac gcggggccag caggagcggg agggcccggg   180
tcggaccac gcaccagca ttcctacctc accttcggt gactccctgg agtcctccac     240
tgagctccgc cgccactgc agtttgtaga agaggaagcg gagttgctcc ggaggtccat    300
ctccgagatc gaagaccaca accggcaact gacccacgag ctcagcaagt ttaagtttga   360
gcctccccgg gagccgggct ggctaggaga gggtgcaagt cctggtgccg gggtgggggc   420
cccctgcag gagagctga agtcagccag gctgcagatc agcgagctca gcgacctgg     480
gctcaaactg cagcacgaga accacgcgct gctgtccaac atccagcgct gcgacctggc   540
agcccacctg ggctgcgtg cccagtcc ccggacagc cggacagc gatgccgaga gtgatgcggg   600
caagaaggag agtgatgggg agagagccg cctgcccag tggg cccaagtggg aaggcctgt    660
tggcggggag agtgactcgg aggagatgtt gcctatcccc tgagaagacg tcgggcttcg    720
gccatcggag gccagcgagc catgccccac acggagccca gcagctcctg aaggcccggg    780
gtacctagtg accctaaaac acgagggcca ggggctagag gggctgcgg gtggtgcgc     840
cacggacacc gacagcttcc tccatgatgc aggagcaggg tgaggggac gcagcaggagc   900
gcctggcctc caggcgaag aggagcaggg tgaaggcttt caagaaagag ctgcaggcct    960
gggaccatc aacgccaaga gcctatcccc cttgcccac ctcacagagt ctcagcagt      1020
ggtgaaccgc attggggatg gcctatcccc cttgcccac ctcccccatc cctctagctt   1080
cctctccact gtgacttccg tgtccggga ctccccccaa gcagctgag gaacctgg      1140
gggcccagac ttgcagtcca gactgaaaga gcagctgag gcagctggag tgcagctcg     1200
agggacgag cgggagagcc tgcgcctccg agcgcgcgg agccgcgcg gagctgcacc      1260
cgggacacc gggagcacg gctggaagaa ccagacctgc ccagaccctgc ttcagcctgg    1320
ggagcacctc tatgcctga gtgcttga actgggaaatg aagaatctg caacctcagg      1380
caccctccat gagcgaacct tcttctacgt caaactcagg atgcagcagg agctccggtc    1440
cttgaagcag aacattttcc aggaaggaga ggagttcact gaggtgaac aacactgcg     1500
gcaagggaag cagatggagg ctcgggggagg ttggagtcca gggggtcac caggcggatg   1560
cctctccagg ctcgggggagc ttgagtcca ggggggcac tcccacact gccagacca      1620
cgacagtgac cgaggctgtg gctttccagt ggctgcagac cgggacagg ccgggtgca     1680
gattggagat cacgacttgc ggctgcagac tcagcgcctt caagcgcag ctgggact      1740
ggtggaaac cagcagctgt tcagcagctg tcagcgcctt caagcgcag ctgagggact      1800
gctgcgggag gatgagcgtg cccgactacg gctgcagcag caatatgcca gcgacaaggc   1860
```

Figure 11n (continued)

```
ggcctgggac gtggagtggg ccgtgctcaa gtgccgtctg gaacagaatt gttgtggata       1920
tcccagaatt aacattgagg aggagactt aggcttcacc aggctgccag ctgggtccac        1980
ggtaaaaacg ttgaagagcc ttgggttgca gagattggag ctggaagaga agactgagaa      2040
caagttggga gaactagget ctccgctga gagcaaggg gccttgaaga aggagagaga         2100
ggtgcaccag aagttcctg cagacagtca cagcctgtc atgacctgc gctggcagat          2160
ccatcacagc gagaagaact ggaaccggga gaagtgaa cttctcgacc gcctggacag         2220
agatcggcag gagtgggagc ggcagaagaa ggaattcttg tggaggatag agcaggaag        2280
cctccgcatg ccccgtccag tggccatgtg gccttgtgca gatgctgact ccatccgtt       2340
tgaagaccgg ccgctgtcca agctgaagga gtcggacagg tgctcggcca gtgagaatct       2400
ctacctgat gccttgtccc tggatgacga gccagaagag cccaccagcc acaggcccga        2460
gagggagttc aggaaccgcc tcctgagga agaagaaaat cacaaaggaa atccttcaaag       2520
ggcgtgtcc gtgtcctcta tgtctgagtt ccagcgtcta atggacatct cccctccct        2580
gcctgagaag ggcctgccgt ccaccagcag caaggaggat gtcaccccac ccctgtctcc      2640
agacgacctc aagtacatcg aggagttcaa caagagctg gactacacac ccaacagggg       2700
ccacaatggt gggggccgg acctttgggc cgacaggacc gagtgggg gggcaggca           2760
cgaggacagc acagagcctt tccccgactc ctcctggtac ctaaccacaa gtgtcaccat       2820
gaccacggac accatgacca gccagagca ctgccagaag cagccactgc ggagccacgt      2880
cctcaccgag cagtcgggt tgcgcgtgtt acacgcccg ctgccgtgc gcagggtcga         2940
cagcatcacg gcgcagtg gtgaggccgc ctccagaaac agcagagcca gagggagccc       3000
gggagacacc aaggggcc ctccagaacc catgtcagc acgcgcccc agtggccttt gcacctccc 3060
caggcactcc cggggactatg tggagggggc cctgcacag acgcgcccc cttgatagtc cctctgtac 3120
ctccctggg tttgcctcc cactgcacag cctgagatg tccaagaact tgagtgatga        3180
catgaaggag gtgccttct ctgtcaggaa tgccatcctg tccgccctg gcgagctgca        3240
agtcaaggag atgcctcgcc agaccaatgg gtccccgacg cctgcgtggc atgggaccc       3300
gaccatcagt gtgggcttgc agactgaagc aggctggggg cggtgctaca cccgtcgt      3360
ccacaagtgt ctcactccaa aggctgggg tgccccctgc catcgagaag gtgcaggcca       3420
gagccttagg agcagacagg tgccccagt atgttctcc caagctgcag aggaagcccc       3480
cacatgctgc tccccaagt atggttctcc caagctgcag aggaagcccc tcccaaaagc      3540
cgaccagcca aataacagga cgtcaccagg gatggcccag aaaggtaca gtgagtcagc       3600
ctgggccgc tccaccacca caagggagag ccccgtgcac accaccatta atgatgcct       3660
ctccagcctc ttcaacatca ttgaccacag cctgagatg caggaccct tccagaaggg       3720
gctgcgggcc ggcagtcggt ctcgctcagc ggaaggtc gcctagccc agagcctg gccaggcca  3780
ggaaacaggc accattccc gaggaaggtc gcctagccc agtgaagcag gacttactg gtcagagat 3840
gtgcaggag gaagggag agggcagcc cagagccgcc agtgaagcag gacttactg ctccccctg  3900
ctacaccctc actgagaacg tgccccggat cctcaacaag aagctgctg aacatgcctt        3960
aaaggaggag aggaggccag ctgcccacg gcccccggt ctccacagtg acagccactc        4020
gctggggac acagccgagc caggcccat ggaggaacta cctttgttctg cactagctcc       4080
atccctagag cctgcttct ccaggcccga gagaccagca accgtcgcc ctccgtccccg       4140
ttgggccca cattcccca ctgcctcaca gcctcagtca cccgagacc cgacgtcctt         4200
```

Figure 11n (continued)

```
ggaggagcat gqtqqcqaqq agccgcccga ggagcagcca caccgagatg caagcttgca    4260
tggattatca cagtatatca caggagagat ctagtttct caaggtcaat gaatgttttt taaaaacaca    4320
ctctgcccaa caggagagat ctagtttct caaggtcaa gaatgttttt taaaaacaca    4380
aagctgctga atgttcaacc tgtgaaactg agatgtttct agaatgaaac agtaaatgtg    4440
cctgtaataa cttaattttt ttcatagctc agaaaactat tttgtctcc atctttttta    4500
cacacagtat attaaacgaa aagtaaata agtataaat agatttaaaa aataaaagtt    4560
ttaaaaaatg tacatttta gagattctga acaccctcgc tgtcaatacc tgactgcctc    4620
tgttaaattt gcactgttac atttgtttc agtttattc catgttgaat tagagtggat    4680
taagttaatt ttattttgtc agtgttactg ttttttacga atttttaat gcttcagact    4740
gtctgattca gtgaactttt tgtagtgaaa aagccatgaa gccagtagac aagacagata    4800
ttctgtatgc tggagggat acaggatgat tttgaaaagg tacaaagtcc tcagtgggct    4860
tagaaattc actgtatgat ccttatatta tcctacttgg cttgcacgtc ttcggtgca    4920
tgtatatacc gctactgtgt cctcgccatc acctaaatgt gactcagtct gttccactgt    4980
aatatgttgt gaatttcctt gtactgtact tttattgttg gtcttcttgc atcgatgatc    5040
caacagcaac accatttta aattattgtg aaagattaa aaaagtcaca ctgcaatgt acagagttta    5100
ctcaaagttt tcttaaggga aaacactaca aaagtcaca agataccaa atggaaacac    5160
atgatgatgc ctctgggtct gtatgagacc gtgatgaagt agaaataaag cccttctgag    5220
atggc                                                               5225
```

Figure 12n Protein sequences of transcript variants of 185P2C9
>185P2C9 v.2 (SEQ ID NO:159).

```
MEDTRGQQER EGPGRDHAPS IPTSPFGDSL ESSTELRRHL QFVEEEAELL RRSISEIEDH     60
NRQLTHELSK FKFEPPREPG WLGEGASPGA GGGAPLQEEL KSARLQISEL SGKVLKLQHE    120
NHALLSNIQR CDLAAHLGLR APSPRDSDAE SDAGKKESDG EESRLPQPKR EGPVGGESDS    180
EEMFEKTSGF GSGKPSEASE PCPTELLKAR EDSEYLVTLK HEAQRLERTV ERLITDTDSF    240
LHDAGLRGGA PLPGPLQGE EEQGEGDQQE PQLLGTINAK MKAFKKELQA FLQQVNRIGD    300
GLSPLPHLTE SSSFLSTVTS VSRDSPIGNL GKELGPDLQS RLKEQLEWQL GPAQGDERES    360
LRLRAARELH RRADGDTGSH GLGGQTCFSL EMEEEHLYAL RWKELEMHSL ALQNTLHERT    420
WSDEKNLMQQ ELRSLKQNIF LFYVKLRWLL KHWRQGKQME EEGEEFTEGE HPETLSRLGE    480
LGVQGGHQAD GPDHDSDRGC GFPVGEHSPH SRVQIGDHSL RLQTADRGQP HKQVENQQL    540
FSAFKALLED FRAELREDER ARLRLQQQYA SDKAAWDVEW AVLKCRLEQL EEKTENKLGE    600
LGSSAESKGA LKKEREVHQK LLADSHSIVM DLRWQIHHSE KWNREKVEL LDRLDRDRQE    660
WERQKKEFLW RIEQIQKENS PRRGGSFICD QKDGNVRPFP HQGSIRMPRP VAMWPCADAD    720
SIPFEDRPLS KLKESDRCSA SENLYLDALS LDDEPEEPPA HRPEREFRNR LPEEEENHKG    780
NLQRAVSVSS MSEFQRLMDI SPFLPEKGLP STSSKEDVTP PLSPDDLKYI EEFNKSWDYT    840
PNRGHNGGGP DLWADRTEVG RAGHEDSTEP FPDSSWYLTT SVTMTTDTMT SPEHCQKQPL    900
RSHVLTEQSG LRVLHSPPAV RRVDSITAAG GEGFPTSRA RGSPGDTKGG PPEPMLSRWP    960
CTSPRHSRDY VEGARRPLDS PLCTSLGFAS PLHSLEMSKN LSDDMKEVAF SVRNAICSGP   1020
```

Figure 12n (continued)

```
GELQVKDMAC QTNGSRTMGT QTVQTISVGL QTEALRGSGV TSSPHKCLTP KAGGGATPVS    1080
SPSRSLRSRQ VAPAIEKVQA KFERTCCSPK YGSPKLQRKP LPKADQPNNR PGNRHQFPRK    1140
VA                                                                  1142

>185P2C9 v.3 (SEQ ID NO:160).
MEDTRGQQER EGPGRDHAPS IPTSPFGDSL ESSTELRRHL QFVEEEAELL RRSISEIEDH      60
NRQLTHELSK FKFEPPREPG WLGEGASPGA GGGAPLQEEL KSARLQISEL SGKVLKLQHE     120
NHALLSNIQR CDLAAHLGLR APSPRDSDAE SDAGKKESDG EESRLPQPKW EGPVGGESDS     180
EEMFEKTSGF GSGKPSEASE PCPTELLKAR EDSEYLVTLK HEAQRLERTV ERLITDTDSF     240
LHDAGLRGGA PLPGPGLQGE EEQGEGDQQE PQLLGTINAK MKAFKKELQA FLEQVNRIGD     300
GLSPLPHLTE SSSFLSTVTS VSRDSPIGNL GKELGPDLQS RLKEQLEWQL GPARGDERES     360
LRLRAARELH RRADGDTGSH GLGGQTCFSL EMEEEHLYAL RWKELEMHSL ALQNTLHERT     420
WSDEKNLMQQ ELRSLKQNIF LFYVKLRWLL KHWRQGKQME EEGEEFTEGE HPETLSRLGE     480
LGVQGGHQAD GPDHDSDRGC GFPVGEHSPH SRVQIGDHSL RLQTADRGQP HKQVVENQQL     540
FSAFKALLED FRAELREDER ARLRLQQQYA SDKAAWDVEW AVLKCRLEQN CCGYPRINIE     600
EETLGFTRLP AGSTVKTLKS LGLQRLELEE KTENKLGELG SSAESKGALK KEREVHQKLL     660
ADSHSLVMDL RWQIHHSEKN WNREKVELLD RLDRDRQEWE RQKKEFLWRI EQGSLRMPRP     720
VAMWPCADAD SIPFEDRPLS KLKESDRCSA SENLYLDALS LDDEPEEPPA HRPEREFRNR     780
LPEEEENHKG NLQRAVSVSS MSEFQRLMDI SPFLPEKGLP STSSKEDVTP PLSPDDLKYI     840
EEFNKSWDYT PNRGHNGGGP DLWADRTEVG RAGHEDSTEP FPDSSWYLTT SVTMTTDTMT     900
SPEHCQKQPL RSHVLTEQSG LRVLHSPPAV RRVDSITAAG GEGPFPTSRA RGSPGDTKGG     960
PPEPMLSRWP CTSPRHSRDY VEGARRPLDS PLCTSLGFAS PLHSLEMSKN LSDDMKEVAF    1020
SVRNAICSGP GELQVKDMAC QTNGSRTMGT QTVQTISVGL QTEALRGSGV TSSPHKCLTP    1080
KAGGGATPVS SPSRSLRSRQ VAPAIEKVQA KFERTCCSPK YGSPKLQRKP LPKADQPNNR    1140
TSPGMAQKGY SESAWARSTT TRESPVHTTI NDGLSSLFNI IDHSPVVQDP FQKGLRAGSR    1200
SRSAEPRPEL GPGQETGTNS RGRSPSPIGV GSEMCREEGG EGTPVKQDLS APPGYTLTEN    1260
VARILNKKLL EHALKEERRQ AAHGPPGLHS DSHSLGDTAE PGPMEELPCS ALAPSLEPCF    1320
SRPERPANRR PPSRWAPHSP TASQPQSPGD PTSLEEHGGE EPPEEQPHRD ASLHGLSQYN    1380
SL                                                                 1382
```

Figure 13n Alignment of nucleotide sequences of 185P2C9 transcript variants (SEQ ID NOS:47, 157, 158).

```
185P2C9v.1    CACGGGGGAAGCAGGCGGGCCCCCAGCACCCGGAGGCCGAGCTGAAGCTGCGGCTAAA     60
185P2C9v.2    CACGGGGGAAGCAGGCGGGCCCCCAGCACCCGGAGGCCGAGCTGAAGCTGCGGCTAAA     60
185P2C9v.3    CACGGGGGAAGCAGGCGGGCCCCCAGCACCCGGAGGCCGAGCTGAAGCTGCGGCTAAA     60
              **********************************************************

185P2C9v.1    GCTGGTGGAGGAGGAAGCCAACATTTGGGCCGAAGATCGTGAGCTGGAGGTGGAGAA    120
                                                                        ***********
```

Figure 13n (continued)

```
185P2C9v.2   GCTGGTGAGGAGGAAGCCAACATCTTGGCCGAAGATCGTGGAGCTGGAGGTGGAGAA  120
185P2C9v.3   GCTGGTGAGGAGGAAGCCAACATCTTGGCCGAAGATCGTGGAGCTGGAGGTGGAGAA  120
             **********************************************************

185P2C9v.1   CCGTGGCCTCAAGGCAGAGATGGAGGACATGCGGGGCCAGCAGGAGCGGGAGGGCCCGGG  180
185P2C9v.2   CCGTGGCCTCAAGGCAGAGATGGAGGACATGCGGGGCCAGCAGGAGCGGGAGGGCCCGGG  180
185P2C9v.3   CCGTGGCCTCAAGGCAGAGATGGAGGACACGCGGGGCCAGCAGGAGCGGGAGGGCCCGGG  180
             *****************************  *****************************

185P2C9v.1   TCGGGACCACGCACCCAGCATTCCTACCTCACCCTTCGGTGACTCCCTGAGTCCTCCAC  240
185P2C9v.2   TCGGGACCACGCACCCAGCATTCCTACCTCACCCTTCGGTGACTCCCTGAGTCCTCCAC  240
185P2C9v.3   TCGGGACCACGCACCCAGCATTCCTACCTCACCCTTCGGTGACTCCCTGAGTCCTCCAC  240
             **********************************************************

185P2C9v.1   TGAGCTCCGCCGCCCACCTGCAGTTTGTAGAAGAGGAAGCGGAGTTGCTCCGGAGGTCCAT  300
185P2C9v.2   TGAGCTCCGCCGCCCACCTGCAGTTTGTAGAAGAGGAAGCGGAGTTGCTCCGGAGGTCCAT  300
185P2C9v.3   TGAGCTCCGCCGCCCACCTGCAGTTTGTAGAAGAGGAAGCGGAGTTGCTCCGGAGGTCCAT  300
             **********************************************************

185P2C9v.1   CTCCGAGATCGAAGACCACCACCGGCAACTGACCCACGAGCTCAGCGAGCTCAGCAAGTTAAGTTTGA  360
185P2C9v.2   CTCCGAGATCGAAGACCACCACCGGCAACTGACCCACGAGCTCAGCGAGCTCAGCAAGTTTAAGTTTGA  360
185P2C9v.3   CTCCGAGATCGAAGACCACCACCGGCAACTGACCCACGAGCTCAGCGAGCTCAGCAAGTTTAAGTTTGA  360
             ****************************************************** ***********

185P2C9v.1   GCCTCCCCGGAGCCGGCTGGCTAGGAGAGGTGCAAGTCCTGGTGCCGGGGGTGGGGC  420
185P2C9v.2   GCCTCCCCGGAGCCGGCTGGCTAGGAGAGGTGCAAGTCCTGGTGCCGGGGGTGGGGC  420
185P2C9v.3   GCCTCCCCGGAGCCGGCTGGCTAGGAGAGGTGCAAGTCCTGGTGCCGGGGGTGGGGC  420
             **********************************************************

185P2C9v.1   CCCCCTGCAGGAGGAGCTGAAGTCAGCCAGGCTGCAGATCAGCGAGCTCAGCGGCAAGGT  480
185P2C9v.2   CCCCCTGCAGGAGGAGCTGAAGTCAGCCAGGCTGCAGATCAGCGAGCTCAGCGGCAAGGT  480
185P2C9v.3   CCCCCTGCAGGAGGAGCTGAAGTCAGCCAGGCTGCAGATCAGCGAGCTCAGCGGCAAGGT  480
             **********************************************************

185P2C9v.1   GCTCAAACTGCAGCACGAGAACCACGCGCTGTCCAACATCCAGCGCTGCCGACCTGGC  540
185P2C9v.2   GCTCAAACTGCAGCACGAGAACCACGCGCTGTCCAACATCCAGCGCTGCCGACCTGGC  540
185P2C9v.3   GCTCAAACTGCAGCACGAGAACCACGCGCTGTCCAACATCCAGCGCTGCCGACCTGGC  540
             **********************************************************
```

Figure 13n (continued)

```
185P2C9v.1   AGCCCACCTGGGCTGCGTGCCCCCAGTCCCCGGACAGCGATGCCGAGAGTGATGCCGGG    600
185P2C9v.2   AGCCCACCTGGGCTGCGTGCCCCCAGTCCCCGGACAGCGATGCCGAGAGTGATGCCGGG    600
185P2C9v.3   AGCCCACCTGGGCTGCGTGCCCCCAGTCCCCGGACAGCGATGCCGAGAGTGATGCCGGG    600
             ************************************************************

185P2C9v.1   CAAGAAGGAGAGTGATGGGGAGGAGAGCCGCCTGCCCCAGCCCAAGCGGGAAGGGCCTGT    660
185P2C9v.2   CAAGAAGGAGAGTGATGGGGAGGAGAGCCGCCTGCCCCAGCCCAAGCGGGAAGGGCCTGT    660
185P2C9v.3   CAAGAAGGAGAGTGATGGGGAGGAGAGCCCTGCCCCAGCCCAAGTGGGAAGGGCCTGT    660
             ********************************   ************ ***********

185P2C9v.1   TGGCGGGGAGAGTGACTCGGAGGAAATGTTTGAGAAGACGTCGGCTTCGGGAGCGGGAA    720
185P2C9v.2   TGGCGGGGAGAGTGACTCGGAGGAGATGTTTGAGAAGACGTCGGCTTCGGGAGCGGGAA    720
185P2C9v.3   TGGCGGGGAGAGTGACTCGGAGGAGATGTTTGAGAAGACGTCGGCTTCGGGAGCGGGAA    720
             ***********************  *********************************

185P2C9v.1   GCCATCGGAGGCCAGCGAGCCATGCCCCACGGAGCTCCTGAAGGCCCGGAGGACTCTGA    780
185P2C9v.2   GCCATCGGAGGCCAGCGAGCCATGCCCCACGGAGCTCCTGAAGGCCCGGAGGACTCTGA    780
185P2C9v.3   GCCATCGGAGGCCAGCGAGCCATGCCCCACGGAGCTCCTGAAGGCCCGGAGGACTCTGA    780
             ************************************************************

185P2C9v.1   GTACCTAGTGACCCTAAAAACACGAGGCCCAGCGGCTAGAGCGGACGGTGGAGCGCCTCAT    840
185P2C9v.2   GTACCTAGTGACCCTAAAAACACGAGGCCCAGCGGCTAGAGCGGACGGTGGAGCGCCTCAT    840
185P2C9v.3   GTACCTAGTGACCCTAAAAACACGAGGCCCAGCGGCTAGAGCGGACGGTGGAGCGCCTCAT    840
             ************************************************************

185P2C9v.1   CACGGACACCGACAGCTTCCTCCATGATGCGGGGCTGCGGGGTGGTGCGCCCTTACCGGG    900
185P2C9v.2   CACGGACACCGACAGCTTCCTCCATGATGCGGGGCTGCGGGGTGGTGCGCCCTTACCGGG    900
185P2C9v.3   CACGGACACCGACAGCTTCCTCCATGATGCGGGGCTGCGGGGTGGTGCGCCCTTACCGGG    900
             ************************************************************

185P2C9v.1   GCCTGGCCCTCCAGGGCGAAGAGGAGCAGGTGAGGGGGAGCAGGACCAGCAGGAGCCCCAGCTGCT    960
185P2C9v.2   GCCTGGCCCTCCAGGGCGAAGAGGAGCAGGTGAGGGGGAGCAGGACCAGCAGGAGCCCCAGCTGCT    960
185P2C9v.3   GCCTGGCCCTCCAGGGCGAAGAGGAGCAGGTGAGGGGGAGCAGGACCAGCAGGAGCCCCAGCTGCT    960
             ************************************************************

185P2C9v.1   GGGGACCATCAACGCCAAGATGAAGGCTTTCAAGAAAGAGCTGCAGGCCTTCCTGCTGAGCA    1020
185P2C9v.2   GGGGACCATCAACGCCAAGATGAAGGCTTTCAAGAAAGAGCTGCAGGCCTTCCTGCTGAGCA    1020
185P2C9v.3   GGGGACCATCAACGCCAAGATGAAGGCTTTCAAGAAAGAGCTGCAGGCCTTCCTGCTGAGCA    1020
             ***********************************************************
```

Figure 13n (continued)

```
185P2C9v.1    GGTGAACCGCATTGGGATGGCCTATCCCCCTTGCCCACCTCACAGAGTCCTCTAGCTT  1080
185P2C9v.2    GGTGAACCGCATTGGGATGGCCTATCCCCCTTGCCCACCTCACAGAGTCCTCTAGCTT  1080
185P2C9v.3    GGTGAACCGCATTGGGATGGCCTATCCCCCTTGCCCACCTCACAGAGTCCTCTAGCTT  1080
              ************************************************************

185P2C9v.1    CCTCTCCACTGTGACTTCCGTGTCCGGGACTCCCCCATCGGGAACCTGGGGAAGGAGCT  1140
185P2C9v.2    CCTCTCCACTGTGACTTCCGTGTCCGGGACTCCCCCATCGGGAACCTGGGGAAGGAGCT  1140
185P2C9v.3    CCTCTCCACTGTGACTTCCGTGTCCGGGACTCCCCCATCGGGAACCTGGGGAAGGAGCT  1140
              ************************************************************

185P2C9v.1    GGGCCCAGACTTGCAGTCCAGACTGAAAGAGCAGCTGGAGTGGCAGCTCGGGCCGGCCCG  1200
185P2C9v.2    GGGCCCAGACTTGCAGTCCAGACTGAAAGAGCAGCTGGAGTGGCAGCTCGGGCCGGCCCA  1200
185P2C9v.3    GGGCCCAGACTTGCAGTCCAGACTGAAAGAGCAGCTGGAGTGGCAGCTCGGGCCGGCCCG  1200
              ************************************************************

185P2C9v.1    AGGGGACGAGCGGGAGAGCCTGCGCCTCCGAGCCGGGAGCTGCACCGCCGCGCGCAGA  1260
185P2C9v.2    AGGGGACGAGCGGGAGAGCCTGCGCCTCCGAGCCGGGAGCTGCACCGCCGCGCGCAGA  1260
185P2C9v.3    AGGGGACGAGCGGGAGAGCCTGCGCCTCCGAGCCGGGAGCTGCACCGCCGCGCGCAGA  1260
              ************************************************************

185P2C9v.1    CGGGGACACCGGAGGAGCCACGGGGCTGGGAGGCCAGACCTGCTTCAGCCTGGAGATGAGGA  1320
185P2C9v.2    CGGGGACACCGGAGGAGCCACGGGGCTGGGAGGCCAGACCTGCTTCAGCCTGGAGATGAGGA  1320
185P2C9v.3    CGGGGACACCGGAGGAGCCACGGGGCTGGGAGGCCAGACCTGCTTCAGCCTGGAGATGAGGA  1320
              ************************************************************

185P2C9v.1    GGAGCACCTCTATGCCTTGAGGTGGAAATGCACAGCCTGGCTTTGCAAAA  1380
185P2C9v.2    GGAGCACCTCTATGCCTTGAGGTGGAAATGCACAGCCTGGCTTTGCAAAA  1380
185P2C9v.3    GGAGCACCTCTATGCCTTGAGGTGGAAATGCACAGCCTGGCTTTGCAAAA  1380
              ************************************************************

185P2C9v.1    CACCCTCCATGAGCGAACCTGGAGTGATGAGAAGAATCTGATGCAGCAGGAGCTCCGGTC  1440
185P2C9v.2    CACCCTCCATGAGCGAACCTGGAGTGATGAGAAGAATCTGATGCAGCAGGAGCTCCGGTC  1440
185P2C9v.3    CACCCTCCATGAGCGAACCTGGAGTGATGAGAAGAATCTGATGCAGCAGGAGCTCCGGTC  1440
              ************************************************************

185P2C9v.1    CTTGAAGCAGAACATTTCCTCTTCTACGTCAAACTCAGGTGCTGCTGAAAACACTGGCG  1500
185P2C9v.2    CTTGAAGCAGAACATTTCCTCTTCTACGTCAAACTCAGGTGCTGCTGAAAACACTGGCG  1500
185P2C9v.3    CTTGAAGCAGAACATTTCCTCTTCTACGTCAAACTCAGGTGCTGCTGAAAACACTGGCG  1500
              ************************************************************
```

Figure 13n (continued)

```
185P2C9v.1  GCAAGGGAAGCAGATGGAGGAGGAAGGAGGAGAGAGAGTTCACTGAGGGTGAACATCCAGAGAC 1560
185P2C9v.2  GCAAGGGAAGCAGATGGAGGAGGAAGGAGGAGAGAGAGTTCACTGAGGGTGAACATCCAGAGAC 1560
185P2C9v.3  GCAAGGGAAGCAGATGGAGGAGGAAGGAGGAGAGAGAGTTCACTGAGGGTGAACATCCAGAGAC 1560
            ****************************************************************

185P2C9v.1  CCTCTCCAGGCTCGGGGAGCTTGCGCTTGGAGTCCAGGGGGTCACCAGGCGGATGGCCCAGACCA 1620
185P2C9v.2  CCTCTCCAGGCTCGGGGAGCTTGCGCTTGGAGTCCAGGGGGTCACCAGGCGGATGGCCCAGACCA 1620
185P2C9v.3  CCTCTCCAGGCTCGGGGAGCTTGCGCTTGGAGTCCAGGGGGTCACCAGGCGGATGGCCCAGACCA 1620
            ****************************************************************

185P2C9v.1  CGACAGTGACCGAGGCTGTGGCTTTCCAGTGGGGAGCACTCCCCACACTCCCGGGTGCA 1680
185P2C9v.2  CGACAGTGACCGAGGCTGTGGCTTTCCAGTGGGGAGCACTCCCCACACTCCCGGGTGCA 1680
185P2C9v.3  CGACAGTGACCGAGGCTGTGGCTTTCCAGTGGGGAGCACTCCCCACACTCCCGGGTGCA 1680
            ************************************************************

185P2C9v.1  GATTGGAGATCACAGCTTGCGCTTGCAGACCGCGGACAGGGACAGCCCCACAAACAGGT 1740
185P2C9v.2  GATTGGAGATCACAGCTTGCGCTTGCAGACCGCGGACAGGGACAGCCCCACAAACAGGT 1740
185P2C9v.3  GATTGGAGATCACAGCTTGCGCTTGCAGACCGCGGACAGGGACAGCCCCACAAACAGGT 1740
            ************************************************************

185P2C9v.1  GGTGGAAAACCAGCAGCTGTTCAGCGCCTTCAAGGCCTTGCTGGAGGACTTCCGTGCGGA 1800
185P2C9v.2  GGTGGAAAACCAGCAGCTGTTCAGCGCCTTCAAGGCCTTGCTGGAGGACTTCCGTGCGGA 1800
185P2C9v.3  GGTGGAAAACCAGCAGCTGTTCAGCGCCTTCAAGGCCTTGCTGGAGGACTTCCGTGCGGA 1800
            ************************************************************

185P2C9v.1  GCTGCGGGAGGATGAGCGTGCCCGACTACGGCTGCAGCAGCAATATGCCAGCGACAAGGC 1860
185P2C9v.2  GCTGCGGGAGGATGAGCGTGCCCGACTACGGCTGCAGCAGCAATATGCCAGCGACAAGGC 1860
185P2C9v.3  GCTGCGGGAGGATGAGCGTGCCCGACTACGGCTGCAGCAGCAATATGCCAGCGACAAGGC 1860
            ************************************************************

185P2C9v.1  GGCCTGGACGTGGAGTGGGCCCGTGCCGTCAAGTGCCGTCTGGAACAG------------ 1906
185P2C9v.2  GGCCTGGACGTGGAGTGGGCCCGTGCCGTCAAGTGCCGTCTGGAACAG------------ 1906
185P2C9v.3  GGCCTGGACGTGGAGTGGGCCCGTGCCGTCAAGTGCCGTCTGGAACAGAATTGTTGTGGATA 1920
            ************************************************

185P2C9v.1  ------------------------------------------------------------
185P2C9v.2  ------------------------------------------------------------
185P2C9v.3  TCCCAGAATTAACATTGAGGAGGAGACTTTAGGCTTCACCAGGCTGCCAGCTGGTCCAC 1980
```

Figure 13n (continued)

```
185P2C9v.1  ------------------------------------------CTGGAAGAGAAGAAGACTGAGAA  1926
185P2C9v.2  ------------------------------------------CTGGAAGAGAAGAAGACTGAGAA  1926
185P2C9v.3  GGTAAAAACGTTGAAGAGCCTTGGGTTGCAGAGATTGGAGCTGGAAGAGAAGAAGACTGAGAA  2040
                                                      ******************

185P2C9v.1  CAAGTTGGGAGAACTAGGCTCCTCCGCTGAGAGCAAGGGGCCTTGAAGAAGGAGAGAGA  1986
185P2C9v.2  CAAGTTGGGAGAACTAGGCTCCTCCGCTGAGAGCAAGGGGCCTTGAAGAAGGAGAGAGA  1986
185P2C9v.3  CAAGTTGGGAGAACTAGGCTCCTCCGCTGAGAGCAAGGGGCCTTGAAGAAGGAGAGAGA  2100
            ***********************************************************

185P2C9v.1  GGTGCACCAGAAGCTCCTGGCAGACAGTCACAGCCTGGTCATGACCTGCGCTGGCAGAT  2046
185P2C9v.2  GGTGCACCAGAAGCTCCTGGCAGACAGTCACAGCCTGGTCATGACCTGCGCTGGCAGAT  2046
185P2C9v.3  GGTGCACCAGAAGCTCCTGGCAGACAGTCACAGCCTGGTCATGACCTGCGCTGGCAGAT  2160
            ***********************************************************

185P2C9v.1  CCATCACAGCGAGAAGAACTGGAACCGGGAGAAGGTGGAACTTCTCGACCGCCTGGACAG  2106
185P2C9v.2  CCATCACAGCGAGAAGAACTGGAACCGGGAGAAGGTGGAACTTCTCGACCGCCTGGACAG  2106
185P2C9v.3  CCATCACAGCGAGAAGAACTGGAACCGGGAGAAGGTGGAACTTCTCGACCGCCTGGACAG  2220
            ***********************************************************

185P2C9v.1  AGATCGGCAGGAGTGGGAGCGGCAGAAGAAGGAATTCTTGTGGAGGATAGAGCAGTTGCA  2166
185P2C9v.2  AGATCGGCAGGAGTGGGAGCGGCAGAAGAAGGAATTCTTGTGGAGGATAGAGCAGTTGCA  2166
185P2C9v.3  AGATCGGCAGGAGTGGGAGCGGCAGAAGAAGGAATTCTTGTGGAGGATAGAGCAG----  2275
            ********************************************************

185P2C9v.1  GAAAGAGAACAGTCCCCGGAGAGGTGGCAGTTTCCTCTGTGATCAAAAAGACGGCAACGT  2226
185P2C9v.2  GAAAGAGAACAGTCCCCGGAGAGGTGGCAGTTTCCTCTGTGATCAAAAAGACGGCAACGT  2226
185P2C9v.3  ------------------------------------------------------------

185P2C9v.1  TCGCCCCCTTTCCCCACCAGGGAAGCCTCCGCATGCCCCGTCCAGTGGCCATGTGGCCTTG  2286
185P2C9v.2  TCGCCCCCTTTCCCCACCAGGGAAGCCTCCGCATGCCCCGTCCAGTGGCCATGTGGCCTTG  2286
185P2C9v.3  ---------GGAAGCCTCCGCATGCCCCGTCCAGTGGCCATGTGGCCTTG  2316
                     ******************************************

185P2C9v.1  TGCAGATGCTGACTCCATCCCGTTTGAAGACCGGCCGCCGCTGTCCAAGCTGAAGGAGTCGGA  2346
185P2C9v.2  TGCAGATGCTGACTCCATCCCGTTTGAAGACCGGCCGCCGCTGTCCAAGCTGAAGGAGTCGGA  2346
185P2C9v.3  TGCAGATGCTGACTCCATCCCGTTTGAAGACCGGCCGCCGCTGTCCAAGCTGAAGGAGTCGGA  2376
            ***************************************************************
```

Figure 13n (continued)

```
185P2C9v.1    CAGGTGCTCGGCCAGTGAGAATCTCTACCTGGATGCCTTGTCCCTGGATGACGAGCCAGA  2406
185P2C9v.2    CAGGTGCTCGGCCAGTGAGAATCTCTACCTGGATGCCTTGTCCCTGGATGACGAGCCAGA  2406
185P2C9v.3    CAGGTGCTCGGCCAGTGAGAATCTCTACCTGGATGCCTTGTCCCTGGATGACGAGCCAGA  2436
              ************************************************************

185P2C9v.1    AGAGCCACCAGCCCACAGCCCGAGAGGGAGTTCAGGAAGCCGCTCCCTGAGGAAGAAGA   2466
185P2C9v.2    AGAGCCACCAGCCCACAGCCCGAGAGGGAGTTCAGGAAGCCGCTCCCTGAGGAAGAAGA   2466
185P2C9v.3    AGAGCCACCAGCCCACAGCCCGAGAGGGAGTTCAGGAAGCCGCTCCCTGAGGAAGAAGA   2496
              ************************************************************

185P2C9v.1    AAATCACAAAGGAAATCTTCAAAGGCCGTGTCCGTGTCCTCCATGTCTGAGTTCCAGCG   2526
185P2C9v.2    AAATCACAAAGGAAATCTTCAAAGGCCGTGTCCGTGTCCTCCATGTCTGAGTTCCAGCG   2526
185P2C9v.3    AAATCACAAAGGAAATCTTCAAAGGCCGTGTCCGTGTCCTCCATGTCTGAGTTCCAGCG   2556
              ************************************************************

185P2C9v.1    TCTAATGGACATCTCCCCCTTCCTGCCTGAGAAGGGCCTGCCGTCCACCAGCAGCAAGGA  2586
185P2C9v.2    TCTAATGGACATCTCCCCCTTCCTGCCTGAGAAGGGCCTGCCGTCCACCAGCAGCAAGGA  2586
185P2C9v.3    TCTAATGGACATCTCCCCCTTCCTGCCTGAGAAGGGCCTGCCGTCCACCAGCAGCAAGGA  2616
              ************************************************************

185P2C9v.1    GGATGTCACCCCCACCCCCTGTCTCCAGACGACCTCAAGTACATCGAGGAGTTCAACAAGAG  2646
185P2C9v.2    GGATGTCACCCCCACCCCCTGTCTCCAGACGACCTCAAGTACATCGAGGAGTTCAACAAGAG  2646
185P2C9v.3    GGATGTCACCCCCACCCCCTGTCTCCAGACGACCTCAAGTACATCGAGGAGTTCAACAAGAG  2676
              ************************************************************

185P2C9v.1    CTGGGACTACACACCCAACAGGGGCCACAATGGTGGGGGCCCGGACCTTTGGGCCGACAG  2706
185P2C9v.2    CTGGGACTACACACCCAACAGGGGCCACAATGGTGGGGGCCCGGACCTTTGGGCCGACAG  2706
185P2C9v.3    CTGGGACTACACACCCAACAGGGGCCACAATGGTGGGGGCCCGGACCTTTGGGCCGACAG  2736
              ************************************************************

185P2C9v.1    GACCGAGGTGGGCGGCAGGGCACGGGACACAGAGCACCTTTCCCGACTCCTCCTG       2766
185P2C9v.2    GACCGAGGTGGGCGGCAGGGCACGGGACACAGAGCACCTTTCCCGACTCCTCCTG       2766
185P2C9v.3    GACCGAGGTGGGCGGCAGGGCACGGGACACAGAGCACCTTTCCCGACTCCTCCTG       2796
              ************************************************************

185P2C9v.1    GTACCTAACCACAAGTGTCACCATGACCACGGACACCATGACCAGCCCAGAGCCACTGCCA  2826
185P2C9v.2    GTACCTAACCACAAGTGTCACCATGACCACGGACACCATGACCAGCCCAGAGCCACTGCCA  2826
185P2C9v.3    GTACCTAACCACAAGTGTCACCATGACCACGGACACCATGACCAGCCCAGAGCCACTGCCA  2856
              ************************************************************
```

Figure 13n (continued)

```
185P2C9v.1    GAAGCAGCCACTGCGGAGCCACGTCCTCACCGAGCAGTCGGGGTTGCGCGTGTTACACAG  2886
185P2C9v.2    GAAGCAGCCACTGCGGAGCCACGTCCTCACCGAGCAGTCGGGGTTGCGCGTGTTACACAG  2886
185P2C9v.3    GAAGCAGCCACTGCGGAGCCACGTCCTCACCGAGCAGTCGGGGTTGCGCGTGTTACACAG  2916
              ************************************************************

185P2C9v.1    CCCGCCTGCCGTGCGCAGGGTCGACAGCATCACGCGGCAGTGGTGAGGTCCCTTTCC     2946
185P2C9v.2    CCCGCCTGCCGTGCGCAGGGTCGACAGCATCACGCGGCAGTGGTGAGGTCCCTTTCC     2946
185P2C9v.3    CCCGCCTGCCGTGCGCAGGGTCGACAGCATCACGCGGCAGTGGTGAGGTCCCTTTCC     2976
              ************************************************************

185P2C9v.1    CACAAGCAGAGCCAGAGGGAGCCCGGAGACACCAAGGGGGCCCTCCAGAACCATGCT     3006
185P2C9v.2    CACAAGCAGAGCCAGAGGGAGCCCGGAGACACCAAGGGGGCCCTCCAGAACCATGCT     3006
185P2C9v.3    CACAAGCAGAGCCAGAGGGAGCCCGGAGACACCAAGGGGGCCCTCCAGAACCATGCT     3036
              ************************************************************

185P2C9v.1    CAGCAGGTGGCCTTGCACCTCCCCCAGGCACTCCCGGACTATGTGGAGGGGCACGGCG   3066
185P2C9v.2    CAGCAGGTGGCCTTGCACCTCCCCCAGGCACTCCCGGACTATGTGGAGGGGCACGGCG   3066
185P2C9v.3    CAGCAGGTGGCCTTGCACCTCCCCCAGGCACTCCCGGACTATGTGGAGGGGCACGGCG   3096
              ************************************************************

185P2C9v.1    CCCCCTTGATAGTCCCCTCTGTACCTCCCCTGGGGTTTGCCTCCCCACTGCACAGCCTGGA  3126
185P2C9v.2    CCCCCTTGATAGTCCCCTCTGTACCTCCCCTGGGGTTTGCCTCCCCACTGCACAGCCTGGA  3126
185P2C9v.3    CCCCCTTGATAGTCCCCTCTGTACCTCCCCTGGGGTTTGCCTCCCCACTGCACAGCCTGGA  3156
              ************************************************************

185P2C9v.1    GATGTCCAAGAACTTGAGTGATGATGACATGAAGGAGTGGCCTTCTCTGTCAGGAATGCCAT  3186
185P2C9v.2    GATGTCCAAGAACTTGAGTGATGATGACATGAAGGAGTGGCCTTCTCTGTCAGGAATGCCAT  3186
185P2C9v.3    GATGTCCAAGAACTTGAGTGATGATGACATGAAGGAGTGGCCTTCTCTGTCAGGAATGCCAT  3216
              ************************************************************

185P2C9v.1    CTGCTCCGGCCCTGCCGAGCTGCAAGTCAAGGACATGGCCTGCCAGACCAATGGGTCCCG   3246
185P2C9v.2    CTGCTCCGGCCCTGCCGAGCTGCAAGTCAAGGACATGGCCTGCCAGACCAATGGGTCCCG   3246
185P2C9v.3    CTGCTCCGGCCCTGCCGAGCTGCAAGTCAAGGACATGGCCTGCCAGACCAATGGGTCCCG   3276
              ************************************************************

185P2C9v.1    GACGATGGGGACCCAGACTGTTCAGACCATCAGTGTGGCTTGCAGACTGAAGCCCTGCG    3306
185P2C9v.2    GACGATGGGGACCCAGACTGTTCAGACCATCAGTGTGGCTTGCAGACTGAAGCCCTGCG    3306
185P2C9v.3    GACGATGGGGACCCAGACTGTTCAGACCATCAGTGTGGCTTGCAGACTGAAGCCCTGCG    3336
              ************************************************************
```

Figure 13n (continued)

```
185P2C9v.1   TGGCAGCGGTGTCACCAGCAGCCCCCACAAGTGTCTCACTCCAAAGGCTGGGGGCGGTGC  3366
185P2C9v.2   TGGCAGCGGTGTCACCAGCAGCCCCCACAAGTGTCTCACTCCAAAGGCTGGGGGCGGTGC  3366
185P2C9v.3   TGGCAGCGGTGTCACCAGCAGCCCCCACAAGTGTCTCACTCCAAAGGCTGGGGGCGGTGC  3396
             ************************************************************

185P2C9v.1   TACACCCGTGTCGTCTCCTTCCCGGAGCCTTAGGAGCAGACAGTGGCCCTGCCATCGA    3426
185P2C9v.2   TACACCCGTGTCGTCTCCTTCCCGGAGCCTTAGGAGCAGACAGTGGCCCTGCCATCGA    3426
185P2C9v.3   TACACCCGTGTCGTCTCCTTCCCGGAGCCTTAGGAGCAGACAGTGGCCCTGCCATCGA    3456
             **********************************************************

185P2C9v.1   GAAGGTGCAGGCCAAGTTTGAACGCACATGCTGCTCCCCAAGTATGTTCTCCCAAGCT    3486
185P2C9v.2   GAAGGTGCAGGCCAAGTTTGAACGCACATGCTGCTCCCCAAGTATGTTCTCCCAAGCT    3486
185P2C9v.3   GAAGGTGCAGGCCAAGTTTGAACGCACATGCTGCTCCCCAAGTATGTTCTCCCAAGCT    3516
             **********************************************************

185P2C9v.1   GCAGAGGAAGCCCTCCCCAAAGCCGACCAGCCAAATAACAGGACGTCACCAGGATGGC   3546
185P2C9v.2   GCAGAGGAAGCCCTCCCCAAAGCCGACCAGCCAAATAACAGG------------------ 3529
185P2C9v.3   GCAGAGGAAGCCCTCCCCAAAGCCGACCAGCCAAATAACAGGACGTCACCAGGATGGC   3576
             ******************************************

185P2C9v.1   CCAGAAAGGGTACAGTGAGTCAGCCTGGGCCCGTCCACCACAAGGGAGAGCCCCGT     3606
185P2C9v.2   ---------------------------------------------------------
185P2C9v.3   CCAGAAAGGGTACAGTGAGTCAGCCTGGGCCCGTCCACCACAAGGGAGAGCCCCGT     3636

185P2C9v.1   GCACACCACCATTAATGATGGCCTCTTCAAGCCTCTTCAACATCATTGACCAGCCCCGT   3666
185P2C9v.2   ---------------------------------------------------------
185P2C9v.3   GCACACCACCATTAATGATGGCCTCTTCAAGCCTCTTCAACATCATTGACCAGCCCCGT   3696

185P2C9v.1   GGTGCAGGACCCCTTCAGAAGGGGCTGCGGCCGCAGTCGGTCTCGCTCAGCAGAGCC    3726
185P2C9v.2   ----------------CCAAGAAACAGGCACCAATTCCCGAGGAAGGTCGCCTAG-
185P2C9v.3   GGTGCAGGACCCCTTCAGAAGGGGCTGCGGCCGCAGTCGGTCTCGCTCAGCAGAGCC    3756

185P2C9v.1   CCGACCAGAGCTGGGCCCAGGCCAAGGAAACAGGCACCAATTCCCGAGGAAGGTCGCCTAG  3786
185P2C9v.2   ----------CCAAGAAACAGGCACCAATTCCCGAGGAAGGTCGCCTAG            3568
185P2C9v.3   CCGACCAGAGCTGGGCCCAGGCCAAGGAAACAGGCACCAATTCCCGAGGAAGGTCGCCTAG  3816
             ************
```

Figure 13n (continued)

```
185P2C9v.1    CCCCATTGGGGTGGGGTCAGAGATGTGCAGGGAGGAAGGGGAGAGGGCACGCCAGTGAA    3846
185P2C9v.2    CCCCATTGGGGTGGGGTCAGAGATGTGCAGGGAGGAAGGGGAGAGGGCACGCCAGTGAA    3628
185P2C9v.3    CCCCATTGGGGTGGGGTCAGAGATGTGCAGGGAGGAAGGGGAGAGGGCACGCCAGTGAA    3876
              ************************************************************

185P2C9v.1    GCAGGACTTATCTGCTCCCCCCTGGCTACACCCTCACTGAGAACGTGGCCCGGATCCTCAA    3906
185P2C9v.2    GCAGGACTTATCTGCTCCCCCCTGGCTACACCCTCACTGAGAACGTGGCCCGGATCCTCAA    3688
185P2C9v.3    GCAGGACTTATCTGCTCCCCCCTGGCTACACCCTCACTGAGAACGTGGCCCGGATCCTCAA    3936
              ************************************************************

185P2C9v.1    CAAGAAGCTGCTGGAACATGCCTTAAAGGAGGAGGAGGCAGGCTGCCCACGGCCCCC    3966
185P2C9v.2    CAAGAAGCTGCTGGAACATGCCTTAAAGGAGGAGGAGGCAGGCTGCCCACGGCCCCC    3748
185P2C9v.3    CAAGAAGCTGCTGGAACATGCCTTAAAGGAGGAGGAGGCAGGCTGCCCACGGCCCCC    3996
              ************************************************************

185P2C9v.1    GGGTCTCCACAGTGACAGCCACTCGCTGGGGACACAGCCGAGCCAGGCCCATGGAGAA    4026
185P2C9v.2    GGGTCTCCACAGTGACAGCCACTCGCTGGGGACACAGCCGAGCCAGGCCCATGGAG--    3806
185P2C9v.3    GGGTCTCCACAGTGACAGCCACTCGCTGGGGACACAGCCGAGCCAGGCCCATGGAG--    4054
              ******************************************************

185P2C9v.1    CCAAAACTGTCTTGCTAACTGCCCCCTGGGGACTCTAGCCCTGCCCCGCCTCACGCTGAACT    4086
185P2C9v.2    -------------------------------------------------------GAACT    3811
185P2C9v.3    -------------------------------------------------------GAACT    4059
                                                                     *****

185P2C9v.1    ACCTTGTTCTGCACTAGCTCCATCCCTAGAGCCCTGCTTCTCCAGGCCCGAGAGACCAGC    4146
185P2C9v.2    ACCTTGTTCTGCACTAGCTCCATCCCTAGAGCCCTGCTTCTCCAGGCCCGAGAGACCAGC    3871
185P2C9v.3    ACCTTGTTCTGCACTAGCTCCATCCCTAGAGCCCTGCTTCTCCAGGCCCGAGAGACCAGC    4119
              ************************************************************

185P2C9v.1    AAACCGTCGCCCTCCGTCCCCGTTGGGCCCCACATTCCCCACTGCCTCACAGCCTCAGTC    4206
185P2C9v.2    AAACCGTCGCCCTCCGTCCCCGTTGGGCCCCACATTCCCCACTGCCTCACAGCCTCAGTC    3931
185P2C9v.3    AAACCGTCGCCCTCCGTCCCCGTTGGGCCCCACATTCCCCACTGCCTCACAGCCTCAGTC    4179
              ************************************************************

185P2C9v.1    ACCCGGAGACCCGACGTCCTTGGAGGAGCATGTGGCGAGGAGCCGCCGAGGAGCAGCC    4266
185P2C9v.2    ACCCGGAGACCCGACGTCCTTGGAGGAGCATGTGGCGAGGAGCCGCCGAGGAGCAGCC    3991
185P2C9v.3    ACCCGGAGACCCGACGTCCTTGGAGGAGCATGTGGCGAGGAGCCGCCGAGGAGCAGCC    4239
              ************************************************************
```

Figure 13n (continued)

```
185P2C9v.1    ACACCGAGATGCAAGCTTGCATGGATTATCACAGTATAATTCACTGTAATTGCATAACC    4326
185P2C9v.2    ACACCGAGATGCAAGCTTGCATGGATTATCACAGTATAATTCACTGTAATTGCATAACC    4051
185P2C9v.3    ACACCGAGATGCAAGCTTGCATGGATTATCACAGTATAATTCACTGTAATTGCATAACC    4299
              ************************************************************

185P2C9v.1    ACACCATCACCATGAACAAAACTCGCCCAACAGGAGAGATCTAGTTTTCTCAAGGTCAA    4386
185P2C9v.2    ACACCATCACCATGAACAAAACTCGCCCAACAGGAGAGATCTAGTTTTCTCAAGGTCAA    4111
185P2C9v.3    ACACCATCACCATGAACAAAACTCGCCCAACAGGAGAGATCTAGTTTTCTCAAGGTCAA    4359
              ************************************************************

185P2C9v.1    AGAATGTTTTAAAAACACAAAGCTGCTGAATGTTCAACCTGTGAAACTGAGATGTTTC    4446
185P2C9v.2    AGAATGTTTTAAAAACACAAAGCTGCTGAATGTTCAACCTGTGAAACTGAGATGTTTC    4171
185P2C9v.3    AGAATGTTTTAAAAACACAAAGCTGCTGAATGTTCAACCTGTGAAACTGAGATGTTTC    4419
              ************************************************************

185P2C9v.1    TAGAATGAAACAGTAAATGTGCCTGTAATAACTTAATTTTTTCATAGCTCAGAAAACTA    4506
185P2C9v.2    TAGAATGAAACAGTAAATGTGCCTGTAATAACTTAATTTTTTCATAGCTCAGAAAACTA    4231
185P2C9v.3    TAGAATGAAACAGTAAATGTGCCTGTAATAACTTAATTTTTTCATAGCTCAGAAAACTA    4479
              ************************************************************

185P2C9v.1    TTTTTGTCTCCATCTTTTTTTACACACAGTATATTAAACGAAAAGGTAAATAAGGTATAAA    4566
185P2C9v.2    TTTTTGTCTCCATCTTTTTTTACACACAGTATATTAAACGAAAAGGTAAATAAGGTATAAA    4291
185P2C9v.3    TTTTTGTCTCCATCTTTTTTTACACACAGTATATTAAACGAAAAGGTAAATAAGGTATAAA    4539
              ************************************************************

185P2C9v.1    TAGATTTAAAAATAAAAGTTTTAAAAAATGTACATTTTAAGAGATTCTGAACACCCTCG    4626
185P2C9v.2    TAGATTTAAAAATAAAAGTTTTAAAAAATGTACATTTTAAGAGATTCTGAACACCCTCG    4351
185P2C9v.3    TAGATTTAAAAATAAAAGTTTTAAAAAATGTACATTTTAAGAGATTCTGAACACCCTCG    4599
              ************************************************************

185P2C9v.1    CTGTCAATACCTGACTGCCTCTGTTAAATTGCACTGTTACATTTTGGTTCAGTTTATTT    4686
185P2C9v.2    CTGTCAATACCTGACTGCCTCTGTTAAATTGCACTGTTACATTTTGGTTCAGTTTATTT    4411
185P2C9v.3    CTGTCAATACCTGACTGCCTCTGTTAAATTGCACTGTTACATTTTGGTTCAGTTTATTT    4659
              ************************************************************

185P2C9v.1    CCATGTTGAATTAGAGTGGATTAAGTTAATTTATTTTGTCACTGTTACTGTTTTTTACG    4746
185P2C9v.2    CCATGTTGAATTAGAGTGGATTAAGTTAATTTATTTTGTCACTGTTACTGTTTTTTACG    4471
185P2C9v.3    CCATGTTGAATTAGAGTGGATTAAGTTAATTTATTTTGTCACTGTTACTGTTTTTTACG    4719
              ************************************************************
```

Figure 13n (continued)

```
185P2C9v.1    AATTTTTTAATGCTTCAGACTGTCTGATTCAGTGAACTTTTTGTAGTGAAAAAGCCATGA    4806
185P2C9v.2    AATTTTTTAATGCTTCAGACTGTCTGATTCAGTGAACTTTTTGTAGTGAAAAAGCCATGA    4531
185P2C9v.3    AATTTTTTAATGCTTCAGACTGTCTGATTCAGTGAACTTTTTGTAGTGAAAAAGCCATGA    4779
              ************************************************************

185P2C9v.1    AGCCAGTAGACAAGACAGATATTCTGTATGCTGGAGGGATACAGGATGATTTGAAAAG     4866
185P2C9v.2    AGCCAGTAGACAAGACAGATATTCTGTATGCTGGAGGGATACAGGATGATTTGAAAAG     4591
185P2C9v.3    AGCCAGTAGACAAGACAGATATTCTGTATGCTGGAGGGATACAGGATGATTTGAAAAG     4839
              **********************************************************

185P2C9v.1    GTACAAAGTCCTCAGTGGGCTTAGAAAATTCACTGTATGATCCTTATATTATCCTACTTG    4926
185P2C9v.2    GTACAAAGTCCTCAGTGGGCTTAGAAAATTCACTGTATGATCCTTATATTATCCTACTTG    4651
185P2C9v.3    GTACAAAGTCCTCAGTGGGCTTAGAAAATTCACTGTATGATCCTTATATTATCCTACTTG    4899
              ************************************************************

185P2C9v.1    GCTTGCACGTCTTCGGGTGCATGTATATACCGCTACTGTGTCCTCCGCCATCACCTAAATG   4986
185P2C9v.2    GCTTGCACGTCTTCGGGTGCATGTATATACCGCTACTGTGTCCTCCGCCATCACCTAAATG   4711
185P2C9v.3    GCTTGCACGTCTTCGGGTGCATGTATATACCGCTACTGTGTCCTCCGCCATCACCTAAATG   4959
              ************************************************************

185P2C9v.1    TGACTCAGTCTGTTCCACTGTAATATGTTGTGAATTTCCTTGTACTGTACTTTTATTGTT    5046
185P2C9v.2    TGACTCAGTCTGTTCCACTGTAATATGTTGTGAATTTCCTTGTACTGTACTTTTATTGTT    4771
185P2C9v.3    TGACTCAGTCTGTTCCACTGTAATATGTTGTGAATTTCCTTGTACTGTACTTTTATTGTT    5019
              ************************************************************

185P2C9v.1    GGTCTTCTTGCATCGATGATCCAACAGCAACACCATTTTTAAATTATTGTGAAAAGATTA    5106
185P2C9v.2    GGTCTTCTTGCATCGATGATCCAACAGCAACACCATTTTTAAATTATTGTGAAAAGATTA    4831
185P2C9v.3    GGTCTTCTTGCATCGATGATCCAACAGCAACACCATTTTTAAATTATTGTGAAAAGATTA    5079
              ************************************************************

185P2C9v.1    ACTGGCAATGTACAGAGTTTACTCAGTTTCTTAAGGGAAAACACTACAAAAGTCAC      5166
185P2C9v.2    ACTGGCAATGTACAGAGTTTACTCAGTTTCTTAAGGGAAAACACTACAAAAGTCAC      4891
185P2C9v.3    ACTGGCAATGTACAGAGTTTACTCAGTTTCTTAAGGGAAAACACTACAAAAGTCAC      5139
              ********************************************************

185P2C9v.1    AAGGATACCAAATGGAAACACATGATGATGCCTCTGGGTCTGTGATGAGACCGTGATGAAG    5226
185P2C9v.2    AAGGATACCAAATGGAAACACATGATGATGCCTCTGGGTCTGTGATGAGACCGTGATGAAG    4951
185P2C9v.3    AAGGATACCAAATGGAAACACATGATGATGCCTCTGGGTCTGTGATGAGACCGTGATGAAG    5199
              **************************************************************
```

Figure 13n (continued)

```
185P2C9v.1        TAGAAATAAAGCCCTTCTGAGATGGC  5252
185P2C9v.2        TAGAAATAAAGCCCTTCTGAGATGGC  4977
185P2C9v.3        TAGAAATAAAGCCCTTCTGAGATGGC  5225
                  *************************
```

Figure 14n  Alignment of protein sequences of 185P2C9 transcript variants (SEQ ID NOS:48, 159, 160).

```
185P2C9v.1   MEDTRGQQEREGPGRDHAPSIPTSPFGDSLESSTELRRHLQFVEEEAELLRRSISEIEDH  60
185P2C9v.2   MEDTRGQQEREGPGRDHAPSIPTSPFGDSLESSTELRRHLQFVEEEAELLRRSISEIEDH  60
185P2C9v.3   MEDTRGQQEREGPGRDHAPSIPTSPFGDSLESSTELRRHLQFVEEEAELLRRSISEIEDH  60
             ************************************************************

185P2C9v.1   NRQLTHELSKFKFEPPREPGWLGEGASPGAGGGAPLQEELKSARLQISELSGKVLKLQHE  120
185P2C9v.2   NRQLTHELSKFKFEPPREPGWLGEGASPGAGGGAPLQEELKSARLQISELSGKVLKLQHE  120
185P2C9v.3   NRQLTHELSKFKFEPPREPGWLGEGASPGAGGGAPLQEELKSARLQISELSGKVLKLQHE  120
             ************************************************************

185P2C9v.1   NHALLSNIQRCDLAAHLGLRAPSPRDSDAESDAGKKESDGEESRLPQPKREGPVGGESDS  180
185P2C9v.2   NHALLSNIQRCDLAAHLGLRAPSPRDSDAESDAGKKESDGEESRLPQPKREGPVGGESDS  180
185P2C9v.3   NHALLSNIQRCDLAAHLGLRAPSPRDSDAESDAGKKESDGEESRLPQPKWEGPVGGESDS  180
             ************************************************** ********

185P2C9v.1   EEMFEKTSGFGSGKPSEASEPCPTELLKAREDSEYLVTLKHEAQRLERTVERLITDTDSF  240
185P2C9v.2   EEMFEKTSGFGSGKPSEASEPCPTELLKAREDSEYLVTLKHEAQRLERTVERLITDTDSF  240
185P2C9v.3   EEMFEKTSGFGSGKPSEASEPCPTELLKAREDSEYLVTLKHEAQRLERTVERLITDTDSF  240
             ************************************************************

185P2C9v.1   LHDAGLRGGAPLPGPGLQGEEEQGEGDQQEPQLLGTINAKMKAFKKELQAFLEQVNRIGD  300
185P2C9v.2   LHDAGLRGGAPLPGPGLQGEEEQGEGDQQEPQLLGTINAKMKAFKKELQAFLEQVNRIGD  300
185P2C9v.3   LHDAGLRGGAPLPGPGLQGEEEQGEGDQQEPQLLGTINAKMKAFKKELQAFLEQQVNRIGD  300
             ******************************************:*********

185P2C9v.1   GLSPLPHLITESSSFLSTVTSVSRDSPIGNLGKELGPDLQSRLKEQLEWQLGPARGDERES  360
185P2C9v.2   GLSPLPHLITESSSFLSTVTSVSRDSPIGNLGKELGPDLQSRLKEQLEWQLGPAQGDERES  360
185P2C9v.3   GLSPLPHLITESSSFLSTVTSVSRDSPIGNLGKELGPDLQSRLKEQLEWQLGPARGDERES  360
             *****************************************:*********
```

Figure 14n (continued)

```
185P2C9v.1      LRLRAARELHRRADGDTGSHGLGGQTCFSLEMEEHLYALRWKELEMHSLALQNTLHERT  420
185P2C9v.2      LRLRAARELHRRADGDTGSHGLGGQTCFSLEMEEHLYALRWKELEMHSLALQNTLHERT  420
185P2C9v.3      LRLRAARELHRRADGDTGSHGLGGQTCFSLEMEEHLYALRWKELEMHSLALQNTLHERT  420
                ***********************************************************

185P2C9v.1      WSDEKNLMQQELRSLKQNIFLFYVKLRWLLKHWRQGKQMEEGEEFTEGEHPETLSRLGE  480
185P2C9v.2      WSDEKNLMQQELRSLKQNIFLFYVKLRWLLKHWRQGKQMEEGEEFTEGEHPETLSRLGE  480
185P2C9v.3      WSDEKNLMQQELRSLKQNIFLFYVKLRWLLKHWRQGKQMEEGEEFTEGEHPETLSRLGE  480
                ***********************************************************

185P2C9v.1      LGVQGGHQADGPDHDSDRGCGFPVGEHSPHSRVQIGDHSLRLQTADRGQPHKQVVENQQL  540
185P2C9v.2      LGVQGGHQADGPDHDSDRGCGFPVGEHSPHSRVQIGDHSLRLQTADRGQPHKQVVENQQL  540
185P2C9v.3      LGVQGGHQADGPDHDSDRGCGFPVGEHSPHSRVQIGDHSLRLQTADRGQPHKQVVENQQL  540
                ***********************************************************

185P2C9v.1      FSAFKALLEDFRAELREDERARLRLQQQYASDKAAWDVEWAVLKCRLEQ----------  589
185P2C9v.2      FSAFKALLEDFRAELREDERARLRLQQQYASDKAAWDVEWAVLKCRLEQ----------  589
185P2C9v.3      FSAFKALLEDFRAELREDERARLRLQQQYASDKAAWDVEWAVLKCRLEQNCCGYPRINIE  600
                *************************************************

185P2C9v.1      ----------LEEKTENKLGELGSSAESKGALKKEREVHQKLL  622
185P2C9v.2      ----------LEEKTENKLGELGSSAESKGALKKEREVHQKLL  622
185P2C9v.3      EETLGFTRLPAGSTVKTLKSLGIQRLELEEKTENKLGELGSSAESKGALKKEREVHQKLL  660
                          ********************************

185P2C9v.1      ADSHSLVMDLRWQIHHSEKNWNREKVELLDRLDRDRQEWERQKKEFLWRIEQLQKENSPR  682
185P2C9v.2      ADSHSLVMDLRWQIHHSEKNWNREKVELLDRLDRDRQEWERQKKEFLWRIEQLQKENSPR  682
185P2C9v.3      ADSHSLVMDLRWQIHHSEKNWNREKVELLDRLDRDRQEWERQKKEFLWRIE--------  711
                ***************************************************

185P2C9v.1      RGGSFICDQKDGNVRPFPHQGSLRMPRPVAMWPCADADSIPFEDRPLSKLKESDRCSASE  742
185P2C9v.2      RGGSFICDQKDGNVRPFPHQGSLRMPRPVAMWPCADADSIPFEDRPLSKLKESDRCSASE  742
185P2C9v.3      --------QGSLRMPRPVAMWPCADADSIPFEDRPLSKLKESDRCSASE  752
                        *****************************************

185P2C9v.1      NLYLDALSLDDEPEEPPAHRPEREFRNRLPEEEENHKGNLQRAVSVSSMSEFQRLMDISP  802
185P2C9v.2      NLYLDALSLDDEPEEPPAHRPEREFRNRLPEEEENHKGNLQRAVSVSSMSEFQRLMDISP  802
185P2C9v.3      NLYLDALSLDDEPEEPPAHRPEREFRNRLPEEEENHKGNLQRAVSVSSMSEFQRLMDISP  812
                ***********************************************************
```

Figure 14n (continued)

```
185P2C9v.1    FLPEKGLPSTSSKEDVTPPLSPDDLKYIEEFNKSWDYTPNRGHNGGPDLWADRTEVGRA 862
185P2C9v.2    FLPEKGLPSTSSKEDVTPPLSPDDLKYIEEFNKSWDYTPNRGHNGGPDLWADRTEVGRA 862
185P2C9v.3    FLPEKGLPSTSSKEDVTPPLSPDDLKYIEEFNKSWDYTPNRGHNGGPDLWADRTEVGRA 872
              ************************************************************

185P2C9v.1    GHEDSTEPFPDSSWYLTTSVTMTTDTMTSPEHCQKQPLRSHVLTEQSGLRVLHSPPAVRR 922
185P2C9v.2    GHEDSTEPFPDSSWYLTTSVTMTTDTMTSPEHCQKQPLRSHVLTEQSGLRVLHSPPAVRR 922
185P2C9v.3    GHEDSTEPFPDSSWYLTTSVTMTTDTMTSPEHCQKQPLRSHVLTEQSGLRVLHSPPAVRR 932
              ************************************************************

185P2C9v.1    VDSITAAGGEGFPTSRARGSPGDTKGGPPEPMLSRWPCTSPRHSRDYVEGARRPLDSPL 982
185P2C9v.2    VDSITAAGGEGFPTSRARGSPGDTKGGPPEPMLSRWPCTSPRHSRDYVEGARRPLDSPL 982
185P2C9v.3    VDSITAAGGEGFPTSRARGSPGDTKGGPPEPMLSRWPCTSPRHSRDYVEGARRPLDSPL 992
              ************************************************************

185P2C9v.1    CTSLGFASPLHSLEMSKNLSDDMKEVAFSVRNAICSGPGELQVKDMACQTNGSRTMGTQT 1042
185P2C9v.2    CTSLGFASPLHSLEMSKNLSDDMKEVAFSVRNAICSGPGELQVKDMACQTNGSRTMGTQT 1042
185P2C9v.3    CTSLGFASPLHSLEMSKNLSDDMKEVAFSVRNAICSGPGELQVKDMACQTNGSRTMGTQT 1052
              ************************************************************

185P2C9v.1    VQTISVGLQTEALRGSGVTSSPHKCLTPKAGGATPVSSPSRSLRSRQVAPAIEKVQAKF 1102
185P2C9v.2    VQTISVGLQTEALRGSGVTSSPHKCLTPKAGGATPVSSPSRSLRSRQVAPAIEKVQAKF 1102
185P2C9v.3    VQTISVGLQTEALRGSGVTSSPHKCLTPKAGGATPVSSPSRSLRSRQVAPAIEKVQAKF 1112
              ************************************************************

185P2C9v.1    ERTCCSPKYGSPKLQRKPLPKADQPNNRTSPGMAQKGYSESAWARSTTTRESPVHTTIND 1162
185P2C9v.2    ERTCCSPKYGSPKLQRKPLPKADQPNN--------------------------------- 1129
185P2C9v.3    ERTCCSPKYGSPKLQRKPLPKADQPNNRTSPGMAQKGYSESAWARSTTTRESPVHTTIND 1172
              ***************************

185P2C9v.1    GLSSLFNIIDHSPVVQDPFQKGLRAGSRSRSAEPRPELGPGQETGTNSRGRSPSPIGVGS 1222
185P2C9v.2    -----------------------RPGNR-------------------------------- 1134
185P2C9v.3    GLSSLFNIIDHSPVVQDPFQKGLRAGSRSRSAEPRPELGPGQETGTNSRGRSPSPIGVGS 1232
                                     *.*.*

185P2C9v.1    EMCREEGGEGTPVKQDLSAPPGYTLTENVARILNKKLLEHALKEERRQAAHGPPGLHSDS 1282
185P2C9v.2    ------------HQFPRKVA---------------------------------------- 1142
185P2C9v.3    EMCREEGGEGTPVKQDLSAPPGYTLTENVARILNKKLLEERRQAAHGPPGLHSDS 1292
                          : :..:**
```

Figure 14n (continued)

```
185P2C9v.1      HSLGDTAEPGPMENQTVLITAP---------------------------------- 1304
185P2C9v.2      ------------------------------------------------------- 
185P2C9v.3      HSLGDTAEPGPMEELPCSALAPSLEPCFSRPERPANRPPSRWAPHSPTASQPQSPGDPT 1352

185P2C9v.1      -------WGL------ 1307
185P2C9v.2      ---------------
185P2C9v.3      SLEEHGGEEPPEEQPHRDASLHGLSQYNSL 1382
```

Figure 11o   Nucleotide sequences of transcript variants of 185P3C2
>185P3C2 v.2 (SEQ ID NO:161).

```
acaactgtct gctgcgcccg aaaaacaagt cggtgcgctg gggacccggg gccggggccg   60
ccttactccg gcctagcccc gcggccctcg gtgcgggctc cagggcatgc tcggtacccc  120
cgcggctcc  agcccagacg ccccggcctc agaaatcgcc cggaaatggg agcttgcgcg  180
aaggctgat  cggcccgctg gggaagctca tggacccgcg ctccctgccg ccctcgact   240
ctgaagatct cttccaggat ctaagtcact tccaggagac gtggctcgct gaagctcagg  300
taccagacag tgatgagcag tttgttcctg atttccattc agaaaaccta gctttccaca  360
gcccaccac  caggatcaag aaggagcccc agagtcccg  cacagacccg gcccgtcct   420
gcagcaggaa gccgccactc ccctaccacc atgcgagca  gtgccttta  tccagtgcct  480
atgacccccc cagacaaatc gccatcaagt ccctgcccc  tggtgccctt ggacagtcgc  540
ccctacagcc ctttcccggg gcagagcaac ggaatttcct gagatcctct ggcacctccc  600
agcccacccg tggccatggg tacctcgggg aacatagctc cgtcttccag cagccccctgg 660
acatttgcca ctccttcaca tctcaggagg gggccggga  acccctccca gcccctacc   720
acaccagct  gtcggagccc tgcccaccct atccccagca gagcttaag  caagaatacc  780
atgatccct  gtatgaacag gcgggccagc cagccgtgga ccaggtggg  gtcaatgggc  840
acaggtaccc agggcgggg  gtggtgatca aacaggaaca gacggactc  gcctacgact  900
cagatgtcac cgggtgcgca tcaattgtacc tccacacaga gaagcttctct gggccctctc  960
caggtgacgg ggccatggc  tatgctatg  agaaacctct gcgaccattc ccagatgatg 1020
tctgcttgt  ccctgagaaa tttgaaggag acatcaagca ggaaggggtc ggtgcattte 1080
gagagggcc  gccctaccag cgccggggtg cgctcgctcc cctgcagct  gtggcaattt ctggtgcct 1140
tgctggatga cccaacaaat gcccatttca ttgcctggac tctgggggga atggagttca 1200
agctcattga gctgaggag  gtcgccaggc gtcgtacaagt ttgtgtga  gcccgaggcc atcatgccaa 1260
tgaattacga caagctgagc cgctcgctcc gatactatta ttgtgtgtga gcccgaggcc ctcttctctt 1320
aggtggctgg tgagcgttac gtgtacaagt ctcaagctc  tcaaggctga gtttgaccgg cctgtcagtg 1380
tggccttccc gggacaatcag cgtccagctc atgagcccc gcctacctc  ccagagctga 1440
aggaggacac agtcccttg  tccacttgg  atgagagccc cgcctactc  ccagagctga 1500
ctggccccgc ccagccattt ggccccaagg gtggctactc ttactagccc ccagcggctg 1560
```

Figure 11o (continued)

```
ttcccctgc cgcagtgtgg tgctgccctg tgtacatata aatgaatctg gtgttgggga  1620
aaccttcatc tgaaaccgac agatgtctct gggcagatc cccactgtcc taccagttgc  1680
cctagcccag actctgagct gctcaccgga gtcattggga aggaaaagtg gagaaatggc  1740
aagtctagag tccctgggg gtttcacctg ggccctggag gaattcagct  1800
cagcttcttc ctaggtccaa gcccccaca ccttttcccc aaccacagag aacaagagtt  1860
tgttctgttc tggggacag agaaggcgct tcccaacttc atactggcag gagggtgagg  1920
aggttcactg agctcccag atctcccact gcgggagac agaagctgg actctgcccc  1980
acgctgtggc cctggaggat cccggtttgt cagttcttgg tgtctgtgt tcccagaggc  2040
agcggaggt tgaagaaagg aacctgggat gagggtgct gggtataagc agagaggat  2100
gggttcctgc tccaagggac cctttgcctt tcttctgccc tttcctaggc ccaggcctgg  2160
gtttgtactt ccacctccac cacatctgcc agaccttaat aaagccccc acttctccca  2220
tt                                                                 2222

>185P3C2 v.3 (SEQ ID NO:162).
acaactgtct gctgcgcccg aaaaacaagt cggtgcgctg gggacccggg gccggggccg    60
ccttactccg gcctagcccg gcgccctcg gtgcgggctg caggcatgc tcggtacccc    120
ccgcgctcc agcccagacg ccccggcctc agtctcggc cccgcttgg ggcccgcc     180
gtcggcgcg agggagcggc cggatgagc gaggatgaa agccggatac ttggaccagc     240
aagtgcccta caccttcagc agcaaatcgc ccggaaatgg gagcttgcgc gaagcgctga     300
tcggcccgct gggaagctc atgaccgg gctccctgcc gccctcgac tctgaagatc     360
tcttccagga tctaagtcac ttccaggaga cgtggctcgc tgaagctcag gtaccagaca     420
gtgatgagca gtttgttcct gatttccatt cagaaaaact agcttcccac agccccacca     480
ccaggatcaa gaaggagccc cagagtcccc gcacagaccc gccctgtcc tgcagcagga     540
agccgccact cccctaccac catgcgagc agtgccttta ctccagtgcc tatgaccccc     600
ccagacaaat cgccatcaag tccctgccc tggtgccct tggacagtcg ccctacagc     660
cctttcccg gcagagcaa cggaatttcc tgagatctc tggcacctcc cagccccacc     720
ctgccatgg gtacctcggg gaacatagat gtcaccgggt gcgcatcaat gtacctccac     780
acagagggct tctctgggcc ctctccagt gacggggcca tgggctatgg ctatgagaaa     840
cctctgcgac cattccagga tgatgtctgc gttgtcctg agaaatttga aggagacatc     900
aagcaggaag gggtcgtgc atttcgagag gggccgcct accagcgccg gggtgccctg     960
cagctgtggc aatttctggt ggccttgctg gatgaccaa caaatgccca tttcattgcc    1020
tgggggcc gggaatgga gttcaagctc attgagcctg aggagtcgc caggtctgg    1080
ggcatccaga agaaccgtga agccatgaat tacgacaagc tgagccgtc gctcgatac    1140
tattatgaga aagcatcat ctctttggcc tcagaagctg gctgtgagc gttacgtgta    1200
caagtttgtg    1200 tgtgagccg agccctcctt tcttggcc gacacagtcc ctttgtccca    1260
tgtgagccg agccctcctt ctctttggcc gacacagtcc ctttgtccca agctctcaag    1260
gctgagtttg accggcctgt cagtgaggag gctgctggc cccgcccagc cttgatgag    1320
agcccgcct acctcccaga gctgtcgc cccgccagc catttgccc caagggtggc    1380
tactcttact agccccagc ggctgttccc ctgccgcag gtgggtgctg ccctgtgtac    1440
atataaatga atctggtgtt ggggaaacct tcatctgaaa cccacagatg tctctggggc    1500
```

Figure 11o (continued)

```
agatccccac tgtcctacca gttgcctag cccagactct gagctgtca ccggagtcat 1560
tgggaaggaa aagtggagaa atgcaagtc cagctcagct tagagtctca gaaactcccc tggggtttc 1620
acctgggccc tggaggaatt cagctcagct tcttcctagg tccaagccc ccacaccttt 1680
tccccaacca cagagaacaa gagttgttc tgtctgggg gacagagaag gcgctccca 1740
acttcatact ggcaggaggg tgaggagtt cactgagctc ccagatctc caactgcggg 1800
gagacagaag cctgagctct gccccacgct gtggccctg agggtcccgg tttgtcagtt 1860
cttgtgctc tgtgttccca gaggcaggcg gaggttgaag aaaggaacct gggatgaggg 1920
gtgctggta taagcagaga gggatgggtt cctgctccaa gggaccctt gccttcttc 1980
tgcccttcc taggcccagg cctggtttg tacttccacc tccaccacat ctgccagacc 2040
ttaataaagg ccccccactc tcccatt 2067

>185P3C2 v.4 (SEQ ID NO:163).
acaactgtct gctgcgcccg aaaaacaagt cggtgcgctg gggacccgg gccggggccg 60
ccttactccg gcctagcccc gcgcccctcg gtgcgggctc caggcatgc tcggtacccc 120
ccgcggctcc agcccagacg cccgcctc agtctcggc cccgcttgg ggcccggcc 180
gtgcggcgcg agggagcggc cggatggagc ggaggatgaa agccggatac ttggaccagc 240
aagtgccta caccttcagc agcaaatgc ccggaaatgg gagcttgcgc gaagcgctga 300
tcggcccgct gggaagctc atgaaccgg gctccctgcc gccctcgac tctgaagatc 360
tcttccagga tctaagtcac ttccaggaga cgtgctgga cgtaagtcag gtaccagaca 420
gtgatgagca gtttgttcct gattccatt cagaaaacct agctttccac agcccacca 480
ccagatcaa gaaggagccc cagagtcccc gcacagaccc gccctgtcc tgcagcagga 540
agccgccact ccctaccac catgccgagc agtgcctta ctccagtgcc tatgacccc 600
ccagacaaat cgccatcaag tccctgccc ctggtgcct ctggacagtcg ccctacagc 660
cctttcccg ggcagagcaa cggaatttcc tgagatcctc tggcacctcc cagccccacc 720
ctggccatgg gtacctcggg gaacatagct cgtcttcca gcagcccctg gacatttgcc 780
actccttcac atctcaggga gggggccggg aacccctcc agagctttaa gcagaatac caacaccagc 840
tgtcgagcc ctgcccaccc tatcccacgc accaggtgg gtcaatggg cacaggtacc 900
tgtatgaaca gcggggccag ggtgtgatc aaacaggaac agacggactt cgctaagac tcagatgtca 960
caggggcggg atcaatgtac ctcacacag aggcttctc tggccctct ccaggctatg 1020
ccggtgcgc acctctgcga ccattcccag atgatgtctg cgttgtccct gagaaatttg 1080
gctatgagaa caagcaggaa gggtcggtg catttcgaga gggcgccc taccagcgcc 1140
aaggagacat caagctgtgg caatttctgg tggccttgct ggatgaccca acaaatgccc 1200
gggtgcct gcagctgtgg ctggacgggc cgggaatgg agttcaagct cattgagcct aggaggtcg 1260
atttcattgc ctggacgggc cggcatca cagccatgaa ttacgacaag ctgagccgct 1320
ccagcctg ggcatccag aagaaccgg accggcctg tctcttttgc cttccggac ggacacagtc cctttgtccc 1440
cgctccgata ctattatgag aaggcatca tctcttttgc cttccggac ggacacagtc cctttgtccc 1500
acaagtttgt gtgtgaggc ggctgagtt gaccggcctg tcagtgagga ggacacagtc cctttgtccc 1560
cagctctcaa ggctgagttt gaccggcctg tcagtgagga ggacacagtc cctttgtccc 1560
acttggatga gagcccccgc tacctcccag agctggctgg cccgcccag ccatttggcc 1620
```

Figure 11o (continued)

```
ccaagggtgg ctactcttac tagccccag tagcccccag cggctgttcc cctgcgca gtgggtgct 1680
gccctgtgta catataaatg aatctgtgt tgggaaacc ttcatctgaa accacagat 1740
gtctctgggg cagatcccca ctgtcctacc agttgccta gcccagactc tgagctgctc 1800
accggagtca ttggaagga aaagtggaga aatgcaagt ctagagtctc agaaactccc 1860
ctggggttt cacctggcc ctggaggaat tcagtcagc ttcttcctag gtccaagccc 1920
cccacacctt ttcccaacc acagagaaca agagtttgtt ctgttctggg ggacagagaa 1980
ggcgcttccc aacttcatac tggcaggagg gtgaggagt tcactgagct cccagatct 2040
cccactgcgg ggagacagaa gcctggactc tgcccacgc tgtggcctg gagggtcccg 2100
gtttgtcagt tctggtgct ctgtgttccc agagcaggc gaggttgaa gaaaggaacc 2160
tgggatgagg ggtgctgggt ataagcagag agggatgggt tcctgctcca agggaccctt 2220
tgccttctt ctgcccttc ctaggcccag gcctggttt gtacttccac ctccaccaca 2280
tctgccagac cttaataaag gccccactt ctcccatt 2318
```

>185P3C2 v.5 (SEQ ID NO:164).

```
acaactgtct gctgcgcccg aaaaacaagt cgtgcgctg gggacccggg gcggggccg 60
ccttactccg gcctagcccc gcggccctcg gtgcggctc caggcatgc tcgtactccc 120
ccgcggctcc agcccagacg cccggcctc agtctcggc cccgcttgg ggccgcttgg 180
gtgcggcgcg agggagcggc cgatgagc ggagatgaa agccggatac ttggaccagc 240
aagtgccta caccttcagc agcgtgagcg ccgcgccgg ctccacgccc gccaacgccc 300
gcaccagcc cctactctca ccacagcccc cctcccgca gtccagcgg agtcctgggc 360
tgccccgccc ctgagtcacc cgaggacccc aacctgtcc ccagaactgc gcgcctcagg 420
gtgactcgcg ggcattctcc ccgcttctcg cagaatcgc ccggaaatgg gagcttgcgc 480
gaagcgctga tcggccccgct gggaagctc atggaccgg gctccctgcc gcccctcgac 540
tctgaagatc tcttccagga tctaagtcac ttcaggaga ctggctcgc tgaagctcag 600
gtaccagaca gtgatgagca gttgttcctt gatttccatt cagaaaacct agctttccac 660
agcccacca ccaggatcaa gaaggagccc cagagtcccc gcacagaccc ggcctgtcc 720
tgcagcagga agccgccact ccctaccac catgggagc agtgccttta ctccagtgcc 780
tatgaccccc ccagacaaat cgccatgaag tcccctgccc ctgtgcccct tgacagtcg 840
ccctacagc cctttcccg ggcagagcaa cggaatttcc tgagatctc tgcaccctcc 900
cagcccacc ctggccatgg gtacctcggg gaacatagct cgtcttcca gcagcccctg 960
gacatttgcc actccttcac atctcaggga gggccggg aaccctccc agcccctac 1020
caacaccagc tgtcggagcc ctgccaccc tatcccagc agcttaa gcaagaatac 1080
catgatccc tgtatgaaca gcggggccag ccaggcgtgg accaggtgg ggtcaatgg 1140
cacagtacc caggggcgg gtggtgatc aaacaggaac agacgactt cgcctacgac 1200
tcagatgtca ccggtgcgc atcaatgtac ctccaacag aggcttctc tggccctct 1260
ccaggtgacg gggccatggg ctatggcat gagaaacctc tgcaccatt ccagatgat 1320
gtctgcgttg tccctgagaa atttgaagga gacatcaagc aggaagggt cggtgcattt 1380
cagaggggc cgcctacca gcgccgggt gccctgcagc tgtggcaatt tctggtgcc 1440
ttgctggatg accaacaaa tgcccatttc attgcctga cggccgggg aatggagttc 1500
```

Figure 11o (continued)

```
aagctcattg agcctgagga ggtcgcgagg ctctgggca tccagaagaa cggccagcc    1560
atgaattacg acaagctgag ccgctcgctc cgatactatt atgagaaagg catcatgcag  1620
aaggtggctg gtgagcgtta cgtgtacaag tttgtgtgtg agcccgaggc ctcttctct   1680
ttggccttcc cggacaatca gcgtccagct ctcaaggctg agtttgaccg gctgtcagt   1740
gaggaggaca cagtccctt gtcccacttg gatgagagcc ccgcctacct cccagagctg   1800
gctggcccg cccagccatt tggcccccaag gtggctact cttactagcc ccagcggct    1860
gtccccctg ccgcaggtgg gtgctgcct gtgtacatat aaatgaatct gtgttgggg    1920
aaaccttcat ctgaaaccca cagatgtctc tgggcagat ccccactgtc ctaccagttg   1980
ccctagccca gactctgagc tgctcaccgg agtcattggg aaggaaaagt ggagaaatgg   2040
caagtctaga gtctcagaaa ctcccctggg ggtttcacct gggccctgga ggaattcagc   2100
tcagcttctt cctaggtcca agccccccac accttttccc caaccacaga aacaagagt   2160
ttgttctgtt ctgggggaca gagaaggcgc ttcccaactt catactggca ggagggtgag   2220
gaggttcact gagctcccca gatctcccac tgcggggaga cagaagcctg gactctgccc   2280
cacgctgtgg ccctggaggg tcccggtttg tcagttcttg gtgctctgtg ttcccagagg   2340
caggcgagg ttgaagaaag gaactggga tgggggtgc tagggtataag cagagaggga   2400
tgggttcctg ctccaagga ccctgccct ttcctgcct ctttcctagg ccaggcctg     2460
ggtttgtact tccacctcca ccacatctgc cagacacttaa taaggccccc cacttctccc   2520
att                                                              2523
```

Figure 12o Protein sequences of transcript variants of 185P3C2

>185P3C2 v.2 (SEQ ID NO:165).

```
NCLLRPKNKS VRWGPGAGAA LLRPSPAALG AGSRACSVPP AAPAQTPRPQ KSPGNGSLRE   60
ALIGPLGKLM DPGSLPPLDS EDLFQDLSHF QETWLAEAQV PDSDEQFVPD FHSENLAFHS  120
PTTRIKKEPQ SPRTDPALSC SRKPPLPYHH GEQCLYSSAY DPPRQIAIKS PAPGALGQSP  180
LQPFPRAEQR NFLRSSGTSQ PHPGHGYLGE HSSVFQQPLD ICHSFTSQGG GREPLPAPYQ  240
HQLSEPCPPY PQQSFKQEYH DPLYEQAGQP AVDQGGVNGH RYPGAGVVIK QEQTDFAYDS  300
DVTGCASMYL HTEGFSGPSP GDGAMGYGYE KPLRPFPDDV CVVPEKFEGD IKQEGVGAFR  360
EGPPYQRRGA LQLWQFIVAL LDDPTNAHFI AWTGRGMEFK LIEPEEVARL WGIQKNRPAM  420
NYDKLSRSLR YYYEKGIMQK VAGERYVYKF VCEPEALFSL AFPDNQRPAL KAEFDRPVSE  480
EDTVPLSHLD ESPAYLPELA GPAQPFGPKG GYSY                             514
```

>185P3C2 v.3A (SEQ ID NO:166).

```
NCLLRPKNKS VRWGPGAGAA LLRPSPAALG AGSRACSVPP AAPAQTPRPQ VSAPAWGPGR   60
AARGSGRMER RMKAGYLDQQ VPYTFSSKSP GNGSLREALI GPLGKLMDPG SLPPLDSEDL  120
FQDLSHFQET WLAEAQVPDS DEQFVPDFHS ENLAFHSPTT RIKKEPQSPR TDPALSCSRK  180
PPLPYHHGEQ CLYSSAYDPP RQIAIKSPAP GALGQSPLQP FPRAEQRNFL RSSGTSQPHP  240
GHGYLGEHRC HRVRINVPPH RGLLWALSR                                   269
```

Figure 12o (continued)

```
>185P3C2 v.3B (SEQ ID NO 167).
MGTSGNIDVT GCASMYLHTE GFSGPSPGDG AMGYGYEKPL RPFPDDVCVV PEKFEGDIKQ      60
EGVGAFREGP PYQRRGALQL WQFLVALLDD PTNAHFIAWT GRGMEFKLIE PEEVARLWGI    120
QKNRPAMNYD KLSRSLRYYY EKGIMQKVAG ERYVYKFVCE PEALFSLAFP DNQRPALKAE    180
FDRPVSEEDT VPLSHLDESP AYLPELAGPA QPFGPKGGYS Y                        221

>185P3C2 v.4 (SEQ ID NO 168).
NCLLRPKNKS VRWGPGAGAA LLRPSPAALG AGSRACSVPP AAPAQTPRPQ VSAPAWGPGR     60
AARGSGRMER RMKAGYLDQQ VPYTFSSKSP GNGSLREALI GPLGKLMDPG SLPPLDSEDL    120
FQDLSHFQET WLAEAQVPDS DEQFVPDFHS ENLAFHSPTT RIKKEPQSPR TDPALSCSRK    180
PPLPYHHGEQ CLYSSAYDPP RQIAIKSPAP GALGQSPLQP FPRAEQRNFL RSSGTSQPHP    240
GHGYLGEHSS VFQQPLDICH SFTSQGGRE PLPAPYQHQL SEPCPPYPQQ SFKQEYHDPL     300
YEQAGQPAVD QGGVNGHRYP GAGVVIKQEQ TDFAYDSDVT GCASMYLHTE GFSGPSPGYG    360
YEKPLRPFPD DVCVVPEKFE GDIKQEGVGA FREGPPYQRR GALQLWQFLV ALLDDPTNAH    420
FIAWTGRGME FKLIEPEEVA RLWGIQKNRP AMNYDKLSRS LRYYYEKGIM QKVAGERYVY    480
KFVCEPEALF SLAFPDNQRP ALKAEFDRPV SEEDTVPLSH LDESPAYLPE LAGPAQPFGP    540
KGGYSY                                                              546

>185P3C2 v.5 (SEQ ID NO 169).
MDPGSLPPLD SEDLFQDLSH FQETWLAEAQ VPDSDEQFVP DFHSENLAFH SPTTRIKKEP     60
QSPRTDPALS CSRKPPLPYH HGEQCLYSSA YDPPRQIAIK SPAPGALGQS PLQPFPRAEQ    120
RNFLRSSGTS QPHPGHGYLG EHSSVFQQPL DICHSFTSQG GGREPLPAPY QHQLSEPCPP    180
YPQQSFKQEY HDPLYEQAGQ PAVDQGGVNG HRYPGAGVVI KQEQTDFAYD SDVTGCASMY    240
LHTEGFSGPS PGDGAMGYGY EKPLRPFPDD VCVVPEKFEG DIKQEGVGAF REGPPYQRRG    300
ALQLWQFLVA LLDDPTNAHF IAWTGRGMEF KLIEPEEVAR LWGIQKNRPA MNYDKLSRSL    360
RYYYEKGIMQ KVAGERYVYK FVCEPEALFS LAFPDNQRPA LKAEFDRPVS EEDTVPLSHL    420
DESPAYLPEL AGPAQPFGPK GGYSY                                          445
```

Figure 13o Alignment of nucleotide sequences of 185P3C2 transcript variants (SEQ ID NOS:53, 161, 162, 163, 164).

```
185P3C2v.1  ACAACTGTCTGCTGCGCCCGAAAAACAAGTCGGTGCGCTGGGACCCGGGGCGCGGGGCCG   60
185P3C2v.2  ACAACTGTCTGCTGCGCCCGAAAAACAAGTCGGTGCGCTGGGACCCGGGGCGCGGGGCCG   60
185P3C2v.3  ACAACTGTCTGCTGCGCCCGAAAAACAAGTCGGTGCGCTGGGACCCGGGGCGCGGGGCCG   60
185P3C2v.4  ACAACTGTCTGCTGCGCCCGAAAAACAAGTCGGTGCGCTGGGACCCGGGGCGCGGGGCCG   60
185P3C2v.5  ACAACTGTCTGCTGCGCCCGAAAAACAAGTCGGTGCGCTGGGACCCGGGGCGCGGGGCCG   60
            ************************************************************
```

Figure 13o (continued)

```
185P3C2v.1  CCTTACTCCGGCCTAGCCCCGGCCCCTCGGTCCGGGCTCCAGGGCATGCTCGGTACCCC  120
185P3C2v.2  CCTTACTCCGGCCTAGCCCCGGCCCCTCGGTGCGGGCTCCAGGGCATGCTCGGTACCCC  120
185P3C2v.3  CCTTACTCCGGCCTAGCCCCGGCCCCTCGGTGCGGGCATGCTCCAGGGCATGCTCGGTACCCC  120
185P3C2v.4  CCTTACTCCGGCCTAGCCCCGGCCCCTCGGTGCGGGCTCCAGGGCATGCTCGGTACCCC  120
185P3C2v.5  CCTTACTCCGGCCTAGCCCCGGCCCCTCGGTGCGGGCTCCAGGGCATGCTCGGTACCCC  120
            ************************************ ***********************

185P3C2v.1  CCGCGGCTCCAGCCCAGACGCCCCGGCTCTCAGGTCTCGGCCCCCGCTTGGGGCCCCGGCC  180
185P3C2v.2  CCGCGGCTCCAGCCCAGACGCCCCGGCCTCAG-----------------------------  152
185P3C2v.3  CCGCGGCTCCAGCCCAGACGCCCCGGCTCTCAGTCTCGGCCCCCCGCTTGGGGCCCCGGCC  180
185P3C2v.4  CCGCGGCTCCAGCCCAGACGCCCCGGCTCTCAGTCTCGGCCCCCCGCTTGGGGCCCCGGCC  180
185P3C2v.5  CCGCGGCTCCAGCCCAGACGCCCCGGCTCTCAGTCTCGGCCCCCCGCTTGGGGCCCCGGCC  180
            ****************************** *****

185P3C2v.1  GTGCGGCGCGAGGGAGCGGCCGGATGGAGCGGAGGATGAAAGCCGGATACTTGGACCAGC  240
185P3C2v.2  ------------------------------------------------------------
185P3C2v.3  GTGCGGCGCGAGGGAGCGGCCGGATGGAGCGGAGGATGAAAGCCGGATACTTGGACCAGC  240
185P3C2v.4  GTGCGGCGCGAGGGAGCGGCCGGATGGAGCGGAGGATGAAAGCCGGATACTTGGACCAGC  240
185P3C2v.5  GTGCGGCGCGAGGGAGCGGCCGGATGGAGCGGAGGATGAAAGCCGGATACTTGGACCAGC  240

185P3C2v.1  AAGTGCCCTACACCTTCAGCAGC-------------------------------------  263
185P3C2v.2  ------------------------------------------------------------
185P3C2v.3  AAGTGCCCTACACCTTCAGCAGC-------------------------------------  263
185P3C2v.4  AAGTGCCCTACACCTTCAGCAGC-------------------------------------  263
185P3C2v.5  AAGTGCCCTACACCTTCAGCAGCGTGAGCGCCTCCACGCCCGCCGCCCCGCCCCC       300

185P3C2v.1  ------------------------------------------------------------
185P3C2v.2  ------------------------------------------------------------
185P3C2v.3  ------------------------------------------------------------
185P3C2v.4  ------------------------------------------------------------
185P3C2v.5  GCACCCAGCCCCTACTCTCACCACAGCCCCCTCCCCGACTCCCAGCGGAGTCCTGGGC    360

```
185P3C2v.5   TGCCCCGCCCCTGAGTCACCGAGACCCGAACCTCGTCCCCAGACTAAGCGCCTCAGG  420

185P3C2v.1   ------------------------------------AAATCGCCCGGAAATGGGAGCTTGCGC  290
185P3C2v.2   ------------------------------------AAATCGCCCGGAAATGGGAGCTTGCGC  179
185P3C2v.3   ------------------------------------AAATCGCCCGGAAATGGGAGCTTGCGC  290
185P3C2v.4   ------------------------------------AAATCGCCCGGAAATGGGAGCTTGCGC  290
185P3C2v.5   GTGACTCGCGGGCATTCTCCCCGCTTCTCGCAGAAATCGCCCGGAAATGGGAGCTTGCGC  480
                                                 ***************************

185P3C2v.1   GAAGCGCTGATCGGCCCGCTGGGGAAGCTCATGACCCGGGCTCCCTGCCGCCCCTCGAC  350
185P3C2v.2   GAAGCGCTGATCGGCCCGCTGGGGAAGCTCATGACCCGGGCTCCCTGCCGCCCCTCGAC  239
185P3C2v.3   GAAGCGCTGATCGGCCCGCTGGGGAAGCTCATGACCCGGGCTCCCTGCCGCCCCTCGAC  350
185P3C2v.4   GAAGCGCTGATCGGCCCGCTGGGGAAGCTCATGACCCGGGCTCCCTGCCGCCCCTCGAC  350
185P3C2v.5   GAAGCGCTGATCGGCCCGCTGGGGAAGCTCATGACCCGGGCTCCCTGCCGCCCCTCGAC  540
             ************************************************************

185P3C2v.1   TCTGAAGATCTCTTCCAGGATCTAAGTCACTTCCAGGAGACGTGGCTCGCTGAAGCTCAG  410
185P3C2v.2   TCTGAAGATCTCTTCCAGGATCTAAGTCACTTCCAGGAGACGTGGCTCGCTGAAGCTCAG  299
185P3C2v.3   TCTGAAGATCTCTTCCAGGATCTAAGTCACTTCCAGGAGACGTGGCTCGCTGAAGCTCAG  410
185P3C2v.4   TCTGAAGATCTCTTCCAGGATCTAAGTCACTTCCAGGAGACGTGGCTCGCTGAAGCTCAG  410
185P3C2v.5   TCTGAAGATCTCTTCCAGGATCTAAGTCACTTCCAGGAGACGTGGCTCGCTGAAGCTCAG  600
             ************************************************************

185P3C2v.1   GTACCAGACAGTGATGAGCAGTTTGTTCCTGATTTCCATTCAGAAAAACCTAGCTTTCCAC  470
185P3C2v.2   GTACCAGACAGTGATGAGCAGTTTGTTCCTGATTTCCATTCAGAAAAACCTAGCTTTCCAC  359
185P3C2v.3   GTACCAGACAGTGATGAGCAGTTTGTTCCTGATTTCCATTCAGAAAAACCTAGCTTTCCAC  470
185P3C2v.4   GTACCAGACAGTGATGAGCAGTTTGTTCCTGATTTCCATTCAGAAAAACCTAGCTTTCCAC  470
185P3C2v.5   GTACCAGACAGTGATGAGCAGTTTGTTCCTGATTTCCATTCAGAAAAACCTAGCTTTCCAC  660
             ************************************************************

185P3C2v.1   AGCCCCACCACCAGGATCAAGAAGGAGCCCAGAGTCCCCGCACAGACCCGGCCCTGTCC  530
185P3C2v.2   AGCCCCACCACCAGGATCAAGAAGGAGCCCAGAGTCCCCGCACAGACCCGGCCCTGTCC  419
185P3C2v.3   AGCCCCACCACCAGGATCAAGAAGGAGCCCAGAGTCCCCGCACAGACCCGGCCCTGTCC  530
185P3C2v.4   AGCCCCACCACCAGGATCAAGAAGGAGCCCAGAGTCCCCGCACAGACCCGGCCCTGTCC  530
185P3C2v.5   AGCCCCACCACCAGGATCAAGAAGGAGCCCAGAGTCCCCGCACAGACCCGGCCCTGTCC  720
             ************************************************************

185P3C2v.1   TGCAGCAGGAAGCCGCACTCCCCTACCACCATGGCGAGCAGTGCCTTTACTCCAGTGCC  590
```

Figure 13o (continued)

```
185P3C2v.2   TGCAGCAGGAAGCCGCCACTCCCTACCACCATGGCGAGCAGTGCCTTTACTCCAGTGCC  479
185P3C2v.3   TGCAGCAGGAAGCCGCCACTCCCTACCACCATGGCGAGCAGTGCCTTTACTCCAGTGCC  590
185P3C2v.4   TGCAGCAGGAAGCCGCCACTCCCTACCACCATGGCGAGCAGTGCCTTTACTCCAGTGCC  590
185P3C2v.5   TGCAGCAGGAAGCCGCCACTCCCTACCACCATGGCGAGCAGTGCCTTTACTCCAGTGCC  780
             ************************************************************

185P3C2v.1   TATGACCCCCCAGACAAATCGCCATCAAGTCCCCTGCCCCTGGTGCCCTTGGACAGTCG  650
185P3C2v.2   TATGACCCCCCAGACAAATCGCCATCAAGTCCCCTGCCCCTGGTGCCCTTGGACAGTCG  539
185P3C2v.3   TATGACCCCCCAGACAAATCGCCATCAAGTCCCCTGCCCCTGGTGCCCTTGGACAGTCG  650
185P3C2v.4   TATGACCCCCCAGACAAATCGCCATCAAGTCCCCTGCCCCTGGTGCCCTTGGACAGTCG  650
185P3C2v.5   TATGACCCCCCAGACAAATCGCCATCAAGTCCCCTGCCCCTGGTGCCCTTGGACAGTCG  840
             ************************************************************

185P3C2v.1   CCCCTACAGCCCTTTCCCCGGGCAGAGAGCAACGAATTTCCTGAGATCCTCTGGCACCTCC  710
185P3C2v.2   CCCCTACAGCCCTTTCCCCGGGCAGAGAGCAACGAATTTCCTGAGATCCTCTGGCACCTCC  599
185P3C2v.3   CCCCTACAGCCCTTTCCCCGGGCAGAGAGCAACGAATTTCCTGAGATCCTCTGGCACCTCC  710
185P3C2v.4   CCCCTACAGCCCTTTCCCCGGGCAGAGAGCAACGAATTTCCTGAGATCCTCTGGCACCTCC  710
185P3C2v.5   CCCCTACAGCCCTTTCCCCGGGCAGAGAGCAACGAATTTCCTGAGATCCTCTGGCACCTCC  900
             ************************************************************

185P3C2v.1   CAGCCCCACCCTGGCCATGGTACCTCGGGAACATAGCTCCGTCTTCCAGCAGCCCTG  770
185P3C2v.2   CAGCCCCACCCTGGCCATGGTACCTCGGGAACATAGCTCCGTCTTCCAGCAGCCCTG  659
185P3C2v.3   CAGCCCCACCCTGGCCATGGTACCTCGGGAACATAG------------------------  748
185P3C2v.4   CAGCCCCACCCTGGCCATGGTACCTCGGGAACATAGCTCCGTCTTCCAGCAGCCCTG  770
185P3C2v.5   CAGCCCCACCCTGGCCATGGTACCTCGGGAACATAGCTCCGTCTTCCAGCAGCCCTG  960
             ***********************************

185P3C2v.1   GACATTTGCCACTCCTTCACATCTCAGGGAGGGGCCGGGAACCCCTCCAGCCCCCTAC  830
185P3C2v.2   GACATTTGCCACTCCTTCACATCTCAGGGAGGGGCCGGGAACCCCTCCAGCCCCCTAC  719
185P3C2v.3   ------------------------------------------------------------
185P3C2v.4   GACATTTGCCACTCCTTCACATCTCAGGGAGGGGCCGGGAACCCCTCCAGCCCCCTAC  830
185P3C2v.5   GACATTTGCCACTCCTTCACATCTCAGGGAGGGGCCGGGAACCCCTCCAGCCCCCTAC 1020

185P3C2v.1   CAACACCAGCTGTCGGAGCCCTGCCCACCCTATCCCCAGCAGAGCTTTAAGCAAGAATAC  890
185P3C2v.2   CAACACCAGCTGTCGGAGCCCTGCCCACCCTATCCCCAGCAGAGCTTTAAGCAAGAATAC  779
185P3C2v.3   ------------------------------------------------------------
185P3C2v.4   CAACACCAGCTGTCGGAGCCCTGCCCACCCTATCCCCAGCAGAGCTTTAAGCAAGAATAC  890
185P3C2v.5   CAACACCAGCTGTCGGAGCCCTGCCCACCCTATCCCCAGCAGAGCTTTAAGCAAGAATAC 1080
```

Figure 13o (continued)

```
185P3C2v.1  CATGATCCCCTGTATGAACAGGCGGGCCAGCCAGCCGTGGACCAGGTGGGGTCAATGGG  950
185P3C2v.2  CATGATCCCCTGTATGAACAGGCGGGCCAGCCAGCCGTGGACCAGGTGGGGTCAATGGG  839
185P3C2v.3  ------------------------------------------------------------
185P3C2v.4  CATGATCCCCTGTATGAACAGGCGGGCCAGCCAGCCGTGGACCAGGTGGGGTCAATGGG  950
185P3C2v.5  CATGATCCCCTGTATGAACAGGCGGGCCAGCCAGCCGTGGACCAGGTGGGGTCAATGGG  1140

185P3C2v.1  CACAGGTACCCAGGGGCGGGGGTGGTGGTGATCAAACAGGAACAGACGACTTCGCCTACGAC  1010
185P3C2v.2  CACAGGTACCCAGGGGCGGGGGTGGTGGTGATCAAACAGGAACAGACGACTTCGCCTACGAC  899
185P3C2v.3  ------------------------------------------------------------
185P3C2v.4  CACAGGTACCCAGGGGCGGGGGTGGTGGTGATCAAACAGGAACAGACGACTTCGCCTACGAC  1010
185P3C2v.5  CACAGGTACCCAGGGGCGGGGGTGGTGGTGATCAAACAGGAACAGACGACTTCGCCTACGAC  1200

185P3C2v.1  TCAGATGTCACCGGTGCGCATCAATGTACCTCCACACAGAGGGCTTCTCTGGGCCCTCT  1070
185P3C2v.2  TCAGATGTCACCGGTGCGCATCAATGTACCTCCACACAGAGGGCTTCTCTGGGCCCTCT  959
185P3C2v.3  ---ATGTCACCGGTGCGCATCAATGTACCTCCACACAGAGGGCTTCTCTGGGCCCTCT  804
185P3C2v.4  TCAGATGTCACCGGTGCGCATCAATGTACCTCCACACAGAGGGCTTCTCTGGGCCCTCT  1070
185P3C2v.5  TCAGATGTCACCGGTGCGCATCAATGTACCTCCACACAGAGGGCTTCTCTGGGCCCTCT  1260
               *************************************************

185P3C2v.1  CCAGGTGACGGGGCCATGGGCTATGGCTATGAGAAACCTCTGCGACCATTCCCAGATGAT  1130
185P3C2v.2  CCAGGTGACGGGGCCATGGGCTATGGCTATGAGAAACCTCTGCGACCATTCCCAGATGAT  1019
185P3C2v.3  CCAGG------------CTATGGCTATGAGAAACCTCTGCGACCATTCCCAGATGAT  864
185P3C2v.4  CCAGGTGACGGGGCCATGGGCTATGGCTATGAGAAACCTCTGCGACCATTCCCAGATGAT  1115
185P3C2v.5  CCAGGTGACGGGGCCATGGGCTATGGCTATGAGAAACCTCTGCGACCATTCCCAGATGAT  1320
               *****      ***********************************

185P3C2v.1  GTCTGCGTTGTCCCTGAGAAATTTGAAGGAGACATCAAGCAGGAAGGGGTCGGTGCATTT  1190
185P3C2v.2  GTCTGCGTTGTCCCTGAGAAATTTGAAGGAGACATCAAGCAGGAAGGGGTCGGTGCATTT  1079
185P3C2v.3  GTCTGCGTTGTCCCTGAGAAATTTGAAGGAGACATCAAGCAGGAAGGGGTCGGTGCATTT  924
185P3C2v.4  GTCTGCGTTGTCCCTGAGAAATTTGAAGGAGACATCAAGCAGGAAGGGGTCGGTGCATTT  1175
185P3C2v.5  GTCTGCGTTGTCCCTGAGAAATTTGAAGGAGACATCAAGCAGGAAGGGGTCGGTGCATTT  1380
               ************************************************

185P3C2v.1  CGAGAGGGGCCGCCCTACCAGCCGCCGCCCCTGCCCTGCAGCTGTGCCAGTTTCTGGTGGCC  1250
185P3C2v.2  CGAGAGGGGCCGCCCTACCAGCCGCCGCCCCTGCCCTGCAGCTGTGCCAGTTTCTGGTGGCC  1139
```

Figure 13o (continued)

```
185P3C2v.3    CGAGAGGGGCCGCCCTACCAGCGCCGCGGGTGCCCTGCAGCTGTGGCAATTTCTGGTGGCC    984
185P3C2v.4    CGAGAGGGGCCGCCCTACCAGCGCCGCGGGTGCCCTGCAGCTGTGGCAATTTCTGGTGGCC   1235
185P3C2v.5    CGAGAGGGGCCGCCCTACCAGCGCCGCGGGTGCCCTGCAGCTGTGGCAATTTCTGGTGGCC   1440
              ************************************************************

185P3C2v.1    TTGCTGGATGACCCAACAAATGCCCATTTCATTGCCTGGACGGGCCGGGAATGGAGTTC    1310
185P3C2v.2    TTGCTGGATGACCCAACAAATGCCCATTTCATTGCCTGGACGGGCCGGGAATGGAGTTC    1199
185P3C2v.3    TTGCTGGATGACCCAACAAATGCCCATTTCATTGCCTGGACGGGCCGGGAATGGAGTTC    1044
185P3C2v.4    TTGCTGGATGACCCAACAAATGCCCATTTCATTGCCTGGACGGGCCGGGAATGGAGTTC    1295
185P3C2v.5    TTGCTGGATGACCCAACAAATGCCCATTTCATTGCCTGGACGGGCCGGGAATGGAGTTC    1500
              ************************************************************

185P3C2v.1    AAGCTCATTGAGCCTGAGGAGGTCGCCAGGCTCGGGGCATCCAGAAGAACCGGCCAGCC    1370
185P3C2v.2    AAGCTCATTGAGCCTGAGGAGGTCGCCAGGCTCGGGGCATCCAGAAGAACCGGCCAGCC    1259
185P3C2v.3    AAGCTCATTGAGCCTGAGGAGGTCGCCAGGCTCGGGGCATCCAGAAGAACCGGCCAGCC    1104
185P3C2v.4    AAGCTCATTGAGCCTGAGGAGGTCGCCAGGCTCGGGGCATCCAGAAGAACCGGCCAGCC    1355
185P3C2v.5    AAGCTCATTGAGCCTGAGGAGGTCGCCAGGCTCGGGGCATCCAGAAGAACCGGCCAGCC    1560
              ************************************************************

185P3C2v.1    ATGAATTACGACAAGCTGAGCGCTGAGCGCCTCGCTCCGATACTATTATGAGAAAGGCATCATGCAG    1430
185P3C2v.2    ATGAATTACGACAAGCTGAGCGCTGAGCGCCTCGCTCCGATACTATTATGAGAAAGGCATCATGCAG    1319
185P3C2v.3    ATGAATTACGACAAGCTGAGCGCTGAGCGCCTCGCTCCGATACTATTATGAGAAAGGCATCATGCAG    1164
185P3C2v.4    ATGAATTACGACAAGCTGAGCGCTGAGCGCCTCGCTCCGATACTATTATGAGAAAGGCATCATGCAG    1415
185P3C2v.5    ATGAATTACGACAAGCTGAGCGCTGAGCGCCTCGCTCCGATACTATTATGAGAAAGGCATCATGCAG    1620
              ************************************************************

185P3C2v.1    AAGGTGGCTGGTGAGCGTTACGTTACGTGTACAAGTTTGTGTGTGAGCCCGAGCCCTCTTCTCT    1490
185P3C2v.2    AAGGTGGCTGGTGAGCGTTACGTTACGTGTACAAGTTTGTGTGTGAGCCCGAGCCCTCTTCTCT    1379
185P3C2v.3    AAGGTGGCTGGTGAGCGTTACGTTACGTGTACAAGTTTGTGTGTGAGCCCGAGCCCTCTTCTCT    1224
185P3C2v.4    AAGGTGGCTGGTGAGCGTTACGTTACGTGTACAAGTTTGTGTGTGAGCCCGAGCCCTCTTCTCT    1475
185P3C2v.5    AAGGTGGCTGGTGAGCGTTACGTTACGTGTACAAGTTTGTGTGTGAGCCCGAGCCCTCTTCTCT    1680
              ************************************************************

185P3C2v.1    TTGGCCTTCCCGGACAATCAGCTCCAGCTCTCAAGGCTCGAGTTTGACCGGCCTGTCAGT    1550
185P3C2v.2    TTGGCCTTCCCGGACAATCAGCTCCAGCTCTCAAGGCTCGAGTTTGACCGGCCTGTCAGT    1439
185P3C2v.3    TTGGCCTTCCCGGACAATCAGCTCCAGCTCTCAAGGCTCGAGTTTGACCGGCCTGTCAGT    1284
185P3C2v.4    TTGGCCTTCCCGGACAATCAGCTCCAGCTCTCAAGGCTCGAGTTTGACCGGCCTGTCAGT    1535
185P3C2v.5    TTGGCCTTCCCGGACAATCAGCTCCAGCTCTCAAGGCTCGAGTTTGACCGGCCTGTCAGT    1740
              ************************************************************
```

Figure 13o (continued)

```
185P3C2v.1    GAGGAGGACACAGTCCCTTTGTCCCACTTGGATGAGAGCCCCGCCTACCTCCCAGAGCTG  1610
185P3C2v.2    GAGGAGGACACAGTCCCTTTGTCCCACTTGGATGAGAGAGCCCCGCCTACCTCCCAGAGCTG 1499
185P3C2v.3    GAGGAGGACACAGTCCCTTTGTCCCACTTGGATGAGAGAGCCCCGCCTACCTCCCAGAGCTG 1344
185P3C2v.4    GAGGAGGACACAGTCCCTTTGTCCCACTTGGATGAGAGAGCCCCGCCTACCTCCCAGAGCTG 1595
185P3C2v.5    GAGGAGGACACAGTCCCTTTGTCCCACTTGGATGAGAGAGCCCCGCCTACCTCCCAGAGCTG 1800
              ************************************* ********************

185P3C2v.1    GCTGGCCCCGCCCCAGCCATTTGGCCCCAAGGGTGGCTACTCTTACTAGCCCCAGCGGCT  1670
185P3C2v.2    GCTGGCCCCGCCCCAGCCATTTGGCCCCAAGGGTGGCTACTCTTACTAGCCCCAGCGGCT  1559
185P3C2v.3    GCTGGCCCCGCCCCAGCCATTTGGCCCCAAGGGTGGCTACTCTTACTAGCCCCAGCGGCT  1404
185P3C2v.4    GCTGGCCCCGCCCCAGCCATTTGGCCCCAAGGGTGGCTACTCTTACTAGCCCCAGCGGCT  1655
185P3C2v.5    GCTGGCCCCGCCCCAGCCATTTGGCCCCAAGGGTGGCTACTCTTACTAGCCCCAGCGGCT  1860
              ************************************************************

185P3C2v.1    GTTCCCCTGCCGCAGGTGGGTGCTGCCCCTGTGTACATATAAATGAATCTGGTGTTGGGG  1730
185P3C2v.2    GTTCCCCTGCCGCAGGTGGGTGCTGCCCCTGTGTACATATAAATGAATCTGGTGTTGGGG  1619
185P3C2v.3    GTTCCCCTGCCGCAGGTGGGTGCTGCCCCTGTGTACATATAAATGAATCTGGTGTTGGGG  1464
185P3C2v.4    GTTCCCCTGCCGCAGGTGGGTGCTGCCCCTGTGTACATATAAATGAATCTGGTGTTGGGG  1715
185P3C2v.5    GTTCCCCTGCCGCAGGTGGGTGCTGCCCCTGTGTACATATAAATGAATCTGGTGTTGGGG  1920
              ************************************************************

185P3C2v.1    AAACCTTCATCTGAAACCACACAGATGTCTCTGGGGCAGATCCCCACTGTCCTACCAGTTG 1790
185P3C2v.2    AAACCTTCATCTGAAACCACACAGATGTCTCTGGGGCAGATCCCCACTGTCCTACCAGTTG 1679
185P3C2v.3    AAACCTTCATCTGAAACCACACAGATGTCTCTGGGGCAGATCCCCACTGTCCTACCAGTTG 1524
185P3C2v.4    AAACCTTCATCTGAAACCACACAGATGTCTCTGGGGCAGATCCCCACTGTCCTACCAGTTG 1775
185P3C2v.5    AAACCTTCATCTGAAACCACACAGATGTCTCTGGGGCAGATCCCCACTGTCCTACCAGTTG 1980
              ************************************************************

185P3C2v.1    CCCTAGCCCAGACTCTGAGCTGCTCACCGAGTCATTGGGAAGGAAAAGTGGAGAAATGG   1850
185P3C2v.2    CCCTAGCCCAGACTCTGAGCTGCTCACCGAGTCATTGGGAAGGAAAAGTGGAGAAATGG   1739
185P3C2v.3    CCCTAGCCCAGACTCTGAGCTGCTCACCGAGTCATTGGGAAGGAAAAGTGGAGAAATGG   1584
185P3C2v.4    CCCTAGCCCAGACTCTGAGCTGCTCACCGAGTCATTGGGAAGGAAAAGTGGAGAAATGG   1835
185P3C2v.5    CCCTAGCCCAGACTCTGAGCTGCTCACCGAGTCATTGGGAAGGAAAAGTGGAGAAATGG   2040
              ************************************************************

185P3C2v.1    CAAGTCTAGAGTCTCAGAAACTCCCCTGGGGGTTTCACCTGGCCCTGGAGGAATTCAGC   1910
185P3C2v.2    CAAGTCTAGAGTCTCAGAAACTCCCCTGGGGGTTTCACCTGGCCCTGGAGGAATTCAGC   1799
185P3C2v.3    CAAGTCTAGAGTCTCAGAAACTCCCCTGGGGGTTTCACCTGGCCCTGGAGGAATTCAGC   1644
185P3C2v.4    CAAGTCTAGAGTCTCAGAAACTCCCCTGGGGGTTTCACCTGGCCCTGGAGGAATTCAGC   1895
```

Figure 13o (continued)

```
185P3C2v.5      CAAGTCTAGAGTCTCAGAAACTCCCCTGGGGGTTTCACCTGGGCCCTGGAGGAATTCAGC  2100
                ************************************************************

185P3C2v.1      TCAGCTTCTTCCTAGTCCAAGCCCCCCACACCTTTTCCCCAACCACAGAGAACAAGAGT  1970
185P3C2v.2      TCAGCTTCTTCCTAGTCCAAGCCCCCCACACCTTTTCCCCAACCACAGAGAACAAGAGT  1859
185P3C2v.3      TCAGCTTCTTCCTAGTCCAAGCCCCCCACACCTTTTCCCCAACCACAGAGAACAAGAGT  1704
185P3C2v.4      TCAGCTTCTTCCTAGTCCAAGCCCCCCACACCTTTTCCCCAACCACAGAGAACAAGAGT  1955
185P3C2v.5      TCAGCTTCTTCCTAGTCCAAGCCCCCCACACCTTTTCCCCAACCACAGAGAACAAGAGT  2160
                ************************************************************

185P3C2v.1      TTGTTCTGTTCTGGGGACAGAGAAGGCGCTTCCCAACTTCATACTGGCAGGAGGGTGAG  2030
185P3C2v.2      TTGTTCTGTTCTGGGGACAGAGAAGGCGCTTCCCAACTTCATACTGGCAGGAGGGTGAG  1919
185P3C2v.3      TTGTTCTGTTCTGGGGACAGAGAAGGCGCTTCCCAACTTCATACTGGCAGGAGGGTGAG  1764
185P3C2v.4      TTGTTCTGTTCTGGGGACAGAGAAGGCGCTTCCCAACTTCATACTGGCAGGAGGGTGAG  2015
185P3C2v.5      TTGTTCTGTTCTGGGGACAGAGAAGGCGCTTCCCAACTTCATACTGGCAGGAGGGTGAG  2220
                ************************************************************

185P3C2v.1      GAGGTTCACTGAGCTCCCCAGATCTCCCACTGCGGGAGACAGAAGCCTGGACTCTGCCC  2090
185P3C2v.2      GAGGTTCACTGAGCTCCCCAGATCTCCCACTGCGGGAGACAGAAGCCTGGACTCTGCCC  1979
185P3C2v.3      GAGGTTCACTGAGCTCCCCAGATCTCCCACTGCGGGAGACAGAAGCCTGGACTCTGCCC  1824
185P3C2v.4      GAGGTTCACTGAGCTCCCCAGATCTCCCACTGCGGGAGACAGAAGCCTGGACTCTGCCC  2075
185P3C2v.5      GAGGTTCACTGAGCTCCCCAGATCTCCCACTGCGGGAGACAGAAGCCTGGACTCTGCCC  2280
                ************************************************************

185P3C2v.1      CACGCTGTGGCCCTGGAGGGTCCCGGTTGTCAGTTCTTGGTCTCTGTCTCTGTTCCCAGAGG  2150
185P3C2v.2      CACGCTGTGGCCCTGGAGGGTCCCGGTTGTCAGTTCTTGGTCTCTGTCTCTGTTCCCAGAGG  2039
185P3C2v.3      CACGCTGTGGCCCTGGAGGGTCCCGGTTGTCAGTTCTTGGTCTCTGTCTCTGTTCCCAGAGG  1884
185P3C2v.4      CACGCTGTGGCCCTGGAGGGTCCCGGTTGTCAGTTCTTGGTCTCTGTCTCTGTTCCCAGAGG  2135
185P3C2v.5      CACGCTGTGGCCCTGGAGGGTCCCGGTTGTCAGTTCTTGGTCTCTGTCTCTGTTCCCAGAGG  2340
                ************************************************************

185P3C2v.1      CAGGCGGAGGTTGAAGAAAGGAACCTGGGATGAGGGGTGCTGGGTATAAGCAGAGAGGGA  2210
185P3C2v.2      CAGGCGGAGGTTGAAGAAAGGAACCTGGGATGAGGGGTGCTGGGTATAAGCAGAGAGGGA  2099
185P3C2v.3      CAGGCGGAGGTTGAAGAAAGGAACCTGGGATGAGGGGTGCTGGGTATAAGCAGAGAGGGA  1944
185P3C2v.4      CAGGCGGAGGTTGAAGAAAGGAACCTGGGATGAGGGGTGCTGGGTATAAGCAGAGAGGGA  2195
185P3C2v.5      CAGGCGGAGGTTGAAGAAAGGAACCTGGGATGAGGGGTGCTGGGTATAAGCAGAGAGGGA  2400
                ************************************************************

185P3C2v.1      TGGGTTCCTGCTCCAAGGGACCCCTTTGCCTTTCTTCTGCCCTTTCCTAGGCCCAGGCCTG  2270
```

Figure 13o (continued)

```
185P3C2v.2   TGGGTTCCTGCTCCAAGGGAGACCCTTTGCCTTTCTCTGCCCTTTCCTAGGCCCAGGCCTG  2159
185P3C2v.3   TGGGTTCCTGCTCCAAGGGAGACCCTTTGCCTTTCTCTGCCCTTTCCTAGGCCCAGGCCTG  2004
185P3C2v.4   TGGGTTCCTGCTCCAAGGGAGACCCTTTGCCTTTCTCTGCCCTTTCCTAGGCCCAGGCCTG  2255
185P3C2v.5   TGGGTTCCTGCTCCAAGGGAGACCCTTTGCCTTTCTCTGCCCTTTCCTAGGCCCAGGCCTG  2460
             ************************************************************

185P3C2v.1   GGTTTGTACTTCCACCTCCACCACATCTGCCAGACCTTAATAAAGGCCCCCACTTCTCCC   2330
185P3C2v.2   GGTTTGTACTTCCACCTCCACCACATCTGCCAGACCTTAATAAAGGCCCCCACTTCTCCC   2219
185P3C2v.3   GGTTTGTACTTCCACCTCCACCACATCTGCCAGACCTTAATAAAGGCCCCCACTTCTCCC   2064
185P3C2v.4   GGTTTGTACTTCCACCTCCACCACATCTGCCAGACCTTAATAAAGGCCCCCACTTCTCCC   2315
185P3C2v.5   GGTTTGTACTTCCACCTCCACCACATCTGCCAGACCTTAATAAAGGCCCCCACTTCTCCC   2520
             ************************************************************

185P3C2v.1   ATT  2333
185P3C2v.2   ATT  2222
185P3C2v.3   ATT  2067
185P3C2v.4   ATT  2318
185P3C2v.5   ATT  2523
             ***
```

Figure 14o   Alignment of protein sequences of 185P3C2 transcript variants
(SEQ ID NOS:54, 165, 166, 167, 168, 169).

```
185P3C2v.1    NCLLRPKNKSVRWGPGAGAALLRPSPAALGAGSRACSVPPAAPAQTPRPQVSAPAWGPGR  60
185P3C2v.2    NCLLRPKNKSVRWGPGAGAALLRPSPAALGAGSRACSVPPAAPAQTPRP----------  49
185P3C2v.3A   NCLLRPKNKSVRWGPGAGAALLRPSPAALGAGSRACSVPPAAPAQTPRPQVSAPAWGPGR  60
185P3C2v.3B   ------------------------------------------------------------
185P3C2v.4    NCLLRPKNKSVRWGPGAGAALLRPSPAALGAGSRACSVPPAAPAQTPRPQVSAPAWGPGR  60
185P3C2v.5    ------------------------------------------------------------

185P3C2v.1    AARGSGRMERRMKAGYLDQQVPYTFSSKSPGNGSLREALIGPLGKLMDPGSLPPLDSEDL  120
185P3C2v.2    ----------------------QKSPGNGSLREALIGPLGKLMDPGSLPPLDSEDL   83
185P3C2v.3A   AARGSGRMERRMKAGYLDQQVPYTFSSKSPGNGSLREALIGPLGKLMDPGSLPPLDSEDL  120
185P3C2v.3B   ------------------------------------------------------------
185P3C2v.4    AARGSGRMERRMKAGYLDQQVPYTFSSKSPGNGSLREALIGPLGKLMDPGSLPPLDSEDL  120
185P3C2v.5    --MDPGSLPPLDSEDL   14
                                                            ***************
```

Figure 14o (continued)

```
185P3C2v.1    FQDLSHFQETWLAEAQVPDSDEQFVPDFHSENLAFHSPTTRIKKEPQSPRTDPALSCSRK    180
185P3C2v.2    FQDLSHFQETWLAEAQVPDSDEQFVPDFHSENLAFHSPTTRIKKEPQSPRTDPALSCSRK    143
185P3C2v.3A   FQDLSHFQETWLAEAQVPDSDEQFVPDFHSENLAFHSPTTRIKKEPQSPRTDPALSCSRK    180
185P3C2v.3B   ------------------------------------------------------------
185P3C2v.4    FQDLSHFQETWLAEAQVPDSDEQFVPDFHSENLAFHSPTTRIKKEPQSPRTDPALSCSRK    180
185P3C2v.5    FQDLSHFQETWLAEAQVPDSDEQFVPDFHSENLAFHSPTTRIKKEPQSPRTDPALSCSRK    74
                                                                          ************************************************************

185P3C2v.1    PPLPYHHGEQCLYSSAYDPPRQIAIKSPAPGALGQSPLQPFPRAEQRNFLRSSGTSQPHP    240
185P3C2v.2    PPLPYHHGEQCLYSSAYDPPRQIAIKSPAPGALGQSPLQPFPRAEQRNFLRSSGTSQPHP    203
185P3C2v.3A   PPLPYHHGEQCLYSSAYDPPRQIAIKSPAPGALGQSPLQPFPRAEQRNFLRSSGTSQPHP    240
185P3C2v.3B   ------------------------------------------------------MGTSG-    5
185P3C2v.4    PPLPYHHGEQCLYSSAYDPPRQIAIKSPAPGALGQSPLQPFPRAEQRNFLRSSGTSQPHP    240
185P3C2v.5    PPLPYHHGEQCLYSSAYDPPRQIAIKSPAPGALGQSPLQPFPRAEQRNFLRSSGTSQPHP    134
                                                                          ************************************************************

185P3C2v.1    GHGYLGEHSSVFQQPLDICHSFTSQGGGREPLPAPYQHLSEPCPPYPQQSFKQEYHDPL    300
185P3C2v.2    GHGYLGEHSSVFQQPLDICHSFTSQGGGREPLPAPYQHLSEPCPPYPQQSFKQEYHDPL    263
185P3C2v.3A   GHGYLGEHR----------CHRVR------------------------------------    254
185P3C2v.3B   ------------------------------------------------------------
185P3C2v.4    GHGYLGEHSSVFQQPLDICHSFTSQGGGREPLPAPYQHLSEPCPPYPQQSFKQEYHDPL    300
185P3C2v.5    GHGYLGEHSSVFQQPLDICHSFTSQGGGREPLPAPYQHLSEPCPPYPQQSFKQEYHDPL    194
              *********        *     *   .

185P3C2v.1    YEQAGQPAVDQGGVNGHRYPGAGVVIKQEQTDFAYDSDVTGCASMYLHTEGFSGPSPGDG    360
185P3C2v.2    YEQAGQPAVDQGGVNGHRYPGAGVVIKQEQTDFAYDSDVTGCASMYLHTEGFSGPSPGDG    323
185P3C2v.3A   --------------IN--------------------------------------------    256
185P3C2v.3B   -----------------------------NIDVTGCASMYLHTEGFSGPSPGDG         30
185P3C2v.4    YEQAGQPAVDQGGVNGHRYP-----GAGVVIKQEQTDFAYDSDVTGCASMYLHTEGFSGP   355
185P3C2v.5    YEQAGQPAVDQGGVNGHRYPGAGVVIKQEQTDFAYDSDVTGCASMYLHTEGFSGPSPGDG    254
                 :*

185P3C2v.1    AMGYGYEKPLRPFPDDVCVVPEKFEGDIKQEGVGAFREGPPYQRRGALQLWQFLVALLDD    420
185P3C2v.2    AMGYGYEKPLRPFPDDVCVVPEKFEGDIKQEGVGAFREGPPYQRRGALQLWQFLVALLDD    383
185P3C2v.3A   ---------------------------------VPPHR---------------------    261
185P3C2v.3B   AMGYGYEKPLRPFPDDVCVVPEKFEGDIKQEGVGAFREGPPYQRRGALQLWQFLVALLDD    90
185P3C2v.4    SPGYGYEKPLRPFPDDVCVVPEKFEGDIKQEGVGAFREGPPYQRRGALQLWQFLVALLDD    415
185P3C2v.5    AMGYGYEKPLRPFPDDVCVVPEKFEGDIKQEGVGAFREGPPYQRRGALQLWQFLVALLDD    314
                                                **::
```

Figure 14o (continued)

```
185P3C2v.1    PTNAHFIAWTGRGMEFKLIEPEEVARLWGIQKNRPAMNYDKLSRSLRYYYEKGIMQKVAG 480
185P3C2v.2    PTNAHFIAWTGRGMEFKLIEPEEVARLWGIQKNRPAMNYDKLSRSLRYYYEKGIMQKVAG 443
185P3C2v.3A   ------------------------------GLLWALSR---------------------- 269
185P3C2v.3B   PTNAHFIAWTGRGMEFKLIEPEEVARLWGIQKNRPAMNYDKLSRSLRYYYEKGIMQKVAG 150
185P3C2v.4    PTNAHFIAWTGRGMEFKLIEPEEVARLWGIQKNRPAMNYDKLSRSLRYYYEKGIMQKVAG 475
185P3C2v.5    PTNAHFIAWTGRGMEFKLIEPEEVARLWGIQKNRPAMNYDKLSRSLRYYYEKGIMQKVAG 374
                                            . **.:.:

185P3C2v.1    ERYVYKFVCEPEALFSLAFPDNQRPALKAEFDRPVSEEDTVPLSHLDESPAYLPELAGPA 540
185P3C2v.2    ERYVYKFVCEPEALFSLAFPDNQRPALKAEFDRPVSEEDTVPLSHLDESPAYLPELAGPA 503
185P3C2v.3A   ------------------------------------------------------------
185P3C2v.3B   ERYVYKFVCEPEALFSLAFPDNQRPALKAEFDRPVSEEDTVPLSHLDESPAYLPELAGPA 210
185P3C2v.4    ERYVYKFVCEPEALFSLAFPDNQRPALKAEFDRPVSEEDTVPLSHLDESPAYLPELAGPA 535
185P3C2v.5    ERYVYKFVCEPEALFSLAFPDNQRPALKAEFDRPVSEEDTVPLSHLDESPAYLPELAGPA 434

185P3C2v.1    QPFGPKGGYSY 551
185P3C2v.2    QPFGPKGGYSY 514
185P3C2v.3A   -----------
185P3C2v.3B   QPFGPKGGYSY 221
185P3C2v.4    QPFGPKGGYSY 546
185P3C2v.5    QPFGPKGGYSY 445
```

Figure 11r Nucleotide sequences of transcript variants of 192P2G7
>192P2G7 v.2 (SEQ ID NO:170).

```
ccacgcgtcc gggcgggcg cggcgcggg cgcgtgcggg ctgcgagccg ggagcgcgcg       60
gcgcgacgg cgacgggcgc ggcatggcgg agacgaggc cgagacccc agcaccccgg      120
gggagttcga gagcaagtac ttcgagttcc atgccgagcg gctgccgccc ttctgccgcg    180
ggaagatgaa ggagatcgcc aacttcccgg tgcgcccaag cgacgtgtgg atcgtcacct    240
acccccaagtc cggaactgcc ctctcccgc ctcatcaaga gccacctgcc ctaccgcttt    300
ctgccctctg acctccacaa aggtctctgc atatggctcg caaaccaag                360
gatctggtgg tgtcttatta tcagttccac cgctctctgc ggaccatgag ctaccgaggc    420
accttcaag aattctgccg gaggtttatg aatgataagc tgggctacg ctcctgtttt      480
gagcacgtgc aggagttctg ggagcacccgc atgagctcga acgtgcttt tctcaagtat    540
gaagacatgc atcgggacct ggtgacgatg gtggagcagc tggagcact gccaccagct    600
tcctgtgaca agcccagct ggaagccctg acgggaagag acgggccag ggtgaccag      660
tgctgcaacg ctgaggccct gcccgtgggc cgggaagag ttgggctgtg gaaggacatc    720
```

Figure 11r (continued)

```
ttcaccgtct ccatgaatga gaagtttgac ttggtgtata aacagaagat gggaaagtgt    780
gacctcacgt ttgactttta tttataataa cagaaacaac aacctgcatg ctcacaatac    840
ccagacagtc tactagccaa aagtcctgta tgcattcatt tattccttgc tggacaaact    900
ctggaagcag cgtgtgaaac agcggggaaa gggaagagcg gcgtgagcgg agggagtgtg    960
atgttccca acgaaaagca gctgtctcgc ctttagaacg tgcagcctct ccatgtctga   1020
ttacaaacag tctccacatt gcagttccaa tgcctggac cgtaaggata aagcctgtaa   1080
tatatgcaac tagaatgtct gccttttcaa cccgtatta tttattgtat tttatagagc   1140
ttttcactgg aaatctacat aaatgtcagt aaaccaaata aaagttcatt tccaagggga   1200
atcaggagcg agccacaccc gaatggtaga aagatctcag ggttaactct ttattttttgt   1260
agttttatta tctaaggcac agccattctg ttctcacttg gtcctgagat agtggtgaga   1320
acaggagatg agttggtct gttggggga atctggacac ttgttttattc tgacggagtt   1380
cacttcttca gaaccttcct gaaatgagca gaaattgttc actagtcctt cagaatggac   1440
gtccttctgc cagagactc cagcggccgg ctccaaagc ccaatgcaga ggagcccgcg   1500
gagcatgtgc tgaggaaagt ctgcctgatg aggctggcag gtggagtct aatgcagtca   1560
ggagcatttg catgcagtgg gtggagagtc ggccaccaga ggaccagagtt gcgctcggaa   1620
tttgagctga attccacagc cttactttgt ttcctgaagt gatagcctac taatgctggc   1680
aagcagatgc ttaatagtaa atttctaaaa tcccgggtc tttatcattc agttgttct    1740
gtgcacctga gcgctcagc cgtgggagga ccattttgcg agtgtagccc tgtttcactc   1800
ggatcaggtt gcacgccg ctgcgtgtc tgtccacctc atccctccgt gtatctgagg    1860
gagtaaaggt gagtctttta tgcttcact gctcaattt ctcaccaca ttcgctgaag    1920
cgatggagag tcggggcca gtagccagcc aaccccgtgg ggaccgggt tgtctgtcat    1980
ttatgtggct ggaaagcacc caaagtgtg gcaggaggg tgctgctgt ggaaggggtc    2040
tccgttcttg gtgctgtatt tgaaacgggt gtagagagaa gcttgtgtt ttgttttgtaa   2100
tggggagaag cgtggccagg cagtggcacg tggcatcgca tggtgggctc ggcagcacct   2160
tgcctgtgtt tctgtgaggg agcgtgcttt ctgtgaaatt tctgtcttg tttctatttt   2220
tagtactgta tcgatgttac tgagcactac acatgatcct tctgtgcttg cttgcatctt   2280
taataaagac atgttccgg caaaaaaaaa aaaaaaaaa aaaaaaaa aaaaaaaaa       2340
aaaaaaaaaa aaaa                                                    2364
```

>192P2G7 v.3 (SEQ ID NO:171).

```
ccacgcgtcc gccgcgggcc cggcgcgcgg cgcgtgcgcg ctgcgagccg ggaggcgcgg     60
gcgcgacgg cgacgcggc ggcatgcgg agagcgaggc cgagacccccc agcaccccgg    120
gggagttcga gagcaagtac ttcgagttcc atggcgtgcg gctgccgccc ttctgccgcg    180
ggaagatgga ggagatcgcc aacttccgg tgcggcccag cgacgtgtgg cgacgtcacct    240
accccaagtc cgtggctac gctcctggt ttgagcacgt gcaggacat gggagcacc       300
gcatggactc gaacgtgctt tttctcaagt atgaagacat gtcctgtgta cggaagcccc    360
tggtggagca gctgccaga ttcctggggg tgtcctgtga caggcccag cgctgaagcc     420
tgacggagca ctgccaccag ctggtgacc agtgctgcaa cgctgaggcc ctgcccgtgg    480
gccgggggaag agttggctg tggaaggaca tcttcaccgt ctccatgaat gagaagtttg    540
```

Figure 11r (continued)

```
acttgtgta taaacagaag atgggaaagt gtgacctcac gtttgacttt tatttataat    600
aacagaaaca acaacctgca tgctcacaat accagacaag tctactagcc aaaagtcctg    660
tatgcattca tttattcctt gctggacaaa ctctggaagc agcgtgtgaa acagcggggg    720
aagggaagag cgcgtgagc gggaggagtg tgatgattcc caaccgaaag cagctgtctc    780
gcctttagaa cgtgcagcct ctccatgtct gattacaaac agtcccaca ttgcagttcc    840
aatggcctgg accgtaagga taaagcctgt aatatatgca actagaatgt ctgccttttc    900
aacccgtat tatttattgt atttatataga gctttcact ggaaatctac ataaatgtca    960
gtaaaccaaa taaaagttca tttccaaggg gaatcaggag cgagccacac ccgaatggta   1020
gaaagatctc aggtttaact cttatttt gtagtttta tatctaaggc acagccattc    1080
tgttctcact tgattctgag atagtggtga gaacagagga tgagtgggt ctgttggggg   1140
gaatctggac acttgtttat tctgacgag ttcacttctt cagaaccttc ctgaaatgag   1200
cagaaattgt tcactaggtc ttcagaatgg acgtcctct gccagagact tccagcgggc   1260
ggctccaaag gcccaatgca gaggagcccg cggagcatt gctgaggga gtctgcctgg   1320
tgaggctggc agtgggagt ctaatgcagt caggagcatt tgcatgcagt gggtggagag   1380
tcggccacca aaggaccgag ttgcgctcgg aatttgagct gaattccaca gccttacttt   1440
gtttcctgaa gtgatagcct actaatgctg gcaagcagat gcttaatagt aaatttctaa   1500
aatccccggg tctttatcat tcagtttgtt ctgtgcacct gagcgctca gccgtgggag   1560
gaccattttg caagtttgag cctgttcac tcggatcagg ttgcacggc cgcctgcgtg   1620
tctgtccacc tcatcctcc gtgtatctga gggagtaaag gtggtcttt tattgcttca   1680
ctgcctaatt ttctcaccca cattcgctga agcgatgag agtcggggc cagtagccag   1740
ccaacccgt gggaccggg gtttgtctgc atttatgtgg ctggaaagca cccaaagtgg   1800
tggtcaggag gtcgctgct gtgaaggg tctccgttct tgtgctgta tttgaaacgg   1860
gtgtagagag aagcttgtgt ttttgttgt aatgggaga agcgtggcca ggcagtggca   1920
cgtggcatcg catggtgggc tcggcagcac ctgcctgtg tttcctgag ggaggctgct   1980
ttctgtgaaa cttctttata ttttctatt ttagtactg tatgatgtt actgagcact   2040
acacatgatc cttctgtgct tgcttgcatc tttaataaag acatgttccc ggcaaaaaaa   2100
aaaaaaaaaa aaaaaaaaaa aaaaaaaaaa aaaaaaaaaa aaaaaa                 2156
```

Figure 12r Protein sequences of transcript variants of 192P2G7
>192P2G7 v.2 (SEQ ID NO:172).
```
MACGCRPSAA GRWRRSPTSR CGPATCGSSP TPSPELTSPR LIKSHLPYRF LPSDLHNGDS     60
KVIYMARNPK DLVVSYYQFH RSLRTMSYRG TFQEFCRRFM NDKLGYGSWF EHVQEFWEHR    120
MDSNVLFLKY EDMHRDIVTM VEQLARFLGV SCDKAQLEAL TEHCQLVDQ CCNAEALPVG     180
RGRVGLWKDI FTVSMNEKFD LVYKQKMGKC DLTFDFYL                            218
```

>192P2G7 v.3 (SEQ ID NO 173).
```
MAESEAETPS TPGEFESKYF EFHGVRLPPF CRGKMEEIAN FPVRPSDVWI VTYPKSVGYG     60
SWFEHVQEFW EHRMDSNVLF LKYEDMHRDL VTMVEQLARF LGVSCDKAQL EALTEHCHQL    120
VDQCCNAEAL PVGRGRVGLW KDIFTVSMNE KFDLVYKQKM GKCDLTFDFY L            171
```

Figure 13r Alignment of nucleotide sequences of 192P2G7 transcript variants
(SEQ ID NOS: 59, 170, 171).

```
192P2G7v.1      CCACGCGTCCGGCGCGGGGCGCGGGGCGCGGGGCGCGGGGCTGCGGGCTGCGAGCGGGCG      60
192P2G7v.2      CCACGCGTCCGGCGCGGGGCGCGGGGCGCGGGGCGCGGGGCTGCGGGCTGCGAGCGGGCG      60
192P2G7v.3      CCACGCGTCCGGCGCGGGGCGCGGGGCGCGGGGCGCGGGGCTGCGGGCTGCGAGCGGGCG      60
                ************************************************************

192P2G7v.1      GCGGCGACGGCGACGGCCGGCGCGGCCGGCGCGGCCATGCGGAGAGCGAGGCCGAGACCCCAGCACCCGG     120
192P2G7v.2      GCGGCGACGGCGACGGCCGGCGCGGCCGGCGCGGCCATGCGGAGAGCGAGGCCGAGACCCCAGCACCCGG     120
192P2G7v.3      GCGGCGACGGCGACGGCCGGCGCGGCCGGCGCGGCCATGCGGAGAGCGAGGCCGAGACCCCAGCACCCGG     120
                ************************************************************

192P2G7v.1      GGGAGTTCGAGAGCAAGTACTTCGAGTTCCATGGCGTGCGGCTGCCGCCCTTCTGCCGCG     180
192P2G7v.2      GGGAGTTCGAGAGCAAGTACTTCGAGTTCCATGGCGTGCGGCTGCCGCCCTTCTGCCGCG     180
192P2G7v.3      GGGAGTTCGAGAGCAAGTACTTCGAGTTCCATGGCGTGCGGCTGCCGCCCTTCTGCCGCG     180
                ************************************************************

192P2G7v.1      GGAAGATGGAGGAGATCGCCAACTTCCCGGTGCGGCCCAGCGACGTGTGGATCGTCACCT     240
192P2G7v.2      GGAAGATGGAGGAGATCGCCAACTTCCCGGTGCGGCCCAGCGACGTGTGGATCGTCACCT     240
192P2G7v.3      GGAAGATGGAGGAGATCGCCAACTTCCCGGTGCGGCCCAGCGACGTGTGGATCGTCACCT     240
                ************************************************************

192P2G7v.1      ACCCCAAGTCCGGCACCCAGCAGCTTGCTGCTGCAGGAGAGTGGTCTACTTGGTGAGCCAGGGCGCTG     300
192P2G7v.2      ACCCCAAGTCCG-------------------------------------------------------     252
192P2G7v.3      ACCCCAAGTCCG-------------------------------------------------------     252
                ************

192P2G7v.1      ACCCCGATGAGATCGGCTTGATGAACATCGACGAGCAGCTCCCGGTCCTGGAGTACCCAC     360
192P2G7v.2      ------------------------------------------------------------
192P2G7v.3      ------------------------------------------------------------

192P2G7v.1      AGCCGGGCCTGGACACATCATCAAGGAACTGACCTCTCCCGCCTCATCAAGAGCCACCTGC     420
192P2G7v.2      -----------------------------GAACTGACCTCTCCCGCCTCATCAAGAGCCACCTGC     289
192P2G7v.3      ------------------------------------------------------------

192P2G7v.1      CCTACCGCTTTCTGCCCTCTGACCTCCACAATGGAGACTCCAAGGTCATCTATATGGCTC     480
192P2G7v.2      CCTACCGCTTTCTGCCCTCTGACCTCCACAATGGAGACTCCAAGGTCATCTATATGGCTC     349
192P2G7v.3      ------------------------------------------------------------
```

Figure 13r (continued)

```
192P2G7v.1    GCAACCCCAAGGATCTGGTGTGTCTTATTATCAGTTCCACGCGTCTCTGCGGACCATGA    540
192P2G7v.2    GCAACCCCAAGGATCTGGTGTGTCTTATTATCAGTTCCACGCGTCTCTGCGGACCATGA    409
192P2G7v.3    ------------------------------------------------------------

192P2G7v.1    GCTACCGAGGCCACCTTTCAAGAATTCTGCCGGAGGTTTATGAATGATAAGCTGGCTACG    600
192P2G7v.2    GCTACCGAGGCCACCTTTCAAGAATTCTGCCGGAGGTTTATGAATGATAAGCTGGCTACG    469
192P2G7v.3    ---------------------------------------TGGGCTACG    261
                                                       *********

192P2G7v.1    GCTCCTGTTTGAGCACGTGCAGGAGTTCTGGGAGCACCGCATGGACTCGAACGTGCTTT    660
192P2G7v.2    GCTCCTGTTTGAGCACGTGCAGGAGTTCTGGGAGCACCGCATGGACTCGAACGTGCTTT    529
192P2G7v.3    GCTCCTGTTTGAGCACGTGCAGGAGTTCTGGGAGCACCGCATGGACTCGAACGTGCTTT    321
              ************************************************************

192P2G7v.1    TTCTCAAGTATGAAGACATGAGCATCGGGACCCTGGTTGACGATGGTGGAGCAGCTGGCCAGAT    720
192P2G7v.2    TTCTCAAGTATGAAGACATGAGCATCGGGACCCTGGTTGACGATGGTGGAGCAGCTGGCCAGAT    589
192P2G7v.3    TTCTCAAGTATGAAGACATGAGCATCGGGACCCTGGTTGACGATGGTGGAGCAGCTGGCCAGAT    381
              ************************************************************

192P2G7v.1    TCCTGGGGGTGTCCTGTGACAAGGCCCAGCTGGAAGCCCTGACGGAGCACTGCCACCAGC    780
192P2G7v.2    TCCTGGGGGTGTCCTGTGACAAGGCCCAGCTGGAAGCCCTGACGGAGCACTGCCACCAGC    649
192P2G7v.3    TCCTGGGGGTGTCCTGTGACAAGGCCCAGCTGGAAGCCCTGACGGAGCACTGCCACCAGC    441
              ************************************************************

192P2G7v.1    TGGTGACCAGTGCTGCAACGCTGAGGCCCTGCCCGTGGGCCGGGAAGAGTTGGGCTGT    840
192P2G7v.2    TGGTGACCAGTGCTGCAACGCTGAGGCCCTGCCCGTGGGCCGGGAAGAGTTGGGCTGT    709
192P2G7v.3    TGGTGACCAGTGCTGCAACGCTGAGGCCCTGCCCGTGGGCCGGGAAGAGTTGGGCTGT    501
              ************************************************************

192P2G7v.1    GGAGGACAICTTCACCGTCTCCATGAATGAGAAGTTTGACTTGGTGTATAAACAGAAGA    900
192P2G7v.2    GGAGGACAICTTCACCGTCTCCATGAATGAGAAGTTTGACTTGGTGTATAAACAGAAGA    769
192P2G7v.3    GGAAGGACAICTTCACCGTCTCCATGAATGAGAAGTTTGACTTGGTGTATAAACAGAAGA    561
              ************************************************************

192P2G7v.1    TGGGAAAGTGTGACCTCACGTTTGACTTTTATTTATAATAACAGAAAACAACAACCTGCAT    960
192P2G7v.2    TGGGAAAGTGTGACCTCACGTTTGACTTTTATTTATAATAACAGAAAACAACAACCTGCAT    829
```

Figure 13r (continued)

```
192P2G7v.3      TGGGAAAGTGTGACCTCACGTTTGACTTTTATTTTATAATAACAGAAACAACAACCTGCAT  621
                * * * * * * * * * * * * * * * * * * * * * * * * * * * * * * * * * * * * * * * * * * * * * * * * * * * * * * * * * * * * * * * *

192P2G7v.1      GCTCACAATACCCAGACAGTCTACTAGCCAAAAGTCCTGTATGCATTCATTTATTCCTTG   1020
192P2G7v.2      GCTCACAATACCCAGACAGTCTACTAGCCAAAAGTCCTGTATGCATTCATTTATTCCTTG   889
192P2G7v.3      GCTCACAATACCCAGACAGTCTACTAGCCAAAAGTCCTGTATGCATTCATTTATTCCTTG   681
                * * * * * * * * * * * * * * * * * * * * * * * * * * * * * * * * * * * * * * * * * * * * * * * * * * * * * * * * * * * * * * * *

192P2G7v.1      CTGGACAAACTCTGGAAGCAGCGTGTGAAACAGCGGGGAAGGAAGAGCGGCGTGAGCG    1080
192P2G7v.2      CTGGACAAACTCTGGAAGCAGCGTGTGAAACAGCGGGGAAGGAAGAGCGGCGTGAGCG    949
192P2G7v.3      CTGGACAAACTCTGGAAGCAGCGTGTGAAACAGCGGGGAAGGAAGAGCGGCGTGAGCG    741
                * * * * * * * * * * * * * * * * * * * * * * * * * * * * * * * * * * * * * * * * * * * * * * * * * * * * * * * * * * * * * * * *

192P2G7v.1      GAGGGAGTGTGATGATTCCCAACCGAAAGCAGCTGTCTCGCCTTTAGAACGTGCAGCCTC   1140
192P2G7v.2      GAGGGAGTGTGATGATTCCCAACCGAAAGCAGCTGTCTCGCCTTTAGAACGTGCAGCCTC   1009
192P2G7v.3      GAGGGAGTGTGATGATTCCCAACCGAAAGCAGCTGTCTCGCCTTTAGAACGTGCAGCCTC   801
                * * * * * * * * * * * * * * * * * * * * * * * * * * * * * * * * * * * * * * * * * * * * * * * * * * * * * * * * * * * * * * * *

192P2G7v.1      TCCATGTCTGATTACAAACAGTCTCCACATTGCAGTTCCAATGGCCTGGACCGTAAGGAT   1200
192P2G7v.2      TCCATGTCTGATTACAAACAGTCTCCACATTGCAGTTCCAATGGCCTGGACCGTAAGGAT   1069
192P2G7v.3      TCCATGTCTGATTACAAACAGTCTCCACATTGCAGTTCCAATGGCCTGGACCGTAAGGAT   861
                * * * * * * * * * * * * * * * * * * * * * * * * * * * * * * * * * * * * * * * * * * * * * * * * * * * * * * * * * * * * * * * *

192P2G7v.1      AAAGCCTGTAATATATGCAACTAGAACTAGTCTGCCTTTTCAACCCCGTATTATTATTGTA 1260
192P2G7v.2      AAAGCCTGTAATATATGCAACTAGAACTAGTCTGCCTTTTCAACCCCGTATTATTATTGTA 1129
192P2G7v.3      AAAGCCTGTAATATATGCAACTAGAACTAGTCTGCCTTTTCAACCCCGTATTATTATTGTA 921
                * * * * * * * * * * * * * * * * * * * * * * * * * * * * * * * * * * * * * * * * * * * * * * * * * * * * * * * * * * * * * * * *

192P2G7v.1      TTTTATAGAGCTTTTCACTGGAAATCTACATAAATGTCAGTAAACCAAATAAAAAGTTCAT 1320
192P2G7v.2      TTTTATAGAGCTTTTCACTGGAAATCTACATAAATGTCAGTAAACCAAATAAAAAGTTCAT 1189
192P2G7v.3      TTTTATAGAGCTTTTCACTGGAAATCTACATAAATGTCAGTAAACCAAATAAAAAGTTCAT 981
                * * * * * * * * * * * * * * * * * * * * * * * * * * * * * * * * * * * * * * * * * * * * * * * * * * * * * * * * * * * * * * * *

192P2G7v.1      TTCCAAGGGAATCAGGAGCGAGCGAGCCACACCCGAATGGTAGAAAGATCTCAGGGTTAACTC 1380
192P2G7v.2      TTCCAAGGGAATCAGGAGCGAGCGAGCCACACCCGAATGGTAGAAAGATCTCAGGGTTAACTC 1249
192P2G7v.3      TTCCAAGGGAATCAGGAGCGAGCGAGCCACACCCGAATGGTAGAAAGATCTCAGGGTTAACTC 1041
                * * * * * * * * * * * * * * * * * * * * * * * * * * * * * * * * * * * * * * * * * * * * * * * * * * * * * * * * * * * * * * * *

192P2G7v.1      TTTATTTTTGTAGTTTTATTATTCTAAGGCACAGCCATTCTGTTCTCACTTGGTTCTGAGA 1440
```

Figure 13r (continued)

```
192P2G7v.2    TTTATTTTTGTAGTTTTATTATCTAAGGCACAGCCATTCTGTTCTTCACTTGGTTCTGAGA    1309
192P2G7v.3    TTTATTTTTGTAGTTTTATTATCTAAGGCACAGCCATTCTGTTCTTCACTTGGTTCTGAGA    1101
              ************************************************************

192P2G7v.1    TAGTGGTGAGAACAGAGGATGAGTTGGGTCTGTTGGGGGGAATCTGACACTTGTTTATT    1500
192P2G7v.2    TAGTGGTGAGAACAGAGGATGAGTTGGGTCTGTTGGGGGGAATCTGACACTTGTTTATT    1369
192P2G7v.3    TAGTGGTGAGAACAGAGGATGAGTTGGGTCTGTTGGGGGGAATCTGACACTTGTTTATT    1161
              ************************************************************

192P2G7v.1    CTGACGGAGTTCACTTCTTCAGAACCTTCCTGAAATGAGCAGAAATTGTTCACTAGGTCT    1560
192P2G7v.2    CTGACGGAGTTCACTTCTTCAGAACCTTCCTGAAATGAGCAGAAATTGTTCACTAGGTCT    1429
192P2G7v.3    CTGACGGAGTTCACTTCTTCAGAACCTTCCTGAAATGAGCAGAAATTGTTCACTAGGTCT    1221
              ************************************************************

192P2G7v.1    TCAGAATGGACGTCCTTCTGCCCAGAGACTTCCAGCGCGGCGCTCCAAAGGCCCAATGCAG    1620
192P2G7v.2    TCAGAATGGACGTCCTTCTGCCCAGAGACTTCCAGCGCGGCGCTCCAAAGGCCCAATGCAG    1489
192P2G7v.3    TCAGAATGGACGTCCTTCTGCCCAGAGACTTCCAGCGCGGCGCTCCAAAGGCCCAATGCAG    1281
              ************************************************************

192P2G7v.1    AGGAGCCCCGCGGGAGCATGTGCTGAGGGAAGTCTGCCTGGTGAGGCTGGCAGGTGGGAGTC    1680
192P2G7v.2    AGGAGCCCCGCGGGAGCATGTGCTGAGGGAAGTCTGCCTGGTGAGGCTGGCAGGTGGGAGTC    1549
192P2G7v.3    AGGAGCCCCGCGGGAGCATGTGCTGAGGGAAGTCTGCCTGGTGAGGCTGGCAGGTGGGAGTC    1341
              ************************************************************

192P2G7v.1    TAATGCAGTCAGGAGCATTTGCATGCAGTGCAGTGCAGTGGAGAGTCGGCCACCAAAGGACCGAGT    1740
192P2G7v.2    TAATGCAGTCAGGAGCATTTGCATGCAGTGCAGTGCAGTGGAGAGTCGGCCACCAAAGGACCGAGT    1609
192P2G7v.3    TAATGCAGTCAGGAGCATTTGCATGCAGTGCAGTGCAGTGGAGAGTCGGCCACCAAAGGACCGAGT    1401
              ************************************************************

192P2G7v.1    TGCGCTCGGAATTTGAGCTGAATTCCACAGCCTTACTTTGTTTCCTGAAGTGATAGCCTA    1800
192P2G7v.2    TGCGCTCGGAATTTGAGCTGAATTCCACAGCCTTACTTTGTTTCCTGAAGTGATAGCCTA    1669
192P2G7v.3    TGCGCTCGGAATTTGAGCTGAATTCCACAGCCTTACTTTGTTTCCTGAAGTGATAGCCTA    1461
              ************************************************************

192P2G7v.1    CTAATGCTGGCAAGCAGATGCTTAATAGTAGTAAATTCTAAAATCCCGGGTCTTTATCATT    1860
192P2G7v.2    CTAATGCTGGCAAGCAGATGCTTAATAGTAGTAAATTCTAAAATCCCGGGTCTTTATCATT    1729
192P2G7v.3    CTAATGCTGGCAAGCAGATGCTTAATAGTAGTAAATTCTAAAATCCCGGGTCTTTATCATT    1521
              ************************************************************
```

Figure 13r (continued)

```
192P2G7v.1    CAGTTTGTTCTGTGCACCTGAGGCGCTCAGCCGTGGAGGACCATTTTGCGAGTGTAGCC  1920
192P2G7v.2    CAGTTTGTTCTGTGCACCTGAGGCGCTCAGCCGTGGAGGACCATTTTGCGAGTGTAGCC  1789
192P2G7v.3    CAGTTTGTTCTGTGCACCTGAGGCGCTCAGCCGTGGAGGACCATTTTGCGAGTGTAGCC  1581
              ************************************************************

192P2G7v.1    CTGTTTCACTCGGATCAGGTTGGCACGGCCGCCTGCGTGTCTGTCCACCTCATCCCTCCG  1980
192P2G7v.2    CTGTTTCACTCGGATCAGGTTGGCACGGCCGCCTGCGTGTCTGTCCACCTCATCCCTCCG  1849
192P2G7v.3    CTGTTTCACTCGGATCAGGTTGGCACGGCCGCCTGCGTGTCTGTCCACCTCATCCCTCCG  1641
              ************************************************************

192P2G7v.1    TGTATCTGAGGGAGTAAAAGTGAGGTCTTTATTGCTTCACTGCCTAATTTTCTCACCCAC  2040
192P2G7v.2    TGTATCTGAGGGAGTAAAAGTGAGGTCTTTATTGCTTCACTGCCTAATTTTCTCACCCAC  1909
192P2G7v.3    TGTATCTGAGGGAGTAAAAGTGAGGTCTTTATTGCTTCACTGCCTAATTTTCTCACCCAC  1701
              ************************************************************

192P2G7v.1    ATTCGCTGAAGCGATGGAGAGTCGGGGGCCAGTAGCCAGCCAACCCCGTGGGGACCGGGG  2100
192P2G7v.2    ATTCGCTGAAGCGATGGAGAGTCGGGGGCCAGTAGCCAGCCAACCCCGTGGGGACCGGGG  1969
192P2G7v.3    ATTCGCTGAAGCGATGGAGAGTCGGGGGCCAGTAGCCAGCCAACCCCGTGGGGACCGGGG  1761
              ************************************************************

192P2G7v.1    TTGTCTGTCATTTATGTGGCTGGAAAGCACCCAAAGTGGTGGTCAGGAGGGTCGCTGCTG  2160
192P2G7v.2    TTGTCTGTCATTTATGTGGCTGGAAAGCACCCAAAGTGGTGGTCAGGAGGGTCGCTGCTG  2029
192P2G7v.3    TTGTCTGTCATTTATGTGGCTGGAAAGCACCCAAAGTGGTGGTCAGGAGGGTCGCTGCTG  1821
              ************************************************************

192P2G7v.1    TGGAAGGGGTCTCCGTTCTTGGTGCTGTATTTGAAACGGGTGTAGAGAGAAGCTTGTGTT  2220
192P2G7v.2    TGGAAGGGGTCTCCGTTCTTGGTGCTGTATTTGAAACGGGTGTAGAGAGAAGCTTGTGTT  2089
192P2G7v.3    TGGAAGGGGTCTCCGTTCTTGGTGCTGTATTTGAAACGGGTGTAGAGAGAAGCTTGTGTT  1881
              ************************************************************

192P2G7v.1    TTTGTTTTGTAATGCCACAAGCGTGGCCAGGCAGTGGCCAGGCAGTGGCATCGCATGTGGGCT  2280
192P2G7v.2    TTTGTTTTGTAATGCCACAAGCGTGGCCAGGCAGTGGCCAGGCAGTGGCATCGCATGTGGGCT  2149
192P2G7v.3    TTTGTTTTGTAATGCCACAAGCGTGGCCAGGCAGTGGCCAGGCAGTGGCATCGCATGTGGGCT  1941
              ************************************************************

192P2G7v.1    CGGCAGCACCTTGCCTGTTCCTGTGTTTCTGTGAGGAGGCTGCTTCTGCTTCTGTGAAATTTCTTATAT  2340
192P2G7v.2    CGGCAGCACCTTGCCTGTTCCTGTGTTTCTGTGAGGAGGCTGCTTCTGCTTCTGTGAAATTTCTTATAT  2209
192P2G7v.3    CGGCAGCACCTTGCCTGTTCCTGTGTTTCTGTGAGGAGGCTGCTTCTGCTTCTGTGAAATTTCTTATAT  2001
              ************************************************************
```

Figure 13r (continued)

```
192P2G7v.1    TTTTCTATTTTTAGTACTGTATGGATGTTACTGAGCACTACACACATGATCCTTCTGTCTT  2400
192P2G7v.2    TTTTCTATTTTTAGTACTGTATGGATGTTACTGAGCACTACACACATGATCCTTCTGTCTT  2269
192P2G7v.3    TTTTCTATTTTTAGTACTGTATGGATGTTACTGAGCACTACACACATGATCCTTCTGTCTT  2061
              ************************************************************

192P2G7v.1    GCTTGCATCTTTAATAAAGACATGTTCCCGGCAAAAAAAAAAAAAAAAAAAAAAAAAAAAA  2460
192P2G7v.2    GCTTGCATCTTTAATAAAGACATGTTCCCGGCAAAAAAAAAAAAAAAAAAAAAAAAAAAAA  2329
192P2G7v.3    GCTTGCATCTTTAATAAAGACATGTTCCCGGCAAAAAAAAAAAAAAAAAAAAAAAAAAAAA  2121
              ************************************************************

192P2G7v.1    AAAAAAAAAAAAAAAAAAAAAAAAAAAAAAAAAAAAAAAAAAAAAAA  2495
192P2G7v.2    AAAAAAAAAAAAAAAAAAAAAAAAAAAAAAAAAAAAAAAAAAAAAAA  2364
192P2G7v.3    AAAAAAAAAAAAAAAAAAAAAAAAAAAAAAAAAAAAAAAAAAAAAAA  2156
              ***********************************************
```

Figure 14r Alignment of protein sequences of 192P2G7 transcript variants
(SEQ ID NOS:60, 172, 173).

```
192P2G7v.1    --------------------MAESEAETPSTPG-EFES-KYFEFHG-VRLPP---------   29
192P2G7v.2    MACGCRPSAAGRWRRSPTSRCGPATCGSSPTPSPELTSPRLIKSHLPYRFLPSDLHNGDS   60
192P2G7v.3    --------------------MAESEAETPSTPG-EFES-KYFEFHG-VRLPP---------   29
                                   *   :.  *.    * :: :  *  *

192P2G7v.1    ----FCRGKMEEIANFPVRPSDVWIVTYPKSGTSLLQEVVYLVSQGADPDEIGLMNIDEQ   85
192P2G7v.2    KVIYMARNPKDLVVSYYQFHRSLRTMSYRGTFQEFCRRFMN-----------------   101
192P2G7v.3    ----FCRGKMEEIANFPVRPSDVWIVTYPKS-----------------------------   56
                  :.*    :  ::::. *      *::*

192P2G7v.1    LPVLEYPQPGLDIIKELTSPRLIKSHLPYRFLPSDLHNGDSKVIYMARNPKDLVVSYYQF  145
192P2G7v.2    ------------------------------------------------------------
192P2G7v.3    ------------------------------------------------------------

192P2G7v.1    HRSLRTMSYRGTFQEFCRRFMNDKLGYGSWFEHVQEFWEHRMDSNVLFLKYEDMHRDLVT  205
192P2G7v.2    ------------------DKLGYGSWFEHVQEFWEHRMDSNVLFLKYEDMHRDLVT  139
192P2G7v.3    ---------------VGYGSWFEHVQEFWEHRMDSNVLFLKYEDMHRDLVT   92
                              :********************************

192P2G7v.1    MVEQLARFLGVSCDKAQLEALTEHCHQLVDQCCNAEALPVGRGRVGLWKDIFTVSMNEKF  265
```

Figure 14r (continued)

```
192P2G7v.2    MVEQLARFLGVSCDKAQLEALTEHCHQLVDQCCNAEALPVGRGRVGLWKDIFTVSMNEKF  199
192P2G7v.3    MVEQLARFLGVSCDKAQLEALTEHCHQLVDQCCNAEALPVGRGRVGLWKDIFTVSMNEKF  152
              ************************************************************

192P2G7v.1    DLVYKQRMGKCDLTFDFYL  284
192P2G7v.2    DLVYKQRMGKCDLTFDFYL  218
192P2G7v.3    DLVYKQRMGKCDLTFDFYL  171
              *******************
```

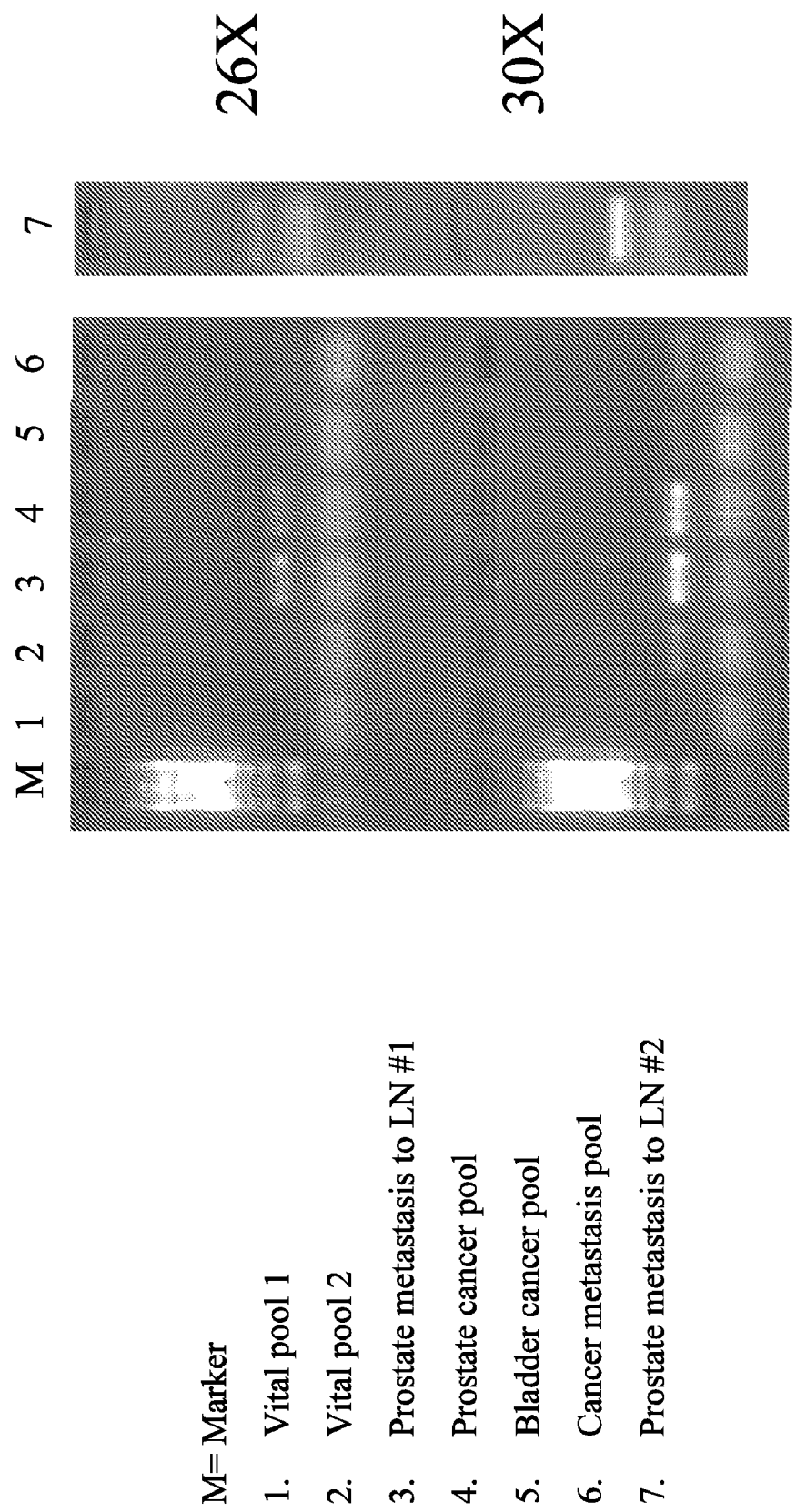
Figure 15  Expression of 74P3B3 by RT-PCR
M= Marker
1. Vital pool 1
2. Vital pool 2
3. Prostate metastasis to LN #1
4. Prostate cancer pool
5. Bladder cancer pool
6. Cancer metastasis pool
7. Prostate metastasis to LN #2

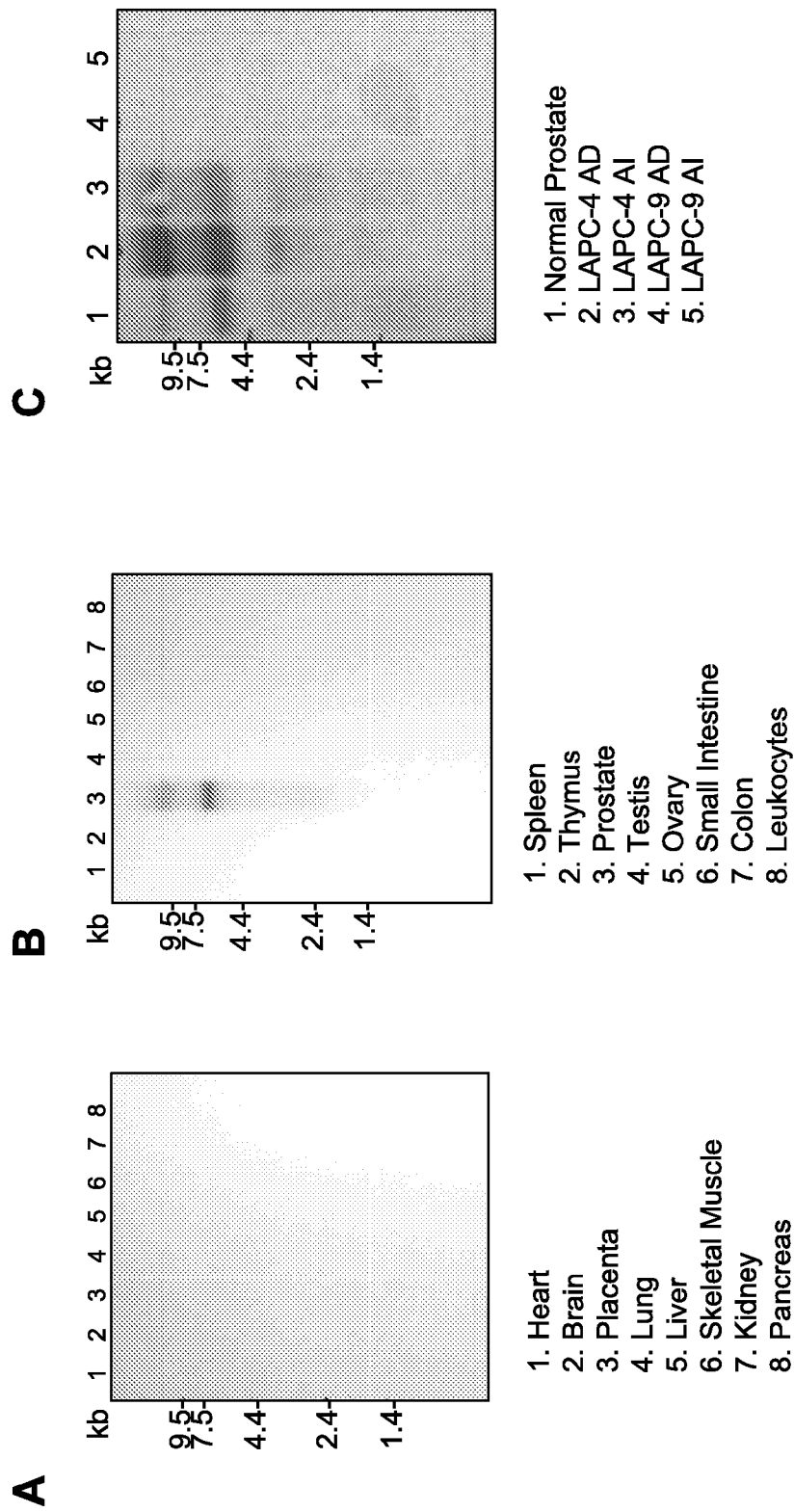
Figure 16 Expression of 74P3B3 in Normal Tissues and Prostate Cancer Xenografts

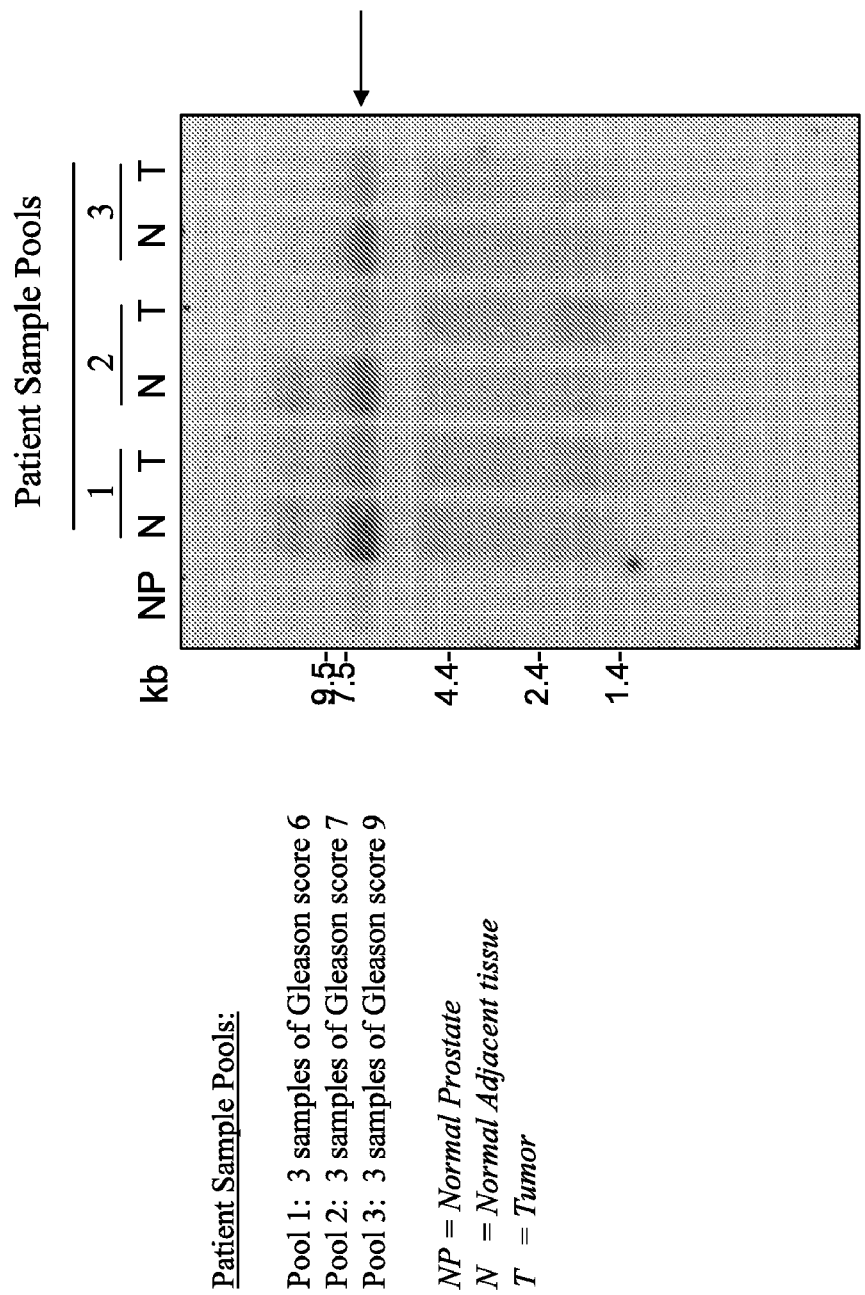
Figure 17 Expression of 74P3B3 in Prostate Cancer Patient Specimens
Patient Sample Pools:
Pool 1: 3 samples of Gleason score 6
Pool 2: 3 samples of Gleason score 7
Pool 3: 3 samples of Gleason score 9
NP = *Normal Prostate*
N = *Normal Adjacent tissue*
T = *Tumor*

Figure 18 Expression of 74P3B3 in Patient Cancer Specimens
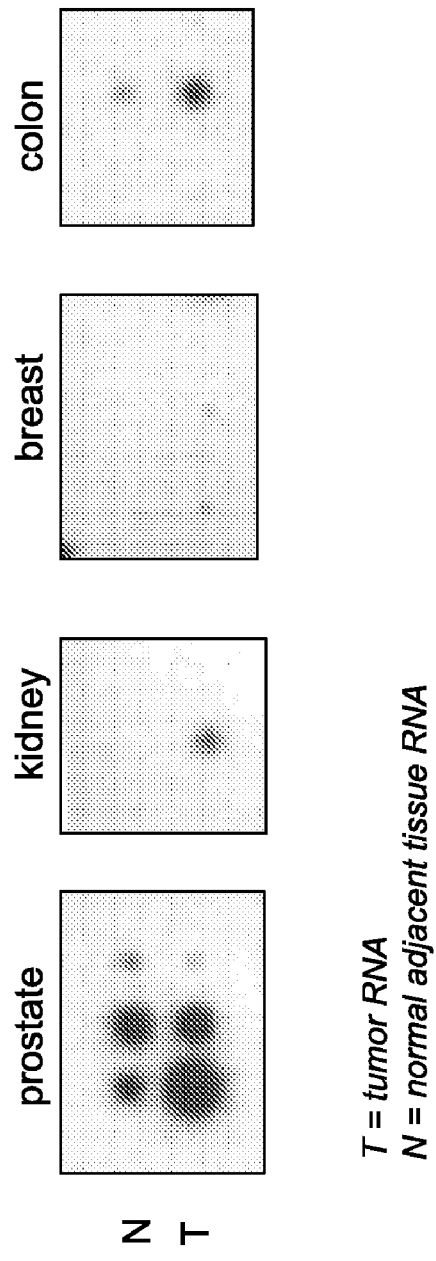
T = tumor RNA
N = normal adjacent tissue RNA

Figure 19  Expression of 83P4B8 by RT-PCR
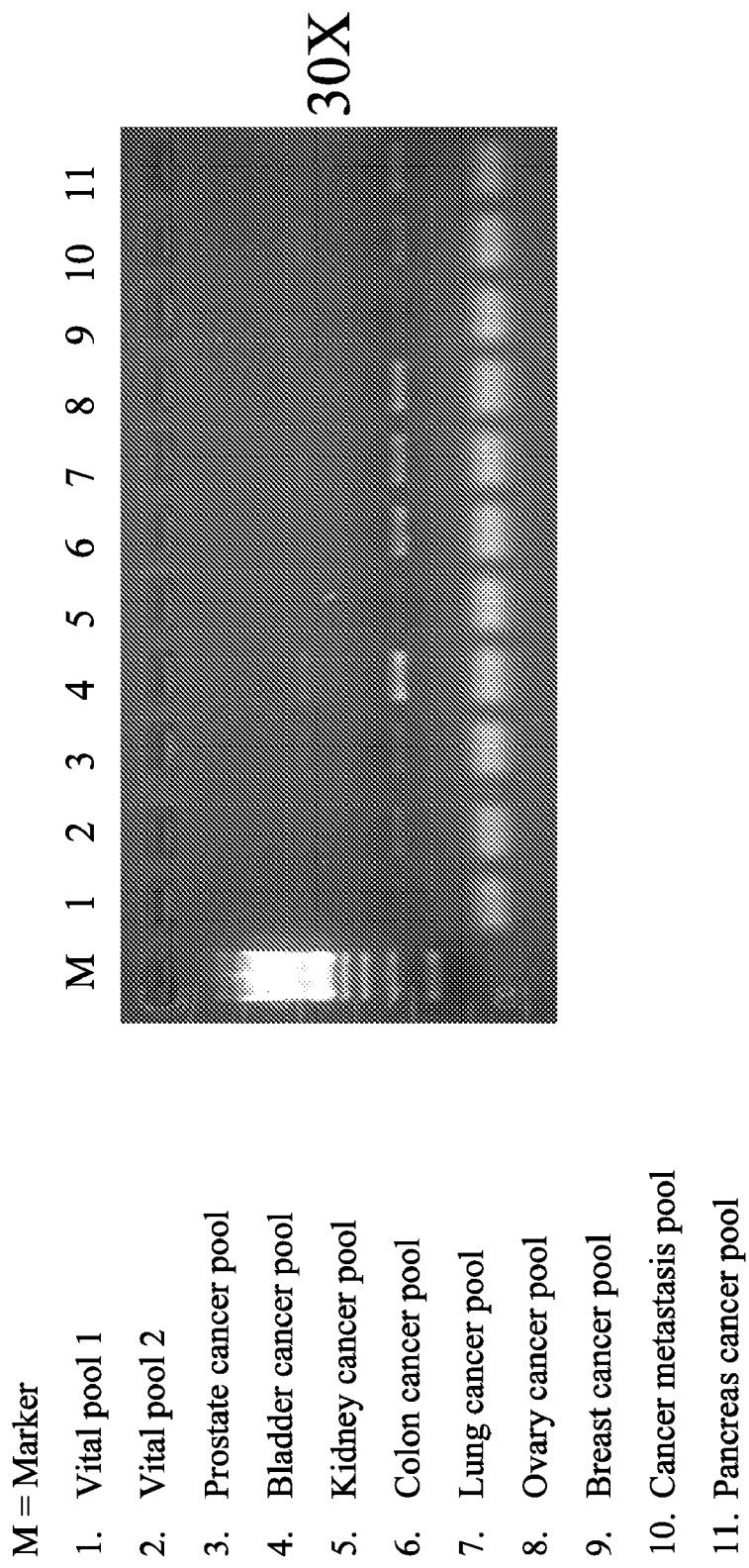
M = Marker
1. Vital pool 1
2. Vital pool 2
3. Prostate cancer pool
4. Bladder cancer pool
5. Kidney cancer pool
6. Colon cancer pool
7. Lung cancer pool
8. Ovary cancer pool
9. Breast cancer pool
10. Cancer metastasis pool
11. Pancreas cancer pool

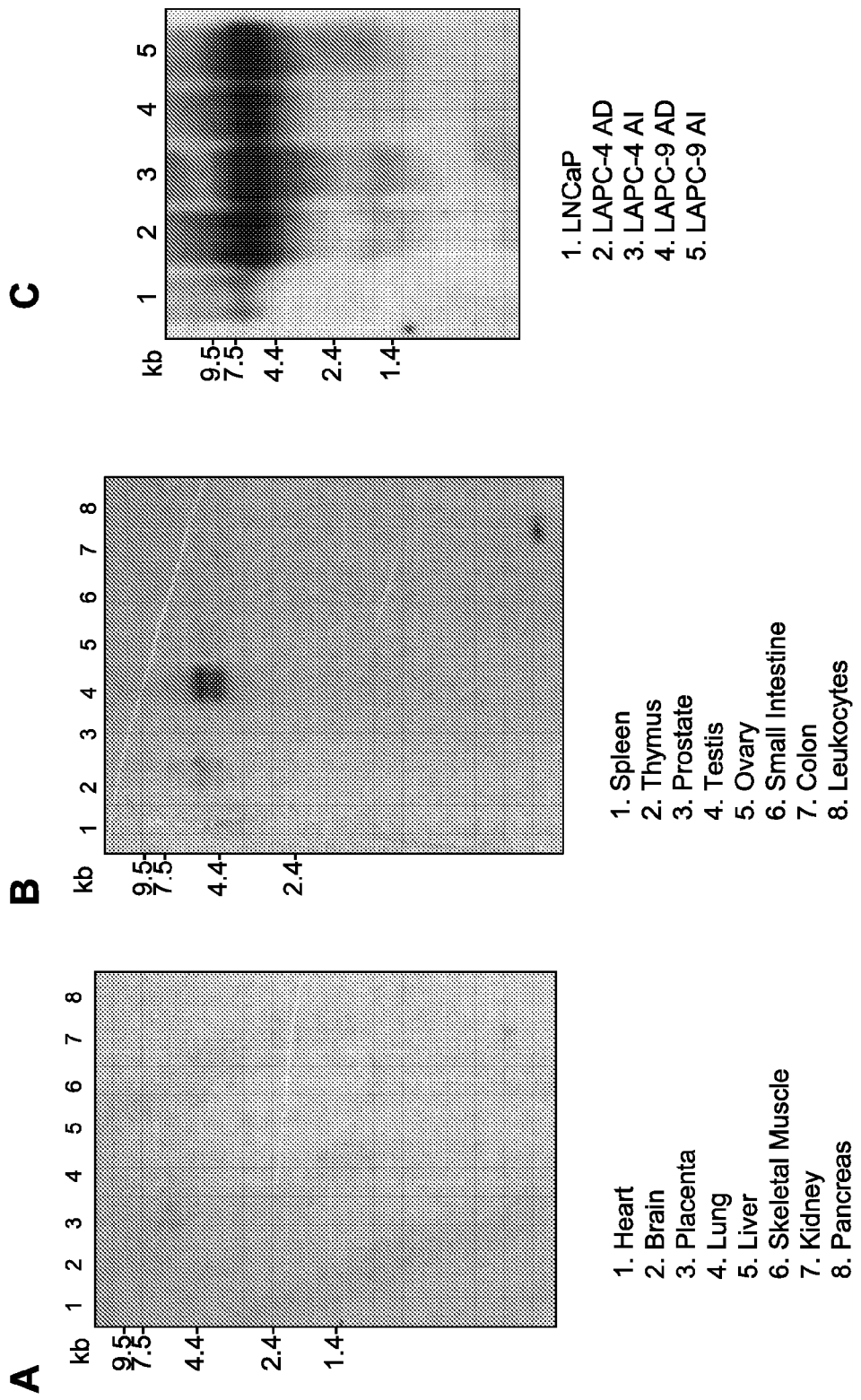
Figure 20 Expression of 83P4B8 in Normal Tissues

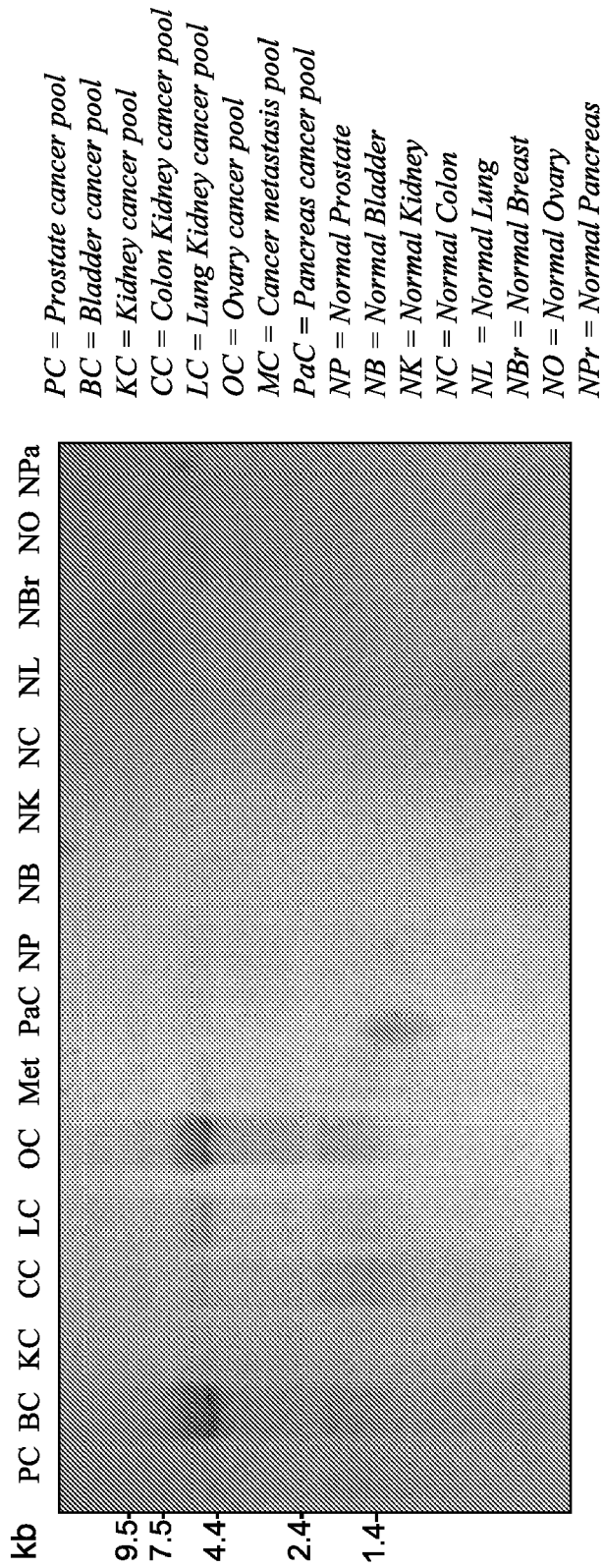
Figure 21 Expression of 83P4B8 in Patient Cancer Specimens and in Normal Tissues

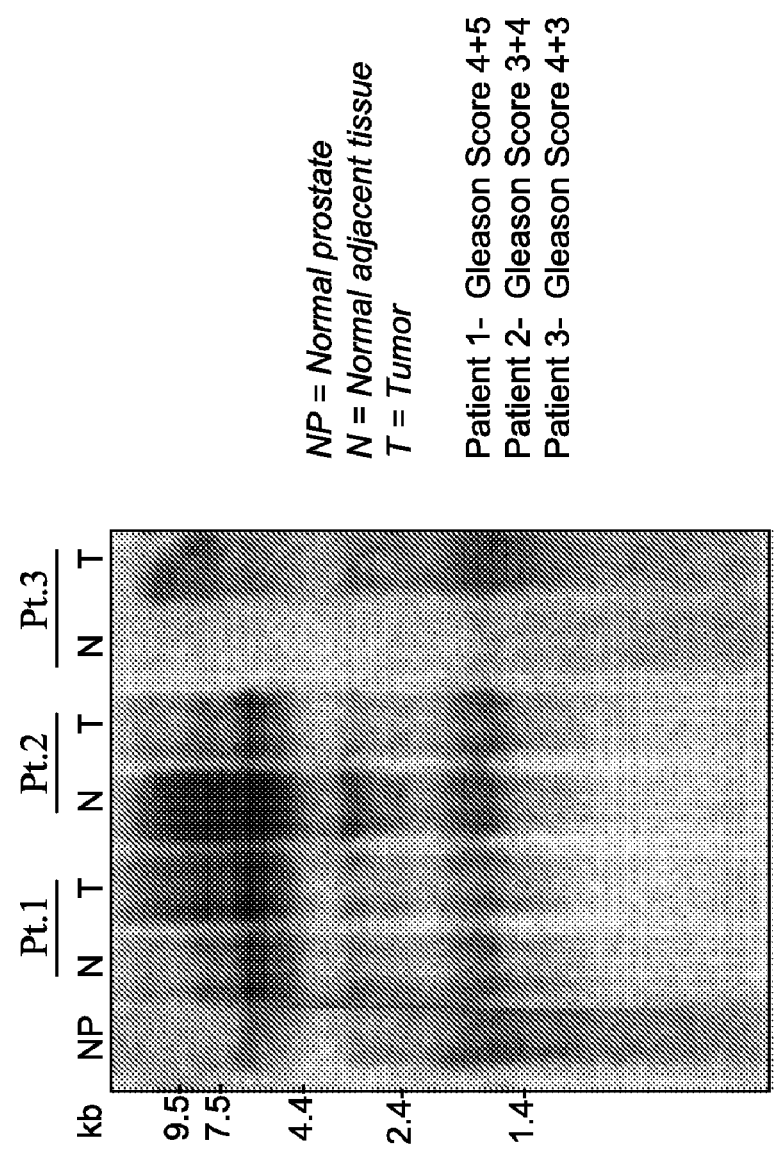
Figure 22 Expression of 83P4B8 in Prostate Cancer Patients Specimens
NP = Normal prostate
N = Normal adjacent tissue
T = Tumor
Patient 1- Gleason Score 4+5
Patient 2- Gleason Score 3+4
Patient 3- Gleason Score 4+3

Figure 23 Expression of 83P4B8 in Colon Cancer Patient Specimens
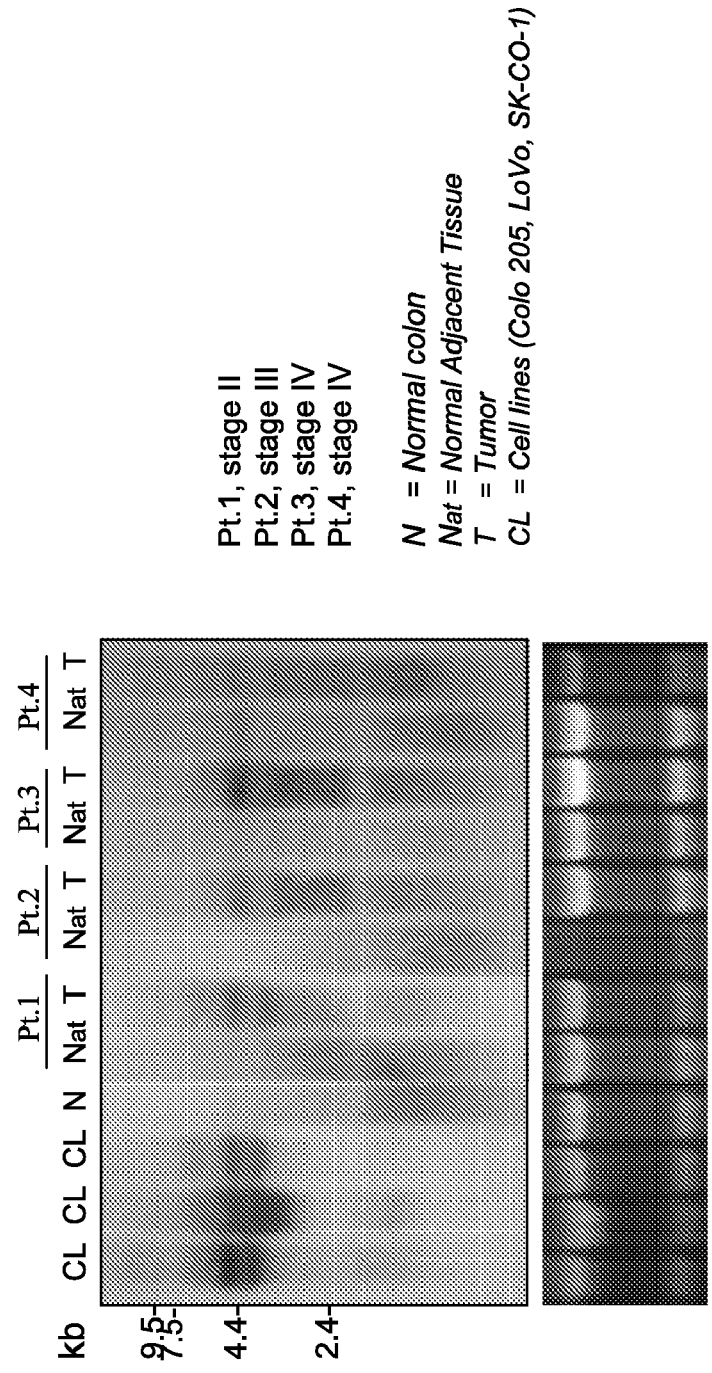

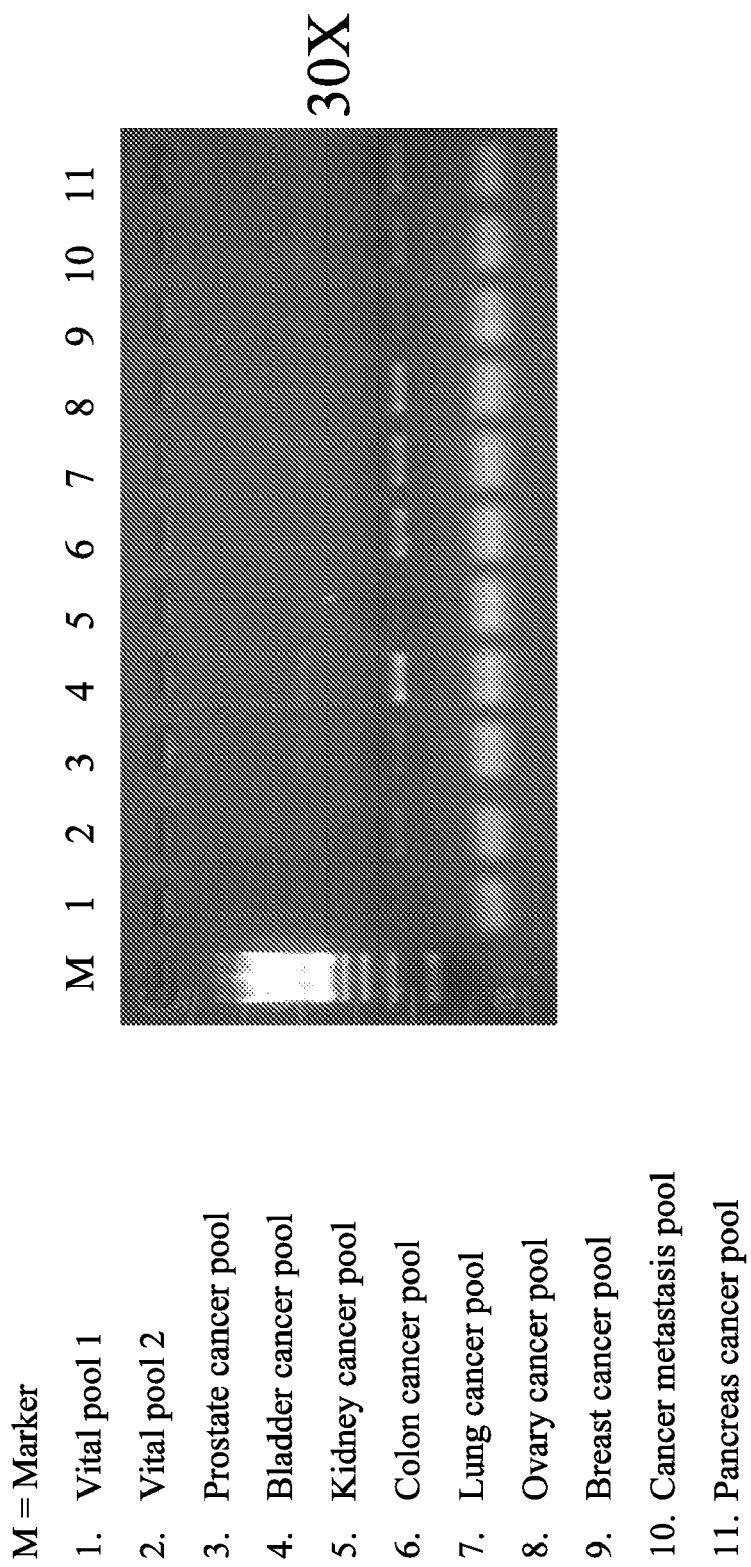
Figure 24 Expression of 109P1D4 by RT-PCR
M = Marker
1. Vital pool 1
2. Vital pool 2
3. Prostate cancer pool
4. Bladder cancer pool
5. Kidney cancer pool
6. Colon cancer pool
7. Lung cancer pool
8. Ovary cancer pool
9. Breast cancer pool
10. Cancer metastasis pool
11. Pancreas cancer pool

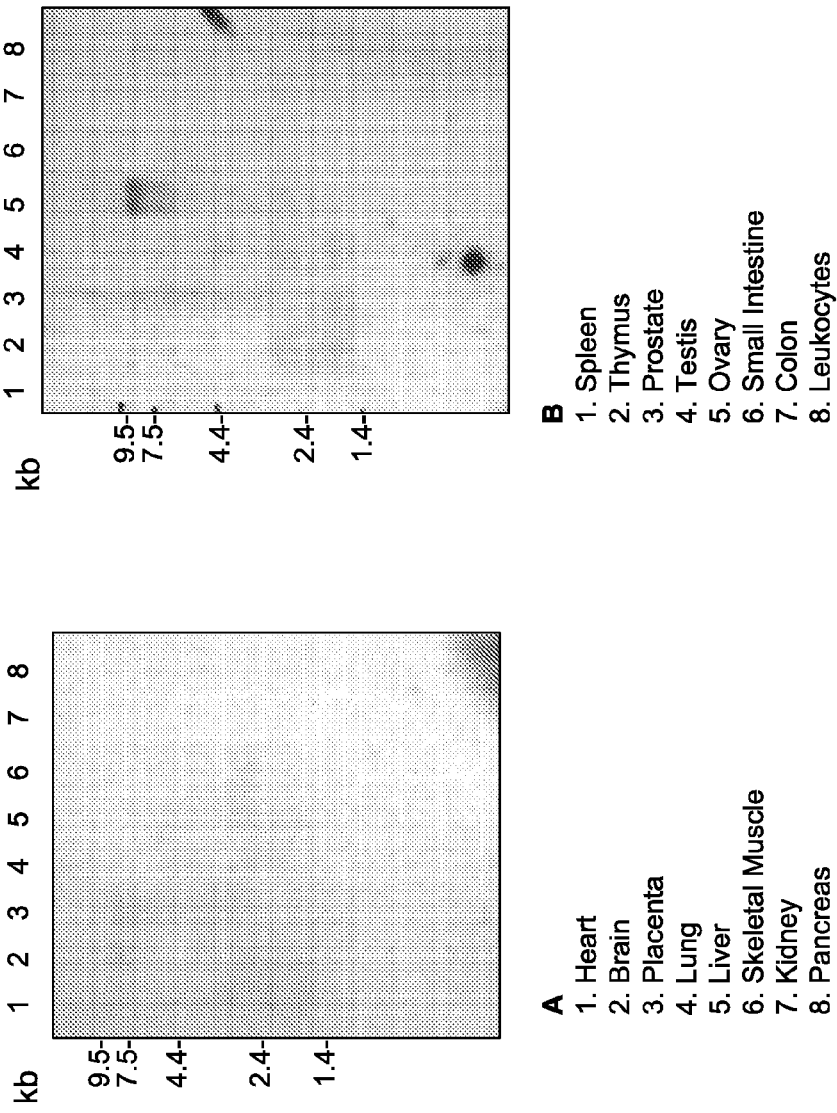
Figure 25 Expression of 109P1D4 in Normal Tissues by Northern Blot

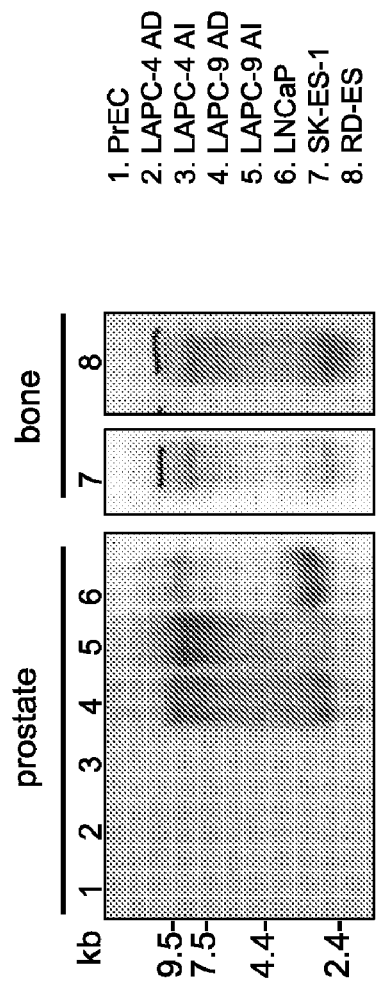
Figure 26 Expression of 109P1D4 in prostate and bone cancer cell lines

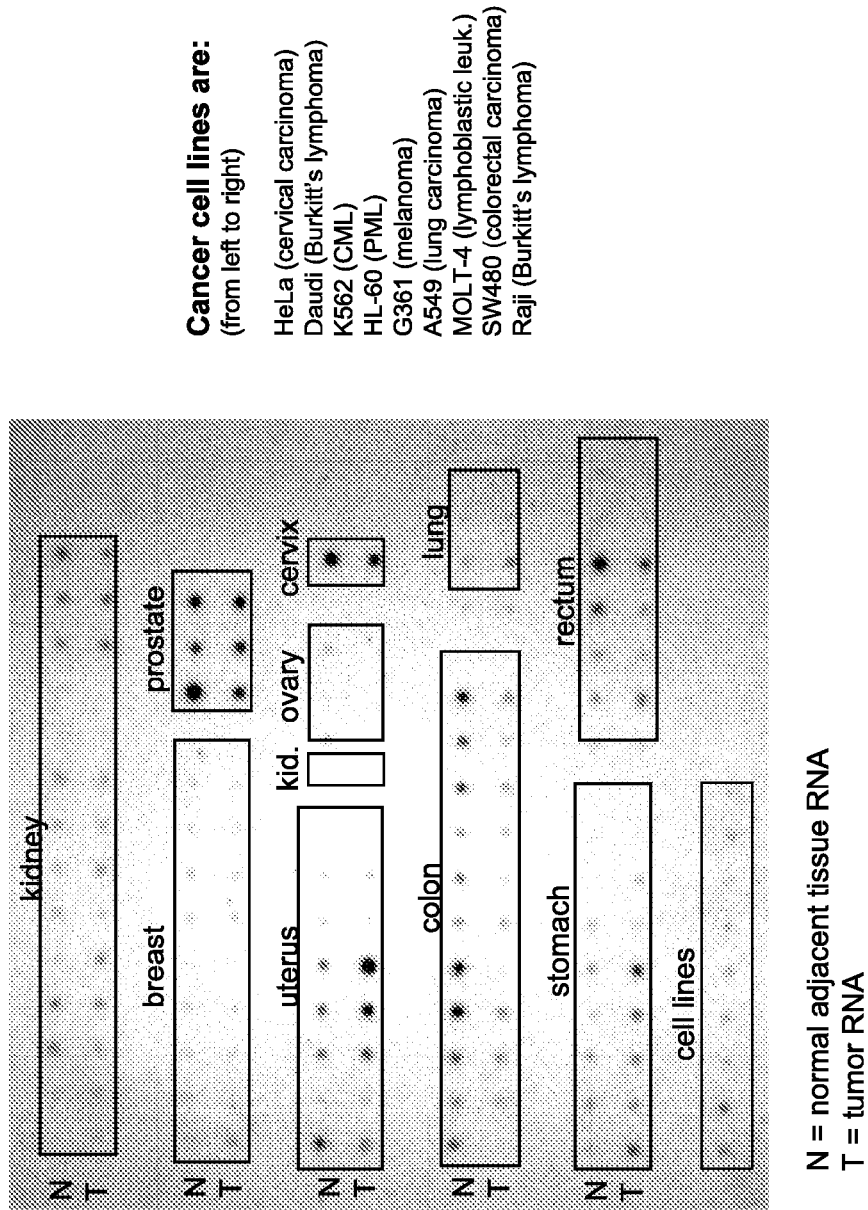
Figure 27 Expression of 109P1D4 in Human Patient Cancer Specimens

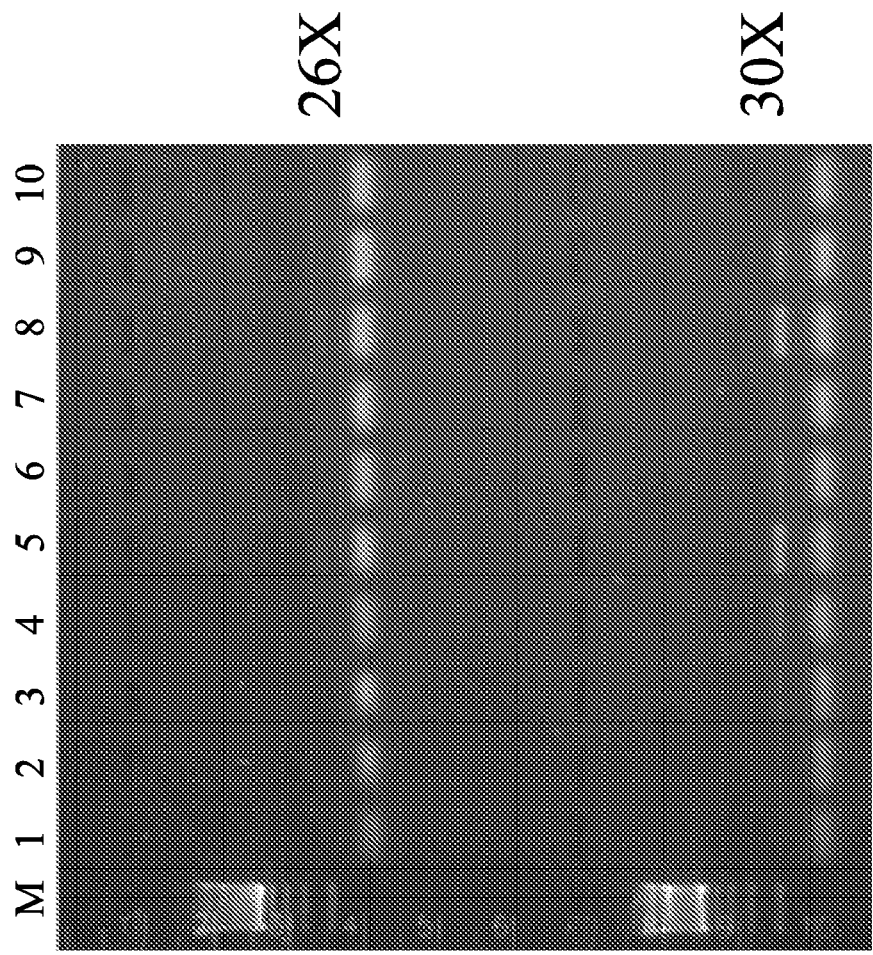
Figure 28 Expression of 151P1C7A by RT-PCR
1. Vital pool 1
2. Vital pool 2
3. Xenograft pool
4. Prostate cancer pool
5. Bladder cancer pool
6. Kidney cancer pool
7. Colon cancer pool
8. Lung cancer pool
9. Cancer metastasis pool
10. H2O

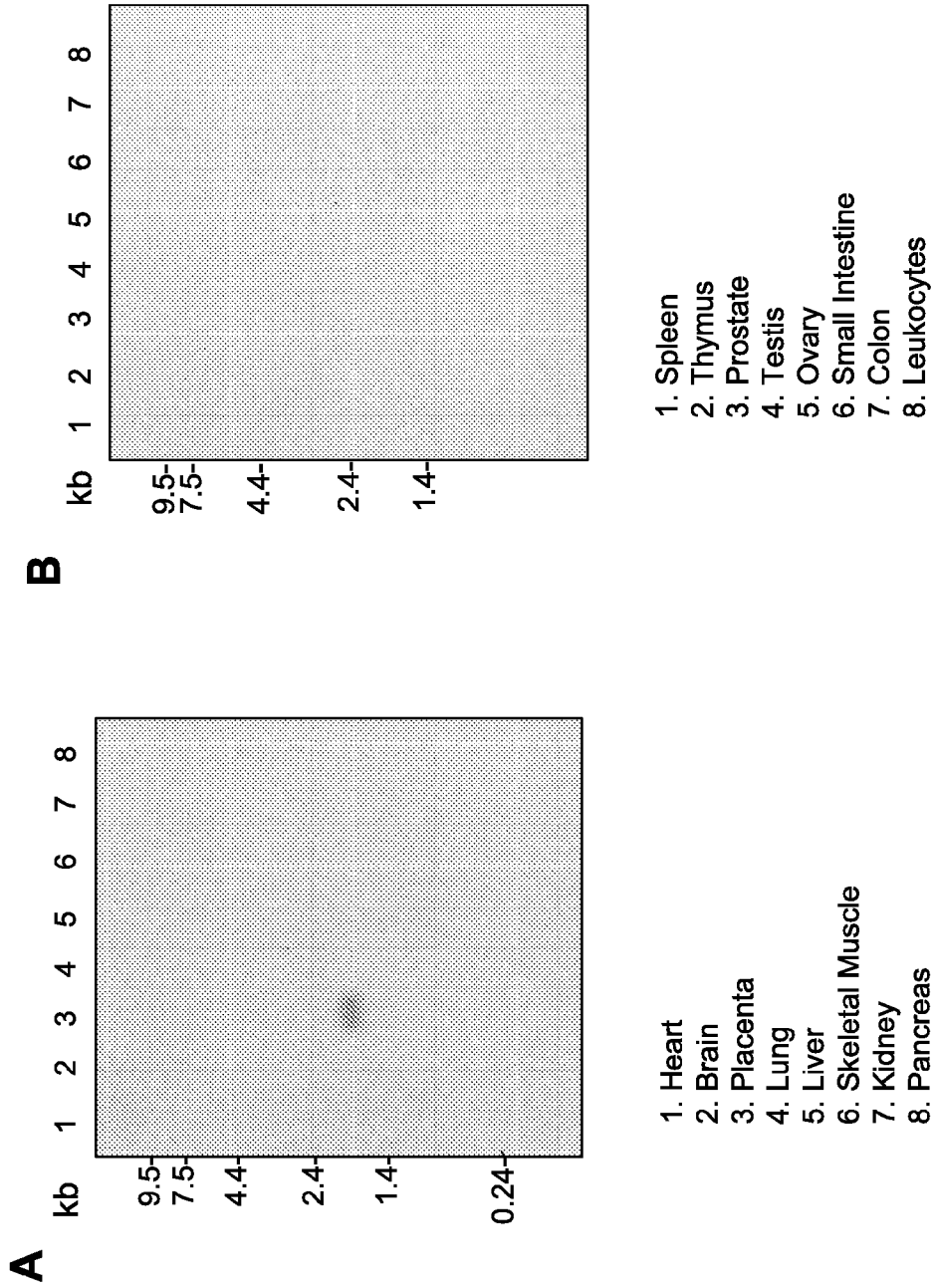
Figure 29 Expression of 151P1C7A in Normal Tissues

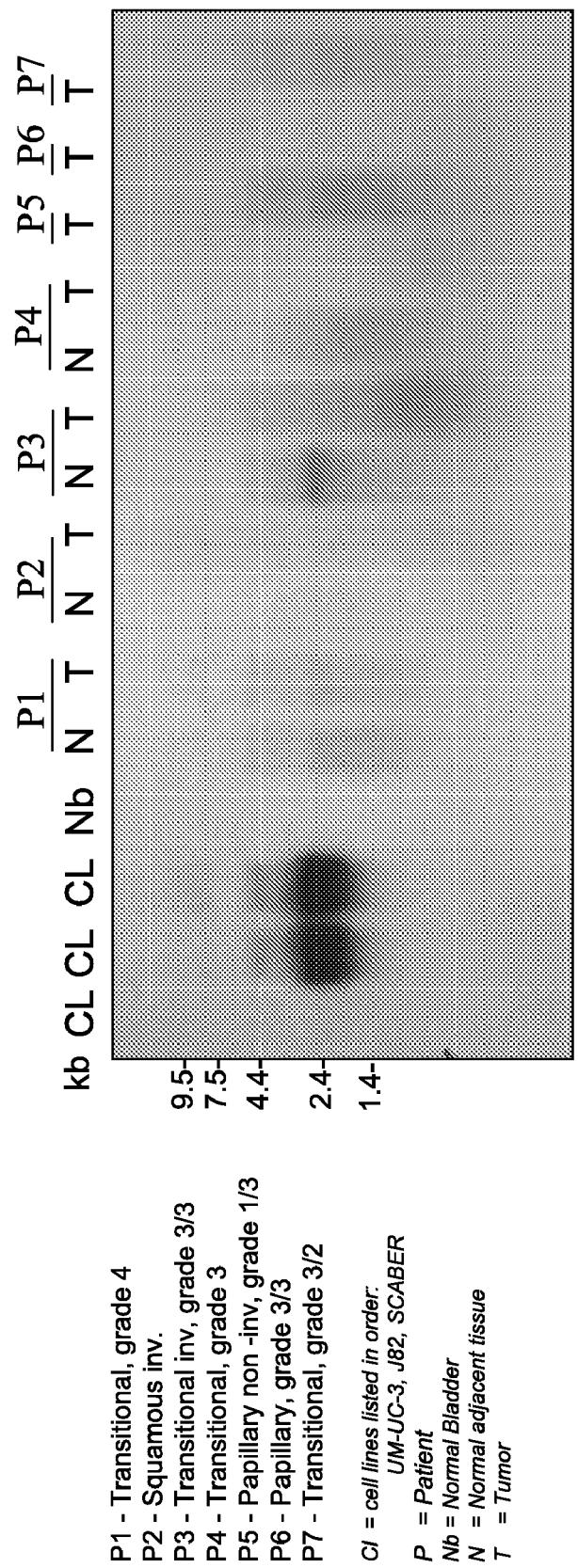
Figure 30  Expression of 151P1C7A in Bladder Cancer Patient Specimens
P1 - Transitional, grade 4
P2 - Squamous inv.
P3 - Transitional inv, grade 3/3
P4 - Transitional, grade 3
P5 - Papillary non -inv, grade 1/3
P6 - Papillary, grade 3/3
P7 - Transitional, grade 3/2
Cl = cell lines listed in order:
     UM-UC-3, J82, SCABER
P = Patient
Nb = Normal Bladder
N = Normal adjacent tissue
T = Tumor

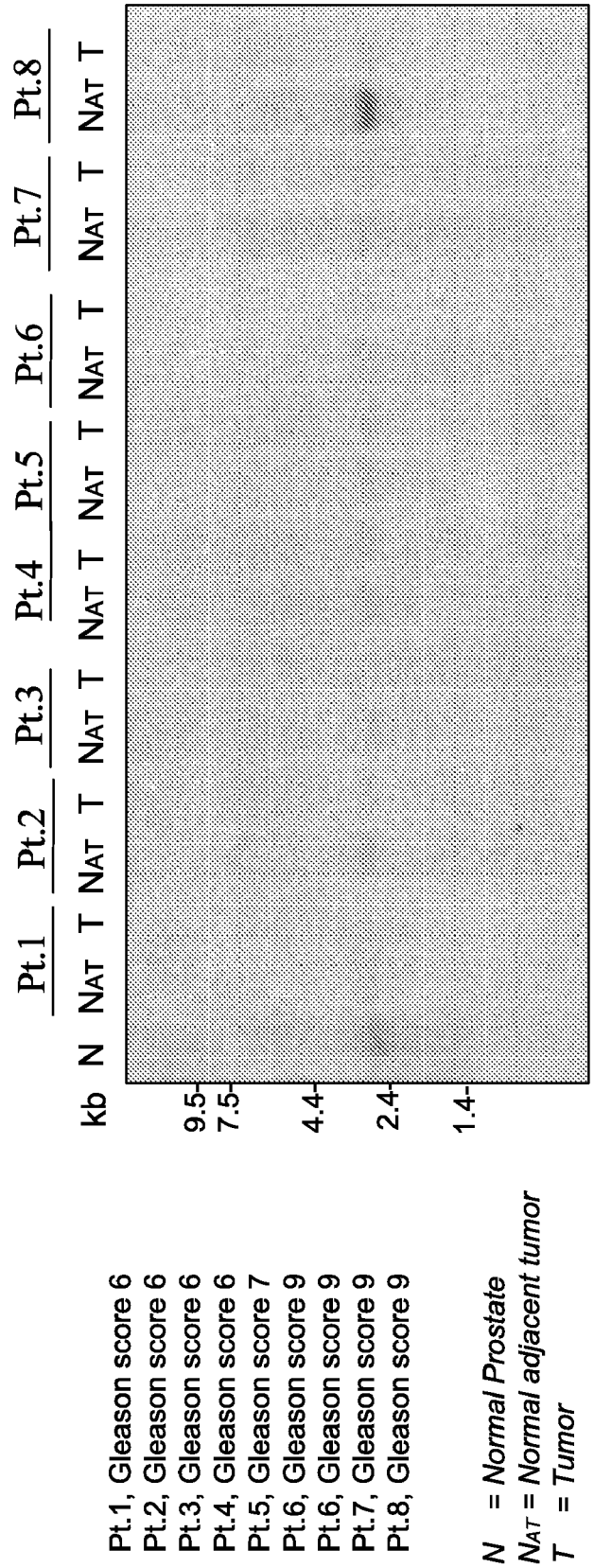
Figure 31 Expression of 151P1C7A in Prostate Cancer Patient Specimens
Pt.1, Gleason score 6
Pt.2, Gleason score 6
Pt.3, Gleason score 6
Pt.4, Gleason score 6
Pt.5, Gleason score 7
Pt.6, Gleason score 9
Pt.6, Gleason score 9
Pt.7, Gleason score 9
Pt.8, Gleason score 9
N = Normal Prostate
N$_{AT}$ = Normal adjacent tumor
T = Tumor

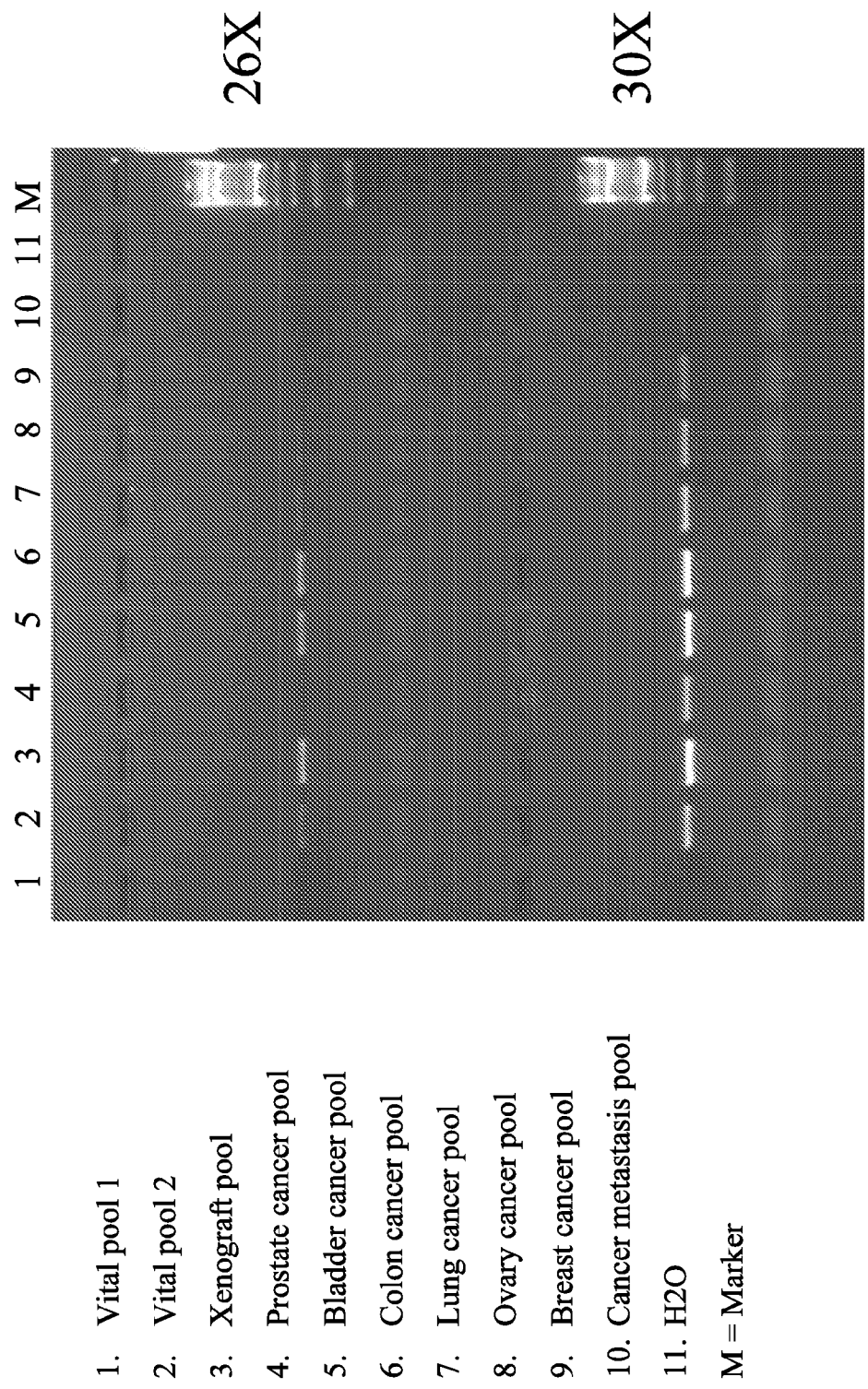
Figure 32 Expression of 151P4E11 by RT-PCR
1. Vital pool 1
2. Vital pool 2
3. Xenograft pool
4. Prostate cancer pool
5. Bladder cancer pool
6. Colon cancer pool
7. Lung cancer pool
8. Ovary cancer pool
9. Breast cancer pool
10. Cancer metastasis pool
11. H2O
M = Marker

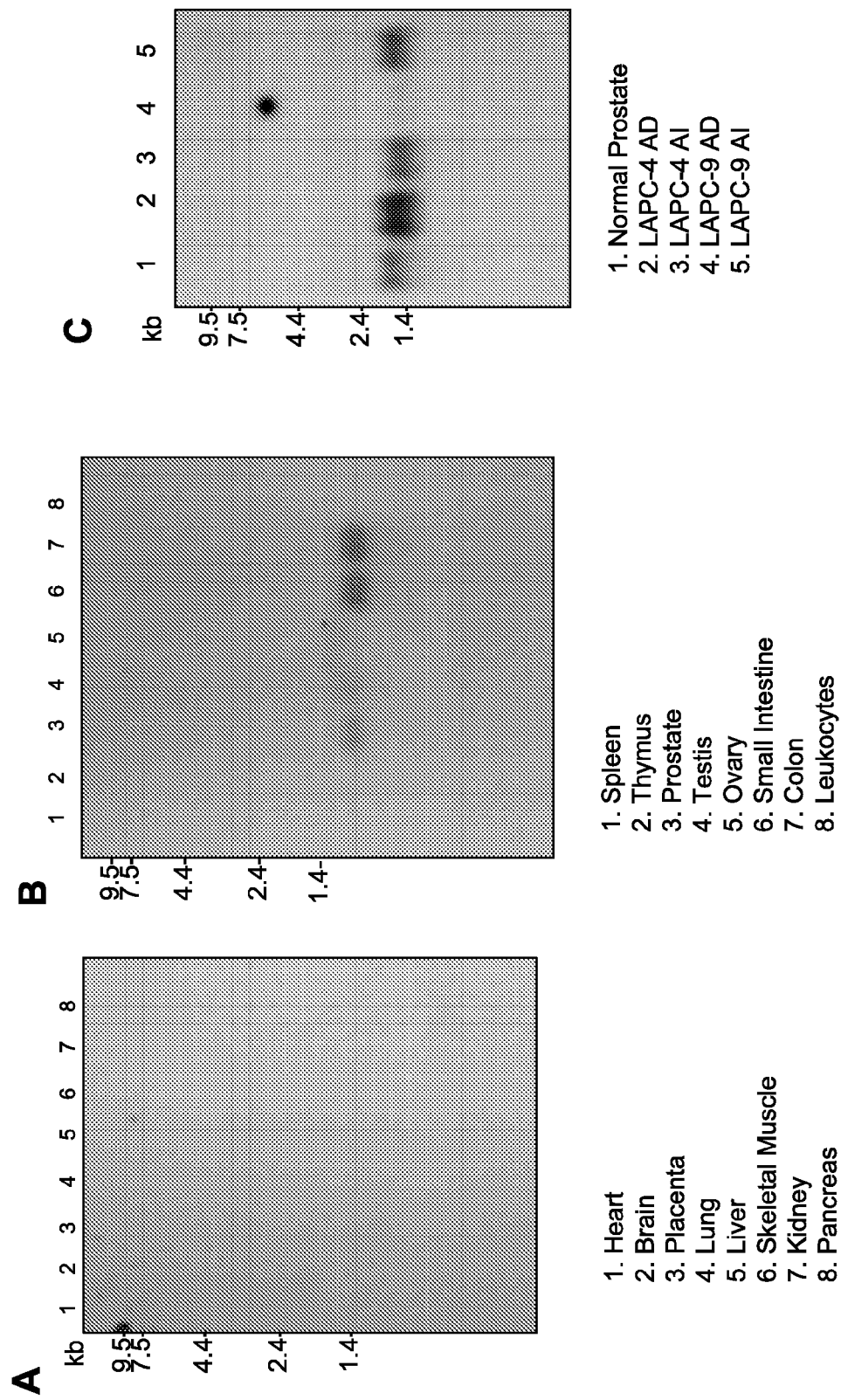
Figure 33 Expression of 151P4E11 in Normal Tissues and in Prostate Cancer Xenografts

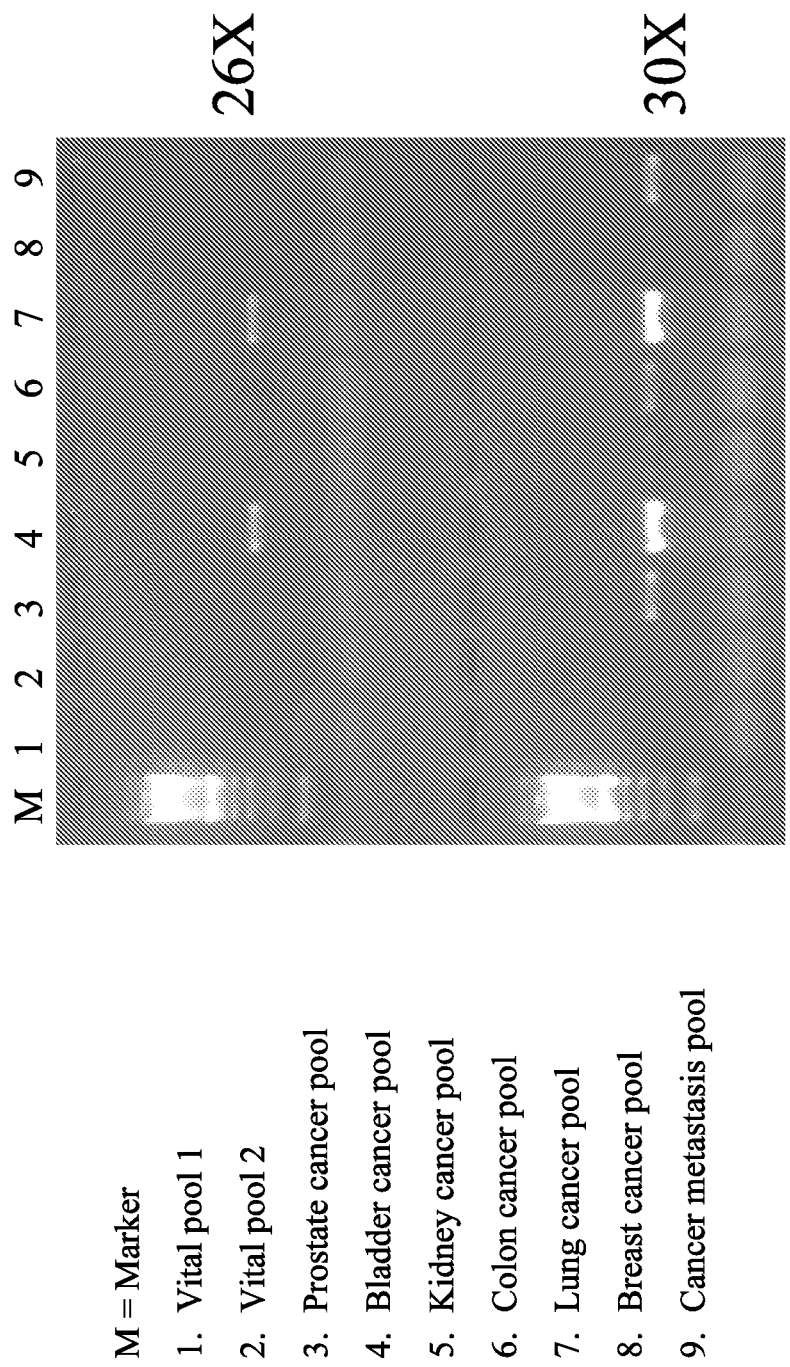
Figure 34 Expression of 154P2A8 by RT-PCR
M = Marker
1. Vital pool 1
2. Vital pool 2
3. Prostate cancer pool
4. Bladder cancer pool
5. Kidney cancer pool
6. Colon cancer pool
7. Lung cancer pool
8. Breast cancer pool
9. Cancer metastasis pool

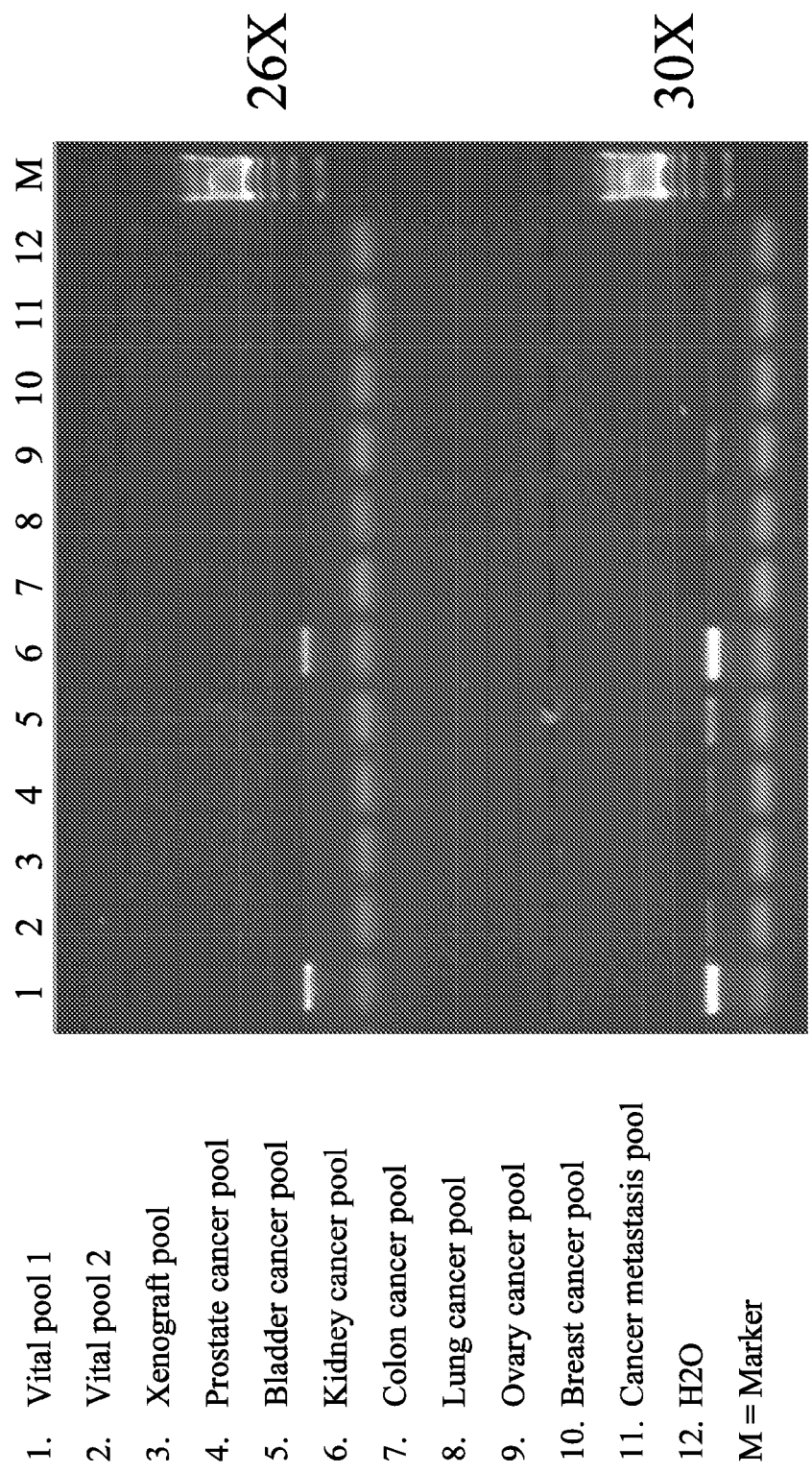
Figure 35 Expression of 156P1D4 by RT-PCR
1. Vital pool 1
2. Vital pool 2
3. Xenograft pool
4. Prostate cancer pool
5. Bladder cancer pool
6. Kidney cancer pool
7. Colon cancer pool
8. Lung cancer pool
9. Ovary cancer pool
10. Breast cancer pool
11. Cancer metastasis pool
12. H2O
M = Marker

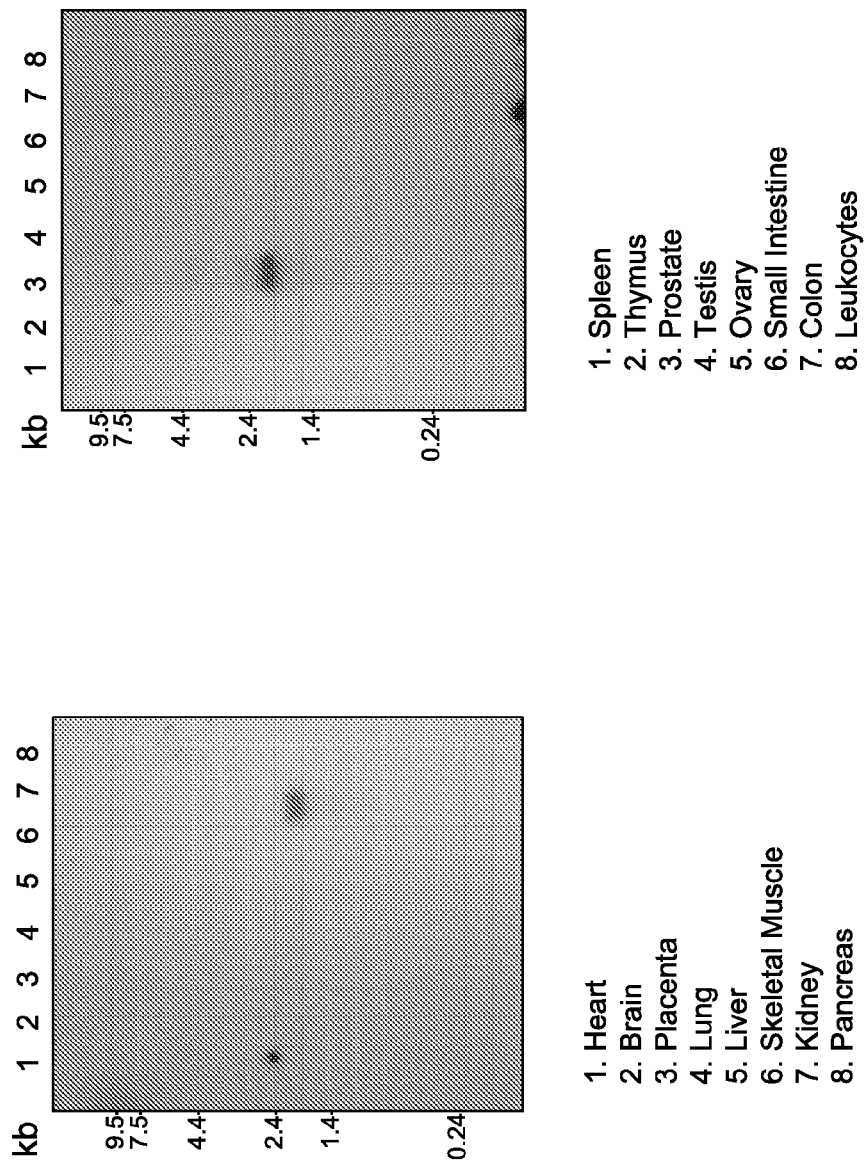
Figure 36  Expression of 156P1D4 in Normal Tissues

Figure 37 Expression of 156P1D4 in Kidney Cancer Patient Specimens

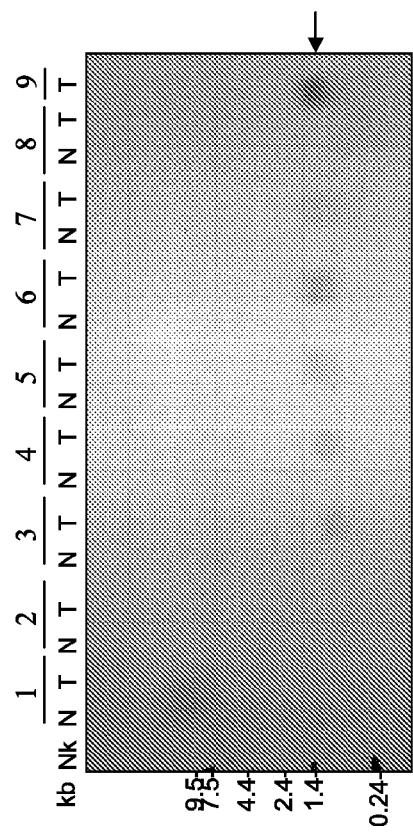

Patient 1 - papillary cell, grade 1
Patient 2 - papillary adenocarc, nuclear, grade 3
Patient 3 - clear cell, Fuhrman grade 2 of 4
Patient 4 - clear cell, grade III
Patient 5 - clear cell, grade II/IV
Patient 6 - clear cell, grade 3
Patient 7 - clear cell, grade III/IV
Patient 8 - chromophobe cell type, grade IV
Patient 9 - met to chest wall

*NK = Normal kidney*
*N = Normal adjacent tissue*
*T = Tumor*

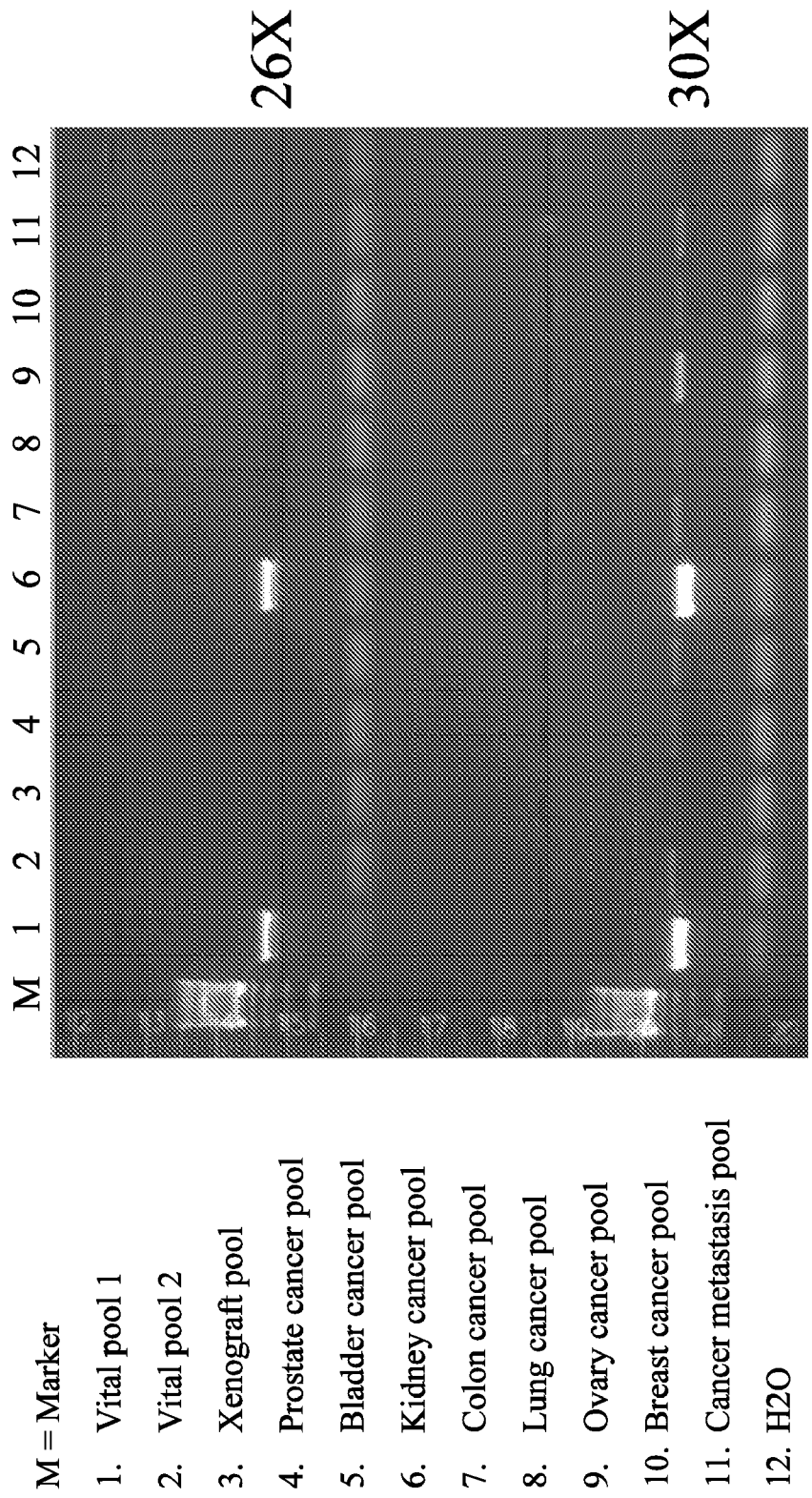
Figure 38 Expression of 156P5C12 by RT-PCR
M = Marker
1. Vital pool 1
2. Vital pool 2
3. Xenograft pool
4. Prostate cancer pool
5. Bladder cancer pool
6. Kidney cancer pool
7. Colon cancer pool
8. Lung cancer pool
9. Ovary cancer pool
10. Breast cancer pool
11. Cancer metastasis pool
12. H2O

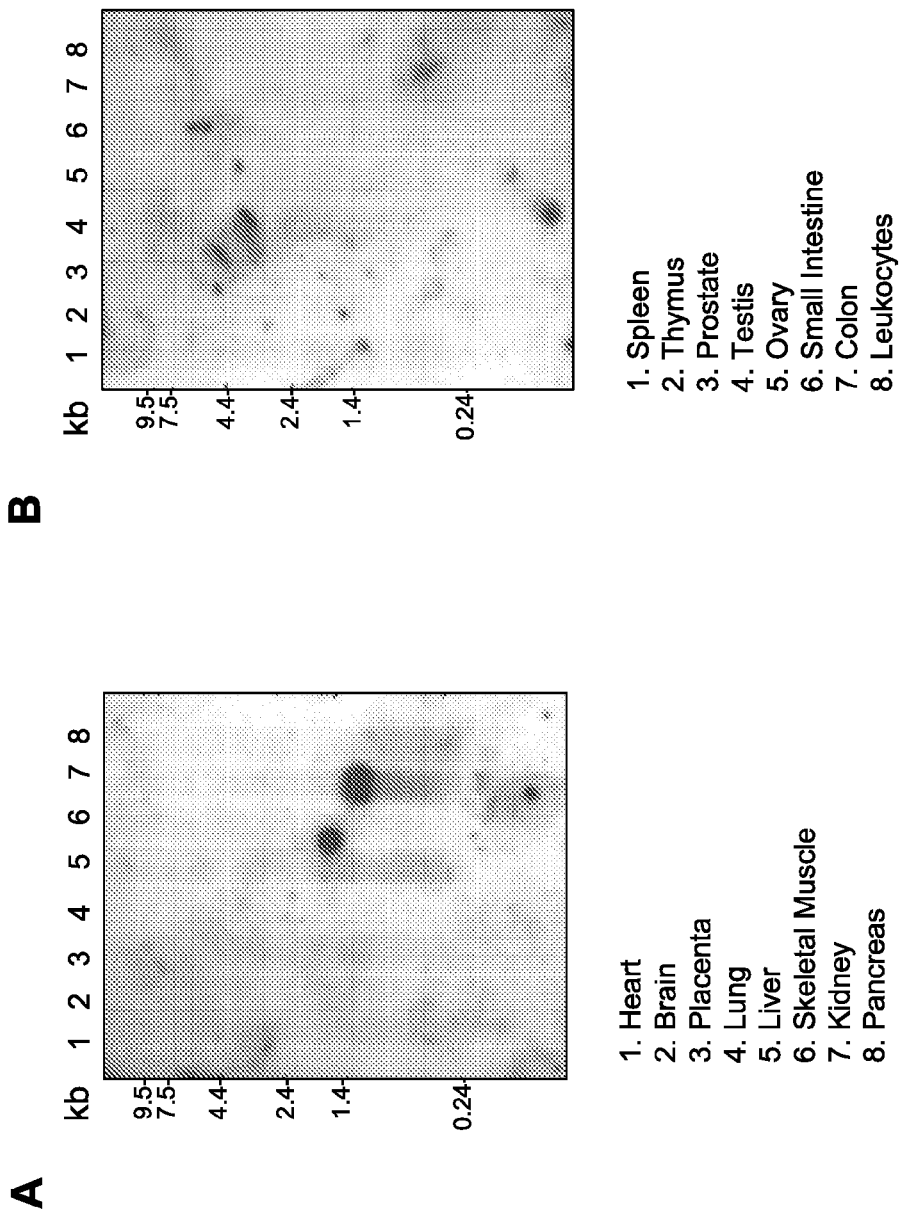
Figure 39  Expression of 156P5C12 in Normal Tissues

Figure 40  Expression of 156P5C12 in Kidney Cancer Patient Specimens
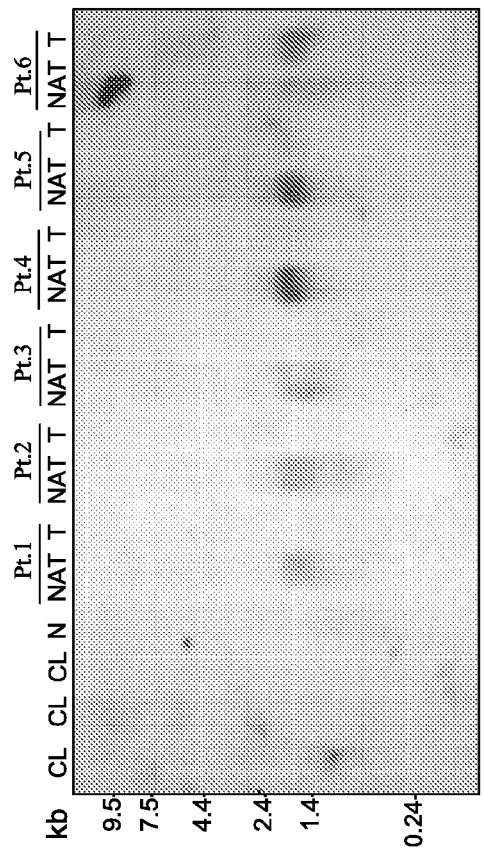
CL = cell lines listed in order:
    769-P, A498, SW839
N = Normal kidney
N_AT = Normal adjacent tumor
T = Tumor
Pt.1, Papillary carcinoma, stage I
Pt.2, Invasive papillary carcinoma
Pt.3, Clear cell type grade 1/3, focally 2/3
Pt.4, Clear cell type, stage III
Pt.5, Clear cell type, stage III
Pt.6, Clear cell type, stage III

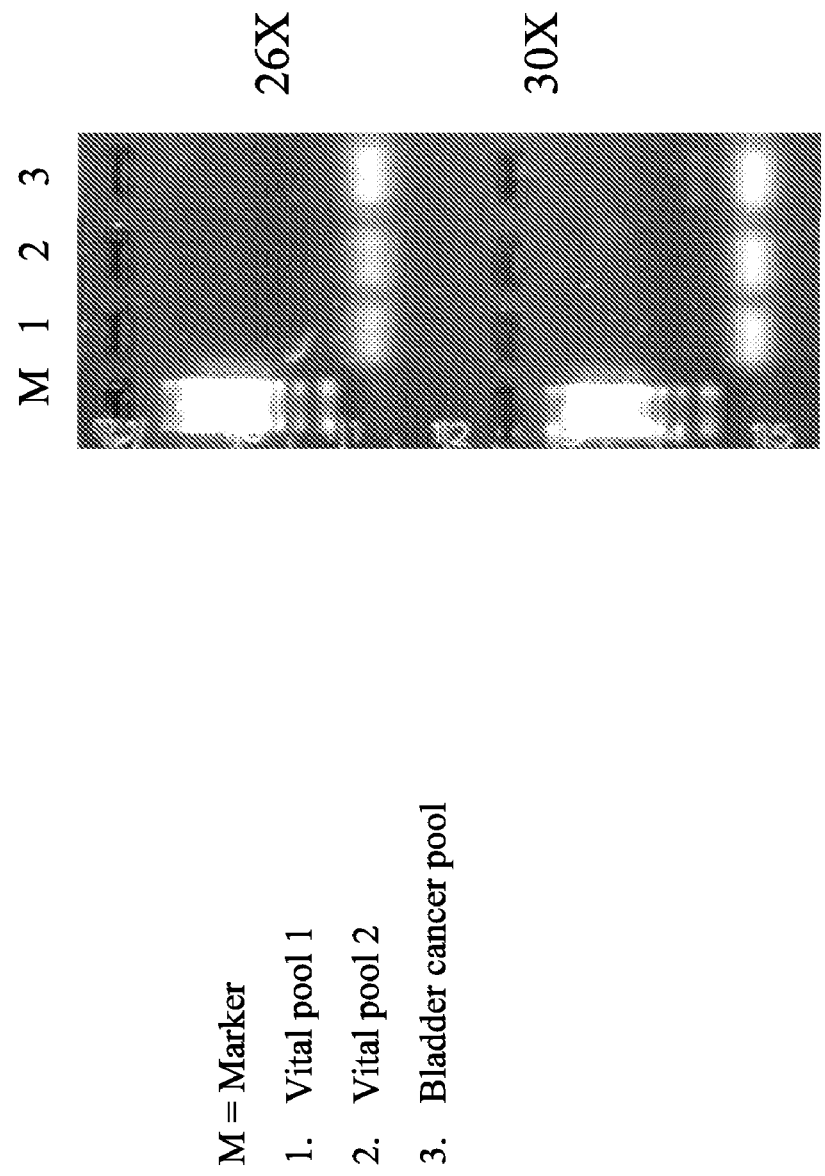
Figure 41 Expression of 159P2B5 by RT-PCR
M = Marker
1. Vital pool 1
2. Vital pool 2
3. Bladder cancer pool

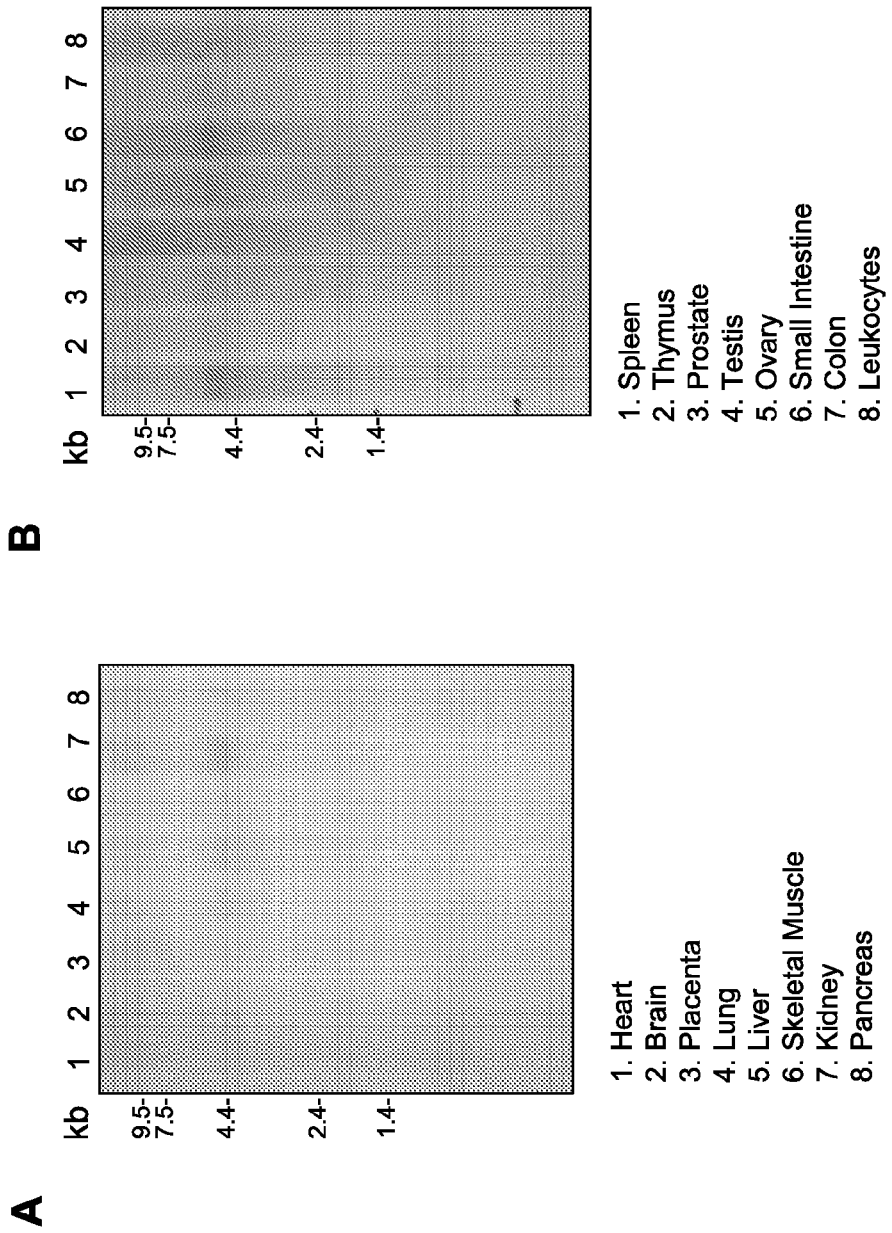
Figure 42 Expression of 159P2B5 in Normal Tissues

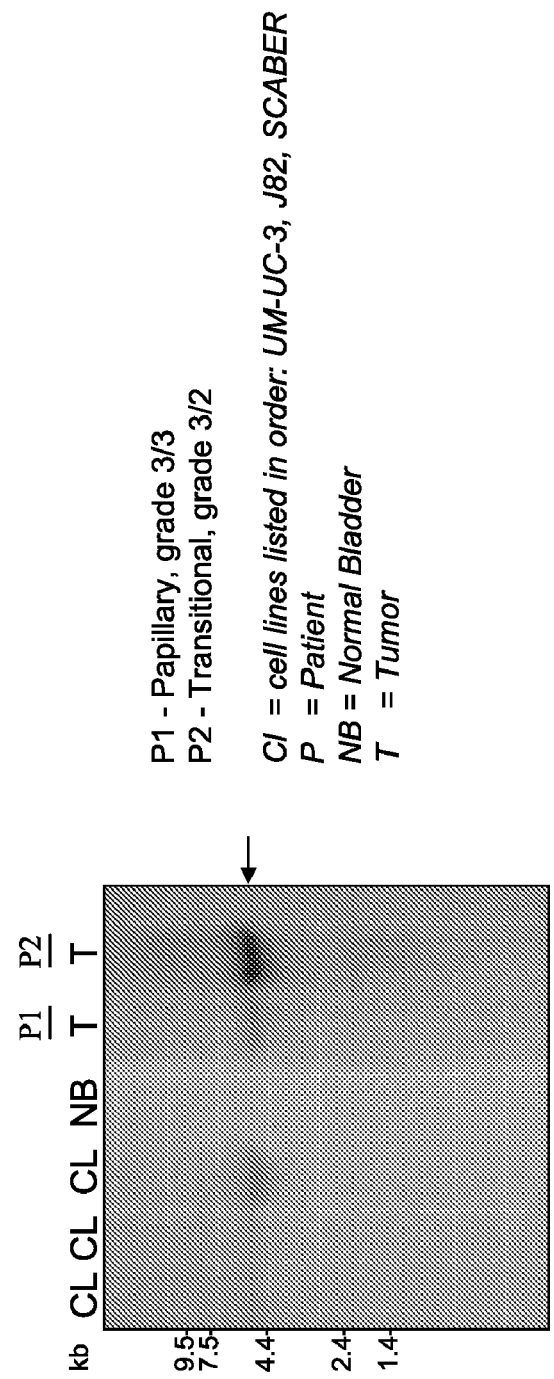
Figure 43  Expression of 159P2B5 in Bladder Cancer Patient Specimens

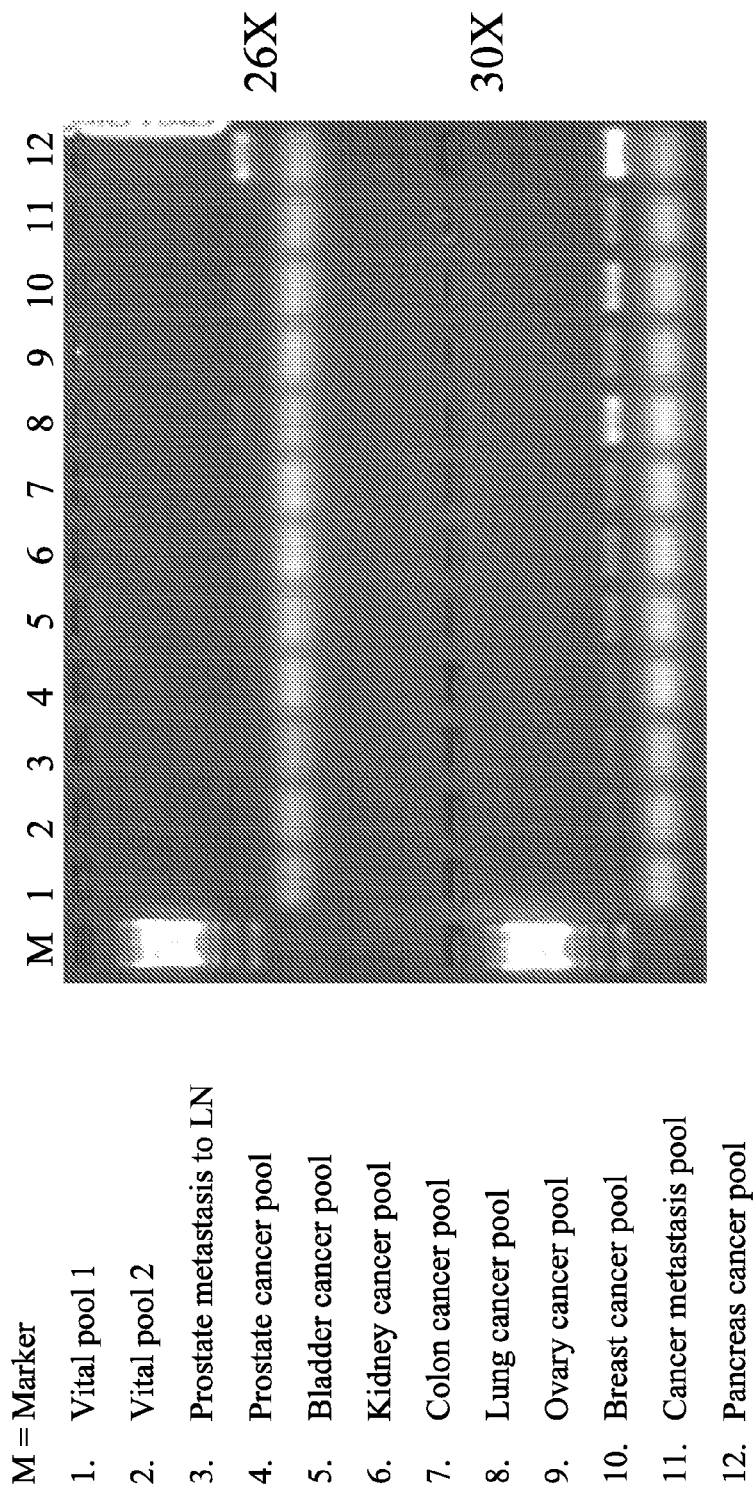
Figure 44 Expression of 161P2B7A by RT-PCR
M = Marker
1. Vital pool 1
2. Vital pool 2
3. Prostate metastasis to LN
4. Prostate cancer pool
5. Bladder cancer pool
6. Kidney cancer pool
7. Colon cancer pool
8. Lung cancer pool
9. Ovary cancer pool
10. Breast cancer pool
11. Cancer metastasis pool
12. Pancreas cancer pool

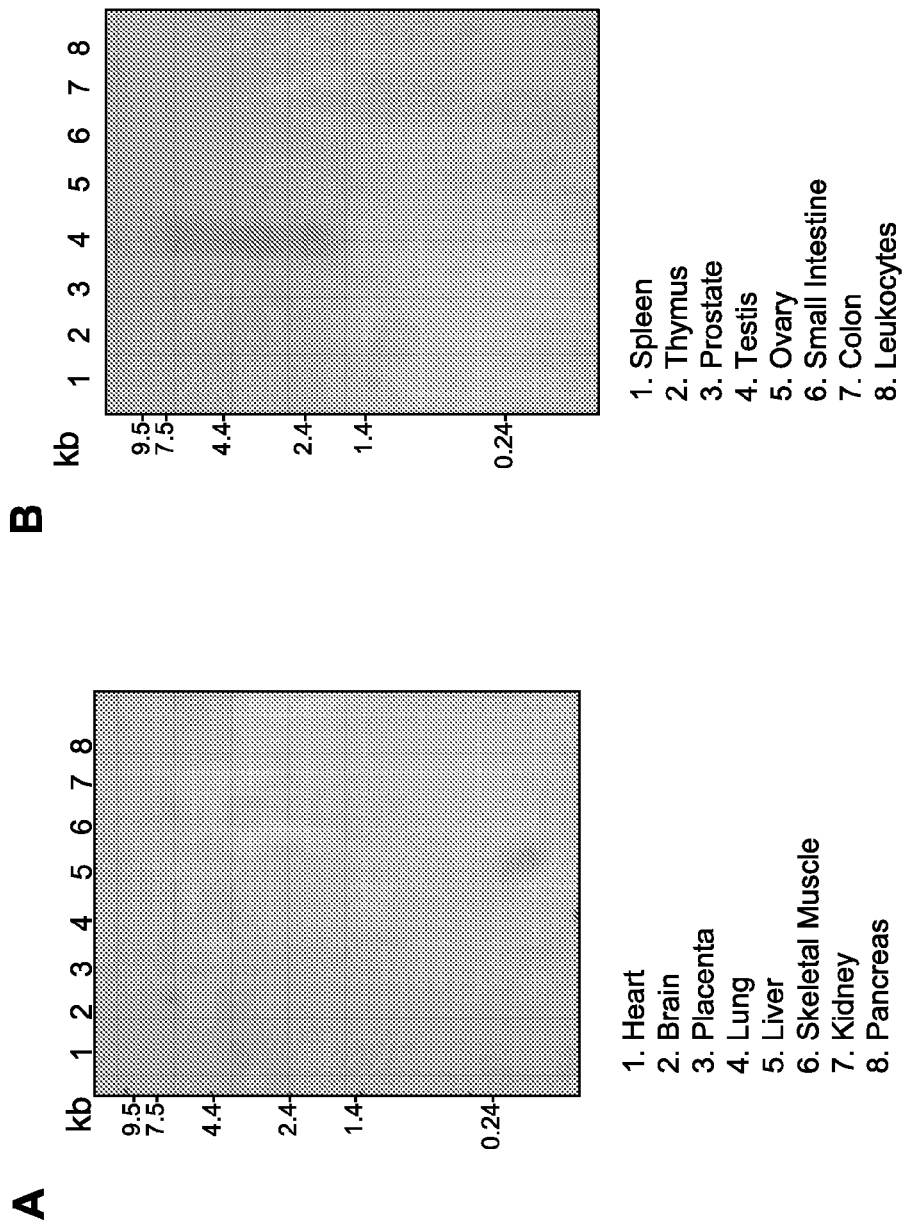
Figure 45 Expression of 161P2B7A in Normal Tissues

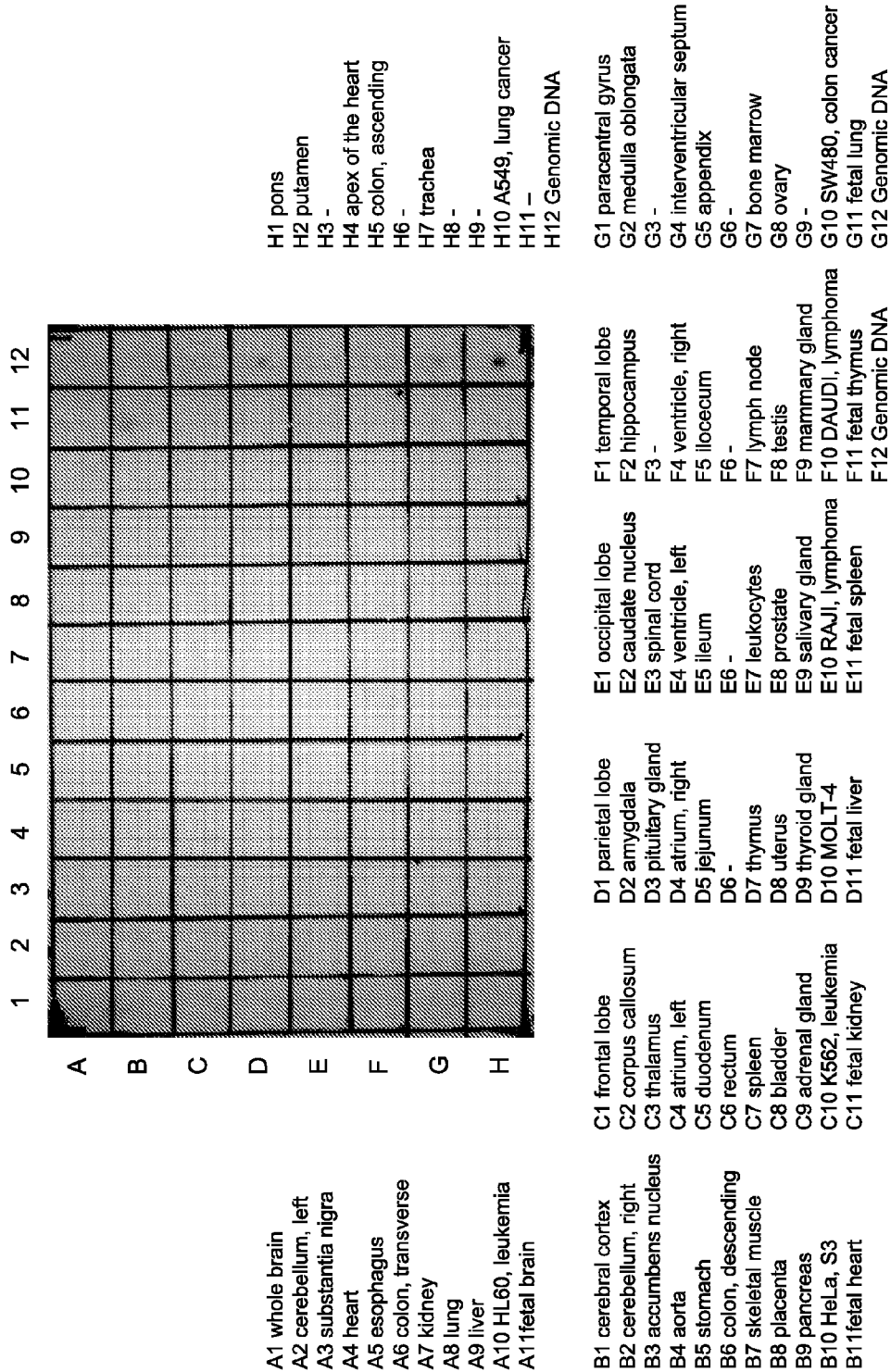

Figure 46 Expression of 161P2B7A in Multiple Normal Tissues

A1 whole brain
A2 cerebellum, left
A3 substantia nigra
A4 heart
A5 esophagus
A6 colon, transverse
A7 kidney
A8 lung
A9 liver
A10 HL60, leukemia
A11 fetal brain B1 cerebral cortex
B2 cerebellum, right
B3 accumbens nucleus
B4 aorta
B5 stomach
B6 colon, descending
B7 skeletal muscle
B8 placenta
B9 pancreas
B10 HeLa, S3
B11 fetal heart C1 frontal lobe
C2 corpus callosum
C3 thalamus
C4 atrium, left
C5 duodenum
C6 rectum
C7 spleen
C8 bladder
C9 adrenal gland
C10 K562, leukemia
C11 fetal kidney D1 parietal lobe
D2 amygdala
D3 pituitary gland
D4 atrium, right
D5 jejunum
D6 -
D7 thymus
D8 uterus
D9 thyroid gland
D10 MOLT-4
D11 fetal liver E1 occipital lobe
E2 caudate nucleus
E3 spinal cord
E4 ventricle, left
E5 ileum
E6 -
E7 leukocytes
E8 prostate
E9 salivary gland
E10 RAJI, lymphoma
E11 fetal spleen F1 temporal lobe
F2 hippocampus
F3 -
F4 ventricle, right
F5 ilocecum
F6 -
F7 lymph node
F8 testis
F9 mammary gland
F10 DAUDI, lymphoma
F11 fetal thymus
F12 Genomic DNA G1 paracentral gyrus
G2 medulla oblongata
G3 -
G4 interventricular septum
G5 appendix
G6 -
G7 bone marrow
G8 ovary
G9 -
G10 SW480, colon cancer
G11 fetal lung
G12 Genomic DNA H1 pons
H2 putamen
H3 -
H4 apex of the heart
H5 colon, ascending
H6 -
H7 trachea
H8 -
H9 -
H10 A549, lung cancer
H11 -
H12 Genomic DNA

Figure 47 Expression of 161P2B7A in Kidney Cancer Patient Specimens
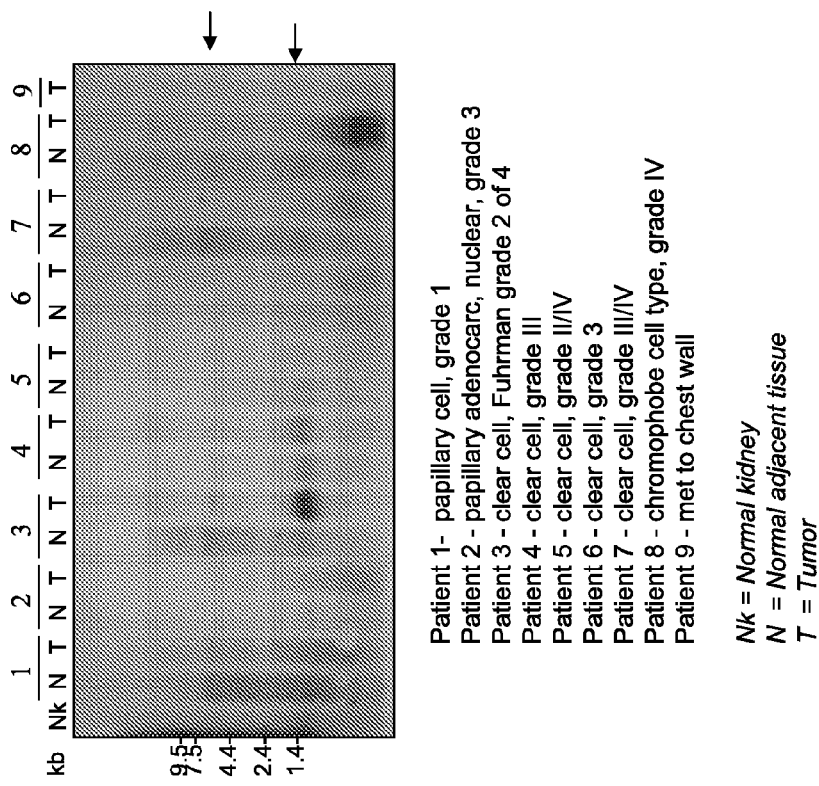

Figure 48 Expression of 161P2B7A in Lung Cancer Patient Specimens
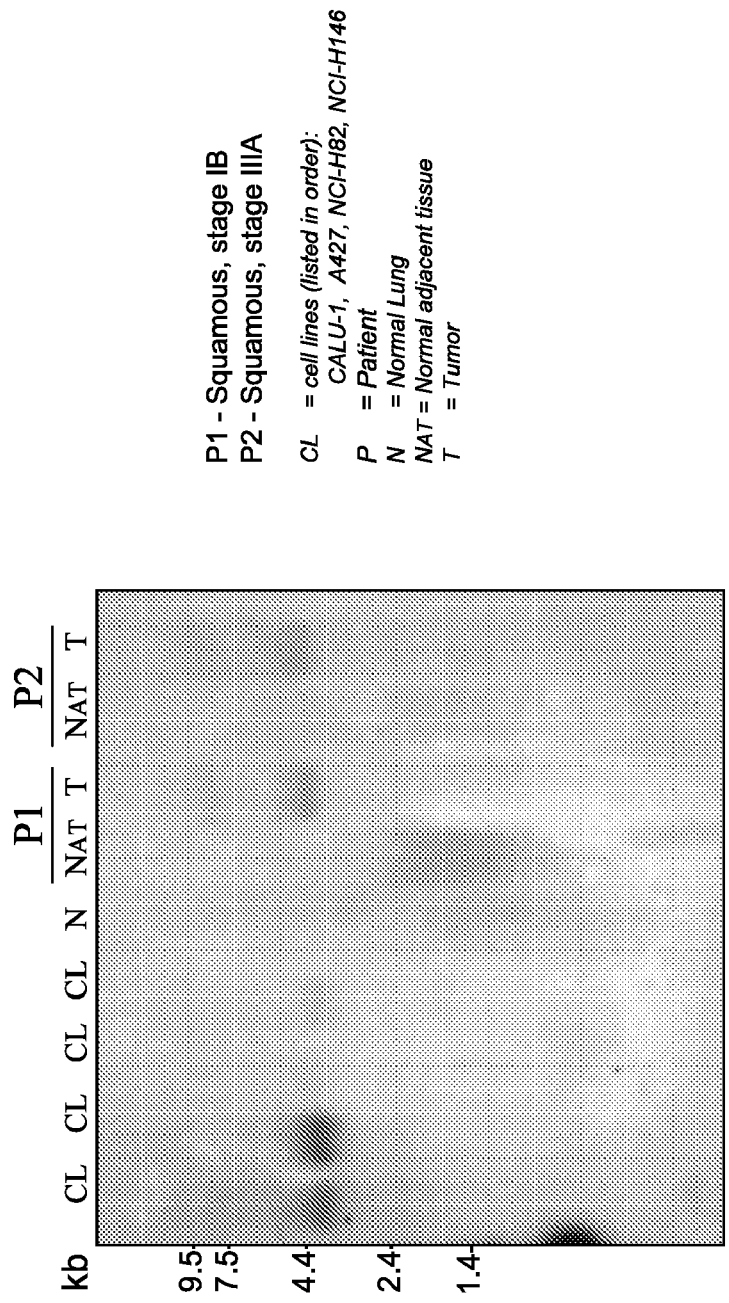

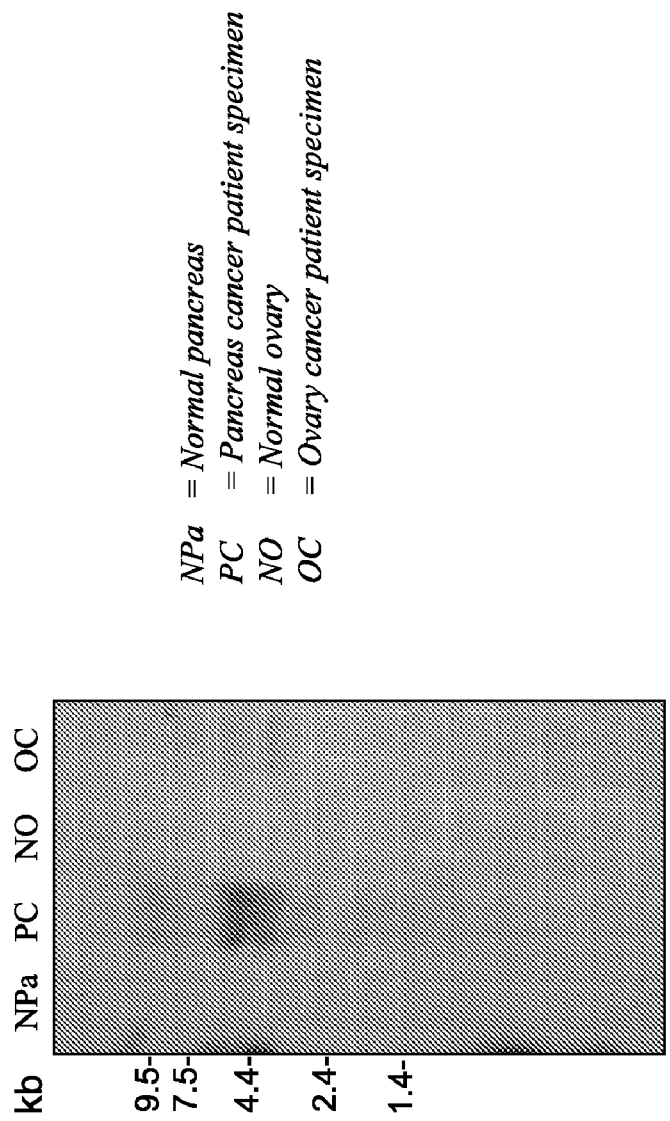
Figure 49 Expression of 161P2B7A in Pancreas and Ovary Cancer Patient Specimens
NPa = Normal pancreas
PC = Pancreas cancer patient specimen
NO = Normal ovary
OC = Ovary cancer patient specimen

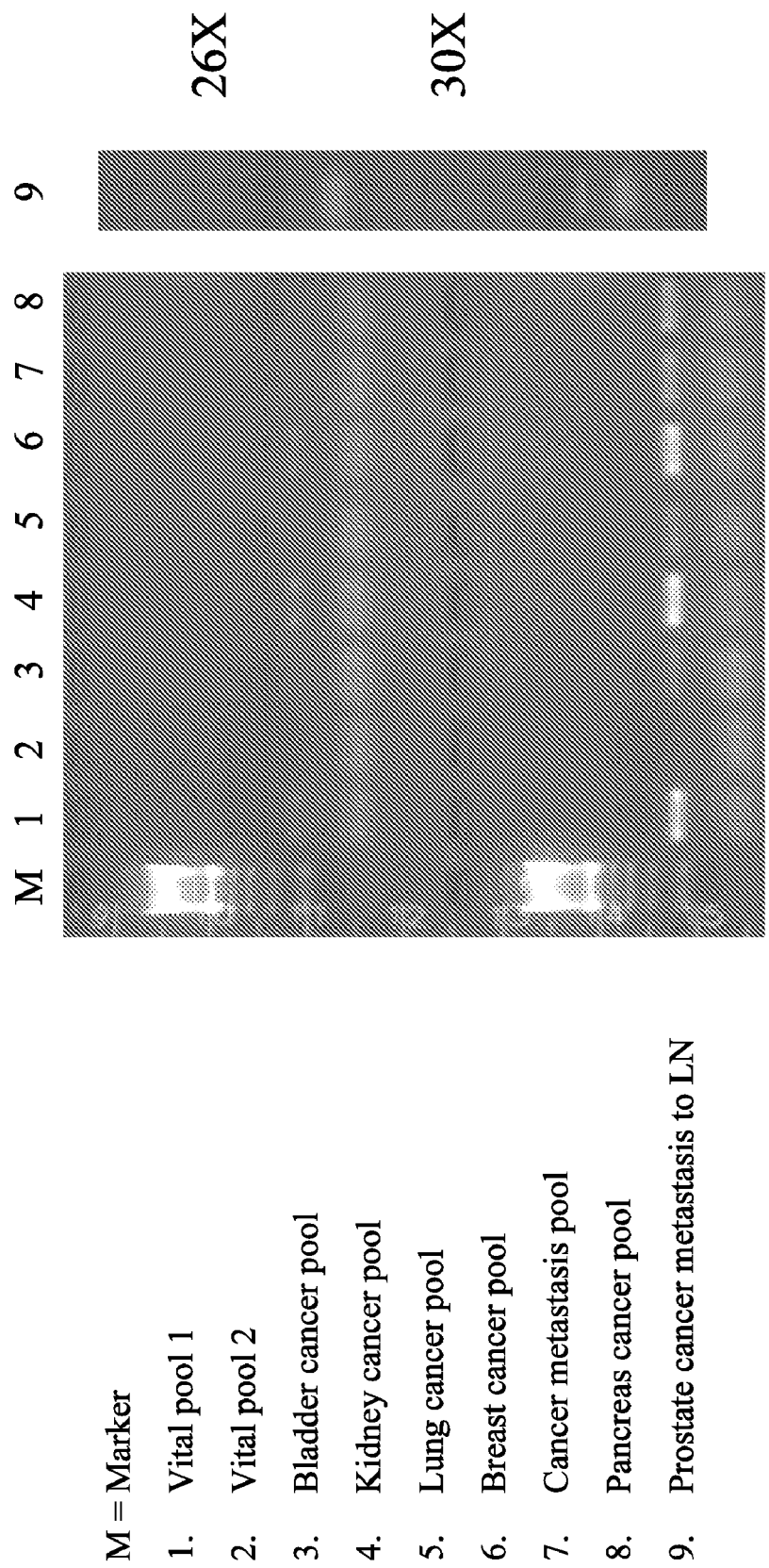
Figure 50 Expression of 179P3G7 by RT-PCR
M = Marker
1. Vital pool 1
2. Vital pool 2
3. Bladder cancer pool
4. Kidney cancer pool
5. Lung cancer pool
6. Breast cancer pool
7. Cancer metastasis pool
8. Pancreas cancer pool
9. Prostate cancer metastasis to LN

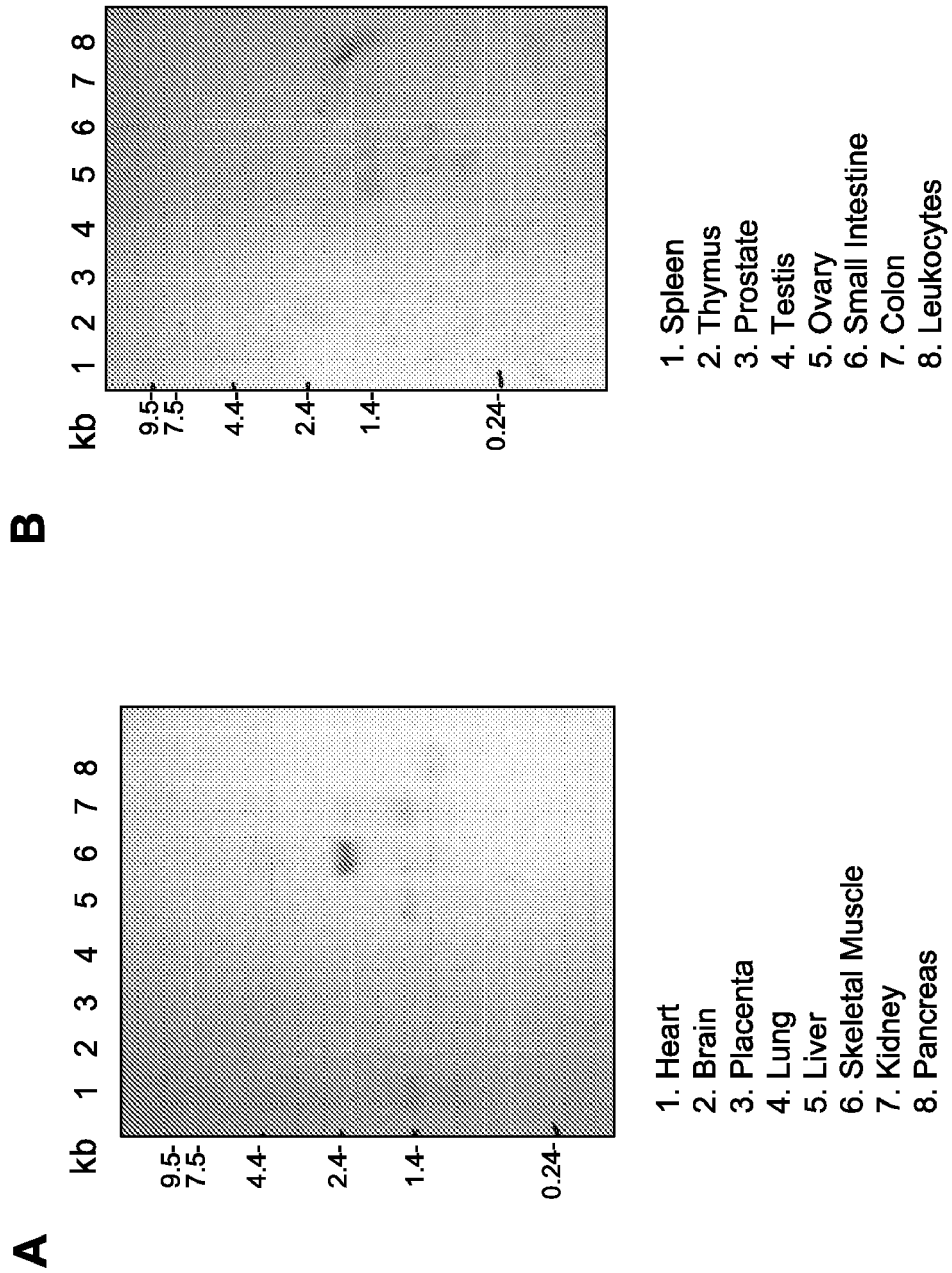
Figure 51 Expression of 179P3G7 in Normal Tissues

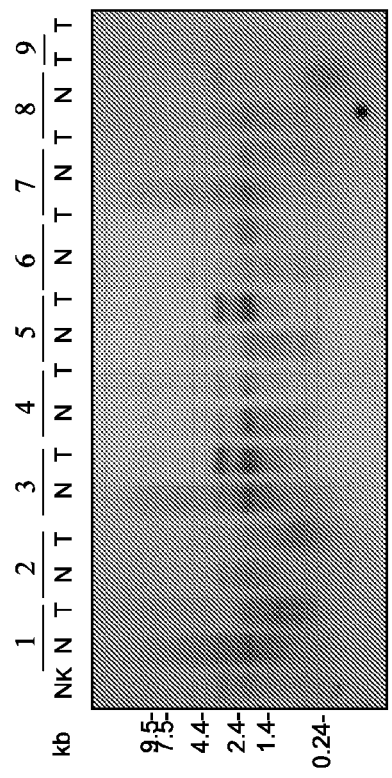
Figure 52 Expression of 179P3G7 in Kidney Cancer Patient Specimens
Patient 1 - papillary cell, grade 1
Patient 2 - papillary adenocarc, nuclear, grade 3
Patient 3 - clear cell, Fuhrman grade 2 of 4
Patient 4 - clear cell, grade III
Patient 5 - clear cell, grade II/IV
Patient 6 - clear cell, grade 3
Patient 7 - clear cell, grade III/IV
Patient 8 - chromophobe cell type, grade IV
Patient 9 - met to chest wall

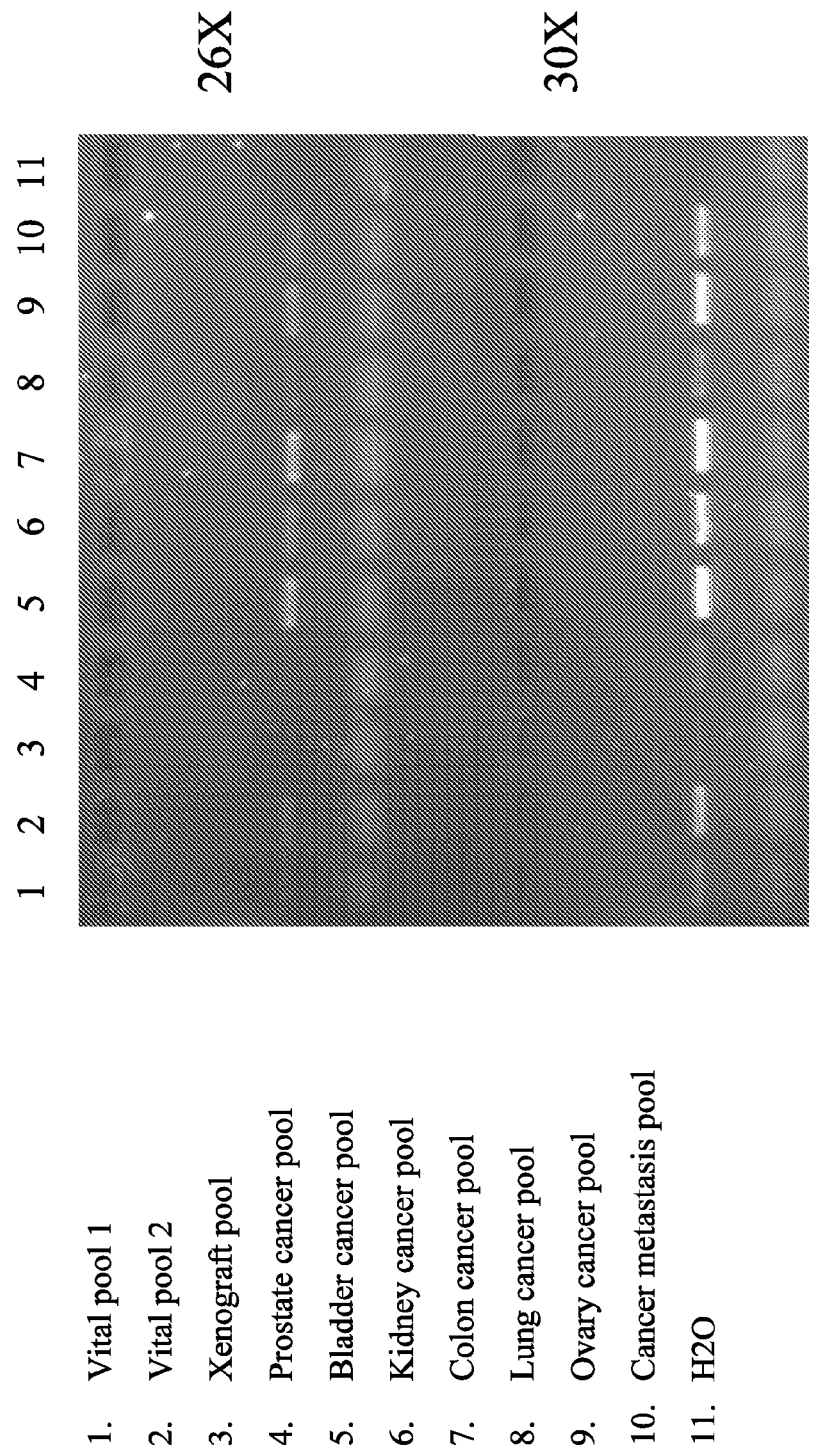
Figure 53 Expression of 184P3C10B by RT-PCR
1. Vital pool 1
2. Vital pool 2
3. Xenograft pool
4. Prostate cancer pool
5. Bladder cancer pool
6. Kidney cancer pool
7. Colon cancer pool
8. Lung cancer pool
9. Ovary cancer pool
10. Cancer metastasis pool
11. H2O

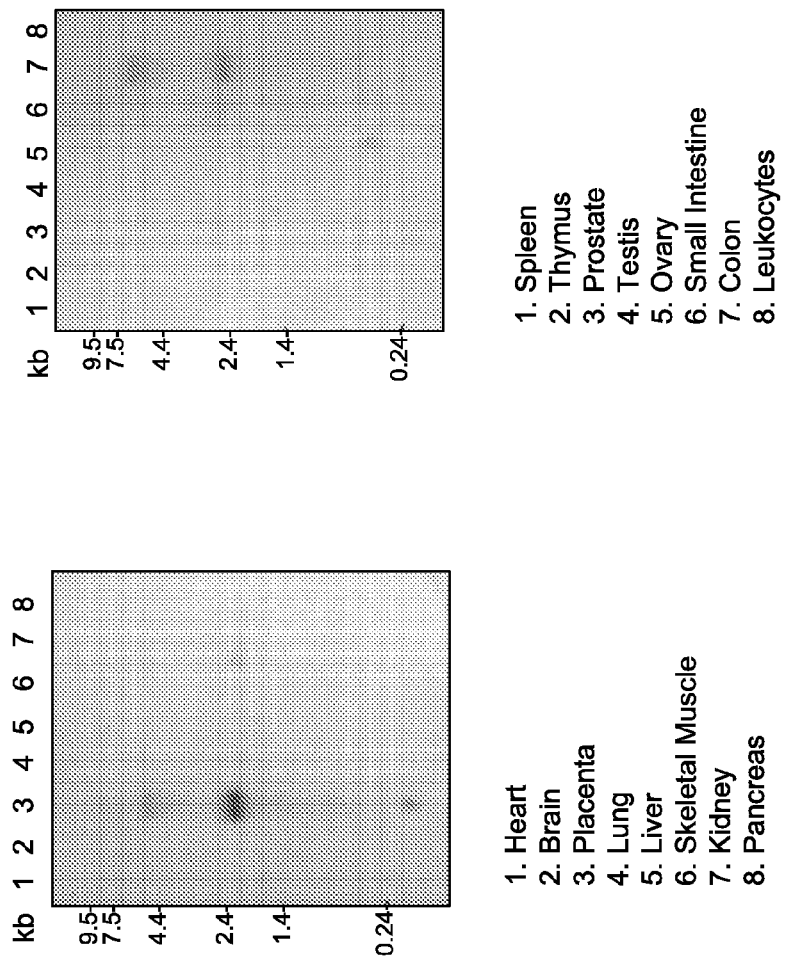
Figure 54 Expression of 184P3C10B in Normal Tissues

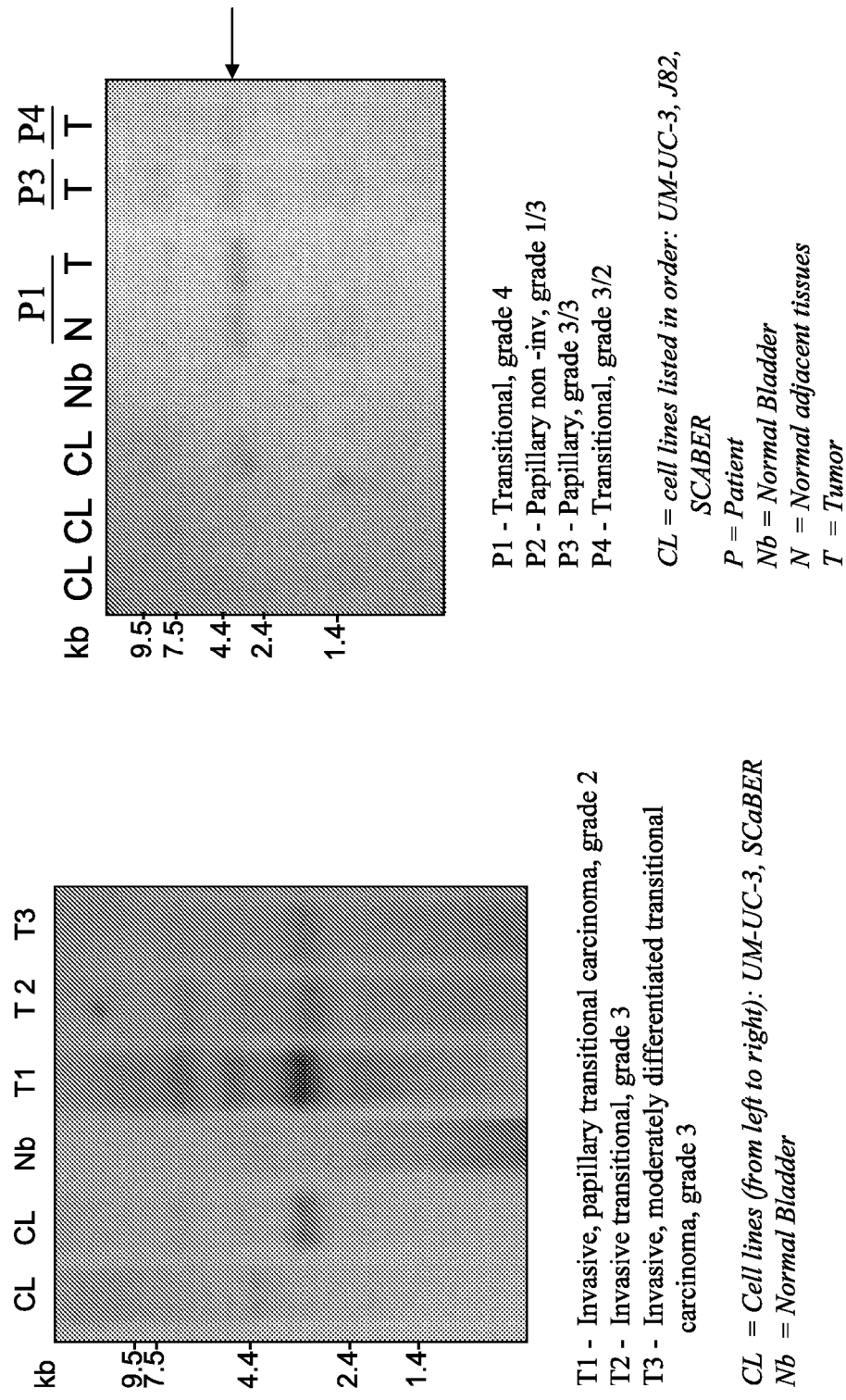
Figure 55 Expression of 184P3C10B in Bladder Cancer Specimens

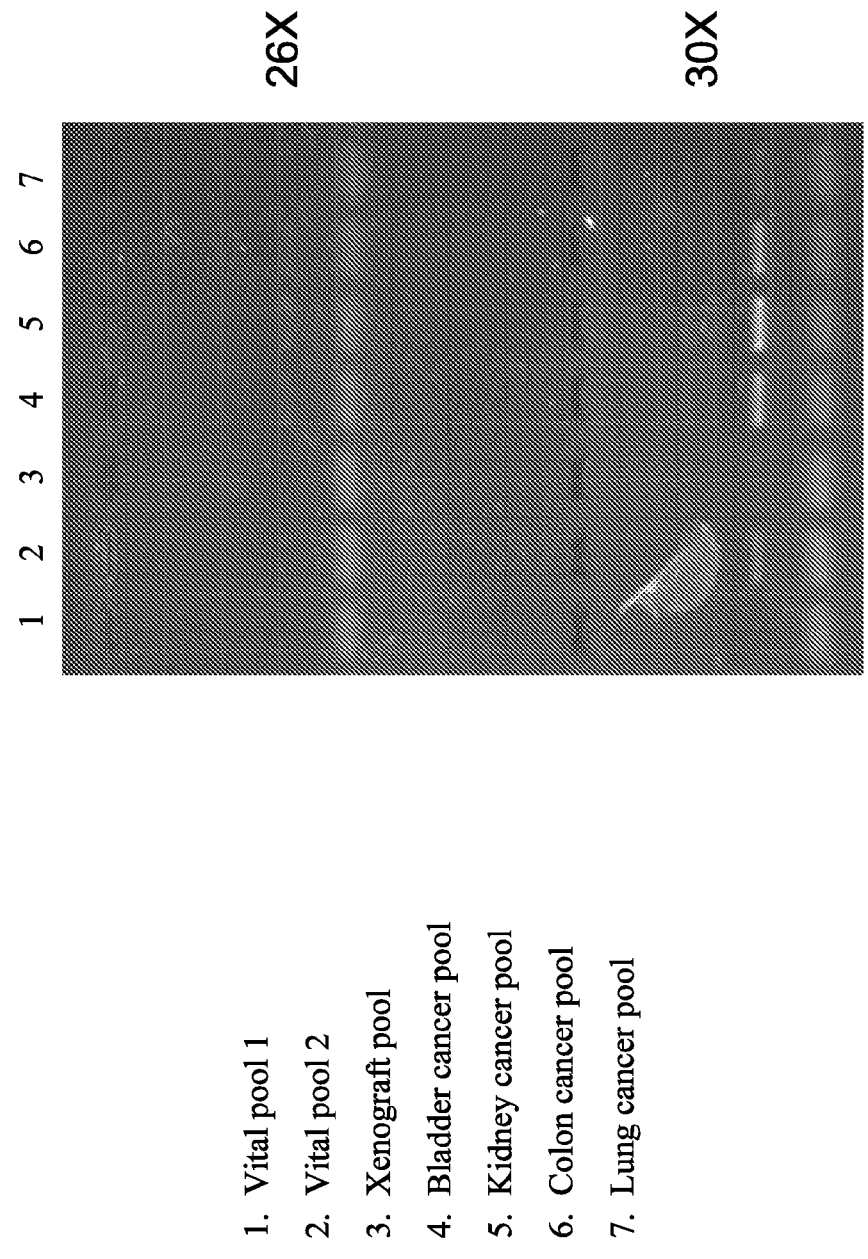
Figure 56 Expression of 184P3G10 by RT-PCR
1. Vital pool 1
2. Vital pool 2
3. Xenograft pool
4. Bladder cancer pool
5. Kidney cancer pool
6. Colon cancer pool
7. Lung cancer pool

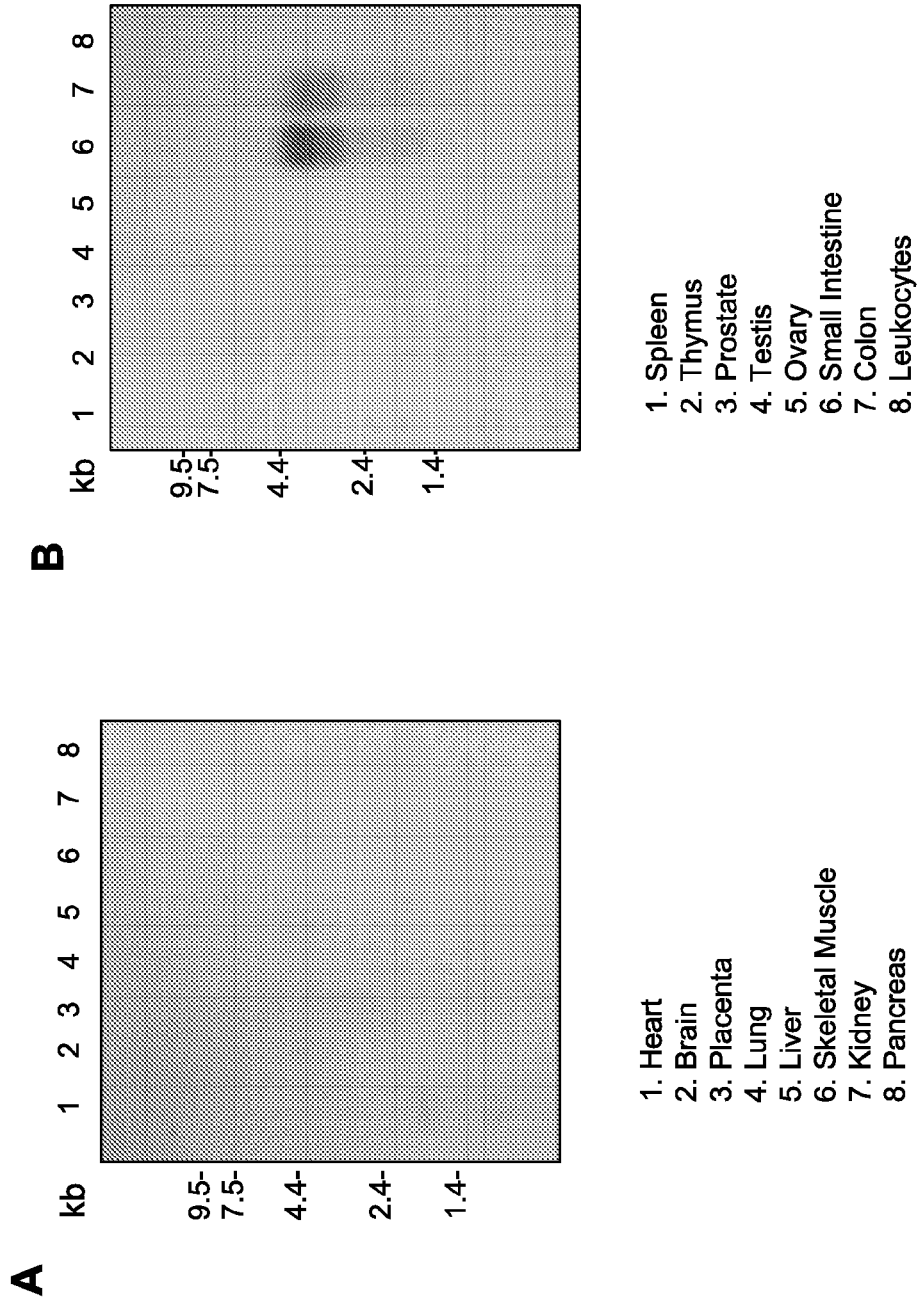
Figure 57 Expression of 184P3G10 in Normal Tissues

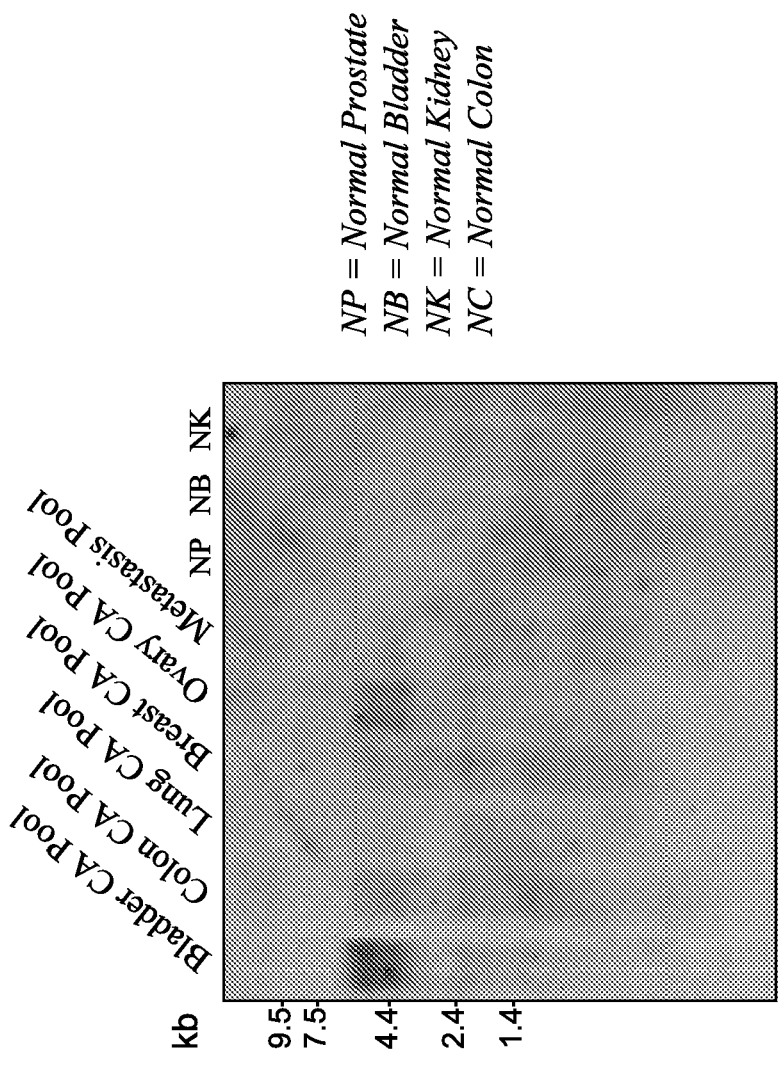
Figure 58 Expression of 184P3G10 in Human Patient Cancer Specimens and in Normal Tissues

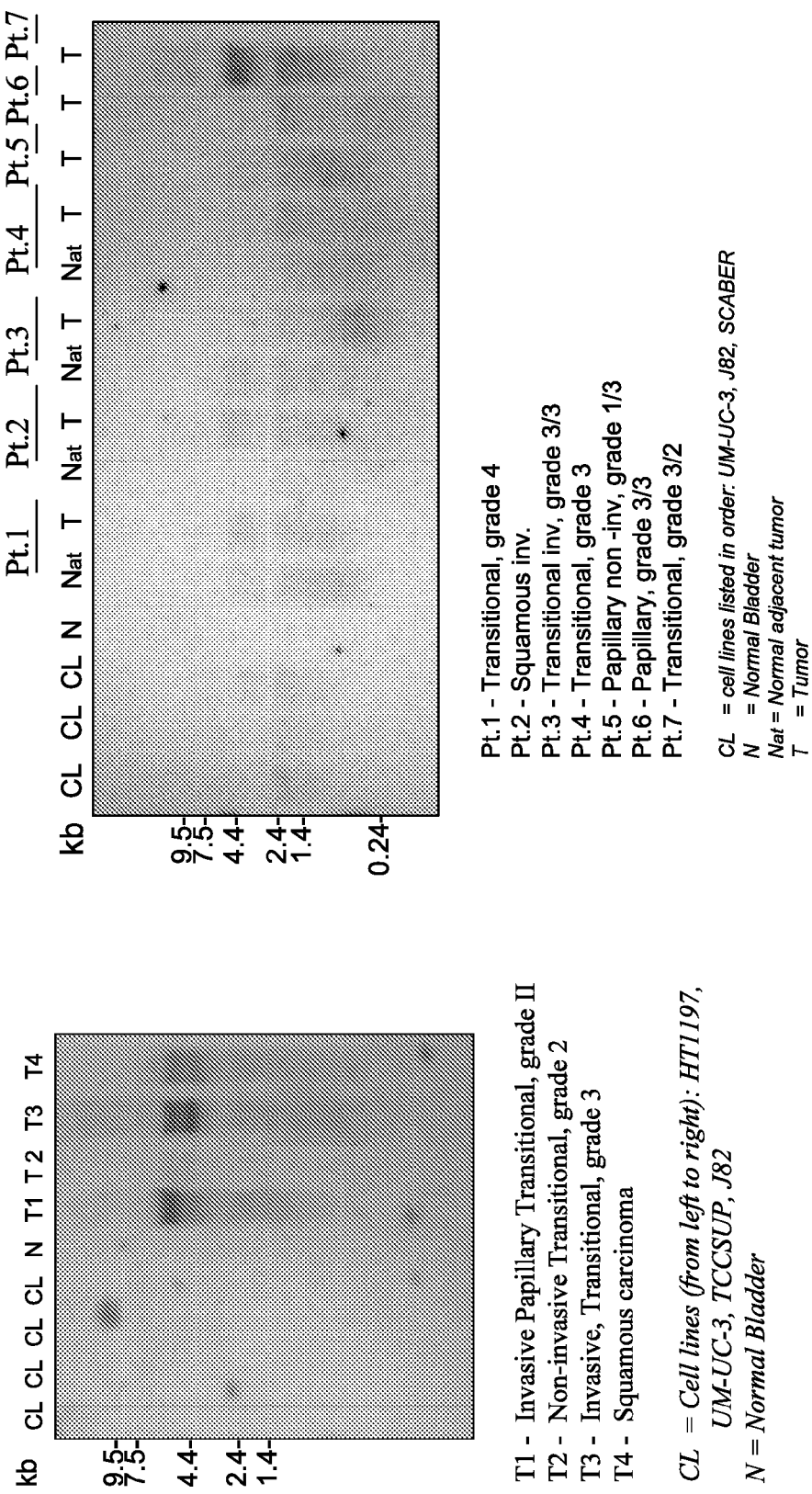

Figure 60    Expression of 185P2C9 by RT-PCR
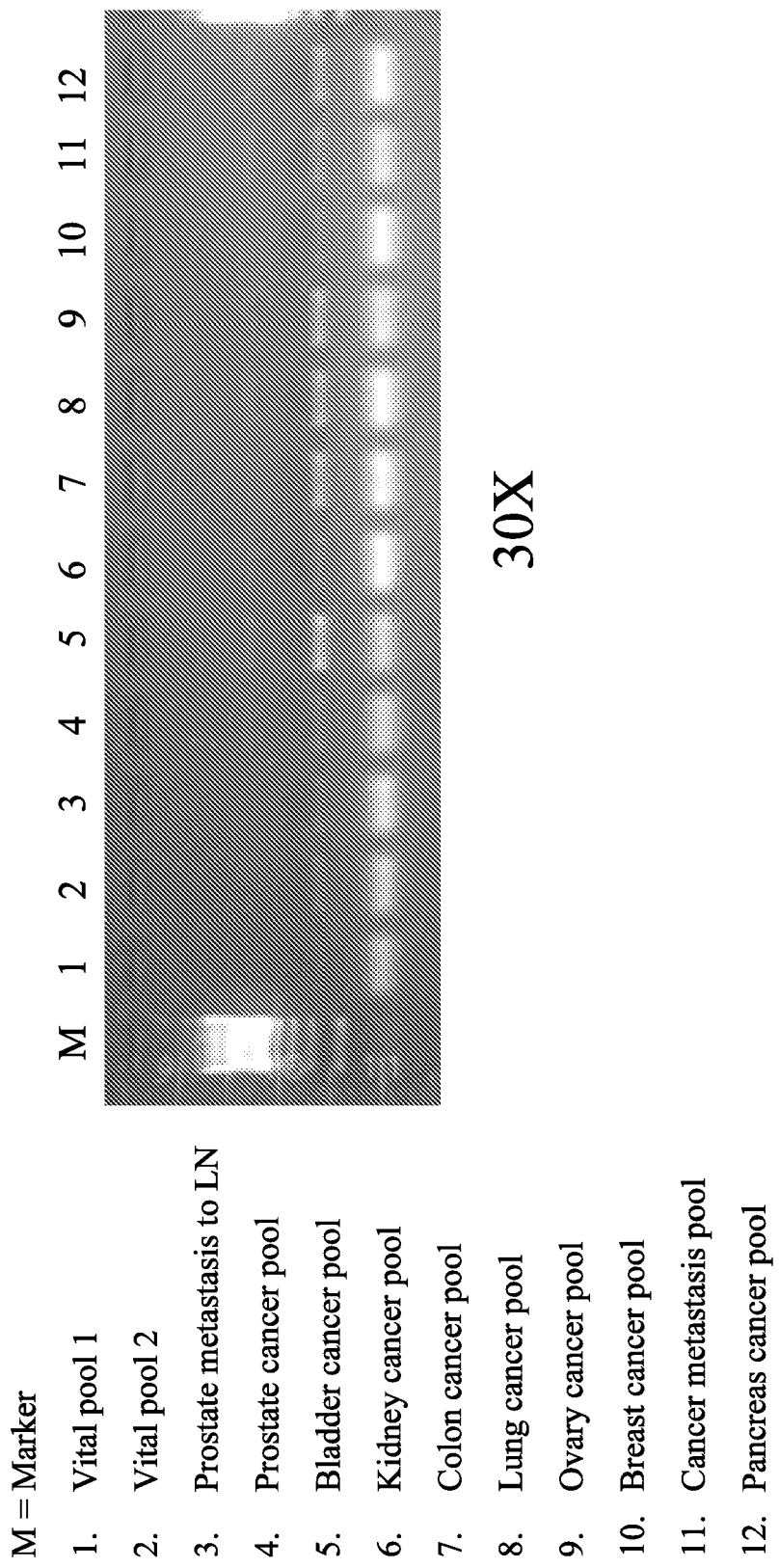
M = Marker
1. Vital pool 1
2. Vital pool 2
3. Prostate metastasis to LN
4. Prostate cancer pool
5. Bladder cancer pool
6. Kidney cancer pool
7. Colon cancer pool
8. Lung cancer pool
9. Ovary cancer pool
10. Breast cancer pool
11. Cancer metastasis pool
12. Pancreas cancer pool

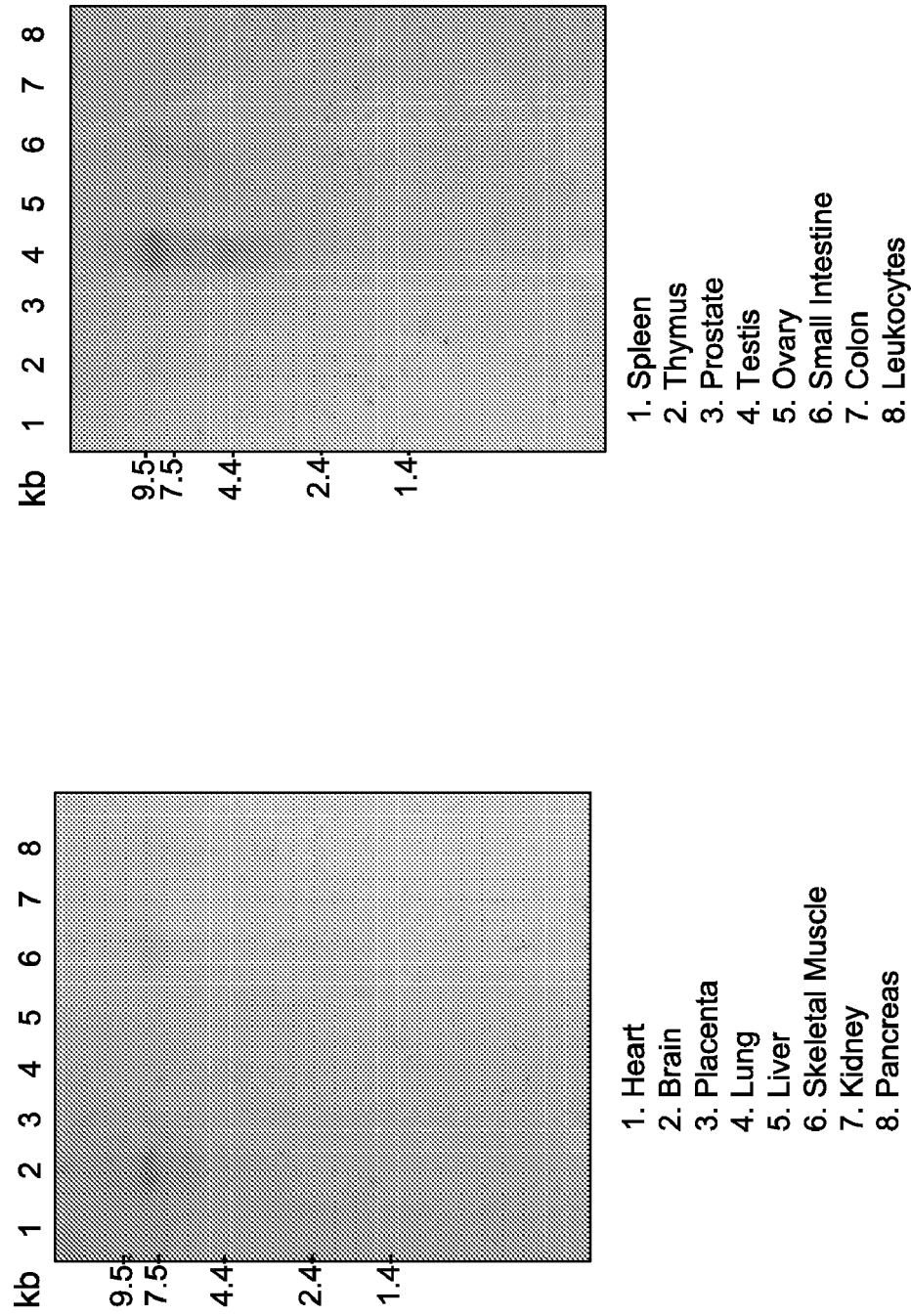
Figure 61  Expression of 185P2C9 in Normal Tissues

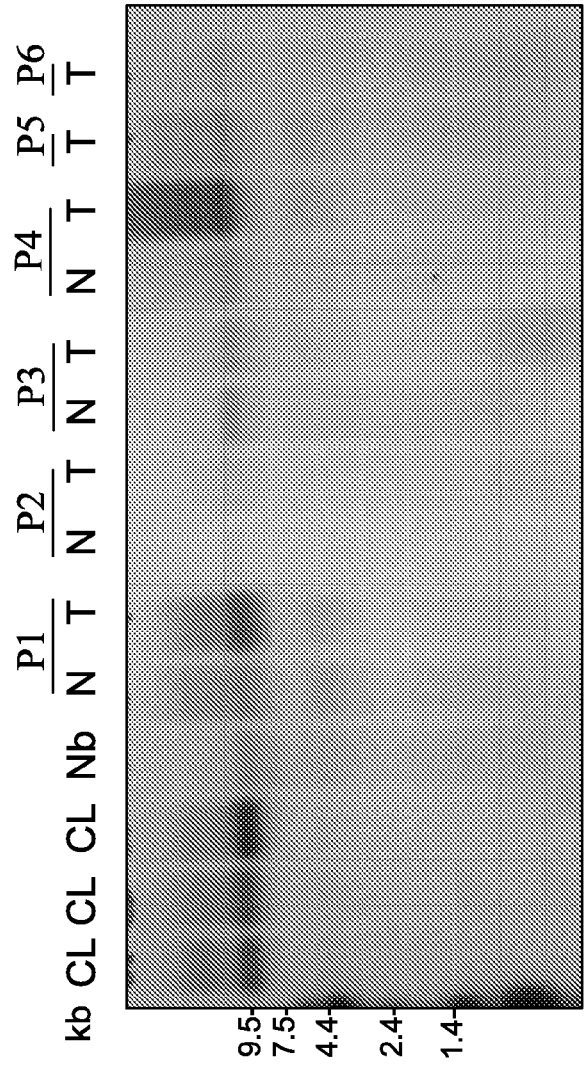
Figure 62 Expression of 185P2C9 in Bladder Cancer Patient Specimens

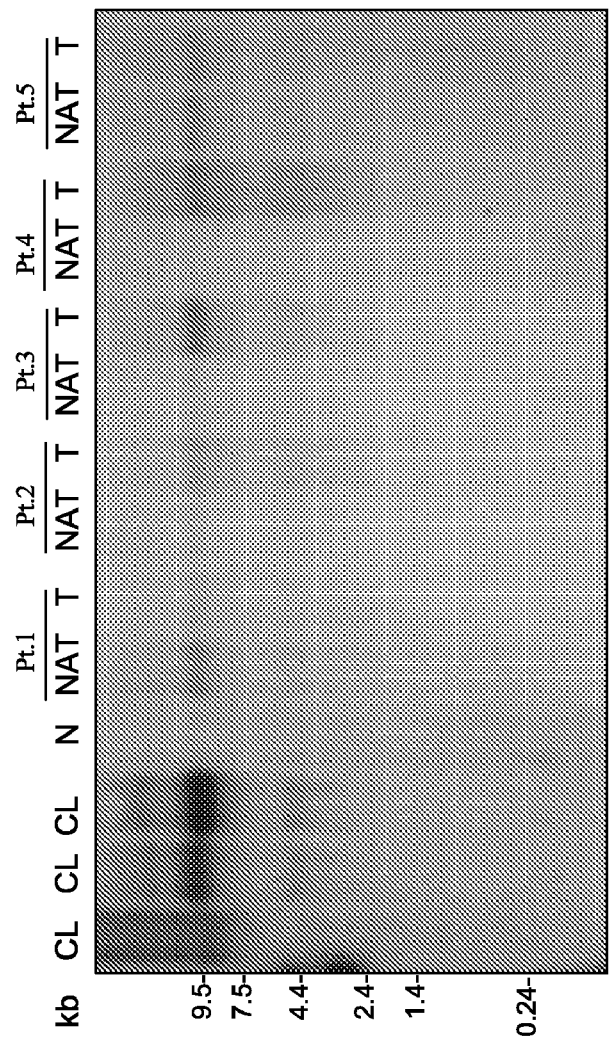
Figure 63  Expression of 185P2C9 in Kidney Cancer Patient Specimens

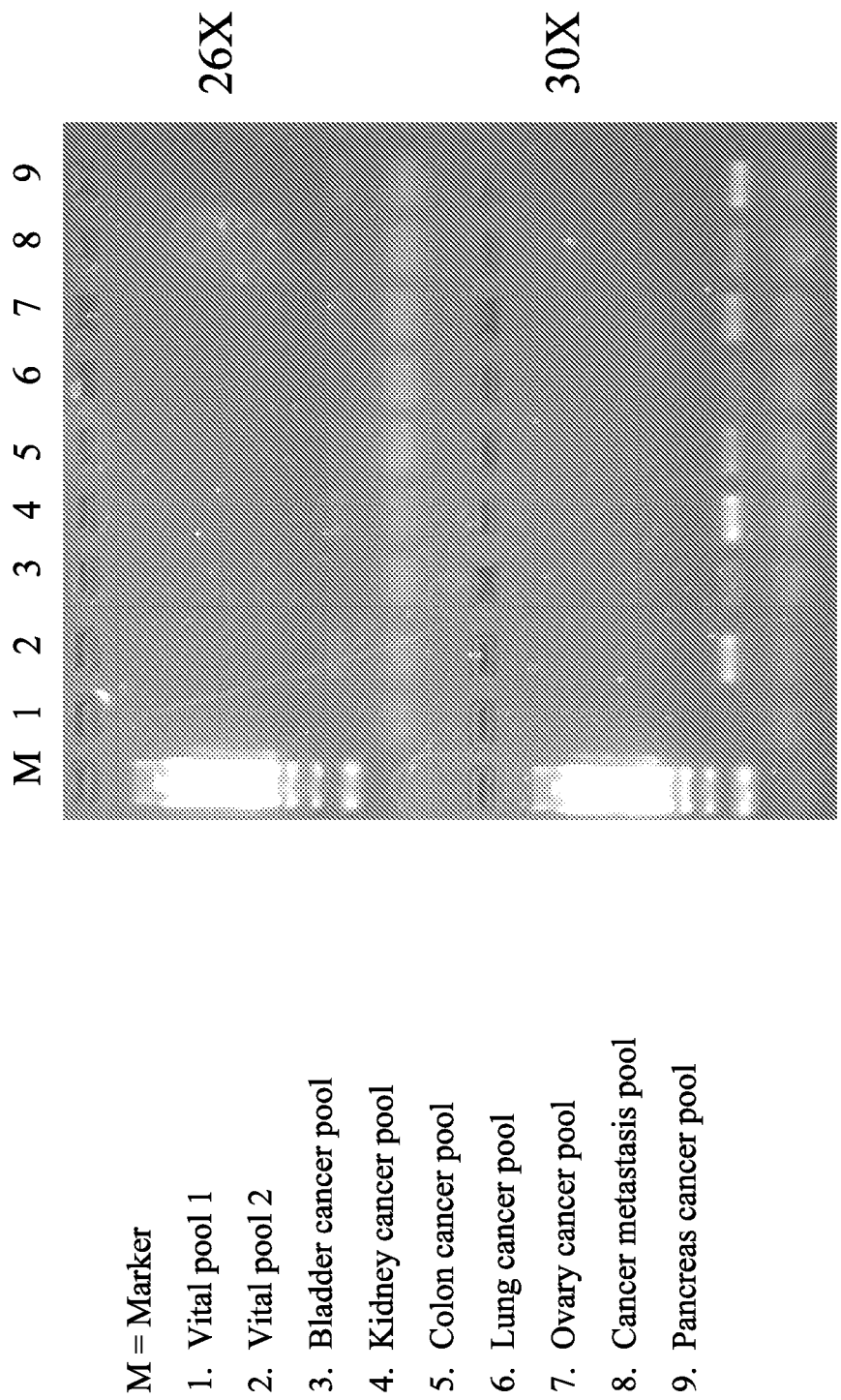
Figure 64 Expression of 186P1H9 by RT-PCR
M = Marker
1. Vital pool 1
2. Vital pool 2
3. Bladder cancer pool
4. Kidney cancer pool
5. Colon cancer pool
6. Lung cancer pool
7. Ovary cancer pool
8. Cancer metastasis pool
9. Pancreas cancer pool

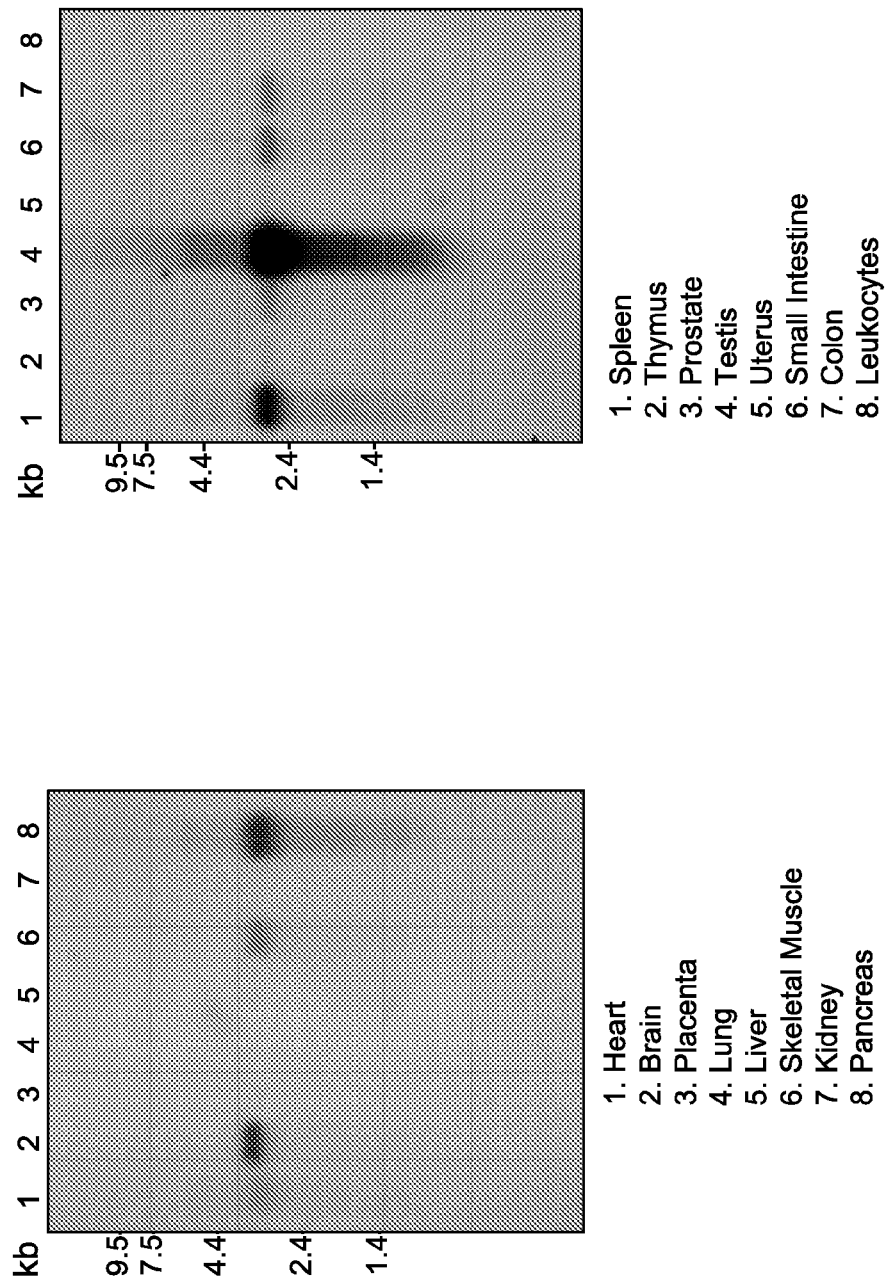
Figure 65    Expression of 186P1H9 in Normal Tissues

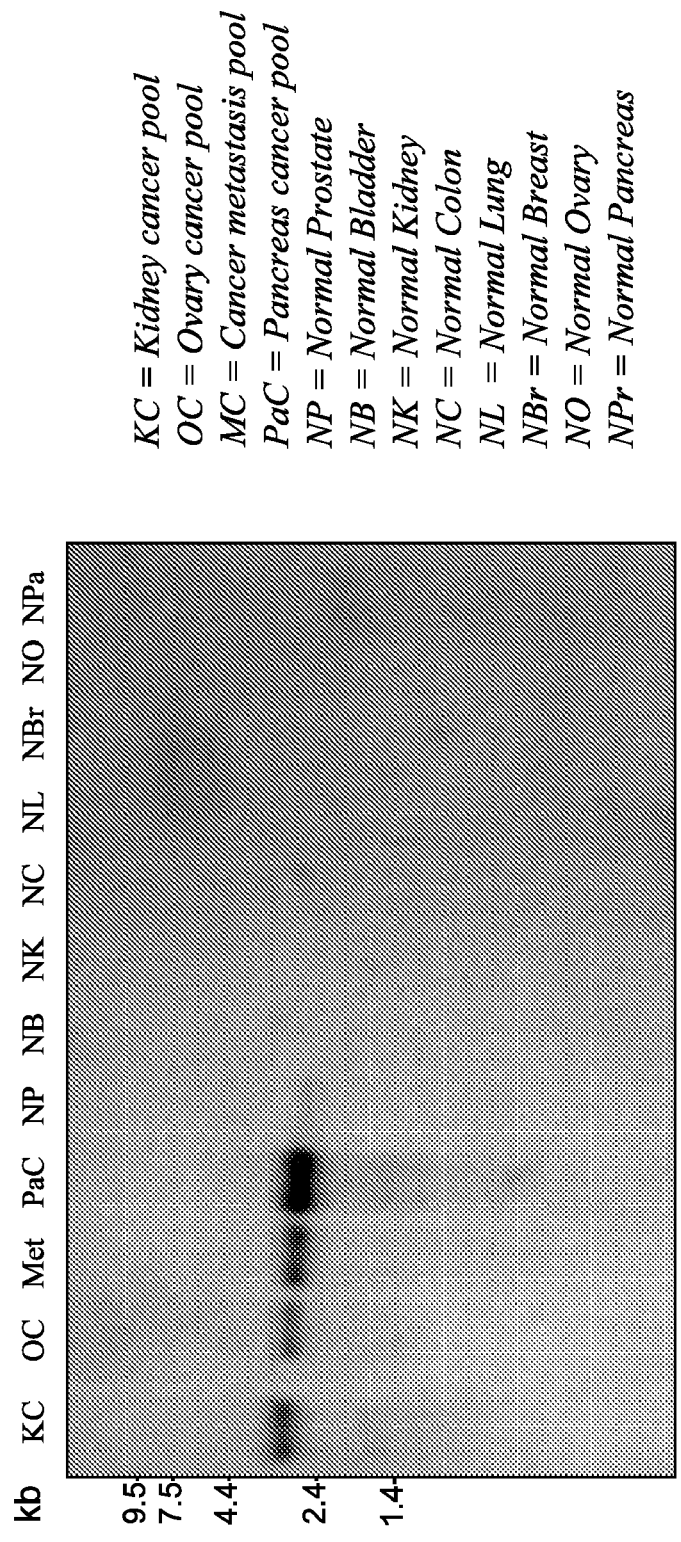
Figure 66 Expression of 186P1H9 in Patient Cancer Specimens and in Normal Tissues

Figure 67 Expression of 186P1H9 in Kidney Cancer Patient Specimens
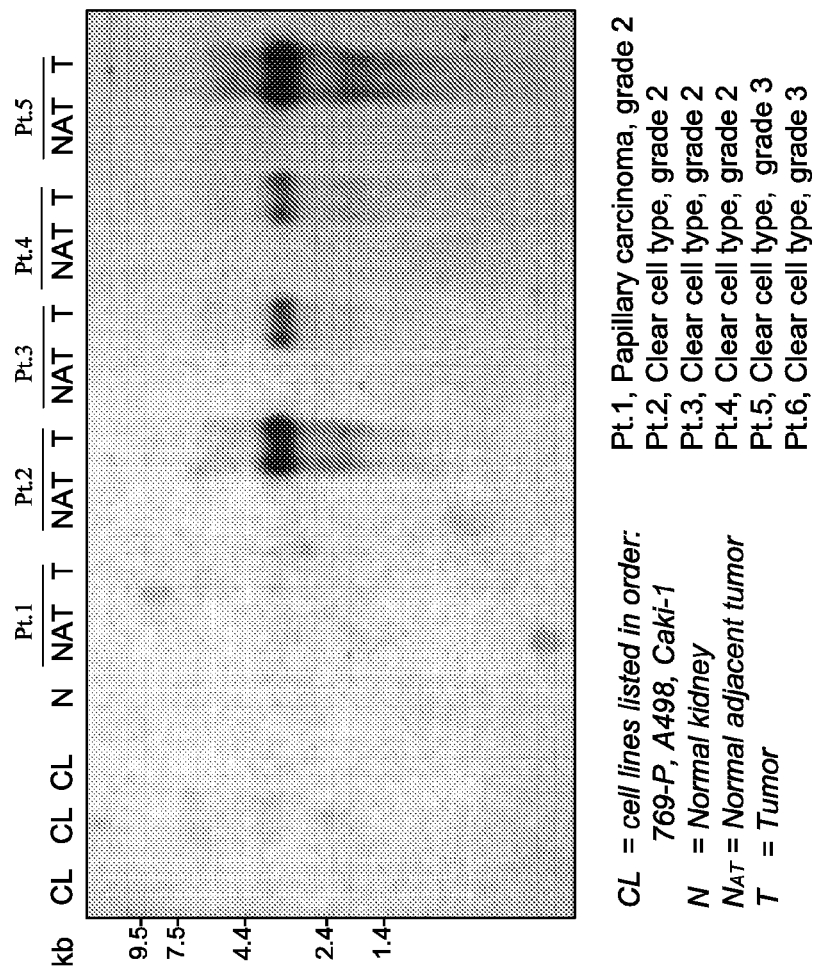

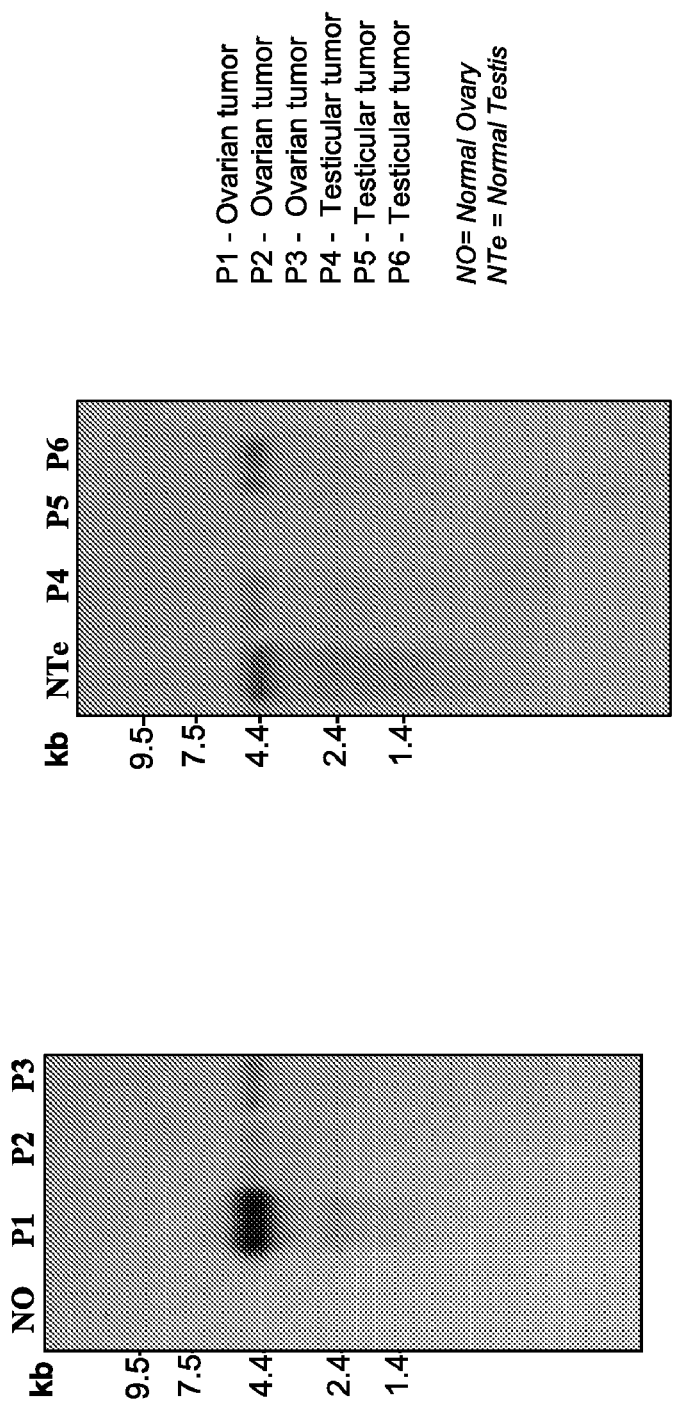
Figure 68 Expression of 186P1H9 in Ovarian and Testicular Cancer Patient Specimens

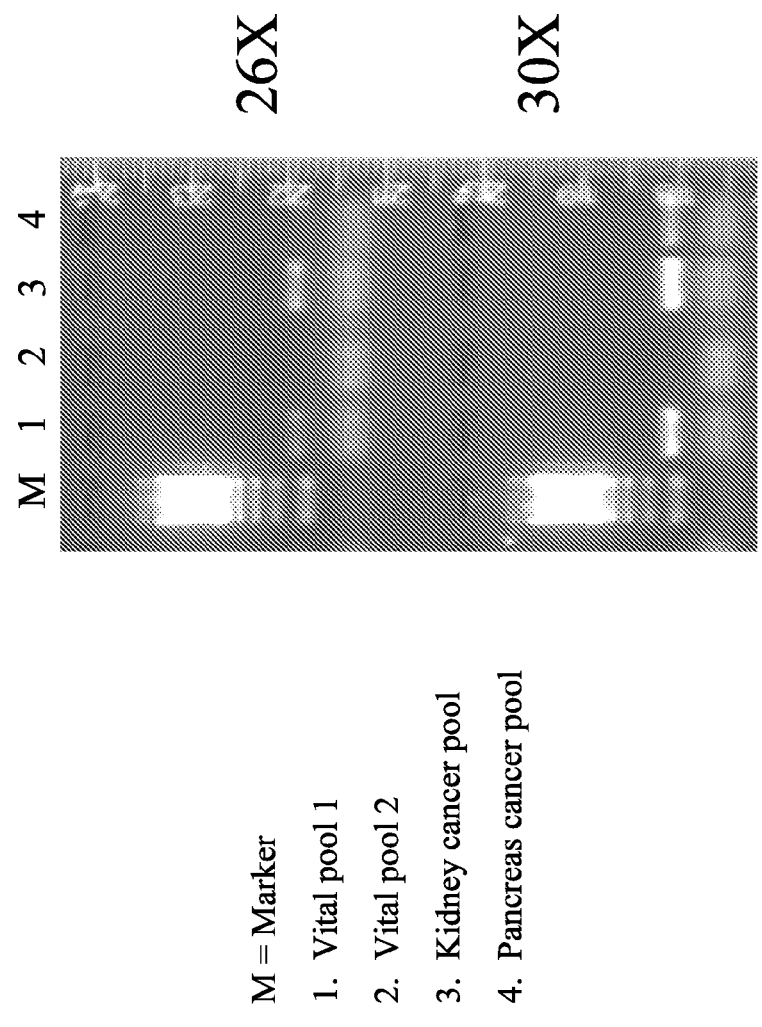
Figure 69 Expression of 187P3F2 by RT-PCR
M = Marker
1. Vital pool 1
2. Vital pool 2
3. Kidney cancer pool
4. Pancreas cancer pool

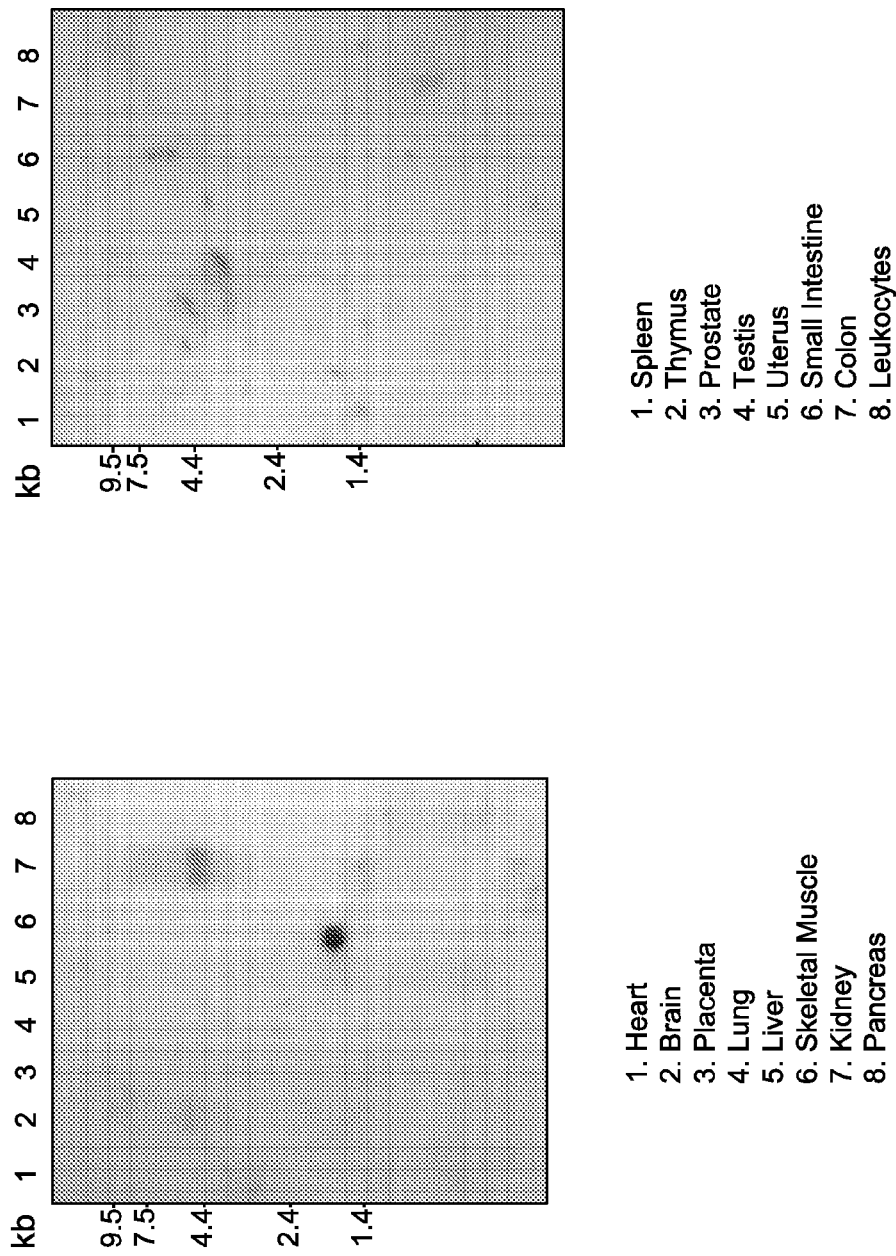
Figure 70  Expression of 187P3F2 in Normal Tissues

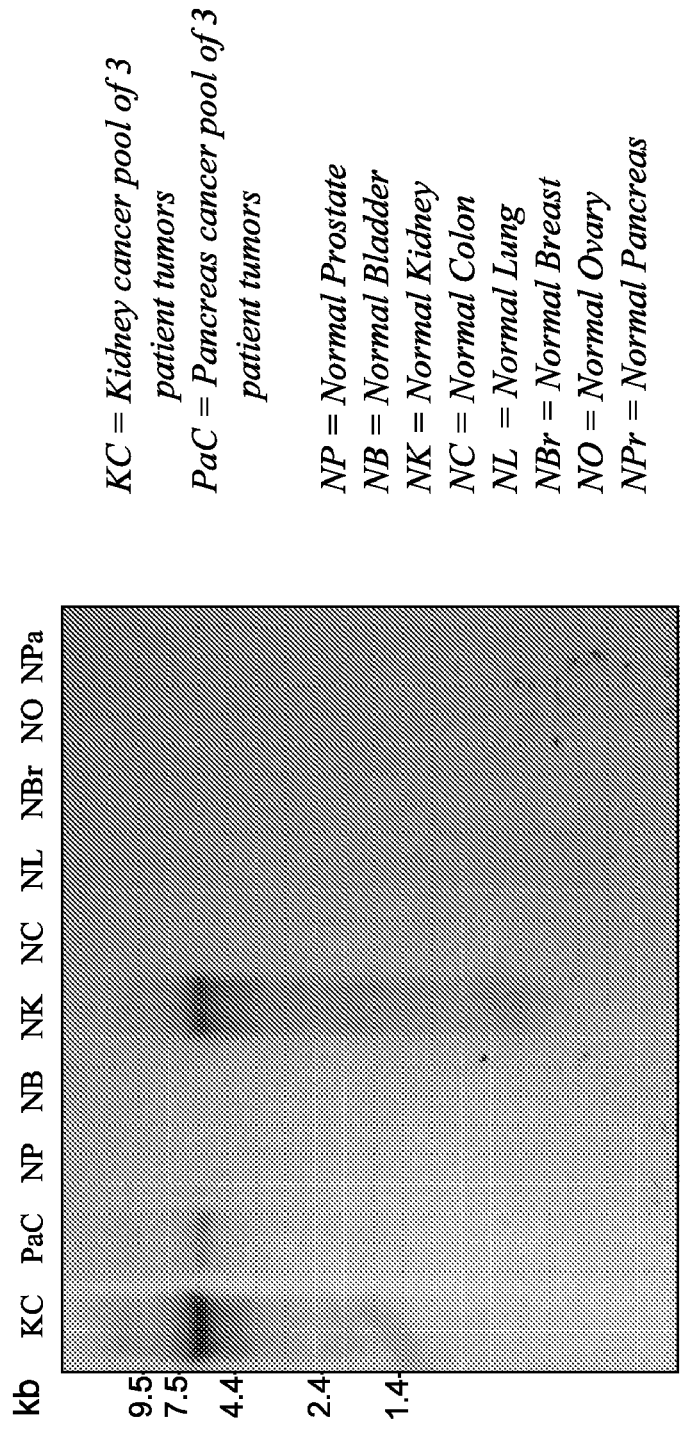
Figure 71 Expression of 187P3F2 in Patient Cancer Specimens and in Normal Tissues

Figure 72 Expression of 187P3F2 in Pancreas Patient Cancer Specimens
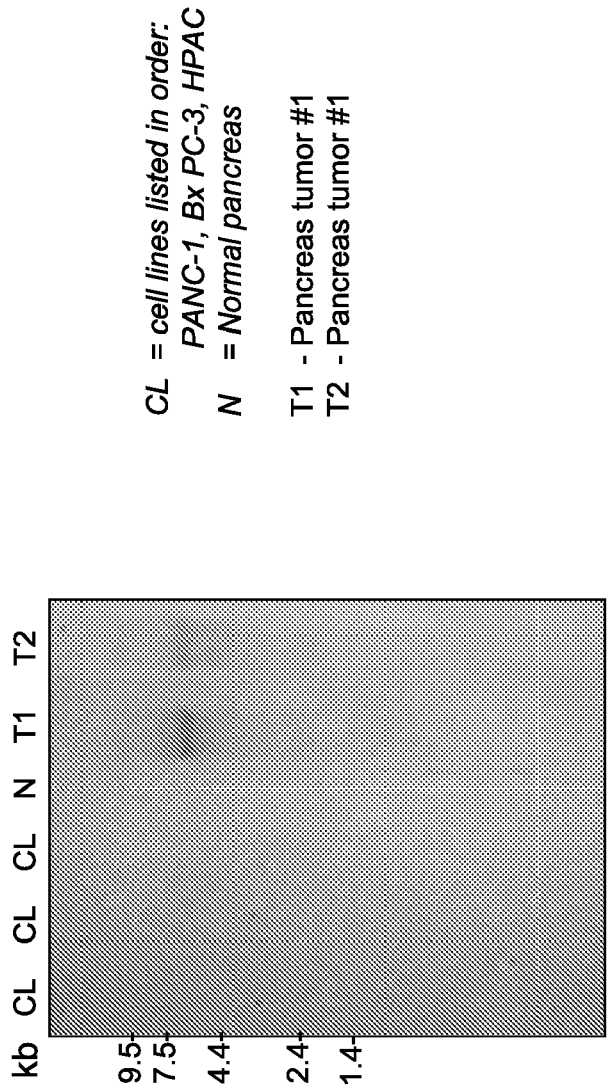

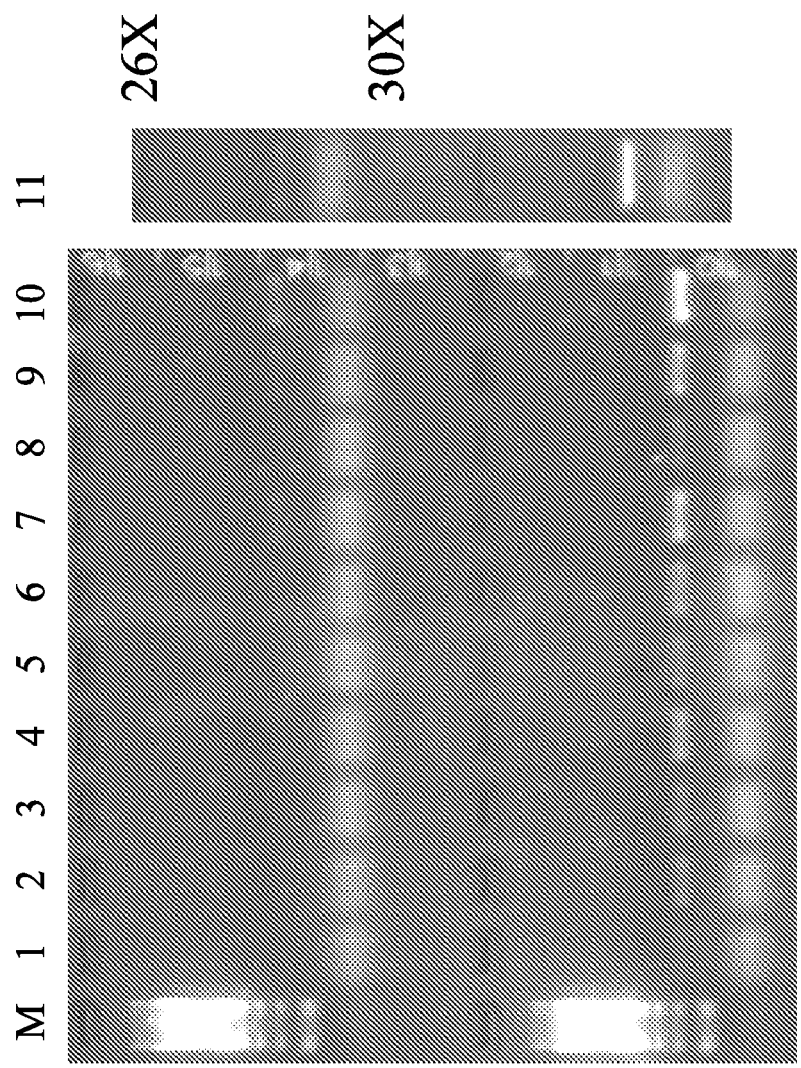
Figure 73 Expression of 192P2G7 by RT-PCR
1. Vital pool 1
2. Vital pool 2
3. Prostate cancer pool
4. Bladder cancer pool
5. Kidney cancer pool
6. Lung cancer pool
7. Ovary cancer pool
8. Breast cancer pool
9. Cancer metastasis pool
10. Pancreas cancer pool
11. Prostate metastasis to LN

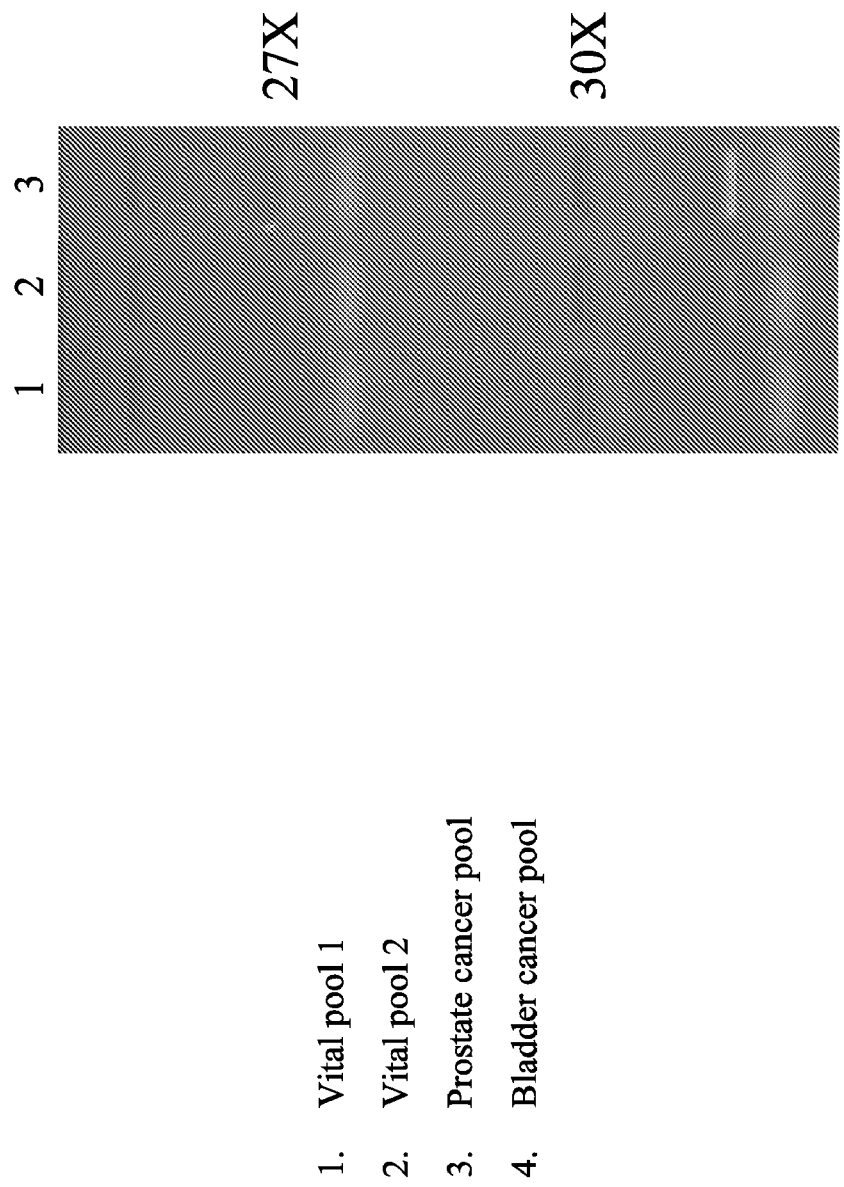
Figure 74  Expression of 185P3C2 by RT-PCR
1. Vital pool 1
2. Vital pool 2
3. Prostate cancer pool
4. Bladder cancer pool

METHODS OF INDUCING AN IMMUNE RESPONSE

CROSS-REFERENCE TO RELATED APPLICATIONS

This application is a divisional of pending U.S. application Ser. No. 10/121,024, filed Apr. 10, 2002, now patented U.S. Pat. No. 7,736,654, which claims the benefit of U.S. Provisional Application Ser. No. 60/283,112, filed Apr. 10, 2001, now expired; U.S. Provisional Application Ser. No. 60/282,739, filed Apr. 10, 2001, now expired; and U.S. Provisional Application Ser. No. 60/286,630, filed Apr. 25, 2001, now expired. The contents of these applications are herein incorporated by reference in their entirety.

SUBMISSION ON COMPACT DISC

The content of the following submission on compact discs is incorporated herein by reference in its entirety: A computer readable form (CRF) of the Sequence Listing on compact disc (file name: 511582004003, date recorded: Sep. 13, 2005, size: 983,040 bytes); a duplicate compact disc copy of the Sequence Listing (COPY 1) (file name: 511582004003, date recorded: Sep. 13, 2005, size: 983,040 bytes); and a duplicate compact disc copy of the Sequence Listing (COPY 2) (file name: 511582004003, date recorded: Sep. 13, 2005, size: 983,040 bytes).

STATEMENT OF RIGHTS TO INVENTIONS MADE UNDER FEDERALLY SPONSORED RESEARCH

Not applicable.

FIELD OF THE INVENTION

The invention described herein relates to a gene and its encoded proteins set forth, e.g., in FIG. 2 expressed in certain cancers, and to diagnostic and therapeutic methods and compositions useful in the management of cancers that express a gene of FIG. 2.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and 8 per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to genes and respective encoded proteins set forth in FIG. 2, that have now been found to be over-expressed in the cancer(s) listed in Table I. Northern blot expression analysis of the genes of FIG. 2 in normal tissues shows a restricted expression pattern in adult tissues. The nucleotide (FIG. 2) and amino acid (FIG. 2, and FIG. 3) sequences of FIG. 2 are provided. The tissue-related expression profile of the genes set forth in FIG. 2 in normal adult tissues, combined with the over-expression observed in the tumors listed in Table I, shows that the genes of FIG. 2 are aberrantly over-expressed in certain cancers, and thus serves as a useful diagnostic, prophylactic, prognostic, and/or therapeutic target for cancers of the tissue(s) such as those listed in Table I.

The invention provides polynucleotides corresponding or complementary to all or part of the genes of FIG. 2, corresponding/related mRNAs, coding and/or complementary sequences, preferably in isolated form, including polynucleotides encoding FIG. 2—related proteins and fragments of 4, 5, 6, 7, 8, 9, 10, 11, 12, 13, 14, 15, 16, 17, 18, 19, 20, 21, 22, 23, 24, 25, or more than 25 contiguous amino acids of a FIG. 2—related protein; at least 30, 35, 40, 45, 50, 55, 60, 65, 70, 80, 85, 90, 95, 100 or more than 100 contiguous amino acids of a FIG. 2—related protein, as well as the peptides/proteins themselves; DNA, RNA, DNA/RNA hybrids, and related molecules such as, polynucleotides or oligonucleotides complementary or having at least a 90% homology to the genes set forth in FIG. 2 or mRNA sequences or parts thereof, and polynucleotides or oligonucleotides that hybridize to the genes set forth in FIG. 2, mRNAs, or to polynucleotides that encode proteins of FIG. 2 or FIG. 3 or analogs or variants thereof; or to polynucleotides that encode proteins of fragments of a peptide of FIG. 2 or FIG. 3 such as set forth in Tables V to XVIII, Table XX, Tables XXIII to XXVI, or analogs or variants thereof; or to polynucleotides that encode fragments/subsequences of a peptide of FIG. 2 or FIG. 3 such as any 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1025, 1050, 1075, 1100, 1125, 1150, 1175, 1200, etc., or more contiguous amino acids of a peptide of FIG. 2 or 3, or an analog or variant thereof.

Also provided are means for isolating cDNAs and the genes encoding proteins set forth in FIG. 2. Recombinant DNA molecules containing genes of FIG. 2 polynucleotides, cells transformed or transduced with such molecules, and host-vector systems for the expression of the genes set forth in FIG. 2 products are also provided. The invention further provides antibodies that bind to the proteins set forth in FIG. 2 and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments there is a proviso that the entire nucleic acid sequence of the genes of FIG. 2 is not encoded and/or the entire amino acid sequence of the proteins of FIG. 2 is not prepared. In certain embodiments, the entire nucleic acid sequence of the genes of FIG. 2 is encoded and/or the entire amino acid sequence of the proteins of FIG. 2 is prepared, either of which are in respective human unit dose forms.

The invention further provides methods for detecting the presence and status of FIG. 2 polynucleotides and proteins in various biological samples, as well as methods for identifying cells that express the genes set forth in FIG. 2. A typical embodiment of this invention provides methods for monitoring the FIG. 2 gene products in a tissue or hematology sample having or suspected of having some form of growth dysregulation such as cancer.

The invention further provides various immunogenic or therapeutic compositions and strategies for treating cancers that express a gene set forth in FIG. 2 such as cancers of tissues listed in Table I, including therapies aimed at inhibiting the transcription, translation, processing or function of the genes of FIG. 2 as well as cancer vaccines. In one aspect, the invention provides compositions, and methods comprising them, for treating a cancer that expresses a gene set forth in FIG. 2 in a human subject wherein the composition comprises a carrier suitable for human use and a human unit dose of one or more than one agent that inhibits the production or function of a gene or proteins of FIG. 2. Preferably, the carrier is a uniquely for use in humans. In another aspect of the invention, the agent is a moiety that is immunoreactive with a protein of FIG. 2. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to a protein of FIG. 2 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with a protein of FIG. 2 as described above. The one or more than one nucleic acid molecule may also be, or encodes, a molecule that inhibits production of a protein set forth in FIG. 2. Non-limiting examples of such molecules include, but are not limited to, those complementary to a nucleotide sequence essential for production of a protein of FIG. 2 (e.g. antisense sequences or molecules that form a triple helix with a nucleotide double helix essential for production of a protein set forth in FIG. 2) or a ribozyme effective to lyse mRNA (sense or antisense) encoded by a gene of FIG. 2.

Please note, to determine the starting position of any peptide set forth in Tables V-XVIII and Tables XXIII to XXVI (collectively HLA Peptide Tables) respective to its parental protein in FIG. 2 or FIG. 3, reference is made to its respective protein.

One embodiment of the invention comprises an HLA peptide, that occurs at least twice in Tables V-XVIII and XXIII to XXVI collectively, or an oligonucleotide that encodes the HLA peptide. Another embodiment of the invention comprises an HLA peptide that occurs at least twice in Tables V-XVIII, or an oligonucleotide that encodes the HLA peptide. Another embodiment of the invention comprises an HLA peptide that occurs at least twice in Tables XXIII to XXVI, or an oligonucleotide that encodes the HLA peptide. Another embodiment of the invention comprises an HLA peptide that occurs at least once in Tables V-XVIII and is embedded within at least one peptide in Tables XXIII to XXVI, or an oligonucleotide that encodes the HLA peptide.

Another embodiment of the invention is antibody epitopes which comprise a peptide region, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9.

BRIEF DESCRIPTION OF THE FIGURES

FIGS. 1A-1R. The SSH sequences of the invention.
FIGS. 2A.1-2R. Genes and respective encoded proteins of the invention.
FIGS. 3A.1-3R. Amino acid sequences of the invention.
FIG. 4. Nucleic acid sequence and protein alignments.

FIGS. 10A-10Z. Secondary structure predictions for the proteins set forth in FIG. 2. The sequence identifiers for the respective amino acids are as follows: 74P3B3 v1 (SEQ ID NO 689), 74P3B3 v2 (SEQ ID NO 690), 83P4B8 (SEQ ID NO 691), 109P1D4 (SEQ ID NO 692), 151P4E11 (SEQ ID NO 693), 151P1C7a (SEQ ID NO 694), 154P2A8 (SEQ ID NO 695), 156P1D4 (SEQ ID NO 696), 156P5C12 (SEQ ID NO 697), 159P2B5 (SEQ ID NO 698), 161P2B7a (SEQ ID NO 699), 179P3G7 (SEQ ID NO 700), 184P3C10B (SEQ ID NO 701), 184P3G10 (SEQ ID NO 702), 185P2C9 v1 (SEQ ID NO 703), 185P2C9 v2 (SEQ ID NO 704), 185P3C2 (SEQ ID NO 705), 186P1H9 (SEQ ID NO 706), 187P3F2 (SEQ ID NO 707), 192P2G7 (SEQ ID NO 708). The secondary structures of the proteins set forth in FIG. 2 were predicted using the HNN—Hierarchical Neural Network method. This method predicts the presence and location of alpha helices, extended strands, and random coils from the primary protein sequence. The percent of the protein in a given secondary structure is also listed for each variant.

Figure 5B:
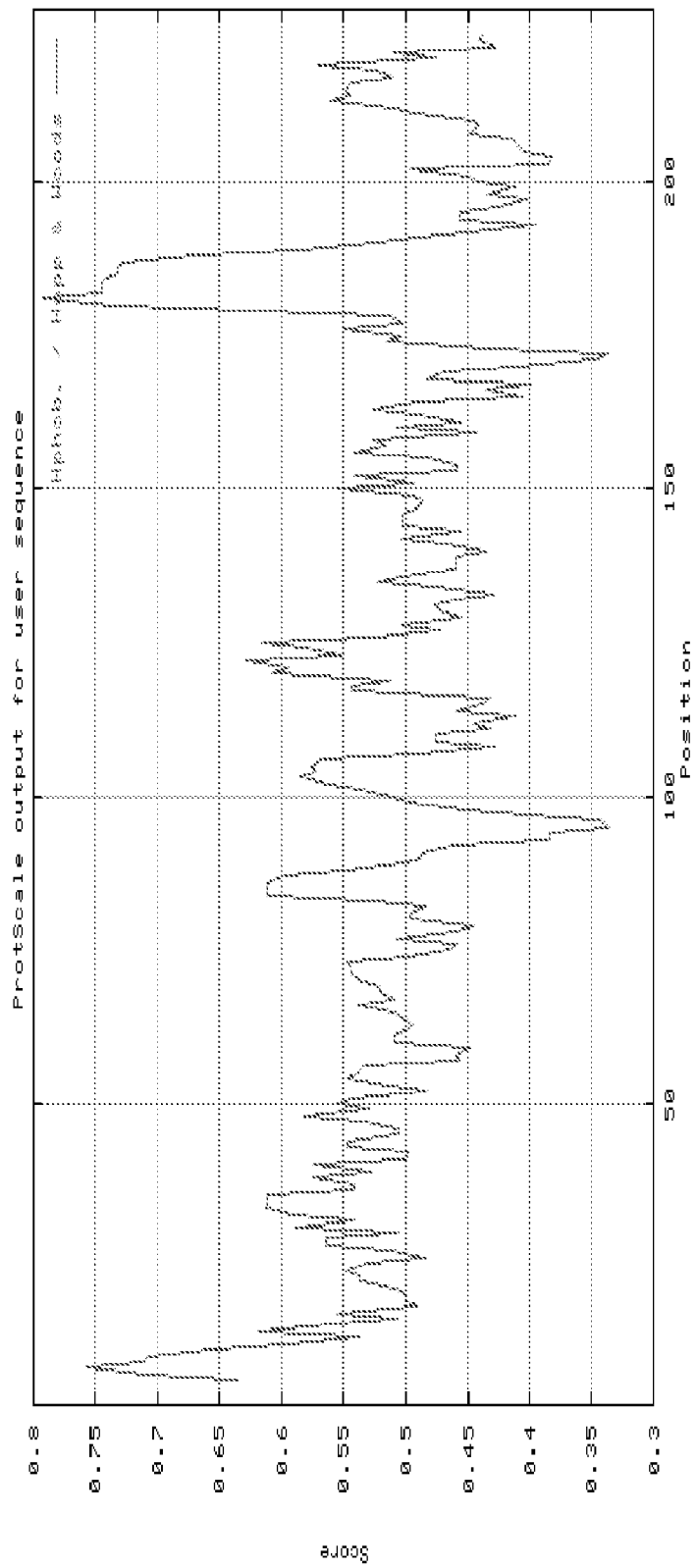
FIGS. 5A-5U. Hydrophilicity amino acid profile of the proteins set forth in FIG. 2 determined by computer algorithm sequence analysis using the method of Hopp and Woods (Hopp T. P., Woods K. R., 1981. Proc. Natl. Acad. Sci. U.S.A. 78:3824-3828).

Transmembrane predictions for the proteins set forth in FIG. 2. Schematic representations of the probability of existence of transmembrane regions and orientation of the proteins of FIG. 2 based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993). Schematic representation of the probability of the existence of transmembrane regions and the extracellular and intracellular orientation of the proteins of FIG. 2 based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998).

FIGS. 11b, 11c, 11e, 11j, 11k, 11m, 11n, 11o, and 11r. The nucleotide sequences of transcript variants of the invention.

FIGS. 12b, 12c, 12e, 12j, 12k, 12m, 12n, 12o, and 12r. These Figures show amino acid sequences of proteins translated from the corresponding transcript variants set forth in FIG. 11.

FIGS. 13b, 13c, 13e, 13j, 13k, 13m, 13n, 13o, and 13r. These Figures display the alignment of the nucleotide sequences of respective transcript variants.

FIGS. 14b, 14c, 14e, 14j, 14k, 14m, 14n, 14o, and 14r. These Figures display the alignment of the protein sequences from the respective transcript variants. The sub-numbering nomenclature of FIG. 11 through FIG. 14 is set forth in the following legend:

| FIG. 11-14 Sub-part | Target |
|---|---|
| A | 074P3B3 |
| B | 083P4B8 |
| C | 109P1D4 |
| D | 151P1C7A |
| E | 151P4E11 |
| F | 154P2A8 |
| G | 156P1D4 |
| H | 156P5C12 |
| I | 159P2B5 |
| J | 161P2B7a |
| K | 179P3G7 |
| L | 184P3C10B |
| M | 184P3G10 |
| N | 185P2C9 |
| O | 185P3C2 |
| P | 186P1H9 |
| Q | 187P3F2 |
| R | 192P2G7 |

FIG. 15. Expression of 74P3B3 by RT-PCR. First strand cDNA was prepared from vital pool 1 (liver, lung and kidney), vital pool 2 (pancreas, colon and stomach), two prostate metastasis to lymph node (LN) harvested from two different patients, prostate cancer pool, bladder cancer pool, and cancer metastasis pool. Normalization was performed by PCR using primers to actin and GAPDH. Semi-quantitative PCR, using primers to 74P3B3, was performed at 26 and 30 cycles of amplification. Results show strong expression of 74P3B3 in the two prostate metastasis to LN specimens and in prostate cancer pool. Expression was also detected in bladder cancer pool, cancer metastasis pool, and vital pool 2 but not in the vital pool 1.

FIG. 16A-16C. Expression of 74P3B3 in normal tissues. Two multiple tissue northern blots (A and B; Clontech) both with 2 µg of mRNA/lane, and a LAPC xenograft blot with 10 µg of total RNA/lane (C) were probed with the 74P3B3 SSH fragment. Size standards in kilobases (kb) are indicated on the side. Results show expression of approximately 7 kB 74P3B3 transcript in prostate but not in the other normal tissues tested. Expression was also detected in LAPC-4AD and LAPC-4AI but not in LAPC-9AD and LAPC-9AI.

FIG. 17. Expression of 74P3B3 in prostate cancer patient specimens. RNA was extracted from normal prostate (NP), pool of 3 prostate cancer patient tumors (T) and their normal adjacent tissues (N). Northern blot with 10 µg of total RNA/lane was probed with 74P3B3 SSH sequence. Size standards in kilobases (kb) are indicated on the side. The results show strong expression of 74P3B3 in normal prostate and in patient prostate cancer specimens.

FIG. 18. Expression of 74P3B3 in patient cancer specimens. Expression of 74P3B3 was assayed in a panel of human cancers (T) and their respective matched normal tissues (N) on RNA dot blots. Upregulated expression of 74P3B3 in tumors compared to normal tissues was observed in prostate, kidney, breast and colon tumors. The expression detected in normal adjacent tissues (isolated from diseased tissues) but not in normal tissues (isolated from healthy donors) may indicate that these tissues are not fully normal and that 74P3B3 may be expressed in early stage tumors.

FIG. 19. Expression of 83P4B8 by RT-PCR. First strand cDNA was prepared from vital pool 1 (liver, lung and kidney), vital pool 2 (pancreas, colon and stomach), prostate cancer pool, bladder cancer pool, kidney cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 83P4B8, was performed at 30 cycles of amplification. Results show strong expression of 83P4B8 in all cancer pools tested. Very low expression was detected in the vital pools.

FIG. 20A-20C. Expression of 83P4B8 in normal tissues. Two multiple tissue northern blots (A and B; Clontech) both with 2 µg of mRNA/lane, and a LAPC xenograft blot with 10 µg of total RNA/lane (C) were probed with the 83P4B8 SSH fragment. Size standards in kilobases (kb) are indicated on the side. Results show expression of two approximately 4.4 kb 83P4B8 transcripts in testis and to lower level in thymus but not in the other normal tissues tested. Expression was also detected in all 4 LAPC prostate cancer xenografts.

FIG. 21. Expression of 83P4B8 in patient cancer specimens and normal tissues. RNA was extracted from a pool of three prostate cancers (PC), bladder cancers (BC), kidney cancers (KC), colon cancers (CC), lung cancers (LC), ovary cancers (OC), cancer metastasis (Met), pancreas cancers (PaC), as well as from normal prostate (NP), normal bladder (NB), normal kidney (NK), normal colon (NC), normal lung (NL), normal breast (NBr) normal ovary (NO) and normal pancreas (NPa). Northern blot with 10 µg of total RNA/lane was probed with 83P4B8 sequence. Size standards in kilobases (kb) are indicated on the side. Results show expression of 83P4B8 in the bladder cancers and ovary cancers. Expression of 83P4B8 was also detected in prostate cancers, kidney cancers, colon cancers, lung cancers, cancer metastasis and pancreas cancer but not in the normal tissues tested.

FIG. 22. Expression of 83P4B8 in prostate cancer patient specimens. RNA was extracted from normal prostate (NP), prostate cancer patient tumors (T) and their normal adjacent tissues (N). Northern blot with 10 µg of total RNA/lane was probed with 83P4B8 SSH sequence. Size standards in kilobases (kb) are indicated on the side. The results show strong expression of 83P4B8 in the patient prostate cancer specimens.

FIG. 23. Expression of 83P4B8 in colon cancer patient specimens. RNA was extracted from colon cancer cell lines (CL), normal colon (N), colon cancer patient tumors (T) and their normal adjacent tissues (Nat). Northern blots with 10 µg of total RNA were probed with the 83P4B8 SSH fragment. Size standards in kilobases are indicated on the side. Results show strong expression of 83P4B8 in the colon tumor tissues and in all three colon cancer cell lines tested, but not in the normal tissues.

FIG. 24. Expression of 109P1D4 by RT-PCR. First strand cDNA was prepared from vital pool 1 (liver, lung and kidney), vital pool 2 (pancreas, colon and stomach), prostate cancer pool, bladder cancer pool, kidney cancer pool, colon cancer pool, lung cancer pool, ovary cancer pool, breast cancer pool, cancer metastasis pool, and pancreas cancer pool. Normalization was performed by PCR using primers to actin and GAPDH. Semi-quantitative PCR, using primers to 109P1D4, was performed at 30 cycles of amplification. Results show strong expression of 109P1D4 in all cancer pools tested. Very low expression was detected in the vital pools FIGS. 25A and 25B. Expression of 109P1D4 in normal tissues. Two multiple tissue northern blots (Clontech), both with 2 µg of mRNA/lane, were probed with the 109P1D4 SSH fragment. Size standards in kilobases (kb) are indicated on the side. Results show expression of approximately 10 kb 109P1D4 transcript in ovary. Weak expression was also detected in placenta and brain, but not in the other normal tissues tested.

FIG. 26. Expression of 109P1D4 in human cancer cell lines. RNA was extracted from a number of human prostate and bone cancer cell lines. Northern blots with 10 µg of total RNA/lane were probed with the 109P1D4 SSH fragment. Size standards in kilobases (kb) are indicated on the side. Results show expression of 109P1D4 in LAPC-9AD, LAPC-9AI, LNCaP prostate cancer cell lines, and in the bone cancer cell lines, SK-ES-1 and RD-ES.

FIG. 27. Expression of 109P1D4 in patient cancer specimens. Expression of 109P1D4 was assayed in a panel of human cancers (T) and their respective matched normal tissues (N) on RNA dot blots. Upregulated expression of 109P1D4 in tumors compared to normal tissues was observed in uterus, lung and stomach. The expression detected in normal adjacent tissues (isolated from diseased tissues) but not in normal tissues (isolated from healthy donors) may indicate that these tissues are not fully normal and that 109P1D4 may be expressed in early stage tumors.

FIG. 28. Expression of 151P1C7A by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, and cancer metastasis pool. Normalization was performed by PCR using primers to actin and GAPDH. Semi-quantitative PCR, using primers to 151P1C7A, was performed at 26 and 30 cycles of amplification. Results show strong expression of 151P1C7A in bladder, lung, and metastasis cancer pools tested. Expression was also detected in xenograft, prostate, kidney and colon cancer pools but not in the vital pools.

FIGS. 29A and 29B. Expression of 151P1C7A in normal tissues. Two multiple tissue northern blots (Clontech), both with 2 µg of mRNA/lane, were probed with the 151P1C7A SSH fragment. Size standards in kilobases (kb) are indicated on the side. Results show expression of an approximately 2 kb 151P1C7A transcript in placenta but not in the other normal tissues tested.

FIG. 30. Expression of 151P1C7A in bladder cancer patient specimens. RNA was extracted from bladder cancer cell lines (CL; UM-UC-3, J82, SCaBER), normal bladder (Nb), bladder cancer patient tumors (T) and their normal adjacent tissue (N) isolated from bladder cancer patients. Northern blots with 10 µg of total RNA were probed with the 151P1C7A SSH sequence. Size standards in kilobases are indicated on the side. Results show expression of 151P1C7A in patient bladder cancer tissues, and in all bladder cancer cell lines tested, but not in normal bladder.

FIG. 31. Expression of 151P1C7A in prostate cancer patient specimens. RNA was extracted from normal prostate (NP), prostate cancer patient tumors (T) and their normal adjacent tissues (N). Northern blot with 10 µg of total RNA/lane was probed with 151P1C7A SSH sequence. Size standards in kilobases (kb) are indicated on the side. Results show expression of 151P1C7A in the patient prostate cancer specimens.

FIG. 32. Expression of 151P4E11 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 151P4E11, was performed at 26 and 30 cycles of amplification. Results show strong expression of 151P4E11 in all cancer pools tested. Expression was detected in vital pool 2 but not in vital pool 1.

FIG. 33A-33C. Expression of 151P4E11 in normal tissues. Two multiple tissue northern blots (A and B; Clontech) both with 2 µg of mRNA/lane, and a LAPC xenograft blot with 10 µg of total RNA/lane (C) were probed with the 151P4E11 SSH fragment. Size standards in kilobases (kb) are indicated on the side. Results show expression of an approximately 1.2 kb 151P4E11 transcript in prostate, testis, colon and small intestine. Expression was also detected in all the LAPC prostate cancer xenografts LAPC-4AD, LAPC-4AI, and LAPC-9AI, but not in LAPC-9AD.

FIG. 34. Expression of 154P2A8 by RT-PCR. First strand cDNA was prepared from vital pool 1 (liver, lung and kidney), vital pool 2 (pancreas, colon and stomach), prostate cancer pool, bladder cancer pool, kidney cancer pool, colon cancer pool, lung cancer pool, and cancer metastasis pool. Normalization was performed by PCR using primers to actin and GAPDH. Semi-quantitative PCR, using primers to 154P2A8, was performed at 26 and 30 cycles of amplification. Results show strong expression of 154P2A8 in bladder cancer pool and lung cancer pool. Expression was also detected in prostate cancer pool, kidney cancer pool, colon cancer pool, and cancer metastasis pool but not in vital pool 1 and vital pool 2.

FIG. 35. Expression of 156P1D4 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 156P1D4, was performed at 26 and 30 cycles of amplification. Results show strong expression of 156P1D4 in kidney cancer pool and vital pool 1. Expression was also detected in xenograft pool, prostate cancer pool, bladder cancer pool, colon cancer pool, lung cancer pool, ovary cancer pool, breast cancer pool, cancer metastasis pool and vital pool 2.

FIG. 36. Expression of 156P1D4 in normal tissues. Two multiple tissue northern blots (Clontech), both with 2 µg of mRNA/lane, were probed with the 156P1D4 SSH fragment. Size standards in kilobases (kb) are indicated on the side. Results show expression of an approximately 2 kb 156P1D4 transcript in kidney and prostate but not in the other normal tissues tested.

FIG. 37. Expression of 156P1D4 in kidney cancer patient specimens. RNA was extracted from normal kidney (Nk), kidney cancer patient tumors (T) and their normal adjacent tissues (N). Northern blots with 10 µg of total RNA were probed with the 156P1D4 SSH fragment. Size standards in kilobases are indicated on the side. Results show strong expression of 156P1D4 in all kidney tumor tissues tested. The expression of 156P1D4 detected in tumor tissues is stronger than in normal tissues.

FIG. 38. Expression of 156P5C12 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 156P5C12, was performed at 26 and 30 cycles of amplification. Results show strong expression of 156P5C12 in kidney cancer pool and vital pool 1. Expression was also detected in xenograft pool, prostate cancer pool, bladder cancer pool, colon cancer pool, lung cancer pool, ovary cancer pool, breast cancer pool, cancer metastasis pool and vital pool 2.

FIGS. 39A and 39B. Expression of 156P5C12 in normal tissues. Two multiple tissue northern blots (Clontech), both with 2 μg of mRNA/lane, were probed with the 156P5C12 SSH fragment. Size standards in kilobases (kb) are indicated on the side. Results show expression of an approximately 1.4 kb 156P5C12 transcript in kidney but not in the other normal tissues tested.

FIG. 40. Expression of 156P5C12 in kidney cancer patient specimens. RNA was extracted from kidney cancer cell lines (CL; 769-P, A498, SW839), normal kidney (N), kidney cancer patient tumors (T) and their normal adjacent tissues (NAT). Northern blots with 10 μg of total RNA were probed with the 156P5C12 SSH fragment. Size standards in kilobases are indicated on the side. Results show expression of 156P5C12 in normal tissues, and in some but not all kidney tumor tissues. Expression was absent in the kidney cancer cell lines tested.

FIG. 41. Expression of 159P2B5 by RT-PCR. First strand cDNA was prepared from vital pool 1 (liver, lung and kidney), vital pool 2 (pancreas, colon and stomach), and bladder cancer pool. Normalization was performed by PCR using primers to actin and GAPDH. Semi-quantitative PCR, using primers to 159P2B5, was performed at 26 and 30 cycles of amplification. Results show expression of 159P2B5 in bladder cancer pool tested but not in the vital pools.

FIGS. 42A and 42B. Expression of 159P2B5 in normal tissues. Two multiple tissue northern blots (Clontech), both with 2 μg of mRNA/lane, were probed with the 159P2B5 SSH fragment. Size standards in kilobases (kb) are indicated on the side. Results show very weak expression of an approximately 4.5 kb 159P2B5 transcript in spleen, kidney and small intestine.

FIG. 43. Expression of 159P2B5 in bladder cancer patient specimens. RNA was extracted from bladder cancer cell lines (CL; UM-UC-3, J82, SCaBER), normal bladder (NB), and bladder cancer patient tumors (T) isolated from bladder cancer patients. Northern blots with 10 μg of total RNA were probed with the 159P2B5 SSH sequence. Size standards in kilobases are indicated on the side. Results show expression of 159P2B5 in patient bladder cancer tissues, and in the SCaBER bladder cancer cell line, but not in normal bladder, nor in the other cancer cell lines tested.

FIG. 44. Expression of 161P2B7A by RT-PCR. First strand cDNA was prepared from vital pool 1 (liver, lung and kidney), vital pool 2 (pancreas, colon and stomach), prostate metastasis to lymph node (LN), prostate cancer pool, bladder cancer pool, kidney cancer pool, colon cancer pool, lung cancer pool, ovary cancer pool, breast cancer pool, cancer metastasis pool and pancreas cancer pool. Normalization was performed by PCR using primers to actin and GAPDH. Semi-quantitative PCR, using primers to 161P2B7A, was performed at 26 and 30 cycles of amplification. Results show strong expression of 161P2B7A in lung cancer pool and pancreas cancer pool. Expression was also detected in prostate metastasis to LN, prostate cancer pool, bladder cancer pool, kidney cancer pool, colon cancer pool, ovary cancer pool, breast cancer pool, and cancer metastasis pool. Very low expression was observed in vital pool 2 but not in vital pool 1.

FIGS. 45A and 45B. Expression of 161P2B7A in normal tissues. Two multiple tissue northern blots (Clontech), both with 2 μg of mRNA/lane, were probed with the 161P2B7A SSH fragment. Size standards in kilobases (kb) are indicated on the side. Results show very low expression of 161P2B7A in testis but not in the other normal tissues tested.

FIG. 46. Expression of 161P2B7A in Multiple Normal Tissues. An mRNA dot blot containing 76 different samples from human tissues was analyzed using a 161P2B7A SSH probe. Expression was not detected in any of the 76 normal tissues tested. The positive genomic DNA control showed very strong signal confirming the validity of the experiment.

FIG. 47. Expression of 161P2B7A in kidney cancer patient specimens. RNA was extracted from normal kidney (Nk), kidney cancer patient tumors (T) and their normal adjacent tissues (N) isolated from kidney cancer patients. Northern blots with 10 μg of total RNA were probed with the 161P2B7A SSH fragment. Size standards in kilobases are indicated on the side. Results show expression of two 161P2B7A transcripts, approximately 1.2 and 7 kb, in kidney cancer specimens but not in normal kidney.

FIG. 48. Expression of 161P2B7A in lung cancer patient specimens. RNA was extracted from lung cancer cell lines (CL), normal lung, lung tumors (T), and their normal adjacent tissues (NAT) isolated from lung cancer patients. Northern blot with 10 μg of total RNA/lane was probed with the 161P2B7A fragment. Size standards in kilobases (kb) are indicated on the side. The results show expression of 161P2B7A in the lung tumors, but not in normal lung tissues. Expression was also detected in the lung cancer cell lines CALU-1, A427 and NCI-146 but not in the small cell lung cancer cell line NCI-H82.

FIG. 49. Expression of 161P2B7A in pancreas and ovary cancer patient specimens. RNA was extracted from normal pancreas (NPa), pancreas cancer (PC), normal ovary (NO), and ovary cancer patient specimen (OC). Northern blot with 10 μg of total RNA/lane was probed with the 161P2B7A fragment. Size standards in kilobases (kb) are indicated on the side. The results show expression of 161P2B7A in the pancreas and ovary cancer patient specimens, but not in the normal tissues.

FIG. 50. Expression of 179P3G7 by RT-PCR. First strand cDNA was prepared from vital pool 1 (liver, lung and kidney), vital pool 2 (pancreas, colon and stomach), bladder cancer pool, kidney cancer pool, lung cancer pool, breast cancer pool, cancer metastasis pool, pancreas cancer pool and pancreas cancer pool. Normalization was performed by PCR using primers to actin and GAPDH. Semi-quantitative PCR, using primers to 179P3G7, was performed at 26 and 30 cycles of amplification. Results show strong expression of 179P3G7 in kidney cancer pool and breast cancer pool. Expression was also detected in bladder cancer pool, lung cancer pool, cancer metastasis pool, pancreas cancer pool and prostate metastasis to LN, and vital pool 1, but not in vital pool 2.

FIGS. 51A and 51B. Expression of 179P3G7 in normal tissues. Two multiple tissue northern blots (Clontech), both with 2 μg of mRNA/lane, were probed with the 179P3G7 SSH fragment. Size standards in kilobases (kb) are indicated on the side. Results show expression of 179P3G7 strongly in skeletal muscle, and weakly in kidney, liver and heart but not in the other normal tissues tested.

FIG. 52. Expression of 179P3G7 in kidney cancer patient specimens. RNA was extracted from normal kidney (Nk), kidney cancer patient tumors (T) and their normal adjacent tissues (N) isolated from kidney cancer patients. Northern blots with 10 μg of total RNA were probed with the 179P3G7 SSH fragment. Size standards in kilobases are indicated on the side. Results show expression of 179P3G7 in kidney cancer specimens. Expression of 179P3G7 is stronger in kidney tumors compared to normal kidney tissues.

FIG. 53. Expression of 184P3C10B by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, ovary cancer pool, and cancer metastasis pool. Normalization was performed by PCR using primers to actin and GAPDH. Semi-quantitative PCR, using primers to 184P3C10B, was performed at 26 and 30 cycles of amplification. Results show expression of 184P3C10B in xenograft pool, prostate cancer pool, bladder cancer pool, kidney cancer pool, colon cancer pool, lung cancer pool, ovary cancer pool, and cancer metastasis pool. Expression was also detected in vital pool 2 but at a much lower level in vital pool 1.

FIG. 54. Expression of 184P3C10B in normal tissues. Two multiple tissue northern blots (Clontech), both with 2 μg of mRNA/lane, were probed with the 184P3C10B SSH fragment. Size standards in kilobases (kb) are indicated on the side. Results show expression of approximately 2.4 and 5 kb 184P3C10B transcripts in placenta and to lower level in colon and small intestine, but not in the other normal tissues tested.

FIG. 55. Expression of 184P3C10B in bladder cancer patient specimens. RNA was extracted from bladder cancer cell lines (CL; UM-UC-3, J82, SCaBER), normal bladder (Nb), bladder cancer patient tumors (T) and their normal adjacent tissue (N) isolated from bladder cancer patients. Northern blots with 10 μg of total RNA were probed with the 184P3C10B SSH sequence. Size standards in kilobases are indicated on the side. Results show expression of 184P3C10B in patient bladder cancer tissues, and in the bladder cancer cell line SCaBER, but not in normal bladder nor in the other bladder cancer cell lines tested.

FIG. 56. Expression of 184P3G10 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), bladder cancer pool, kidney cancer pool, colon cancer pool, and lung cancer pool. Normalization was performed by PCR using primers to actin and GAPDH. Semi-quantitative PCR, using primers to 184P3G10, was performed at 26 and 30 cycles of amplification. Results show strong expression of 184P3G10 in bladder cancer pool, kidney cancer pool, and colon cancer pool. Expression was also detected in xenograft pool, lung cancer pool, vital pool 2 but not in vital pool 1.

FIGS. 57A and 57B. Expression of 184P3G10 in normal tissues. Two multiple tissue northern blots (Clontech) both with 2 μg of mRNA/lane, were probed with the 184P3G10 SSH fragment. Size standards in kilobases (kb) are indicated on the side. Results show expression of two approximately 4.4 kb 184P3G10 transcripts in colon and small intestine, but not in the other normal tissues tested.

FIG. 58. Expression of 184P3G10 in patient cancer specimens and normal tissues. RNA was extracted from a pool of three bladder cancers, colon cancers, lung cancers, breast cancers, ovary cancers, cancer metastasis, as well as from normal prostate (NP), normal bladder (NB), and normal kidney (NK). Northern blot with 10 μg of total RNA/lane was probed with 184P3G10 sequence. Size standards in kilobases (kb) are indicated on the side. Results show strong expression of 184P3G10 in the bladder cancers, colon cancers and ovary cancers. Expression of 184P3G10 was also detected in lung cancers, breast cancers, and cancer metastasis but not in the normal tissues tested.

FIG. 59. Expression of 184P3G10 in bladder cancer patient specimens. RNA was extracted from bladder cancer cell lines (CL; UM-UC-3, J82, SCaBER), normal bladder (N), bladder cancer patient tumors (T) and their normal adjacent tissue (Nat) isolated from bladder cancer patients. Northern blots with 10 μg of total RNA were probed with the 184P3G10 SSH sequence. Size standards in kilobases are indicated on the side. Results show expression of 184P3G10 in patient bladder cancer tissues, but not in normal bladder nor in the bladder cancer cell lines tested.

FIG. 60. Expression of 185P2C9 by RT-PCR. First strand cDNA was prepared from vital pool 1 (liver, lung and kidney), vital pool 2 (pancreas, colon and stomach), prostate metastasis to lymph node (LN), prostate cancer pool, bladder cancer pool, kidney cancer pool, colon cancer pool, lung cancer pool, ovary cancer pool, breast cancer pool, cancer metastasis pool and pancreas cancer pool. Normalization was performed by PCR using primers to actin and GAPDH. Semi-quantitative PCR, using primers to 185P2C9, was performed at 30 cycles of amplification. Results show strong expression of 185P2C9 in bladder cancer pool, colon cancer pool, lung cancer pool, ovary cancer pool and pancreas cancer pool. Expression was also detected in prostate metastasis to LN, prostate cancer pool, kidney cancer pool, breast cancer pool, cancer metastasis pool, vital pool 2 but not in vital pool 1.

FIG. 61. Expression of 185P2C9 in normal tissues. Two multiple tissue northern blots (Clontech), both with 2 μg of mRNA/lane, were probed with the 185P2C9 SSH fragment. Size standards in kilobases (kb) are indicated on the side. Results show expression of and approximately 8.5 kb 185P2C9 transcript in testis and brain, but not in the other normal tissues tested.

FIG. 62. Expression of 185P2C9 in bladder cancer patient specimens. RNA was extracted from bladder cancer cell lines (CL; UM-UC-3, 382, SCaBER), normal bladder (Nb), bladder cancer patient tumors (T) and their normal adjacent tissue (N) isolated from bladder cancer patients. Northern blots with 10 μg of total RNA were probed with the 185P2C9 SSH sequence. Size standards in kilobases are indicated on the side. Results show expression of 185P2C9 in bladder cancer patient tissues, and in the bladder cancer cell lines tested. Expression of 185P2C9 is significantly stronger in bladder tumor tissues compared to normal tissues.

FIG. 63. Expression of 185P2C9 in kidney cancer patient specimens. RNA was extracted from kidney cancer cell lines (CL; 769-P, A498, Caki-1), normal kidney (N), kidney cancer patient tumors (T) and their normal adjacent tissues (NAT) isolated from kidney cancer patients. Northern blots with 10 μg of total RNA were probed with the 185P2C9 SSH fragment. Size standards in kilobases are indicated on the side. Results show expression of 185P2C9 in kidney cancer specimens and kidney cancer cell lines, but not in normal kidney.

FIG. 64. Expression of 186P1H9 by RT-PCR. First strand cDNA was prepared from vital pool 1 (liver, lung and kidney), vital pool 2 (pancreas, colon and stomach), bladder cancer pool, kidney cancer pool, colon cancer pool, lung cancer pool, ovary cancer pool, cancer metastasis pool, and pancreas cancer pool. Normalization was performed by PCR using primers to actin and GAPDH. Semi-quantitative PCR, using primers to 186P1H9, was performed at 26 and 30 cycles of amplification. Results show strong expression of 186P1H9 in kidney cancer pool, colon cancer pool, ovary cancer pool, cancer metastasis pool, and pancreas cancer pool. Expression was also detected in bladder cancer pool, lung cancer pool, vital pool 2 but not in vital pool 1.

FIG. 65. Expression of 186P1H9 in normal tissues. Two multiple tissue northern blots (Clontech) both with 2 µg of mRNA/lane, were probed with the 186P1H9 SSH fragment. Size standards in kilobases (kb) are indicated on the side. Results show expression of an approximately 2.6 kb 186P1H9 transcript in testis, spleen, pancreas and brain. Lower expression is also detected in heart, skeletal muscle, prostate, colon and small intestine.

FIG. 66. Expression of 186P1H9 in patient cancer specimens and normal tissues. RNA was extracted from a pool of three kidney cancers (KC), ovary cancers (OC), cancer metastasis (Met), pancreas cancers (PaC), as well as from normal prostate (NP), normal bladder (NB), and normal kidney (NK), normal colon (NC), normal lung (NL), normal breast (NBr), normal ovary (NO), and normal pancreas (NPa). Northern blot with 10 µg of total RNA/lane was probed with 186P1H9 sequence. Size standards in kilobases (kb) are indicated on the side. Results show strong expression of 186P1H9 in the bladder cancers, ovary cancers, cancer metastasis and pancreas cancers, but not in normal tissues. Expression of 186P1H9 is significantly stronger in patient cancer tissues compared to normal tissues.

FIG. 67. Expression of 186P1H9 in kidney cancer patient specimens. RNA was extracted from kidney cancer cell lines (CL; 769-P, A498, Caki-1), normal kidney (N), kidney cancer patient tumors (T) and their normal adjacent tissues (NAT) isolated from kidney cancer patients. Northern blots with 10 µg of total RNA were probed with the 186P1H9 SSH fragment. Size standards in kilobases are indicated on the side. Results show strong expression of 186P1H9 in kidney cancer patient specimens, but not in normal kidney, nor in the kidney cancer cell lines.

FIG. 68. Expression of 186P1H9 in ovarian and testicular cancer patient specimens. RNA was extracted from normal ovary (NO), ovary cancer patient specimens (P1, P2, P3), normal testis (NTe), and testis cancer patient specimens (P4, P5, P6). Northern blot with 10 µg of total RNA/lane was probed with the 186P1H9 SSH fragment. Size standards in kilobases (kb) are indicated on the side. The results show strong expression of 186P1H9 in the ovary cancer patient specimens, but not in the normal ovary. Expression was also detected in normal and in testis cancer specimens.

FIG. 69. Expression of 187P3F2 by RT-PCR. First strand cDNA was prepared from vital pool 1 (liver, lung and kidney), vital pool 2 (pancreas, colon and stomach), kidney cancer pool, and pancreas cancer pool. Normalization was performed by PCR using primers to actin and GAPDH. Semi-quantitative PCR, using primers to 187P3F2, was performed at 26 and 30 cycles of amplification. Results show strong expression of 187P3F2 in kidney cancer pool, pancreas cancer pool and vital pool 1, but not in vital pool 2.

FIG. 70. Expression of 187P3F2 in normal tissues. Two multiple tissue northern blots (Clontech) both with 2 µg of mRNA/lane, were probed with the 187P3F2 SSH fragment. Size standards in kilobases (kb) are indicated on the side. Results show expression of an 4.5 kb 187P3F2 transcript in kidney and brain, but not in the other tissues tested.

FIG. 71. Expression of 187P3F2 in patient cancer specimens and normal tissues. RNA was extracted from a pool of three kidney cancers (KC), pancreas cancers (PaC), as well as from normal prostate (NP), normal bladder (NB), and normal kidney (NK), normal colon (NC), normal lung (NL), normal breast (NBr), normal ovary (NO), and normal pancreas (NPa). Northern blot with 10 µg of total RNA/lane was probed with 187P3F2 sequence. Size standards in kilobases (kb) are indicated on the side. Results show strong expression of 187P3F2 in kidney cancers, pancreas cancers, and normal kidney, but not in the other normal tissues.

FIG. 72. Expression of 187P3F2 in pancreas cancer patient specimens. RNA was extracted from pancreas cancer cell lines (CL), normal pancreas (N), and pancreas tumor tissues (T) isolated from pancreatic cancer patients. Northern blot with 10 µg of total RNA/lane was probed with the 187P3F2 SSH fragment. Size standards in kilobases (kb) are indicated on the side. The results show strong expression of 187P3F2 in the pancreas cancer specimens, but not in normal pancreas nor in the cancer cell lines tested.

FIG. 73. Expression of 192P2G7 by RT-PCR. First strand cDNA was prepared from vital pool 1 (liver, lung and kidney), vital pool 2 (pancreas, colon and stomach), prostate cancer pool, bladder cancer pool, kidney cancer pool, lung cancer pool, ovary cancer pool, breast cancer pool, cancer metastasis pool, pancreas cancer pool, and prostate metastasis to lymph node (LN). Normalization was performed by PCR using primers to actin and GAPDH. Semi-quantitative PCR, using primers to 186P1H9, was performed at 26 and 30 cycles of amplification. Results show strong expression of 186P1H9 in pancreas cancer pool and prostate metastasis to LN. Expression was also detected in prostate cancer pool, bladder cancer pool, kidney cancer pool, lung cancer pool, ovary cancer pool, breast cancer pool, cancer metastasis pool, vital pool 2 but not in vital pool 1.

FIG. 74. Expression of 185P3C2 by RT-PCR. First strand cDNA was prepared from vital pool 1 (liver, lung and kidney), vital pool 2 (pancreas, colon and stomach), and bladder cancer pool. Normalization was performed by PCR using primers to actin and GAPDH. Semi-quantitative PCR, using primers to 185P3C2, was performed at 26 and 30 cycles of amplification. Results show strong expression of 185P3C2 in bladder cancer pool. Low level expression was detected in vital pool 2, but not in vital pool 1.

DETAILED DESCRIPTION OF THE INVENTION

Outline of Sections
I.) Definitions
II.) Polynucleotides of the Invention
II.A.) Uses Polynucleotides of the Invention
   II.A.1.) Monitoring of Genetic Abnormalities
   II.A.2.) Antisense Embodiments
   II.A.3.) Primers and Primer Pairs
   II.A.4.) Isolation of Nucleic Acid Molecules that Encode Proteins of the Invention
   II.A.5.) Recombinant Nucleic Acid Molecules and Host-Vector Systems
III.) Proteins of the Invention
III.A.) Motif-bearing Protein Embodiments
III.B.) Expression of FIG. 2—related Proteins
III.C.) Modifications of FIG. 2—related Proteins
III.D.) Uses of FIG. 2—related Proteins
IV.) Antibodies of the Invention
V.) Cellular Immune Responses of the Invention
VI.) Transgenic Animals of the Invention
VII.) Methods for the Detection of a Gene or Protein of the Invention
VIII.) Methods for Monitoring the Status of Genes and Proteins of the Invention
IX.) Identification of Molecules That Interact With the Proteins of FIG. 2
X.) Therapeutic Methods and Compositions
X.A.) Anti-Cancer Vaccines X.B.) A Protein of FIG. 2 as a Target for Antibody-Based Therapy
X.C.) A Protein of FIG. 2 as a Target for Cellular Immune Responses
   X.C.1. Minigene Vaccines
   X.C.2. Combinations of CTL Peptides with Helper Peptides
   X.C.3. Combinations of CTL Peptides with T Cell Priming Agents
   X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of the Invention
XII.) Inhibition of the Function of a Protein of the Invention
   XII.A.) Inhibition of a Protein of FIG. 2 with Intracellular Antibodies
   XII.B.) Inhibition of a Protein of FIG. 2 with Recombinant Proteins
   XII.C.) Inhibition of Transcription or Translation in Accordance with the Invention
   XII.D.) General Considerations for Therapeutic Strategies
XII.) KITS

I.) DEFINITIONS

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence of the genes set forth in FIG. 2 (either by removing the underlying glycosylation site or by deleting the glycosylation by chemical and/or enzymatic means), and/or adding one or more glycosylation sites that are not present in the native sequence of a protein set forth in FIG. 2. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a protein of FIG. 2). For example an analog of a protein of FIG. 2 can be specifically bound by an antibody or T cell that specifically binds to the respective protein of FIG. 2.

The term "antibody" is used in the broadest sense. Therefore an "antibody" can be naturally occurring or man-made such as monoclonal antibodies produced by conventional hybridoma technology. Antibodies of the invention comprise monoclonal and polyclonal antibodies as well as fragments containing the antigen-binding domain and/or one or more complementarity determining regions of these antibodies that specifically bind a protein of FIG. 2.

An "antibody fragment" is defined as at least a portion of the variable region of the immunoglobulin molecule that binds to its target, i.e., the antigen-binding region. In one embodiment it specifically covers single antibodies and clones thereof (including agonist, antagonist and neutralizing antibodies) and antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, 8$^{TH}$ ED., Lange Publishing, Los Altos, Calif. (1994)).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/ 100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the genes of FIG. 2 or that encode polypeptides other than proteins of FIG. 2 product or fragments thereof. A skilled artisan can readily employ nucleic acid isolation procedures to obtain an isolated polynucleotide. A protein is said to be "isolated," for example, when physical, mechanical or chemical methods are employed to remove a protein of FIG. 2 from cellular constituents that are normally associated with the protein. A skilled artisan can readily employ standard purification methods to obtain an isolated FIG. 2 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of a FIG. 2—related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymine (T), as shown for example in FIG. 2, can also be uracil (U); this definition pertains to the differences between the chemical structures of DNA and RNA, in particular the observation that one of the four major bases in RNA is uracil (U) instead of thymine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. In another embodiment, for example, the primary anchor residues of a peptide that will bind an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif A "recombinant" DNA or RNA molecule is a DNA or RNA molecule that has been subjected to molecular manipulation in vitro.

Non-limiting examples of small molecules include compounds that bind or interact with the proteins of FIG. 2;

ligands including hormones, neuropeptides, chemokines, odorants, phospholipids, and functional equivalents thereof that bind and preferably inhibit function of a FIG. 2 protein. Such non-limiting small molecules preferably have a molecular weight of less than about 10 kDa, more preferably below about 9, about 8, about 7, about 6, about 5 or about 4 kDa. In certain embodiments, small molecules physically associate with, or bind, a FIG. 2 protein; and are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, erg., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. a protein of FIG. 2 protein shown in FIG. 2 or FIG. 3. An analog is an example of a variant protein. Splice isoforms and single nucleotides polymorphisms (SNPs) are further examples of variants.

The "genes of FIG. 2—related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different genes set forth in FIG. 2 proteins of the invention or fragments thereof, as well as fusion proteins of a gene of FIG. 2 protein and a heterologous polypeptide are also included. Such genes of FIG. 2 proteins are collectively referred to as the genes of FIG. 2—related proteins, the proteins of the invention, or proteins of FIG. 2. The term "genes of FIG. 2—related protein" refers to a polypeptide fragment or a FIG. 2 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100 or more than 100 amino acids. In certain cases the phrase "corresponding to" or "respective" is used instead of the term "-related."

II.) POLYNUCLEOTIDES OF THE INVENTION

One aspect of the invention provides polynucleotides corresponding or complementary to all or part of: a gene of FIG. 2; gene of FIG. 2—related mRNA, a coding sequence of a gene of FIG. 2, an open reading frame of a gene of FIG. 2, each of the foregoing preferably in isolated form. Polynucleotides of the invention include polynucleotides encoding FIG. 2—related proteins and fragments thereof, DNA, RNA, DNA/RNA hybrid, and related molecules, polynucleotides or oligonucleotides complementary to a FIG. 2 gene or mRNA sequence or a part thereof, and polynucleotides or oligonucleotides that hybridize to a FIG. 2 gene, mRNA, or to a FIG. 2 encoding polynucleotide (collectively, "FIG. 2 polynucleotides"). In all instances when referred to in this section, T can also be U in FIG. 2.

Figure 5C:
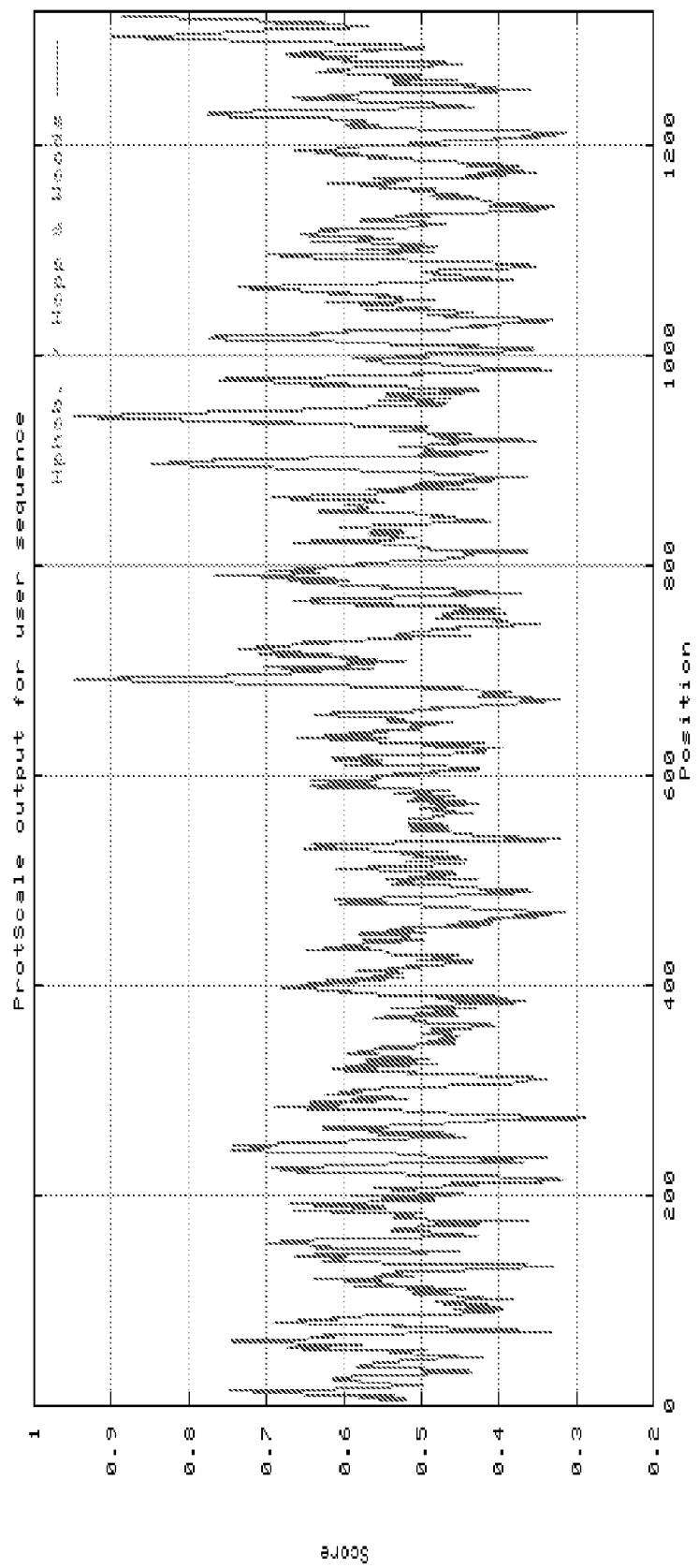
Figure 5D:
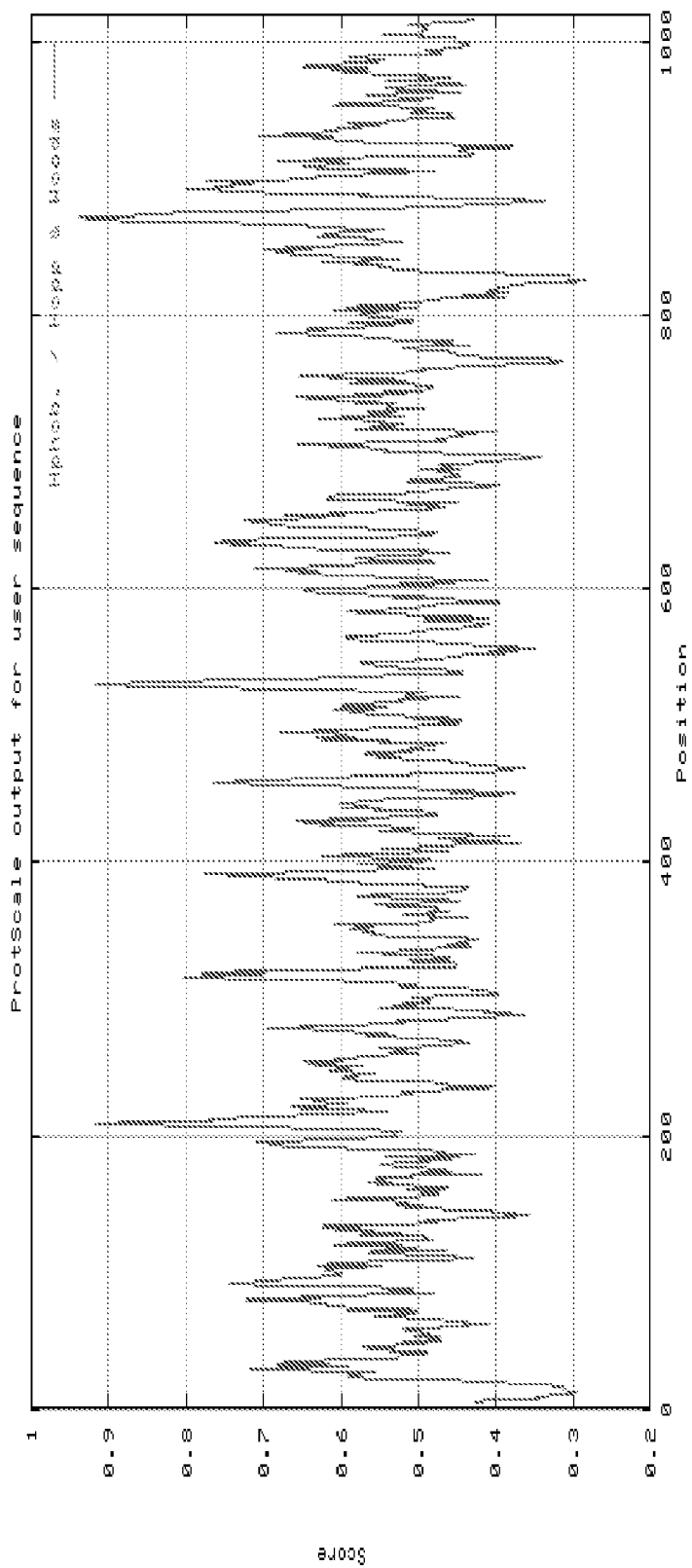
Figure 6B:
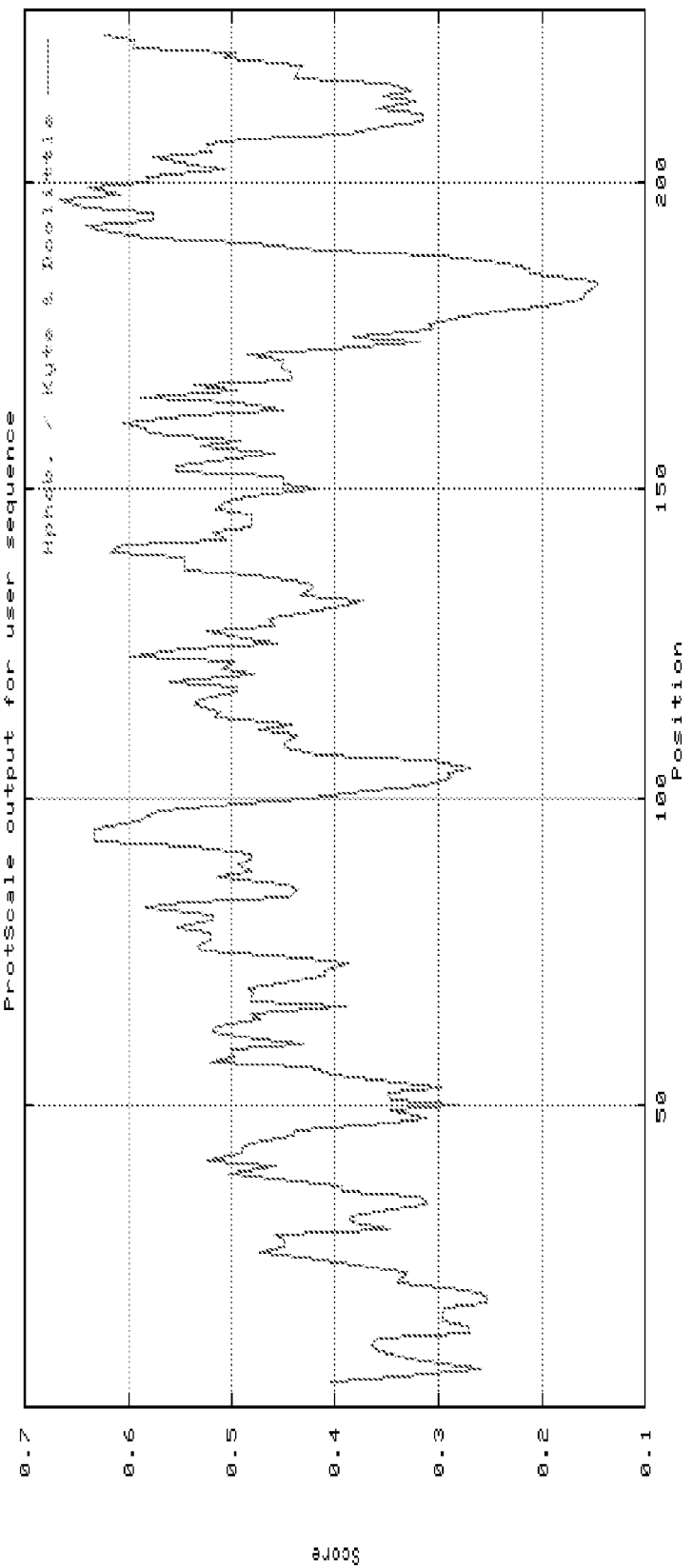
FIGS. 6A-6U. Hydropathicity amino acid profile of the proteins set forth in FIG. 2 determined by computer algorithm sequence analysis using the method of Kyte and Doolittle (Kyte J., Doolittle R. F., 1982. J. Mol. Biol. 157:105-132).
Figure 6C:
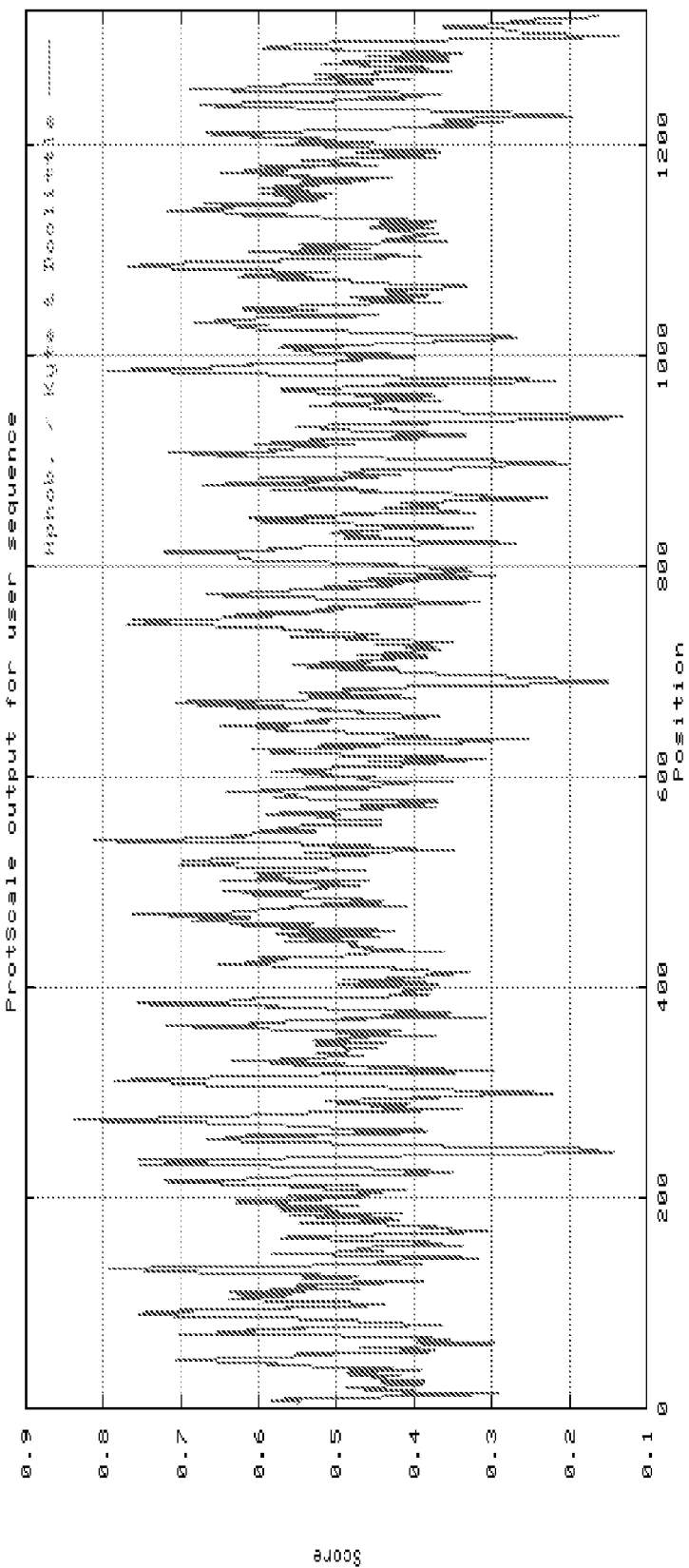
Figure 6D:
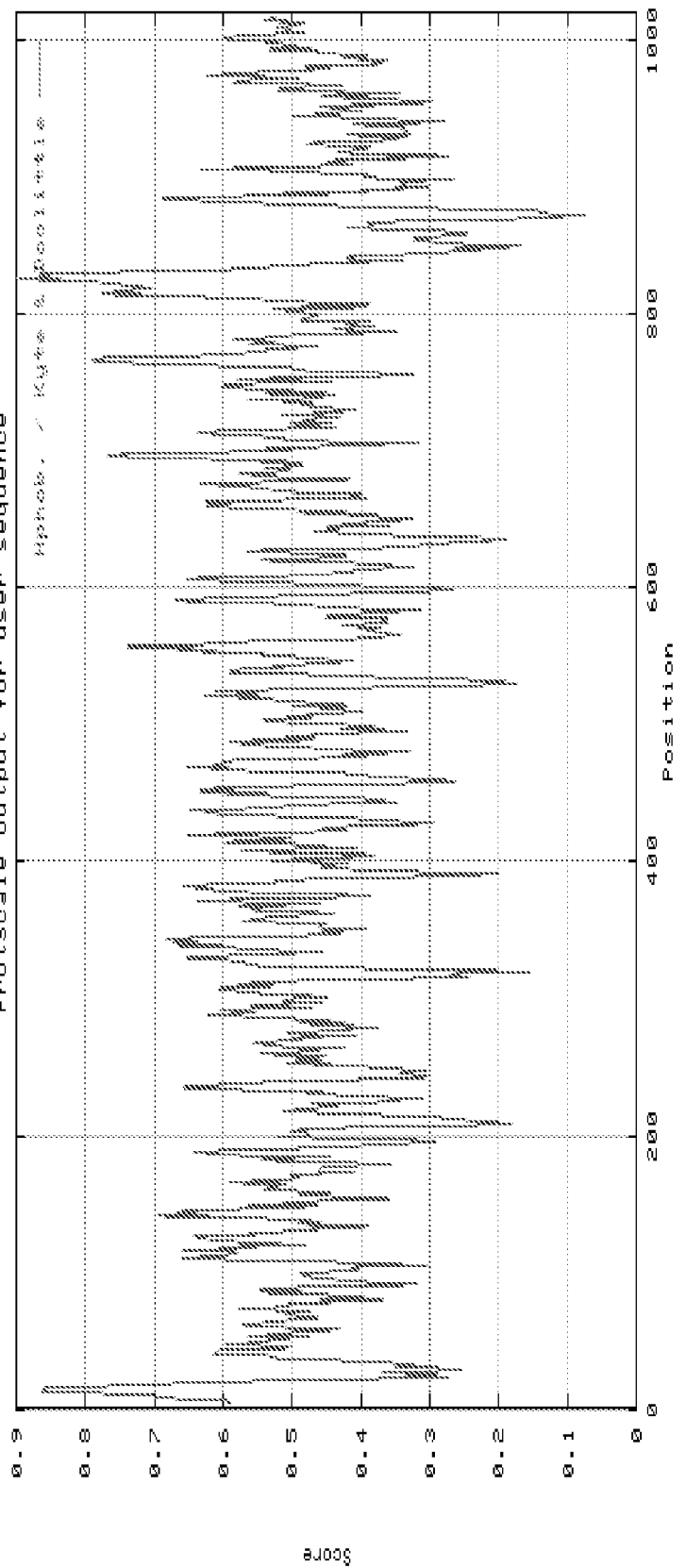
Figure 7A:
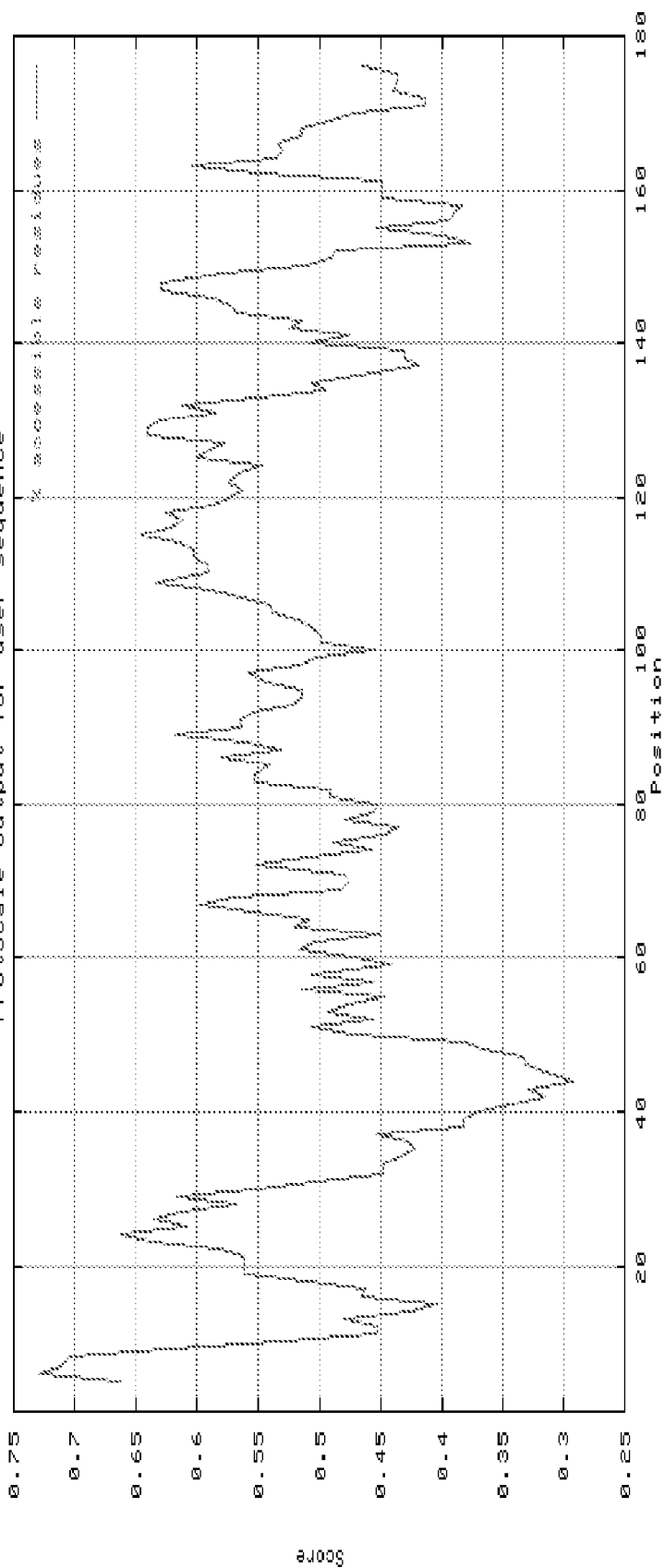
FIGS. 7A-7U. Percent accessible residues amino acid profile of the proteins set forth in FIG. 2 determined by computer algorithm sequence analysis using the method of Janin (Janin J., 1979 Nature 277:491-492).
Figure 7C:
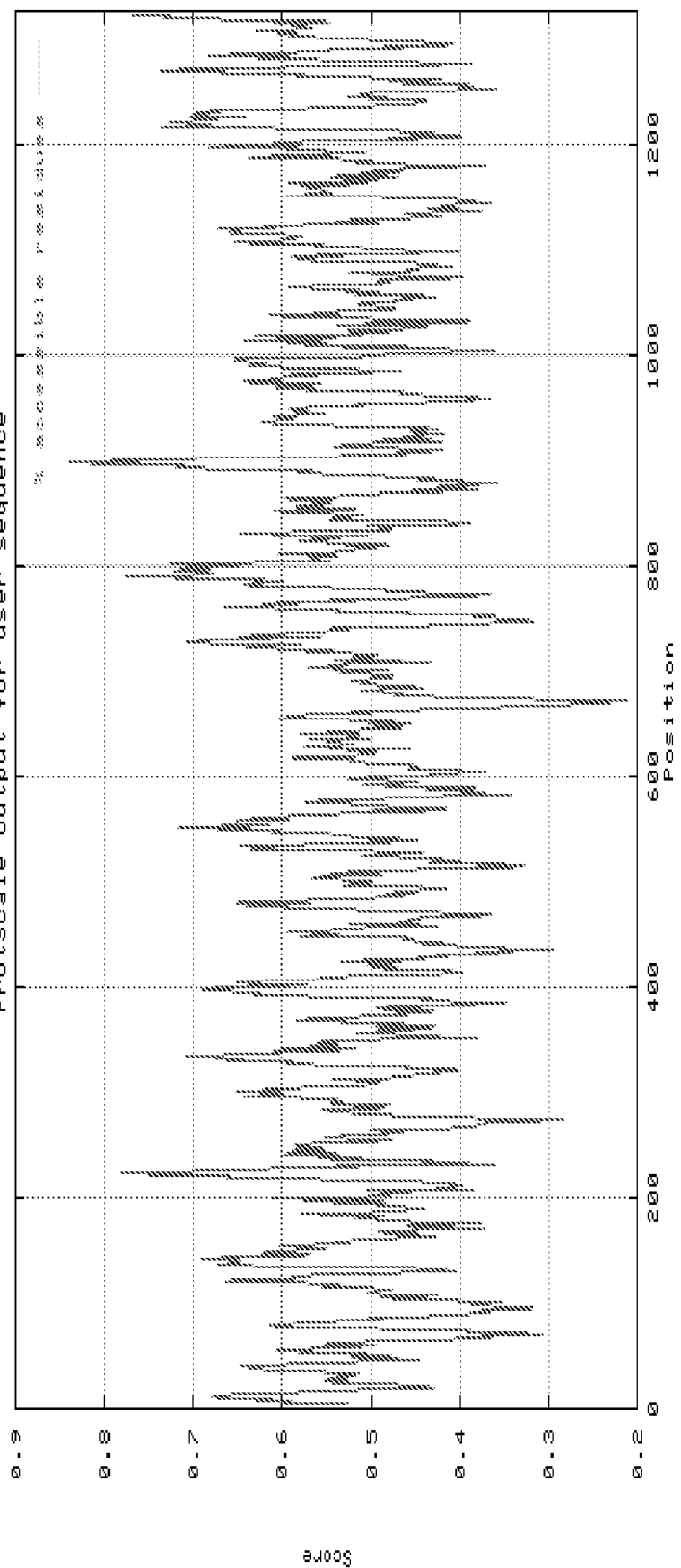
Figure 7D:
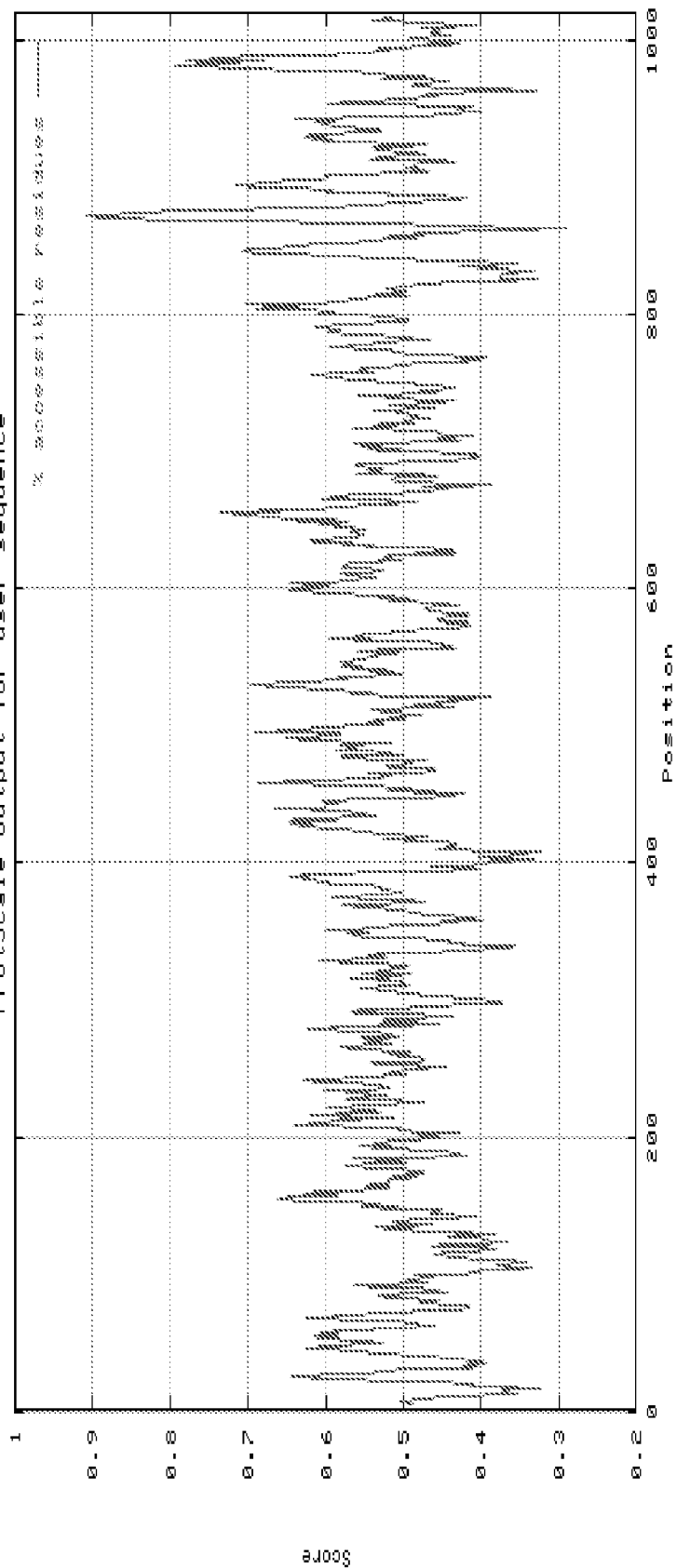
Figure 8A:
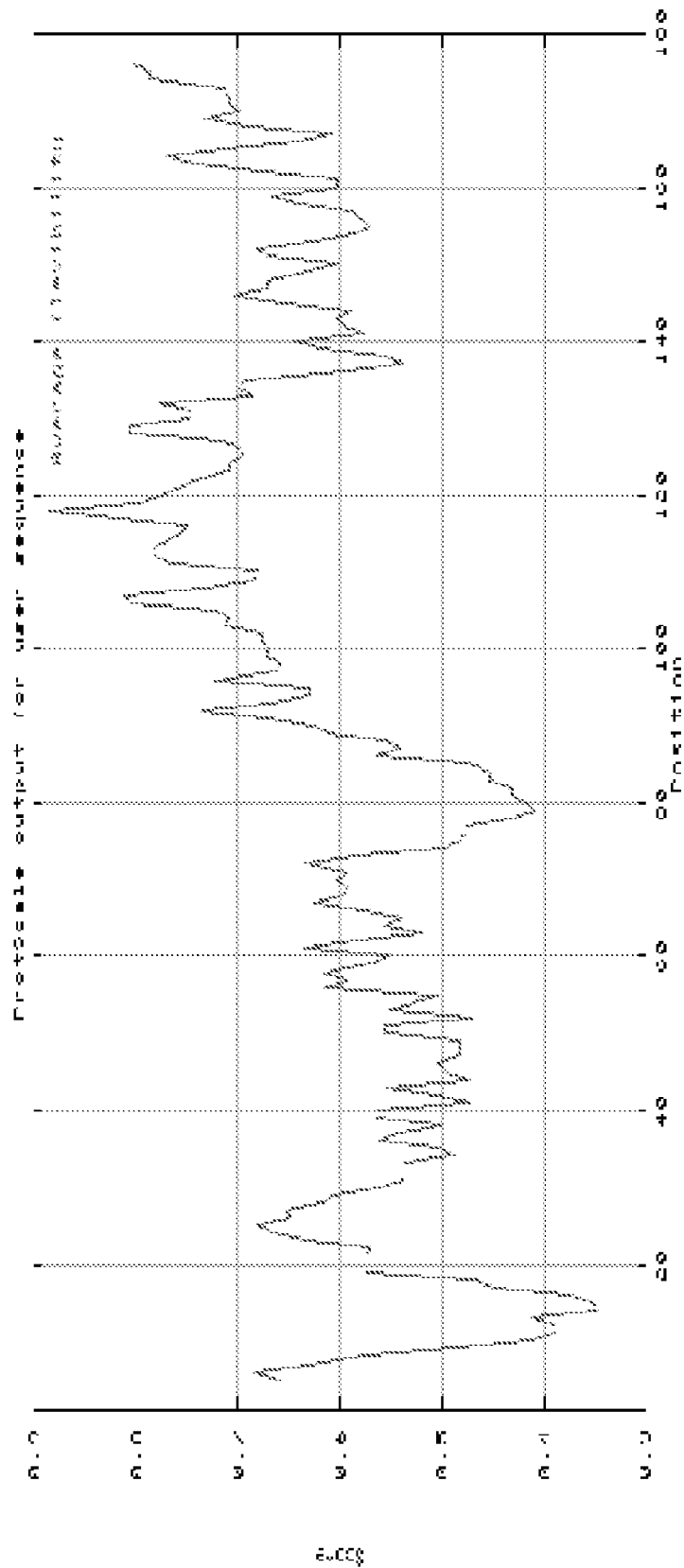
FIGS. 8A-8U. Average flexibility amino acid profile of the proteins set forth in FIG. 2 determined by computer algorithm sequence analysis using the method of Bhaskaran and Ponnuswamy (Bhaskaran R., and Ponnuswamy P. K., 1988. Int. J. Pept. Protein Res. 32:242-255).
Figure 8B:
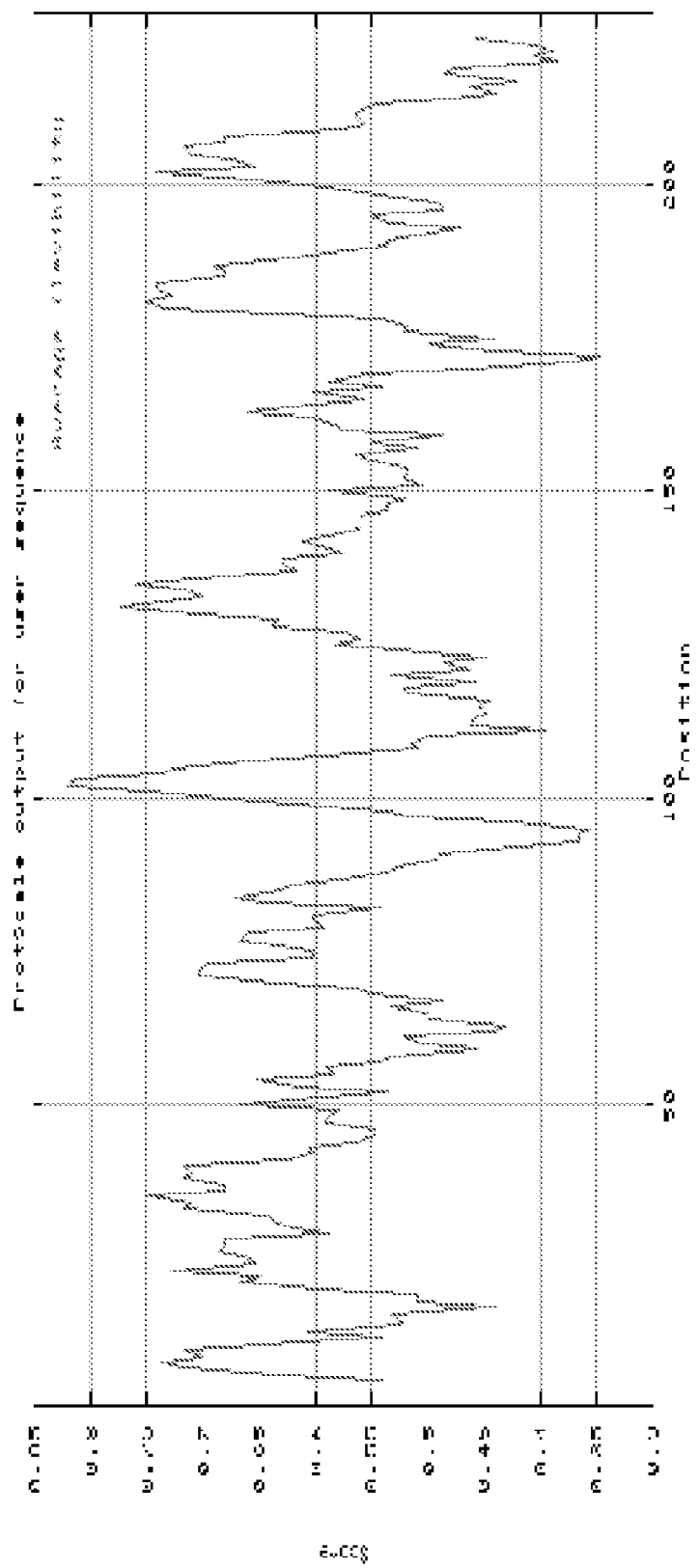
Figure 8C:
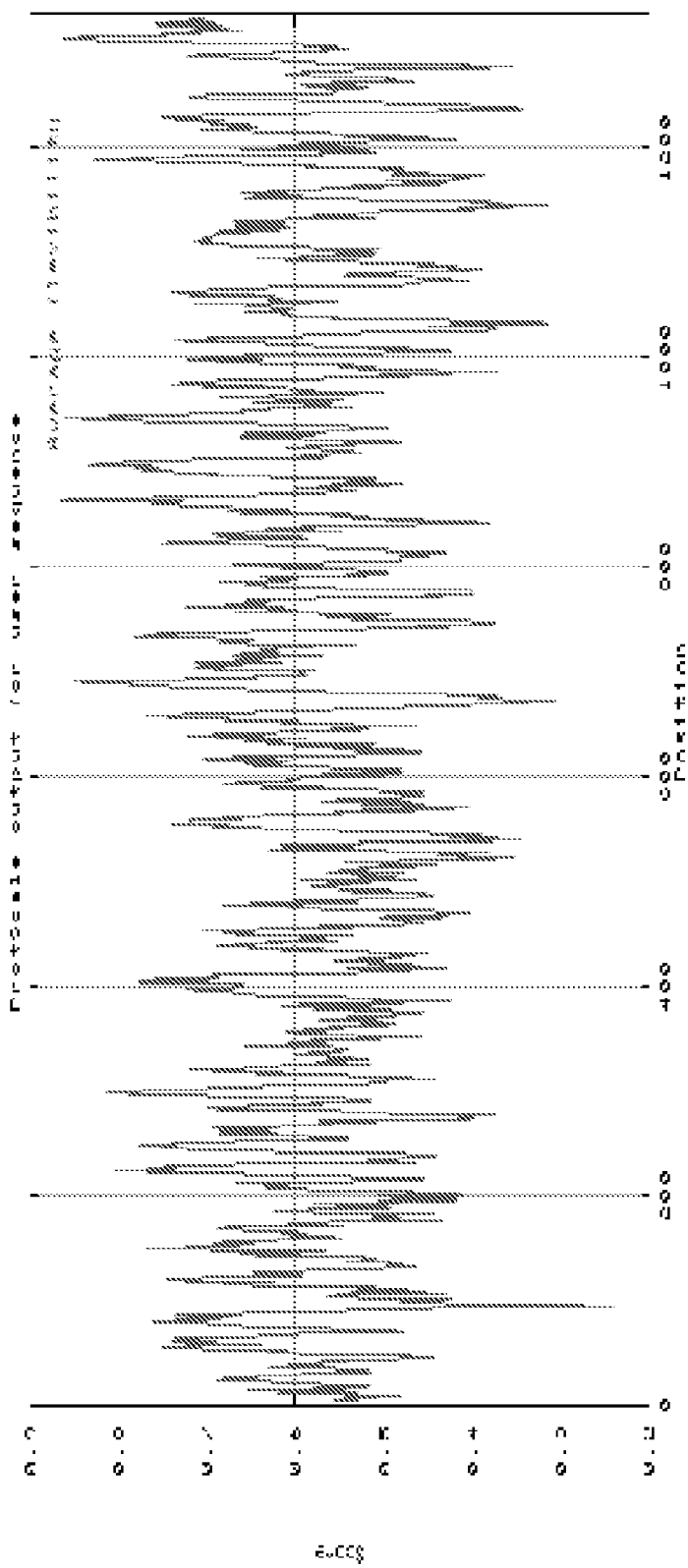
Figure 8D:
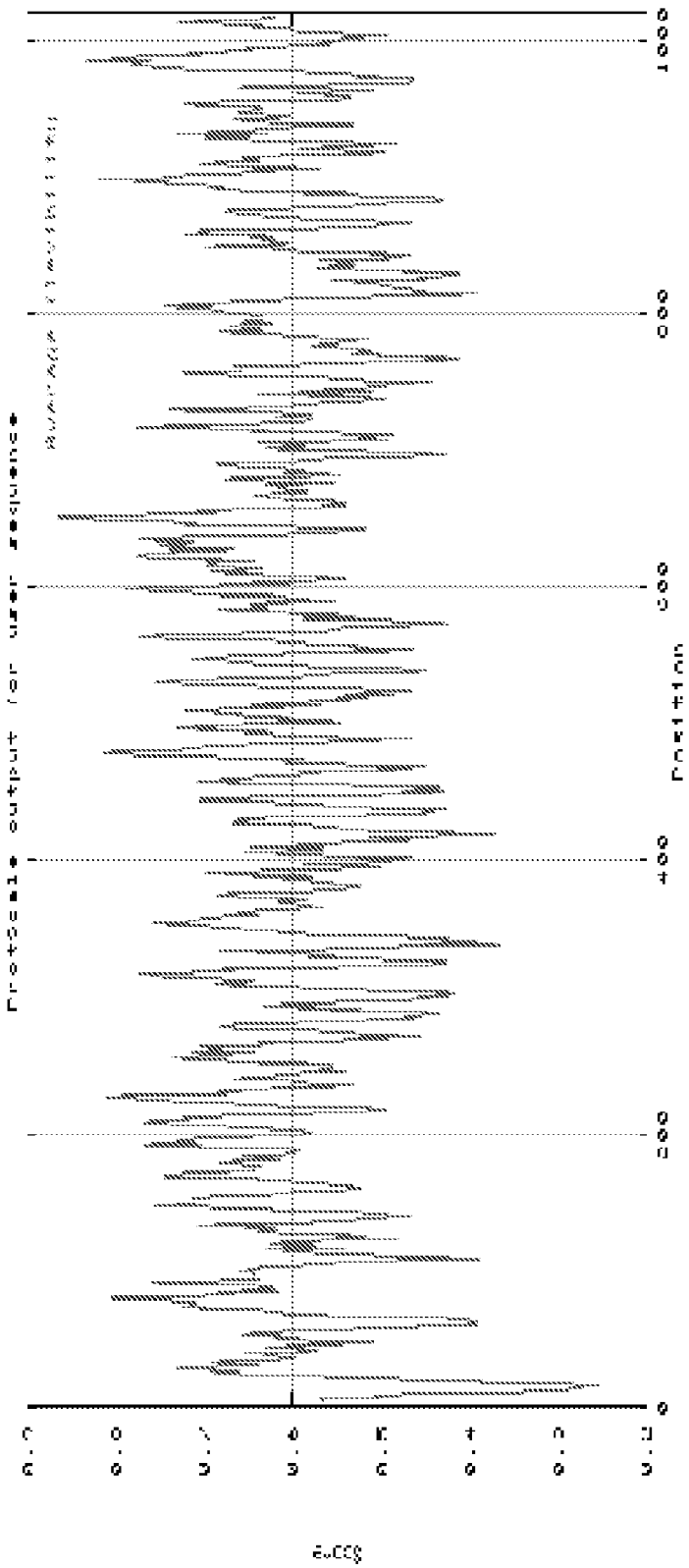
Figure 9A:
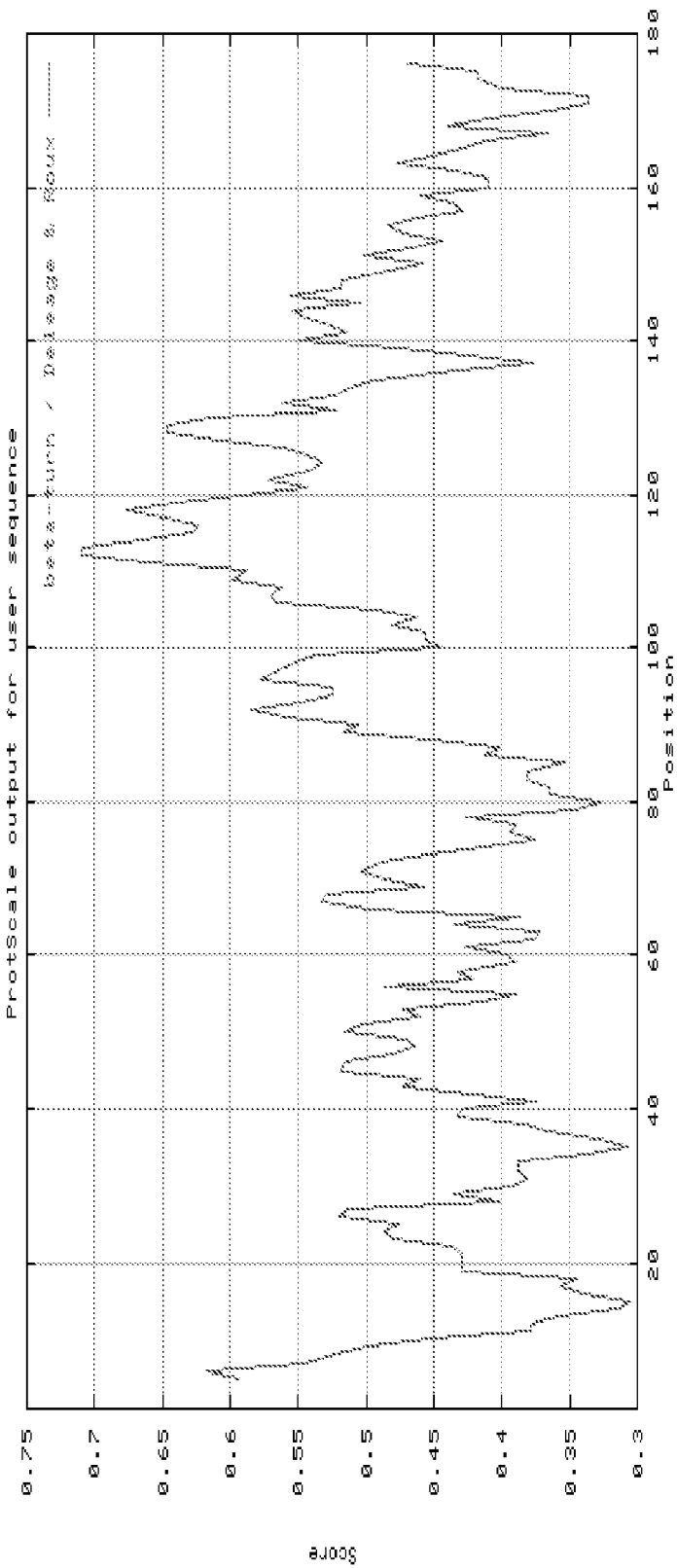
FIGS. 9A-9U. Beta-turn amino acid profile of the proteins set forth in FIG. 2 determined by computer algorithm sequence analysis using the method of Deleage and Roux (Deleage, G., Roux B. 1987 Protein Engineering 1:289-294).
Figure 9B:
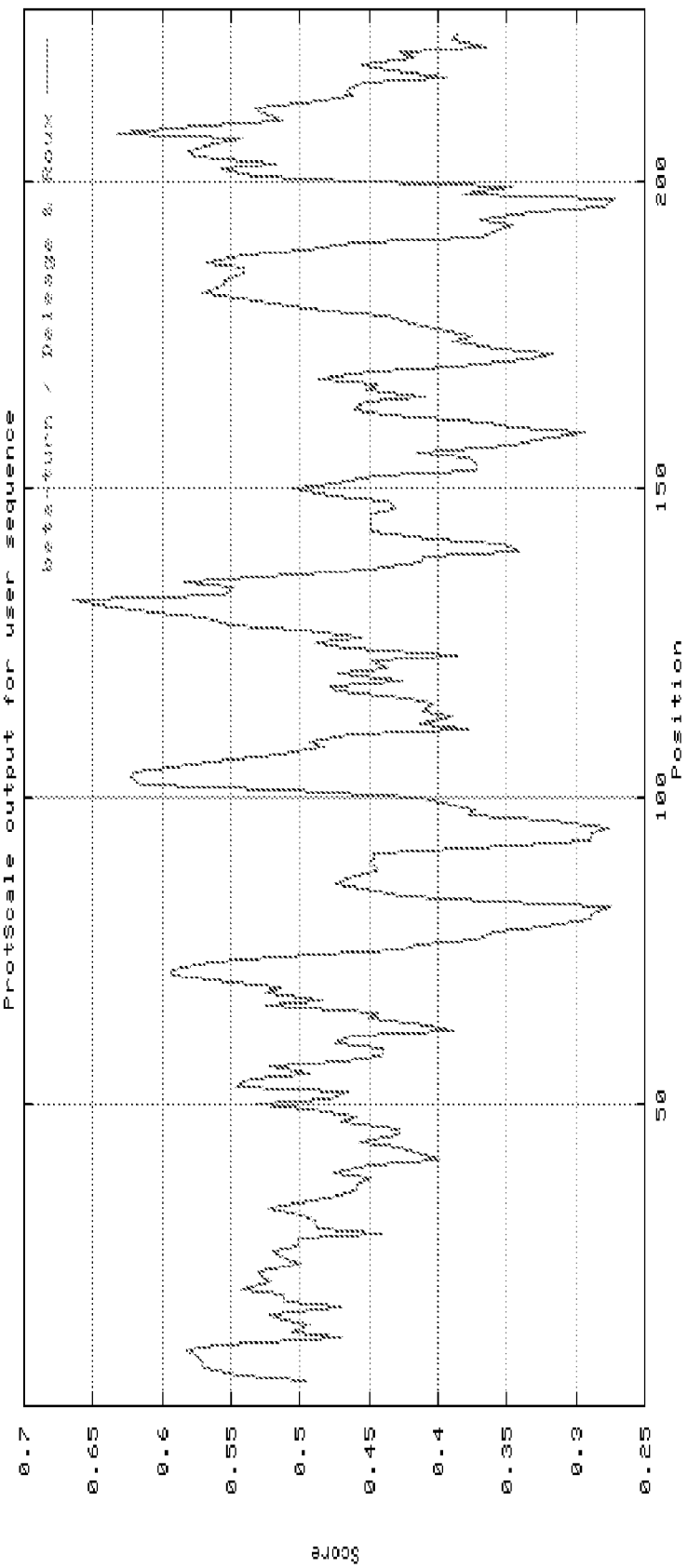
Figure 9D:
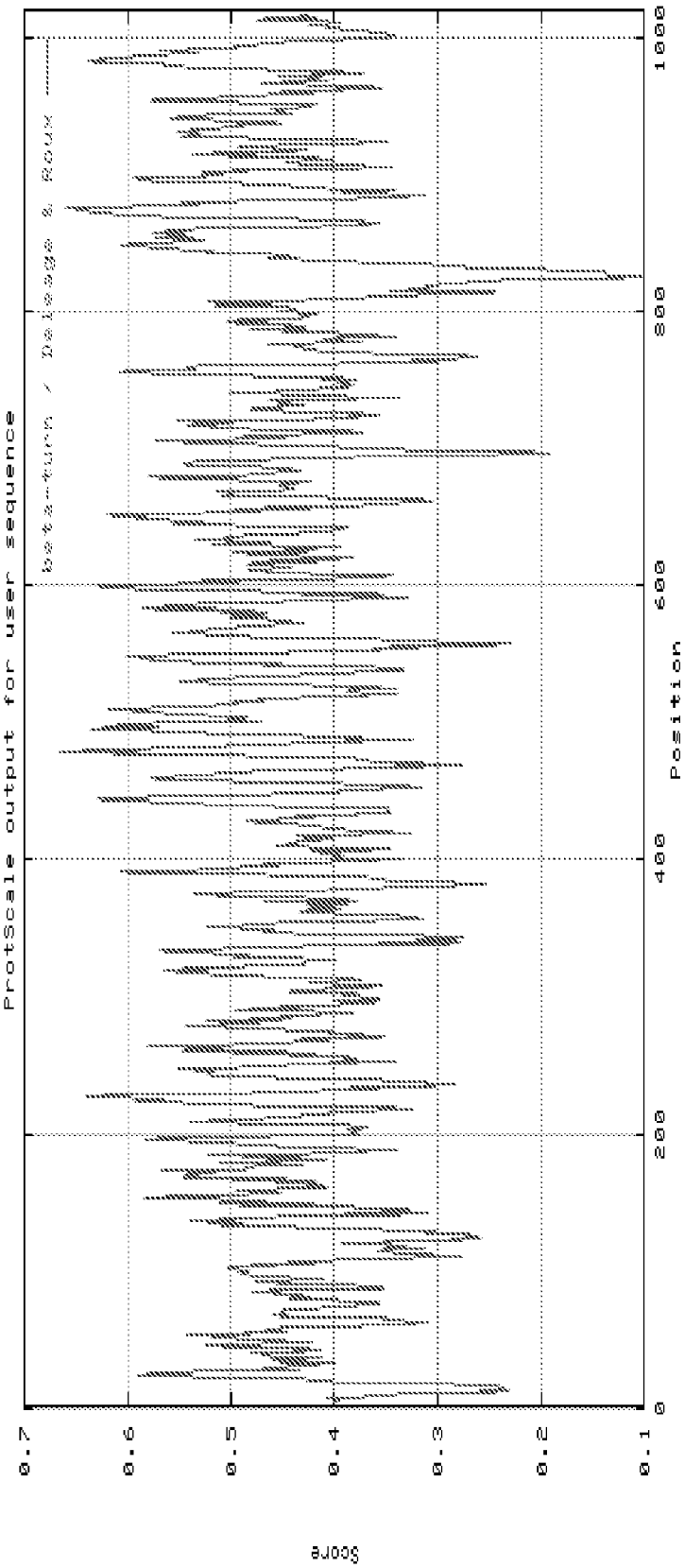

Embodiments of a FIG. 2 polynucleotide include: a FIG. 2 polynucleotide having the sequence shown in FIG. 2, the nucleotide sequence of the genes of FIG. 2 as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of the FIG. 2 nucleotides comprise, without limitation:

(1) a polynucleotide comprising, consisting essentially of, or consisting of a sequence as shown in FIG. 2, wherein T can also be U;

(2) a polynucleotide comprising, consisting essentially of, or consisting of a sequence as shown in FIG. 2, from the first nucleotide residue of a reading frame through the last nucleotide residue of that reading frame, optionally followed by a stop codon, wherein T can also be U;

(3) a polynucleotide comprising, consisting essentially of, or consisting of the sequence as shown in FIG. 2A.1, from nucleotide residue number 289 through nucleotide residue number 828, optionally followed by a stop codon, wherein T can also be U;

(4) a polynucleotide comprising, consisting essentially of, or consisting of the sequence as shown in FIG. 2A.2, from nucleotide residue number 756 through nucleotide residue number 1439, optionally followed by a stop codon, wherein T can also be U;

(5) a polynucleotide comprising, consisting essentially of, or consisting of the sequence as shown in FIG. 2B, from nucleotide residue number 25 through nucleotide residue number 4008, optionally followed by a stop codon, wherein T can also be U;

(6) a polynucleotide comprising, consisting essentially of, or consisting of the sequence as shown in FIG. 2C, from nucleotide residue number 846 through nucleotide residue number 3908, optionally followed by a stop codon, wherein T can also be U;

(7) a polynucleotide comprising, consisting essentially of, or consisting of the sequence as shown in FIG. 2D, from nucleotide residue number 103 through nucleotide residue number 900, optionally followed by a stop codon, wherein T can also be U;

(8) a polynucleotide comprising, consisting essentially of, or consisting of the sequence as shown in FIG. 2E, from nucleotide residue number 3 through nucleotide residue number 371, optionally followed by a stop codon, wherein T can also be U;

(9) a polynucleotide comprising, consisting essentially of, or consisting of the sequence as shown in FIG. 2F, from nucleotide residue number 250 through nucleotide residue number 1323, optionally followed by a stop codon, wherein T can also be U;

(10) a polynucleotide comprising, consisting essentially of, or consisting of the sequence as shown in FIG. 2G, from nucleotide residue number 24 through nucleotide residue number 599, optionally followed by a stop codon, wherein T can also be U;

(11) a polynucleotide comprising, consisting essentially of, or consisting of the sequence as shown in FIG. 2H, from nucleotide residue number 178 through nucleotide residue number 858, optionally followed by a stop codon, wherein T can also be U;

(12) a polynucleotide comprising, consisting essentially of, or consisting of the sequence as shown in FIG. 2I, from nucleotide residue number 1517 through nucleotide residue number 2188, optionally followed by a stop codon, wherein T can also be U;

(13) a polynucleotide comprising, consisting essentially of, or consisting of the sequence as shown in FIG. 2J, from nucleotide residue number 198 through nucleotide residue number 767, optionally followed by a stop codon, wherein T can also be U;

(14) a polynucleotide comprising, consisting essentially of, or consisting of the sequence as shown in FIG. 2K, from nucleotide residue number 72 through nucleotide residue number 1097, optionally followed by a stop codon, wherein T can also be U;

(15) a polynucleotide comprising, consisting essentially of, or consisting of the sequence as shown in FIG. 2L, from nucleotide residue number 118 through nucleotide residue number 1233, optionally followed by a stop codon, wherein T can also be U;

(16) a polynucleotide comprising, consisting essentially of, or consisting of the sequence as shown in FIG. 2M, from nucleotide residue number 14 through nucleotide residue number 2257, optionally followed by a stop codon, wherein T can also be U;

(17) a polynucleotide comprising, consisting essentially of, or consisting of the sequence as shown in FIG. 2N.1, from nucleotide residue number 140 through nucleotide residue number 4060, optionally followed by a stop codon, wherein T can also be U;

(18) a polynucleotide comprising, consisting essentially of, or consisting of the sequence as shown in FIG. 2N.2, from nucleotide residue number 140 through nucleotide residue number 3565, optionally followed by a stop codon, wherein T can also be U;

(19) a polynucleotide comprising, consisting essentially of, or consisting of the sequence as shown in FIG. 2N.3, from nucleotide residue number 140 through nucleotide residue number 4075, optionally followed by a stop codon, wherein T can also be U;

(20) a polynucleotide comprising, consisting essentially of, or consisting of the sequence as shown in FIG. 2(0), from nucleotide residue number 3 through nucleotide residue number 1655, optionally followed by a stop codon, wherein T can also be U;

(21) a polynucleotide comprising, consisting essentially of, or consisting of the sequence as shown in FIG. 2P, from nucleotide residue number 170 through nucleotide residue number 1459, optionally followed by a stop codon, wherein T can also be U;

(22) a polynucleotide comprising, consisting essentially of, or consisting of the sequence as shown in FIG. 2Q, from nucleotide residue number 60 through nucleotide residue number 1559, optionally followed by a stop codon, wherein T can also be U;

(23) a polynucleotide comprising, consisting essentially of, or consisting of the sequence as shown in FIG. 2R, from nucleotide residue number 84 through nucleotide residue number 938, optionally followed by a stop codon, wherein T can also be U;

(24) a polynucleotide that encodes a FIG. 2—related protein that is at least 90% homologous to an entire amino acid sequence shown in FIG. 2A-R;

(25) a polynucleotide that encodes a FIG. 2—related protein that is at least 90% identical to an entire amino acid sequence shown in FIG. 2A-R;

(26) a polynucleotide that encodes at least one peptide set forth in Tables V-XVIII, Table XX, or Tables XXIII to XXVI;

(27) a polynucleotide that encodes a peptide region of at least five amino acids of a peptide of FIG. 3 in any whole number increment up to the entire length of that protein, that includes an amino acid position having a value greater than 0.5 in the Hydrophilicity profile of FIG. 5 for that protein;

(28) a polynucleotide that encodes a peptide region of at least five amino acids of a peptide of FIG. 3 in any whole number increment up to the entire length of the protein, that includes an amino acid position having a value less than 0.5 in the Hydropathicity profile of FIG. 6 for that protein;

(29) a polynucleotide that encodes a peptide region of at least five amino acids of a peptide of FIG. 3 in any whole number increment up to the entire length of the protein, that includes an amino acid position having a value greater than 0.5 in the Percent Accessible Residues profile of FIG. 7 for that protein;

(30) a polynucleotide that encodes a peptide region of at least 5 amino acids of a peptide of FIG. 3 in any whole number increment up to the entire length of that protein, that includes an amino acid position having a value greater than 0.5 in the Average Flexibility profile of FIG. 8 for that protein;

(31) a polynucleotide that encodes a peptide region of at least 5 amino acids of a peptide of FIG. 3 in any whole number increment up to the entire length of the protein, that includes an amino acid position having a value greater than 0.5 in the Beta-turn profile of FIG. 9 for that protein;

(32) a polynucleotide that encodes a FIG. 2—related protein whose sequence is encoded by the cDNAs contained in the plasmid 74P3B3 that was deposited with American Type Culture Collection (ATCC) as Accession No. PTA-1892 on 19 May 2000;

(33) a polynucleotide that is fully complementary to a polynucleotide of any one of (1)-(32);

(34) a polynucleotide that selectively hybridizes under stringent conditions to a polynucleotide of (1) to (33);

(35) a peptide that is encoded by any of (1)-(32); and,

(36) a polynucleotide of any of (1)-(34) or peptide of (35) together with a pharmaceutical excipient and/or in a human unit dose form.

As used herein, a range is understood to specifically disclose all whole unit positions, i.e., integer positions, thereof.

Typical embodiments of the invention disclosed herein include the proteins of FIG. 2 polynucleotides that encode specific portions of the FIG. 2 mRNA sequences (and those which are complementary to such sequences) such as those that encode the proteins and/or fragments thereof, for example:

4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1025, 1050, 1075, 1100, 1125, 1150, 1175, 1200, etc., or more contiguous amino acids of a peptide of the invention.

For example, representative embodiments of the invention disclosed herein include: polynucleotides and their encoded peptides themselves encoding about amino acid 1 to about amino acid 10 of a FIG. 2 protein or variants thereof, polynucleotides encoding about amino acid 10 to about amino acid 20 of a FIG. 2 protein or variants thereof, polynucleotides encoding about amino acid 20 to about amino acid 30 of a FIG. 2 protein or variants thereof, polynucleotides encoding about amino acid 30 to about amino acid 40 of a FIG. 2 protein or variants thereof, polynucleotides encoding about amino acid 40 to about amino acid 50 of a FIG. 2 protein or variants thereof, polynucleotides encoding about amino acid 50 to about amino acid 60 of a FIG. 2 protein or variants thereof, polynucleotides encoding about amino acid 60 to about amino acid 70 of a FIG. 2 protein or variants thereof, polynucleotides encoding about amino acid 70 to about amino acid 80 of a FIG. 2 protein or variants thereof, polynucleotides encoding about amino acid 80 to about amino acid 90 of a FIG. 2 protein or variants thereof, polynucleotides encoding about amino acid 90 to about amino acid 100 of a FIG. 2 protein or variants thereof, or encoding regions from about amino acid 100 to amino acids later in the sequence, in increments of about 10 amino acids, ending at the carboxyl terminal amino acid of a protein of the invention, e.g. a protein set forth in FIG. 2 or FIG. 3. Accordingly polynucleotides encoding portions of the amino acid sequence (in increments of about 10 amino acids), of amino acids 100 through the carboxyl terminal amino acid of a FIG. 2 protein are embodiments of the invention. Wherein it is understood that each particular amino acid position discloses that position plus or minus five amino acid residues.

Polynucleotides encoding relatively long portions of a FIG. 2 protein are also within the scope of the invention. For example, polynucleotides encoding from about amino acid 1 (or 20 or 30 or 40 etc.) to about amino acid 20, (or 30, or 40 or 50 etc.) of a FIG. 2 protein or variants thereof can be generated by a variety of techniques well known in the art. These polynucleotide fragments can include any portion of gene of the invention as shown, e.g., in FIG. 2.

Additional illustrative embodiments of the invention disclosed herein include a protein of FIG. 2 polynucleotide fragments encoding one or more of the biological motifs contained within a FIG. 2 protein sequence or a variant sequence thereof, including one or more of the motif-bearing subsequences of a FIG. 2 protein or variant, e.g., set forth in Tables V-XVIII, Table XX, and/or Tables XXIII to XXVI. In another embodiment, typical polynucleotide fragments of the invention encode one or more of the regions of a FIG. 2 protein or variant thereof that exhibit homology to a known molecule. In another embodiment of the invention, typical polynucleotide fragments encode one or more of the FIG. 2 proteins or variants N-glycosylation sites, cAMP and cGMP-dependent protein kinase phosphorylation sites, casein kinase II phosphorylation sites or N-myristoylation site and amidation sites (see, e.g., Table XX).

II.A.) Uses Polynucleotides of the Invention

II.A.1.) Monitoring of Genetic Abnormalities

The polynucleotides of the preceding paragraphs have a number of different specific uses. The human genes set forth in FIG. 2 maps to the chromosomal locations set forth in Example 3. For example, because a FIG. 2 gene map to a particular chromosome, polynucleotides that encode different regions of the FIG. 2 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the FIG. 2 proteins provide new tools that can be used to delineate, with greater precision than previously possible, cytogenetic abnormalities in the chromosomal region that encodes the proteins set forth in FIG. 2 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as the genes set forth in FIG. 2 are shown to be highly expressed in cancers, the FIG. 2 polynucleotides are used in methods assessing the status of the FIG. 2 gene products in normal versus cancerous tissues. Typically, polynucleotides that encode specific regions of the FIG. 2 proteins are used to assess the presence of perturbations (such as deletions, insertions, point mutations, or alterations resulting in a loss of an antigen etc.) in specific regions of the FIG. 2 genes, such as regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of a gene set forth in FIG. 2. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the FIG. 2 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., a gene of FIG. 2. See for example, Jack Cohen, Oligodeoxynucleotides, Antisense Inhibitors of Gene Expression, CRC Press, 1989; and Synthesis 1:1-5 (1988). The FIG. 2 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112:1253-1254 (1990). Additionally, the FIG. 2 antisense oligonucleotides of the present invention include morpholino antisense oligonucleotides known in the art (see, e.g., Partridge et al., 1996, Antisense & Nucleic Acid Drug Development 6: 169-175).

The FIG. 2 antisense oligonucleotides of the present invention typically can be RNA or DNA that is complementary to and stably hybridizes with the first 100 5' codons or last 100 3' codons of a genomic sequence or the corresponding mRNA of the invention. Absolute complementarity is not required, although high degrees of complementarity are preferred. Use of an oligonucleotide complementary to this region allows for the selective hybridization to mRNA of the invention and not to mRNA specifying other regulatory subunits of protein kinase. In one embodiment, the FIG. 2 antisense oligonucleotides of the present invention are 15 to 30-mer fragments of the antisense DNA molecule that have a sequence that hybridizes to mRNA of the invention. Optionally, a FIG. 2 antisense oligonucleotide is a 30-mer oligonucleotide that is complementary to a region in the first 10 5' codons or last 10 3' codons of a gene set forth in FIG. 2. Alternatively, the antisense molecules are modified to employ ribozymes in the inhibition of expression of a gene set forth in FIG. 2, see, e.g., L. A. Couture & D. T. Stinchcomb; *Trends Genet* 12: 510-515 (1996).

II.A.3.) Primers and Primer Pairs

Further specific embodiments of the nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a FIG. 2 polynucleotide in a sample and as a means for detecting a cell expressing a FIG. 2 protein.

Examples of such probes include polynucleotides comprising all or part of a human gene set forth in FIG. 2. Examples of primer pairs capable of specifically amplifying an mRNA of the invention are also disclosed herein. As will be understood by the skilled artisan, a great many different primers and probes can be prepared based on the sequences provided herein and used effectively to amplify and/or detect an mRNA of the invention.

The FIG. 2 polynucleotides of the invention are useful for a variety of purposes, including but not limited to their use as probes and primers for the amplification and/or detection of the FIG. 2 gene(s), mRNA(s), or fragments thereof; as reagents for the diagnosis and/or prognosis of prostate cancer and other cancers; as coding sequences capable of directing the expression of a FIG. 2 polypeptide; as tools for modulating or inhibiting the expression of a FIG. 2 gene(s) and/or translation of a FIG. 2 transcript(s); and as therapeutic agents.

The present invention includes the use of any probe as described herein to identify and isolate a gene set forth in FIG. 2 or FIG. 2—related nucleic acid sequence of the invention from a naturally occurring source, such as humans or other mammals, as well as the isolated nucleic acid sequence per se, which would comprise all or most of the sequences found in the probe used.

II.A.4.) Isolation of Nucleic Acid Molecules that Encode Proteins of the Invention The cDNA sequences described herein, see, e.g., FIG. 2, enable the isolation of other polynucleotides encoding gene product(s) of the invention, as well as the isolation of polynucleotides encoding homologs of protein of FIG. 2, alternatively spliced isoforms, allelic variants, and mutant forms of agene product of a gene of the invention as well as polynucleotides that encode analogs of the FIG. 2—related proteins. Various molecular cloning methods that can be employed to isolate full length cDNAs encoding a FIG. 2 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing a FIG. 2 gene cDNA can be identified by probing with a labeled cDNA of FIG. 2 or a fragment thereof. For example, in one embodiment, a FIG. 2 cDNA or a portion thereof is synthesized and used as a probe to retrieve overlapping and full-length cDNAs corresponding to a gene set forth in FIG. 2. A gene set forth in FIG. 2 itself can be isolated by screening genomic DNA libraries, bacterial artificial chromosome libraries (BACs), yeast artificial chromosome libraries (YACs), and the like, with a respective gene in FIG. 2 DNA probe or primer.

II.A.5.) Recombinant Nucleic Acid Molecules and Host-Vector Systems

The invention also provides recombinant DNA or RNA molecules containing a polynucleotide, a fragment, analog or homologue thereof in accordance with the invention, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing polynucleotide (fragment, analog or homologue thereof) in accordance with the invention within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of a protein in FIG. 2 or a fragment, analog or homolog thereof can be used to generate FIG. 2 proteins or fragments thereof using any number of host-vector systems routinely used and widely known in the art.

A wide range of host-vector systems suitable for the expression of FIG. 2 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11: 1785). Using these expression vectors, proteins set forth in FIG. 2 can be expressed in several prostate cancer and non-prostate cell lines, including for example 293, 293T, rat-1, NIH 3T3 and TsuPr1. The host-vector systems of the invention are useful for the production of a FIG. 2 protein or fragment thereof. Such host-vector systems can be employed to study the functional properties of proteins set forth in FIG. 2 and of the proteins of FIG. 2 mutations or analogs.

Recombinant human proteins of the invention, e.g., set forth in FIG. 2, or an analog or homolog or fragment thereof can be produced by mammalian cells transfected with a construct containing a FIG. 2—related nucleotide. For example, 293T cells can be transfected with an expression plasmid encoding a protein of FIG. 2 or fragment, analog or homolog thereof, a FIG. 2—related protein is expressed in the 293T cells, and the recombinant protein of the invention is isolated using standard purification methods (e.g., affinity purification using antibodies of the invention, e.g., an antibody that specifically binds a protein of the invention such as one set forth in FIG. 2). In another embodiment, a FIG. 2 coding sequence is subcloned into the retroviral vector pSRαMSVtkneo and used to infect various mammalian cell lines, such as NIH 3T3, TsuPr1, 293 and rat-1 in order to establish cell lines that express a protein of the invention. Various other expression systems well known in the art can also be employed. Expression constructs encoding a leader peptide joined in frame to a FIG. 2 coding sequence can be used for the generation of a secreted form of recombinant FIG. 2 proteins.

As discussed herein, redundancy in the genetic code permits variation in the gene sequences set forth in FIG. 2. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) PROTEINS OF THE INVENTION

Another aspect of the present invention provides FIG. 2—related proteins, i.e., proteins of the invention. Specific embodiments of FIG. 2—related proteins comprise a polypeptide having all or part of the amino acid sequence of a human protein set forth in FIG. 2. Alternatively, embodiments of FIG. 2 proteins comprise variant, homolog or analog polypeptides that have alterations in their amino acid sequence relative to a protein set forth in FIG. 2.

In general, naturally occurring allelic variants of a protein set forth in FIG. 2 shares a high degree of structural identity and homology (e.g., 90% or more homology). Typically, allelic variants of a FIG. 2 protein contain conservative amino acid substitutions within the protein sequences set forth in FIG. 2 described herein or contain a substitution of an amino acid from a corresponding position in a homologue of a protein set forth in FIG. 2. One class of FIG. 2 allelic variants are proteins that share a high degree of homology with at least a small region of a particular FIG. 2 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270(20):11882-6).

Embodiments of the invention disclosed herein include a wide variety of art-accepted variants or analogs of FIG. 2 proteins such as polypeptides having amino acid insertions, deletions and substitutions. FIG. 2 variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis (Wells et al., *Philos. Trans. R. Soc. London SerA*, 317:415 (1986)) or other known techniques can be performed on the cloned DNA to produce variant DNA in accordance with the invention.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, FIG. 2 variants, analogs or homologs, have the distinguishing attribute of having at least one epitope that is "cross reactive" with a protein of FIG. 2. As used in this sentence, "cross reactive" means that an antibody or T cell that specifically binds to a FIG. 2 variant also specifically binds to a FIG. 2 protein having an amino acid sequence set forth in FIG. 3. A polypeptide ceases to be a variant of a protein shown in FIG. 3, when it no longer contains any epitope capable of being recognized by an antibody or T cell that specifically binds to the starting of a FIG. 2 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165 (12): 6949-6955; Hebbes et al., Mol Immunol (1989) 26(9): 865-73; Schwartz et al., J Immunol (1985) 135(4):2598-608.

Other classes of FIG. 2—related protein variants share 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more similarity, homology or identity with an amino acid sequence of FIG. 3, or a fragment thereof. Another specific class of FIG. 2 protein variants or analogs comprise one or more of the FIG. 2 biological motifs described herein (see, e.g., Table V or XVIII, Table XX, or Tables XXIII to XXVI) or presently known in the art. Thus, encompassed by the present invention are analogs of the proteins set forth in FIG. 2 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a protein shown in FIG. 2 or FIG. 3. For example, representative embodiments of the invention comprise peptides/proteins having any: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1025, 1050, 1075, 1100, 1125, 1150, 1175, 1200, etc., or more contiguous amino acids of a protein shown in FIG. 2 or FIG. 3.

Moreover, representative embodiments of the invention disclosed herein include polypeptides consisting of about amino acid 1 to about amino acid 10 of a FIG. 2 protein shown, polypeptides consisting of about amino acid 10 to about amino acid 20 of a FIG. 2 protein, polypeptides consisting of about amino acid 20 to about amino acid 30 of a FIG. 2 protein, polypeptides consisting of about amino acid 30 to about amino acid 40 of a FIG. 2 protein, polypeptides consisting of about amino acid 40 to about amino acid 50 of a FIG. 2 protein, polypeptides consisting of about amino acid 50 to about amino acid 60 of a FIG. 2 protein, polypeptides consisting of about amino acid 60 to about amino acid 70 of a FIG. 2 protein, polypeptides consisting of about amino acid 70 to about amino acid 80 of a FIG. 2 protein, polypeptides consisting of about amino acid 80 to about amino acid 90 of a FIG. 2 protein, polypeptides consisting of about amino acid 90 to about amino acid 100 of a FIG. 2 protein, etc. throughout the entirety of a protein set forth in FIG. 2 amino acid sequence. Moreover, polypeptides consisting of about amino acid 1 (or 20 or 30 or 40 etc.) to about amino acid 20, (or 130, or 140 or 150 etc.) of a FIG. 2 protein are embodiments of the invention. It is to be appreciated that the starting and stopping positions in this paragraph refer to the specified position as well as that position plus or minus 5 residues.

FIG. 2—related proteins are generated using standard peptide synthesis technology or using chemical cleavage methods well known in the art. Alternatively, recombinant methods can be used to generate nucleic acid molecules that encode a FIG. 2—related protein. In one embodiment, nucleic acid molecules provide a means to generate defined fragments of a FIG. 2 protein (or variants, homologs or analogs thereof).

III.A.) Motif-Bearing Protein Embodiments

Additional illustrative embodiments of the invention disclosed herein include polypeptides of the invention that comprise the amino acid residues of one or more of the biological motifs contained within a protein of FIG. 2 polypeptide sequence set forth in FIG. 2 or FIG. 3. Various motifs are known in the art, and a protein can be evaluated for the presence of such motifs by a number of publicly available Internet sites. Accordingly, see, e.g., the motif bearing subsequences of all FIG. 2 proteins set forth and identified in Tables V to XVIII, Table XX, Table XXI, and Tables XXIII to XXVI. Additionally, Table XIX sets forth several frequently occurring motifs based on pfam searches. The columns of Table VIII list (1) motif name abbreviation, (2) percent identity found amongst the different member of the motif family, (3) motif name or description and (4) most common function; location information is included if the motif is relevant for location.

Polypeptides comprising one or more of the motifs set forth in Tables V to XVIII, Table XX, Table XXI, and Tables XXIII to XXVI are useful in elucidating the specific characteristics of a malignant phenotype in view of the observation that the motifs discussed above are associated with growth dysregulation and because the proteins of FIG. 2 are overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables V-XVIII and XXIII to XXVI. CTL epitopes can be determined using specific algorithms to identify peptides within a FIG. 2 protein that are capable of optimally binding to specified HLA alleles. Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/ supermotifs of Table IV). The epitope is analoged by substituting out an amino acid at one of the specified positions, and replacing it with another amino acid specified for that position. For example, one can substitute out a deleterious residue in favor of any other residue, such as a preferred residue as defined in Table IV; substitute a less-preferred residue with a preferred residue as defined in Table IV; or substitute an originally-occurring preferred residue with another preferred residue as defined in Table IV. Substitutions can occur at primary anchor positions or at other positions in a peptide; see, e.g., Table IV.

A variety of references reflect the art regarding the identification and generation of epitopes in a protein of interest as well as analogs thereof. See, for example, WO 9733602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the inventions include polypeptides comprising combinations of the different motifs set forth in Table XIX; and/or, one or more of the predicted CTL epitopes of Tables V to XVIII, and/or, one or more of the predicted HTL epitopes of Tables XXIII to XXVI and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

FIG. 2—related proteins are embodied in many forms, preferably in isolated form. A purified FIG. 2 protein molecule will be substantially free of other proteins or molecules that impair the binding of a protein of FIG. 2 to an antibody, T cell or other ligand. The nature and degree of isolation and purification will depend on the intended use. Embodiments of FIG. 2—related proteins include purified FIG. 2—related proteins and functional, soluble FIG. 2—related proteins. In one embodiment, a functional, soluble FIG. 2 protein or fragment thereof retains the ability to be bound by an antibody, T cell or other ligand.

The invention also provides FIG. 2 proteins comprising biologically active fragments of a FIG. 2 amino acid sequence. Such proteins exhibit properties of the starting FIG. 2 protein, such as the ability to elicit the generation of antibodies that specifically bind an epitope associated with the starting FIG. 2 protein; to be bound by such antibodies; to elicit the activation of HTL or CTL; and/or, to be recognized by HTL or CTL that also specifically bind to the starting protein.

FIG. 2—related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific antibodies that bind to a protein of FIG. 2, or T cells or in identifying cellular factors that bind to a protein set forth in FIG. 2. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a FIG. 2 protein that are capable of optimally binding to specified HLA alleles. Illustrating this, peptide epitopes from the proteins set forth in FIG. 2 that are presented in the context of human MHC class I molecules HLA-A1, A2, A3, A11, A24, B7 and B35 were predicted (Tables V-XVIII). Specifically, the complete amino acid sequence of a FIG. 2 protein and relevant portions of other presented variants, i.e., for HLA Class I predictions 9 flanking residues on either side of a point mutation for 10-mers, and for HLA Class II predictions 14 flanking residues on either side of a point mutation for 15-mers, were entered into the HLA Peptide Motif Search algorithm; for HLA Class II SYFPEITHI was used for HTL epitopes of Tables XXIII to XXVI.

The HLA peptide motif search algorithm was developed by Dr. Ken Parker based on binding of specific peptide sequences in the groove of HLA Class I molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results from a complete protein sequence set forth in FIG. 2 that predicted binding peptides are shown in Tables V-XVII. In Tables V-XVIII, the top 50 ranking candidates, 9-mers and 10-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV are to be "applied" to a FIG. 2 protein in accordance with the invention. As used in this context "applied" means that a FIG. 2 protein is evaluated, e.g., visually or by computer-based patterns finding methods, as appreciated by those of skill in the relevant art. Every subsequence of a FIG. 2 protein of 8, 9, 10, or 11 amino acid residues that bears an HLA Class I motif, or a subsequence of 9 or more amino acid residues that bear an HLA Class II motif are within the scope of the invention.

III.B.) Expression of FIG. 2—Related Proteins

In an embodiment described in the examples that follow, the proteins set forth in FIG. 2 can be conveniently expressed in cells (such as 293T cells) transfected with a commercially available expression vector such as a CMV-driven expression vector encoding a protein of FIG. 2 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted FIG. 2 protein in transfected cells. A secreted HIS-tagged FIG. 2 protein in the culture media can be purified, e.g., using a nickel column using standard techniques.

III.C.) Modifications of FIG. 2—Related Proteins

Modifications of FIG. 2—related proteins such as covalent modifications are included within the scope of this invention. One type of covalent modification includes reacting targeted amino acid residues of a protein of FIG. 2 polypeptide with an organic derivatizing agent that is capable of reacting with selected side chains or the N- or C-terminal residues of a FIG. 2 protein. Another type of covalent modification to a protein of FIG. 2 polypeptide included within the scope of this invention comprises altering the native glycosylation pattern of a protein of the invention. Another type of covalent modification to a protein of FIG. 2 comprises linking a FIG. 2 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

FIG. 2—related proteins of the present invention can also be modified to form a chimeric molecule comprising a protein of FIG. 2 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a FIG. 2 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of a protein set forth in FIG. 2. A chimeric molecule can comprise a fusion of a FIG. 2—related protein with a polyhistidine epitope tag, which provides an epitope to which immobilized nickel can selectively bind, with cytokines or with growth factors. The epitope tag is generally placed at the amino- or carboxyl-terminus of a FIG. 2 protein. In an alternative embodiment, the chimeric molecule can comprise a fusion of a FIG. 2—related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a FIG. 2 polypeptide in place of at least one variable region within an Ig molecule. In a preferred embodiment, the immunoglobulin fusion includes the hinge, CH2 and CH3, or the hinge, CH1, CH2 and CH3 regions of an IgG1 molecule. For the production of immunoglobulin fusions see, e.g., U.S. Pat. No. 5,428,130 issued Jun. 27, 1995.

III.D.) Uses of FIG. 2—Related Proteins

The proteins of the invention have a number of different specific uses. As the proteins set forth in FIG. 2 are highly expressed in one or more cancers, FIG. 2—related proteins are used in methods that assess the status of FIG. 2 gene products in normal versus cancerous tissues, thereby elucidating the malignant phenotype. Typically, polypeptides from specific regions of a FIG. 2 protein are used to assess the presence of perturbations (such as deletions, insertions, point mutations etc.) in those regions (such as regions containing one or more motifs). Exemplary assays utilize antibodies or T cells targeting FIG. 2—related proteins comprising the amino acid residues of one or more of the biological motifs contained within a protein of FIG. 2 polypeptide sequence in order to evaluate the characteristics of this region in normal versus cancerous tissues or to elicit an immune response to the epitope. Alternatively, FIG. 2—related proteins that contain the amino acid residues of one or more of the biological motifs in a FIG. 2 protein are used to screen for factors that interact with that region of the respective protein set forth in FIG. 2.

FIG. 2 protein fragments/subsequences are particularly useful in generating and characterizing domain-specific antibodies (e.g., antibodies recognizing an extracellular or intracellular epitope of a FIG. 2 protein), for identifying agents or cellular factors that bind to a protein in FIG. 2 or a particular structural domain thereof, and in various therapeutic and diagnostic contexts, including but not limited to diagnostic assays, cancer vaccines and methods of preparing such vaccines.

Proteins encoded by a gene of the invention (e.g., a FIG. 2 gene, or analog, homolog or fragment thereof) have a variety of uses, including but not limited to generating antibodies and in methods for identifying ligands and other agents and cellular constituents that bind to a FIG. 2 gene product. Antibodies raised against a FIG. 2 protein or fragment thereof are useful in diagnostic and prognostic assays, and imaging methodologies in the management of human cancers characterized by expression of a FIG. 2 protein, such as those listed in Table I. Such antibodies can be expressed intracellularly and used in methods of treating patients with such cancers. FIG. 2—related nucleic acids or proteins are also used in generating HTL or CTL responses.

Various immunological assays useful for the detection of FIG. 2 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting cells that express a protein set forth in FIG. 2 (e.g., in radioscintigraphic imaging methods). FIG. 2 proteins are also particularly useful in generating cancer vaccines, as further described herein.

IV.) ANTIBODIES OF THE INVENTION

Another aspect of the invention provides antibodies that bind to FIG. 2—related proteins. Preferred antibodies specifically bind to a FIG. 2—related protein and do not bind (or bind weakly) to peptides or proteins that are not FIG. 2—related proteins. For example, antibodies that bind to proteins in FIG. 2 can bind to FIG. 2—related proteins such as the homologs or analogs thereof.

Antibodies of the invention are particularly useful in cancer (see, e.g., the cancers referred to in Table I) diagnostic and prognostic assays, and imaging methodologies. Similarly, such antibodies are useful in the treatment, diagnosis, and/or prognosis of other cancers, to the extent the genes and respective encoded proteins set forth in FIG. 2 are also expressed or overexpressed in these other cancers. Moreover, intracellularly expressed antibodies (e.g., single chain antibodies) are therapeutically useful in treating cancers in which the expression of a gene and encoded protein of FIG. 2 is involved, such as advanced or metastatic prostate cancers.

The invention also provides various immunological assays useful for the detection and quantification a protein of FIG. 2 and mutants thereof. Such assays can comprise one or more FIG. 2 antibodies capable of recognizing and binding a FIG. 2—related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting a cancer expressing a gene of the invention are also provided by the invention, including but not limited to radioscintigraphic imaging methods using labeled FIG. 2 antibodies. Such assays are clinically useful in the detection, monitoring, and prognosis of a gene of the invention-expressing cancer.

Antibodies of the invention are also used in methods for purifying a FIG. 2—related protein and for isolating proteins of the invention, e.g., FIG. 2 homologues and related molecules. For example, a method of purifying a FIG. 2—related protein comprises incubating a FIG. 2 antibody, which has been coupled to a solid matrix, with a lysate or other solution containing a FIG. 2—related protein under conditions that permit the antibody to bind to the FIG. 2—related protein; washing the solid matrix to eliminate impurities; and eluting the FIG. 2—related protein from the coupled antibody. Other uses of antibodies in accordance with the invention include generating anti-idiotypic antibodies that mimic a FIG. 2 protein.

Various methods for the preparation of antibodies are well known in the art. For example, antibodies can be prepared by immunizing a suitable mammalian host using a FIG. 2—related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins in accordance with the invention can also be used, such as a protein of FIG. 2 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a FIG. 2—related protein is synthesized and used as an immunogen.

In addition, naked DNA immunization techniques known in the art are used (with or without a purified FIG. 2—related protein or agene of FIG. 2—expressing cells) to generate an immune response to the encoded immunogen (for review, see Donnelly et al., 1997, Ann. Rev. Immunol. 15: 617-648).

The amino acid sequence of a FIG. 2 protein can be analyzed to select specific regions of the protein for generating antibodies. For example, hydrophobicity and hydrophilicity analyses of FIG. 2 amino acid sequences are used to identify hydrophilic regions in the protein. Regions of a FIG. 2 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Methods for the generation of antibodies in accordance with the invention are further illustrated by way of the Examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of protein immunogen is often conducted by injection over a suitable time period and with use of a suitable adjuvant, as is understood in the art. During the immunization schedule, titers of antibodies can be taken to determine adequacy of antibody formation.

Monoclonal antibodies of the invention can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a FIG. 2—related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a FIG. 2 protein can also be produced in the context of chimeric or complementarity-determining region (CDR) grafted antibodies of multiple species origin. Humanized or human antibodies that specifically bind to a proteins of FIG. 2 can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human monoclonal antibodies of the invention can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human monoclonal antibodies of the invention can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. No. 6,162,963 issued 19 Dec. 2000; U.S. Pat. No. 6,150,584 issued 12 Nov. 2000; and, U.S. Pat. No. 6,114,598 issued 5 Sep. 2000). This method avoids the in vitro manipulation required with phage display technology and efficiently produces high affinity authentic human antibodies.

Reactivity of antibodies of the invention with a FIG. 2—related protein can be established by a number of well known means, including Western blot, immunoprecipitation, ELISA, and FACS analyses using, as appropriate, FIG. 2—related proteins, or protein of FIG. 2—expressing cells or extracts thereof. An FIG. 2 antibody of the invention, or fragment thereof, can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more epitopes are generated using methods generally known in the art. Homodimeric antibodies can also be generated by cross-linking techniques known in the art (e.g., Wolff et al., Cancer Res. 53: 2560-2565).

V.) CELLULAR IMMUNE RESPONSES OF THE INVENTION

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317: 359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160: 3363, 1998; Rammensee, et al., *Immunogenetics* 41:178, 1995; Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al., *Cell* 74:929-937, 1993; Kondo et al., *J. Immunol.* 155: 4307-4312, 1995; Sidney et al., *J. Immunol.* 157:3480-3490, 1996; Sidney et al., *Human Immunol.* 45:79-93, 1996; Sette, A. and Sidney, *J. Immunogenetics* 1999 November; 50(3-4): 201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g. Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g. Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) TRANSGENIC ANIMALS OF THE INVENTION

Nucleic acids that encode a FIG. 2—related protein can also be used to generate either transgenic animals or "knock out" animals that, in turn, are useful in the development and screening of therapeutically useful reagents. In accordance with established techniques, cDNA encoding a protein of FIG. 2 can be used to clone genomic DNA that encodes a protein of FIG. 2. The cloned genomic sequences can then be used to generate transgenic animals containing cells that express DNA that encode a FIG. 2 protein. Methods for generating transgenic animals, particularly animals such as mice or rats, have become conventional in the art and are described, for example, in U.S. Pat. No. 4,736,866 issued 12 Apr. 1988, and U.S. Pat. No. 4,870,009 issued 26 Sep. 1989. Typically, particular cells would be targeted for a nucleic acid sequence of FIG. 2 transgene incorporation with tissue-specific enhancers.

Transgenic animals that include a copy of a transgene encoding a FIG. 2 protein can be used to examine the effect of increased expression of DNA that encodes the FIG. 2 protein. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of FIG. 2 proteins can be used to construct a FIG. 2 protein "knock out" animal that has a defective or altered gene encoding the FIG. 2 protein as a result of homologous recombination between the endogenous gene encoding the FIG. 2 protein and altered genomic DNA encoding the FIG. 2 protein, introduced into an embryonic cell of the animal. For example, cDNA that encodes a FIG. 2 protein can be used to clone genomic DNA encoding the FIG. 2 protein, in accordance with established techniques. A portion of the genomic DNA encoding a FIG. 2 protein can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a protein of FIG. 2.

VII.) METHODS FOR THE DETECTION OF A GENE OR PROTEIN OF THE INVENTION

Another aspect of the present invention relates to methods for detecting FIG. 2 polynucleotides and FIG. 2—related proteins, as well as methods for identifying a cell that expresses a gene set forth in FIG. 2. The expression profile of a gene or protein set forth in FIG. 2 makes it a diagnostic marker for metastasized disease. Accordingly, the status of FIG. 2 gene products provides information useful for predicting a variety of factors including susceptibility to advanced stage disease, rate of progression, and/or tumor aggressiveness. As discussed in detail herein, the status of FIG. 2 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of FIG. 2 polynucleotides in a biological sample, such as serum, bone, prostate, and other tissues, urine, semen, cell preparations, and the like. Detectable FIG. 2 polynucleotides include, for example, a FIG. 2 gene or fragment thereof, a FIG. 2 mRNA, alternative splice variants of FIG. 2 mRNAs, and recombinant DNA or RNA molecules that contain a FIG. 2 polynucleotide. A number of methods for amplifying and/or detecting the presence of FIG. 2 polynucleotides are well known in the art and can be employed in the practice of this aspect of the invention.

In one embodiment, a method for detecting an a FIG. 2 mRNA in a biological sample comprises producing cDNA from the sample by reverse transcription using at least one primer; amplifying the cDNA so produced using FIG. 2 polynucleotides as sense and antisense primers to amplify FIG. 2 cDNAs therein; and detecting the presence of the amplified FIG. 2 cDNA. Optionally, the sequence of the amplified FIG. 2 cDNA can be determined.

In another embodiment, a method of detecting a FIG. 2 gene in a biological sample comprises first isolating genomic DNA from the sample; amplifying the isolated genomic DNA using FIG. 2 polynucleotides as sense and antisense primers; and detecting the presence of the amplified FIG. 2 gene. Any number of appropriate sense and antisense probe combinations can be designed from a FIG. 2 nucleotide sequence and used for this purpose.

The invention also provides assays for detecting the presence of a FIG. 2 protein in a tissue or other biological sample such as serum, semen, bone, prostate, urine, cell preparations, and the like. Methods for detecting a FIG. 2—related protein are also well known and include, for example, immunoprecipitation, immunohistochemical analysis, Western blot analysis, molecular binding assays, ELISA, ELIFA and the like. For example, a method of detecting the presence of a FIG. 2—related protein in a biological sample comprises first contacting the sample with a FIG. 2 antibody, a FIG. 2—reactive fragment thereof, or a recombinant protein containing an antigen binding region of a FIG. 2 antibody; and then detecting the binding of a FIG. 2—related protein in the sample.

Methods for identifying a cell that expresses a gene of FIG. 2 are also within the scope of the invention. In one embodiment, an assay for identifying a cell that expresses a FIG. 2 gene comprises detecting the presence of a FIG. 2 mRNA in the cell. Methods for the detection of particular mRNAs in cells are well known and include, for example, hybridization assays using complementary DNA probes (such as in situ hybridization using labeled riboprobes to a gene of FIG. 2, Northern blot and related techniques) and various nucleic acid amplification assays (such as RT-PCR using complementary primers specific for genes of FIG. 2, and other amplification type detection methods, such as, for example, branched DNA, SISBA, TMA and the like). Alternatively, an assay for identifying a cell that expresses a FIG. 2 gene comprises detecting the presence of a FIG. 2—related protein in the cell or secreted by the cell. Various methods for the detection of proteins are well known in the art and are employed for the detection of FIG. 2—related proteins and cells that express FIG. 2—related proteins.

Expression analysis of FIG. 2 proteins is also useful as a tool for identifying and evaluating agents that modulate FIG. 2 gene expressions. For example, FIG. 2 gene expression is significantly upregulated in prostate cancer, and is expressed in cancers of the tissues listed in Table I. Identification of a molecule or biological agent that inhibits FIG. 2 gene expression or over-expression in cancer cells is of therapeutic value.

For example, such an agent can be identified by using a screen that quantifies a FIG. 2 gene expression by RT-PCR, nucleic acid hybridization or antibody binding.

VIII.) METHODS FOR MONITORING THE STATUS OF GENES AND PROTEINS OF THE INVENTION

Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant gene of FIG. 2 expression in cancers) allows for early detection of such aberrant physiology, before a pathologic state such as cancer has progressed to a stage that therapeutic options are more limited and or the prognosis is worse. In such examinations, the status of the genes and proteins in FIG. 2 in a biological sample of interest can be compared, for example, to the status of that gene and/or protein of FIG. 2 in a corresponding normal sample (e.g. a sample from that individual or alternatively another individual that is not affected by a pathology). An alteration in the status of a gene and/or protein of FIG. 2 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare the status of a gene or protein in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of gene of FIG. 2 expressing cells) as well as the level, and biological activity of expressed gene products (such as FIG. 2 mRNA, polynucleotides and polypeptides). Typically, an alteration in the status of a gene and/or protein of FIG. 2 comprises a change in the location of a protein FIG. 2 and/or cells that express a protein of FIG. 2 and/or an increase in FIG. 2 mRNA and/or protein expression.

The status in a sample of a gene or protein of FIG. 2 can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a FIG. 2 gene and gene product are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of a gene or protein in FIG. 2 in a biological sample is evaluated by various methods utilized by skilled artisans including, but not limited to genomic Southern analysis (to examine, for example perturbations in a FIG. 2 gene), Northern analysis and/or PCR analysis of FIG. 2 mRNA (to examine, for example alterations in the polynucleotide sequences or expression levels of FIG. 2 mRNAs), and, Western and/or immunohistochemical analysis (to examine, for example alterations in polypeptide sequences, alterations in polypeptide localization within a sample, alterations in expression levels of FIG. 2 proteins and/or associations of FIG. 2 proteins with polypeptide binding partners). Detectable FIG. 2 polynucleotides include, for example, a FIG. 2 gene or fragment thereof, a FIG. 2 mRNA, alternative splice variants, FIG. 2 mRNAs, and recombinant DNA or RNA molecules containing a FIG. 2 polynucleotide.

The expression profile of each gene of FIG. 2 makes it a diagnostic marker for local and/or metastasized disease, and provides information on the growth or oncogenic potential of a biological sample. In particular, the status of a gene or protein of FIG. 2 provides information useful for predicting susceptibility to particular disease stages, progression, and/or tumor aggressiveness. The invention provides methods and assays for determining the expression or mutational status of a gene of FIG. 2 and diagnosing cancers that express a gene of FIG. 2, such as cancers of the tissues listed in Table I. For example, because each gene of FIG. 2 mRNA is highly expressed in cancers relative to normal tissue, assays that evaluate the levels of FIG. 2 mRNA transcripts or proteins in a biological sample are used to diagnose a disease associated with dysregulation of a gene set forth in FIG. 2, and can provide prognostic information useful in defining appropriate therapeutic options.

The expression status of the genes and proteins set forth in FIG. 2 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of these genes and proteins in biological samples such as those from individuals suffering from, or suspected of suffering from a pathology characterized by dysregulated cellular growth, such as cancer.

As described above, the status of the genes and proteins in FIG. 2 in a biological sample can be examined by a number of well-known procedures in the art. For example, the status of the genes and proteins in FIG. 2 in a biological sample taken from a specific location in the body can be examined by evaluating the sample for the presence or absence of a FIG. 2 protein expressing cells (e.g. those that express FIG. 2 mRNAs or proteins). This examination can provide evidence of dysregulated cellular growth, for example, when FIG. 2 protein-expressing cells are found in a biological sample that does not normally contain such cells (such as a lymph node), because such alterations in the status of the genes and proteins in FIG. 2 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000); Su et al., Semin. Surg. Oncol. 18(1): 17-28 (2000) and Freeman et al., J Urol 1995 August 154(2 Pt 1):474-8).

In one aspect, the invention provides methods for monitoring FIG. 2 gene products by determining the status of FIG. 2 gene products expressed by cells from an individual suspected of having a disease associated with dysregulated cell growth (such as hyperplasia or cancer) and then comparing the status so determined to the status of FIG. 2 gene products in a corresponding normal sample. The presence of aberrant FIG. 2 gene products in the test sample relative to the normal sample provides an indication of the presence of dysregulated cell growth within the cells of the individual.

In another aspect, the invention provides assays useful in determining the presence of cancer in an individual, comprising detecting a significant increase in FIG. 2 mRNA or protein expression in a test cell or tissue sample relative to expression levels in the corresponding normal cell or tissue. The presence of FIG. 2 mRNA can, for example, be evaluated in tissue samples including but not limited to those listed in Table I. The presence of significant FIG. 2 protein expression or overexpression in any of these tissues is useful to indicate the emergence, presence and/or severity of a cancer, where the corresponding normal tissues do not express FIG. 2 mRNA or express it at lower levels.

In a related embodiment, the genes and proteins in FIG. 2 status is determined at the protein level rather than at the nucleic acid level. For example, such a method comprises determining the level of a FIG. 2 protein expressed by cells in a test tissue sample and comparing the level so determined to the level of a FIG. 2 protein expressed in a corresponding normal sample. In one embodiment, the presence of a FIG. 2 protein is evaluated, for example, using immunohistochemical methods. Antibodies of the invention or binding partners capable of detecting a FIG. 2 protein expression are used in a variety of assay formats well known in the art for this purpose.

In a further embodiment, one can evaluate the status of FIG. 2 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of a FIG. 2 gene can indicate the presence or promotion of a tumor. Such assays therefore have diagnostic and predictive value where a mutation in a FIG. 2 gene indicates a potential loss of function or increase in tumor growth.

A wide variety of assays for observing perturbations in nucleotide and amino acid sequences are well known in the art. For example, the size and structure of nucleic acid or amino acid sequences of FIG. 2, or the gene products of one of these genes are observed by the Northern, Southern, Western, PCR and DNA sequencing protocols as discussed herein. In addition, other methods for observing perturbations in nucleotide and amino acid sequences such as single strand conformation polymorphism analysis are well known in the art (see, e.g., U.S. Pat. No. 5,382,510 issued 7 Sep. 1999, and U.S. Pat. No. 5,952,170 issued 17 Jan. 1995).

Additionally, one can examine the methylation status of a FIG. 2 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al eds., 1995.

Gene amplification is an additional method for assessing the status of a FIG. 2 gene. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect expression of a gene of FIG. 2. The presence of RT-PCR amplifiable FIG. 2 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting FIG. 2 mRNA or a protein of the invention in a tissue sample, its presence indicating susceptibility to cancer, wherein the degree of FIG. 2 mRNA expression correlates to the degree of susceptibility. In a specific embodiment, the presence of a protein of the invention in, e.g., prostate tissue is examined, with the presence of a protein of FIG. 2 in the sample providing an indication of prostate cancer susceptibility (or the emergence or existence of a prostate tumor). Similarly, one can evaluate the integrity a gene in FIG. 2 nucleotide and amino acid sequences in a biological sample, in order to identify perturbations in the structure of these molecules such as insertions, deletions, substitutions and the like. The presence of one or more perturbations in genes or gene products of the invention in the sample is an indication of cancer susceptibility (or the emergence or existence of a tumor).

The invention also comprises methods for gauging tumor aggressiveness. In one embodiment, a method for gauging aggressiveness of a tumor comprises determining the level of FIG. 2 mRNA or a FIG. 2 protein expressed by tumor cells, comparing the level so determined to the level of FIG. 2 mRNA or a FIG. 2 protein expressed in a corresponding normal tissue taken from the same individual or a normal tissue reference sample, wherein the degree of FIG. 2 mRNA or a FIG. 2 protein expression in the tumor sample relative to the normal sample indicates the degree of aggressiveness. In a specific embodiment, aggressiveness of a tumor is evaluated by determining the extent to which a gene of FIG. 2 is expressed in the tumor cells, with higher expression levels indicating more aggressive tumors. Another embodiment is the evaluation of the integrity of FIG. 2 nucleotide and/or amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of FIG. 2 mRNA or a FIG. 2 protein expressed by cells in a sample of the tumor, comparing the level so determined to the level of FIG. 2 mRNA or a FIG. 2 protein expressed in an equivalent tissue sample taken from the same individual at a different time, wherein the degree of FIG. 2 mRNA or a FIG. 2 protein expression in the tumor sample over time provides information on the progression of the cancer. In a specific embodiment, the progression of a cancer is evaluated by determining FIG. 2 gene or protein expression in the tumor cells over time, where increased expression over time indicates a progression of the cancer. Also, one can evaluate the integrity of FIG. 2 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of a FIG. 2 gene and/or FIG. 2 gene products (or perturbations in a FIG. 2 gene and/or FIG. 2 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer, etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of a FIG. 2 gene and/or FIG. 2 gene products (or perturbations in a FIG. 2 gene and/or FIG. 2 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of a FIG. 2 gene and FIG. 2 gene products (or perturbations in a FIG. 2 gene and/or FIG. 2 gene products) and another factor associated with malignancy entails detecting the overexpression of FIG. 2 mRNA and/or protein in a tissue sample; detecting the overexpression of PSA mRNA or protein in a tissue sample (or PSCA or PSM expression, etc.), and observing a coincidence of FIG. 2 mRNA and/or protein and PSA mRNA or protein overexpression (or PSCA or PSM expression). In a specific embodiment, the expression of a gene of FIG. 2 and PSA mRNA in prostate tissue is examined, where the coincidence of a FIG. 2 gene and PSA mRNA overexpression in the sample indicates the existence of prostate cancer, prostate cancer susceptibility or the emergence or status of a prostate tumor.

Methods for detecting and quantifying the expression of FIG. 2 mRNA or protein are described herein, and standard nucleic acid and protein detection and quantification technologies are well known in the art. Standard methods for the detection and quantification of FIG. 2 mRNA include in situ hybridization using labeled FIG. 2 gene riboprobes, Northern blot and related techniques using FIG. 2 polynucleotide probes, RT-PCR analysis using primers specific for FIG. 2 genes, and other amplification type detection methods, such as, for example, branched DNA, SISBA, TMA and the like. In a specific embodiment, semi-quantitative RT-PCR is used to detect and quantify FIG. 2 mRNA expression. Any number of primers capable of amplifying a FIG. 2 gene can be used for this purpose, including but not limited to the various primer sets specifically described herein. In a specific embodiment, polyclonal or monoclonal antibodies specifically reactive with a wild-type FIG. 2 protein can be used in an immunohistochemical assay of biopsied tissue.

IX.) IDENTIFICATION OF MOLECULES THAT INTERACT WITH PROTEINS OF FIG. 2

The FIG. 2 protein and nucleic acid sequences disclosed herein allow a skilled artisan to identify proteins, small molecules and other agents that interact with the genes or proteins in FIG. 2, as well as pathways activated by genes or proteins in FIG. 2 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued 21 Sep. 1999, U.S. Pat. No. 5,925, 523 issued 20 Jul. 1999, U.S. Pat. No. 5,846,722 issued 8 Dec. 1998 and U.S. Pat. No. 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with a protein sequence of the invention, e.g., a protein of FIG. 2. In such methods, peptides that bind to FIG. 2 proteins are identified by screening libraries that encode a random or controlled collection of amino acids. Peptides encoded by the libraries are expressed as fusion proteins of bacteriophage coat proteins, the bacteriophage particles are then screened against a FIG. 2 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with FIG. 2 protein sequences are disclosed for example in U.S. Pat. No. 5,723,286 issued 3 Mar. 1998 and U.S. Pat. No. 5,733,731 issued 31 Mar. 1998.

Alternatively, cell lines that express a protein of FIG. 2 are used to identify protein-protein interactions mediated by the respective proteins of FIG. 2. Such interactions can be examined using immunoprecipitation techniques (see, e.g., Hamilton B. J., et al. Biochem. Biophys. Res. Commun. 1999, 261:646-51). FIG. 2 proteins can be immunoprecipitated from the respective proteins of FIG. 2—expressing cell line using antibodies of the invention that specifically bind that protein. Alternatively, antibodies against His-tag can be used in a cell line engineered to express fusions of a protein of FIG. 2 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with the genes and proteins in FIG. 2 can be identified through related embodiments of such screening assays. For example, small molecules can be identified that interfere with protein function, including molecules that interfere with protein of the invention's ability to mediate phosphorylation and de-phosphorylation, interaction with DNA or RNA molecules as an indication of regulation of cell cycles, second messenger signaling or tumorigenesis. Similarly, small molecules that modulate a proteins of FIG. 2—related ion channel, protein pump, or cell communication functions are identified and used to treat patients that have a cancer that expresses a FIG. 2 gene (see, e.g., Hille, B., Ionic Channels of Excitable Membranes $2^{nd}$ Ed., Sinauer Assoc., Sunderland, Mass., 1992). Moreover, ligands that regulate the function of a protein of the invention can be identified based on their ability to bind proteins of the invention and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of a FIG. 2 protein and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators which activate or inhibit a protein of the invention.

An embodiment of the invention comprises a method of screening for a molecule that interacts with a protein of the invention, e.g., an amino acid sequence shown in FIG. 2 or FIG. 3, comprising the steps of contacting a population of molecules with a FIG. 2 amino acid sequence, allowing the population of molecules and the FIG. 2 amino acid sequence to interact under conditions that facilitate an interaction, determining the presence of a molecule that interacts with the FIG. 2 amino acid sequence, and then separating molecules that do not interact with the FIG. 2 amino acid sequence from molecules that do. In a specific embodiment, the method further comprises purifying, characterizing and identifying a molecule that interacts with the FIG. 2 amino acid sequence. The identified molecule can be used to modulate a function performed by a protein of the invention. In a preferred embodiment, the protein in FIG. 2 amino acid sequence is contacted with a library of peptides.

X.) THERAPEUTIC METHODS AND COMPOSITIONS

The identification of a FIG. 2 as a protein that is normally expressed in a restricted set of tissues, but which is also expressed in certain cancers, opens a number of therapeutic approaches to the treatment of such cancers. As contemplated herein, the genes and proteins in FIG. 2 function as a transcription factor involved in activating tumor-promoting genes or repressing genes that block tumorigenesis.

Accordingly, therapeutic approaches that inhibit the activity of a FIG. 2 protein are useful for patients suffering from a cancer that expresses a gene of FIG. 2. These therapeutic approaches generally fall into two classes. One class comprises various methods for inhibiting the binding or association of a FIG. 2 protein with its binding partner or with other proteins. Another class comprises a variety of methods for inhibiting the transcription of a FIG. 2 gene or translation of FIG. 2 mRNA.

X.A.) Anti-Cancer Vaccines

The invention provides cancer vaccines comprising a FIG. 2—related protein or a FIG. 2—related nucleic acid. In view of the expression of a FIG. 2 protein, cancer vaccines prevent and/or treat genes of FIG. 2—expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a FIG. 2—related protein, or a nucleic acid sequence that encodes a FIG. 2—related protein and recombinant vectors capable of expressing and presenting immunogen of the invention (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3):123-32) Briefly, such methods of generating an immune response (e.g. humoral and/or cell-mediated) in a mammal, comprise the steps of: exposing the mammal's immune system to an immunoreactive epitope (e.g. an epitope present in a protein of the invention, e.g., shown in FIG. 3 or analog or homolog thereof) so that the mammal generates an immune response that is specific for that epitope (e.g. generates antibodies that specifically recognize that epitope). In a preferred method, an immunogen contains a biological motif, see e.g., Tables V-XVIII, Tables XXIII to XXVI; or a peptide of a size range from a protein in FIG. 2 indicated in FIG. 5, FIG. 6, FIG. 7, FIG. 8, and/or FIG. 9.

The entire FIG. 2 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with a protein of FIG. 2—associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within a FIG. 2 protein that bind corresponding HLA alleles. In a preferred embodiment, an of the invention contains one or more amino acid sequences identified using techniques well known in the art, such as the sequences shown in Tables V-XVIII or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule, as a convention 15-mer peptides that bind to HLA class II alleles are generally presented (see, e.g., Tables XXIII to XXVI). Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a FIG. 2 protein) so that an immune response is generated. A typical embodiment consists of a method for generating an immune response to a protein in FIG. 2 in a host, by contacting the host with a sufficient amount of at least one protein in FIG. 2 B cell or cytotoxic T-cell epitope or analog thereof; and at least one periodic interval thereafter re-contacting the host with the B cell or cytotoxic T-cell epitope or analog thereof. A specific embodiment consists of a method of generating an immune response against a FIG. 2—related protein or a man-made multiepitopic peptide comprising: administering an immunogen of the invention (e.g. a FIG. 2 protein or a peptide fragment thereof, an FIG. 2 fusion protein or analog etc.) in a vaccine preparation to a human or another mammal. Typically, such vaccine preparations further contain a suitable adjuvant (see, e.g., U.S. Pat. No. 6,146, 635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against an immunogen of the invention by: administering in vivo to muscle or skin of the individual's body a DNA molecule that comprises a DNA sequence that encodes an immunogen of the invention, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics a protein set forth in FIG. 2, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing FIG. 2 proteins. Constructs comprising DNA encoding a FIG. 2—related protein/immunogen and appropriate regulatory sequences can be injected directly into muscle or skin of an individual, such that the cells of the muscle or skin take-up the construct and express the encoded FIG. 2 protein/immunogen. Alternatively, a vaccine comprises a FIG. 2—related protein. Expression of the FIG. 2—related protein immunogen results in the generation of prophylactic or therapeutic humoral and cellular immunity against cells that bear the FIG. 2—related protein. Various prophylactic and therapeutic genetic immunization techniques known in the art can be used. Nucleic acid-based delivery is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. *J. Natl. Cancer Inst.* 87:982-990 (1995)). Non-viral delivery systems can also be employed by introducing naked DNA encoding a FIG. 2—related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a FIG. 2—related nucleic acid molecule. In one embodiment, the full-length human gene of FIG. 2 cDNA is employed. In another embodiment, FIG. 2 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present antigen of the invention to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present peptide immunogens of the invention to T cells in the context of MHC class I or II molecules. In one embodiment, autologous dendritic cells are pulsed with immunogenic peptides capable of binding to MHC class I and/or class II molecules. In another embodiment, dendritic cells are pulsed with the complete FIG. 2 protein. Yet another embodiment involves engineering the overexpression of a FIG. 2 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186:1177-1182). Cells that express proteins of the invention can also be engineered to express immune modulators, such as GM-CSF, and used as immunizing agents.

X.B.) A Protein of FIG. 2 as a Target for Antibody-Based Therapy

Proteins of the invention, e.g. FIG. 2, are attractive targets for antibody-based therapeutic strategies. A number of antibody strategies are known in the art for targeting both extracellular and intracellular molecules (see, e.g., complement and ADCC mediated killing as well as the use of intrabodies). Because of the expression profiles of the proteins set forth in FIG. 2, e.g., expressed by cancer cells of various lineages at higher levels compared to corresponding normal cells, systemic administration of proteins in FIG. 2—immunoreactive compositions are prepared that exhibit excellent sensitivity without toxic, non-specific and/or non-target effects caused by binding of the immunoreactive composition to non-target organs and tissues. Antibodies specifically reactive with domains of FIG. 2 proteins are useful to systemically treat cancers that express a protein of FIG. 2, either as conjugates with a toxin or therapeutic agent, or as naked antibodies capable of inhibiting cell proliferation or function.

Antibodies of the invention can be introduced into a patient such that the antibody binds to a protein of the invention and modulate a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of proteins of the invention, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a protein of the invention such as a protein sequence shown in FIG. 2 or FIG. 3. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. a protein of FIG. 2), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an antibody that specifically binds a protein of FIG. 2) that binds to a marker (e.g. a protein of FIG. 2) expressed, accessible to binding or localized on the cell surfaces. A typical embodiment is a method of delivering a cytotoxic and/or therapeutic agent to a cell expressing a FIG. 2 protein, comprising conjugating the cytotoxic agent to an antibody that immunospecifically binds to a protein in FIG. 2 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using antibodies o the invention can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, antibodies of the invention can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although antibody therapy directed to a protein of the invention is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of expression of a gene of FIG. 2, preferably using immunohistochemical assessments of tumor tissue, quantitative imaging of a protein of the invention, or other techniques that reliably indicate the presence and degree of a FIG. 2 protein expression. Immunohistochemical analysis of tumor biopsies or surgical specimens is preferred for this purpose. Methods for immunohistochemical analysis of tumor tissues are well known in the art.

Monoclonal antibodies of the invention that treat cancers (e.g., of a tissue of Table I) include those that initiate a potent immune response against the tumor or those that are directly cytotoxic. In this regard, monoclonal antibodies (mAbs) of the invention can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, mAbs of the invention that exert a direct biological effect on tumor growth are useful to treat cancers that express proteins in FIG. 2. Mechanisms by which directly cytotoxic mAbs act include: inhibition of cell growth, modulation of cellular differentiation, modulation of tumor angiogenesis factor profiles, and the induction of apoptosis. The mechanism(s) by which a particular mAbs of the invention exert an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target of proteins in FIG. 2 antigens with high affinity but exhibit low or no antigenicity in the patient.

Therapeutic methods of the invention contemplate the administration of single mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, mAbs of the invention can be administered concomitantly with other therapeutic modalities, including but not limited to various chemotherapeutic agents, androgen-blockers, immune modulators (e.g., IL-2, GM-CSF), surgery or radiation. The mAbs of the invention are administered in their "naked" or unconjugated form, or can have a therapeutic agent(s) conjugated to them.

Antibody formulations of the invention are administered via any route capable of delivering the antibodies to a tumor cell. Routes of administration include, but are not limited to, intravenous, intraperitoneal, intramuscular, intratumor, intradermal, and the like. Treatment generally involves repeated administration of an antibody preparation of the invention, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of expression of the protein of the invention in the patient, the extent of circulating shed protein of the invention, the desired steady-state antibody concentration level, frequency of treatment, and the influence of chemotherapeutic or other agents used in combination with the treatment method of the invention, as well as the health status of a particular patient.

Optionally, patients should be evaluated for the levels of a protein of the invention in a given sample (e.g. the levels of circulating FIG. 2 protein antigen and/or proteins of FIG. 2—expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic antibodies of the invention can also be used in anti-cancer therapy as a vaccine for inducing an immune response to cells that express a FIG. 2—related protein. In particular, the generation of anti-idiotypic antibodies is well known in the art; this methodology can readily be adapted to generate anti-idiotypic anti-protein of FIG. 2 antibodies that mimic an epitope on a FIG. 2—related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) A Protein of FIG. 2 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis *J. Immunol.* 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress an antigen of a protein of FIG. 2, or the host derives at least some therapeutic benefit when the antigen was tumor-associated.

In some embodiments, it may be desirable to combine the class I peptide components with components that induce or facilitate neutralizing antibody and/or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived from a protein of the invention, the PADRE® universal helper T cell epitope (or multiple HTL epitopes from a protein of the invention), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves: 1.) to generate a CTL response; and, 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 (QYIKANSKFIGITE; SEQ ID NO: 174), *Plasmodium falciparum* circumsporozoite (CS) protein at positions 378-398 (DIEKKIAKMEKASSVFNVVNS; SEQ ID NO: 175), and *Streptococcus* 18 kD protein at positions 116-131 (GAVDSILGGVATYGAA; SEQ ID NO: 176). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 177), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g. incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinyl-seryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to specifically prime an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/ IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to a protein of FIG. 2. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses a protein of FIG. 2.

X.D. Adoptive Immunotherapy

Antigenic peptides of the invention, e.g., peptides derived from a protein of FIG. 2, are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses a FIG. 2 protein. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses a protein of FIG. 2. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of a protein of FIG. 2—associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses a protein of FIG. 2, a vaccine comprising CTLs specific for the respective protein of FIG. 2 may be more efficacious in killing tumor cells in patient with advanced disease than alternative embodiments.

It is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosages for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., *Remington's Pharmaceutical Sciences*, 17$^{th}$ Edition, A. Gennaro, Editor, Mack Publishing Co., Easton, Pa., 1985). For example a peptide dose for initial immunization can be from about 1 to about 50,000 µg, generally 100-5,000 µg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of 5-10$^7$ to 5×10$^9$ pfu.

For antibodies, a treatment generally involves repeated administration of the antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-FIG. 2 protein mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of expression of the protein of the invention in the patient, the extent of circulating shed of protein of the invention antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg m$^2$ of body area weekly; 1-600 mg m$^2$ of body area weekly; 225-400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) DIAGNOSTIC AND PROGNOSTIC EMBODIMENTS OF THE INVENTION

As disclosed herein, polynucleotides, polypeptides, reactive cytotoxic T cells (CTL), reactive helper T cells (HTL) and anti-polypeptide antibodies of the invention are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in Example 4).

Proteins of FIG. 2 can be analogized to the prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640(1999)). A variety of other diagnostic markers are also used in similar contexts including p53 and K-ras (see, e.g., Tulchinsky et al., Int J Mol Med 1999 July 4(1):99-102 and Minimoto et al., Cancer Detect Prev 2000; 24(1):1-12). Therefore, this disclosure of FIG. 2 polynucleotides and polypeptides (as well as FIG. 2—related polynucleotide probes and anti-FIG. 2 protein antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods, which utilize the polynucleotides, polypeptides, reactive T cells and antibodies of the invention, are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the FIG. 2 polynucleotides described herein can be utilized in the same way to detect the respective FIG. 2 protein overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the FIG. 2 polypeptides described herein can be utilized to generate antibodies for use in detecting the respective proteins of FIG. 2 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing FIG. 2 polynucleotides and/or polypeptides can be used to provide evidence of metastasis. For example, when a biological sample from tissue that does not normally contain gene or protein of FIG. 2—expressing cells (e.g., a lymph node) is found to contain a protein of FIG. 2—expressing cells, this finding is indicative of metastasis.

Alternatively polynucleotides and/or polypeptides of the invention can be used to provide evidence of cancer, for example, when cells in a biological sample that do not normally express FIG. 2 genes or express FIG. 2 genes at a different level are found to express FIG. 2 genes or have an increased expression of FIG. 2 genes (see, e.g., the expression in the cancers of tissues listed in Table I and in patient samples etc. shown in the accompanying Figures). In such assays, artisans may further wish to generate supplementary evidence of metastasis by testing the biological sample for the presence of a second tissue restricted marker (in addition to a protein of FIG. 2) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, a gene of FIG. 2 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mot. Biol. 98:121-154 (1998)). An additional illustration of the use of such fragments is provided in Example 4, where a gene of FIG. 2 polynucleotide fragments are used as a probe to show the expression of respective gene of FIG. 2 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a FIG. 2 polynucleotide or variant thereof) under conditions of high stringency.

Furthermore, PSA polypeptides which contain an epitope that can be recognized by an antibody or T cell that specifically binds to that epitope are used in methods of monitoring PSA. Polypeptide fragments, polypeptide analogs or variants of a protein of FIG. 2 can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the biological motifs of a protein of FIG. 2 discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a protein of FIG. 2).

As shown herein, the FIG. 2 polynucleotides and polypeptides (as well as the FIG. 2 polynucleotide probes and anti-proteins of FIG. 2 antibodies or T cells used to identify the presence of these molecules) exhibit specific properties that make them useful in diagnosing cancers such as those listed in Table I. Diagnostic assays that measure the presence of gene of FIG. 2 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as FIG. 2 polynucleotides and polypeptides (as well as the gene of FIG. 2 polynucleotide probes and anti-proteins of FIG. 2 antibodies used to identify the presence of these molecules) need to be employed to confirm a metastases of prostatic origin.

Finally, in addition to their use in diagnostic assays, the FIG. 2 polynucleotides disclosed herein have a number of other utilities such as their use in the identification of onco-genetic associated chromosomal abnormalities in the chromosomal region to which a FIG. 2 gene maps (see Example 3 below). Moreover, in addition to their use in diagnostic assays, the FIG. 2—related proteins and polynucleotides disclosed herein have other utilities such as their use in the forensic analysis of tissues of unknown origin (see, e.g., Takahama K Forensic Sci Int 1996 Jun. 28; 80(1-2): 63-9).

Additionally, FIG. 2—related proteins or polynucleotides of the invention can be used to treat a pathologic condition characterized by the over-expression of FIG. 2 proteins. For example, the amino acid or nucleic acid sequences in FIG. 2 or FIG. 3, or fragments of either, can be used to generate an immune response to a protein of FIG. 2 antigen. Antibodies or other molecules that react with proteins of the invention FIG. 2 can be used to modulate the function of this molecule, and thereby provide a therapeutic benefit.

XII.) INHIBITION OF THE FUNCTION OF A PROTEIN IN THE INVENTION

The invention includes various methods and compositions for inhibiting the binding of proteins in FIG. 2 to its binding partner or its association with other protein(s) as well as methods for inhibiting the function of proteins in FIG. 2.

XII.A.) Inhibition of a Protein of FIG. 2 with Intracellular Antibodies

In one approach, a recombinant vector that encodes single chain antibodies that specifically bind to a FIG. 2 protein are introduced into proteins of FIG. 2 expressing cells via gene transfer technologies. Accordingly, the encoded single chain anti-protein of FIG. 2 antibodies are expressed intracellularly, and bind to the respective FIG. 2 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture proteins of FIG. 2 in the nucleus, thereby preventing the activity of that protein(s) within the nucleus. Nuclear targeting signals are engineered into such FIG. 2—related intrabodies in order to achieve the desired targeting. Such FIG. 2—related intrabodies are designed to bind specifically to a particular FIG. 2 protein domain. In another embodiment, cytosolic intrabodies that specifically bind to a FIG. 2 protein are used to prevent the protein in FIG. 2 from gaining access to the nucleus, thereby preventing it from exerting any biological activity within the nucleus (e.g., preventing proteins of FIG. 2 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of a Protein of FIG. 2 with Recombinant Proteins

In another approach, recombinant molecules bind to a FIG. 2 protein and thereby inhibit the function of a protein of FIG. 2. For example, these recombinant molecules prevent or inhibit FIG. 2 proteins from accessing/binding to its binding partner(s) or associating with other protein(s). Such recombinant molecules can, for example, contain the reactive part(s) of an antibody molecule specific for a protein of FIG. 2. In a particular embodiment, the FIG. 2 protein binding domain of a corresponding binding partner is engineered into a dimeric fusion protein, whereby the fusion protein comprises two protein of FIG. 2 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of proteins of the invention, see, e.g., FIG. 2, whereby the dimeric fusion protein specifically binds to a FIG. 2 protein and blocks the interaction of a FIG. 2 protein with one or more binding partners. Such dimeric fusion proteins are further combined into multimeric proteins using known antibody linking technologies.

XII.C.) Inhibition of Transcription or Translation in Accordance with the Invention The present invention also comprises various methods and compositions for inhibiting the transcription of a FIG. 2 gene. Similarly, the invention also provides methods and compositions for inhibiting the translation of the genes in FIG. 2—related mRNA into protein.

In one approach, a method of inhibiting the transcription of a FIG. 2 gene comprises contacting the FIG. 2 gene with a respective FIG. 2 antisense polynucleotide. In another approach, a method of inhibiting gene of FIG. 2—related mRNA translation comprises contacting a gene of FIG. 2—related mRNA with an antisense polynucleotide. In another approach, a gene of FIG. 2 specific ribozyme is used to cleave a gene of FIG. 2—related message, thereby inhibiting translation. Such antisense and ribozyme based methods can also be directed to the regulatory regions of a FIG. 2 gene, such as a promoter and/or enhancer element for a gene of FIG. 2. Similarly, proteins capable of inhibiting agene of FIG. 2 transcription factor are used to inhibit the gene of FIG. 2 mRNA transcription. The various polynucleotides and compositions useful in the aforementioned methods have been described above. The use of antisense and ribozyme molecules to inhibit transcription and translation is well known in the art.

Other factors that inhibit the transcription of a FIG. 2 gene by interfering with that gene's transcriptional activation are also useful to treat cancers expressing genes of FIG. 2. Similarly, factors that interfere with a gene of FIG. 2 gene processing are useful to treat cancers that express genes of FIG. 2. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing proteins of the invention, see, e.g., FIG. 2, (e.g., antisense, ribozyme, polynucleotides encoding intrabodies and other gene/protein of FIG. 2 inhibitory molecules). A number of gene therapy approaches are known in the art. Recombinant vectors encoding FIG. 2 antisense polynucleotides, ribozymes, factors capable of interfering with transcription of a gene of FIG. 2, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of a protein of FIG. 2 to one or more of its binding partners, etc.

In vivo, the effects of a therapeutic composition of the invention can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) KITS

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a FIG. 2—related protein or a FIG. 2 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequences in FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes; carrier, package, container, vial and/or tube labels listing contents and/or instructions for use, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

EXAMPLES

Various aspects of the invention are further described and illustrated by way of the several examples that follow, none of which are intended to limit the scope of the invention.

Example 1

SSH-Generated Isolation of a cDNA Fragment of the Target of the Invention Gene

The suppression subtractive hybridization (SSH) cDNA fragments shown in FIG. 1 were derived from many different subtractions utilizing LAPC xenografts in differing states of androgen dependence and/or castration as well as using cancer patient derived tissues. The cancer patient tissue SSHs utilized prostate, bladder, and kidney with tumors representing all stages and grades of the diseases. Information for additional sequences disclosed in FIG. 2 and FIG. 3 were derived from other clones and the use of various sequence databases.

Materials and Methods

LAPC Xenografts and Human Tissues:

LAPC xenografts were obtained from Dr. Charles Sawyers (UCLA) and generated as described (Klein et al., 1997, Nature Med. 3: 402-408; Craft et al., 1999, Cancer Res. 59: 5030-5036). Androgen dependent and independent LAPC xenografts were grown in male SCID mice and were passaged as small tissue chunks in recipient males. LAPC xenografts were derived from LAPC tumors. To generate the androgen independent (AI) xenografts, male mice bearing androgen dependent (AD) tumors were castrated and maintained for 2-3 months. After the tumors re-grew, the tumors were harvested and passaged in castrated males or in female SCID mice. Tissues from prostate, bladder, kidney, colon, lung, pancreas, ovary and breast cancer patients as well as the corresponding normal tissues were stored frozen at −70 C prior to RNA isolation.

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
5'TTTTGATCAAGCTT₃₀3'           (SEQ ID NO: 178)

Adaptor 1:
5'CTAATACGACTCACTATAGGGCTCGAGCGGCC (SEQ ID NO: 179)
GCCCGGGCAG3'

3'GGCCCGTCCTAG5'                (SEQ ID NO: 180)

Adaptor 2:
5'GTAATACGACTCACTATAGGGCAGCGTGGTCG (SEQ ID NO: 181)
CGGCCGAG3'

3'CGGCTCCTAG5'                  (SEQ ID NO: 182)

PCR primer 1:
5'CTAATACGACTCACTATAGGGC3'      (SEQ ID NO: 183)

Nested primer (NP)1:
5'TCGAGCGGCCGCCCGGGCAGGA3'      (SEQ ID NO: 184)

Nested primer (NP)2:
5'AGCGTGGTCGCGGCCGAGGA3'        (SEQ ID NO: 185)
```

Suppression Subtractive Hybridization:

Suppression Subtractive Hybridization (SSH) was used to identify cDNAs corresponding to genes that are differentially expressed in cancer. The SSH reaction utilized cDNA from the prostate cancer xenografts, LAPC-4 AD, LAPC-4 AI, LAPC-9 AD, and LAPC-9AI as well as from prostate, bladder, and kidney cancer patients. Specifically, to isolate genes that are involved in the progression of androgen dependent (AD) prostate cancer to androgen independent (AI) cancer, experiments were conducted with the LAPC-9 AD and LAPC-4 AD xenograft in male SCID mice. Mice that harbored these xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that are turned on or off during the transition to androgen independence.

The cDNAs derived from LAPC-4 AD and LAPC-9 AD tumors (post-castration) were used as the source of the "tester" cDNAs, while the cDNAs from LAPC4-AD and LAPC-9 AD tumors (grown in intact male mouse) were used as the source of the "driver" cDNAs respectively. Some SSHs also used any combination of the LAPC-4 AD, LAPC-4 AI, LAPC-9AD, and LAPC9-AI xenografts as "tester" or "driver". In addition, cDNAs derived from patient tumors of prostate, bladder and kidney cancer were used as "tester" while cDNAs derived from normal prostate, bladder, and kidney were used as "driver" respectively. Double stranded cDNAs corresponding to tester and driver cDNAs were synthesized from 2 μg of poly(A)⁺ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 μl of Dpn II digested cDNA from the relevant xenograft source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 μl of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

A full-length cDNA clone can be identified by assembling EST fragments homologous to the SSH fragment into a large contiguous sequence with an ORF and amplifying the ORF by PCR using xenograft, prostate, bladder, kidney, prostate cancer, bladder cancer, or kidney cancer first strand cDNA.

Example 2

Full Length Cloning of a Target of the Invention

Full length cDNA clones were isolated by a variety of methods known in the art. For example, cDNA phage libraries were constructed from normal and cancer tissues using methods based on those set forth in Current Protocols in Molecular Biology, Ed Ausubel et al., page 5.01, to 5.11.1, through supplement 52, Wiley and Sons; Molecular Cloning, $2^{nd}$ Edition, Sambrook et al. Eds, pp. 8.2 to 8.45, 1989, Cold Spring Harbor Press) and full length cDNA clone isolated using probes derived from SSH clones and methods based on (Ausubel et al., supra, pp. 6.0.1 to 6.5.2; Sambrook et al. Eds, supra, 1989, pp. 8.46 to 8.86). In addition, some full length cDNAs were cloned using PCR with primers derived from the extreme ends of ORFs identified in ESTs assembled into contigs. The PCR product is subsequently cloned into pCR2.1 cloning vector (Invitrogen, Carlsbad, Calif.). Sequences of the cloned genes are listed in FIG. 2.

Example 3

Chromosomal Mapping

Chromosomal localization can implicate genes in disease pathogenesis. Several chromosome mapping approaches are available including fluorescent in situ hybridization (FISH), human/hamster radiation hybrid (RH) panels (Walter et al., 1994; Nature Genetics 7:22; Research Genetics, Huntsville Al), human-rodent somatic cell hybrid panels such as is available from the Coriell Institute (Camden, N.J.), and genomic viewers utilizing BLAST homologies to sequenced and mapped genomic clones (NCBI, Bethesda, Md.).

Using FIG. 2 gene sequences and the NCBI BLAST tool, placed the genes of FIG. 2 to the chromosome locations listed in Table XXII.

Accordingly, as the human genes set forth in FIG. 2 map to the designated chromosomes, polynucleotides encoding different regions of the of FIG. 2 protein can be used to characterize cytogenetic abnormalities on a respective chromosome For example, when chromosomal abnormalities in a chromosome listed in Table XXII have been identified as frequent cytogenetic abnormalities in different cancers (see, e.g., Lai et al., 2000, Clin. Cancer Res. 6(8):3172-6; Oya and Schulz, 2000, Br. J. Cancer 83(5):626-31; Svaren et al., Sep. 12, 2000, J. Biol. Chem.); polynucleotides encoding specific regions of the of a FIG. 2 protein provide new tools that are used to delineate, with greater precision than previously possible, the specific nature of the cytogenetic abnormalities in this region of the respective chromosome that contribute to the malignant phenotype. In this context, these polynucleotides satisfy a need in the art for expanding the sensitivity of chromosomal screening in order to identify more subtle and less common chromosomal abnormalities (see, e.g., Evans et al., 1994, Am. J. Obstet. Gynecol. 171(4):1055-1057).

Example 4

Expression Analysis of a Gene of the Invention in Normal Tissues and Patient Specimens Expression analysis by RT-PCR and Northern analysis demonstrated that normal tissue expression of a gene of FIG. 2 is restricted predominantly to the tissues set forth in Table I.

Therapeutic applications for a gene of FIG. 2 include use as a small molecule therapy and/or a vaccine (T cell or antibody) target. Diagnostic applications for a gene of FIG. 2 include use as a diagnostic marker for local and/or metastasized disease. The restricted expression of a gene of FIG. 2 in normal tissues makes it useful as a tumor target for diagnosis and therapy. Expression analysis of a gene of FIG. 2 provides information useful for predicting susceptibility to advanced stage disease, rate of progression, and/or tumor aggressiveness. Expression status of a gene of FIG. 2 in patient samples, tissue arrays and/or cell lines may be analyzed by: (i) immunohistochemical analysis; (ii) in situ hybridization; (iii) RT-PCR analysis on laser capture micro-dissected samples; (iv) Western blot analysis; and (v) Northern analysis.

RT-PCR analysis and Northern blotting were used to evaluate gene expression in a selection of normal and cancerous urological tissues. The results are summarized in FIGS. 15-74.

RT-PCR Expression Analysis:

First strand cDNAs can be generated from 1 µg of mRNA with oligo (dT)12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgc-cgcgctcgtcgtcgacaa3' (SEQ ID NO: 186) and 5'agccacacg-cagctcattgtagaagg 3' (SEQ ID NO: 187) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCL, 1.5 mM $MgCl_2$, 50 mM KCl, pH8.3) and 1× Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the gene, 5 µl of normalized first strand cDNA are analyzed by PCR using 26, and 30 cycles of amplification. Semi-quantitative expression analysis can be achieved by comparing the PCR products at cycle numbers that give light band intensities. RT-PCR expression analysis is performed on first strand cDNAs generated using pools of tissues from multiple samples. The cDNA normalization was demonstrated in every experiment using beta-actin PCR.

Northern Blot Expression Analysis:

Expression of mRNA in normal and cancerous human tissues was analyzed by northern blotting. Expression in normal tissues was analyzed using two multiple tissue blots (Clontech; Palo Alto, Calif.), comprising a total of 16 different normal human tissues, using labeled SSH fragment as a probe. To further analyze expression in prostate cancer tissues, northern blotting was performed on RNA derived from the LAPC xenografts and/or prostate cancer patient samples. In addition, expression in other cancers was studied using patient samples and/or various cancer cell lines.

FIG. 15 shows expression of 74P3B3 by RT-PCR. First strand cDNA was prepared from vital pool 1 (liver, lung and kidney), vital pool 2 (pancreas, colon and stomach), two prostate metastasis to lymph node (LN) harvested from two different patients, prostate cancer pool, bladder cancer pool, and cancer metastasis pool. Normalization was performed by PCR using primers to actin and GAPDH. Semi-quantitative PCR, using primers to 74P3B3, was performed at 26 and 30 cycles of amplification. Results show strong expression of 74P3B3 in the two prostate metastasis to LN specimens and in prostate cancer pool. Expression was also detected in bladder cancer pool, cancer metastasis pool, and vital pool 2 but not in the vital pool 1.

FIG. 16 shows expression of 74P3B3 in normal tissues. Two multiple tissue northern blots (A and B; Clontech) both with 2 µg of mRNA/lane, and a LAPC xenograft blot with 10 µg of total RNA/lane (C) were probed with the 74P3B3 SSH fragment. Size standards in kilobases (kb) are indicated on the side. Results show expression of approximately 7 kb 74P3B3 transcript in prostate but not in the other normal tissues tested. Expression was also detected in LAPC-4AD and LAPC-4AI but not in LAPC-9AD and LAPC-9AI.

FIG. 17 shows expression of 74P3B3 in prostate cancer patient specimens. RNA was extracted from normal prostate (NP), pool of 3 prostate cancer patient tumors (T) and their normal adjacent tissues (N). Northern blot with 10 mg of total RNA/lane was probed with 74P3B3 SSH sequence. Size standards in kilobases (kb) are indicated on the side. The results show strong expression of 74P3B3 in normal prostate and in patient prostate cancer specimens.

FIG. 18 shows expression of 74P3B3 in patient cancer specimens. Expression of 74P3B3 was assayed in a panel of human cancers (T) and their respective matched normal tissues (N) on RNA dot blots. Upregulated expression of 74P3B3 in tumors compared to normal tissues was observed in prostate, kidney, breast and colon tumors. The expression detected in normal adjacent tissues (isolated from diseased tissues) but not in normal tissues (isolated from healthy donors) may indicate that these tissues are not fully normal and that 74P3B3 may be expressed in early stage tumors.

FIG. 19 shows expression of 83P4B8 by RT-PCR. First strand cDNA was prepared from vital pool 1 (liver, lung and kidney), vital pool 2 (pancreas, colon and stomach), prostate cancer pool, bladder cancer pool, kidney cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 83P4B8, was performed at 30 cycles of amplification. Results show strong expression of 83P4B8 in all cancer pools tested. Very low expression was detected in the vital pools.

FIG. 20 shows expression of 83P4B8 in normal tissues. Two multiple tissue northern blots (A and B; Clontech) both with 2 µg of mRNA/lane, and a LAPC xenograft blot with 10 µg of total RNA/lane (C) were probed with the 83P4B8 SSH fragment. Size standards in kilobases (kb) are indicated on the side. Results show expression of two approximately 4.4 kb 83P4B8 transcripts in testis and to lower level in thymus but not in the other normal tissues tested. Expression was also detected in all 4 LAPC prostate cancer xenografts.

FIG. 21 shows expression of 83P4B8 in patient cancer specimens and normal tissues. RNA was extracted from a pool of three prostate cancers (PC), bladder cancers (BC), kidney cancers (KC), colon cancers (CC), lung cancers (LC), ovary cancers (OC), cancer metastasis (Met), pancreas cancers (PaC), as well as from normal prostate (NP), normal bladder (NB), normal kidney (NK), normal colon (NC), normal lung (NL), normal breast (NBr) normal ovary (NO) and normal pancreas (NPa). Northern blot with 10 mg of total RNA/lane was probed with 83P4B8 sequence. Size standards in kilobases (kb) are indicated on the side. Results show expression of 83P4B8 in the bladder cancers and ovary cancers. Expression of 83P4B8 was also detected in prostate cancers, kidney cancers, colon cancers, lung cancers, cancer metastasis and pancreas cancer but not in the normal tissues tested.

FIG. 22 shows expression of 83P4B8 in prostate cancer patient specimens. RNA was extracted from normal prostate (NP), prostate cancer patient tumors (T) and their normal adjacent tissues (N). Northern blot with 10 mg of total RNA/lane was probed with 83P4B8 SSH sequence. Size standards in kilobases (kb) are indicated on the side. The results show strong expression of 83P4B8 in the patient prostate cancer specimens.

FIG. 23 shows expression of 83P4B8 in colon cancer patient specimens. RNA was extracted from colon cancer cell lines (CL), normal colon (N), colon cancer patient tumors (T) and their normal adjacent tissues (Nat). Northern blots with 10 µg of total RNA were probed with the 83P4B8 SSH fragment. Size standards in kilobases are indicated on the side. Results show strong expression of 83P4B8 in the colon tumor tissues and in all three colon cancer cell lines tested, but not in the normal tissues.

FIG. 24 shows expression of 109P1D4 by RT-PCR. First strand cDNA was prepared from vital pool 1 (liver, lung and kidney), vital pool 2 (pancreas, colon and stomach), prostate cancer pool, bladder cancer pool, kidney cancer pool, colon cancer pool, lung cancer pool, ovary cancer pool, breast cancer pool, cancer metastasis pool, and pancreas cancer pool. Normalization was performed by PCR using primers to actin and GAPDH. Semi-quantitative PCR, using primers to 109P1D4, was performed at 30 cycles of amplification. Results show strong expression of 109P1D4 in all cancer pools tested. Very low expression was detected in the vital pools FIG. 25 shows expression of 109P1D4 in normal tissues. Two multiple tissue northern blots (Clontech), both with 2 µg of mRNA/lane, were probed with the 109P1D4 SSH fragment. Size standards in kilobases (kb) are indicated on the side. Results show expression of approximately 10 kb 109P1D4 transcript in ovary. Weak expression was also detected in placenta and brain, but not in the other normal tissues tested.

FIG. 26 shows expression of 109P1D4 in human cancer cell lines. RNA was extracted from a number of human prostate and bone cancer cell lines. Northern blots with 10 µg of total RNA/lane were probed with the 109P1D4 SSH fragment. Size standards in kilobases (kb) are indicated on the side. Results show expression of 109P1D4 in LAPC-9AD, LAPC-9AI, LNCaP prostate cancer cell lines, and in the bone cancer cell lines, SK-ES-1 and RD-ES.

FIG. 27 shows expression of 109P1D4 in patient cancer specimens. Expression of 109P1D4 was assayed in a panel of human cancers (T) and their respective matched normal tissues (N) on RNA dot blots. Upregulated expression of 109P1D4 in tumors compared to normal tissues was observed in uterus, lung and stomach. The expression detected in normal adjacent tissues (isolated from diseased tissues) but not in normal tissues (isolated from healthy donors) may indicate that these tissues are not fully normal and that 109P1D4 may be expressed in early stage tumors.

FIG. 28 shows expression of 151P1C7A by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, and cancer metastasis pool. Normalization was performed by PCR using primers to actin and GAPDH. Semi-quantitative PCR, using primers to 151P1C7A, was performed at 26 and 30 cycles of amplification. Results show strong expression of 151P1C7A in bladder, lung, and metastasis cancer pools tested. Expression was also detected in xenograft, prostate, kidney and colon cancer pools but not in the vital pools.

FIG. 29 shows expression of 151P1C7A in normal tissues. Two multiple tissue northern blots (Clontech), both with 2 μg of mRNA/lane, were probed with the 151P1C7A SSH fragment. Size standards in kilobases (kb) are indicated on the side. Results show expression of an approximately 2 kb 151P1C7A transcript in placenta but not in the other normal tissues tested.

FIG. 30 shows expression of 151P1C7A in bladder cancer patient specimens. RNA was extracted from bladder cancer cell lines (CL; UM-UC-3, J82, SCaBER), normal bladder (Nb), bladder cancer patient tumors (T) and their normal adjacent tissue (N) isolated from bladder cancer patients. Northern blots with 10 μg of total RNA were probed with the 151P1C7A SSH sequence. Size standards in kilobases are indicated on the side. Results show expression of 151P1C7A in patient bladder cancer tissues, and in all bladder cancer cell lines tested, but not in normal bladder.

FIG. 31 shows expression of 151P1C7A in prostate cancer patient specimens. RNA was extracted from normal prostate (NP), prostate cancer patient tumors (T) and their normal adjacent tissues (N). Northern blot with 10 mg of total RNA/lane was probed with 151P1C7A SSH sequence. Size standards in kilobases (kb) are indicated on the side. Results show expression of 151P1C7A in the patient prostate cancer specimens.

FIG. 32 shows expression of 151P4E11 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 151P4E11, was performed at 26 and 30 cycles of amplification. Results show strong expression of 151P4E11 in all cancer pools tested. Expression was detected in vital pool 2 but not in vital pool 1.

FIG. 33 shows expression of 151P4E11 in normal tissues. Two multiple tissue northern blots (A and B; Clontech) both with 2 μg of mRNA/lane, and a LAPC xenograft blot with 10 μg of total RNA/lane (C) were probed with the 151P4E11 SSH fragment. Size standards in kilobases (kb) are indicated on the side. Results show expression of an approximately 1.2 kb 151P4E11 transcript in prostate, testis, colon and small intestine. Expression was also detected in all the LAPC prostate cancer xenografts LAPC-4AD, LAPC-4AI, and LAPC-9AI, but not in LAPC-9AD.

FIG. 34 shows expression of 154P2A8 by RT-PCR. First strand cDNA was prepared from vital pool 1 (liver, lung and kidney), vital pool 2 (pancreas, colon and stomach), prostate cancer pool, bladder cancer pool, kidney cancer pool, colon cancer pool, lung cancer pool, and cancer metastasis pool. Normalization was performed by PCR using primers to actin and GAPDH. Semi-quantitative PCR, using primers to 154P2A8, was performed at 26 and 30 cycles of amplification. Results show strong expression of 154P2A8 in bladder cancer pool and lung cancer pool. Expression was also detected in prostate cancer pool, kidney cancer pool, colon cancer pool, and cancer metastasis pool but not in vital pool 1 and vital pool 2.

FIG. 35 shows expression of 156P1D4 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 156P1D4, was performed at 26 and 30 cycles of amplification. Results show strong expression of 156P1D4 in kidney cancer pool and vital pool 1. Expression was also detected in xenograft pool, prostate cancer pool, bladder cancer pool, colon cancer pool, lung cancer pool, ovary cancer pool, breast cancer pool, cancer metastasis pool and vital pool 2.

FIG. 36 shows expression of 156P1D4 in normal tissues. Two multiple tissue northern blots (Clontech), both with 2 μg of mRNA/lane, were probed with the 156P1D4 SSH fragment. Size standards in kilobases (kb) are indicated on the side. Results show expression of an approximately 2 kb 156P1D4 transcript in kidney and prostate but not in the other normal tissues tested.

FIG. 37 shows expression of 156P1D4 in kidney cancer patient specimens. RNA was extracted from normal kidney (Nk), kidney cancer patient tumors (T) and their normal adjacent tissues (N). Northern blots with 10 μg of total RNA were probed with the 156P1D4 SSH fragment. Size standards in kilobases are indicated on the side. Results show strong expression of 156P1D4 in all kidney tumor tissues tested. The expression of 156P1D4 detected in tumor tissues is stronger than in normal tissues.

FIG. 38 shows expression of 156P5C12 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, ovary cancer pool, breast cancer pool, and cancer metastasis pool. Normalization was performed by PCR using primers to actin and GAPDH. Semi-quantitative PCR, using primers to 156P5C12, was performed at 26 and 30 cycles of amplification. Results show strong expression of 156P5C12 in kidney cancer pool and vital pool 1. Expression was also detected in xenograft pool, prostate cancer pool, bladder cancer pool, colon cancer pool, lung cancer pool, ovary cancer pool, breast cancer pool, cancer metastasis pool and vital pool 2.

FIG. 39 shows expression of 156P5C12 in normal tissues. Two multiple tissue northern blots (Clontech), both with 2 μg of mRNA/lane, were probed with the 156P5C12 SSH fragment. Size standards in kilobases (kb) are indicated on the side. Results show expression of an approximately 1.4 kb 156P5C12 transcript in kidney but not in the other normal tissues tested.

FIG. 40 shows expression of 156P5C12 in kidney cancer patient specimens. RNA was extracted from kidney cancer cell lines (CL; 769-P, A498, SW839), normal kidney (N), kidney cancer patient tumors (T) and their normal adjacent tissues (NAT). Northern blots with 10 μg of total RNA were probed with the 156P5C12 SSH fragment. Size standards in kilobases are indicated on the side. Results show expression of 156P5C12 in normal tissues, and in some but not all kidney tumor tissues. Expression was absent in the kidney cancer cell lines tested.

FIG. 41 shows expression of 159P2B5 by RT-PCR. First strand cDNA was prepared from vital pool 1 (liver, lung and kidney), vital pool 2 (pancreas, colon and stomach), and bladder cancer pool. Normalization was performed by PCR using primers to actin and GAPDH. Semi-quantitative PCR, using primers to 159P2B5, was performed at 26 and 30 cycles of amplification. Results show expression of 159P2B5 in bladder cancer pool tested but not in the vital pools.

FIG. 42 shows expression of 159P2B5 in normal tissues. Two multiple tissue northern blots (Clontech), both with 2 μg of mRNA/lane, were probed with the 159P2B5 SSH fragment. Size standards in kilobases (kb) are indicated on the side. Results show very weak expression of an approximately 4.5 kb 159P2B5 transcript in spleen, kidney and small intestine.

FIG. 43 shows expression of 159P2B5 in bladder cancer patient specimens. RNA was extracted from bladder cancer cell lines (CL; UM-UC-3, J82, SCaBER), normal bladder (NB), and bladder cancer patient tumors (T) isolated from bladder cancer patients. Northern blots with 10 μg of total RNA were probed with the 159P2B5 SSH sequence. Size standards in kilobases are indicated on the side. Results show expression of 159P2B5 in patient bladder cancer tissues, and in the SCaBER bladder cancer cell line, but not in normal bladder, nor in the other cancer cell lines tested.

FIG. 44 shows expression of 161P2B7A by RT-PCR. First strand cDNA was prepared from vital pool 1 (liver, lung and kidney), vital pool 2 (pancreas, colon and stomach), prostate metastasis to lymph node (LN), prostate cancer pool, bladder cancer pool, kidney cancer pool, colon cancer pool, lung cancer pool, ovary cancer pool, breast cancer pool, cancer metastasis pool and pancreas cancer pool. Normalization was performed by PCR using primers to actin and GAPDH. Semi-quantitative PCR, using primers to 161P2B7A, was performed at 26 and 30 cycles of amplification. Results show strong expression of 161P2B7A in lung cancer pool and pancreas cancer pool. Expression was also detected in prostate metastasis to LN, prostate cancer pool, bladder cancer pool, kidney cancer pool, colon cancer pool, ovary cancer pool, breast cancer pool, and cancer metastasis pool. Very low expression was observed in vital pool 2 but not in vital pool 1.

FIG. 45 shows expression of 161P2B7A in normal tissues. Two multiple tissue northern blots (Clontech), both with 2 μg of mRNA/lane, were probed with the 161P2B7A SSH fragment. Size standards in kilobases (kb) are indicated on the side. Results show very low expression of 161P2B7A in testis but not in the other normal tissues tested.

FIG. 46 shows expression of 161P2B7A in Multiple Normal Tissues. An mRNA dot blot containing 76 different samples from human tissues was analyzed using a 161P2B7A SSH probe. Expression was not detected in any of the 76 normal tissues tested. The positive genomic DNA control showed very strong signal confirming the validity of the experiment.

FIG. 47 shows expression of 161P2B7A in kidney cancer patient specimens. RNA was extracted from normal kidney (Nk), kidney cancer patient tumors (T) and their normal adjacent tissues (N) isolated from kidney cancer patients. Northern blots with 10 μg of total RNA were probed with the 161P2B7A SSH fragment. Size standards in kilobases are indicated on the side. Results show expression of two 161P2B7A transcripts, approximately 1.2 and 7 kb, in kidney cancer specimens but not in normal kidney.

FIG. 48 shows expression of 161P2B7A in lung cancer patient specimens. RNA was extracted from lung cancer cell lines (CL), normal lung, lung tumors (T), and their normal adjacent tissues (NAT) isolated from lung cancer patients. Northern blot with 10 mg of total RNA/lane was probed with the 161P2B7A fragment. Size standards in kilobases (kb) are indicated on the side. The results show expression of 161P2B7A in the lung tumors, but not in normal lung tissues. Expression was also detected in the lung cancer cell lines CALU-1, A427 and NCI-146 but not in the small cell lung cancer cell line NCI-H82.

FIG. 49 shows expression of 161P2B7A in pancreas and ovary cancer patient specimens. RNA was extracted from normal pancreas (NPa), pancreas cancer (PC), normal ovary (NO), and ovary cancer patient specimen (OC). Northern blot with 10 mg of total RNA/lane was probed with the 161P2B7A fragment. Size standards in kilobases (kb) are indicated on the side. The results show expression of 161P2B7A in the pancreas and ovary cancer patient specimens, but not in the normal tissues.

FIG. 50 shows expression of 179P3G7 by RT-PCR. First strand cDNA was prepared from vital pool 1 (liver, lung and kidney), vital pool 2 (pancreas, colon and stomach), bladder cancer pool, kidney cancer pool, lung cancer pool, breast cancer pool, cancer metastasis pool, pancreas cancer pool and pancreas cancer pool. Normalization was performed by PCR using primers to actin and GAPDH. Semi-quantitative PCR, using primers to 179P3G7, was performed at 26 and 30 cycles of amplification. Results show strong expression of 179P3G7 in kidney cancer pool and breast cancer pool. Expression was also detected in bladder cancer pool, lung cancer pool, cancer metastasis pool, pancreas cancer pool and prostate metastasis to LN, and vital pool 1, but not in vital pool 2.

FIG. 51 shows expression of 179P3G7 in normal tissues. Two multiple tissue northern blots (Clontech), both with 2 μg of mRNA/lane, were probed with the 179P3G7 SSH fragment. Size standards in kilobases (kb) are indicated on the side. Results show expression of 179P3G7 strongly in skeletal muscle, and weakly in kidney, liver and heart but not in the other normal tissues tested.

FIG. 52 shows expression of 179P3G7 in kidney cancer patient specimens. RNA was extracted from normal kidney (Nk), kidney cancer patient tumors (T) and their normal adjacent tissues (N) isolated from kidney cancer patients. Northern blots with 10 μg of total RNA were probed with the 179P3G7 SSH fragment. Size standards in kilobases are indicated on the side. Results show expression of 179P3G7 in kidney cancer specimens. Expression of 179P3G7 is stronger in kidney tumors compared to normal kidney tissues.

FIG. 53 shows expression of 184P3C10B by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), prostate cancer pool, bladder cancer pool, kidney cancer pool, colon cancer pool, lung cancer pool, ovary cancer pool, and cancer metastasis pool. Normalization was performed by PCR using primers to actin and GAPDH. Semi-quantitative PCR, using primers to 184P3C10B, was performed at 26 and 30 cycles of amplification. Results show expression of 184P3C10B in xenograft pool, prostate cancer pool, bladder cancer pool, kidney cancer pool, colon cancer pool, lung cancer pool, ovary cancer pool, and cancer metastasis pool. Expression was also detected in vital pool 2 but at a much lower level in vital pool 1.

FIG. 54 shows expression of 184P3C10B in normal tissues. Two multiple tissue northern blots (Clontech), both with 2 µg of mRNA/lane, were probed with the 184P3C10B SSH fragment. Size standards in kilobases (kb) are indicated on the side. Results show expression of approximately 2.4 and 5 kb 184P3C10B transcripts in placenta and to lower level in colon and small intestine, but not in the other normal tissues tested.

FIG. 55 shows expression of 184P3C10B in bladder cancer patient specimens. RNA was extracted from bladder cancer cell lines (CL; UM-UC-3, J82, SCaBER), normal bladder (Nb), bladder cancer patient tumors (T) and their normal adjacent tissue (N) isolated from bladder cancer patients. Northern blots with 10 µg of total RNA were probed with the 184P3C10B SSH sequence. Size standards in kilobases are indicated on the side. Results show expression of 184P3C10B in patient bladder cancer tissues, and in the bladder cancer cell line SCaBER, but not in normal bladder nor in the other bladder cancer cell lines tested.

FIG. 56 shows expression of 184P3G10 by RT-PCR. First strand cDNA was prepared from vital pool 1 (liver, lung and kidney), vital pool 2 (pancreas, colon and stomach), LAPC prostate cancer xenograft pool (LAPC-4AD, LAPC-4AI, LAPC-9AD and LAPC-9AI), bladder cancer pool, kidney cancer pool, colon cancer pool, and lung cancer pool. Normalization was performed by PCR using primers to actin and GAPDH. Semi-quantitative PCR, using primers to 184P3G10, was performed at 26 and 30 cycles of amplification. Results show strong expression of 184P3G10 in bladder cancer pool, kidney cancer pool, and colon cancer pool. Expression was also detected in xenograft pool, lung cancer pool, vital pool 2 but not in vital pool 1.

FIG. 57 shows expression of 184P3G10 in normal tissues. Two multiple tissue northern blots (Clontech) both with 2 µg of mRNA/lane, were probed with the 184P3G10 SSH fragment. Size standards in kilobases (kb) are indicated on the side. Results show expression of two approximately 4.4 kb 184P3G10 transcripts in colon and small intestine, but not in the other normal tissues tested.

FIG. 58 shows expression of 184P3G10 in patient cancer specimens and normal tissues. RNA was extracted from a pool of three bladder cancers, colon cancers, lung cancers, breast cancers, ovary cancers, cancer metastasis, as well as from normal prostate (NP), normal bladder (NB), and normal kidney (NK). Northern blot with 10 mg of total RNA/lane was probed with 184P3G10 sequence. Size standards in kilobases (kb) are indicated on the side. Results show strong expression of 184P3G10 in the bladder cancers, colon cancers and ovary cancers. Expression of 184P3G10 was also detected in lung cancers, breast cancers, and cancer metastasis but not in the normal tissues tested.

FIG. 59 shows expression of 184P3G10 in bladder cancer patient specimens. RNA was extracted from bladder cancer cell lines (CL; UM-UC-3, J82, SCaBER), normal bladder (N), bladder cancer patient tumors (T) and their normal adjacent tissue (Nat) isolated from bladder cancer patients. Northern blots with 10 µg of total RNA were probed with the 184P3G10 SSH sequence. Size standards in kilobases are indicated on the side. Results show expression of 184P3G10 in patient bladder cancer tissues, but not in normal bladder nor in the bladder cancer cell lines tested.

FIG. 60 shows expression of 185P2C9 by RT-PCR. First strand cDNA was prepared from vital pool 1 (liver, lung and kidney), vital pool 2 (pancreas, colon and stomach), prostate metastasis to lymph node (LN), prostate cancer pool, bladder cancer pool, kidney cancer pool, colon cancer pool, lung cancer pool, ovary cancer pool, breast cancer pool, cancer metastasis pool and pancreas cancer pool. Normalization was performed by PCR using primers to actin and GAPDH. Semi-quantitative PCR, using primers to 185P2C9, was performed at 30 cycles of amplification. Results show strong expression of 185P2C9 in bladder cancer pool, colon cancer pool, lung cancer pool, ovary cancer pool and pancreas cancer pool. Expression was also detected in prostate metastasis to LN, prostate cancer pool, kidney cancer pool, breast cancer pool, cancer metastasis pool, vital pool 2 but not in vital pool 1.

FIG. 61 shows expression of 185P2C9 in normal tissues. Two multiple tissue northern blots (Clontech), both with 2 µg of mRNA/lane, were probed with the 185P2C9 SSH fragment. Size standards in kilobases (kb) are indicated on the side. Results show expression of and approximately 8.5 kb 185P2C9 transcript in testis and brain, but not in the other normal tissues tested.

FIG. 62 shows expression of 185P2C9 in bladder cancer patient specimens. RNA was extracted from bladder cancer cell lines (CL; UM-UC-3, J82, SCaBER), normal bladder (Nb), bladder cancer patient tumors (T) and their normal adjacent tissue (N) isolated from bladder cancer patients. Northern blots with 10 µg of total RNA were probed with the 185P2C9 SSH sequence. Size standards in kilobases are indicated on the side. Results show expression of 185P2C9 in bladder cancer patient tissues, and in the bladder cancer cell lines tested. Expression of 185P2C9 is significantly stronger in bladder tumor tissues compared to normal tissues.

FIG. 63 shows expression of 185P2C9 in kidney cancer patient specimens. RNA was extracted from kidney cancer cell lines (CL; 769-P, A498, Caki-1), normal kidney (N), kidney cancer patient tumors (T) and their normal adjacent tissues (NAT) isolated from kidney cancer patients. Northern blots with 10 µg of total RNA were probed with the 185P2C9 SSH fragment. Size standards in kilobases are indicated on the side. Results show expression of 185P2C9 in kidney cancer specimens and kidney cancer cell lines, but not in normal kidney.

FIG. 64 shows expression of 186P1H9 by RT-PCR. First strand cDNA was prepared from vital pool 1 (liver, lung and kidney), vital pool 2 (pancreas, colon and stomach), bladder cancer pool, kidney cancer pool, colon cancer pool, lung cancer pool, ovary cancer pool, cancer metastasis pool, and pancreas cancer pool. Normalization was performed by PCR using primers to actin and GAPDH. Semi-quantitative PCR, using primers to 186P1H9, was performed at 26 and 30 cycles of amplification. Results show strong expression of 186P1H9 in kidney cancer pool, colon cancer pool, ovary cancer pool, cancer metastasis pool, and pancreas cancer pool. Expression was also detected in bladder cancer pool, lung cancer pool, and vital pool 2 but not in vital pool 1.

FIG. 65 shows expression of 186P1H9 in normal tissues. Two multiple tissue northern blots (Clontech) both with 2 µg of mRNA/lane, were probed with the 186P1H9 SSH fragment. Size standards in kilobases (kb) are indicated on the side. Results show expression of an approximately 2.6 kb 186P1H9 transcript in testis, spleen, pancreas and brain. Lower expression is also detected in heart, skeletal muscle, prostate, colon and small intestine.

FIG. 66 shows expression of 186P1H9 in patient cancer specimens and normal tissues. RNA was extracted from a pool of three kidney cancers (KC), ovary cancers (OC), cancer metastasis (Met), pancreas cancers (PaC), as well as from normal prostate (NP), normal bladder (NB), and normal kidney (NK), normal colon (NC), normal lung (NL), normal breast (NBr), normal ovary (NO), and normal pancreas (NPa). Northern blot with 10 mg of total RNA/lane was probed with 186P1H9 sequence. Size standards in kilobases (kb) are indicated on the side. Results show strong expression of 186P1H9 in the bladder cancers, ovary cancers, cancer metastasis and pancreas cancers, but not in normal tissues. Expression of 186P1H9 is significantly stronger in patient cancer tissues compared to normal tissues.

FIG. 67 shows expression of 186P1H9 in kidney cancer patient specimens. RNA was extracted from kidney cancer cell lines (CL; 769-P, A498, Caki-1), normal kidney (N), kidney cancer patient tumors (T) and their normal adjacent tissues (NAT) isolated from kidney cancer patients. Northern blots with 10 µg of total RNA were probed with the 186P1H9 SSH fragment. Size standards in kilobases are indicated on the side. Results show strong expression of 186P1H9 in kidney cancer patient specimens, but not in normal kidney, nor in the kidney cancer cell lines.

FIG. 68 shows expression of 186P1H9 in ovarian and testicular cancer patient specimens. RNA was extracted from normal ovary (NO), ovary cancer patient specimens (P1, P2, P3), normal testis (NTe), and testis cancer patient specimens (P4, P5, P6). Northern blot with 10 mg of total RNA/lane was probed with the 186P1H9 SSH fragment. Size standards in kilobases (kb) are indicated on the side. The results show strong expression of 186P1H9 in the ovary cancer patient specimens, but not in the normal ovary. Expression was also detected in normal and in testis cancer specimens.

FIG. 69 shows expression of 187P3F2 by RT-PCR. First strand cDNA was prepared from vital pool 1 (liver, lung and kidney), vital pool 2 (pancreas, colon and stomach), kidney cancer pool, and pancreas cancer pool. Normalization was performed by PCR using primers to actin and GAPDH. Semi-quantitative PCR, using primers to 187P3F2, was performed at 26 and 30 cycles of amplification. Results show strong expression of 187P3F2 in kidney cancer pool, pancreas cancer pool and vital pool 1, but not in vital pool 2.

FIG. 70 shows expression of 187P3F2 in normal tissues. Two multiple tissue northern blots (Clontech) both with 2 µg of mRNA/lane, were probed with the 187P3F2 SSH fragment. Size standards in kilobases (kb) are indicated on the side. Results show expression of a 4.5 kb 187P3F2 transcript in kidney and brain, but not in the other tissues tested.

FIG. 71 shows expression of 187P3F2 in patient cancer specimens and normal tissues. RNA was extracted from a pool of three kidney cancers (KC), pancreas cancers (PaC), as well as from normal prostate (NP), normal bladder (NB), and normal kidney (NK), normal colon (NC), normal lung (NL), normal breast (NBr), normal ovary (NO), and normal pancreas (NPa). Northern blot with 10 mg of total RNA/lane was probed with 187P3F2 sequence. Size standards in kilobases (kb) are indicated on the side. Results show strong expression of 187P3F2 in kidney cancers, pancreas cancers, and normal kidney, but not in the other normal tissues.

FIG. 72 shows expression of 187P3F2 in pancreas cancer patient specimens. RNA was extracted from pancreas cancer cell lines (CL), normal pancreas (N), and pancreas tumor tissues (T) isolated from pancreatic cancer patients. Northern blot with 10 mg of total RNA/lane was probed with the 187P3F2 SSH fragment. Size standards in kilobases (kb) are indicated on the side. The results show strong expression of 187P3F2 in the pancreas cancer specimens, but not in normal pancreas nor in the cancer cell lines tested.

FIG. 73 shows expression of 192P2G7 by RT-PCR. First strand cDNA was prepared from vital pool 1 (liver, lung and kidney), vital pool 2 (pancreas, colon and stomach), prostate cancer pool, bladder cancer pool, kidney cancer pool, lung cancer pool, ovary cancer pool, breast cancer pool, cancer metastasis pool, pancreas cancer pool, and prostate metastasis to lymph node (LN). Normalization was performed by PCR using primers to actin and GAPDH. Semi-quantitative PCR, using primers to 186P1H9, was performed at 26 and 30 cycles of amplification. Results show strong expression of 186P1H9 in pancreas cancer pool and prostate metastasis to LN. Expression was also detected in prostate cancer pool, bladder cancer pool, kidney cancer pool, lung cancer pool, ovary cancer pool, breast cancer pool, cancer metastasis pool, vital pool 2 but not in vital pool 1.

FIG. 74 shows expression of 185P3C2 by RT-PCR. First strand cDNA was prepared from vital pool 1 (liver, lung and kidney), vital pool 2 (pancreas, colon and stomach), and bladder cancer pool. Normalization was performed by PCR using primers to actin and GAPDH. Semi-quantitative PCR, using primers to 185P3C2, was performed at 26 and 30 cycles of amplification. Results show strong expression of 185P3C2 in bladder cancer pool. Low level expression was detected in vital pool 2, but not in vital pool 1.

Example 5

Transcript Variants of Genes of the Invention

Transcript variants are variants of matured mRNA from the same gene by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or may encode proteins with different functions, and may be expressed in the same tissue at the same time, or at different tissue, or at different times, proteins encoded by transcript variants can have similar or different cellular or extracellular localizations, i.e., be secreted.

Transcript variants are identified by a variety of art-accepted methods. For example, alternative transcripts and splice variants are identified full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs available in the art are used that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4): 516-22). For a general discussion of splice variant identification protocols see., e.g., Southan, C., A genomic perspective on human proteases, FEBS Lett. 2001 Jun. 8; 498(2-3):214-8; de Souza, S. J., et al., Identification of human chromosome 22 transcribed sequences with ORF expressed sequence tags, Proc. Natl. Acad Sci USA. 2000 Nov. 7; 97(23): 12690-3.

To further confirm the parameters of a transcript variant, a variety of techniques available in the art are used, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17; 1433(1-2): 321-6; Ferranti P, et al., Differential splicing of pre-messenger RNA produces multiple forms of mature caprine alpha (s1)-casein, Eur J. Biochem. 1997 Oct. 1; 249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2):211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is a particular expression profile of the target genes related to cancer. Alternative transcripts and splice variants of these genes may also be involved in cancers in the same or different tissues, thus serving as tumor-associated markers/antigens.

Using the full-length gene and EST sequences, five transcript variants were identified for 83P4B8, seven for 109P1D4, one for 151P4E11, two for 161P2B7A, one for 179P3G7, four for 184P3G10, two for 185P2C9, four for 185P3C2, and two for 192P2G7, as displayed in FIGS. 11-14.

FIG. 11 through FIG. 14 are set forth herein on a gene-by-gene basis. The following list shows the numbering of figures and the corresponding genes. nucleotide sequence of a transcript variant. FIG. 11 displays the nucleotide sequences of transcript variants. FIG. 12 shows amino acid sequences of proteins translated from the corresponding transcript variants. FIG. 13 displays the alignment of nucleotide sequences of transcript variants. FIG. 14 displays the alignment of protein sequences from the corresponding transcript variants. Number of Transcript Variants for Target Genes and the Numbering of Associated Figures.

| Target Gene | Number of Trans. Var. | Figure Number |
|---|---|---|
| 83P4B8 | 5 | FIG. 11b-14b |
| 109P1D4 | 7 | FIG. 11c-14c |
| 151P4E11 | 1 | FIG. 11e-14e |
| 161P2B7A | 2 | FIG. 11j-14j |
| 179P3G7 | 1 | FIG. 11k-14k |
| 184P3G10 | 4 | FIG. 11m-14m |
| 185P2C9 | 2 | FIG. 11n-14n |
| 185P3C2 | 4 | FIG. 11o-14o |
| 192P2G7 | 2 | FIG. 11r-14r |

Example 6

Production of Recombinant Targets of the Invention in Prokaryotic Systems

To express a recombinant gene of FIG. 2 in prokaryotic cells, full or partial length gene cDNA sequences are cloned into any one of a variety of expression vectors known in the art. One or more of the following regions of genes set forth in FIG. 2, or variants or analogs thereof, are expressed in these constructs: regions that encode the entire, respective, amino acid sequence of a particular target, or any 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more contiguous amino acids from a protein of FIG. 2, variants, or analogs thereof.

A. In Vitro Transcription and Translation Constructs:

pCRII: To generate sense and anti-sense RNA probes for RNA in situ investigations, pCRII constructs (Invitrogen, Carlsbad Calif.) are generated encoding either all of or fragments of a cDNA. The pCRII vector has Sp6 and T7 promoters flanking the insert to drive the transcription of RNA for use as probes in RNA in situ hybridization experiments. These probes are used to analyze the cell and tissue expression of a gene at the RNA level. Transcribed RNA representing the cDNA amino acid coding region of the gene is used in in vitro translation systems such as the TnT™ Coupled Reticulolysate System (Promega, Corp., Madison, Wis.) to synthesize a protein of the invention.

B. Bacterial Constructs:

pGEX Constructs: To generate recombinant proteins of the invention in bacteria that are fused to the Glutathione S-transferase (GST) protein, all of or parts of a cDNA protein coding sequence of the invention are fused to the GST gene by cloning into pGEX-6P-1 or any other GST-fusion vector of the pGEX family (Amersham Pharmacia Biotech, Piscataway, N.J.). These constructs allow controlled expression of recombinant target of the invention protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as the PreScission™ recognition site in pGEX-6P-1, can be employed to permit cleavage of the GST tag from target of the invention-related protein. The ampicillin resistance gene and pBR322 origin permits selection and maintenance of the pGEX plasmids in E. coli.

pMAL Constructs: To generate, in bacteria, recombinant target of the invention proteins that are fused to maltose-binding protein (MBP), all of or parts of the target of the invention cDNA protein coding sequence are fused to the MBP gene by cloning into the pMAL-c2X and pMAL-p2X vectors (New England Biolabs, Beverly, Mass.). These constructs allow controlled expression of recombinant target of the invention protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from a target of the invention. The pMAL-c2X and pMAL-p2X vectors are optimized to express the recombinant protein in the cytoplasm or periplasm respectively. Periplasm expression enhances folding of proteins with disulfide bonds.

pET Constructs: To express a target of the invention in bacterial cells, all of or parts of the target of the invention cDNA protein coding sequence are cloned into the pET family of vectors (Novagen, Madison, Wis.). These vectors allow tightly controlled expression of recombinant target of the invention protein in bacteria with and without fusion to proteins that enhance solubility, such as NusA and thioredoxin (Trx), and epitope tags, such as 6×His and S-Tag™ that aid purification and detection of the recombinant protein. For example, constructs are made utilizing pET NusA fusion system 43.1 such that regions of the target of the invention protein are expressed as amino-terminal fusions to NusA. In one embodiment, a NusA-fusion protein encompassing certain amino acids of a FIG. 2 protein with a C-terminal 6×His tag are expressed in E. coli, purified by metal chelate affinity chromatography, and used as an immunogen for generation of antibodies.

C. Yeast Constructs:

pESC Constructs: To express a target of the invention in the yeast species Saccharomyces cerevisiae for generation of recombinant protein and functional studies, all of or parts of a target of the invention cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of a target of the invention. In addition, expression in yeast yields similar post-translational modifications, such as glycosylations and phosphorylations, that are found when expressed in eukaryotic cells.

pESP Constructs: To express a target of the invention in the yeast species Saccharomyces pombe, all of or parts of a target of the invention cDNA protein coding sequence are cloned into the pESP family of vectors. These vectors allow controlled high level of expression of a target of the invention protein sequence that is fused at either the amino terminus or at the carboxyl terminus to GST which aids purification of the recombinant protein. A Flag™ epitope tag allows detection of the recombinant protein with anti-Flag™ antibody.

Example 7

Production of Recombinant Target of the Invention in Eukaryotic Systems

A. Mammalian Constructs:

To express a recombinant target of the invention in eukaryotic cells, the full or partial length target of the invention cDNA sequences can be cloned into any one of a variety of expression vectors known in the art. One or more of the following peptide regions of a protein of the invention are expressed in these constructs: any 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more contiguous amino acids from a protein of FIG. 2, variants, or analogs thereof. In certain embodiments a region of a specific variant of a target of the invention is expressed that encodes an amino acid at a specific position which differs from the amino acid of any other respective variant found at that position. In other embodiments, a region of a variant of the invention is expressed that lies partly or entirely within a sequence that is unique to that variant respective to other variants of that target.

The constructs can be transfected into any one of a wide variety of mammalian cells such as 293T cells. Transfected 293T cell lysates can be probed with the anti-target of the invention polyclonal serum, described herein.

pcDNA4/HisMax Constructs: To express a target of the invention in mammalian cells, a target of the invention ORF, or portions thereof, are cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs: To express a target of the invention in mammalian cells, a target of the invention ORF, or portions thereof, with a consensus Kozak translation initiation site are cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in E. coli.

pcDNA3.1/CT-GFP-TOPO Construct: To express a target of the invention in mammalian cells and to allow detection of the recombinant proteins using fluorescence, a target of the invention ORF, or portions thereof, with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in E. coli. Additional constructs with an amino-terminal GFP fusion are made in pcDNA3.1/NT-GFP-TOPO spanning the entire length of a target of the invention protein.

PAPtag: A target of the invention ORF, or portions thereof, is cloned into pAPtag-5 (GenHunter Corp. Nashville, Tenn.). This construct generates an alkaline phosphatase fusion at the carboxyl-terminus of a target of the invention protein while fusing the IgGκ signal sequence to the amino-terminus. Constructs are also generated in which alkaline phosphatase with an amino-terminal IgGκ signal sequence is fused to the amino-terminus of a target of the invention protein. The resulting recombinant target of the invention proteins are optimized for secretion into the media of transfected mammalian cells and can be used to identify proteins such as ligands or receptors that interact with a target of the invention protein. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in E. coli.

ptag5: A target of the invention ORF, or portions thereof, is cloned into pTag-5. This vector is similar to pAPtag but without the alkaline phosphatase fusion. This construct generates a target of the invention protein with an amino-terminal IgGκ signal sequence and myc and 6×His epitope tags at the carboxyl-terminus that facilitate detection and affinity purification. The resulting recombinant target of the invention protein is optimized for secretion into the media of transfected mammalian cells, and is used as immunogen or ligand to identify proteins such as ligands or receptors that interact with target of the invention proteins. Protein expression is driven from the CMV promoter. The Zeocin resistance gene present in the vector allows for selection of mammalian cells expressing the protein, and the ampicillin resistance gene permits selection of the plasmid in E. coli.

PsecFc: A target of the invention ORF, or portions thereof, is also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of a target of the invention protein, while fusing the IgGK signal sequence to N-terminus. Target of the invention fusions utilizing the murine IgG1 Fc region are also used. The resulting recombinant target of the invention proteins are optimized for secretion into the media of transfected mammalian cells, and can be used as immunogens or to identify proteins such as ligands or receptors that interact with a target of the invention protein. Protein expression is driven from the CMV promoter. The hygromycin resistance gene present in the vector allows for selection of mammalian cells that express the recombinant protein, and the ampicillin resistance gene permits selection of the plasmid in E. coli.

pSRα Constructs: To generate mammalian cell lines that express a target of the invention constitutively, a target of the invention ORF, or portions thereof, are cloned into pSRα constructs. Amphotropic and ecotropic retroviruses are generated by transfection of pSRα constructs into the 293T-10A1 packaging line or co-transfection of pSRα and a helper plasmid (containing deleted packaging sequences) into the 293 cells, respectively. The retrovirus is used to infect a variety of mammalian cell lines, resulting in the integration of the cloned gene, a target of the invention, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in E. coli. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of a target of the invention sequence to allow detection using anti-Flag antibodies. For example, the FLAG™ sequence 5' gat tac aag gat gac gac gat aag 3' (SEQ ID NO: 188) is added to cloning primer at the 3' end of the ORF. Additional pSRα constructs are made to produce both amino-terminal and carboxyl-terminal GFP and myc/6×His fusion proteins of the full-length target of the invention proteins.

Additional Viral Vectors: Additional constructs are made for viral-mediated delivery and expression of a target of the invention. High virus titer leading to high level expression of a target of the invention is achieved in viral delivery systems such as adenoviral vectors and herpes amplicon vectors. A target of the invention coding sequence or fragments thereof is amplified by PCR and subcloned into the AdEasy shuttle vector (Stratagene). Recombination and virus packaging are performed according to the manufacturer's instructions to generate adenoviral vectors. Alternatively, target of the invention coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of a target of the invention in mammalian cells, coding sequences of a target of the invention, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant targets of the invention. These vectors are thereafter used to control expression of a target of the invention in various cell lines such as PC3, NIH 3T3, 293 or rat-1 cells.

B. Baculovirus Expression Systems

To generate recombinant target of the invention proteins in a baculovirus expression system, a target of the invention ORF, or portions thereof, are cloned into the baculovirus transfer vector pBlueBac 4.5 (Invitrogen), which provides a His-tag at the N-terminus. Specifically, pBlueBac-target of the invention nucleic acid sequence is co-transfected with helper plasmid pBac-N-Blue (Invitrogen) into SF9 (Spodoptera frugiperda) insect cells to generate recombinant baculovirus (see Invitrogen instruction manual for details). Baculovirus is then collected from cell supernatant and purified by plaque assay.

Recombinant target of the invention protein is then generated by infection of HighFive insect cells (Invitrogen) with purified baculovirus. Recombinant target of the invention protein can be detected using anti-target of the invention or anti-His-tag antibody. Target of the invention protein can be purified and used in various cell-based assays or as immunogen to generate polyclonal and monoclonal antibodies specific for a target of the invention.

Example 8

Antigenicity Profiles and Secondary Structure

FIG. 5, FIG. 6, FIG. 7, FIG. 8, and FIG. 9 depict graphically five amino acid profiles of the target of the invention amino acid sequences.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of the target of the invention proteins. Each of the above amino acid profiles were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus be available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible for immune recognition, such as by antibodies.

Antigenic sequences of the target of the invention proteins indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-target of the invention antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the target of the invention variant proteins. In particular, peptide immunogens for target of the invention proteins can comprise, a peptide region of at least 5 amino acids of a protein of the invention in any whole number increment up to an entire protein that includes an amino acid position having a value greater than 0.5 in the Hydrophilicity profile of FIG. 5; a peptide region of at least 5 amino acids of a protein of the invention in any whole number increment up to the entire protein that includes an amino acid position having a value less than 0.5 in the Hydropathicity profile of FIG. 6; a peptide region of at least 5 amino acids of a protein of the invention in any whole number increment up to the entire protein that includes an amino acid position having a value greater than 0.5 in the Percent Accessible Residues profile of FIG. 7; a peptide region of at least 5 amino acids of a protein of the invention in any whole number increment up to the entire protein that includes an amino acid position having a value greater than 0.5 in the Average Flexibility profile on FIG. 8; and, a peptide region of at least 5 amino acids of a protein of the invention in any whole number increment up to the entire protein that includes an amino acid position having a value greater than 0.5 in the Beta-turn profile of FIG. 9.

All immunogens of the invention, whether peptides or nucleic acids, can be embodied in human unit dose form, or comprised by a composition that includes a pharmaceutical excipient compatible with human physiology.

The secondary structure of a protein of the invention, namely the predicted presence and location of alpha helices, extended strands, and random coils, is predicted from the primary amino acid sequence using the HNN—Hierarchical Neural Network method. The analysis provides the data set forth in FIG. 10 on a protein by protein basis.

Analysis for the presence of transmembrane domains in a protein of the invention was carried out using a variety of transmembrane prediction algorithms. The programs provide the data summarized in Table XXI on a protein by protein basis.

Example 9

Generation of Polyclonal Antibodies of the Invention

Polyclonal antibodies can be raised in a mammal, for example, by one or more injections of an immunizing agent (e.g., a protein of the invention) and, if desired, an adjuvant. Typically, the immunizing agent and/or adjuvant will be injected in the mammal by multiple subcutaneous or intraperitoneal injections. In addition to immunizing with a full length protein of the invention such as that set forth in FIG. 2, computer algorithms are employed in design of immunogens that, based on amino acid sequence analysis contain characteristics of being antigenic and available for recognition by the immune system of the immunized host (see the Example entitled "Antigenicity Profiles"). Such regions would be predicted to be hydrophilic, flexible, in beta-turn conformations, and/or be exposed on the surface of the protein (see, e.g., FIG. 5, FIG. 6, FIG. 7, FIG. 8, and FIG. 9 for amino acid profiles that indicate such regions of a protein of the invention).

For example, of FIG. 2 recombinant bacterial fusion proteins or peptides containing hydrophilic, flexible, beta-turn regions, generally found in regions between transmembrane domains and at the amino and carboxyl termini, are used as antigens to generate polyclonal antibodies in New Zealand White rabbits. Examples of such regions can be extracellular or intracellular. In addition, the amino-terminal region of a variant that is not present in a respective variant can be used as an immunogen. Antibodies to such regions are useful to distinguish one variant protein from another variant of that target. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids from a protein of the invention is conjugated to KLH and used to immunize the rabbit. Alternatively the immunizing agent can include all or portions of the of a protein of the invention e.g. in FIG. 2, analogs or fusion proteins thereof. For example, a FIG. 2 amino acid sequence can be fused using recombinant DNA techniques to any one of a variety of fusion protein partners that are well known in the art, such as glutathione-5-transferase (GST) and HIS tagged fusion proteins. Such fusion proteins are purified from induced bacteria using the appropriate affinity matrix.

In one embodiment, a GST-fusion protein encoding amino acids of a protein of the invention is produced and purified and used as immunogen. Other recombinant bacterial fusion proteins that can be employed include maltose binding protein, LacZ, thioredoxin, NusA, or an immunoglobulin constant region (see the Example entitled "Production of Recombinant Targets of the Invention in Prokaryotic Systems" and Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L. (1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the Example entitled "Production of Recombinant Targets of the Invention in Eukaryotic Systems"), and retain post-translational modifications such as glycosylations found in native protein. In one embodiment, amino acids from a protein of the invention are cloned into the Tag5 mammalian secretion vector. The recombinant protein is purified by metal chelate chromatography from tissue culture supernatants of 293T cells stably expressing the recombinant vector. The purified Tag5-produced protein of the invention is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with Tag5-produced protein of the invention, a full-length FIG. 2 cDNA is cloned into pCDNA 3.1 myc-his expression vector (Invitrogen, see the Example entitled "Production of Recombinant Targets of the Invention in Eukaryotic Systems"). After transfection of the constructs into 293T cells, cell lysates are probed with the respective anti-protein of the invention antibodies and with anti-His antibody (Santa Cruz Biotechnologies, Santa Cruz, Calif.) to determine specific reactivity of the antibodies to the respective denatured protein of the invention using the Western blot technique. Immunoprecipitation and flow cytometric analyses of 293T and other recombinant of FIG. 2—expressing cells determine recognition of native protein by the antibodies. In addition, Western blot, immunoprecipitation, fluorescent microscopy, and flow cytometric techniques using cells that endogenously express the protein of the invention are carried out to test specificity.

Anti-serum from rabbits immunized with target of the invention fusion proteins, such as GST and MBP fusion proteins, are purified by depletion of antibodies reactive to the fusion partner sequence by passage over an affinity column containing the fusion partner either alone or in the context of an irrelevant fusion protein. For example, antiserum derived from a GST- of a FIG. 2 fusion protein is first purified by passage over a column of GST protein covalently coupled to AffiGel matrix (BioRad, Hercules, Calif.). The antiserum is then affinity purified by passage over a column composed of a MBP-fusion protein also comprising those amino acids covalently coupled to Affigel matrix. The serum is then further purified by protein G affinity chromatography to isolate the IgG fraction. Sera from other His-tagged antigens and peptide immunized rabbits as well as fusion partner depleted sera are affinity purified by passage over a column matrix composed of the original protein immunogen or free peptide.

Example 10

Generation of Monoclonal Antibodies (mAbs) of the Invention

In one embodiment, therapeutic mAbs to a protein of the invention comprise those that react with epitopes of the protein that would disrupt or modulate the biological function of a protein of the invention, for example antibodies that disrupt its interaction with ligands and binding partners. Therapeutic mAbs also comprise those that specifically bind epitopes of a protein of the invention exposed on the cell surface and thus are useful in targeting mAb-toxin conjugates. Immunogens for generation of such mAbs include those designed to encode or contain an entire protein of the invention, regions of a protein of the invention predicted to be antigenic from computer analysis of the amino acid sequence (see, e.g., FIG. 5, FIG. 6, FIG. 7, FIG. 8, or FIG. 9, and the Example entitled "Antigenicity Profiles"), and regions such as extracellular domains. Immunogens include peptides, recombinant bacterial proteins, and mammalian expressed Tag 5 proteins and human and murine IgG FC fusion proteins. In addition, cells expressing high levels of a protein of the invention, such as 293T-protein of the invention or 300.19-protein of the invention murine Pre-B cells, are used to immunize mice.

To generate mAbs to a protein of the invention, mice are first immunized intraperitoneally (IP) with, typically, 10-50 μg of protein immunogen or $10^7$ protein of the invention-expressing cells mixed in complete Freund's adjuvant. Mice are then subsequently immunized IP every 2-4 weeks with, typically, 10-50 μg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding a protein of the invention sequence is used to immunize mice by direct injection of the plasmid DNA. For example, amino acids from a protein of the invention are cloned into the Tag5 mammalian secretion vector and the recombinant vector is used as immunogen. In another example the same amino acids are cloned into an Fc-fusion secretion vector in which the protein of the invention sequence is fused at the amino-terminus to an IgK leader sequence and at the carboxyl-terminus to the coding sequence of the human or murine IgG Fc region. This recombinant vector is then used as immunogen. The plasmid immunization protocols are used in combination with purified proteins expressed from the same vector and with cells expressing protein of the invention.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating monoclonal antibodies reactive with a protein of the invention, a Tag5-protein of the invention antigen is expressed and purified from stably transfected 293T cells. Balb C mice are initially immunized intraperitoneally with 25 μg of the Tag5-protein of the invention mixed in complete Freund's adjuvant. Mice are subsequently immunized every two weeks with 25 μg of the antigen mixed in incomplete Freund's adjuvant for a total of three immunizations. ELISA using the Tag5 antigen determines the titer of serum from immunized mice. Reactivity and specificity of serum to full length protein of the invention is monitored by Western blotting, immunoprecipitation and flow cytometry using 293T cells transfected with an expression vector encoding the protein of the invention cDNA (see e.g., the Example entitled "Production of Recombinant Targets of the Invention in Eukaryotic Systems"). Other recombinant protein of the invention-expressing cells or cells endogenously expressing a protein of the invention are also used. Mice showing the strongest reactivity are rested and given a final injection of Tag5 antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify protein of the invention-specific antibody-producing clones.

The binding affinity of a monoclonal antibody is determined using standard technologies. Affinity measurements quantify the strength of antibody to epitope binding and are used to help define which monoclonal antibodies reactive with proteins of the invention are suitable for diagnostic or therapeutic use, as appreciated by one of skill in the art. The BIAcore system (Uppsala, Sweden) is a useful method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 11

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and IC$_{50}$≧[HLA], the measured IC$_{50}$ values are reasonable approximations of the true K$_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the IC$_{50}$ of a positive control for inhibition by the IC$_{50}$ for each tested peptide (typically unlabeled versions of the radiolabeled probe peptide). For database purposes, and inter-experiment comparisons, relative binding values are compiled. These values can subsequently be converted back into IC$_{50}$ nM values by dividing the IC$_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides.

Example 12

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" (and, e.g., Tables V-XVIII, and Tables XXIII to XXVI) employ the protein sequence data from the protein set forth in FIGS. 2 and 3.

Computer searches for epitopes bearing HLA Class I or Class II supermotifs or motifs are performed as follows. All translated FIG. 2 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or ΔG) of peptide-HLA molecule interactions can be approximated as a linear polynomial function of the type:

$$"\Delta G" = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount j$_i$ to the free energy of binding of the peptide irrespective of the sequence of the rest of the peptide.

The method of derivation of specific algorithm coefficients has been described in Gulukota et al., *J. Mol. Biol.* 267:1258-126, 1997; (see also Sidney et al., *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of j$_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Peptides

Protein sequences from FIG. 2 proteins are scanned utilizing motif identification software, to identify 8-, 9-10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-Bearing Epitopes

The FIG. 2 protein sequence(s) scanned above are also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The FIG. 2 protein(s) scanned above are also analyzed for the presence of 8-, 9-10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of ≦500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the FIG. 2 proteins is performed to identify HLA-A1- and A24-motif-containing sequences.

High affinity and/or cross-reactive binding epitopes that bear other motif and/or supermotifs are identified using analogous methodology.

Example 13

Confirmation of Immunogenicity

Cross-reactive candidate CTL A2-supermotif-bearing peptides that are identified as described herein are selected to confirm in vitro immunogenicity. Conformation is performed using the following methodology:

Target Cell Lines for Cellular Screening:

The 221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 μg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the Detacha-Bead® reagent. Typically about $200\text{-}250 \times 10^6$ PBMC are processed to obtain $24 \times 10^6$ CD8+ T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of $20 \times 10^6$ cells/ml. The magnetic beads are washed 3 times with PBS/AB serum, added to the cells (140 μl beads/$20 \times 10^6$ cells) and incubated for 1 hour at 4° C. with continuous mixing. The beads and cells are washed 4× with PBS/AB serum to remove the nonadherent cells and resuspended at $100 \times 10^6$ cells/ml (based on the original cell number) in PBS/AB serum containing 100 μl/ml Detacha-Bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 μg/ml of peptide at a cell concentration of $1\text{-}2 \times 10^6$/ml in the presence of 3 μg/ml $\beta_2$-microglobulin for 4 hours at 20° C. The DC are then irradiated (4,200 rads), washed 1 time with medium and counted again.

Setting up induction cultures: 0.25 ml cytokine-generated DC (at $1 \times 10^5$ cells/ml) are co-cultured with 0.25 ml of CD8+ T-cells (at $2 \times 10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5 \times 10^6$ cells/ml and irradiated at ~4200 rads. The PBMCs are plated at $2 \times 10^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml $\beta_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 50 IU/ml (Tsai et al., *Critical Reviews in Immunology*, 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 µCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3 \times 10^6$/ml (an NK-sensitive erythroblastoma cell line used to reduce non-specific lysis). Target cells (100 µl) and effectors (100 µl) are plated in 96 well round-bottom plates and incubated for 5 hours at 37° C. At that time, 100 µl of supernatant are collected from each well and percent lysis is determined according to the formula:

[(cpm of the test sample–cpm of the spontaneous $^{51}$Cr release sample)/(cpm of the maximal $^{51}$Cr release sample–cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 µg/ml 0.1M NaHCO$_3$, pH8.2) overnight at 4° C. The plates are washed with Ca$^{2+}$, Mg$^{2+}$-free PBS/0.05% Tween 20 and blocked with PBS/10% FCS for two hours, after which the CTLs (100 µl/well) and targets (100 µl/well) are added to each well, leaving empty wells for the standards and blanks (which received media only). The target cells, either peptide-pulsed or endogenous targets, are used at a concentration of $1 \times 10^6$ cells/ml. The plates are incubated for 48 hours at 37° C. with 5% CO$_2$.

Recombinant human IFN-gamma is added to the standard wells starting at 400 pg or 1200 pg/100 microliter/well and the plate incubated for two hours at 37° C. The plates are washed and 100 µl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, $5 \times 10^4$ CD8+ cells are added to a T25 flask containing the following: $1 \times 10^6$ irradiated (4,200 rad) PBMC (autologous or allogeneic) per ml, $2 \times 10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 µM 2-mercaptoethanol, L-glutamine and penicillin/streptomycin. Recombinant human IL2 is added 24 hours later at a final concentration of 200 IU/ml and every three days thereafter with fresh media at 50 IU/ml. The cells are split if the cell concentration exceeds $1 \times 10^6$/ml and the cultures are assayed between days 13 and 15 at E:T ratios of 30, 10, 3 and 1:1 in the $^{51}$Cr release assay or at $1 \times 10^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and $5 \times 10^4$ CD8$^+$ cells are added to a T25 flask containing the following: $1 \times 10^6$ autologous PBMC per ml which have been peptide-pulsed with 10 µg/ml peptide for two hours at 37° C. and irradiated (4,200 rad); $2 \times 10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses a FIG. 2 protein. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 14

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with protein(s) of FIG. 2—expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and I. Chen, John Wiley & Sons, England, 1999).

Thus, by the use of single amino acid substitutions, the binding properties and/or cross-reactivity of peptide ligands for HLA supertype molecules can be modulated.

Example 15

Identification of HLA-DR Binding Motifs in Proteins of FIG. 2

Peptide epitopes bearing an HLA class II supermotif or motif are identified and confirmed as outlined below using methodology similar to that described for HLA Class I peptides.

Selection of HLA-DR-Supermotif-Bearing Epitopes.

To identify HLA class II HTL epitopes derived from a protein of FIG. 2, a FIG. 2 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160:3363-3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but also additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The protein in FIG. 2—derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. Proteins in FIG. 2—derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, FIG. 2 antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity of 1 µM or better, i.e., less than 1 µM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 16

Immunogenicity of HTL Epitopes Derived from a Protein of FIG. 2

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have proteins of FIG. 2—expressing tumors.

Example 17

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf-1-(SQRT(1-af)) (see, e.g., Sidney et al., *Human Immunol.* 45:79-93, 1996). To obtain overall phenotypic frequencies, cumulative gene frequencies are calculated, and the cumulative antigen frequencies derived by the use of the inverse formula $[af=1-(1-Cgf)^2]$.

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%. An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 18

CTL Recognition of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}Cr$ labeled Jurkat-A2.1/$K^b$ target cells in the absence or presence of peptide, and also tested on $^{51}Cr$ labeled target cells bearing the endogenously synthesized antigen, i.e. cells that are stably transfected with a gene of FIG. 2—related expression vector.

The results demonstrate that CTL lines obtained from animals primed with peptide epitopes recognize endogenously synthesized FIG. 2 antigens. The choice of transgenic mouse model to be used for such an analysis depends upon the epitope(s) that are being evaluated. In addition to HLA-A*0201/$K^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 19

Activity of CTL-HTL Conjugated Epitopes in Transgenic Mice

This example illustrates the induction of CTLs and HTLs in transgenic mice, by use of a protein of FIG. 2—derived CTL and HTL peptide vaccine compositions. The vaccine compositions used herein comprise peptides to be administered to a patient with a protein of FIG. 2—expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al, *J. Immunol.* 159:4753-4761, 1997). For example, A2/$K^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/$K^b$ chimeric gene (e.g., Vitiello et al., *J. Exp. Med* 173:1007, 1991)

In vitro CTL activation: One week after priming, spleen cells (30×10$^6$ cells/flask) are co-cultured at 37° C. with syngeneic, irradiated (3000 rads), peptide coated lymphoblasts (10×10$^6$ cells/flask) in 10 ml of culture medium/T25 flask. After six days, effector cells are harvested and assayed for cytotoxic activity.

Assay for cytotoxic activity: Target cells (1.0 to 1.5×10$^6$) are incubated at 37° C. in the presence of 200 µl of $^{51}$Cr. After 60 minutes, cells are washed three times and resuspended in R10 medium. Peptide is added where required at a concentration of 1 µg/ml. For the assay, 10$^4$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100× (experimental release−spontaneous release)/(maximum release−spontaneous release). To facilitate comparison between separate CTL assays run under the same conditions, % $^{51}$Cr release data is expressed as lytic units/10$^6$ cells. One lytic unit is arbitrarily defined as the number of effector cells required to achieve 30% lysis of 10,000 target cells in a six hour $^{51}$Cr release assay. To obtain specific lytic units/10$^6$, the lytic units/10$^6$ obtained in the absence of peptide is subtracted from the lytic units/10$^6$ obtained in the presence of peptide. For example, if 30% $^{51}$Cr release is obtained at the effector (E):target (T) ratio of 50:1 (i.e., 5×10$^5$ effector cells for 10,000 targets) in the absence of peptide and 5:1 (i.e., 5×10$^4$ effector cells for 10,000 targets) in the presence of peptide, the specific lytic units would be: [(1/50,000)−(1/500,000)]×10$^6$=18 LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity". Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 20

Selection of CTL and HTL Epitopes for Inclusion in a Vaccine Specific for a Protein of FIG. 2

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with FIG. 2 protein clearance. The number of epitopes used depends on observations of patients who spontaneously clear a FIG. 2 protein. For example, if it has been observed that patients who spontaneously clear a FIG. 2 protein generate an immune response to at least three (3) epitopes from a protein of FIG. 2 antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in FIG. 2 proteins, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress a FIG. 2 protein.

Example 21

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived from a protein of FIG. 2, are selected such that multiple supermotifs/motifs are represented to ensure broad population coverage. Similarly, HLA class II epitopes are selected from a FIG. 2 protein to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 22

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/$K^b$ transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-$A^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci USA* 95:7648-53, 1998; Hanke and McMichael, *Immunol. Letters* 66:177-181, 1999; and Robinson et al., *Nature Med* 5:526-34, 1999).

For example, the efficacy of the DNA minigene used in a prime boost protocol is initially evaluated in transgenic mice. In this example, A2.1/$K^b$ transgenic mice are immunized 1M with 100 μg of a DNA minigene encoding the immunogenic peptides including at least one HLA-A2 supermotif-bearing peptide. After an incubation period (ranging from 3-9 weeks), the mice are boosted IP with $10^7$ pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 23

Peptide Compositions for Prophylactic Uses

Vaccine compositions of the present invention can be used to prevent a gene of FIG. 2 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a protein of FIG. 2—associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100-5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against protein of FIG. 2—associated disease.

Alternatively, a composition typically comprising transfecting agents is used for the administration of a nucleic acid-based vaccine in accordance with methodologies known in the art and disclosed herein.

Example 24

Polyepitopic Vaccine Compositions Derived from Native Protein Sequence of FIG. 2

A native FIG. 2 protein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested"

epitopes is selected; it can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from a protein antigen of the invention and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (excluding an analoged embodiment) directs the immune response to multiple peptide sequences that are actually present in native proteins of the invention, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 25

Polyepitopic Vaccine Compositions from Multiple Antigens

The protein peptide epitopes of the present invention are used in conjunction with epitopes from other target tumor-associated antigens (such as from one or more proteins of FIG. 2), to create a vaccine composition that is useful for the prevention or treatment of cancer that expresses protein(s) of the invention and such other antigens. For example, a vaccine composition can be provided as a single polypeptide that incorporates multiple epitopes from a protein of the invention as well as tumor-associated antigens that are often expressed with the particular target cancer that is also associated with expression of a protein of the invention, or can be administered as a composition comprising a cocktail of one or more discrete epitopes. Alternatively, the vaccine can be administered as a minigene construct or as dendritic cells which have been loaded with the peptide epitopes in vitro.

Example 26

Use of Peptides to Evaluate an Immune Response

Peptides of the invention may be used to analyze an immune response for the presence of specific antibodies, CTL or HTL directed to a protein of the invention. Such an analysis can be performed in a manner described by Ogg et al., Science 279:2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, a protein of FIG. 2 HLA-A*0201-specific CTL frequencies from HLA A*0201-positive individuals at different stages of disease or following immunization comprising a protein of FIG. 2 peptide containing an A*0201 motif. Tetrameric complexes are synthesized as described (Musey et al., N. Engl. J. Med. 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tricolor analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the protein of the invention epitopes, and thus the status of exposure to proteins of the invention, or exposure to a vaccine that elicits a protective or therapeutic response.

Example 27

Use of Peptide Epitopes to Evaluate Recall Responses

The peptide epitopes of the invention are used as reagents to evaluate T cell responses, such as acute or recall responses, in patients. Such an analysis may be performed on patients who have recovered from a protein of the invention-associated disease or who have been vaccinated with a protein of the invention vaccine.

For example, the class I restricted CTL response of persons who have been vaccinated may be analyzed. The vaccine may be any protein of the invention vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128-140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 µl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., *Nature Med.* 2:1104, 1108, 1996; Rehermann et al., *J. Clin. Invest.* 97:1655-1665, 1996; and Rehermann et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to proteins of the invention or a protein of the invention-related vaccine.

Similarly, Class II restricted HTL responses may also be analyzed. Purified PBMC are cultured in a 96-well flat bottom plate at a density of $1.5 \times 10^5$ cells/well and are stimulated with 10 µg/ml synthetic peptide of the invention, a whole protein of the invention antigens, or PHA. Cells are routinely plated in replicates of 4-6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 28

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;
Group II: 3 subjects are injected with placebo and 6 subjects are injected with 50 µg peptide composition;
Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 29

Phase it Trials in Patients Expressing a Gene of the Invention

Phase II trials are performed to study the effect of administering the CTL-HTL peptide compositions to patients having a cancer that expresses genes of the invention. The main objectives of the trial are to determine an effective dose and regimen for inducing CTLs in cancer patients that express a gene(s) of the invention, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses a gene of the invention.

Clinical manifestations or antigen-specific T-cell responses are monitored to assess the effects of administering the peptide compositions. The vaccine composition is found to be both safe and efficacious in the treatment of a gene of the invention-associated disease.

Example 30

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of 'Minigene' Multi-Epitope DNA Plasmids" in the form of naked nucleic acid administered IM (or SC or ID) in the amounts of 0.5-5 mg at multiple sites. The nucleic acid (0.1 to 1000 µg) can also be administered using a gene gun. Following an incubation period of 3-4 weeks, a booster dose is then administered. The booster can be recombinant fowlpox virus administered at a dose of $5 \times 10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against of FIG. 2 is generated.

Example 31

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the proteins of the invention from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., Nature Med. 4:328, 1998; Nature Med. 2:52, 1996 and Prostate 32:272, 1997). Although $2-50 \times 10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5 \times 10^6$ DC, then the patient will be injected with a total of $2.5 \times 10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to protein antigens of the invention can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 32

An Alternative Method of Identifying Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigens of interest, e.g. antigens of FIG. 2. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., J. Immunol. 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode proteins of the invention, to isolate peptides corresponding to proteins of FIG. 2 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 33

Complementary Polynucleotides

Sequences complementary to FIG. 2 protein-encoding sequences, or any parts thereof, are used to detect, decrease, or inhibit expression of naturally occurring proteins of the invention. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequences of proteins of the invention. To inhibit transcription, a complementary oligonucleotide is designed from the most unique 5' sequence and used to prevent promoter binding to the coding sequence. To inhibit translation, a complementary oligonucleotide is designed to prevent ribosomal binding to a FIG. 2 protein-encoding transcript.

Example 34

Purification of Naturally-Occurring or Recombinant FIG. 2 Proteins Using Specific Antibodies Naturally occurring or recombinant FIG. 2 proteins are substantially purified by immunoaffinity chromatography using antibodies specific for a protein of the invention. An immunoaffinity column is constructed by covalently coupling, e.g., anti-protein of FIG. 2 antibodies to an activated chromatographic resin, such as CNBr-activated SEPHAROSE (Amersham Pharmacia Biotech). After the coupling, the resin is blocked and washed according to the manufacturer's instructions.

Media containing protein(s) of the invention are passed over the immunoaffinity column, and the column is washed under conditions that allow the preferential absorbance of proteins of the invention (e.g., high ionic strength buffers in the presence of detergent). The column is eluted under conditions that disrupt antibody/FIG. 2 protein binding (e.g., a buffer of pH 2 to pH 3, or a high concentration of a chaotrope, such as urea or thiocyanate ion), and GCR.P is collected.

Example 35

Identification of Molecules which Interact with Proteins of the Invention

FIG. 2 proteins, or biologically active fragments thereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled FIG. 2 proteins, washed, and any wells with labeled FIG. 2 protein complexes are assayed. Data obtained using different concentrations of FIG. 2 proteins are used to calculate values for the number, affinity, and association of FIG. 2 proteins with the candidate molecules.

Example 36

In Vivo Assay for Tumor Growth Promotion

The effect of a FIG. 2 protein on tumor cell growth is evaluated in vivo by gene overexpression in tumor-bearing mice. For example, SCID mice are injected subcutaneously on each flank with $1 \times 10^6$ of either PC3, DU145 or 3T3 cells containing tkNeo empty vector or a nucleic acid sequence of the invention. At least two strategies can be used: (1) Constitutive expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tet, etc., provided such promoters are compatible with the host cell systems. Tumor volume is then monitored at the appearance of palpable tumors and followed over time to determine if the cells expressing a gene of the invention grow at a faster rate and whether tumors of a FIG. 2 protein-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine if a protein of the invention has an effect on local growth in the prostate or on the ability of the cells to metastasize, specifically to lungs, lymph nodes, and bone marrow.

The assay is also useful to determine the inhibitory effect of candidate therapeutic compositions, such as for example, FIG. 2 protein-related intrabodies, FIG. 2 gene-related antisense molecules and ribozymes.

Example 37

Tumors In Vivo, with Monoclonals Specific to a FIG. 2 Protein

The significant expression of a FIG. 2 proteins in cancer tissues of Table I and its restrictive expression in normal tissues, together with its expected cell surface expression, makes FIG. 2 proteins excellent targets for antibody therapy. Similarly, FIG. 2 proteins are a target for T cell-based immunotherapy. Thus, for FIG. 2 genes expressed, e.g., in prostate cancer, the therapeutic efficacy of anti-FIG. 2 protein mAbs in human prostate cancer xenograft mouse models is evaluated by using androgen-independent LAPC-4 and LAPC-9 xenografts (Craft, N., et al., Cancer Res, 1999. 59(19): p. 5030-6) and the androgen independent recombinant cell line PC3- of FIG. 2 (see, e.g., Kaighn, M. E., et al., Invest Urol, 1979. 17(1): p. 16-23); analogous models are used for other cancers.

Antibody efficacy on tumor growth and metastasis formation is studied, e.g., in a mouse orthotopic prostate cancer xenograft models and mouse kidney xenograft models. The antibodies can be unconjugated, as discussed in this Example, or can be conjugated to a therapeutic modality, as appreciated in the art. Anti-FIG. 2 protein mAbs inhibit formation of both the androgen-dependent LAPC-9 and androgen-independent PC3-FIG. 2 protein tumor xenografts. Anti-FIG. 2 protein mAbs also retard the growth of established orthotopic tumors and prolonged survival of tumor-bearing mice. These results indicate the utility of anti-FIG. 2 protein mAbs in the treatment of local and advanced stages of prostate cancer. (See, e.g., Saffran, D., et al., PNAS 10:1073-1078.)

Administration of the anti-FIG. 2 protein mAbs lead to retardation of established orthotopic tumor growth and inhibition of metastasis to distant sites, resulting in a significant prolongation in the survival of tumor-bearing mice. These studies indicate that proteins of the invention are attractive targets for immunotherapy and demonstrate the therapeutic potential of anti-FIG. 2 protein mAbs for the treatment of local and metastatic cancer. This example demonstrates that unconjugated FIG. 2 protein-related monoclonal antibodies are effective to inhibit the growth of human prostate tumor xenografts and human kidney xenografts grown in SCID mice; accordingly a combination of such efficacious monoclonal antibodies is also effective.

Tumor Inhibition Using Multiple Unconjugated mAbs

Materials and Methods

FIG. 2 Protein-Related Monoclonal Antibodies:

Monoclonal antibodies are raised against proteins of the invention as described in Example 10. The antibodies are characterized by ELISA, Western blot, FACS, and immunoprecipitation for their capacity to bind to the respective protein of the invention. Epitope mapping data for, e.g., the anti-FIG. 2 protein mAbs, as determined by ELISA and Western analysis, indicate that the antibodies recognize epitopes on the respective FIG. 2 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at $-20°$ C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC-9 prostate tumor xenografts.

Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., supra). The prostate carcinoma cell line PC3 (American Type Culture Collection) is maintained in RPMI supplemented with L-glutamine and 10% FBS.

Recombinant PC3 and 3T3-cell populations expressing a protein of the invention are generated by retroviral gene transfer as described in Hubert, R. S., et al., STEAP: a prostate-specific cell-surface antigen highly expressed in human prostate tumors. Proc Natl Acad Sci USA, 1999. 96(25): p. 14523-8. Anti-protein of the invention staining is detected by using an FITC-conjugated goat anti-mouse antibody (Southern Biotechnology Associates) followed by analysis on a Coulter Epics-XL flow cytometer.

Xenograft Mouse Models.

Subcutaneous (s.c.) tumors are generated by injection of $1 \times 10^6$ LAPC-9, PC3, recombinant PC3-protein of the invention, 3T3 or recombinant 3T3-protein of the invention cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of, e.g., anti-FIG. 2 protein mAbs are determined by a capture ELISA kit (Bethyl Laboratories, Montgomery, Tex.). (See, e.g., Saffran, D., et al., PNAS 10:1073-1078.)

Orthotopic injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 or PC3 cells ($5 \times 10^5$) mixed with Matrigel are injected into each dorsal lobe in a 10-μl volume. To monitor tumor growth, mice are bled on a weekly basis for determination of PSA levels. The mice are segregated into groups for the appropriate treatments, with anti-protein of the invention or control mAbs being injected i.p.

Anti-FIG. 2 Protein mAbs Inhibit Growth of Respective FIG. 2 Protein-Expressing Xenograft-Cancer Tumors The effect of anti-FIG. 2 protein mAbs on tumor formation is tested by using LAPC-9 and recombinant PC3-protein of the invention orthotopic models. As compared with the s.c. tumor model, the orthotopic model, which requires injection of tumor cells directly in the mouse prostate or kidney, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allowed us to follow the therapeutic effect of mAbs on clinically relevant end points.

Accordingly, tumor cells are injected into the mouse prostate or kidney, and 2 days later, the mice are segregated into two groups and treated with either: a) 200-500 μg, of anti-FIG. 2 protein Ab, or b) PBS three times per week for two to five weeks.

A major advantage of the orthotopic prostate-cancer model is the ability to study the development of metastases. Formation of metastasis in mice bearing established orthotopic tumors is studied by IHC analysis on lung sections using an antibody against a prostate-specific cell-surface protein STEAP expressed at high levels in LAPC-9 xenografts (Hubert, R. S., et al., Proc Natl Acad Sci USA, 1999. 96(25): p. 14523-8).

Mice bearing established orthotopic LAPC-9 or recombinant PC3-FIG. 2 protein tumors are administered 1000 μg injections of either anti-FIG. 2 protein mAbs or PBS over a 4-week period. Mice in both groups are allowed to establish a high tumor burden (PSA levels greater than 300 ng/ml for IAPC-9), to ensure a high frequency of metastasis formation in mouse lungs. Mice then are killed and their prostate and lungs are analyzed for the presence of tumor cells by IHC analysis.

These studies demonstrate a broad anti-tumor efficacy of anti-FIG. 2 protein antibodies on initiation and progression of prostate cancer in xenograft mouse models. Anti-FIG. 2 protein antibodies inhibit tumor formation of both androgen-dependent and androgen-independent tumors, retard the growth of already established tumors, and prolong the survival of treated mice. Moreover, anti-FIG. 2 protein mAbs demonstrate a dramatic inhibitory effect on the spread of local prostate tumor to distal sites, even in the presence of a large tumor burden. Thus, anti-FIG. 2 protein mAbs are efficacious on major clinically relevant end points (tumor growth), prolongation of survival, and health.

Example 38

Therapeutic and Diagnostic Use of Antibodies Specific to a Protein of FIG. 2

Anti-protein of FIG. 2 monoclonal antibodies are safely and effectively used for diagnostic, prophylactic, prognostic and/or therapeutic purposes in humans. Western blot and immunohistochemical analysis of cancer tissues and cancer xenografts with anti-protein of FIG. 2 mAb show strong extensive staining in carcinoma but significantly lower or undetectable levels in normal tissues. Detection of a protein of FIG. 2 in carcinoma and in metastatic disease demonstrates the usefulness of the mAb as a diagnostic and/or prognostic indicator. Anti-protein of FIG. 2 antibodies are therefore used in diagnostic applications such as immunohistochemistry of biopsy specimens to detect cancer from suspect patients.

As determined by flow cytometry, anti-protein of FIG. 2 mAbs specifically bind to carcinoma cells. Thus, anti-protein of FIG. 2 antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of a protein of FIG. 2. Shedding or release of an extracellular domain of a protein of FIG. 2 into the extracellular milieu, such as that seen for alkaline phosphodiesterase B10 (Meerson, N. R., Hepatology 27:563-568 (1998)), allows diagnostic detection of a protein of FIG. 2 by corresponding anti-protein of FIG. 2 antibodies in serum and/or urine samples from suspect patients.

Anti-protein of FIG. 2 antibodies that specifically bind protein of FIG. 2 are used in therapeutic applications for the treatment of cancers that express that protein of FIG. 2. Anti-protein of FIG. 2 antibodies are used as an unconjugated modality and as a conjugated form in which the antibodies are attached to one of various therapeutic or imaging modalities well known in the art, such as a prodrugs, enzymes or radio-isotopes. In preclinical studies, unconjugated and conjugated anti-protein of FIG. 2 antibodies are tested for efficacy of tumor prevention and growth inhibition in the SCID mouse cancer xenograft models, e.g., kidney cancer models AGS-K3 and AGS-K6, (see, e.g., the Example entitled "Monoclonal Antibody-mediated Inhibition of Prostate Tumors In vivo"). Conjugated and unconjugated anti-protein of FIG. 2 antibodies are used as a therapeutic modality in human clinical trials either alone or in combination with other treatments as described in the following Examples.

Example 39

Human Clinical Trials for the Treatment and Diagnosis of Human Carcinomas Through Use of Human Antibodies Specific for a Protein of FIG. 2 In Vivo Antibodies are used in accordance with the present invention which recognize an epitope of a FIG. 2 protein, and are used in the treatment of certain tumors such as those listed in Table I. Based upon a number of factors, including FIG. 2 protein expression levels, tumors such as those listed in Table I are presently preferred indications. In connection with each of these indications, three clinical approaches are successfully pursued.

I.) Adjunctive therapy: In adjunctive therapy, patients are treated with antibodies of the invention, e.g., antibodies that specifically bind a protein of the invention, in combination with a chemotherapeutic or antineoplastic agent and/or radiation therapy. Primary cancer targets, such as those listed in Table I, are treated under standard protocols by the addition anti-FIG. 2 protein antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-FIG. 2 protein antibodies are utilized in several adjunctive clinical trials in combination with the chemotherapeutic or antineoplastic agents adriamycin (advanced prostate carcinoma), cisplatin (advanced head and neck and lung carcinomas), taxol (breast cancer), and doxorubicin (preclinical).

II.) Monotherapy: In connection with the use of the anti-FIG. 2 protein antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-FIG. 2 protein antibodies, the radiolabeled antibodies are utilized as a diagnostic and/or imaging agent. In such a role, the labeled antibodies localize to both solid tumors, as well as, metastatic lesions of cells expressing a protein of the invention. In connection with the use of the anti-FIG. 2 protein antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-FIG. 2 protein antibody is used as an imaging agent in a Phase I human clinical trial in patients having a carcinoma that expresses a protein of the invention (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified Dose and Route of Administration As appreciated by those of ordinary skill in the art, dosing considerations can be determined through comparison with the analogous products that are in the clinic. Thus, anti-FIG. 2 protein antibodies can be administered with doses in the range of 5 to 400 mg/m$^2$, with the lower doses used, e.g., in connection with safety studies. The affinity of anti-FIG. 2 protein antibodies relative to the affinity of a known antibody for its target is one parameter used by those of skill in the art for determining analogous dose regimens. Further, anti-FIG. 2 protein antibodies that are fully human antibodies, as compared to the chimeric antibody, have slower clearance; accordingly, dosing in patients with such fully human anti-FIG. 2 protein antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults. Three distinct delivery approaches are useful for delivery of anti-FIG. 2 protein antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-FIG. 2 protein antibodies in connection with adjunctive therapy, monotherapy, and as an imaging agent. Trials initially demonstrate safety and thereafter confirm efficacy in repeat doses. Trials are open label comparing standard chemotherapy with standard therapy plus anti-FIG. 2 protein antibodies. As will be appreciated, one criteria that can be utilized in connection with enrollment of patients is FIG. 2 protein expression levels in their tumors as determined e.g. from biopsy specimens. As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express a protein of the invention. Standard tests and follow-ups are utilized to monitor each of these safety concerns. Anti-FIG. 2 protein antibodies are found to be safe upon human administration.

Example 40

Human Clinical Trial Adjunctive Therapy with Human Antibody (Specific to a Protein of FIG. 2) and Chemotherapeutic Agent A phase I human clinical trial is initiated to assess the safety of six intravenous doses of a human anti-FIG. 2 protein antibody in connection with the treatment of a solid tumor, e.g., a cancer of a tissue listed in Table I. In the study, the safety of single doses of anti-FIG. 2 protein antibodies when utilized as an adjunctive therapy to an antineoplastic or chemotherapeutic agent, such as cisplatin, topotecan, doxorubicin, adriamycin, taxol, or the like, is assessed. The trial design includes delivery of six single doses of an anti-FIG. 2 protein antibody with dosage of antibody escalating from approximately about 25 mg/m$^2$ to about 275 mg/m$^2$ over the course of the treatment in accordance with the following schedule:

|  | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express a protein of the invention. Standard tests and follow-up are utilized to monitor each of these safety concerns. Patients are also assessed for clinical outcome, and particularly reduction in tumor mass as evidenced by MRI or other imaging.

The anti-FIG. 2 protein antibodies are demonstrated to be safe and efficacious, Phase II trials confirm the efficacy and refine optimum dosing.

Example 41

Human Clinical Trial: Monotherapy with Human Antibody Specific to a Protein of FIG. 2

Anti-FIG. 2 protein antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-FIG. 2 protein antibodies.

Example 42

Human Clinical Trial: Diagnostic Imaging with Antibody Specific to a Protein of FIG. 2

Once again, as the adjunctive therapy discussed above is safe within the safety criteria discussed above, a human clinical trial is conducted concerning the use of anti-FIG. 2 protein antibodies as a diagnostic imaging agent. The protocol is designed in a substantially similar manner to those described in the art, such as in Divgi et al *J. Natl. Cancer Inst.* 83:97-104 (1991). The antibodies are found to be both safe and efficacious when used as a diagnostic modality.

Example 43

Effects on Tumor Growth and Promotion

The genes in FIG. 2 contribute to the growth of cancer cells. The role of these genes in tumor growth is investigated in a variety of primary and transfected cell lines including prostate, colon, bladder and kidney cell lines as well as NIH 3T3 cells engineered to stably express the gene of interest. Parental cells lacking the gene of interest and cells expressing that gene are evaluated for cell growth using a well-documented proliferation assay (Fraser S P, Grimes J A, Djamgoz M B. Prostate. 2000; 44:61, Johnson D E, Ochieng J, Evans S L. Anticancer Drugs. 1996, 7:288).

To determine the role of genes in FIG. 2 in the transformation process, the effect of individual genes in colony forming assays is investigated. Parental NIH3T3 cells lacking the gene of interest are compared to NHI-3T3 cells expressing that gene, using a soft agar assay under stringent and more permissive conditions (Song Z. et al. Cancer Res. 2000; 60:6730). It is found that genes set forth in FIG. 2 asversely affect transformation.

To determine the role of the genes of FIG. 2 in invasion and metastasis of cancer cells, a well-established assay is used, e.g., a Transwell Insert System assay (Becton Dickinson) (Cancer Res. 1999; 59:6010). Control cells, including prostate, colon, bladder and kidney cell lines lacking the gene of interest are compared to cells expressing that gene. Cells are loaded with the fluorescent dye, calcein, and plated in the top well of the Transwell insert coated with a basement membrane analog. Invasion is determined by fluorescence of cells in the lower chamber relative to the fluorescence of the entire cell population. It is found that genes set forth in FIG. 2 adversely invasion and/or metastasis.

The genes in FIG. 2 also play a role in cell cycle modulation and apoptosis. Parental cells and cells expressing the gene of interest are compared for differences in cell cycle regulation using a well-established BrdU assay (Abdel-Malek Z A. J Cell Physiol. 1988, 136:247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing the gene of interest, including normal and tumor prostate, colon and lung cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by genes of FIG. 2 play a critical role in regulating tumor progression and tumor load.

When a genes set for in FIG. 2, and/or its respective gene product, plays a role in cell growth, transformation, invasion or apoptosis, it is used as a target for diagnostic, prognostic, preventative and therapeutic purposes.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Lengthy table referenced here

US07951375-20110531-T00001

Please refer to the end of the specification for access instructions.

Lengthy table referenced here

US07951375-20110531-T00002

Please refer to the end of the specification for access instructions.

Lengthy table referenced here

US07951375-20110531-T00003

Please refer to the end of the specification for access instructions.

Lengthy table referenced here

US07951375-20110531-T00004

Please refer to the end of the specification for access instructions.

Lengthy table referenced here

US07951375-20110531-T00005

Please refer to the end of the specification for access instructions.

Lengthy table referenced here

US07951375-20110531-T00006

Please refer to the end of the specification for access instructions.

Lengthy table referenced here

US07951375-20110531-T00007

Please refer to the end of the specification for access instructions.

Lengthy table referenced here

US07951375-20110531-T00008

Please refer to the end of the specification for access instructions.

Lengthy table referenced here

US07951375-20110531-T00009

Please refer to the end of the specification for access instructions.

| Lengthy table referenced here |
| --- |
| US07951375-20110531-T00010 |
| Please refer to the end of the specification for access instructions. |

| Lengthy table referenced here |
| --- |
| US07951375-20110531-T00011 |
| Please refer to the end of the specification for access instructions. |

| Lengthy table referenced here |
| --- |
| US07951375-20110531-T00012 |
| Please refer to the end of the specification for access instructions. |

| Lengthy table referenced here |
| --- |
| US07951375-20110531-T00013 |
| Please refer to the end of the specification for access instructions. |

| Lengthy table referenced here |
| --- |
| US07951375-20110531-T00014 |
| Please refer to the end of the specification for access instructions. |

| Lengthy table referenced here |
| --- |
| US07951375-20110531-T00015 |
| Please refer to the end of the specification for access instructions. |

LENGTHY TABLES

The patent contains a lengthy table section. A copy of the table is available in electronic form from the USPTO web site (http://seqdata.uspto.gov/?pageRequest=docDetail&DocID=US07951375B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07951375B2). An electronic copy of the "Sequence Listing" will also be available from the USPTO upon request and payment of the fee set forth in 37 CFR 1.19(b)(3).

The invention claimed is:

1. A method of inducing an immunospecific immune response, comprising:
    exposing cells of the immune system of a mammal to a peptide consisting of residues 168 to 177 of the protein of SEQ ID NO: 40, and
    inducing the immunospecific immune response to the peptide.

2. The method of claim 1, wherein the peptide comprises or at least one B cell epitope.

3. The method of claim 2, whereby the peptide induces a B cell to generate antibodies that specifically bind to the protein.

4. The method of claim 2, wherein the peptide activates the antibody producing activity of a B cell.

5. The method of claim 1, wherein the immune response comprises production of an antibody that binds specifically to the peptide.

* * * * *